US012617777B2

(12) United States Patent
Abbott et al.

(10) Patent No.: US 12,617,777 B2
(45) Date of Patent: May 5, 2026

(54) GPR84 ANTAGONISTS AND USES THEREOF

(71) Applicant: Liminal BioSciences Limited, Cambridge (GB)

(72) Inventors: Shaun Abbott, Pointe Claire (CA); Mylène De Léséleuc, Montreal (CA); Julien Martel, Laval (CA); Elyse Bourque, L'Étang-du-Nord (CA); Jeremy Green, Waltham, MA (US); Alexandre Larivée, Montreal (CA); Jean-Benoìt Giguère, Montreal (CA); Elodie Landagaray, Montreal (CA); Claudio Sturino, L'ile-Bizard (CA); Nadia Michel Nasser, Laval (CA)

(73) Assignee: Liminal BioSciences Limited, Cheshire (GB)

( * ) Notice: Subject to any disclaimer, the term of this patent is extended or adjusted under 35 U.S.C. 154(b) by 0 days.

(21) Appl. No.: 17/649,752

(22) Filed: Feb. 2, 2022

(65) Prior Publication Data

US 2023/0113202 A1 Apr. 13, 2023

Related U.S. Application Data

(60) Provisional application No. 63/144,720, filed on Feb. 2, 2021.

(51) Int. Cl.

| | |
|---|---|
| *C07D 405/06* | (2006.01) |
| *C07D 249/06* | (2006.01) |
| *C07D 401/14* | (2006.01) |
| *C07D 405/12* | (2006.01) |
| *C07D 405/14* | (2006.01) |
| *C07D 409/06* | (2006.01) |
| *C07D 409/14* | (2006.01) |
| *C07D 413/06* | (2006.01) |
| *C07D 471/08* | (2006.01) |
| *C07D 471/10* | (2006.01) |
| *C07D 487/10* | (2006.01) |
| *C07D 491/056* | (2006.01) |

(52) U.S. Cl.

CPC ......... *C07D 405/06* (2013.01); *C07D 249/06* (2013.01); *C07D 401/14* (2013.01); *C07D 405/12* (2013.01); *C07D 405/14* (2013.01); *C07D 409/06* (2013.01); *C07D 409/14* (2013.01); *C07D 413/06* (2013.01); *C07D 471/08* (2013.01); *C07D 471/10* (2013.01); *C07D 487/10* (2013.01); *C07D 491/056* (2013.01)

(58) Field of Classification Search

CPC .. C07D 401/14; C07D 249/06; C07D 405/06; C07D 405/12; C07D 409/06; C07D 409/14; C07D 413/06; C07D 471/08; C07D 471/10; C07D 487/10; C07D 491/056

See application file for complete search history.

(56) References Cited

U.S. PATENT DOCUMENTS

| | | | |
|---|---|---|---|
| 5,112,839 | A | 5/1992 | Gericke et al. |
| 5,234,923 | A | 8/1993 | Poss et al. |
| 5,294,722 | A | 3/1994 | Kim |
| 5,356,911 | A | 10/1994 | Muller-Gliemann et al. |
| 5,374,615 | A | 12/1994 | Poss |
| 5,378,720 | A | 1/1995 | Hlasta et al. |
| 5,407,948 | A | 4/1995 | Fey et al. |
| 5,466,701 | A | 11/1995 | Hlasta et al. |
| 5,470,975 | A | 11/1995 | Atwal |
| 5,510,362 | A | 4/1996 | Matassa et al. |
| 5,512,576 | A | 4/1996 | Desai et al. |
| 5,599,823 | A | 2/1997 | Muller-Gliemann et al. |
| 5,607,957 | A | 3/1997 | Castro Pineiro et al. |
| 5,869,428 | A | 2/1999 | Morishima et al. |
| 6,265,350 | B1 | 7/2001 | Schnatterer et al. |
| 6,642,390 | B2 | 11/2003 | Kolb et al. |
| 6,670,307 | B2 | 12/2003 | Schnatterer et al. |
| 6,949,571 | B2 | 9/2005 | Nagato et al. |
| 7,067,540 | B2 | 6/2006 | Devadas et al. |
| 7,105,548 | B2 | 9/2006 | Cosford et al. |
| 7,183,287 | B2 | 2/2007 | Durley |
| 7,253,190 | B2 | 8/2007 | Cosford et al. |
| 7,268,151 | B2 | 9/2007 | Cosford et al. |
| 7,319,108 | B2 | 1/2008 | Schwink et al. |
| 7,332,508 | B2 | 2/2008 | Sorensen et al. |
| 7,348,334 | B2 | 3/2008 | Iqbal et al. |
| 7,371,767 | B2 | 5/2008 | Cosford et al. |
| 7,563,811 | B2 | 7/2009 | Nagato et al. |
| 7,569,592 | B2 | 8/2009 | Cosford et al. |
| 7,629,363 | B2 | 12/2009 | Devadas et al. |
| 7,728,017 | B2 | 6/2010 | Lauffer et al. |
| 7,759,367 | B2 | 7/2010 | Smith |

(Continued)

FOREIGN PATENT DOCUMENTS

| | | | |
|---|---|---|---|
| CA | 2020370 | A1 | 1/1991 |
| CA | 2809478 | A1 | 9/2014 |

(Continued)

OTHER PUBLICATIONS

Registry No. 1043552-81-3, File Registry on STN, entered STN Aug. 25, 2008.*
Registry No. 876592-08-4, File Registry on STN, entered STN Mar. 13, 2006.*
Kalisiak et al. Organic Letters, 2008, vol. 10, No. 15, 3171-3174.*
Registry No. 208990-89-0, File Registry on STN, entered STN Jul. 26, 1998.*
Al Mahmud, Z. et al., "Three classes of ligands each bind to distinct sites on the orphan G protein-coupled receptor GPR84," *Scientific Reports*, pp. 1-15 (2017).
Ando, M. et al., "Discovery of novel phenethylpyridone derivatives as potent melanin-concentrating hormone 1 receptor antagonists," Bioorganic & Medicinal Chemistry Letters vol. 19, pp. 5186-5190 (2009).

(Continued)

*Primary Examiner* — Rebecca L Anderson
(74) *Attorney, Agent, or Firm* — Dechert LLP

(57) ABSTRACT

The present invention provides compounds, compositions thereof, and methods of using the same for the inhibition of GPR84, and the treatment of GPR84-mediated disorders.

26 Claims, No Drawings

(56) References Cited

U.S. PATENT DOCUMENTS

| | | | | |
|---|---|---|---|---|
| 7,795,271 | B2 | 9/2010 | Durley | |
| 7,799,924 | B2 | 9/2010 | Sorensen et al. | |
| 7,879,896 | B2 | 2/2011 | Allegretti et al. | |
| 7,932,390 | B2 | 4/2011 | Chen et al. | |
| 7,939,549 | B2 | 5/2011 | Nagato et al. | |
| 7,973,060 | B2 | 7/2011 | Kim et al. | |
| 7,989,441 | B2 | 8/2011 | Chen et al. | |
| 7,989,478 | B2 | 8/2011 | Tomigahara et al. | |
| 7,998,987 | B2 | 8/2011 | Lauffer et al. | |
| 8,013,005 | B2 | 9/2011 | Allegretti et al. | |
| 8,017,635 | B2 | 9/2011 | Lyga et al. | |
| 8,084,471 | B2 | 12/2011 | Hamilton et al. | |
| 8,158,659 | B2 | 4/2012 | Allegretti et al. | |
| 8,236,846 | B2 | 8/2012 | Allegretti et al. | |
| 8,242,150 | B2 * | 8/2012 | Fischer ................ | C07D 471/04 548/255 |
| 8,299,101 | B2 | 10/2012 | Nez et al. | |
| 8,299,104 | B2 | 10/2012 | Schwink et al. | |
| 8,344,013 | B2 | 1/2013 | Allegretti et al. | |
| 8,349,875 | B2 | 1/2013 | Allegretti et al. | |
| 8,399,493 | B2 | 3/2013 | Bolea et al. | |
| 8,518,975 | B2 | 8/2013 | Aslanian et al. | |
| 8,569,351 | B2 | 10/2013 | Allegretti et al. | |
| 8,623,879 | B2 | 1/2014 | Giovannini et al. | |
| 8,623,901 | B2 | 1/2014 | Giovannini et al. | |
| 8,664,220 | B2 | 3/2014 | Clark et al. | |
| 8,664,254 | B2 | 3/2014 | Choi et al. | |
| 8,778,983 | B2 | 7/2014 | Clark et al. | |
| 8,841,323 | B2 | 9/2014 | Imogai et al. | |
| 8,895,755 | B2 | 11/2014 | Allegretti et al. | |
| 8,906,939 | B2 | 12/2014 | Cid-Nunez et al. | |
| 8,927,543 | B2 | 1/2015 | Labeguere et al. | |
| 9,012,485 | B2 | 4/2015 | Choi et al. | |
| 9,034,900 | B2 | 5/2015 | Bennett et al. | |
| 9,067,891 | B2 | 6/2015 | Cid-Nunez et al. | |
| 9,096,603 | B2 | 8/2015 | Giovannini et al. | |
| 9,102,679 | B2 | 8/2015 | Giovannini et al. | |
| 9,114,138 | B2 | 8/2015 | Cid-Nunez et al. | |
| 9,115,114 | B2 | 8/2015 | Bennett et al. | |
| 9,132,122 | B2 | 9/2015 | Cid-Nunez et al. | |
| 9,139,565 | B2 | 9/2015 | Oyelere et al. | |
| 9,150,514 | B2 | 10/2015 | Allegretti et al. | |
| 9,181,233 | B2 | 11/2015 | Heiser et al. | |
| 9,187,437 | B2 | 11/2015 | Das et al. | |
| 9,255,095 | B2 | 2/2016 | Labeguere et al. | |
| 9,266,834 | B2 | 2/2016 | Imogai et al. | |
| 9,271,978 | B2 | 3/2016 | Liu et al. | |
| 9,272,990 | B2 | 3/2016 | Seiders et al. | |
| 9,273,008 | B2 | 3/2016 | Choi et al. | |
| 9,359,379 | B2 | 6/2016 | Buckman et al. | |
| 9,533,967 | B2 | 1/2017 | Short et al. | |
| 9,540,322 | B2 | 1/2017 | Jorgensen et al. | |
| 9,547,197 | B2 | 1/2017 | Lim | |
| 9,598,367 | B2 | 3/2017 | Liu et al. | |
| 9,598,372 | B2 | 3/2017 | Boloor | |
| 9,643,922 | B2 | 5/2017 | Jorgensen et al. | |
| 9,675,593 | B2 | 6/2017 | Buckman et al. | |
| 9,861,637 | B2 | 1/2018 | Liu et al. | |
| 9,963,440 | B2 | 5/2018 | Short et al. | |
| 10,000,456 | B2 | 6/2018 | Clark et al. | |
| 10,023,592 | B2 | 7/2018 | Boloor | |
| 10,047,083 | B2 | 8/2018 | Labeguere et al. | |
| 10,125,102 | B2 | 11/2018 | Kotian et al. | |
| 10,130,625 | B2 | 11/2018 | Sintim et al. | |
| 10,202,343 | B2 | 2/2019 | Jorgensen et al. | |
| 10,329,260 | B2 | 6/2019 | Kotian et al. | |
| 10,336,724 | B2 | 7/2019 | Tsai et al. | |
| 10,376,497 | B2 | 8/2019 | Buckman et al. | |
| 10,428,082 | B2 | 10/2019 | Janganati et al. | |
| 10,508,127 | B2 | 12/2019 | Rosch et al. | |
| 10,562,915 | B2 | 2/2020 | Boloor | |
| 10,568,879 | B2 | 2/2020 | Menet et al. | |
| 10,633,345 | B2 | 4/2020 | Kotian et al. | |
| 10,653,674 | B2 | 5/2020 | Short et al. | |
| 10,689,346 | B2 | 6/2020 | Kotian et al. | |
| 10,898,474 | B2 | 1/2021 | Buckman et al. | |
| 2004/0259917 | A1 | 12/2004 | Cosford et al. | |
| 2005/0176775 | A1 | 8/2005 | Devadas et al. | |
| 2007/0060608 | A1 | 3/2007 | Vanderslice et al. | |
| 2007/0088033 | A1 | 4/2007 | Devadas et al. | |
| 2007/0167621 | A1 | 7/2007 | Durley | |
| 2007/0299065 | A1 | 12/2007 | Mederski et al. | |
| 2008/0280949 | A1 | 11/2008 | Albert et al. | |
| 2009/0137557 | A1 | 5/2009 | Ku et al. | |
| 2009/0170847 | A1 | 7/2009 | Lee et al. | |
| 2009/0270350 | A1 | 10/2009 | Devadas et al. | |
| 2010/0249092 | A1 | 9/2010 | Singh et al. | |
| 2010/0298384 | A1 | 11/2010 | Takhi et al. | |
| 2011/0045101 | A1 | 2/2011 | Selby et al. | |
| 2011/0281845 | A1 | 11/2011 | Chen et al. | |
| 2011/0313001 | A1 | 12/2011 | Fischer et al. | |
| 2012/0028931 | A1 | 2/2012 | Leonardi et al. | |
| 2013/0109652 | A1 | 5/2013 | Imogai et al. | |
| 2013/0253019 | A1 | 9/2013 | Hutchinson et al. | |
| 2013/0281503 | A1 | 10/2013 | Melander et al. | |
| 2014/0073634 | A1 | 3/2014 | Jones et al. | |
| 2016/0122333 | A1 | 5/2016 | Short et al. | |
| 2016/0256440 | A1 | 9/2016 | Short et al. | |
| 2017/0114323 | A1 | 4/2017 | Theunissen et al. | |
| 2018/0237424 | A1 | 8/2018 | Legeai-Mallet et al. | |
| 2019/0209548 | A1 | 7/2019 | Sintim et al. | |
| 2019/0209656 | A1 | 7/2019 | Petry et al. | |
| 2019/0270706 | A1 | 9/2019 | Jorgensen et al. | |
| 2019/0321343 | A1 | 10/2019 | Buckman et al. | |
| 2020/0038391 | A1 | 2/2020 | Cid-Nunez et al. | |
| 2020/0039943 | A1 | 2/2020 | Veiseh et al. | |
| 2020/0148703 | A1 | 5/2020 | Boloor | |
| 2020/0206196 | A1 | 7/2020 | Stewart et al. | |
| 2020/0247762 | A1 | 8/2020 | Mccormick et al. | |
| 2020/0255413 | A1 | 8/2020 | Teng et al. | |
| 2020/0270231 | A1 | 8/2020 | Aliper et al. | |
| 2020/0270234 | A1 | 8/2020 | Aliper et al. | |
| 2020/0331874 | A1 | 10/2020 | Shapiro et al. | |
| 2020/0331894 | A1 | 10/2020 | Tsai et al. | |

FOREIGN PATENT DOCUMENTS

| | | | |
|---|---|---|---|
| CN | 104513213 | A | 4/2015 |
| CN | 104844533 | A | 8/2015 |
| CN | 104876912 | A | 9/2015 |
| CN | 106316975 | A | 1/2017 |
| CN | 104876912 | B | 7/2017 |
| CN | 109369623 | A | 2/2019 |
| CN | 109456250 | A | 3/2019 |
| CN | 104844533 | B | 4/2019 |
| CN | 110396089 | A | 11/2019 |
| CN | 109369623 | B | 4/2020 |
| EP | 0407342 | A2 | 1/1991 |
| EP | 0488532 | A1 | 6/1992 |
| EP | 3372590 | A1 | 9/2018 |
| EP | 3403649 | A1 | 11/2018 |
| GB | 2263639 | A | 8/1993 |
| KR | 1020150136294 | A | 12/2015 |
| KR | 101666759 | B1 | 10/2016 |
| WO | WO-199318029 | A1 | 9/1993 |
| WO | WO-199320066 | A1 | 10/1993 |
| WO | WO-1996016952 | A1 | 6/1996 |
| WO | WO-1999052893 | A1 | 10/1999 |
| WO | WO-1999065901 | A1 | 12/1999 |
| WO | WO-2001096308 | A1 | 12/2001 |
| WO | WO-2002081454 | A1 | 10/2002 |
| WO | WO-2003029210 | A2 | 4/2003 |
| WO | WO-2003047577 | A2 | 6/2003 |
| WO | WO-2003051315 | A2 | 6/2003 |
| WO | WO-2003051833 | A2 | 6/2003 |
| WO | WO-2003053922 | A2 | 7/2003 |
| WO | WO-2003059904 | A1 | 7/2003 |
| WO | WO-2003068230 | A1 | 8/2003 |
| WO | WO-2003090699 | A1 | 11/2003 |
| WO | WO-2004030637 | A2 | 4/2004 |
| WO | WO-2004044046 | A2 | 5/2004 |
| WO | WO-2004054973 | A2 | 7/2004 |
| WO | WO-2004087677 | A2 | 10/2004 |
| WO | WO-2004089306 | A2 | 10/2004 |

(56) References Cited

FOREIGN PATENT DOCUMENTS

| | | | |
|---|---|---|---|
| WO | WO-2005018557 | A2 | 3/2005 |
| WO | WO-2005028439 | A1 | 3/2005 |
| WO | WO-2005070925 | A1 | 8/2005 |
| WO | WO-2006030032 | A1 | 3/2006 |
| WO | WO-2006058597 | A1 | 6/2006 |
| WO | WO-2006130403 | A1 | 12/2006 |
| WO | WO-2006133147 | A2 | 12/2006 |
| WO | WO-2007006591 | A2 | 1/2007 |
| WO | WO-2007018469 | A1 | 2/2007 |
| WO | WO-2007043835 | A1 | 4/2007 |
| WO | WO-2007062370 | A2 | 5/2007 |
| WO | WO-2007064797 | A2 | 6/2007 |
| WO | WO-2007083978 | A1 | 7/2007 |
| WO | WO-2007091176 | A1 | 8/2007 |
| WO | WO-2007104783 | A2 | 9/2007 |
| WO | WO-2007132948 | A1 | 11/2007 |
| WO | WO-2007136125 | A1 | 11/2007 |
| WO | WO-2007143597 | A2 | 12/2007 |
| WO | WO-2008000697 | A1 | 1/2008 |
| WO | WO-2008025886 | A1 | 3/2008 |
| WO | WO-2008030408 | A2 | 3/2008 |
| WO | WO-2008064317 | A1 | 5/2008 |
| WO | WO-2008064318 | A2 | 5/2008 |
| WO | WO-2008107479 | A1 | 9/2008 |
| WO | WO-2008107480 | A1 | 9/2008 |
| WO | WO-2008107481 | A1 | 9/2008 |
| WO | WO-2008133896 | A2 | 11/2008 |
| WO | WO-2008143649 | A2 | 11/2008 |
| WO | WO-2008156580 | A1 | 12/2008 |
| WO | WO-2009016498 | A1 | 2/2009 |
| WO | WO-2009032277 | A1 | 3/2009 |
| WO | WO-2009033704 | A1 | 3/2009 |
| WO | WO-2009087949 | A1 | 7/2009 |
| WO | WO-2009121919 | A1 | 10/2009 |
| WO | WO-2009137538 | A2 | 11/2009 |
| WO | WO-2009137651 | A2 | 11/2009 |
| WO | WO-2010021693 | A2 | 2/2010 |
| WO | WO-2010077582 | A1 | 7/2010 |
| WO | WO-2010112437 | A1 | 10/2010 |
| WO | WO-2010131145 | A1 | 11/2010 |
| WO | WO-2010131146 | A1 | 11/2010 |
| WO | WO-2010131147 | A1 | 11/2010 |
| WO | WO-2011029633 | A1 | 3/2011 |
| WO | WO-2011041461 | A2 | 4/2011 |
| WO | WO-2011041462 | A2 | 4/2011 |
| WO | WO-2011057112 | A1 | 5/2011 |
| WO | WO-2011107530 | A2 | 9/2011 |
| WO | WO-2011126903 | A2 | 10/2011 |
| WO | WO-2011140202 | A2 | 11/2011 |
| WO | WO-2011159632 | A1 | 12/2011 |
| WO | WO-2011159633 | A1 | 12/2011 |
| WO | WO-2011159635 | A1 | 12/2011 |
| WO | WO-2012011707 | A2 | 1/2012 |
| WO | WO-2012040532 | A1 | 3/2012 |
| WO | WO-2012041158 | A1 | 4/2012 |
| WO | WO-2012050868 | A1 | 4/2012 |
| WO | WO-2012058531 | A2 | 5/2012 |
| WO | WO-2012078593 | A2 | 6/2012 |
| WO | WO-2012164085 | A1 | 12/2012 |
| WO | WO-2013078320 | A1 | 5/2013 |
| WO | WO-2013092791 | A1 | 6/2013 |
| WO | WO-2014031928 | A2 | 2/2014 |
| WO | WO-2014048065 | A1 | 4/2014 |
| WO | WO-2014055548 | A1 | 4/2014 |
| WO | WO-2014095798 | A1 | 6/2014 |
| WO | WO-2014096965 | A2 | 6/2014 |
| WO | WO-2014113485 | A1 | 7/2014 |
| WO | WO-2014179144 | A1 | 11/2014 |
| WO | WO-2015058160 | A1 | 4/2015 |
| WO | WO-2015134998 | A1 | 9/2015 |
| WO | WO-2015162216 | A1 | 10/2015 |
| WO | WO-2015196072 | A2 | 12/2015 |
| WO | WO-2015197550 | A1 | 12/2015 |
| WO | WO-2016014674 | A1 | 1/2016 |
| WO | WO-2016058704 | A1 | 4/2016 |
| WO | WO-2016139227 | A1 | 9/2016 |
| WO | WO-2016169911 | A1 | 10/2016 |
| WO | WO-2017040459 | A1 | 3/2017 |
| WO | WO-2017069601 | A1 | 4/2017 |
| WO | WO-2017132528 | A1 | 8/2017 |
| WO | WO-2017207754 | A1 | 12/2017 |
| WO | WO-2018067615 | A1 | 4/2018 |
| WO | WO-2018195439 | A2 | 10/2018 |
| WO | WO-2018208985 | A2 | 11/2018 |
| WO | WO-2018210822 | A1 | 11/2018 |
| WO | WO-2018227228 | A1 | 12/2018 |
| WO | WO-2019060693 | A1 | 3/2019 |
| WO | WO 2019/067702 | * | 4/2019 |
| WO | WO-2019076329 | A1 | 4/2019 |
| WO | WO-2019096944 | A1 | 5/2019 |
| WO | WO-2019165158 | A1 | 8/2019 |
| WO | WO-202003313 | A1 | 1/2020 |
| WO | WO-2020006724 | A1 | 1/2020 |
| WO | WO-2020008013 | A1 | 1/2020 |
| WO | WO-2020011811 | A1 | 1/2020 |
| WO | WO-2020011812 | A1 | 1/2020 |
| WO | WO-2020011816 | A1 | 1/2020 |
| WO | WO-2020013646 | A1 | 1/2020 |
| WO | WO-2020020851 | A1 | 1/2020 |
| WO | WO-2020023846 | A1 | 1/2020 |
| WO | WO-2020033413 | A2 | 2/2020 |
| WO | WO-2020055164 | A1 | 3/2020 |
| WO | WO-2020033413 | A3 | 5/2020 |
| WO | WO-2020118194 | A1 | 6/2020 |
| WO | WO-2020131597 | A1 | 6/2020 |
| WO | WO-2020170202 | A1 | 8/2020 |
| WO | WO-2020170203 | A1 | 8/2020 |
| WO | WO-2021123394 | A1 | 6/2021 |
| WO | WO-2022167457 | A1 | 8/2022 |

OTHER PUBLICATIONS

Cosin-Roger, J. et al., "Metabolite Sensing CPCRs: Promising Therapeutic Targets for Cancer Treatment," *Cells*, vol. 9, pp. 1-33 (2020).

Dietrich, P.A., et .al., "GPR84 sustains aberrant β-catenin signaling in leukemic stem cells for maintenance of MLL leukemogenesis," *Blood*, vol. 124, No. 22, pp. 3284-3294 (2013).

Fredriksson, R. et al., "The G-Protein-Coupled Receptors in the Human Genome Form Five Main Families. Phylogenetic Analysis, Paralogon Groups, and Fingerprints," *Mol. Pharmacol.*, vol. 63, No. 6, pp. 1256-1272 (2003).

Gamo, K. et al., "G-Protein-Coupled Receptor Screen Reveals a Role for Chemokine Receptor CCR5 in Suppressing Microglial Neurotoxicity," *The Journal of Neuroscience*, 28(46), pp. 11980-11988 (2008).

International Search Report and Written Opinion for International Application No. PCT/EP2022/052400, dated Jul. 27, 2022.

International Search Report and Written Opinion for International Application No. PCT/EP2022/052419, dated Jul. 11, 2022.

Labeguere, F et al., "Discovery of 9-Cyclopropylethynyl-2-((S-1-[1,4]dioxan-2-ylmethoxy)-6,7- dihydropyrimido[6, 1-a]isoquinolin-4-one (GLPG1205), a Unique GPR84 Negative Allosteric Modulator Undergoing Evaluation in a Phase II Clinical Trial," *J. Med. Chem.*, vol. 63, pp. 13526-13545 (2020).

Mancini, S.J. et al., "On-target and off-target effects of novel orthosteric and allosteric activators of GPR84," *Scientific Reports*, vol. 9, pp. 1-15 (2019).

Nanthakumar, C.B. et al., "Dissecting fibrosis: therapeutic insights from the small-molecule toolbox," *Nature Reviews*, vol. 14, pp. 693-720 (2015).

News & Analysis, BioBusiness Briefs, Target Watch, "GPR84: an immune response dial," vol. 19, p. 374 (2020).

Partial International Search Report for International Application PCT/EP/2022/052400 dated May 10, 2022.

Partial International Search Report for International Application PCT/EP/2022/052419 dated May 20, 2022.

Raghu G. and Selman, M. "Nintedanib and Pirfenidone, New Antifibrotic Treatments Indicated for Idiopathic Pulmonary Fibrosis

(56) References Cited

OTHER PUBLICATIONS

Offer Hopes and Raises Questions," *Am. J. Resp. and Crit. Care Med.*, vol. 191, No. 3, pp. 252-254 (2015).
Reddy, N. et al., "Dual catalysis by Cu(i): facile single step click and intramolecular C—O bond formation leading to triazole tethered dihydrobenzodioxines/benzoxazines/benzoxathiines/ benzodioxepines," *Organic & Biomolecular Chemistry*, vol. 11, No. 42, pp. 7350-7360 (2013).
Thanigaimalai, P. et al., ("6-(Ar)Alkylamino-Substituted Uracil Derivatives: Lipid Mimetics with Potent Activity at the Orphan G Protein-Coupled Receptor 84 (GPR84)," *ACS Omega*, vol. 3, No. 3, pp. 3365-3383 (2018).
Vincetti, P. et al., "Discovery of Multitarget Antivirals Acting on Both the Dengue Virus NS5—NS3 Interaction and the Host Src/Fyn Kinases," *J. Med. Chem.*, vol. 58, pp. 4964-4975 (2015).
Wacker, D. et al., "How ligands illuminate GPCR molecular pharmacology," *Cell*, pp. 1-29, (2017).
Yu, J. et al., "Synthesis and antitumor activity of novel 2,3-diethanethio-2,3,5-trideoxy-5-triazolo nucleoside anlogues," *European J. Med. Chem., Elsevier*, Amsterdam, NL, vol. 45, No. 7, pp. 3219-3222 (2010).
Bouchard C., et al. in "G protein-coupled receptor 84, a microglia-associated protein expressed in neuroinflammatory conditions." Glia. 2007; 55(8):790-800.
Gagnon, L., et al. in "A Newly Discovered Antifibrotic Pathway Regulated by Two Fatty Acid Receptors: GPR40 and GPR84." American J. of Path., 2018, 188(5); 1132-1148.
Jenkins, L. et al., "Discovery and Characterization of Novel Antagonists of the Proinflammatory Orphan Receptor GPR84." ACS Pharmacology & Translational Science, 2021, 4(5): 1598-1613.
Kalisiak, J. et al., "Efficient Synthesis of 2-Substituted-1,2,3-triazoles," Org. Lett., 10(15):3171-3174 (2008).
Labeguère F., et al. in "Discovery of 9-Cyclopropylethynyl-2-((S)-1-[1,4]dioxan-2-ylmethoxy)-6,7-dihydropyrimido[6, 1-a]isoquinolin-4-one (GLPG1205), a Unique GPR84 Negative Allosteric Modulator Undergoing Evaluation in a Phase II Clinical Trial." J Med Chem. 2020; 63(22):13526-13545.
Lee, D. et al., "Efficient Syntheses of 1,2,3-Triazoloamide Derivatives Using Solid- and Solution-Phase Synthetic Approaches," Molecules, vol. 20, No. 11, (2015) pp. 19984-20013.
Luscombe V. B., et al. in "20 Years an Orphan: Is GPR84 a Plausible Medium-Chain Fatty Acid-Sensing Receptor?" DNA Cell Biol., vol. 39, No. 11 (2020) pp. 1926-1937.
Mohammadi, L. et al., "Synthesis of nanomagnetic supported thiourea-copper(I) catalyst and its application the syntheses of triazoles and benzamides," Applied Organometallic Chemistry, Longman Group UK, Ltd, Hoboken, USA, vol. 32, No. 1 (2017).
Nguyen Q. T., et al. in "PBI-4050 reduces pulmonary hypertension, lung fibrosis, and right ventricular dysfunction in heart failure." Cardiovasc Res. 2020; 116(1):171-182.
Nicol, L. S., et al. in "The role of G-protein receptor 84 in experimental neuropathic pain." J. Neurosci. 2015; 35(23):8959-69.
Puengel, T., et al. in "The Medium-Chain Fatty Acid Receptor GPR84 Mediates Myeloid Cell Infiltration Promoting Steatohepatitis and Fibrosis." J Clin Med. 2020; 9(4):1140.
Recio C., et al. in "Activation of the Immune-Metabolic Receptor GPR84 Enhances Inflammation and Phagocytosis in Macrophages." Front Immunol. 2018; 9:1419.
Simard, J. C., et al. in "Fatty acid mimetic PBI-4547 restores metabolic homeostasis via GPR84 in mice with non-alcoholic fatty liver disease." Sci Rep. 2020; 10, 12778.
STN Registry Database, Registry No. 1043552-81-3 for "4-[4-(1,1-Dimethylethyl)phenyl]-1H-1,2,3- triazole-1-methanol," entered on Aug. 25, 2008, 3 pages.
STN Registry Database, Registry No. 876592-08-4 for "4-Phenyl-1H-1,2,3-triazole-1-methanol" entered on Mar. 13, 2006, 3 pages.
Vincetti, P. et al., "Discovery of Multitarget Antivirals Acting on Both the Dengue Virus NS5—NS3 Interaction and the Host Src/Fyn Kinases," Journal of Medicinal Chemistry, vol. 58, No. 12 (2015) pp. 4964-4975.
Wei L., et al. in "Agonists for G-protein-coupled receptor 84 (GPR84) alter cellular morphology and motility but do not induce pro-inflammatory responses in microglia." J Neuroinflammation. 2017;14(1):198.
Yin, C. et al. in "Regulatory role of Gpr84 in the switch of alveolar macrophages from CD11blo to CD11bhi status during lung injury process." Mucosal Immun. 2020; 13(6): 892-907.
Luscombe in "20 Years an Orphan: Is GPR84 a Plausible Medium-Chain Fatty Acid-Sensing Receptor ?" *DNA and Cell Biology* (2020), vol. 39(11), pp. 1926-1937.
Chen in "Modulation of the G-Protein-Coupled Receptor 84 (GPR84) by Agonists and Antagonists" *J. Med. Chem.* 2020, 63, 1539915409.
Marsango in "Therapeutic validation of an orphan G protein-coupled receptor: The case of GPR84" *Br J Pharmacol.* 2022;179:35293541.
Desrivot in "Effect of GLPG1205, a GPR84 Modulator, on CYP2C9, CYP2C19, and CYP1A2 Enzymes: In Vitro and Phase 1 Studies" *Clinical Pharmacology in Drug Development* 2021, 10(9) 1007-1017.
Torkildsen in "Disease-modifying treatments for multiple sclerosis—a review of approved medications" *European Journal of Neurology* 2015, 23 (Suppl. 1):18-27.
Alavi in "The role of orphan G protein-coupled receptors in the pathophysiology of multiple sclerosis: A review," *Life Sciences* 224 2019) 33-40.
Bae in *Cancer Targeted Drug Delivery*, Springer: New York, 2013, Page v.
Hayat, M.A. in Autophagy Cancer, Other Pathologies, Inflammation, Immunity, Infection, and Aging vol. 5 Academic Press: San Diego, 2015, p. xxi.
Carlo C. Maley and Mel Greaves in *Frontiers in Cancer Research*, Springer: 2016, pp. 18-19.
Damia in "Contemporary pre-clinical development of anticancer agents—What are the optimal preclinical models?" *European Journal of Cancer* (2009) vol. 45, pp. 2768-2781.
Sharma in "Cell line-based platforms to evaluate the therapeutic efficacy of candidate anticancer agents" *Nature Reviews Cancer*, Apr. 2010, vol. 10, pp. 241-253.
Ocana, A. in "Preclinical development of molecular targeted agents for cancer" *Nat. Rev. Clin. Oncol.* 2011, 8, 200-209.
Ledford in "US cancer institute overhauls cell lines" *Nature* Feb. 25, 2016, vol. 530, p. 391.
Johnson, et al. "Relationships between drug activity in NCI preclinical in vitro and in vivo models and early clinical trials." *British Journal of Cancer* 2001, 84, 1424-1431.
Bendele in "Animal models of rheumatoid arthritis" *J Musculoskel Neuron Interact* 2001; 1(4):377-385.
University of Cambridge John van Geest Centre for Brain Repair School of Clinical Medicine "Alzheimer's disease and tauopathy" Online "http://www.brc.cam.ac.uk/research/alzheimers-disease-and-tauopathy/" accessed Sep. 10, 2015.
Tomohiro Chiba in "Emerging Therapeutic Strategies in Alzheimer's Disease" *Intech* 2013, 181-225.
Le Bars, et al. in "Animal Models of Nociception," *Pharmacological Reviews* 2001, 53, 597-652, at p. 634.
Costigan in "Neuropathic Pain: A Maladaptive Response of the Nervous System to Damage," *Annu. Rev. Neurosci.* 2009. 32:1-32.
Elborn in "Cystic fibrosis" The Lancet, Published online Apr. 29, 2016, Online "http://dx.doi.org/10.1016/S0140-6736(16)00576-6" 1-13.
Schober in "New Advances in the Treatment of Metastatic Pancreatic Cancer" *Digestion* 2015; vol. 92, pp. 175-184.
Zhao in "Vaccine adjuvants: mechanisms and platforms" *Signal Transduction and Targeted Therapy* (2023) vol. 8, p. 283.

* cited by examiner

GPR84 ANTAGONISTS AND USES THEREOF

CROSS REFERENCE TO RELATED APPLICATIONS

This application claims the benefit of and priority to U.S. Provisional Patent Application Ser. No. 63/144,720, filed Feb. 2, 2021; the contents of which are hereby incorporated by reference.

TECHNICAL FIELD OF THE INVENTION

The present invention relates to compounds and methods useful for antagonizing G-protein coupled receptor 84 (GPR84). The invention also provides pharmaceutically acceptable compositions comprising compounds of the present invention and methods of using said compositions in the treatment of various disorders.

BACKGROUND OF THE INVENTION

The G-protein coupled receptor 84 (GPR84), also known as EX33, GPCR4, and G protein-coupled receptor 84, is a medium chain fatty acid receptor mainly expressed in immune cells and upregulated under inflammatory conditions.

GPR84 was isolated and characterized from human B cells (Wittenberger et al. 2001. *J. Mol. Biol.* 307, 799-813) as the result of an expressed sequence tag data mining strategy, and also using a degenerate primer reverse transcriptase-polymerase chain reaction (RT-PCR) approach aimed to identify novel chemokine receptors expressed in neutrophils (Yousefi S et al. 2001. *J. Leukoc. Biol.* 69, 1045-1052). GPR84 remained an orphan GPCR until the identification of medium-chain Free Fatty Acids (FFAs) with carbon chain lengths of 9-14 as ligands for this receptor (Wang J et al. 2006. *J. Biol. Chem.* 281, 34457-34464). GPR84 was described to be activated by capric acid (C10:0), undecanoic acid (C11:0) and lauric acid (C12:0) with potencies of 5 μM, 9 μM and 11 μM, respectively. Three small molecules were also described to have some GPR84 agonist activity: 3,3'-diindolylmethane (DIM) (Wang et al. 2006), embelin (Hakak Y et al. 2007. WO2007027661 (A2)) and 6-n-octylaminouracil (6-OAU) (Suzuki M et al. 2013. *J. Biol. Chem.* 288, 10684-10691).

GPR84 has been shown to be expressed in immune cells at least but not limited to polymorphonuclear leukocytes (PMN), neutrophils, monocytes, T cells and B cells. (Hakak et al. 2007; Venkataraman C, Kuo F. 2005. *Immunol. Lett.* 101, 144-153; Wang et al. 2006; Yousefi et al. 2001). Higher levels of GPR84 were measured in neutrophils and eosinophils than in T-cells and B-cells. GPR84 expression was demonstrated in tissues that may play a role in the propagation of the inflammatory response such as lung, spleen, bone marrow.

For example, in a recent review, du Bois reported the current status of therapies for lung interstitial diseases, such as idiopathic pulmonary fibrosis (IPF). There are almost 300 distinct injurious or inflammatory causes of interstitial lung disease that can result in diffuse lung scarring, and the initial stages of the IPF pathology are very likely to involve inflammation (du Bois R M. 2010. *Nat. Rev. Drug Discov.* 9, 129-140), and combination therapies involving anti-inflammatory treatment could be advantageously used.

The expression of GPR84 was highly up-regulated in monocytes/macrophages upon LPS stimulation (Wang et al. 2006).

GPR84 knock-out (KO) mice are viable and indistinguishable from wild-type littermate controls (Venkataraman & Kuo 2005). The proliferation of T and B cells in response to various mitogens is reported to be normal in GPR84-deficient mice (Venkataraman & Kuo 2005). T helper 2 (Th2) differentiated T cells from GPR84 KO mice secreted higher levels of IL4, IL5, IL13, the 3 major $Th_2$ cytokines, compared to wild-type littermate controls. In contrast, the production of the Th1 cytokine, INFγ, was similar in Th1 differentiated T cells from GPR84 KO mice and wild-type littermate (Venkataraman & Kuo 2005).

In addition, capric acid, undecanoic acid and lauric acid dose dependently increased the secretion of interleukin-12 p40 subunit (IL-12 p40) from RAW264.7 murine macrophage-like cells stimulated with LPS. The pro-inflammatory cytokine IL-12 plays a pivotal role in promoting cell-mediated immunity to eradicate pathogens by inducing and maintaining T helper 1 (Th1) responses and inhibiting T helper 2 (Th2) responses. Medium-chain FFAs, through their direct actions on GPR84, may affect Th1/Th2 balance.

Berry et al. identified a whole-blood 393-gene transcriptional signature for active tuberculosis (TB) (Berry M P R et al. 2010. *Nature* 466, 973-977). GPR84 was part of this whole-blood 393-gene transcriptional signature for active TB indicating a potential role for GPR84 in infectious diseases.

GPR84 expression was also described in microglia, the primary immune effector cells of the central nervous system (CNS) of myeloid-monocytic origin (Bouchard C et al. 2007. *Glia* 55, 790-800). As observed in peripheral immune cells, GPR84 expression in microglia was highly inducible under inflammatory conditions such as TNFα and IL1 treatment but also notably endotoxemia and experimental autoimmune encephalomyelitis (EAE), suggesting a role in neuroinflammatory processes. Those results suggest that GPR84 would be up-regulated in CNS not only during endotoxemia and multiple sclerosis, but also in all neurological conditions in which TNFα or IL-1β pro-inflammatory cytokines are produced, including brain injury, infection, Alzheimer's disease (AD), Parkinson's disease (PD).

GPR84 expression was also observed in adipocytes and shown to be enhanced by inflammatory stimuli (Nagasaki H et al. 2012. *FEBS Lett.* 586, 368-372). The results suggest that the expression of GPR84 is triggered by TNFα from infiltrating macrophages and exacerbates the vicious cycle between adiposity and diabetes/obesity, and therefore the inhibition of GPR84 activity might be beneficial for the treatment of endocrine and/or metabolic diseases.

GPR84 expression is also upregulated in microglia surrounding the neurons, after nerve injury. (Gamo et al, 2008. *J. Neurosi.* 28(46), 11980-11988). Furthermore, in GPR84 knock-out mice, hypersensitivity to mechanical stimuli were significantly reduced or completely absent in mouse models of inflammatory and neuropathic pain (Nicol L S C et al. 2015. *J. Neurosci.* 35, 8959-8969). Molecules which block the activation of GPR84 may therefore have the potential to deliver broad-spectrum analgesia.

GPR84 expression is increased in human leukemic stem cells (LSC) from acute myeloid leukemia (AML) patients compared to hematopoietic stem cells from healthy donors. GPR84 simultaneously augments β-catenin signaling and an oncogenic transcription program essential for establishment of MLL leukemia (Dietrich et al, 2014. *Blood* 124(22), 3284-3294). Suppression of GPR84 significantly inhibited cell growth in pre-LSCs, reduced LSC frequency and impaired reconstitution of stem cell-derived MLL leukemia, which represents a particularly aggressive and drug-resistant subtype of AML. Targeting the oncogenic GPR84/β-catenin signaling axis may represent a novel therapeutic strategy for AML and possibly other leukemias.

GPR84 expression is increased by 49.9 times in M1 type macrophages isolated from aortic atherosclerotic lesions of LDLR−/− mice fed a western diet (Kadl A et al. 2010. *Circ. Res.* 107, 737-746). Therefore, molecules targeting GPR84 may have a potential benefit in treatment of atherosclerosis.

In experimental esophagitis, GPR84 is upregulated in the esophageal tissue, mainly in the epithelial cells, and is significantly decreased in rats treated with either omeprazole (proton pump inhibitor) or STW5, an herbal preparation shown to ameliorate esophagitis without affecting refluxate pH (Abdel-Aziz H et al. 2015. *Mol. Med.* 21, 1011-1024). This finding is supported by Western blot and immunohistochemistry in rat tissue and HET-1A cells, a human esophageal squamous cell line. GPR84 was also found to be significantly upregulated in esophageal biopsies from patients with grade B reflux esophagitis. Molecules that block the GPR84 receptor activity may therefore represent a new therapeutic paradigm for the treatment of esophagitis.

Therefore, the identification and development of novel compounds, processes for their preparation and their use in the preparation of a medicament would be highly desirable for patients suffering from inflammatory conditions, pain, neuroinflammatory conditions, neurodegenerative conditions, infectious diseases, autoimmune diseases, endocrine and/or metabolic diseases, cardiovascular diseases, leukemia, and/or diseases involving impairment of immune cell functions.

Additionally, the identification and development of novel compounds for use in the preparation of a medicament for the prophylaxis and/or treatment of one or more fibrotic diseases, and more particularly NASH and/or IPF remains highly desirable.

SUMMARY OF THE INVENTION

It has now been found that compounds of this invention, and pharmaceutically acceptable compositions thereof, are effective as antagonists of GPR84. In certain embodiments, the invention provides for compounds of the formulae presented herein.

Compounds of the present invention, and pharmaceutically acceptable compositions thereof, are useful for treating a variety of diseases, disorders or conditions, associated with GPR84. Such diseases, disorders, or conditions include those described herein.

Compounds provided by this invention are also useful for the study of GPR84 in biological and pathological phenomena; the study of fibrotic processes occurring in bodily tissues; and the comparative evaluation of new GPR84 inhibitors or other regulators of neutrophil and macrophage chemotaxis in vitro or in vivo.

DETAILED DESCRIPTION OF CERTAIN EMBODIMENTS

1. General Description of Certain Embodiments of the Invention:

In certain aspects, the present invention provides a compound of formula I:

I

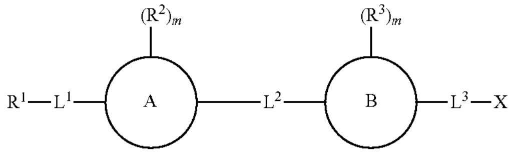

or a pharmaceutically acceptable salt thereof, wherein each of Ring A, Ring B, $L^1$, $L^2$, $L^3$, $R^1$, $R^2$, $R^3$, X, m, and n, is as defined below and described in embodiments herein, both singly and in combination.

In some embodiments, the present invention provides a pharmaceutical composition comprising a compound of formula I and a pharmaceutically acceptable carrier, adjuvant, or diluent.

In some embodiments, the present invention provides a method of treating a GPR84-mediated disease, disorder, or condition comprising administering to a patient in need thereof, a compound of formula I, or a pharmaceutically acceptable salt thereof.

2. Compounds and Definitions:

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, $75^{th}$ Ed. Additionally, general principles of organic chemistry are described in "Organic Chemistry", Thomas Sorrell, University Science Books, Sausalito: 1999, and "March's Advanced Organic Chemistry", $5^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

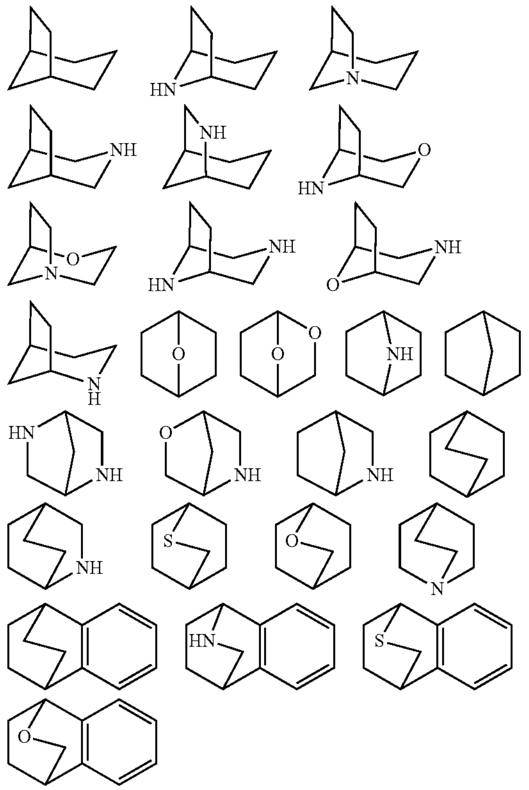

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where unless otherwise specified, the radical or point of attachment is on the heteroaromatic ring or on one of the rings to which the heteroaromatic ring is fused. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, and tetrahydroisoquinolinyl. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^{+}NR$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, 2-oxa-6-azaspiro[3.3]heptane, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $-(CH_2)_{0-4}R^o$; $-(CH_2)_{0-4}OR^o$; $-O(CH_2)_{0-4}R^o$, $-O-(CH_2)_{0-4}C(O)OR^o$; $-(CH_2)_{0-4}CH(OR^o)_2$; $-(CH2)_{0-4}SR^o$; $-(CH_2)_{0-4}Ph$, which may be substituted with $R^o$; $-(CH_2)_{0-4}O(CH_2)_{0-1}Ph$ which may be substituted with $R^o$; $-CH{=}CHPh$, which may be substituted with $R^o$; $-(CH_2)_{0-4}O(CH_2)_{0-1}$-pyridyl which may be substituted with $R^o$; $-NO_2$; $-CN$; $-N_3$; $-(CH_2)_{0-4}N(R^o)_2$; $-(CH_2)_{0-4}N(R^o)C(O)R^o$; $-N(R^o)C(S)R^o$; $-(CH_2)_{0-4}N(R^o)C(O)NR^o{}_2$; $-N(R^o)C(S)NR^o{}_2$; $-(CH_2)_{0-4}N(R^o)C(O)OR^o$; $-N(R^o)N(R^o)C(O)R^o$; $-N(R^o)N(R^o)C(O)NR^o{}_2$; $-N(R^o)N(R^o)C(O)OR^o$; $-N(R^o)C(NR^o)N(R^o)_2$; $-(CH_2)_{0-4}C(O)R^o$; $-C(S)R^o$; $-(CH_2)_{0-4}C(O)OR^o$; $-(CH_2)_{0-4}C(O)SR^o$; $-(CH_2)_{0-4}C(O)OSiR^o{}_3$; $-(CH_2)_{0-4}OC(O)R^o$; $-OC(O)(CH_2)_{0-4}SR^o$; $-SC(S)SR^o$; $-(CH_2)_{0-4}SC(O)R^o$; $-(CH_2)_{0-4}C(O)NR^o{}_2$; $-C(S)NR^o{}_2$; $-C(S)SR^o$; $-SC(S)SR^o$, $-(CH_2)_{0-4}OC(O)NR^o{}_2$; $-C(O)N(OR^o)R^o$; $-C(O)C(O)R^o$; $-C(O)CH_2C(O)R^o$; $-C(NOR^o)R^o$; $-(CH_2)_{0-4}SSR^o$; $-(CH_2)_{0-4}S(O)_2R^o$; $-(CH_2)_{0-4}S(O)_2OR^o$; $-(CH_2)_{0-4}OS(O)_2R^o$; $-S(O)_2NR^o{}_2$; $-(CH_2)_{0-4}S(O)R^o$; $-N(R^o)S(O)_2NR^o{}_2$; $-N(R^o)S(O)_2R^o$; $-N(OR^o)R^o$; $-C(NH)NR^o{}_2$; $-P(O)_2R^o$; $-P(O)R^o{}_2$; $-OP(O)R^o{}_2$; $-OP(O)(OR^o)_2$; $-SiR^o{}_3$; $-(C_{1-4}$ straight or branched alkylene)$O-N(R^o)_2$; or $-(C_{1-4}$ straight or branched alkylene)$C(O)O-N(R^o)_2$, wherein each $R^o$ may be substituted (e.g., with one, two, or more substituents) as defined below and is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^o$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^o$ (or the ring formed by taking two independent occurrences of $R^o$ together with their intervening atoms), are independently halogen, $-(CH_2)_{0-2}R^\bullet$,-(halo$R^\bullet$), $-(CH_2)_{0-2}OH$, $-(CH_2)_{0-2}OR^\bullet$, $-(CH_2)_{0-2}CH(OR^\bullet)_2$; $-O$(halo$R^\bullet$), $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet{}_2$, $-NO_2$, $-SiR^o{}_3$, $-OSiR^o{}_3$, $-C(O)SR^\bullet$, $-(C_{1-4}$ straight or branched alkylene)$C(O)OR^\bullet$, or $-SSR^\bullet$ wherein each $R^\bullet$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^o$ include $=O$ and $=S$.

Suitable divalent substituents on a saturated carbon atom of an "optionally substituted" group include the following: $=O$, $=S$, $=NNR^*{}_2$, $=NNHC(O)R^*$, $=NNHC(O)OR^*$, $=NNHS(O)_2R^*$, $=NR^*$, $=NOR^*$, $-O(C(R^*{}_2))_{2-3}O-$, or $-S(C(R^*{}_2))_{2-3}S-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR^*{}_2)_{2-3}O-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —$R^\bullet$, -(halo$R^\bullet$), —OH, —$OR^\bullet$, —O(halo$R^\bullet$), —CN, —C(O)OH, —C(O)$OR^\bullet$, —$NH_2$, —$NHR^\bullet$, —$NR^\bullet_2$, or —$NO_2$, wherein each $R^\bullet$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —$R^\dagger$, —$NR^\dagger_2$, —C(O)$R^\dagger$, —C(O)$OR^\dagger$, —C(O)C(O)$R^\dagger$, —C(O)$CH_2$C(O)$R^\dagger$, —$S(O)_2R^\dagger$, —$S(O)_2NR^\dagger_2$, —C(S)$NR^\dagger_2$, —C(NH)$NR^\dagger_2$, or —$N(R^\dagger)S(O)_2R^\dagger$; wherein each $R^\dagger$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, —$R^\bullet$, -(halo$R^\bullet$), —OH, —$OR^\bullet$, —O(halo$R^\bullet$), —CN, —C(O)OH, —C(O)$OR^\bullet$, —$NH_2$, —$NHR^\bullet$, —$NR^\bullet_2$, or —$NO_2$, wherein each $R^\bullet$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in *J. Pharmaceutical Sciences,* 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention.

In certain embodiments, $R^1$ of a provided compound comprises one or more deuterium atoms. In certain embodiments, $R^2$ of a provided compound comprises one or more deuterium atoms. In certain embodiments, $R^3$ of a provided compound comprises one or more deuterium atoms. In certain embodiments, $R^4$ of a provided compound comprises one or more deuterium atoms. In certain embodiments, $R^5$ of a provided compound comprises one or more deuterium atoms. In certain embodiments, $L^1$ of a provided compound comprises one or more deuterium atoms. In certain embodiments, $L^2$ of a provided compound comprises one or more deuterium atoms. In certain embodiments, $L^3$ of a provided compound comprises one or more deuterium atoms. In certain embodiments, Ring A of a provided compound comprises one or more deuterium atoms. In certain embodiments, Ring B of a provided compound comprises one or more deuterium atoms. In certain embodiments, Ring C of a provided compound comprises one or more deuterium atoms. In certain embodiments, R of a provided compound may be substituted with one or more deuterium atoms. In certain embodiments, $R^z$ of a provided compound may be substituted with one or more deuterium atoms. In certain embodiments, X of a provided compound may be substituted with one or more deuterium atoms.

The structures as drawn represent relative configurations, unless labeled as absolute configurations. The invention contemplates individual enantiomers and racemic mixtures.

As used herein, a "GPR84 antagonist" or a "GPR84 inhibitor" is a molecule that reduces, inhibits, or otherwise diminishes one or more of the biological activities of GPR84 (e.g. Gai signaling, increased immune cell migration, and secretion of proinflammatory cytokines). Antagonism using the GPR84 antagonist does not necessarily indicate a total elimination of the GPR84 activity. Instead, the activity could decrease by a statistically significant amount including, for example, a decrease of at least about 5%, 10%, 15%, 20%, 25%, 30%, 35%, 40%, 45%, 50%, 55%, 60%, 65%, 70%, 75%, 80%, 85%, 95% or 100% of the activity of GPR84 compared to an appropriate control. In some embodiments, the GPR84 antagonist reduces, inhibits, or otherwise diminishes the activity of GPR84. The presently disclosed compounds bind directly to GPR84 and inhibit its activity.

By “specific antagonist” is intended an agent that reduces, inhibits, or otherwise diminishes the activity of a defined target greater than that of an unrelated target. For example, a GPR84 specific antagonist reduces at least one biological activity of GPR84 by an amount that is statistically greater than the inhibitory effect of the antagonist on any other protein (e.g., other GPCRs). In some embodiments, the $IC_{50}$ of the antagonist for the target is about 90%, 80%, 70%, 60%, 50%, 40%, 30%, 20%, 10%, 5%, 1%, 0.1%, 0.01%, 0.001% or less of the $IC_{50}$ of the antagonist for a non-target. The presently disclosed compounds may or may not be a specific GPR84 antagonist. A specific GPR84 antagonist reduces the biological activity of GPR84 by an amount that is statistically greater than the inhibitory effect of the antagonist on any other protein (e.g., other GPCRs). In certain embodiments, the GPR84 antagonist specifically inhibits the activity of GPR84. In some of these embodiments, the $IC_{50}$ of the GPR84 antagonist for GPR84 is about 90%, 80%, 70%, 60%, 50%, 40%, 30%, 20%, 10%, 0.1%, 0.01%, 0.001%, or less of the $IC_{50}$ of the GPR84 antagonist for a closely related GPCR (e.g. a free fatty acid receptor (FFAR) such as GPR40 (FFAR1), GPR41 (FFAR3), GPR43 (FFAR2), or GPR120 (FFAR4)) or other type of GPCR (e.g., a Class A GPCR).

A compound of the present invention may be tethered to a detectable moiety. It will be appreciated that such compounds are useful as imaging agents. One of ordinary skill in the art will recognize that a detectable moiety may be attached to a provided compound via a suitable substituent. As used herein, the term “suitable substituent” refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties may be directly attached to a provided compound or via a tethering group, such as a bivalent saturated or unsaturated hydrocarbon chain. In some embodiments, such moieties may be attached via click chemistry. In some embodiments, such moieties may be attached via a 1,3-cycloaddition of an azide with an alkyne, optionally in the presence of a copper catalyst. Methods of using click chemistry are known in the art and include those described by Rostovtsev et al., *Angew. Chem. Int. Ed.* 2002, 41, 2596-99 and Sun et al., *Bioconjugate Chem.*, 2006, 17, 52-57. In some embodiments, such moieties may be attached via a strained alkyne. Methods of using strained alkynes to enable rapid Cu-free click chemistry are known in the art and include those described by Jewett et al., *J. Am. Chem. Soc.* 2010, 132(11), 3688-3690.

As used herein, the term “detectable moiety” is used interchangeably with the term “label” and relates to any moiety capable of being detected, e.g., primary labels and secondary labels. Primary labels, such as radioisotopes (e.g., tritium, $^{32}P$, $^{33}P$, $^{35}S$, or $^{14}C$), mass-tags, and fluorescent labels are signal generating reporter groups which can be detected without further modifications. Detectable moieties also include luminescent and phosphorescent groups.

The term “secondary label” as used herein refers to moieties such as biotin and various protein antigens that require the presence of a second intermediate for production of a detectable signal. For biotin, the secondary intermediate may include streptavidin-enzyme conjugates. For antigen labels, secondary intermediates may include antibody-enzyme conjugates. Some fluorescent groups act as secondary labels because they transfer energy to another group in the process of nonradiative fluorescent resonance energy transfer (FRET), and the second group produces the detected signal.

The terms “fluorescent label”, “fluorescent dye”, and “fluorophore” as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxy-rhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, Texas Red-X.

The term “mass-tag” as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360,8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

A compound of the present invention may be tethered to an E3 ligase binding moiety. It will be appreciated that such compounds are useful as degraders (see, for example, Kostic and Jones, *Trends Pharmacol. Sci.*, 2020, 41(5), 305-31; Ottis and Crews, *ACS Chem. Biol.* 2017, 12(4), 892-898). One of ordinary skill in the art will recognize that an E3 ligase binding moiety may be attached to a provided compound via a suitable substituent as defined above. Such degraders have been found to be useful for the targeted degradation of G-protein coupled receptors (Li et al. *Acta Pharm. Sin. B.* 2020, 10(9), 1669-1679).

As used herein, the term “E3 ligase binding moiety” is used interchangeably with the term “E3 ligase binder” and relates to any moiety capable of binding to and/or recruiting an E3 ligase (e.g., cIAP1, MDM2, cereblon, VHL, APC/C) for targeted degradation.

A compound of the present invention may be tethered to a lysosome targeting moiety. It will be appreciated that such compounds are useful as degraders (see, for example, Banik et al. 2020. *Nature* 584, 291-297). One of ordinary skill in the art will recognize that a lysosome targeting moiety may be attached to a provided compound via a suitable substituent as defined above. Such degraders have been found to be useful for the targeted degradation of secreted and membrane proteins (Banik et al. 2020).

As used herein, the term "lysosome targeting moiety" is used interchangeably with the term "lysosome binding moiety" and relates to any moiety capable of binding to and/or recruiting a cell surface lysosome targeting receptor (e.g., cation-independent mannose-6-phosphate receptor, CI-M6PR) for targeted degradation.

The terms "measurable affinity" and "measurably inhibit," as used herein, means a measurable change in a GPR84 activity between a sample comprising a compound of the present invention, or composition thereof, and a GPR84 GPCR, and an equivalent sample comprising a GPR84 GPCR, in the absence of said compound, or composition thereof.

3. Description of Exemplary Embodiments:

As described above, in certain embodiments, the present invention provides a compound of formula I.

I

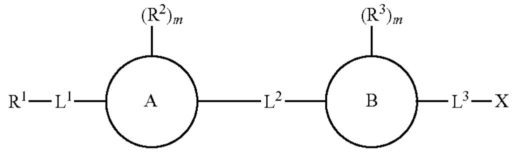

or a pharmaceutically acceptable salt thereof, wherein:

Ring A is a 5-6 membered monocyclic heteroaryl ring having 1-4 heteroatoms independently selected from nitrogen, oxygen, and sulfur; a 4-8 membered saturated or partially unsaturated monocyclic heterocyclic ring having 1-2 heteroatoms independently selected from nitrogen, oxygen, and sulfur; phenyl; an 8-10 membered bicyclic heteroaromatic ring (having 1-5 heteroatoms independently selected from nitrogen, oxygen, and sulfur); or a 3-7 membered saturated or partially unsaturated monocyclic carbocyclic ring;

Ring B is a 5-membered monocyclic heteroaryl ring having 1-4 heteroatoms independently selected from nitrogen, oxygen, and sulfur; or a 5-membered saturated or partially unsaturated monocyclic heterocyclic ring having 1-3 heteroatoms independently selected from nitrogen, oxygen, and sulfur;

$R^1$ is selected from (i) a 3-7 membered saturated or partially unsaturated monocyclic carbocyclic ring; a 5-6 membered monocyclic heteroaryl ring having 1-4 heteroatoms independently selected from nitrogen, oxygen, and sulfur; a 4-8 membered saturated or partially unsaturated monocyclic heterocyclic ring having 1-2 heteroatoms independently selected from nitrogen, oxygen, and sulfur; a 7-11 membered saturated or partially unsaturated spiro or bridged bicyclic heterocyclic ring having 1-2 heteroatoms independently selected from nitrogen, oxygen, and sulfur; phenyl; and a $C_{1-6}$ aliphatic; each of which is substituted with p instances of $R^4$; and (ii) hydrogen;

each instance of $R^2$, $R^4$, and $R^5$ is independently hydrogen, deuterium, $R^z$, halogen, —CN, —$NO_2$, —OR, —SR, —$NR_2$, —$S(O)_2R$, —$S(O)_2NR_2$, —S(O)R, —$S(O)NR_2$, —$CF_2R$, —$CF_3$, —$CR_2(CN)$, —$CR_2(OR)$, —$CR_2(NR_2)$, —C(O)R, —C(O)OR, —C(O)$NR_2$, —C(O)N(R)OR, —OC(O)R, —OC(O)$NR_2$, —C(S)$NR_2$, —N(R)C(O)OR, —N(R)C(O)R, —N(R)C(O)$NR_2$, —N(R)C(NR)$NR_2$, —N(R)$NR_2$, —N(R)$S(O)_2NR_2$, —N(R)$S(O)_2R$, —N═$S(O)R_2$, —S(NR)(O)R, —N(R)S(O)R, —N(R)CN, —Si(OR)$R_2$, —$SiR_3$, —P(O)(R)$NR_2$, —P(O)(R)OR or —P(O)$R_2$; or two $R^2$ groups are optionally taken together to form ═O;

two $R^4$ groups are optionally taken together to form ═O;

two $R^5$ groups are optionally taken together to form ═O;

two $R^2$ groups are optionally taken together with their intervening atoms to form a 5-8 membered saturated, partially unsaturated, or aryl fused ring having 0-3 heteroatoms independently selected from nitrogen, oxygen and sulfur;

two $R^4$ groups are optionally taken together with their intervening atoms to form a 5-8 membered saturated, partially unsaturated, or aryl fused ring having 0-3 heteroatoms independently selected from nitrogen, oxygen and sulfur; or two $R^5$ groups are optionally taken together with their intervening atoms to form a 5-8 membered saturated, partially unsaturated, or aryl fused ring having 0-3 heteroatoms independently selected from nitrogen, oxygen and sulfur;

each instance of $R^z$ is independently selected from an optionally substituted group selected from $C_{1-6}$ aliphatic; phenyl; a 3-7 membered saturated or partially unsaturated monocyclic carbocyclic ring; a 4-7 membered saturated or partially unsaturated heterocyclic ring having 1-2 heteroatoms independently selected from nitrogen, oxygen, and sulfur; and a 5-6 membered heteroaryl ring having 1-4 heteroatoms independently selected from nitrogen, oxygen, and sulfur;

$R^3$ is hydrogen or an optionally substituted $C_{1-6}$ aliphatic group; or two $R^3$ groups are optionally taken together to form ═O; or an R2 group and an R3 group are optionally taken together with their intervening atoms to form an optionally substituted 5-8 membered saturated or partially unsaturated fused ring having 0-3 heteroatoms independently selected from nitrogen, oxygen or sulfur;

$L^1$ is one of the following:

(a) a $C_{1-6}$ bivalent straight or branched saturated or unsaturated hydrocarbon chain wherein 1-3 methylene units of the chain are independently and optionally replaced with —O—,-Cy-, —C(O)—, —C(S)—, —$C(R)_2$—, —CH(R)—, —CH(OR)—, —$C(F)_2$—, —N(R)—, —S—, —S(O)—, or —$S(O)_2$—; or (b) a covalent bond;

each -Cy- is independently an optionally substituted bivalent ring selected from phenylene; 3-7 membered saturated or partially unsaturated carbocyclylene; 4-7 membered saturated or partially unsaturated heterocyclylene having 1-2 heteroatoms independently selected from nitrogen, oxygen, and sulfur; a 7-11 membered saturated or partially unsaturated spiro or bridged bicyclic heterocyclylene having 1-2 heteroatoms independently selected from nitrogen, oxygen, and sulfur; or a 5-6 membered heteroarylene having 1-4 heteroatoms independently selected from nitrogen, oxygen, and sulfur;

$L^2$ is a covalent bond or a $C_{1-4}$ bivalent straight or branched saturated or unsaturated hydrocarbon chain wherein 1-2 methylene units of the chain are independently and optionally replaced with —O—, —C(O)—, —C(S)—, —$C(R)_2$—, —CH(R)—, —CR(OR)—, —$C(F)_2$—, —N(R)—, —S—, —S(O)—, —CH($CR_3$)—, —C=($CH_2$)—, or —$S(O)_2$—;

$L^3$ is one of the following:

(a) a $C_{1-4}$ bivalent straight or branched saturated or unsaturated hydrocarbon chain wherein 1-2 methylene units of the chain are independently and optionally replaced with —O—, —C(O)—, —C(S)—, —$C(R)_2$—, —CH(R)—, —CH(OR)—, —$C(F)_2$—, —N(R)—, —S—, —S(O)—, or —$S(O)_2$—; or (b) a covalent bond;

X is one of the following:

(a) a 4-8 membered saturated or partially unsaturated monocyclic heterocyclic ring having 1-2 heteroatoms independently selected from nitrogen, oxygen, and sulfur; a 6-11 membered saturated or partiallay unsaturated bridged or spiro cyclic, bicyclic heterocyclic ring having 1-2 heteroatoms independently selected from nitrogen, oxygen, and sulfur; a 6-10 membered saturated or partiallay unsaturated bridged tricyclic heterocyclic ring having 1-2 heteroatoms independently selected from nitrogen, oxygen, and sulfur; an 8-10 membered partially aromatic or heteroaromatic bicyclic heterocyclic ring having 1-4 heteroatoms independently selected from nitrogen, oxygen, and sulfur; a 5-6 membered monocyclic heteroaryl ring having 1-4 heteroatoms independently selected from nitrogen, oxygen, and sulfur; a 3-7 membered saturated or partially unsaturated monocyclic carbocyclic ring; or phenyl; each of which is substituted with q instances of $R^5$; or (b) —$CH_2$(OR), —CH(R)(OR), or —$C(R)_2$(OR);

each instance of R is independently hydrogen, or an optionally substituted group selected from $C_{1-6}$ aliphatic; phenyl; an 8-10 membered bicyclic aryl ring, a 3-7 membered saturated or partially unsaturated monocyclic carbocyclic ring; a 4-8 membered saturated or partially unsaturated monocyclic heterocyclic ring having 1-2 heteroatoms independently selected from nitrogen, oxygen, and sulfur; a 5-6 membered monocyclic heteroaryl ring having 1-4 heteroatoms independently selected from nitrogen, oxygen, and sulfur; and an 8-10 membered bicyclic heteroaryl ring having 1-5 heteroatoms independently selected from nitrogen, oxygen, and sulfur; or two R groups on the same atom are optionally taken together with the atom to form an optionally substituted 3-7 membered monocyclic saturated, partially unsaturated, or heteroaryl ring having, in addition to the atom, 0-3 heteroatoms independently selected from nitrogen, oxygen, and sulfur;

m is 0, 1, 2, 3, or 4;

n is 0, 1, 2, 3, or 4;

p is 0, 1, 2, 3, 4, or 5; and q is 0, 1, 2, 3, 4, or 5.

As defined generally above, Ring A is a 5-6 membered monocyclic heteroaryl ring having 1-4 heteroatoms independently selected from nitrogen, oxygen, and sulfur; a 4-8 membered saturated or partially unsaturated monocyclic heterocyclic ring having 1-2 heteroatoms independently selected from nitrogen, oxygen, and sulfur; phenyl; an 8-10 membered bicyclic heteroaromatic ring (having 1-5 heteroatoms independently selected from nitrogen, oxygen, and sulfur); or a 3-7 membered saturated or partially unsaturated monocyclic carbocyclic ring.

In some embodiments, Ring A is a 5-6 membered monocyclic heteroaryl ring having 1-4 heteroatoms independently selected from nitrogen, oxygen, and sulfur. In some embodiments, Ring A is a 4-8 membered saturated or partially unsaturated monocyclic heterocyclic ring having 1-2 heteroatoms independently selected from nitrogen, oxygen, and sulfur. In some embodiments, Ring A is phenyl. In some embodiments, Ring A is an 8-10 membered bicyclic heteroaromatic ring (having 1-5 heteroatoms independently selected from nitrogen, oxygen, and sulfur). In some embodiments, Ring A is a 3-7 membered saturated or partially unsaturated monocyclic carbocyclic ring.

In some embodiments, Ring A is

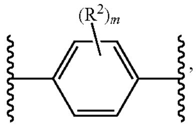,
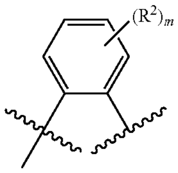,
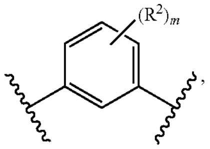,
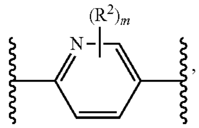,
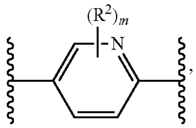,
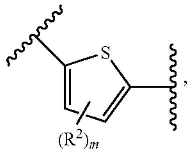,
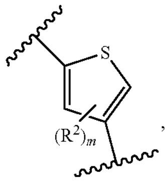,
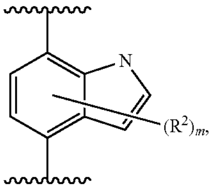,
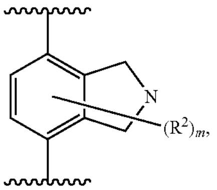,
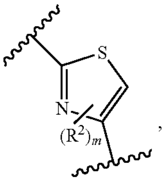,
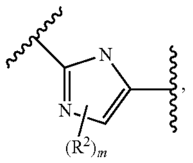,
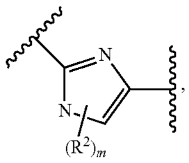,
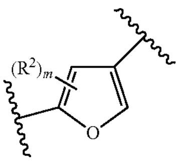,
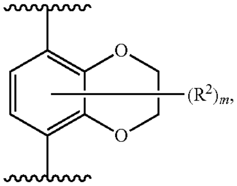

-continued

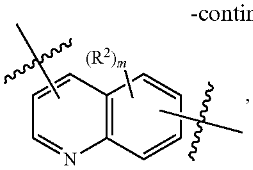, 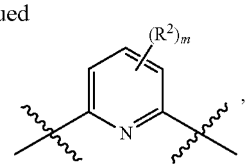,

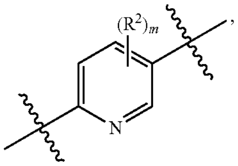, 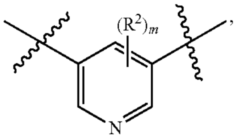,

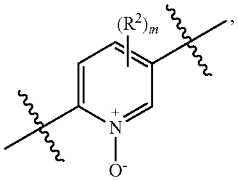, 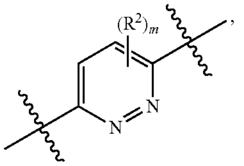,

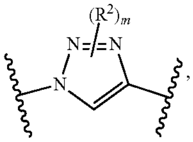, or 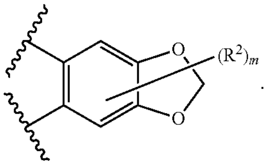.

In some embodiments, the  on the left side of Ring A is connected to $L^1$ and the  on the right side of Ring A is connected to $L^2$. In some embodiments, the  on the right side of Ring A is connected to $L^1$ and the  on the left side of Ring A is connected to $L^2$.

In some embodiments, Ring A is selected from those depicted in Table 1, below.

As defined generally above, Ring B is a 5-membered monocyclic heteroaryl ring having 1-4 heteroatoms independently selected from nitrogen, oxygen, and sulfur; or a 5-membered saturated or partially unsaturated monocyclic heterocyclic ring having 1-3 heteroatoms independently selected from nitrogen, oxygen, and sulfur.

In some embodiments, Ring B is a 5-membered monocyclic heteroaryl ring having 1-4 heteroatoms independently selected from nitrogen, oxygen, and sulfur.

In some embodiments, Ring B is a 5-membered saturated or partially unsaturated monocyclic heterocyclic ring having 1-3 heteroatoms independently selected from nitrogen, oxygen, and sulfur.

In some embodiments, Ring B is

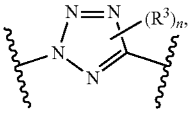, 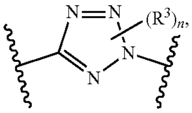,

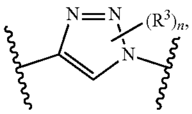, 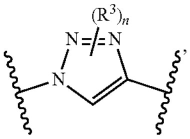,

-continued

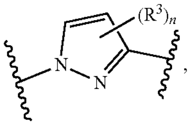, 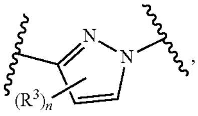,

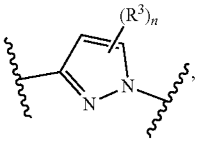, 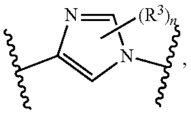,

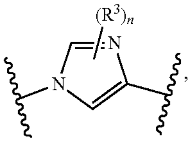, 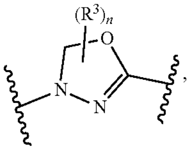,

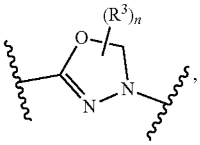, 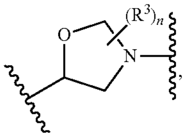,

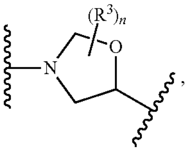, 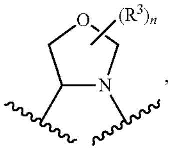,

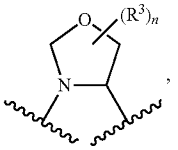, 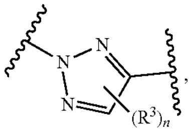,

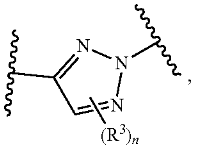, 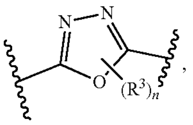,

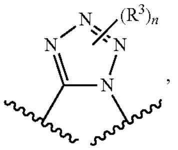, 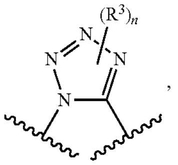,

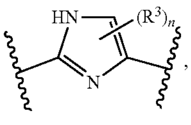, 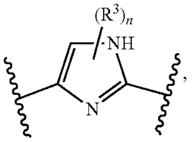,

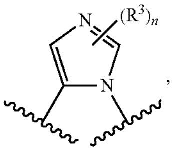, 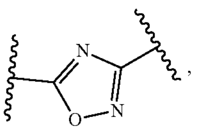, or

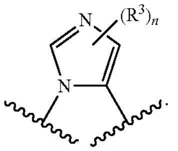.

In some embodiments, two $R^3$ groups are taken together to form =O and Ring B is

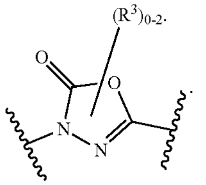

In some embodiments, two $R^3$ groups are taken together to form =O and Ring B is

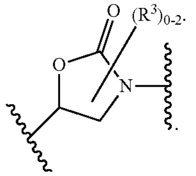

In some embodiments, two $R^3$ groups are taken together to form =O and Ring B is

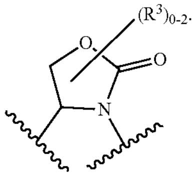

In some embodiments, the  on the left side of Ring B is connected to $L^2$ and the  on the right side of Ring B is connected to $L^3$. In some embodiments, the  on the right side of Ring B is connected to $L^2$ and the  on the left side of Ring B is connected to $L^3$.

In some embodiments, Ring B is selected from those depicted in Table 1, below.

As defined generally above, $R^1$ is selected from (i) a 3-7 membered saturated or partially unsaturated monocyclic carbocyclic ring; a 5-6 membered monocyclic heteroaryl ring having 1-4 heteroatoms independently selected from nitrogen, oxygen, and sulfur; a 4-8 membered saturated or partially unsaturated monocyclic heterocyclic ring having 1-2 heteroatoms independently selected from nitrogen, oxygen, and sulfur; a 7-11 membered saturated or partially unsaturated spiro bicyclic heterocyclic ring having 1-2 heteroatoms independently selected from nitrogen, oxygen, and sulfur; phenyl; and a $C_{1-6}$ aliphatic; each of which is substituted with p instances of $R^4$; and (ii) hydrogen.

In some embodiments, $R^1$ is a 3-7 membered saturated or partially unsaturated monocyclic carbocyclic ring substituted with p instances of $R^4$. In some embodiments, $R^1$ is a 5-6 membered monocyclic heteroaryl ring having 1-4 heteroatoms independently selected from nitrogen, oxygen, and sulfur, substituted with p instances of $R^4$. In some embodiments, $R^1$ is a 4-8 membered saturated or partially unsaturated monocyclic heterocyclic ring having 1-2 heteroatoms independently selected from nitrogen, oxygen, and sulfur, substituted with p instances of $R^4$. In some embodiments, $R^1$ is a 7-11 membered saturated or partially unsaturated spiro or bridged bicyclic heterocyclic ring having 1-2 heteroatoms independently selected from nitrogen, oxygen, and sulfur, substituted with p instances of $R^4$. In some embodiments, $R^1$ is a $C_{1-6}$ aliphatic group substituted with p instances of $R^4$. In some embodiments, $R^1$ is phenyl substituted with p instances of $R^4$. In some embodiments, $R^1$ is hydrogen.

In some embodiments, $R^1$ is

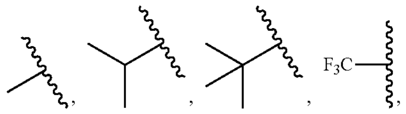

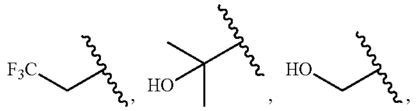

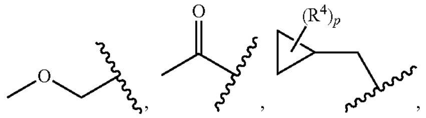

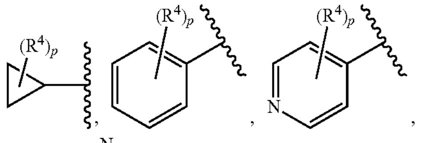

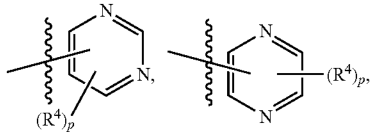

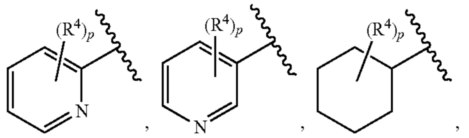

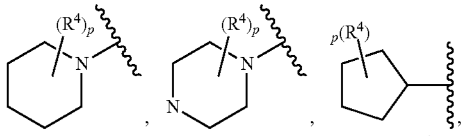

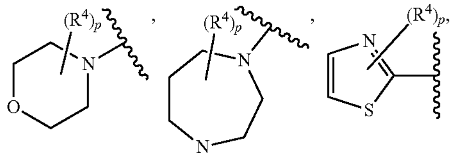

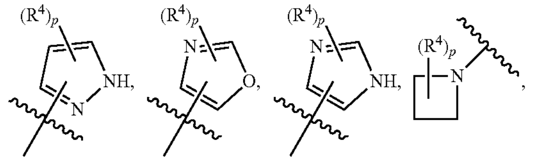

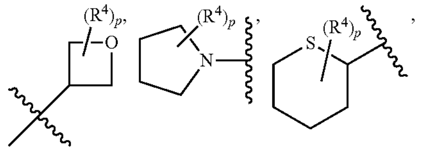

-continued

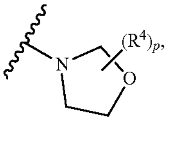 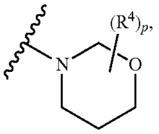

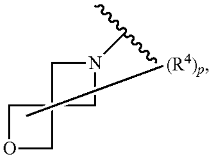 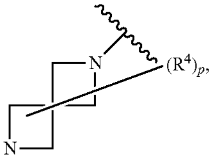

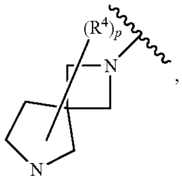, 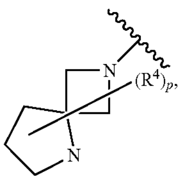 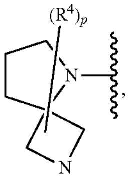

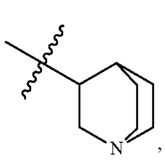, 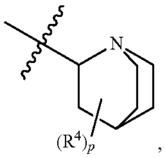, 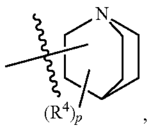,

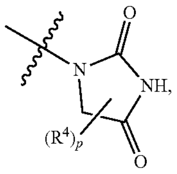 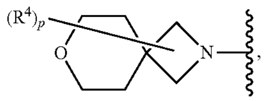 or

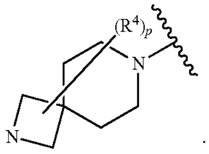

In some embodiments, two $R^4$ groups are taken together to form =O and $R^1$ is

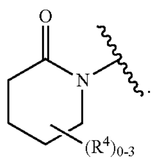

In some embodiments, two $R^4$ groups are taken together to form =O and $R^1$ is

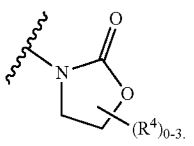

In some embodiments, two $R^4$ groups are taken together to form =O and $R^1$ is

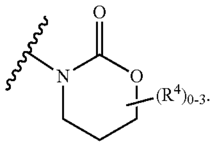

In some embodiments, two sets of $R^4$ groups are taken together to each form =O and $R^1$ is

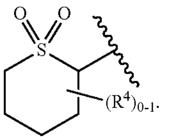

In some embodiments, $R^1$ is

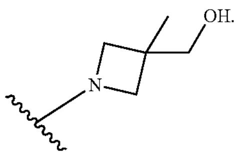 [SMILES: *N1CC(C)(CO)C1]

In some embodiments, $-L^1-R^1$ is

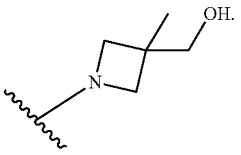 [SMILES: *N1CC(C)(CO)C1]

In some embodiments, $R^1$ is selected from those depicted in Table 1, below.

As defined generally above, each instance of $R^2$, $R^4$, and $R^5$ is independently hydrogen, deuterium, $R^z$, halogen, —CN, —$NO_2$, —OR, —SR, —$NR_2$, —$S(O)_2R$, —$S(O)_2NR_2$, —S(O)R, —$S(O)NR_2$, —$CF_2R$, —$CF_3$, —$CR_2(CN)$, —$CR_2(OR)$, —$CR_2(NR_2)$, —C(O)R, —C(O)OR, —$C(O)NR_2$, —C(O)N(R)OR, —OC(O)R, —$OC(O)NR_2$, —$C(S)NR_2$, —N(R)C(O)OR, —N(R)C(O)R, —$N(R)C(O)NR_2$, —$N(R)C(NR)NR_2$, —$N(R)NR_2$, —$N(R)S(O)_2NR_2$, —$N(R)S(O)_2R$, —N=$S(O)R_2$, —S(NR)(O)R, —N(R)S(O)R, —N(R)CN, —$Si(OR)R_2$, —$SiR_3$, —$P(O)(R)NR_2$, —P(O)(R)OR or —$P(O)R_2$.

In some embodiments, $R^2$ is hydrogen, deuterium, $R^z$, halogen, —CN, —$NO_2$, —OR, —SR, —$NR_2$, —$S(O)_2R$, —$S(O)_2NR_2$, —S(O)R, —$S(O)NR_2$, —$CF_2R$, —$CF_3$, —$CR_2(CN)$, —$CR_2(OR)$, —$CR_2(NR_2)$, —C(O)R, —C(O)OR, —$C(O)NR_2$, —C(O)N(R)OR, —OC(O)R, —$OC(O)NR_2$, —$C(S)NR_2$, —N(R)C(O)OR, —N(R)C(O)R, —$N(R)C(O)NR_2$, —$N(R)C(NR)NR_2$, —$N(R)NR_2$, —$N(R)S(O)_2NR_2$, —$N(R)S(O)_2R$, —N=$S(O)R_2$, —S(NR)(O)R, —N(R)S(O)R, —N(R)CN, —$Si(OR)R_2$, —$SiR_3$, —$P(O)(R)NR_2$, —P(O)(R)OR or —$P(O)R_2$. In some embodiments, $R^2$ is hydrogen. In some embodiments, $R^2$ is $R^z$, halogen, —CN, —$NO_2$, —OR, —SR, —$NR_2$, —$S(O)_2R$, —$S(O)_2NR_2$, —S(O)R, —$S(O)NR_2$, —$CF_2R$, —$CF_3$, —$CR_2(CN)$, —$CR_2(OR)$, —$CR_2(NR_2)$, —C(O)R, —C(O)OR, —$C(O)NR_2$, —C(O)N(R)OR, —OC(O)R, —$OC(O)NR_2$, —C(S)

$NR_2$, —N(R)C(O)OR, —N(R)C(O)R, —N(R)C(O)$NR_2$, —N(R)C(NR)$NR_2$, —N(R)$NR_2$, —N(R)$S(O)_2NR_2$, —N(R)$S(O)_2R$, —N═$S(O)R_2$, —S(NR)(O)R, —N(R)S(O)R, —N(R)CN, —Si(OR)$R_2$, —$SiR_3$, —P(O)(R)$NR_2$, —P(O)(R)OR or —P(O)$R_2$.

In some embodiments, $R^2$ is methyl, ethyl, n-propyl, isopropyl, fluoro, chloro, —$CF_3$, —$OCH_3$, —$N(CH_3)_2$, —$OCH_2CH_2OH$, —$CH_2CF_3$, —C(O)$CH_3$, —S(O)$CH_3$, —$S(O)_2CH_3$, -OiPr, —$SCH_3$, —CN, —C(O)$NH_2$, —C(O)$OCH_3$, —$CH_2OH$, —$CH_2CN$, —$CO_2H$, —$OCF_3$, —$OCHF_2$,

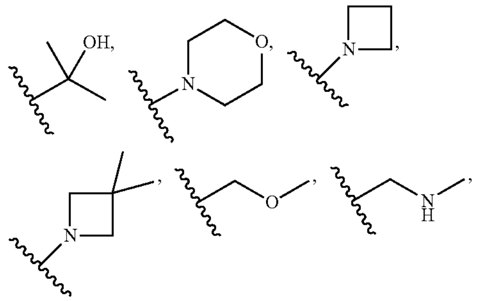

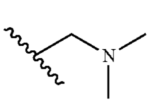

, or

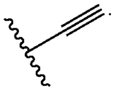

In some embodiments, $R^2$ is selected from those depicted in Table 1, below.

As defined generally above, $R^4$ is hydrogen, deuterium, $R^z$, halogen, —CN, —$NO_2$, —OR, —SR, —$NR_2$, —$S(O)_2R$, —$S(O)_2NR_2$, —S(O)R, —S(O)$NR_2$, —$CF_2R$, —$CF_3$, —$CR_2$(CN), —$CR_2$(OR), —$CR_2$($NR_2$), —C(O)R, —C(O)OR, —C(O)$NR_2$, —C(O)N(R)OR, —OC(O)R, —OC(O)$NR_2$, —C(S)$NR_2$, —N(R)C(O)OR, —N(R)C(O)R, —N(R)C(O)$NR_2$, —N(R)C(NR)$NR_2$, —N(R)$NR_2$, —N(R)$S(O)_2NR_2$, —N(R)$S(O)_2R$, —N═$S(O)R_2$, —S(NR)(O)R, —N(R)S(O)R, —N(R)CN, —Si(OR)$R_2$, —$SiR_3$, —P(O)(R)$NR_2$, —P(O)(R)OR or —P(O)$R_2$. In some embodiments, $R^4$ is hydrogen. In some embodiments, $R^4$ is $R^z$, halogen, —CN, —$NO_2$, —OR, —SR, —$NR_2$, —$S(O)_2R$, —$S(O)_2NR_2$, —S(O)R, —S(O)$NR_2$, —$CF_2R$, —$CF_3$, —$CR_2$(CN), —$CR_2$(OR), —$CR_2$($NR_2$), —C(O)R, —C(O)OR, —C(O)$NR_2$, —C(O)N(R)OR, —OC(O)R, —OC(O)$NR_2$, —C(S)$NR_2$, —N(R)C(O)OR, —N(R)C(O)R, —N(R)C(O)$NR_2$, —N(R)C(NR)$NR_2$, —N(R)$NR_2$, —N(R)$S(O)_2NR_2$, —N(R)$S(O)_2R$, —N═$S(O)R_2$, —S(NR)(O)R, —N(R)S(O)R, —N(R)CN, —Si(OR)$R_2$, —$SiR_3$, —P(O)(R)$NR_2$, —P(O)(R)OR or —P(O)$R_2$.

In some embodiments, $R^4$ is methyl, fluoro, —$OCH_3$, —$N(CH_3)_2$, —OH, —$CF_3$, —C(O)$NH_2$, —CN,

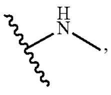

,

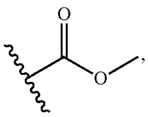

, or

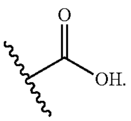

In some embodiments, $R^4$ is selected from those depicted in Table 1, below.

As defined generally above, $R^5$ is hydrogen, deuterium, $R^z$, halogen, —CN, —$NO_2$, —OR, —SR, —$NR_2$, —$S(O)_2R$, —$S(O)_2NR_2$, —S(O)R, —S(O)$NR_2$, —$CF_2R$, —$CF_3$, —$CR_2$(CN), —$CR_2$(OR), —$CR_2$($NR_2$), —C(O)R, —C(O)OR, —C(O)$NR_2$, —C(O)N(R)OR, —OC(O)R, —OC(O)$NR_2$, —C(S)$NR_2$, —N(R)C(O)OR, —N(R)C(O)R, —N(R)C(O)$NR_2$, —N(R)C(NR)$NR_2$, —N(R)$NR_2$, —N(R)$S(O)_2NR_2$, —N(R)$S(O)_2R$, —N═$S(O)R_2$, —S(NR)(O)R, —N(R)S(O)R, —N(R)CN, —Si(OR)$R_2$, —$SiR_3$, —P(O)(R)$NR_2$, —P(O)(R)OR or —P(O)$R_2$.

In some embodiments, $R^5$ is methyl, fluoro,

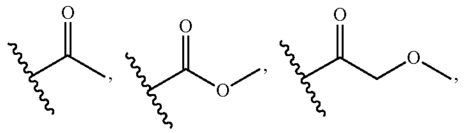

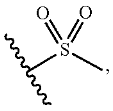

, or

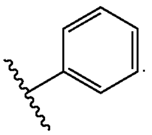

In some embodiments, $R^5$ is hydrogen. In some embodiments, $R^5$ is $R^z$, halogen, —CN, —$NO_2$, —OR, —SR, —$NR_2$, —$S(O)_2R$, —$S(O)_2NR_2$, —S(O)R, —S(O)$NR_2$, —$CF_2R$, —$CF_3$, —$CR_2$(CN), —$CR_2$(OR), —$CR_2$($NR_2$), —C(O)R, —C(O)OR, —C(O)$NR_2$, —C(O)N(R)OR, —OC(O)R, —OC(O)$NR_2$, —C(S)$NR_2$, —N(R)C(O)OR, —N(R)C(O)R, —N(R)C(O)$NR_2$, —N(R)C(NR)$NR_2$, —N(R)$NR_2$, —N(R)$S(O)_2NR_2$, —N(R)$S(O)_2R$, —N═$S(O)R_2$, —S(NR)(O)R, —N(R)S(O)R, —N(R)CN, —Si(OR)$R_2$, —$SiR_3$, —P(O)(R)$NR_2$, —P(O)(R)OR or —P(O)$R_2$.

In some embodiments, $R^5$ is selected from those depicted in Table 1, below.

As defined generally above, two $R^2$ groups are optionally taken together to form ═O.

In some embodiments, two $R^2$ groups are taken together to form ═O.

As defined generally above, two $R^4$ groups are optionally taken together to form ═O.

In some embodiments, two $R^4$ groups are taken together to form ═O.

As defined generally above, two $R^5$ groups are optionally taken together to form ═O.

In some embodiments, two $R^5$ groups are taken together to form ═O.

As defined generally above, two $R^2$ groups are optionally taken together with their intervening atoms to form a 5-8 membered saturated, partially unsaturated, or aryl fused ring having 0-3 heteroatoms independently selected from nitrogen, oxygen and sulfur.

In some embodiments, two $R^2$ groups are taken together with their intervening atoms to form a 5-8 membered saturated, partially unsaturated, or aryl fused ring having 0-3 heteroatoms independently selected from nitrogen, oxygen and sulfur.

As defined generally above, two $R^4$ groups are optionally taken together with their intervening atoms to form a 5-8 membered saturated, partially unsaturated, or aryl fused ring having 0-3 heteroatoms independently selected from nitrogen, oxygen and sulfur.

In some embodiments, two $R^4$ groups are taken together with their intervening atoms to form a 5-8 membered saturated, partially unsaturated, or aryl fused ring having 0-3 heteroatoms independently selected from nitrogen, oxygen and sulfur.

As defined generally above, two $R^5$ groups are optionally taken together with their intervening atoms to form a 5-8 membered saturated, partially unsaturated, or aryl fused ring having 0-3 heteroatoms independently selected from nitrogen, oxygen and sulfur.

In some embodiments, two $R^5$ groups are taken together with their intervening atoms to form a 5-8 membered saturated, partially unsaturated, or aryl fused ring having 0-3 heteroatoms independently selected from nitrogen, oxygen and sulfur.

As defined generally above, each instance of $R^z$ is independently selected from an optionally substituted group selected from $C_{1-6}$ aliphatic; phenyl; a 4-7 membered saturated or partially unsaturated heterocyclic ring having 1-2 heteroatoms independently selected from nitrogen, oxygen, and sulfur; and a 5-6 membered heteroaryl ring having 1-4 heteroatoms independently selected from nitrogen, oxygen, and sulfur.

In some embodiments, $R^z$ is selected from an optionally substituted group selected from $C_{1-6}$ aliphatic; phenyl; a 4-7 membered saturated or partially unsaturated heterocyclic ring having 1-2 heteroatoms independently selected from nitrogen, oxygen, and sulfur; and a 5-6 membered heteroaryl ring having 1-4 heteroatoms independently selected from nitrogen, oxygen, and sulfur.

In some embodiments, $R^z$ is selected from those depicted in Table 1, below.

As defined generally above, $R^3$ is hydrogen or an optionally substituted $C_{1-6}$ aliphatic group. In some embodiments, $R^3$ is hydrogen. In some embodiments, $R^3$ is an optionally substituted $C_{1-6}$ aliphatic group. In some embodiments, $R^3$ is methyl. In some embodiments, $R^3$ is selected from those depicted in Table 1, below.

As defined generally above, two $R^3$ groups are optionally taken together to form =O. In some embodiments, two $R^3$ groups are taken together to form =O.

As defined generally above, an $R^2$ group and an $R^3$ group are optionally taken together with their intervening atoms to form a 5-8 membered saturated or partially unsaturated fused ring having 0-3 heteroatoms independently selected from nitrogen, oxygen or sulfur.

In some embodiments, an $R^2$ group and an $R^3$ group are taken together with their intervening atoms to form a 5-8 membered saturated or partially unsaturated fused ring having 0-3 heteroatoms independently selected from nitrogen, oxygen or sulfur.

As defined generally above, $L^1$ is one of the following: (a) a $C_{1-6}$ bivalent straight or branched saturated or unsaturated hydrocarbon chain wherein 1-3 methylene units of the chain are independently and optionally replaced with —O—, -Cy-, —C(O)—, —C(S)—, —$C(R)_2$—, —CH(R)—, —CH(OR)—, —$C(F)_2$—, —N(R)—, —S—, —S(O)—, or —$S(O)_2$—; or (b) a covalent bond.

In some embodiments, $L^1$ is a $C_{1-6}$ bivalent straight or branched saturated or unsaturated hydrocarbon chain wherein 1-3 methylene units of the chain are independently and optionally replaced with —O—, -Cy-, —C(O)—, —C(S)—, —$C(R)_2$—, —CH(R)—, —CH(OR)—, —$C(F)_2$—, —N(R)—, —S—, —S(O)—, or —$S(O)_2$—.

In some embodiments, $L^1$ is a covalent bond.

In some embodiments, $L^1$ is

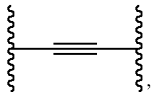,
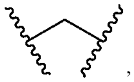,
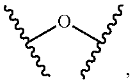,

-continued

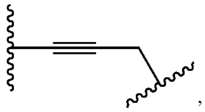,
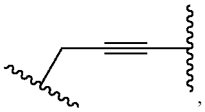,
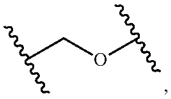,
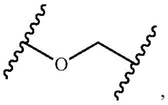,
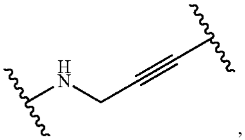,
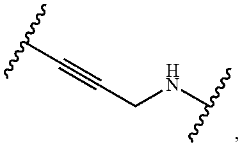,
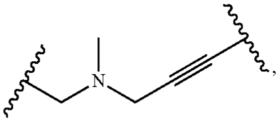,
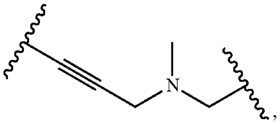,
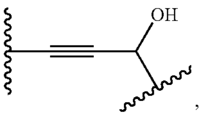,
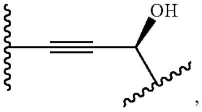,
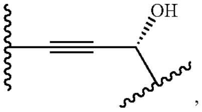,
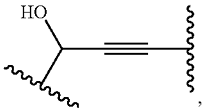,
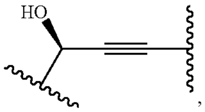,
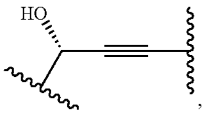,
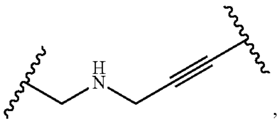,
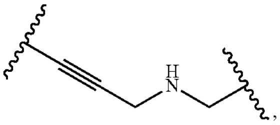,
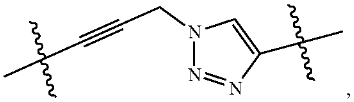,
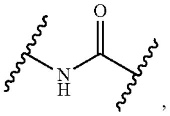,
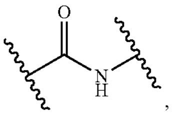,
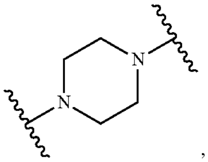,
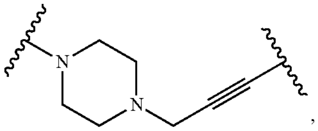,
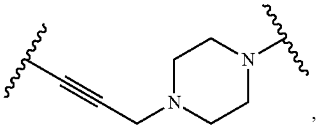, -continued
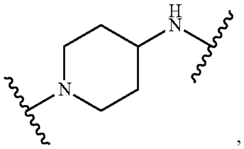,
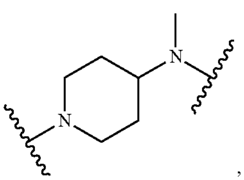,
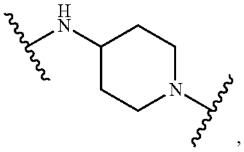,
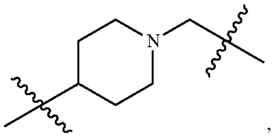,
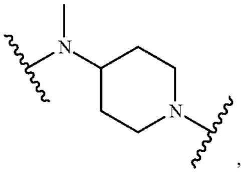,
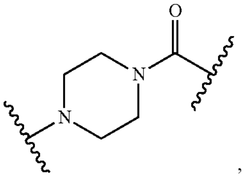,
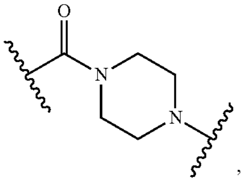,
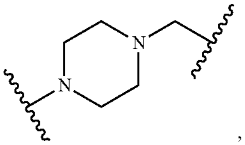,
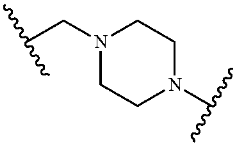,
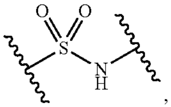,
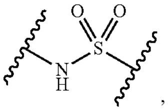,
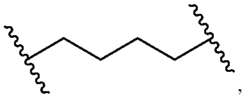,
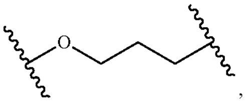,
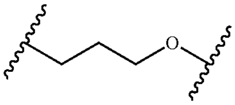,
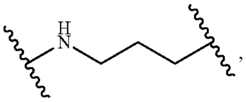,
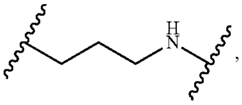,
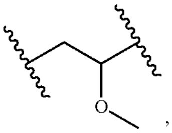,
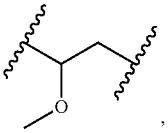,
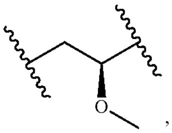,
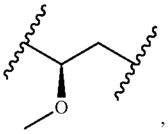,
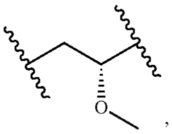,
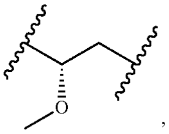,
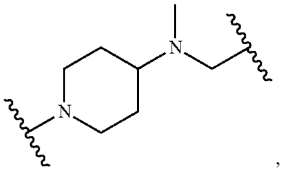,
-continued
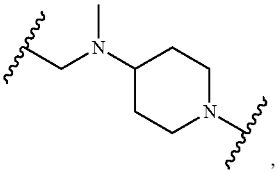,
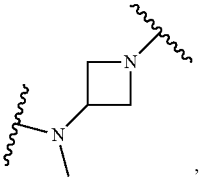,
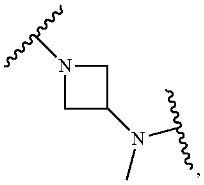,
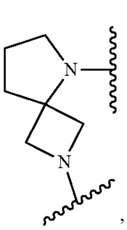,
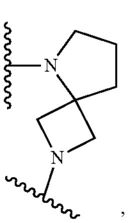,
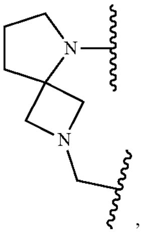,
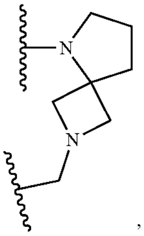,
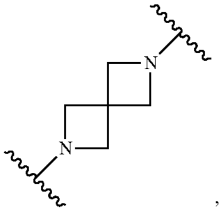,
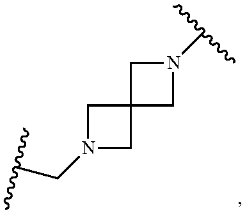,
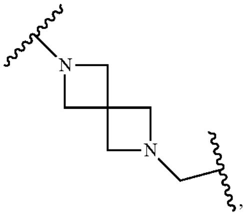,
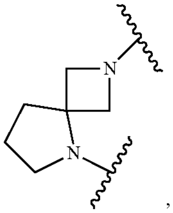,
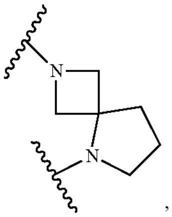,
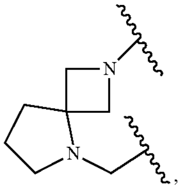,
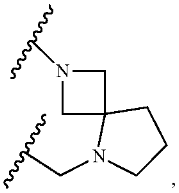,
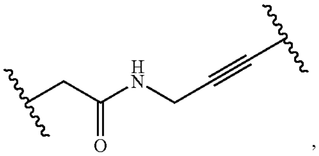, -continued
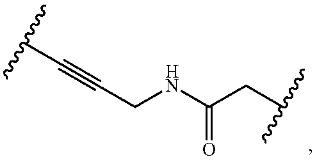,
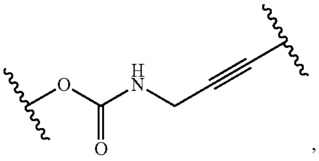,
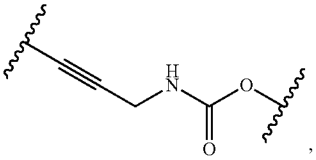,
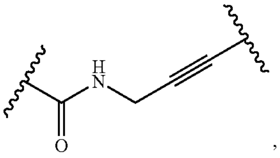,
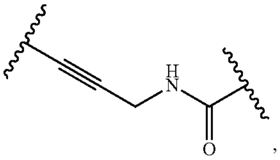,
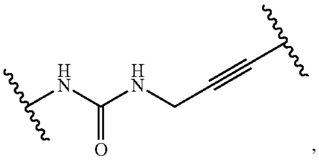,
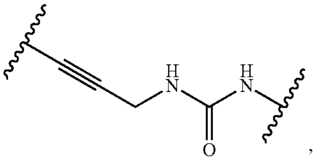,
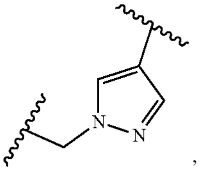, 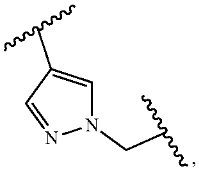,
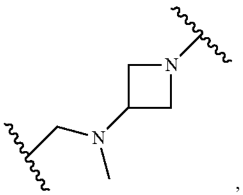, 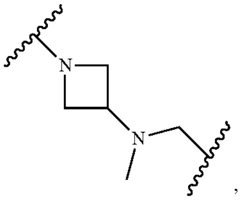,
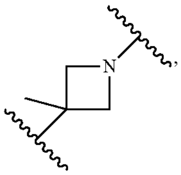, 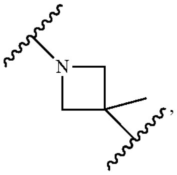,
-continued
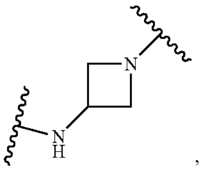, 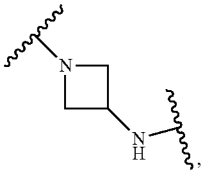,
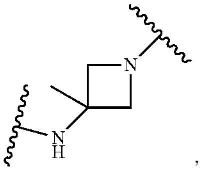, 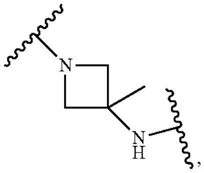,
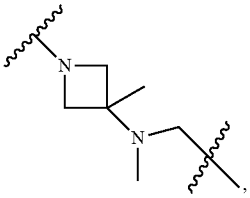, 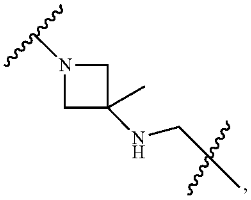,
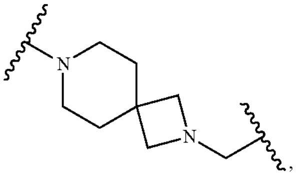,
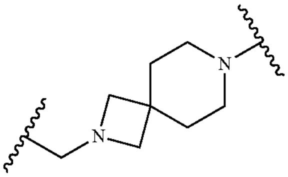, 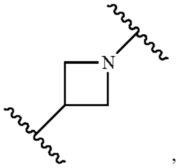,
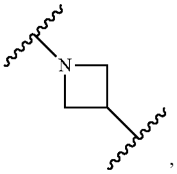, 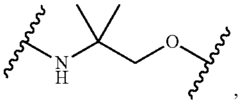,
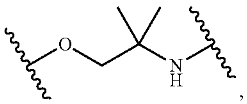, 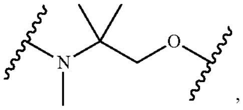,
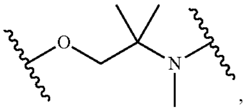, 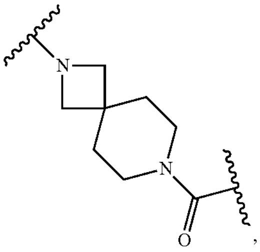,
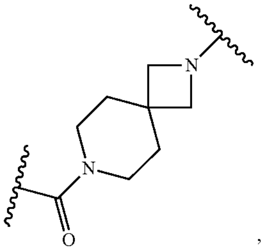, -continued
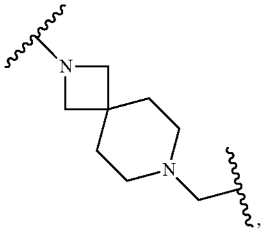,
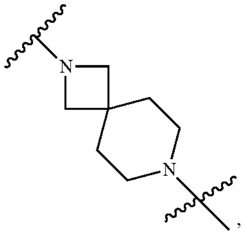,
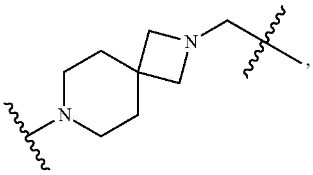,
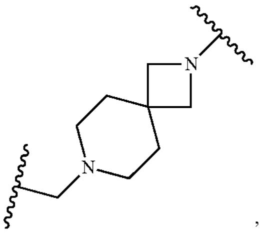,
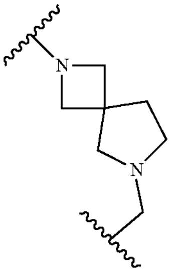,
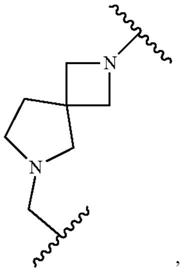,
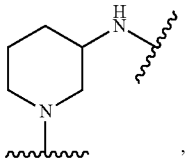,
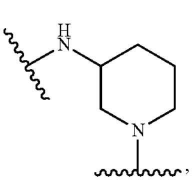,
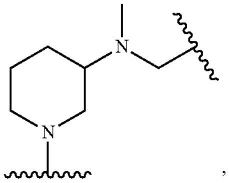,
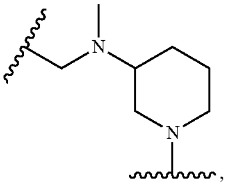,
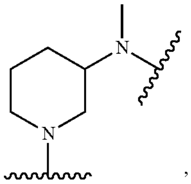,
-continued
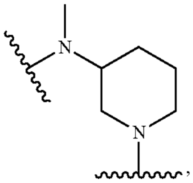,
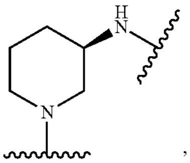,
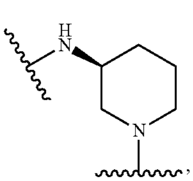,
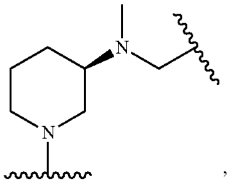,
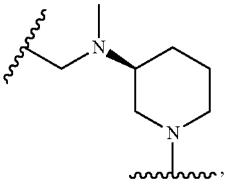,
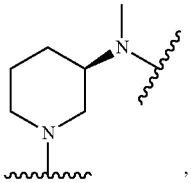,
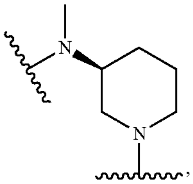,
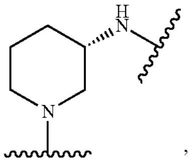,
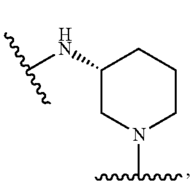,
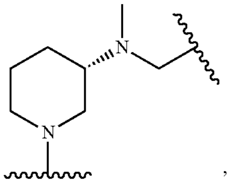,
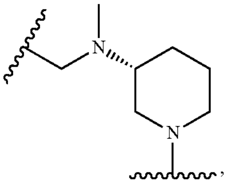,
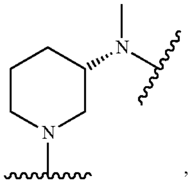,
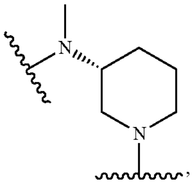,
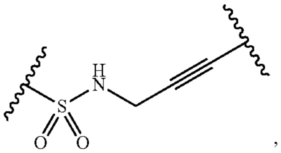,
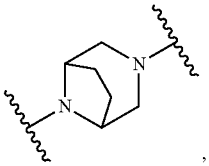,
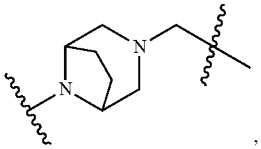,
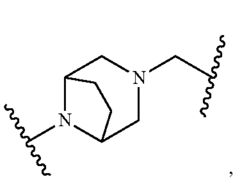,
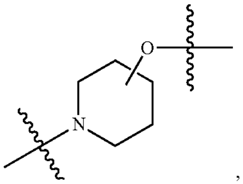, -continued

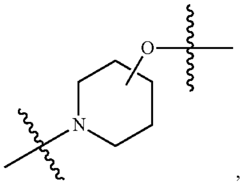, 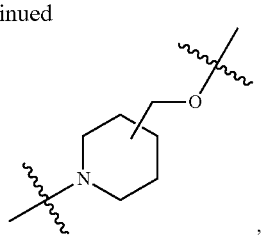,

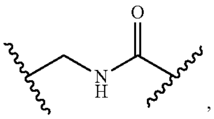, or 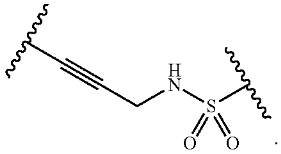.

In some embodiments the  on the left side of $L^1$ is connected to $R^1$ and the  on the right side of $L^1$ is connected to Ring A. In some embodiments, the  on the right side of $L^1$ is connected to $R^1$ and the  on the left side of $L^1$ is connected to Ring A.

In some embodiments, $L^1$ is selected from those depicted in Table 1, below.

As defined generally above, each -Cy- is independently an optionally substituted bivalent ring selected from phenylene; 3-7 membered saturated or partially unsaturated carbocyclylene; 4-7 membered saturated or partially unsaturated heterocyclylene having 1-2 heteroatoms independently selected from nitrogen, oxygen, and sulfur; a 7-11 membered saturated or partially unsaturated spiro or bridged bicyclic heterocyclylene having 1-2 heteroatoms independently selected from nitrogen, oxygen, and sulfur; or a 5-6 membered heteroarylene having 1-4 heteroatoms independently selected from nitrogen, oxygen, and sulfur.

In some embodiments, -Cy- is an optionally substituted bivalent ring selected from phenylene; 3-7 membered saturated or partially unsaturated carbocyclylene; 4-7 membered saturated or partially unsaturated heterocyclylene having 1-2 heteroatoms independently selected from nitrogen, oxygen, and sulfur; a 7-11 membered saturated or partially unsaturated spiro or bridged bicyclic heterocyclylene having 1-2 heteroatoms independently selected from nitrogen, oxygen, and sulfur; or a 5-6 membered heteroarylene having 1-4 heteroatoms independently selected from nitrogen, oxygen, and sulfur.

In some embodiments, -Cy- is selected from those depicted in Table 1, below.

As defined generally above, $L^2$ is a covalent bond or a $C_{1-4}$ bivalent straight or branched saturated or unsaturated hydrocarbon chain wherein 1-2 methylene units of the chain are independently and optionally replaced with —O—, —C(O)—, —C(S)—, —C(R)$_2$—, —CH(R)—, —CR(OR)—, —C(F)$_2$—, —N(R)—, —S—, —S(O)—, —CH(CR$_3$), —C═(CH$_2$)—, or —S(O)$_2$—.

In some embodiments, $L^2$ is a covalent bond,

In some embodiments, $L^2$ is a $C_{1-4}$ bivalent straight or branched saturated or unsaturated hydrocarbon chain wherein 1-2 methylene units of the chain are independently and optionally replaced with —O—, —C(O)—, —C(S)—, —C(R)$_2$—, —CH(R)—, —CR(OR)—, —C(F)$_2$—, —N(R)—S—, —S(O)—, —CH(CR$_3$), —C═(CH$_2$)—, or —S(O)$_2$—.

In some embodiments, $L^2$ is

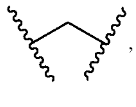, 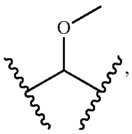, 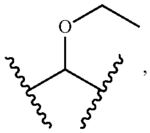,

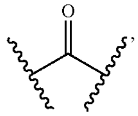, 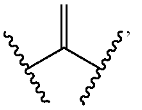, 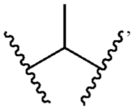,

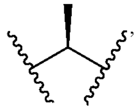, 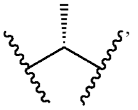, 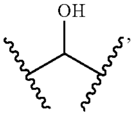,

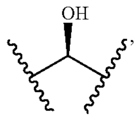, 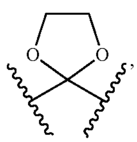, 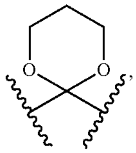,

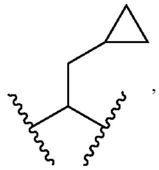, 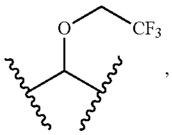, 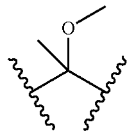,

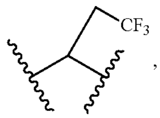, 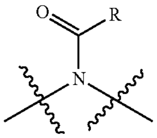, 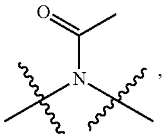,

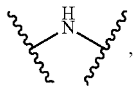, 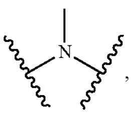, or 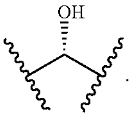.

In some embodiments, $L^2$ is selected from those depicted in Table 1, below.

As defined generally above, $L^3$ is one of the following: (a) a $C_{1-4}$ bivalent straight or branched saturated or unsaturated hydrocarbon chain wherein 1-2 methylene units of the chain are independently and optionally replaced with —O—, —C(O)—, —C(S)—, —C(R)$_2$—, —CH(R)—, —CH(OR)—, —C(F)$_2$—, —N(R)—, —S—, —S(O)—, or —S(O)$_2$—; or (b) a covalent bond.

In some embodiments, $L^3$ is a $C_{1-4}$ bivalent straight or branched saturated or unsaturated hydrocarbon chain wherein 1-2 methylene units of the chain are independently and optionally replaced with —O—, —C(O)—, —C(S)—, —C(R)$_2$—, —CH(R)—, —CH(OR)—, —C(F)$_2$—, —N(R)—, —S—, —S(O)—, or —S(O)$_2$—.

In some embodiments, $L^3$ is a covalent bond.

In some embodiments, $L^3$ is

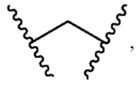, 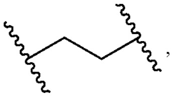, 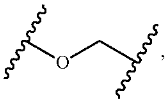,

-continued

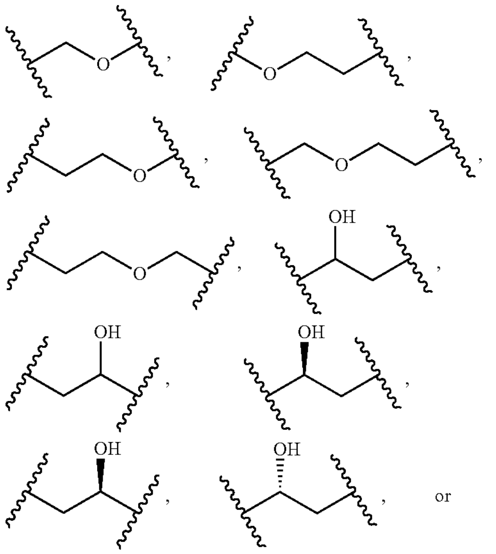

or

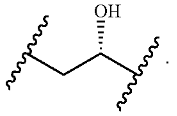

In some embodiments, the  on the left side of $L^3$ is connected to Ring B and the  on the right side of $L^3$ is connected to X. In some embodiments, the  on the right side of $L^3$ is connected to Ring B and the  on the left side of $L^3$ is connected to X.

In some embodiments, $L^3$ is selected from those depicted in Table 1, below.

As defined generally above, X is one of the following: (a) a 4-8 membered saturated or partially unsaturated monocyclic heterocyclic ring having 1-2 heteroatoms independently selected from nitrogen, oxygen, and sulfur; a 6-11 membered saturated or partiallay unsaturated bridged or spiro cyclic, bicyclic heterocyclic ring having 1-2 heteroatoms independently selected from nitrogen, oxygen, and sulfur; a 6-10 membered saturated or partiallay unsaturated bridged tricyclic heterocyclic ring having 1-2 heteroatoms independently selected from nitrogen, oxygen, and sulfur; an 8-10 membered partially aromatic or heteroaromatic bicyclic heterocyclic ring having 1-4 heteroatoms independently selected from nitrogen, oxygen, and sulfur; a 5-6 membered monocyclic heteroaryl ring having 1-4 heteroatoms independently selected from nitrogen, oxygen, and sulfur; a 3-7 membered saturated or partially unsaturated monocyclic carbocyclic ring; or phenyl; each of which is substituted with q instances of $R^5$; or (b) —$CH_2$(OR), —CH(R)(OR), or —$C(R)_2$(OR).

In some embodiments, X is a 4-8 membered saturated or partially unsaturated monocyclic heterocyclic ring having 1-2 heteroatoms independently selected from nitrogen, oxygen, and sulfur; a 6-11 membered saturated or partiallay unsaturated bridged or spiro cyclic, bicyclic heterocyclic ring having 1-2 heteroatoms independently selected from nitrogen, oxygen, and sulfur; a 6-10 membered saturated or partiallay unsaturated bridged tricyclic heterocyclic ring having 1-2 heteroatoms independently selected from nitrogen, oxygen, and sulfur; an 8-10 membered partially aromatic or heteroaromatic bicyclic heterocyclic ring having 1-4 heteroatoms independently selected from nitrogen, oxygen, and sulfur; a 5-6 membered monocyclic heteroaryl ring having 1-4 heteroatoms independently selected from nitrogen, oxygen, and sulfur; a 3-7 membered saturated or partially unsaturated monocyclic carbocyclic ring; or phenyl; each of which is substituted with q instances of $R^5$.

In some embodiments, X is —$CH_2$(OR), —CH(R)(OR), or —$C(R)_2$(OR).

In some embodiments, X is

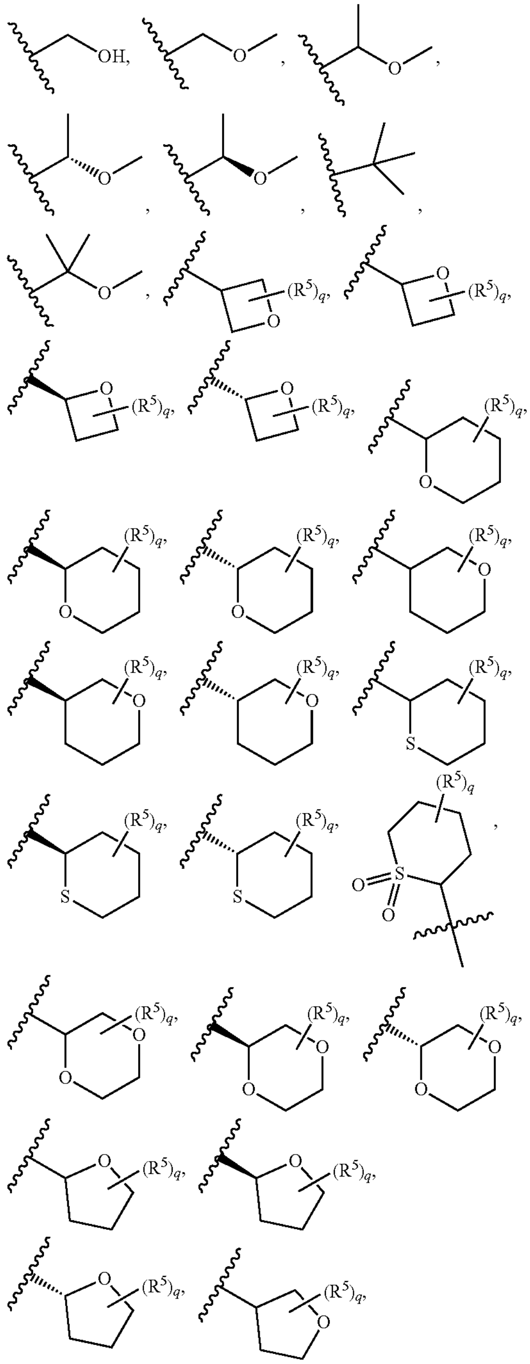

-continued
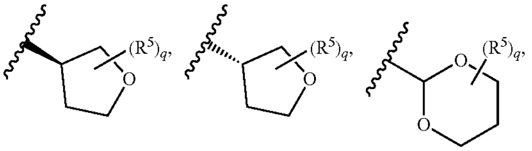
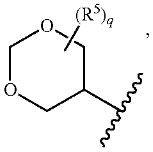
,
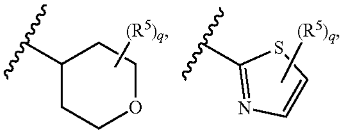
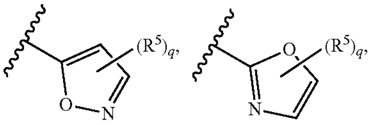
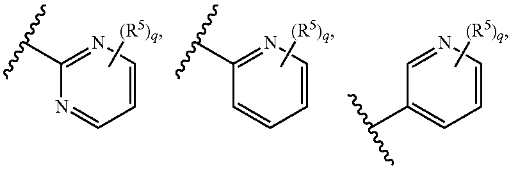
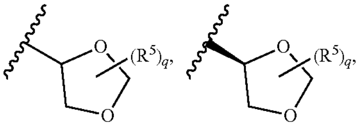
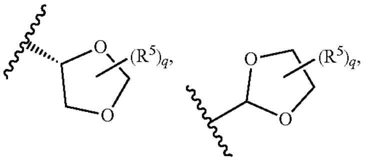
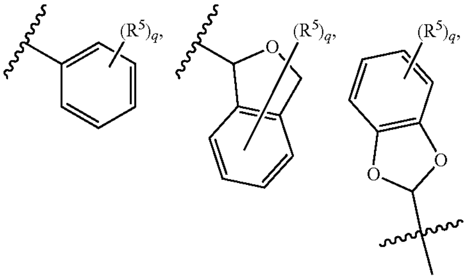
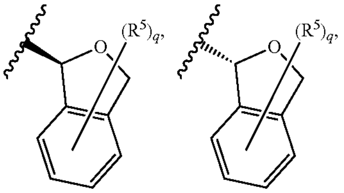
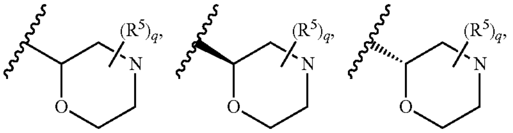
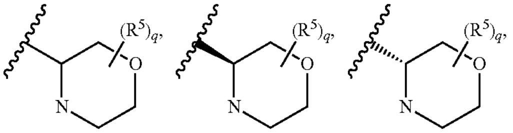
-continued
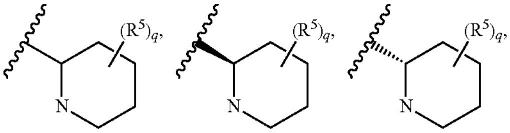
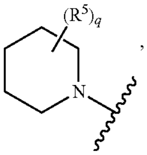
,
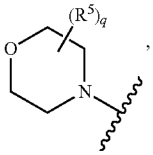
,
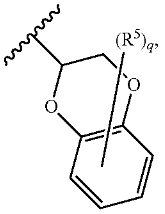
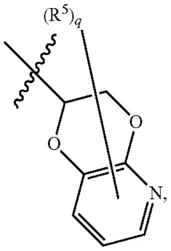
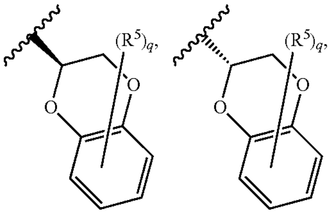
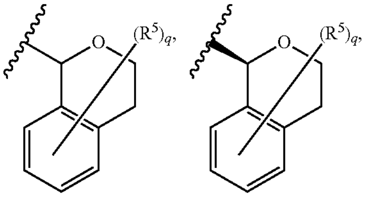
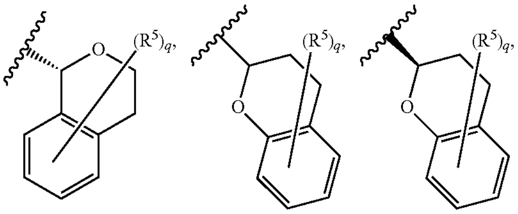
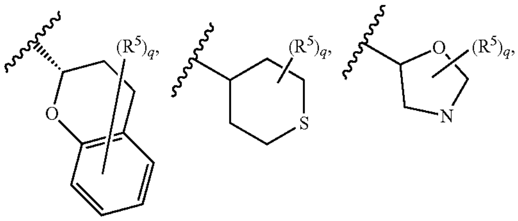
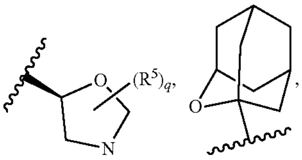
,
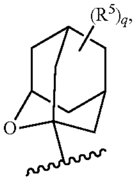

-continued

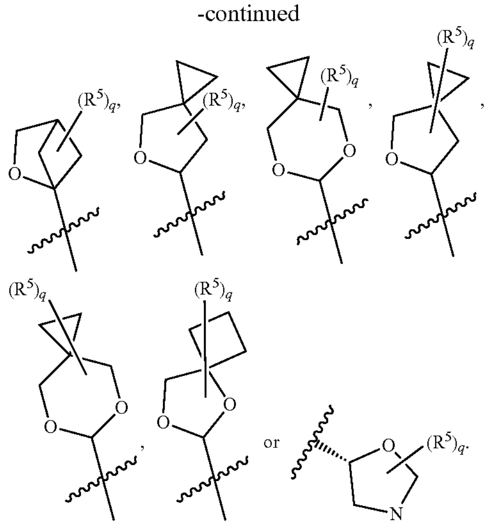

or

In some embodiments, two $R^5$ groups are taken together to form ═O and X is

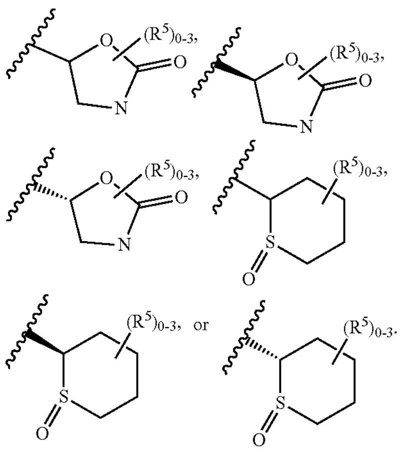

or

In some embodiments, two sets of $R^5$ groups are taken together to each form ═O and X

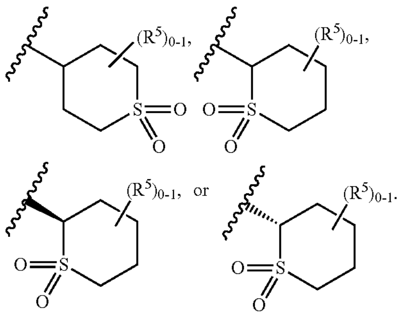

or

In some embodiments, X is selected from those depicted in Table 1, below.

As defined generally above, each instance of R is independently hydrogen, or an optionally substituted group selected from $C_{1-6}$ aliphatic; phenyl; an 8-10 membered bicyclic aryl ring, a 3-7 membered saturated or partially unsaturated monocyclic carbocyclic ring; a 4-8 membered saturated or partially unsaturated monocyclic heterocyclic ring having 1-2 heteroatoms independently selected from nitrogen, oxygen, and sulfur; a 5-6 membered monocyclic heteroaryl ring having 1-4 heteroatoms independently selected from nitrogen, oxygen, and sulfur; and an 8-10 membered bicyclic heteroaryl ring having 1-5 heteroatoms independently selected from nitrogen, oxygen, and sulfur; or: two R groups on the same nitrogen are optionally taken together with the nitrogen to form an optionally substituted 4-7 membered monocyclic saturated, partially unsaturated, or heteroaryl ring having, in addition to the nitrogen, 0-3 heteroatoms independently selected from nitrogen, oxygen, and sulfur.

In some embodiments, R is hydrogen. In some embodiments, R is an optionally substituted group selected from $C_{1-6}$ aliphatic; phenyl; an 8-10 membered bicyclic aryl ring, a 3-7 membered saturated or partially unsaturated monocyclic carbocyclic ring; a 4-8 membered saturated or partially unsaturated monocyclic heterocyclic ring having 1-2 heteroatoms independently selected from nitrogen, oxygen, and sulfur; a 5-6 membered monocyclic heteroaryl ring having 1-4 heteroatoms independently selected from nitrogen, oxygen, and sulfur; and an 8-10 membered bicyclic heteroaryl ring having 1-5 heteroatoms independently selected from nitrogen, oxygen, and sulfur.

In some embodiments, two R groups on the same nitrogen are taken together with the nitrogen to form an optionally substituted 4-7 membered monocyclic saturated, partially unsaturated, or heteroaryl ring having, in addition to the nitrogen, 0-3 heteroatoms independently selected from nitrogen, oxygen, and sulfur.

In some embodiments, R is selected from those depicted in Table 1, below.

As defined generally above, m is 0, 1, 2, 3, or 4.

In some embodiments, m is 0, 1, 2, 3, or 4. In some embodiments, m is 0. In some embodiments, m is 1. In some embodiments, m is 2. In some embodiments, m is 3. In some embodiments, m is 4.

In some embodiments, m is selected from those depicted in Table 1, below.

As defined generally above, n is 0, 1, 2, 3, or 4.

In some embodiments, n is 0, 1, 2, 3, or 4. In some embodiments, n is 0. In some embodiments, n is 1. In some embodiments, n is 2. In some embodiments, n is 3. In some embodiments, n is 4.

In some embodiments, n is selected from those depicted in Table 1, below.

As defined generally above, p is 0, 1, 2, 3, 4, or 5.

In some embodiments, p is 0, 1, 2, 3, 4, or 5. In some embodiments, p is 0. In some embodiments, p is 1. In some embodiments, p is 2. In some embodiments, p is 3. In some embodiments, p is 4. In some embodiments, p is 5.

In some embodiments, p is selected from those depicted in Table 1, below.

As defined generally above, q is 0, 1, 2, 3, 4, or 5.

In some embodiments, q is 0, 1, 2, 3, 4, or 5. In some embodiments, q is 0. In some embodiments, q is 1. In some embodiments, q is 2. In some embodiments, q is 3. In some embodiments, q is 4. In some embodiments, q is 5.

In some embodiments, q is selected from those depicted in Table 1, below.

In some embodiments, the present invention provides a compound of formula I, wherein Ring A is phenyl, Ring B is triazolyl, and $L^2$ is a covalent bond, to provide a compound of formula I-a:

I-a

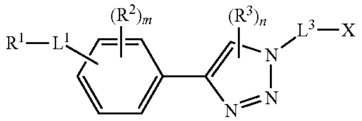

or a pharmaceutically acceptable salt thereof, wherein each of $L^1$, $L^3$, $R^1$, $R^2$, $R^3$, X, m, and n is as defined above and described in embodiments herein, both singly and in combination.

In some embodiments, the present invention provides a compound of formula I, wherein Ring A is pyridyl, Ring B is triazolyl, and $L^2$ is a covalent bond, to provide a compound of formula I-b-1, I-b-2, or I-b-3:

I-b-1

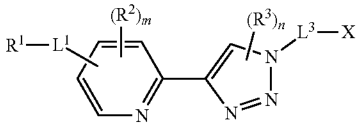

I-b-2

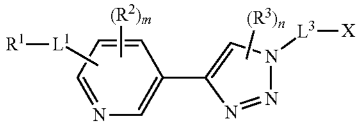

I-b-3

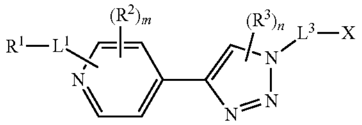

or a pharmaceutically acceptable salt thereof, wherein each of $L^1$, $L^3$, $R^1$, $R^2$, $R^3$, X, m, and n is as defined above and described in embodiments herein, both singly and in combination.

In some embodiments, the present invention provides a compound of formula I, wherein Ring A is thiophenyl, Ring B is triazolyl, and $L^2$ is a covalent bond, to provide a compound of formula I-c:

I-c

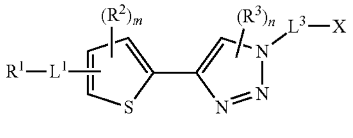

or a pharmaceutically acceptable salt thereof, wherein each of $L^1$, $L^3$, $R^1$, $R^2$, $R^3$, X, m, and n is as defined above and described in embodiments herein, both singly and in combination.

In some embodiments, the present invention provides a compound of formula I, wherein $L^1$ is acetylenyl, $L^2$ is a covalent bond, Ring A is phenyl, thiophenyl, or pyridyl, and Ring B is triazolyl, to provide a compound of formula I-f-1, I-f-2, I-f-3, I-f-4, I-f-5, I-f-6, I-f-7, I-f-8, or I-f-9:

I-f-1

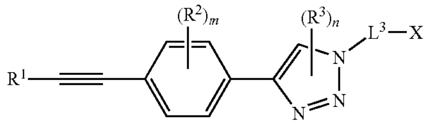

I-f-2

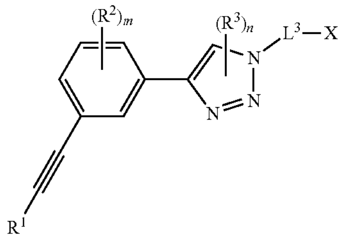

I-f-3

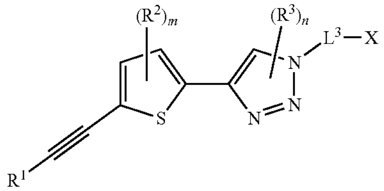

I-f-4

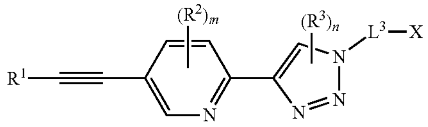

I-f-5

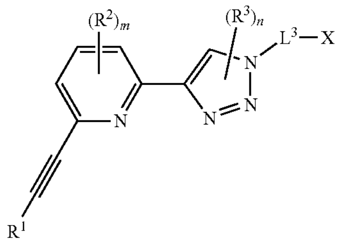

I-f-6

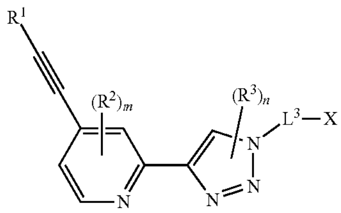

I-f-7

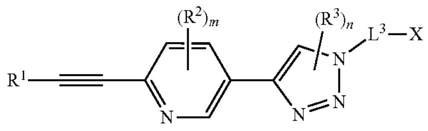

I-f-8

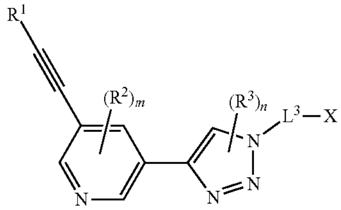

-continued

I-f-9

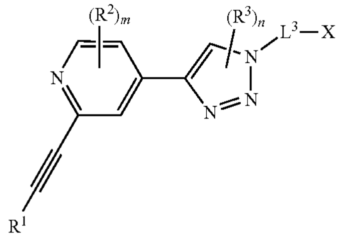

or a pharmaceutically acceptable salt thereof, wherein each of $L^3$, $R^1$, $R^2$, $R^3$, X, m, and n is as defined above and described in embodiments herein, both singly and in combination.

In some embodiments, the present invention provides a compound of formula I, wherein Ring B is triazolyl, $L^3$ is methylene, and X is oxetanyl, to provide a compound of formula I-g-1, I-g-2, or I-g-3:

I-g-1

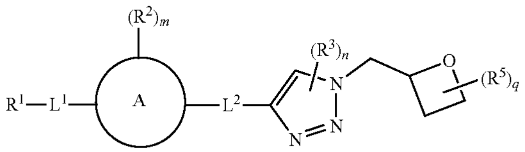

I-g-2

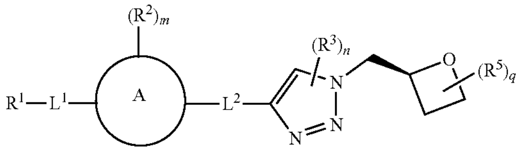

I-g-3

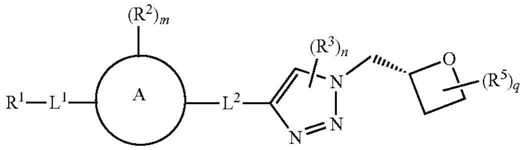

or a pharmaceutically acceptable salt thereof, wherein each of $L^1$, $L^2$, $R^1$, $R^2$, $R^3$, $R^5$, m, n, and q is as defined above and described in embodiments herein, both singly and in combination.

In some embodiments, the present invention provides a compound of formula I, wherein Ring B is triazolyl, $L^3$ is methylene, and X is furanyl, to provide a compound of formula I-h-1, I-h-2, or I-h-3:

I-h-1

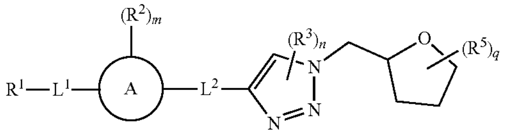

-continued

I-h-2

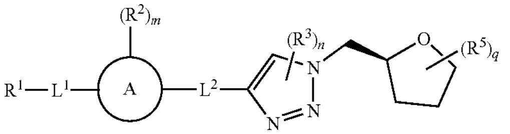

I-h-3

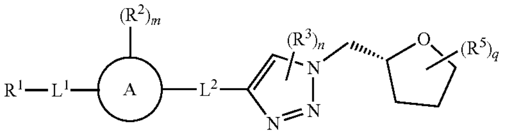

or a pharmaceutically acceptable salt thereof, wherein each of $L^1$, $L^2$, $R^1$, $R^2$, $R^3$, $R^5$, m, n, and q is as defined above and described in embodiments herein, both singly and in combination.

In some embodiments, the present invention provides a compound of formula I, wherein Ring B is triazolyl, $L^3$ is methylene, and X is tetrahydropyranyl, to provide a compound of formula I-i-1, I-i-2, or I-i-3:

I-i-1

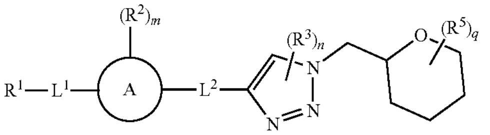

I-i-2

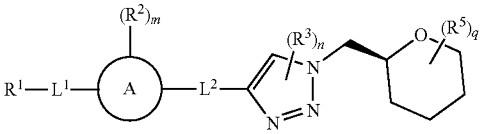

I-i-3

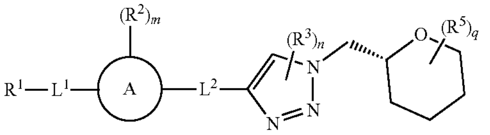

or a pharmaceutically acceptable salt thereof, wherein each of $L^1$, $L^2$, $R^1$, $R^2$, $R^3$, $R^5$, m, n, and q is as defined above and described in embodiments herein, both singly and in combination.

In some embodiments, the present invention provides a compound of formula I, wherein Ring B is triazolyl, $L^3$ is methylene, and X is 1,4-dioxanyl, to provide a compound of formula I-j-1, I-j-2, or I-j-3:

I-j-1

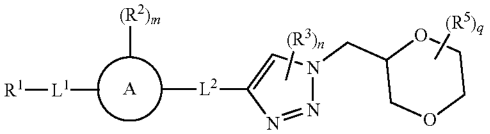

-continued

I-j-2

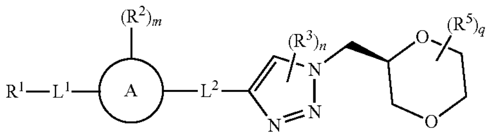

I-j-3

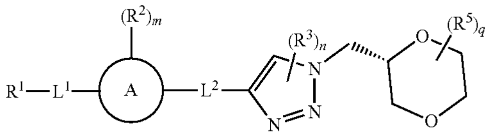

or a pharmaceutically acceptable salt thereof, wherein each of $L^1$, $L^2$, $R^1$, $R^2$, $R^3$, $R^5$, m, n, and q is as defined above and described in embodiments herein, both singly and in combination.

In some embodiments, the present invention provides a compound of formula I, wherein Ring B is triazolyl, Ring A is phenyl, and $L^2$ is selected from —O—, —N(H)—, —N(Ac)—, —$N(CH_3)$—, —S—, —S(O)—, or —$S(O)_2$—, to provide a compound of formula I-k-1:

I-k-1

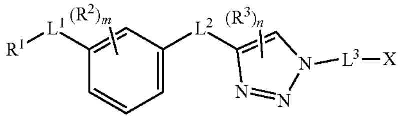

or a pharmaceutically acceptable salt thereof, wherein each of $L^1$, $L^3$, $R^1$, $R^2$, $R^3$, X, m, and n, is as defined above and described in embodiments herein, both singly and in combination.

In certain embodiments, the compound of formula I is a compound of formula I-k-2:

I-k-2

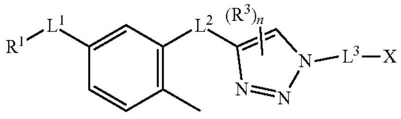

or a pharmaceutically acceptable salt thereof, wherein each of $L^1$, $L^3$, $R^1$, $R^3$, X, and n, is as defined above and described in embodiments herein, both singly and in combination.

In certain embodiments, the compound of formula is a compound of formula I-k-3:

I-k-3

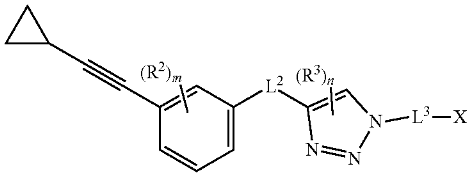

or a pharmaceutically acceptable salt thereof, wherein each of $L^3$, $R^2$, $R^3$, X, m, and n, is as defined above and described in embodiments herein, both singly and in combination.

In certain embodiments, the compound of formula I is a compound of formula I-k-4, I-k-5, or I-k-6:

I-k-4

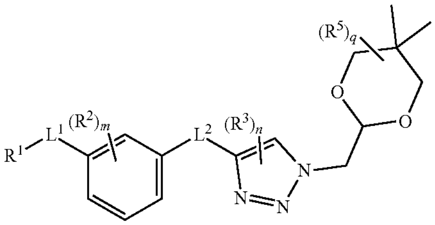

I-k-5

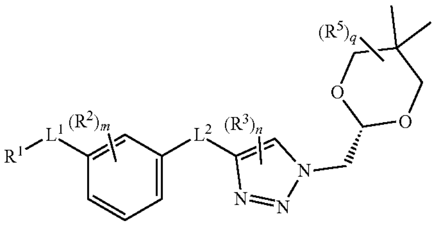

I-k-6

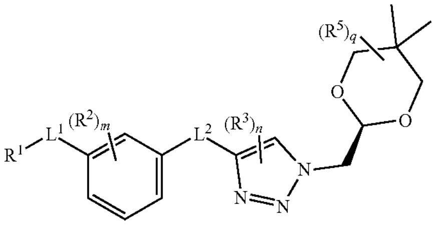

or a pharmaceutically acceptable salt thereof, wherein each of $L^1$, $R^1$, $R^2$, $R^3$, $R^5$, m, q, and n, is as defined above and described in embodiments herein, both singly and in combination. In certain embodiments, in I-k-5 and I-k-6 q is not 0 and $R^5$ is not hydrogen.

In certain embodiments, the compound of formula I is a compound of formula I-l-1, I-l-2, or I-l-3:

I-l-1

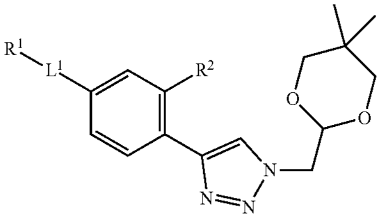

I-l-2

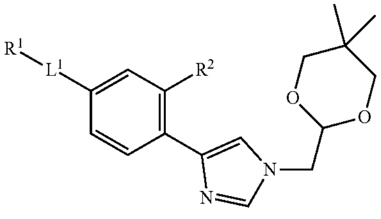

-continued

I-l-3

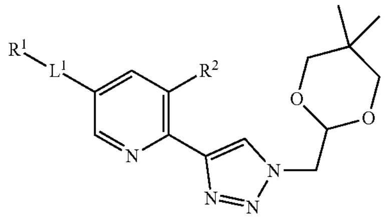

or a pharmaceutically acceptable salt thereof, wherein each of $L^1$, $R^1$, and $R^2$, is as defined above and described in embodiments herein, both singly and in combination.

In certain embodiments, the compound of formula I is a compound of formula I-m-1, I-m-2, or I-m-3:

I-m-1

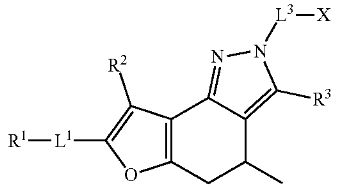

I-m-2

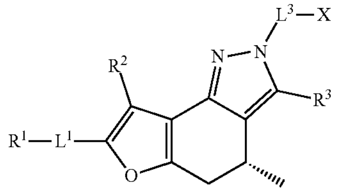

I-m-3

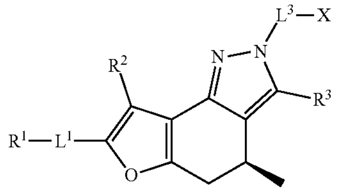

or a pharmaceutically acceptable salt thereof, wherein each of $L^1$, $R^1$, $R^2$, $R^3$, $L^3$, and X is as defined above and described in embodiments herein, both singly and in combination.

In certain embodiments, the compound of formula I is a compound of formula I-n-1, I-n-2, or I-n-3:

I-n-1

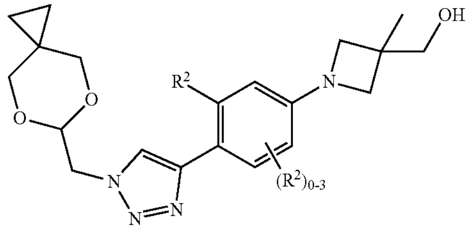

-continued

I-n-2

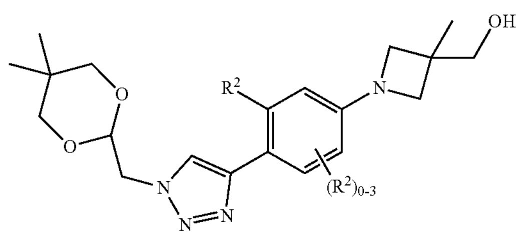

I-n-3

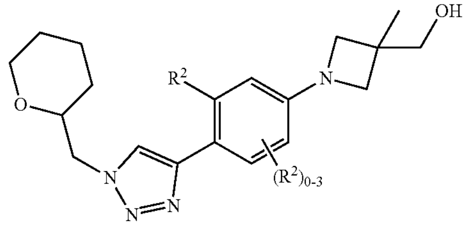

or a pharmaceutically acceptable salt thereof, wherein each of $R^2$ is as defined above and described in embodiments herein, both singly and in combination.

In certain embodiments, the compound of formula I is a compound of formula I-o-1, I-o-2, or I-o-3:

I-o-1

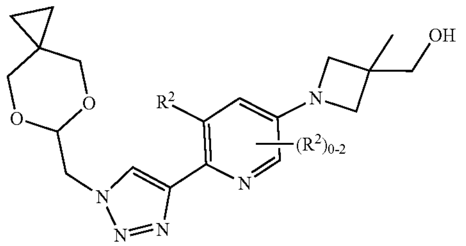

I-o-2

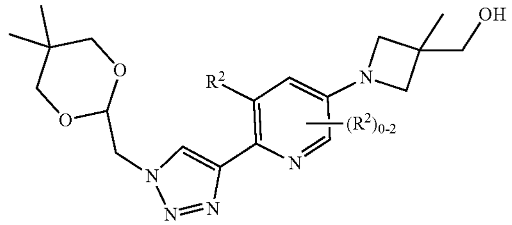

I-o-3

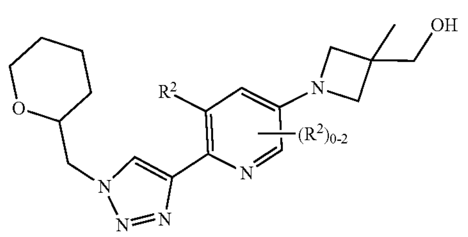

or a pharmaceutically acceptable salt thereof, wherein each of $R^2$ is as defined above and described in embodiments herein, both singly and in combination. In some embodiments, the $R^2$s on the right in the formulae of the present paragraph are H and the $R^2$ meta to the nitrogen of the pyridine (Ring B) is not H.

In certain embodiments, the compound of formula I is a compound of formula I-p-1, I-p-2, or I-p-3:

I-p-1

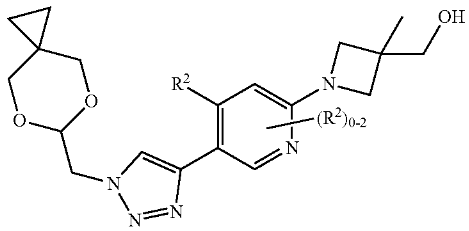

I-p-2

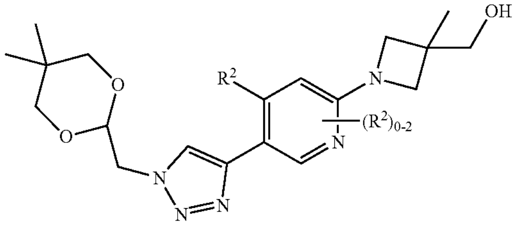

I-p-3

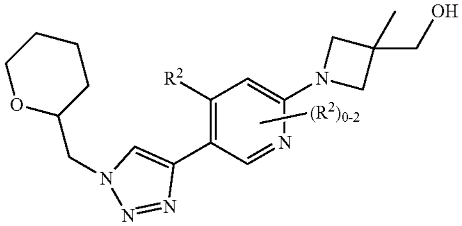

or a pharmaceutically acceptable salt thereof, wherein each of $R^2$ is as defined above and described in embodiments herein, both singly and in combination. In some embodiments, the $R^2$ meta to the point of attachment to the triazole (and para to the N of the pyridine), in the formulae of the present paragraph is not H.

In certain embodiments, the compound of formula I is a compound of formula I-q-1, I-q-2, or I-q-3:

I-q-1

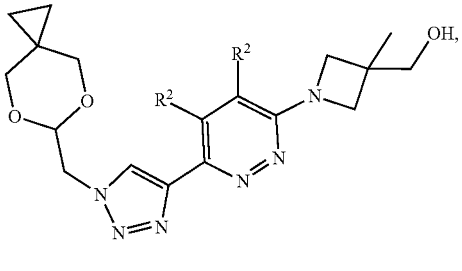

I-q-2

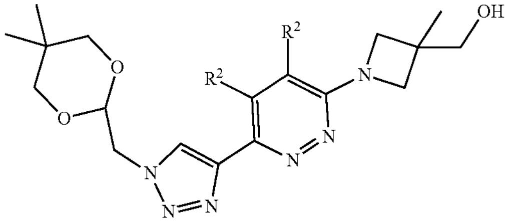

-continued

I-q-3

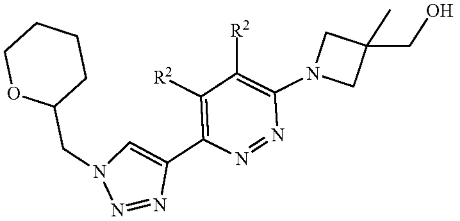

or a pharmaceutically acceptable salt thereof, wherein each of $R^2$ is as defined above and described in embodiments herein, both singly and in combination. In some embodiments, the $R^2$ on the left of the $R^2$s in the formulae of the present paragraph is H.

In certain embodiments, the compound of formula I is a compound of formula I-r-1, I-r-2, or I-r-3:

I-r-1

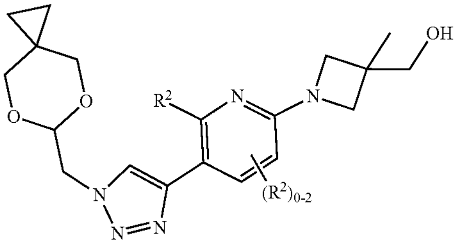

I-r-2

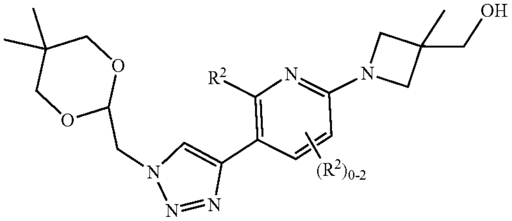

I-r-3

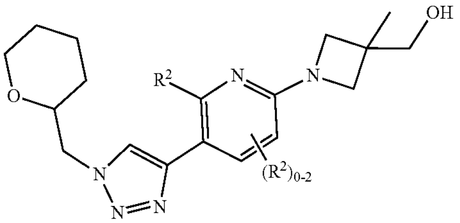

or a pharmaceutically acceptable salt thereof, wherein each of $R^2$ is as defined above and described in embodiments herein, both singly and in combination. In some embodiments, the $R^2$s on the right in the formulae of the present paragraph (parenthesized) are H and the $R^2$ ortho to the nitrogen of the pyridine (Ring B) is not H. In some embodiments, the $R^2$ ortho to the pyridine N in the formulae of the present paragraph is methyl.

In certain embodiments, the compound of formula I is a compound of formula I-s-1, I-s-2, or I-s-3:

I-s-1

I-s-2

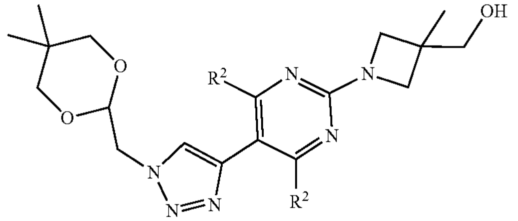

I-s-3

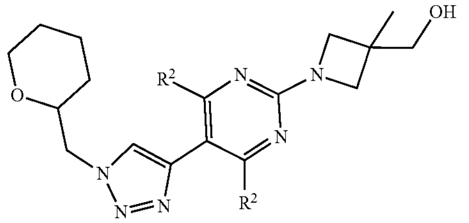

or a pharmaceutically acceptable salt thereof, wherein each of $R^2$ is as defined above and described in embodiments herein, both singly and in combination. In some embodiments, the $R^2$ on the right (facing downwards) of the $R^2$s in the formulae of the present paragraph is H. In some embodiments the $R^2$ on the left (facing upwards) of the $R^2$s in the formulae of the present paragraph is not H.

In certain embodiments, the compound of formula I is a compound of formula I-t-1, I-t-2, or I-t-3:

I-t-1

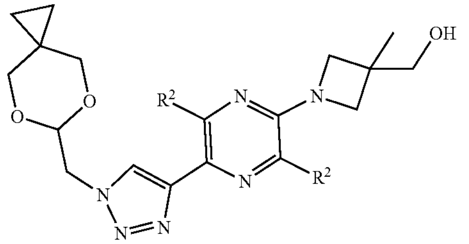

I-t-2

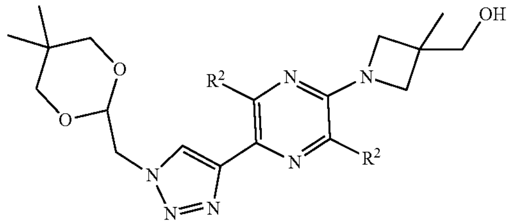

-continued

I-t-3

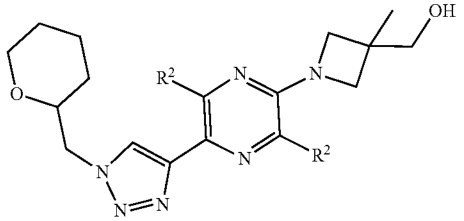

or a pharmaceutically acceptable salt thereof, wherein each of $R^2$ is as defined above and described in embodiments herein, both singly and in combination. In some embodiments, the $R^2$ on the right of the $R^2$s in the formulae of the present paragraph is H. In some embodiments, the $R^2$ meta to the point of attachment to the triazole in the formulae of the present paragraph is not H.

In certain embodiments, the compound of formula I is a compound of formula I-u-1, I-u-2, or I-u-3:

I-u-1

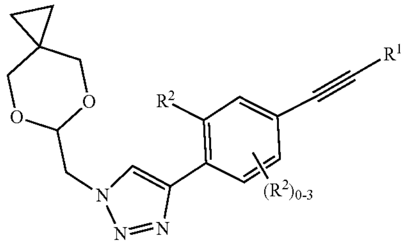

I-u-2

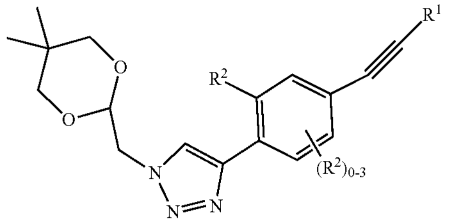

I-u-3

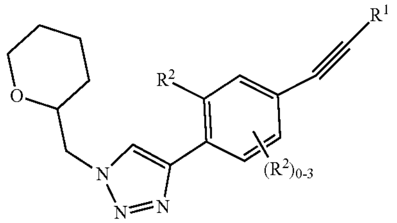

or a pharmaceutically acceptable salt thereof, wherein each of $R^2$ is as defined above and described in embodiments herein, both singly and in combination. In some embodiments, $R^1$ is cyclopropyl or —$CH_2OR$. In some embodiments, this R is H or methyl. In some embodiments, the $R^2$s on the right in the formulae of the present paragraph are H and the $R^2$ shown ortho to the attachment point of the triazole is not H.

In certain embodiments, the compound of formula I is a compound of formula I-v-1, I-v-2, or I-v-3:

I-v-1

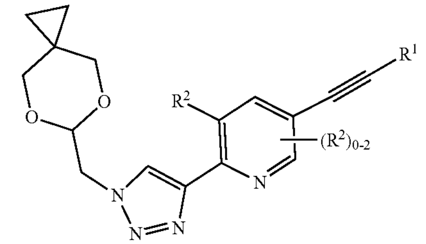

I-v-2

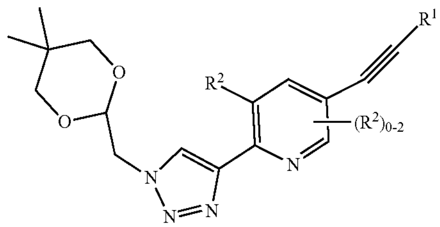

I-v-3

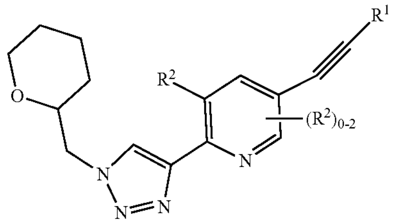

or a pharmaceutically acceptable salt thereof, wherein each of $R^2$ is as defined above and described in embodiments herein, both singly and in combination. In some embodiments, $R^1$ is cyclopropyl or —$CH_2OR$. In some embodiments, this R is H or methyl. In some embodiments, the $R^2$s on the right in the formulae of the present paragraph are H and the $R^2$ meta to the nitrogen of the pyridine (Ring B) is not H.

In certain embodiments, the compound of formula I is a compound of formula I-w-1, I-w-2, or I-w-3:

I-w-1

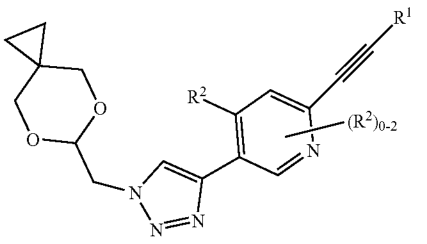

I-w-2

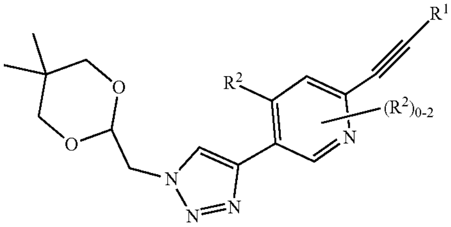

-continued

I-w-3

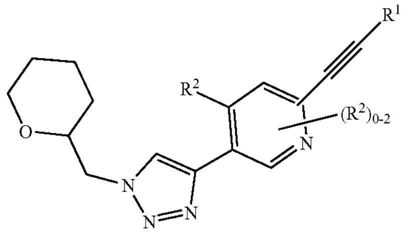

or a pharmaceutically acceptable salt thereof, wherein each of $R^2$ is as defined above and described in embodiments herein, both singly and in combination. In some embodiments, $R^1$ is cyclopropyl or —$CH_2OR$. In some embodiments, this R is H or methyl. In some embodiments, the $R^2$s on the right in the formulae of the present paragraph are H and the $R^2$ para to the nitrogen of the pyridine is not H.

In certain embodiments, the compound of formula I is a compound of formula I-x-1, I-x-2, or I-x-3:

I-x-1

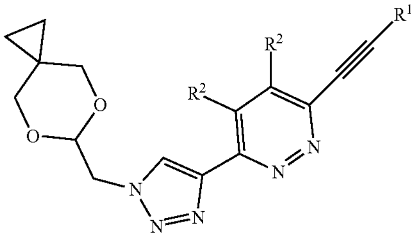

I-x-2

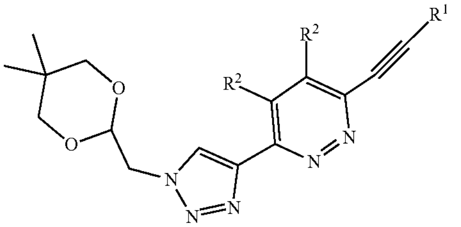

I-x-3

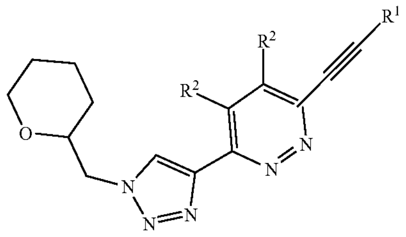

or a pharmaceutically acceptable salt thereof, wherein each of $R^2$ is as defined above and described in embodiments herein, both singly and in combination. In some embodiments, the $R^2$ on the right in the formulae of the present paragraph is H. In some embodiments, $R^1$ is cyclopropyl or —$CH_2OR$. In some embodiments, this R is H or methyl.

In certain embodiments, the compound of formula I is a compound of formula I-y-1, I-y-2, or I-y-3:

I-y-1

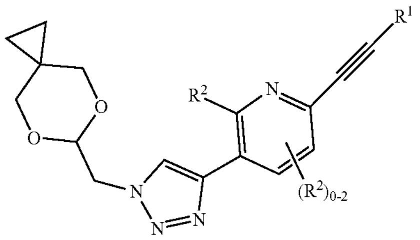

I-y-2

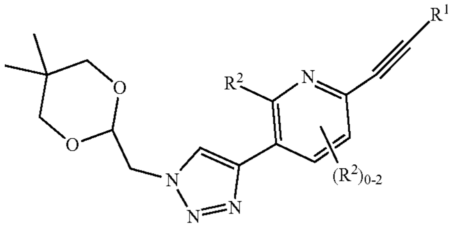

I-y-3

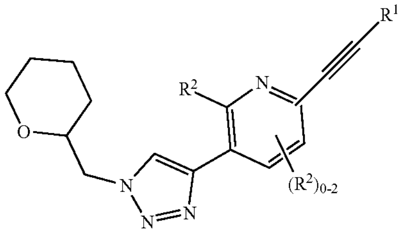

or a pharmaceutically acceptable salt thereof, wherein each of $R^2$ is as defined above and described in embodiments herein, both singly and in combination. In some embodiments, the $R^2$s on the right in the formulae of the present paragraph are H and the $R^2$ ortho to the nitrogen of the pyridine is not H. In some embodiments, $R^1$ is cyclopropyl or —$CH_2OR$. In some embodiments, this R is H or methyl.

In certain embodiments, the compound of formula I is a compound of formula I-z-1, I-z-2, or I-z-3:

I-z-1

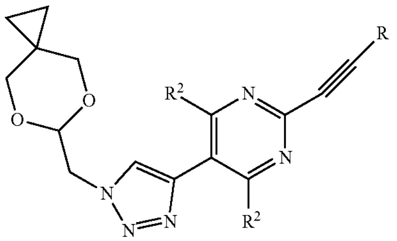

I-z-2

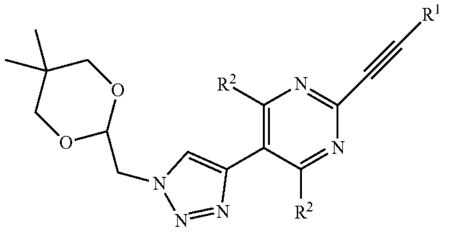

-continued

I-z-3

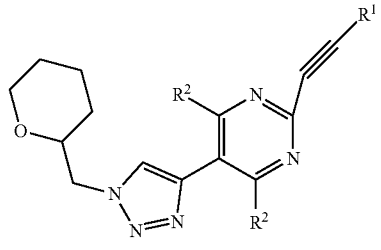

or a pharmaceutically acceptable salt thereof, wherein each of $R^2$ is as defined above and described in embodiments herein, both singly and in combination. In some embodiments, the $R^2$ on the right in the formulae of the present paragraph's $R^2$s (the $R^2$ facing downwards) is H. In some embodiments, $R^1$ is cyclopropyl or —$CH_2OR$. In some embodiments, this R is H or methyl.

In certain embodiments, the compound of formula I is a compound of formula I-aa-1, I-aa-2, or I-aa-3:

I-aa-1

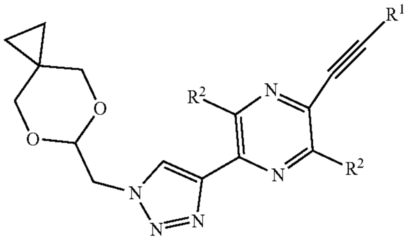

I-aa-2

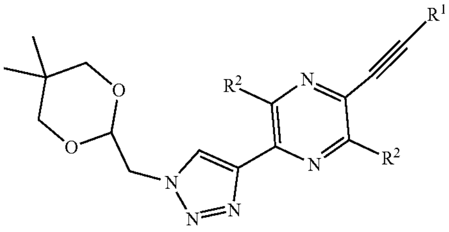

I-aa-3

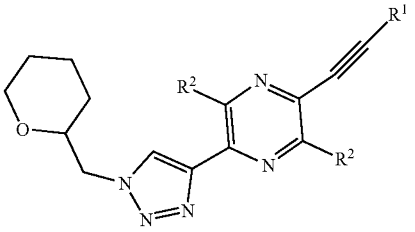

or a pharmaceutically acceptable salt thereof, wherein each of $R^2$ is as defined above and described in embodiments herein, both singly and in combination. In some embodiments, the $R^2$ on the right of the $R^2$s in the formulae of the present paragraph, is H. In some embodiments, $R^1$ is cyclopropyl or —$CH_2OR$. In some embodiments, this R is H or methyl.

In certain embodiments, the compound of formula I is a compound of formula I-bb-1, I-bb-2, or I-bb-3:

I-bb-1

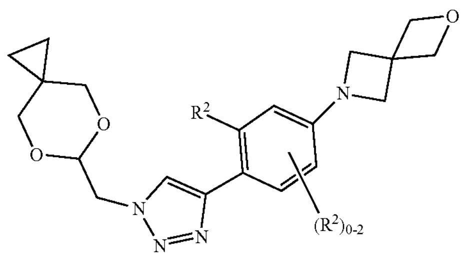

I-bb-2

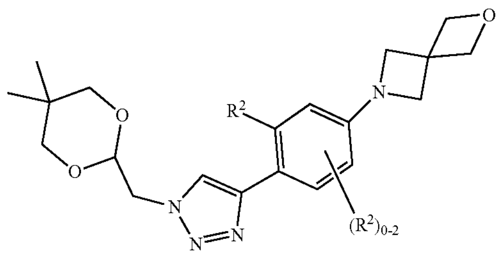

I-bb-3

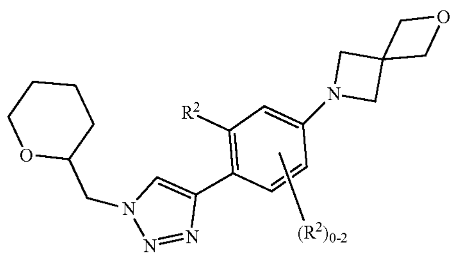

or a pharmaceutically acceptable salt thereof, wherein each of $R^2$ is as defined above and described in embodiments herein, both singly and in combination. In some embodiments, the $R^2$s on the right of the $R^2$ ortho to the triazole attachment site, of the formulae of the present paragraph are H.

In certain embodiments, the compound of formula I is a compound of formula I-cc-1, I-cc-2, or I-cc-3:

I-cc-1

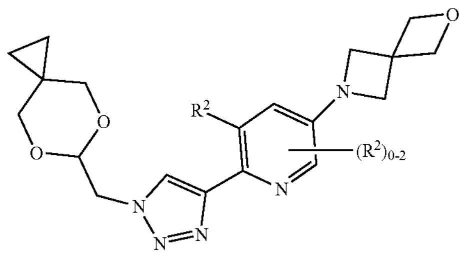

-continued

I-cc-2

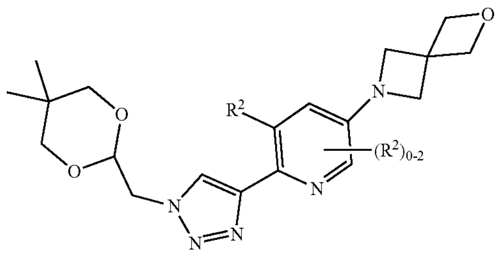

I-cc-3

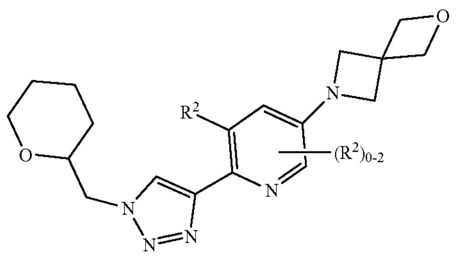

or a pharmaceutically acceptable salt thereof, wherein each of $R^2$ is as defined above and described in embodiments herein, both singly and in combination.

In certain embodiments, the compound of formula I is a compound of formula I-dd-1, I-dd-2, or I-dd-3:

I-dd-1

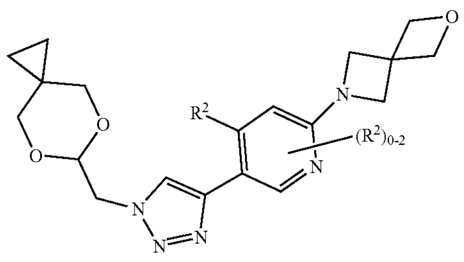

I-dd-2

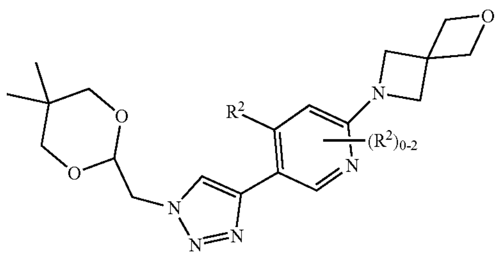

I-dd-3

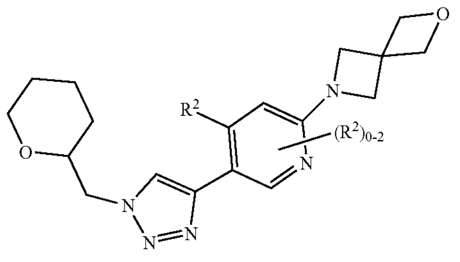

or a pharmaceutically acceptable salt thereof, wherein each of $R^2$ is as defined above and described in embodiments herein, both singly and in combination.

In certain embodiments, the compound of formula I is a compound of formula I-ee-1, I-ee-2, or I-ee-3:

I-ee-1

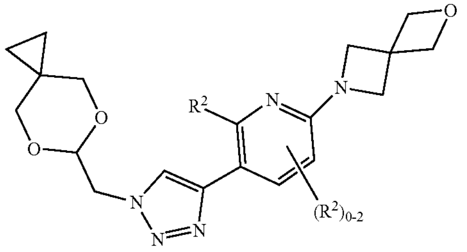

I-ee-2

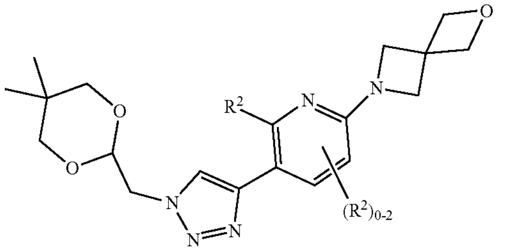

I-ee-3

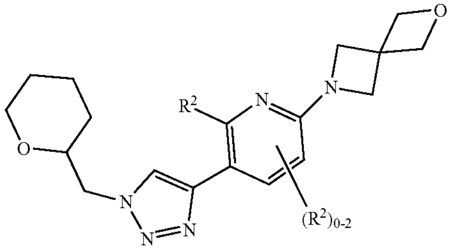

or a pharmaceutically acceptable salt thereof, wherein each of $R^2$ is as defined above and described in embodiments herein, both singly and in combination. In some embodiments, the 0-2 $R^2$ on the right of the $R^2$ ortho to the pyridine nitrogen, of the formulae of the present paragraph are H.

In certain embodiments, the compound of formula I is a compound of formula I-ff-1, I-ff-2, or I-ff-3:

I-ff-1

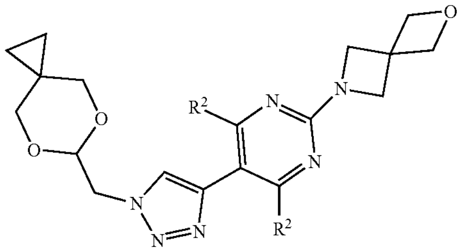

I-ff-2

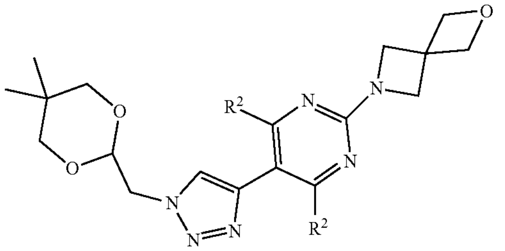

-continued

I-ff-3

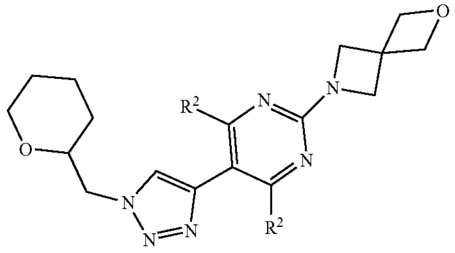

or a pharmaceutically acceptable salt thereof, wherein each of $R^2$ is as defined above and described in embodiments herein, both singly and in combination. In some embodiments, the $R^2$ on the right (facing downwards) of the $R^2$s of the formulae of the present paragraph is H.

In certain embodiments, the compound of formula I is a compound of formula I-gg-1, I-gg-2, or I-gg-3:

I-gg-1

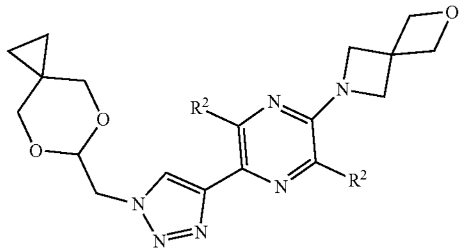

I-gg-2

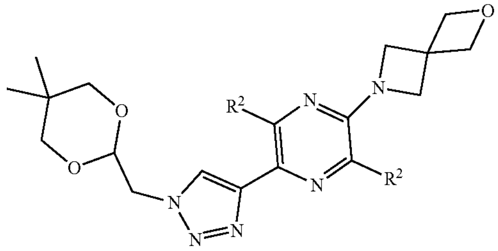

I-gg-3

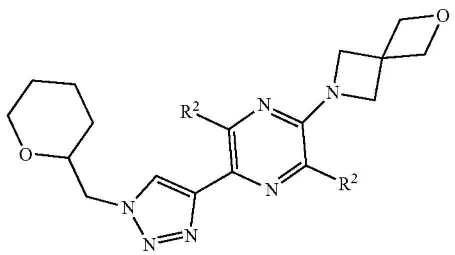

or a pharmaceutically acceptable salt thereof, wherein each of $R^2$ is as defined above and described in embodiments herein, both singly and in combination. In some embodiments, the $R^2$ on the right of the $R^2$s of the formulae of the present paragraph is H.

In certain embodiments, the compound of formula I is a compound of formula I-hh-1, I-hh-2, or I-hh-3:

I-hh-1

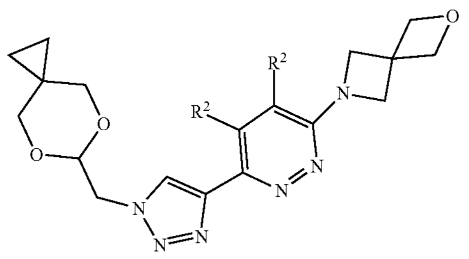

I-gg-2

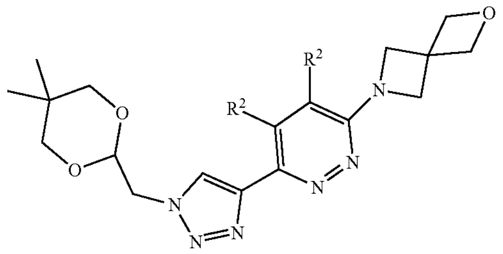

I-gg-3

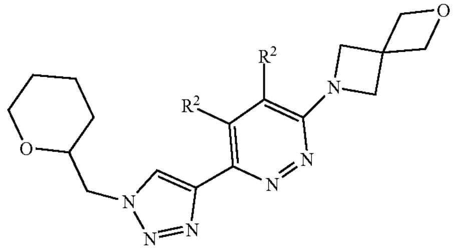

or a pharmaceutically acceptable salt thereof, wherein each of $R^2$ is as defined above and described in embodiments herein, both singly and in combination. In some embodiments, the $R^2$s on the right of the $R^2$s in the formulae of the present paragraph, are H and the $R^2$ ortho to the attachment of the triazole is not H.

In certain embodiments, the compound of formula I is a compound of formula I-hh-1, I-hh-2, or I-hh-3:

I-hh-1

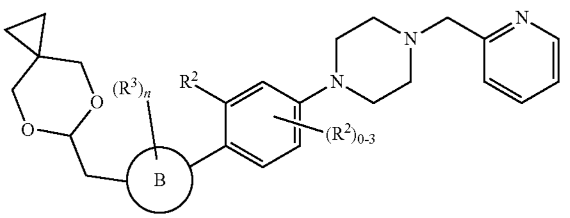

I-hh-2

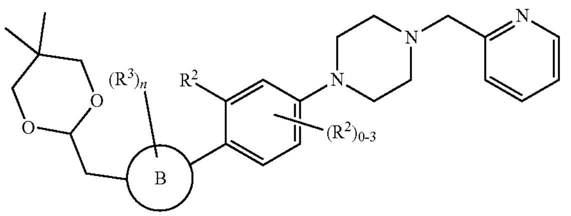

-continued

I-hh-3

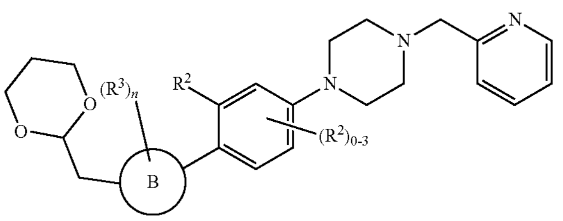

Or a pharmaceutically acceptable salt thereof, wherein each of $R^2$ is as defined above and described in embodiments herein, both singly and in combination. In some embodiments, the 0-3 $R^2$s to the right (of the $R^2$ ortho to phenyl's point of attachment to Ring B) in the formulae of the present paragraph are H. In some embodiments, the $R^2$ ortho to phenyl's point of attachment to Ring B, is not H. In some embodiments, ring B is

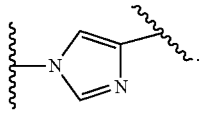 [SMILES: *c1cn(*)cn1]

In certain embodiments, the compound of formula I is a compound of any one of formulae I-ii-1 or I-ii-2:

I-ii-1

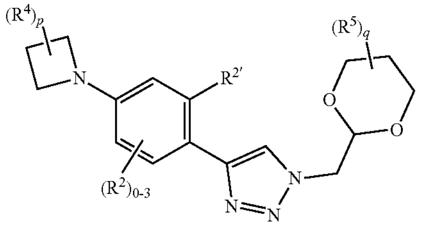

I-ii-2

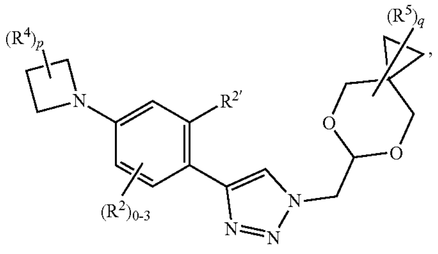

or a pharmaceutically acceptable salt thereof, wherein $R^{2'}$ is an $R^2$. In some embodiments, $R^{2'}$ is $—NR_2$. In some embodiments, $R^{2'}$ is $—N(CH_3)_2$.

In certain embodiments, the compound of formula I is a compound of any one of formulae I-jj-1 or I-jj-2:

I-jj-1

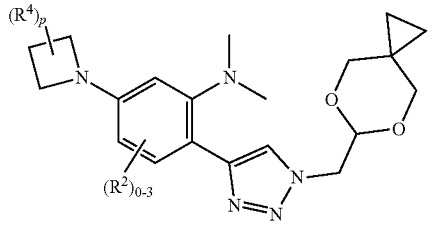

I-jj-2

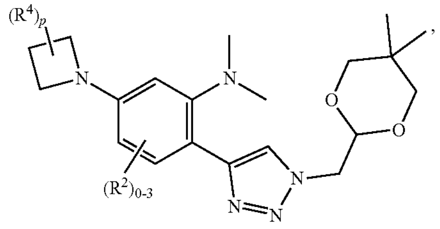

or a pharmaceutically acceptable salt thereof.

In certain embodiments, the compound of formula I is a compound of any one of formulae I-kk-1 or I-kk-2:

I-kk-1

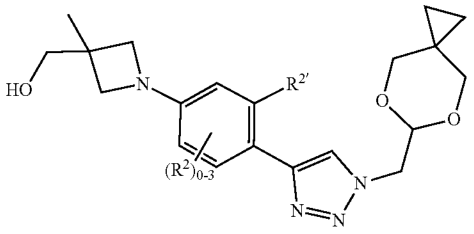

I-kk-2

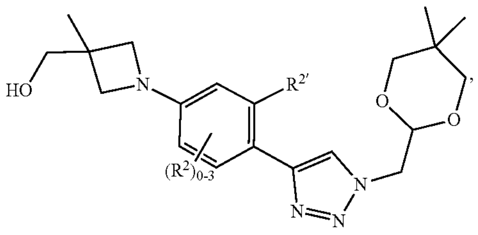

or a pharmaceutically acceptable salt thereof, wherein $R^{2'}$ is an $R^2$. In some embodiments, $R^{2'}$ is —$NR_2$. In some embodiments, $R^{2'}$ is —$N(CH_3)_2$.

In certain embodiments, the compound of formula I is a compound of any one of formulae I-11-1 or I-11-2:

I-ll-1

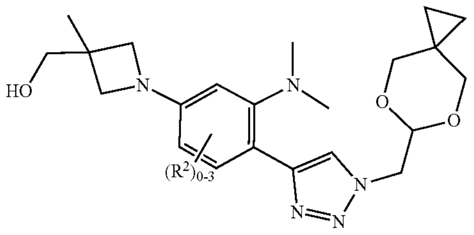

-continued

I-ll-2

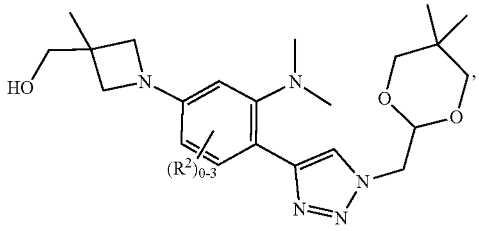

or a pharmaceutically acceptable salt thereof. In some embodiments, one $R^2$ is F.

In certain embodiments, the present invention provides a compound of formula I-1*:

I-1

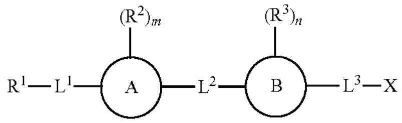

or a pharmaceutically acceptable salt thereof, wherein:

Ring A is a 5-6 membered monocyclic heteroaryl ring having 1-4 heteroatoms independently selected from nitrogen, oxygen, and sulfur; a 4-8 membered saturated or partially unsaturated monocyclic heterocyclic ring having 1-2 heteroatoms independently selected from nitrogen, oxygen, and sulfur; phenyl; or a 3-7 membered saturated or partially unsaturated monocyclic carbocyclic ring;

Ring B is a 5-membered monocyclic heteroaryl ring having 1-4 heteroatoms independently selected from nitrogen, oxygen, and sulfur; or a 5-membered saturated or partially unsaturated monocyclic heterocyclic ring having 1-3 heteroatoms independently selected from nitrogen, oxygen, and sulfur;

$R^1$ is selected from (i) a 3-7 membered saturated or partially unsaturated monocyclic carbocyclic ring; a 5-6 membered monocyclic heteroaryl ring having 1-4 heteroatoms independently selected from nitrogen, oxygen, and sulfur; a 4-8 membered saturated or partially unsaturated monocyclic heterocyclic ring having 1-2 heteroatoms independently selected from nitrogen, oxygen, and sulfur; a 7-11 membered saturated or partially unsaturated spiro bicyclic heterocyclic ring having 1-2 heteroatoms independently selected from nitrogen, oxygen, and sulfur; phenyl; and a $C_{1-6}$ aliphatic; each of which is substituted with p instances of $R^4$; and (ii) hydrogen;

each instance of $R^2$, $R^4$, and $R^5$ is independently hydrogen, deuterium, $R^z$, halogen, —CN, —$NO_2$, —OR, —SR, —$NR_2$, —$S(O)_2R$, —$S(O)_2NR_2$, —S(O)R, —$S(O)NR_2$, —$CF_2R$, —$CF_3$, —$CR_2(CN)$, —$CR_2(OR)$, —$CR_2(NR_2)$, —C(O)R, —C(O)OR, —$C(O)NR_2$, —C(O)N(R)OR, —OC(O)R, —$OC(O)NR_2$, —$C(S)NR_2$, —N(R)C(O)OR, —N(R)C(O)R, —$N(R)C(O)NR_2$, —$N(R)C(NR)NR_2$, —$N(R)NR_2$, —$N(R)S(O)_2NR_2$, —$N(R)S(O)_2R$, —N═$S(O)R_2$, —S(NR)(O)R, —N(R)S(O)R, —N(R)CN, —$Si(OR)R_2$, —$SiR_3$, —$P(O)(R)NR_2$, —P(O)(R)OR or —$P(O)R_2$; or two $R^2$ groups are optionally taken together to form ═O;

two $R^4$ groups are optionally taken together to form =O;

two $R^5$ groups are optionally taken together to form =O;

two $R^2$ groups are optionally taken together with their intervening atoms to form a 5-8 membered saturated, partially unsaturated, or aryl fused ring having 0-3 heteroatoms independently selected from nitrogen, oxygen and sulfur;

two $R^4$ groups are optionally taken together with their intervening atoms to form a 5-8 membered saturated, partially unsaturated, or aryl fused ring having 0-3 heteroatoms independently selected from nitrogen, oxygen and sulfur; or two $R^5$ groups are optionally taken together with their intervening atoms to form a 5-8 membered saturated, partially unsaturated, or aryl fused ring having 0-3 heteroatoms independently selected from nitrogen, oxygen and sulfur;

each instance of $R^z$ is independently selected from an optionally substituted group selected from $C_{1-6}$ aliphatic; phenyl; a 4-7 membered saturated or partially unsaturated heterocyclic ring having 1-2 heteroatoms independently selected from nitrogen, oxygen, and sulfur; and a 5-6 membered heteroaryl ring having 1-4 heteroatoms independently selected from nitrogen, oxygen, and sulfur;

$R^3$ is hydrogen or an optionally substituted $C_{1-6}$ aliphatic group; or two $R^3$ groups are optionally taken together to form =O; or an $R^2$ group and an $R^3$ group are optionally taken together with their intervening atoms to form a 5-8 membered saturated or partially unsaturated fused ring having 0-3 heteroatoms independently selected from nitrogen, oxygen or sulfur;

$L^1$ is one of the following:

(a) a $C_{1-6}$ bivalent straight or branched saturated or unsaturated hydrocarbon chain wherein 1-3 methylene units of the chain are independently and optionally replaced with —O—,-Cy-, —C(O)—, —C(S)—, —$C(R)_2$—, —CH(R)—, —CH(OR)—, —$C(F)_2$—, —N(R)—, —S—, —S(O)—, or —$S(O)_2$—; or (b) a covalent bond;

each -Cy- is independently an optionally substituted bivalent ring selected from phenylene; 3-7 membered saturated or partially unsaturated carbocyclylene; 4-7 membered saturated or partially unsaturated heterocyclylene having 1-2 heteroatoms independently selected from nitrogen, oxygen, and sulfur; a 7-11 membered saturated or partially unsaturated spiro bicyclic heterocyclylene having 1-2 heteroatoms independently selected from nitrogen, oxygen, and sulfur; or a 5-6 membered heteroarylene having 1-4 heteroatoms independently selected from nitrogen, oxygen, and sulfur;

$L^2$ is a covalent bond or a $C_{1-4}$ bivalent straight or branched saturated or unsaturated hydrocarbon chain wherein 1-2 methylene units of the chain are independently and optionally replaced with —O—, —C(O)—, —C(S)—, —$C(R)_2$—, —CH(R)—, —CH(OR)—, —$C(F)_2$—, —N(R)—, —S—, —S(O)—, or —$S(O)_2$—;

$L^3$ is one of the following:

(a) a $C_{1-4}$ bivalent straight or branched saturated or unsaturated hydrocarbon chain wherein 1-2 methylene units of the chain are independently and optionally replaced with —O—, —C(O)—, —C(S)—, —$C(R)_2$—, —CH(R)—, —CH(OR)—, —$C(F)_2$—, —N(R)—, —S—, —S(O)—, or —$S(O)_2$—; or (b) a covalent bond;

X is one of the following:

(c) a 4-8 membered saturated or partially unsaturated monocyclic heterocyclic ring having 1-2 heteroatoms independently selected from nitrogen, oxygen, and sulfur; an 8-10 membered partially aromatic or heteroaromatic bicyclic heterocyclic ring having 1-4 heteroatoms independently selected from nitrogen, oxygen, and sulfur; a 5-6 membered monocyclic heteroaryl ring having 1-4 heteroatoms independently selected from nitrogen, oxygen, and sulfur; a 3-7 membered saturated or partially unsaturated monocyclic carbocyclic ring; or phenyl; each of which is substituted with q instances of $R^5$; or (d) —$CH_2$(OR), —CH(R)(OR), or —$C(R)_2$(OR);

each instance of R is independently hydrogen, or an optionally substituted group selected from $C_{1-6}$ aliphatic; phenyl; an 8-10 membered bicyclic aryl ring, a 3-7 membered saturated or partially unsaturated monocyclic carbocyclic ring; a 4-8 membered saturated or partially unsaturated monocyclic heterocyclic ring having 1-2 heteroatoms independently selected from nitrogen, oxygen, and sulfur; a 5-6 membered monocyclic heteroaryl ring having 1-4 heteroatoms independently selected from nitrogen, oxygen, and sulfur; and an 8-10 membered bicyclic heteroaryl ring having 1-5 heteroatoms independently selected from nitrogen, oxygen, and sulfur; or two R groups on the same nitrogen are optionally taken together with the nitrogen to form an optionally substituted 4-7 membered monocyclic saturated, partially unsaturated, or heteroaryl ring having, in addition to the nitrogen, 0-3 heteroatoms independently selected from nitrogen, oxygen, and sulfur;

m is 0, 1, 2, 3, or 4;

n is 0, 1, 2, 3, or 4;

p is 0, 1, 2, 3, 4, or 5; and q is 0, 1, 2, 3, 4, or 5.

Compounds of Formula I-1* may be more particularly defined. For example, in some embodiments, Ring A is a 5-6 membered monocyclic heteroaryl ring having 1-4 heteroatoms independently selected from nitrogen, oxygen, and sulfur. In some embodiments, Ring A is a 4-8 membered saturated or partially unsaturated monocyclic heterocyclic ring having 1-2 heteroatoms independently selected from nitrogen, oxygen, and sulfur. In some embodiments, Ring A is phenyl. In some embodiments, Ring A is a 3-7 membered saturated or partially unsaturated monocyclic carbocyclic ring.

In some embodiments, Ring A is

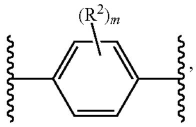,
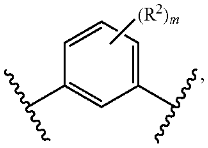,
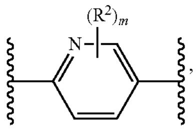,
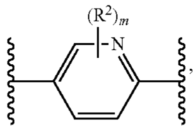,

-continued

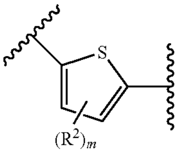,
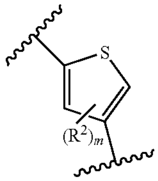,
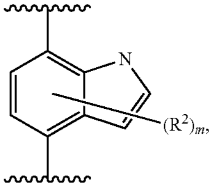
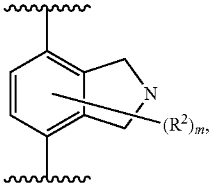
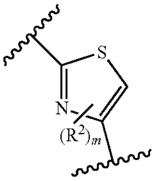,
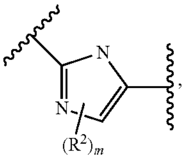
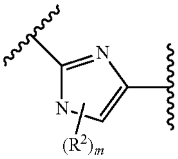
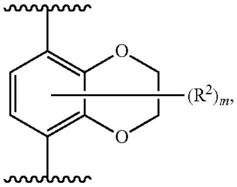 or
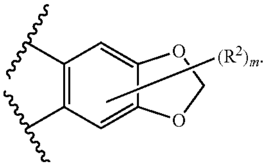

In some embodiments, Ring A is selected from those depicted in Table 1, below.

In some embodiments, Ring B is a 5-membered monocyclic heteroaryl ring having 1-4 heteroatoms independently selected from nitrogen, oxygen, and sulfur. In some embodiments, Ring B is a 5-membered saturated or partially unsaturated monocyclic heterocyclic ring having 1-3 heteroatoms independently selected from nitrogen, oxygen, and sulfur.

In some embodiments, Ring B is

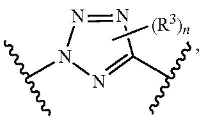
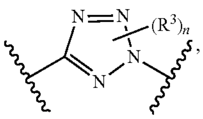
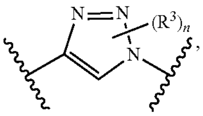
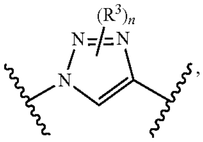
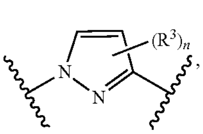
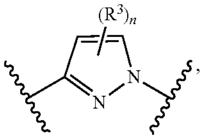

-continued

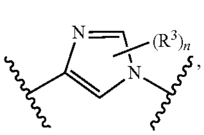
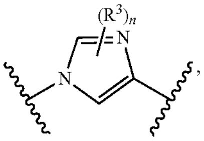
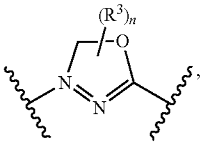
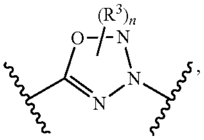
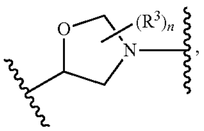
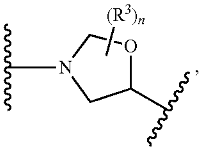
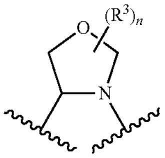,
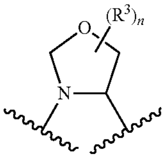,
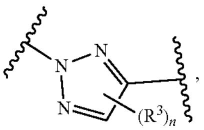
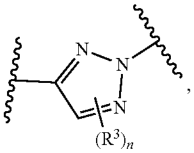
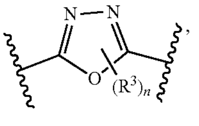
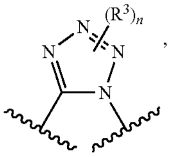,
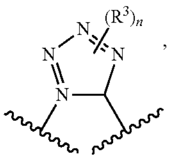,
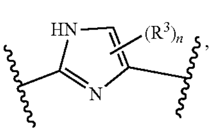
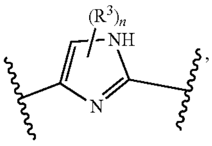
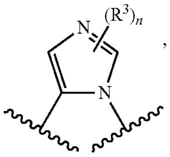, or
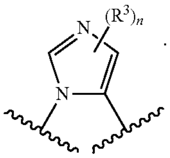.

In some embodiments, two $R^3$ groups are taken together to form =O and Ring B is

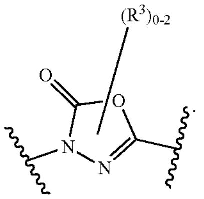

In some embodiments, two $R^3$ groups are taken together to form =O and Ring B is

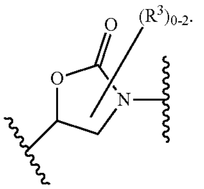

In some embodiments, two $R^3$ groups are taken together to form =O and Ring B is

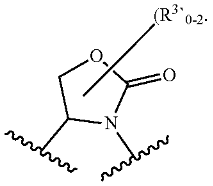

In some embodiments, Ring B is selected from those depicted in Table 1, below.

In some embodiments, $R^1$ is a 3-7 membered saturated or partially unsaturated monocyclic carbocyclic ring substituted with p instances of $R^4$. In some embodiments, $R^1$ is a 5-6 membered monocyclic heteroaryl ring having 1-4 heteroatoms independently selected from nitrogen, oxygen, and sulfur, substituted with p instances of $R^4$. In some embodiments, $R^1$ is a 4-8 membered saturated or partially unsaturated monocyclic heterocyclic ring having 1-2 heteroatoms independently selected from nitrogen, oxygen, and sulfur, substituted with p instances of $R^4$. In some embodiments, $R^1$ is a 7-11 membered saturated or partially unsaturated spiro bicyclic heterocyclic ring having 1-2 heteroatoms independently selected from nitrogen, oxygen, and sulfur, substituted with p instances of $R^4$. In some embodiments, $R^1$ is a $C_{1-6}$ aliphatic group substituted with p instances of R4. In some embodiments, $R^1$ is phenyl substituted with p instances of $R^4$. In some embodiments, $R^1$ is hydrogen.

In some embodiments, $R^1$ is

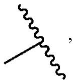, 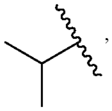, 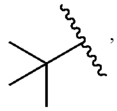, 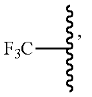,

-continued

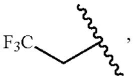, 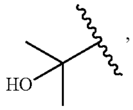, 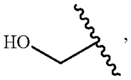,

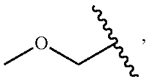, 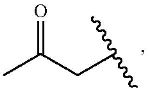, 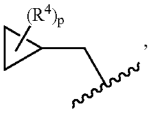,

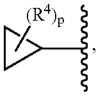, 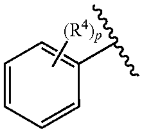, 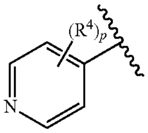,

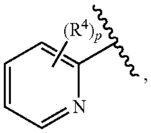, 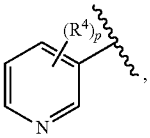, 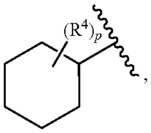,

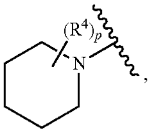, 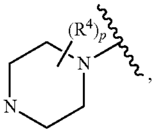, 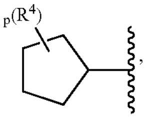,

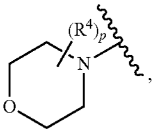, 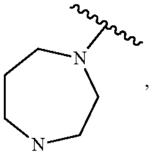, 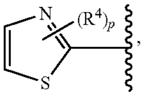,

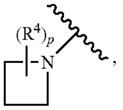, 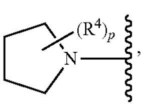, 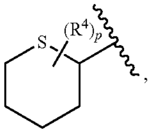,

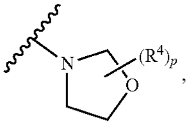, 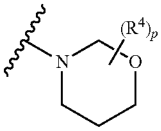,

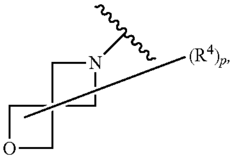 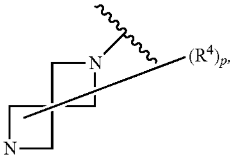

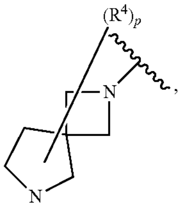, 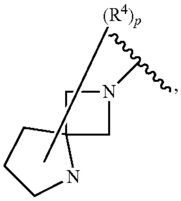,

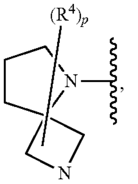 or 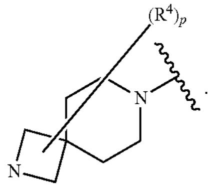.

In some embodiments, two $R^4$ groups are taken together to form ═O and $R^1$ is

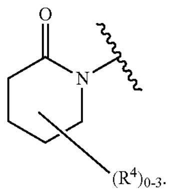

In some embodiments, two $R^4$ groups are taken together to form ═O and $R^1$ is

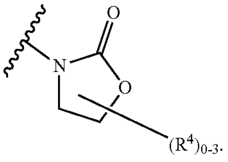

In some embodiments, two $R^4$ groups are taken together to form ═O and $R^1$ is

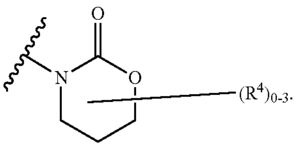

In some embodiments, two sets of R4 groups are taken together to each form ═O and $R^1$ is

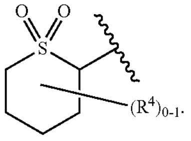

In some embodiments, $R^1$ is selected from those depicted in Table 1, below.

In some embodiments, $R^2$ is hydrogen, deuterium, $R^z$, halogen, —CN, —$NO_2$, —OR, —SR, —$NR_2$, —$S(O)_2R$, —$S(O)_2NR_2$, —S(O)R, —$S(O)NR_2$, —$CF_2R$, —$CF_3$, —$CR_2(CN)$, —$CR_2(OR)$, —$CR_2(NR_2)$, —C(O)R, —C(O)OR, —$C(O)NR_2$, —C(O)N(R)OR, —OC(O)R, —OC(O)$NR_2$, —$C(S)NR_2$, —N(R)C(O)OR, —N(R)C(O)R, —N(R)C(O)$NR_2$, —N(R)C(NR)$NR_2$, —N(R)$NR_2$, —N(R)$S(O)_2NR_2$, —N(R)$S(O)_2R$, —N═S(O)$R_2$, —S(NR)(O)R, —N(R)S(O)R, —N(R)CN, —Si(OR)$R_2$, —$SiR_3$, —P(O)(R)$NR_2$, —P(O)(R)OR or —P(O)$R_2$.

In some embodiments, $R^2$ is methyl, ethyl, n-propyl, isopropyl, fluoro, chloro, —$CF_3$, —$OCH_3$, —$N(CH_3)_2$, —$OCH_2CH_2OH$, —$CH_2CF_3$, —C(O)$CH_3$, —S(O)$CH_3$, —$S(O)_2CH_3$, -OiPr, —$SCH_3$, —CN, —C(O)$NH_2$, —C(O)$OCH_3$, —$CH_2OH$, —$CH_2CN$, —$CO_2H$, —$OCF_3$, —$OCHF_2$,

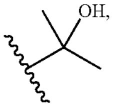 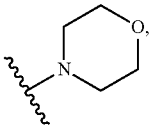

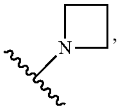 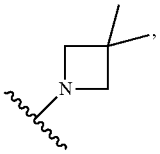

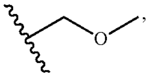 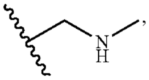

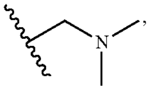 or 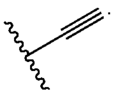

In some embodiments, $R^2$ is selected from those depicted in Table 1, below.

In some embodiments, $R^4$ is hydrogen, deuterium, $R^z$, halogen, —CN, —$NO_2$, —OR, —SR, —$NR_2$, —$S(O)_2R$, —$S(O)_2NR_2$, —S(O)R, —$S(O)NR_2$, —$CF_2R$, —$CF_3$, —$CR_2(CN)$, —$CR_2(OR)$, —$CR_2(NR_2)$, —C(O)R, —C(O)OR, —$C(O)NR_2$, —C(O)N(R)OR, —OC(O)R, —OC(O)$NR_2$, —$C(S)NR_2$, —N(R)C(O)OR, —N(R)C(O)R, —N(R)C(O)$NR_2$, —N(R)C(NR)$NR_2$, —N(R)$NR_2$, —N(R)$S(O)_2NR_2$, —N(R)$S(O)_2R$, —N═S(O)$R_2$, —S(NR)(O)R, —N(R)S(O)R, —N(R)CN, —Si(OR)$R_2$, —$SiR_3$, —P(O)(R)$NR_2$, —P(O)(R)OR or —P(O)$R_2$. In some embodiments, $R^4$ is methyl, fluoro, —$OCH_3$, —$N(CH_3)_2$, —OH, —$CF_3$, —C(O)$NH_2$, —CN

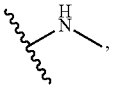 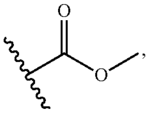 or

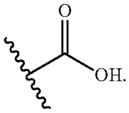

In some embodiments, $R^4$ is selected from those depicted in Table 1, below.

In some embodiments, $R^5$ is hydrogen, deuterium, $R^z$, halogen, —CN, —$NO_2$, —OR, —SR, —$NR_2$, —$S(O)_2R$, —$S(O)_2NR_2$, —S(O)R, —$S(O)NR_2$, —$CF_2R$, —$CF_3$, —$CR_2(CN)$, —$CR_2(OR)$, —$CR_2(NR_2)$, —C(O)R, —C(O)OR, —$C(O)NR_2$, —C(O)N(R)OR, —OC(O)R, —OC(O)$NR_2$, —$C(S)NR_2$, —N(R)C(O)OR, —N(R)C(O)R, —N(R)C(O)$NR_2$, —N(R)C(NR)$NR_2$, —N(R)$NR_2$, —N(R)$S(O)_2NR_2$, —N(R)$S(O)_2R$, —N═S(O)$R_2$, —S(NR)(O)R, —N(R)S(O)R, —N(R)CN, —Si(OR)$R_2$, —$SiR_3$, —P(O)(R)$NR_2$, —P(O)(R)OR or —P(O)$R_2$. In some embodiments, $R^5$ is methyl, fluoro,

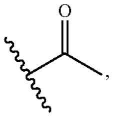 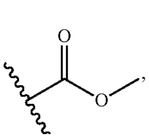

-continued

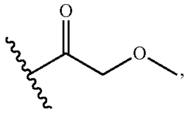,
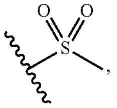, or
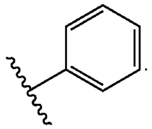.

In some embodiments, $R^5$ is selected from those depicted in Table 1, below.

In some embodiments, two $R^2$ groups are taken together to form =O. As defined generally above, two $R^4$ groups are optionally taken together to form =O. In some embodiments, two $R^4$ groups are taken together to form =O. As defined generally above, two $R^5$ groups are optionally taken together to form =O. In some embodiments, two $R^5$ groups are taken together to form =O.

In some embodiments, two $R^2$ groups are taken together with their intervening atoms to form a 5-8 membered saturated, partially unsaturated, or aryl fused ring having 0-3 heteroatoms independently selected from nitrogen, oxygen and sulfur.

In some embodiments, two $R^4$ groups are taken together with their intervening atoms to form a 5-8 membered saturated, partially unsaturated, or aryl fused ring having 0-3 heteroatoms independently selected from nitrogen, oxygen and sulfur.

In some embodiments, two $R^5$ groups are taken together with their intervening atoms to form a 5-8 membered saturated, partially unsaturated, or aryl fused ring having 0-3 heteroatoms independently selected from nitrogen, oxygen and sulfur.

In some embodiments, $R^z$ is selected from an optionally substituted group selected from $C_{1-6}$ aliphatic; phenyl; a 4-7 membered saturated or partially unsaturated heterocyclic ring having 1-2 heteroatoms independently selected from nitrogen, oxygen, and sulfur; and a 5-6 membered heteroaryl ring having 1-4 heteroatoms independently selected from nitrogen, oxygen, and sulfur.

In some embodiments, $R^z$ is selected from those depicted in Table 1, below.

In some embodiments, $R^3$ is hydrogen. In some embodiments, $R^3$ is an optionally substituted $C_{1-6}$ aliphatic group.

In some embodiments, $R^3$ is methyl.

In some embodiments, $R^3$ is selected from those depicted in Table 1, below.

In some embodiments, two $R^3$ groups are taken together to form =O.

In some embodiments, an $R^2$ group and an $R^3$ group are taken together with their intervening atoms to form a 5-8 membered saturated or partially unsaturated fused ring having 0-3 heteroatoms independently selected from nitrogen, oxygen or sulfur.

In some embodiments, $L^1$ is one of the following: (a) a $C_{1-6}$ bivalent straight or branched saturated or unsaturated hydrocarbon chain wherein 1-3 methylene units of the chain are independently and optionally replaced with —O—, -Cy-, —C(O)—, —C(S)—, —$C(R)_2$—, —CH(R)—, —CH(OR)—, —$C(F)_2$—, —N(R)—, —S—, —S(O)—, or —$S(O)_2$—; or (b) a covalent bond. In some embodiments, $L^1$ is a $C_{1-6}$ bivalent straight or branched saturated or unsaturated hydrocarbon chain wherein 1-3 methylene units of the chain are independently and optionally replaced with —O—, -Cy-, —C(O)—, —C(S)—, —$C(R)_2$—, —CH(R)—, —CH(OR)—, —$C(F)_2$—, —N(R)—, —S—, —S(O)—, or —$S(O)_2$—

In some embodiments, $L^1$ is a covalent bond.

In some embodiments, $L^1$ is,

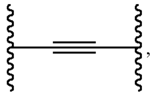,
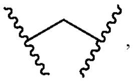,
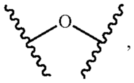,
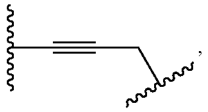,
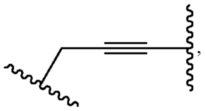,
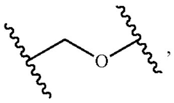,
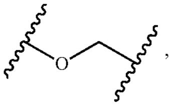,
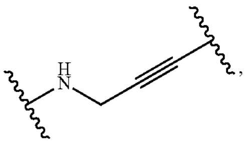,
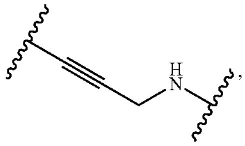,
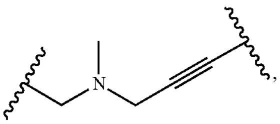,
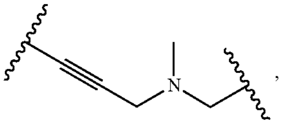,
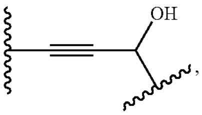,
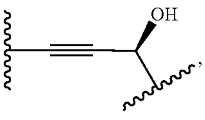,
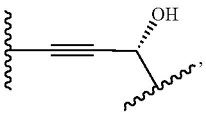,
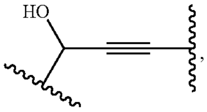,
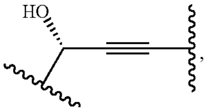,
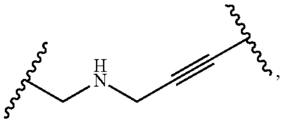,
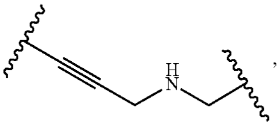,
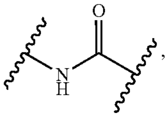,
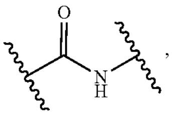,
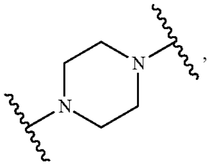,
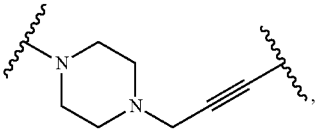, -continued
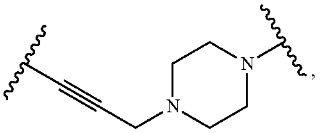,
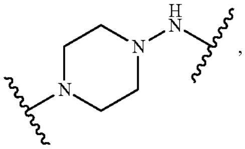, 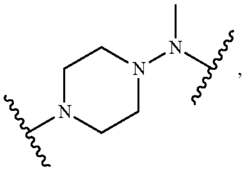,
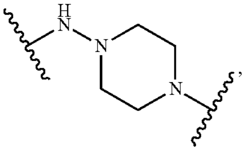, 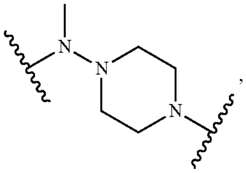,
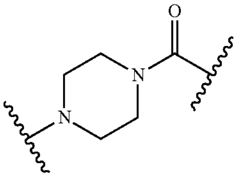, 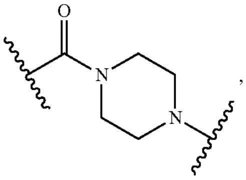,
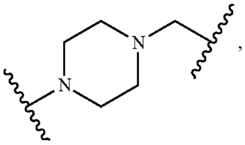, 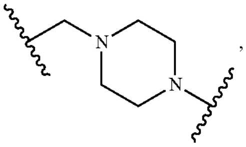,
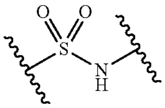, 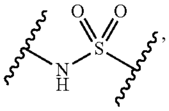,
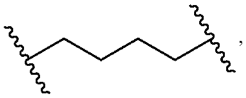, 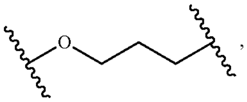,
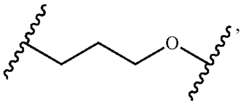, 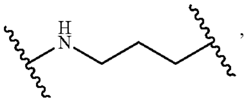,
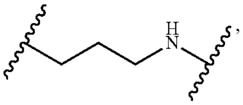, 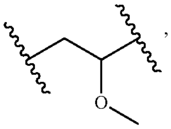,
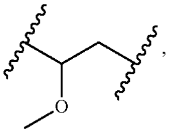, 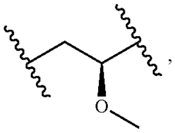,
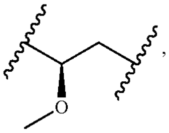, 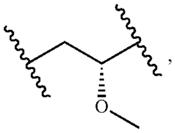,
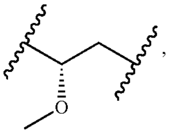, 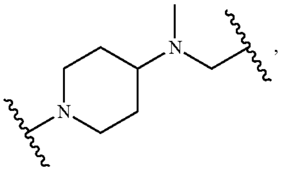,
-continued
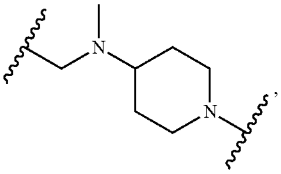, 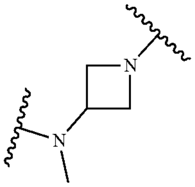,
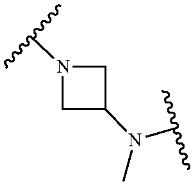, 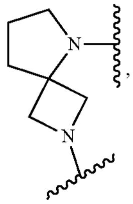, 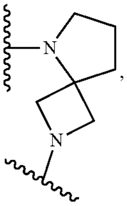,
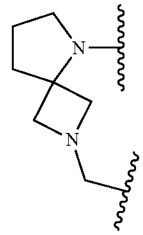, 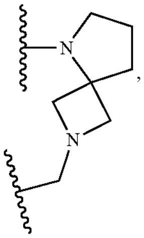,
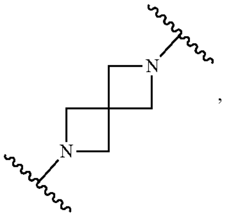, 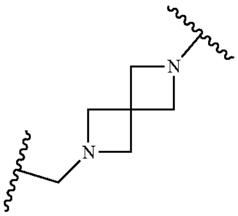,
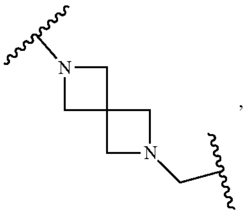, 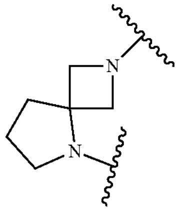,
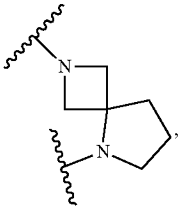, 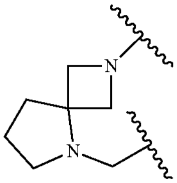,
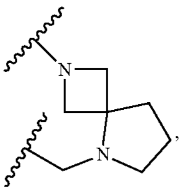, 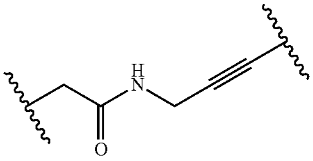,
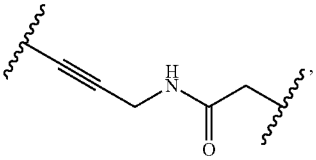, -continued
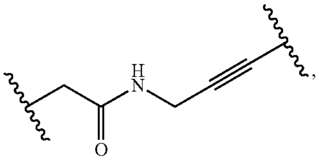,
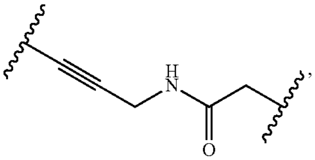,
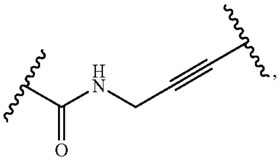,
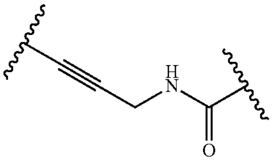,
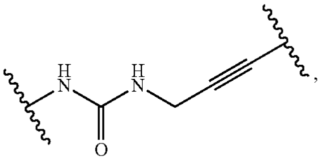,
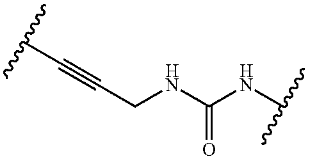,
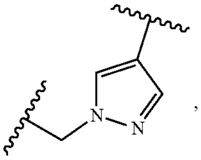, 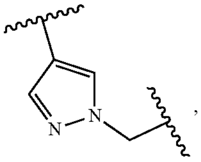,
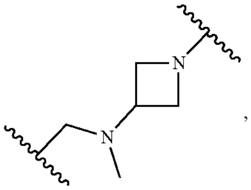, 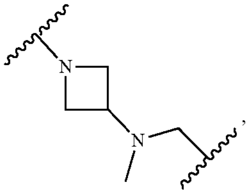,
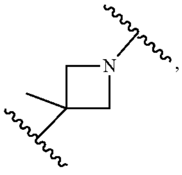, 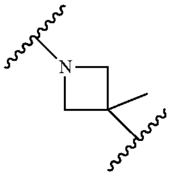,
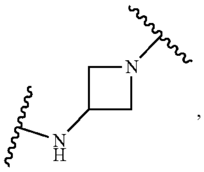, 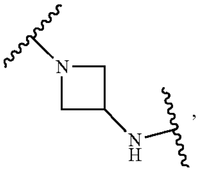,
-continued
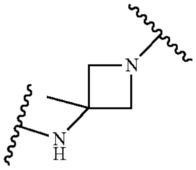, 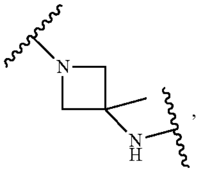,
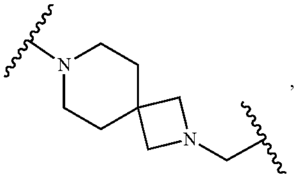,
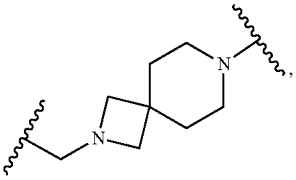, 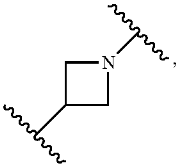,
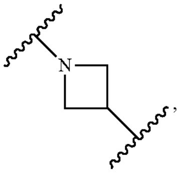, 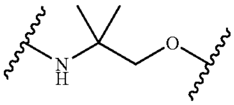,
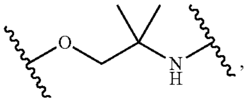, 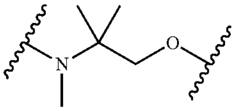,
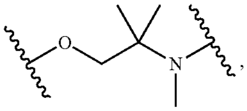, 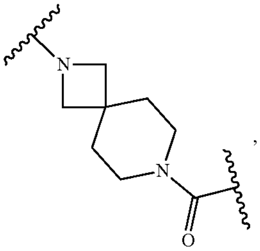,
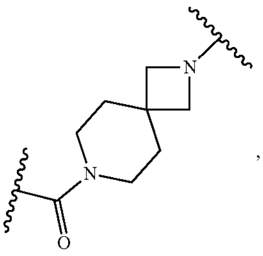,
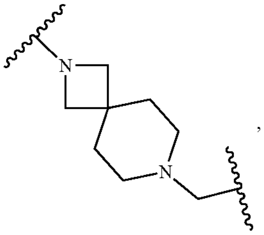, -continued

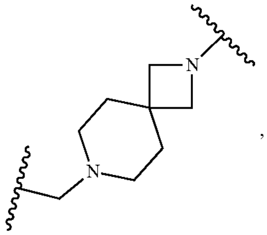
,
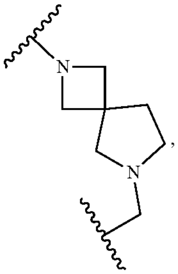
,
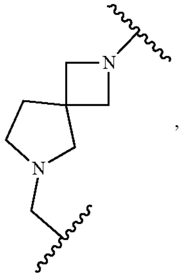
,
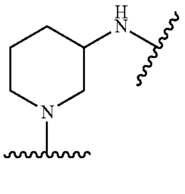
,
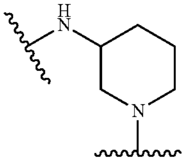
,
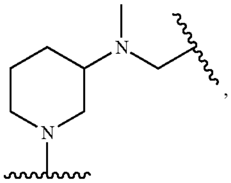
,
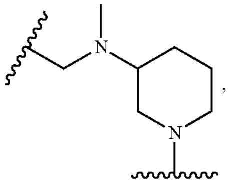
,
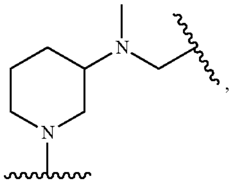
,
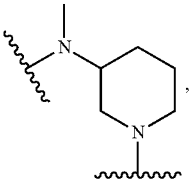
,
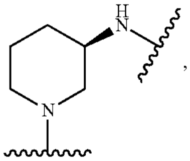
,
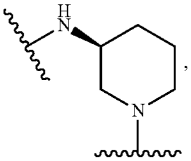
,
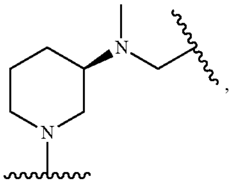
,
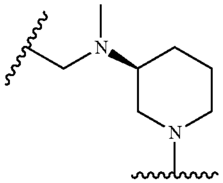
,
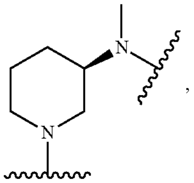
,
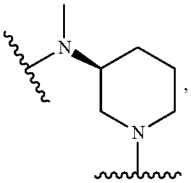
,
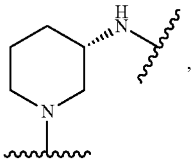
, -continued

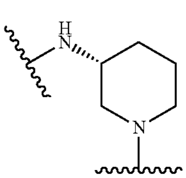
,
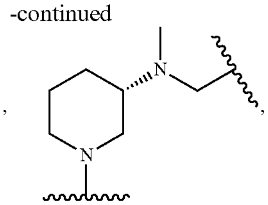
,
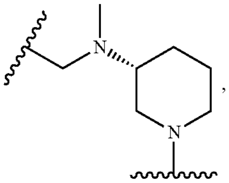
,
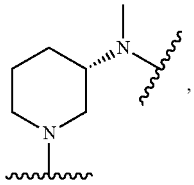
,
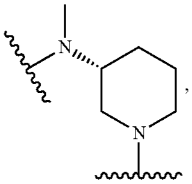
,
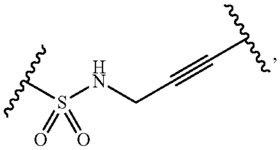
,
or
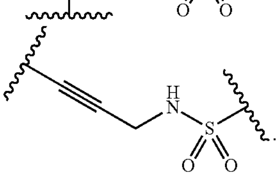
.

In some embodiments, $L^1$ is selected from those depicted in Table 1, below.

In some embodiments, -Cy- is an optionally substituted bivalent ring selected from phenylene; 3-7 membered saturated or partially unsaturated carbocyclylene; 4-7 membered saturated or partially unsaturated heterocyclylene having 1-2 heteroatoms independently selected from nitrogen, oxygen, and sulfur; a 7-11 membered saturated or partially unsaturated spiro bicyclic heterocyclylene having 1-2 heteroatoms independently selected from nitrogen, oxygen, and sulfur; or a 5-6 membered heteroarylene having 1-4 heteroatoms independently selected from nitrogen, oxygen, and sulfur. In some embodiments, -Cy- is selected from those depicted in Table 1, below.

In some embodiments, $L^2$ is a covalent bond or a $C_{1-4}$ bivalent straight or branched saturated or unsaturated hydrocarbon chain wherein 1-2 methylene units of the chain are independently and optionally replaced with —O—, —C(O)—, —C(S)—, —C(R)$_2$—, —CH(R)—, —CH(OR)—, —C(F)$_2$—, —N(R)—, —S—, —S(O)—, or —S(O)$_2$—. In some embodiments, $L^2$ is a covalent bond. In some embodiments, $L^2$ is a $C_{1-4}$ bivalent straight or branched saturated or unsaturated hydrocarbon chain wherein 1-2 methylene units of the chain are independently and optionally replaced with —O—, —C(O)—, —C(S)—, —C(R)$_2$—, —CH(R)—, —CH(OR)—, —C(F)$_2$—, —N(R)—, —S—, —S(O)—, or —S(O)$_2$—.

In some embodiments, $L^2$ is

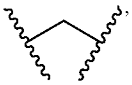
,
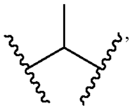
,
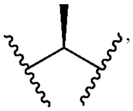
,
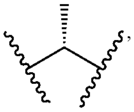
,

-continued

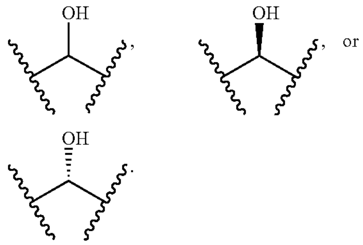

In some embodiments, $L^2$ is selected from those depicted in Table 1, below.

In some embodiments, $L^3$ is a $C_{1-4}$ bivalent straight or branched saturated or unsaturated hydrocarbon chain wherein 1-2 methylene units of the chain are independently and optionally replaced with —O—, —C(O)—, —C(S)—, —$C(R)_2$—, —CH(R)—, —CH(OR)—, —$C(F)_2$—, —N(R)—, —S—, —S(O)—, or —$S(O)_2$—.

In some embodiments, $L^3$ is a covalent bond.

In some embodiments, $L^3$ is

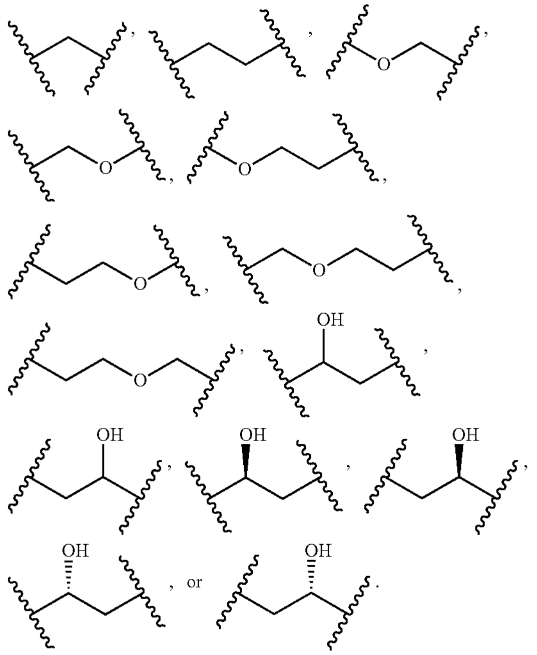

In some embodiments, $L^3$ is selected from those depicted in Table 1, below.

In some embodiments, X is a 4-8 membered saturated or partially unsaturated monocyclic heterocyclic ring having 1-2 heteroatoms independently selected from nitrogen, oxygen, and sulfur; an 8-10 membered partially aromatic or heteroaromatic bicyclic heterocyclic ring having 1-4 heteroatoms independently selected from nitrogen, oxygen, and sulfur; a 5-6 membered monocyclic heteroaryl ring having 1-4 heteroatoms independently selected from nitrogen, oxygen, and sulfur; a 3-7 membered saturated or partially unsaturated monocyclic carbocyclic ring; or phenyl; each of which is substituted with q instances of $R^5$. In some embodiments, X is —$CH_2$(OR), —CH(R)(OR), or —$C(R)_2$(OR).

In some embodiments, X is

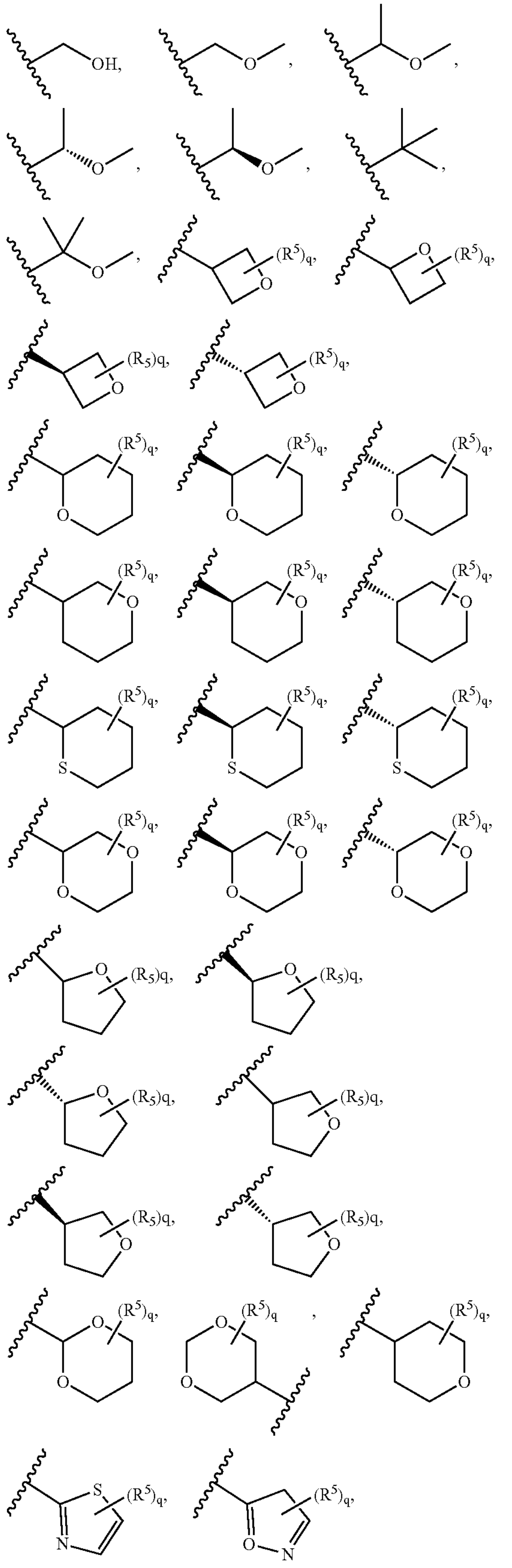

-continued
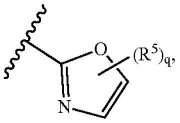 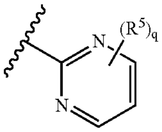 ,
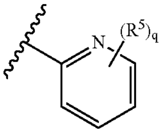 , 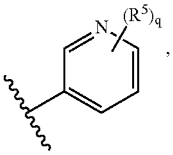 ,
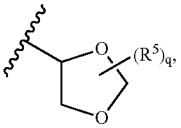 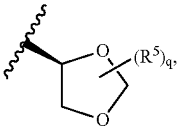
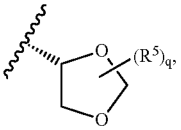 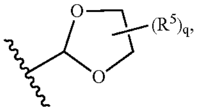
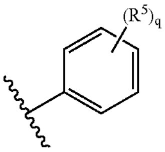 , 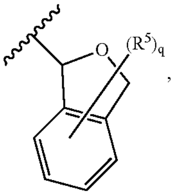 ,
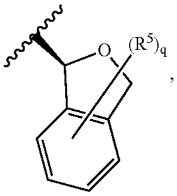 , 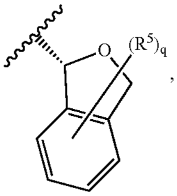 ,
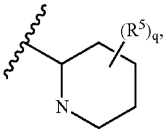 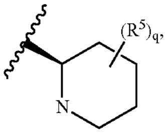 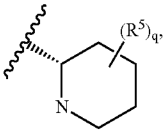
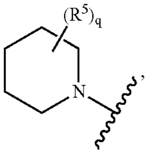 , 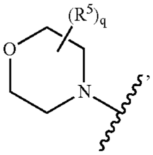 , 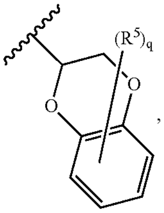 ,
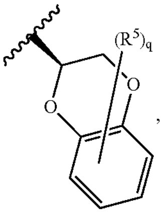 , 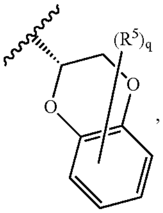 ,
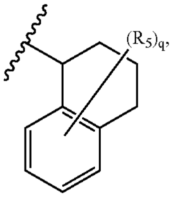 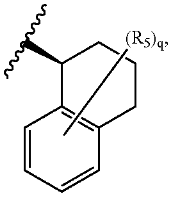
-continued
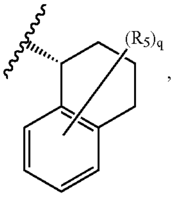 , 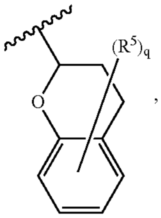 ,
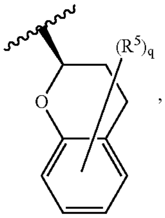 , 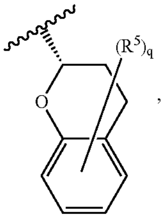 , 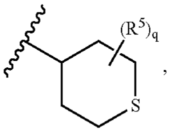 ,
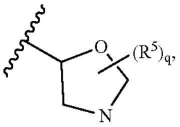 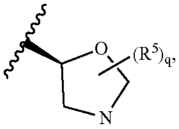 or
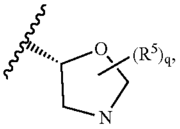
In some embodiments, two $R^5$ groups are taken together to form =O and X is
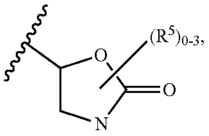 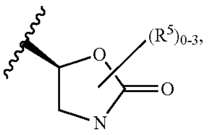
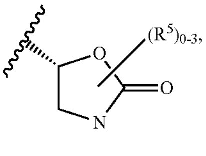 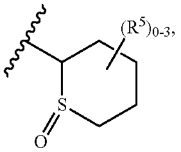
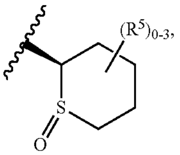 or 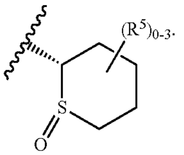
In some embodiments, two sets of $R^5$ groups are taken together to each form =O and X is
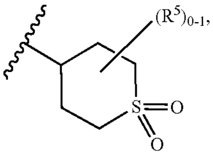 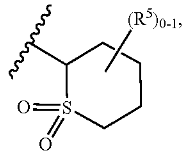

-continued

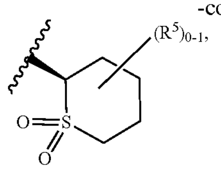 or 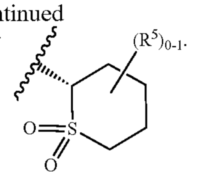

In some embodiments, X is selected from those depicted in Table 1, below.

In some embodiments, R is hydrogen. In some embodiments, R is an optionally substituted group selected from $C_{1-6}$ aliphatic; phenyl; an 8-10 membered bicyclic aryl ring, a 3-7 membered saturated or partially unsaturated monocyclic carbocyclic ring; a 4-8 membered saturated or partially unsaturated monocyclic heterocyclic ring having 1-2 heteroatoms independently selected from nitrogen, oxygen, and sulfur; a 5-6 membered monocyclic heteroaryl ring having 1-4 heteroatoms independently selected from nitrogen, oxygen, and sulfur; and an 8-10 membered bicyclic heteroaryl ring having 1-5 heteroatoms independently selected from nitrogen, oxygen, and sulfur.

In some embodiments, two R groups on the same nitrogen are taken together with the nitrogen to form an optionally substituted 4-7 membered monocyclic saturated, partially unsaturated, or heteroaryl ring having, in addition to the nitrogen, 0-3 heteroatoms independently selected from nitrogen, oxygen, and sulfur.

In some embodiments, R is selected from those depicted in Table 1, below.

In some embodiments, m is 0, 1, 2, 3, or 4. In some embodiments, m is 0. In some embodiments, m is 1. In some embodiments, m is 2. In some embodiments, m is 3. In some embodiments, m is 4. In some embodiments, m is selected from those depicted in Table 1, below.

In some embodiments, n is 0, 1, 2, 3, or 4. In some embodiments, n is 0. In some embodiments, n is 1. In some embodiments, n is 2. In some embodiments, n is 3. In some embodiments, n is 4. In some embodiments, n is selected from those depicted in Table 1, below.

In some embodiments, p is 0, 1, 2, 3, 4, or 5. In some embodiments, p is 0. In some embodiments, p is 1. In some embodiments, p is 2. In some embodiments, p is 3. In some embodiments, p is 4. In some embodiments, p is 5. In some embodiments, p is selected from those depicted in Table 1, below.

In some embodiments, q is 0, 1, 2, 3, 4, or 5. In some embodiments, q is 0. In some embodiments, q is 1. In some embodiments, q is 2. In some embodiments, q is 3. In some embodiments, q is 4. In some embodiments, q is 5. In some embodiments, q is selected from those depicted in Table 1, below.

In some embodiments, the present invention provides a compound of formula I-1*, wherein Ring A is phenyl, Ring B is triazolyl, and $L^2$ is a covalent bond, to provide a compound of formula I-a*:

I-a*

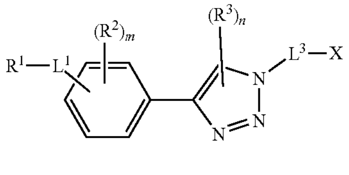

or a pharmaceutically acceptable salt thereof, wherein each of $L^1$, $L^3$, $R^1$, $R^2$, $R^3$, X, m, and n is as defined above and described in embodiments herein, both singly and in combination.

In some embodiments, the present invention provides a compound of formula I-1*, wherein Ring A is pyridyl, Ring B is triazolyl, and $L^2$ is a covalent bond, to provide a compound of formula I-b-1*, I-b-2*, or I-b-3*:

I-b-1*

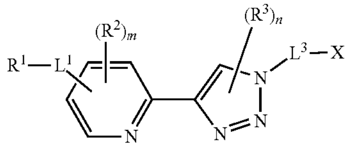

I-b-2*

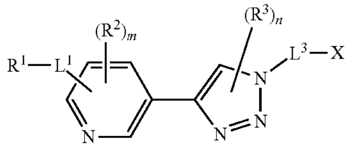

I-b-3*

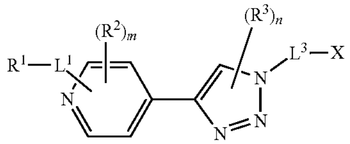

or a pharmaceutically acceptable salt thereof, wherein each of $L^1$, $L^3$, $R^1$, $R^2$, $R^3$, X, m, and n is as defined above and described in embodiments herein, both singly and in combination.

In some embodiments, the present invention provides a compound of formula I-1*, wherein Ring A is thiophenyl, Ring B is triazolyl, and $L^2$ is a covalent bond, to provide a compound of formula I-c*:

I-c*

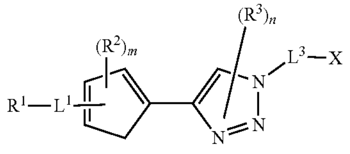

or a pharmaceutically acceptable salt thereof, wherein each of $L^1$, $L^3$, $R^1$, $R^2$, $R^3$, X, m, and n is as defined above and described in embodiments herein, both singly and in combination.

In some embodiments, the present invention provides a compound of formula I-1*, wherein $L^1$ is acetylenyl, $L^2$ is a covalent bond, Ring A is phenyl, thiophenyl, or pyridyl, and Ring B is triazolyl, to provide a compound of formula I-f-1*, I-f-2*, I-f-3*, I-f-4*, I-f-5*, 1-f-6*, I-f-7*, I-f-8*, or 1-f-9*:

i-f-1*

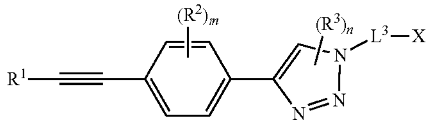

-continued i-f-2*

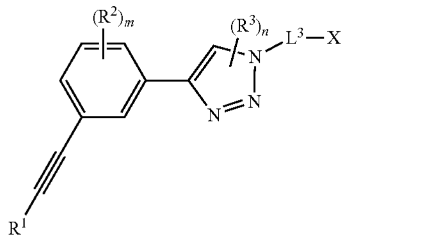

i-f-3*

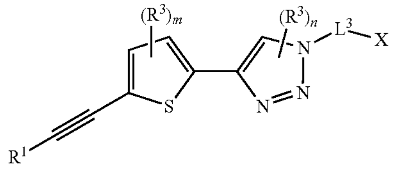

i-f-4*

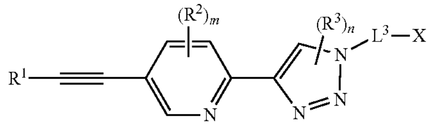

i-f-5*

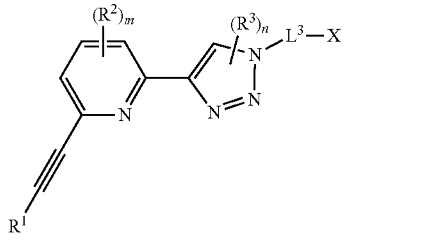

i-f-6*

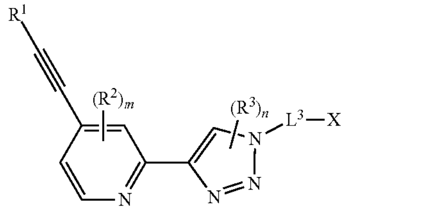

i-f-7*

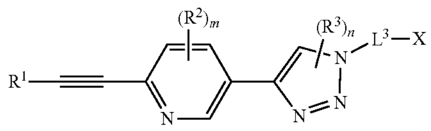

i-f-8*

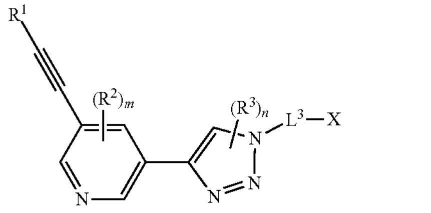

-continued i-f-9*

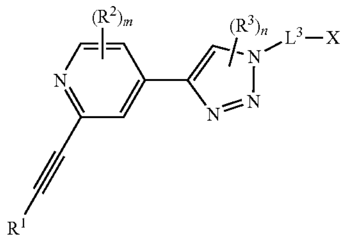

or a pharmaceutically acceptable salt thereof, wherein each of $L^3$, $R^1$, $R^2$, $R^3$, X, m, and n is as defined above and described in embodiments herein, both singly and in combination.

In some embodiments, the present invention provides a compound of formula I-1*, wherein Ring B is triazolyl, $L^3$ is methylene, and X is oxetanyl, to provide a compound of formula I-g-1*, I-g-2*, or I-g-3*:

I-g-1*

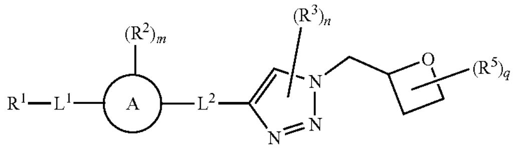

I-g-2*

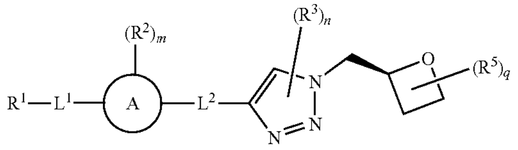

I-g-3*

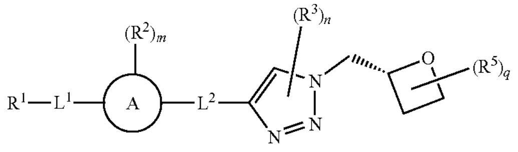

or a pharmaceutically acceptable salt thereof, wherein each of $L^1$, $L^2$, $R^1$, $R^2$, $R^3$, $R^5$, m, n, and q is as defined above and described in embodiments herein, both singly and in combination.

In some embodiments, the present invention provides a compound of formula I-1*, wherein Ring B is triazolyl, $L^3$ is methylene, and X is furanyl, to provide a compound of formula I-h-1*, I-h-2*, or I-h-3*:

I-h-1*

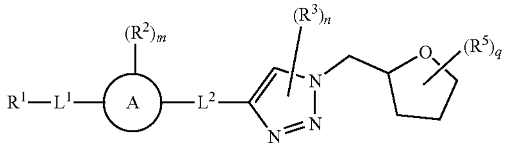

-continued

I-h-2*

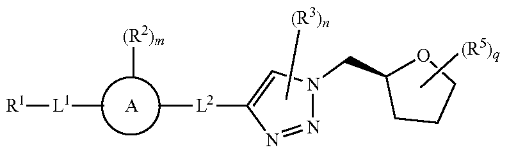

I-h-3*

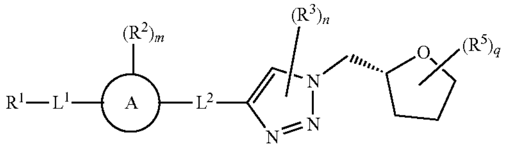

or a pharmaceutically acceptable salt thereof, wherein each of $L^1$, $L^2$, $R^1$, $R^2$, $R^3$, $R^5$, m, n, and q is as defined above and described in embodiments herein, both singly and in combination.

In some embodiments, the present invention provides a compound of formula I-1*, wherein Ring B is triazolyl, $L^3$ is methylene, and X is tetrahydropyranyl, to provide a compound of formula I-i-1*, I-i-2*, or I-i-3*:

I-i-1*

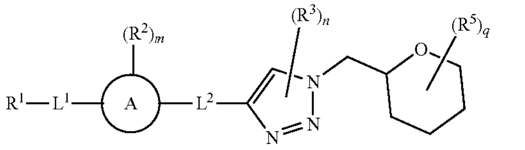

I-i-2*

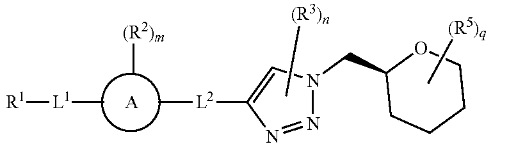

-continued

I-i-3*

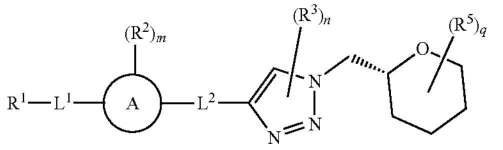

or a pharmaceutically acceptable salt thereof, wherein each of $L^1$, $L^2$, $R^1$, $R^2$, $R^3$, $R^5$, m, n, and q is as defined above and described in embodiments herein, both singly and in combination.

In some embodiments, the present invention provides a compound of formula I-1*, wherein Ring B is triazolyl, $L^3$ is methylene, and X is 1,4-dioxanyl, to provide a compound of formula I-j-1*, I-j-2*, or I-j-3*.

I-j-1*

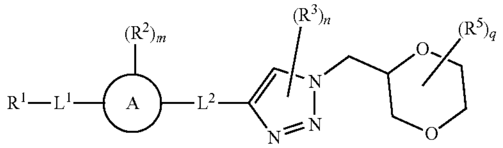

I-j-2*

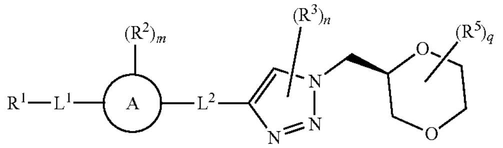

I-j-3*

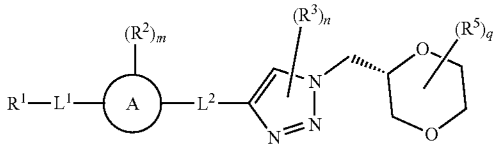

or a pharmaceutically acceptable salt thereof, wherein each of $L^1$, $L^2$, $R^1$, $R^2$, $R^3$, $R^5$, m, n, and q is as defined above and described in embodiments herein, both singly and in combination.

Exemplary compounds of the invention are set forth in Table 1, below.

TABLE 1

| Selected Compounds | |
|---|---|
| Compound | Structure |
| I-1 | 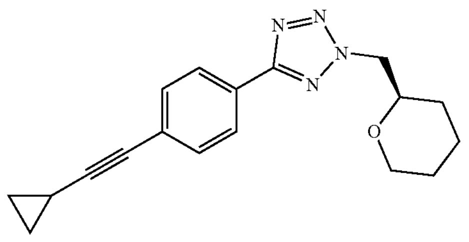 [SMILES: C(#CC1CC1)c1ccc(-c2nnn(C[C@H]3CCCCO3)n2)cc1] |

TABLE 1-continued
| Selected Compounds | |
|---|---|
| Compound | Structure |
| I-2 | 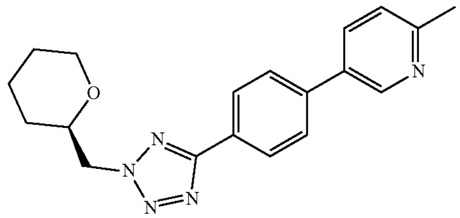 [SMILES: Cc1ccc(-c2ccc(-c3nnn(C[C@H]4CCCCO4)n3)cc2)cn1] |
| I-3 | 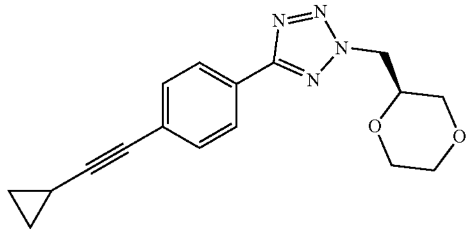 [SMILES: C(#CC1CC1)c1ccc(-c2nnn(C[C@H]3COCCO3)n2)cc1] |
| I-4 | 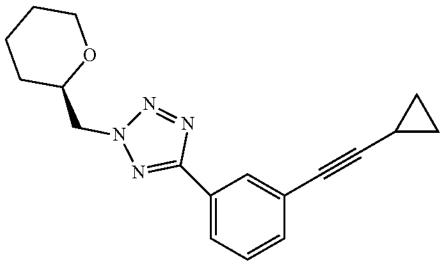 [SMILES: C(#CC1CC1)c1cccc(-c2nnn(C[C@H]3CCCCO3)n2)c1] |
| I-5 | 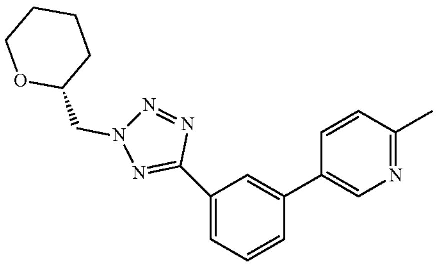 [SMILES: Cc1ccc(-c2cccc(-c3nnn(C[C@H]4CCCCO4)n3)c2)cn1] |
| I-6 | 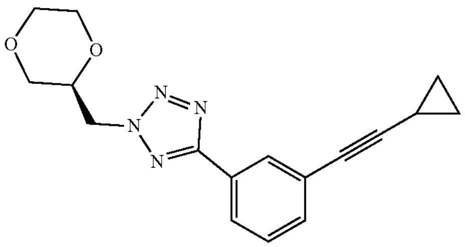 [SMILES: C(#CC1CC1)c1cccc(-c2nnn(C[C@H]3COCCO3)n2)c1] |
| I-7 | 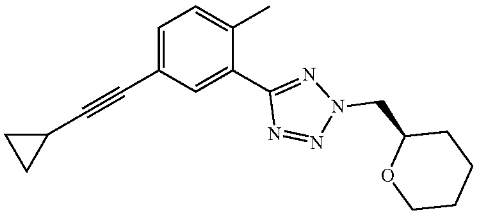 |

TABLE 1-continued
| Selected Compounds | |
|---|---|
| Compound | Structure |
| I-8 | 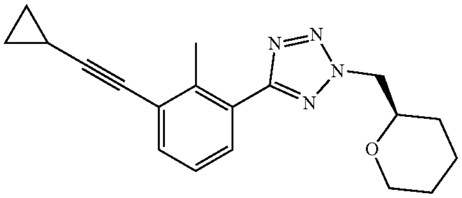 |
| I-9 | 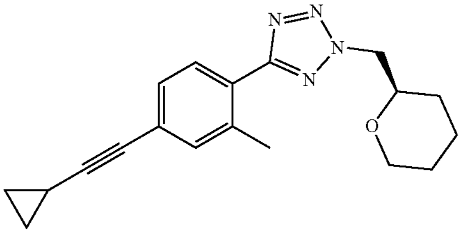 [SMILES: Cc1cc(C#CC2CC2)ccc1-c1nnn(C[C@H]2CCCCO2)n1] |
| I-10 | 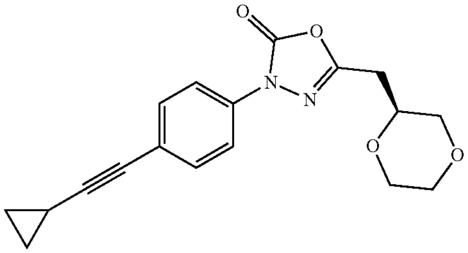 [SMILES: O=c1oc(C[C@H]2COCCO2)nn1-c1ccc(C#CC2CC2)cc1] |
| I-11 | 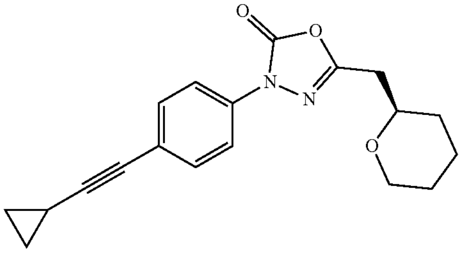 [SMILES: O=c1oc(C[C@H]2CCCCO2)nn1-c1ccc(C#CC2CC2)cc1] |
| I-12 | 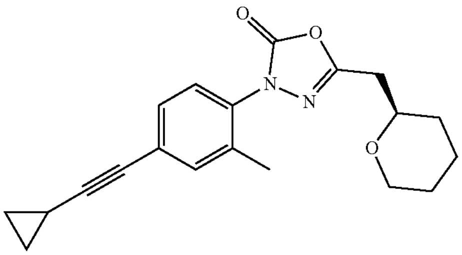 [SMILES: Cc1cc(C#CC2CC2)ccc1-n1nc(C[C@H]2CCCCO2)oc1=O] |
| I-13 | 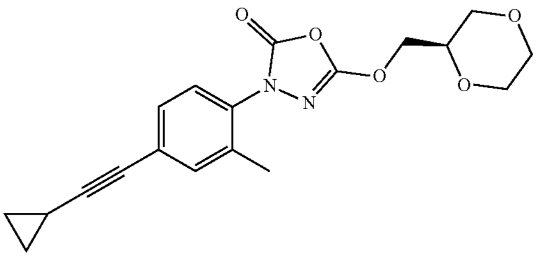 [SMILES: Cc1cc(C#CC2CC2)ccc1-n1nc(OC[C@H]2COCCO2)oc1=O] |

TABLE 1-continued
| Selected Compounds | |
|---|---|
| Compound | Structure |
| I-14 | 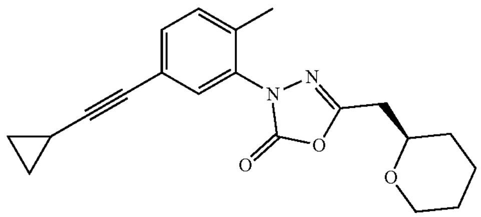 [SMILES: Cc1ccc(C#CC2CC2)cc1-n1nc(C[C@H]2CCCCO2)oc1=O] |
| I-15 | 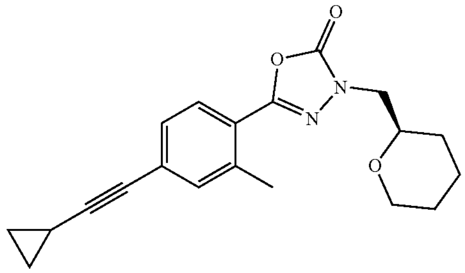 [SMILES: Cc1cc(C#CC2CC2)ccc1-c1nn(C[C@H]2CCCCO2)c(=O)o1] |
| I-16 | 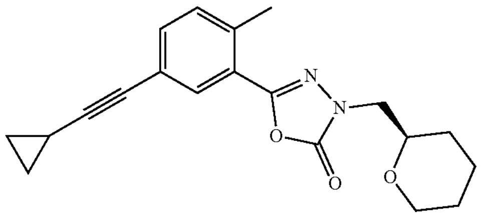 [SMILES: Cc1ccc(C#CC2CC2)cc1-c1nn(C[C@H]2CCCCO2)c(=O)o1] |
| I-17 | 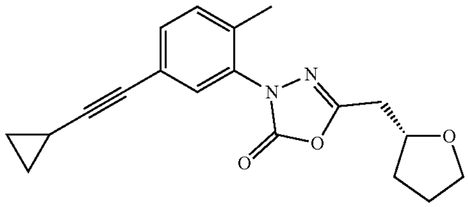 [SMILES: Cc1ccc(C#CC2CC2)cc1-n1nc(C[C@H]2CCCO2)oc1=O] |
| I-18 | 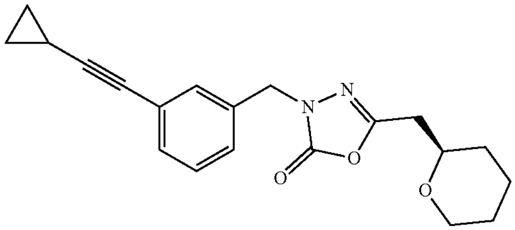 [SMILES: O=c1oc(C[C@H]2CCCCO2)nn1Cc1cccc(C#CC2CC2)c1] |
| I-19 | 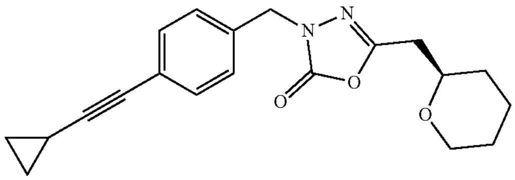 [SMILES: O=c1oc(C[C@H]2CCCCO2)nn1Cc1ccc(C#CC2CC2)cc1] |

TABLE 1-continued
| Selected Compounds | |
|---|---|
| Compound | Structure |
| I-20 | 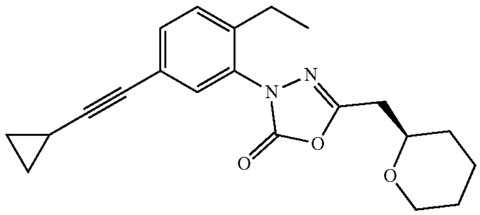 [SMILES: CCc1ccc(C#CC2CC2)cc1-n1nc(C[C@H]2CCCCO2)oc1=O] |
| I-22 | 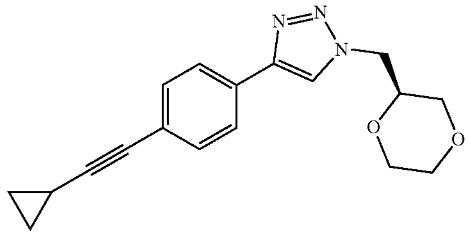 |
| I-23 | 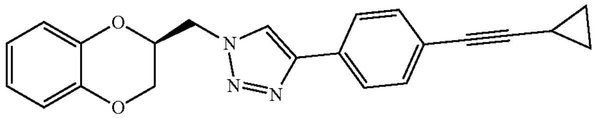 [SMILES: C(#CC1CC1)c1ccc(-c2cn(C[C@H]3COc4ccccc4O3)nn2)cc1] |
| I-24 | 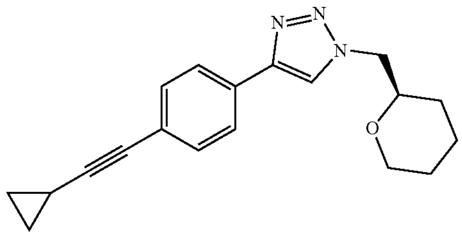 [SMILES: C(#CC1CC1)c1ccc(-c2cn(C[C@H]3CCCCO3)nn2)cc1] |
| I-25 | 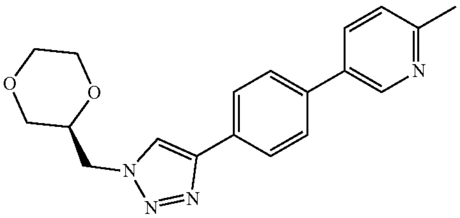 [SMILES: Cc1ccc(-c2ccc(-c3cn(C[C@H]4COCCO4)nn3)cc2)cn1] |
| I-26 | 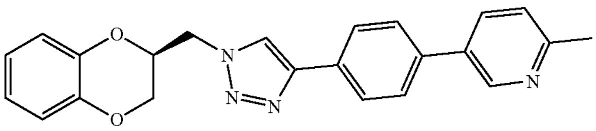 [SMILES: Cc1ccc(-c2ccc(-c3cn(C[C@H]4COc5ccccc5O4)nn3)cc2)cn1] |
| I-27 | 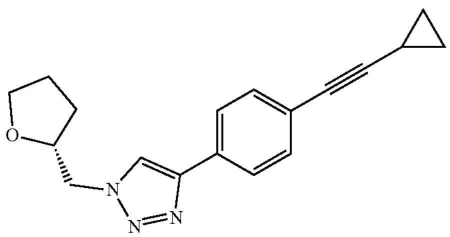 [SMILES: C(#CC1CC1)c1ccc(-c2cn(C[C@H]3CCCO3)nn2)cc1] |

TABLE 1-continued
| Selected Compounds | |
|---|---|
| Compound | Structure |
| I-28 | 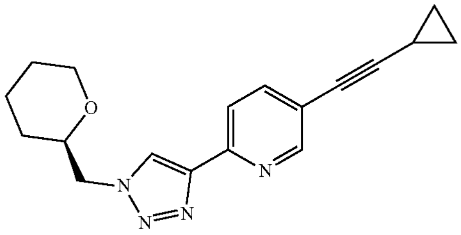 [SMILES: C(#CC1CC1)c1ccc(-c2cn(C[C@H]3CCCCO3)nn2)nc1] |
| I-29 | 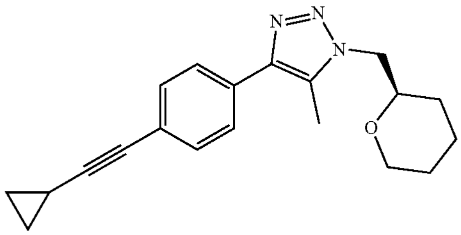 [SMILES: Cc1c(-c2ccc(C#CC3CC3)cc2)nnn1C[C@H]1CCCCO1] |
| I-30 | 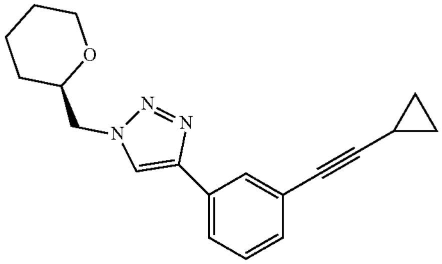 [SMILES: C(#CC1CC1)c1cccc(-c2cn(C[C@H]3CCCCO3)nn2)c1] |
| I-31 | 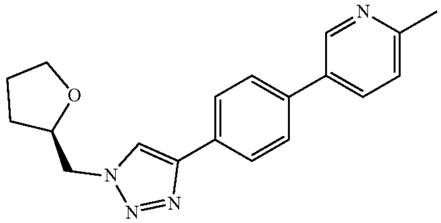 [SMILES: Cc1ccc(-c2ccc(-c3cn(C[C@H]4CCCO4)nn3)cc2)cn1] |
| I-32 | 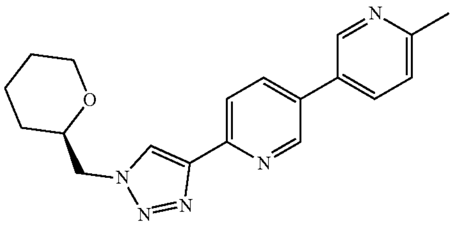 [SMILES: Cc1ccc(-c2ccc(-c3cn(C[C@H]4CCCCO4)nn3)nc2)cn1] |
| I-33 | 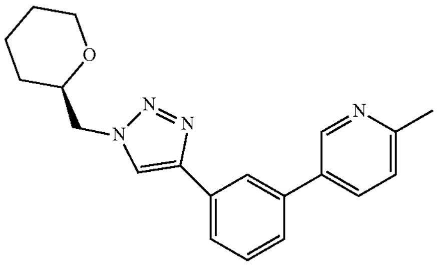 [SMILES: Cc1ccc(-c2cccc(-c3cn(C[C@H]4CCCCO4)nn3)c2)cn1] |

TABLE 1-continued
| Compound | Structure |
| --- | --- |
| I-34 | 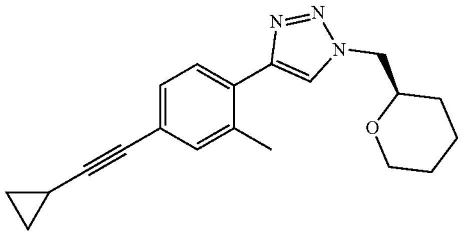 |
| I-35 | 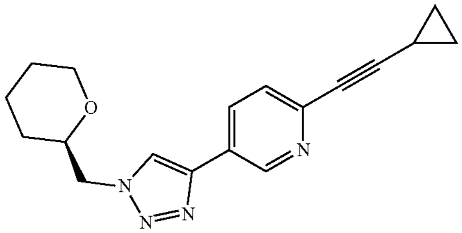 [SMILES: C(#CC1CC1)c1ccc(-c2cn(C[C@H]3CCCCO3)nn2)cn1] |
| I-36 | 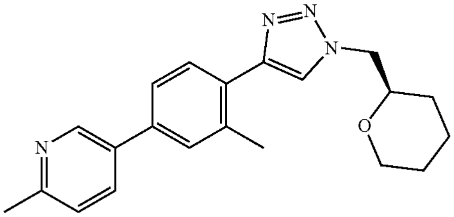 [SMILES: Cc1ccc(-c2ccc(-c3cn(C[C@H]4CCCCO4)nn3)c(C)c2)cn1] |
| I-37 | 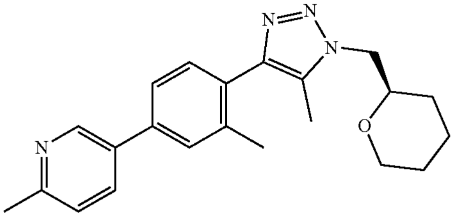 [SMILES: Cc1ccc(-c2ccc(-c3nnn(C[C@H]4CCCCO4)c3C)c(C)c2)cn1] |
| I-38 | 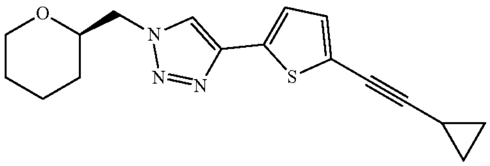 [SMILES: C(#CC1CC1)c1ccc(-c2cn(C[C@H]3CCCCO3)nn2)s1] |
| I-39 | 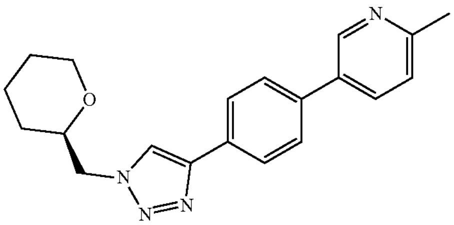 [SMILES: Cc1ccc(-c2ccc(-c3cn(C[C@H]4CCCCO4)nn3)cc2)cn1] |

TABLE 1-continued
| Selected Compounds | |
|---|---|
| Compound | Structure |
| I-40 | 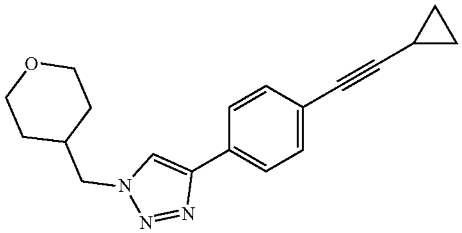 [SMILES: C(#CC1CC1)c1ccc(-c2cn(CC3CCOCC3)nn2)cc1] |
| I-41 | 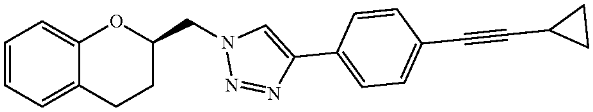 [SMILES: C(#CC1CC1)c1ccc(-c2cn(C[C@H]3CCc4ccccc4O3)nn2)cc1] |
| I-42 | 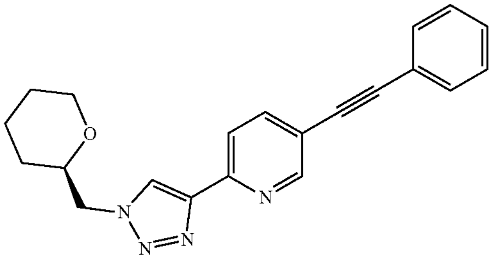 [SMILES: C(#Cc1ccc(-c2cn(C[C@H]3CCCCO3)nn2)nc1)c1ccccc1] |
| I-43 | 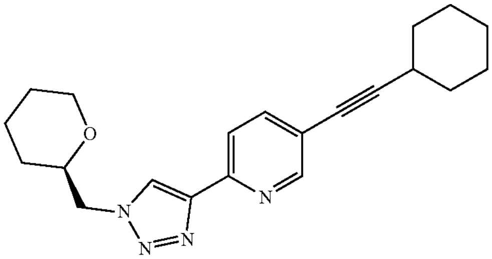 [SMILES: C(#CC1CCCCC1)c1ccc(-c2cn(C[C@H]3CCCCO3)nn2)nc1] |
| I-44 | 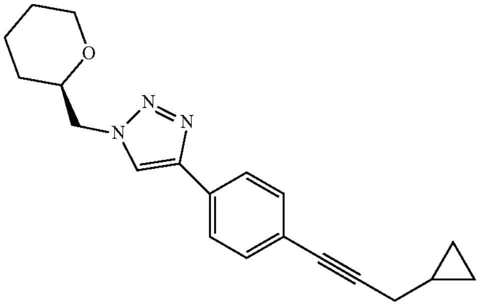 [SMILES: C(#Cc1ccc(-c2cn(C[C@H]3CCCCO3)nn2)cc1)CC1CC1] |
| I-45 | 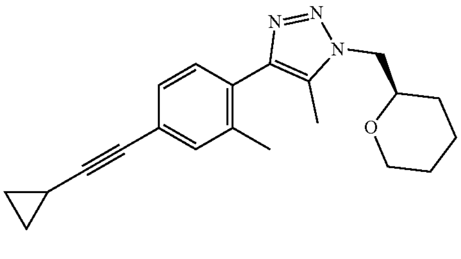 [SMILES: Cc1cc(C#CC2CC2)ccc1-c1nnn(C[C@H]2CCCCO2)c1C] |

TABLE 1-continued
| Selected Compounds | |
|---|---|
| Compound | Structure |
| I-46 | 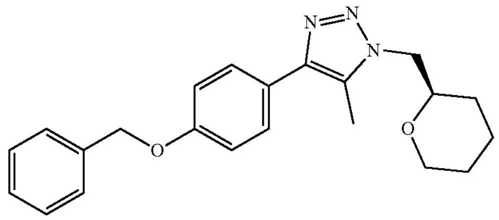 [SMILES: Cc1c(-c2ccc(OCc3ccccc3)cc2)nnn1C[C@H]1CCCCO1] |
| I-47 | 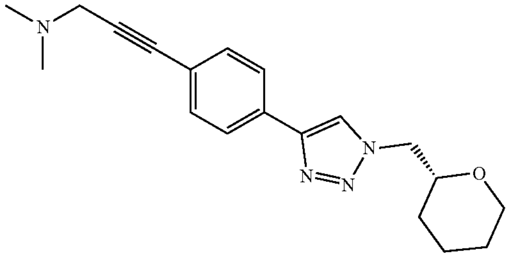 [SMILES: CN(C)CC#Cc1ccc(-c2cn(C[C@H]3CCCCO3)nn2)cc1] |
| I-48 | 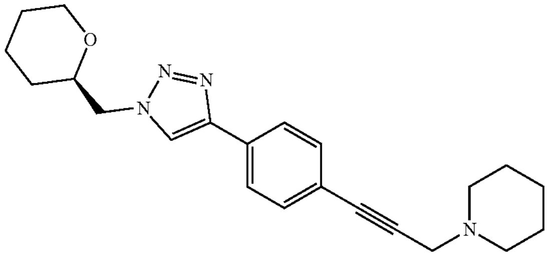 [SMILES: C(#Cc1ccc(-c2cn(C[C@H]3CCCCO3)nn2)cc1)CN1CCCCC1] |
| I-49 | 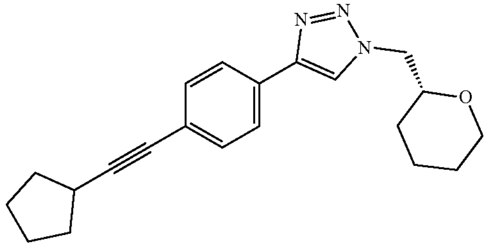 [SMILES: C(#CC1CCCC1)c1ccc(-c2cn(C[C@H]3CCCCO3)nn2)cc1] |
| I-50 | 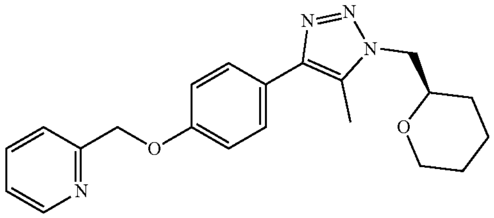 [SMILES: Cc1c(-c2ccc(OCc3ccccn3)cc2)nnn1C[C@H]1CCCCO1] |
| I-51 | 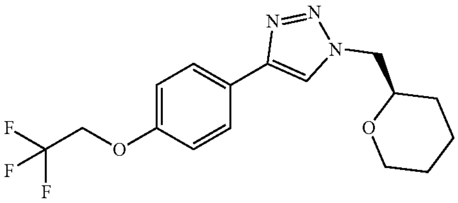 [SMILES: FC(F)(F)COc1ccc(-c2cn(C[C@H]3CCCCO3)nn2)cc1] |

TABLE 1-continued
| Selected Compounds | |
| --- | --- |
| Compound | Structure |
| I-52 | 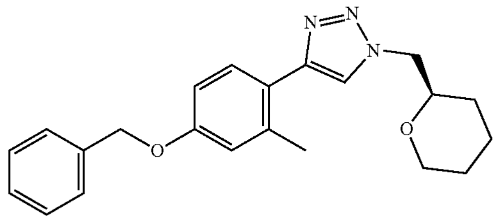 [SMILES: Cc1cc(OCc2ccccc2)ccc1-c1cn(C[C@H]2CCCCO2)nn1] |
| I-53 | 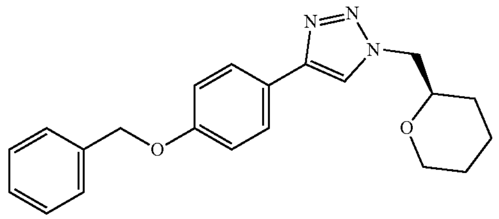 [SMILES: c1ccc(COc2ccc(-c3cn(C[C@H]4CCCCO4)nn3)cc2)cc1] |
| I-54 | 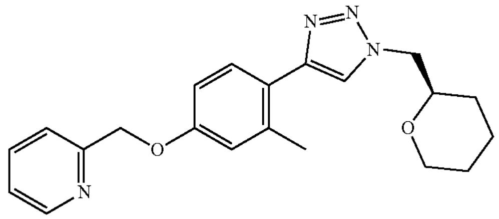 [SMILES: Cc1cc(OCc2ccccn2)ccc1-c1cn(C[C@H]2CCCCO2)nn1] |
| I-55 | 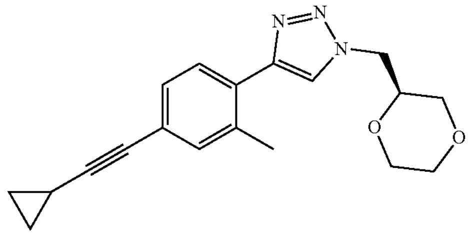 [SMILES: Cc1cc(C#CC2CC2)ccc1-c1cn(C[C@H]2COCCO2)nn1] |
| I-56 | 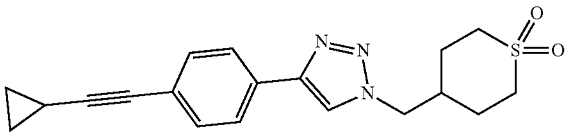 [SMILES: O=S1(=O)CCC(Cn2cc(-c3ccc(C#CC4CC4)cc3)nn2)CC1] |
| I-57 | 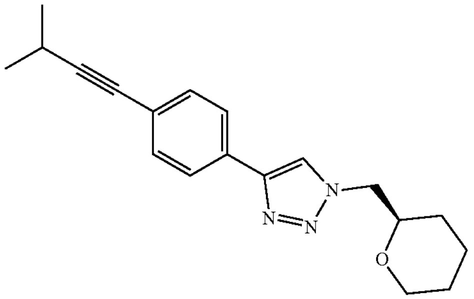 [SMILES: CC(C)C#Cc1ccc(-c2cn(C[C@H]3CCCCO3)nn2)cc1] |
| I-58 | 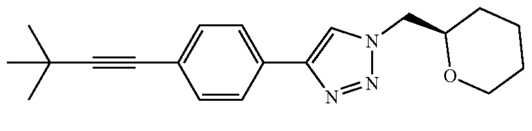 [SMILES: CC(C)(C)C#Cc1ccc(-c2cn(C[C@H]3CCCCO3)nn2)cc1] |

TABLE 1-continued
| Selected Compounds | |
|---|---|
| Compound | Structure |
| I-59 | 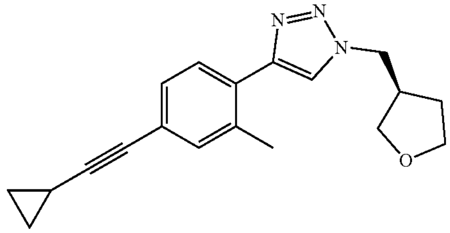 [SMILES: Cc1cc(C#CC2CC2)ccc1-c1cn(C[C@H]2CCOC2)nn1] |
| I-60 | 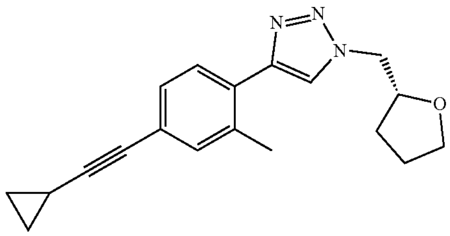 [SMILES: Cc1cc(C#CC2CC2)ccc1-c1cn(C[C@H]2CCCO2)nn1] |
| I-61 | 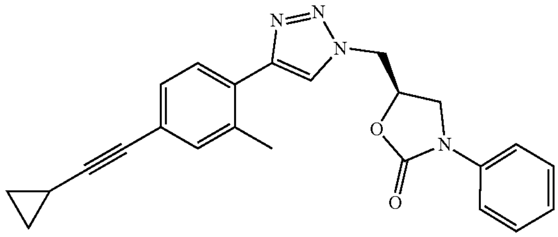 [SMILES: Cc1cc(C#CC2CC2)ccc1-c1cn(C[C@H]2CN(c3ccccc3)C(=O)O2)nn1] |
| I-62 | 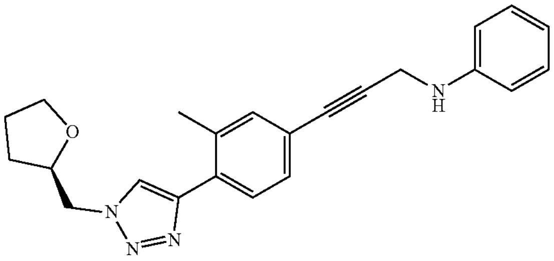 [SMILES: Cc1cc(C#CCNc2ccccc2)ccc1-c1cn(C[C@H]2CCCO2)nn1] |
| I-63 | 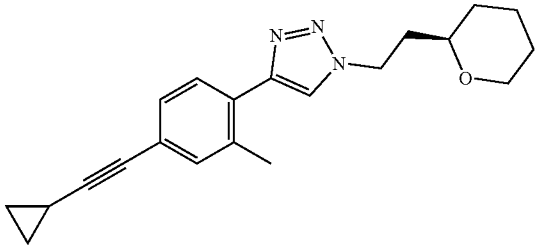 [SMILES: Cc1cc(C#CC2CC2)ccc1-c1cn(CC[C@H]2CCCCO2)nn1] |
| I-64 | 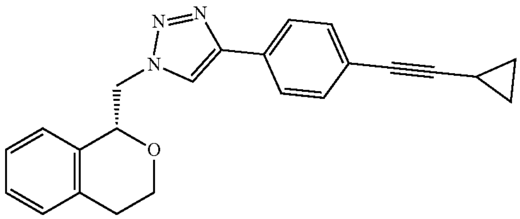 [SMILES: C(#CC1CC1)c1ccc(-c2cn(C[C@@H]3OCCc4ccccc43)nn2)cc1] |

TABLE 1-continued
| Selected Compounds | |
|---|---|
| Compound | Structure |
| I-65 | 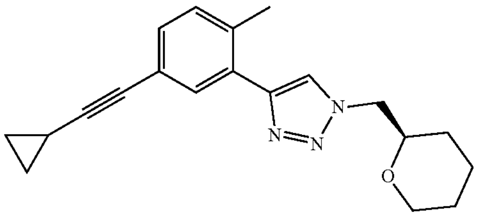 [SMILES: Cc1ccc(C#CC2CC2)cc1-c1cn(C[C@H]2CCCCO2)nn1] |
| I-66 | 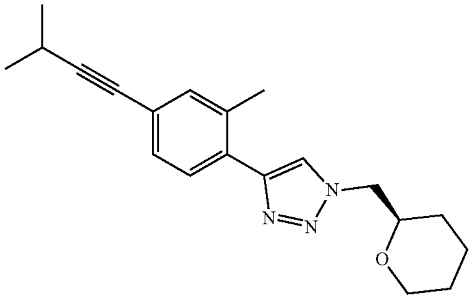 [SMILES: Cc1cc(C#CC(C)C)ccc1-c1cn(C[C@H]2CCCCO2)nn1] |
| I-67 | 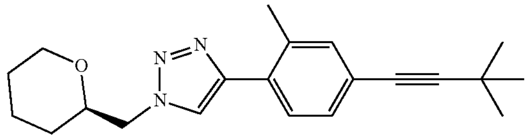 [SMILES: Cc1cc(C#CC(C)(C)C)ccc1-c1cn(C[C@H]2CCCCO2)nn1] |
| I-68 | 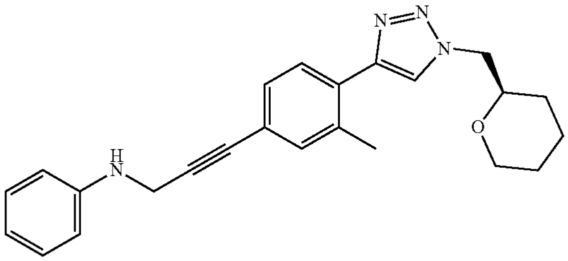 [SMILES: Cc1cc(C#CCNc2ccccc2)ccc1-c1cn(C[C@H]2CCCCO2)nn1] |
| I-69 | 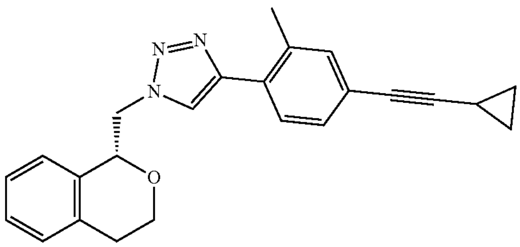 [SMILES: Cc1cc(C#CC2CC2)ccc1-c1cn(C[C@@H]2OCCc3ccccc32)nn1] |
| I-70 | 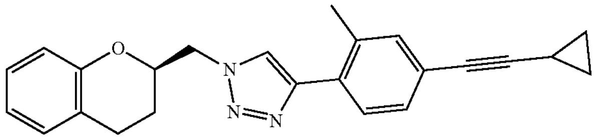 [SMILES: Cc1cc(C#CC2CC2)ccc1-c1cn(C[C@H]2CCc3ccccc3O2)nn1] |

TABLE 1-continued
| Selected Compounds | |
|---|---|
| Compound | Structure |
| I-71 | 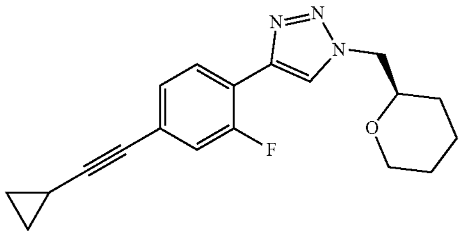 [SMILES: Fc1cc(C#CC2CC2)ccc1-c1cn(C[C@H]2CCCCO2)nn1] |
| I-72 | 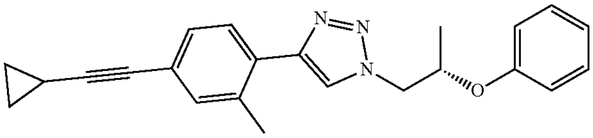 [SMILES: Cc1cc(C#CC2CC2)ccc1-c1cn(C[C@H](C)Oc2ccccc2)nn1] |
| I-73 | 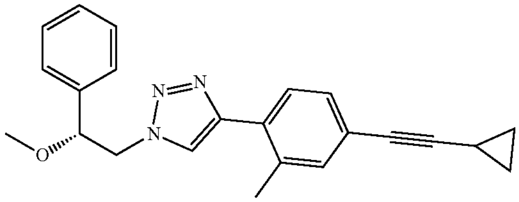 [SMILES: CO[C@@H](Cn1cc(-c2ccc(C#CC3CC3)cc2C)nn1)c1ccccc1] |
| I-74 | 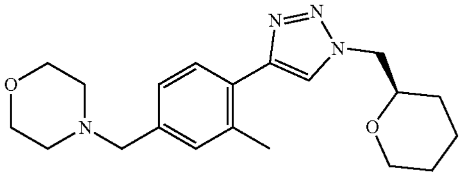 [SMILES: Cc1cc(CN2CCOCC2)ccc1-c1cn(C[C@H]2CCCCO2)nn1] |
| I-75 | 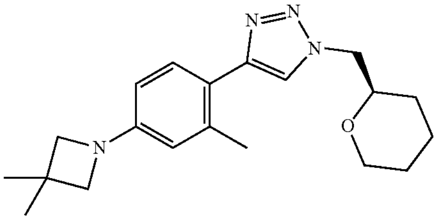 [SMILES: Cc1cc(N2CC(C)(C)C2)ccc1-c1cn(C[C@H]2CCCCO2)nn1] |
| I-76 | 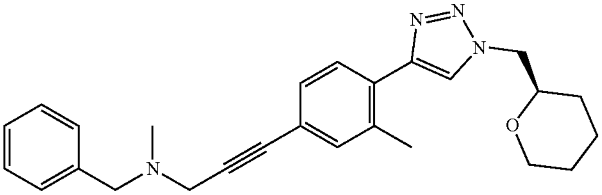 [SMILES: Cc1cc(C#CCN(C)Cc2ccccc2)ccc1-c1cn(C[C@H]2CCCCO2)nn1] |
| I-77 | 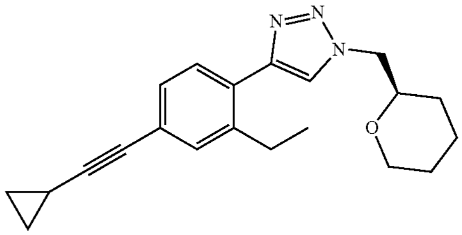 |

TABLE 1-continued
| Selected Compounds | |
| --- | --- |
| Compound | Structure |
| I-78 | 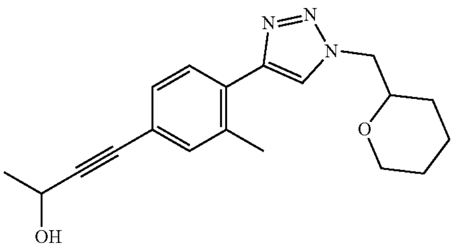 [SMILES: Cc1cc(C#CC(C)O)ccc1-c1cn(CC2CCCCO2)nn1] |
| I-79 | 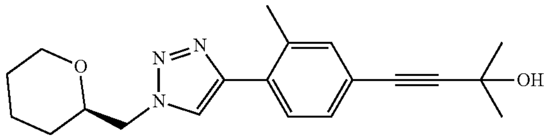 [SMILES: Cc1cc(C#CC(C)(C)O)ccc1-c1cn(C[C@H]2CCCCO2)nn1] |
| I-80 | 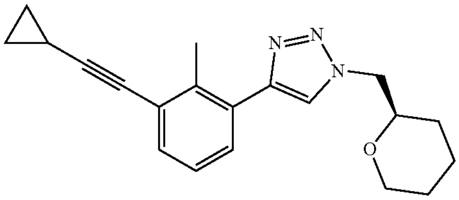 [SMILES: Cc1c(C#CC2CC2)cccc1-c1cn(C[C@H]2CCCCO2)nn1] |
| I-81 | 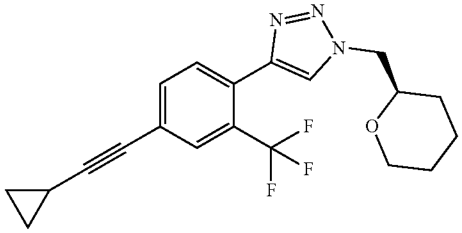 [SMILES: FC(F)(F)c1cc(C#CC2CC2)ccc1-c1cn(C[C@H]2CCCCO2)nn1] |
| I-82 | 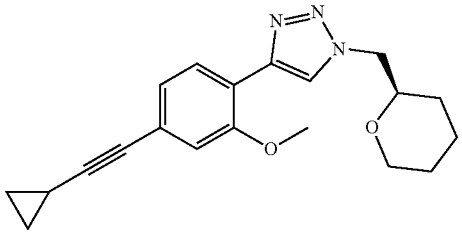 [SMILES: COc1cc(C#CC2CC2)ccc1-c1cn(C[C@H]2CCCCO2)nn1] |
| I-83 | 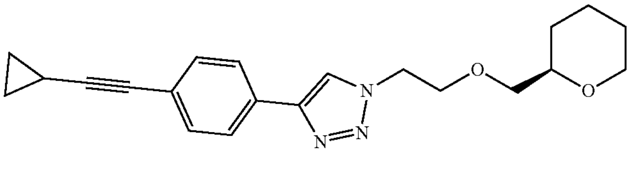 [SMILES: C(#CC1CC1)c1ccc(-c2cn(CCOC[C@H]3CCCCO3)nn2)cc1] |
| I-84 | 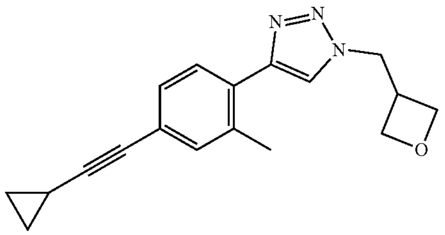 [SMILES: Cc1cc(C#CC2CC2)ccc1-c1cn(CC2COC2)nn1] |

TABLE 1-continued
| Selected Compounds | |
|---|---|
| Compound | Structure |
| I-85 | 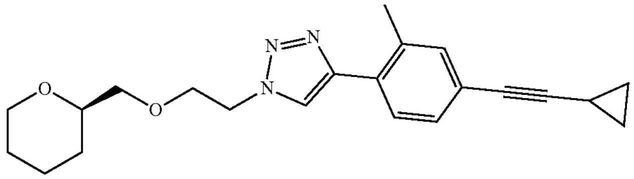 [SMILES: Cc1cc(C#CC2CC2)ccc1-c1cn(CCOC[C@H]2CCCCO2)nn1] |
| I-86 | 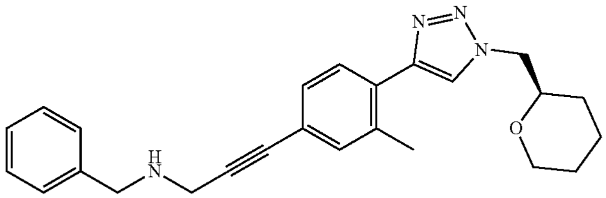 [SMILES: Cc1cc(C#CCNCc2ccccc2)ccc1-c1cn(C[C@H]2CCCCO2)nn1] |
| I-87 | 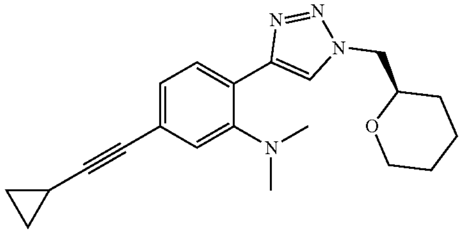 [SMILES: CC(C)c1cc(C#CC2CC2)ccc1-c1cn(C[C@H]2CCCCO2)nn1] |
| I-88 | 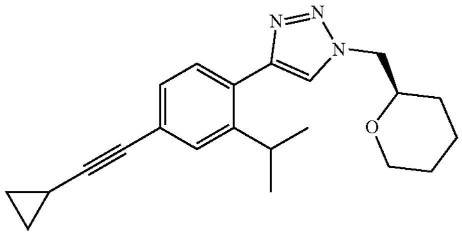 |
| I-89 | 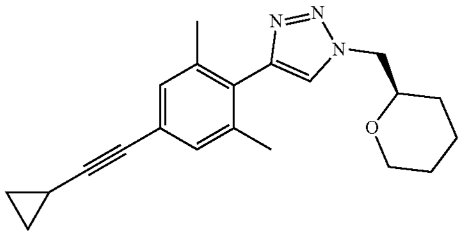 [SMILES: Cc1cc(C#CC2CC2)cc(C)c1-c1cn(C[C@H]2CCCCO2)nn1] |
| I-90 | 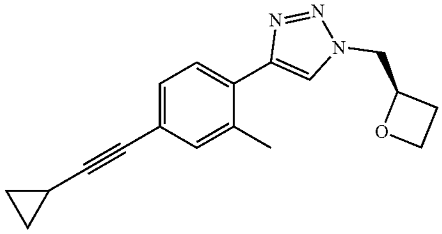 [SMILES: Cc1cc(C#CC2CC2)ccc1-c1cn(C[C@H]2CCO2)nn1] |

TABLE 1-continued
| Selected Compounds | |
|---|---|
| Compound | Structure |
| I-91 | 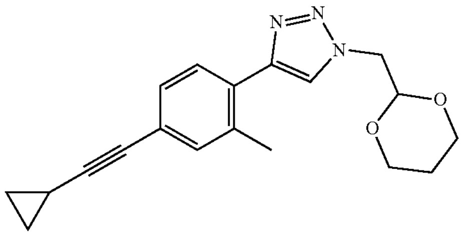 [SMILES: Cc1cc(C#CC2CC2)ccc1-c1cn(CC2OCCCO2)nn1] |
| I-92 | 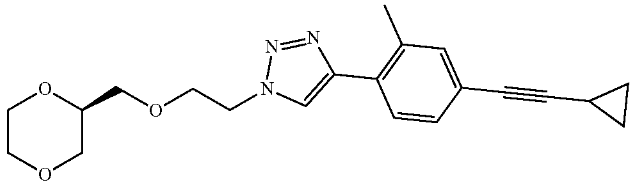 [SMILES: Cc1cc(C#CC2CC2)ccc1-c1cn(CCOC[C@H]2COCCO2)nn1] |
| I-93 | 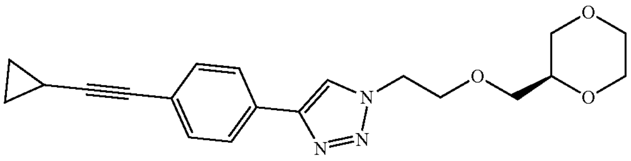 [SMILES: C(#CC1CC1)c1ccc(-c2cn(CCOC[C@H]3COCCO3)nn2)cc1] |
| I-94 | 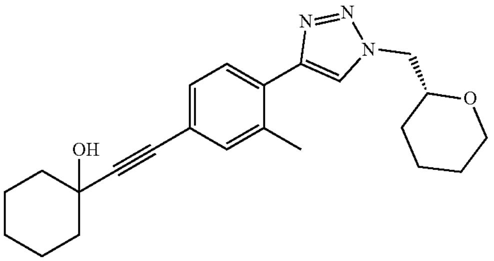 [SMILES: Cc1cc(C#CC2(O)CCCCC2)ccc1-c1cn(C[C@H]2CCCCO2)nn1] |
| I-95 | 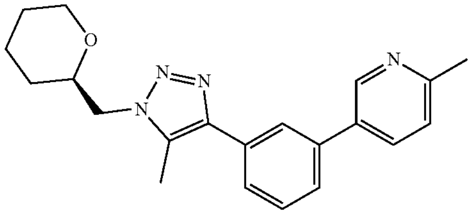 [SMILES: Cc1ccc(-c2cccc(-c3nnn(C[C@H]4CCCCO4)c3C)c2)cn1] |
| I-96 | 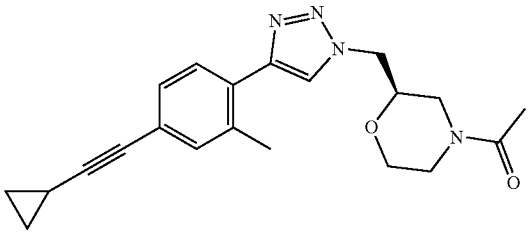 [SMILES: CC(=O)N1CCO[C@@H](Cn2cc(-c3ccc(C#CC4CC4)cc3C)nn2)C1] |
| I-97 | 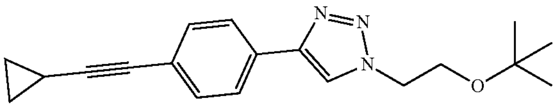 [SMILES: CC(C)(C)OCCn1cc(-c2ccc(C#CC3CC3)cc2)nn1] |

TABLE 1-continued
| Selected Compounds | |
|---|---|
| Compound | Structure |
| I-98 | 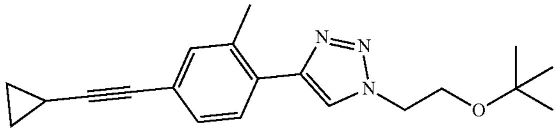 [SMILES: Cc1cc(C#CC2CC2)ccc1-c1cn(CCOC(C)(C)C)nn1] |
| I-99 | 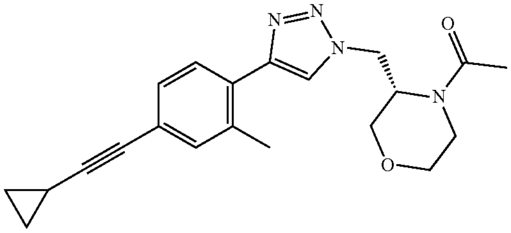 [SMILES: CC(=O)N1CCOC[C@@H]1Cn1cc(-c2ccc(C#CC3CC3)cc2C)nn1] |
| I-100 | 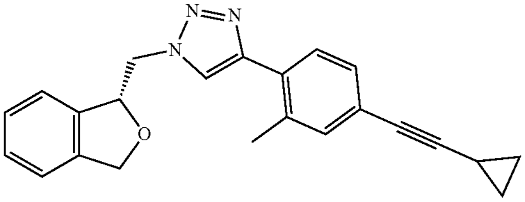 [SMILES: Cc1cc(C#CC2CC2)ccc1-c1cn(C[C@@H]2OCc3ccccc32)nn1] |
| I-101 | 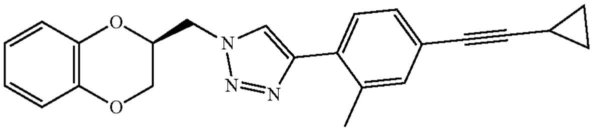 [SMILES: Cc1cc(C#CC2CC2)ccc1-c1cn(C[C@H]2COc3ccccc3O2)nn1] |
| I-102 | 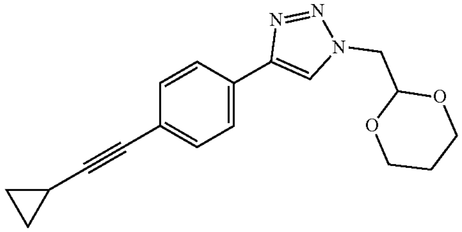 [SMILES: C(#CC1CC1)c1ccc(-c2cn(CC3OCCCO3)nn2)cc1] |
| I-103 | 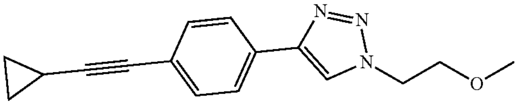 [SMILES: COCCn1cc(-c2ccc(C#CC3CC3)cc2)nn1] |
| I-104 | 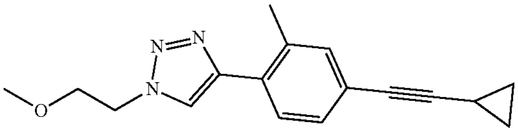 [SMILES: COCCn1cc(-c2ccc(C#CC3CC3)cc2C)nn1] |
| I-105 | 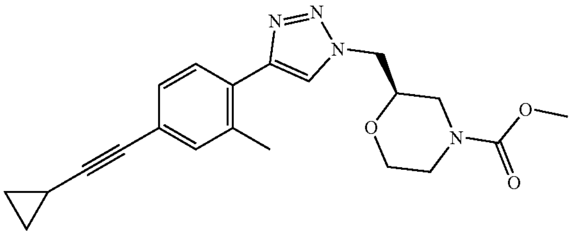 [SMILES: COC(=O)N1CCO[C@@H](Cn2cc(-c3ccc(C#CC4CC4)cc3C)nn2)C1] |

TABLE 1-continued
| Selected Compounds | |
|---|---|
| Compound | Structure |
| I-106 | 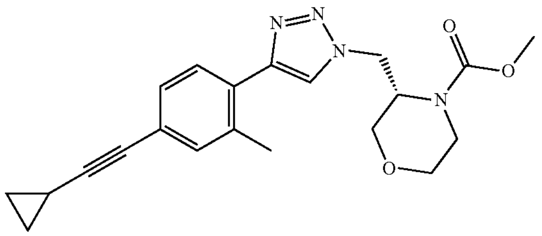 [SMILES: COC(=O)N1CCOC[C@@H]1Cn1cc(-c2ccc(C#CC3CC3)cc2C)nn1] |
| I-107 | 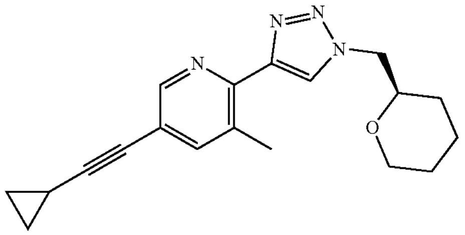 [SMILES: Cc1cc(C#CC2CC2)cnc1-c1cn(C[C@H]2CCCCO2)nn1] |
| I-108 | 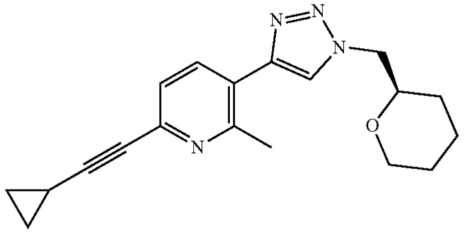 [SMILES: Cc1nc(C#CC2CC2)ccc1-c1cn(C[C@H]2CCCCO2)nn1] |
| I-109 | 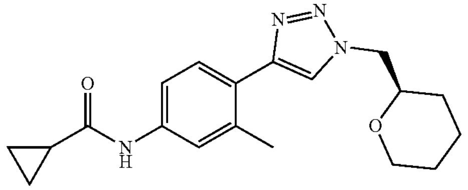 [SMILES: Cc1cc(NC(=O)C2CC2)ccc1-c1cn(C[C@H]2CCCCO2)nn1] |
| I-110 | 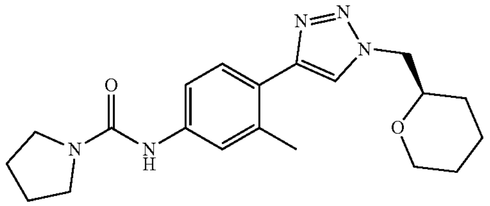 [SMILES: Cc1cc(NC(=O)N2CCCC2)ccc1-c1cn(C[C@H]2CCCCO2)nn1] |
| I-111 | 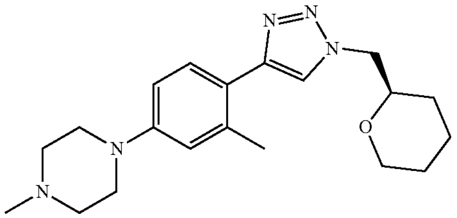 [SMILES: Cc1cc(N2CCN(C)CC2)ccc1-c1cn(C[C@H]2CCCCO2)nn1] |

TABLE 1-continued
| Selected Compounds | |
|---|---|
| Compound | Structure |
| I-112 | 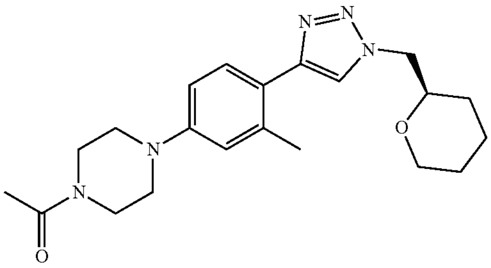 [SMILES: CC(=O)N1CCN(c2ccc(-c3cn(C[C@H]4CCCCO4)nn3)c(C)c2)CC1] |
| I-113 | 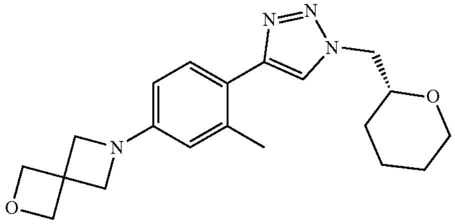 [SMILES: Cc1cc(N2CC3(COC3)C2)ccc1-c1cn(C[C@H]2CCCCO2)nn1] |
| I-114 | 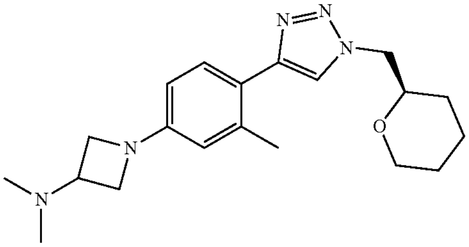 [SMILES: Cc1cc(N2CC(N(C)C)C2)ccc1-c1cn(C[C@H]2CCCCO2)nn1] |
| I-115 | 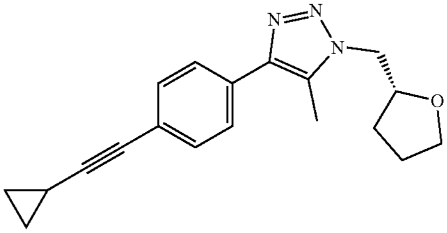 [SMILES: Cc1c(-c2ccc(C#CC3CC3)cc2)nnn1C[C@H]1CCCO1] |
| I-116 | 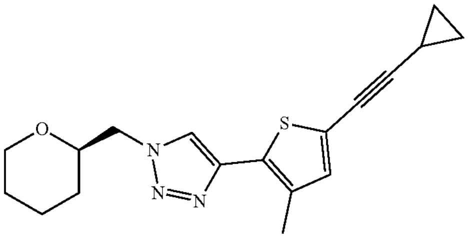 [SMILES: Cc1cc(C#CC2CC2)sc1-c1cn(C[C@H]2CCCCO2)nn1] |
| I-117 | 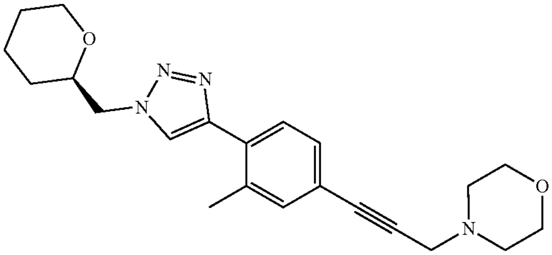 [SMILES: Cc1cc(C#CCN2CCOCC2)ccc1-c1cn(C[C@H]2CCCCO2)nn1] |

TABLE 1-continued
| Selected Compounds | |
|---|---|
| Compound | Structure |
| I-118 | 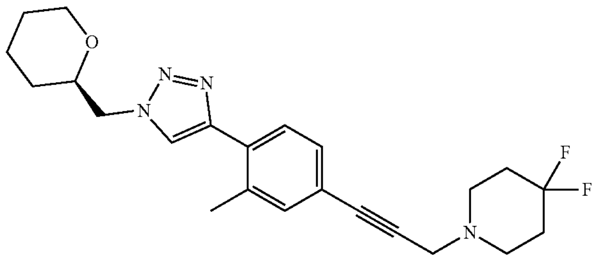 [SMILES: Cc1cc(C#CCN2CCC(F)(F)CC2)ccc1-c1cn(C[C@H]2CCCCO2)nn1] |
| I-119 | 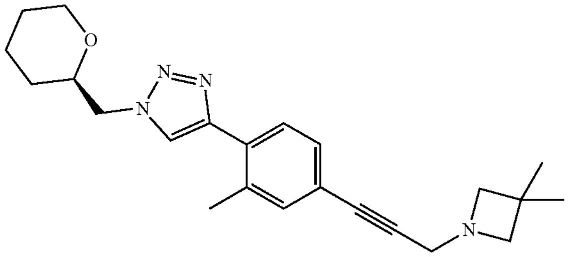 [SMILES: Cc1cc(C#CCN2CC(C)(C)C2)ccc1-c1cn(C[C@H]2CCCCO2)nn1] |
| I-120 | 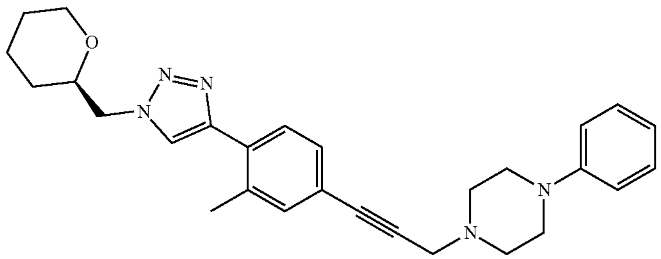 [SMILES: Cc1cc(C#CCN2CCN(c3ccccc3)CC2)ccc1-c1cn(C[C@H]2CCCCO2)nn1] |
| I-121 | 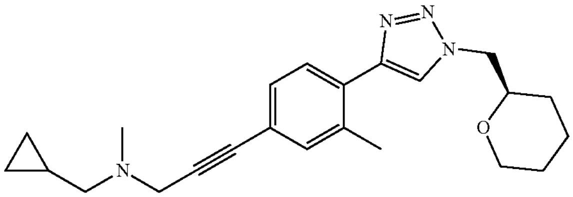 [SMILES: Cc1cc(C#CCN(C)CC2CC2)ccc1-c1cn(C[C@H]2CCCCO2)nn1] |
| I-122 | 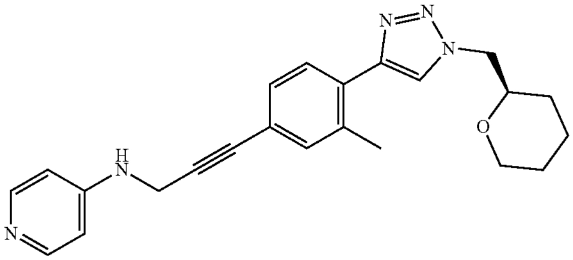 [SMILES: Cc1cc(C#CCNc2ccncc2)ccc1-c1cn(C[C@H]2CCCCO2)nn1] |
| I-123 | 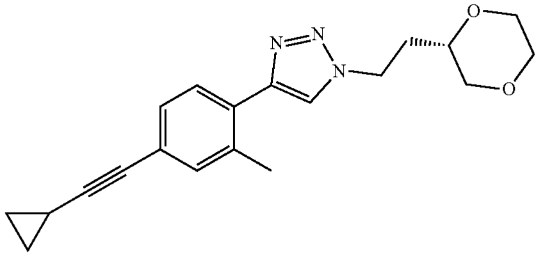 [SMILES: Cc1cc(C#CC2CC2)ccc1-c1cn(CC[C@H]2COCCO2)nn1] |

TABLE 1-continued
| Selected Compounds | |
|---|---|
| Compound | Structure |
| I-124 | 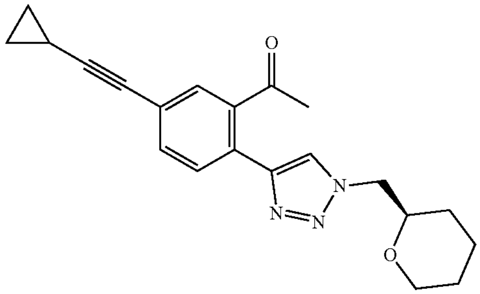 [SMILES: CC(=O)c1cc(C#CC2CC2)ccc1-c1cn(C[C@H]2CCCCO2)nn1] |
| I-125 | 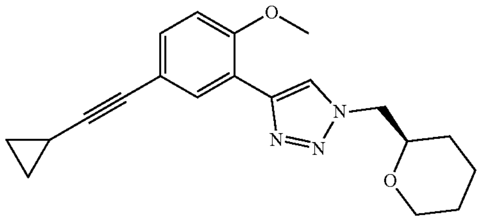 [SMILES: COc1ccc(C#CC2CC2)cc1-c1cn(C[C@H]2CCCCO2)nn1] |
| I-126 | 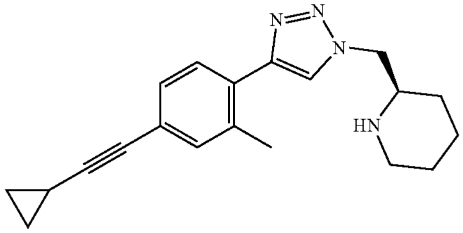 [SMILES: Cc1cc(C#CC2CC2)ccc1-c1cn(C[C@H]2CCCCN2)nn1] |
| I-127 | 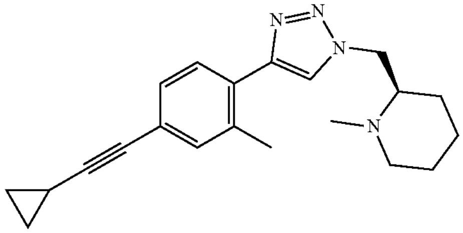 [SMILES: Cc1cc(C#CC2CC2)ccc1-c1cn(C[C@H]2CCCCN2C)nn1] |
| I-128 | 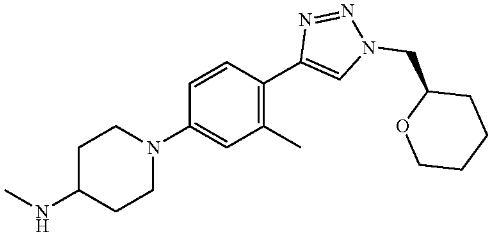 [SMILES: CNC1CCN(c2ccc(-c3cn(C[C@H]4CCCCO4)nn3)c(C)c2)CC1] |
| I-129 | 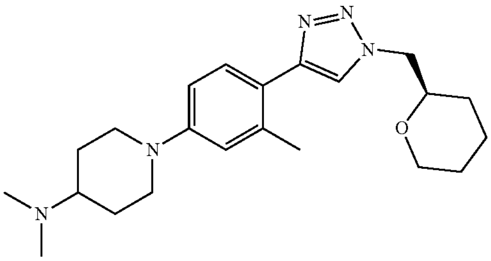 [SMILES: Cc1cc(N2CCC(N(C)C)CC2)ccc1-c1cn(C[C@H]2CCCCO2)nn1] |

TABLE 1-continued
| Selected Compounds | |
|---|---|
| Compound | Structure |
| I-130 | 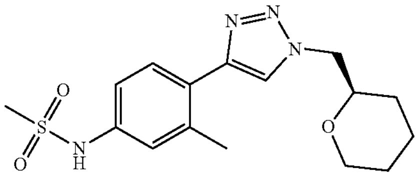 [SMILES: Cc1cc(NS(C)(=O)=O)ccc1-c1cn(C[C@H]2CCCCO2)nn1] |
| I-131 | 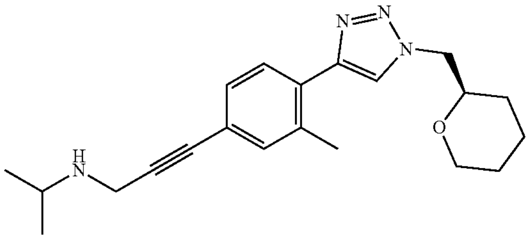 [SMILES: Cc1cc(C#CCNC(C)C)ccc1-c1cn(C[C@H]2CCCCO2)nn1] |
| I-132 | 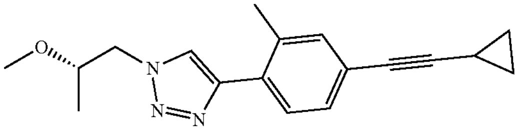 [SMILES: CO[C@@H](C)Cn1cc(-c2ccc(C#CC3CC3)cc2C)nn1] |
| I-133 | 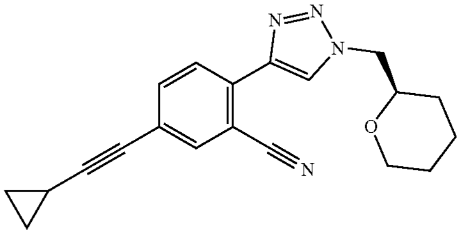 [SMILES: N#Cc1cc(C#CC2CC2)ccc1-c1cn(C[C@H]2CCCCO2)nn1] |
| I-134 | 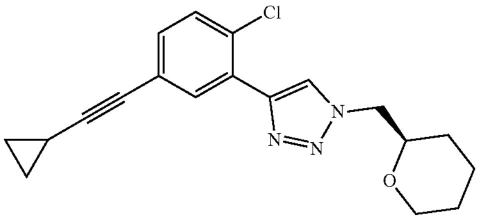 [SMILES: Clc1ccc(C#CC2CC2)cc1-c1cn(C[C@H]2CCCCO2)nn1] |
| I-135 | 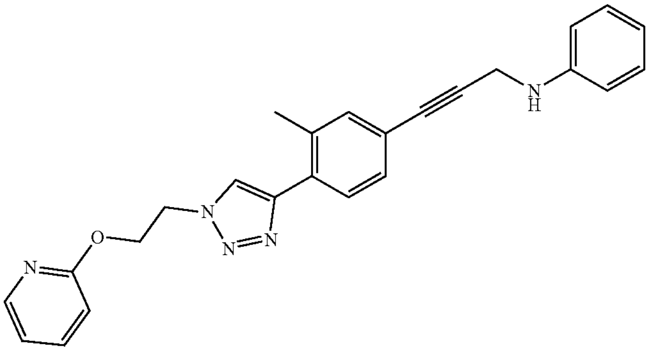 [SMILES: Cc1cc(C#CCNc2ccccc2)ccc1-c1cn(CCOc2ccccn2)nn1] |

TABLE 1-continued
| Selected Compounds | |
| --- | --- |
| Compound | Structure |
| I-136 | 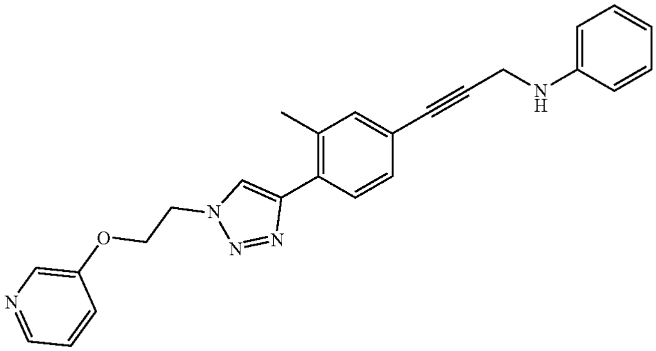 [SMILES: Cc1cc(C#CCNc2ccccc2)ccc1-c1cn(CCOc2cccnc2)nn1] |
| I-137 | 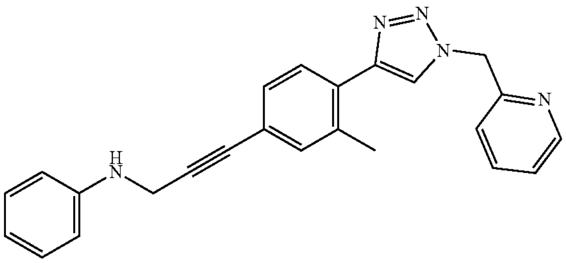 [SMILES: Cc1cc(C#CCNc2ccccc2)ccc1-c1cn(Cc2ccccn2)nn1] |
| I-138 | 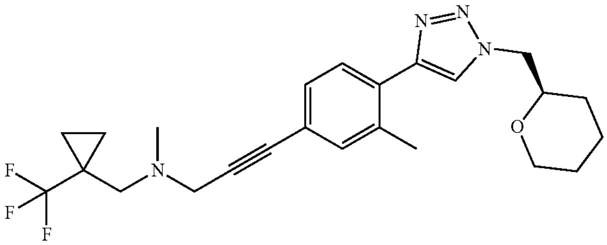 [SMILES: Cc1cc(C#CCN(C)CC2(C(F)(F)F)CC2)ccc1-c1cn(C[C@H]2CCCCO2)nn1] |
| I-139 | 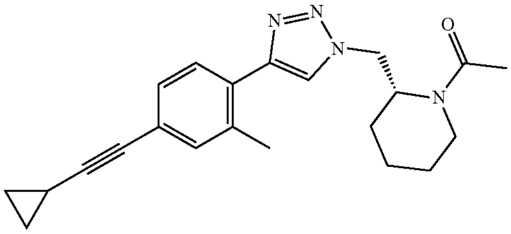 |
| I-140 | 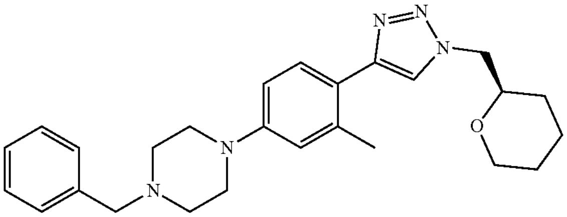 [SMILES: Cc1cc(N2CCN(Cc3ccccc3)CC2)ccc1-c1cn(C[C@H]2CCCCO2)nn1] |

TABLE 1-continued
| Selected Compounds | |
|---|---|
| Compound | Structure |
| I-141 | 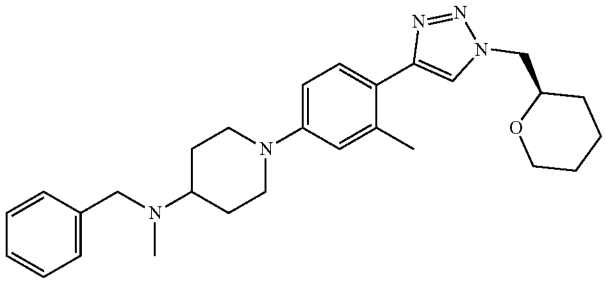 [SMILES: Cc1cc(N2CCC(N(C)Cc3ccccc3)CC2)ccc1-c1cn(C[C@H]2CCCCO2)nn1] |
| I-142 | 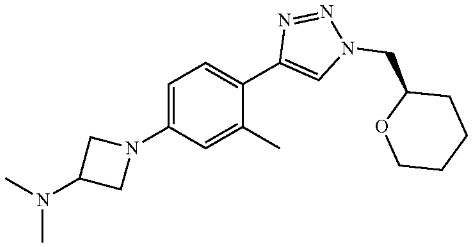 [SMILES: Cc1cc(N2CC(N(C)C)C2)ccc1-c1cn(C[C@H]2CCCCO2)nn1] |
| I-143 | 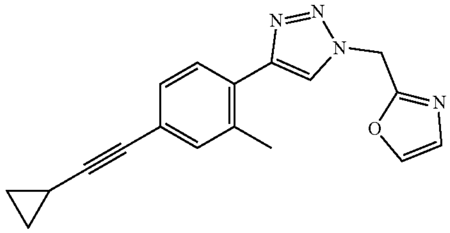 [SMILES: Cc1cc(C#CC2CC2)ccc1-c1cn(Cc2ncco2)nn1] |
| I-144 | 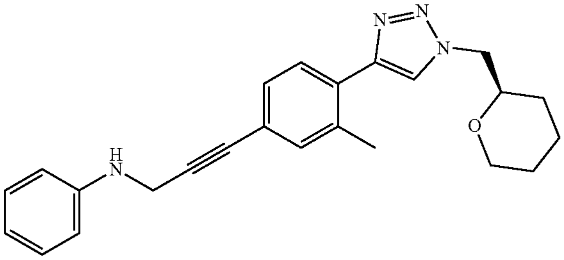 [SMILES: Cc1cc(C#CCNc2ccccc2)ccc1-c1cn(C[C@H]2CCCCO2)nn1] |
| I-145 | 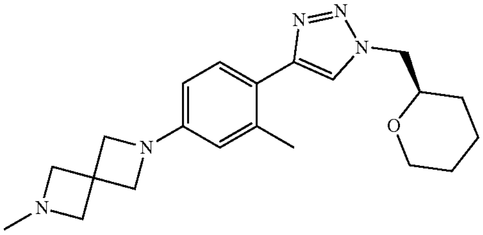 [SMILES: Cc1cc(N2CC3(CN(C)C3)C2)ccc1-c1cn(C[C@H]2CCCCO2)nn1] |
| I-146 | 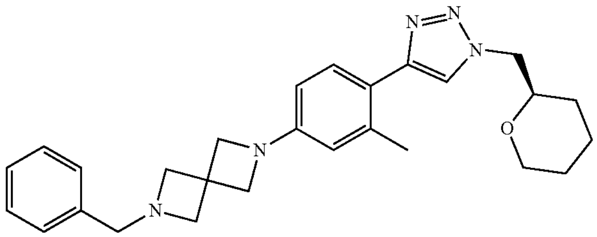 [SMILES: Cc1cc(N2CC3(CN(Cc4ccccc4)C3)C2)ccc1-c1cn(C[C@H]2CCCCO2)nn1] |

TABLE 1-continued
| Selected Compounds | |
|---|---|
| Compound | Structure |
| I-147 | 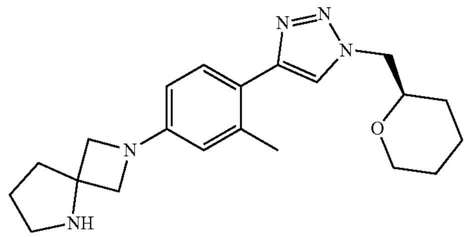 [SMILES: Cc1cc(N2CC3(CCCN3)C2)ccc1-c1cn(C[C@H]2CCCCO2)nn1] |
| I-148 | 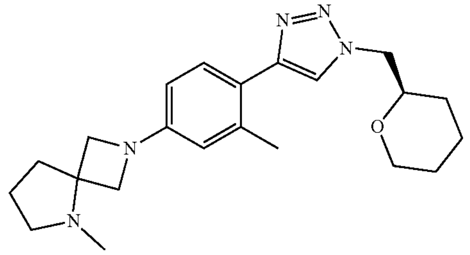 [SMILES: Cc1cc(N2CC3(CCCN3C)C2)ccc1-c1cn(C[C@H]2CCCCO2)nn1] |
| I-149 | 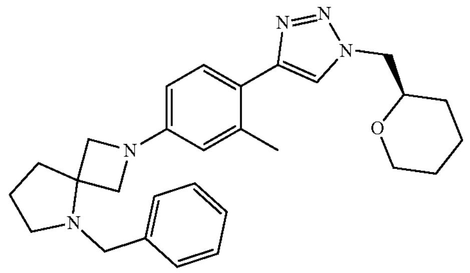 [SMILES: Cc1cc(N2CC3(CCCN3Cc3ccccc3)C2)ccc1-c1cn(C[C@H]2CCCCO2)nn1] |
| I-150 | 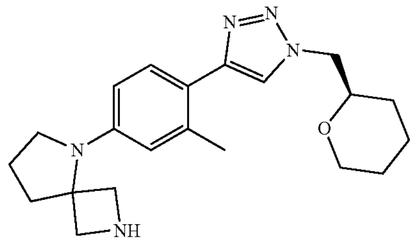 [SMILES: Cc1cc(N2CCCC23CNC3)ccc1-c1cn(C[C@H]2CCCCO2)nn1] |
| I-151 | 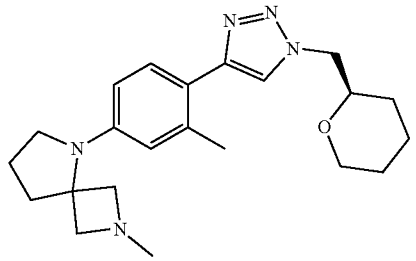 [SMILES: Cc1cc(N2CCCC23CN(C)C3)ccc1-c1cn(C[C@H]2CCCCO2)nn1] |

TABLE 1-continued
Selected Compounds
| Compound | Structure |
| --- | --- |
| I-152 | 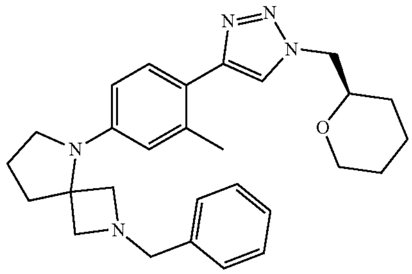 [SMILES: Cc1cc(N2CCCC23CN(Cc2ccccc2)C3)ccc1-c1cn(C[C@H]2CCCCO2)nn1] |
| I-153 | 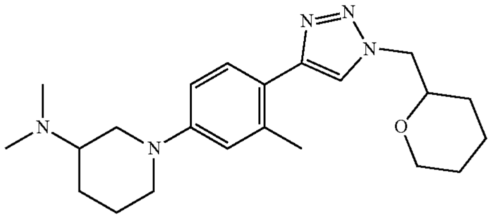 [SMILES: Cc1cc(N2CCCC(N(C)C)C2)ccc1-c1cn(CC2CCCCO2)nn1] |
| I-154 | 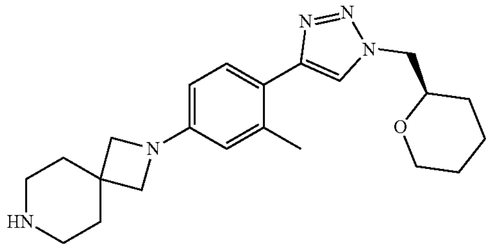 [SMILES: Cc1cc(N2CC3(CCNCC3)C2)ccc1-c1cn(C[C@H]2CCCCO2)nn1] |
| I-155 | 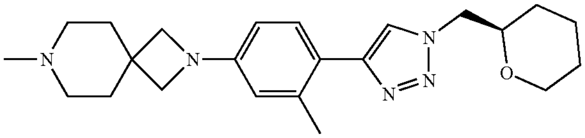 [SMILES: Cc1cc(N2CC3(CCN(C)CC3)C2)ccc1-c1cn(C[C@H]2CCCCO2)nn1] |
| I-156 | 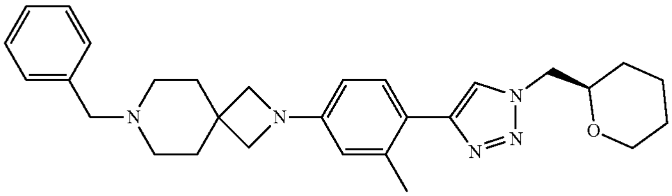 [SMILES: Cc1cc(N2CC3(CCN(Cc4ccccc4)CC3)C2)ccc1-c1cn(C[C@H]2CCCCO2)nn1] |
| I-157 | 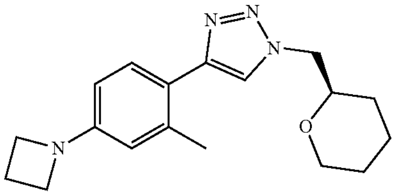 [SMILES: Cc1cc(N2CCC2)ccc1-c1cn(C[C@H]2CCCCO2)nn1] |
| I-158 | 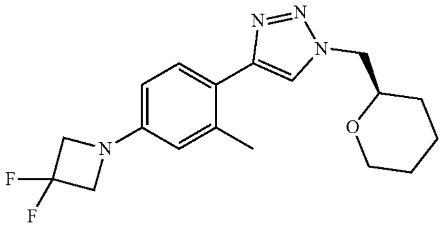 [SMILES: Cc1cc(N2CC(F)(F)C2)ccc1-c1cn(C[C@H]2CCCCO2)nn1] |

TABLE 1-continued
| Selected Compounds | |
|---|---|
| Compound | Structure |
| I-159 | 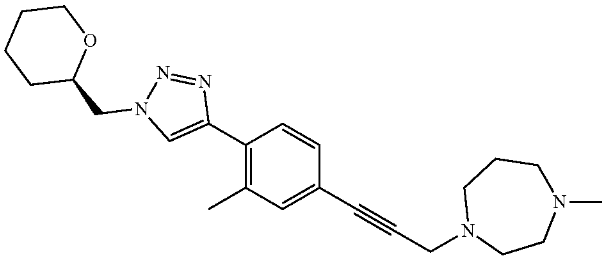 [SMILES: Cc1cc(C#CCN2CCCN(C)CC2)ccc1-c1cn(C[C@H]2CCCCO2)nn1] |
| I-160 | 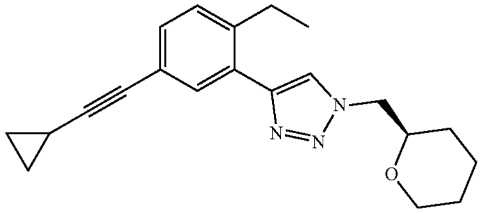 [SMILES: CCc1ccc(C#CC2CC2)cc1-c1cn(C[C@H]2CCCCO2)nn1] |
| I-161 | 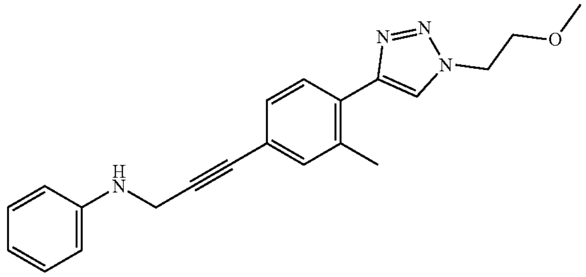 [SMILES: COCCn1cc(-c2ccc(C#CCNc3ccccc3)cc2C)nn1] |
| I-162 | 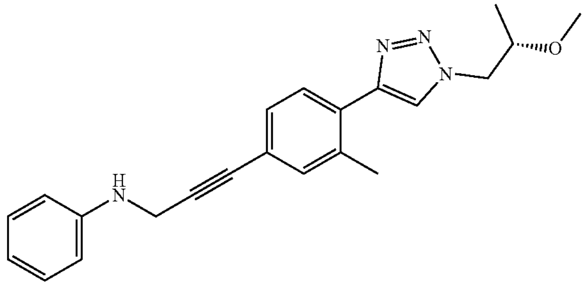 [SMILES: CO[C@@H](C)Cn1cc(-c2ccc(C#CCNc3ccccc3)cc2C)nn1] |
| I-163 | 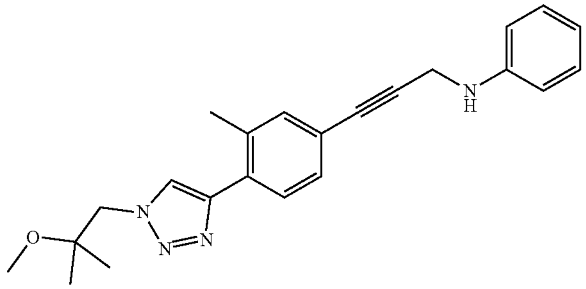 [SMILES: COC(C)(C)Cn1cc(-c2ccc(C#CCNc3ccccc3)cc2C)nn1] |

TABLE 1-continued
| Selected Compounds | |
|---|---|
| Compound | Structure |
| I-164 | 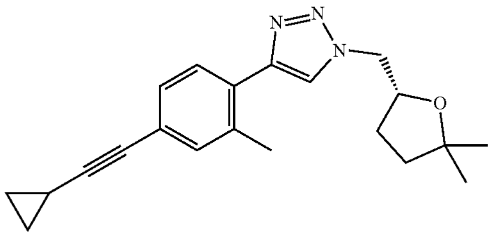 [SMILES: Cc1cc(C#CC2CC2)ccc1-c1cn(C[C@H]2CCC(C)(C)O2)nn1] |
| I-165 | 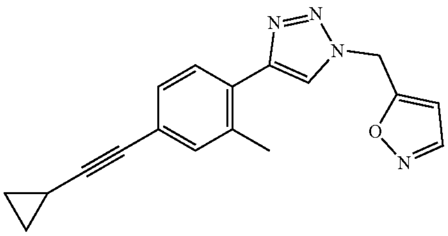 [SMILES: Cc1cc(C#CC2CC2)ccc1-c1cn(Cc2ccno2)nn1] |
| I-166 | 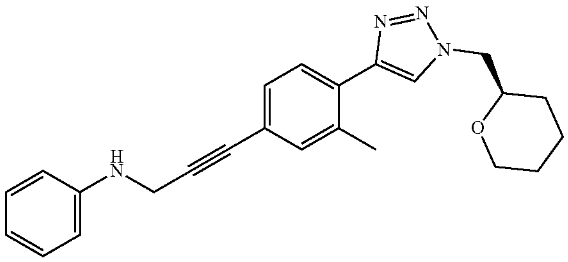 [SMILES: Cc1cc(C#CCNc2ccccc2)ccc1-c1cn(C[C@H]2CCCCO2)nn1] |
| I-167 | 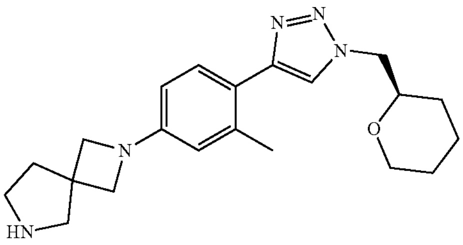 [SMILES: Cc1cc(N2CC3(CCNC3)C2)ccc1-c1cn(C[C@H]2CCCCO2)nn1] |
| I-168 | 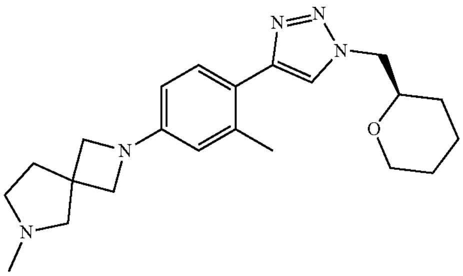 [SMILES: Cc1cc(N2CC3(CCN(C)C3)C2)ccc1-c1cn(C[C@H]2CCCCO2)nn1] |

TABLE 1-continued
| Selected Compounds | |
|---|---|
| Compound | Structure |
| I-169 | 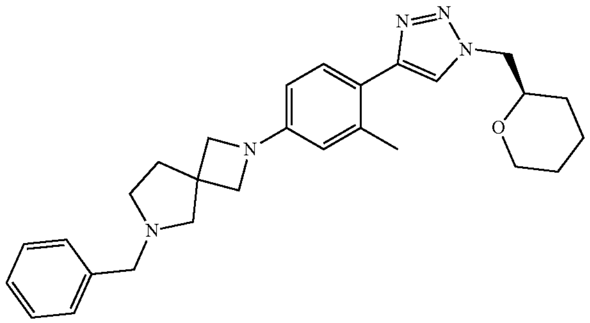 [SMILES: Cc1cc(N2CC3(CCN(Cc4ccccc4)C3)C2)ccc1-c1cn(C[C@H]2CCCCO2)nn1] |
| I-170 | 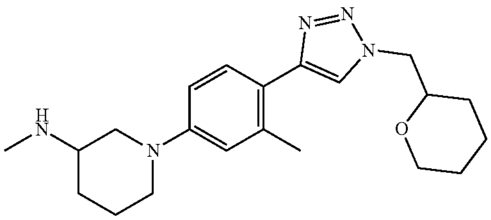 [SMILES: CNC1CCCN(c2ccc(-c3cn(CC4CCCCO4)nn3)c(C)c2)C1] |
| I-171 | 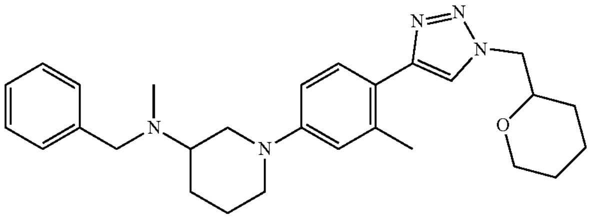 [SMILES: Cc1cc(N2CCCC(N(C)Cc3ccccc3)C2)ccc1-c1cn(CC2CCCCO2)nn1] |
| I-172 | 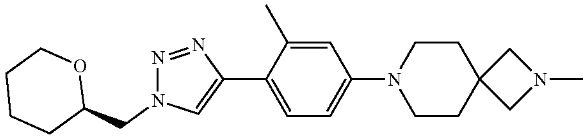 [SMILES: Cc1cc(N2CCC3(CC2)CN(C)C3)ccc1-c1cn(C[C@H]2CCCCO2)nn1] |
| I-173 | 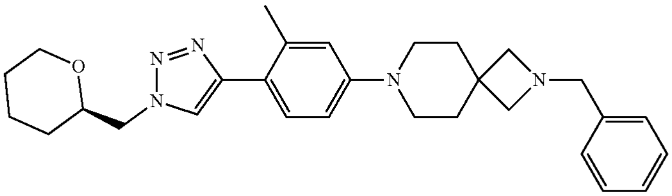 [SMILES: Cc1cc(N2CCC3(CC2)CN(Cc2ccccc2)C3)ccc1-c1cn(C[C@H]2CCCCO2)nn1] |
| I-174 | 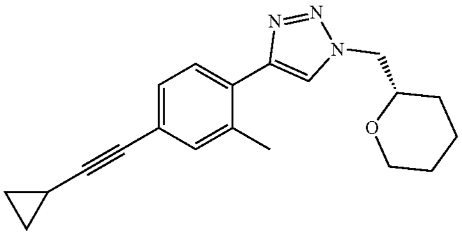 [SMILES: Cc1cc(C#CC2CC2)ccc1-c1cn(C[C@@H]2CCCCO2)nn1] |

TABLE 1-continued
| Selected Compounds | |
|---|---|
| Compound | Structure |
| I-175 | 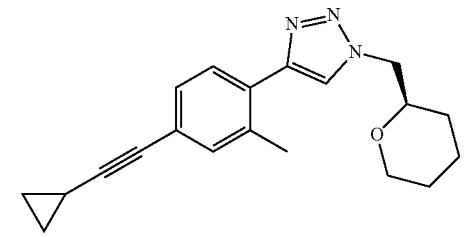 [SMILES: Cc1cc(C#CC2CC2)ccc1-c1cn(C[C@H]2CCCCO2)nn1] |
| I-176 | 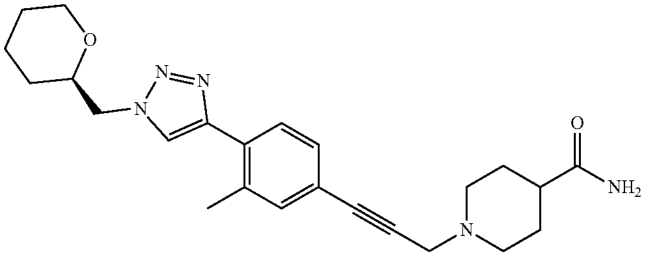 [SMILES: Cc1cc(C#CCN2CCC(C(N)=O)CC2)ccc1-c1cn(C[C@H]2CCCCO2)nn1] |
| I-177 | 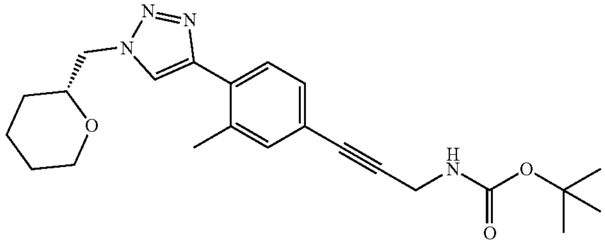 [SMILES: Cc1cc(C#CCNC(=O)OC(C)(C)C)ccc1-c1cn(C[C@H]2CCCCO2)nn1] |
| I-178 | 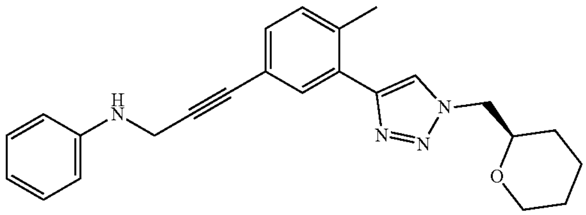 [SMILES: Cc1ccc(C#CCNc2ccccc2)cc1-c1cn(C[C@H]2CCCCO2)nn1] |
| I-179 | 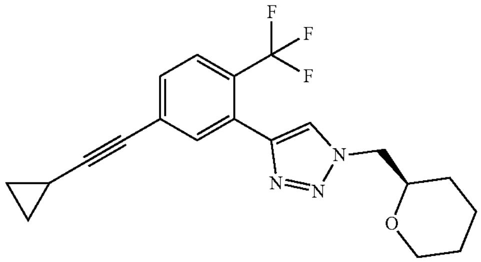 [SMILES: FC(F)(F)c1ccc(C#CC2CC2)cc1-c1cn(C[C@H]2CCCCO2)nn1] |
| I-180 | 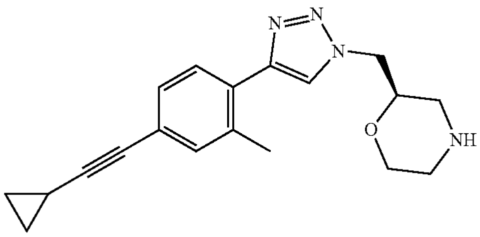 [SMILES: Cc1cc(C#CC2CC2)ccc1-c1cn(C[C@H]2CNCCO2)nn1] |

TABLE 1-continued
| Selected Compounds | |
|---|---|
| Compound | Structure |
| I-181 | 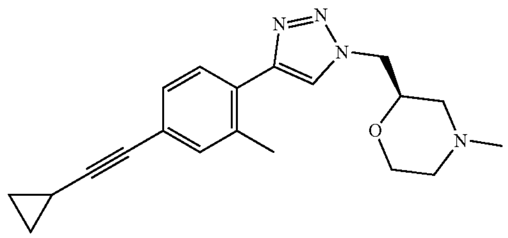 [SMILES: Cc1cc(C#CC2CC2)ccc1-c1cn(C[C@H]2CN(C)CCO2)nn1] |
| I-182 | 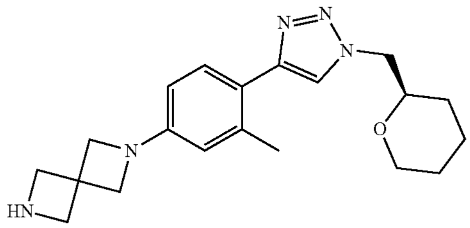 [SMILES: Cc1cc(N2CC3(CNC3)C2)ccc1-c1cn(C[C@H]2CCCCO2)nn1] |
| I-183 | 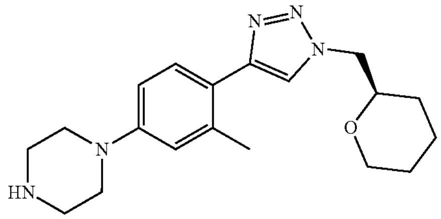 [SMILES: Cc1cc(N2CCNCC2)ccc1-c1cn(C[C@H]2CCCCO2)nn1] |
| I-184 | 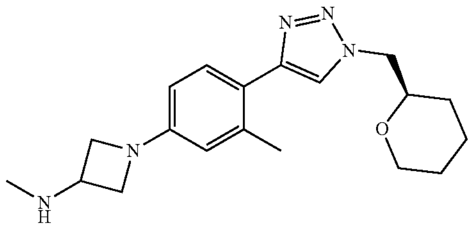 [SMILES: CNC1CN(c2ccc(-c3cn(C[C@H]4CCCCO4)nn3)c(C)c2)C1] |
| I-185 | 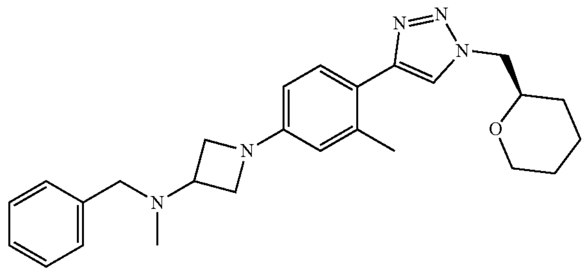 [SMILES: Cc1cc(N2CC(N(C)Cc3ccccc3)C2)ccc1-c1cn(C[C@H]2CCCCO2)nn1] |
| I-186 | 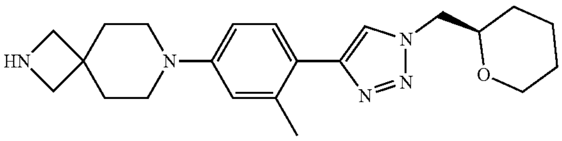 [SMILES: Cc1cc(N2CCC3(CC2)CNC3)ccc1-c1cn(C[C@H]2CCCCO2)nn1] |

TABLE 1-continued
| Selected Compounds | |
|---|---|
| Compound | Structure |
| I-187 | 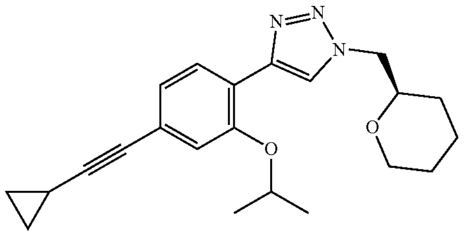 [SMILES: CC(C)Oc1cc(C#CC2CC2)ccc1-c1cn(C[C@H]2CCCCO2)nn1] |
| I-188 | 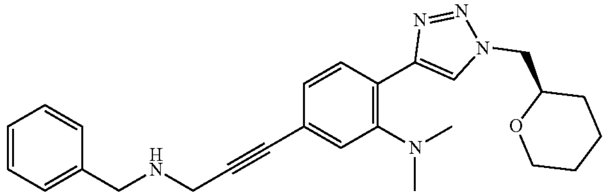 [SMILES: CN(C)c1cc(C#CCNCc2ccccc2)ccc1-c1cn(C[C@H]2CCCCO2)nn1] |
| I-189 | 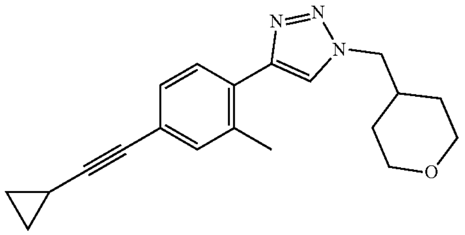 [SMILES: Cc1cc(C#CC2CC2)ccc1-c1cn(CC2CCOCC2)nn1] |
| I-190 | 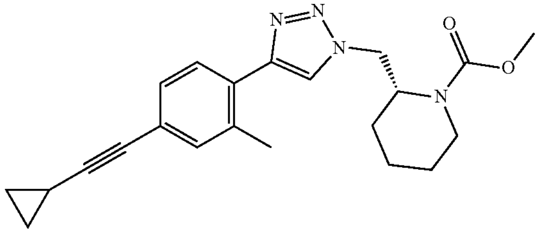 [SMILES: COC(=O)N1CCCC[C@@H]1Cn1cc(-c2ccc(C#CC3CC3)cc2C)nn1] |
| I-191 | 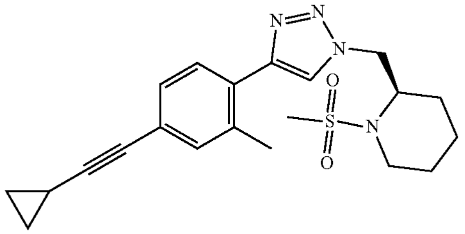 [SMILES: Cc1cc(C#CC2CC2)ccc1-c1cn(C[C@H]2CCCCN2S(C)(=O)=O)nn1] |

TABLE 1-continued
| Selected Compounds | |
|---|---|
| Compound | Structure |
| I-192 | 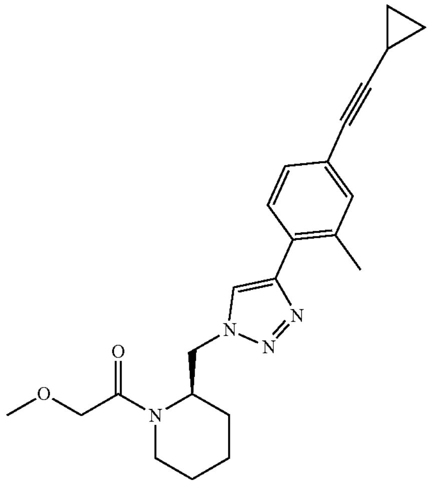 [SMILES: COCC(=O)N1CCCC[C@@H]1Cn1cc(-c2ccc(C#CC3CC3)cc2C)nn1] |
| I-193 | 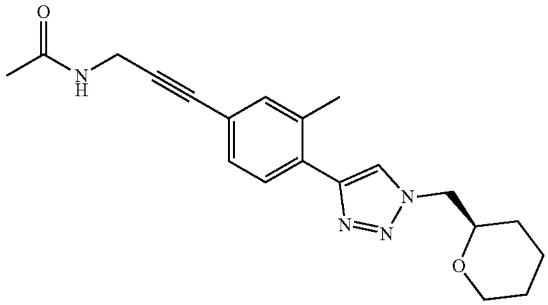 [SMILES: CC(=O)NCC#Cc1ccc(-c2cn(C[C@H]3CCCCO3)nn2)c(C)c1] |
| I-194 | 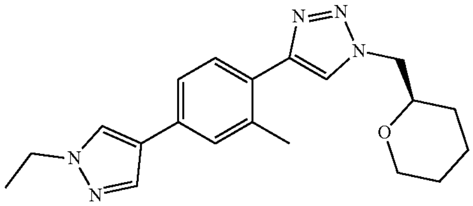 [SMILES: CCn1cc(-c2ccc(-c3cn(C[C@H]4CCCCO4)nn3)c(C)c2)cn1] |
| I-195 | 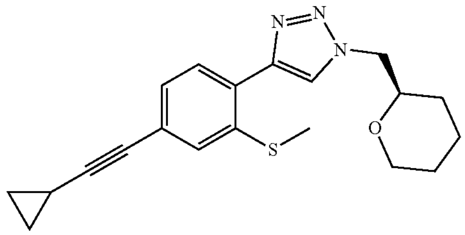 |
| I-196 | 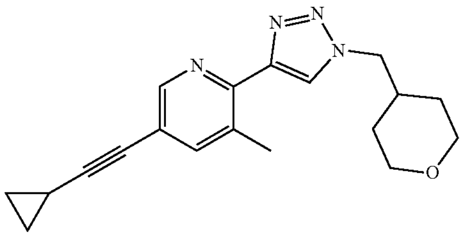 [SMILES: Cc1cc(C#CC2CC2)cnc1-c1cn(CC2CCOCC2)nn1] |

TABLE 1-continued
| Selected Compounds | |
|---|---|
| Compound | Structure |
| I-197 | 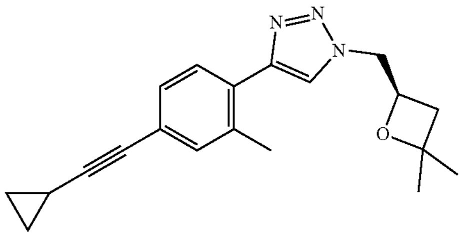 [SMILES: Cc1cc(C#CC2CC2)ccc1-c1cn(C[C@H]2CC(C)(C)O2)nn1] |
| I-198 | 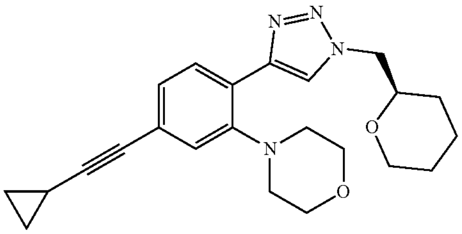 [SMILES: C(#CC1CC1)c1ccc(-c2cn(C[C@H]3CCCCO3)nn2)c(N2CCOCC2)c1] |
| I-199 | 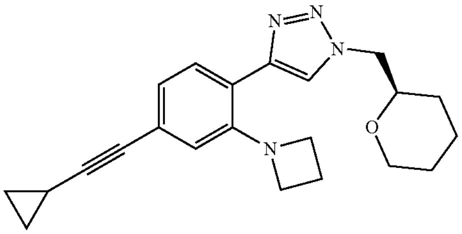 [SMILES: C(#CC1CC1)c1ccc(-c2cn(C[C@H]3CCCCO3)nn2)c(N2CCC2)c1] |
| I-200 | 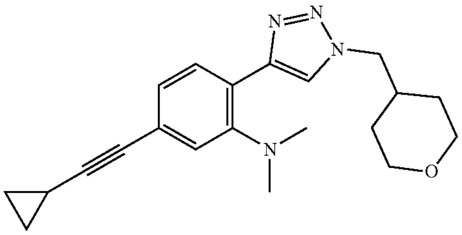 [SMILES: CN(C)c1cc(C#CC2CC2)ccc1-c1cn(CC2CCOCC2)nn1] |
| I-201 | 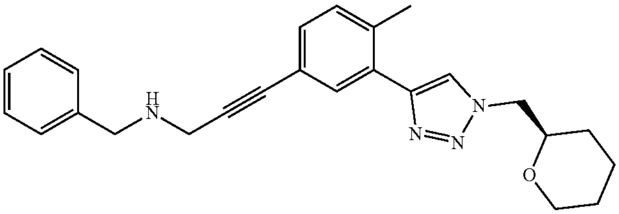 [SMILES: Cc1ccc(C#CCNCc2ccccc2)cc1-c1cn(C[C@H]2CCCCO2)nn1] |
| I-202 | 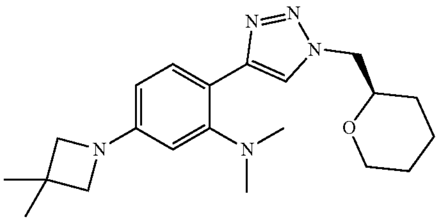 [SMILES: CN(C)c1cc(N2CC(C)(C)C2)ccc1-c1cn(C[C@H]2CCCCO2)nn1] |

TABLE 1-continued
| Selected Compounds | |
|---|---|
| Compound | Structure |
| I-203 | 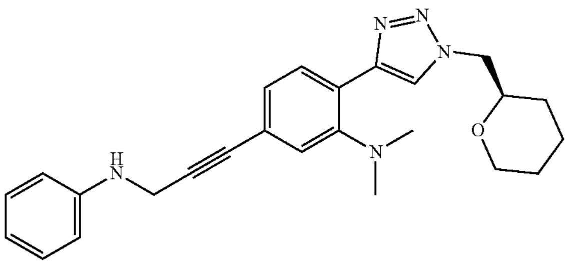 [SMILES: CN(C)c1cc(C#CCNc2ccccc2)ccc1-c1cn(C[C@H]2CCCCO2)nn1] |
| I-204 | 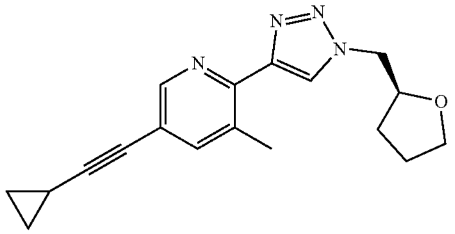 [SMILES: Cc1cc(C#CC2CC2)cnc1-c1cn(C[C@@H]2CCCO2)nn1] |
| I-205 | 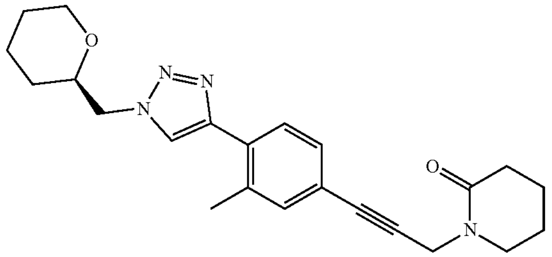 [SMILES: Cc1cc(C#CCN2CCCCC2=O)ccc1-c1cn(C[C@H]2CCCCO2)nn1] |
| I-206 | 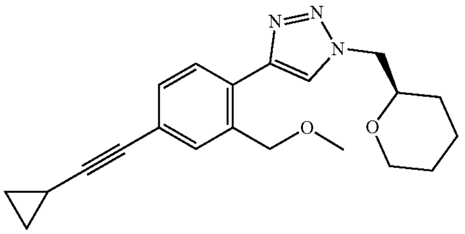 [SMILES: COCc1cc(C#CC2CC2)ccc1-c1cn(C[C@H]2CCCCO2)nn1] |
| I-207 | 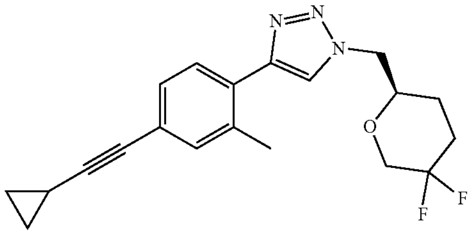 [SMILES: Cc1cc(C#CC2CC2)ccc1-c1cn(C[C@H]2CCC(F)(F)CO2)nn1] |
| I-208 | 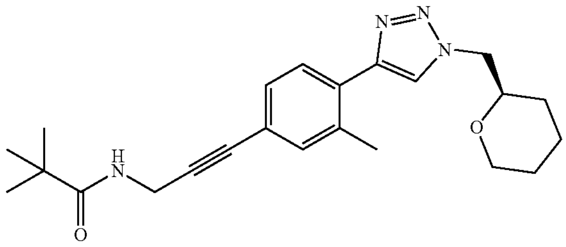 [SMILES: Cc1cc(C#CCNC(=O)C(C)(C)C)ccc1-c1cn(C[C@H]2CCCCO2)nn1] |

TABLE 1-continued
| Selected Compounds | |
|---|---|
| Compound | Structure |
| I-209 | 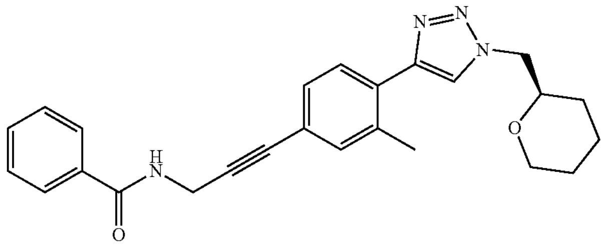 [SMILES: Cc1cc(C#CCNC(=O)c2ccccc2)ccc1-c1cn(C[C@H]2CCCCO2)nn1] |
| I-210 | 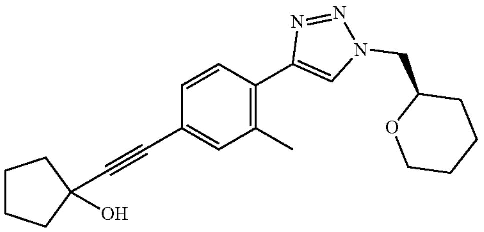 [SMILES: Cc1cc(C#CC2(O)CCCC2)ccc1-c1cn(C[C@H]2CCCCO2)nn1] |
| I-211 | 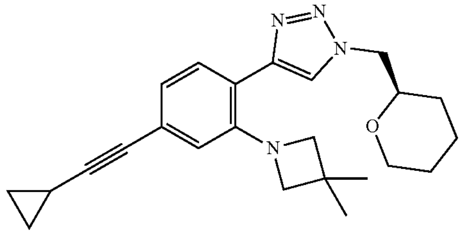 [SMILES: CC1(C)CN(c2cc(C#CC3CC3)ccc2-c2cn(C[C@H]3CCCCO3)nn2)C1] |
| I-212 | 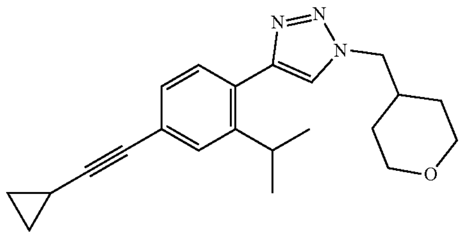 [SMILES: CC(C)c1cc(C#CC2CC2)ccc1-c1cn(CC2CCOCC2)nn1] |
| I-213 | 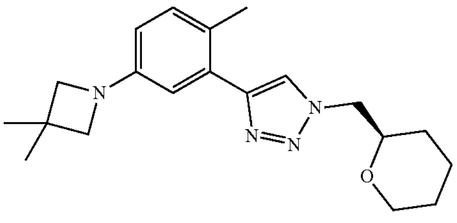 [SMILES: Cc1ccc(N2CC(C)(C)C2)cc1-c1cn(C[C@H]2CCCCO2)nn1] |
| I-214 | 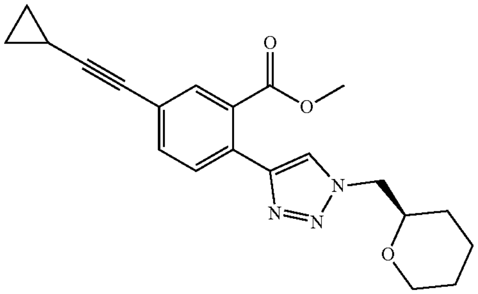 [SMILES: COC(=O)c1cc(C#CC2CC2)ccc1-c1cn(C[C@H]2CCCCO2)nn1] |

TABLE 1-continued
| Selected Compounds | |
|---|---|
| Compound | Structure |
| I-215 | 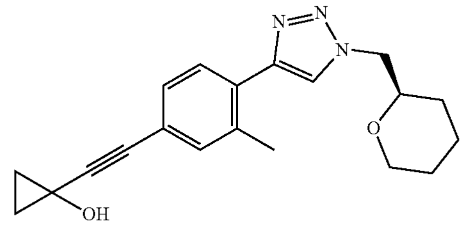 [SMILES: Cc1cc(C#CC2(O)CC2)ccc1-c1cn(C[C@H]2CCCCO2)nn1] |
| I-216 | 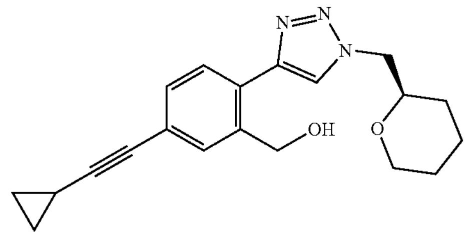 [SMILES: OCc1cc(C#CC2CC2)ccc1-c1cn(C[C@H]2CCCCO2)nn1] |
| I-217 | 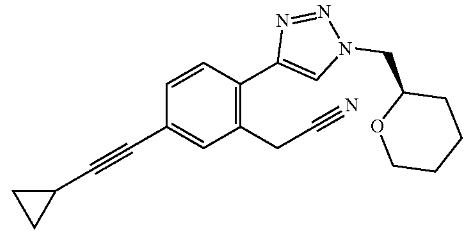 [SMILES: N#CCc1cc(C#CC2CC2)ccc1-c1cn(C[C@H]2CCCCO2)nn1] |
| I-218 | 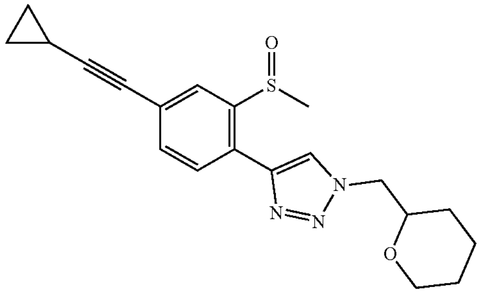 [SMILES: CS(=O)c1cc(C#CC2CC2)ccc1-c1cn(CC2CCCCO2)nn1] |
| I-219 | 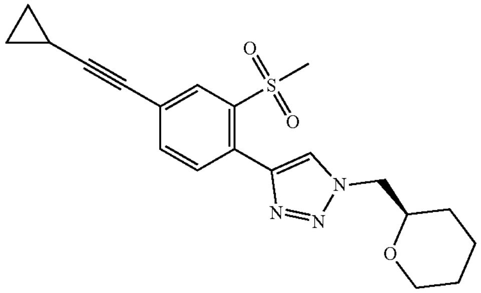 [SMILES: CS(=O)(=O)c1cc(C#CC2CC2)ccc1-c1cn(C[C@H]2CCCCO2)nn1] |
| I-220 | 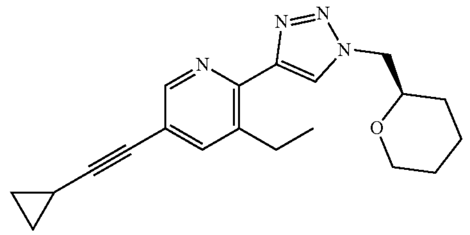 [SMILES: CCc1cc(C#CC2CC2)cnc1-c1cn(C[C@H]2CCCCO2)nn1] |

TABLE 1-continued
| Selected Compounds | |
|---|---|
| Compound | Structure |
| I-221 | 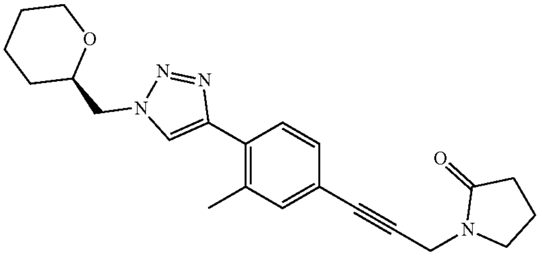 [SMILES: Cc1cc(C#CCN2CCCC2=O)ccc1-c1cn(C[C@H]2CCCCO2)nn1] |
| I-222 | 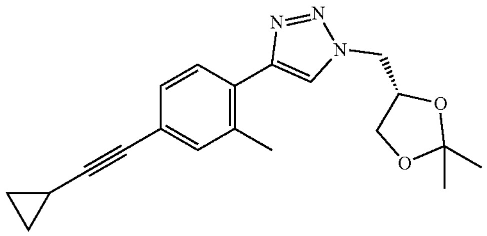 [SMILES: Cc1cc(C#CC2CC2)ccc1-c1cn(C[C@H]2COC(C)(C)O2)nn1] |
| I-223 | 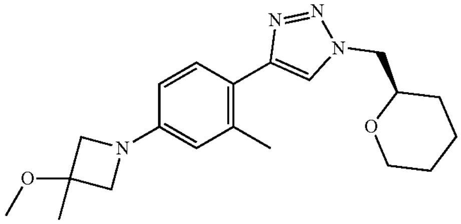 [SMILES: COC1(C)CN(c2ccc(-c3cn(C[C@H]4CCCCO4)nn3)c(C)c2)C1] |
| I-224 | 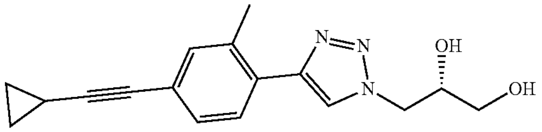 [SMILES: Cc1cc(C#CC2CC2)ccc1-c1cn(C[C@H](O)CO)nn1] |
| I-225 | 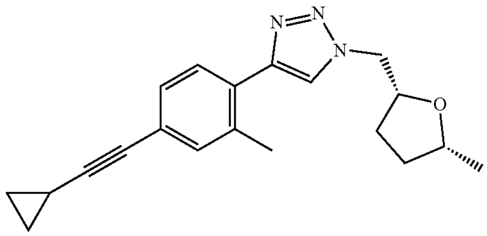 [SMILES: Cc1cc(C#CC2CC2)ccc1-c1cn(C[C@H]2CC[C@@H](C)O2)nn1] |
| I-226 | 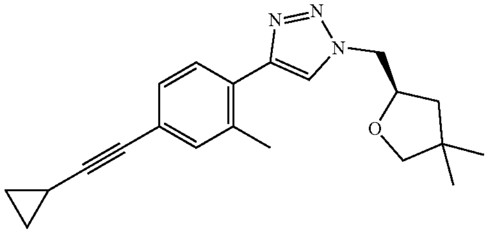 [SMILES: Cc1cc(C#CC2CC2)ccc1-c1cn(C[C@H]2CC(C)(C)CO2)nn1] |

TABLE 1-continued
| Selected Compounds | |
|---|---|
| Compound | Structure |
| I-227 | 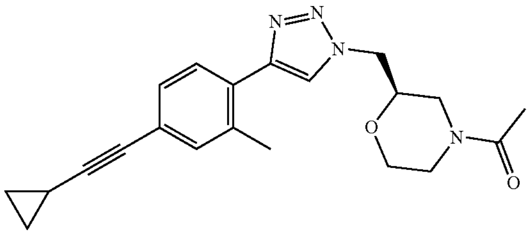 [SMILES: CC(=O)N1CCO[C@@H](Cn2cc(-c3ccc(C#CC4CC4)cc3C)nn2)C1] |
| I-228 | 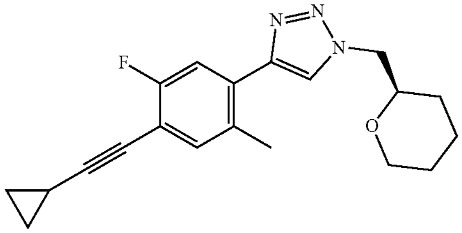 [SMILES: Cc1cc(C#CC2CC2)c(F)cc1-c1cn(C[C@H]2CCCCO2)nn1] |
| I-229 | 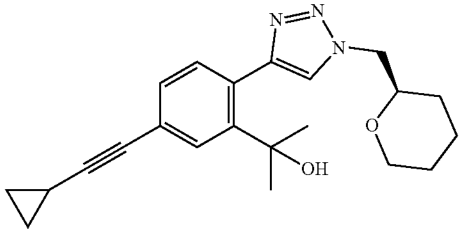 [SMILES: CC(C)(O)c1cc(C#CC2CC2)ccc1-c1cn(C[C@H]2CCCCO2)nn1] |
| I-230 | 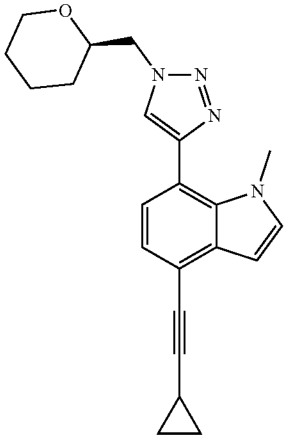 [SMILES: Cn1ccc2c(C#CC3CC3)ccc(-c3cn(C[C@H]4CCCCO4)nn3)c21] |
| I-231 | 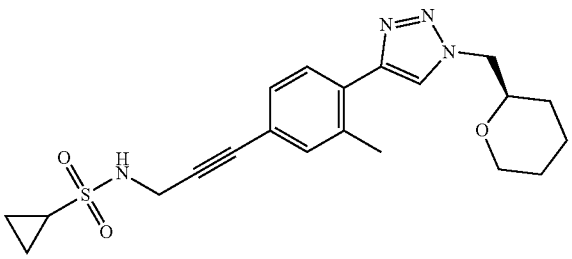 [SMILES: Cc1cc(C#CCNS(=O)(=O)C2CC2)ccc1-c1cn(C[C@H]2CCCCO2)nn1] |

TABLE 1-continued
| Selected Compounds | |
|---|---|
| Compound | Structure |
| I-232 | 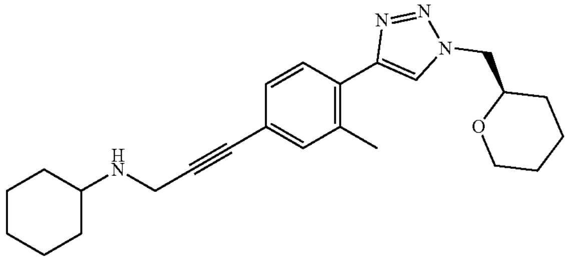 [SMILES: Cc1cc(C#CCNC2CCCCC2)ccc1-c1cn(C[C@H]2CCCCO2)nn1] |
| I-233 | 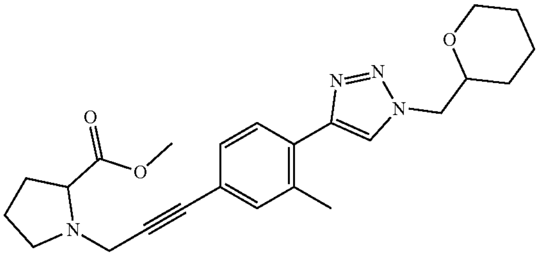 [SMILES: COC(=O)C1CCCN1CC#Cc1ccc(-c2cn(CC3CCCCO3)nn2)c(C)c1] |
| I-234 | 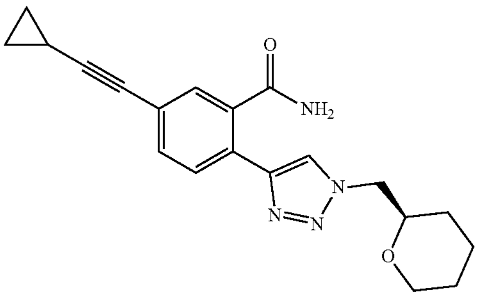 [SMILES: NC(=O)c1cc(C#CC2CC2)ccc1-c1cn(C[C@H]2CCCCO2)nn1] |
| I-235 | 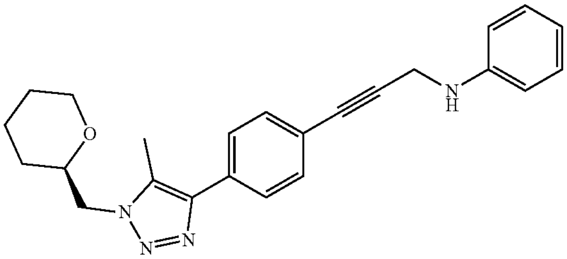 [SMILES: Cc1c(-c2ccc(C#CCNc3ccccc3)cc2)nnn1C[C@H]1CCCCO1] |
| I-236 | 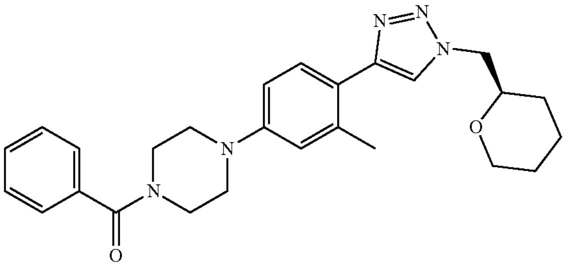 [SMILES: Cc1cc(N2CCN(C(=O)c3ccccc3)CC2)ccc1-c1cn(C[C@H]2CCCCO2)nn1] |

TABLE 1-continued
| Selected Compounds | |
|---|---|
| Compound | Structure |
| I-237 | 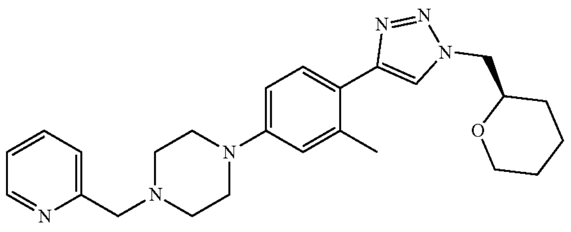 [SMILES: Cc1cc(N2CCN(Cc3ccccn3)CC2)ccc1-c1cn(C[C@H]2CCCCO2)nn1] |
| I-238 | 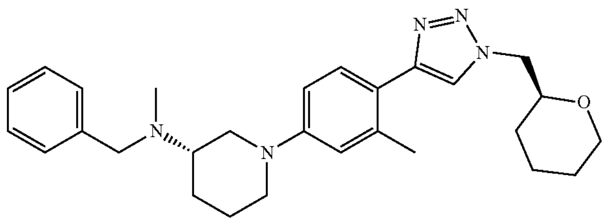 [SMILES: Cc1cc(N2CCC[C@H](N(C)Cc3ccccc3)C2)ccc1-c1cn(C[C@@H]2CCCCO2)nn1] |
| I-239 | 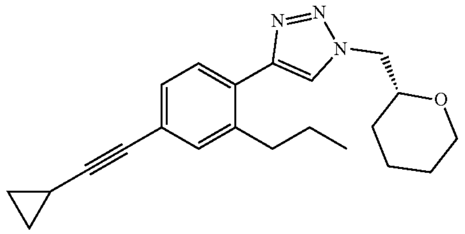 [SMILES: CCCc1cc(C#CC2CC2)ccc1-c1cn(C[C@H]2CCCCO2)nn1] |
| I-240 | 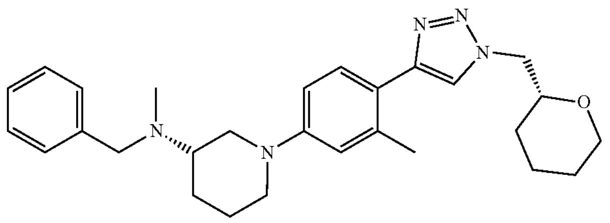 |
| I-241 | 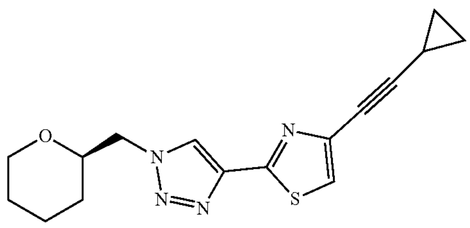 |
| I-242 | 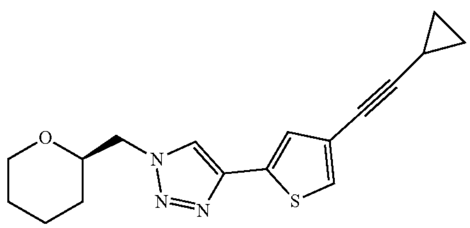 [SMILES: C(#CC1CC1)c1csc(-c2cn(C[C@H]3CCCCO3)nn2)c1] |

TABLE 1-continued
| Selected Compounds | |
|---|---|
| Compound | Structure |
| I-243 | 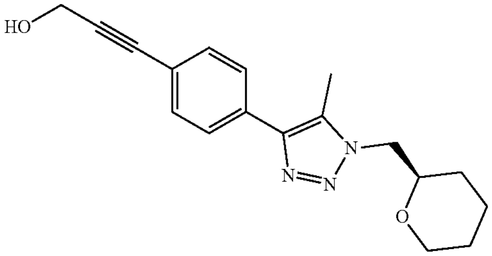 [SMILES: Cc1c(-c2ccc(C#CCO)cc2)nnn1C[C@H]1CCCCO1] |
| I-244 | 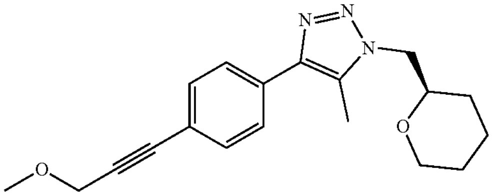 [SMILES: COCC#Cc1ccc(-c2nnn(C[C@H]3CCCCO3)c2C)cc1] |
| I-245 | 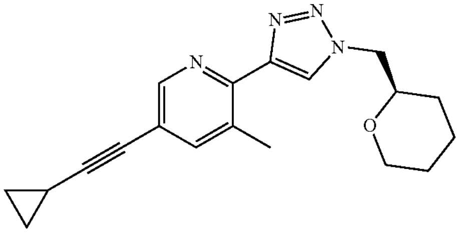 [SMILES: Cc1cc(C#CC2CC2)cnc1-c1cn(C[C@H]2CCCCO2)nn1] |
| I-246 | 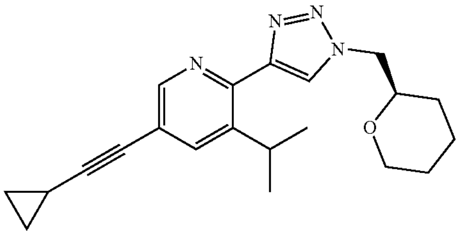 [SMILES: CC(C)c1cc(C#CC2CC2)cnc1-c1cn(C[C@H]2CCCCO2)nn1] |
| I-247 | 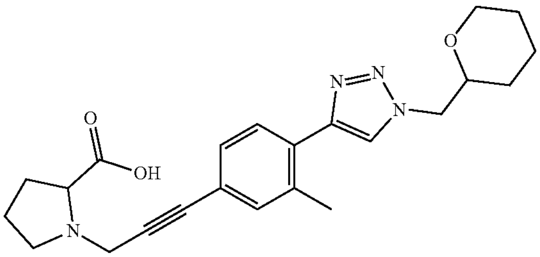 [SMILES: Cc1cc(C#CCN2CCCC2C(=O)O)ccc1-c1cn(CC2CCCCO2)nn1] |
| I-248 | 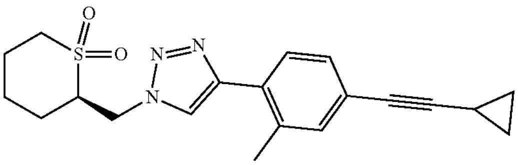 [SMILES: Cc1cc(C#CC2CC2)ccc1-c1cn(C[C@H]2CCCCS2(=O)=O)nn1] |

TABLE 1-continued
| Selected Compounds | |
|---|---|
| Compound | Structure |
| I-249 | 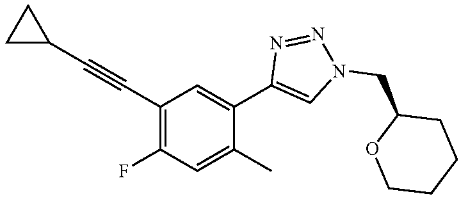 [SMILES: Cc1cc(F)c(C#CC2CC2)cc1-c1cn(C[C@H]2CCCCO2)nn1] |
| I-250 | 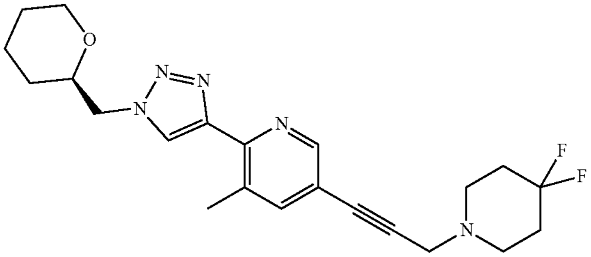 [SMILES: Cc1cc(C#CCN2CCC(F)(F)CC2)cnc1-c1cn(C[C@H]2CCCCO2)nn1] |
| I-251 | 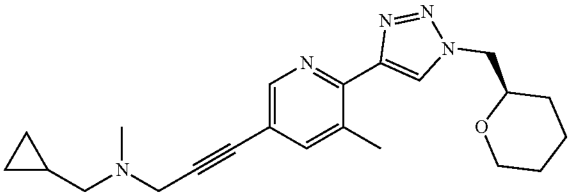 [SMILES: Cc1cc(C#CCN(C)CC2CC2)cnc1-c1cn(C[C@H]2CCCCO2)nn1] |
| I-252 | 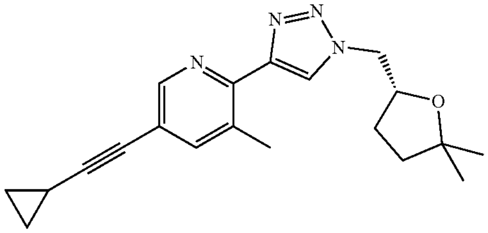 [SMILES: Cc1cc(C#CC2CC2)cnc1-c1cn(C[C@H]2CCC(C)(C)O2)nn1] |
| I-253 | 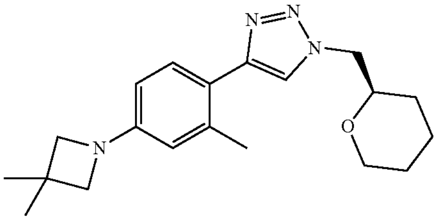 [SMILES: Cc1cc(N2CC(C)(C)C2)ccc1-c1cn(C[C@H]2CCCCO2)nn1] |
| I-254 | 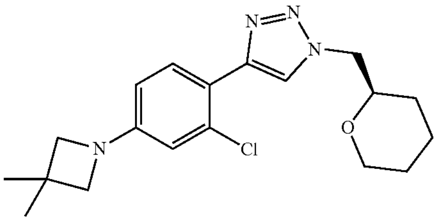 [SMILES: CC1(C)CN(c2ccc(-c3cn(C[C@H]4CCCCO4)nn3)c(Cl)c2)C1] |

TABLE 1-continued
| Selected Compounds | |
|---|---|
| Compound | Structure |
| I-255 | 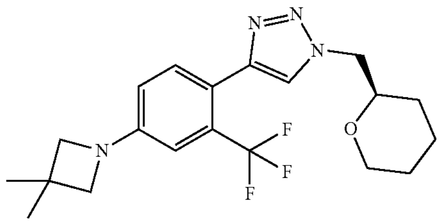 [SMILES: CC1(C)CN(c2ccc(-c3cn(C[C@H]4CCCCO4)nn3)c(C(F)(F)F)c2)C1] |
| I-256 | 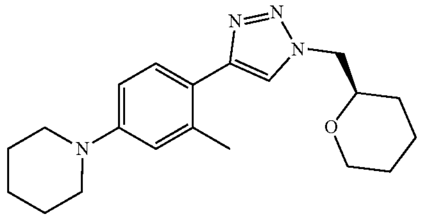 [SMILES: Cc1cc(N2CCCCC2)ccc1-c1cn(C[C@H]2CCCCO2)nn1] |
| I-257 | 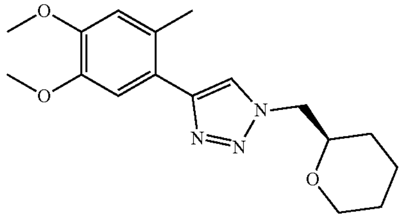 [SMILES: COc1cc(C)c(-c2cn(C[C@H]3CCCCO3)nn2)cc1OC] |
| I-258 | 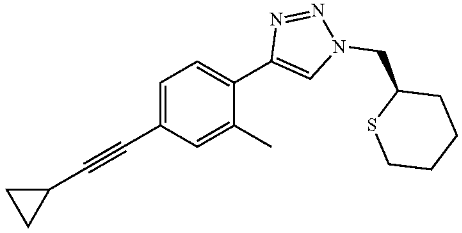 |
| I-259 | 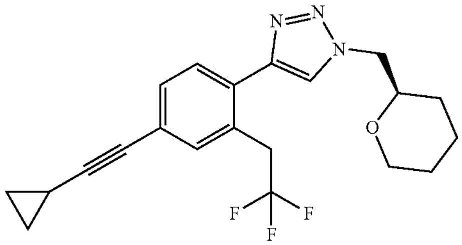 [SMILES: FC(F)(F)Cc1cc(C#CC2CC2)ccc1-c1cn(C[C@H]2CCCCO2)nn1] |
| I-260 | 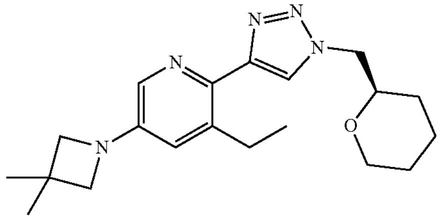 [SMILES: CCc1cc(N2CC(C)(C)C2)cnc1-c1cn(C[C@H]2CCCCO2)nn1] |

TABLE 1-continued
| Selected Compounds | |
|---|---|
| Compound | Structure |
| I-261 | 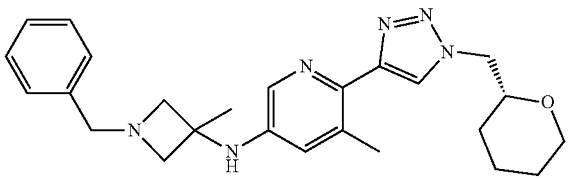 [SMILES: Cc1cc(NC2(C)CN(Cc3ccccc3)C2)cnc1-c1cn(C[C@H]2CCCCO2)nn1] |
| I-262 | 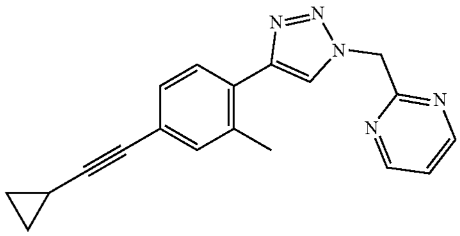 [SMILES: Cc1cc(C#CC2CC2)ccc1-c1cn(Cc2ncccn2)nn1] |
| I-263 | 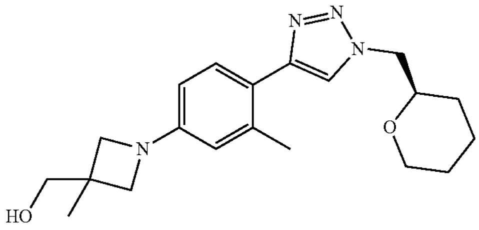 [SMILES: Cc1cc(N2CC(C)(CO)C2)ccc1-c1cn(C[C@H]2CCCCO2)nn1] |
| I-264 | 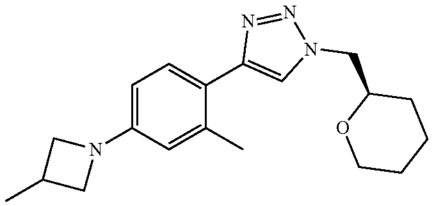 [SMILES: Cc1cc(N2CC(C)C2)ccc1-c1cn(C[C@H]2CCCCO2)nn1] |
| I-265 | 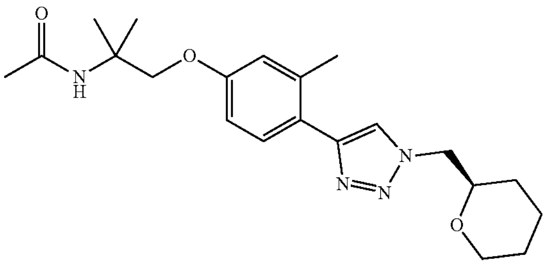 [SMILES: CC(=O)NC(C)(C)COc1ccc(-c2cn(C[C@H]3CCCCO3)nn2)c(C)c1] |
| I-266 | 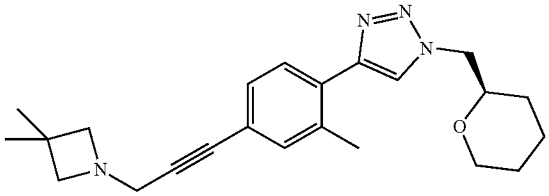 [SMILES: Cc1cc(C#CCN2CC(C)(C)C2)ccc1-c1cn(C[C@H]2CCCCO2)nn1] |

TABLE 1-continued
| Selected Compounds | |
|---|---|
| Compound | Structure |
| I-267 | 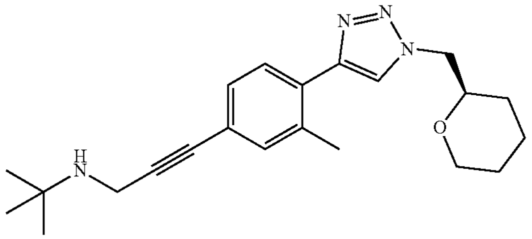 [SMILES: Cc1cc(C#CCNC(C)(C)C)ccc1-c1cn(C[C@H]2CCCCO2)nn1] |
| I-268 | 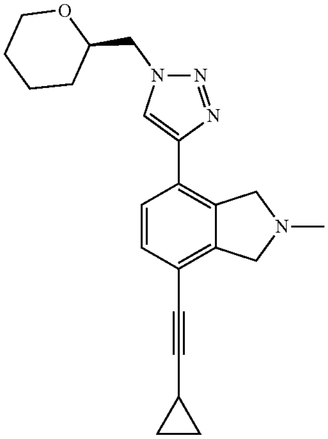 [SMILES: CN1Cc2c(C#CC3CC3)ccc(-c3cn(C[C@H]4CCCCO4)nn3)c2C1] |
| I-269 | 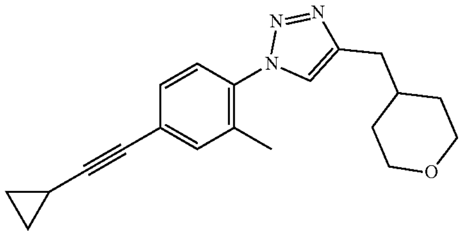 [SMILES: Cc1cc(C#CC2CC2)ccc1-n1cc(CC2CCOCC2)nn1] |
| I-270 | 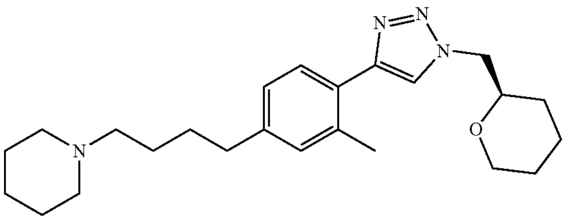 [SMILES: Cc1cc(CCCCN2CCCCC2)ccc1-c1cn(C[C@H]2CCCCO2)nn1] |
| I-271 | 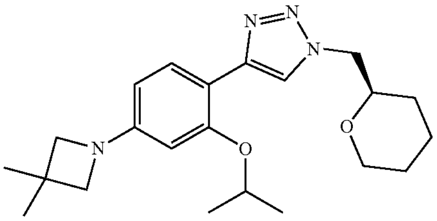 [SMILES: CC(C)Oc1cc(N2CC(C)(C)C2)ccc1-c1cn(C[C@H]2CCCCO2)nn1] |

TABLE 1-continued
| Selected Compounds | |
|---|---|
| Compound | Structure |
| I-272 | 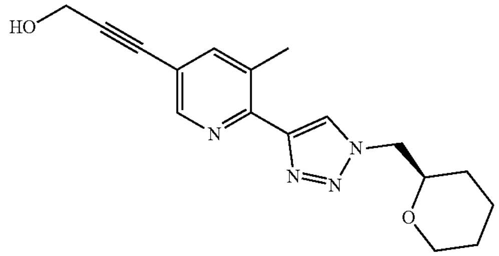 [SMILES: Cc1cc(C#CCO)cnc1-c1cn(C[C@H]2CCCCO2)nn1] |
| I-273 | 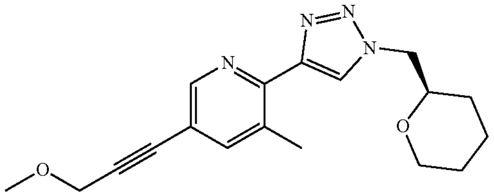 [SMILES: COCC#Cc1cnc(-c2cn(C[C@H]3CCCCO3)nn2)c(C)c1] |
| I-274 | 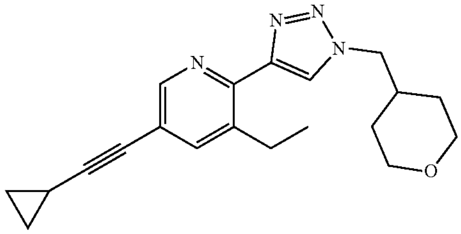 [SMILES: CCc1cc(C#CC2CC2)cnc1-c1cn(CC2CCOCC2)nn1] |
| I-275 | 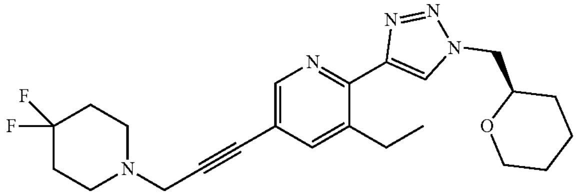 [SMILES: CCc1cc(C#CCN2CCC(F)(F)CC2)cnc1-c1cn(C[C@H]2CCCCO2)nn1] |
| I-276 | 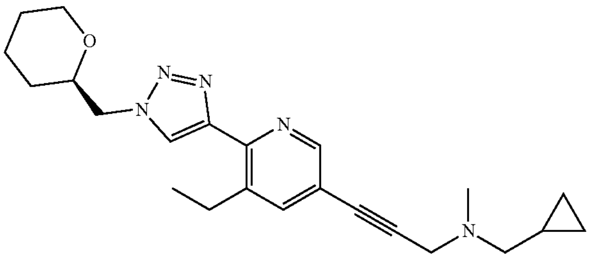 [SMILES: CCc1cc(C#CCN(C)CC2CC2)cnc1-c1cn(C[C@H]2CCCCO2)nn1] |
| I-277 | 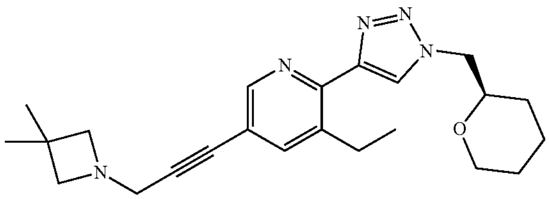 [SMILES: CCc1cc(C#CCN2CC(C)(C)C2)cnc1-c1cn(C[C@H]2CCCCO2)nn1] |

TABLE 1-continued
| Selected Compounds | |
|---|---|
| Compound | Structure |
| I-278 | 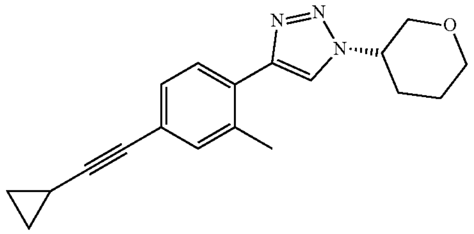 |
| I-279 | 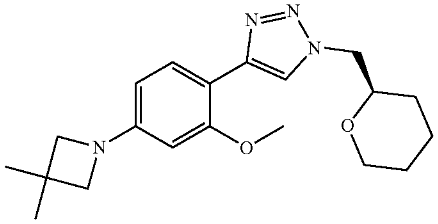 [SMILES: COc1cc(N2CC(C)(C)C2)ccc1-c1cn(C[C@H]2CCCCO2)nn1] |
| I-280 | 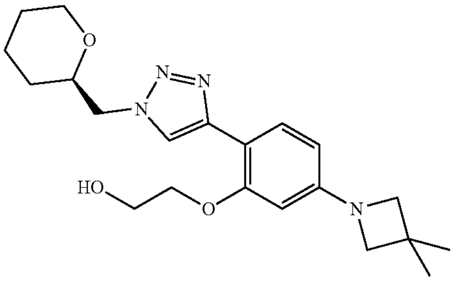 [SMILES: CC1(C)CN(c2ccc(-c3cn(C[C@H]4CCCCO4)nn3)c(OCCO)c2)C1] |
| I-281 | 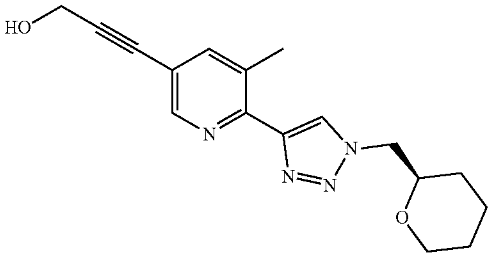 [SMILES: Cc1cc(C#CCO)cnc1-c1cn(C[C@H]2CCCCO2)nn1] |
| I-282 | 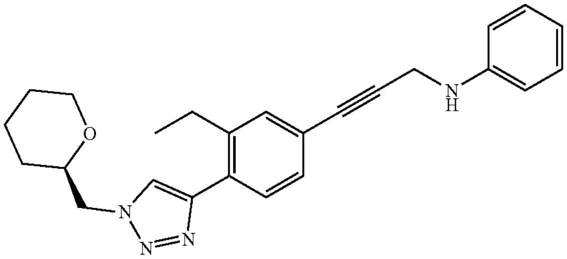 [SMILES: CCc1cc(C#CCNc2ccccc2)ccc1-c1cn(C[C@H]2CCCCO2)nn1] |
| I-283 | 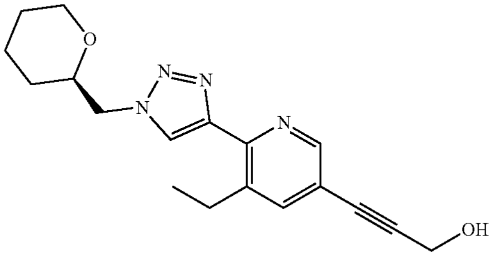 [SMILES: CCc1cc(C#CCO)cnc1-c1cn(C[C@H]2CCCCO2)nn1] |

TABLE 1-continued
| Selected Compounds | |
|---|---|
| Compound | Structure |
| I-284 | 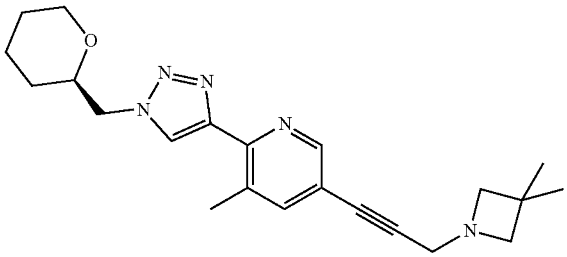 [SMILES: Cc1cc(C#CCN2CC(C)(C)C2)cnc1-c1cn(C[C@H]2CCCCO2)nn1] |
| I-285 | 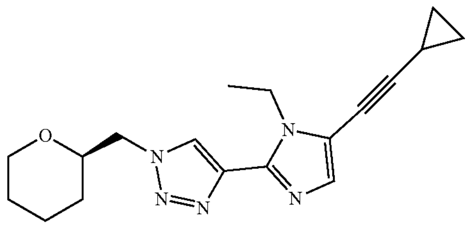 [SMILES: CCn1c(C#CC2CC2)cnc1-c1cn(C[C@H]2CCCCO2)nn1] |
| I-286 | 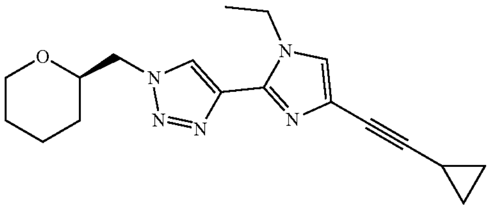 [SMILES: CCn1cc(C#CC2CC2)nc1-c1cn(C[C@H]2CCCCO2)nn1] |
| I-287 | 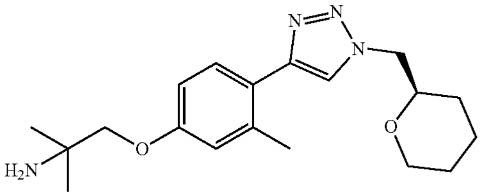 [SMILES: Cc1cc(OCC(C)(C)N)ccc1-c1cn(C[C@H]2CCCCO2)nn1] |
| I-288 | 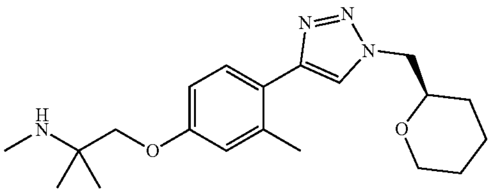 [SMILES: CNC(C)(C)COc1ccc(-c2cn(C[C@H]3CCCCO3)nn2)c(C)c1] |
| I-289 | 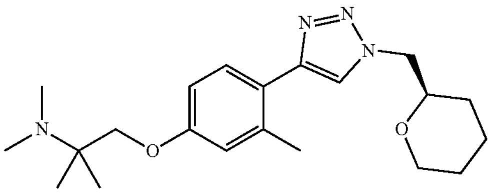 [SMILES: Cc1cc(OCC(C)(C)N(C)C)ccc1-c1cn(C[C@H]2CCCCO2)nn1] |

TABLE 1-continued
| Selected Compounds | |
|---|---|
| Compound | Structure |
| I-290 | 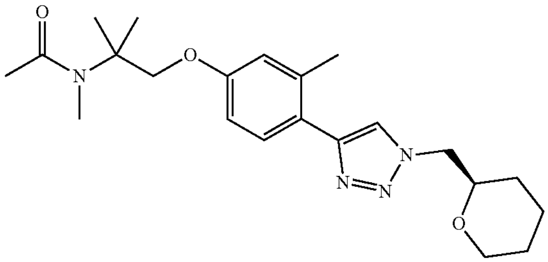 [SMILES: CC(=O)N(C)C(C)(C)COc1ccc(-c2cn(C[C@H]3CCCCO3)nn2)c(C)c1] |
| I-291 | 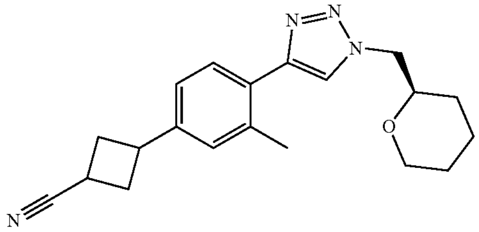 [SMILES: Cc1cc(C2CC(C#N)C2)ccc1-c1cn(C[C@H]2CCCCO2)nn1] |
| I-292 | 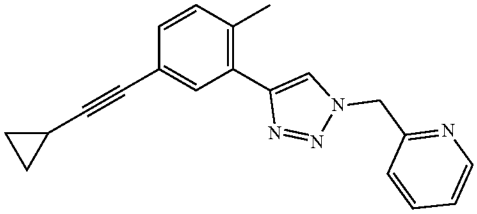 [SMILES: Cc1ccc(C#CC2CC2)cc1-c1cn(Cc2ccccn2)nn1] |
| I-293 | 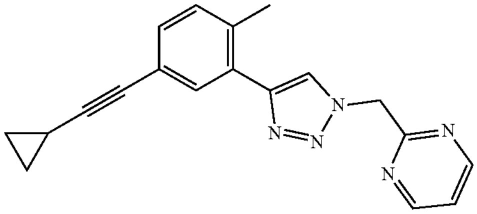 [SMILES: Cc1ccc(C#CC2CC2)cc1-c1cn(Cc2ncccn2)nn1] |
| I-294 | 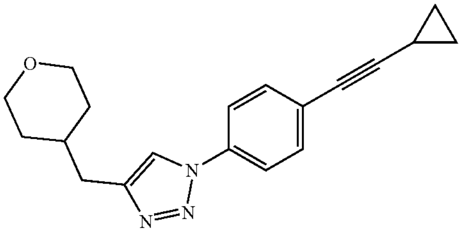 [SMILES: C(#CC1CC1)c1ccc(-n2cc(CC3CCOCC3)nn2)cc1] |
| I-295 | 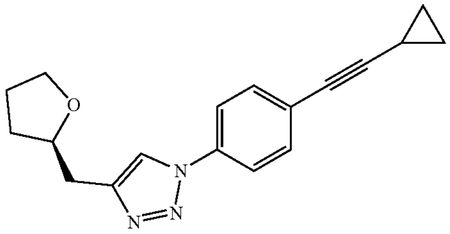 [SMILES: C(#CC1CC1)c1ccc(-n2cc(C[C@H]3CCCO3)nn2)cc1] |

TABLE 1-continued
| Selected Compounds | |
|---|---|
| Compound | Structure |
| I-296 | 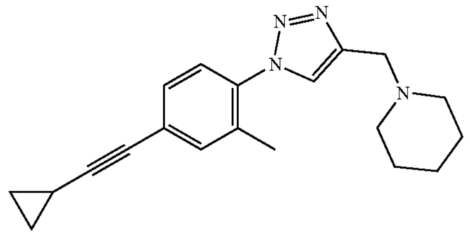 [SMILES: Cc1cc(C#CC2CC2)ccc1-n1cc(CN2CCCCC2)nn1] |
| I-297 | 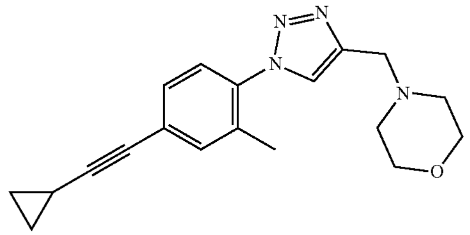 [SMILES: Cc1cc(C#CC2CC2)ccc1-n1cc(CN2CCOCC2)nn1] |
| I-298 | 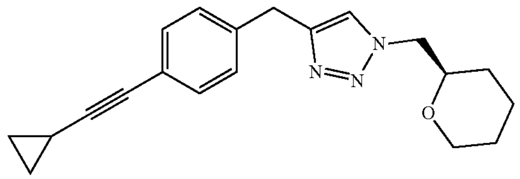 [SMILES: C(#CC1CC1)c1ccc(Cc2cn(C[C@H]3CCCCO3)nn2)cc1] |
| I-299 | 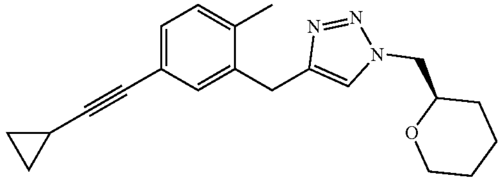 [SMILES: Cc1ccc(C#CC2CC2)cc1Cc1cn(C[C@H]2CCCCO2)nn1] |
| I-300 | 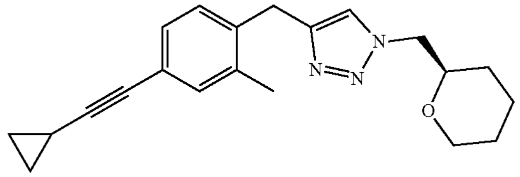 [SMILES: Cc1cc(C#CC2CC2)ccc1Cc1cn(C[C@H]2CCCCO2)nn1] |
| I-301 | 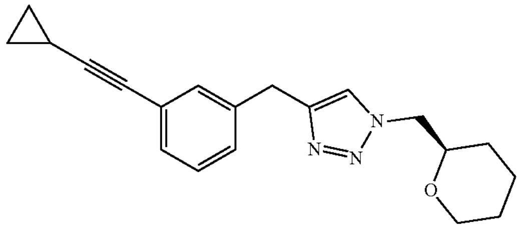 [SMILES: C(#CC1CC1)c1cccc(Cc2cn(C[C@H]3CCCCO3)nn2)c1] |
| I-302 | 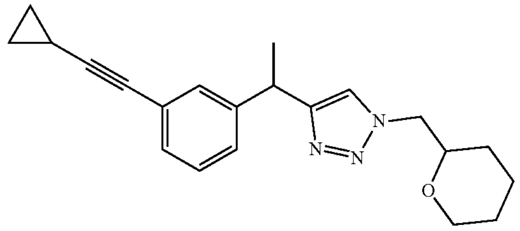 [SMILES: CC(c1cccc(C#CC2CC2)c1)c1cn(CC2CCCCO2)nn1] |

TABLE 1-continued
| Selected Compounds | |
|---|---|
| Compound | Structure |
| I-303 | 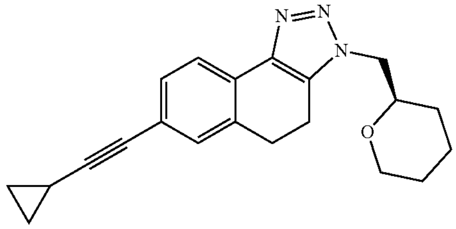 [SMILES: C(#CC1CC1)c1ccc2c(c1)CCc1c-2nnn1C[C@H]1CCCCO1] |
| I-304 | 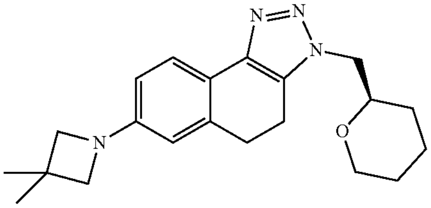 [SMILES: CC1(C)CN(c2ccc3c(c2)CCc2c-3nnn2C[C@H]2CCCCO2)C1] |
| I-305 | 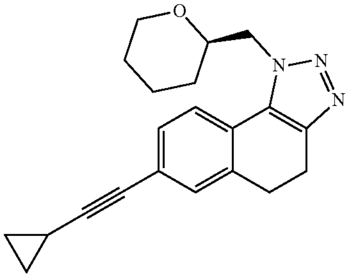 [SMILES: C(#CC1CC1)c1ccc2c(c1)CCc1nnn(C[C@H]3CCCCO3)c1-2] |
| I-306 | 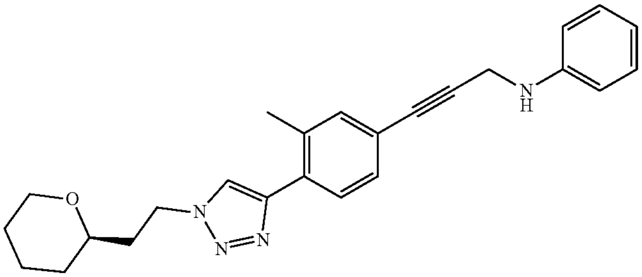 [SMILES: Cc1cc(C#CCNc2ccccc2)ccc1-c1cn(CC[C@H]2CCCCO2)nn1] |
| I-307 | 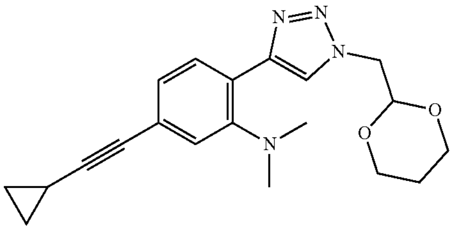 |
| I-308 | 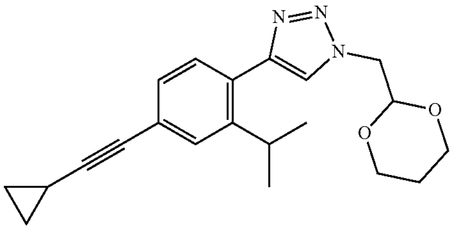 [SMILES: CC(C)c1cc(C#CC2CC2)ccc1-c1cn(CC2OCCCO2)nn1] |

TABLE 1-continued
| Selected Compounds | |
|---|---|
| Compound | Structure |
| I-309 | 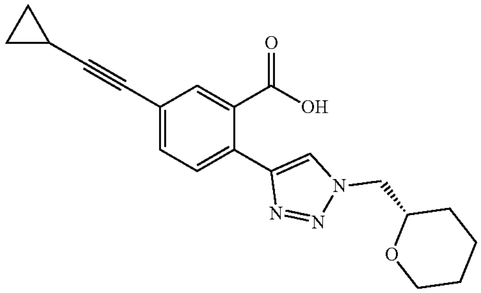 [SMILES: O=C(O)c1cc(C#CC2CC2)ccc1-c1cn(C[C@@H]2CCCCO2)nn1] |
| I-310 | 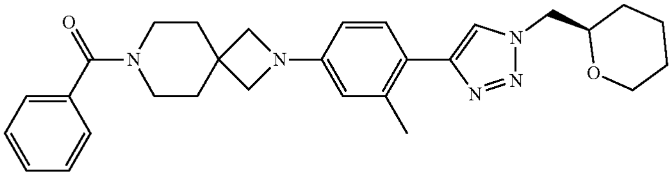 [SMILES: Cc1cc(N2CC3(CCN(C(=O)c4ccccc4)CC3)C2)ccc1-c1cn(C[C@H]2CCCCO2)nn1] |
| I-311 | 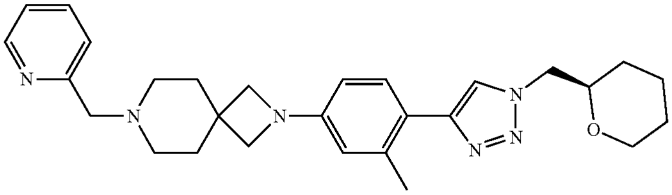 [SMILES: Cc1cc(N2CC3(CCN(Cc4ccccn4)CC3)C2)ccc1-c1cn(C[C@H]2CCCCO2)nn1] |
| I-312 | 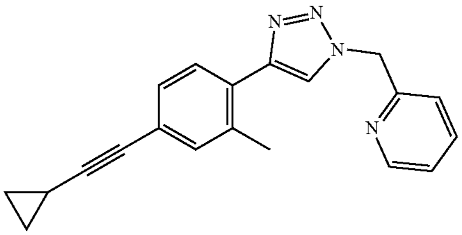 [SMILES: Cc1cc(C#CC2CC2)ccc1-c1cn(Cc2ccccn2)nn1] |
| I-313 | 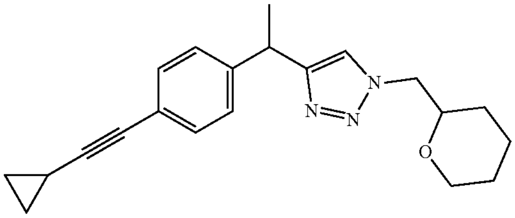 [SMILES: CC(c1ccc(C#CC2CC2)cc1)c1cn(CC2CCCCO2)nn1] |
| I-314 | 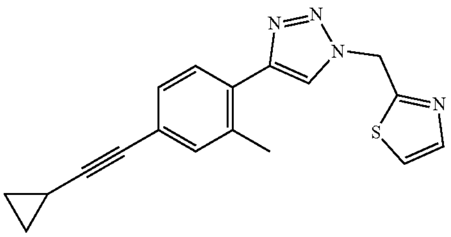 [SMILES: Cc1cc(C#CC2CC2)ccc1-c1cn(Cc2nccs2)nn1] |

TABLE 1-continued
| Selected Compounds | |
|---|---|
| Compound | Structure |
| I-315 | 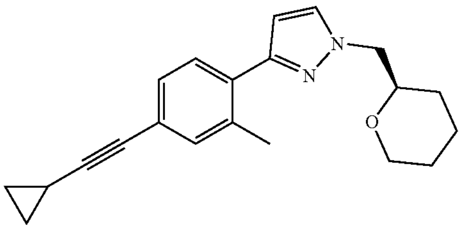 [SMILES: Cc1cc(C#CC2CC2)ccc1-c1ccn(C[C@H]2CCCCO2)n1] |
| I-316 | 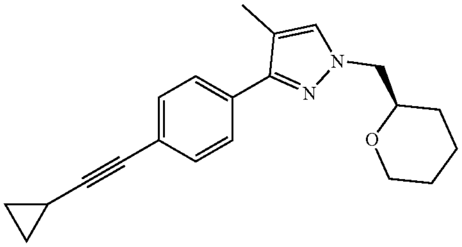 [SMILES: Cc1cn(C[C@H]2CCCCO2)nc1-c1ccc(C#CC2CC2)cc1] |
| I-317 | 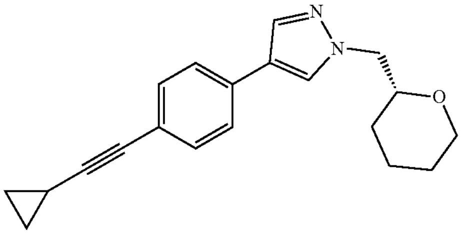 [SMILES: C(#CC1CC1)c1ccc(-c2cnn(C[C@H]3CCCCO3)c2)cc1] |
| I-318 | 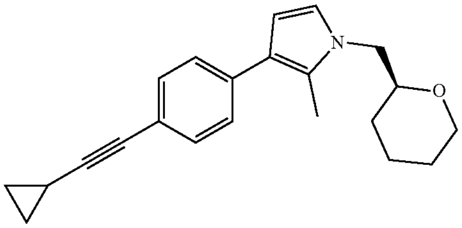 [SMILES: Cc1c(-c2ccc(C#CC3CC3)cc2)ccn1C[C@@H]1CCCCO1] |
| I-319 | 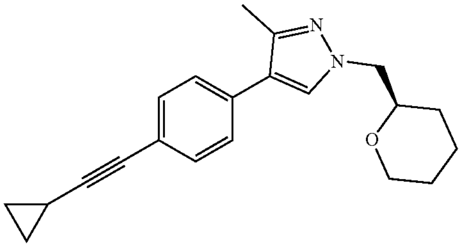 [SMILES: Cc1nn(C[C@H]2CCCCO2)cc1-c1ccc(C#CC2CC2)cc1] |
| I-320 | 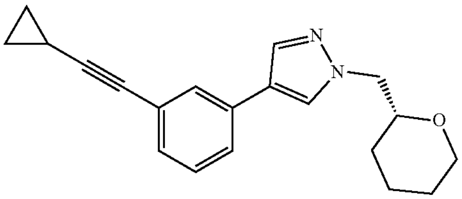 [SMILES: C(#CC1CC1)c1cccc(-c2cnn(C[C@H]3CCCCO3)c2)c1] |

TABLE 1-continued
| Selected Compounds | |
|---|---|
| Compound | Structure |
| I-321 | 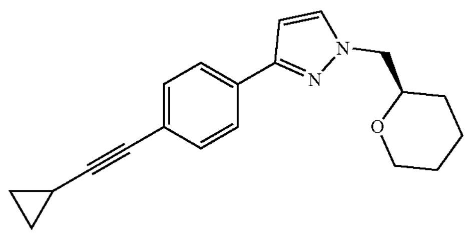 [SMILES: C(#CC1CC1)c1ccc(-c2ccn(C[C@H]3CCCCO3)n2)cc1] |
| I-322 | 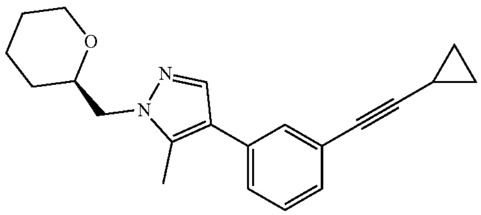 [SMILES: Cc1c(-c2cccc(C#CC3CC3)c2)cnn1C[C@H]1CCCCO1] |
| I-323 | 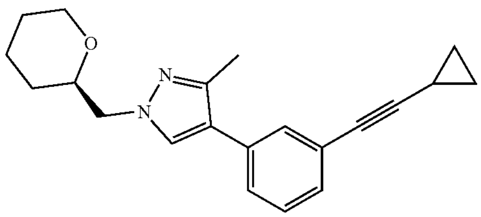 [SMILES: Cc1nn(C[C@H]2CCCCO2)cc1-c1cccc(C#CC2CC2)c1] |
| I-324 | 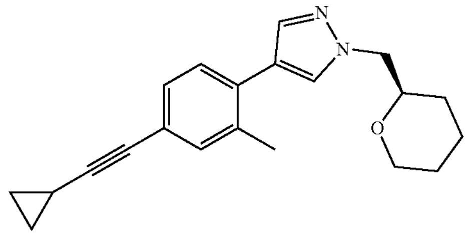 [SMILES: Cc1cc(C#CC2CC2)ccc1-c1cnn(C[C@H]2CCCCO2)c1] |
| I-325 | 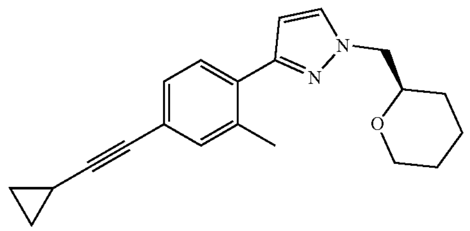 [SMILES: Cc1cc(C#CC2CC2)ccc1-c1ccn(C[C@H]2CCCCO2)n1] |
| I-326 | 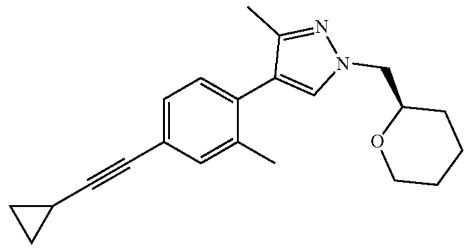 [SMILES: Cc1cc(C#CC2CC2)ccc1-c1cn(C[C@H]2CCCCO2)nc1C] |

TABLE 1-continued
| Selected Compounds | |
|---|---|
| Compound | Structure |
| I-327 | 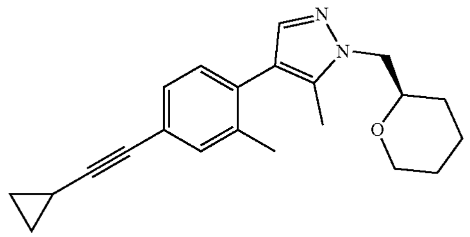 [SMILES: Cc1cc(C#CC2CC2)ccc1-c1cnn(C[C@H]2CCCCO2)c1C] |
| I-328 | 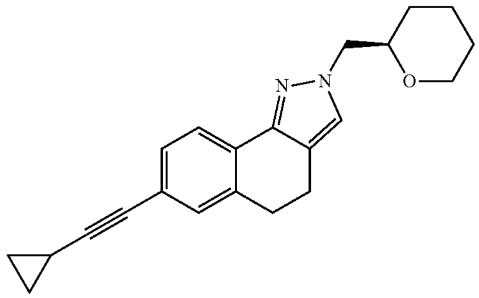 [SMILES: C(#CC1CC1)c1ccc2c(c1)CCc1cn(C[C@H]3CCCCO3)nc1-2] |
| I-329 | 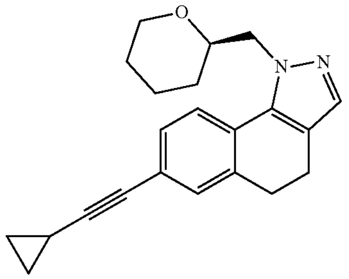 [SMILES: C(#CC1CC1)c1ccc2c(c1)CCc1cnn(C[C@H]3CCCCO3)c1-2] |
| I-330 | 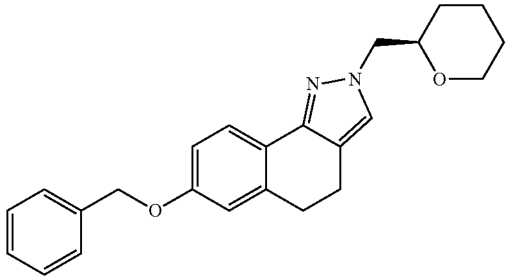 [SMILES: c1ccc(COc2ccc3c(c2)CCc2cn(C[C@H]4CCCCO4)nc2-3)cc1] |
| I-331 | 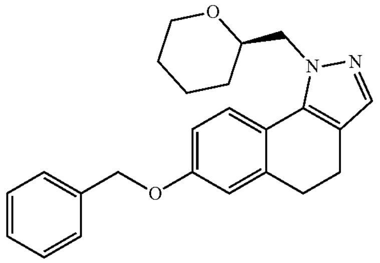 [SMILES: c1ccc(COc2ccc3c(c2)CCc2cnn(C[C@H]4CCCCO4)c2-3)cc1] |

TABLE 1-continued
| Selected Compounds | |
|---|---|
| Compound | Structure |
| I-332 | 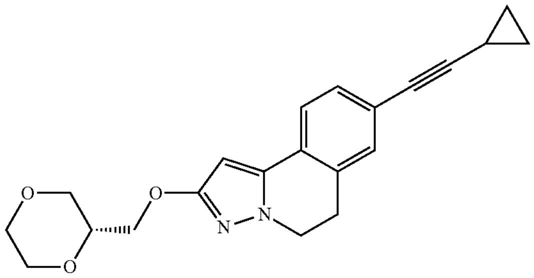 [SMILES: C(#CC1CC1)c1ccc2c(c1)CCn1nc(OC[C@H]3COCCO3)cc1-2] |
| I-333 | 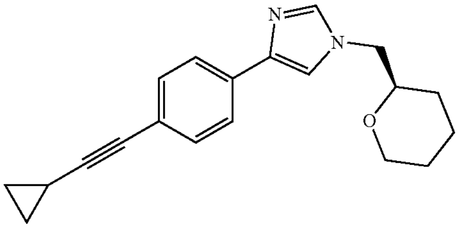 [SMILES: C(#CC1CC1)c1ccc(-c2cn(C[C@H]3CCCCO3)cn2)cc1] |
| I-334 | 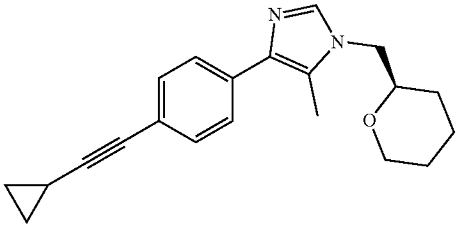 [SMILES: Cc1c(-c2ccc(C#CC3CC3)cc2)ncn1C[C@H]1CCCCO1] |
| I-335 | 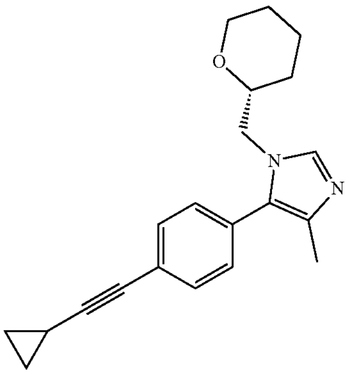 [SMILES: Cc1ncn(C[C@H]2CCCCO2)c1-c1ccc(C#CC2CC2)cc1] |
| I-336 | 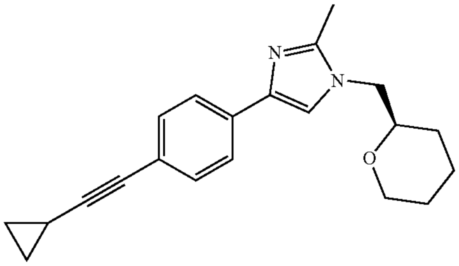 [SMILES: Cc1nc(-c2ccc(C#CC3CC3)cc2)cn1C[C@H]1CCCCO1] |

TABLE 1-continued
| Selected Compounds | |
|---|---|
| Compound | Structure |
| I-337 | 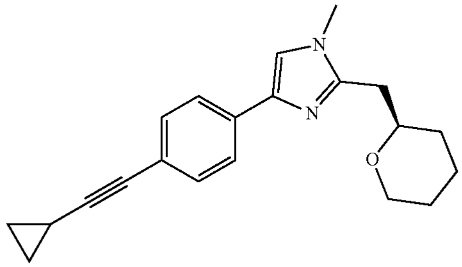 [SMILES: Cn1cc(-c2ccc(C#CC3CC3)cc2)nc1C[C@H]1CCCCO1] |
| I-338 | 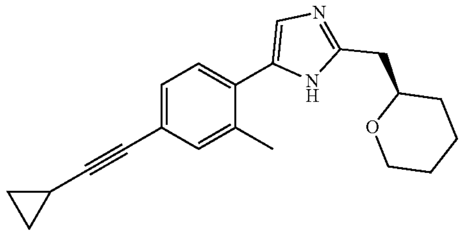 [SMILES: Cc1cc(C#CC2CC2)ccc1-c1cnc(C[C@H]2CCCCO2)[nH]1] |
| I-339 | 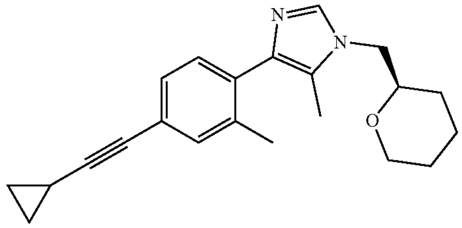 [SMILES: Cc1cc(C#CC2CC2)ccc1-c1ncn(C[C@H]2CCCCO2)c1C] |
| I-340 | 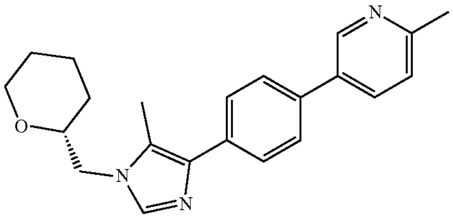 [SMILES: Cc1ccc(-c2ccc(-c3ncn(C[C@H]4CCCCO4)c3C)cc2)cn1] |
| I-341 | 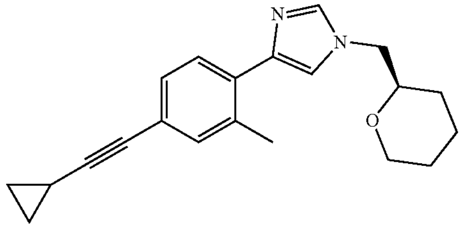 [SMILES: Cc1cc(C#CC2CC2)ccc1-c1cn(C[C@H]2CCCCO2)cn1] |
| I-342 | 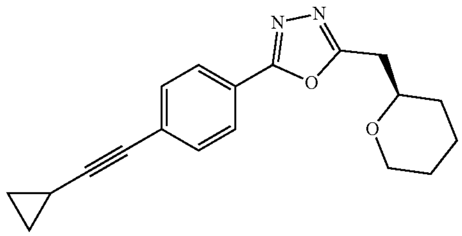 [SMILES: C(#CC1CC1)c1ccc(-c2nnc(C[C@H]3CCCCO3)o2)cc1] |

TABLE 1-continued
| Selected Compounds | |
|---|---|
| Compound | Structure |
| I-343 | 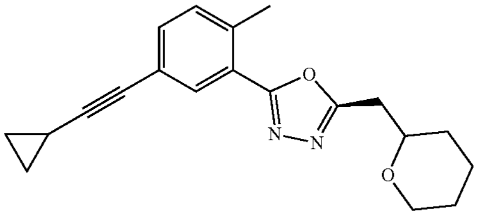 |
| I-344 | 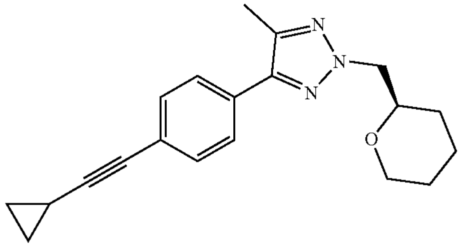 [SMILES: Cc1nn(C[C@H]2CCCCO2)nc1-c1ccc(C#CC2CC2)cc1] |
| I-345 | 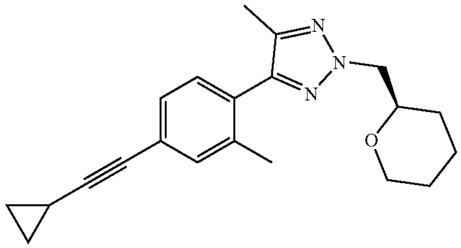 [SMILES: Cc1cc(C#CC2CC2)ccc1-c1nn(C[C@H]2CCCCO2)nc1C] |
| I-346 | 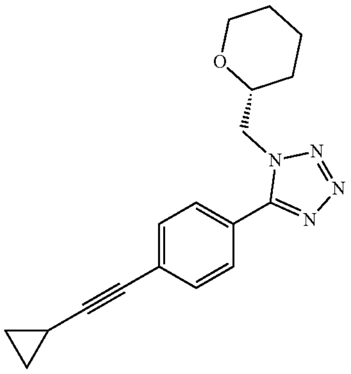 [SMILES: C(#CC1CC1)c1ccc(-c2nnnn2C[C@H]2CCCCO2)cc1] |
| I-350 | 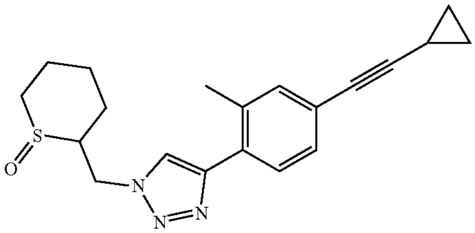 [SMILES: Cc1cc(C#CC2CC2)ccc1-c1cn(CC2CCCCS2=O)nn1] |

TABLE 1-continued
| Selected Compounds | |
|---|---|
| Compound | Structure |
| I-351 | 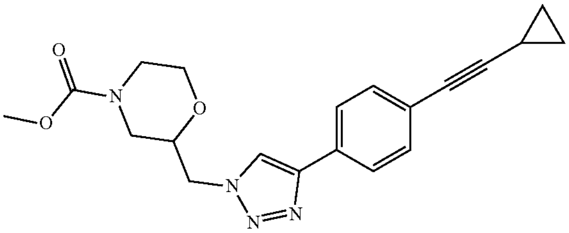 [SMILES: COC(=O)N1CCOC(Cn2cc(-c3ccc(C#CC4CC4)cc3)nn2)C1] |
| I-352 | 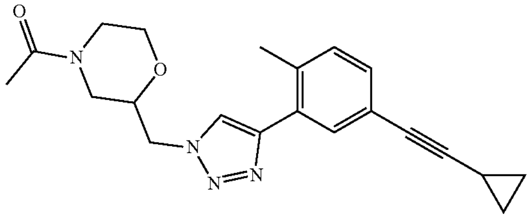 [SMILES: CC(=O)N1CCOC(Cn2cc(-c3cc(C#CC4CC4)ccc3C)nn2)C1] |
| I-353 | 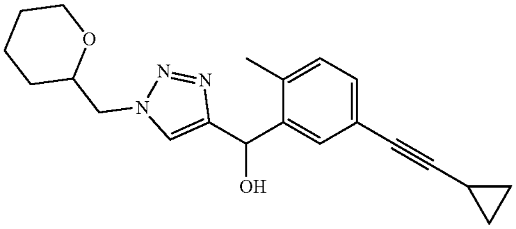 [SMILES: Cc1ccc(C#CC2CC2)cc1C(O)c1cn(CC2CCCCO2)nn1] |
| I-354 | 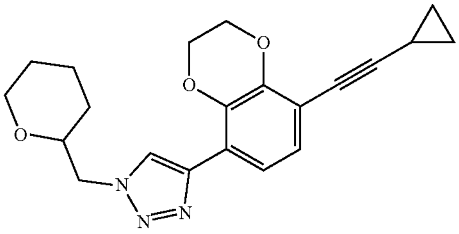 [SMILES: C(#CC1CC1)c1ccc(-c2cn(CC3CCCCO3)nn2)c2c1OCCO2] |
| I-355 | 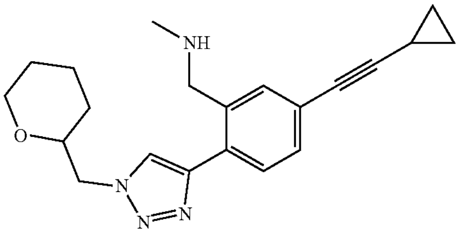 [SMILES: CNCc1cc(C#CC2CC2)ccc1-c1cn(CC2CCCCO2)nn1] |
| I-356 | 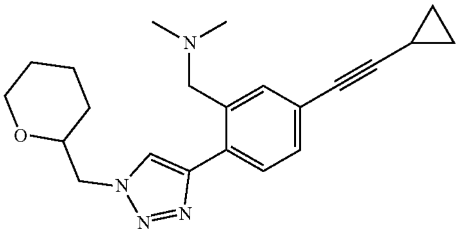 [SMILES: CN(C)Cc1cc(C#CC2CC2)ccc1-c1cn(CC2CCCCO2)nn1] |

TABLE 1-continued
| Selected Compounds | |
|---|---|
| Compound | Structure |
| I-357 | 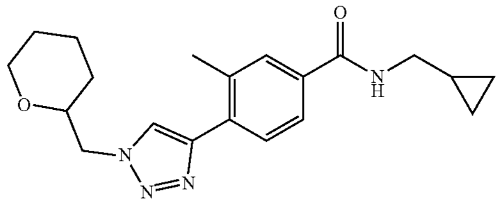 [SMILES: Cc1cc(C(=O)NCC2CC2)ccc1-c1cn(CC2CCCCO2)nn1] |
| I-358 | 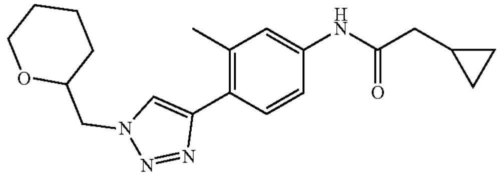 [SMILES: Cc1cc(NC(=O)CC2CC2)ccc1-c1cn(CC2CCCCO2)nn1] |
| I-359 | 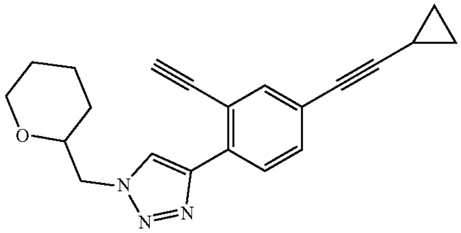 [SMILES: C#Cc1cc(C#CC2CC2)ccc1-c1cn(CC2CCCCO2)nn1] |
| I-360 | 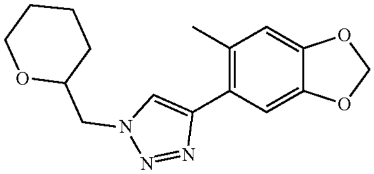 [SMILES: Cc1cc2c(cc1-c1cn(CC3CCCCO3)nn1)OCO2] |
| I-361 | 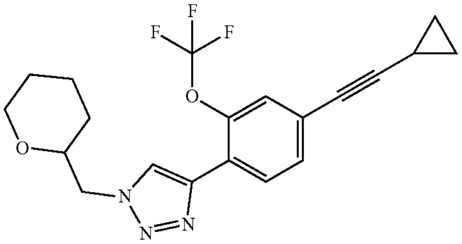 [SMILES: FC(F)(F)Oc1cc(C#CC2CC2)ccc1-c1cn(CC2CCCCO2)nn1] |
| I-362 | 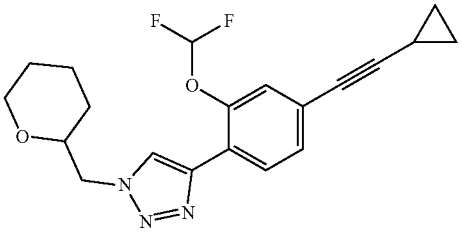 [SMILES: FC(F)Oc1cc(C#CC2CC2)ccc1-c1cn(CC2CCCCO2)nn1] |
| I-363 | 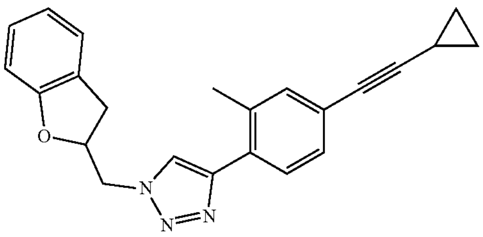 [SMILES: Cc1cc(C#CC2CC2)ccc1-c1cn(CC2Cc3ccccc3O2)nn1] |

TABLE 1-continued
| Selected Compounds | |
|---|---|
| Compound | Structure |
| I-364 | 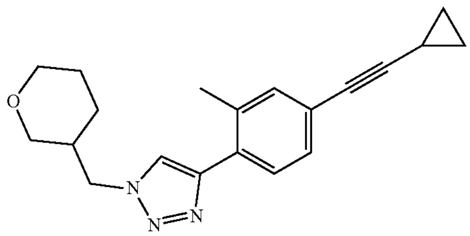 [SMILES: Cc1cc(C#CC2CC2)ccc1-c1cn(CC2CCCOC2)nn1] |
| I-365 | 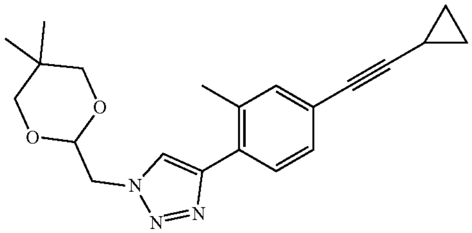 [SMILES: Cc1cc(C#CC2CC2)ccc1-c1cn(CC2OCC(C)(C)CO2)nn1] |
| I-366 | 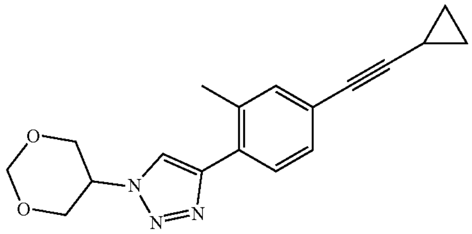 [SMILES: Cc1cc(C#CC2CC2)ccc1-c1cn(C2COCOC2)nn1] |
| I-367 | 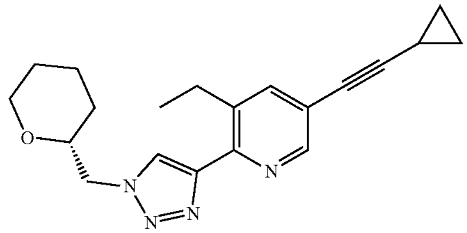 [SMILES: CCc1cc(C#CC2CC2)cnc1-c1cn(C[C@H]2CCCCO2)nn1] |
| I-368 | 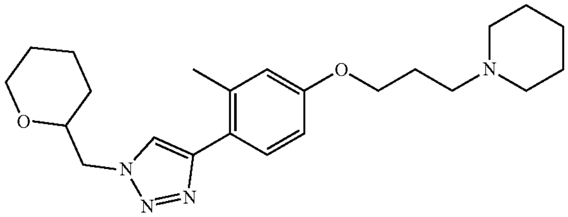 [SMILES: Cc1cc(OCCCN2CCCCC2)ccc1-c1cn(CC2CCCCO2)nn1] |
| I-369 | 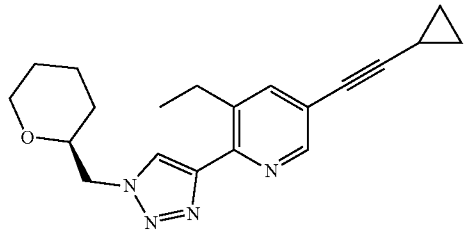 [SMILES: CCc1cc(C#CC2CC2)cnc1-c1cn(C[C@@H]2CCCCO2)nn1] |

TABLE 1-continued
| Selected Compounds | |
|---|---|
| Compound | Structure |
| I-370 | 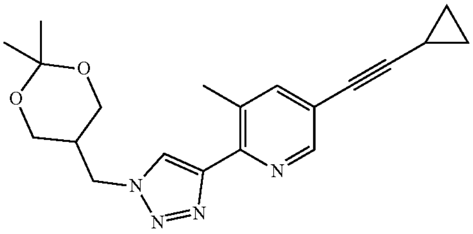 [SMILES: Cc1cc(C#CC2CC2)cnc1-c1cn(CC2COC(C)(C)OC2)nn1] |
| I-371 | 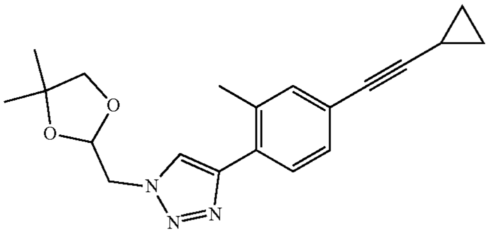 [SMILES: Cc1cc(C#CC2CC2)ccc1-c1cn(CC2OCC(C)(C)O2)nn1] |
| I-372 | 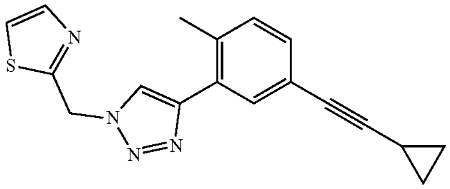 [SMILES: Cc1ccc(C#CC2CC2)cc1-c1cn(Cc2nccs2)nn1] |
| I-373 | 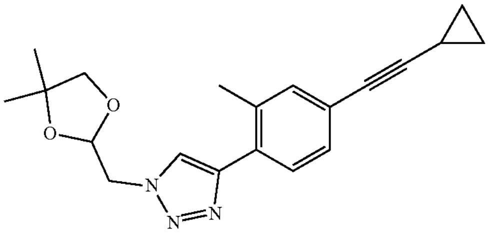 [SMILES: Cc1cc(C#CC2CC2)ccc1-c1cn(CC2OCC(C)(C)O2)nn1] |
| I-374 | 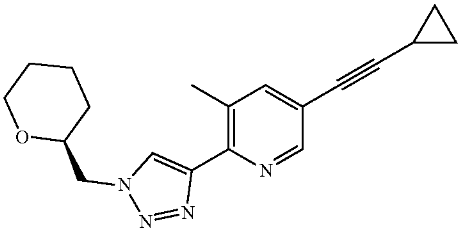 [SMILES: Cc1cc(C#CC2CC2)cnc1-c1cn(C[C@@H]2CCCCO2)nn1] |
| I-375 | 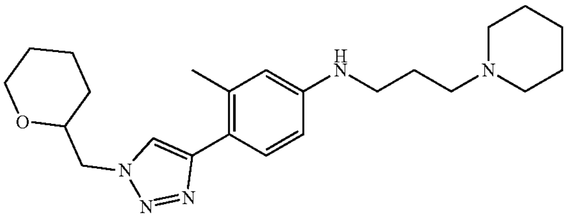 [SMILES: Cc1cc(NCCCN2CCCCC2)ccc1-c1cn(CC2CCCCO2)nn1] |

TABLE 1-continued
| Selected Compounds | |
|---|---|
| Compound | Structure |
| I-376 | 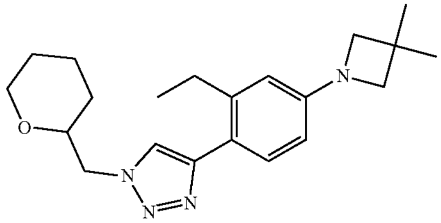 [SMILES: CCc1cc(N2CC(C)(C)C2)ccc1-c1cn(CC2CCCCO2)nn1] |
| I-377 | 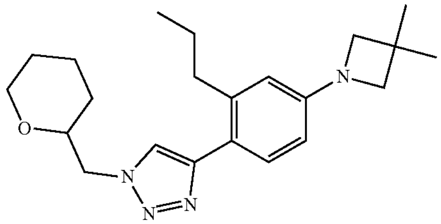 [SMILES: CCCc1cc(N2CC(C)(C)C2)ccc1-c1cn(CC2CCCCO2)nn1] |
| I-378 | 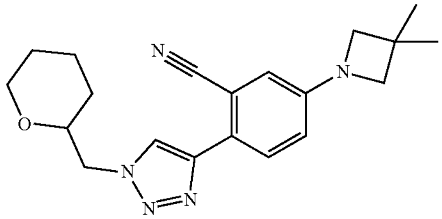 [SMILES: CC1(C)CN(c2ccc(-c3cn(CC4CCCCO4)nn3)c(C#N)c2)C1] |
| I-379 | 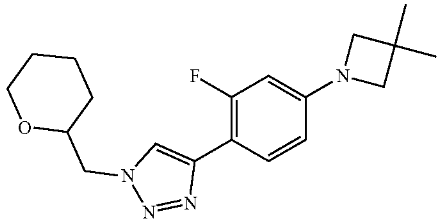 [SMILES: CC1(C)CN(c2ccc(-c3cn(CC4CCCCO4)nn3)c(F)c2)C1] |
| I-380 | 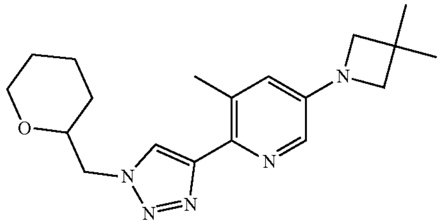 |
| I-381 | 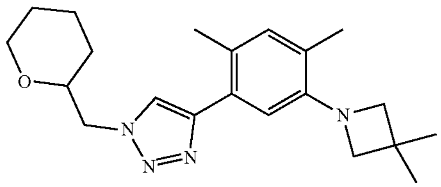 |
| I-382 | 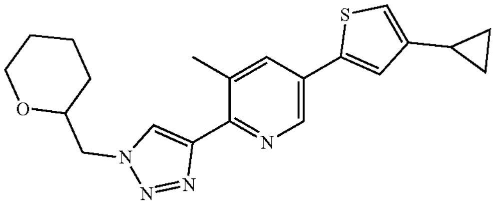 [SMILES: Cc1cc(-c2cc(C3CC3)cs2)cnc1-c1cn(CC2CCCCO2)nn1] |

TABLE 1-continued
| Selected Compounds | |
|---|---|
| Compound | Structure |
| I-383 | 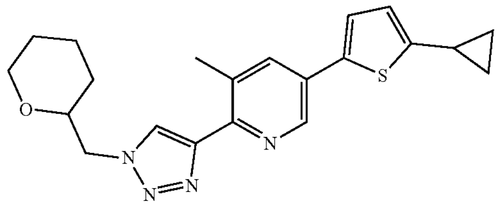 [SMILES: Cc1cc(-c2ccc(C3CC3)s2)cnc1-c1cn(CC2CCCCO2)nn1] |
| I-384 | 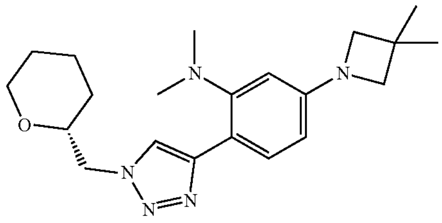 [SMILES: CN(C)c1cc(N2CC(C)(C)C2)ccc1-c1cn(C[C@H]2CCCCO2)nn1] |
| I-385 | 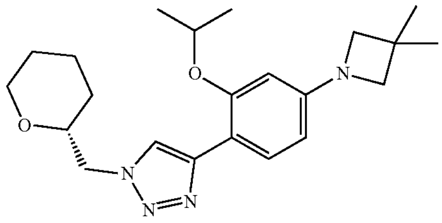 [SMILES: CC(C)Oc1cc(N2CC(C)(C)C2)ccc1-c1cn(C[C@H]2CCCCO2)nn1] |
| I-386 | 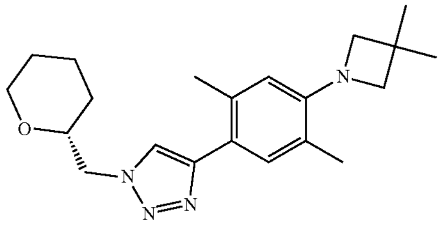 |
| I-387 | 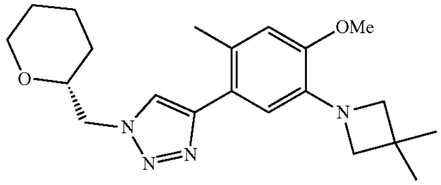 |
| I-388 | 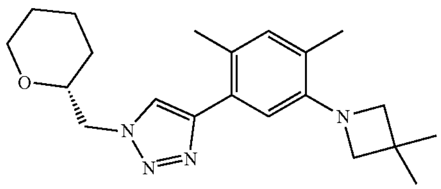 |
| I-389 | 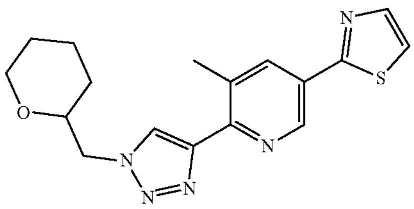 [SMILES: Cc1cc(-c2nccs2)cnc1-c1cn(CC2CCCCO2)nn1] |

TABLE 1-continued
| Selected Compounds | |
|---|---|
| Compound | Structure |
| I-390 | 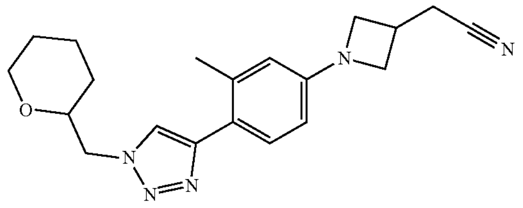 |
| I-391 | 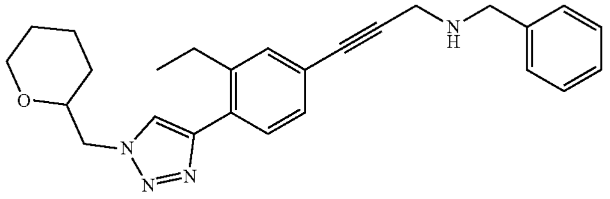 [SMILES: CCc1cc(C#CCNCc2ccccc2)ccc1-c1cn(CC2CCCCO2)nn1] |
| I-392 | 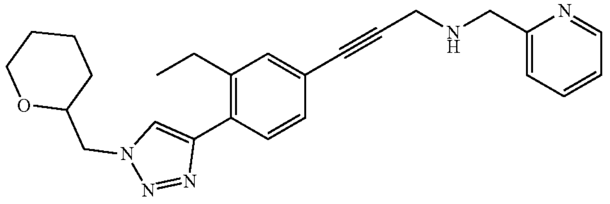 [SMILES: CCc1cc(C#CCNCc2ccccn2)ccc1-c1cn(CC2CCCCO2)nn1] |
| I-393 | 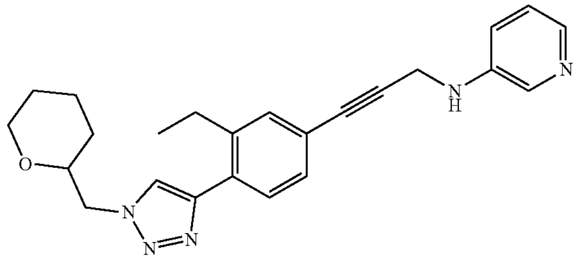 [SMILES: CCc1cc(C#CCNc2cccnc2)ccc1-c1cn(CC2CCCCO2)nn1] |
| I-394 | 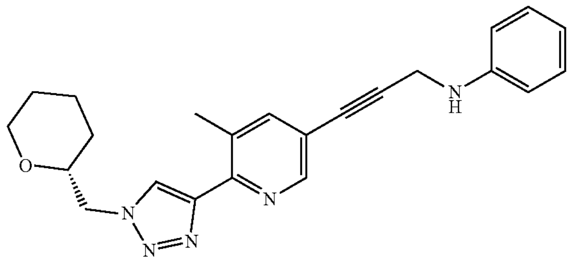 [SMILES: Cc1cc(C#CCNc2ccccc2)cnc1-c1cn(C[C@H]2CCCCO2)nn1] |
| I-395 | 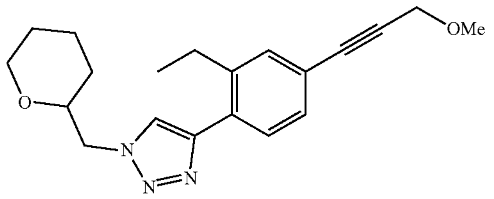 [SMILES: CCc1cc(C#CCOC)ccc1-c1cn(CC2CCCCO2)nn1] |

TABLE 1-continued
| Selected Compounds | |
|---|---|
| Compound | Structure |
| I-396 | 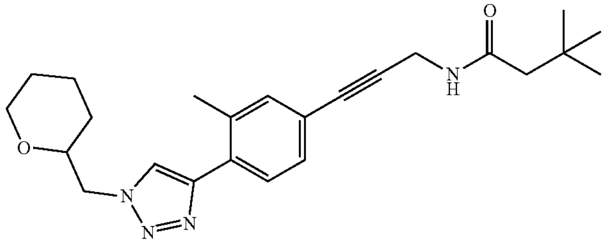 [SMILES: Cc1cc(C#CCNC(=O)CC(C)(C)C)ccc1-c1cn(CC2CCCCO2)nn1] |
| I-397 | 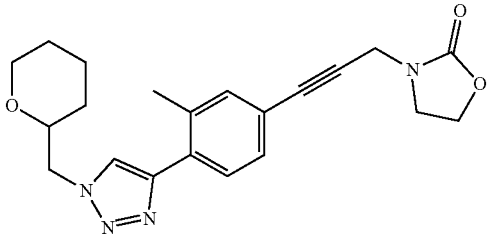 [SMILES: Cc1cc(C#CCN2CCOC2=O)ccc1-c1cn(CC2CCCCO2)nn1] |
| I-398 | 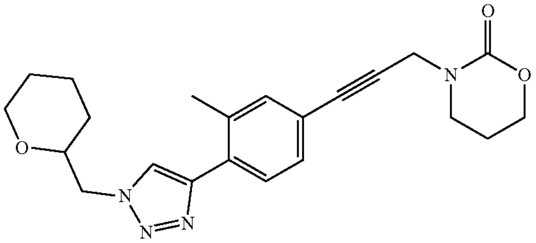 [SMILES: Cc1cc(C#CCN2CCCOC2=O)ccc1-c1cn(CC2CCCCO2)nn1] |
| I-400 | 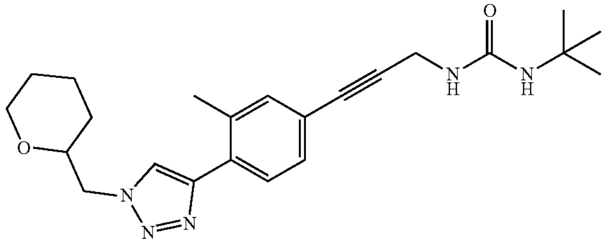 [SMILES: Cc1cc(C#CCNC(=O)NC(C)(C)C)ccc1-c1cn(CC2CCCCO2)nn1] |
| I-401 | 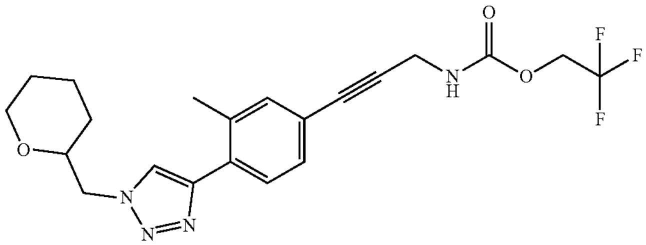 [SMILES: Cc1cc(C#CCNC(=O)OCC(F)(F)F)ccc1-c1cn(CC2CCCCO2)nn1] |
| I-402 | 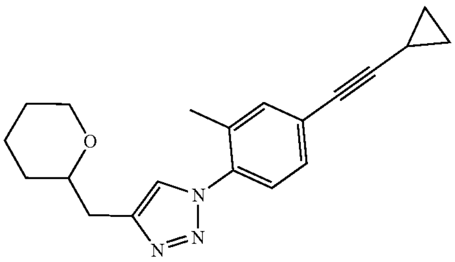 [SMILES: Cc1cc(C#CC2CC2)ccc1-n1cc(CC2CCCCO2)nn1] |

TABLE 1-continued
| Selected Compounds | |
|---|---|
| Compound | Structure |
| I-403 | 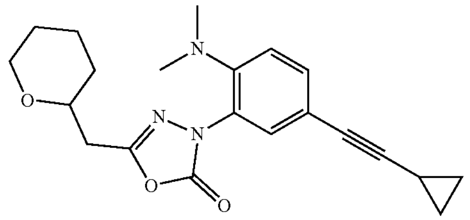 [SMILES: CN(C)c1ccc(C#CC2CC2)cc1-n1nc(CC2CCCCO2)oc1=O] |
| I-404 | 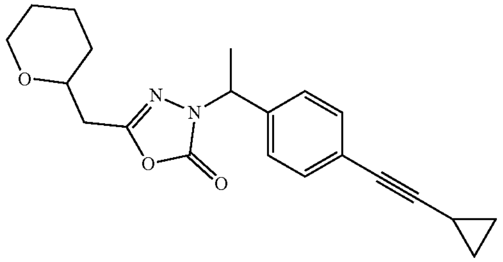 [SMILES: CC(c1ccc(C#CC2CC2)cc1)n1nc(CC2CCCCO2)oc1=O] |
| I-405 | 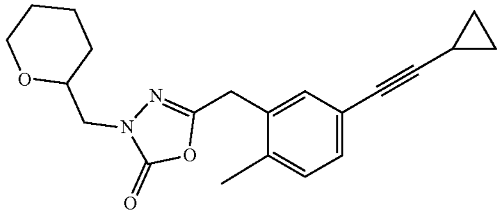 [SMILES: Cc1ccc(C#CC2CC2)cc1Cc1nn(CC2CCCCO2)c(=O)o1] |
| I-406 | 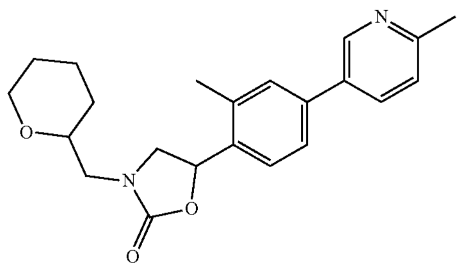 [SMILES: Cc1ccc(-c2ccc(C3CN(CC4CCCCO4)C(=O)O3)c(C)c2)cn1] |
| I-407 | 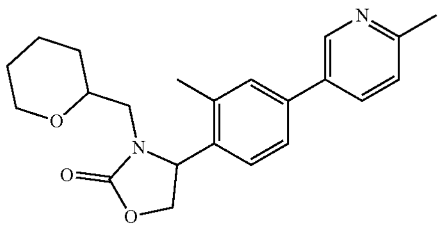 [SMILES: Cc1ccc(-c2ccc(C3COC(=O)N3CC3CCCCO3)c(C)c2)cn1] |
| I-408 | 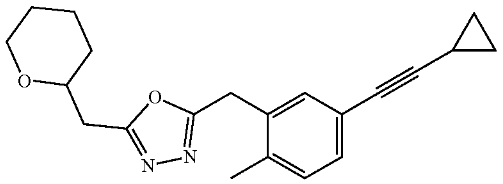 [SMILES: Cc1ccc(C#CC2CC2)cc1Cc1nnc(CC2CCCCO2)o1] |

TABLE 1-continued
| Selected Compounds | |
|---|---|
| Compound | Structure |
| I-409 | 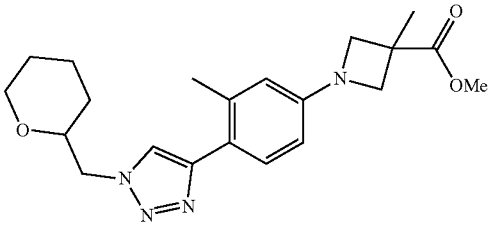 [SMILES: COC(=O)C1(C)CN(c2ccc(-c3cn(CC4CCCCO4)nn3)c(C)c2)C1] |
| I-410 | 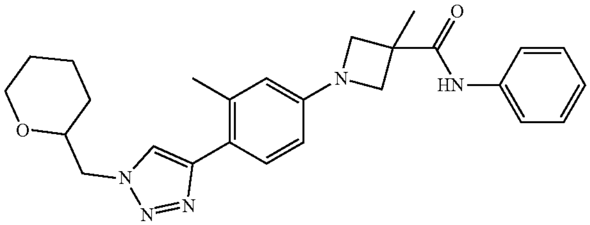 [SMILES: Cc1cc(N2CC(C)(C(=O)Nc3ccccc3)C2)ccc1-c1cn(CC2CCCCO2)nn1] |
| I-411 | 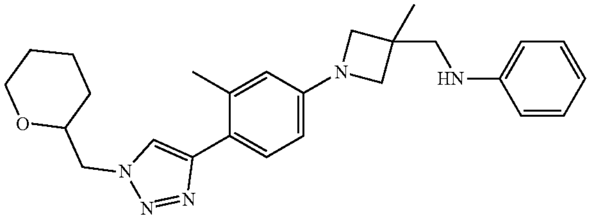 [SMILES: Cc1cc(N2CC(C)(CNc3ccccc3)C2)ccc1-c1cn(CC2CCCCO2)nn1] |
| I-412 | 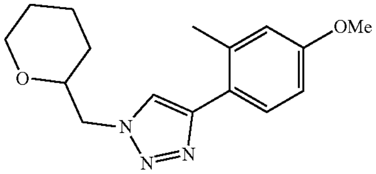 [SMILES: COc1ccc(-c2cn(CC3CCCCO3)nn2)c(C)c1] |
| I-413 | 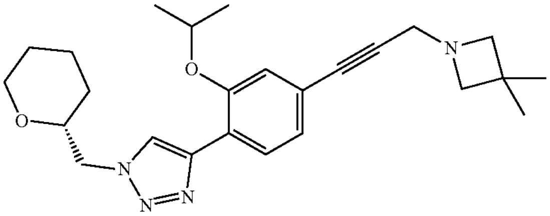 [SMILES: CC(C)Oc1cc(C#CCN2CC(C)(C)C2)ccc1-c1cn(C[C@H]2CCCCO2)nn1] |
| I-414 | 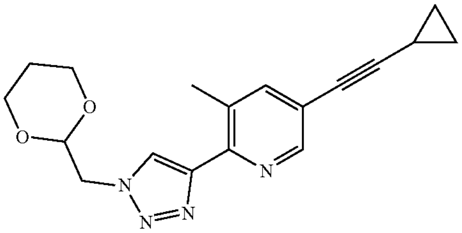 |
| I-415 | 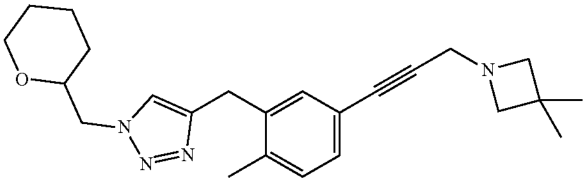 [SMILES: Cc1ccc(C#CCN2CC(C)(C)C2)cc1Cc1cn(CC2CCCCO2)nn1] |

TABLE 1-continued
| Selected Compounds | |
|---|---|
| Compound | Structure |
| I-416 | 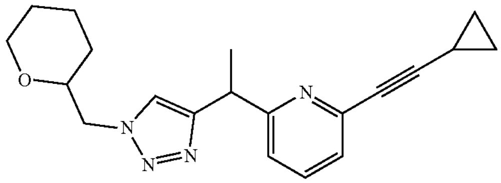 [SMILES: CC(c1cn(CC2CCCCO2)nn1)c1cccc(C#CC2CC2)n1] |
| I-417 | 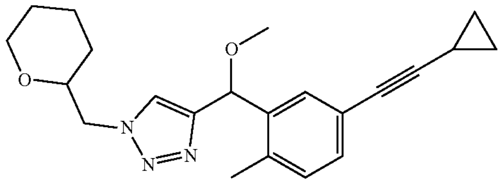 [SMILES: COC(c1cn(CC2CCCCO2)nn1)c1cc(C#CC2CC2)ccc1C] |
| I-418 | 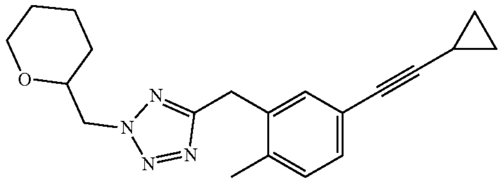 [SMILES: Cc1ccc(C#CC2CC2)cc1Cc1nnn(CC2CCCCO2)n1] |
| I-419 | 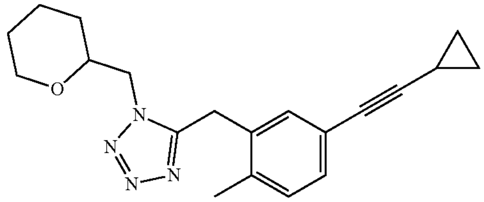 [SMILES: Cc1ccc(C#CC2CC2)cc1Cc1nnnn1CC1CCCCO1] |
| I-420 | 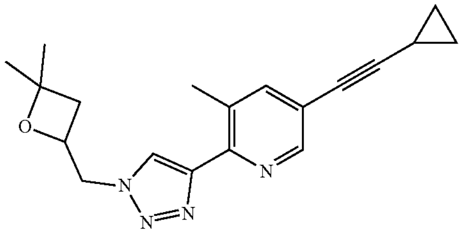 [SMILES: Cc1cc(C#CC2CC2)cnc1-c1cn(CC2CC(C)(C)O2)nn1] |
| I-421 | 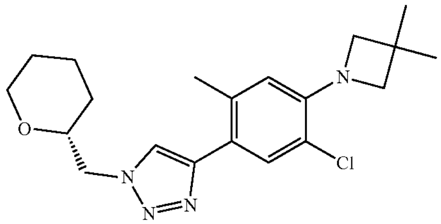 |
| I-422 | 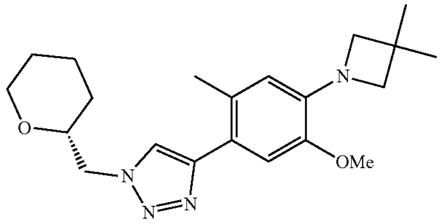 [SMILES: COc1cc(-c2cn(C[C@H]3CCCCO3)nn2)c(C)cc1N1CC(C)(C)C1] |

TABLE 1-continued
| Selected Compounds | |
|---|---|
| Compound | Structure |
| I-423 | 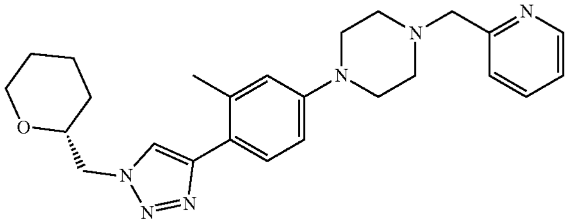 [SMILES: Cc1cc(N2CCN(Cc3ccccn3)CC2)ccc1-c1cn(C[C@H]2CCCCO2)nn1] |
| I-424 | 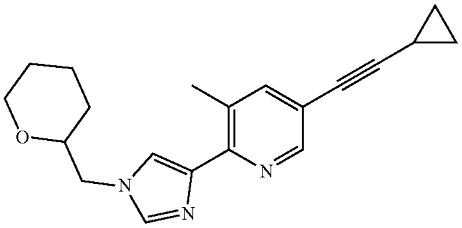 [SMILES: Cc1cc(C#CC2CC2)cnc1-c1cn(CC2CCCCO2)cn1] |
| I-425 | 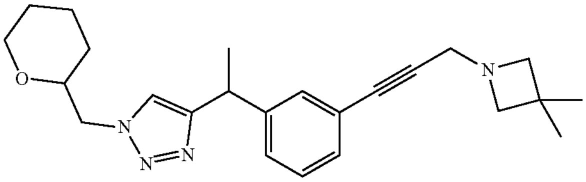 [SMILES: CC(c1cccc(C#CCN2CC(C)(C)C2)c1)c1cn(CC2CCCCO2)nn1] |
| I-426 | 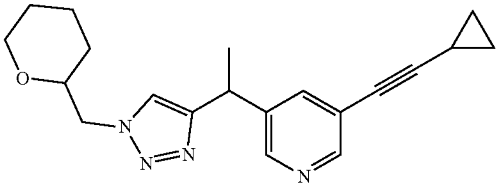 [SMILES: CC(c1cncc(C#CC2CC2)c1)c1cn(CC2CCCCO2)nn1] |
| I-427 | 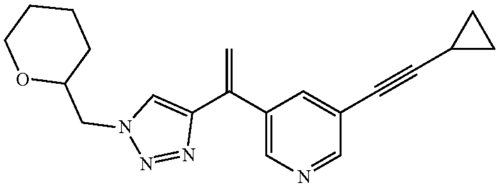 |
| I-428 | 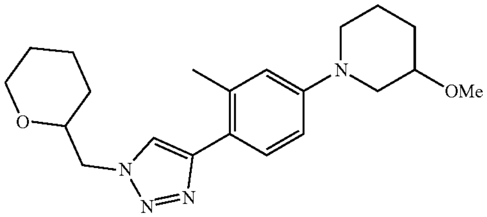 [SMILES: COC1CCCN(c2ccc(-c3cn(CC4CCCCO4)nn3)c(C)c2)C1] |
| I-429 | 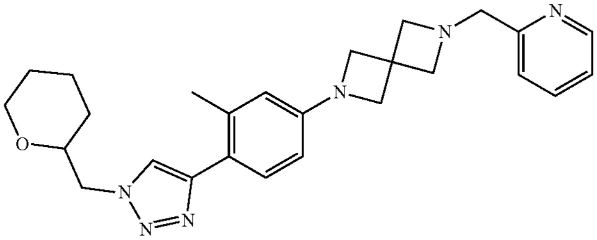 [SMILES: Cc1cc(N2CC3(CN(Cc4ccccn4)C3)C2)ccc1-c1cn(CC2CCCCO2)nn1] |

TABLE 1-continued
| Selected Compounds | |
|---|---|
| Compound | Structure |
| I-430 | 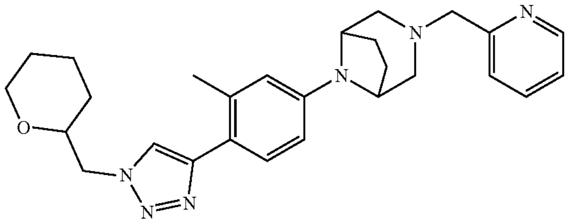 [SMILES: Cc1cc(N2C3CCC2CN(Cc2ccccn2)C3)ccc1-c1cn(CC2CCCCO2)nn1] |
| I-431 | 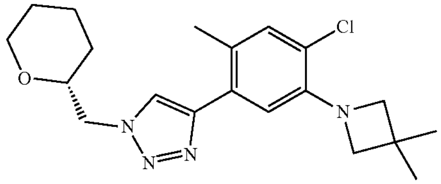 |
| I-432 | 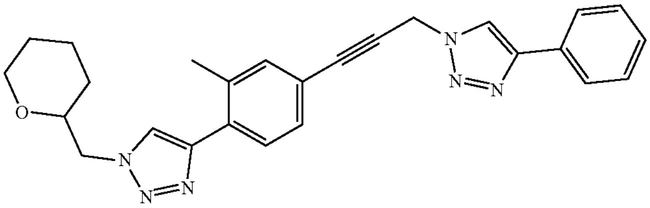 [SMILES: Cc1cc(C#CCn2cc(-c3ccccc3)nn2)ccc1-c1cn(CC2CCCCO2)nn1] |
| I-433 | 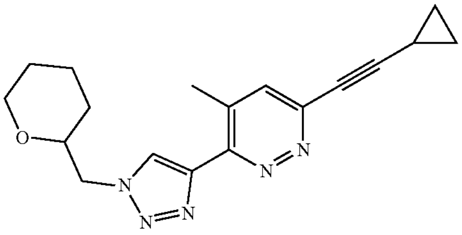 [SMILES: Cc1cc(C#CC2CC2)nnc1-c1cn(CC2CCCCO2)nn1] |
| I-434 | 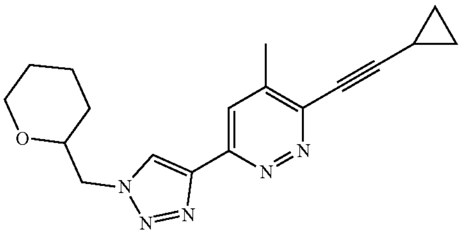 [SMILES: Cc1cc(-c2cn(CC3CCCCO3)nn2)nnc1C#CC1CC1] |
| I-435 | 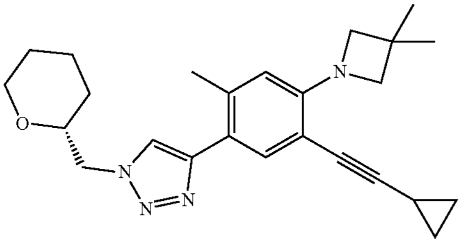 [SMILES: Cc1cc(N2CC(C)(C)C2)c(C#CC2CC2)cc1-c1cn(C[C@H]2CCCCO2)nn1] |

TABLE 1-continued
| Selected Compounds | |
|---|---|
| Compound | Structure |
| I-436 | 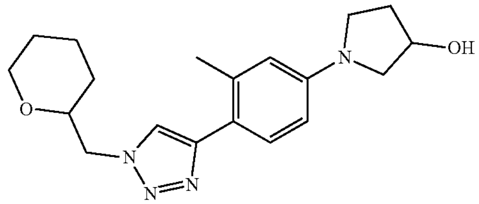 [SMILES: Cc1cc(N2CCC(O)C2)ccc1-c1cn(CC2CCCCO2)nn1] |
| I-437 | 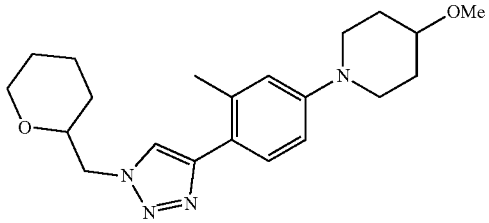 [SMILES: COC1CCN(c2ccc(-c3cn(CC4CCCCO4)nn3)c(C)c2)CC1] |
| I-438 | 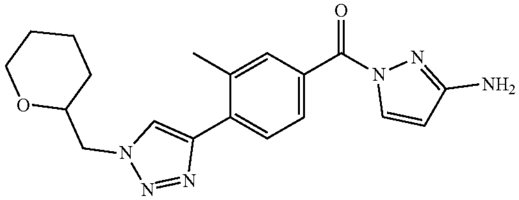 [SMILES: Cc1cc(C(=O)n2ccc(N)n2)ccc1-c1cn(CC2CCCCO2)nn1] |
| I-439 | 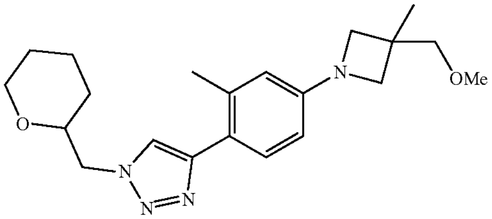 [SMILES: COCC1(C)CN(c2ccc(-c3cn(CC4CCCCO4)nn3)c(C)c2)C1] |
| I-440 | 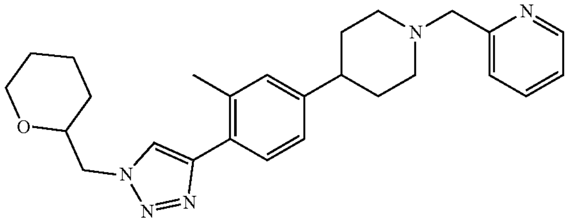 [SMILES: Cc1cc(C2CCN(Cc3ccccn3)CC2)ccc1-c1cn(CC2CCCCO2)nn1] |
| I-441 | 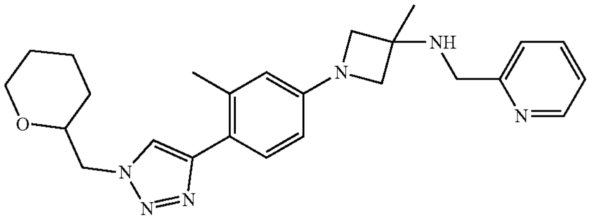 |

TABLE 1-continued
| Selected Compounds | |
|---|---|
| Compound | Structure |
| I-442 | 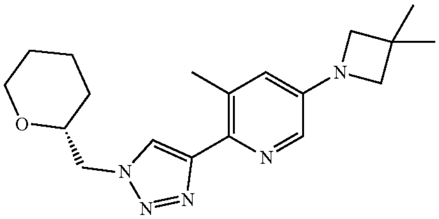 [SMILES: Cc1cc(N2CC(C)(C)C2)cnc1-c1cn(C[C@H]2CCCCO2)nn1] |
| I-443 | 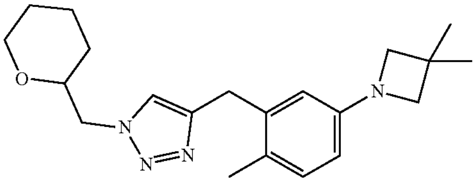 [SMILES: Cc1ccc(N2CC(C)(C)C2)cc1Cc1cn(CC2CCCCO2)nn1] |
| I-444 | 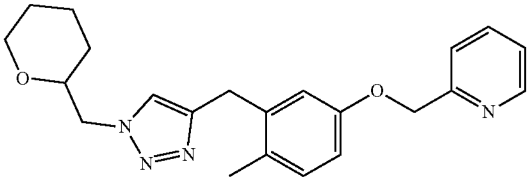 [SMILES: Cc1ccc(OCc2ccccn2)cc1Cc1cn(CC2CCCCO2)nn1] |
| I-445 | 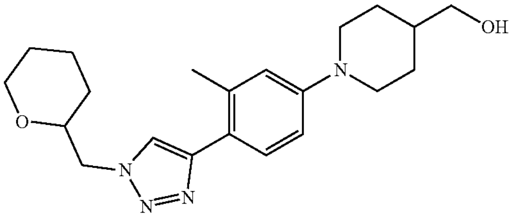 [SMILES: Cc1cc(N2CCC(CO)CC2)ccc1-c1cn(CC2CCCCO2)nn1] |
| I-446 | 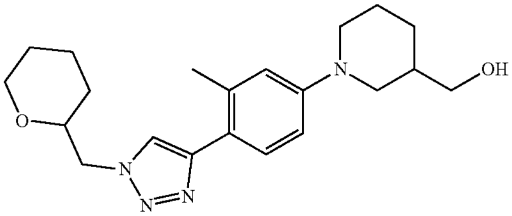 [SMILES: Cc1cc(N2CCCC(CO)C2)ccc1-c1cn(CC2CCCCO2)nn1] |
| I-447 | 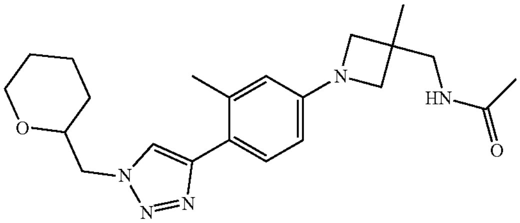 [SMILES: CC(=O)NCC1(C)CN(c2ccc(-c3cn(CC4CCCCO4)nn3)c(C)c2)C1] |
| I-448 | 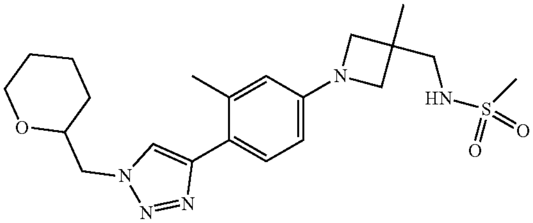 [SMILES: Cc1cc(N2CC(C)(CNS(C)(=O)=O)C2)ccc1-c1cn(CC2CCCCO2)nn1] |

TABLE 1-continued
| Selected Compounds | |
|---|---|
| Compound | Structure |
| I-449 | 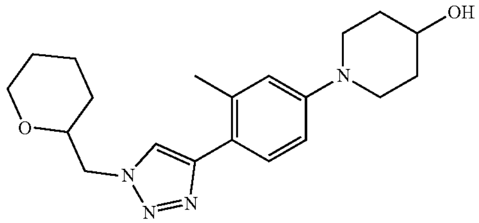 [SMILES: Cc1cc(N2CCC(O)CC2)ccc1-c1cn(CC2CCCCO2)nn1] |
| I-450 | 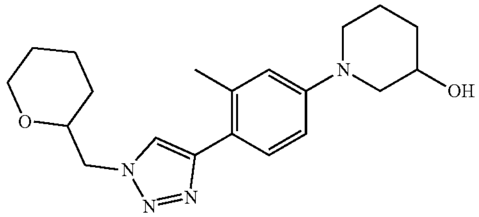 [SMILES: Cc1cc(N2CCCC(O)C2)ccc1-c1cn(CC2CCCCO2)nn1] |
| I-451 | 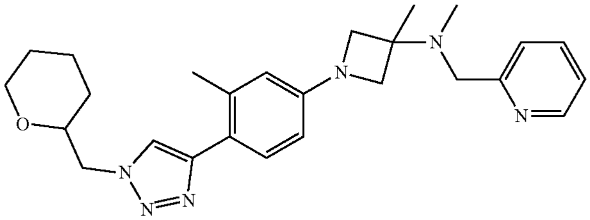 |
| I-452 | 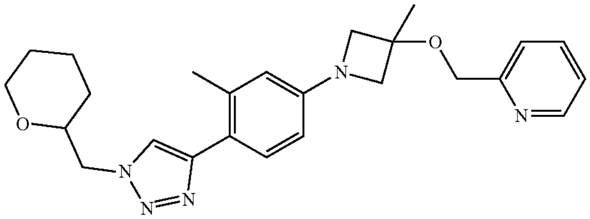 [SMILES: Cc1cc(N2CC(C)(N(C)Cc3ccccn3)C2)ccc1-c1cn(CC2CCCCO2)nn1] |
| I-453 | 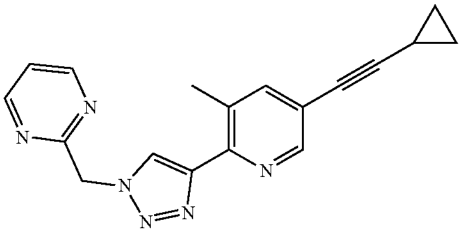 [SMILES: Cc1cc(C#CC2CC2)cnc1-c1cn(Cc2ncccn2)nn1] |
| I-454 | 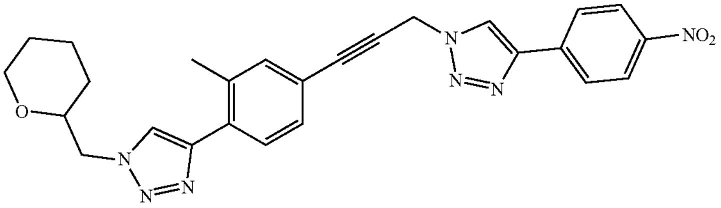 [SMILES: Cc1cc(C#CCn2cc(-c3ccc([N+](=O)[O-])cc3)nn2)ccc1-c1cn(CC2CCCCO2)nn1] |

TABLE 1-continued
| Selected Compounds | |
|---|---|
| Compound | Structure |
| I-455 | 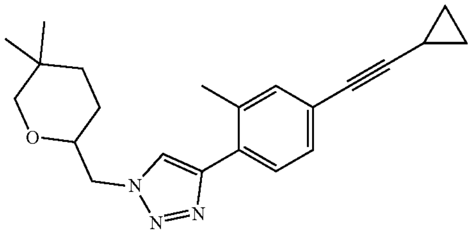 [SMILES: Cc1cc(C#CC2CC2)ccc1-c1cn(CC2CCC(C)(C)CO2)nn1] |
| I-456 | 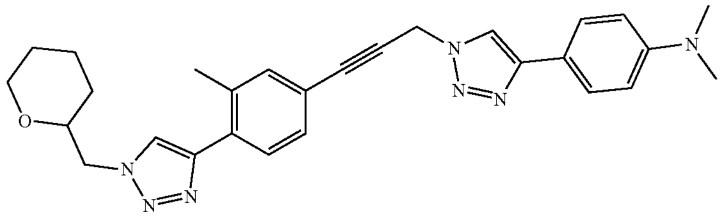 [SMILES: Cc1cc(C#CCn2cc(-c3ccc(N(C)C)cc3)nn2)ccc1-c1cn(CC2CCCCO2)nn1] |
| I-457 | 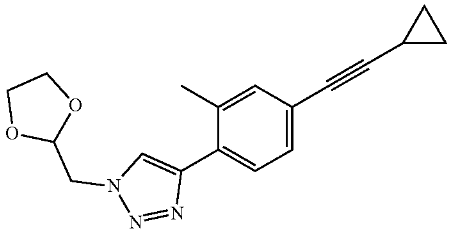 [SMILES: Cc1cc(C#CC2CC2)ccc1-c1cn(CC2OCCO2)nn1] |
| I-458 | 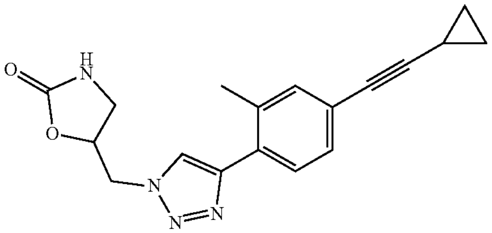 [SMILES: Cc1cc(C#CC2CC2)ccc1-c1cn(CC2CNC(=O)O2)nn1] |
| I-459 | 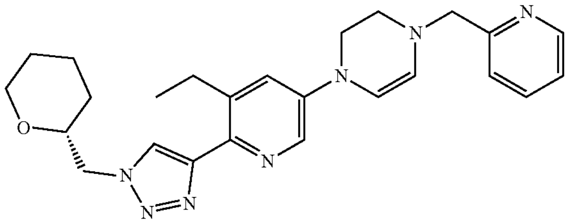 [SMILES: CCc1cc(N2C=CN(Cc3ccccn3)CC2)cnc1-c1cn(C[C@H]2CCCCO2)nn1] |
| I-460 | 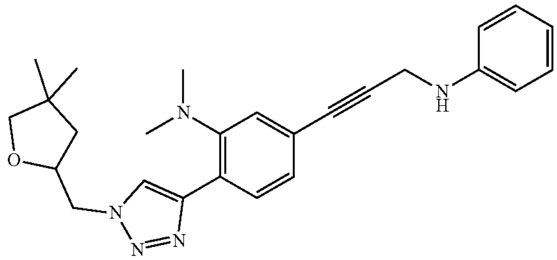 [SMILES: CN(C)c1cc(C#CCNc2ccccc2)ccc1-c1cn(CC2CC(C)(C)CO2)nn1] |

TABLE 1-continued
| Selected Compounds | |
|---|---|
| Compound | Structure |
| I-461 | 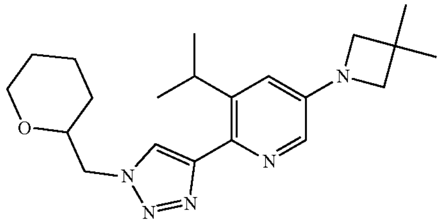 [SMILES: CC(C)c1cc(N2CC(C)(C)C2)cnc1-c1cn(CC2CCCCO2)nn1] |
| I-462 | 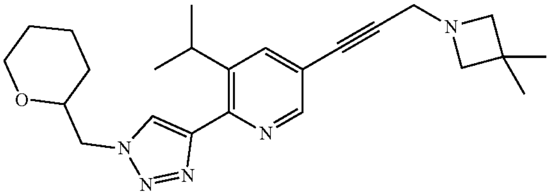 [SMILES: CC(C)c1cc(C#CCN2CC(C)(C)C2)cnc1-c1cn(CC2CCCCO2)nn1] |
| I-463 | 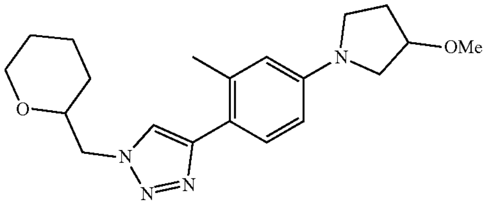 [SMILES: COC1CCN(c2ccc(-c3cn(CC4CCCCO4)nn3)c(C)c2)C1] |
| I-464 | 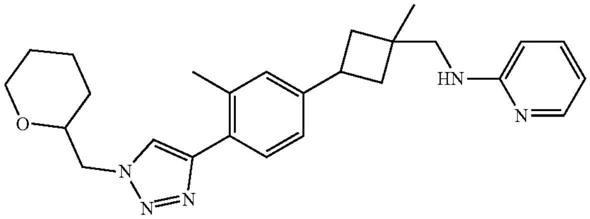 |
| I-465 | 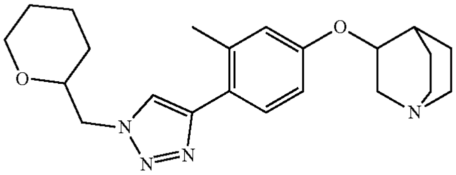 [SMILES: Cc1cc(OC2CN3CCC2CC3)ccc1-c1cn(CC2CCCCO2)nn1] |
| I-466 | 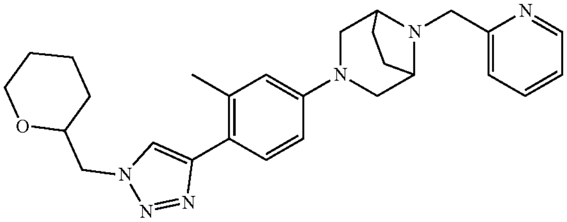 [SMILES: Cc1cc(N2CC3CCC(C2)N3Cc2ccccn2)ccc1-c1cn(CC2CCCCO2)nn1] |
| I-467 | 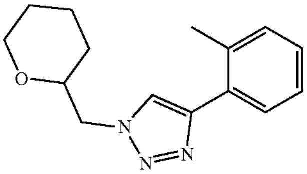 [SMILES: Cc1ccccc1-c1cn(CC2CCCCO2)nn1] |

TABLE 1-continued
| Selected Compounds | |
|---|---|
| Compound | Structure |
| I-468 | 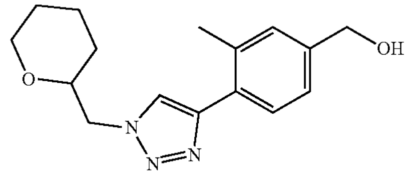 [SMILES: Cc1cc(CO)ccc1-c1cn(CC2CCCCO2)nn1] |
| I-469 | 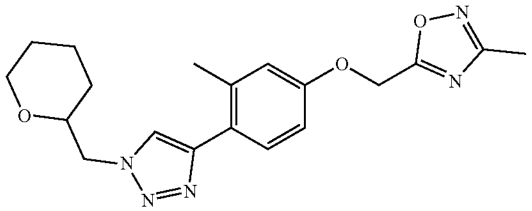 [SMILES: Cc1noc(COc2ccc(-c3cn(CC4CCCCO4)nn3)c(C)c2)n1] |
| I-470 | 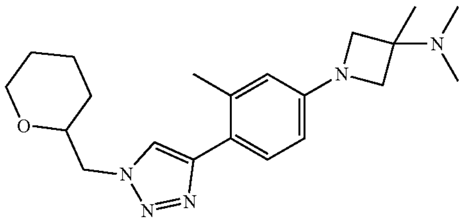 [SMILES: Cc1cc(N2CC(C)(N(C)C)C2)ccc1-c1cn(CC2CCCCO2)nn1] |
| I-471 | 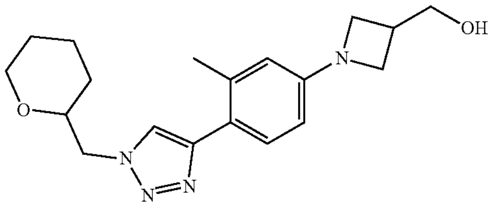 [SMILES: Cc1cc(N2CC(CO)C2)ccc1-c1cn(CC2CCCCO2)nn1] |
| I-472 | 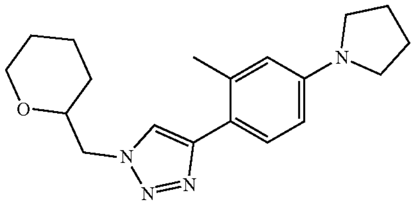 [SMILES: Cc1cc(N2CCCC2)ccc1-c1cn(CC2CCCCO2)nn1] |
| I-473 | 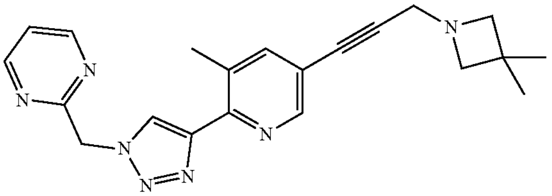 [SMILES: Cc1cc(C#CCN2CC(C)(C)C2)cnc1-c1cn(Cc2ncccn2)nn1] |
| I-474 | 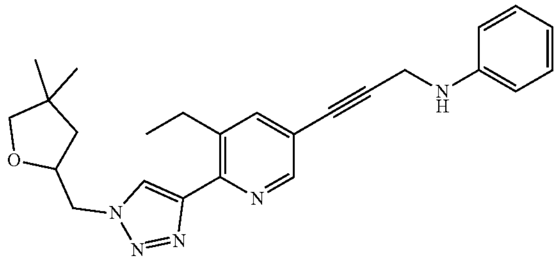 [SMILES: CCc1cc(C#CCNc2ccccc2)cnc1-c1cn(CC2CC(C)(C)CO2)nn1] |

TABLE 1-continued
| Selected Compounds | |
|---|---|
| Compound | Structure |
| I-475 | 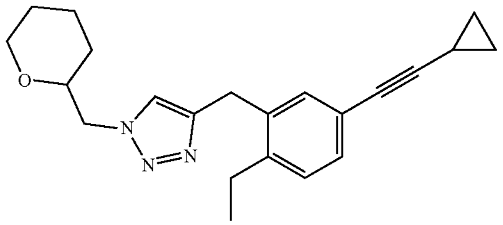 [SMILES: CCc1ccc(C#CC2CC2)cc1Cc1cn(CC2CCCCO2)nn1] |
| I-476 | 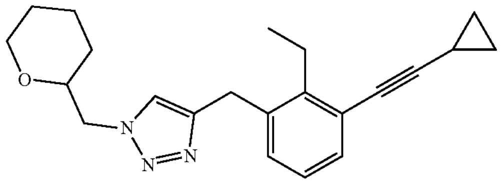 [SMILES: CCc1c(C#CC2CC2)cccc1Cc1cn(CC2CCCCO2)nn1] |
| I-477 | 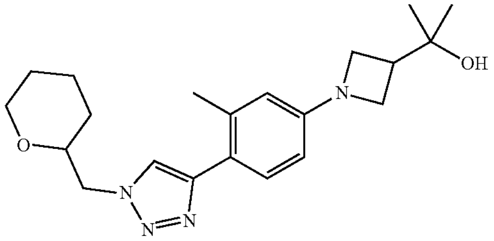 [SMILES: Cc1cc(N2CC(C(C)(C)O)C2)ccc1-c1cn(CC2CCCCO2)nn1] |
| I-478 | 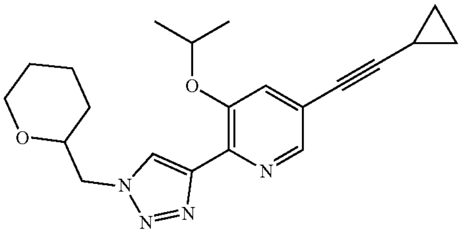 [SMILES: CC(C)Oc1cc(C#CC2CC2)cnc1-c1cn(CC2CCCCO2)nn1] |
| I-479 | 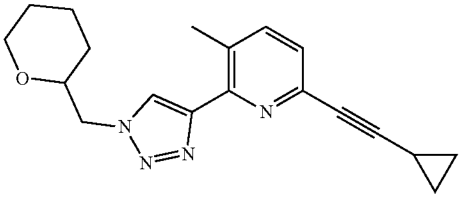 [SMILES: Cc1ccc(C#CC2CC2)nc1-c1cn(CC2CCCCO2)nn1] |
| I-480 | 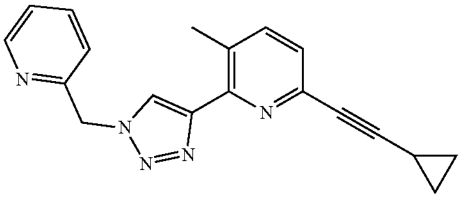 [SMILES: Cc1ccc(C#CC2CC2)nc1-c1cn(Cc2ccccn2)nn1] |
| I-481 | 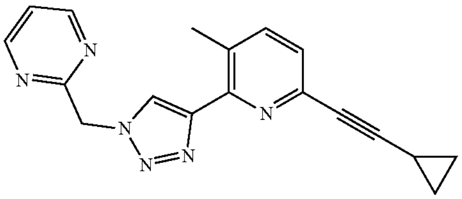 |

TABLE 1-continued
| Selected Compounds | |
|---|---|
| Compound | Structure |
| I-482 | 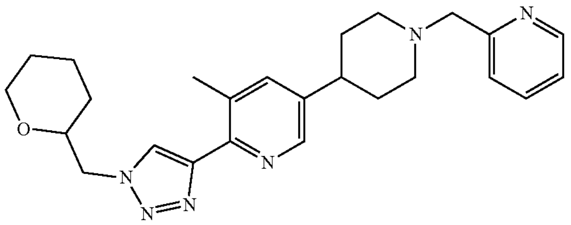 [SMILES: Cc1cc(C2CCN(Cc3ccccn3)CC2)cnc1-c1cn(CC2CCCCO2)nn1] |
| I-483 | 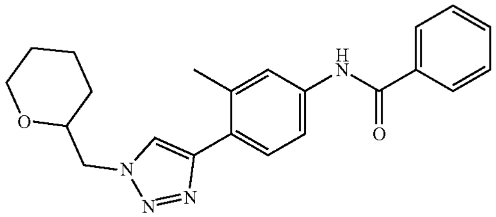 [SMILES: Cc1cc(NC(=O)c2ccccc2)ccc1-c1cn(CC2CCCCO2)nn1] |
| I-484 | 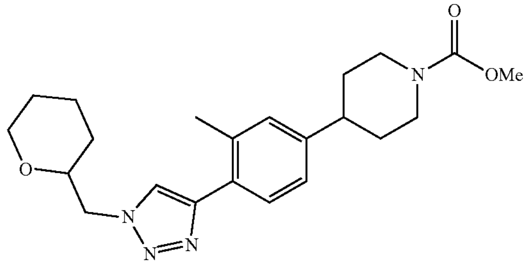 [SMILES: COC(=O)N1CCC(c2ccc(-c3cn(CC4CCCCO4)nn3)c(C)c2)CC1] |
| I-485 | 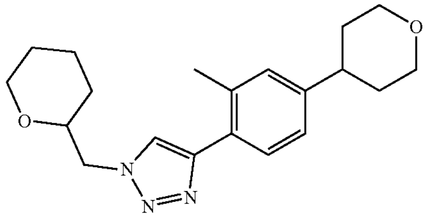 [SMILES: Cc1cc(C2CCOCC2)ccc1-c1cn(CC2CCCCO2)nn1] |
| I-486 | 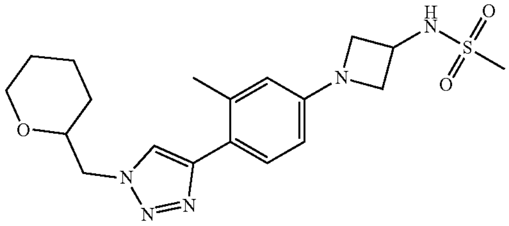 [SMILES: Cc1cc(N2CC(NS(C)(=O)=O)C2)ccc1-c1cn(CC2CCCCO2)nn1] |
| I-487 | 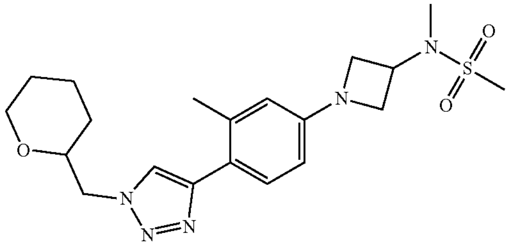 [SMILES: Cc1cc(N2CC(N(C)S(C)(=O)=O)C2)ccc1-c1cn(CC2CCCCO2)nn1] |

TABLE 1-continued
| Selected Compounds | |
|---|---|
| Compound | Structure |
| I-488 | 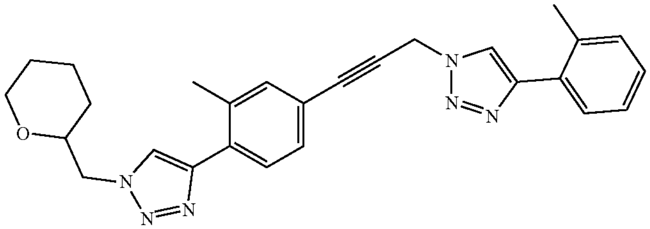 [SMILES: Cc1ccccc1-c1cn(CC#Cc2ccc(-c3cn(CC4CCCCO4)nn3)c(C)c2)nn1] |
| I-489 | 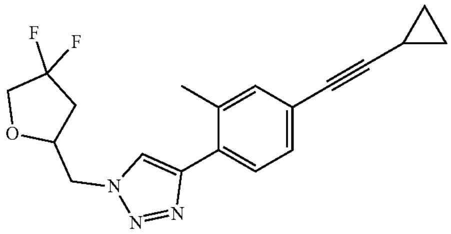 [SMILES: Cc1cc(C#CC2CC2)ccc1-c1cn(CC2CC(F)(F)CO2)nn1] |
| I-490 | 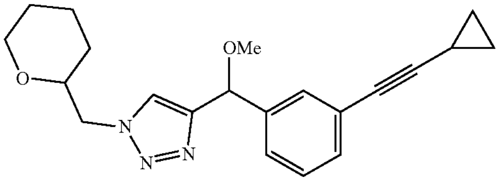 [SMILES: COC(c1cccc(C#CC2CC2)c1)c1cn(CC2CCCCO2)nn1] |
| I-491 | 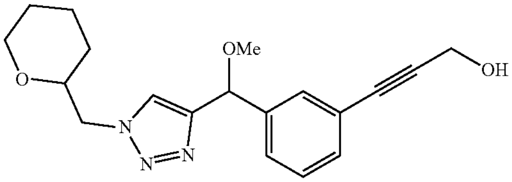 [SMILES: COC(c1cccc(C#CCO)c1)c1cn(CC2CCCCO2)nn1] |
| I-492 | 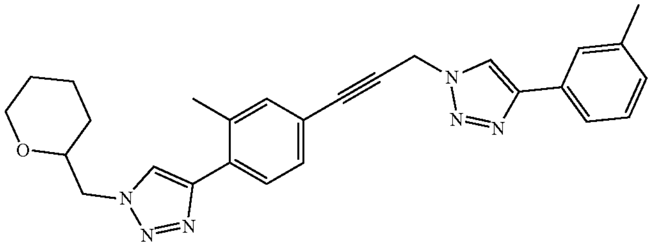 [SMILES: Cc1cccc(-c2cn(CC#Cc3ccc(-c4cn(CC5CCCCO5)nn4)c(C)c3)nn2)c1] |
| I-493 | 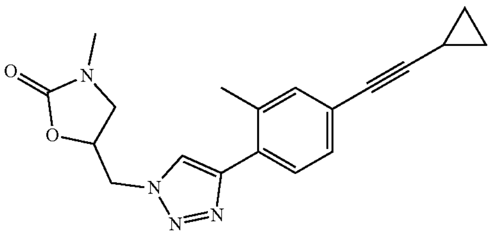 [SMILES: Cc1cc(C#CC2CC2)ccc1-c1cn(CC2CN(C)C(=O)O2)nn1] |

TABLE 1-continued
| Selected Compounds | |
|---|---|
| Compound | Structure |
| I-494 | 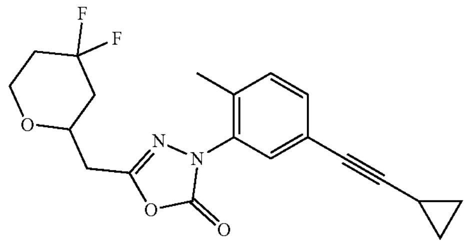 [SMILES: Cc1ccc(C#CC2CC2)cc1-n1nc(CC2CC(F)(F)CCO2)oc1=O] |
| I-495 | 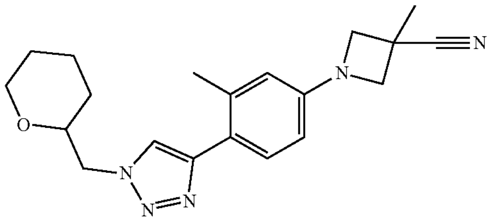 [SMILES: Cc1cc(N2CC(C)(C#N)C2)ccc1-c1cn(CC2CCCCO2)nn1] |
| I-496 | 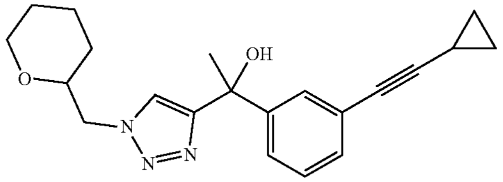 [SMILES: CC(O)(c1cccc(C#CC2CC2)c1)c1cn(CC2CCCCO2)nn1] |
| I-497 | 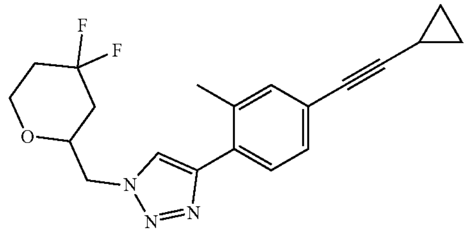 [SMILES: Cc1cc(C#CC2CC2)ccc1-c1cn(CC2CC(F)(F)CCO2)nn1] |
| I-498 | 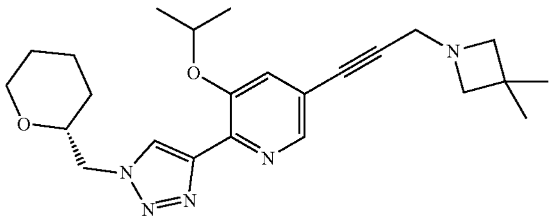 |
| I-499 | 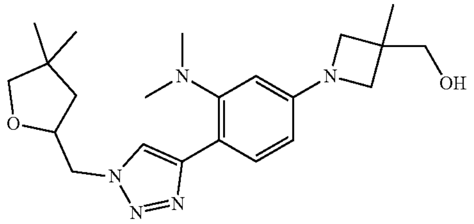 [SMILES: CN(C)c1cc(N2CC(C)(CO)C2)ccc1-c1cn(CC2CC(C)(C)CO2)nn1] |

TABLE 1-continued
| Selected Compounds | |
|---|---|
| Compound | Structure |
| I-500 | 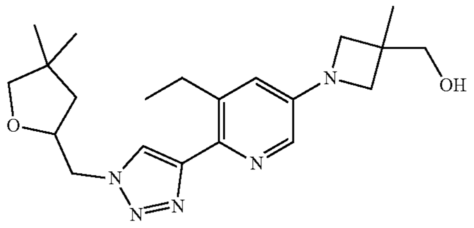 [SMILES: CCc1cc(N2CC(C)(CO)C2)cnc1-c1cn(CC2CC(C)(C)CO2)nn1] |
| I-501 | 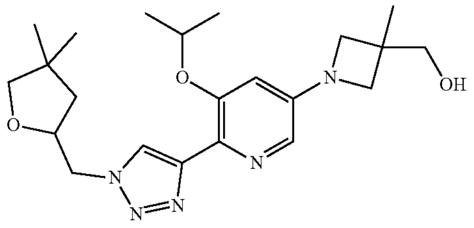 [SMILES: CC(C)Oc1cc(N2CC(C)(CO)C2)cnc1-c1cn(CC2CC(C)(C)CO2)nn1] |
| I-502 | 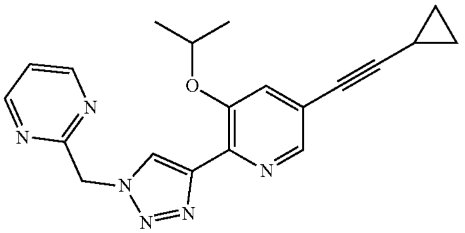 [SMILES: CC(C)Oc1cc(C#CC2CC2)cnc1-c1cn(Cc2ncccn2)nn1] |
| I-503 | 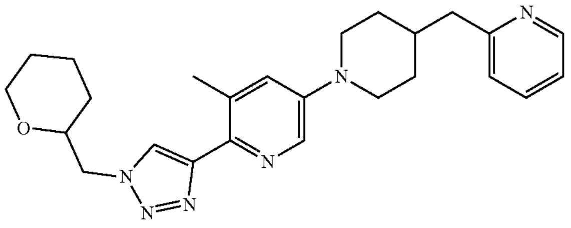 [SMILES: Cc1cc(N2CCC(Cc3ccccn3)CC2)cnc1-c1cn(CC2CCCCO2)nn1] |
| I-504 | 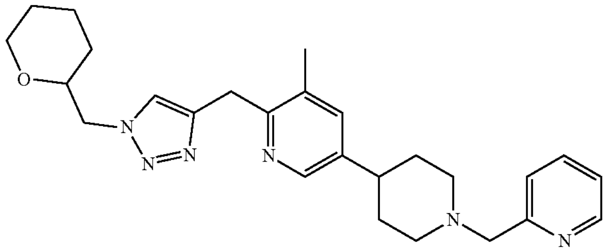 [SMILES: Cc1cc(C2CCN(Cc3ccccn3)CC2)cnc1Cc1cn(CC2CCCCO2)nn1] |
| I-505 | 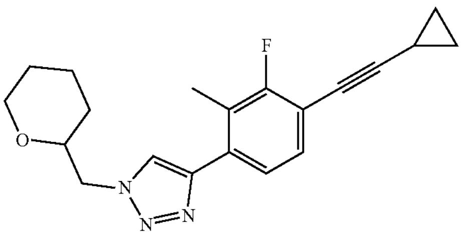 [SMILES: Cc1c(-c2cn(CC3CCCCO3)nn2)ccc(C#CC2CC2)c1F] |

TABLE 1-continued
| Selected Compounds | |
|---|---|
| Compound | Structure |
| I-506 | 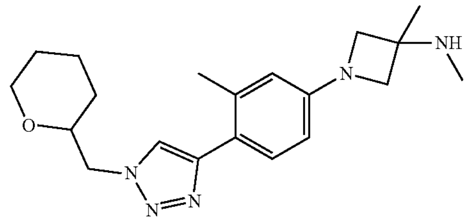 [SMILES: CNC1(C)CN(c2ccc(-c3cn(CC4CCCCO4)nn3)c(C)c2)C1] |
| I-507 | 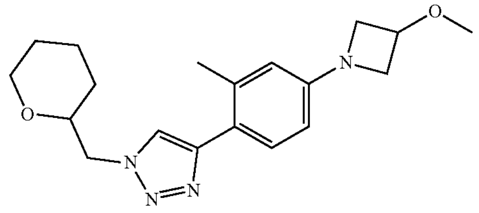 [SMILES: COC1CN(c2ccc(-c3cn(CC4CCCCO4)nn3)c(C)c2)C1] |
| I-508 | 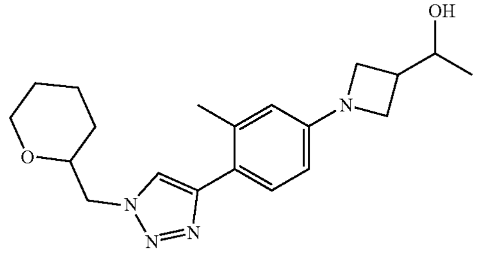 [SMILES: Cc1cc(N2CC(C(C)O)C2)ccc1-c1cn(CC2CCCCO2)nn1] |
| I-509 | 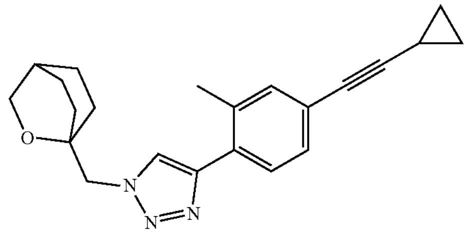 [SMILES: Cc1cc(C#CC2CC2)ccc1-c1cn(CC23CCC(CC2)CO3)nn1] |
| I-510 | 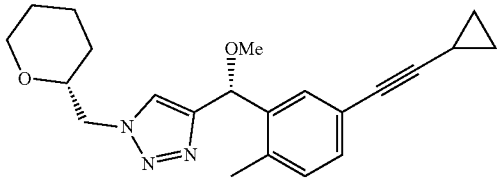 [SMILES: CO[C@@H](c1cn(C[C@H]2CCCCO2)nn1)c1cc(C#CC2CC2)ccc1C] |
| I-511 | 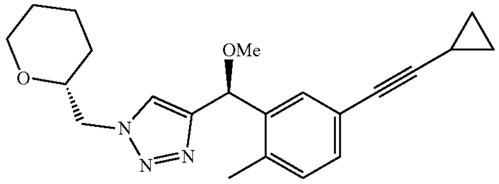 [SMILES: CO[C@H](c1cn(C[C@H]2CCCCO2)nn1)c1cc(C#CC2CC2)ccc1C] |
| I-512 | 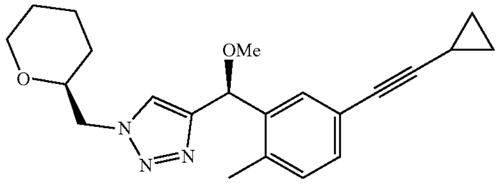 [SMILES: CO[C@H](c1cn(C[C@@H]2CCCCO2)nn1)c1cc(C#CC2CC2)ccc1C] |

TABLE 1-continued
| Selected Compounds | |
|---|---|
| Compound | Structure |
| I-513 | 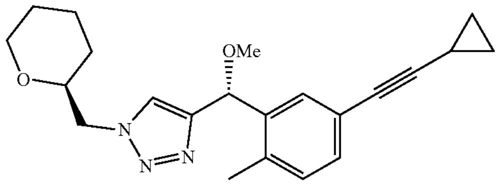 [SMILES: CO[C@@H](c1cn(C[C@@H]2CCCCO2)nn1)c1cc(C#CC2CC2)ccc1C] |
| I-514 | 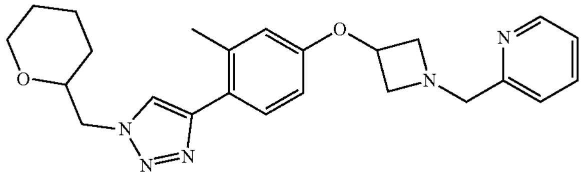 [SMILES: Cc1cc(OC2CN(Cc3ccccn3)C2)ccc1-c1cn(CC2CCCCO2)nn1] |
| I-515 | 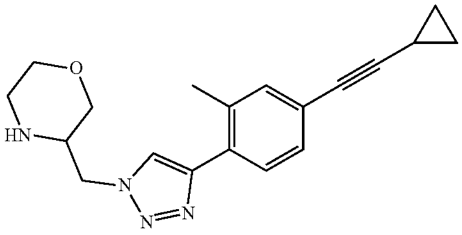 [SMILES: Cc1cc(C#CC2CC2)ccc1-c1cn(CC2COCCN2)nn1] |
| I-516 | 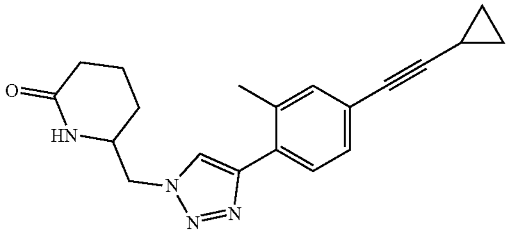 [SMILES: Cc1cc(C#CC2CC2)ccc1-c1cn(CC2CCCC(=O)N2)nn1] |
| I-517 | 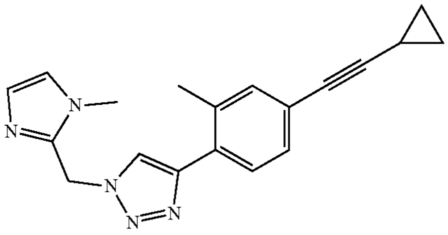 [SMILES: Cc1cc(C#CC2CC2)ccc1-c1cn(Cc2nccn2C)nn1] |
| I-518 | 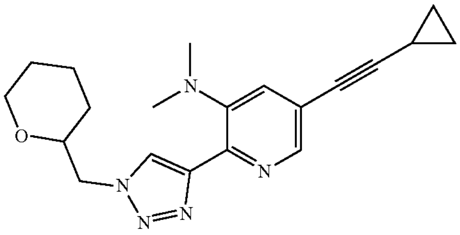 [SMILES: CN(C)c1cc(C#CC2CC2)cnc1-c1cn(CC2CCCCO2)nn1] |

TABLE 1-continued
| Selected Compounds | |
|---|---|
| Compound | Structure |
| I-519 | 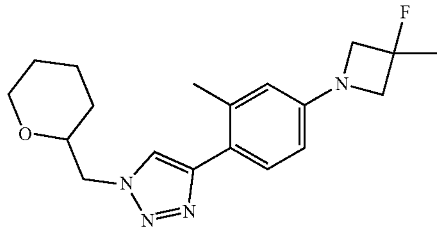 [SMILES: Cc1cc(N2CC(C)(F)C2)ccc1-c1cn(CC2CCCCO2)nn1] |
| I-520 | 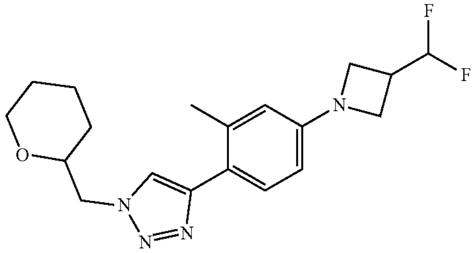 [SMILES: Cc1cc(N2CC(C(F)F)C2)ccc1-c1cn(CC2CCCCO2)nn1] |
| I-521 | 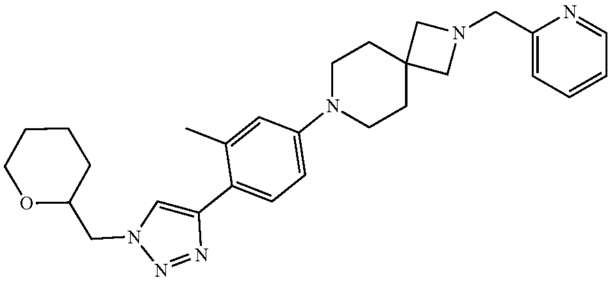 [SMILES: Cc1cc(N2CCC3(CC2)CN(Cc2ccccn2)C3)ccc1-c1cn(CC2CCCCO2)nn1] |
| I-522 | 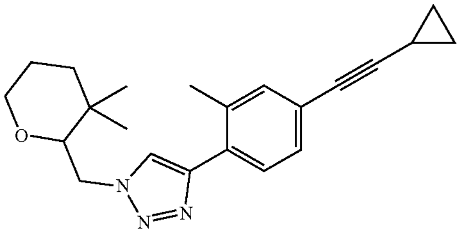 [SMILES: Cc1cc(C#CC2CC2)ccc1-c1cn(CC2OCCCC2(C)C)nn1] |
| I-523 | 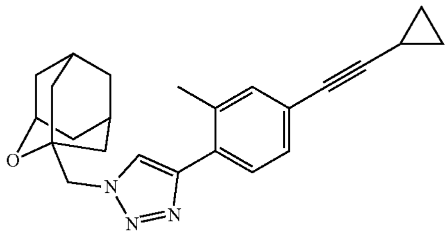 [SMILES: Cc1cc(C#CC2CC2)ccc1-c1cn(CC23CC4CC(CC(C4)O2)C3)nn1] |
| I-524 | 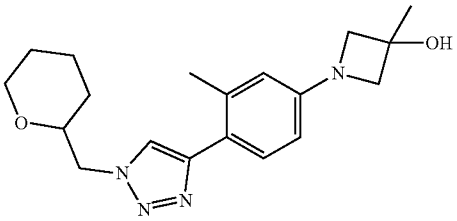 [SMILES: Cc1cc(N2CC(C)(O)C2)ccc1-c1cn(CC2CCCCO2)nn1] |

TABLE 1-continued
| Selected Compounds | |
|---|---|
| Compound | Structure |
| I-525 | 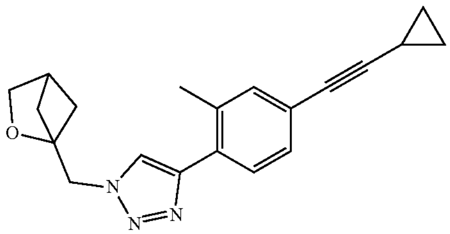 [SMILES: Cc1cc(C#CC2CC2)ccc1-c1cn(CC23CC(CO2)C3)nn1] |
| I-526 | 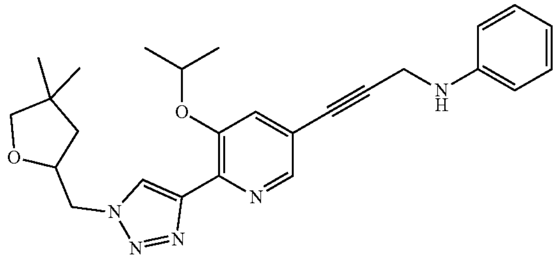 [SMILES: CC(C)Oc1cc(C#CCNc2ccccc2)cnc1-c1cn(CC2CC(C)(C)CO2)nn1] |
| I-527 | 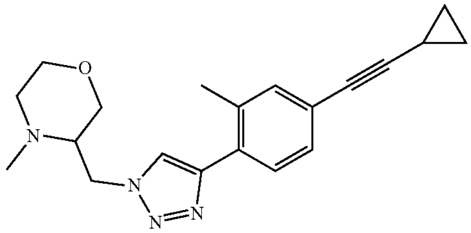 [SMILES: Cc1cc(C#CC2CC2)ccc1-c1cn(CC2COCCN2C)nn1] |
| I-528 | 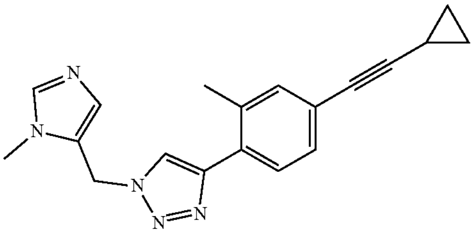 [SMILES: Cc1cc(C#CC2CC2)ccc1-c1cn(Cc2cncn2C)nn1] |
| I-529 | 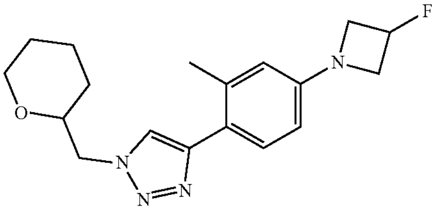 [SMILES: Cc1cc(N2CC(F)C2)ccc1-c1cn(CC2CCCCO2)nn1] |
| I-530 | 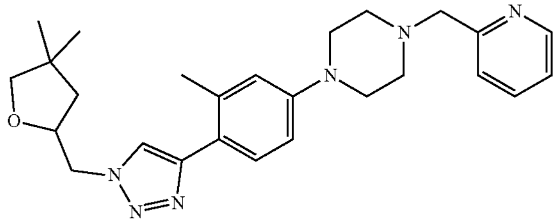 [SMILES: Cc1cc(N2CCN(Cc3ccccn3)CC2)ccc1-c1cn(CC2CC(C)(C)CO2)nn1] |

TABLE 1-continued
| Selected Compounds | |
|---|---|
| Compound | Structure |
| I-531 | 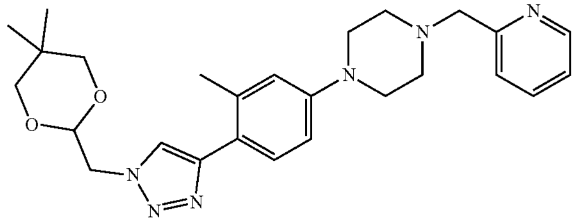 [SMILES: Cc1cc(N2CCN(Cc3ccccn3)CC2)ccc1-c1cn(CC2OCC(C)(C)CO2)nn1] |
| I-532 | 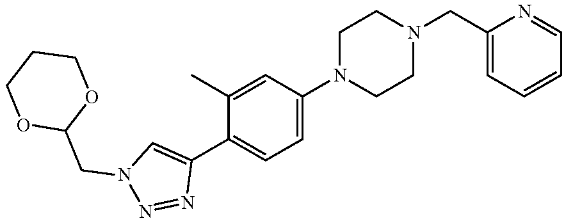 [SMILES: Cc1cc(N2CCN(Cc3ccccn3)CC2)ccc1-c1cn(CC2OCCCO2)nn1] |
| I-533 | 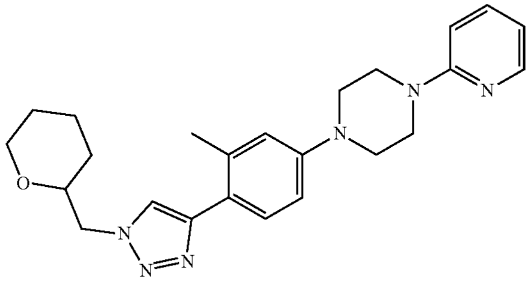 [SMILES: Cc1cc(N2CCN(c3ccccn3)CC2)ccc1-c1cn(CC2CCCCO2)nn1] |
| I-534 | 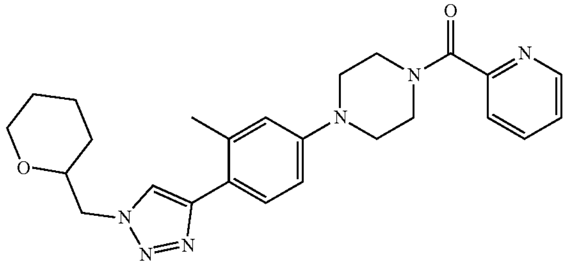 [SMILES: Cc1cc(N2CCN(C(=O)c3ccccn3)CC2)ccc1-c1cn(CC2CCCCO2)nn1] |
| I-535 | 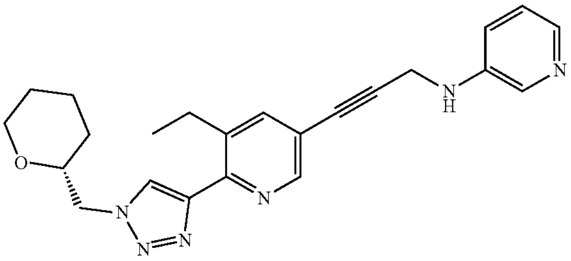 [SMILES: CCc1cc(C#CCNc2cccnc2)cnc1-c1cn(C[C@H]2CCCCO2)nn1] |
| I-536 | 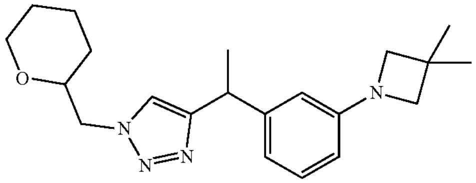 [SMILES: CC(c1cccc(N2CC(C)(C)C2)c1)c1cn(CC2CCCCO2)nn1] |

TABLE 1-continued
| Selected Compounds | |
|---|---|
| Compound | Structure |
| I-537 | 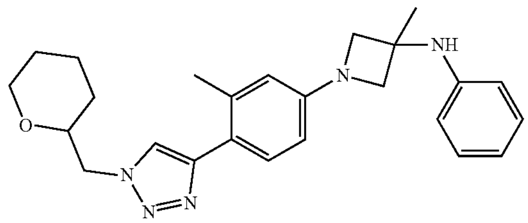 [SMILES: Cc1cc(N2CC(C)(Nc3ccccc3)C2)ccc1-c1cn(CC2CCCCO2)nn1] |
| I-538 | 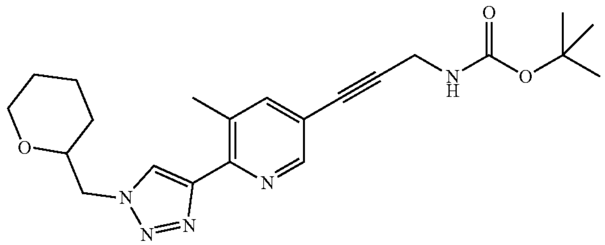 [SMILES: Cc1cc(C#CCNC(=O)OC(C)(C)C)cnc1-c1cn(CC2CCCCO2)nn1] |
| I-539 | 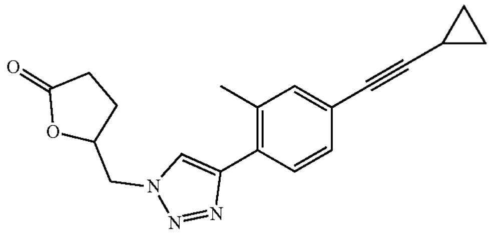 [SMILES: Cc1cc(C#CC2CC2)ccc1-c1cn(CC2CCC(=O)O2)nn1] |
| I-540 | 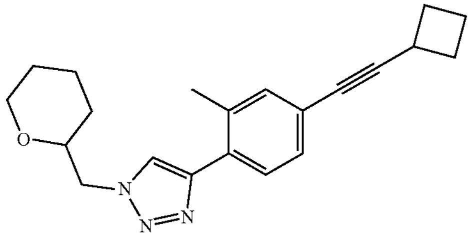 [SMILES: Cc1cc(C#CC2CCC2)ccc1-c1cn(CC2CCCCO2)nn1] |
| I-541 | 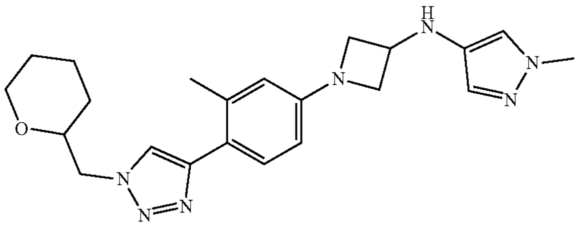 [SMILES: Cc1cc(N2CC(Nc3cnn(C)c3)C2)ccc1-c1cn(CC2CCCCO2)nn1] |
| I-542 | 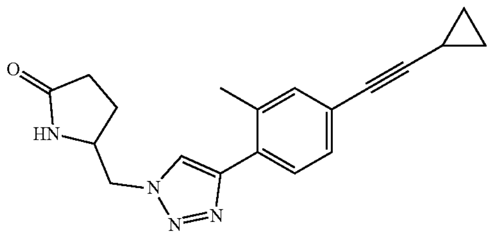 [SMILES: Cc1cc(C#CC2CC2)ccc1-c1cn(CC2CCC(=O)N2)nn1] |

TABLE 1-continued
| Selected Compounds | |
|---|---|
| Compound | Structure |
| I-543 | 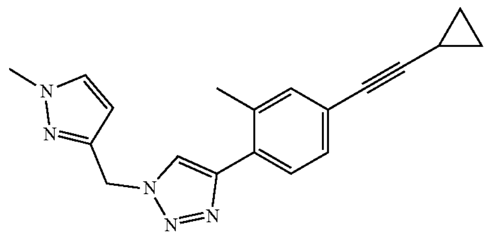 [SMILES: Cc1cc(C#CC2CC2)ccc1-c1cn(Cc2ccn(C)n2)nn1] |
| I-544 | 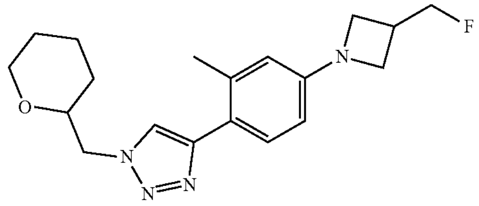 [SMILES: Cc1cc(N2CC(CF)C2)ccc1-c1cn(CC2CCCCO2)nn1] |
| I-545 | 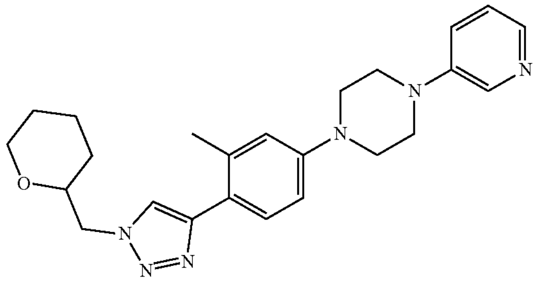 [SMILES: Cc1cc(N2CCN(c3cccnc3)CC2)ccc1-c1cn(CC2CCCCO2)nn1] |
| I-546 | 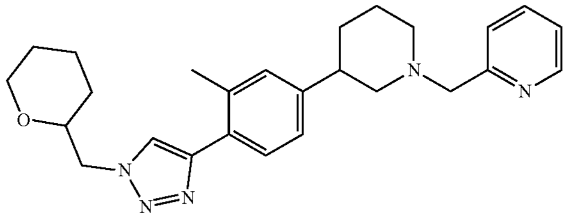 [SMILES: Cc1cc(C2CCCN(Cc3ccccn3)C2)ccc1-c1cn(CC2CCCCO2)nn1] |
| I-547 | 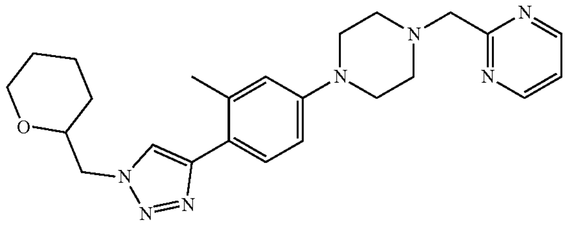 [SMILES: Cc1cc(N2CCN(Cc3ncccn3)CC2)ccc1-c1cn(CC2CCCCO2)nn1] |
| I-548 | 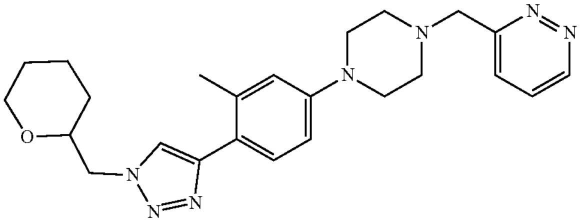 [SMILES: Cc1cc(N2CCN(Cc3cccnn3)CC2)ccc1-c1cn(CC2CCCCO2)nn1] |

TABLE 1-continued
| Selected Compounds | |
|---|---|
| Compound | Structure |
| I-549 | 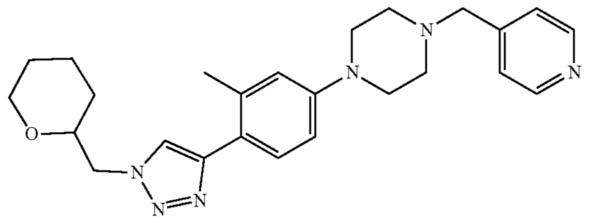 [SMILES: Cc1cc(N2CCN(Cc3ccncc3)CC2)ccc1-c1cn(CC2CCCCO2)nn1] |
| I-550 | 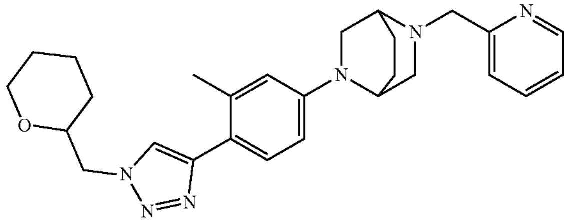 [SMILES: Cc1cc(N2CC3CCC2CN3Cc2ccccn2)ccc1-c1cn(CC2CCCCO2)nn1] |
| I-551 | 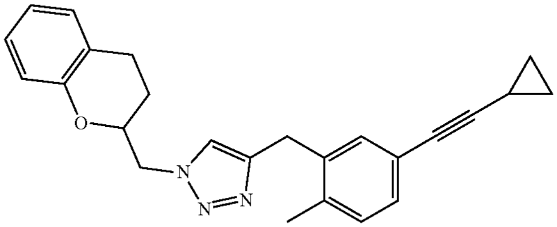 [SMILES: Cc1ccc(C#CC2CC2)cc1Cc1cn(CC2CCc3ccccc3O2)nn1] |
| I-552 | 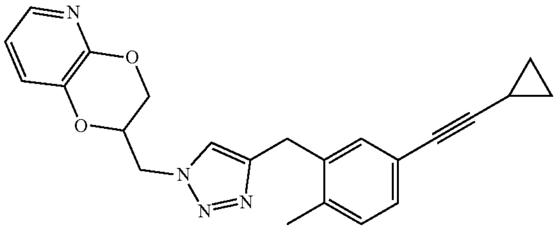 [SMILES: Cc1ccc(C#CC2CC2)cc1Cc1cn(CC2COc3ncccc3O2)nn1] |
| I-553 | 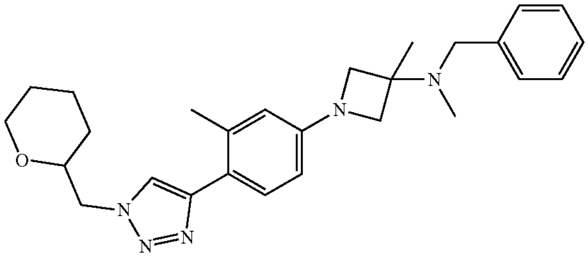 [SMILES: Cc1cc(N2CC(C)(N(C)Cc3ccccc3)C2)ccc1-c1cn(CC2CCCCO2)nn1] |
| I-554 | 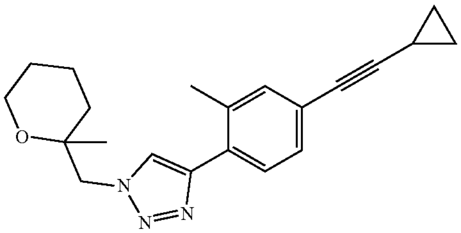 [SMILES: Cc1cc(C#CC2CC2)ccc1-c1cn(CC2(C)CCCCO2)nn1] |

TABLE 1-continued
| Selected Compounds | |
|---|---|
| Compound | Structure |
| I-555 | 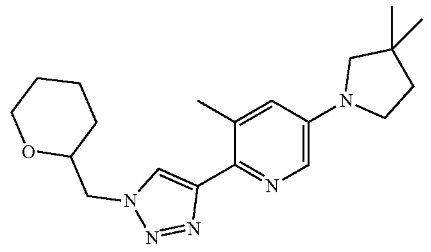 [SMILES: Cc1cc(N2CCC(C)(C)C2)cnc1-c1cn(CC2CCCCO2)nn1] |
| I-556 | 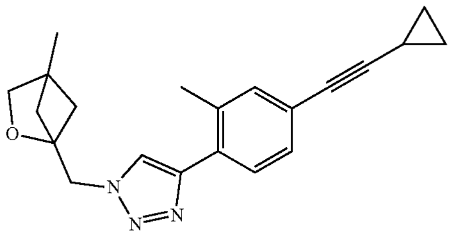 [SMILES: Cc1cc(C#CC2CC2)ccc1-c1cn(CC23CC(C)(CO2)C3)nn1] |
| I-557 | 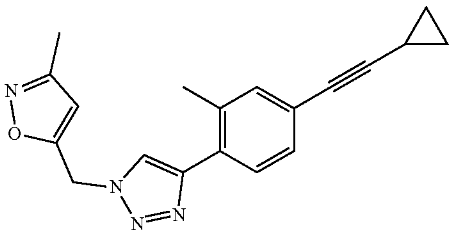 [SMILES: Cc1cc(Cn2cc(-c3ccc(C#CC4CC4)cc3C)nn2)on1] |
| I-558 | 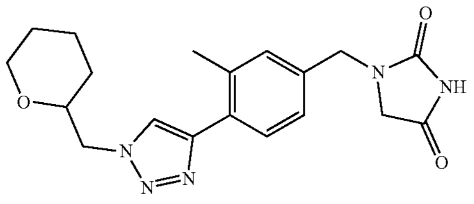 [SMILES: Cc1cc(CN2CC(=O)NC2=O)ccc1-c1cn(CC2CCCCO2)nn1] |
| I-559 | 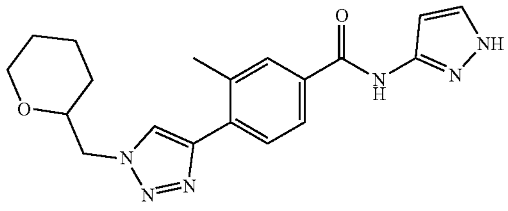 [SMILES: Cc1cc(C(=O)Nc2cc[nH]n2)ccc1-c1cn(CC2CCCCO2)nn1] |
| I-560 | 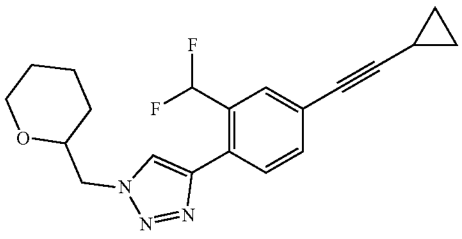 |

TABLE 1-continued
| Selected Compounds | |
|---|---|
| Compound | Structure |
| I-561 | 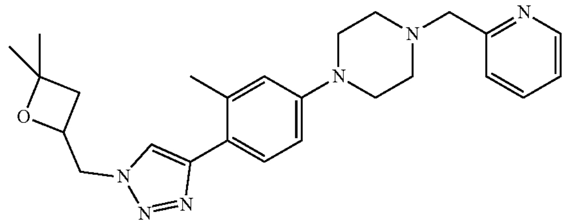 [SMILES: Cc1cc(N2CCN(Cc3ccccn3)CC2)ccc1-c1cn(CC2CC(C)(C)O2)nn1] |
| I-562 | 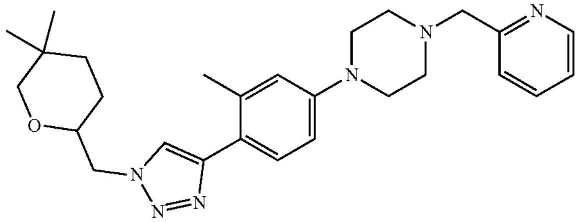 [SMILES: Cc1cc(N2CCN(Cc3ccccn3)CC2)ccc1-c1cn(CC2CCC(C)(C)CO2)nn1] |
| I-563 | 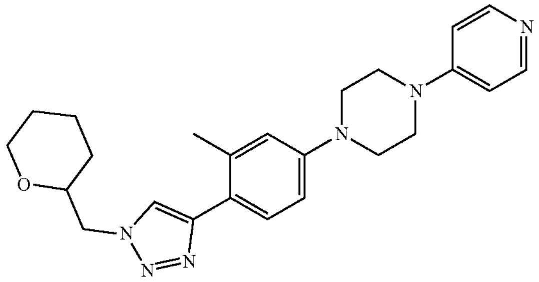 [SMILES: Cc1cc(N2CCN(c3ccncc3)CC2)ccc1-c1cn(CC2CCCCO2)nn1] |
| I-564 | 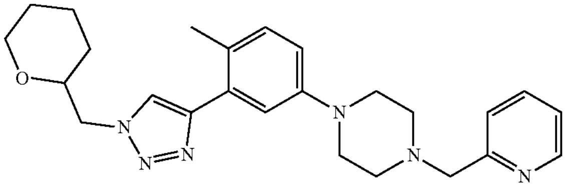 [SMILES: Cc1ccc(N2CCN(Cc3ccccn3)CC2)cc1-c1cn(CC2CCCCO2)nn1] |
| I-565 | 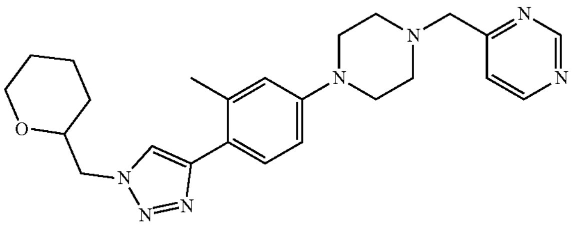 [SMILES: Cc1cc(N2CCN(Cc3ccncn3)CC2)ccc1-c1cn(CC2CCCCO2)nn1] |
| I-566 | 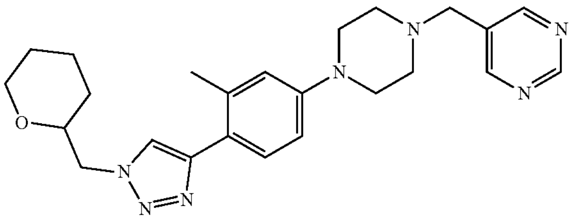 [SMILES: Cc1cc(N2CCN(Cc3cncnc3)CC2)ccc1-c1cn(CC2CCCCO2)nn1] |

TABLE 1-continued
| Selected Compounds | |
|---|---|
| Compound | Structure |
| I-567 | 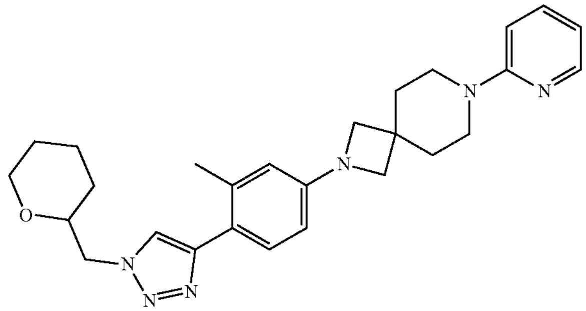 [SMILES: Cc1cc(N2CC3(CCN(c4ccccn4)CC3)C2)ccc1-c1cn(CC2CCCCO2)nn1] |
| I-568 | 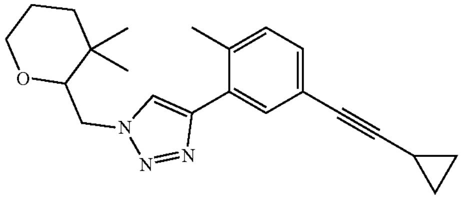 [SMILES: Cc1ccc(C#CC2CC2)cc1-c1cn(CC2OCCCC2(C)C)nn1] |
| I-569 | 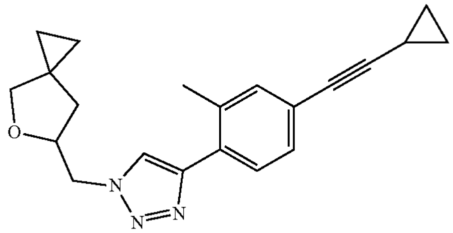 [SMILES: Cc1cc(C#CC2CC2)ccc1-c1cn(CC2CC3(CC3)CO2)nn1] |
| I-570 | 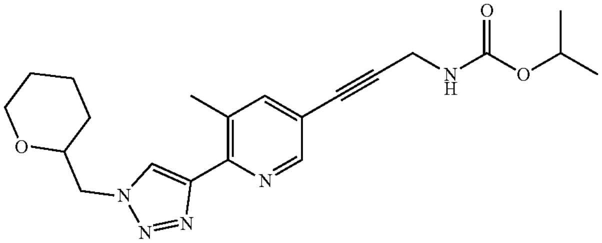 [SMILES: Cc1cc(C#CCNC(=O)OC(C)C)cnc1-c1cn(CC2CCCCO2)nn1] |
| I-571 | 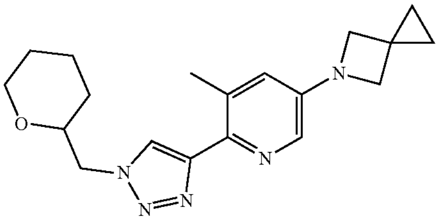 [SMILES: Cc1cc(N2CC3(CC3)C2)cnc1-c1cn(CC2CCCCO2)nn1] |
| I-572 | 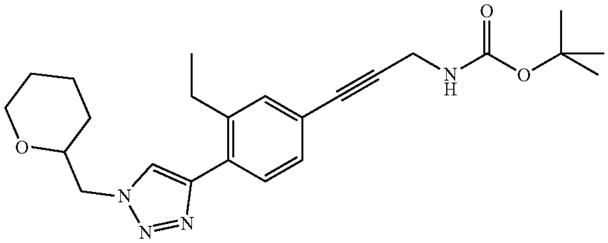 [SMILES: CCc1cc(C#CCNC(=O)OC(C)(C)C)ccc1-c1cn(CC2CCCCO2)nn1] |

TABLE 1-continued
| Selected Compounds | |
|---|---|
| Compound | Structure |
| I-573 | 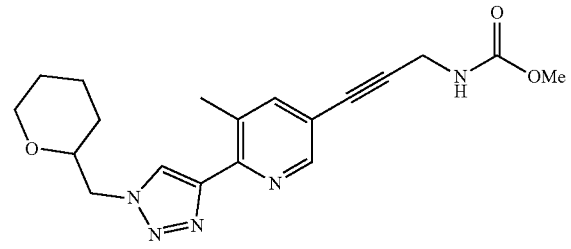 [SMILES: COC(=O)NCC#Cc1cnc(-c2cn(CC3CCCCO3)nn2)c(C)c1] |
| I-574 | 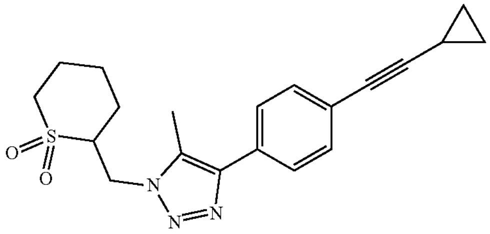 [SMILES: Cc1c(-c2ccc(C#CC3CC3)cc2)nnn1CC1CCCCS1(=O)=O] |
| I-575 | 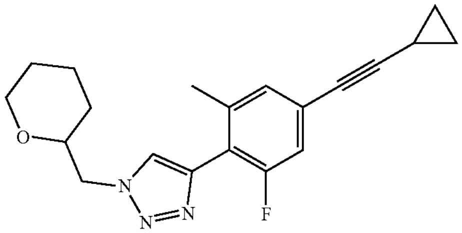 [SMILES: Cc1cc(C#CC2CC2)cc(F)c1-c1cn(CC2CCCCO2)nn1] |
| I-576 | 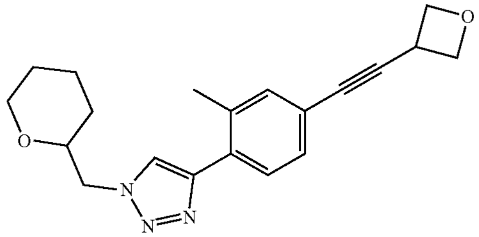 [SMILES: Cc1cc(C#CC2COC2)ccc1-c1cn(CC2CCCCO2)nn1] |
| I-577 | 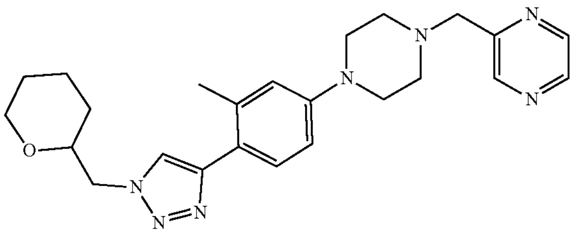 [SMILES: Cc1cc(N2CCN(Cc3cnccn3)CC2)ccc1-c1cn(CC2CCCCO2)nn1] |
| I-578 | 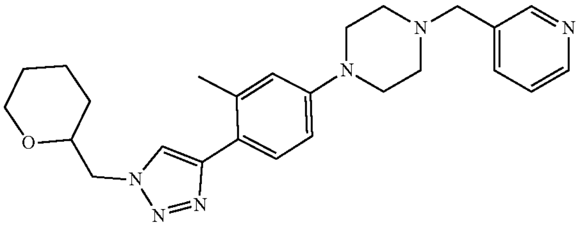 [SMILES: Cc1cc(N2CCN(Cc3cccnc3)CC2)ccc1-c1cn(CC2CCCCO2)nn1] |

TABLE 1-continued
| Selected Compounds | |
|---|---|
| Compound | Structure |
| I-579 | 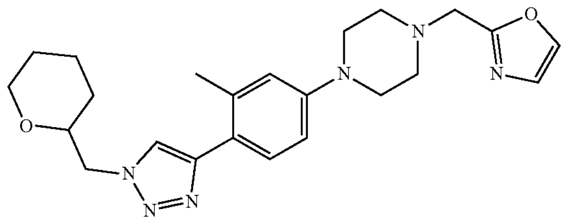 [SMILES: Cc1cc(N2CCN(Cc3ncco3)CC2)ccc1-c1cn(CC2CCCCO2)nn1] |
| I-580 | 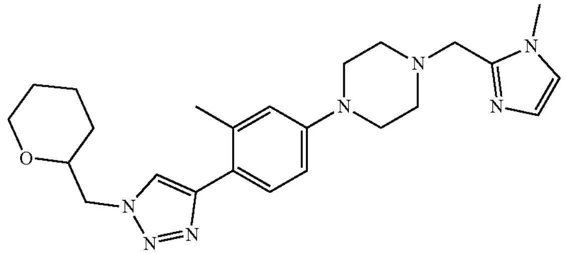 [SMILES: Cc1cc(N2CCN(Cc3nccn3C)CC2)ccc1-c1cn(CC2CCCCO2)nn1] |
| I-581 | 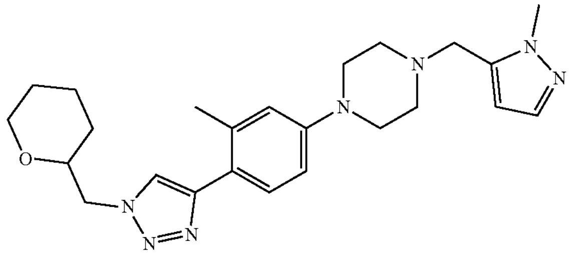 [SMILES: Cc1cc(N2CCN(Cc3ccnn3C)CC2)ccc1-c1cn(CC2CCCCO2)nn1] |
| I-582 | 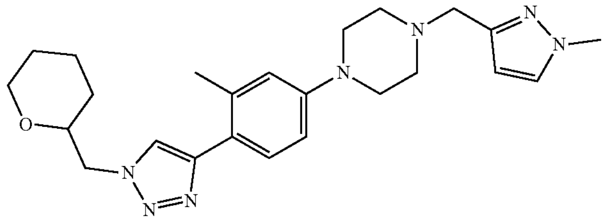 [SMILES: Cc1cc(N2CCN(Cc3ccn(C)n3)CC2)ccc1-c1cn(CC2CCCCO2)nn1] |
| I-583 | 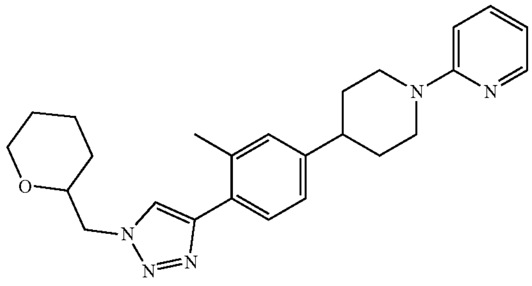 [SMILES: Cc1cc(C2CCN(c3ccccn3)CC2)ccc1-c1cn(CC2CCCCO2)nn1] |
| I-584 | 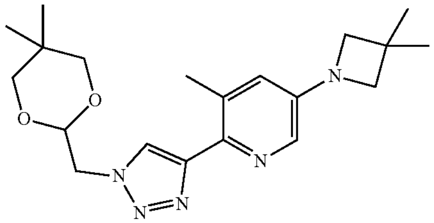 |

TABLE 1-continued
Selected Compounds
| Compound | Structure |
| --- | --- |
| I-585 | 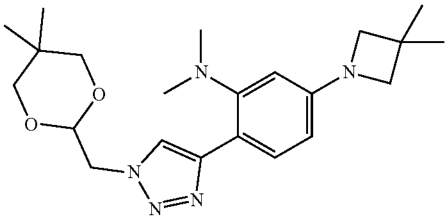 |
| I-586 | 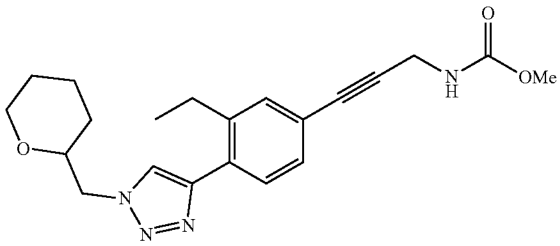 [SMILES: CCc1cc(C#CCNC(=O)OC)ccc1-c1cn(CC2CCCCO2)nn1] |
| I-587 | 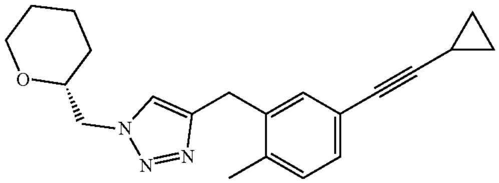 [SMILES: Cc1ccc(C#CC2CC2)cc1Cc1cn(C[C@H]2CCCCO2)nn1] |
| I-588 | 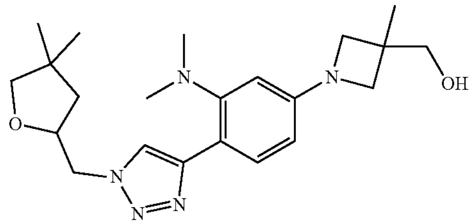 Enantiomer I |
| I-589 | 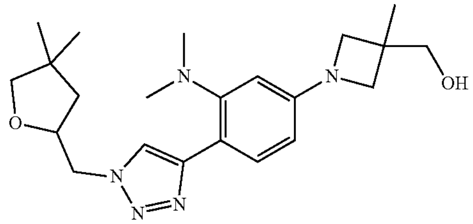 Enantiomer II |
| I-590 | 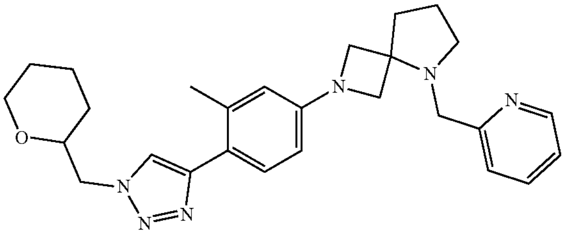 [SMILES: Cc1cc(N2CC3(CCCN3Cc3ccccn3)C2)ccc1-c1cn(CC2CCCCO2)nn1] |

TABLE 1-continued
| Selected Compounds | |
|---|---|
| Compound | Structure |
| I-591 | 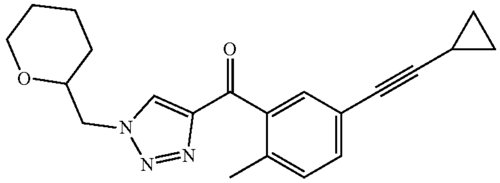 [SMILES: Cc1ccc(C#CC2CC2)cc1C(=O)c1cn(CC2CCCCO2)nn1] |
| I-592 | 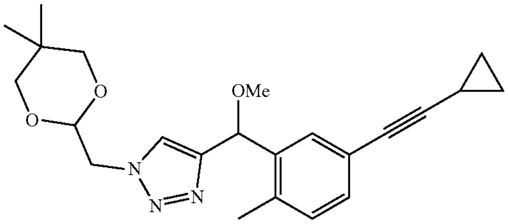 [SMILES: COC(c1cn(CC2OCC(C)(C)CO2)nn1)c1cc(C#CC2CC2)ccc1C] |
| I-593 | 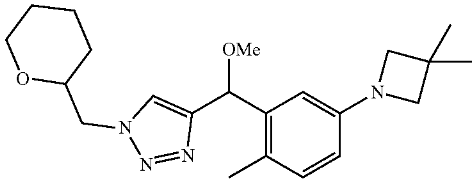 [SMILES: COC(c1cn(CC2CCCCO2)nn1)c1cc(N2CC(C)(C)C2)ccc1C] |
| I-594 | 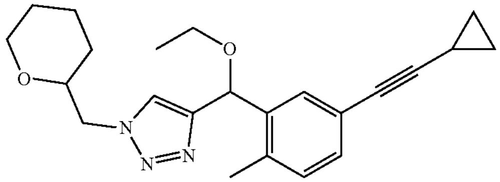 [SMILES: CCOC(c1cn(CC2CCCCO2)nn1)c1cc(C#CC2CC2)ccc1C] |
| I-595 | 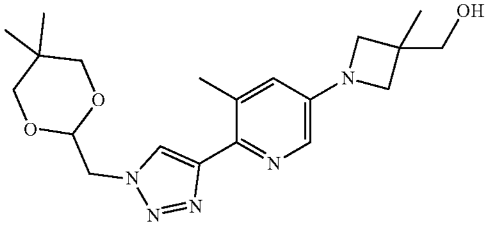 [SMILES: Cc1cc(N2CC(C)(CO)C2)cnc1-c1cn(CC2OCC(C)(C)CO2)nn1] |
| I-596 | 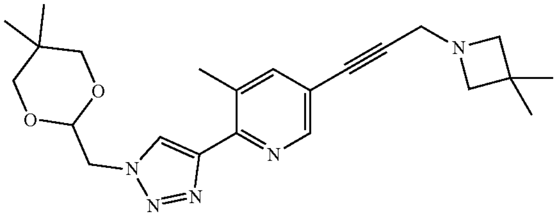 |
| I-597 | 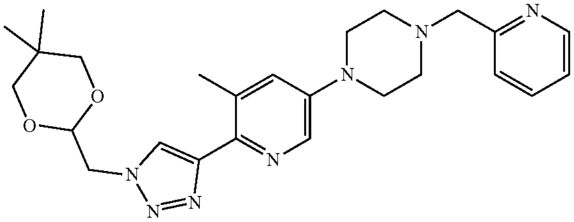 [SMILES: Cc1cc(N2CCN(Cc3ccccn3)CC2)cnc1-c1cn(CC2OCC(C)(C)CO2)nn1] |

TABLE 1-continued
| Selected Compounds | |
|---|---|
| Compound | Structure |
| I-598 | 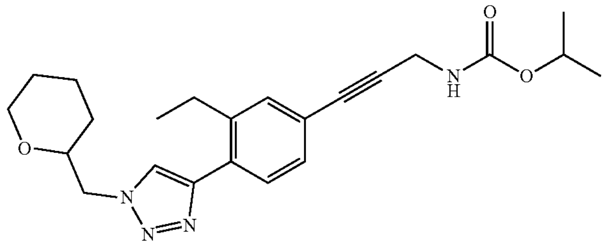 [SMILES: CCc1cc(C#CCNC(=O)OC(C)C)ccc1-c1cn(CC2CCCCO2)nn1] |
| I-599 | 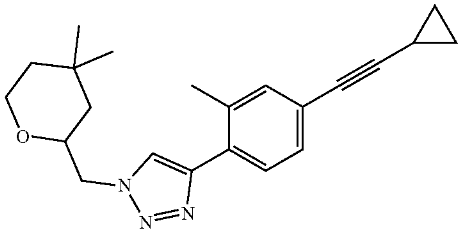 [SMILES: Cc1cc(C#CC2CC2)ccc1-c1cn(CC2CC(C)(C)CCO2)nn1] |
| I-600 | 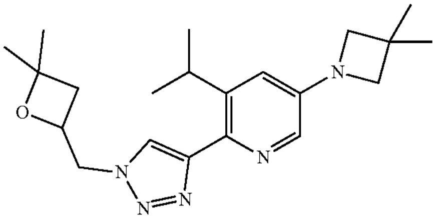 |
| I-601 | 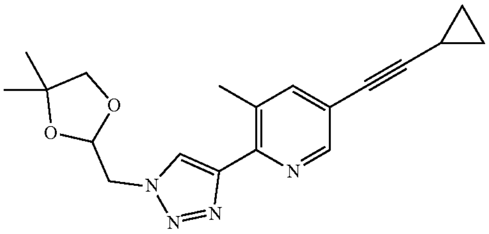 [SMILES: Cc1cc(C#CC2CC2)cnc1-c1cn(CC2OCC(C)(C)O2)nn1] |
| I-602 | 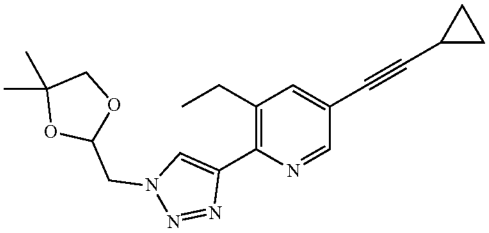 [SMILES: CCc1cc(C#CC2CC2)cnc1-c1cn(CC2OCC(C)(C)O2)nn1] |
| I-603 | 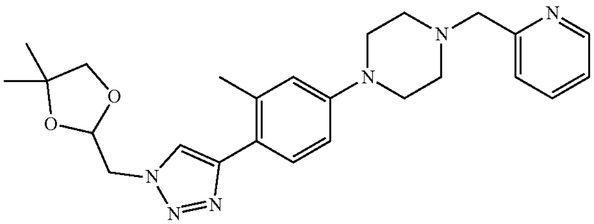 [SMILES: Cc1cc(N2CCN(Cc3ccccn3)CC2)ccc1-c1cn(CC2OCC(C)(C)O2)nn1] |

TABLE 1-continued
| Selected Compounds | |
|---|---|
| Compound | Structure |
| I-604 | 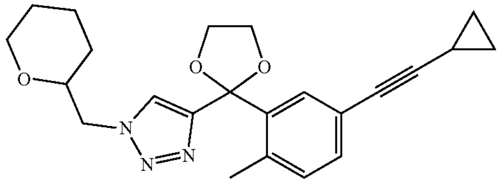 [SMILES: Cc1ccc(C#CC2CC2)cc1C1(c2cn(CC3CCCCO3)nn2)OCCO1] |
| I-605 | 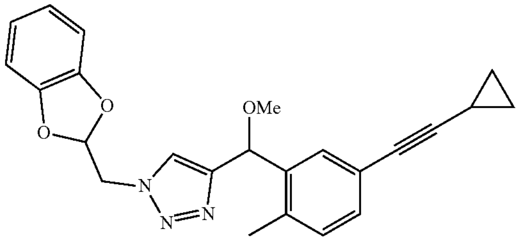 [SMILES: COC(c1cn(CC2Oc3ccccc3O2)nn1)c1cc(C#CC2CC2)ccc1C] |
| I-606 | 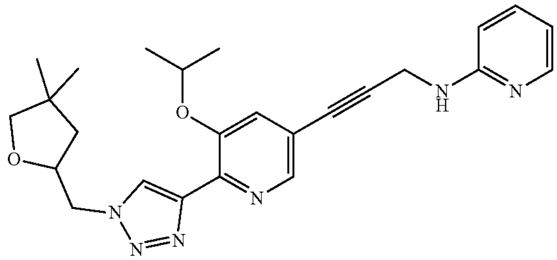 [SMILES: CC(C)Oc1cc(C#CCNc2ccccn2)cnc1-c1cn(CC2CC(C)(C)CO2)nn1] |
| I-607 | 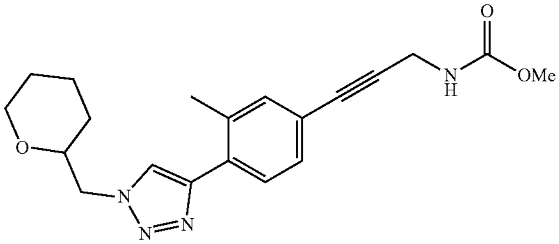 [SMILES: COC(=O)NCC#Cc1ccc(-c2cn(CC3CCCCO3)nn2)c(C)c1] |
| I-608 | 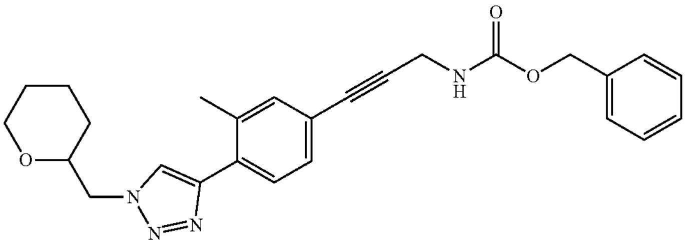 [SMILES: Cc1cc(C#CCNC(=O)OCc2ccccc2)ccc1-c1cn(CC2CCCCO2)nn1] |
| I-609 | 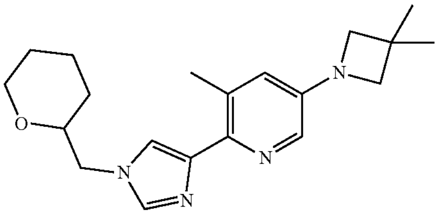 [SMILES: Cc1cc(N2CC(C)(C)C2)cnc1-c1cn(CC2CCCCO2)cn1] |

TABLE 1-continued
| Selected Compounds | |
| --- | --- |
| Compound | Structure |
| I-610 | 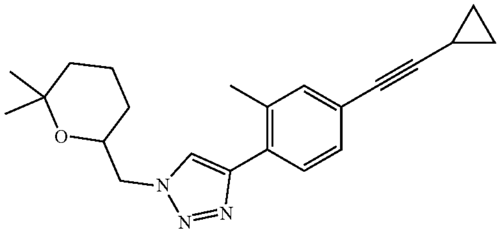 [SMILES: Cc1cc(C#CC2CC2)ccc1-c1cn(CC2CCCC(C)(C)O2)nn1] |
| I-611 | 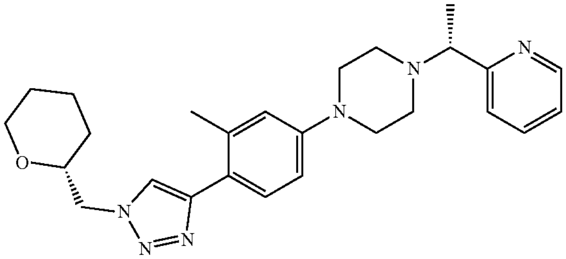 [SMILES: Cc1cc(N2CCN([C@H](C)c3ccccn3)CC2)ccc1-c1cn(C[C@H]2CCCCO2)nn1] |
| I-612 | 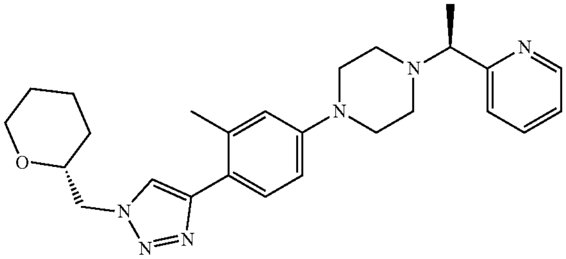 [SMILES: Cc1cc(N2CCN([C@@H](C)c3ccccn3)CC2)ccc1-c1cn(C[C@H]2CCCCO2)nn1] |
| I-613 | 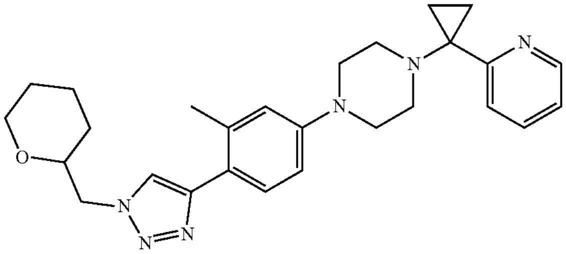 [SMILES: Cc1cc(N2CCN(C3(c4ccccn4)CC3)CC2)ccc1-c1cn(CC2CCCCO2)nn1] |
| I-614 | 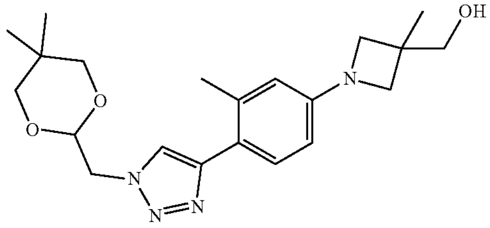 [SMILES: Cc1cc(N2CC(C)(CO)C2)ccc1-c1cn(CC2OCC(C)(C)CO2)nn1] |
| I-615 | 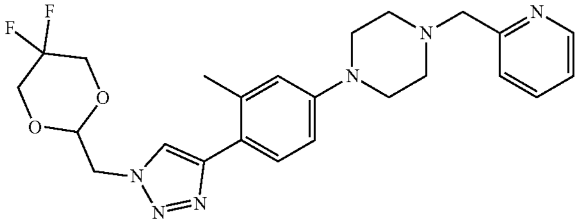 [SMILES: Cc1cc(N2CCN(Cc3ccccn3)CC2)ccc1-c1cn(CC2OCC(F)(F)CO2)nn1] |

TABLE 1-continued
| Selected Compounds | |
|---|---|
| Compound | Structure |
| I-616 | 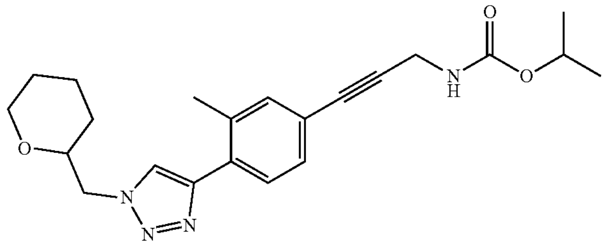 [SMILES: Cc1cc(C#CCNC(=O)OC(C)C)ccc1-c1cn(CC2CCCCO2)nn1] |
| I-617 | 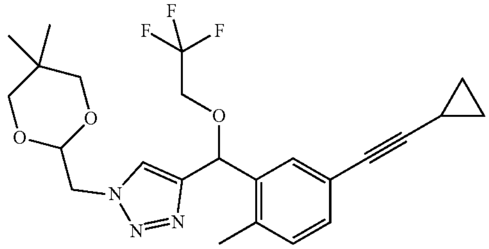 [SMILES: Cc1ccc(C#CC2CC2)cc1C(OCC(F)(F)F)c1cn(CC2OCC(C)(C)CO2)nn1] |
| I-618 | 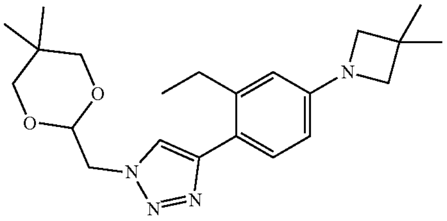 |
| I-619 | 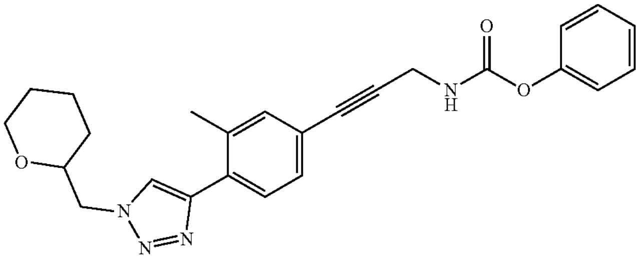 [SMILES: Cc1cc(C#CCNC(=O)Oc2ccccc2)ccc1-c1cn(CC2CCCCO2)nn1] |
| I-620 | 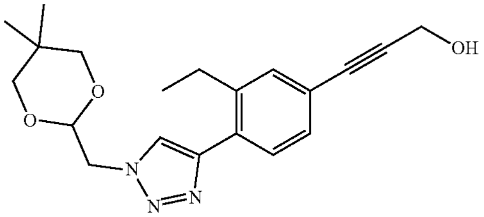 [SMILES: CCc1cc(C#CCO)ccc1-c1cn(CC2OCC(C)(C)CO2)nn1] |
| I-621 | 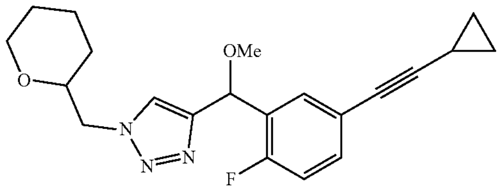 [SMILES: COC(c1cn(CC2CCCCO2)nn1)c1cc(C#CC2CC2)ccc1F] |

TABLE 1-continued
| Selected Compounds | |
|---|---|
| Compound | Structure |
| I-622 | 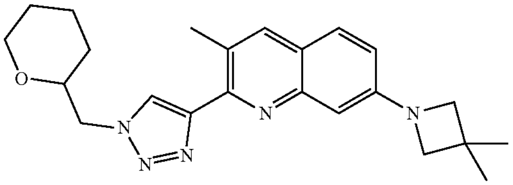 [SMILES: Cc1cc2ccc(N3CC(C)(C)C3)cc2nc1-c1cn(CC2CCCCO2)nn1] |
| I-623 | 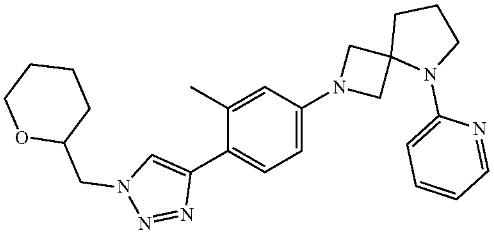 [SMILES: Cc1cc(N2CC3(CCCN3c3ccccn3)C2)ccc1-c1cn(CC2CCCCO2)nn1] |
| I-624 | 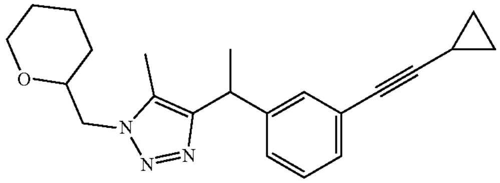 [SMILES: Cc1c(C(C)c2cccc(C#CC3CC3)c2)nnn1CC1CCCCO1] |
| I-625 | 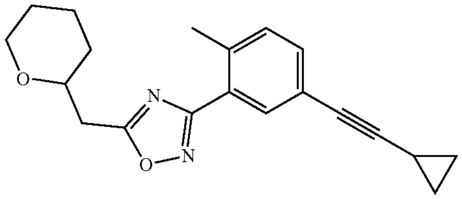 [SMILES: Cc1ccc(C#CC2CC2)cc1-c1noc(CC2CCCCO2)n1] |
| I-626 | 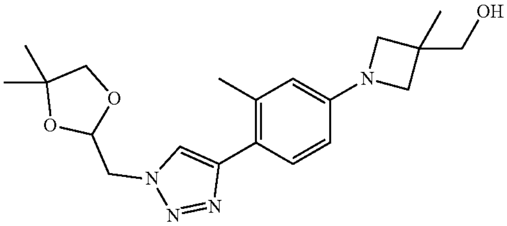 [SMILES: Cc1cc(N2CC(C)(CO)C2)ccc1-c1cn(CC2OCC(C)(C)O2)nn1] |
| I-627 | 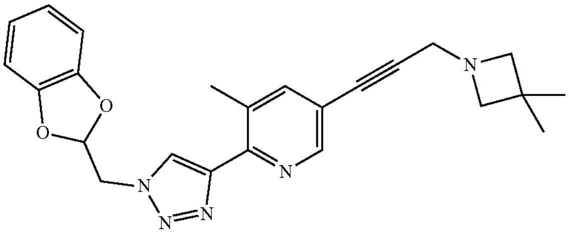 [SMILES: Cc1cc(C#CCN2CC(C)(C)C2)cnc1-c1cn(CC2Oc3ccccc3O2)nn1] |
| I-628 | 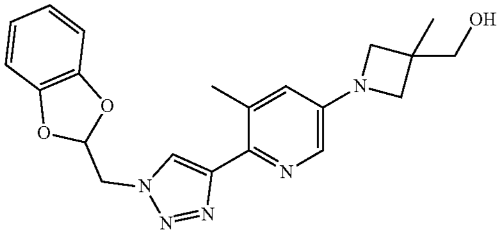 [SMILES: Cc1cc(N2CC(C)(CO)C2)cnc1-c1cn(CC2Oc3ccccc3O2)nn1] |

TABLE 1-continued
| Selected Compounds | |
|---|---|
| Compound | Structure |
| I-629 | 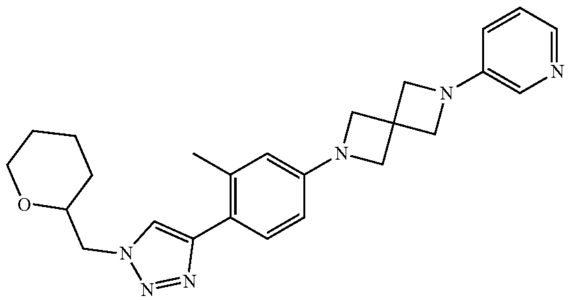 [SMILES: Cc1cc(N2CC3(CN(c4cccnc4)C3)C2)ccc1-c1cn(CC2CCCCO2)nn1] |
| I-630 | 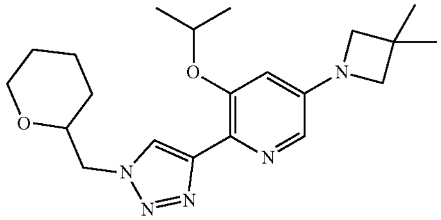 [SMILES: CC(C)Oc1cc(N2CC(C)(C)C2)cnc1-c1cn(CC2CCCCO2)nn1] |
| I-631 | 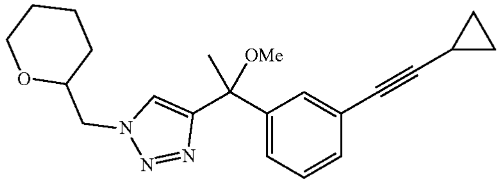 [SMILES: COC(C)(c1cccc(C#CC2CC2)c1)c1cn(CC2CCCCO2)nn1] |
| I-632 | 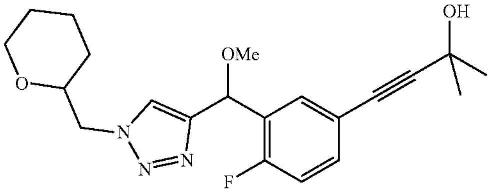 [SMILES: COC(c1cn(CC2CCCCO2)nn1)c1cc(C#CC(C)(C)O)ccc1F] |
| I-633 | 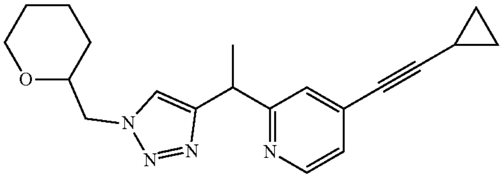 [SMILES: CC(c1cc(C#CC2CC2)ccn1)c1cn(CC2CCCCO2)nn1] |
| I-634 | 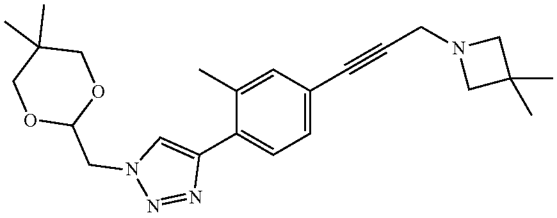 |

TABLE 1-continued
| Selected Compounds | |
|---|---|
| Compound | Structure |
| I-635 | 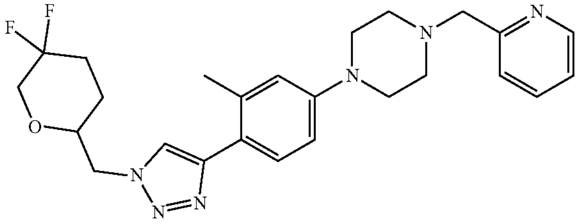 Enantiomer I |
| I-636 | 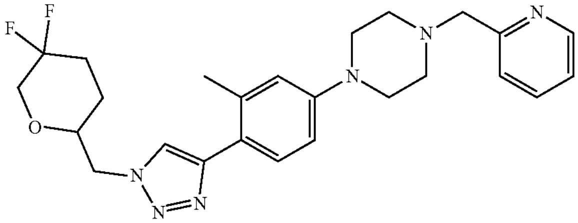 Enantiomer II |
| I-637 | 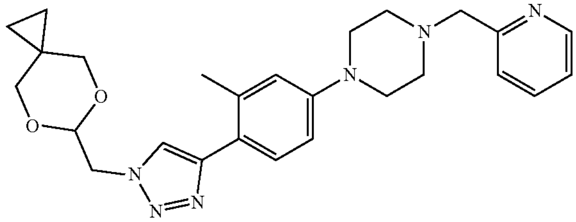 [SMILES: Cc1cc(N2CCN(Cc3ccccn3)CC2)ccc1-c1cn(CC2OCC3(CC3)CO2)nn1] |
| I-638 | 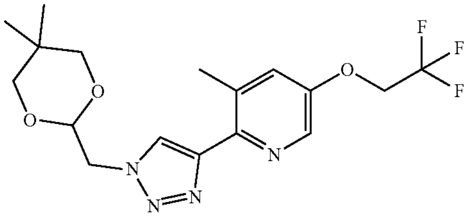 [SMILES: Cc1cc(OCC(F)(F)F)cnc1-c1cn(CC2OCC(C)(C)CO2)nn1] |
| I-639 | 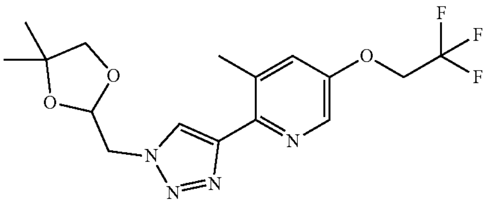 [SMILES: Cc1cc(OCC(F)(F)F)cnc1-c1cn(CC2OCC(C)(C)O2)nn1] |
| I-640 | 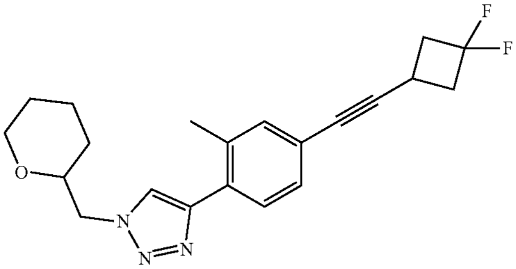 [SMILES: Cc1cc(C#CC2CC(F)(F)C2)ccc1-c1cn(CC2CCCCO2)nn1] |

TABLE 1-continued
| Selected Compounds | |
|---|---|
| Compound | Structure |
| I-641 | 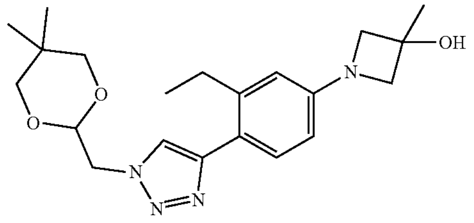 [SMILES: CCc1cc(N2CC(C)(O)C2)ccc1-c1cn(CC2OCC(C)(C)CO2)nn1] |
| I-642 | 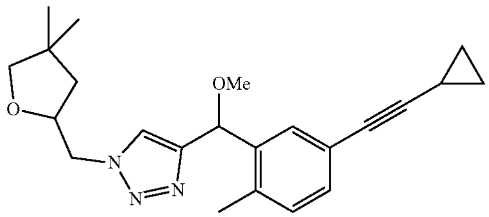 [SMILES: COC(c1cn(CC2CC(C)(C)CO2)nn1)c1cc(C#CC2CC2)ccc1C] |
| I-643 | 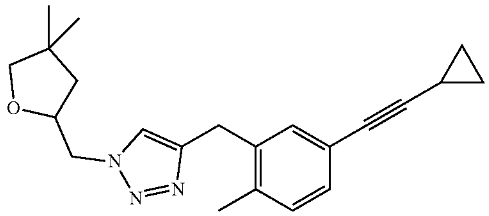 [SMILES: Cc1ccc(C#CC2CC2)cc1Cc1cn(CC2CC(C)(C)CO2)nn1] |
| I-644 | 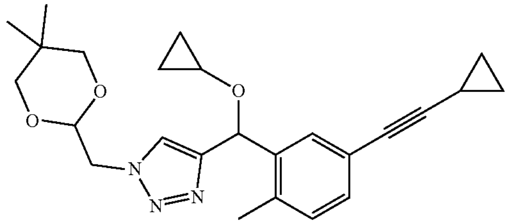 [SMILES: Cc1ccc(C#CC2CC2)cc1C(OC1CC1)c1cn(CC2OCC(C)(C)CO2)nn1] |
| I-645 | 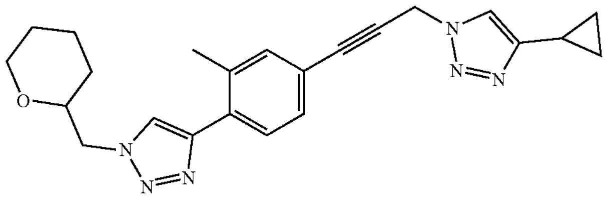 [SMILES: Cc1cc(C#CCn2cc(C3CC3)nn2)ccc1-c1cn(CC2CCCCO2)nn1] |
| I-646 | 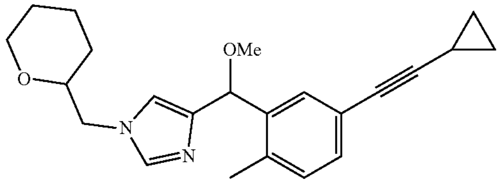 [SMILES: COC(c1cn(CC2CCCCO2)cn1)c1cc(C#CC2CC2)ccc1C] |
| I-647 | 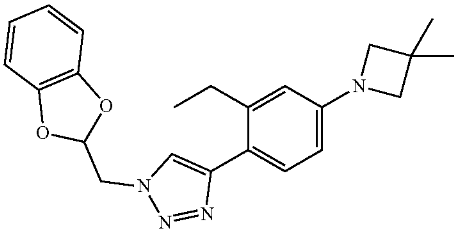 [SMILES: CCc1cc(N2CC(C)(C)C2)ccc1-c1cn(CC2Oc3ccccc3O2)nn1] |

TABLE 1-continued
| Compound | Structure |
|---|---|
| I-648 | 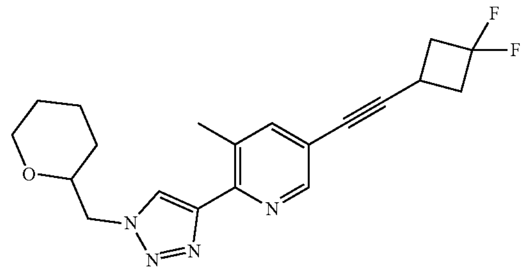 [SMILES: Cc1cc(C#CC2CC(F)(F)C2)cnc1-c1cn(CC2CCCCO2)nn1] |
| I-649 | 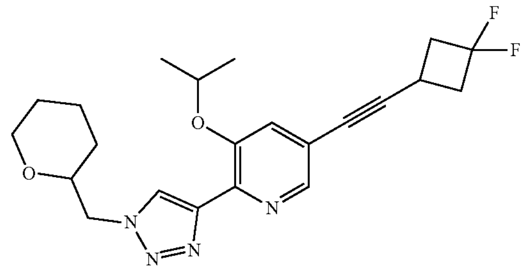 [SMILES: CC(C)Oc1cc(C#CC2CC(F)(F)C2)cnc1-c1cn(CC2CCCCO2)nn1] |
| I-650 | 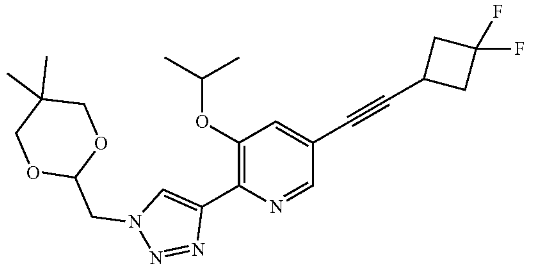 [SMILES: CC(C)Oc1cc(C#CC2CC(F)(F)C2)cnc1-c1cn(CC2OCC(C)(C)CO2)nn1] |
| I-651 | 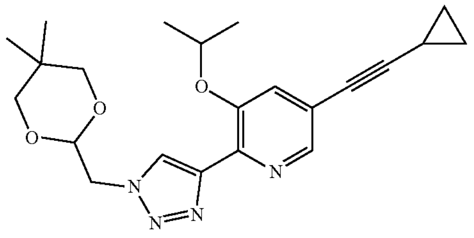 [SMILES: CC(C)Oc1cc(C#CC2CC2)cnc1-c1cn(CC2OCC(C)(C)CO2)nn1] |
| I-652 | 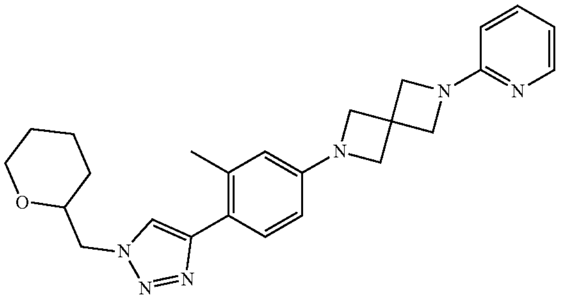 [SMILES: Cc1cc(N2CC3(C2)CN(c2ccccn2)C3)ccc1-c1cn(CC2CCCCO2)nn1] |
Selected Compounds TABLE 1-continued
| Selected Compounds | |
|---|---|
| Compound | Structure |
| I-653 | 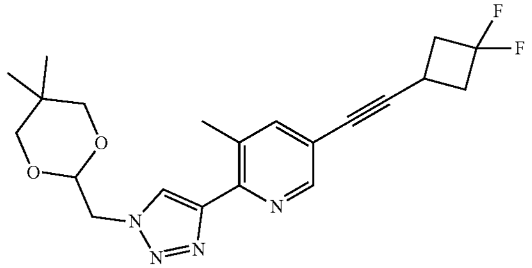 [SMILES: Cc1cc(C#CC2CC(F)(F)C2)cnc1-c1cn(CC2OCC(C)(C)CO2)nn1] |
| I-654 | 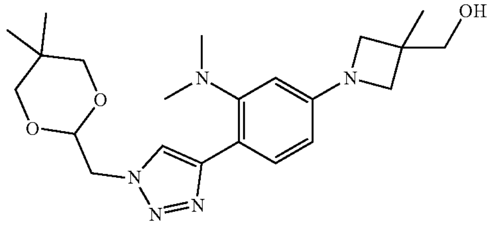 |
| I-655 | 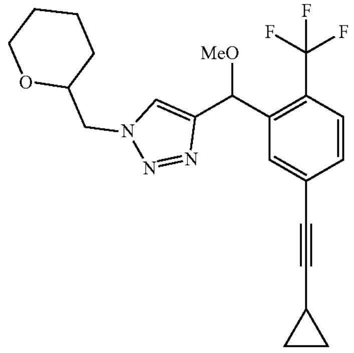 [SMILES: COC(c1cn(CC2CCCCO2)nn1)c1cc(C#CC2CC2)ccc1C(F)(F)F] |
| I-656 | 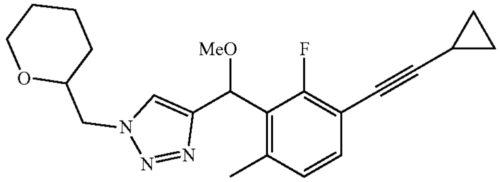 [SMILES: COC(c1cn(CC2CCCCO2)nn1)c1c(C)ccc(C#CC2CC2)c1F] |
| I-657 | 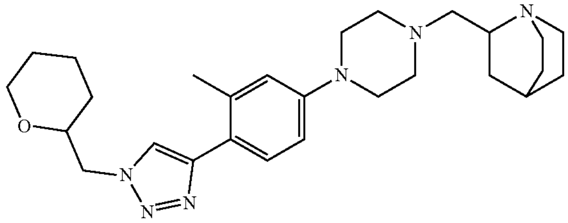 [SMILES: Cc1cc(N2CCN(CC3CC4CCN3CC4)CC2)ccc1-c1cn(CC2CCCCO2)nn1] |
| I-658 | 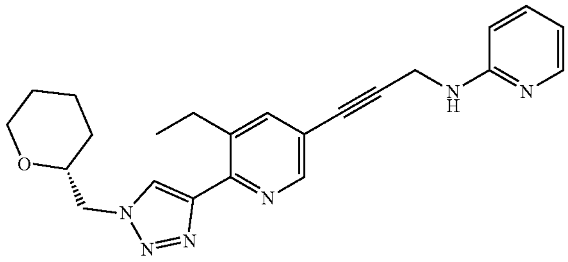 [SMILES: CCc1cc(C#CCNc2ccccn2)cnc1-c1cn(C[C@H]2CCCCO2)nn1] |

TABLE 1-continued
| Selected Compounds | |
|---|---|
| Compound | Structure |
| I-659 | 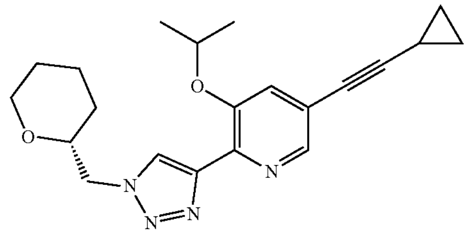 |
| I-660 | 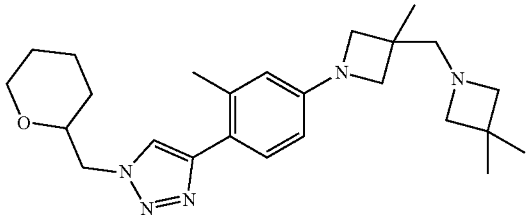 [SMILES: Cc1cc(N2CC(C)(CN3CC(C)(C)C3)C2)ccc1-c1cn(CC2CCCCO2)nn1] |
| I-661 | 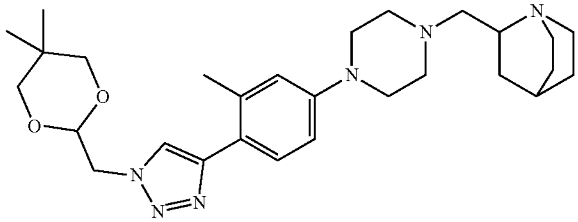 [SMILES: Cc1cc(N2CCN(CC3CC4CCN3CC4)CC2)ccc1-c1cn(CC2OCC(C)(C)CO2)nn1] |
| I-662 | 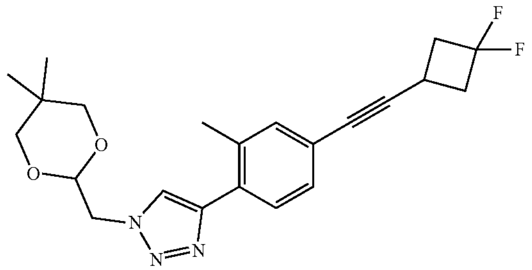 [SMILES: Cc1cc(C#CC2CC(F)(F)C2)ccc1-c1cn(CC2OCC(C)(C)CO2)nn1] |
| I-663 | 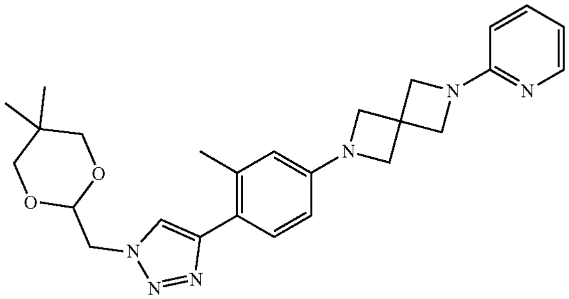 [SMILES: Cc1cc(N2CC3(C2)CN(c2ccccn2)C3)ccc1-c1cn(CC2OCC(C)(C)CO2)nn1] |
| I-664 | 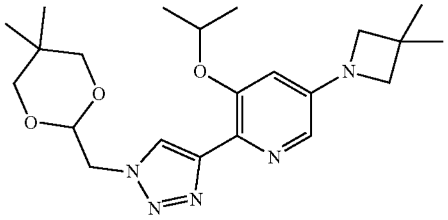 |

TABLE 1-continued
| Selected Compounds | |
|---|---|
| Compound | Structure |
| I-665 | 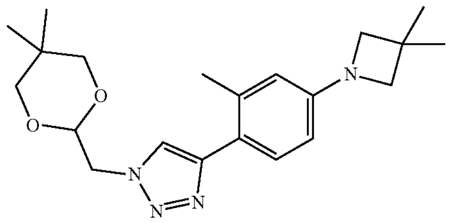 |
| I-666 | 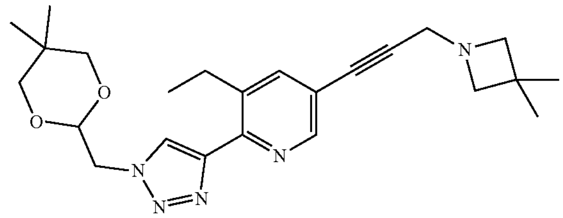 |
| I-667 | 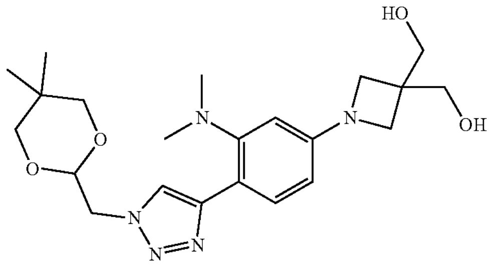 [SMILES: CN(C)c1cc(N2CC(CO)(CO)C2)ccc1-c1cn(CC2OCC(C)(C)CO2)nn1] |
| I-668 | 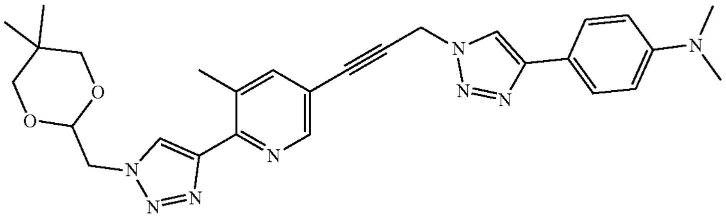 |
| I-669 | 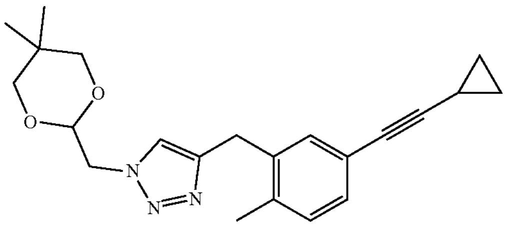 [SMILES: Cc1ccc(C#CC2CC2)cc1Cc1cn(CC2OCC(C)(C)CO2)nn1] |
| I-670 | 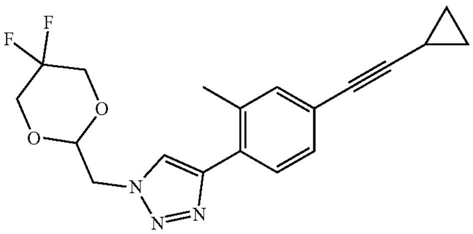 [SMILES: Cc1cc(C#CC2CC2)ccc1-c1cn(CC2OCC(F)(F)CO2)nn1] |

TABLE 1-continued
| Selected Compounds | |
|---|---|
| Compound | Structure |
| I-671 | 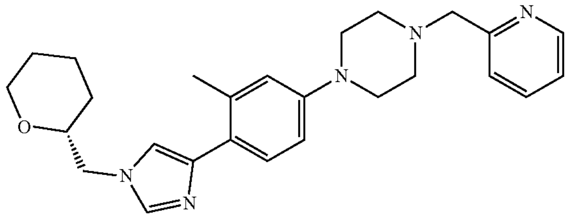 [SMILES: Cc1cc(N2CCN(Cc3ccccn3)CC2)ccc1-c1cn(C[C@H]2CCCCO2)cn1] |
| I-672 | 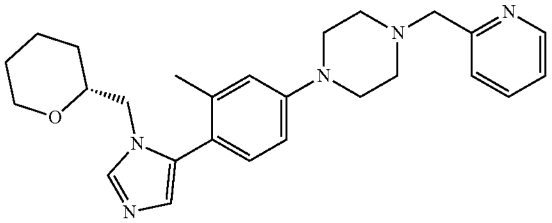 [SMILES: Cc1cc(N2CCN(Cc3ccccn3)CC2)ccc1-c1cncn1C[C@H]1CCCCO1] |
| I-673 | 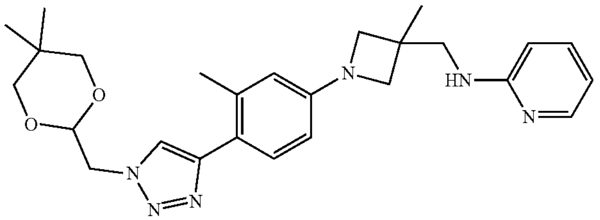 [SMILES: Cc1cc(N2CC(C)(CNc3ccccn3)C2)ccc1-c1cn(CC2OCC(C)(C)CO2)nn1] |
| I-674 | 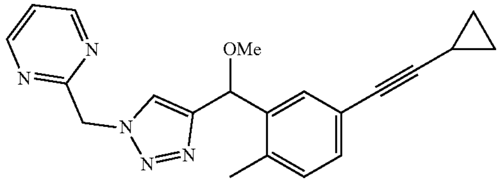 [SMILES: COC(c1cn(Cc2ncccn2)nn1)c1cc(C#CC2CC2)ccc1C] |
| I-675 | 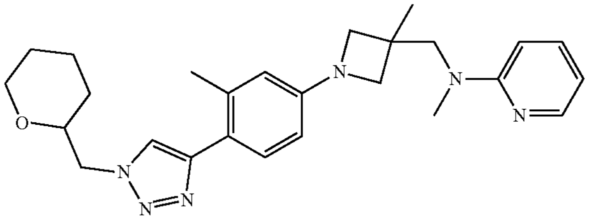 [SMILES: Cc1cc(N2CC(C)(CN(C)c3ccccn3)C2)ccc1-c1cn(CC2CCCCO2)nn1] |
| I-676 | 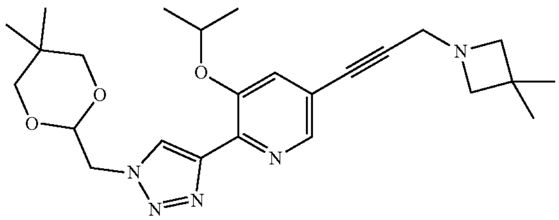 |
| I-677 | 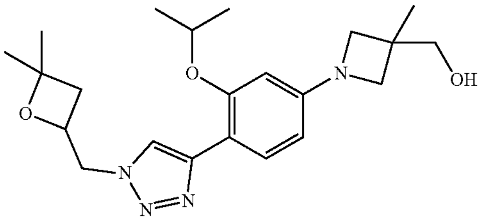 [SMILES: CC(C)Oc1cc(N2CC(C)(CO)C2)ccc1-c1cn(CC2CC(C)(C)O2)nn1] |

TABLE 1-continued
| Selected Compounds | |
|---|---|
| Compound | Structure |
| I-678 | 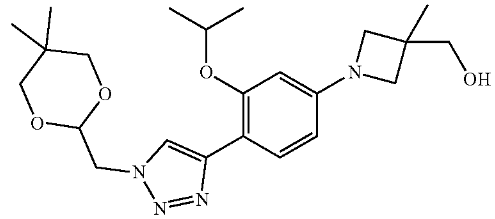 [SMILES: CC(C)Oc1cc(N2CC(C)(CO)C2)ccc1-c1cn(CC2OCC(C)(C)CO2)nn1] |
| I-679 | 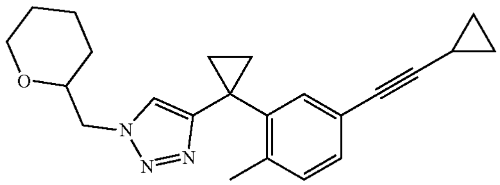 [SMILES: Cc1ccc(C#CC2CC2)cc1C1(c2cn(CC3CCCCO3)nn2)CC1] |
| I-680 | 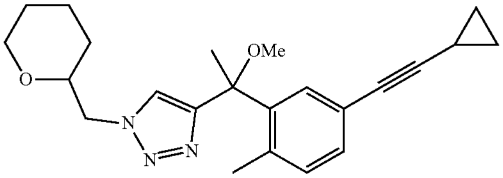 [SMILES: COC(C)(c1cn(CC2CCCCO2)nn1)c1cc(C#CC2CC2)ccc1C] |
| I-681 | 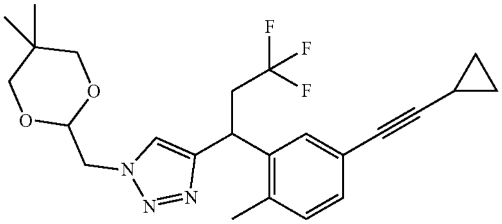 [SMILES: Cc1ccc(C#CC2CC2)cc1C(CC(F)(F)F)c1cn(CC2OCC(C)(C)CO2)nn1] |
| I-682 | 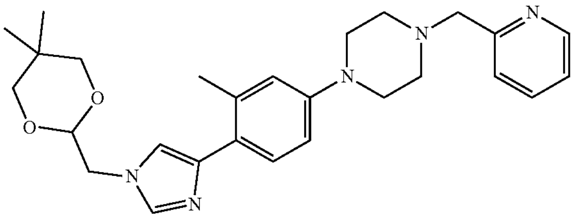 [SMILES: Cc1cc(N2CCN(Cc3ccccn3)CC2)ccc1-c1cn(CC2OCC(C)(C)CO2)cn1] |
| I-683 | 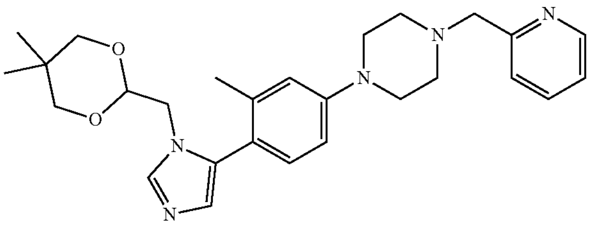 [SMILES: Cc1cc(N2CCN(Cc3ccccn3)CC2)ccc1-c1cncn1CC1OCC(C)(C)CO1] |

TABLE 1-continued
| Selected Compounds | |
|---|---|
| Compound | Structure |
| I-684 | 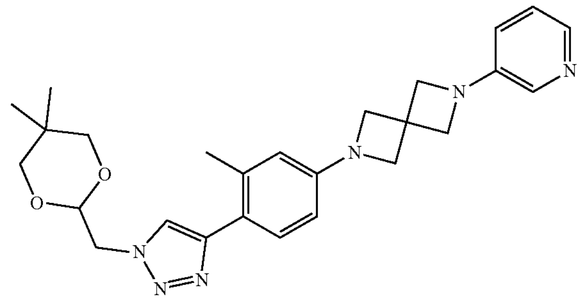 [SMILES: Cc1cc(N2CC3(CN(c4cccnc4)C3)C2)ccc1-c1cn(CC2OCC(C)(C)CO2)nn1] |
| I-685 | 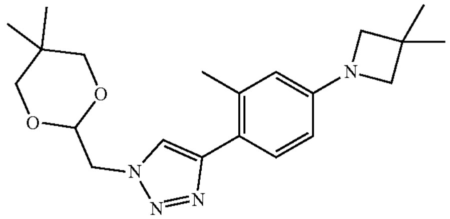 |
| I-686 | 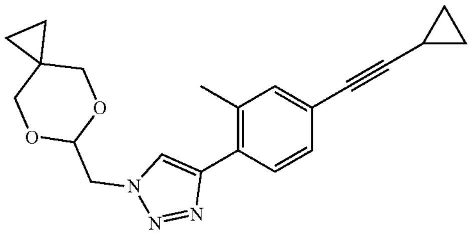 [SMILES: Cc1cc(C#CC2CC2)ccc1-c1cn(CC2OCC3(CC3)CO2)nn1] |
| I-687 | 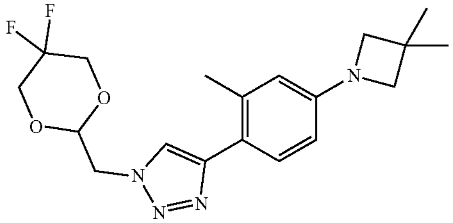 [SMILES: Cc1cc(N2CC(C)(C)C2)ccc1-c1cn(CC2OCC(F)(F)CO2)nn1] |
| I-688 | 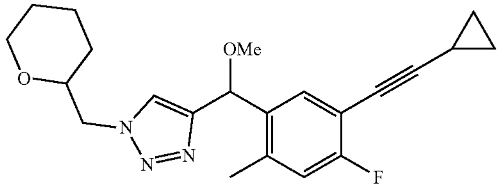 [SMILES: COC(c1cn(CC2CCCCO2)nn1)c1cc(C#CC2CC2)c(F)cc1C] |
| I-689 | 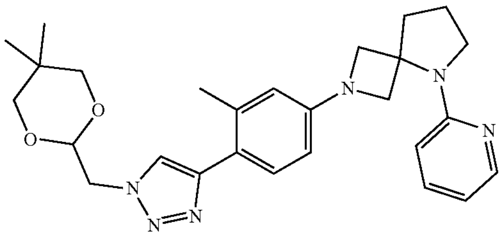 [SMILES: Cc1cc(N2CC3(CCCN3c3ccccn3)C2)ccc1-c1cn(CC2OCC(C)(C)CO2)nn1] |

TABLE 1-continued
| Selected Compounds | |
|---|---|
| Compound | Structure |
| I-690 | 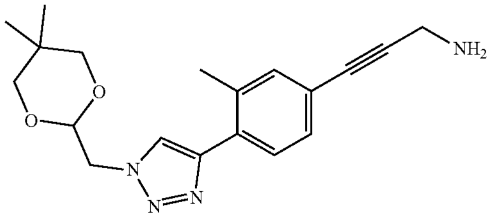 [SMILES: Cc1cc(C#CCN)ccc1-c1cn(CC2OCC(C)(C)CO2)nn1] |
| I-691 | 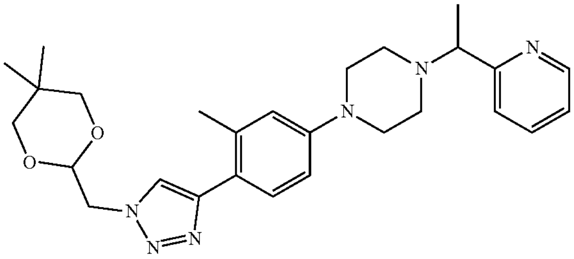 [SMILES: Cc1cc(N2CCN(C(C)c3ccccn3)CC2)ccc1-c1cn(CC2OCC(C)(C)CO2)nn1] |
| I-692 | 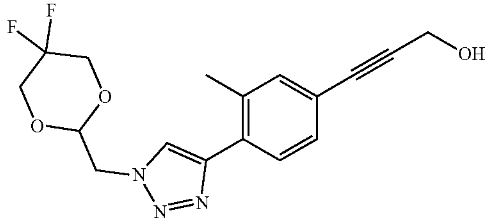 [SMILES: Cc1cc(C#CCO)ccc1-c1cn(CC2OCC(F)(F)CO2)nn1] |
| I-693 | 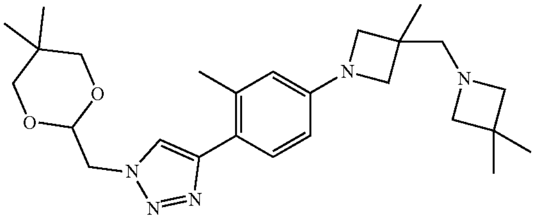 |
| I-694 | 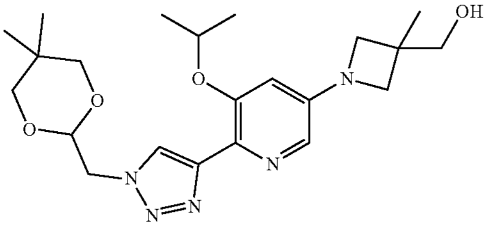 [SMILES: CC(C)Oc1cc(N2CC(C)(CO)C2)cnc1-c1cn(CC2OCC(C)(C)CO2)nn1] |
| I-695 | 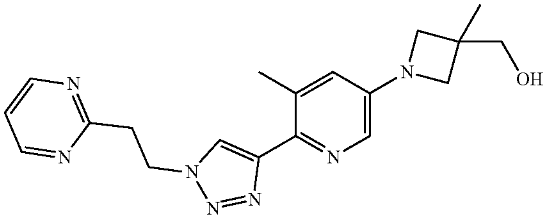 [SMILES: Cc1cc(N2CC(C)(CO)C2)cnc1-c1cn(CCc2ncccn2)nn1] |

TABLE 1-continued
| Selected Compounds | |
|---|---|
| Compound | Structure |
| I-696 | 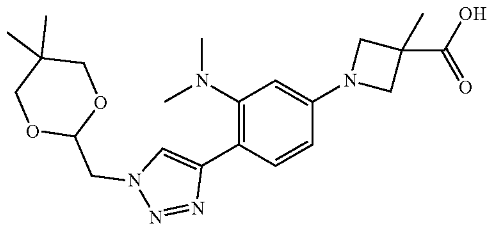 [SMILES: CN(C)c1cc(N2CC(C)(C(=O)O)C2)ccc1-c1cn(CC2OCC(C)(C)CO2)nn1] |
| I-697 | 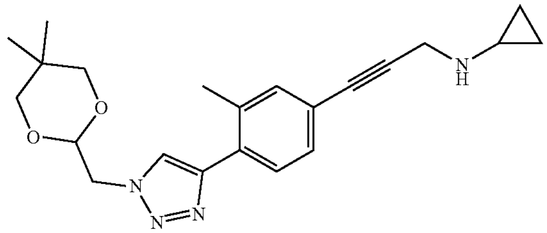 [SMILES: Cc1cc(C#CCNC2CC2)ccc1-c1cn(CC2OCC(C)(C)CO2)nn1] |
| I-698 | 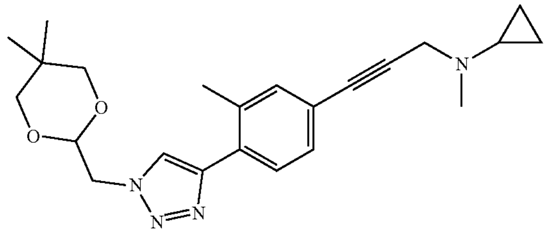 [SMILES: Cc1cc(C#CCN(C)C2CC2)ccc1-c1cn(CC2OCC(C)(C)CO2)nn1] |
| I-699 | 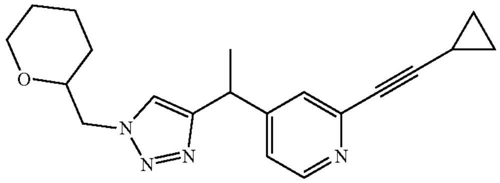 [SMILES: CC(c1ccnc(C#CC2CC2)c1)c1cn(CC2CCCCO2)nn1] |
| I-700 | 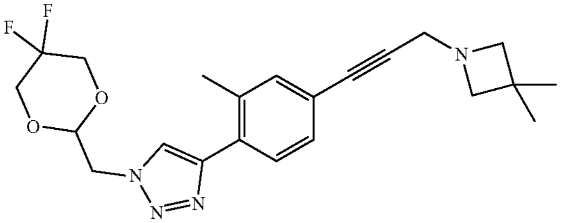 [SMILES: Cc1cc(C#CCN2CC(C)(C)C2)ccc1-c1cn(CC2OCC(F)(F)CO2)nn1] |
| I-701 | 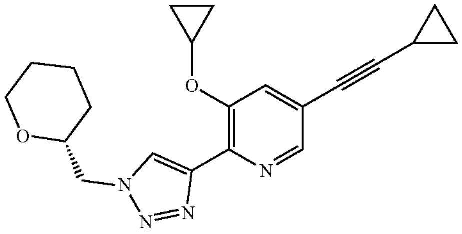 [SMILES: C(#CC1CC1)c1cnc(-c2cn(C[C@H]3CCCCO3)nn2)c(OC2CC2)c1] |

TABLE 1-continued
| Selected Compounds | |
|---|---|
| Compound | Structure |
| I-702 | 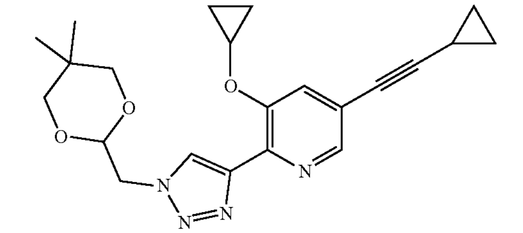 [SMILES: CC1(C)COC(Cn2cc(-c3ncc(C#CC4CC4)cc3OC3CC3)nn2)OC1] |
| I-703 | 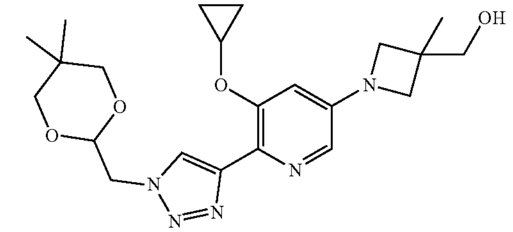 [SMILES: CC1(C)COC(Cn2cc(-c3ncc(N4CC(C)(CO)C4)cc3OC3CC3)nn2)OC1] |
| I-704 | 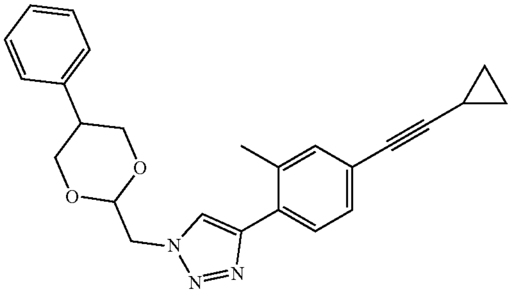 [SMILES: Cc1cc(C#CC2CC2)ccc1-c1cn(CC2OCC(c3ccccc3)CO2)nn1] |
| I-705 | 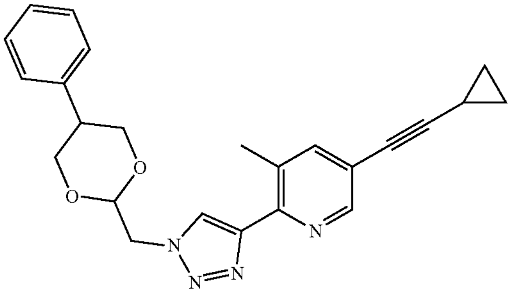 [SMILES: Cc1cc(C#CC2CC2)cnc1-c1cn(CC2OCC(c3ccccc3)CO2)nn1] |
| I-706 | 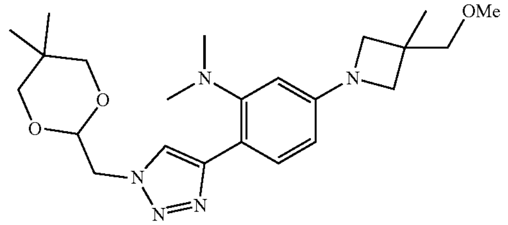 [SMILES: COCC1(C)CN(c2ccc(-c3cn(CC4OCC(C)(C)CO4)nn3)c(N(C)C)c2)C1] |
| I-707 | 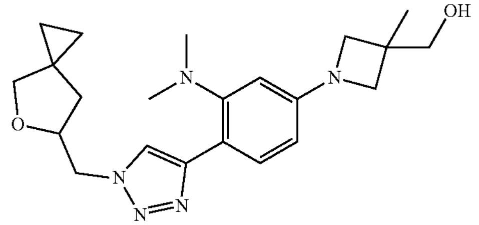 [SMILES: CN(C)c1cc(N2CC(C)(CO)C2)ccc1-c1cn(CC2CC3(CC3)CO2)nn1] |

TABLE 1-continued
| Selected Compounds | |
|---|---|
| Compound | Structure |
| I-708 | 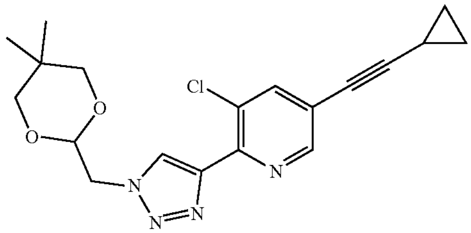 [SMILES: CC1(C)COC(Cn2cc(-c3ncc(C#CC4CC4)cc3Cl)nn2)OC1] |
| I-709 | 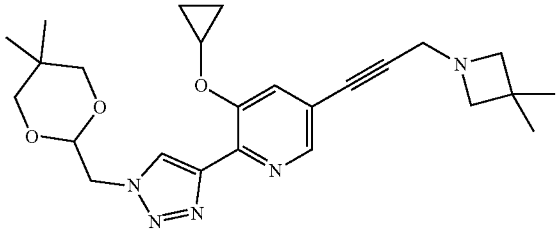 |
| I-710 | 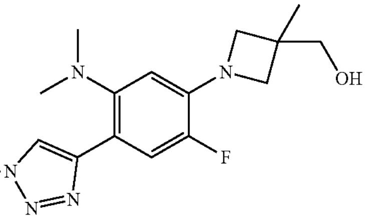 |
| I-711 | 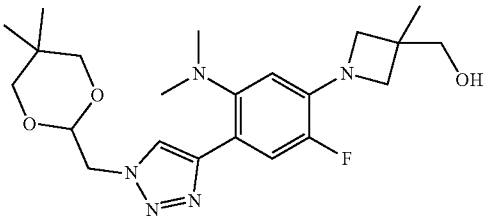 [SMILES: CN(C)c1cc(N2CC(C)(CO)C2)c(F)cc1-c1cn(CC2OCC(C)(C)CO2)nn1] |
| I-712 | 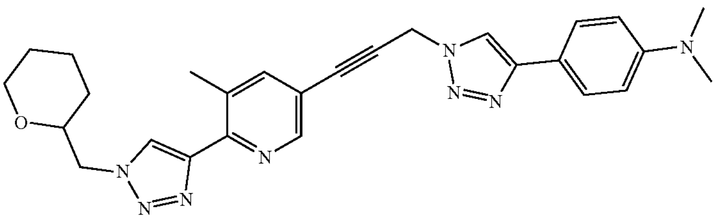 [SMILES: Cc1cc(C#CCn2cc(-c3ccc(N(C)C)cc3)nn2)cnc1-c1cn(CC2CCCCO2)nn1] |
| I-713 | 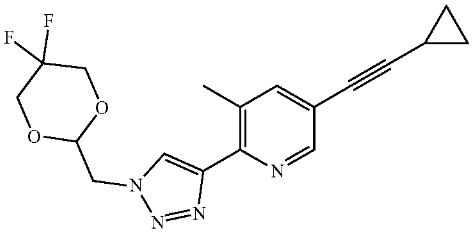 [SMILES: Cc1cc(C#CC2CC2)cnc1-c1cn(CC2OCC(F)(F)CO2)nn1] |

TABLE 1-continued
| Selected Compounds | |
|---|---|
| Compound | Structure |
| I-714 | 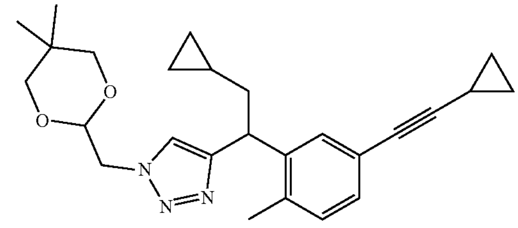 |
| I-715 | 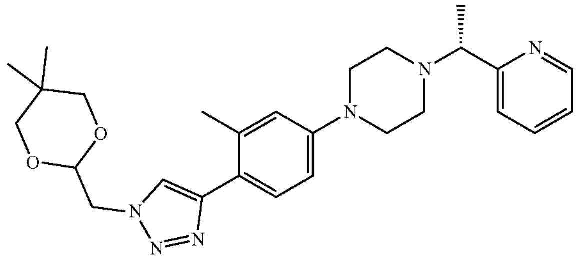 [SMILES: Cc1cc(N2CCN([C@H](C)c3ccccn3)CC2)ccc1-c1cn(CC2OCC(C)(C)CO2)nn1] |
| I-716 | 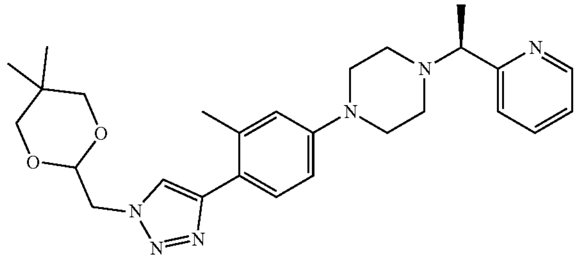 [SMILES: Cc1cc(N2CCN([C@@H](C)c3ccccn3)CC2)ccc1-c1cn(CC2OCC(C)(C)CO2)nn1] |
| I-717 | 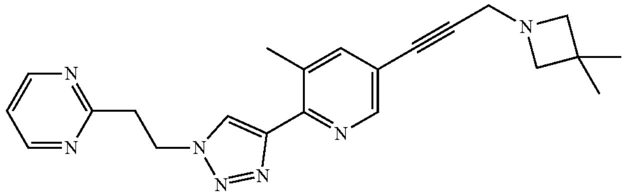 [SMILES: Cc1cc(C#CCN2CC(C)(C)C2)cnc1-c1cn(CCc2ncccn2)nn1] |
| I-718 | 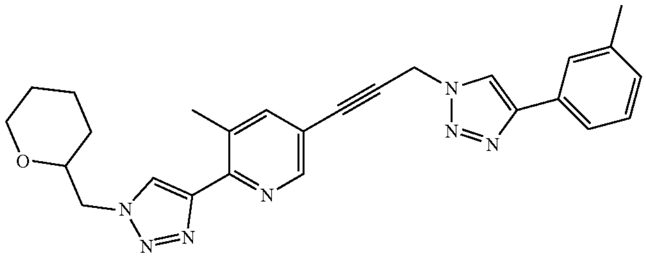 [SMILES: Cc1cccc(-c2cn(CC#Cc3cnc(-c4cn(CC5CCCCO5)nn4)c(C)c3)nn2)c1] |
| I-719 | 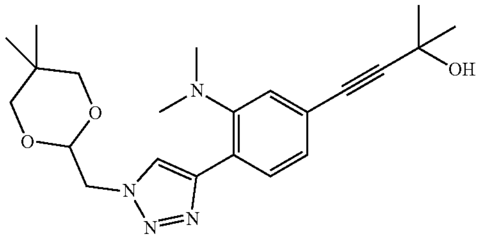 [SMILES: CN(C)c1cc(C#CC(C)(C)O)ccc1-c1cn(CC2OCC(C)(C)CO2)nn1]

TABLE 1-continued
| Selected Compounds | |
|---|---|
| Compound | Structure |
| I-720 | 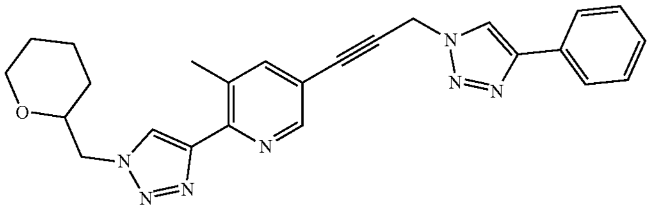 [SMILES: Cc1cc(C#CCn2cc(-c3ccccc3)nn2)cnc1-c1cn(CC2CCCCO2)nn1] |
| I-721 | 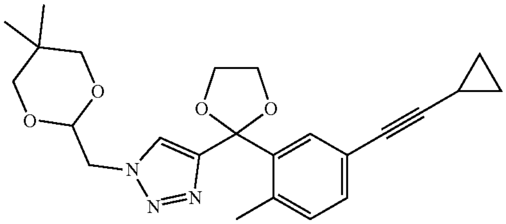 [SMILES: Cc1ccc(C#CC2CC2)cc1C1(c2cn(CC3OCC(C)(C)CO3)nn2)OCCO1] |
| I-722 | 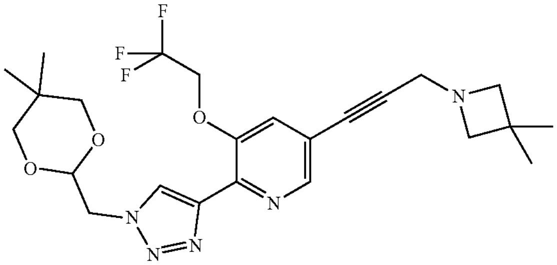 |
| I-723 | 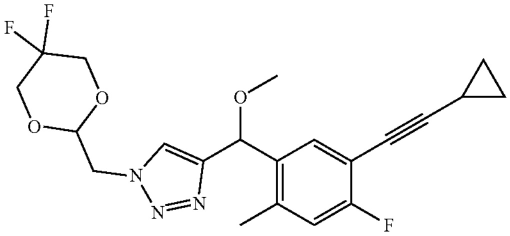 [SMILES: COC(c1cn(CC2OCC(F)(F)CO2)nn1)c1cc(C#CC2CC2)c(F)cc1C] |
| I-724 | 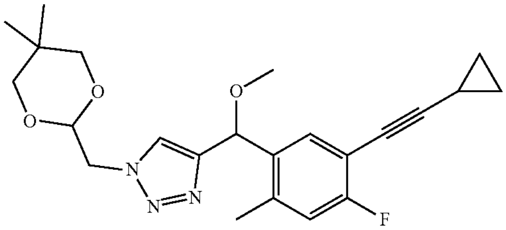 [SMILES: COC(c1cn(CC2OCC(C)(C)CO2)nn1)c1cc(C#CC2CC2)c(F)cc1C] |
| I-725 | 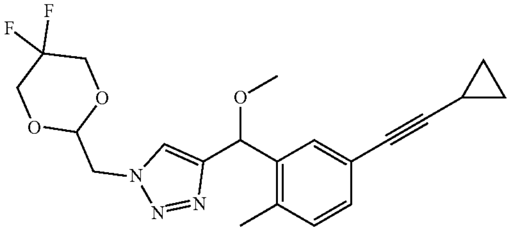 [SMILES: COC(c1cn(CC2OCC(F)(F)CO2)nn1)c1cc(C#CC2CC2)ccc1C] |

TABLE 1-continued
| Selected Compounds | |
|---|---|
| Compound | Structure |
| I-726 | 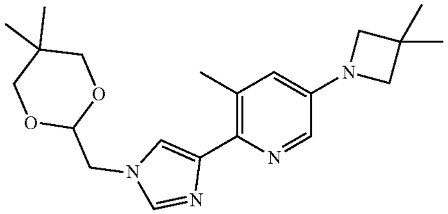 |
| I-727 | 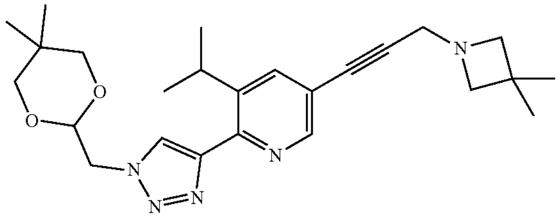 |
| I-728 | 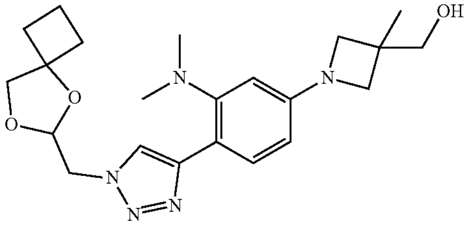 [SMILES: CN(C)c1cc(N2CC(C)(CO)C2)ccc1-c1cn(CC2OCC3(CCC3)O2)nn1] |
| I-729 | 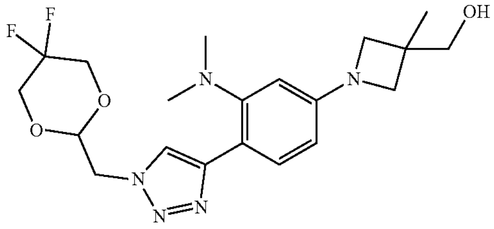 [SMILES: CN(C)c1cc(N2CC(C)(CO)C2)ccc1-c1cn(CC2OCC(F)(F)CO2)nn1] |
| I-730 | 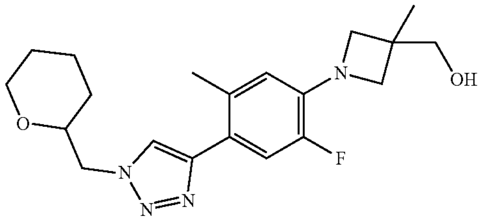 [SMILES: Cc1cc(N2CC(C)(CO)C2)c(F)cc1-c1cn(CC2CCCCO2)nn1] |
| I-731 | 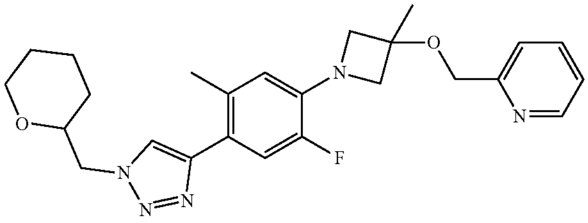 [SMILES: Cc1cc(N2CC(C)(OCc3ccccn3)C2)c(F)cc1-c1cn(CC2CCCCO2)nn1] |

TABLE 1-continued
| Selected Compounds | |
|---|---|
| Compound | Structure |
| I-732 | 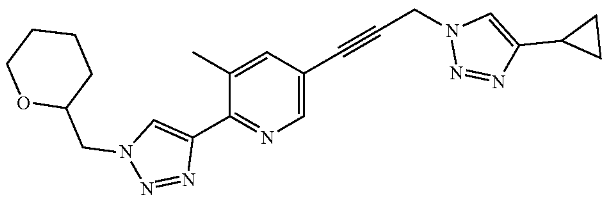 [SMILES: Cc1cc(C#CCn2cc(C3CC3)nn2)cnc1-c1cn(CC2CCCCO2)nn1] |
| I-733 | 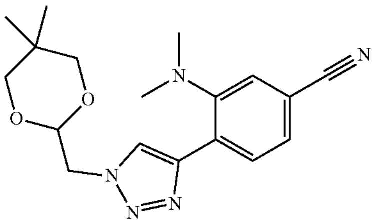 [SMILES: CN(C)c1cc(C#N)ccc1-c1cn(CC2OCC(C)(C)CO2)nn1] |
| I-734 | 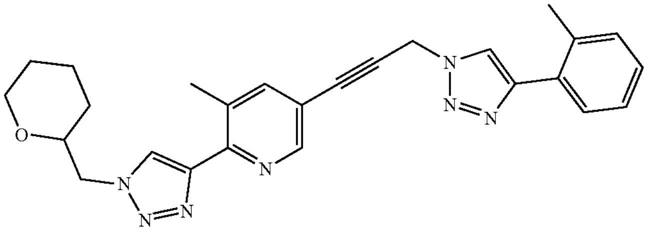 [SMILES: Cc1ccccc1-c1cn(CC#Cc2cnc(-c3cn(CC4CCCCO4)nn3)c(C)c2)nn1] |
| I-735 | 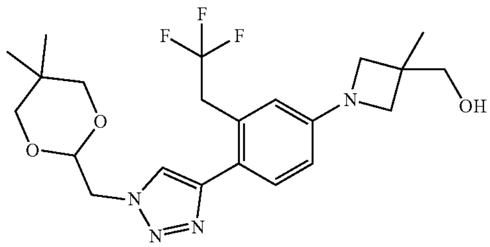 [SMILES: CC1(C)COC(Cn2cc(-c3ccc(N4CC(C)(CO)C4)cc3CC(F)(F)F)nn2)OC1] |
| I-736 | 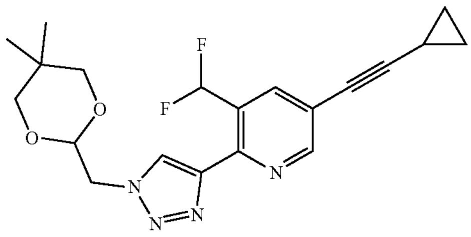 [SMILES: CC1(C)COC(Cn2cc(-c3ncc(C#CC4CC4)cc3C(F)F)nn2)OC1] |
| I-737 | 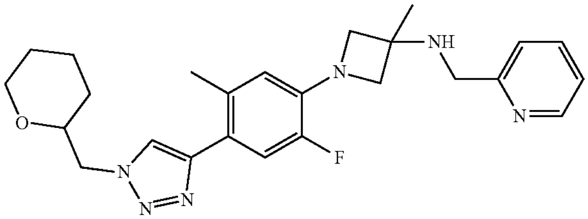 [SMILES: Cc1cc(N2CC(C)(NCc3ccccn3)C2)c(F)cc1-c1cn(CC2CCCCO2)nn1] |

TABLE 1-continued
| Selected Compounds | |
|---|---|
| Compound | Structure |
| I-738 | 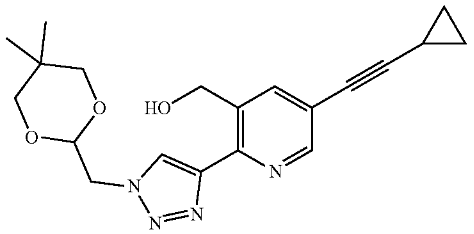 [SMILES: CC1(C)COC(Cn2cc(-c3ncc(C#CC4CC4)cc3CO)nn2)OC1] |
| I-739 | 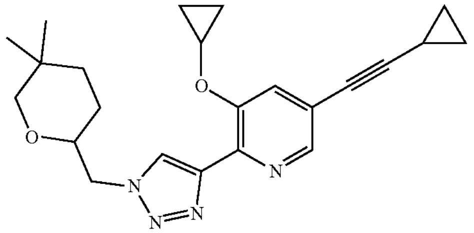 [SMILES: CC1(C)CCC(Cn2cc(-c3ncc(C#CC4CC4)cc3OC3CC3)nn2)OC1] |
| I-740 | 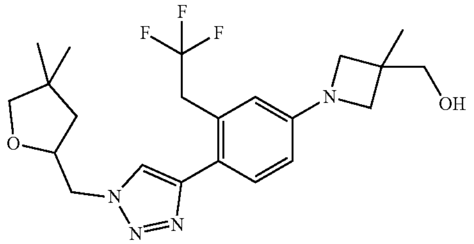 [SMILES: CC1(C)COC(Cn2cc(-c3ccc(N4CC(C)(CO)C4)cc3CC(F)(F)F)nn2)C1] |
| I-741 | 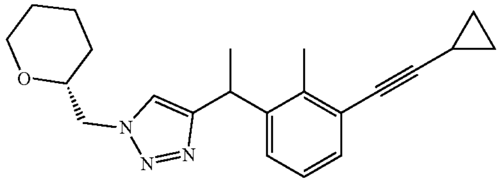 [SMILES: Cc1c(C#CC2CC2)cccc1C(C)c1cn(C[C@H]2CCCCO2)nn1] |
| I-742 | 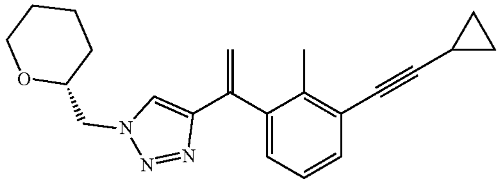 [SMILES: C=C(c1cn(C[C@H]2CCCCO2)nn1)c1cccc(C#CC2CC2)c1C] |
| I-743 | 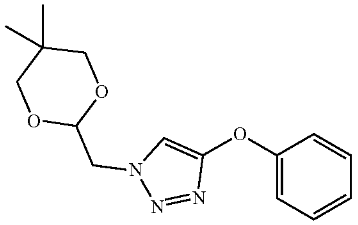 [SMILES: CC1(C)COC(Cn2cc(Oc3ccccc3)nn2)OC1] |

TABLE 1-continued
| Selected Compounds | |
|---|---|
| Compound | Structure |
| I-744 | 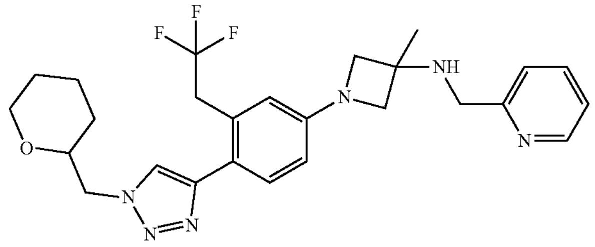 [SMILES: CC1(NCc2ccccn2)CN(c2ccc(-c3cn(CC4CCCCO4)nn3)c(CC(F)(F)F)c2)C1] |
| I-745 | 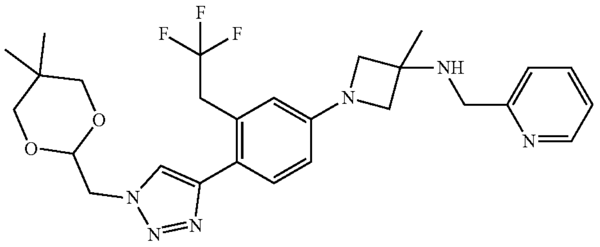 [SMILES: CC1(C)COC(Cn2cc(-c3ccc(N4CC(C)(NCc5ccccn5)C4)cc3CC(F)(F)F)nn2)OC1] |
| I-746 | 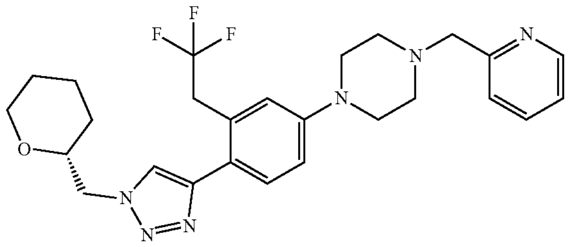 [SMILES: FC(F)(F)Cc1cc(N2CCN(Cc3ccccn3)CC2)ccc1-c1cn(C[C@H]2CCCCO2)nn1] |
| I-747 | 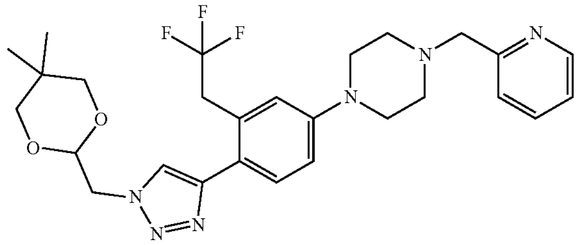 [SMILES: CC1(C)COC(Cn2cc(-c3ccc(N4CCN(Cc5ccccn5)CC4)cc3CC(F)(F)F)nn2)OC1] |
| I-748 | 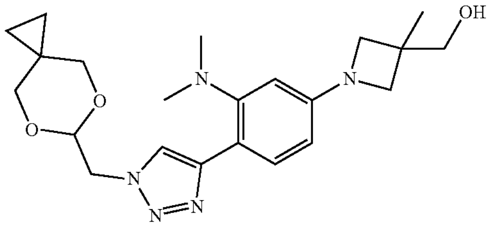 [SMILES: CN(C)c1cc(N2CC(C)(CO)C2)ccc1-c1cn(CC2OCC3(CC3)CO2)nn1] |
| I-749 | 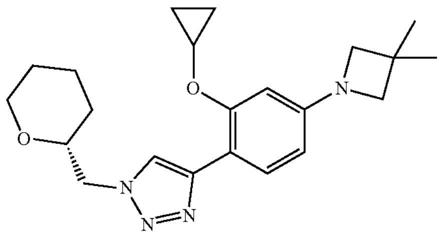 [SMILES: CC1(C)CN(c2ccc(-c3cn(C[C@H]4CCCCO4)nn3)c(OC3CC3)c2)C1] |

TABLE 1-continued
| Selected Compounds | |
|---|---|
| Compound | Structure |
| I-750 | 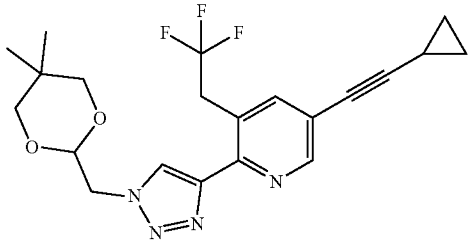 [SMILES: CC1(C)COC(Cn2cc(-c3ncc(C#CC4CC4)cc3CC(F)(F)F)nn2)OC1] |
| I-751 | 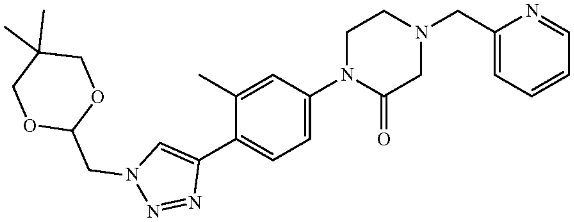 [SMILES: Cc1cc(N2CCN(Cc3ccccn3)CC2=O)ccc1-c1cn(CC2OCC(C)(C)CO2)nn1] |
| I-752 | 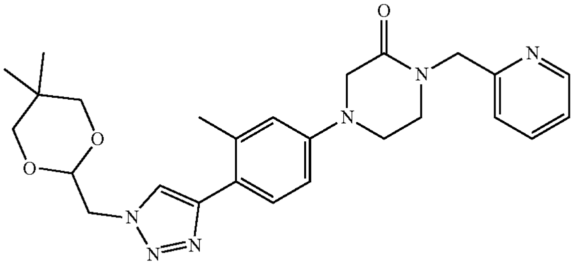 [SMILES: Cc1cc(N2CCN(Cc3ccccn3)C(=O)C2)ccc1-c1cn(CC2OCC(C)(C)CO2)nn1] |
| I-753 | 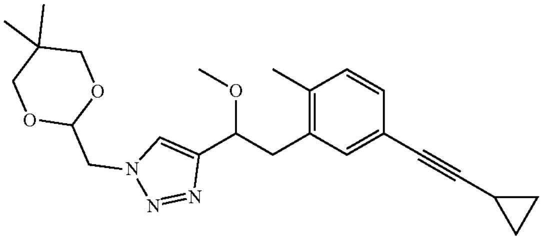 [SMILES: COC(Cc1cc(C#CC2CC2)ccc1C)c1cn(CC2OCC(C)(C)CO2)nn1] |
| I-754 | 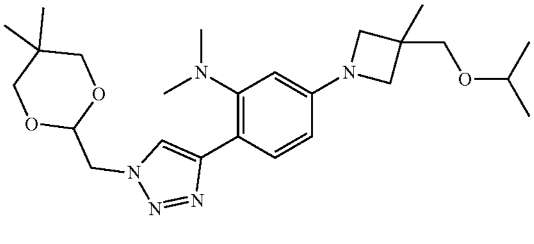 [SMILES: CC(C)OCC1(C)CN(c2ccc(-c3cn(CC4OCC(C)(C)CO4)nn3)c(N(C)C)c2)C1] |
| I-755 | 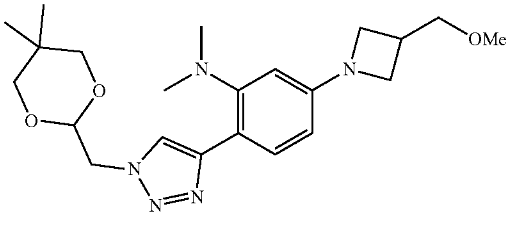 [SMILES: COCC1CN(c2ccc(-c3cn(CC4OCC(C)(C)CO4)nn3)c(N(C)C)c2)C1] |

TABLE 1-continued
| Selected Compounds | |
|---|---|
| Compound | Structure |
| I-756 | 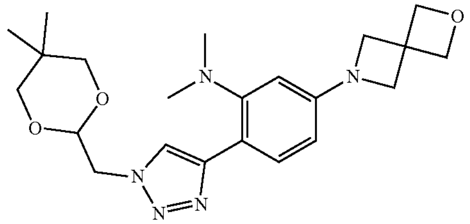 [SMILES: CN(C)c1cc(N2CC3(COC3)C2)ccc1-c1cn(CC2OCC(C)(C)CO2)nn1] |
| I-757 | 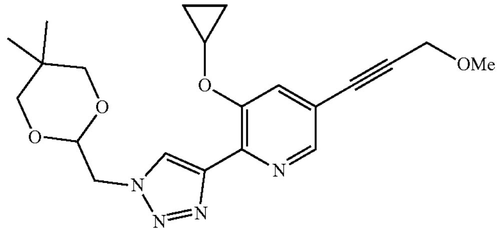 [SMILES: COCC#Cc1cnc(-c2cn(CC3OCC(C)(C)CO3)nn2)c(OC2CC2)c1] |
| I-758 | 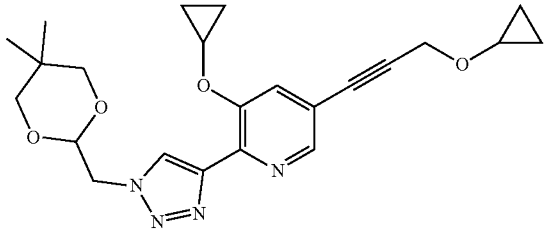 |
| I-759 | 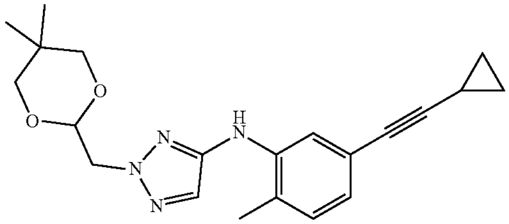 [SMILES: Cc1ccc(C#CC2CC2)cc1Nc1cnn(CC2OCC(C)(C)CO2)n1] |
| I-760 | 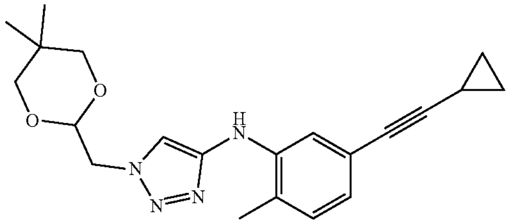 [SMILES: Cc1ccc(C#CC2CC2)cc1Nc1cn(CC2OCC(C)(C)CO2)nn1] |
| I-761 | 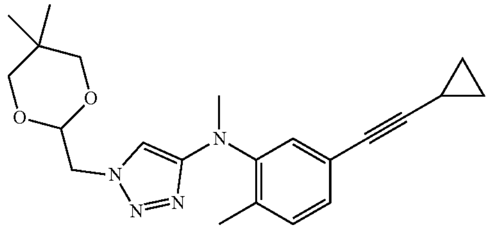 [SMILES: Cc1ccc(C#CC2CC2)cc1N(C)c1cn(CC2OCC(C)(C)CO2)nn1] |

TABLE 1-continued
| Selected Compounds | |
|---|---|
| Compound | Structure |
| I-762 | 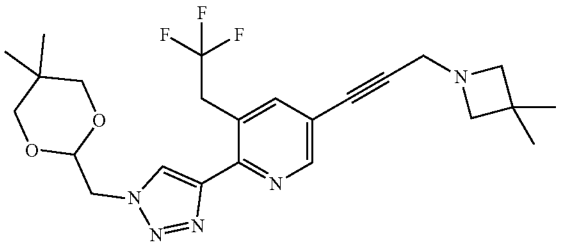 |
| I-763 | 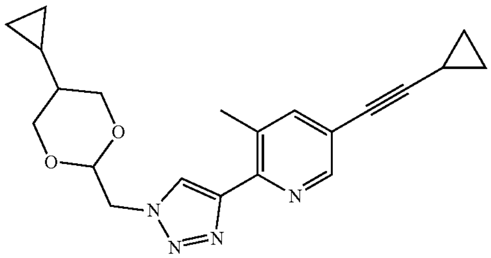 [SMILES: Cc1cc(C#CC2CC2)cnc1-c1cn(CC2OCC(C3CC3)CO2)nn1] |
| I-764 | 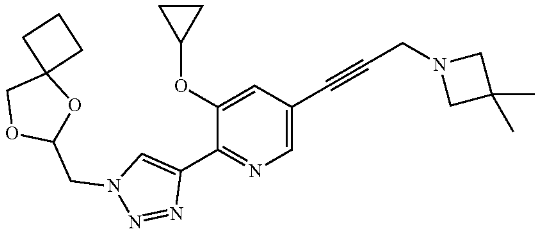 [SMILES: CC1(C)CN(CC#Cc2cnc(-c3cn(CC4OCC5(CCC5)O4)nn3)c(OC3CC3)c2)C1] |
| I-765 | 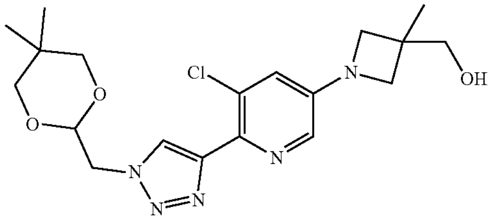 [SMILES: CC1(C)COC(Cn2cc(-c3ncc(N4CC(C)(CO)C4)cc3Cl)nn2)OC1] |
| I-766 | 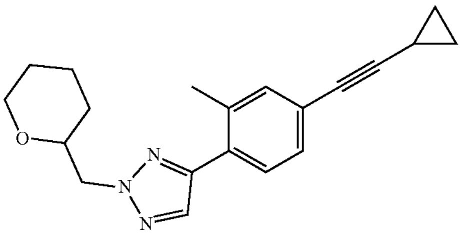 [SMILES: Cc1cc(C#CC2CC2)ccc1-c1cnn(CC2CCCCO2)n1] |
| I-767 | 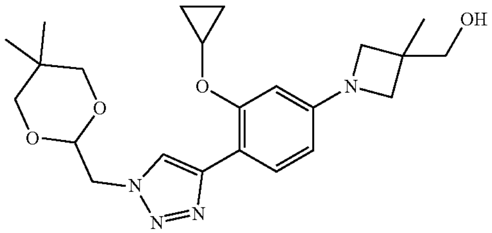 [SMILES: CC1(C)COC(Cn2cc(-c3ccc(N4CC(C)(CO)C4)cc3OC3CC3)nn2)OC1] |

TABLE 1-continued
| Selected Compounds | |
|---|---|
| Compound | Structure |
| I-768 | 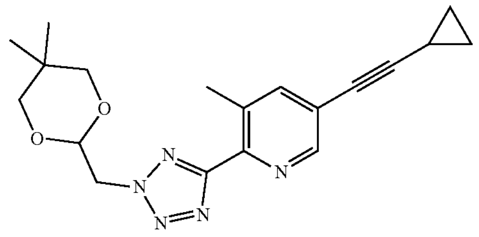 [SMILES: Cc1cc(C#CC2CC2)cnc1-c1nnn(CC2OCC(C)(C)CO2)n1] |
| I-769 | 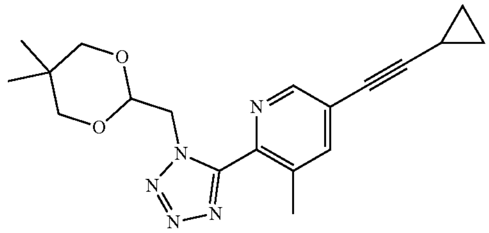 [SMILES: Cc1cc(C#CC2CC2)cnc1-c1nnnn1CC1OCC(C)(C)CO1] |
| I-770 | 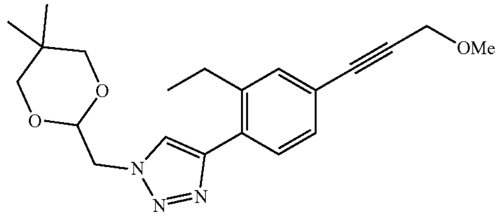 [SMILES: CCc1cc(C#CCOC)ccc1-c1cn(CC2OCC(C)(C)CO2)nn1] |
| I-771 | 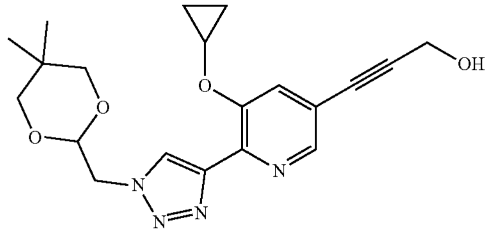 [SMILES: CC1(C)COC(Cn2cc(-c3ncc(C#CCO)cc3OC3CC3)nn2)OC1] |
| I-772 | 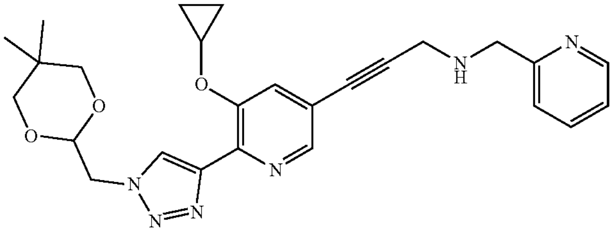 [SMILES: CC1(C)COC(Cn2cc(-c3ncc(C#CCNCc4ccccn4)cc3OC3CC3)nn2)OC1] |
| I-773 | 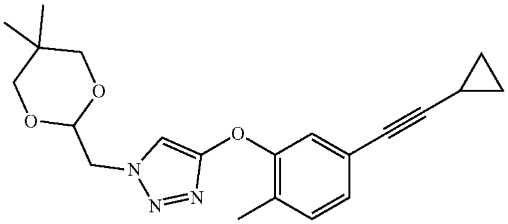 [SMILES: Cc1ccc(C#CC2CC2)cc1Oc1cn(CC2OCC(C)(C)CO2)nn1] |

TABLE 1-continued
| Selected Compounds | |
|---|---|
| Compound | Structure |
| I-774 | 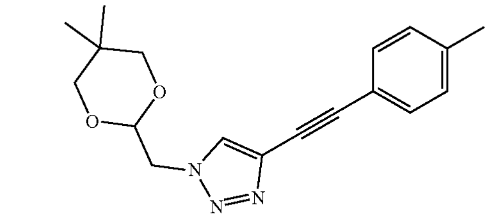 |
| I-775 | 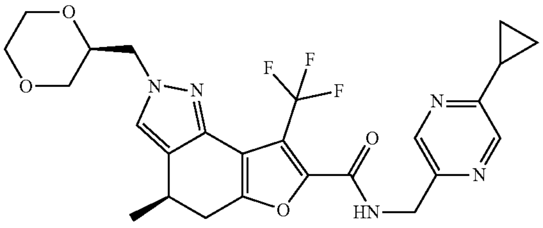<br>(A)<br>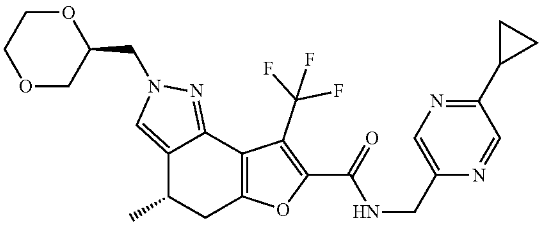<br>(B) |
| I-776 | 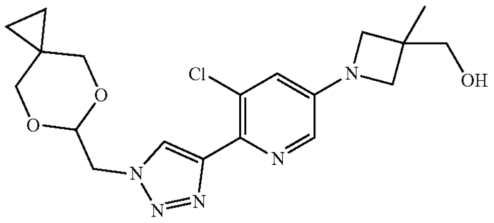 [SMILES: CC1(CO)CN(c2cnc(-c3cn(CC4OCC5(CC5)CO4)nn3)c(Cl)c2)C1] |
| I-777 | 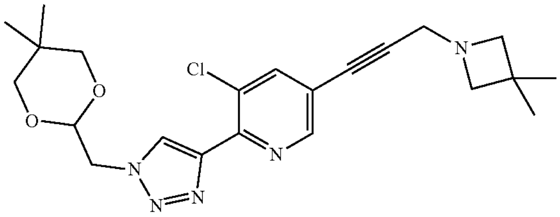 |
| I-778 | 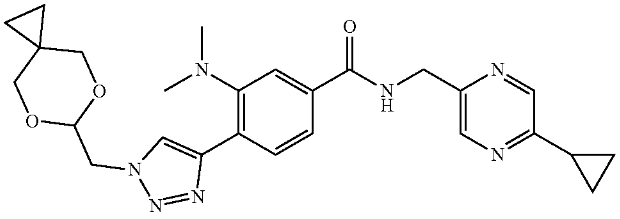 [SMILES: CN(C)c1cc(C(=O)NCc2cnc(C3CC3)cn2)ccc1-c1cn(CC2OCC3(CC3)CO2)nn1] |

TABLE 1-continued
| Selected Compounds | |
|---|---|
| Compound | Structure |
| I-779 | 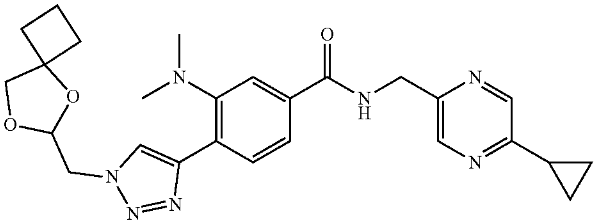 [SMILES: CN(C)c1cc(C(=O)NCc2cnc(C3CC3)cn2)ccc1-c1cn(CC2OCC3(CCC3)O2)nn1] |
| I-780 | 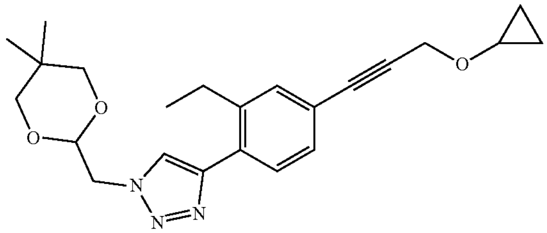 [SMILES: CCc1cc(C#CCOC2CC2)ccc1-c1cn(CC2OCC(C)(C)CO2)nn1] |
| I-781 | 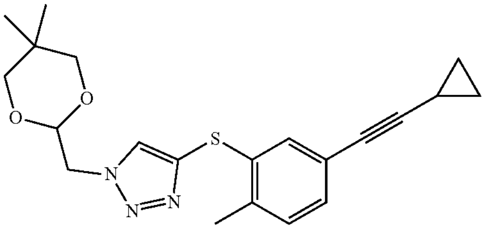 [SMILES: Cc1ccc(C#CC2CC2)cc1Sc1cn(CC2OCC(C)(C)CO2)nn1] |
| I-782 | 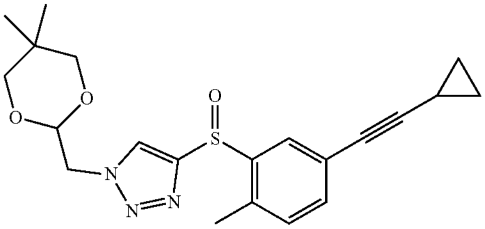 [SMILES: Cc1ccc(C#CC2CC2)cc1S(=O)c1cn(CC2OCC(C)(C)CO2)nn1] |
| I-783 | 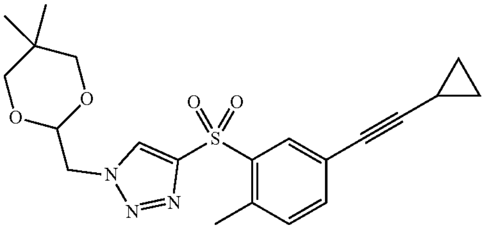 [SMILES: Cc1ccc(C#CC2CC2)cc1S(=O)(=O)c1cn(CC2OCC(C)(C)CO2)nn1] |
| I-784 | 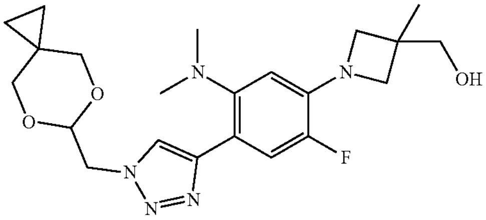 [SMILES: CN(C)c1cc(N2CC(C)(CO)C2)c(F)cc1-c1cn(CC2OCC3(CC3)CO2)nn1] |

TABLE 1-continued
| Selected Compounds | |
|---|---|
| Compound | Structure |
| I-785 | 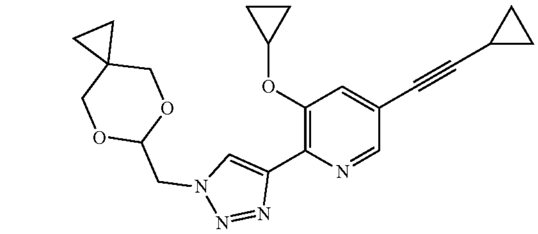 [SMILES: C(#CC1CC1)c1cnc(-c2cn(CC3OCC4(CC4)CO3)nn2)c(OC2CC2)c1] |
| I-786 | 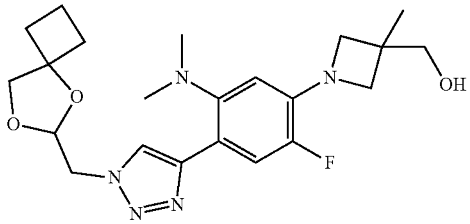 [SMILES: CN(C)c1cc(N2CC(C)(CO)C2)c(F)cc1-c1cn(CC2OCC3(CCC3)O2)nn1] |
| I-787 | 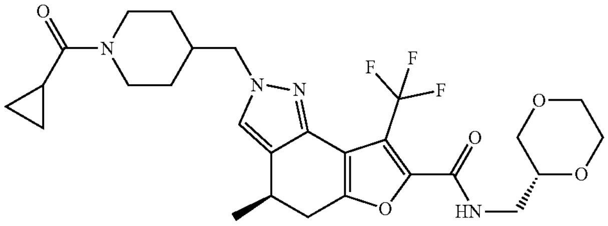 (A) 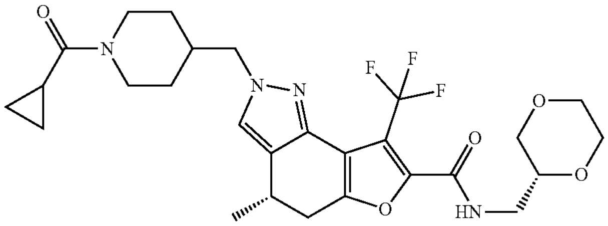 (B) |
| I-788 | 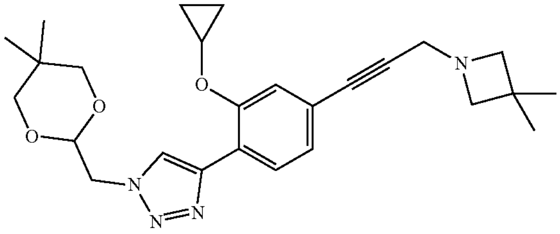 |
| I-789 | 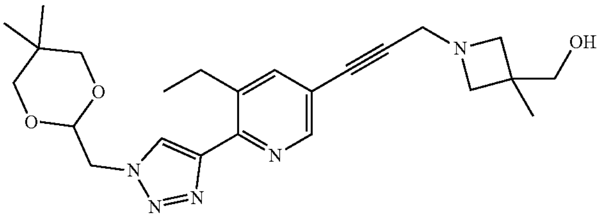 [SMILES: CCc1cc(C#CCN2CC(C)(CO)C2)cnc1-c1cn(CC2OCC(C)(C)CO2)nn1] |

TABLE 1-continued
| Selected Compounds | |
|---|---|
| Compound | Structure |
| I-790 | 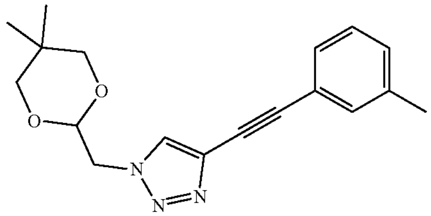 |
| I-791 | 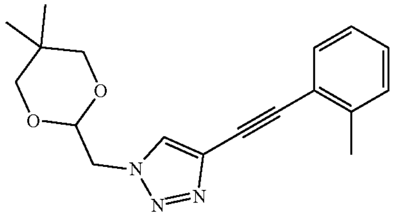 [SMILES: Cc1ccccc1C#Cc1cn(CC2OCC(C)(C)CO2)nn1] |
| I-792 | 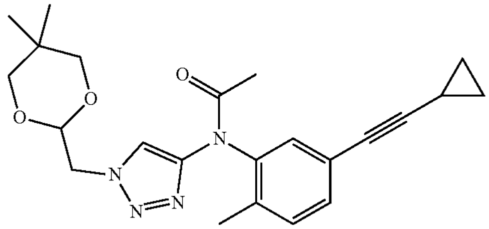 [SMILES: CC(=O)N(c1cn(CC2OCC(C)(C)CO2)nn1)c1cc(C#CC2CC2)ccc1C] |
| I-793 | 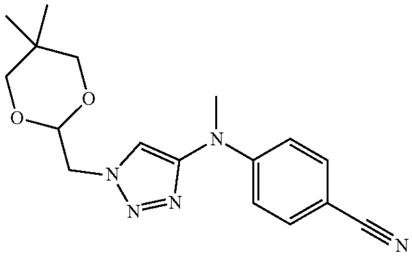 [SMILES: CN(c1ccc(C#N)cc1)c1cn(CC2OCC(C)(C)CO2)nn1] |
| I-794 | 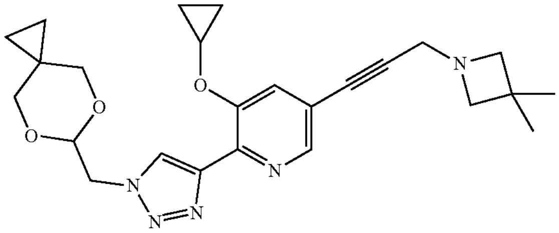 [SMILES: CC1(C)CN(CC#Cc2cnc(-c3cn(CC4OCC5(CC5)CO4)nn3)c(OC3CC3)c2)C1] |
| I-795 | 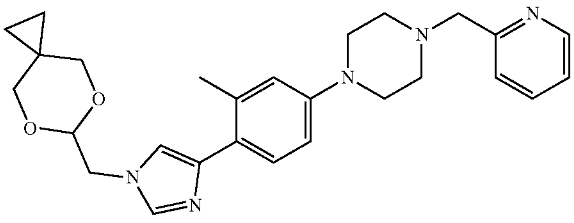 [SMILES: Cc1cc(N2CCN(Cc3ccccn3)CC2)ccc1-c1cn(CC2OCC3(CC3)CO2)cn1] |

TABLE 1-continued
| Selected Compounds | |
|---|---|
| Compound | Structure |
| I-796 | 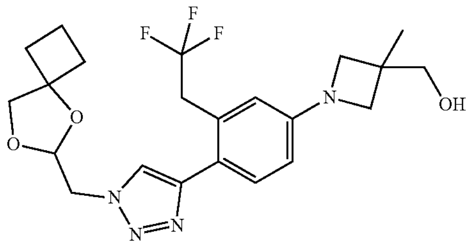 [SMILES: CC1(CO)CN(c2ccc(-c3cn(CC4OCC5(CCC5)O4)nn3)c(CC(F)(F)F)c2)C1] |
| I-797 | 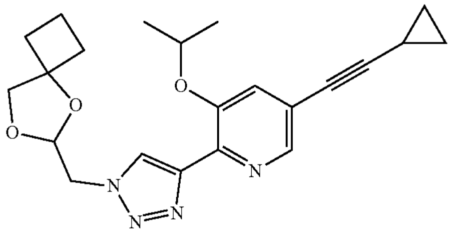 [SMILES: CC(C)Oc1cc(C#CC2CC2)cnc1-c1cn(CC2OCC3(CCC3)O2)nn1] |
| I-798 | 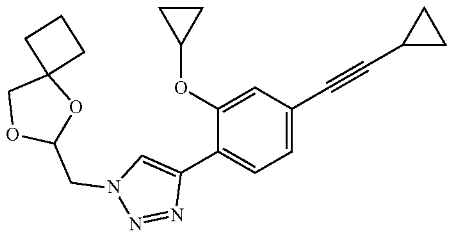 [SMILES: C(#CC1CC1)c1ccc(-c2cn(CC3OCC4(CCC4)O3)nn2)c(OC2CC2)c1] |
| I-799 | 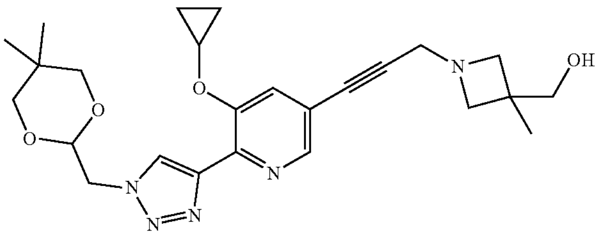 [SMILES: CC1(C)COC(Cn2cc(-c3ncc(C#CCN4CC(C)(CO)C4)cc3OC3CC3)nn2)OC1] |
| I-800 | 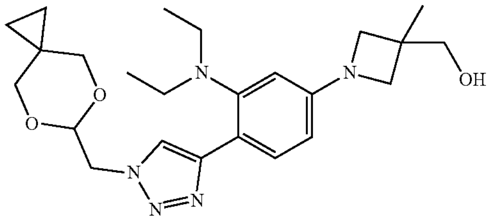 [SMILES: CCN(CC)c1cc(N2CC(C)(CO)C2)ccc1-c1cn(CC2OCC3(CC3)CO2)nn1] |
| I-801 | 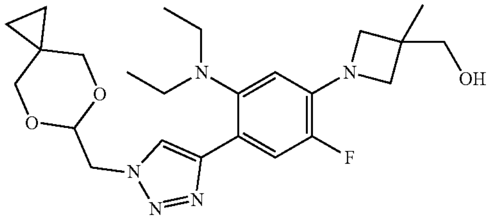 [SMILES: CCN(CC)c1cc(N2CC(C)(CO)C2)c(F)cc1-c1cn(CC2OCC3(CC3)CO2)nn1] |

TABLE 1-continued
| Selected Compounds | |
|---|---|
| Compound | Structure |
| I-802 | 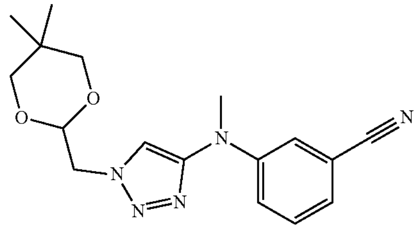 [SMILES: CN(c1cccc(C#N)c1)c1cn(CC2OCC(C)(C)CO2)nn1] |
| I-803 | 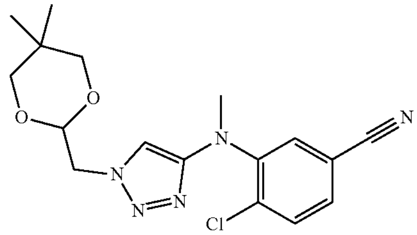 [SMILES: CN(c1cn(CC2OCC(C)(C)CO2)nn1)c1cc(C#N)ccc1Cl] |
| I-804 | 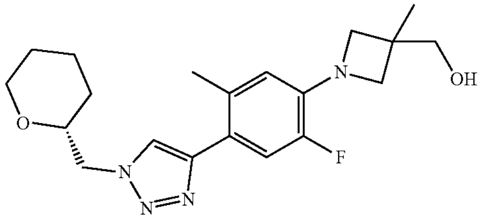 |
| I-805 | 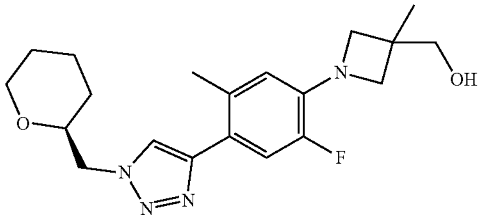 [SMILES: Cc1cc(N2CC(C)(CO)C2)c(F)cc1-c1cn(C[C@@H]2CCCCO2)nn1] |
| I-806 | 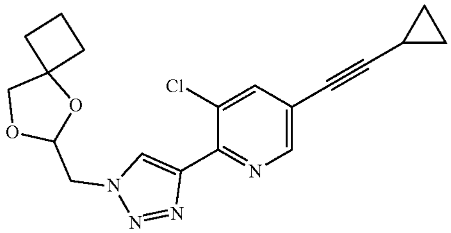 [SMILES: Clc1cc(C#CC2CC2)cnc1-c1cn(CC2OCC3(CCC3)O2)nn1] |
| I-807 | 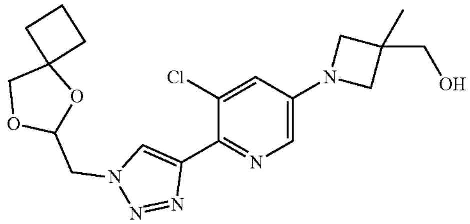 [SMILES: CC1(CO)CN(c2cnc(-c3cn(CC4OCC5(CCC5)O4)nn3)c(Cl)c2)C1] |

TABLE 1-continued
| Selected Compounds | |
|---|---|
| Compound | Structure |
| I-808 | 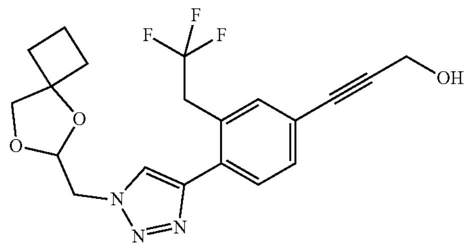 [SMILES: OCC#Cc1ccc(-c2cn(CC3OCC4(CCC4)O3)nn2)c(CC(F)(F)F)c1] |
| I-809 | 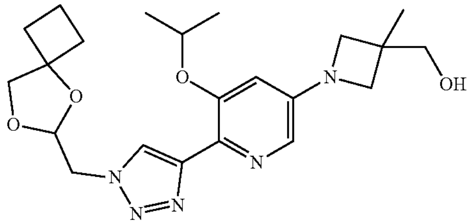 [SMILES: CC(C)Oc1cc(N2CC(C)(CO)C2)cnc1-c1cn(CC2OCC3(CCC3)O2)nn1] |
| I-810 | 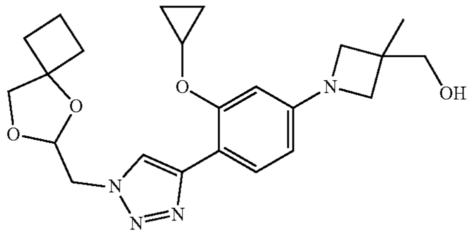 [SMILES: CC1(CO)CN(c2ccc(-c3cn(CC4OCC5(CCC5)O4)nn3)c(OC3CC3)c2)C1] |
| I-811 | 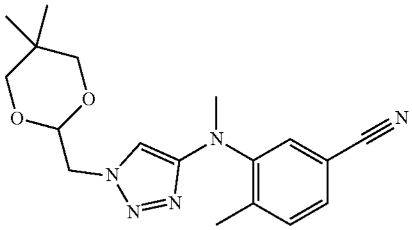 [SMILES: Cc1ccc(C#N)cc1N(C)c1cn(CC2OCC(C)(C)CO2)nn1] |
| I-812 | 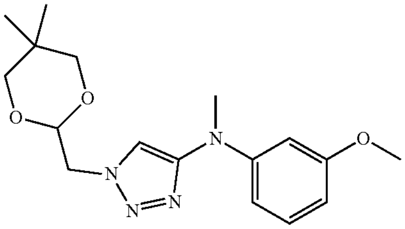 [SMILES: COc1cccc(N(C)c2cn(CC3OCC(C)(C)CO3)nn2)c1] |
| I-813 | 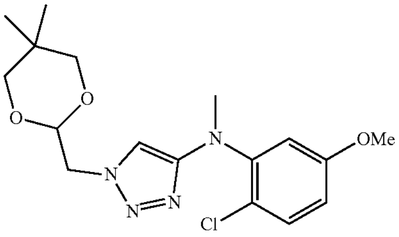 [SMILES: COc1ccc(Cl)c(N(C)c2cn(CC3OCC(C)(C)CO3)nn2)c1] |

TABLE 1-continued
| Selected Compounds | |
|---|---|
| Compound | Structure |
| I-814 | 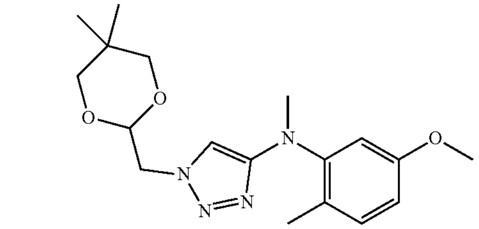 [SMILES: COc1ccc(C)c(N(C)c2cn(CC3OCC(C)(C)CO3)nn2)c1] |
| I-815 | 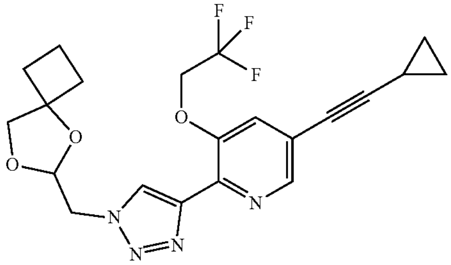 [SMILES: FC(F)(F)COc1cc(C#CC2CC2)cnc1-c1cn(CC2OCC3(CCC3)O2)nn1] |
| I-816 | 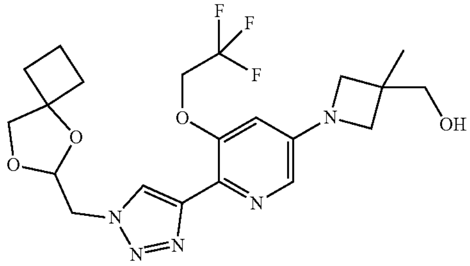 [SMILES: CC1(CO)CN(c2cnc(-c3cn(CC4OCC5(CCC5)O4)nn3)c(OCC(F)(F)F)c2)C1] |
| I-817 | 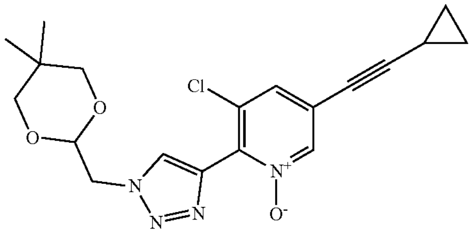 [SMILES: CC1(C)COC(Cn2cc(-c3c(Cl)cc(C#CC4CC4)c[n+]3[O-])nn2)OC1] |
| I-818 | 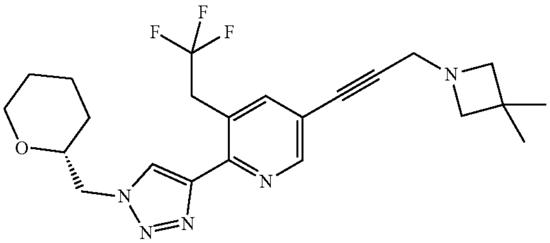 [SMILES: CC1(C)CN(CC#Cc2cnc(-c3cn(C[C@H]4CCCCO4)nn3)c(CC(F)(F)F)c2)C1] |
| I-819 | 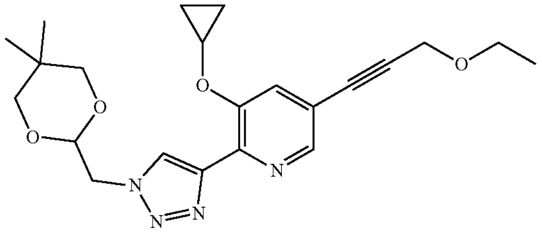 [SMILES: CCOCC#Cc1cnc(-c2cn(CC3OCC(C)(C)CO3)nn2)c(OC2CC2)c1] |

TABLE 1-continued
| Selected Compounds | |
|---|---|
| Compound | Structure |
| I-820 | 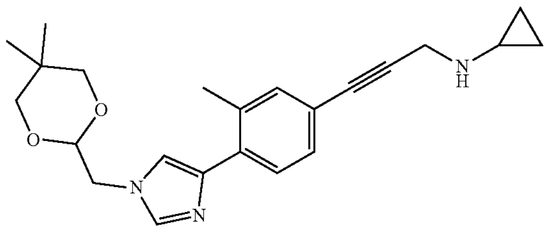 [SMILES: Cc1cc(C#CCNC2CC2)ccc1-c1cn(CC2OCC(C)(C)CO2)cn1] |
| I-821 | 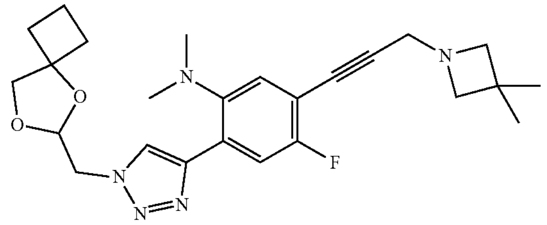 [SMILES: CN(C)c1cc(C#CCN2CC(C)(C)C2)c(F)cc1-c1cn(CC2OCC3(CCC3)O2)nn1] |
| I-822 | 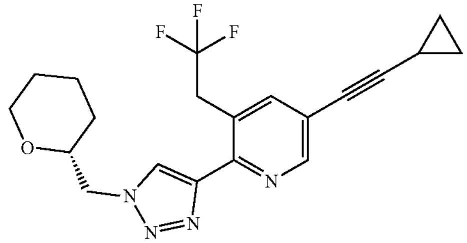 [SMILES: FC(F)(F)Cc1cc(C#CC2CC2)cnc1-c1cn(C[C@H]2CCCCO2)nn1] |
| I-823 | 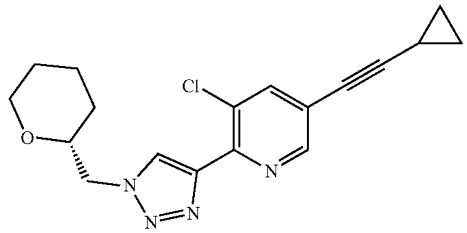 [SMILES: Clc1cc(C#CC2CC2)cnc1-c1cn(C[C@H]2CCCCO2)nn1] |
| I-824 | 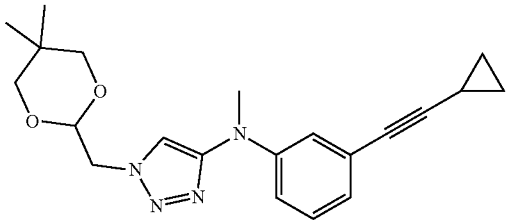 [SMILES: CN(c1cccc(C#CC2CC2)c1)c1cn(CC2OCC(C)(C)CO2)nn1] |
| I-825 | 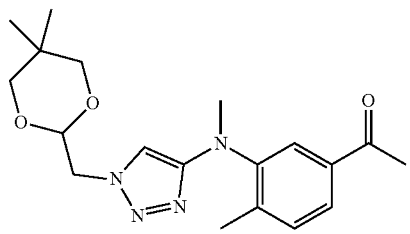 [SMILES: CC(=O)c1ccc(C)c(N(C)c2cn(CC3OCC(C)(C)CO3)nn2)c1] |

TABLE 1-continued
| Compound | Structure |
| --- | --- |
| I-826 | 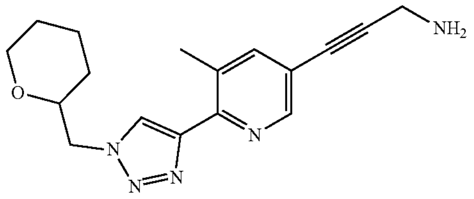 [SMILES: Cc1cc(C#CCN)cnc1-c1cn(CC2CCCCO2)nn1] |
| I-827 | 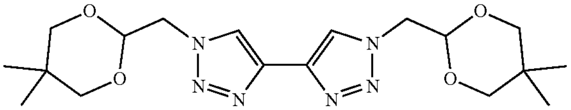 |
| I-828 | 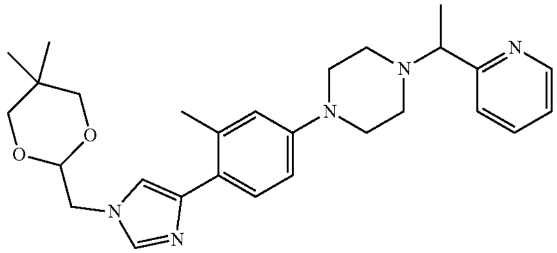 [SMILES: Cc1cc(N2CCN(C(C)c3ccccn3)CC2)ccc1-c1cn(CC2OCC(C)(C)CO2)cn1] |
| I-829 | 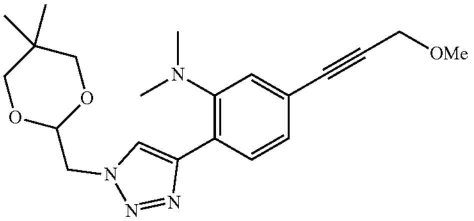 [SMILES: COCC#Cc1ccc(-c2cn(CC3OCC(C)(C)CO3)nn2)c(N(C)C)c1] |
| I-830 | 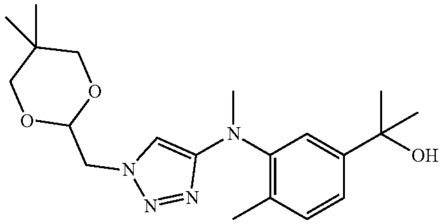 [SMILES: Cc1ccc(C(C)(C)O)cc1N(C)c1cn(CC2OCC(C)(C)CO2)nn1] |
| I-831 | 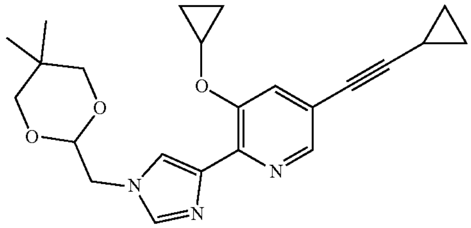 [SMILES: CC1(C)COC(Cn2cnc(-c3ncc(C#CC4CC4)cc3OC3CC3)c2)OC1] |
| I-832 | 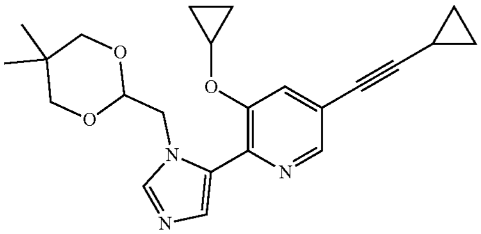 [SMILES: CC1(C)COC(Cn2cncc2-c2ncc(C#CC3CC3)cc2OC2CC2)OC1] |
Selected Compounds TABLE 1-continued
| Selected Compounds | |
|---|---|
| Compound | Structure |
| I-833 | 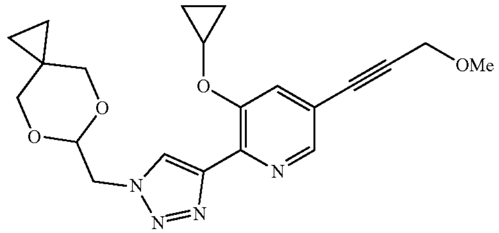 [SMILES: COCC#Cc1cnc(-c2cn(CC3OCC4(CC4)CO3)nn2)c(OC2CC2)c1] |
| I-834 | 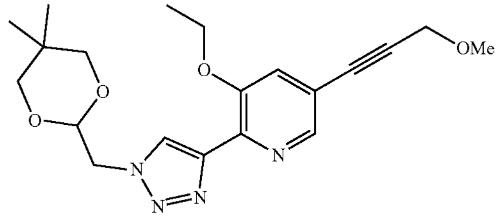 [SMILES: CCOc1cc(C#CCOC)cnc1-c1cn(CC2OCC(C)(C)CO2)nn1] |
| I-835 | 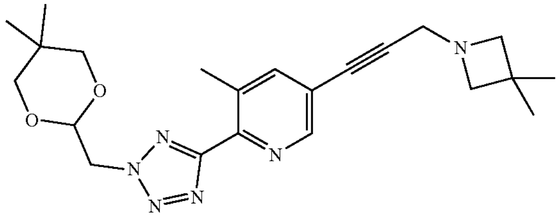 |
| I-836 | 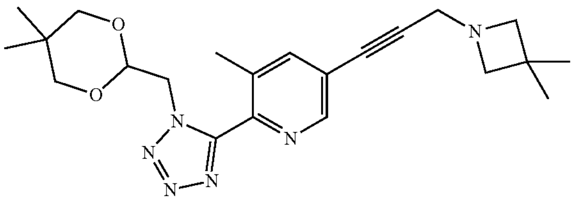 |
| I-837 | 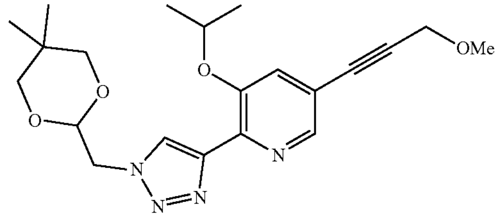 [SMILES: COCC#Cc1cnc(-c2cn(CC3OCC(C)(C)CO3)nn2)c(OC(C)C)c1] |
| I-838 | 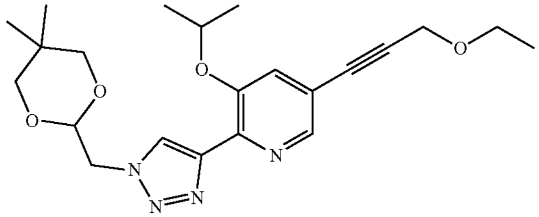 [SMILES: CCOCC#Cc1cnc(-c2cn(CC3OCC(C)(C)CO3)nn2)c(OC(C)C)c1] |

TABLE 1-continued
| Selected Compounds | |
|---|---|
| Compound | Structure |
| I-839 | 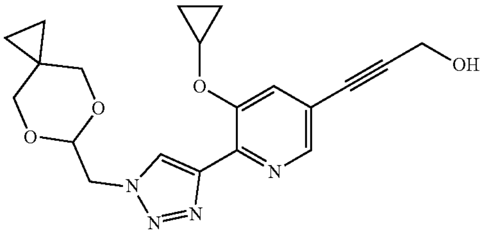 [SMILES: OCC#Cc1cnc(-c2cn(CC3OCC4(CC4)CO3)nn2)c(OC2CC2)c1] |
| I-840 | 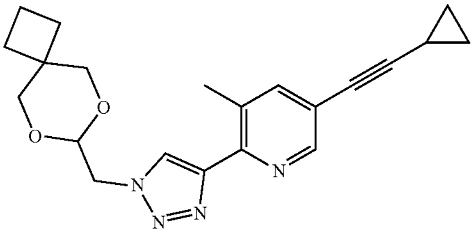 [SMILES: Cc1cc(C#CC2CC2)cnc1-c1cn(CC2OCC3(CCC3)CO2)nn1] |
| I-841 | 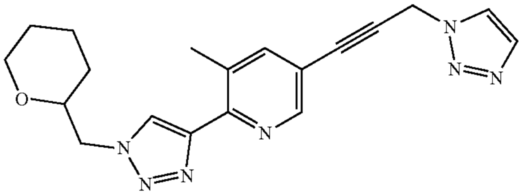 [SMILES: Cc1cc(C#CCn2ccnn2)cnc1-c1cn(CC2CCCCO2)nn1] |
| I-842 | 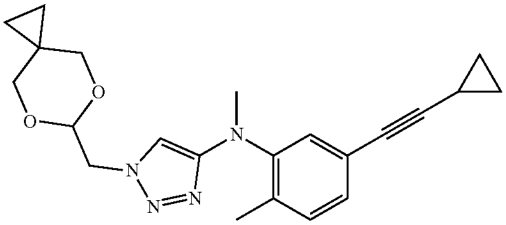 [SMILES: Cc1ccc(C#CC2CC2)cc1N(C)c1cn(CC2OCC3(CC3)CO2)nn1] |
| I-843 | 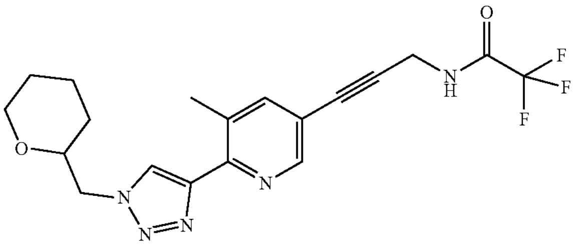 [SMILES: Cc1cc(C#CCNC(=O)C(F)(F)F)cnc1-c1cn(CC2CCCCO2)nn1] |
| I-844 | 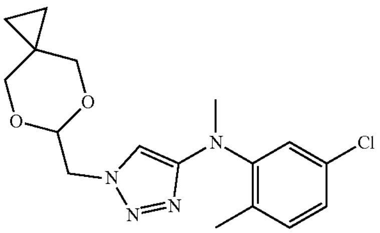 [SMILES: Cc1ccc(Cl)cc1N(C)c1cn(CC2OCC3(CC3)CO2)nn1] |

TABLE 1-continued
| Selected Compounds | |
|---|---|
| Compound | Structure |
| I-845 | 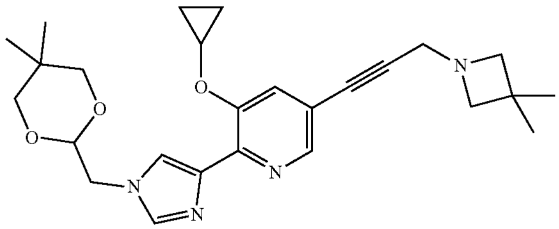 |
| I-846 | 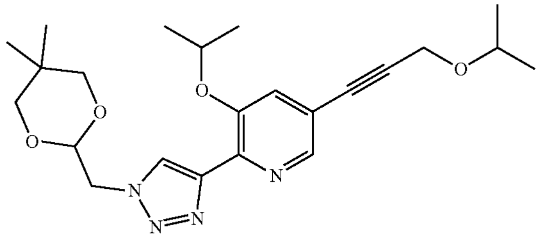 [SMILES: CC(C)OCC#Cc1cnc(-c2cn(CC3OCC(C)(C)CO3)nn2)c(OC(C)C)c1] |
| I-847 | 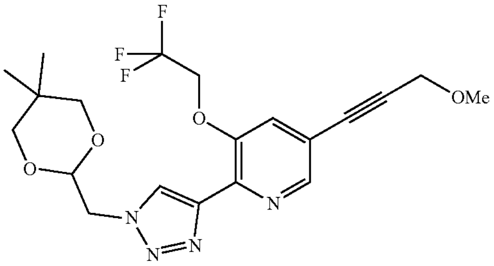 [SMILES: COCC#Cc1cnc(-c2cn(CC3OCC(C)(C)CO3)nn2)c(OCC(F)(F)F)c1] |
| I-848 | 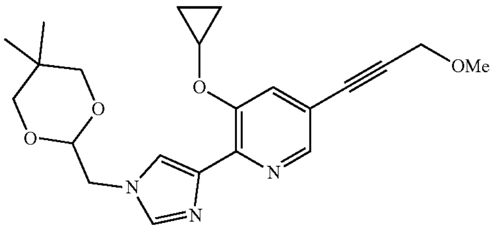 [SMILES: COCC#Cc1cnc(-c2cn(CC3OCC(C)(C)CO3)cn2)c(OC2CC2)c1] |
| I-849 | 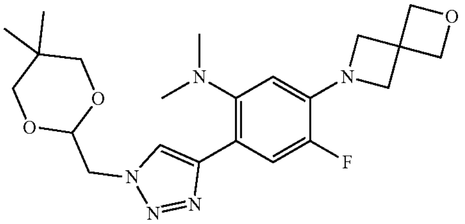 [SMILES: CN(C)c1cc(N2CC3(COC3)C2)c(F)cc1-c1cn(CC2OCC(C)(C)CO2)nn1] |
| I-850 | 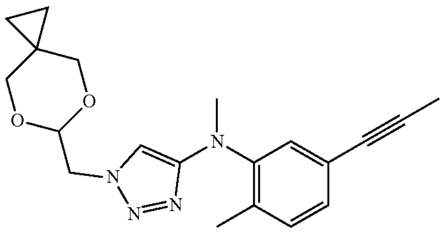 [SMILES: CC#Cc1ccc(C)c(N(C)c2cn(CC3OCC4(CC4)CO3)nn2)c1] |

TABLE 1-continued
| Selected Compounds | |
|---|---|
| Compound | Structure |
| I-851 | 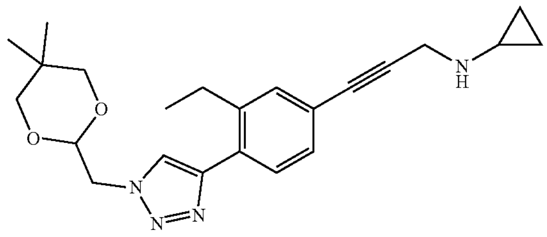 [SMILES: CCc1cc(C#CCNC2CC2)ccc1-c1cn(CC2OCC(C)(C)CO2)nn1] |
| I-852 | 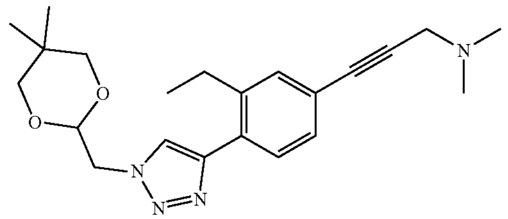 |
| I-853 | 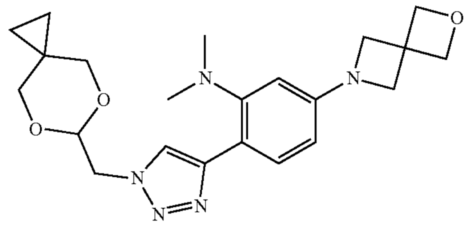 [SMILES: CN(C)c1cc(N2CC3(COC3)C2)ccc1-c1cn(CC2OCC3(CC3)CO2)nn1] |
| I-854 | 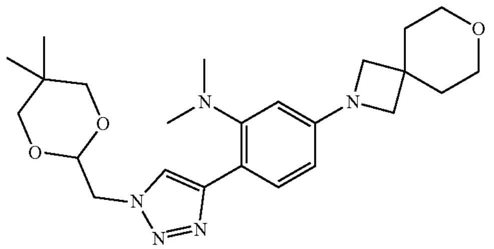 [SMILES: CN(C)c1cc(N2CC3(CCOCC3)C2)ccc1-c1cn(CC2OCC(C)(C)CO2)nn1] |
| I-855 | 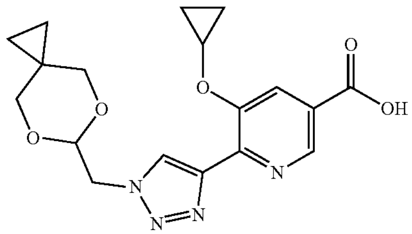 [SMILES: O=C(O)c1cnc(-c2cn(CC3OCC4(CC4)CO3)nn2)c(OC2CC2)c1] |
| I-856 | 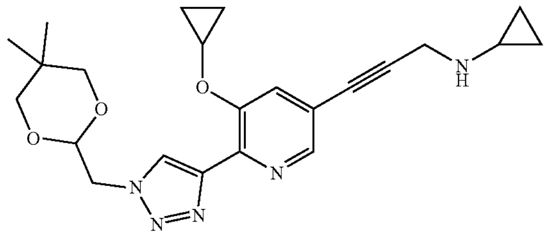 [SMILES: CC1(C)COC(Cn2cc(-c3ncc(C#CCNC4CC4)cc3OC3CC3)nn2)OC1] |

TABLE 1-continued
| Selected Compounds | |
|---|---|
| Compound | Structure |
| I-857 | 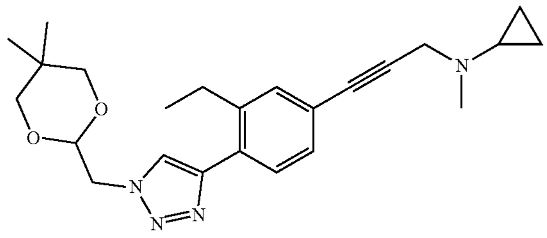 [SMILES: CCc1cc(C#CCN(C)C2CC2)ccc1-c1cn(CC2OCC(C)(C)CO2)nn1] |
| I-858 | 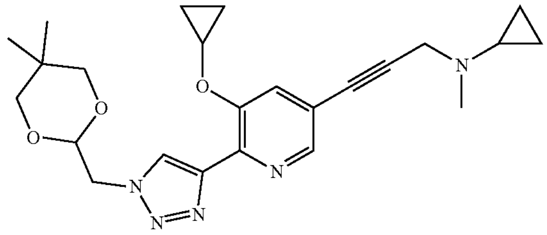 [SMILES: CN(CC#Cc1cnc(-c2cn(CC3OCC(C)(C)CO3)nn2)c(OC2CC2)c1)C1CC1] |
| I-859 | 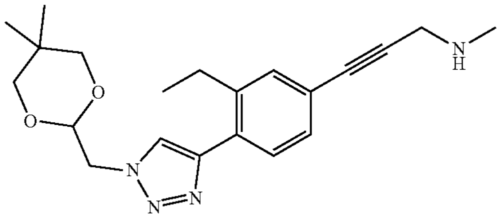 |
| I-860 | 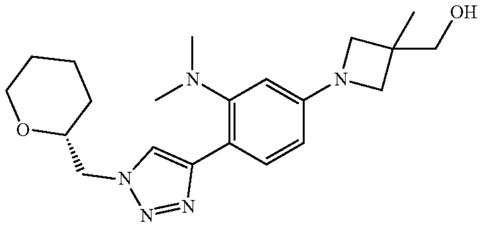 [SMILES: CN(C)c1cc(N2CC(C)(CO)C2)ccc1-c1cn(C[C@H]2CCCCO2)nn1] |
| I-861 | 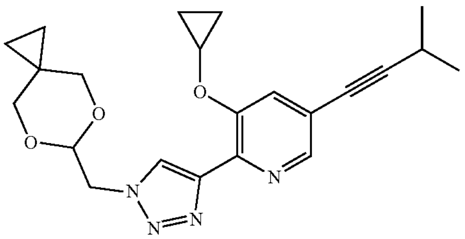 [SMILES: CC(C)C#Cc1cnc(-c2cn(CC3OCC4(CC4)CO3)nn2)c(OC2CC2)c1] |
| I-862 | 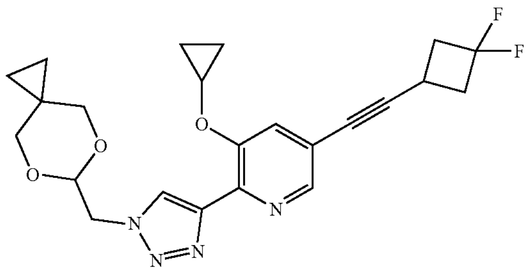 [SMILES: FC1(F)CC(C#Cc2cnc(-c3cn(CC4OCC5(CC5)CO4)nn3)c(OC3CC3)c2)C1] |

TABLE 1-continued
| Selected Compounds | |
|---|---|
| Compound | Structure |
| I-863 | 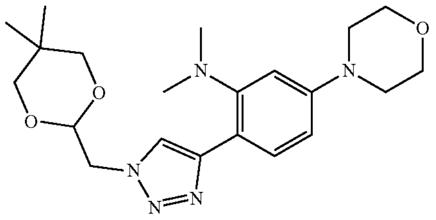 [SMILES: CN(C)c1cc(N2CCOCC2)ccc1-c1cn(CC2OCC(C)(C)CO2)nn1] |
| I-864 | 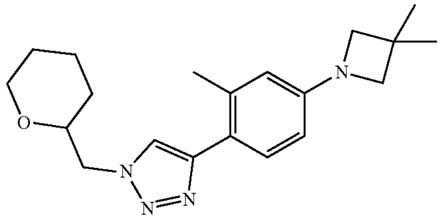 [SMILES: Cc1cc(N2CC(C)(C)C2)ccc1-c1cn(CC2CCCCO2)nn1] |
| I-865 | 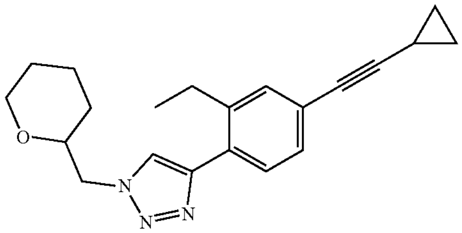 [SMILES: CCc1cc(C#CC2CC2)ccc1-c1cn(CC2CCCCO2)nn1] |
| I-866 | 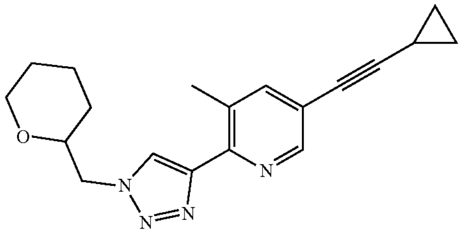 [SMILES: Cc1cc(C#CC2CC2)cnc1-c1cn(CC2CCCCO2)nn1] |
| I-867 | 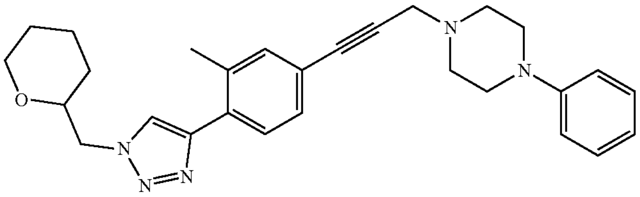 [SMILES: Cc1cc(C#CCN2CCN(c3ccccc3)CC2)ccc1-c1cn(CC2CCCCO2)nn1] |
| I-868 | 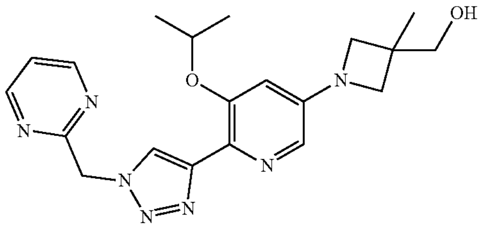 [SMILES: CC(C)Oc1cc(N2CC(C)(CO)C2)cnc1-c1cn(Cc2ncccn2)nn1] |

TABLE 1-continued
| Selected Compounds | |
|---|---|
| Compound | Structure |
| I-869 | 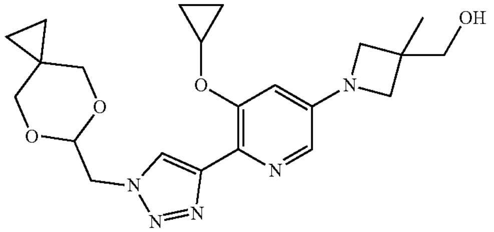 [SMILES: CC1(CO)CN(c2cnc(-c3cn(CC4OCC5(CC5)CO4)nn3)c(OC3CC3)c2)C1] |
| I-870 | 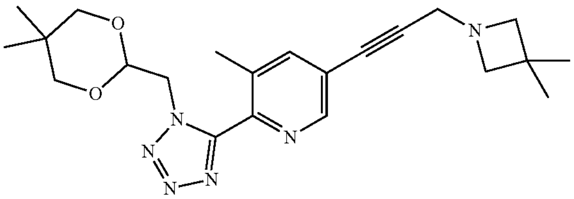 |
| I-871 | 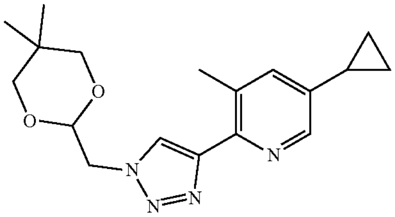 [SMILES: Cc1cc(C2CC2)cnc1-c1cn(CC2OCC(C)(C)CO2)nn1] |
| I-872 | 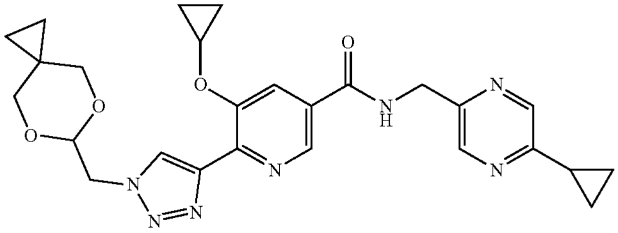 [SMILES: O=C(NCc1cnc(C2CC2)cn1)c1cnc(-c2cn(CC3OCC4(CC4)CO3)nn2)c(OC2CC2)c1] |
| I-873 | 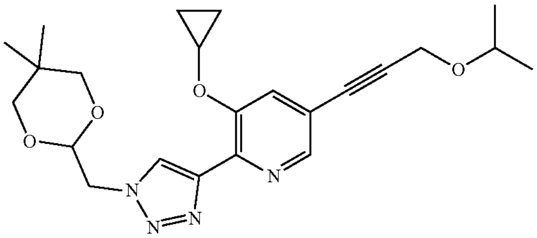 [SMILES: CC(C)OCC#Cc1cnc(-c2cn(CC3OCC(C)(C)CO3)nn2)c(OC2CC2)c1] |
| I-874 | 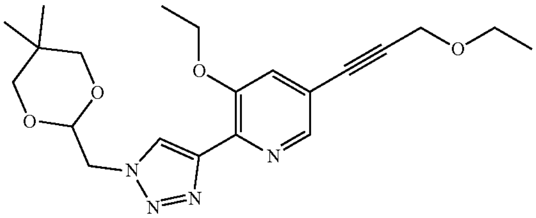 [SMILES: CCOCC#Cc1cnc(-c2cn(CC3OCC(C)(C)CO3)nn2)c(OCC)c1] |

TABLE 1-continued
| Selected Compounds | |
|---|---|
| Compound | Structure |
| I-875 | 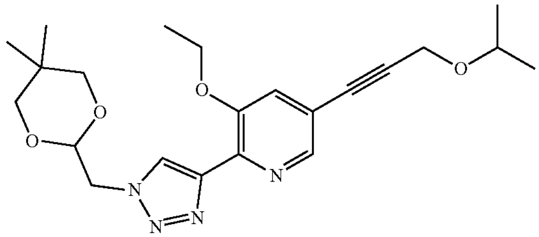 [SMILES: CCOc1cc(C#CCOC(C)C)cnc1-c1cn(CC2OCC(C)(C)CO2)nn1] |
| I-876 | 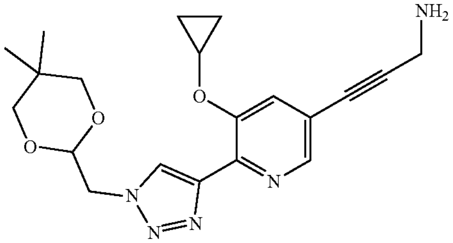 [SMILES: CC1(C)COC(Cn2cc(-c3ncc(C#CCN)cc3OC3CC3)nn2)OC1] |
| I-877 | 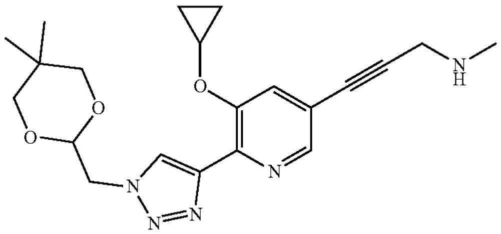 |
| I-878 | 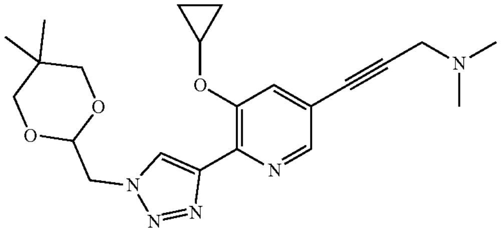 |
| I-879 | 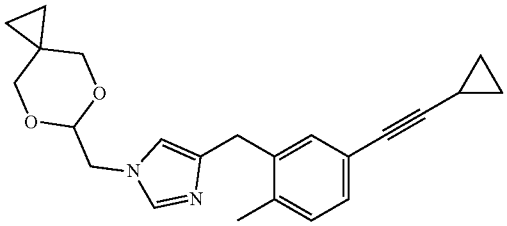 [SMILES: Cc1ccc(C#CC2CC2)cc1Cc1cn(CC2OCC3(CC3)CO2)cn1] |
| I-880 | 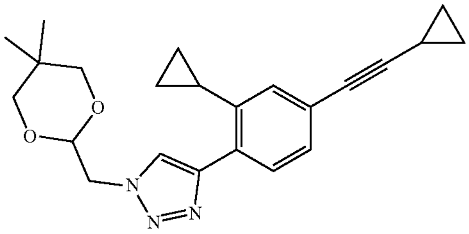 [SMILES: CC1(C)COC(Cn2cc(-c3ccc(C#CC4CC4)cc3C3CC3)nn2)OC1] |

TABLE 1-continued

| Selected Compounds | |
|---|---|
| Compound | Structure |
| I-881 | 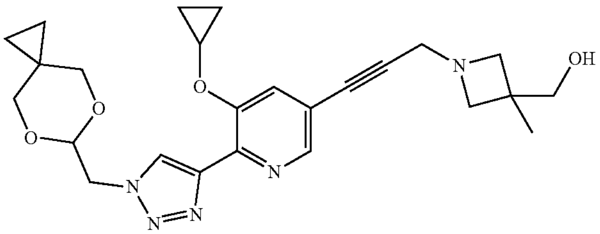 [SMILES: CC1(CO)CN(CC#Cc2cnc(-c3cn(CC4OCC5(CC5)CO4)nn3)c(OC3CC3)c2)C1] |
| I-882 | 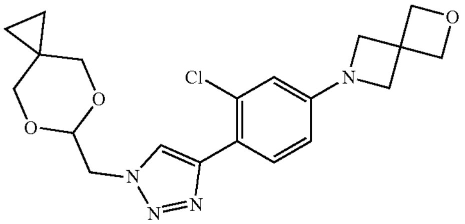 [SMILES: Clc1cc(N2CC3(COC3)C2)ccc1-c1cn(CC2OCC3(CC3)CO2)nn1] |
| I-883 | 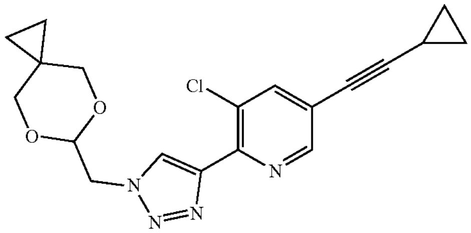 [SMILES: Clc1cc(C#CC2CC2)cnc1-c1cn(CC2OCC3(CC3)CO2)nn1] |

In some embodiments, the present invention provides a compound set forth in Table 1, above, or a pharmaceutically acceptable salt thereof. In some embodiments, the present invention provides a compound set forth in Table 1, above. In some embodiments, the present invention provides a pharmaceutical composition comprising a compound set forth in Table 1 above, or a pharmaceutically acceptable salt thereof, together with a pharmaceutically acceptable carrier, excipient, or diluent.

In some embodiments, the present invention provides a compound of formula I as defined above, or a pharmaceutically acceptable salt thereof, or a pharmaceutical composition comprising a compound of formula I as defined above, or a pharmaceutically acceptable salt thereof, and a pharmaceutically acceptable carrier, adjuvant, or vehicle for use as a medicament.

In chemical structures in Table 1, above, and the Examples, below, stereogenic centers are described according to the Enhanced Stereo Representation format (MDL/Biovia, e.g. using labels "or1", "or2", "abs", "and1").

In some embodiments, the invention also provides compounds of formula I described herein or pharmaceutical compositions described herein for use in a method for inhibiting GPR84 as described herein, in a method for modulating an immune response in a subject in need thereof as described herein and/or in a method for treating a GPR84-dependent disorder as described herein.

In some embodiments, the invention also provides compounds of formula I described herein or pharmaceutical compositions described herein for use in a method for inhibiting GPR84 as described herein.

In some embodiments, the invention also provides compounds of formula I described herein or pharmaceutical compositions described herein for use in a method for modulating an immune response in a subject in need thereof as described herein.

In some embodiments, the invention also provides compounds of formula I described herein or pharmaceutical compositions described herein for use in a method for treating a GPR84-dependent disorder as described herein.

In some embodiments, the invention also provides the use of a compound of formula I described herein or a pharmaceutical composition described herein for the manufacture of a medicament for inhibiting GPR84, a medicament for modulating an immune response in a subject in need thereof and/or a medicament for treating a GPR84-dependent disorder.

In some embodiments, the invention also provides the use of a compound of formula I described herein or a pharmaceutical composition described herein for the manufacture of a medicament for inhibiting GPR84.

In some embodiments, the invention also provides the use of a compound of formula I described herein or a pharmaceutical composition described herein for the manufacture of a medicament for modulating an immune response in a subject in need thereof.

In some embodiments, the invention also provides the use of a compound of formula I described herein, or a pharmaceutical composition described herein for the manufacture of a medicament treating a GPR84-dependent disorder.

In some embodiments, the invention also provides the use of compounds of formula I described herein or pharmaceutical compositions described herein in a method for inhibiting GPR84 as described herein, in a method for modulating an immune response in a subject in need thereof as described herein and/or in a method for treating a GPR84-dependent disorder as described herein.

In some embodiments, the invention also provides the use of compounds of formula I described herein, or pharmaceutical compositions described herein in a method for inhibiting GPR84 as described herein.

In some embodiments, the invention also provides the use of compounds of formula I described herein, or pharmaceutical compositions described herein in a method for modulating an immune response in a subject in need thereof as described herein.

In some embodiments, the invention also provides the use of compounds of formula I described herein, or pharmaceutical compositions described herein in a method for treating a GPR84-dependent disorder as described herein.

4. General Methods of Providing the Present Compounds

The compounds of this invention may be prepared or isolated in general by synthetic and/or semi-synthetic methods known to those skilled in the art for analogous compounds and by methods described in detail in the Examples, herein.

5. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit GPR84, or a mutant thereof, in a biological sample or in a patient. In certain embodiments, the amount of compound in compositions of this invention is such that is effective to measurably inhibit GPR84, or a mutant thereof, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of GPR84, or a mutant thereof.

The subject matter disclosed herein includes prodrugs, metabolites, derivatives, and pharmaceutically acceptable salts of compounds of the invention. Metabolites include compounds produced by a process comprising contacting a compound of the invention with a mammal for a period of time sufficient to yield a metabolic product thereof. If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like. If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

A compound of the invention can be in the form of a "prodrug," which includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Prodrugs which are converted to active forms through other mechanisms in vivo are also included. In aspects, the compounds of the invention are prodrugs of any of the formulae herein.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

The compounds and compositions described herein are generally useful for the inhibition of signaling activity of one or more GPCRs. In some embodiments the GPCR inhibited by the compounds and methods of the invention is GPR84.

The presently disclosed compounds find use in inhibiting the activity of GPR84. GPR84 is a Gi-coupled G-protein-coupled receptor (GPCR) that is expressed on the surface of immune cells. GPR84 modulates the innate immune response in conditions such as fibrotic disorders.

Multiple studies have indicated GPR84 may be a potential target for the treatment of obesity and/or metabolic dysfunction.

GPR84 gene expression in human differentiated adipocytes in culture is highly upregulated by the major pro-inflammatory cytokines TNF-alpha and IL-1beta (Muredda et al. 2017. *Arch. Physiol. Biochem.* 124(2), 97-108). These data confirm activation of pro-inflammatory GPR84 signaling in the context of inflammation in fat cells, first described by Nagasaki in 2012 (Nagasaki et al, 2012, FEBS Letters, 586, 368-372).

IL-33, a member of the IL-1beta superfamily, in an autocrine manner, strongly upregulates GPR84 mRNA expression in human differentiated adipocytes, which correlates with enhanced production of pro-inflammatory cytokines and chemokines such as IL-1beta, CCL2, IL6, CXCL2 and CSF3 (Zaibi et al. 2018. *Cytokine,* 110, 189-193). This suggests GPR84 activation by pro-inflammatory stimuli in fat cells leads to further pro-inflammatory cytokine release and identifies the presence of a putative autocrine positive feedback loop.

GPR84 expression in liver is upregulated in patients with NASH and correlates with disease severity. GPR84 is upregulated in activated human and mouse macrophages and neutrophils. GPR84 mediated myeloid cell infiltration promoting steatohepatitis and fibrosis. Pharmacological inhibition of GPR84 significantly reduced macrophage accumulation, inflammation and fibrosis in NASH models, similarly to selonsertib (ASK1 inhibitor). These findings suggest GPR84 promotes myeloid cell infiltration in liver injury and is a valid therapeutic target for steatohepatitis and fibrosis in NAFLD/NASH (Puengel et al. 2020. *J. Clin. Med.* 9(4), 1140).

GPR84 deletion in mice was associated with decreased NAFLD-induced liver injury. Treatment with PBI-4547 (putative GPR84 antagonist) reduced NAFLD induced injury in liver, adipose tissue and promoted fatty acid oxidation (Simard et al. 2020. *Sci. Rep.* 10(1), 12778).

Mice with global deletion of Gpr84 [Gpr84 knockout (KO)] exhibit a mild impairment in glucose tolerance when fed a MCFA-enriched diet. The study demonstrated the regulation of mitochondrial metabolism in murine skeletal muscle by the medium-chain fatty acid receptor GPR84, an important player in glycemic control (Montgomery M K, et al. 2019. *FASEB J.* 33(11), 12264-12276).

Nutrient-sensing receptors located on enteroendocrine (EEC) cells modulate appetite via detection of luminal contents. Peiris et al. assessed the effects of obesity and gastric bypass-induced weight loss on expression of nutrient-sensing G-protein coupled receptors (GPCRs) and found that GPR84 expression was increased in obese mice. Further, obesity-induced overexpression of GPR84 further increased after Roux-en-Y gastric bypass surgery (RYGB). Several nutrient-sensing receptors including GPR84 induced activation of colonic EEC. Profound adaptive changes to the expression of these receptors occur in response to diet and weight loss induced by RYGB or calorie restriction. (Peiris M, et al. 2018. *Nutrients.* 10(10), 1529)

Du Toit et al. studied the effect of GPR84 deletion on obesity and diabetes development in mice fed long chain fatty acid (LCFA) or medium chain fatty acid rich (MCFA) diets and found no effect on body weight or glucose tolerance in mice fed either a high MCFA or LCFA diet. GPR84 may influence lipid metabolism, as GPR84 KO mice had smaller livers and increased myocar-dial triglyceride accumulation when fed LCFA diets, and increased liver triglyceride accumulation in responses to increased dietary MCFAs. (Du Toit et al. 2018 *Eur. J. Nutr.* 57(5), 1737-1746)

A review by Hara et al. indicated that GPR84 and other free fatty acid receptors (FFARs) primarily involved in energy metabolism are considered as key therapeutic targets in the pathology of obesity and type 2 diabetes. (Hara et al. 2014. *Biochim. Biophys. Acta.* 1841(9), 1292-300)

Nagasaki et al. conducted studies in mice that showed a high-fat diet up-regulated GPR84 expression in fat pads. These results suggest that GPR84 emerges in adipocytes in response to TNFα from infiltrating macrophages and exacerbates the vicious cycle between adiposity and diabesity. (Nagasaki H. et al. 2012. *FEBS Lett.* 586(4), 368-72)

Fibrosis is a process that can be triggered by chronic tissue damage because of toxic substances, viral infection, inflammation, or mechanical stress (Nanthakumar et al., 2015. *Nature Reviews Drug Discovery* 14, 693-720); and may be defined as the abnormal or excessive production and accumulation of extracellular matrix (ECM).

In particular, fibrosis is a key driver of progressive organ dysfunction in many inflammatory and metabolic diseases, including idiopathic pulmonary fibrosis (IPF), advanced liver disease (e.g. non-alcoholic steatohepatitis (NASH)) and advanced kidney disease. These conditions remain poorly treated despite advances in the understanding of the disease mechanism and, more recently, an increase in the number of clinical trials reflecting the need to identify new treatments, particularly in IPF (Nanthakumar et al., 2015).

Non-alcoholic fatty liver disease (NAFLD) is initially characterized by pure steatosis with progression to non-alcoholic steatohepatitis (NASH), mainly caused by excess energy intake and physical inactivity apart from genetic defects, and closely associated with obesity, insulin resistance, and other related metabolic complications. (Neuschwander-Tetri B A and Caldwell S H, 2003, *Hepatology* 37, 1202-1219). If untreated, NASH leads to lethal liver failure.

The mechanisms that promote the progression from NAFLD to NASH and end-stage liver diseases are complex and may be triggered by an acute inflammatory insult and oxidative stress. (Day and James 1998, *Hepatology* 27, 1463-1466).

GPR84 (also known as EX33) has been isolated and characterized from human B cells (Wittenberger et al. 2001, *J. Mol. Biol.* 307, 799-813) and also using a degenerate primer reverse transcriptase-polymerase chain reaction (RT-PCR) approach (Yousefi et al., 2001). It remained an orphan GPCR until the identification of medium-chain Free Fatty Acids (FFAs) with carbon chain lengths of 9-14 as ligands for this receptor (Wang et al., 2006).

GPR84 is activated by medium-chain FFAs, such as capric acid (Cl 0:0), undecanoic acid (Cl 1:0) and lauric acid (12:0) which amplify lipopolysaccharide stimulated production of pro-inflammatory cytokines/chemokines (TNFα, IL-6, IL-8, CCL2 and others), and is highly expressed in neutrophils and monocytes (macrophages) (Miyamoto et al. 2016, *Int. J. Mol. Sci.* 17(4) 450).

In contrast, GPR84-ligand mediated chemotaxis of neutrophils and monocytes/macrophages is inhibited by GPR84 antagonists (Suzuki M et al. 2013. *J. Biol. Chem.* 288, 10684-10691).

Although the recruitment of monocytes/macrophages to livers may appear to occur concomitantly with fibrogenesis in patients with chronic liver diseases (Marra et al 1998. *Am. J. Pathol.* 152, 423-430; Zimmermann et al. 2010. *PLOS ONE* 5, el 1049), this has not resulted in novel therapies.

No approved drug for the treatment of NASH is available at present, and consequently liver transplant remains the last option for end stage disease status. In the case of IPF for example, only two drugs have been approved despite their undesirable side effects (Brunnemer et al. 2018. *Respiration*

95, 301-309; Lancaster et al., 2017, *Eur. Respir. Rev.* 26, 170057; Richeldi et al., 2014, *N. Engl. J. Med.* 370, 2071-2082), and therefore there is clear need for improved therapies (Raghu, 2015, *Am J Respir Crit Care Med* 191(3) 252-4).

Potent and selective GPR84 inhibitor GLPG1205 at once-daily doses of 3 and 10 mg/kg, reduced disease activity index score and neutrophil infiltration in a mouse dextran sodium sulfate-induced chronic inflammatory bowel disease model, with efficacy similar to positive-control compound sulfasalazine. (Labeguere F, et al. 2020. *J Med Chem.* 63(22), 13526-13545)

A study by Nguyen et al. showed that PBI-4050 (a GPR84 antagonist/GPR40 agonist) reduces pulmonary hypertension, lung fibrosis, and right ventricular dysfunction in heart failure. This points to GPR84 antagonists being a novel promising therapy for targeting lung remodeling in group II pulmonary hypertension (Nguyen et al. 2020. *Cardiovasc Res.* 116(1), 171-182).

A study by Gagnon et al. showed that GPR40 and GPR84 may represent promising molecular targets in fibrosis pathways. Administering PBI-4050, an antagonist of GPR84 as well as an agonist of GPR40, significantly attenuated fibrosis in many injury contexts, as evidenced by the antifibrotic activity observed in kidney, liver, heart, lung, pancreas, and skin fibrosis models (Gagnon et al. 2018. *Am J Pathol.* 188(5), 1132-1148).

Studies have also linked GPR84 to acute lung injury and/or inflammation.

A review by Alavi et al. summarized studies on GPR17, GPR30, GPR37, GPR40, GPR50, GPR54, GPR56, GPR65, GPR68, GPR75, GPR84, GPR97, GPR109, GPR124, and GPR126 that reported considerable effects in the prevention and/or treatment of multiple sclerosis (MS) in preclinical studies (Alavi et al. 2019. *Life Sci.* 224, 33-40).

GPR84 expression in several murine tissues is enhanced under inflammatory stimuli, such as in endotoxemia, hyperglycemia and hypercholesterolemia. These stimuli also increase GPR84 expression in macrophages, while a selective GPR84 receptor agonist (6-OAU) triggered enhanced secretion of pro-inflammatory cytokines and phagocytosis in macrophages (Recio et al. 2018. *Front. Immunol.* 9, 1419). The results reveal that GPR84 functions as an enhancer of inflammatory signaling in macrophages once inflammation is established and that molecules that antagonize the GPR84 receptor may be potential therapeutic tools in inflammatory and metabolic diseases.

Discovery of DL-175, a potent and selective structurally novel molecule which leads to distinct functional effects in macrophages, compared to other GPR84 ligands (Lucy et al. 2019. *ACS Chem. Biol.* 14(9), 2055-2064). This study confirms GPR84 agonism leads to enhanced chemotaxis and/or phagocytosis in macrophages (aka macrophage activation)

GPR84 was among a few pro-inflammatory neutrophil-associated genes highly enriched in the analysis of RNA-seq data sets from BALF cells from COVID-19 patients (Didangelos, A. 2020. *mSphere.* 5(3), e00367-20).

In acute lung inflammation models, LPS-induced a switch of alveolar macrophages from $CD11^{lo}$ to more inflamed $CD11^{hi}$ status, worsening the lung injury process (Yin et al. 2020. *Mucosal Immunol.* 13(6), 892-907). GPR84 was highly expressed in diseased lung tissues and involved in cytokine release, phagocytosis, and the status switch of alveolar macrophages. GPR84 may represent a potential therapeutic target for acute respiratory distress syndrome.

Köse et al. prepared the first GPR84 agonist radioligand (tritiated) for studying the binding affinities of receptor ligands. They note that GPR84 was found to be involved in inflammatory processes relevant to gastroesophageal reflux disease, inflammatory bowel disease, multiple sclerosis, neuropathic pain, and Alzheimer's disease. Moreover, GPR84 has been linked to obesity and diabetes. Preliminary evidence indicates that GPR84 might be associated with leukemogenesis, osteoclastogenesis, as well as organ fibrosis, a pathological outcome of many inflammatory and metabolic diseases. (Köse M, et al. 2020. *J. Med. Chem.* 63(5), 2391-2410).

A global analysis of glycoproteins by Miller et al. identified markers of endotoxin tolerant monocytes and GPR84 as a modulator of TNFα expression. (Müller M M, et al. 2017 *Sci Rep.* 7(1), 838).

A study by Venkataraman et al. demonstrated that GPR84 regulates IL-4 production by T lymphocytes in response to CD3 crosslinking revealing a novel role for GPR84 in regulating early IL-4 gene expression in activated T cells (Venkataraman C, et al. 2005. *Immunol Lett.* 101(2), 144-53).

Additionally, GPR84 has been linked to neuropathic pain and/or neuropathy.

Gao et al. have shown that DOK3 is involved in microglial cell activation in neuropathic pain by interacting with GPR84, uncovering a physical association between DOK3 and GPR84 in the induction of inflammatory responses. They hypothesize that targeting the adaptor protein DOK3 may open new avenues for pharmaceutical approaches to the alleviation of neuropathic pain in the spinal cord (Gao W S, et al. 2020. *Aging* (Albany NY). 12).

Studies by Kozela et al. on behavioral effects of CBD in a pharmacological model of schizophrenia-like cognitive deficits induced by repeated ketamine (KET) administration demonstrated that CBD reversed transcriptional changes induced by KET including the Gpr84 gene (Kozela E, et al. 2020. *Mol Neurobiol.* 57(3), 1733-1747).

A study by Wei et al. demonstrated that agonists for G-protein-coupled receptor 84 (GPR84) alter cellular morphology and motility but do not induce pro-inflammatory responses in microglia. The study suggests that micro-glial GPR84 could be a therapeutic target in microglia-associated diseases such as multiple sclerosis and Alzheimer's disease (Wei L, et al. 2017. *J Neuroinflammation.* 14(1), 198).

Nicol et al. studied the role of GPR84 in experimental neuropathic pain and demonstrated that GPR84 is a proinflammatory receptor that contributes to nociceptive signaling via the modulation of macrophages, whereas in its absence the response of these cells to an inflammatory insult is impaired (Nicol L S, et al. 2015. *J Neurosci.* 35(23), 8959-69).

Mededdu et al. found that expression of Gpr84 was induced in both microglia and astrocytes and was upregulated in the CNS following virus infection indicating that Gpr 84 expression may be a useful measurement of glial activation during insult or injury to the CNS (Madeddu S, et al. 2015. *PLoS One.* 10(7), e0127336).

Bouchard et al. found that mice suffering from endotoxemia express GPR84 in microglia in a strong and sustained manner, making GPR84 a sensitive marker of microglial activation, which may play an important regulatory role in neuroimmunological processes, acting downstream to the effects of proinflammatory mediators (Bouchard C, et al. 2007. *Glia.* 55(8), 790-800).

GPR84 has also been linked to inflammatory bowel disease as a potential disease target.

Planell et al. identified GPR84 as a transcriptional Blood Biomarker useful as a Non-invasive Surrogate Marker of Mucosal Healing and Endoscopic Response in Ulcerative Colitis. At 14 weeks of treatment, response to anti-TNF therapy induced alterations in blood HP, CD177, GPR84, and S100A12 transcripts that correlated with changes in endoscopic activity (Planell N, et al. 2017. *J Crohns Colitis.* 11(11), 1335-1346).

Studies by Abdel-Aziz et al. found that GPR84 and TREM-1 signaling contribute to the pathogenesis of reflux esophagitis, indicating that GPR84 plays an important role in the pathogenesis of Gastro-esophageal reflux disease (GERD), (Abdel-Aziz, et al. 2016 *Mol Med.* 21(1), 1011-1024).

Dietrich et al. demonstrated that GPR84 sustains aberrant β-catenin signaling in leukemic stem cells (LSCs) for maintenance of stem cell-derived mixed-lineage leukemia (MLL) leukemogenesis, a previously unrecognized role of GPR84 in maintaining fully developed acute myeloid leukemia (AML) by sustaining aberrant β-catenin signaling in LSCs, and suggesting that targeting the oncogenic GPR84/β-catenin signaling axis may represent a novel therapeutic strategy for AML (Dietrich P A, et al. 2014. *Blood.* 124(22), 3284-94).

By mining the Cancer Genome Atlas (TCGA) Database for tumor microenvironment-related genes of prognostic value in hepatocellular carcinoma (HCC), Deng et al. identified GPR84 among a set of differentially expressed genes (DEGs) useful as a candidate biomarker for HCC prognosis (Deng Z, et al. 2019. *Biomed Res Int.* 2019, 2408348).

GeneChip expression profiling by Wang et al. revealed the alterations of energy metabolism related genes including GPR84 in osteocytes under large gradient high magnetic fields. The identification of sensitive genes such as GPR84 to special environments may provide some potential targets for preventing and treating bone loss or osteoporosis (Wang Y, et al. 2015. *PLoS One.* 10(1), e0116359).

Studies by Park et al. demonstrated that GPR84 controls osteoclastogenesis through inhibition of NF-xB and MAPK signaling pathways, revealing that GPR84 functions as a negative regulator of osteoclastogenesis, suggesting that it may be a potential therapeutic target for osteoclast-mediated bone-destructive diseases (Park J W, et al. 2018. *J Cell Physiol.* 233(2), 1481-1489).

Whole-genome transcription and DNA methylation analysis of peripheral blood mononuclear cells by Zhu et al. identified aberrant gene regulation pathways in systemic lupus erythematosus. The gene expressions for MX1, GPR84, and E2F2 were increased in systemic lupus erythematosus (SLE) lupus nephritis (LN)+ as compared to SLE LN-patients (Zhu H, et al. 2016. *Arthritis Res Ther.* 18, 162).

In one embodiment, the subject matter disclosed herein is directed to a method of inhibiting GPR84, the method comprising contacting GPR84 with an effective amount of a compound of the invention or a pharmaceutical composition described herein.

In certain embodiments, the subject matter disclosed herein is directed to a method for modulating an immune response in a subject in need thereof, wherein the method comprises administering to the subject an effective amount of a compound of the invention or a pharmaceutical composition described herein.

The presently disclosed compounds bind directly to GPR84 and inhibit its signaling activity. In some embodiments, the presently disclosed compounds reduce, inhibit, or otherwise diminish the GPR84-mediated inflammatory response.

The presently disclosed compounds may or may not be a specific GPR84 antagonist. A specific GPR84 antagonist reduces the biological activity of GPR84 by an amount that is statistically greater than the inhibitory effect of the antagonist on any other protein (e.g., other GPCRs). In certain embodiments, the presently disclosed compounds specifically inhibit the signaling activity of GPR84. In some of these embodiments, the $IC_{50}$ of the GPR84 antagonist for GPR84 is about 90%, 80%, 70%, 60%, 50%, 40%, 30%, 20%, 10%, 0.1%, 0.01%, 0.001%, or less of the $IC_{50}$ of the GPR84 antagonist for another GPCR activated by free fatty acids (FFA) or other type of GPCR (e.g., Class A GPCR).

The presently disclosed compounds can be used in a method for inhibiting GPR84. Such methods comprise contacting GPR84 with an effective amount of a presently disclosed compound. By "contact" is intended bringing the compound within close enough proximity to an isolated GPR84 GPCR or a cell expressing GPR84 (e.g., T cell or B cell) such that the compound is able to bind to and inhibit the activity of GPR84. The compound can be contacted with GPR84 in vitro or in vivo via administration of the compound to a subject.

Any method known in the art to measure the signaling activity of GPR84 may be used to determine if GPR84 has been inhibited, including in vitro assays or the measurement of a downstream biological effect of GPR84 signaling activity.

The presently disclosed compounds can be used to treat a GPR84-dependent disorder. As used herein, a "GPR84-dependent disorder" is a pathological condition in which GPR84 activity is necessary for the genesis or maintenance of the pathological condition. In some embodiments, the GPR84-dependent disorder is an inflammatory condition.

The presently disclosed compounds also find use in modulating an immune response in a subject in need thereof. Such methods comprise administering an effective amount of a compound of the invention.

As used herein, "modulating an immune response" refers to modulation of any immunogenic response to an antigen.

In another aspect of the invention, this invention provides novel compounds of the invention for use in therapy.

In a further aspect of the invention, this invention provides a method of treating a mammal susceptible to or afflicted with a condition from among those listed herein, and particularly, such condition as may be associated with aberrant activity of GPR84 and/or aberrant GPR84 expression and/or aberrant GPR84 distribution, for example inflammatory conditions, pain, neuroinflammatory conditions, neurodegenerative conditions, infectious diseases, autoimmune diseases, endocrine and/or metabolic diseases, cardiovascular diseases, leukemia, and/or diseases involving impairment of immune cell functions, which method comprises administering a therapeutically effective amount of a compound of the invention, or one or more of the pharmaceutical compositions herein described.

In a further aspect, the present invention provides a compound of the invention for use in the treatment or prevention of a condition selected from those listed herein, particularly such conditions as may be associated with aberrant activity of GPR84 and/or aberrant GPR84 expression and/or aberrant GPR84 distribution expression such as inflammatory conditions, pain, neuroinflammatory conditions, neurodegenerative conditions, infectious diseases, autoimmune diseases, endocrine and/or metabolic diseases, cardiovascular diseases, leukemia, and/or diseases involving impairment of immune cell functions.

In additional aspects, this invention provides methods for synthesizing a compound of the invention, with representative synthetic protocols and pathways disclosed herein.

Accordingly, it is a principal object of this invention to provide a compound of the invention, which can modify the activity of GPR84 and thus prevent or treat any conditions that may be causally related thereto.

It is further an object of this invention to provide a compound of the invention that can treat or alleviate conditions or diseases or symptoms of same, such as inflammatory conditions, pain, neuroinflammatory conditions, neurodegenerative conditions, infectious diseases, autoimmune diseases, endocrine and/or metabolic diseases, cardiovascular diseases, leukemia, and/or diseases involving impairment of immune cell functions, that may be causally related to the activity and/or expression and/or distribution of GPR84.

A still further object of this invention is to provide pharmaceutical compositions that may be used in the treatment or prevention of a variety of disease states, including the diseases associated with aberrant activity of GPR84 and/or aberrant GPR84 expression and/or aberrant GPR84 distribution such as inflammatory conditions, pain, neuroinflammatory conditions, neurodegenerative conditions, infectious diseases, autoimmune diseases, endocrine and/or metabolic diseases, cardiovascular diseases, leukemia, and/or diseases involving impairment of immune cell functions.

Other objects and advantages will become apparent to those skilled in the art from a consideration of the ensuing detailed description.

The present disclosure provides methods of modulating (e.g., inhibiting) GPR84 activity, said method comprising administering to a patient a compound provided herein, or a pharmaceutically acceptable salt thereof.

In one aspect, provided herein is a method for treating of cancer in a subject in need thereof comprising administering to the subject an effective amount of a compound of the invention or a pharmaceutically acceptable salt, prodrug, metabolite, or derivative thereof.

In the methods described herein, a compound of the invention or a pharmaceutical composition thereof is administered to a subject that has cancer.

In certain embodiments, the subject matter disclosed herein is directed to a method for treating a GPR84-dependent disorder, the method comprising administering to a subject in need thereof an effective amount of a compound of the invention or a pharmaceutical composition described herein. In certain aspects of this embodiment, the GPR84-dependent disorder is a cancer.

In some embodiments, the subject matter disclosed herein is directed to a method for treatment of chronic viral infections. In some embodiments, the subject matter disclosed herein is directed to the use of an GPR84 inhibitor as an adjuvant treatment for increasing the efficacy of vaccination.

In some embodiments, the invention provides a pharmaceutical composition comprising an effective amount of a compound of the invention, or a pharmaceutically acceptable salt, hydrate, solvate, or prodrug thereof, and a pharmaceutically acceptable carrier.

In certain aspects, the invention provides a method of treating cell proliferation disorders, including cancers.

In one aspect, the invention provides a method of treating a cell proliferation disorder in a subject, comprising administering a therapeutically effective amount of a compound of the invention, or a pharmaceutically acceptable salt, hydrate, solvate, or prodrug thereof, to the subject.

In certain embodiments, the cell proliferation disorder is cancer.

Examples of cancers that are treatable using the compounds of the present disclosure include, but are not limited to, chronic or acute leukemias including acute myeloid leukemia, chronic myeloid leukemia, acute lymphoblastic leukemia, chronic lymphocytic leukemia, solid tumors of childhood, lymphocytic lymphoma, and combinations of said cancers.

In some embodiments, cancers that are treatable using the compounds of the present disclosure include, but are not limited to, hematological cancers (e.g., lymphoma, leukemia such as acute lymphoblastic leukemia (ALL), acute myelogenous leukemia (AML), chronic lymphocytic leukemia (CLL), chronic myelogenous leukemia (CML), DLBCL, and combinations of said cancers.

In certain embodiments, the cancer is leukemia. In another embodiment the cancer is selected from the group consisting of acute myeloid leukemia and chronic myelogenous leukemia.

In certain embodiments, the cancer is selected from leukemia and cancers of the blood. In particular embodiments, the cancer is present in an adult patient; in additional embodiments, the cancer is present in a pediatric patient. In particular embodiments, the cancer is AIDS-related.

In specific embodiments, the cancer is selected from leukemia and cancers of the blood. In particular embodiments, the cancer is selected from the group consisting of myeloproliferative neoplasms, myelodysplastic syndromes, myelodysplastic/myeloproliferative neoplasms, acute myeloid leukemia (AML), myelodysplastic syndrome (MDS), chronic myelogenous leukemia (CML), myeloproliferative neoplasm (MPN), post-MPN AML, post-MDS AML, del(5q)-associated high risk MDS or AML, blast-phase chronic myelogenous leukemia, angioimmunoblastic lymphoma, acute lymphoblastic leukemia, Langerans cell histiocytosis, hairy cell leukemia, and plasma cell neoplasms including plasmacytomas and multiple myelomas. Leukemias referenced herein may be acute or chronic.

In some embodiments, diseases and indications that are treatable using the compounds of the present disclosure include, but are not limited to hematological cancers.

Exemplary hematological cancers include lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular), Hodgkin lymphoma, myeloproliferative diseases (e.g., primary myelofibrosis (PMF), polycythemia vera (PV), essential thrombocytosis (ET)), myelodysplasia syndrome (MDS), T-cell acute lymphoblastic lymphoma (T-ALL), multiple myeloma, cutaneous T-cell lymphoma, Waldenstrom's Macroglobulinemia, hairy cell lymphoma, chronic myelogenic lymphoma and Burkitt's lymphoma.

As used herein the term "inflammatory condition(s)" refers to the group of conditions including inflammatory bowel diseases (IBD) (e.g., Crohn's disease, ulcerative colitis), rheumatoid arthritis, vasculitis, lung diseases (e.g., chronic obstructive pulmonary disease (COPD) and lung interstitial diseases (e.g., idiopathic pulmonary fibrosis (IPF))), psoriasis, gout, allergic airway disease (e.g., asthma, rhinitis), and endotoxin-driven disease states (e.g., complications after bypass surgery or chronic endotoxin states contributing to e.g., chronic cardiac failure). Particularly the term refers to rheumatoid arthritis, allergic airway disease (e.g., asthma) and inflammatory bowel diseases. In a further particular aspect, the term refers to uveitis, periodontitis, esophagitis, neutrophilic dermatoses (e.g., pyoderma gangrenosum, Sweet's syndrome), severe asthma, and skin and/or colon inflammation caused by oncology treatments aimed at activating the immune response.

As used herein the term "pain" refers to diseases or disorders characterized by unpleasant feeling often caused by intense or damaging stimuli, and include but is not limited to nociceptive pain, inflammatory pain (associated with tissue damage and inflammatory cell infiltration) and neuropathic or dysfunctional pain (caused by damage to or abnormal function of the nervous system), and/or pain associated or caused by the conditions mentioned herein. Pain can be acute or chronic.

As used herein the term "neuroinflammatory conditions" refers to diseases or disorders characterized by abrupt neurologic deficits associated with inflammation, demyelination, and axonal damage, and includes but is not limited to conditions such as Guillain-Barre syndrome (GBS), multiple sclerosis, axonal degeneration, and autoimmune encephalomyelitis.

As used herein the term "neurodegenerative conditions" refers to diseases or disorders characterized by progressive loss of structure or function of neurons, including death of neurons, and includes but is not limited to conditions such as dementia, degenerative dementia, senile dementia, vascular dementia, dementia associated with intracranial space occupying lesions, mild cognitive impairment associated with ageing, age associated memory impairment, and/or peripheral neuropathies. In particular, the term refers to retinopathies, glaucoma, macular degeneration, stroke, cerebral ischemia, traumatic brain injury, Alzheimer's disease, Pick's disease, Huntingdon's chorea, Parkinson's disease, Creutzfeldt-Jakob disease, Amyotrophic lateral sclerosis (ALS), motor neurone disease (MND), Spinocerebellar ataxia (SCA), and/or Spinal muscular atrophy (SMA). More particularly, the term refers to retinopathies, glaucoma, macular degeneration, stroke, cerebral ischemia, traumatic brain injury, Alzheimer's disease, Pick's disease, Huntingdon's chorea, Parkinson's disease, Creutzfeldt-Jakob disease, and/or Amyotrophic lateral sclerosis (ALS).

As used herein, the term "infectious diseases" refers to bacterial infectious diseases and includes but is not limited to conditions such as sepsis, septicemia, endotoxemia, systemic inflammatory response syndrome (SIRS), gastritis, enteritis, enterocolitis, tuberculosis, and other infections involving, for example, *Yersinia, Salmonella, Chlamydia, Shigella*, or enterobacteria species.

As used herein the term "autoimmune disease(s)" refers to the group of diseases including obstructive airways disease (including conditions such as COPD (chronic obstructive pulmonary disease)), psoriasis, asthma (e.g., intrinsic asthma, extrinsic asthma, dust asthma, infantile asthma) particularly chronic or inveterate asthma (for example late asthma and airway hyperreponsiveness), bronchitis, including bronchial asthma, systemic lupus erythematosus (SLE), multiple sclerosis, type I diabetes mellitus and complications associated therewith, atopic eczema (atopic dermatitis), contact dermatitis and further eczematous dermatitis, vasculitis, inflammatory bowel disease (e.g., Crohn's disease and ulcerative colitis), atherosclerosis and amyotrophic lateral sclerosis. Particularly the term refers to COPD, asthma, psoriasis, systemic lupus erythematosis, type I diabetes mellitus, vasculitis and inflammatory bowel disease.

As used herein the term "endocrine and/or metabolic disease(s)" refers to the group of conditions involving the body's over- or under-production of certain hormones, while metabolic disorders affect the body's ability to process certain nutrients and vitamins. Endocrine disorders include hypothyroidism, congenital adrenal hyperplasia, diseases of the parathyroid gland, diabetes mellitus, diseases of the adrenal glands (including Cushing's syndrome and Addison's disease), and ovarian dysfunction (including polycystic ovary syndrome), among others. Some examples of metabolic disorders include cystic fibrosis, phenylketonuria (PKU), diabetes, hyperlipidemia, gout, and rickets. A particular example of metabolic disorders is obesity.

As used herein the term "cardiovascular diseases" refers to diseases affecting the heart or blood vessels or both. In particular, cardiovascular disease includes arrhythmia (atrial or ventricular or both); atherosclerosis and its sequelae; angina; cardiac rhythm disturbances; myocardial ischemia; myocardial infarction; cardiac or vascular aneurysm; vasculitis, stroke; peripheral obstructive arteriopathy of a limb, an organ, or a tissue; reperfusion injury following ischemia of the brain, heart, kidney or other organ or tissue; endotoxic, surgical, or traumatic shock; hypertension, valvular heart disease, heart failure, abnormal blood pressure; shock; vasoconstriction (including that associated with migraines); vascular abnormality, inflammation, insufficiency limited to a single organ or tissue. Particularly, the term refers to atherosclerosis.

As used herein the term "leukemia" refers to neoplastic diseases of the blood and blood forming organs. Such diseases can cause bone marrow and immune system dysfunction, which renders the host highly susceptible to infection and bleeding. In particular the term leukemia refers to acute myeloid leukaemia (AML) and acute lymphoblastic leukemia (ALL).

As used herein, the term "diseases" involving impairment of immune cell functions' includes conditions with symptoms such as recurrent and drawn out viral and bacterial infections, and slow recovery. Other invisible symptoms may be the inability to kill off parasites, yeasts and bacterial pathogens in the intestines or throughout the body.

As used herein the term "fibrotic diseases" refers to diseases characterized by excessive scarring due to excessive production, deposition, and contraction of extracellular matrix, and are that are associated with the abnormal accumulation of cells and/or fibronectin and/or collagen and/or increased fibroblast recruitment and include but are not limited to fibrosis of individual organs or tissues such as the heart, kidney, liver, joints, lung, pleural tissue, peritoneal tissue, skin, cornea, retina, musculoskeletal and digestive tract. In particular, the term fibrotic diseases refers to idiopathic pulmonary fibrosis (IPF); cystic fibrosis, other diffuse parenchymal lung diseases of different etiologies including iatrogenic drug-induced fibrosis, occupational and/or environmental induced fibrosis, granulomatous diseases (sarcoidosis, hypersensitivity pneumonia), collagen vascular disease, alveolar proteinosis, Langerhans cell granulomatosis, lymphangioleiomyomatosis, inherited diseases (Hermansky-Pudlak Syndrome, tuberous sclerosis, neurofibromatosis, metabolic storage diseases, familial interstitial lung disease); radiation induced fibrosis; chronic obstructive pulmonary disease; scleroderma; bleomycin induced pulmonary fibrosis; chronic asthma; silicosis; asbestos induced pulmonary fibrosis; acute respiratory distress syndrome (ARDS); kidney fibrosis; tubulointerstitium fibrosis; glomerular nephritis; diabetic nephropathy, focal segmental glomerular sclerosis; IgA nephropathy; hypertension; Alport; gut fibrosis; liver fibrosis; cirrhosis; alcohol induced liver fibrosis; toxic/drug induced liver fibrosis; hemochromatosis; alcoholic steato hepatitis (ASH), nonalcoholic steatohepatitis (NASH), nonalcoholic fatty liver disease (NAFLD); cholestasis, biliary duct injury; primary sclerosing cholangitis (PSC), primary biliary cirrhosis (PBC); infection induced liver fibrosis; viral induced liver fibrosis; and autoimmune hepatitis; corneal scarring; hypertrophic scarring; Dupuytren disease, keloids, cutaneous fibrosis; cutaneous scleroderma; systemic sclerosis, spinal cord injury/fibrosis; myelofibrosis; Duchenne muscular dystrophy (DMD) associated musculoskeletal fibrosis, vascular restenosis; atherosclerosis; arteriosclerosis; Wegener's granulomatosis; Peyronie's disease, or chronic lymphocytic. More particularly, the term "fibrotic diseases" refers to idiopathic pulmonary fibrosis (IPF), Dupuytren disease, nonalcoholic steatohepatitis (NASH), nonalcoholic fatty liver disease (NAFLD), Alcoholic steatohepatitis, (ASH), portal hypertension, systemic sclerosis, renal fibrosis, and cutaneous fibrosis. Most particularly, the term "fibrotic diseases" refers to nonalcoholic steatohepatitis (NASH), and/or nonalcoholic fatty liver disease (NAFLD). Alternatively, most particularly, the term "fibrotic diseases" refers to IPF.

In some embodiments, the compounds of the invention are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

The presently disclosed compounds may be administered in any suitable manner known in the art. In some embodiments, the compound of the invention or a pharmaceutically acceptable salt, prodrug, metabolite, or derivative thereof is administered intravenously, intramuscularly, subcutaneously, topically, orally, transdermally, intraperitoneally, intraorbitally, by implantation, by inhalation, intrathecally, intraventricularly, intratumorally, or intranasally.

In some embodiments, the GPR84 antagonist is administered continuously. In other embodiments, the GPR84 antagonist is administered intermittently. Moreover, treatment of a subject with an effective amount of a GPR84 antagonist can include a single treatment or can include a series of treatments.

It is understood that appropriate doses of the active compound depends upon a number of factors within the knowledge of the ordinarily skilled physician or veterinarian. The dose(s) of the active compound will vary, for example, depending upon the age, body weight, general health, gender, and diet of the subject, the time of administration, the route of administration, the rate of excretion, and any drug combination.

It will also be appreciated that the effective dosage of a compound of the invention or a pharmaceutically acceptable salt, prodrug, metabolite, or derivative thereof used for treatment may increase or decrease over the course of a particular treatment. Changes in dosage may result and become apparent from the results of diagnostic assays.

In some embodiments, the GPR84 antagonist is administered to the subject at a dose of between about 0.001 μg/kg and about 1000 mg/kg, including but not limited to about 0.001 μg/kg, 0.01 μg/kg, 0.05 μg/kg, 0.1 μg/kg, 0.5 μg/kg, 1 μg/kg, 10 μg/kg, 25 μg/kg, 50 μg/kg, 100 μg/kg, 250 μg/kg, 500 μg/kg, 1 mg/kg, 5 mg/kg, 10 mg/kg, 25 mg/kg, 50 mg/kg, 100 mg/kg, and 200 mg/kg.

In the methods described herein, the method can further comprise administering a chemotherapeutic agent to the subject. In certain aspects of this embodiment, the chemotherapeutic agent is administered to the subject simultaneously with the compound or the composition. In certain aspects of this embodiment, the chemotherapeutic agent is administered to the subject prior to administration of the compound or the composition. In certain aspects of this embodiment, the chemotherapeutic agent is administered to the subject after administration of the compound or the composition.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The term "administration" or "administering" includes routes of introducing the compound(s) to a subject to perform their intended function. Examples of routes of administration which can be used include injection (subcutaneous, intravenous, parenterally, intraperitoneally, intrathecal), topical, oral, inhalation, rectal and transdermal.

The term "effective amount" includes an amount effective, at dosages and for periods of time necessary, to achieve the desired result. An effective amount of compound may vary according to factors such as the disease state, age, and weight of the subject, and the ability of the compound to elicit a desired response in the subject. Dosage regimens may be adjusted to provide the optimum therapeutic response.

The phrases "systemic administration," "administered systemically", "peripheral administration" and "administered peripherally" as used herein mean the administration of a compound(s), drug or other material, such that it enters the patient's system and, thus, is subject to metabolism and other like processes.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The term "subject" refers to animals such as mammals, including, but not limited to, primates (e.g., humans), cows, sheep, goats, horses, dogs, cats, rabbits, rats, mice and the like. In certain embodiments, the subject is a human.

In one embodiment, the present invention provides compounds of the invention, or pharmaceutical compositions comprising a compound of the invention, for use in the prophylaxis and/or treatment of one or more fibrotic diseases. In a particular embodiment, the fibrotic disease is NASH and/or NAFLD. In a most particular embodiment, the fibrotic disease is NASH. In another most particular embodiment, the fibrotic disease is idiopathic pulmonary fibrosis (IPF).

In another embodiment, the present invention provides compounds of the invention, or pharmaceutical compositions comprising a compound of the invention for use in the manufacture of a medicament for use in the prophylaxis and/or treatment of one or more fibrotic diseases. In a particular embodiment, the fibrotic disease is NASH and/or NAFLD. In a most particular embodiment, the fibrotic disease is NASH. In another most particular embodiment, the fibrotic disease is idiopathic pulmonary fibrosis (IPF).

In additional method of treatment aspects, this invention provides methods of prophylaxis and/or treatment of a mammal afflicted with fibrotic diseases, which methods comprise the administration of an effective amount of a compound of the invention or one or more of the pharmaceutical compositions herein described for the treatment or prophylaxis of said condition. In a particular embodiment, the fibrotic disease is NASH and/or NAFLD. In a most particular embodiment, the fibrotic disease is NASH. In another most particular embodiment, the fibrotic disease is idiopathic pulmonary fibrosis (IPF).

In one embodiment, the present invention provides pharmaceutical compositions comprising a compound of the invention, and another therapeutic agent. In a particular embodiment, the other therapeutic agent is a fibrotic disease treatment agent. In a particular embodiment, the fibrotic disease is NASH and/or NAFLD. In a most particular embodiment, the fibrotic disease is NASH. In another most particular embodiment, the fibrotic disease is idiopathic pulmonary fibrosis (IPF).

In one embodiment, the present invention provides compounds of the invention, or pharmaceutical compositions comprising a compound of the invention, for use in the prophylaxis and/or treatment of a subject presenting a NAS score of at least 3, at least 4, at least 5, at least 6 or at least 7.

In another embodiment, the present invention provides compounds of the invention, or pharmaceutical compositions comprising a compound of the invention for use in the manufacture of a medicament for use in the prophylaxis and/or treatment of a subject presenting a NAS score >5.

In additional method of treatment aspects, this invention provides methods of prophylaxis and/or treatment of a mammal presenting a NAS score >5, which methods comprise the administration of an effective amount of a compound of the invention or one or more of the pharmaceutical compositions herein described for the treatment or prophylaxis of said fibrotic diseases, in particular NASH, and/or NAFLD, more particularly NASH.

In further method of treatment embodiments, the methods of prophylaxis and/or treatment of a mammal comprises measuring the forced vital capacity (FVC) in the subject, wherein the FVC does not decrease following treatment. In a particular embodiment, FVC does not decrease over a period of 12, 16, 20 or 26 weeks of treatment. [0158] In another embodiment, the method comprises measuring the FVC in the subject, wherein the FVC increases by at least 1 mL, at least 2 mL, at least 3 mL, at least 4 mL, at least 5 mL, at least 6 mL, at least 7 mL or at least 8 mL. In a particular embodiment, the FVC increases by at least 1 mL, at least 2 mL, at least 3 mL, at least 4 mL, at least 5 mL, at least 6 mL, at least 7 mL or at least 8 mL over a period of 12, 16, 20 or 26 weeks of treatment.

In one embodiment, the method comprises measuring the airway volume wherein said airway volume decrease is no more than 5 mL/L, no more than 4 mL/1, or no more than 3 mL/L. In a particular embodiment the airway volume decrease is no more than 5 mL/L, no more than 4 mL/1, or no more than 3 mL/L after 12, 16, 20 or 26 weeks of treatment.

Combination Therapies

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated."

In certain embodiments, a provided combination, or composition thereof, is administered in combination with another therapeutic agent.

A compound of the invention may be used as a therapeutic agent for the treatment of conditions in mammals that are causally related or attributable to aberrant activity of GPR84 and/or aberrant GPR84 expression and/or aberrant GPR84 distribution.

Accordingly, a compound and pharmaceutical compositions of the invention find use as therapeutics for the prophylaxis and/or treatment of inflammatory conditions, pain, neuroinflammatory conditions, neurodegenerative conditions, infectious diseases, autoimmune diseases, endocrine and/or metabolic diseases, cardiovascular diseases, leukemia, and/or diseases involving impairment of immune cell functions, in mammals including humans.

Accordingly, in one aspect, the present invention provides the compound of the invention, or a pharmaceutical composition comprising the compound of the invention for use as a medicament.

In another aspect, the present invention provides the compound of the invention, or a pharmaceutical composition comprising the compound of the invention for use in the manufacture of a medicament.

In yet another aspect, the present invention provides a method of treating a mammal having, or at risk of having a disease disclosed herein. In a particular aspect, the present invention provides a method of treating a mammal having, or at risk of having inflammatory conditions, pain, neuroinflammatory conditions, neurodegenerative conditions, infectious diseases, autoimmune diseases, endocrine and/or metabolic diseases, cardiovascular diseases, leukemia, and/or diseases involving impairment of immune cell functions, in mammals including humans, said method comprising administering an effective amount of a compound of the invention, or one or more of the pharmaceutical compositions herein described.

In one aspect, the present invention provides the compound of the invention, or a pharmaceutical composition comprising the compound of the invention for use in the prophylaxis and/or treatment of inflammatory conditions. In a specific embodiment, the inflammatory condition is selected from inflammatory bowel disease (IBD), rheumatoid arthritis, vasculitis, chronic obstructive pulmonary disease (COPD), and idiopathic pulmonary fibrosis (IPF). In another specific embodiment, the inflammatory condition is selected from uveitis, periodontitis, esophagitis, neutrophilic dermatoses (e.g., pyoderma gangrenosum, Sweet's syndrome), severe asthma, and skin and/or colon inflammation caused by oncology treatments aimed at activating the immune response.

In another aspect, the present invention provides the compound of the invention, or a pharmaceutical composition comprising the compound of the invention for use in the manufacture of a medicament for the prophylaxis and/or treatment of inflammatory conditions. In a specific embodiment, the inflammatory condition is selected from inflammatory bowel disease (IBD), rheumatoid arthritis, vasculitis, chronic obstructive pulmonary disease (COPD), and idiopathic pulmonary fibrosis (IPF). In another specific embodiment, the inflammatory condition is selected from uveitis, periodontitis, esophagitis, neutrophilic dermatoses (e.g., pyoderma gangrenosum, Sweet's syndrome), severe asthma, and skin and/or colon inflammation caused by oncology treatments aimed at activating the immune response.

In another aspect, the present invention provides a method of treating a mammal having, or at risk of having a disease selected from inflammatory conditions (for example inflammatory bowel diseases (IBD), rheumatoid arthritis, vasculitis), lung diseases (e.g., chronic obstructive pulmonary disease (COPD) and lung interstitial diseases (e.g., idiopathic pulmonary fibrosis (IPF))), neuroinflammatory conditions, infectious diseases, autoimmune diseases, endocrine and/or metabolic diseases, and/or diseases involving impairment of immune cell functions, which method comprises administering an effective amount of a compound of the invention, or one or more of the pharmaceutical compositions herein described.

In additional method of treatment aspects, this invention provides methods of treatment and/or prophylaxis of a mammal susceptible to or afflicted with inflammatory conditions, which method comprises administering an effective amount of a compound of the invention, or one or more of the pharmaceutical compositions herein described. In a specific embodiment, the inflammatory condition is selected from inflammatory bowel disease (IBD), rheumatoid arthritis, vasculitis, chronic obstructive pulmonary disease (COPD), and idiopathic pulmonary fibrosis (IPF). In another specific embodiment, the inflammatory condition is selected from uveitis, periodontitis, esophagitis, neutrophilic dermatoses (e.g., pyoderma gangrenosum, Sweet's syndrome), severe asthma, and skin and/or colon inflammation caused by oncology treatments aimed at activating the immune response.

In one aspect, the present invention provides the compound of the invention, or a pharmaceutical composition comprising the compound of the invention for use in the prophylaxis and/or treatment of pain. In a specific embodiment, the pain is acute or chronic and is selected from nociceptive pain, inflammatory pain, and neuropathic or dysfunctional pain.

In another aspect, the present invention provides the compound of the invention, or a pharmaceutical composition comprising the compound of the invention for use in the manufacture of a medicament for the prophylaxis and/or treatment of pain. In a specific embodiment, the pain is acute or chronic and is selected from nociceptive pain, inflammatory pain, and neuropathic or dysfunctional pain.

In additional method of treatment aspects, this invention provides methods of treatment and/or prophylaxis of a mammal susceptible to or afflicted with pain, which method comprises administering an effective amount of a compound of the invention, or one or more of the pharmaceutical compositions herein described. In a specific embodiment, the pain is acute or chronic and is selected from nociceptive pain, inflammatory pain, and neuropathic or dysfunctional pain.

In one aspect, the present invention provides a compound of the invention, or a pharmaceutical composition comprising the compound of the invention for use in the prophylaxis and/or treatment of neuroinflammatory conditions, Guillain-Barre syndrome (GBS), multiple sclerosis, axonal degeneration, autoimmune encephalomyelitis.

In another aspect, the present invention provides a compound of the invention, or a pharmaceutical composition comprising the compound of the invention for use in the manufacture of a medicament for the prophylaxis and/or treatment of neuroinflammatory conditions, Guillain-Barre syndrome (GBS), multiple sclerosis, axonal degeneration, autoimmune encephalomyelitis.

In additional method of treatment aspects, this invention provides methods of treatment and/or prophylaxis of a mammal susceptible to or afflicted with neuroinflammatory conditions, Guillain-Barre syndrome (GBS), multiple sclerosis, axonal degeneration, autoimmune encephalomyelitis, which method comprises administering an effective amount of a compound of the invention, or one or more of the pharmaceutical compositions herein described.

In one aspect, the present invention provides a compound of the invention, or a pharmaceutical composition comprising the compound of the invention for use in the prophylaxis and/or treatment of infectious disease(s). In a specific embodiment, the infectious disease(s) is selected from sepsis, septicemia, endotoxemia, systemic inflammatory response syndrome (SIRS), gastritis, enteritis, enterocolitis, tuberculosis, and other infections involving, for example, *Yersinia, Salmonella, Chlamydia, Shigella*, enterobacteria species.

In another aspect, the present invention provides a compound of the invention, or a pharmaceutical composition comprising the compound of the invention for use in the manufacture of a medicament for the prophylaxis and/or treatment of infectious disease(s). In a specific embodiment, the infectious disease(s) is selected from sepsis, septicemia, endotoxemia, systemic inflammatory response syndrome (SIRS), gastritis, enteritis, enterocolitis, tuberculosis, and other infections involving, for example, *Yersinia, Salmonella, Chlamydia, Shigella*, enterobacteria species.

In additional method of treatment aspects, this invention provides methods of treatment and/or prophylaxis of a mammal susceptible to or afflicted with infectious disease(s), which method comprises administering an effective amount of a compound of the invention, or one or more of the pharmaceutical compositions herein described. In a specific embodiment, the infectious disease is selected from sepsis, septicemia, endotoxemia, systemic inflammatory response syndrome (SIRS), gastritis, enteritis, enterocolitis, tuberculosis, and other infections involving, for example, *Yersinia, Salmonella, Chlamydia, Shigella*, enterobacteria species.

In one aspect, the present invention provides the compound of the invention, or a pharmaceutical composition comprising the compound of the invention for use in the prophylaxis and/or treatment of autoimmune diseases, and/or diseases involving impairment of immune cell functions. In a specific embodiment, the autoimmune diseases and/or diseases involving impairment of immune cell functions is selected from COPD, asthma, psoriasis, systemic lupus erythematosis, type I diabetes mellitus, vasculitis and inflammatory bowel disease.

In another aspect, the present invention provides the compound of the invention, or a pharmaceutical composition comprising the compound of the invention for use in the manufacture of a medicament for the prophylaxis and/or treatment of autoimmune diseases and/or diseases involving impairment of immune cell functions. In a specific embodiment, the autoimmune diseases, and/or diseases involving impairment of immune cell functions is selected from COPD, asthma, psoriasis, systemic lupus erythematosis, type I diabetes mellitus, vasculitis and inflammatory bowel disease.

In additional method of treatment aspects, this invention provides methods of treatment and/or prophylaxis of a mammal susceptible to or afflicted with autoimmune diseases and/or diseases involving impairment of immune cell functions, which method comprises administering an effective amount of a compound of the invention, or one or more of the pharmaceutical compositions herein described. In a specific embodiment, the autoimmune diseases and/or diseases involving impairment of immune cell functions is selected from COPD, asthma, psoriasis, systemic lupus erythematosis, type I diabetes mellitus, vasculitis and inflammatory bowel disease.

In one aspect, the present invention provides the compound of the invention, or a pharmaceutical composition comprising the compound of the invention for use in the prophylaxis and/or treatment of endocrine and/or metabolic diseases. In a specific embodiment, the endocrine and/or metabolic diseases is selected from hypothyroidism, congenital adrenal hyperplasia, diseases of the parathyroid gland, diabetes mellitus, diseases of the adrenal glands (including Cushing's syndrome and Addison's disease), ovarian dysfunction (including polycystic ovary syndrome), cystic fibrosis, phenylketonuria (PKU), diabetes, hyperlipidemia, gout, and rickets.

In another aspect, the present invention provides the compound of the invention, or a pharmaceutical composition comprising the compound of the invention for use in the manufacture of a medicament for the prophylaxis and/or treatment of endocrine and/or metabolic diseases. In a specific embodiment, the endocrine and/or metabolic diseases is selected from hypothyroidism, congenital adrenal hyperplasia, diseases of the parathyroid gland, diabetes mellitus, diseases of the adrenal glands (including Cushing's syndrome and Addison's disease), ovarian dysfunction (including polycystic ovary syndrome), cystic fibrosis, phenylketonuria (PKU), diabetes, hyperlipidemia, gout, and rickets.

In additional method of treatment aspects, this invention provides methods of treatment and/or prophylaxis of a mammal susceptible to or afflicted with endocrine and/or metabolic diseases, which method comprises administering an effective amount of a compound of the invention, or one or more of the pharmaceutical compositions herein described. In a specific embodiment, the endocrine and/or metabolic diseases is selected from hypothyroidism, congenital adrenal hyperplasia, diseases of the parathyroid gland, diabetes mellitus, diseases of the adrenal glands (including Cushing's syndrome and Addison's disease), ovarian dysfunction (including polycystic ovary syndrome), cystic fibrosis, phenylketonuria (PKU), diabetes, hyperlipidemia, gout, and rickets.

As a further aspect of the invention there is provided a compound of the invention for use as a medicament especially in the treatment or prevention of the aforementioned conditions and diseases. Also provided herein is the use of the compound in the manufacture of a medicament for the treatment or prevention of one of the aforementioned conditions and diseases.

A particular regimen of the present method comprises the administration to a subject in suffering from an inflammatory condition, of an effective amount of a compound of the invention for a period of time sufficient to reduce the level of inflammation in the subject, and preferably terminate, the processes responsible for said inflammation. A special embodiment of the method comprises administering of an effective amount of a compound of the invention to a subject suffering from or susceptible to the development of inflammatory condition, for a period of time sufficient to reduce or prevent, respectively, inflammation of said patient, and preferably terminate, the processes responsible for said inflammation.

Injection dose levels range from about 0.1 mg/kg/h to at least 10 mg/kg/h, all for from about 1 to about 120 h and especially 24 to 96 h. A preloading bolus of from about 0.1 mg/kg to about 10 mg/kg or more may also be administered to achieve adequate steady state levels. The maximum total dose is not expected to exceed about 2 g/day for a 40 to 80 kg human patient.

Transdermal doses are generally selected to provide similar or lower blood levels than are achieved using injection doses.

When used to prevent the onset of a condition, a compound of the invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

A compound of the invention can be administered as the sole active agent or it can be administered in combination with other therapeutic agents, including other compounds that demonstrate the same or a similar therapeutic activity, and that are determined to be safe and efficacious for such combined administration. In a specific embodiment, co-administration of two (or more) agents allows for significantly lower doses of each to be used, thereby reducing the side effects seen.

In one embodiment, a compound of the invention is co-administered with another therapeutic agent for the treatment and/or prevention of an inflammatory condition; particular agents include, but are not limited to, immunoregulatory agents e.g., azathioprine, corticosteroids (e.g., prednisolone or dexamethasone), cyclophosphamide, cyclosporin A, tacrolimus, Mycophenolate Mofetil, muromonab-CD3 (OKT3, e.g., Orthocolone®), ATG, aspirin, acetaminophen, ibuprofen, naproxen, and piroxicam.

In one embodiment, a compound of the invention is co-administered with another therapeutic agent for the treatment and/or prevention of arthritis (e.g., rheumatoid arthritis); particular agents include but are not limited to analgesics, non-steroidal anti-inflammatory drugs (NSAIDS), steroids, synthetic DMARDS (for example but without limitation methotrexate, leflunomide, sulfasalazine, auranofin, sodium aurothiomalate, penicillamine, chloroquine, hydroxychloroquine, azathioprine, and cyclosporin), and biological DMARDS (for example but without limitation Infliximab, Etanercept, Adalimumab, Rituximab, Golimumab, Certolizumab pegol, Tocilizumab, Interleukin 1 blockers and Abatacept).

In one embodiment, a compound of the invention is co-administered with another therapeutic agent for the treatment and/or prevention of autoimmune diseases; particular agents include but are not limited to: glucocorticoids, cytostatic agents (e.g., purine analogs), alkylating agents, (e.g., nitrogen mustards (cyclophosphamide), nitrosoureas, platinum compounds, and others), antimetabolites (e.g., e.g., methotrexate, azathioprine and mercaptopurine), cytotoxic antibiotics (e.g., e.g., dactinomycin anthracyclines, mitomycin C, bleomycin, and mithramycin), antibodies (e.g., anti-CD20, anti-CD25 or anti-CD3 (OTK3) monoclonal antibodies, Atgam® and Thymoglobuline®), cyclosporin, tacrolimus, rapamycin (sirolimus), interferons (e.g., IFN-β), TNF binding proteins (e.g., infliximab (Remicade®), etanercept (Enbrel®), or adalimumab (Humira®)), mycophenolate, Fingolimod, and Myriocin.

In one embodiment, a compound of the invention is co-administered with another therapeutic agent for the treatment and/or prevention of infectious diseases; particular agents include but are not limited to antibiotics. In a particular embodiment, a compound of the invention is co-administered with another therapeutic agent for the treatment and/or prevention of infections of any organ of the human body; particular agents include but are not limited to: aminoglycosides, ansamycins, carbacephem, carbapenems, cephalosporins, glycopeptides, lincosamides, macrolides, monobactams, nitrofurans, penicillins, polypeptides, quinolones, sulfonamides, tetracyclins, anti-mycobacterial agents, as well as chloramphenicol, fosfomycin, linezolid, metronidazole, mupirocin, rifamycin, thiamphenicol and tinidazole.

In one embodiment, a compound of the invention is co-administered with another therapeutic agent for the treatment and/or prevention of vasculitis, particular agents include but are not limited to steroids (for example prednisone, prednisolone), cyclophosphamide and eventually antibiotics in case of cutaneous infections (for example cephalexin).

In one embodiment, a compound of the invention is co-administered with another therapeutic agent for the treatment and/or prevention of esophagitis; particular agents include but are not limited to: anti-acids (e.g., formulations containing aluminum hydroxide, magnesium hydroxide, and/or simethicone), H2-antagonists (e.g., cimetidine, ranitidine, famotidine), proton pump inhibitors (e.g., omeprazole, esomeprazole, lansoprazole, rabeprazole, pantoprazole), and glucocorticoids (e.g., prednisone, budesonide).

In one embodiment, a compound of the invention is co-administered with another therapeutic agent for the treatment and/or prevention of IPF, particular agents include but are not limited to pirfenidone and bosentan.

In one embodiment, a compound of the invention is co-administered with another therapeutic agent for the treatment and/or prevention of asthma and/or rhinitis and/or COPD; particular agents include but are not limited to: beta2-adrenoceptor agonists (e.g., salbutamol, levalbuterol, terbutaline and bitolterol), epinephrine (inhaled or tablets), anticholinergics (e.g., ipratropium bromide), glucocorticoids (oral or inhaled) Long-acting β2-agonists (e.g., salmeterol, formoterol, bambuterol, and sustained-release oral albuterol), combinations of inhaled steroids and long-acting bronchodilators (e.g., fluticasone/salmeterol, budesonide/formoterol), leukotriene antagonists and synthesis inhibitors (e.g., montelukast, zafirlukast and zileuton), inhibitors of mediator release (e.g., cromoglycate and ketotifen), phosphodiesterase-4 inhibitors (e.g., Roflumilast), biological regulators of IgE response (e.g., omalizumab), antihistamines (e.g., ceterizine, cinnarizine, fexofenadine), and vasoconstrictors (e.g., oxymethazoline, xylomethazoline, nafazoline and tramazoline).

Additionally, a compound of the invention may be administered in combination with emergency therapies for asthma and/or COPD, such therapies include oxygen or heliox administration, nebulized salbutamol or terbutaline (optionally combined with an anticholinergic (e.g., ipratropium), systemic steroids (oral or intravenous, e.g., prednisone, prednisolone, methylprednisolone, dexamethasone, or hydrocortisone), intravenous salbutamol, non-specific beta-agonists, injected or inhaled (e.g., epinephrine, isoetharine, isoproterenol, metaproterenol), anticholinergics (IV or nebulized, e.g., glycopyrrolate, atropine, ipratropium), methylxanthines (theophylline, aminophylline, bamiphylline), inhalation anesthetics that have a bronchodilatory effect (e.g., isoflurane, halothane, enflurane), ketamine, and intravenous magnesium sulfate.

In one embodiment, a compound of the invention is co-administered with another therapeutic agent for the treatment and/or prevention of inflammatory bowel disease (IBD); particular agents include but are not limited to: glucocorticoids (e.g., prednisone, budesonide) synthetic disease modifying, immunomodulatory agents (e.g., methotrexate, leflunomide, sulfasalazine, mesalazine, azathioprine, 6-mercaptopurine and ciclosporin) and biological disease modifying, immunomodulatory agents (infliximab, adalimumab, rituximab, and abatacept).

In one embodiment, a compound of the invention is co-administered with another therapeutic agent for the treatment and/or prevention of pain, such as non-narcotic and narcotic analgesics; particular agents include but are not limited to: paracetamol, acetylsalicylic acid, NSAID's, codeine, dihydrocodeine, tramadol, pentazocine, pethidine, tilidine, buprenorfine, fentanyl, hydromorfon, methadon, morfine, oxycodon, piritramide, tapentadol or combinations thereof.

Course of treatment for leukemia comprises chemotherapy, biological therapy, targeted therapy, radiation therapy, bone marrow transplantation and/or combinations thereof.

Examples of further therapeutic agents for Acute Lymphoblastic Leukemia (ALL) comprise methotrexate, nelarabine, asparaginase *Erwinia chrysanthemi*, blinatumomab, daunorubicin, clofarabine, cyclophosphamide, cytarabine, dasatinib, doxorubicin, imatinib, ponatinib vincristine, mercaptopurine, pegaspargase, and/or prednisone.

Examples of further therapeutic agents for Acute Myeloid Leukemia (AML) comprise arsenic trioxide, daunorubicin, cyclophosphamide, cytarabine, doxorubicin, idarubicin, mitoxantrone, and/or vincristine.

Examples of further therapeutic agents for Chronic Lymphocytic Leukemia (CLL) comprise alemtuzumab, chlorambucil, ofatumumab, bendamustine, cyclophosphamide, fludarabine, obinutuzumab, ibrutinib, idelalisib, mechlorethamine, prednisone, and/or rituximab.

Examples of further therapeutic agents for Chronic Myelogenous Leukemia (CML) comprise bosutinib, busulfan, cyclophosphamide, cytarabine, dasatinib, imatinib, ponatinib, mechlorethamine, nilotinib, and/or omacetaxine.

Examples of further therapeutic agents for Hairy Cell Leukemia comprise cladiribine, pentostatin, and/or interferon alfa-2b.

By co-administration is included any means of delivering two or more therapeutic-agents to the patient as part of the same treatment regime, as will be apparent to the skilled person. Whilst the two or more agents may be administered simultaneously in a single formulation this is not essential. The agents may be administered in different formulations and at different times.

In one embodiment, a compound of the invention is co-administered with one or more further therapeutic agents for the treatment and/or prophylaxis of a fibrotic disease. In a particular embodiment, a compound of the invention is co-administered with one or two further therapeutic agents for the treatment and/or prophylaxis of a fibrotic disease. In a more particular embodiment, a compound of the invention is co-administered with one further therapeutic agent for the treatment and/or prophylaxis of a fibrotic disease.

In one embodiment, the further therapeutic agent for the treatment and/or prophylaxis of a fibrotic disease include, but are not limited to 5-methyl-1-phenyl-2-(1H)-pyridone (pirfenidone); nintedanib (Ofev® or Vargatef®); STX-100 (ClinicalTrials.gov Identifier NCT01371305), FG-3019 (ClinicalTrials.gov Identifier NCT01890265), lebrikizumab (CAS n #953400-68-5); tralokinumab (CAS n #1044515-88-9), CC-90001 (ClinicalTrials.gov Identifier NCT03142191), tipelukast (MN-001; ClinicalTrials.gov Identifier NCT02503657), ND-L02-s0201 (ClinicalTrials.gov Identifier NCT03538301), KD025 (ClinicalTrials.gov Identifier NCT02688647), TD139 (ClinicalTrials.gov Identifier NCT02257177), VAY736 (ClinicalTrials.gov Identifier NCT03287414), PRM-151 (ClinicalTrials.gov Identifier NCT02550873) and PBI-4050 (ClinicalTrials.gov Identifier NCT02538536). In a particular embodiment, the further therapeutic agent for the treatment and/or prophylaxis of a fibrotic disease is an autotaxin (or ectonucleotide pyrophosphatase/phosphodiesterase 2 or NPP2 or ENPP2) inhibitor, examples of which are described in WO 2014/139882, such as GLPG1690.

In one embodiment, a compound of the invention is co-administered with another therapeutic agent for the treatment and/or prophylaxis of NASH, particular agents include but are not limited to weight loss treatment agents (for example Sibutramine, or Orlistat), insulin-sensitizing agents (for example Metformin, Thiazolidinedione, Rosiglitazone, or Pioglitazone), lipid-lowering agents (for example Gemfibrozil), Antioxidants (for example Vitamine E, N-acetylcysteine, Betaine, or Pentoxifylline), Angiotensin-converting enzyme inhibitors, Angiotensin-receptor blockers, Monounsaturated fatty acids, or Polyunsaturated fatty acids. FXR agonists (for example Obeticholic acid), LOXL2 antagonists (for example Simtuzumab), ASK1 antagonists (for example Selonsertib), PPAR agonists (for example clofibrate, gemfibrozil, ciprofibrate, bezafibrate, fenofibrate, thiazolidinediones, ibuprofen, GW-9662, aleglitazar, muraglitazar or tesaglitazar), Acetyl CoA-Carboxylase (ACC) antagonists (for example NDI-010976, PF-05221304), CCR2/CCR5 (for example Cenicriviroc), VAP1 antagonist.

Examples of agents the combinations of this invention may also be combined with include, without limitation: treatments for Alzheimer's Disease such as Aricept® and Excelon®; treatments for HIV such as ritonavir; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents that prolong or improve pharmacokinetics such as cytochrome P450 inhibitors (i.e., inhibitors of metabolic breakdown) and CYP3A4 inhibitors (e.g., ketokenozole and ritonavir), and agents for treating immunodeficiency disorders such as gamma globulin.

In certain embodiments, combination therapies of the present invention, or a pharmaceutically acceptable composition thereof, are administered in combination with a monoclonal antibody or an siRNA therapeutic.

Those additional agents may be administered separately from a provided combination therapy, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a combination of the present invention may be administered with another therapeutic agent simultaneously or sequentially in separate unit dosage forms or together in a single unit dosage form.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In one embodiment, the present invention provides a composition comprising a compound of formula I and one or more additional therapeutic agents. The therapeutic agent may be administered together with a compound of formula I, or may be administered prior to or following administration of a compound of formula I. Suitable therapeutic agents are described in further detail below. In certain embodiments, a compound of formula I may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In other embodiments, a compound of formula I may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

In another embodiment, the present invention provides a method of treating an inflammatory disease, disorder or condition by administering to a patient in need thereof a compound of formula I and one or more additional therapeutic agents. Such additional therapeutic agents may be small molecules or recombinant biologic agents and include, for example, acetaminophen, non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol, febuxostat (Uloric®), sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), canakinumab (Ilaris®), anti-Jak inhibitors such as tofacitinib, antibodies such as rituximab (Rituxan®), "anti-T-cell" agents such as abatacept (Orencia®), "anti-IL-6" agents such as tocilizumab (Actemra®), diclofenac, cortisone, hyaluronic acid (Synvisc® or Hyalgan®), monoclonal antibodies such as tanezumab, anticoagulants such as heparin (Calcinparine® or Liquaemin®) and warfarin (Coumadin®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot®, anticholinergics or antispasmodics such as dicyclomine (Bentyl®), Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as beclomethasone dipropionate (Beclovent®, Qvar®, and Vanceril®), triamcinolone acetonide (Azmacort®), mometasone (Asthmanex®), budesonide (Pulmocort®), and flunisolide (Aerobid®), Afviar®, Symbicort®, Dulera®, cromolyn sodium (Intal®), methylxanthines such as theophylline (Theo-Dur®, Theolair®, Slo-bid®, Uniphyl®, Theo-24®) and aminophylline, IgE antibodies such as omalizumab (Xolair®), nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), doxorubicin (Hydrodaunorubicin®), vincristine (Oncovin®), bortezomib (Velcade®), and dexamethasone (Decadron®) in combination with lenalidomide (Revlimid®), or any combination(s) thereof.

In another embodiment, the present invention provides a method of treating rheumatoid arthritis comprising administering to a patient in need thereof a compound of formula I and one or more additional therapeutic agents selected from non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), antibodies such as rituximab (Rituxan®), "anti-T-cell" agents such as abatacept (Orencia®) and "anti-IL-6" agents such as tocilizumab (Actemra®).

In some embodiments, the present invention provides a method of treating osteoarthritis comprising administering to a patient in need thereof a compound of formula I and one or more additional therapeutic agents selected from acetaminophen, non-steroidal anti-inflammatory drugs (NSAIDS) such as aspirin, ibuprofen, naproxen, etodolac (Lodine®) and celecoxib, diclofenac, cortisone, hyaluronic acid (Synvisc® or Hyalgan®) and monoclonal antibodies such as tanezumab.

In some embodiments, the present invention provides a method of treating cutaneous lupus erythematosus or systemic lupus erythematosus comprising administering to a patient in need thereof a compound of formula I and one or more additional therapeutic agents selected from acetaminophen, non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, antimalarials such as hydroxychloroquine (Plaquenil®) and chloroquine (Aralen®), cyclophosphamide (Cytoxan®), methotrexate (Rheumatrex®), azathioprine (Imuran®) and anticoagulants such as heparin (Calcinparine® or Liquaemin®) and warfarin (Coumadin®).

In some embodiments, the present invention provides a method of treating Crohn's disease, ulcerative colitis, or inflammatory bowel disease comprising administering to a patient in need thereof a compound of formula I and one or more additional therapeutic agents selected from mesalamine (Asacol®) sulfasalazine (Azulfidine®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot® and anticholinergics or antispasmodics such as dicyclomine (Bentyl®), anti-TNF therapies, steroids, and antibiotics such as Flagyl or ciprofloxacin.

In some embodiments, the present invention provides a method of treating asthma comprising administering to a patient in need thereof a compound of formula I and one or more additional therapeutic agents selected from Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, cromolyn sodium (Intal®), methylxanthines such as theophylline (Theo-Dur®, Theolair®, Slo-bid®, Uniphyl®, Theo-24®) and aminophylline, and IgE antibodies such as omalizumab (Xolair®).

In some embodiments, the present invention provides a method of treating COPD comprising administering to a patient in need thereof a compound of formula I and one or more additional therapeutic agents selected from beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), methylxanthines such as theophylline (Theo-Dur®, Theolair®, Slo-bid®, Uniphyl®, Theo-24®) and aminophylline, inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, In another embodiment, the present invention provides a method of treating a hematological malignancy comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a PI3K inhibitor, a SYK inhibitor, and combinations thereof.

In another embodiment, the present invention provides a method of treating a solid tumor comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a PI3K inhibitor, a SYK inhibitor, and combinations thereof.

In another embodiment, the present invention provides a method of treating a hematological malignancy comprising administering to a patient in need thereof a compound of formula I and a Hedgehog (Hh) signaling pathway inhibitor. In some embodiments, the hematological malignancy is DLBCL (Ramirez et al "Defining causative factors contributing in the activation of hedgehog signaling in diffuse large B-cell lymphoma" Leuk. Res. (2012), published onine July 17, and incorporated herein by reference in its entirety).

In another embodiment, the present invention provides a method of treating diffuse large B-cell lymphoma (DLBCL) comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, and combinations thereof.

In another embodiment, the present invention provides a method of treating multiple myeloma comprising administering to a patient in need thereof a compound of formula I and one or more additional therapeutic agents selected from bortezomib (Velcade®), and dexamethasone (Decadron®), a hedgehog signaling inhibitor, a BTK inhibitor, a JAK/pan-JAK inhibitor, a TYK2 inhibitor, a PI3K inhibitor, a SYK inhibitor in combination with lenalidomide (Revlimid®).

In another embodiment, the present invention provides a method of treating or lessening the severity of a disease comprising administering to a patient in need thereof a compound of formula I and a BTK inhibitor, wherein the disease is selected from inflammatory bowel disease, arthritis, cutaneous lupus erythematosus, systemic lupus erythematosus (SLE), vasculitis, idiopathic thrombocytopenic purpura (ITP), rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, autoimmune thyroiditis, Sjogren's syndrome, multiple sclerosis, systemic sclerosis, Lyme neuroborreliosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, autoimmune gastritis, pernicious anemia, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, membranous glomerulonephropathy, endometriosis, interstitial cystitis, pemphigus vulgaris, bullous pemphigoid, neuromyotonia, scleroderma, vulvodynia, a hyperproliferative disease, rejection of transplanted organs or tissues, Acquired Immunodeficiency Syndrome (AIDS, also known as HIV), type 1 diabetes, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis, asthma, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis, B-cell proliferative disorder, e.g., diffuse large B cell lymphoma, follicular lymphoma, chronic lymphocytic lymphoma, chronic lymphocytic leukemia, acute lymphocytic leukemia, B-cell prolymphocytic leukemia, lymphoplasmacytic lymphoma/Waldenstrom macroglobulinemia, splenic marginal zone lymphoma, multiple myeloma (also known as plasma cell myeloma), non-Hodgkin's lymphoma, Hodgkin's lymphoma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, or lymphomatoid granulomatosis, breast cancer, prostate cancer, or cancer of the mast cells (e.g., mastocytoma, mast cell leukemia, mast cell sarcoma, systemic mastocytosis), bone cancer, colorectal cancer, pancreatic cancer, diseases of the bone and joints including, without limitation, rheumatoid arthritis, seronegative spondyloarthropathies (including ankylosing spondylitis, psoriatic arthritis and Reiter's disease), Behcet's disease, Sjogren's syndrome, systemic sclerosis, osteoporosis, bone cancer, bone metastasis, a thromboembolic disorder, (e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, deep venous thrombosis), inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, diabetes, septic shock, cutaneous lupus erythematosus, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleraderma, mycosis fungoides, acute inflammatory responses (such as acute respiratory distress syndrome and ischemia/reperfusion injury), and Graves' disease.

In another embodiment, the present invention provides a method of treating or lessening the severity of a disease comprising administering to a patient in need thereof a compound of formula I and a PI3K inhibitor, wherein the disease is selected from a cancer, a neurodegenative disorder, an angiogenic disorder, a viral disease, an autoimmune disease, an inflammatory disorder, a hormone-related disease, conditions associated with organ transplantation, immunodeficiency disorders, a destructive bone disorder, a proliferative disorder, an infectious disease, a condition associated with cell death, thrombin-induced platelet aggregation, chronic myelogenous leukemia (CML), chronic lymphocytic leukemia (CLL), liver disease, pathologic immune conditions involving T cell activation, a cardiovascular disorder, and a CNS disorder.

In another embodiment, the present invention provides a method of treating or lessening the severity of a disease comprising administering to a patient in need thereof a compound of formula I and a PI3K inhibitor, wherein the disease is selected from benign or malignant tumor, carcinoma or solid tumor of the brain, kidney (e.g., renal cell carcinoma (RCC)), liver, adrenal gland, bladder, breast, stomach, gastric tumors, ovaries, colon, rectum, prostate, pancreas, lung, vagina, endometrium, cervix, testis, genitourinary tract, esophagus, larynx, skin, bone or thyroid, sarcoma, glioblastomas, neuroblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, (including, for example, non-Hodgkin's Lymphoma (NHL) and Hodgkin's lymphoma (also termed Hodgkin's or Hodgkin's disease)), a mammary carcinoma, follicular carcinoma, undifferentiated carcinoma, papillary carcinoma, seminoma, melanoma, or a leukemia, diseases include Cowden syndrome, Lhermitte-Dudos disease and Bannayan-Zonana syndrome, or diseases in which the PI3K/PKB pathway is aberrantly activated, asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection, acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy, bronchitis of whatever type or genesis including, but not limited to, acute, arachidic, catarrhal, croupus, chronic or phthinoid bronchitis, pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis, Loffler's syndrome, eosinophilic, pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction, psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), cutaneous lupus erythematosus, systemic lupus erythematosus, rheumatoid arthritis, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy, restenosis, cardiomegaly, atherosclerosis, myocardial infarction, ischemic stroke and congestive heart failure, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

In some embodiments the present invention provides a method of treating or lessening the severity of a disease comprising administering to a patient in need thereof a compound of formula I and a Bcl-2 inhibitor, wherein the disease is an inflammatory disorder, an autoimmune disorder, a proliferative disorder, an endocrine disorder, a neurological disorder, or a disorder associated with transplantation. In some embodiments, the disorder is a proliferative disorder, lupus, or lupus nephritis. In some embodiments, the proliferative disorder is chronic lymphocytic leukemia, diffuse large B-cell lymphoma, Hodgkin's disease, small-cell lung cancer, non-small-cell lung cancer, myelodysplastic syndrome, lymphoma, a hematological neoplasm, or solid tumor.

In some embodiments, the disease is an autoimmune disorder, an inflammatory disorder, a proliferative disorder, an endocrine disorder, a neurological disorder, or a disorder associated with transplantation. In some embodiments the JH2 binding compound is a compound of formula I. Other suitable JH2 domain binding compounds include those described in WO2014074660A1, WO2014074661A1, WO2015089143A1, the entirety of each of which is incorporated herein by reference. Suitable JH1 domain binding compounds include those described in WO2015131080A1, the entirety of which is incorporated herein by reference.

The compounds and compositions, according to the method of the present invention, may be administered using any amount and any route of administration effective for treating or lessening the severity of an autoimmune disorder, an inflammatory disorder, a proliferative disorder, an endocrine disorder, a neurological disorder, or a disorder associated with transplantation. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting GPR84 activity in a biological sample comprising the step of contacting said biological sample with a compound of this invention, or a composition comprising said compound.

According to another embodiment, the invention relates to a method of inhibiting GPR84, or a mutant thereof, activity in a biological sample comprising the step of contacting said biological sample with a compound of this invention, or a composition comprising said compound.

The term “biological sample”, as used herein, includes, without limitation, cell cultures or extracts thereof, biopsied material obtained from a mammal or extracts thereof; and blood, saliva, urine, feces, semen, tears, or other body fluids or extracts thereof.

Inhibition of GPR84 (or a mutant thereof) activity in a biological sample is useful for a variety of purposes that are known to one of skill in the art. Examples of such purposes include, but are not limited to, blood transfusion, organ-transplantation, biological specimen storage, and biological assays.

Another embodiment of the present invention relates to a method of inhibiting GPR84 activity in a patient comprising the step of administering to said patient a compound of the present invention, or a composition comprising said compound.

According to another embodiment, the invention relates to a method of inhibiting activity of GPR84, or a mutant thereof, in a patient comprising the step of administering to said patient a compound of the present invention, or a composition comprising said compound. According to certain embodiments, the invention relates to a method of reversibly or irreversibly inhibiting one or more of GPR84, or a mutant thereof, activity in a patient comprising the step of administering to said patient a compound of the present invention, or a composition comprising said compound. In other embodiments, the present invention provides a method for treating a disorder mediated by GPR84, or a mutant thereof, in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as “appropriate for the disease, or condition, being treated.”

A compound of the current invention may also be used to advantage in combination with other therapeutic compounds. In some embodiments, the other therapeutic compounds are antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal©); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from AstraZeneca, PD181461 from Pfizer and leucovorin. The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™. Letrozole is marketed under the trade names Femara™ or Femar™ Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™ Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™

The term "topoisomerase II inhibitor" as used herein includes, but is not limited to the anthracyclines such as doxorubicin (including liposomal formulation, such as Caelyx™) daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed. under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; *vinca* alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™ Docetaxel is marketed under the trade name Taxotere™. Vinblastine sulfate is marketed under the trade name Vinblastin R.P™. Vincristine sulfate is marketed under the trade name Farmistin™

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the AxI receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; llmofosine; RO 318220 and RO 320432; GO 6976; lsis 3521; LY333531/LY379196; isochinoline compounds; FTIs; PD184352 or QAN697 (a P13K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); 1) compounds targeting, decreasing or inhibiting the activity of the epidermal growth factor family of receptor tyrosine kinases (EGFR1 ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, Cl-1033, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof; see WO2008118802), navitoclax (and analogs thereof, see U.S. Pat. No. 7,390,799), NH-1 (Shenayng Pharmaceutical University), obatoclax (and analogs thereof, see WO2004106328), 5-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

Further examples of BTK inhibitory compounds, and conditions treatable by such compounds in combination with compounds of this invention can be found in WO2008039218 and WO2011090760, the entirety of which are incorporated herein by reference.

Further examples of SYK inhibitory compounds, and conditions treatable by such compounds in combination with compounds of this invention can be found in WO2003063794, WO2005007623, and WO2006078846, the entirety of which are incorporated herein by reference.

Further examples of PI3K inhibitory compounds, and conditions treatable by such compounds in combination with compounds of this invention can be found in WO2004019973, WO2004089925, WO2007016176, U.S. Pat. No. 8,138,347, WO2002088112, WO2007084786, WO2007129161, WO2006122806, WO2005113554, and WO2007044729 the entirety of which are incorporated herein by reference.

Further examples of JAK inhibitory compounds, and conditions treatable by such compounds in combination with compounds of this invention can be found in WO2009114512, WO2008109943, WO2007053452, WO2000142246, and WO2007070514, the entirety of which are incorporated herein by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC125, such as okadaic acid or a derivative thereof.

Compounds which induce cell differentiation processes include, but are not limited to, retinoic acid, α-γ- or δ-tocopherol or α-γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™ Pamidronic acid is marketed under the trade name Aredia™. Alendronic acid is marketed under the trade name Fosamax™. Ibandronic acid is marketed under the trade name Bondranat™ Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; ALK inhibitors, which are compounds which target, decrease or inhibit anaplastic lymphoma kinase, and Bcl-2 inhibitors.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino, 17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PR064553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412. In some embodiments, the present invention provides a method of treating AML associated with an ITD and/or D835Y mutation, comprising administering a compound of the present invention together with a one or more FLT3 inhibitors. In some embodiments, the FLT3 inhibitors are selected from quizartinib (AC220), a staurosporine derivative (e.g. midostaurin or lestaurtinib), sorafenib, tandutinib, LY-2401401, LS-104, EB-10, famitinib, NOV-110302, NMS-P948, AST-487, G-749, SB-1317, 5-209, SC-110219, AKN-028, fedratinib, tozasertib, and sunitinib. In some embodiments, the FLT3 inhibitors are selected from quizartinib, midostaurin, lestaurtinib, sorafenib, and sunitinib.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., 4$^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; ZD6474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™)

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The compounds of the invention are also useful as co-therapeutic compounds for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. A compound of the invention may be mixed with the other drug substance in a fixed pharmaceutical composition or it may be administered separately, before, simultaneously with or after the other drug substance. Accordingly the invention includes a combination of a compound of the invention as hereinbefore described with an anti-inflammatory, bronchodilatory, antihistamine or anti-tussive drug substance, said compound of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate; non-steroidal glucocorticoid receptor agonists; LTB4 antagonists such LY293111, CGS025019C, CP-195543, SC-53228, BIIL 284, ONO 4057, SB 209247; LTD4 antagonists such as montelukast and zafirlukast; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (*Asta Medica*), CDC-801 (Celgene), SeICID™ CC-10004 (Celgene), VM554/UM565 (Vernalis), T-440 (Tanabe), KW-4490 (Kyowa Hakko Kogyo); A2a agonists; A2b antagonists; and beta-2 adrenoceptor agonists such as albuterol (salbutamol), metaproterenol, terbutaline, salmeterol fenoterol, procaterol, and especially, formoterol and pharmaceutically acceptable salts thereof. Suitable bronchodilatory drugs include anticholinergic or antimuscarinic compounds, in particular ipratropium bromide, oxitropium bromide, tiotropium salts and CHF 4226 (Chiesi), and glycopyrrolate.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine.

Other useful combinations of compounds of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, and Takeda antagonists such as N-[[4-[[[6,7-dihydro-2-(4-methylphenyl)-5H-benzo-cyclohepten-8-yl]carbonyl]amino]phenyl]-methyl]tetrahydro-N,N-dimethyl-2H-pyran-4-aminium chloride (TAK-770).

The structure of the active compounds identified by code numbers, generic or trade names may be taken from the actual edition of the standard compendium "The Merck Index" or from databases, e.g. Patents International (e.g. IMS World Publications).

Exemplary Immuno-Oncology Agents

In some embodiments, one or more other therapeutic agent is an immuno-oncology agent. As used herein, the term "an immuno-oncology agent" refers to an agent which is effective to enhance, stimulate, and/or up-regulate immune responses in a subject. In some embodiments, the administration of an immuno-oncology agent with a compound of the invention has a synergic effect in treating a cancer.

An immuno-oncology agent can be, for example, a small molecule drug, an antibody, or a biologic or small molecule. Examples of biologic immuno-oncology agents include, but are not limited to, cancer vaccines, antibodies, and cytokines. In some embodiments, an antibody is a monoclonal antibody. In some embodiments, a monoclonal antibody is humanized or human.

In some embodiments, an immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses.

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fni4, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α1β2, FAS, FASL, RELT, DR6, TROY, NGFR.

In some embodiments, an immuno-oncology agent is a cytokine that inhibits T cell activation (e.g., IL-6, IL-10, TGF-β, VEGF, and other immunosuppressive cytokines) or a cytokine that stimulates T cell activation, for stimulating an immune response.

In some embodiments, a combination of a compound of the invention and an immuno-oncology agent can stimulate T cell responses. In some embodiments, an immuno-oncology agent is: (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4; or (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

In some embodiments, an immuno-oncology agent is an antagonist of inhibitory receptors on NK cells or an agonist of activating receptors on NK cells. In some embodiments, an immuno-oncology agent is an antagonist of KIR, such as lirilumab.

In some embodiments, an immuno-oncology agent is an agent that inhibits or depletes macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

In some embodiments, an immuno-oncology agent is selected from agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell energy or exhaustion) and agents that trigger innate immune activation and/or inflammation at tumor sites.

In some embodiments, an immuno-oncology agent is a CTLA-4 antagonist. In some embodiments, a CTLA-4 antagonist is an antagonistic CTLA-4 antibody. In some embodiments, an antagonistic CTLA-4 antibody is YERVOY (ipilimumab) or tremelimumab.

In some embodiments, an immuno-oncology agent is a PD-1 antagonist. In some embodiments, a PD-1 antagonist is administered by infusion. In some embodiments, an immuno-oncology agent is an antibody or an antigen-binding portion thereof that binds specifically to a Programmed Death-1 (PD-1) receptor and inhibits PD-1 activity. In some embodiments, a PD-1 antagonist is an antagonistic PD-1 antibody. In some embodiments, an antagonistic PD-1 antibody is OPDIVO (nivolumab), KEYTRUDA (pembrolizumab), or MEDI-0680 (AMP-514; WO2012/145493). In some embodiments, an immuno-oncology agent may be pidilizumab (CT-011). In some embodiments, an immuno-oncology agent is a recombinant protein composed of the extracellular domain of PD-L2 (B7-DC) fused to the Fc portion of IgG1, called AMP-224.

In some embodiments, an immuno-oncology agent is a PD-L1 antagonist. In some embodiments, a PD-L1 antagonist is an antagonistic PD-L1 antibody. In some embodiments, a PD-L1 antibody is MPDL3280A (RG7446; WO2010/077634), durvalumab (MEDI4736), BMS-936559 (WO2007/005874), and MSB0010718C (WO2013/79174).

In some embodiments, an immuno-oncology agent is a LAG-3 antagonist. In some embodiments, a LAG-3 antagonist is an antagonistic LAG-3 antibody. In some embodiments, a LAG3 antibody is BMS-986016 (WO10/19570, WO14/08218), or IMP-731 or AIP-321 (WO08/132601, WO009/44273).

In some embodiments, an immuno-oncology agent is a CD137 (4-1BB) agonist. In some embodiments, a CD137 (4-1BB) agonist is an agonistic CD137 antibody. In some embodiments, a CD137 antibody is urelumab or PF-05082566 (WO12/32433).

In some embodiments, an immuno-oncology agent is a GITR agonist. In some embodiments, a GITR agonist is an agonistic GITR antibody. In some embodiments, a GITR antibody is BMS-986153, BMS-986156, TRX-518 (WO006/105021, WO009/009116), or MK-4166 (WO11/028683).

In some embodiments, an immuno-oncology agent is an indoleamine (2,3)-dioxygenase (IDO) antagonist. In some embodiments, an IDO antagonist is selected from epacadostat (INCB024360, Incyte); indoximod (NLG-8189, NewLink Genetics Corporation); capmanitib (INC280, Novartis); GDC-0919 (Genentech/Roche); PF-06840003 (Pfizer); BMS:F001287 (Bristol-Myers Squibb); Phy906/KD108 (Phytoceutica); an enzyme that breaks down kynurenine (Kynase, Ikena Oncology, formerly known as Kyn Therapeutics); and NLG-919 (WO09/73620, WO009/1156652, WO11/56652, WO12/142237).

In some embodiments, an immuno-oncology agent is an OX40 agonist. In some embodiments, an OX40 agonist is an agonistic OX40 antibody. In some embodiments, an OX40 antibody is MEDI-6383 or MEDI-6469.

In some embodiments, an immuno-oncology agent is an OX40L antagonist. In some embodiments, an OX40L antagonist is an antagonistic OX40 antibody. In some embodiments, an OX40L antagonist is RG-7888 (WO06/029879).

In some embodiments, an immuno-oncology agent is a CD40 agonist. In some embodiments, a CD40 agonist is an agonistic CD40 antibody. In some embodiments, an immuno-oncology agent is a CD40 antagonist. In some embodiments, a CD40 antagonist is an antagonistic CD40 antibody. In some embodiments, a CD40 antibody is lucatumumab or dacetuzumab.

In some embodiments, an immuno-oncology agent is a CD27 agonist. In some embodiments, a CD27 agonist is an agonistic CD27 antibody. In some embodiments, a CD27 antibody is varlilumab.

In some embodiments, an immuno-oncology agent is MGA271 (to B7H3) (WO11/109400).

In some embodiments, an immuno-oncology agent is abagovomab, adecatumumab, afutuzumab, alemtuzumab, anatumomab mafenatox, apolizumab, atezolimab, avelumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MPDL3280A, nivolumab, obinutuzumab, ocaratuzumab, ofatumumab, olatatumab, pembrolizumab, pidilizumab, rituximab, ticilimumab, samalizumab, or tremelimumab.

In some embodiments, an immuno-oncology agent is an immunostimulatory agent. For example, antibodies blocking the PD-1 and PD-L1 inhibitory axis can unleash activated tumor-reactive T cells and have been shown in clinical trials to induce durable anti-tumor responses in increasing numbers of tumor histologies, including some tumor types that conventionally have not been considered immunotherapy sensitive. See, e.g., Okazaki, T. et al. (2013) Nat. Immunol. 14, 1212-1218; Zou et al. (2016) Sci. Transl. Med. 8. The anti-PD-1 antibody nivolumab (OPDIVO©, Bristol-Myers Squibb, also known as ONO-4538, MDX1106 and BMS-936558), has shown potential to improve the overall survival in patients with RCC who had experienced disease progression during or after prior anti-angiogenic therapy.

In some embodiments, the immunomodulatory therapeutic specifically induces apoptosis of tumor cells. Approved immunomodulatory therapeutics which may be used in the present invention include pomalidomide (POMALYST®, Celgene); lenalidomide (REVLIMID®, Celgene); ingenol mebutate (PICATO®, LEO Pharma).

In some embodiments, an immuno-oncology agent is a cancer vaccine. In some embodiments, the cancer vaccine is selected from sipuleucel-T (PROVENGE®, Dendreon/Valeant Pharmaceuticals), which has been approved for treatment of asymptomatic, or minimally symptomatic metastatic castrate-resistant (hormone-refractory) prostate cancer; and talimogene laherparepvec (AILYGIC®, BioVex/Amgen, previously known as T-VEC), a genetically modified oncolytic viral therapy approved for treatment of unresectable cutaneous, subcutaneous and nodal lesions in melanoma. In some embodiments, an immuno-oncology agent is selected from an oncolytic viral therapy such as pexastimogene devacirepvec (PexaVec/JX-594, SillaJen/formerly Jennerex Biotherapeutics), a thymidine kinase-(TK-) deficient vaccinia virus engineered to express GM-CSF, for hepatocellular carcinoma (NCT02562755) and melanoma (NCT00429312); pelareorep (REOLYSIN®, Oncolytics Biotech), a variant of respiratory enteric orphan virus (reovirus) which does not replicate in cells that are not RAS-activated, in numerous cancers, including colorectal cancer (NCT01622543); prostate cancer (NCT01619813); head and neck squamous cell cancer (NCT01166542); pancreatic adenocarcinoma (NCT00998322); and non-small cell lung cancer (NSCLC) (NCT 00861627); enadenotucirev (NG-348, PsiOxus, formerly known as ColoAd1), an adenovirus engineered to express a full length CD80 and an antibody fragment specific for the T-cell receptor CD3 protein, in ovarian cancer (NCT02028117); metastatic or advanced epithelial tumors such as in colorectal cancer, bladder cancer, head and neck squamous cell carcinoma and salivary gland cancer (NCT02636036); ONCOS-102 (Targovax/formerly Oncos), an adenovirus engineered to express GM-CSF, in melanoma (NCT03003676); and peritoneal disease, colorectal cancer or ovarian cancer (NCT02963831); GL-ONC1 (GLV-1h68/GLV-1h153, Genelux GmbH), vaccinia viruses engineered to express beta-galactosidase (beta-gal)/beta-glucoronidase or beta-gal/human sodium iodide symporter (hNIS), respectively, were studied in peritoneal carcinomatosis (NCT01443260); fallopian tube cancer, ovarian cancer (NCT 02759588); or CG0070 (Cold Genesys), an adenovirus engineered to express GM-CSF, in bladder cancer (NCT02365818).

In some embodiments, an immuno-oncology agent is selected from JX-929 (SillaJen/formerly Jennerex Biotherapeutics), a TK- and vaccinia growth factor-deficient vaccinia virus engineered to express cytosine deaminase, which is able to convert the prodrug 5-fluorocytosine to the cytotoxic drug 5-fluorouracil; TGO1 and TG02 (Targovax/formerly Oncos), peptide-based immunotherapy agents targeted for difficult-to-treat RAS mutations; and TILT-123 (TILT Biotherapeutics), an engineered adenovirus designated: Ad5/3-E2F-delta24-hTNFα-IRES-hIL20; and VSV-GP (ViraTherapeutics) a vesicular stomatitis virus (VSV) engineered to express the glycoprotein (GP) of lymphocytic choriomeningitis virus (LCMV), which can be further engineered to express antigens designed to raise an antigen-specific $CD8^+$ T cell response.

In some embodiments, an immuno-oncology agent is a T-cell engineered to express a chimeric antigen receptor, or CAR. The T-cells engineered to express such chimeric antigen receptor are referred to as a CAR-T cells.

CARs have been constructed that consist of binding domains, which may be derived from natural ligands, single chain variable fragments (scFv) derived from monoclonal antibodies specific for cell-surface antigens, fused to endodomains that are the functional end of the T-cell receptor (TCR), such as the CD3-zeta signaling domain from TCRs, which is capable of generating an activation signal in T lymphocytes. Upon antigen binding, such CARs link to endogenous signaling pathways in the effector cell and generate activating signals similar to those initiated by the TCR complex.

For example, in some embodiments the CAR-T cell is one of those described in U.S. Pat. No. 8,906,682 (June et al; hereby incorporated by reference in its entirety), which discloses CAR-T cells engineered to comprise an extracellular domain having an antigen binding domain (such as a domain that binds to CD19), fused to an intracellular signaling domain of the T cell antigen receptor complex zeta chain (such as CD3 zeta). When expressed in the T cell, the CAR is able to redirect antigen recognition based on the antigen binding specificity. In the case of CD19, the antigen is expressed on malignant B cells. Over 200 clinical trials are currently in progress employing CAR-T in a wide range of indications. [https://clinicaltrials.gov/ct2/results?term=chimeric+antigen+receptors&pg=1].

In some embodiments, an immunostimulatory agent is an activator of retinoic acid receptor-related orphan receptor γ (RORγt). RORγt is a transcription factor with key roles in the differentiation and maintenance of Type 17 effector subsets of CD4+(Th17) and CD8+(Tc17) T cells, as well as the differentiation of IL-17 expressing innate immune cell subpopulations such as NK cells. In some embodiments, an activator of RORγt is LYC-55716 (Lycera), which is currently being evaluated in clinical trials for the treatment of solid tumors (NCT02929862).

In some embodiments, an immunostimulatory agent is an agonist or activator of a toll-like receptor (TLR). Suitable activators of TLRs include an agonist or activator of TLR9 such as SD-101 (Dynavax). SD-101 is an immunostimulatory CpG which is being studied for B-cell, follicular and other lymphomas (NCT02254772). Agonists or activators of TLR8 which may be used in the present invention include motolimod (VTX-2337, VentiRx Pharmaceuticals) which is being studied for squamous cell cancer of the head and neck (NCTO2124850) and ovarian cancer (NCT02431559).

Other immuno-oncology agents that can be used in the present invention include urelumab (BMS-663513, Bristol-Myers Squibb), an anti-CD137 monoclonal antibody; varlilumab (CDX-1127, Celldex Therapeutics), an anti-CD27 monoclonal antibody; BMS-986178 (Bristol-Myers Squibb), an anti-OX40 monoclonal antibody; lirilumab (IPH2102/BMS-986015, Innate Pharma, Bristol-Myers Squibb), an anti-KIR monoclonal antibody; monalizumab (IPH2201, Innate Pharma, AstraZeneca) an anti-NKG2A monoclonal antibody; andecaliximab (GS-5745, Gilead Sciences), an anti-MMP9 antibody; MK-4166 (Merck & Co.), an anti-GITR monoclonal antibody.

In some embodiments, an immunostimulatory agent is selected from elotuzumab, mifamurtide, an agonist or activator of a toll-like receptor, and an activator of RORγt.

In some embodiments, an immunostimulatory therapeutic is recombinant human interleukin 15 (rhIL-15). rhIL-15 has been tested in the clinic as a therapy for melanoma and renal cell carcinoma (NCT01021059 and NCT01369888) and leukemias (NCT02689453). In some embodiments, an immunostimulatory agent is recombinant human interleukin 12 (rhIL-12). In some embodiments, an IL-15 based immunotherapeutic is heterodimeric IL-15 (hetIL-15, Novartis/Admune), a fusion complex composed of a synthetic form of endogenous IL-15 complexed to the soluble IL-15 binding protein IL-15 receptor alpha chain (IL15:sIL-15RA), which has been tested in Phase 1 clinical trials for melanoma, renal cell carcinoma, non-small cell lung cancer and head and neck squamous cell carcinoma (NCT02452268). In some embodiments, a recombinant human interleukin 12 (rhIL-12) is NM-ILL-12 (Neumedicines, Inc.), NCT02544724, or NCT02542124.

In some embodiments, an immuno-oncology agent is selected from those descripted in Jerry L. Adams et al., "Big opportunities for small molecules in immuno-oncology," Cancer Therapy 2015, Vol. 14, pages 603-622, the content of which is incorporated herein by reference in its entirety. In some embodiments, an immuno-oncology agent is selected from the examples described in Table 1 of Jerry L. Adams et al. In some embodiments, an immuno-oncology agent is a small molecule targeting an immuno-oncoloby target selected from those listed in Table 2 of Jerry L. Adams et al. In some embodiments, an immuno-oncology agent is a small molecule agent selectd from those listed in Table 2 of Jerry L. Adams et al.

In some embodiments, an immuno-oncology agent is selected from the small molecule immuno-oncology agents described in Peter L. Toogood, "Small molecule immuno-oncology therapeutic agents," Bioorganic & Medicinal Chemistry Letters 2018, Vol. 28, pages 319-329, the content of which is incorporated herein by refenrece in its entirety. In some embodiments, an immuno-oncology agent is an agent targeting the pathways as described in Peter L. Toogood.

In some embodiments, an immuno-oncology agent is selected from those described in Sandra L. Ross et al., "Bispecific T cell engager (BITE®) antibody constructs can mediate bystander tumor cell killing", PLoS ONE 12(8): e0183390, the conten of which is incorporated herein by reference in its entirety. In some embodiments, an immuno-oncology agent is a bispecific T cell engager (BITE®) antibody construct. In some embodiments, a bispecific T cell engager (BITE®) antibody construct is a CD19/CD3 bispecific antibody construct. In some embodimens, a bispecific T cell engager (BITE®) antibody construct is an EGFR/CD3 bispecific antibody construct. In some embodiments, a bispecific T cell engager (BITE®) antibody construct activates T cells. In some embodiments, a bispecific T cell engager (BITE®) antibody construct activates T cells, which release cytokines inducing upregulation of intercellular adhesion molecule 1 (ICAM-1) and FAS on bystander cells. In some embodiments, a bispecific T cell engager (BITE®) antibody construct activates T cells which result in induced bystander cell lysis. In some embodiments, the bystander cells are in solid tumors. In some embodiments, the bystander cells being lysed are in proximity to the BITE®-activated T cells. In some embodiment, the bystander cells comprise tumor-associated antigen (TAA) negative cancer cells. In some embodiment, the bystander cells comprise EGFR-negative cancer cells. In some embodiments, an immuno-oncology agent is an antibody which blocks the PD-L1/PD1 axis and/or CTLA4. In some embodiments, an immuno-oncology agent is an ex vivo expanded tumor-infiltrating T cell. In some embodiments, an immuno-oncology agent is a bispecific antibody construct or chimeric antigen receptors (CARs) that directly connect T cells with tumor-associated surface antigens (TAAs).

Exemplary Immune Checkpoint Inhibitors

In some embodiments, an immuno-oncology agent is an immune checkpoint inhibitor as described herein.

The term "checkpoint inhibitor" as used herein relates to agents useful in preventing cancer cells from avoiding the immune system of the patient. One of the major mechanisms of anti-tumor immunity subversion is known as "T-cell exhaustion," which results from chronic exposure to antigens that has led to up-regulation of inhibitory receptors. These inhibitory receptors serve as immune checkpoints in order to prevent uncontrolled immune reactions.

PD-1 and co-inhibitory receptors such as cytotoxic T-lymphocyte antigen 4 (CTLA-4, B and T Lymphocyte Attenuator (BTLA; CD272), T cell Immunoglobulin and Mucin domain-3 (Tim-3), Lymphocyte Activation Gene-3 (Lag-3; CD223), and others are often referred to as a checkpoint regulators. They act as molecular "gatekeepers" that allow extracellular information to dictate whether cell cycle progression and other intracellular signaling processes should proceed.

In some embodiments, an immune checkpoint inhibitor is an antibody to PD-1. PD-1 binds to the programmed cell death 1 receptor (PD-1) to prevent the receptor from binding to the inhibitory ligand PDL-1, thus overriding the ability of tumors to suppress the host anti-tumor immune response.

In some embodiments, the checkpoint inhibitor is a biologic therapeutic or a small molecule. In some embodiments, the checkpoint inhibitor is a monoclonal antibody, a humanized antibody, a fully human antibody, a fusion protein or a combination thereof. In some embodiments, the checkpoint inhibitor inhibits a checkpoint protein selected from CTLA-4, PDL1, PDL2, PDl, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In some embodiments, the checkpoint inhibitor interacts with a ligand of a checkpoint protein selected from CTLA-4, PDL1, PDL2, PDl, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In some embodiments, the checkpoint inhibitor is an immunostimulatory agent, a T cell growth factor, an interleukin, an antibody, a vaccine or a combination thereof. In some embodiments, the interleukin is IL-7 or IL-15. In some embodiments, the interleukin is glycosylated IL-7. In an additional aspect, the vaccine is a dendritic cell (DC) vaccine.

Checkpoint inhibitors include any agent that blocks or inhibits in a statistically significant manner, the inhibitory pathways of the immune system. Such inhibitors can include small molecule inhibitors or can include antibodies, or antigen binding fragments thereof, that bind to and block or inhibit immune checkpoint receptors or antibodies that bind to and block or inhibit immune checkpoint receptor ligands. Illustrative checkpoint molecules that can be targeted for blocking or inhibition include, but are not limited to, CTLA-4, PDL1, PDL2, PD1, B7-H3, B7-H4, BTLA, HVEM, GAL9, LAG3, TIM3, VISTA, KIR, 2B4 (belongs to the CD2 family of molecules and is expressed on all NK, γδ, and memory $CD8^+$ (αβ) T cells), CD160 (also referred to as BY55), CGEN-15049, CHK 1 and CHK2 kinases, A2aR, and various B-7 family ligands. B7 family ligands include, but are not limited to, B7-1, B7-2, B7-DC, B7-H1, B7-H2, B7-H3, B7-H4, B7-H5, B7-H6 and B7-H7. Checkpoint inhibitors include antibodies, or antigen binding fragments thereof, other binding proteins, biologic therapeutics, or small molecules, that bind to and block or inhibit the activity of one or more of CTLA-4, PDL1, PDL2, PD1, BTLA, HVEM, TIM3, GAL9, LAG3, VISTA, KIR, 2B4, CD 160 and CGEN-15049. Illustrative immune checkpoint inhibitors include, but are not limited to, Tremelimumab (CTLA-4 blocking antibody), anti-OX40, PD-L1 monoclonal Antibody (Anti-B7-H1; MEDI4736), MK-3475 (PD-1 blocker), Nivolumab (anti-PD1 antibody), CT-011 (anti-PD1 antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody), and ipilimumab (anti-CTLA-4 checkpoint inhibitor). Checkpoint protein ligands include, but are not limited to PD-L1, PD-L2, B7-H3, B7-H4, CD28, CD86 and TIM-3.

In certain embodiments, the immune checkpoint inhibitor is selected from a PD-1 antagonist, a PD-L1 antagonist, and a CTLA-4 antagonist. In some embodiments, the checkpoint inhibitor is selected from the group consisting of nivolumab (OPDIVO®), ipilimumab (YERVOY®), and pembrolizumab (KEYTRUDA®). In some embodiments, the checkpoint inhibitor is selected from nivolumab (anti-PD-1 antibody, OPDIVO®, Bristol-Myers Squibb); pembrolizumab (anti-PD-1 antibody, KEYTRUDA®, Merck); ipilimumab (anti-CTLA-4 antibody, YERVOY®, Bristol-Myers Squibb); durvalumab (anti-PD-L1 antibody, IMFINZI®, AstraZeneca); and atezolizumab (anti-PD-L1 antibody, TECENTRIQ®, Genentech).

In some embodiments, the checkpoint inhibitor is selected from the group consisting of lambrolizumab (MK-3475), nivolumab (BMS-936558), pidilizumab (CT-011), AMP-224, MDX-1105, MEDI4736, MPDL3280A, BMS-936559, ipilimumab, lirlumab, IPH2101, pembrolizumab (KEYTRUDA®), and tremelimumab.

In some embodiments, an immune checkpoint inhibitor is REGN2810 (Regeneron), an anti-PD-1 antibody tested in patients with basal cell carcinoma (NCT03132636); NSCLC (NCT03088540); cutaneous squamous cell carcinoma (NCT02760498); lymphoma (NCT02651662); and melanoma (NCT03002376); pidilizumab (CureTech), also known as CT-011, an antibody that binds to PD-1, in clinical trials for diffuse large B-cell lymphoma and multiple myeloma; avelumab (BAVENCIO®, Pfizer/Merck KGaA), also known as MSB0010718C), a fully human IgG1 anti-PD-L1 antibody, in clinical trials for non-small cell lung cancer, Merkel cell carcinoma, mesothelioma, solid tumors, renal cancer, ovarian cancer, bladder cancer, head and neck cancer, and gastric cancer; or PDR001 (Novartis), an inhibitory antibody that binds to PD-1, in clinical trials for non-small cell lung cancer, melanoma, triple negative breast cancer and advanced or metastatic solid tumors. Tremelimumab (CP-675,206; Astrazeneca) is a fully human monoclonal antibody against CTLA-4 that has been in studied in clinical trials for a number of indications, including: mesothelioma, colorectal cancer, kidney cancer, breast cancer, lung cancer and non-small cell lung cancer, pancreatic ductal adenocarcinoma, pancreatic cancer, germ cell cancer, squamous cell cancer of the head and neck, hepatocellular carcinoma, prostate cancer, endometrial cancer, metastatic cancer in the liver, liver cancer, large B-cell lymphoma, ovarian cancer, cervical cancer, metastatic anaplastic thyroid cancer, urothelial cancer, fallopian tube cancer, multiple myeloma, bladder cancer, soft tissue sarcoma, and melanoma. AGEN-1884 (Agenus) is an anti-CTLA4 antibody that is being studied in Phase 1 clinical trials for advanced solid tumors (NCT02694822).

In some embodiments, a checkpoint inhibitor is an inhibitor of T-cell immunoglobulin mucin containing protein-3 (TIM-3). TIM-3 inhibitors that may be used in the present invention include TSR-022, LY3321367 and MBG453. TSR-022 (Tesaro) is an anti-TIM-3 antibody which is being studied in solid tumors (NCT02817633). LY3321367 (Eli Lilly) is an anti-TIM-3 antibody which is being studied in solid tumors (NCT03099109). MBG453 (Novartis) is an anti-TIM-3 antibody which is being studied in advanced malignancies (NCT02608268).

In some embodiments, a checkpoint inhibitor is an inhibitor of T cell immunoreceptor with Ig and ITIM domains, or TIGIT, an immune receptor on certain T cells and NK cells. TIGIT inhibitors that may be used in the present invention include BMS-986207 (Bristol-Myers Squibb), an anti-TIGIT monoclonal antibody (NCT02913313); OMP-313M32 (Oncomed); and anti-TIGIT monoclonal antibody (NCT03119428).

In some embodiments, a checkpoint inhibitor is an inhibitor of Lymphocyte Activation Gene-3 (LAG-3). LAG-3 inhibitors that may be used in the present invention include BMS-986016 and REGN3767 and IMP321. BMS-986016 (Bristol-Myers Squibb), an anti-LAG-3 antibody, is being studied in glioblastoma and gliosarcoma (NCT02658981). REGN3767 (Regeneron), is also an anti-LAG-3 antibody, and is being studied in malignancies (NCT03005782). IMP321 (Immutep S.A.) is an LAG-3-Ig fusion protein, being studied in melanoma (NCT02676869); adenocarcinoma (NCT02614833); and metastatic breast cancer (NCT00349934).

Checkpoint inhibitors that can be used in the present invention include OX40 agonists. OX40 agonists that are being studied in clinical trials include PF-04518600/PF-8600 (Pfizer), an agonistic anti-OX40 antibody, in metastatic kidney cancer (NCT03092856) and advanced cancers and neoplasms (NCT02554812; NCT05082566); GSK3174998 (Merck), an agonistic anti-OX40 antibody, in Phase 1 cancer trials (NCT02528357); MEDI0562 (Medimmune/AstraZeneca), an agonistic anti-OX40 antibody, in advanced solid tumors (NCT02318394 and NCT02705482); MEDI6469, an agonistic anti-OX40 antibody (Medimmune/AstraZeneca), in patients with colorectal cancer (NCT02559024), breast cancer (NCT01862900), head and neck cancer (NCT02274155) and metastatic prostate cancer (NCT01303705); and BMS-986178 (Bristol-Myers Squibb) an agonistic anti-OX40 antibody, in advanced cancers (NCT02737475).

Checkpoint inhibitors that can be used in the present invention include CD137 (also called 4-1BB) agonists. CD137 agonists that are being studied in clinical trials include utomilumab (PF-05082566, Pfizer) an agonistic anti-CD137 antibody, in diffuse large B-cell lymphoma (NCT02951156) and in advanced cancers and neoplasms (NCT02554812 and NCT05082566); urelumab (BMS-663513, Bristol-Myers Squibb), an agonistic anti-CD137 antibody, in melanoma and skin cancer (NCT02652455) and glioblastoma and gliosarcoma (NCT02658981); and CTX-471 (Compass Therapeutics), an agonistic anti-CD137 antibody in metastatic or locally advanced malignancies (NCT03881488).

Checkpoint inhibitors that can be used in the present invention include CD27 agonists. CD27 agonists that are being studied in clinical trials include varlilumab (CDX-1127, Celldex Therapeutics) an agonistic anti-CD27 antibody, in squamous cell head and neck cancer, ovarian carcinoma, colorectal cancer, renal cell cancer, and glioblastoma (NCT02335918); lymphomas (NCT01460134); and glioma and astrocytoma (NCT02924038).

Checkpoint inhibitors that can be used in the present invention include glucocorticoid-induced tumor necrosis factor receptor (GITR) agonists. GITR agonists that are being studied in clinical trials include TRX518 (Leap Therapeutics), an agonistic anti-GITR antibody, in malignant melanoma and other malignant solid tumors (NCT01239134 and NCT02628574); GWN323 (Novartis), an agonistic anti-GITR antibody, in solid tumors and lymphoma (NCT 02740270); INCAGN01876 (Incyte/Agenus), an agonistic anti-GITR antibody, in advanced cancers (NCT02697591 and NCT03126110); MK-4166 (Merck), an agonistic anti-GITR antibody, in solid tumors (NCT02132754) and MEDI1873 (Medimmune/AstraZeneca), an agonistic hexameric GITR-ligand molecule with a human IgG1 Fc domain, in advanced solid tumors (NCT02583165).

Checkpoint inhibitors that can be used in the present invention include inducible T-cell co-stimulator (ICOS, also known as CD278) agonists. ICOS agonists that are being studied in clinical trials include MEDI-570 (Medimmune), an agonistic anti-ICOS antibody, in lymphomas (NCT02520791); GSK3359609 (Merck), an agonistic anti-ICOS antibody, in Phase 1 (NCT02723955); JTX-2011 (Jounce Therapeutics), an agonistic anti-ICOS antibody, in Phase 1 (NCT02904226).

Checkpoint inhibitors that can be used in the present invention include killer IgG-like receptor (KTR) inhibitors. KTR inhibitors that are being studied in clinical trials include lirilumab (IPH2102/BMS-986015, Innate Pharma/Bristol-Myers Squibb), an anti-KIR antibody, in leukemias (NCT01687387, NCT02399917, NCT02481297, NCT02599649), multiple myeloma (NCT02252263), and lymphoma (NCT01592370); IPH2101 (1-7F9, Innate Pharma) in myeloma (NCT01222286 and NCT01217203); and IPH4102 (Innate Pharma), an anti-KIR antibody that binds to three domains of the long cytoplasmic tail (KIR3DL2), in lymphoma (NCT02593045).

Checkpoint inhibitors that can be used in the present invention include CD47 inhibitors of interaction between CD47 and signal regulatory protein alpha (SIRPa). CD47/SIRPa inhibitors that are being studied in clinical trials include ALX-148 (Alexo Therapeutics), an antagonistic variant of (SIRPa) that binds to CD47 and prevents CD47/SIRPa-mediated signaling, in phase 1 (NCT03013218); TTI-621 (SIRPa-Fc, *Trillium* Therapeutics), a soluble recombinant fusion protein created by linking the N-terminal CD47-binding domain of SIRPa with the Fc domain of human IgG1, acts by binding human CD47, and preventing it from delivering its "do not eat" signal to macrophages, is in clinical trials in Phase 1 (NCT02890368 and NCT02663518); CC-90002 (Celgene), an anti-CD47 antibody, in leukemias (NCT02641002); and Hu5F9-G4 (Forty Seven, Inc.), in colorectal neoplasms and solid tumors (NCT02953782), acute myeloid leukemia (NCT02678338) and lymphoma (NCT02953509).

Checkpoint inhibitors that can be used in the present invention include CD73 inhibitors. CD73 inhibitors that are being studied in clinical trials include MEDI9447 (Medimmune), an anti-CD73 antibody, in solid tumors (NCT02503774); and BMS-986179 (Bristol-Myers Squibb), an anti-CD73 antibody, in solid tumors (NCT02754141).

Checkpoint inhibitors that can be used in the present invention include agonists of stimulator of interferon genes protein (STING, also known as transmembrane protein 173, or TMEM173). Agonists of STING that are being studied in clinical trials include MK-1454 (Merck), an agonistic synthetic cyclic dinucleotide, in lymphoma (NCT03010176); and ADU-S100 (MIW815, Aduro Biotech/Novartis), an agonistic synthetic cyclic dinucleotide, in Phase 1 (NCT02675439 and NCT03172936).

Checkpoint inhibitors that can be used in the present invention include CSF1R inhibitors. CSF1R inhibitors that are being studied in clinical trials include pexidartinib (PLX3397, Plexxikon), a CSF1R small molecule inhibitor, in colorectal cancer, pancreatic cancer, metastatic and advanced cancers (NCT02777710) and melanoma, non-small cell lung cancer, squamous cell head and neck cancer, gastrointestinal stromal tumor (GIST) and ovarian cancer (NCT02452424); and IMC-CS4 (LY3022855, Lilly), an anti-CSF-1R antibody, in pancreatic cancer (NCT03153410), melanoma (NCT03101254), and solid tumors (NCT02718911); and BLZ945 (4-[2((1R,2R)-2-hydroxycyclohexylamino)-benzothiazol-6-yloxyl]-pyridine-2-carboxylic acid methylamide, Novartis), an orally available inhibitor of CSF1R, in advanced solid tumors (NCT02829723).

Checkpoint inhibitors that can be used in the present invention include NKG2A receptor inhibitors. NKG2A receptor inhibitors that are being studied in clinical trials include monalizumab (IPH2201, Innate Pharma), an anti-NKG2A antibody, in head and neck neoplasms (NCT02643550) and chronic lymphocytic leukemia (NCT02557516).

In some embodiments, the immune checkpoint inhibitor is selected from nivolumab, pembrolizumab, ipilimumab, avelumab, durvalumab, atezolizumab, or pidilizumab.

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 μg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a GPR84 inhibitor. Implantable devices coated with a compound of this invention are another embodiment of the present invention.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein. Additional compounds of the invention were prepared by methods substantially similar to those described herein in the Examples and methods known to one skilled in the art.

General information: All evaporations were carried out in vacuo with a rotary evaporator. Analytical samples were dried in vacuo (1-5 mmHg) at rt. Thin layer chromatography (TLC) was performed on silica gel plates, spots were visualized by UV light (214 and 254 nm). Purification by column and flash chromatography was carried out using silica gel (200-300 mesh). Solvent systems are reported as mixtures by volume. All NMR spectra were recorded on a Bruker 400 (400 MHz) spectrometer. 1H chemical shifts are reported in δ values in ppm with the deuterated solvent as the internal standard. Data are reported as follows: chemical shift, multiplicity (s=singlet, d=doublet, t=triplet, q=quartet, br=broad, m=multiplet), coupling constant (Hz), integration. LCMS spectra were obtained on an Agilent 1200 series 6110 or 6120 mass spectrometer with electrospray ionization and excepted as otherwise indicated,* the general LCMS condition was as follows: Waters X Bridge C18 column (50 mm*4.6 mm*3.5 um); Flow Rate: 2.0 mL/min, the column temperature: 40° C.

* Other methods:

"A"=Acquity BEH C18 1.7 μm column (2.1 nn×50 mm); Flow Rate: 0.8 mL/min, the column temperature: 50° C. Eluting with MeCN containing 0.1% TFA, in water containing 0.1% TFA; 1 to 100% over 5 min.

"B"=Same column and flow rate as in "A." Eluting with MeCN in 10 mM aqueous ammonium acetate; 0 to 100% over 5 min.

"C"=CSH C18, 3.5 μm column (4.6 mm×30 mm); Flow Rate: 0.8 mL/min, the column temperature: 40° C. Eluting with MeCN in 10 mM aqueous ammonium formate; 5% MeCN for 0.5 min, 5% to 100% MeCN over 5 minutes; hold 100% MeCN for 1.5 minute General procedure A (The formation of triazole derivatives from hydrazide and primary amine): To a mixture of 4-methyl-N'-(1-phenylethylidene)benzenesulfonohydrazide (1.0 eq.), $Cu(OAc)_2$ (2.0 eq.), NaOAc (2.0 eq.) and N-Acetylglycine (2.0 eq.) in toluene, was added amine hydrochloride (1.0 eq.). The reaction mixture was stirred at 110° C. for 24 hours until the reaction was complete (by LCMS). The suspension was diluted with $H_2O$ and extracted with ethyl acetate. The combined organic phases were washed with brine, dried over anhydrous $Na_2SO_4$ and concentrated to dryness. The crude product was purified by prep-HPLC to afford the desired triazole intermediate.

General procedure B (Cyclization reaction to get triazole derivatives by Click Reaction): To a solution of $CuSO_4.5H_2O$ (0.05~0.1 eq.) in water, was added sodium ascorbate (0.2 eq.). The resulting mixture was added to a solution of terminal alkyne (1.0 eq.) and alkyl azide (1.5 eq.) in DMF. The reaction mixture was stirred at room temperature for overnight then diluted with water, extracted with ethyl acetate and the combined organic phases were washed with brine, dried over anhydrous $Na_2SO_4$ and concentrated to dryness. The crude product was purified by Prep-TLC to afford the desired triazole intermediate.

General procedure C (Alkyl azide derivatives formation from primary/secondary alcohol): Sodium azide (1.2 eq.) was added to a solution of primary/secondary alcohol (1.0 eq.) in DMSO. The reaction mixture was heated to 50-90° C. for 24 h until the reaction was complete (by LCMS), then it was cooled down to room temperature, diluted with water and extracted with dichloromethane. The combined organic phases were washed with water and brine, dried over anhydrous Na2SO4 and concentrated to dryness to afford the desired alkyl azide, which was used for the next step directly.

General procedure D (Alkyl azide derivatives formation from primary amine): To a solution of primary amine (1.0 eq.) in MeOH was added $K_2CO_3$ (2.0 eq.), $CuSO_4.5H_2O$ (0.2 eq.) and Imidazole-1-sulfonyl azide hydrochloride (1.0 eq.). The reaction was stirred at room temperature for 5 h. After the consumption of starting material (by LCMS), water was added, the reaction mixture was extracted with ethyl acetate, washed with water, dried over anhydrous Na2SO4 and concentrated to dryness. The crude product was purified by prep-HPLC to get the desired alkyl azide intermediate.

General procedure E (Terminal alkynes formation by Seyferth-Gilbert Homologation): A mixture of aldehyde (1.0 eq.), dimethyl 1-diazo-2-oxopropylphosphonate (1.1 eq.) and potassium carbonate (2.0 eq.) in methanol was stirred at room temperature for 4 h. The mixture was filtered and the filtrate was concentrated to dryness, the crude product was purified by c.c. to afford the desired terminal alkynes intermediate.

General procedure F (Sonogashira Coupling, Method 1): To a mixture of aromatic bromide/iodide (1.0 eq.), ethynylcyclopropane (2.0~6.0 eq.), X-phos (0.1 eq) and Bis(acetonitrile)dichloropalladium(II) (0.1 eq.) in acetonitrile was added and $K_2CO_3$ (2.0 eq.), the reaction mixture was heated to 90° C. for overnight until the reaction was complete (by LCMS), then it was cooled down to room temperature, diluted with water and extracted with dichloromethane. The combined organic phases were washed with water and brine, dried over anhydrous Na2SO4 and concentrated to dryness. The crude product was purified by c.c. and Prep-HPLC to afford the desired product.

General procedure G (Sonogashira Coupling, Method 2): To a stirred solution of aromatic bromide/iodide (1.0 eq.), ethynylcyclopropane (2.0~6.0 eq.) and TEA (5.0 eq.) in DMF was added $PdCl_2(PPh_3)_2$ (0.1 eq.) and CuI (0.05-0.10 eq.). The reaction mixture was stirred at 80° C. for 16 hours until the reaction was complete (by LCMS), then it was cooled down to room temperature, diluted with water and extracted with dichloromethane. The combined organic phases were washed with water and brine, dried over anhydrous $Na_2SO_4$ and concentrated to dryness. The crude product was purified by c.c. and Prep-HPLC to afford the desired product.

General procedure H (Suzuki Coupling): To a stirred solution of aromatic bromide (1.0 eq.), boric acid/boric ester (1.2-1.5 eq.) and $K_2CO_3$ (2.0 eq.) in dioxane was added $Pd(dppf)Cl_2$ (0.1 eq). The reaction mixture was stirred at 100° C. for 5 hours until the reaction was complete (by LCMS), then it was cooled down to room temperature, diluted with water and extracted with ethyl acetate. The combined organic phases were washed with water and brine, dried over anhydrous $Na_2SO_4$ and concentrated to dryness. The crude product was purified by prep-HPLC to afford the desired product.

General procedure I: (Buchwald Coupling): To a stirred solution of aromatic bromide/iodide (1.0 eq.), 3,3-dimethylazetidine hydrochloride (1.5 eq.), BINAP (0.1 eq) and X-Phos (0.1 eq.) in DMF was added $Pd_2(dba)_3$ (0.1 eq.) and $Cs_2CO_3$ (3.0 eq.). The reaction mixture was stirred at 100° C. for 16 hours until the reaction was complete (by LCMS), then it was cooled down to room temperature, diluted with water and extracted with ethyl acetate. The combined organic phases were washed with water and brine, dried over anhydrous $Na_2SO_4$ and concentrated to dryness. The crude was purified by prep-HPLC to give the desired product.

General procedure J: (Esterification of the alcohol derivatives to mesylate ester with $Ms_2O$): To a solution of the alcohol derivatives (1.0 eq.) and $Et_3N$ (3.0 eq.) in DCM was added $Ms_2O$ (1.5 eq.) at 0° C. The mixture was stirred at room temperature for 30-90 min then quenched with water and extracted with DCM. The combined organic phases were washed with water and brine, dried over anhydrous $Na_2SO_4$ and concentrated to give the crude mesylate ester, which was used to the next step directly.

General procedure K: (Substitution on the primary/secondary amine with mesylate): To a stirred solution of mesylate ester (1.0 eq.), primary/secondary amine (1.0 eq.) in DMF was added $K_2CO_3$ (3.0 eq.). The reaction mixture was stirred at room temperature for overnight. $H_2O$ and EA were added and the organic phases were collected and evaporated under reduced pressure. The residue was purified by prep-HPLC to give the desired product.

Example 1: Synthesis of I-45

Synthetic Scheme of I-45

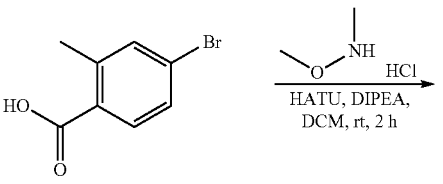

1.1

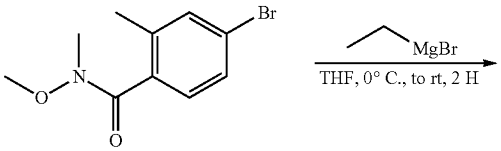

1.2

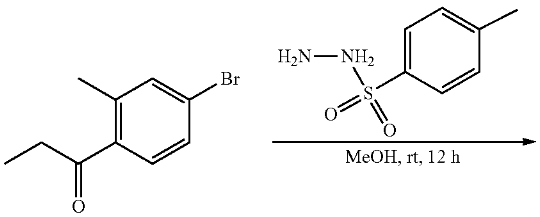

1.3

-continued

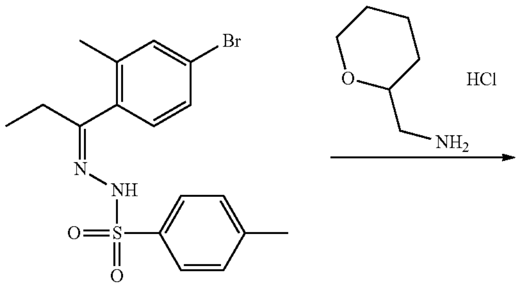

1.4

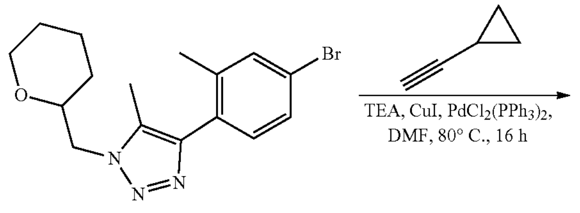

1.5

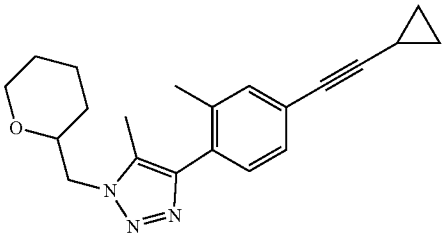

I-45

1. The Synthesis of Intermediate 1.2

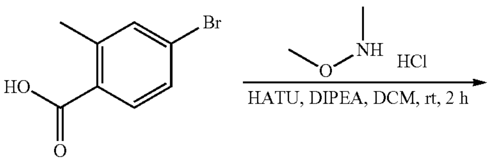

1.1

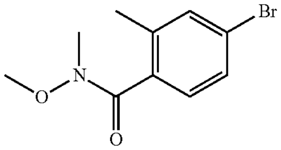

1.2

To a solution of 1.1 (5.4 g, 25 mmol) in DCM (30 mL) was added DIPEA (12.9 g, 100 mmol) and HATU (9.5 g, 25 mmol). The reaction was stirred at room temperature for 15 min, then N,O-dimethylhydroxylamine hydrochloride (2.4 g, 25 mmol) was added and the mixture was stirred at room temperature for 2 h. After the consumption of starting material (by LCMS), water (30 mL) was added, extracted with ethyl acetate (30 mL×3), washed with water (30 mL×3), dried over anhydrous $Na_2SO_4$ and concentrated. The crude product was purified by prep-HPLC to get 1.2 (4.0 g, 62% yield) as yellow oil. LC-MS m/z: 258.11 $[M+H]^+$.

2. The Synthesis of Intermediate 1.3

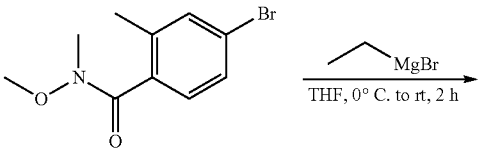

1.2

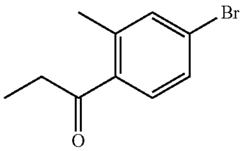

1.3

To a stirred solution of 1.2 (4.0 g, 15.6 mmol) in dry THF (20 mL) was slowly added ethylmagnesium bromide (2.0 M/THF, 15.5 mL, 31.0 mmol) at 0° C. The reaction mixture was stirred at RT for 2 h. Saturated $NH_4Cl$ (a.q.) was added and the mixture was extracted with EA (30 mL×2), the organic layer was washed with water, dried over anhydrous $Na_2SO_4$ and evaporated to dryness. The crude product was purified by prep-HPLC to give 1.3 (3.0 g, yield: 86%) as yellow oil. LC-MS m/z: 227.1 $[M+H]^+$.

3. The Synthesis of Intermediate 1.4

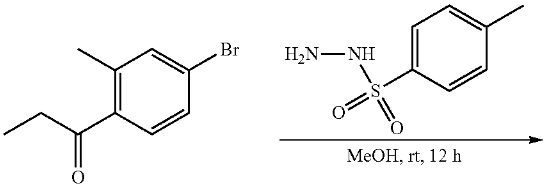

1.3

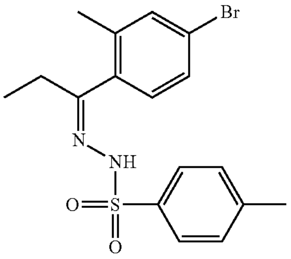

1.4

To a solution of compound 1.3 (3.0 g, 13.3 mmol) in MeOH (20 mL) was added 4-methylbenzenesulfonohydrazide (2.5 g, 13.3 mmol). The mixture was stirred at room temperature for 12 h. After the reaction was complete (by LCMS), the mixture was concentrated to dryness. The crude product was purified by prep-HPLC to get 1.4 (3.0 g, 57% yield) as a white solid. LC-MS m/z: 395.31 $[M+H]^+$.

4. The Synthesis of Intermediate 1.5

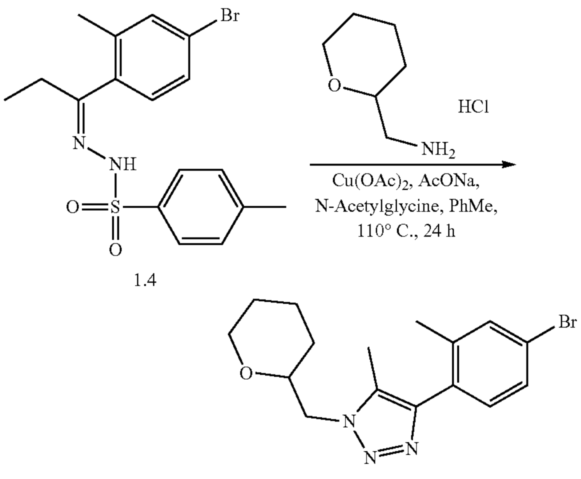

1.4

1.5

To a stirred solution of 1.4 (1.0 g, 2.5 mmol), $Cu(OAc)_2$ (0.90 g, 5.0 mmol) AcONa (0.40 g, 5.0 mmol) and N-Acetylglycine (0.60 g, 5.0 mmol) in PhMe (20 mL) was added (tetrahydro-2H-pyran-2-yl)methanamine hydrochloride (0.40 g, 2.5 mmol). The reaction mixture was stirred at 110° C. for 24 hours until the reaction was complete (by LCMS). The suspension was diluted with $H_2O$ (20 mL) and extracted with EA (20 mL×2), the combined organic layers were concentrated. The crude product was purified by prep-HPLC to give 1.5 (0.40 g, yield: 46%) as a white solid. LC-MS m/z: 350.25 $[M+H]^+$.

5. The Synthesis of I-45

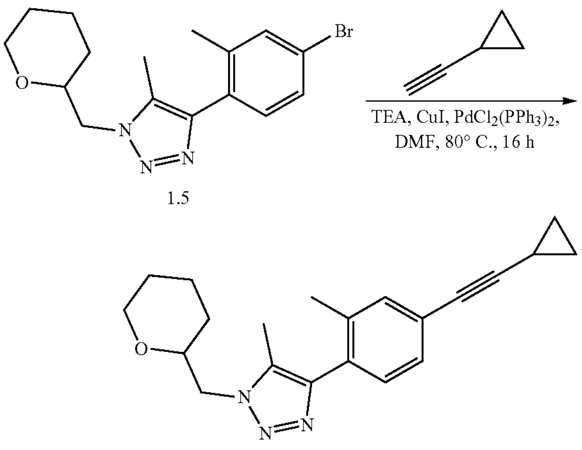

1.5

I-45

To a stirred solution of 1.5 (0.40 g, 1.2 mmol), ethynylcyclopropane (0.30 g, 4 mmol) and TEA (0.50 g, 5 mmol) in DMF (5 mL) was added $PdCl_2(PPh_3)_2$ (80 mg) and CuI (80 mg). The reaction mixture was stirred at 80° C. for 16 hours until the reaction was complete (by LCMS). The suspension was diluted with $H_2O$ (20 mL) and extracted with EA (20 mL×2), the combined organic layers were concentrated. The crude product was purified by prep-HPLC to give I-45 (23 mg, yield: 6%) as yellow oil.

Additional exemplary compounds were prepared following methods substantially similar to the method described above and herein. Data for these compounds are provided below.

TABLE 2

Characterization Data for Additional Exemplary Compounds

| Compound No. | Chemical Structure | [M + H] observed | $^1$H NMR (400 MHz) |
|---|---|---|---|
| I-45 | 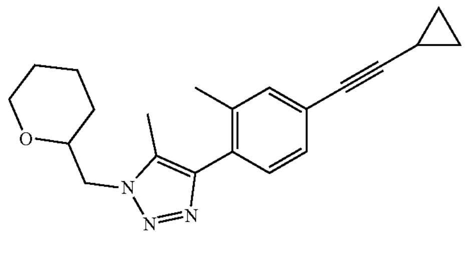 [SMILES: Cc1cc(C#CC2CC2)ccc1-c1nnn(CC2CCCCO2)c1C] | 335.4 | $^1$H NMR (400 MHz, DMSO-$d_6$) δ 7.33 (s, 1H), 7.23-7.25 (m, 1H), 7.17-7.19 (m, 1H), 4.28-4.40 (m, 2H), 3.83-3.85 (m, 1H), 3.71-3.85 (m, 1H), 3.28-3.34 (m, 1H), 2.22 (s, 3H), 2.21 (s, 3H), 1.78-1.81 (m, 1H), 1.64-1.67 (m, 1H), 1.45-1.57 (m, 4H), 1.23-1.26 (m, 1H), 0.87-0.92 (m, 2H), 0.72-0.76 (m, 2H). |
| I-37 | 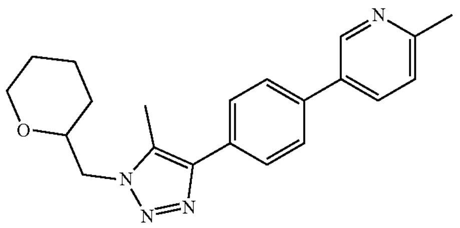 [SMILES: Cc1ccc(-c2ccc(-c3nnn(CC4CCCCO4)c3C)cc2)cn1] | 349.3 | $^1$H NMR (400 MHz, DMSO-$d_6$): δ 8.82 (d, J = 2.0 Hz, 1H), 8.02 (dd, J = 2.4 Hz, 8.0 Hz, 1H), 7.81-7.83 (m, 4H), 7.36 (d, J = 8.0 Hz, 1H), 4.31-4.44 (m, 2H), 3.82-3.85 (m, 1H), 3.68-3.75 (m, 1H), 3.26-3.30 (m, 1H), 2.52 (s, 3H), 2.50 (s, 3H), 1.67-1.81 (m, 2H), 1.40-1.52 (m, 3H), 1.22-1.32 (m, 1H). |

TABLE 2-continued

| Compound No. | Chemical Structure | [M + H] observed | $^1$H NMR (400 MHz) |
|---|---|---|---|
| Characterization Data for Additional Exemplary Compounds | | | |
| I-54 | 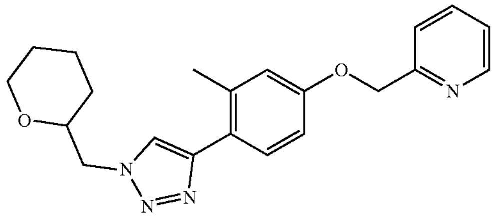 [SMILES: Cc1cc(OCc2ccccn2)ccc1-c1cn(CC2CCCCO2)nn1] | 365.3 | $^1$H NMR (400 MHz, DMSO-$d_6$) δ 8.58 (d, J = 4.8 Hz, 1H), 8.21 (s, 1H), 7.82-7.86 (m, 1H), 7.65 (d, J = 8.4 Hz, 1H), 7.52 (d, J = 8.0 Hz, 1H), 7.35 (dd, J = 5.2 Hz, 6.8 Hz, 1H), 6.99 (d, J = 2.4 Hz, 1H), 6.94 (dd, J = 2.4 Hz, 8.4 Hz, 1H), 5.21 (s, 2H), 4.36-4.47 (m, 2H), 3.84-3.87 (m, 1H), 3.71-3.77 (m, 1H), 3.29-3.31 (m, 1H), 2.40 (s, 3H), 1.78-1.81 (m, 1H), 1.63 (d, J = 12.8 Hz, 1H), 1.40-1.51 (m, 3H), 1.18-1.24 (m, 1H). |
| I-50 | 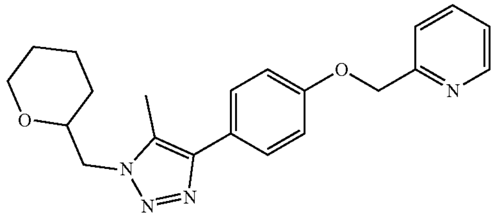 [SMILES: Cc1c(-c2ccc(OCc3ccccn3)cc2)nnn1CC1CCCCO1] | 365.3 | $^1$H NMR (400 MHz, DMSO-$d_6$) δ 8.60 (d, J = 4.8 Hz, 1H), 7.83-7.87 (m, 1H), 7.61 (d, J = 7.2 Hz, 2H), 7.54 (d, J = 8.0 Hz, 1H), 7.34-7.38 (m, 1H), 7.12 (d, J = 8.8 Hz, 2H), 5.23 (s, 2H), 4.27-4.39 (m, 2H), 3.81-3.84 (m, 1H), 3.68-3.70 (m, 1H), 3.23-3.30 (m, 1H), 2.41 (s, 3H), 1.77-1.82 (m, 1H), 1.65-1.68 (m, 1H), 1.36-1.55 (m, 3H), 1.21-1.31 (m, 1H). |
| I-51 | 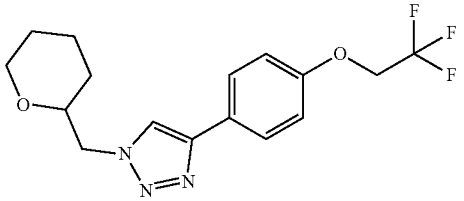 [SMILES: FC(F)(F)COc1ccc(-c2cn(CC3CCCCO3)nn2)cc1] | 342.3 | $^1$H NMR (400 MHz, DMSO-$d_6$) δ 8.43 (s, 1H), 7.80-7.84 (m, 2H), 7.12-7.16 (m, 2H), 4.81 (dd, J = 17.6 Hz, 8.8 Hz, 2H), 4.33-4.48 (m, 2H), 3.84-3.88 (m, 1H), 3.68-3.74 (m, 1H), 3.28-3.32 (m, 1H), 1.78-1.81 (m, 1H), 1.63-1.66 (m, 1H), 1.39-1.52 (m, 3H), 1.19-1.25 (m, 3H). |
| I-52 | 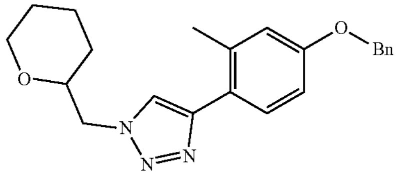 [SMILES: Cc1cc(OCc2ccccc2)ccc1-c1cn(CC2CCCCO2)nn1] | 364.3 | $^1$H NMR (400 MHz, DMSO-$d_6$) δ 8.20 (s, 1H), 7.64 (d, J = 8.4 Hz, 1H), 7.46-7.47 (m, 2H), 7.38-7.42 (m, 2H), 7.32-7.35 (m, 1H), 6.97 (d, J = 2.4 Hz, 1H), 6.92 (dd, J = 2.4 Hz, 8.4 Hz, 1H), 5.13 (s, 2H), 4.35-4.47 (m, 2H), 3.84-3.87 (m, 1H), 3.71-3.77 (m, 1H), 3.29-3.33 (m, 1H), 2.40 (s, 3H), 1.78-1.81 (m, 1H), 1.62-1.65 (m, 1H), 1.40-1.52 (m, 3H), 1.18-1.24 (m, 1H). |
| I-46 | 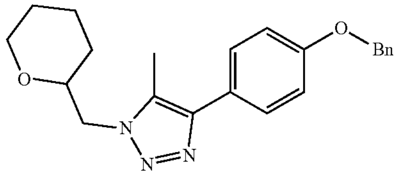 [SMILES: Cc1c(-c2ccc(OCc3ccccc3)cc2)nnn1CC1CCCCO1] | 364.3 | $^1$H NMR (400 MHz, DMSO-$d_6$): δ 7.58-7.61 (m, 2H), 7.47-7.48 (m, 2H), 7.39-7.42 (m, 2H), 7.32-7.36 (m, 1H), 7.10-7.13 (m, 2H), 5.15 (s, 2H), 4.26-4.40 (m, 2H), 3.81-3.84 (m, 1H), 3.65-3.72 (m, 1H), 3.24-3.31 (m, 1H), 2.41 (s, 3H), 1.78-1.81 (m, 1H), 1.65-1.68 (m, 1H), 1.39-1.52 (m, 3H), 1.23-1.30 (m, 1H). |
| I-53 | 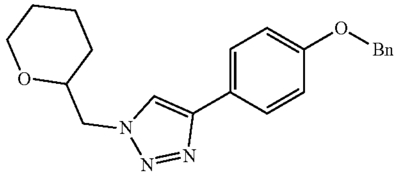 [SMILES: c1ccc(COc2ccc(-c3cn(CC4CCCCO4)nn3)cc2)cc1] | 350.3 | $^1$H NMR (400 MHz, DMSO-$d_6$) δ 8.38 (s, 1H), 7.77 (d, J = 8.8 Hz, 2H), 7.47 (d, J = 6.8 Hz, 2H), 7.40 (t, J = 7.6 Hz, 2H), 7.32-7.36 (m, 1H), 7.09 (d, J = 8.8 Hz, 2H), 5.14 (s, 2H), 4.32-4.46 (m, 2H), 3.84-3.87 (m, 1H), 3.68-3.74 (m, 1H), 3.28-3.33 (m, 1H), 1.65-1.81 (m, 1H), 1.62-1.65 (m, 1H), 1.39-1.51 (m, 3H), 1.15-1.25 (m, 1H). |
| I-115 | 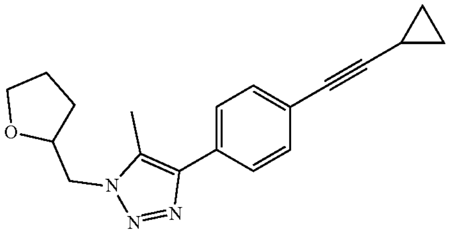 [SMILES: Cc1c(-c2ccc(C#CC3CC3)cc2)nnn1CC1CCCO1] | 308.2 | $^1$H NMR (400 MHz, DMSO-$d_6$): δ 7.66 (d, J = 8.4 Hz, 2H), 7.44 (d, J = 8.0 Hz, 2H), 4.44-4.49 (m, 1H), 4.33-4.38 (m, 1H), 4.18-4.24 (m, 1H), 3.69-3.75 (m, 1H), 3.59-3.65 (m, 1H), 2.47 (s, 3H), 1.97-2.05 (m, 1H), 1.69-1.83 (m, 3H), 1.53-1.59 (m, 1H), 0.88-0.92 (m, 2H), 0.73-0.77 (m, 2H). |

TABLE 2-continued

Characterization Data for Additional Exemplary Compounds

| Compound No. | Chemical Structure | [M + H] observed | $^1H$ NMR (400 MHz) |
|---|---|---|---|
| I-248 | 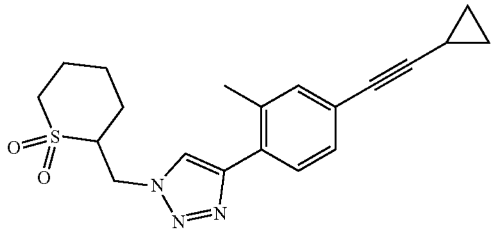 [SMILES: Cc1cc(C#CC2CC2)ccc1-c1cn(CC2CCCCS2(=O)=O)nn1] | 370.0 | $^1H$ NMR (400 MHz, $CDCl_3$) δ 7.82 (s, 1H), 7.73 (d, J = 7.6 Hz, 1H), 7.26-7.29 (m, 2H), 5.02 (dd, J = 5.6 Hz, 14.4 Hz, 1H), 4.65 (dd, J = 6.8 Hz, 14.8 Hz, 1H), 3.45-3.52 (m, 1H), 3.14-3.19 (m, 1H), 2.95-3.03 (m, 1H), 2.43 (s, 3H), 2.06-2.15 (m, 3H), 1.79-1.96 (m, 2H), 1.42-1.56 (m, 2H), 0.79-0.90 (m, 4H). |
| I-227 | 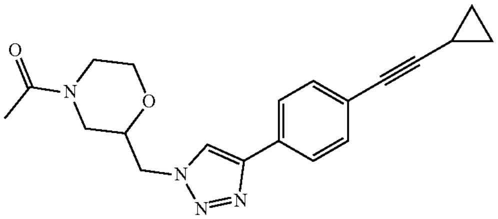 [SMILES: CC(=O)N1CCOC(Cn2cc(-c3ccc(C#CC4CC4)cc3)nn2)C1] | 351.3 | $^1H$ NMR (400 MHz, $CDCl_3$) δ 7.87 (d, J = 11.2 Hz, 1H), 7.74-7.76 (m, 2H), 7.43 (dd, J = 3.2 Hz, 8.0 Hz, 2H), 3.40-3.61 (m, 3H), 3.97 (d, J = 11.6 Hz, 1H), 3.48-3.82 (m, 3H), 2.89-3.29 (m, 1H), 2.46-2.72 (m, 1H), 2.10 (s, 3H), 1.44-1.48 (m, 1H), 0.80-0.91 (m, 4H). |
| I-96 | 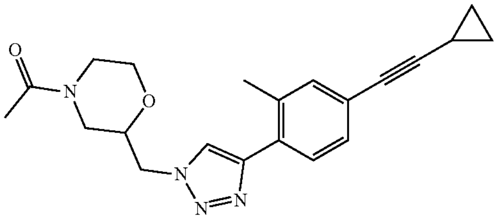 [SMILES: CC(=O)N1CCOC(Cn2cc(-c3ccc(C#CC4CC4)cc3C)nn2)C1] | 365.1 | $^1H$ NMR (400 MHz, $CDCl_3$): δ 7.72-7.79 (m, 2H), 7.26-7.30 (m, 2H), 4.39-4.61 (m, 3H), 3.96 (d, J = 11.6 Hz, 1H), 3.48-3.83 (m, 3H), 2.89-3.28 (m, 1H), 2.46-2.75 (m, 1H), 2.43 (s, 3H), 2.10 (s, 3H), 1.42-1.49 (m, 1H), 0.79-0.90 (m, 4H). |
| I-105 | 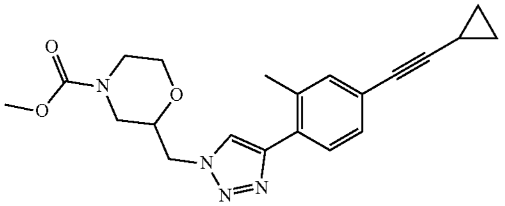 [SMILES: COC(=O)N1CCOC(Cn2cc(-c3ccc(C#CC4CC4)cc3C)nn2)C1] | 381.1 | $^1H$ NMR (400 MHz, $CDCl_3$): δ 7.78 (s, 1H), 7.73 (d, J = 7.6 Hz, 1H), 7.28-7.30 (m, 2H), 4.55-4.59 (m, 1H), 4.41-4.46 (m, 1H), 3.82-4.09 (m, 4H), 3.71 (s, 3H), 3.49-3.55 (m, 1H), 2.95 (brs., 1H), 2.68 (t, J = 8.0 Hz, 1H), 2.43 (s, 3H), 1.43-1.49 (m, 1H), 0.79-0.90 (m, 4H). |
| I-99 | 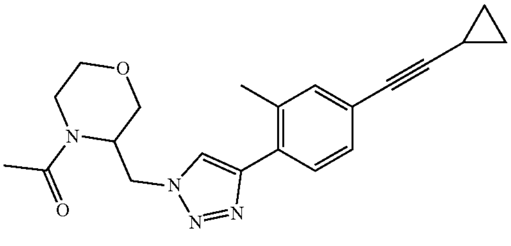 [SMILES: CC(=O)N1CCOCC1Cn1cc(-c2ccc(C#CC3CC3)cc2C)nn1] | 365.1 | $^1H$ NMR (400 MHz, $CDCl_3$): δ 7.52-7.77 (m, 2H), 7.26-7.30 (m, 2H), 4.77-5.04 (m, 2H), 4.45-4.59 (m, 1H), 3.60-4.31 (m, 4H), 3.04-3.52 (m, 2H), 2.39-2.42 (m, 3H), 1.95 (s, 2H), 1.74 (s, 1H), 1.42-1.49 (m, 1H), 0.79-0.90 (m, 4H). |
| I-106 | 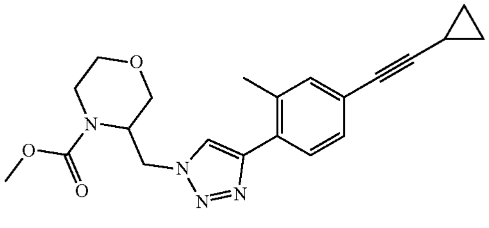 [SMILES: COC(=O)N1CCOCC1Cn1cc(-c2ccc(C#CC3CC3)cc2C)nn1] | 381.1 | $^1H$ NMR (400 MHz, $CDCl_3$): δ 7.59-7.72 (m, 2H), 7.27-7.29 (m, 2H), 4.52-4.80 (m, 3H), 3.37-3.96 (m, 9 H), 2.42 (s, 3H), 1.42-1.49 (m, 1H), 0.79-0.90 (m, 4H). |

TABLE 2-continued

| Compound No. | Chemical Structure | [M + H] observed | $^1$H NMR (400 MHz) |
|---|---|---|---|
| Characterization Data for Additional Exemplary Compounds | | | |
| I-180 | 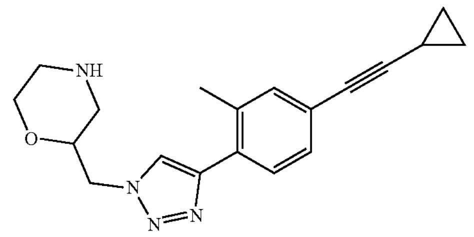 [SMILES: Cc1cc(C#CC2CC2)ccc1-c1cn(CC2CNCCO2)nn1] | 323.2 | $^1$H NMR (400 MHz, $CDCl_3$) δ 7.79 (s, 1H), 7.74 (d, J = 8.0 Hz, 1H), 7.27-7.30 (m, 2H), 4.49-4.53 (m, 1H), 4.36-4.41 (m, 1H), 3.83-3.91 (m, 2H), 3.55-3.62 (m, 1H), 2.98 (dd, J = 2.0 Hz, 12.0 Hz, 1H), 2.80-2.83 (m, 2H), 2.51-2.57 (m, 1H), 2.43 (s, 3H), 1.42-1.49 (m, 1H), 0.79-0.90 (m, 4H). |
| I-181 | 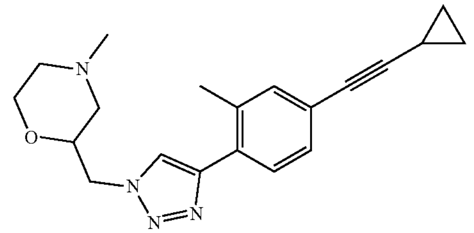 [SMILES: Cc1cc(C#CC2CC2)ccc1-c1cn(CC2CN(C)CCO2)nn1] | 337.3 | $^1$H NMR (400 MHz, $CDCl_3$) δ 7.79 (s, 1H), 7.75 (d, J = 7.6 Hz, 1H), 7.27-7.30 (m, 2H), 4.52-4.56 (m, 1H), 4.41-4.46 (m, 1H), 3.88-3.95 (m, 2H), 3.62-3.69 (m, 1H), 2.79 (d, J = 11.2 Hz, 1H), 2.63 (d, J = 11.2 Hz, 1H), 2.43 (s, 3H), 2.27 (s, 3H), 2.04-2.11 (m, 1H), 1.78 (t, J = 10.8 Hz, 1H), 1.42-1.49 (m, 1H), 0.79-0.90 (m, 4H). |
| I-243 | 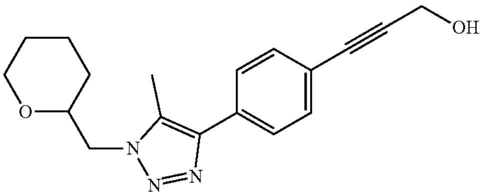 [SMILES: Cc1c(-c2ccc(C#CCO)cc2)nnn1CC1CCCCO1] | 312.0 | $^1$H NMR (400 MHz, DMSO-$d_6$) δ 7.72 (d, J = 8.4 Hz, 2H), 7.51 (d, J = 8.4 Hz, 2H), 5.36 (t, J = 6.0 Hz, 1H), 4.30-4.43 (m, 4H), 3.81-3.83 (m, 1H), 3.67-3.71 (m, 1H), 3.24-3.31 (m, 1H), 2.47 (s, 3H), 1.78-1.81 (m, 1H), 1.66-1.69 (m, 1H), 1.37-1.54 (m, 3H), 1.21-1.31 (m, 1H). |
| I-244 | 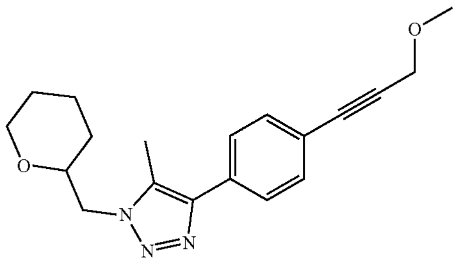 [SMILES: COCC#Cc1ccc(-c2nnn(CC3CCCCO3)c2C)cc1] | 326.0 | $^1$H NMR (400 MHz, DMSO-$d_6$) δ 7.73 (d, J = 6.8 Hz, 2H), 7.55 (d, J = 6.8 Hz, 2H), 4.30-4.43 (m, 4H), 3.81-3.84 (m, 1H), 3.66-3.72 (m, 1H), 3.35 (s, 3H), 3.24-3.31 (m, 1H), 2.47 (s, 3H), 1.78-1.81 (m, 1H), 1.66-1.69 (m, 1H), 1.39-1.54 (m, 3H), 1.21-1.31 (m, 1H). |
| I-258 | 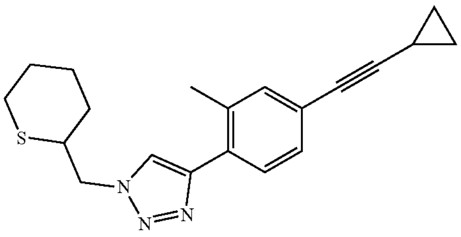 [SMILES: Cc1cc(C#CC2CC2)ccc1-c1cn(CC2CCCCS2)nn1] | 338.0 | $^1$H NMR (400 MHz, $CDCl_3$) δ 7.74 (d, J = 7.6 Hz, 1H), 7.71 (s, 1H), 7.26-7.29 (m, 2H), 4.53-4.58 (m, 1H), 4.42-4.47 (m, 1H), 3.24-3.27 (m, 1H), 2.66-2.69 (m, 2H), 2.44 (s, 3H), 1.91-1.98 (m, 3H), 1.60-1.75 (m, 1H), 1.39-1.51 (m, 3H), 0.79-0.90 (m, 4H). |
| I-350 | 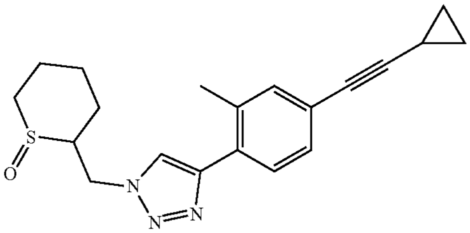 [SMILES: Cc1cc(C#CC2CC2)ccc1-c1cn(CC2CCCCS2=O)nn1] | 354.0 | $^1$H NMR (400 MHz, $CDCl_3$) δ 7.80-7.84 (m, 1H), 7.72-7.77 (m, 1H), 7.26-7.30 (m, 2H), 4.55-4.96 (m, 2H), 2.69-3.51 (m, 2.6H), 2.43-2.44 (m, 3H), 2.37-2.41 (m, 0.4H), 2.06-2.21 (m, 2H), 1.52-1.81 (m, 2H), 1.36-1.52 (m, 3H), 0.79-0.90 (m, 4H). |

TABLE 2-continued

Characterization Data for Additional Exemplary Compounds

| Compound No. | Chemical Structure | [M + H] observed | $^{1}H$ NMR (400 MHz) |
|---|---|---|---|
| I-351 | 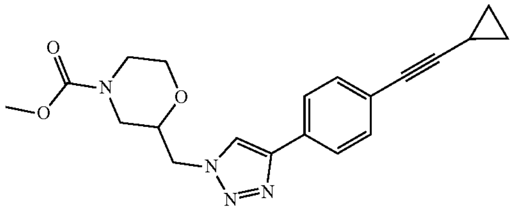 [SMILES: COC(=O)N1CCOC(Cn2cc(-c3ccc(C#CC4CC4)cc3)nn2)C1] | 367.1 | $^{1}H$ NMR (400 MHz, $CDCl_3$) δ 7.87 (s, 1H), 7.75 (d, J = 8.0 Hz, 2H), 7.43 (d, J = 8.0 Hz, 2H), 4.54-4.58 (m, 1H), 4.38-4.44 (m, 1H), 4.04-4.08 (m, 1H), 3.80-3.97 (m, 3H), 3.72 (s, 3H), 3.49-3.54 (m, 1H), 2.95 (brs., 1H), 2.68 (t, J = 12.0 Hz, 1H), 1.43-1.50 (m, 1H), 0.80-0.91 (m, 4H). |
| I-352 | 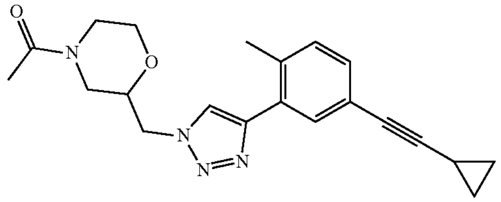 [SMILES: CC(=O)N1CCOC(Cn2cc(-c3cc(C#CC4CC4)ccc3C)nn2)C1] | 365.0 | 1HNMR (400 MHz, CDC13) δ 7.77-7.79 (m, 2H), 7.28-7.29 (m, 1H), 7.16-7.19 (m, 1H), 4.40-4.63 (m, 3H), 3.95-3.98 (m, 1H), 3.48-3.84 (m, 3H), 2.90-3.29 (m, 1H), 2.49-2.72 (m, 1H), 2.47 (s, 3H), 2.11 (s, 3H), 1.41-1.48 (m, 1H), 0.78-0.89 (m, 4H). |
| I-353 | 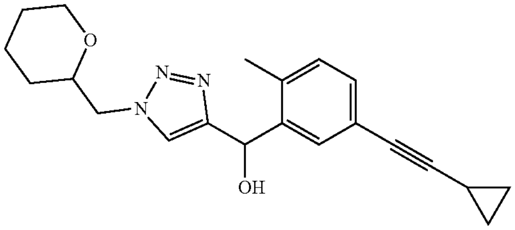 [SMILES: Cc1ccc(C#CC2CC2)cc1C(O)c1cn(CC2CCCCO2)nn1] | 352.2 | 1H NMR (400 MHz, DMSO-d6) δ 7.74 (d, J = 12.4 Hz, 1H), 7.46 (dd, J = 1.6 Hz, 9.2 Hz, 1H), 7.06-7.15 (m, 2H), 5.91 (s, 2H), 4.26-4.36 (m, 2H), 3.80-3.84 (m, 1H), 3.61-3.66 (m, 1H), 3.24-3.34 (m, 1H), 2.20 (d, J = 2.4 Hz, 3H), 1.75-1.78 (m, 1H), 1.40-1.58 (m, 5H), 1.09-1.15 (m, 1H), 0.84-0.89 (m, 2H), 0.68-0.73 (m, 2H). |
| I-95 | 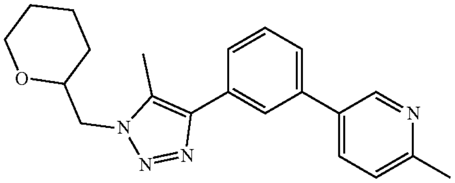 [SMILES: Cc1ccc(-c2cccc(-c3nnn(CC4CCCCO4)c3C)c2)cn1] | 349.1 | 1H NMR (400 MHz, $CDCl_3$) δ 8.75 (s, 1H), 7.95-7.88 (m, 1H), 7.81 (dd, J = 8.0, 2.3 Hz, 1H), 7.66 (ddt, J = 5.7, 4.0, 1.6 Hz, 1H), 7.51 (dd, J = 3.9, 1.3 Hz, 2H), 7.21 (d, J = 8.0 Hz, 1H), 4.36 (dd, J = 14.3, 3.6 Hz, 1H), 4.21 (dd, J = 14.3, 7.7 Hz, 1H), 3.95-3.83 (m, 1H), 3.75 (ddt, J = 11.1, 5.6, 2.8 Hz, 1H), 3.44-3.21 (m, 1H), 2.58 (s, 3H), 2.48 (s, 3H), 1.85 (dd, J = 6.6, 3.1 Hz, 1H), 1.68 (d, J = 12.3 Hz, 1H), 1.49 (td, J = 12.8, 12.3, 6.3 Hz, 3H), 1.41-1.24 (m, 1H). |

Example 2: Synthesis of I-315

Synthetic Scheme of I-315

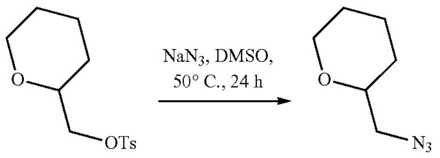

2-Int-2

2-Int-4

-continued

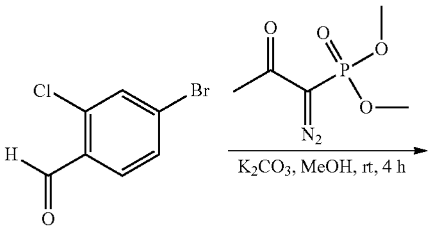

2.1

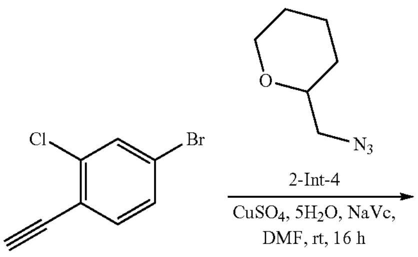

2.2

-continued

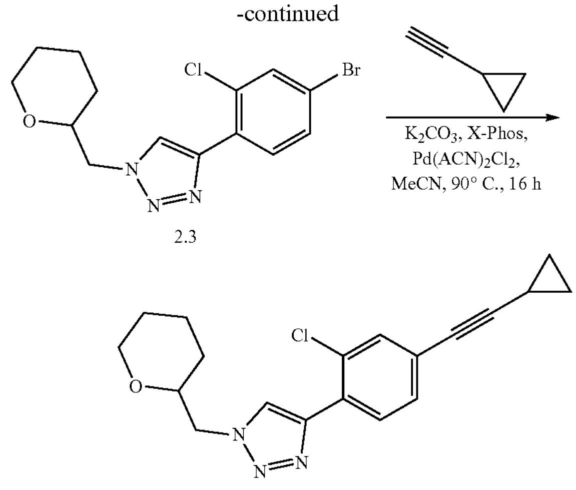

2.3

I-315

1. The Synthesis of Intermediate 2-Int-4

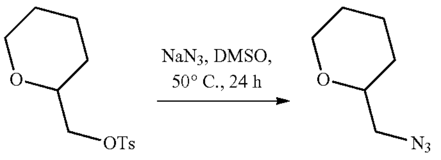

2-Int-2

2-Int-4

Sodium azide (1.5 g, 22 mmol) was added to a solution of compound 2-Int-2 (5.0 g, 18.5 mmol) in DMSO (20 mL). The reaction mixture was heated to 50° C. for 24 h and then cooled down to room temperature, diluted with water (80 mL), extracted with dichloromethane (3×10 ml). The combined organics phase were washed with water (3×10 ml) and brine (10 ml), dried over $Na_2SO_4$ and concentrated to dryness to afford 2-Int-4 (2.6 g) as brown oil. $^1$H NMR (400 MHz, $CDCl_3$) δ: 3.99-4.06 (m, 1H), 3.41-3.52 (m, 2H), 3.24-3.32 (m, 1H), 3.16-3.22 (m, 1H), 1.83-1.91 (m, 1H), 1.45-1.62 (m, 4H), 1.30-1.40 (m, 1H).

2. The Synthesis of Intermediate 2.2

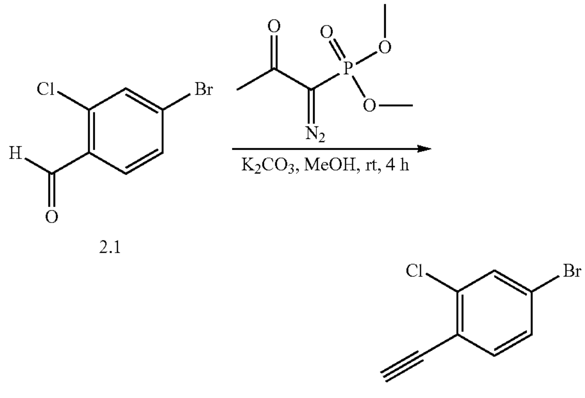

2.1

2.2

A mixture of 2.1 (500 mg, 2.3 mmol), dimethyl 1-diazo-2-oxopropylphosphonate (482 mg, 2.5 mmol) and potassium carbonate (630 mg, 4.6 mmol) in methanol (5 mL) was stirred at room temperature for 4 h. The mixture was filtered and the filtrate was concentrated to afford 2.2 (450 mg, yield: 92%) as an off-white solid. $^1$H NMR (400 MHz, $CDCl_3$) δ 7.59 (d, J 1.2 Hz, 1H), 7.35-7.40 (m, 2H), 3.42 (s, 1H).

3. The Synthesis of Intermediate 2.3

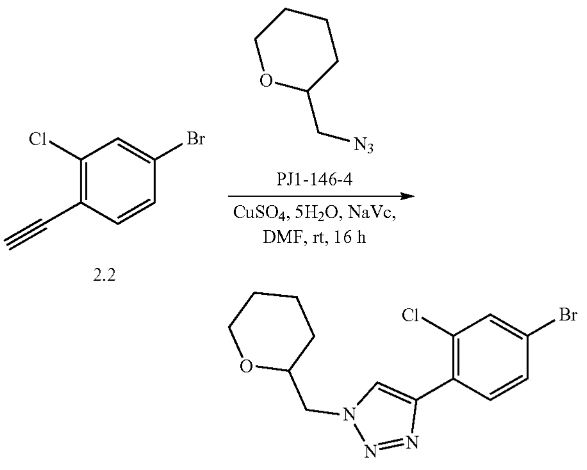

2.2

2.3

To a solution of $CuSO_4.5H_2O$ (24 mg, 0.096 mmol) in water (1 ml) was added sodium ascorbate (37 mg, 0.19 mmol). The resulting mixture was added to a solution of compound 2.2 (200 mg, 0.9 mmol) and 2.4 (197 mg, 1.4 mmol) in DMF (4 ml). The reaction mixture was stirred at room temperature for overnight and then diluted with water (16 mL), extracted with ethyl acetate (3×10 ml). The combined organic phases were washed with brine (10 ml), dried over Na2SO4 and concentrated to dryness. The crude product was purified by Prep-TLC (petroleum ether/ethyl acetate=3/1) to afford 2.3 (331 mg, yield: 100%) as a white solid. $^1$H NMR (400 MHz, $CDCl_3$) δ 8.30 (s, 1H), 8.14 (d, J 8.8 Hz, 1H), 7.63 (d, J 2.0 Hz, 1H), 7.50 (dd, J 8.4, 2.0 Hz, 1H), 4.49-4.55 (m, 1H), 4.31-4.39 (m, 1H), 3.97-4.03 (m, 1H), 3.68-3.76 (m, 1H), 3.36-3.44 (m, 1H), 1.84-1.93 (m, 1H), 1.65-1.72 (m, 1H), 1.49-1.60 (m, 3H), 1.22-1.34 (m, 1H).

4. The Synthesis of Intermediate I-315

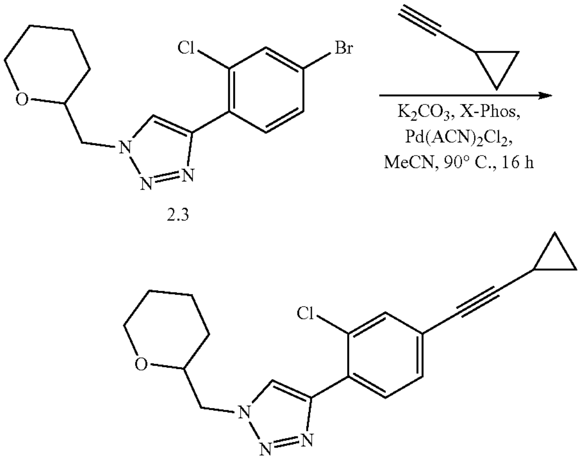

2.3

I-315

A solution of 2.3 (331 mg, 0.9 mmol), ethynylcyclopropane (369 mg, 5.6 mmol), X-phos (56 mg, 0.12 mmol), Bis(acetonitrile)dichloropalladium(II) (24 mg, 0.09 mmol) and potassium carbonate (257 mg, 1.9 mmol) in acetonitrile (10 mL) was heated to 90° C. for overnight. The reaction mixture was cooled down to room temperature and then filtered through diatomite, rinsing with ethyl acetate. The filtrate was concentrated and purified by column chromatography (petroleum ether, petroleum ether/ethyl acetate=3/1) and Prep-HPLC to afford I-315 (24.4 mg, yield: 8%) as a white solid.

Additional exemplary compounds were prepared following methods substantially similar to the method described above and herein. Data for these compounds are provided below.

TABLE 3

Characterization Data for Additional Exemplary Compounds

| Compound No. | Chemical Structure | [M + H] observed | $^1$H NMR (400 MHz) |
|---|---|---|---|
| I-315 | 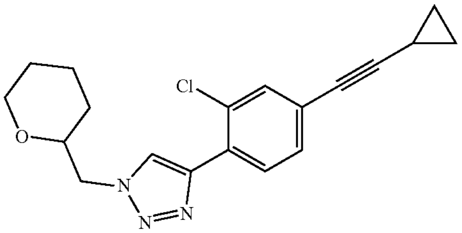 [SMILES: Clc1cc(C#CC2CC2)ccc1-c1cn(CC2CCCCO2)nn1] | 342.2 | $^1$H NMR (400 MHz, $CDCl_3$): δ 8.30 (s, 1H), 8.16 (d, J = 8.0 Hz, 1H), 7.46 (d, J = 1.6 Hz, 1H), 7.35 (dd, J = 8.0 Hz, 1.6 Hz, 1H), 4.48-4.54 (m, 1H), 4.32-4.38 (m, 1H), 3.98-4.01 (m, 1H), 3.68-3.74 (m, 1H), 3.36-3.43 (m, 1H), 1.87-1.89 (m, 1H), 1.64-1.72 (m, 1H), 1.42-1.59 (m, 4H), 1.22-1.34 (m, 1H), 0.80-0.92 (m, 4H). |
| I-65 | 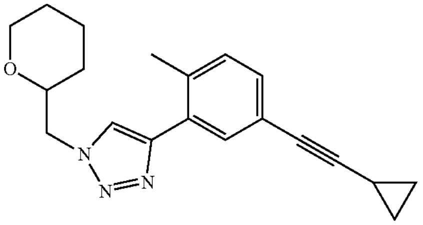 [SMILES: Cc1ccc(C#CC2CC2)cc1-c1cn(CC2CCCCO2)nn1] | 322.3 | $^1$H NMR (400 MHz, DMSO-$d_6$) δ 8.36 (s, 1H), 7.73 (s, 1H), 7.23-7.27 (m, 2H), 4.37-4.49 (m, 2H), 3.84-3.88 (m, 1H), 3.72-3.78 (m, 1H), 3.29-3.32 (m, 1H), 2.43 (s, 3H), 1.79-1.82 (m, 1H), 1.64 (d, J = 12.4 Hz, 1H), 1.39-1.57 (m, 4H), 1.16-1.26 (m, 1H), 0.86-0.91 (m, 2H), 0.72-0.76 (m, 2H). |
| I-160 | 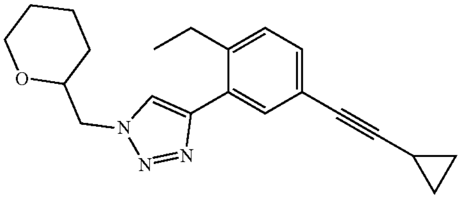 [SMILES: CCc1ccc(C#CC2CC2)cc1-c1cn(CC2CCCCO2)nn1] | 336.2 | $^1$H NMR (400 MHz, $CDCl_3$) δ 7.78 (s, 1H), 7.65 (d, J = 1.6 Hz, 1H), 7.31 (dd, J = 8.4 Hz, 2.0 Hz, 1H),7.21 (d, J = 8.0 Hz, 1H), 4.51 (dd, J = 14.0 Hz, 3.2 Hz, 1H), 4.34 (dd, J = 14.0 Hz, 7.2 Hz, 1H), 3.98-4.01 (m, 1H), 3.67-3.73 (m, 1H), 3.38-3.44 (m, 1H), 2.82 (q, J = 7.6 Hz, 2H), 1.88-1.89 (m, 1H), 1.68 (d, J = 13.2 Hz, 1H), 1.53-1.54 (m, 3H), 1.41-1.48 (m, 1H), 1.25-1.32 (m, 1H), 1.18 (t, J = 7.6 Hz, 3H), 0.78-0.88 (m, 4H). |
| I-134 | 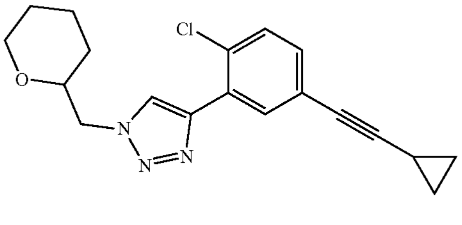 [SMILES: Clc1ccc(C#CC2CC2)cc1-c1cn(CC2CCCCO2)nn1] | 342.3 | $^1$H NMR (400 MHz, DMSO-$d_6$) δ 8.59 (s, 1H), 8.03 (s, 1H), 7.52 (d, J = 8.0 Hz, 1H), 7.34 (d, J = 8.0 Hz, 1H), 4.40-4.52 (m, 2H), 3.85 (d, J = 11.2 Hz, 1H), 3.73-3.75 (m, 1H), 3.28-3.30 (m, 1H), 1.80 (d, J = 10 Hz, 1H), 1.39-1.65 (m, 5H), 1.18-1.23 (m, 1H), 0.88-0.91 (m, 2H), 0.76-0.78 (m, 2H). |
| I-125 | 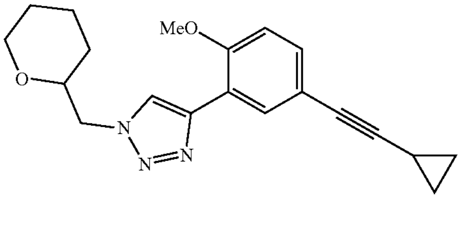 [SMILES: COc1ccc(C#CC2CC2)cc1-c1cn(CC2CCCCO2)nn1] | 338.0 | $^1$H NMR (400 MHz, $CDCl_3$): δ 8.38 (d, J = 2.0 Hz, 1H), 8.09 (s, 1H), 7.31 (dd, J = 2.0, 8.4 Hz, 1H), 6.86 (d, J = 8.4 Hz, 1H), 4.46 (dd, J = 3.6, 14.4 Hz, 1H), 4.31 (dd, J = 7.2, 14.0 Hz, 1H), 3.97-4.00 (m, 1H), 3.92 (s, 3H), 3.69-3.75 (m, 1H), 3.36-3.43 (m, 1H), 1.86-1.89 (m, 1H), 1.51-1.69 (m, 4H), 1.40-1.47 (m, 1H), 1.25-1.34 (m, 1H), 0.77-0.87 (m, 4H). |

TABLE 3-continued

Characterization Data for Additional Exemplary Compounds

| Compound No. | Chemical Structure | [M + H] observed | $^1$H NMR (400 MHz) |
|---|---|---|---|
| I-179 | 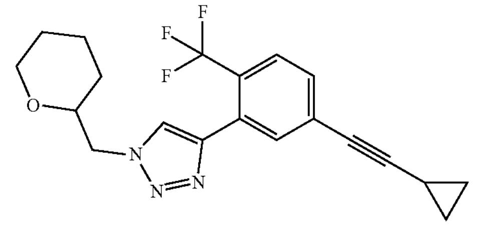 [SMILES: FC(F)(F)c1ccc(C#CC2CC2)cc1-c1cn(CC2CCCCO2)nn1] | 376.3 | $^1$H NMR (400 MHz, $CDCl_3$): δ 7.98 (s, 1H), 7.92 (d, J = 0.8 Hz, 1H), 7.64 (d, J = 8.0 Hz, 1H), 7.43 (dd, J = 8.4, 0.8 Hz, 1H), 4.51 (dd, J = 14.4, 3.2 Hz, 1H), 4.36 (dd, J = 14.4, 7.6 Hz, 1H), 3.96-4.02 (m, 1H), 3.65-3.73 (m, 1H), 3.36-3.44 (m, 1H), 1.83-1.94 (m, 1H), 1.62-1.69 (m, 1H), 1.42-1.58 (m, 4H), 1.18-1.30 (m, 1H), 0.80-0.93 (m, 4H). |
| I-164 | 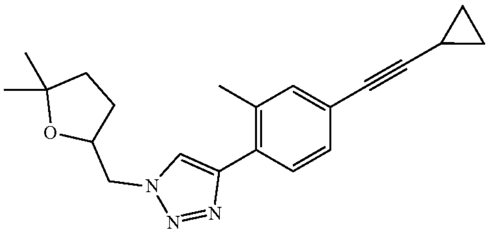 [SMILES: Cc1cc(C#CC2CC2)ccc1-c1cn(CC2CCC(C)(C)O2)nn1] | 336.3 | $^1$H NMR (400 MHz, $CDCl_3$): δ 7.83 (s, 1H), 7.74 (d, J = 8.0 Hz, 1H), 7.28 (d, J = 10.4 Hz, 2H), 4.45-4.60 (m, 2H), 4.32-4.41 (m, 1H), 2.44 (s, 3H), 2.04-2.14 (m, 1H), 1.70-1.82 (m, 2H), 1.42-1.60 (m, 2H), 1.23 (s, 3H), 1.17 (s, 3H), 0.78-0.91 (m, 4H). |
| I-200 | 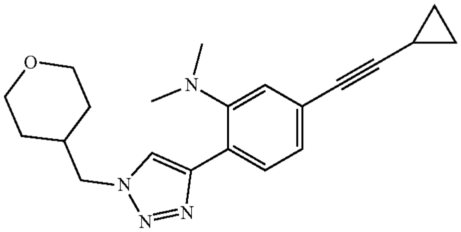 [SMILES: CN(C)c1cc(C#CC2CC2)ccc1-c1cn(CC2CCOCC2)nn1] | 351.0 | $^1$H NMR (400 MHz, DMSO-$d_6$) δ 8.48 (s, 1H), 7.97 (d, J = 7.6 Hz, 1H), 7.08-7.14 (m, 2H), 4.34 (d, J = 7.2 Hz, 2H), 3.83 (dd, J = 8.8 Hz, 11.6 Hz, 2H), 3.23-3.29 (m, 2H), 2.58 (s, 6H), 2.08-2.17 (m, 1H), 1.52-1.58 (m, 1H), 1.40-1.44 (m, 2H), 1.22-1.33 (m, 2H), 0.85-0.92 (m, 2H), 0.73-0.76 (m, 2H). |
| I-307 | 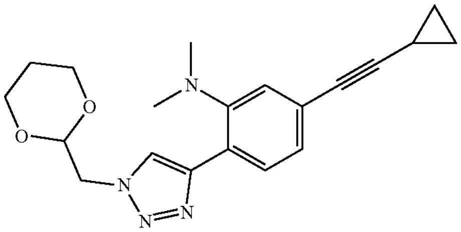 | 353.0 | $^1$H NMR (400 MHz, DMSO-$d_6$): δ 8.43 (s, 1H), 7.98 (d, J = 8.0 Hz, 1H), 7.14 (s, 1H), 7.10 (d, J = 8.0 Hz, 1H), 4.97 (t, J = 4.4 Hz, 1H), 4.53 (d, J = 4.8 Hz, 2H), 3.98-4.06 (m, 2H), 3.70-3.79 (m, 2H), 2.57 (s, 6H), 1.77-1.92 (m, 1H), 1.50-1.59 (m, 1H), 1.36 (d, J = 11.6 Hz, 1H), 0.84-0.93 (m, 2H), 0.71-0.78 (m, 2H). |
| I-241 | 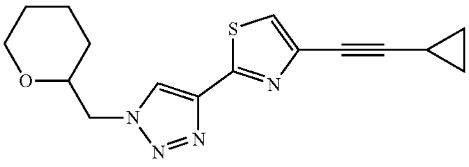 | 315.0 | $^1$H NMR (400 MHz, DMSO-$d_6$) δ 8.59 (s, 1H), 7.84 (s, 1H), 4.40-4.54 (m, 2H), 3.84-3.87 (m, 1H), 3.71-3.77 (m, 1H), 3.28-3.29 (d, 1H, J = 3.2 Hz), 1.78-1.81 (m, 1H), 1.53-1.61 (m, 2H), 1.39-1.52 (m, 3H), 1.16-1.24 (m, 1H), 0.85-0.94 (m, 2H), 0.75-0.78 (m, 2H). |
| I-242 | 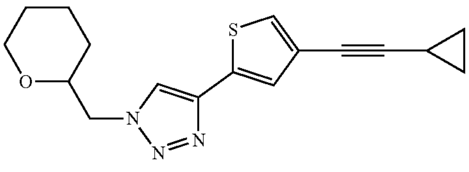 [SMILES: C(#CC1CC1)c1csc(-c2cn(CC3CCCCO3)nn2)c1] | 314.0 | $^1$H NMR (400 MHz, $CDCl_3$) δ 7.80 (s, 1H), 7.27-7.28 (m, 2H), 4.48 (dd, J = 3.2 Hz, 14.0 Hz, 1H), 4.25-4.31 (m, 1H), 3.97-4.01 (m, 1H), 3.64-3.70 (m, 1H), 3.36-3.42 (m, 1H), 1.87-1.89 (m, 1H), 1.65-1.68 (m, 1H), 1.49-1.58 (m, 3H), 1.40-1.47 (m, 1H), 1.21-1.30 (m, 1H), 0.82-0.89 (m, 2H), 0.77-0.81 (m, 2H). |
| I-270 | 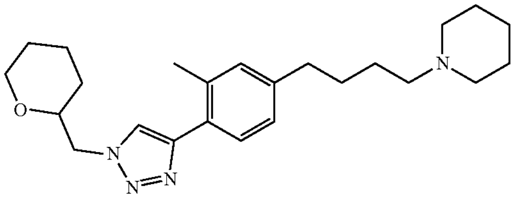 [SMILES: Cc1cc(CCCCN2CCCCC2)ccc1-c1cn(CC2CCCCO2)nn1] | 397.2 | $^1$H NMR (400 MHz, DMSO-$d_6$) δ 8.24 (s, 1H), 7.64 (d, J = 7.6 Hz, 1H), 7.10-7.13 (m, 2H), 4.37-4.49 (m, 2H), 3.84-3.87 (m, 1H), 3.71-3.77 (m, 1H), 3.28-3.35 (m, 1H), 2.69-2.74 (m, 1H), 2.41 (s, 3H), 2.03-2.25 (m, 6H), 1.78-1.81 (m, 1H), 1.61-1.72 (m, 3H), 1.45-1.51 (m, 7H), 1.34-1.41 (m, 2H), 1.19-1.26 (m, 4H). |

TABLE 3-continued

| Compound No. | Chemical Structure | [M + H] observed | $^1H$ NMR (400 MHz) |
|---|---|---|---|
| Characterization Data for Additional Exemplary Compounds | | | |
| I-257 | 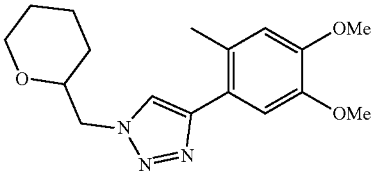 [SMILES: COc1cc(C)c(-c2cn(CC3CCCCO3)nn2)cc1OC] | 318.0 | $^1H$ NMR (400 MHz, DMSO-$d_6$) δ 8.23 (s, 1H), 7.33 (s, 1H), 6.89 (s, 1H), 4.36-4.48 (m, 2H), 3.86-3.87 (m, 1H), 3.71-3.78 (m, 7H), 3.29-3.32 (m, 1H), 2.36 (s, 3H), 1.79-1.81 (m, 1H), 1.62-1.65 (d, 1H, J = 12.4 Hz), 1.39-1.52 (m, 3H), 1.19-1.26 (m, 1H). |
| I-374 | 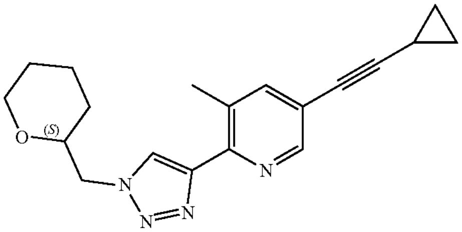 | 323.0 | $^1H$ NMR (400 MHz, DMSO-$d_6$) δ 8.47 (s, 1H), 8.43 (d, J = 1.6 Hz, 1H), 7.73 (d, J = 1.2 Hz, 1H), 4.39-4.53 (m, 2H), 3.84-3.88 (m, 1H) 3.73-3.75 (m, 1H), 3.28-3.30 (m, 1H), 2.62 (s, 3H), 1.76-1.84 (m, 1H), 1.56-1.68 (m, 2H), 1.38-1.52 (m, 3H), 1.08-1.23 (m, 1H), 0.85-0.88 (m, 2H), 0.67-0.80 (m, 2H). |
| I-35 | 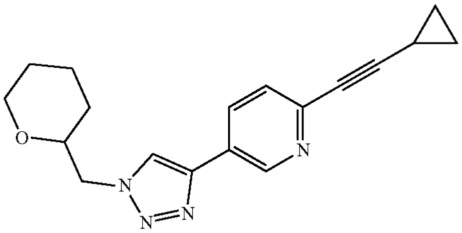 [SMILES: C(#CC1CC1)c1ccc(-c2cn(CC3CCCCO3)nn2)cn1] | 309.2 | $^1H$ NMR (400 MHz, $CDCl_3$) δ 8.92 (dd, J = 2.3, 0.8 Hz, 1H), 8.12 (dd, J = 8.1, 2.3 Hz, 1H), 7.97 (s, 1H), 7.40 (dd, J = 8.2, 0.8 Hz, 1H), 4.51 (dd, J = 14.2, 2.9 Hz, 1H), 4.31 (dd, J = 14.2, 7.6 Hz, 1H), 4.00 (dd, J = 11.0, 2.0 Hz, 1H), 3.69 (ddt, J = 10.2, 7.6, 2.5 Hz, 1H), 3.39 (td, J = 11.3, 4.2 Hz, 1H), 1.94-1.80 (m, 1H), 1.68 (d, J = 12.4 Hz, 1H), 1.60-1.43 (m, 4H), 1.33-1.20 (m, 1H), 0.90 (d, J = 6.4 Hz, 4H). |
| I-38 | 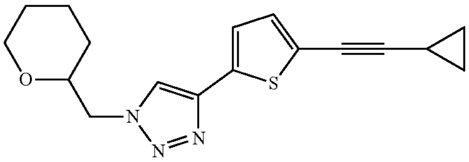 [SMILES: C(#CC1CC1)c1ccc(-c2cn(CC3CCCCO3)nn2)s1] | 314.1 | $^1H$ NMR (400 MHz, $CDCl_3$) δ 7.78 (s, 1H), 7.18 (d, J = 3.8 Hz, 1H), 7.04 (d, J = 3.7 Hz, 1H), 4.47 (dd, J = 14.2, 2.9 Hz, 1H), 4.27 (dd, J = 14.2, 7.6 Hz, 1H), 4.02-3.94 (m, 1H), 3.66 (ddt, J = 10.0, 7.6, 2.6 Hz, 1H), 3.43-3.33 (m, 1H), 1.92-1.80 (m, 1H), 1.70-1.62 (m, 1H), 1.58-1.43 (m, 4H), 1.32-1.19 (m, 1H), 0.92-0.80 (m, 4H). |

Example 3: Synthesis of I-77

Synthetic Scheme of I-77

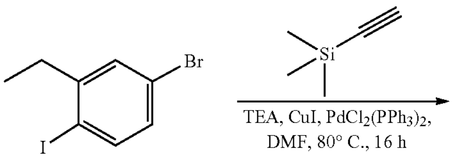

3.1

-continued

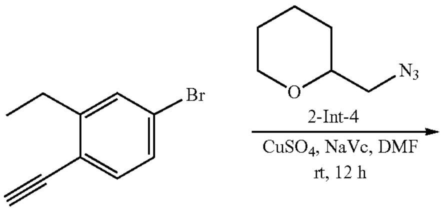

3.3

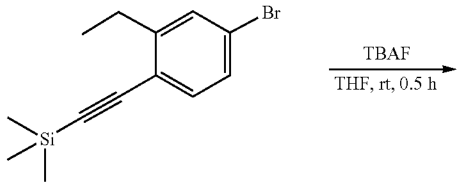

3.2

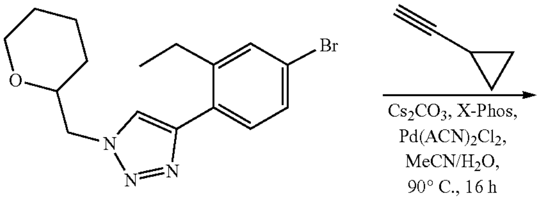

3.4

-continued

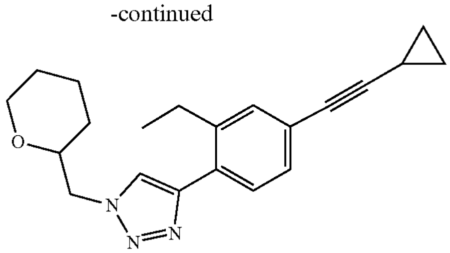

I-77

1. The Synthesis of Intermediate 3.2

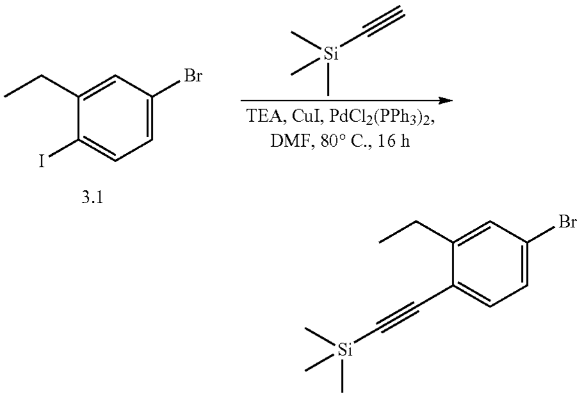

3.1

3.2

To a stirred solution of 3.1 (500 mg, 1.6 mmol), ethynyltrimethylsilane (470 mg, 4.8 mmol) and TEA (5 mL) in DMF (5 mL) was added $PdCl_2(PPh_3)_2$ (50 mg) and CuI (100 mg). The reaction mixture was stirred at 80° C. for 16 hours until the reaction was complete. The suspension was diluted with $H_2O$ (20 mL) and extracted with EA (20 mL×2), concentrated. The crude product was purified by flash column chromatography (silica gel, PE/EA=100:1) to give 3.2 (420 mg, yield: 93.7%) as yellow oil. $^1$H NMR (400 MHz, DMSO-$d_6$): δ 7.03-7.11 (m, 3H), 2.57 (q, J=7.6 Hz, 2H), 1.02-1.09 (m, 3H), 0.06 (s, 9H).

2. The Synthesis of Intermediate 3.3

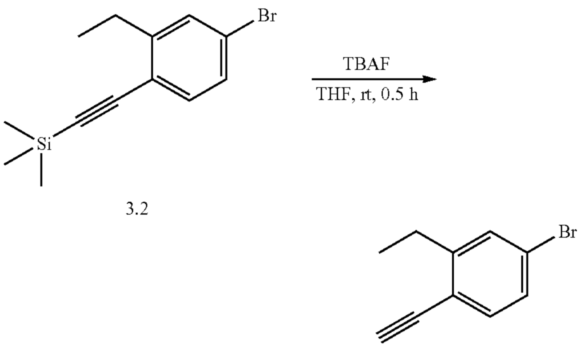

3.2

To a stirred solution of 3.2 (420 mg, 1.5 mmol) in THF (10 mL) was added TBAF (10 mL). The reaction mixture was stirred at RT for 0.5 h until the reaction was complete. The reaction was poured into water and extracted with DCM (20 mL×2). The reaction mixture was concentrated and the crude product was purified by flash column chromatography (silica gel, PE/EA=100:1) to give 3.3 (280 mg, yield: 89.7%) as yellow oil.

3. The Synthesis of Intermediate 3.4

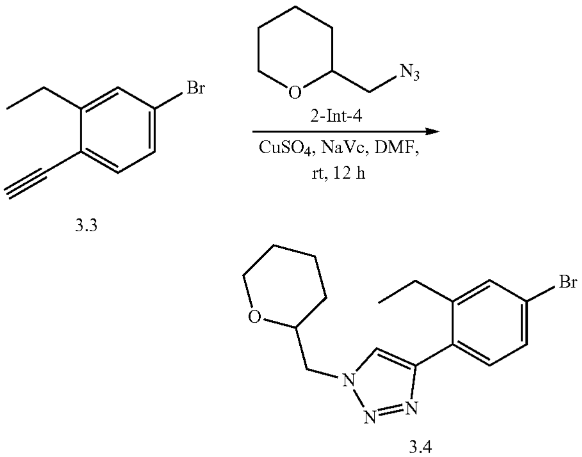

3.3

3.4

To a stirred solution of 3.3 (280 mg, 1.3 mmol) in DMF (10 mL) was added 2-(azidomethyl)tetrahydro-2H-pyran, 2-Int-4 (182 mg, 1.3 mmol), $CuSO_4$ (26 mg, 0.13 mmol) and sodium ascorbate (52 mg, 0.26 mmol). The reaction mixture was stirred at RT for 12 h until the reaction was complete. The reaction was poured into ice water and extracted with DCM (20 mL×2). The reaction mixture was concentrated and the crude product was purified by flash column chromatography (silica gel, PE/EA=2:1) to give 3.4 (270 mg, yield: 59.5%) as yellow oil.

4. The Synthesis of I-77

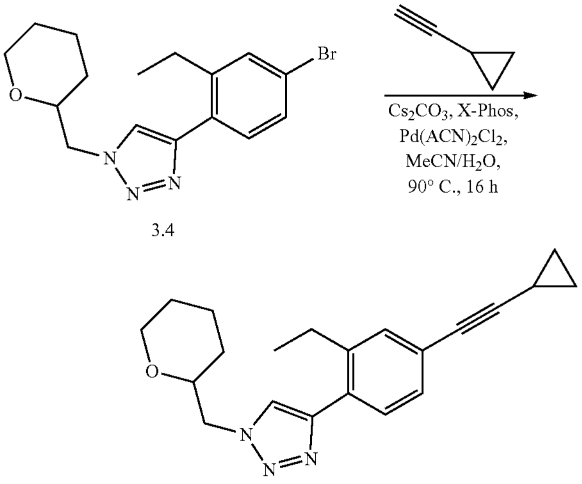

3.4

I-77

To a stirred solution of 3.4 (270 mg, 0.77 mmol), ethynylcyclopropane (153 mg, 2.31 mmol) and $Cs_2CO_3$ (753 mg, 2.31 mmol) in $CH_3CN$ (10 mL) was added $Pd(ACN)_2Cl_2$ (30 mg), X-Phos (60 mg) and $H_2O$ (5 mL). The reaction mixture was stirred at 90° C. for 16 hours until the reaction was complete. The suspension was diluted with $H_2O$ (20 mL) and extracted with EA (20 mL×2), concentrated. The crude product was purified by prep-HPLC to give 1-77 (53.02 mg, yield: 20.5%) as a yellow solid.

Additional exemplary compounds were prepared following methods substantially similar to the method described above and herein. Data for these compounds are provided below.

TABLE 4

Characterization Data for Additional Exemplary Compounds

| Compound No. | Chemical Structure | [M + H] observed | $^1$H NMR (400 MHz) |
|---|---|---|---|
| I-80 | 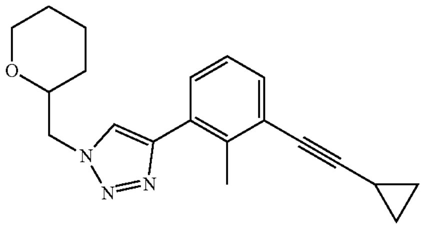 [SMILES: Cc1c(C#CC2CC2)cccc1-c1cn(CC2CCCCO2)nn1] | 322.3 | $^1$H NMR (400 MHz, DMSO-$d_6$) δ 8.30 (s, 1H), 7.61 (d, J = 7.6 Hz, 1.2 Hz, 1H), 7.35 (dd, J = 7.6 Hz, 1.2 Hz, 1H), 7.23 (t, J = 7.6 Hz, 1H), 4.38-4.50 (m, 2H), 3.84-3.88 (m, 1H), 3.71-3.78 (m, 1H), 3.29-3.35 (m, 1H), 2.48 (s, 3H), 1.78-1.81 (m, 1H), 1.57-1.66 (m, 2H), 1.39-1.54 (m, 3H), 1.16-1.26 (m, 1H), 0.90-0.94 (m, 2H), 0.74-0.78 (m, 2H). |
| I-77 | 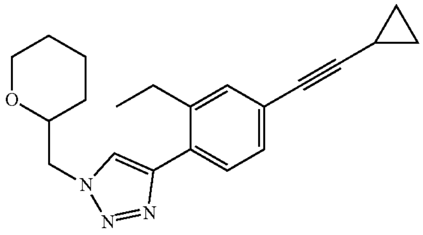 [SMILES: CCc1cc(C#CC2CC2)ccc1-c1cn(CC2CCCCO2)nn1] | 336.3 | $^1$H NMR (400 MHz, $CDCl_3$): δ 7.78 (s, 1H), 7.61 (d, J = 8.0 Hz, 1H), 7.32 (d, J = 2.0 Hz, 1H), 7.26-7.28 (m, 1H), 4.49-4.53 (m, 1H), 4.30-4.36 (m, 1H), 3.97-4.00 (m, 1H), 3.67-3.73 (m, 1H), 3.37-3.43 (m, 1H), 2.79 (q, J = 7.6 Hz, 2H), 1.86-1.90 (m, 1H), 1.62-1.69 (m, 1H), 1.43-1.57 (m, 4H), 1.23-1.40 (m, 1H), 1.20 (t, J = 7.6 Hz, 3H), 0.80-0.90 (m, 4H). |
| I-88 | 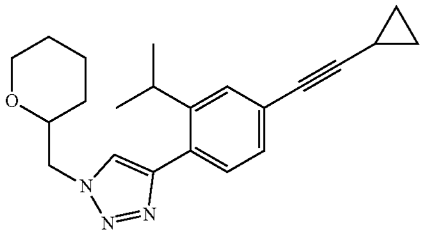 | 350.0 | $^1$H NMR (400 MHz, DMSO-$d_6$): δ 8.22 (s, 1H), 7.43 (d, J = 8.0 Hz, 1H), 7.39 (d, J = 1.6 Hz, 1H), 7.23 (dd, J = 1.6 Hz, 7.6 Hz, 1H), 4.38-4.49 (m, 2H), 3.84-3.88 (m, 1H), 3.71-3.77 (m, 1H), 3.38-3.44 (m, 1H), 3.29-3.33 (m, 1H), 1.78-1.81 (m, 1H), 1.39-1.65 (m, 5H), 1.16-1.23 (m,7H), 0.87-0.92 (m, 2H), 0.74-0.77 (m, 2H). |
| I-89 | 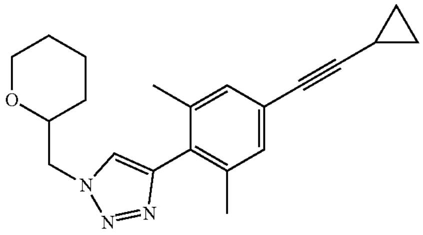 [SMILES: Cc1cc(C#CC2CC2)cc(C)c1-c1cn(CC2CCCCO2)nn1] | 335.4 | $^1$H NMR (400 MHz, DMSO-$d_6$): δ 8.08 (s, 1H), 7.14 (s, 2H), 4.39-4.49 (m, 2H), 3.85-3.88 (m, 1H), 3.71-3.74 (m, 1H), 3.34-3.36 (m, 1H), 2.04 (s, 6H), 1.77-1.80 (m, 1H), 1.37-1.60 (m, 5H), 1.12-1.23 (m, 1H), 0.87-0.91 (m, 2H), 0.71-0.75 (m, 2H). |
| I-81 | 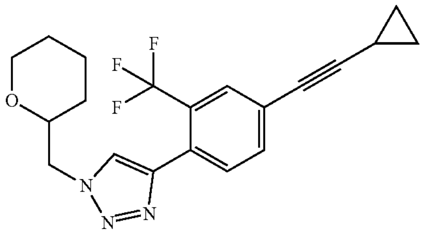 [SMILES: FC(F)(F)c1cc(C#CC2CC2)ccc1-c1cn(CC2CCCCO2)nn1] | 375.9 | $^1$H NMR (400 MHz, DMSO-$d_6$): δ 8.24 (s, 1H), 7.71-7.84 (m, 3H), 4.41-4.54 (m, 2H), 3.84-3.88 (m, 1H), 3.71-3.72 (m, 1H), 3.29-3.32 (m, 1H), 1.75-1.85 (m, 1H), 1.31-1.68 (m, 5H), 1.10-1.23 (m, 1H), 0.91-0.97 (m, 2H), 0.77-0.84 (m, 2H). |

TABLE 4-continued

Characterization Data for Additional Exemplary Compounds

| Compound No. | Chemical Structure | [M + H] observed | $^1$H NMR (400 MHz) |
|---|---|---|---|
| I-82 | 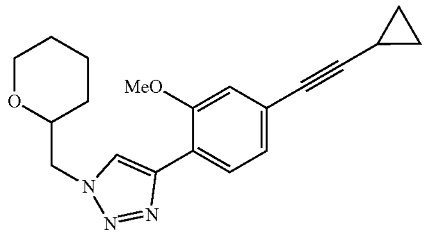 [SMILES: COc1cc(C#CC2CC2)ccc1-c1cn(CC2CCCCO2)nn1] | 338.3 | $^1$H NMR (400 MHz, DMSO-$d_6$): δ 8.32 (s, 1H), 8.09 (d, J = 8.0 Hz, 1H), 7.03-7.09 (m, 2H), 4.40-4.47 (m, 2H), 3.92 (s, 3H), 3.81-3.88 (m, 1H), 3.69-3.72 (m, 1H), 3.25-3.33 (m, 1H), 1.75-1.82 (m, 1H), 1.37-1.62 (m, 5H), 1.17-1.25 (m, 1H), 0.88-0.93 (m, 2H), 0.73-0.78 (m, 2H). |
| I-124 | 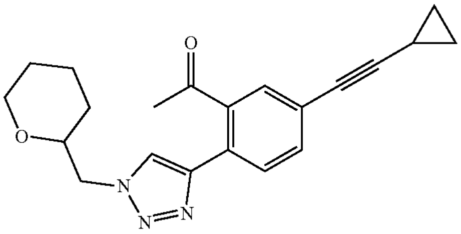 [SMILES: CC(=O)c1cc(C#CC2CC2)ccc1-c1cn(CC2CCCCO2)nn1] | 350.0 | $^1$H NMR (400 MHz, $CDCl_3$): δ 7.84 (s, 1H), 7.69 (dd, J = 7.2 Hz, 1.6 Hz, 1H), 7.46-7.51 (m, 2H), 4.46-4.51 (m, 1H), 4.28-4.34 (m, 1H), 3.97-4.01 (m, 1H), 3.65-3.71 (m, 1H), 3.35-3.41 (m, 1H), 2.38 (s, 3H), 1.61-1.68 (m, 1H), 1.43-1.53 (m, 5H), 1.24-1.28 (m, 1H), 0.81-0.93 (m, 4H). |
| I-234 | 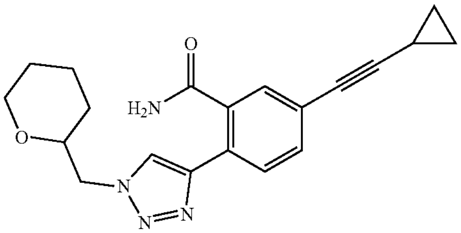 [SMILES: NC(=O)c1cc(C#CC2CC2)ccc1-c1cn(CC2CCCCO2)nn1] | 351.2 | $^1$H NMR (400 MHz, $CDCl_3$) δ 7.93 (s, 1H), 7.77 (d, J = 8.0 Hz, 1H), 7.57 (d, J = 1.6 Hz, 1H), 7.45 (dd, J = 8.0 Hz, 1.6 Hz, 1H), 6.45 (s, 1H), 6.06 (s, 1H), 4.40-4.44 (m, 1H), 4.25-4.31 (m, 1H), 3.94-3.97 (m, 1H), 3.65-3.70 (m, 1H), 3.33-3.39 (m, 1H), 1.85-189 (m, 1H), 1.63 (d, J = 12.4 Hz, 1H), 1.43-1.56 (m, 4H), 1.20-1.29 (m, 1H), 0.84-0.92 (m, 2H), 0.80-0.83 (m, 2H). |
| I-116 | 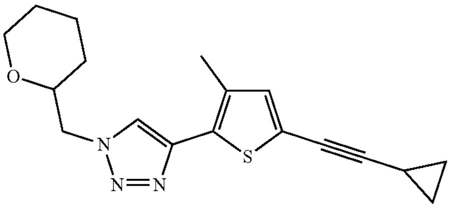 [SMILES: Cc1cc(C#CC2CC2)sc1-c1cn(CC2CCCCO2)nn1] | 327.9 | $^1$H NMR (400 MHz, DMSO-$d_6$) δ 8.31 (s, 1H), 7.05 (s, 1H), 4.35-4.49 (m, 2H), 3.81-3.88 (m, 1H), 3.70-3.78 (m, 1H), 2.27 (s, 3H), 1.78-1.82 (m, 1H), 1.14-1.68 (m, 7H), 0.86-0.93 (m, 2H), 0.72-0.78 (m, 2H). |
| I-228 | 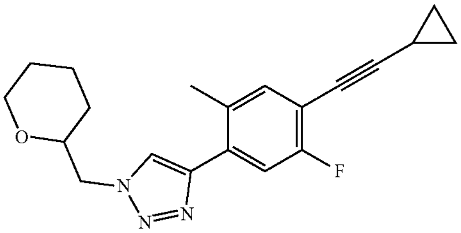 [SMILES: Cc1cc(C#CC2CC2)c(F)cc1-c1cn(CC2CCCCO2)nn1] | 340.2 | $^1$H NMR (400 MHz, DMSO-$d_6$) δ 8.43 (s, 1H), 7.64 (d, J = 10.8 Hz, 1H), 7.38 (d, J = 7.6 Hz, 1H), 4.38-4.51 (m, 2H), 3.83-3.86 (m, 1H) 3.71-3.76 (m, 1H), 3.27-3.31 (m, 1H), 2.39 (s, 3H), 1.78-1.81 (m, 1H), 1.58-1.66 (m, 2H), 1.39-1.54 (m, 3H), 1.16-1.26 (m, 1H), 0.89-0.95 (m, 2H), 0.75-0.79 (m, 2H). |
| I-268 | 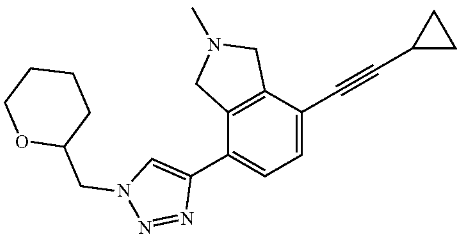 [SMILES: CN1Cc2c(C#CC3CC3)ccc(-c3cn(CC4CCCCO4)nn3)c2C1] | 363.0 | $^1$H NMR (400 MHz, DMSO-$d_6$) δ 8.40 (s, 1H), 7.66 (d, J = 8.4 Hz, 1H), 7.25 (d, J = 8.0 Hz, 1H), 4.36-4.49 (m, 2H), 4.12 (s, 2H), 3.83-3.87 (m, 3H), 3.70-3.76 (m, 1H), 3.27-3.32 (m, 1H), 2.53 (s, 3H), 1.78-1.81 (m, 1H), 1.52-1.65 (m, 2H), 1.39-1.51 (m, 3H), 1.15-1.25 (m, 1H), 0.85-0.94 (m, 2H), 0.72-0.76 (m, 2H). |

TABLE 4-continued

| Characterization Data for Additional Exemplary Compounds | | | |
|---|---|---|---|
| Compound No. | Chemical Structure | [M + H] observed | $^1H$ NMR (400 MHz) |
| I-354 | 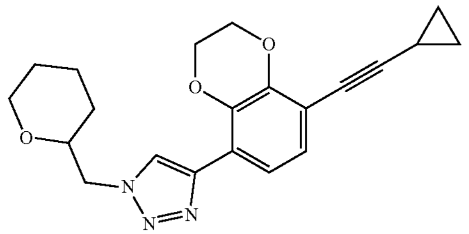 [SMILES: C(#CC1CC1)c1ccc(-c2cn(CC3CCCCO3)nn2)c2c1OCCO2] | 366.2 | $^1H$ NMR (400 MHz, DMSO-$d_6$) δ 8.31 (s, 1H), 7.60 (d, J = 8.0 Hz, 1H), 6.94 (d, J = 8.0 Hz, 1H), 4.35-4.49 (m, 6H), 3.83-3.86 (m, 1H), 3.68-3.73 (m, 1H), 3.31 (s, 1H), 1.78-1.80 (m, 1H), 1.42-1.65 (m, 5H), 1.14-1.23 (m, 1H), 0.87-0.91 (m, 2H), 0.70-0.74 (m, 2H). |
| I-229 | 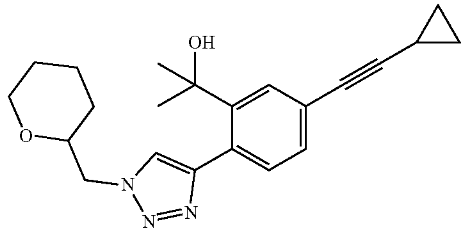 [SMILES: CC(C)(O)c1cc(C#CC2CC2)ccc1-c1cn(CC2CCCCO2)nn1] | 366.1 | $^1H$ NMR (400 MHz, DMSO-$d_6$): δ 8.24 (s, 1H), 7.69 (s, 1H), 7.24-7.30 (m, 2H), 5.69 (s, 1H), 4.48 (dd, J = 14.0 Hz, 3.6 Hz, 1H), 4.39 (dd, J = 14.0 Hz, 7.6 Hz, 1H), 3.82-3.88 (m, 1H), 3.67-3.75 (m, 1H), 3.28-3.36 (m, 1H), 1.75-1.84 (m, 1H), 1.53-1.65 (m, 2H), 1.36-1.51 (m, 3H), 1.31 (s, 3H), 1.30 (s, 3H), 1.10-1.22 (m, 1H), 0.87-0.93 (m, 2H), 0.73-0.78 (m, 2H). |
| I-212 | 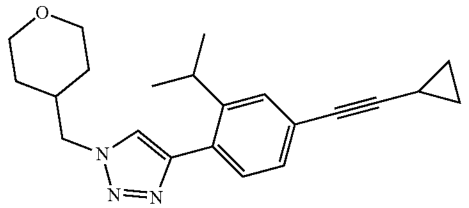 [SMILES: CC(C)c1cc(C#CC2CC2)ccc1-c1cn(CC2CCOCC2)nn1] | 350.0 | $^1H$ NMR (400 MHz, DMSO-$d_6$) δ 8.32 (s, 1H), 7.43 (d, J = 8.0 Hz, 1H), 7.39 (d, J = 1.6 Hz, 2H), 7.23 (dd, J = 8.4 Hz, 1.6 Hz, 1H), 4.33 (d, J = 7.2 Hz, 2H), 3.85 (dd, J = 11.2 Hz, 2.8 Hz, 2H), 3.38-3.45 (m, 1H), 3.24 (t, J = 2.0 Hz, 1H), 2.12-2.16 (m, 1H), 1.53-1.58 (m, 1H), 1.41-1.45 (m, 2H), 1.23-1.33 (m, 2H), 1.17 (s, 3H), 1.15 (s, 3H), 0.87-0.92 (m, 2H), 0.73-0.78 (m, 2H). |
| I-308 | 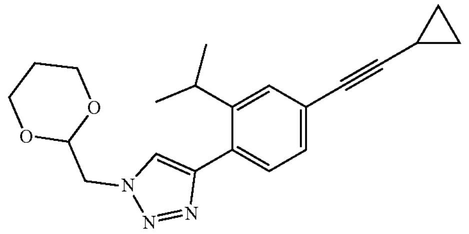 [SMILES: CC(C)c1cc(C#CC2CC2)ccc1-c1cn(CC2OCCCO2)nn1] | 352.0 | $^1H$ NMR (400 MHz, DMSO-$d_6$) δ 8.24 (s, 1H), 7.40 (d, J = 8.0 Hz, 1H), 7.40 (d, J = 1.6 Hz, 1H), 7.24 (dd, J = 8.8 Hz, 1.6 Hz, 1H), 5.01 (t, J = 4.8 Hz, 1H), 4.52 (d, J = 4.8 Hz, 2H) 4.03 (dd, J = 10.8 Hz, 2.8 Hz, 2H), 3.73-3.79 (m, 2H), 3.35-3.41 (m, 1H), 1.86-1.90 (m, 1H), 1.53-1.58 (m, 1H), 1.38 (d, J = 13.2 Hz, 1H), 1.17 (d, J = 6.8 Hz, 6H), 0.87-0.92 (m, 2H), 0.74-0.78 (m, 2H). |
| I-214 | 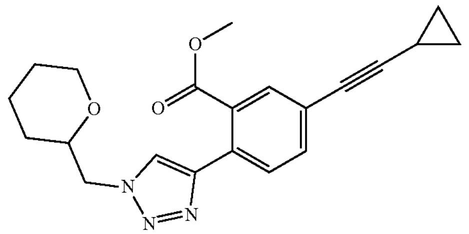 [SMILES: COC(=O)c1cc(C#CC2CC2)ccc1-c1cn(CC2CCCCO2)nn1] | 366.3 | $^1H$ NMR (400 MHz, DMSO-$d_6$): δ 8.28 (s, 1H), 7.74 (dd, J = 7.6, 2.4 Hz, 1H), 7.54-7.60 (m, 2H), 4.47 (dd, J = 14.0 Hz, 3.6 Hz, 1H), 4.39 (dd, J = 14.0 Hz, 7.6 Hz, 1H), 3.83-3.89 (m, 1H), 3.73 (s, 3H), 3.67-3.75 (m, 1H), 3.28-3.36 (m, 1H), 1.76-1.84 (m, 1H), 1.53-1.66 (m, 2H), 1.38-1.52 (m, 3H), 1.13-1.24 (m, 1H), 0.88-0.95 (m, 2H), 0.74-0.80 (m, 2H). |
| I-309 | 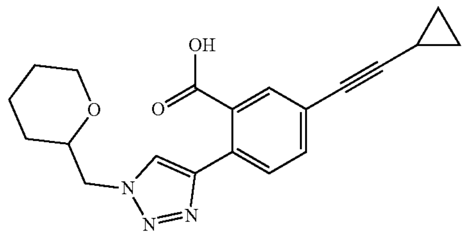 [SMILES: O=C(O)c1cc(C#CC2CC2)ccc1-c1cn(CC2CCCCO2)nn1] | 352.3 | $^1H$ NMR (400 MHz, DMSO-$d_6$): δ 13.05 (br, 1H), 8.26 (s, 1H), 7.72 (d, J = 8.0 Hz, 1H), 7.57 (d, J = 1.6 Hz, 1H), 7.53 (dd, J = 8.0, 1.6 Hz, 1H), 4.46 (dd, J = 14.0, 3.6 Hz, 1H), 4.39 (dd, J = 14.0, 7.6 Hz, 1H), 3.83-3.89 (m, 1H), 3.66-3.74 (m, 1H), 3.27-3.36 (m, 1H), 1.75-1.83 (m, 1H), 1.53-1.65 (m, 2H), 1.38-1.51 (m, 3H), 1.13-1.26 (m, 1H), 0.88-0.94 (m, 2H), 0.75-0.80 (m, 2H). |

TABLE 4-continued

Characterization Data for Additional Exemplary Compounds

| Compound No. | Chemical Structure | [M + H] observed | $^1$H NMR (400 MHz) |
|---|---|---|---|
| I-355 | 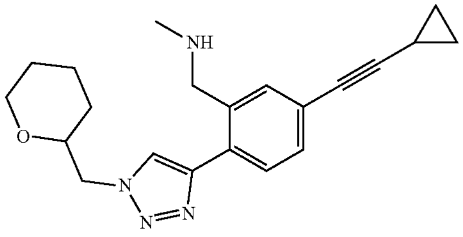 [SMILES: CNCc1cc(C#CC2CC2)ccc1-c1cn(CC2CCCCO2)nn1] | 351.0 | $^1$H NMR (400 MHz, $CDCl_3$) δ 8.03 (s, 1H), 7.62 (d, J = 8.0 Hz, 1H), 7.45 (d, J = 1.2 Hz, 1H), 7.34 (dd, J = 1.6 Hz, 8.0 Hz, 1H), 4.50 (dd, J = 3.2 Hz, 14.0 Hz, 1H), 4.31-4.36 (m, 1H), 3.98-4.01 (m, 1H), 3.78 (s, 2H), 3.68-3.74 (m, 1H), 3.38-3.45 (m, 1H), 2.47 (s, 3H), 1.88-1.90 (m, 1H), 1.67-1.70 (m, 1H), 1.43-1.58 (m, 4H), 1.26-1.30 (m, 1H), 0.79-0.91 (m, 4H). |
| I-356 | 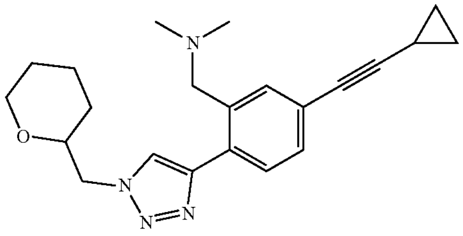 [SMILES: CN(C)Cc1cc(C#CC2CC2)ccc1-c1cn(CC2CCCCO2)nn1] | 365.1 | $^1$H NMR (400 MHz, $CDCl_3$) δ 8.26 (s, 1H), 7.85-7.87 (m, 1H), 7.37-7.39 (m, 2H), 4.50 (dd, J = 2.8 Hz, 14.0 Hz, 1H), 4.31-4.37 (m, 1H), 3.98-4.01 (m, 1H), 3.69-3.73 (m, 1H), 3.35-3.44 (m, 3H), 2.24 (s, 6H), 1.87-1.90 (m, 1H), 1.67-1.70 (m, 1H), 1.48-1.58 (m, 2H), 1.44-1.47 (m, 2H), 1.27-1.30 (m, 1H), 0.80-0.94 (m, 4H). |
| I-357 | 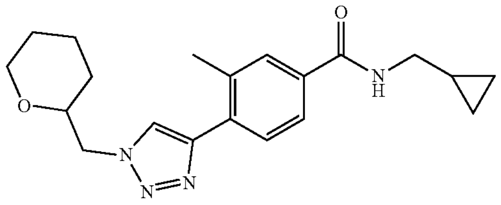 [SMILES: Cc1cc(C(=O)NCC2CC2)ccc1-c1cn(CC2CCCCO2)nn1] | 355.1 | $^1$H NMR (400 MHz, DMSO-$d_6$) δ 8.58 (t, J = 5.2 Hz, 1H), 8.41 (s, 1H), 7.73-7.90 (m, 3H), 4.37-4.53 (m, 2H), 3.72-3.91 (m, 2H), 3.27-3.35 (m, 1H), 3.15 (t, J = 6.0 Hz, 2H), 2.50 (s, 3H), 1.76-1.85 (m, 1H), 1.66 (d, J = 8.0 Hz, 1H), 1.40-1.53 (m, 3H), 1.16-1.28 (m, 1H), 0.98-1.08 (m, 1H), 0.40-0.49 (m, 2H), 0.20-0.37 (m, 2H). |
| I-358 | 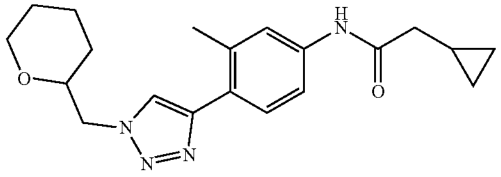 [SMILES: Cc1cc(NC(=O)CC2CC2)ccc1-c1cn(CC2CCCCO2)nn1] | 355.3 | $^1$H NMR (400 MHz, DMSO-$d_6$) δ 9.83 (s, 1H), 8.23 (s, 1H), 7.67 (d, J = 8.0 Hz, 1H), 7.50-7.54 (m, 2H), 4.36-4.48 (m, 2H), 3.84-3.88 (m, 1H), 3.71-3.77 (m, 1H), 3.29-3.25 (m, 1H), 2.40 (s, 3H), 2.21 (d, J = 7.6 Hz, 2H), 1.79-1.81 (m, 1H), 1.62-1.65 (m, 1H), 1.39-1.52 (m, 3H), 1.19-1.25 (m, 1H), 1.03-1.08 (m, 1H), 0.46-0.51 (m, 2H), 0.18-0.22 (m, 2H). |
| I-359 | 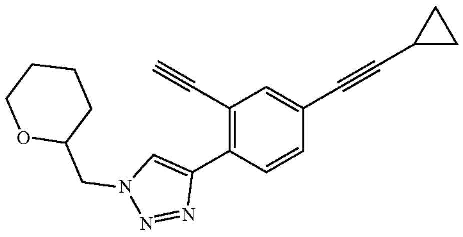 [SMILES: C#Cc1cc(C#CC2CC2)ccc1-c1cn(CC2CCCCO2)nn1] | 332.1 | $^1$H NMR (400 MHz, DMSO-$d_6$) δ 8.67 (s, 1H), 8.06 (d, J = 8.0 Hz, 1H), 7.54 (d, J = 1.6 Hz, 1H), 7.48 (dd, J = 1.6 Hz, 8.0 Hz, 1H), 4.58 (s, 1H), 4.41-4.55 (m, 2H), 3.86-3.89 (m, 1H), 3.67-3.72 (m, 1H), 3.28-3.34 (m, 1H), 1.77-1.81 (m, 1H), 1.43-1.66 (m, 5H), 1.16-1.20 (m, 1H), 0.88-0.93 (m, 2H), 0.74-0.79 (m, 2H). |
| I-360 | 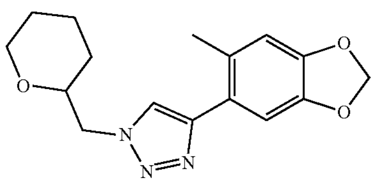 [SMILES: Cc1cc2c(cc1-c1cn(CC3CCCCO3)nn1)OCO2] | 302.1 | $^1$H NMR (400 MHz, DMSO-$d_6$) δ 8.22 (s, 1H), 7.26 (s, 1H), 6.89 (s, 1H), 6.02 (s, 2H), 4.35-4.47 (m, 2H), 3.84-3.87 (m, 1H), 3.67-3.80 (m, 1H), 3.29-3.34 (m, 1H), 2.33 (s, 3H), 1.78-1.81 (m, 1H), 1.62-1.65 (m, 1H), 1.40-1.53 (m, 3H), 1.16-1.24 (m, 1H). |

TABLE 4-continued

| Compound No. | Chemical Structure | [M + H] observed | $^1$H NMR (400 MHz) |
|---|---|---|---|
| | Characterization Data for Additional Exemplary Compounds | | |
| I-34 | 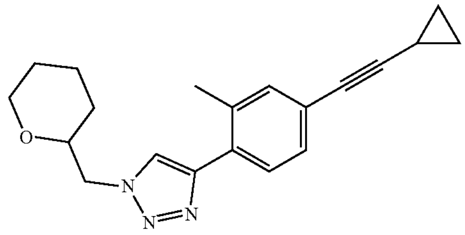 [SMILES: Cc1cc(C#CC2CC2)ccc1-c1cn(CC2CCCCO2)nn1] | 322.2 | $^1$H NMR (400 MHz, DMSO-d6) δ 7.80 (s, 1H), 7.75 (d, J = 8.3 Hz, 1H), 7.30-7.26 (m, 2H), 4.51 (dd, J = 14.2, 3.0 Hz, 1H), 4.32 (dd, J = 14.2, 7.5 Hz, 1H), 4.02-3.94 (m, 1H), 3.69 (dtd, J = 9.9, 5.2, 2.7 Hz, 1H), 3.44-3.34 (m, 1H), 2.43 (s, 3H), 1.88 (dq, J = 6.2, 3.9, 2.9 Hz, 1H), 1.71-1.63 (m, 1H), 1.58-1.50 (m, 3H), 1.50-1.40 (m, 1H), 1.33-1.19 (m, 1H), 0.91-0.77 (m, 4H). |
| I-39 | 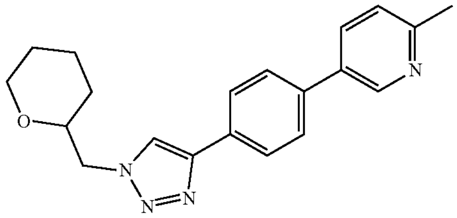 [SMILES: Cc1ccc(-c2ccc(-c3cn(CC4CCCCO4)nn3)cc2)cn1] | 335.2 | $^1$H NMR (400 MHz, $CDCl_3$) δ 8.76 (s, 1H), 7.97-7.91 (m, 3H), 7.80 (dd, J = 8.0, 2.2 Hz, 1H), 7.63 (d, J = 8.2 Hz, 2H), 7.23 (d, J = 8.0 Hz, 1H), 4.51 (dd, J = 14.1, 2.8 Hz, 1H), 4.32 (dd, J = 14.1, 7.5 Hz, 1H), 4.00 (d, J = 10.8 Hz, 1H), 3.75-3.66 (m, 1H), 3.45-3.35 (m, 1H), 2.60 (s, 3H), 1.88 (s, 1H), 1.68 (d, J = 12.9 Hz, 1H), 1.60-1.45 (m, 3H), 1.34-1.21 (m, 1H). |
| I-40 | 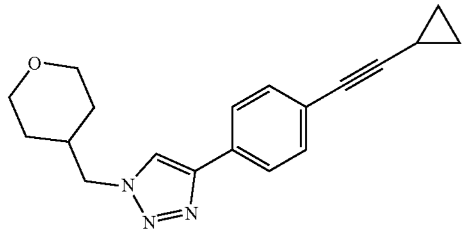 [SMILES: C(#CC1CC1)c1ccc(-c2cn(CC3CCOCC3)nn2)cc1] | 328.2 | $^1$H NMR (400 MHz, $CDCl_3$) δ 7.73 (d, J = 8.6 Hz, 2H), 7.70 (s, 1H), 7.42 (d, J = 8.6 Hz, 2H), 4.26 (d, J = 7.3 Hz, 2H), 3.97 (dd, J = 11.6, 2.6 Hz, 2H), 3.36 (td, J = 11.8, 2.2 Hz, 2H), 2.20 (ttt, J = 11.3, 7.4, 3.8 Hz, 1H), 1.59-1.51 (m, 2H), 1.50-1.33 (m, 3H), 0.92-0.77 (m, 4H). |
| I-41 | 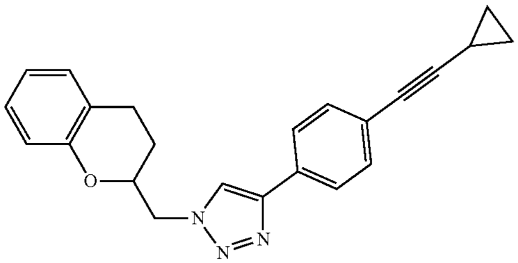 [SMILES: C(#CC1CC1)c1ccc(-c2cn(CC3CCc4ccccc4O3)nn2)cc1] | 356.2 | C $^1$H NMR (400 MHz, $CDCl_3$) δ 7.96 (s, 1H), 7.78-7.72 (m, 2H), 7.43 (d, J = 8.6 Hz, 2H), 7.11 (td, J = 8.1, 1.4 Hz, 1H), 7.05 (d, J = 7.5 Hz, 1H), 6.91-6.81 (m, 2H), 4.73 (dd, J = 14.3, 3.5 Hz, 1H), 4.64 (dd, J = 14.3, 6.3 Hz, 1H), 4.42 (tdd, J = 8.5, 3.4, 2.2 Hz, 1H), 2.90 (ddd, J = 17.3, 11.5, 6.0 Hz, 1H), 2.78 (ddd, J = 16.6, 5.5, 2.8 Hz, 1H), 2.10 (ddt, J = 13.5, 5.9, 2.8 Hz, 1H), 1.67 (dtd, J = 13.4, 11.6, 5.7 Hz, 1H), 1.46 (tt, J = 8.2, 5.1 Hz, 1H), 0.93-0.78 (m, 4H). |
| I-42 | 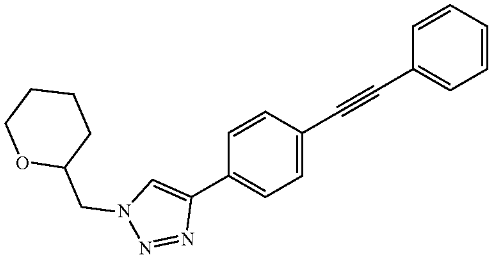 [SMILES: C(#Cc1ccc(-c2cn(CC3CCCCO3)nn2)cc1)c1ccccc1] | 344.2 | $^1$H NMR (400 MHz, $CDCl_3$ δ 7.93 (s, 1H), 7.85 (d, J = 8.2 Hz, 2H), 7.59 (d, J = 8.2 Hz, 2H), 7.57-7.51 (m, 2H), 7.42-7.29 (m, 3H), 4.51 (dd, J = 14.2, 2.9 Hz, 1H), 4.32 (dd, J = 14.2, 7.6 Hz, 1H), 4.00 (dd, J = 11.2, 1.9 Hz, 1H), 3.69 (ddt, J = 10.1, 7.5, 2.6 Hz, 1H), 3.40 (td, J = 11.3, 3.9 Hz, 1H), 1.93-1.82 (m, 1H), 1.72-1.64 (m, 1H), 1.60-1.45 (m, 3H), 1.34-1.21 (m, 1H). |
| I-43 | 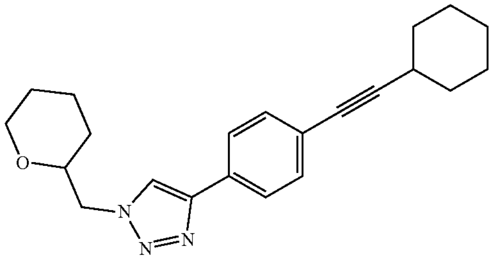 [SMILES: C(#CC1CCCCC1)c1ccc(-c2cn(CC3CCCCO3)nn2)cc1] | 350.2 | $^1$H NMR (400 MHz, $CDCl_3$ δ 7.89 (s, 1H), 7.76 (d, J = 8.6 Hz, 2H), 7.44 (d, J = 8.5 Hz, 2H), 4.49 (dd, J = 14.2, 3.0 Hz, 1H), 4.30 (dd, J = 14.2, 7.6 Hz, 1H), 3.99 (dt, J = 11.7, 2.0 Hz, 1H), 3.73-3.63 (m, 1H), 3.39 (td, J = 11.3, 3.8 Hz, 1H), 2.59 (tt, J = 9.1, 3.7 Hz, 1H), 1.94-1.82 (m, 3H), 1.82-1.71 (m, 2H), 1.67 (d, J = 10.9 Hz, 1H), 1.61-1.48 (m, 6H), 1.48-1.20 (m, 5H). |

TABLE 4-continued

Characterization Data for Additional Exemplary Compounds

| Compound No. | Chemical Structure | [M + H] observed | $^1$H NMR (400 MHz) |
|---|---|---|---|
| I-44 | 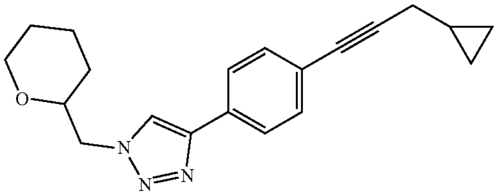 [SMILES: C(#Cc1ccc(-c2cn(CC3CCCCO3)nn2)cc1)CC1CC1] | 322.2 | $^1$H NMR (400 MHz, $CDCl_3$ δ 7.89 (s, 1H), 7.77 (d, J = 8.6 Hz, 2H), 7.45 (d, J = 8.5 Hz, 2H), 4.49 (dd, J = 14.2, 3.0 Hz, 1H), 4.30 (dd, J = 14.2, 7.5 Hz, 1H), 3.99 (dt, J = 11.7, 1.9 Hz, 1H), 3.68 (ddt, J = 9.9, 7.6, 2.6 Hz, 1H), 3.39 (td, J = 11.3, 3.8 Hz, 1H), 2.48 (d, J = 5.9 Hz, 2H), 1.88 (dd, J = 6.0, 3.1 Hz, 1H), 1.73-1.62 (m, 1H), 1.60-1.44 (m, 3H), 1.33-1.20 (m, 1H), 1.08-0.95 (m, 1H), 0.56-0.47 (m, 2H), 0.34-0.27 (m, 2H). |
| I-47 | 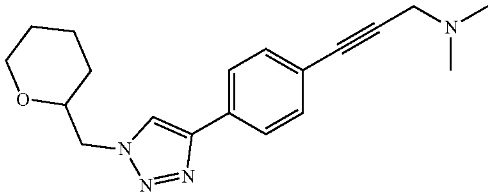 [SMILES: CN(C)CC#Cc1ccc(-c2cn(CC3CCCCO3)nn2)cc1] | 325.2 | $^1$H NMR ($CDCl_3$, 400 MHz) δ 7.89 (s, 1H), 7.77 (d, J = 8.6 Hz, 2H), 7.47 (d, J = 8.6 Hz, 2H), 4.47 (dd, J = 14.2, 3.0 Hz, 1H), 4.28 (dd, J = 14.2, 7.6 Hz, 1H), 4.01-3.93 (m, 1H), 3.66 (ddt, J = 12.8, 7.5, 2.6 Hz, 1H), 3.46 (s, 2H), 3.42-3.31 (m, 1H), 2.36 (s, 6H), 1.89-1.79 (m, 1H), 1.69-1.61 (m, 1H), 1.56-1.45 (m, 2H), 1.31-1.18 (m, 1H) ppm. |
| I-49 | 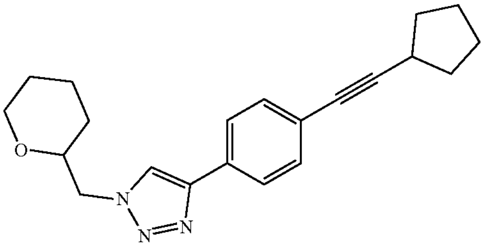 [SMILES: C(#CC1CCCC1)c1ccc(-c2cn(CC3CCCCO3)nn2)cc1] | 336.2 | $^1$H NMR (400 MHz, $CDCl_3$) δ 7.84 (s, 1H), 7.72 (d, J = 8.3 Hz, 2H), 7.39 (d, J = 8.3 Hz, 2H), 4.41 (dd, J = 14.2, 3.0 Hz, 1H), 4.23 (dd, J = 14.2, 7.6 Hz, 1H), 3.92 (d, J = 11.0 Hz, 1H), 3.61 (td, J = 8.4, 2.5 Hz, 1H), 3.31 (td, J = 11.2, 4.0 Hz, 1H), 2.79 (p, J = 7.5 Hz, 1H), 2.03-1.89 (m, 2H), 1.89-1.76 (m, 1H), 1.76-1.61 (m, 4H), 1.61-1.50 (m, 3H), 1.50-1.39 (m, 3H), 1.32-1.08 (m, 1H). |
| I-55 | 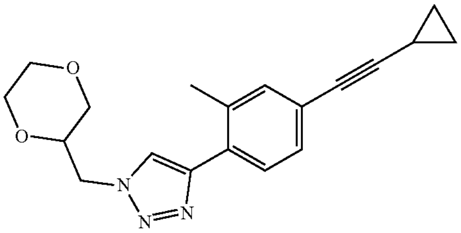 [SMILES: Cc1cc(C#CC2CC2)ccc1-c1cn(CC2COCCO2)nn1] | 324.2 | $^1$H NMR (400 MHz, $CDCl_3$) δ 7.78 (s, 1H), 7.73 (d, J = 7.9 Hz, 1H), 7.31-7.26 (m, 2H), 4.50 (dd, J = 14.4, 3.5 Hz, 1H), 4.38 (dd, J = 14.4, 6.8 Hz, 1H), 3.99 (ddt, J = 10.0, 6.5, 3.1 Hz, 1H), 3.86 (dd, J = 11.6, 2.6 Hz, 1H), 3.81 (dd, J = 11.2, 2.7 Hz, 1H), 3.77-3.67 (m, 2H), 3.60-3.50 (m, 1H), 3.28 (dd, J = 11.5, 10.1 Hz, 1H), 2.43 (s, 3H), 1.51-1.40 (m, 1H), 0.92-0.78 (m, 5H). |
| I-57 | 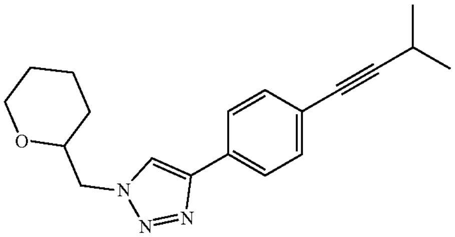 [SMILES: CC(C)C#Cc1ccc(-c2cn(CC3CCCCO3)nn2)cc1] | 310.2 | $^1$H NMR ($CDCl_3$, 400 MHz) δ 7.89 (s, 1H), 7.76 (d, J = 8.2 Hz, 2H), 7.44 (d, J = 8.3 Hz, 2H), 4.49 (dd, J = 14.2, 3.0 Hz, 1H), 4.30 (dd, J = 14.2, 7.6 Hz, 1H), 4.10-3.84 (m, 1H), 3.77-3.60 (m, 1H), 3.39 (td, J = 11.3, 3.8 Hz, 1H), 2.78 (dq, J = 13.8, 6.9 Hz, 1H), 1.91-1.84 (m, 1H), 1.67 (d, J = 13.6 Hz, 1H), 1.59-1.46 (m, 3H), 1.38-1.23 (m, 7H). |
| I-58 | 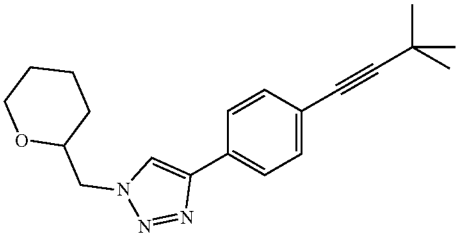 [SMILES: CC(C)(C)C#Cc1ccc(-c2cn(CC3CCCCO3)nn2)cc1] | 324.1 | $^1$H NMR ($CDCl_3$, 400 MHz) δ 7.89 (s, 1H), 7.82-7.69 (m, 2H), 7.51-7.32 (m, 2H), 4.49 (dd, J = 14.2, 3.0 Hz, 1H), 4.30 (dd, J = 14.2, 7.6 Hz, 1H), 3.99 (dt, J = 11.9, 2.0 Hz, 1H), 3.68 (ddt, J = 12.8, 7.6, 2.6 Hz, 1H), 3.46-3.32 (m, 1H), 1.93-1.80 (m, 1H), 1.68-1.62 (m, 1H), 1.58-1.47 (m, 5H), 1.32 (s, 9H), 1.28-1.22 (m, 1H). |

TABLE 4-continued

Characterization Data for Additional Exemplary Compounds

| Compound No. | Chemical Structure | [M + H] observed | $^1$H NMR (400 MHz) |
|---|---|---|---|
| I-59 | 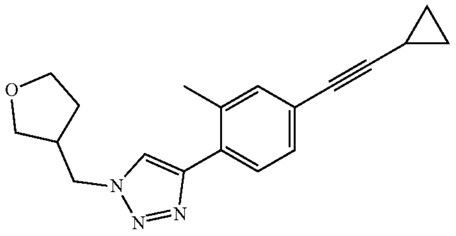 [SMILES: Cc1cc(C#CC2CC2)ccc1-c1cn(CC2CCOC2)nn1] | 308.1 | $^1$H NMR (400 MHz, $CDCl_3$) δ 7.72 (d, J = 7.8 Hz, 1H), 7.65 (s, 1H), 7.32-7.27 (m, 2H), 4.40 (dd, J = 7.6, 1.2 Hz, 2H), 3.95 (td, J = 8.3, 5.4 Hz, 1H), 3.88-3.74 (m, 2H), 3.66 (dd, J = 9.1, 4.9 Hz, 1H), 3.00-2.86 (m, 1H), 2.43 (s, 3H), 2.11 (dtd, J = 13.4, 8.1, 5.5 Hz, 1H), 1.74 (td, J = 12.7, 7.5 Hz, 1H), 1.51-1.40 (m, 1H), 0.87 (dtd, J = 10.5, 5.0, 2.6 Hz, 2H), 0.84-0.79 (m, 2H). |
| I-60 | 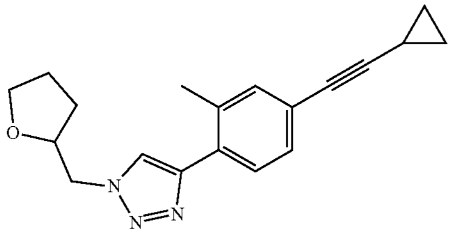 [SMILES: Cc1cc(C#CC2CC2)ccc1-c1cn(CC2CCCO2)nn1] | 308.1 | $^1$H NMR (400 MHz, $CDCl_3$ δ 7.83 (s, 1H), 7.73 (d, J = 7.8 Hz, 1H), 7.27 (d, J = 10.8 Hz, 2H), 4.60 (dd, J = 14.2, 3.4 Hz, 1H), 4.44 (dd, J = 14.2, 5.8 Hz, 1H), 4.28 (tq, J = 6.9, 3.4 Hz, 1H), 3.87-3.72 (m, 2H), 2.43 (s, 3H), 2.07 (dtd, J = 12.3, 7.3, 4.8 Hz, 1H), 1.93-1.82 (m, 1H), 1.79-1.57 (m, 3H), 1.51-1.40 (m, 1H), 0.90-0.84 (m, 2H), 0.84-0.78 (m, 2H). |
| I-61 | 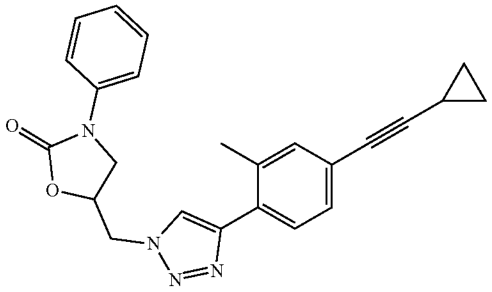 [SMILES: Cc1cc(C#CC2CC2)ccc1-c1cn(CC2CN(c3ccccc3)C(=O)O2)nn1] | 399.2 | $^1$H NMR (400 MHz, $CDCl_3$) δ 7.88 (s, 1H), 7.65 (d, J = 7.9 Hz, 1H), 7.42-7.36 1H), 2H), 7.35-7.30 (m, 2H), 7.29-7.23 (m, 2H), 7.16-7.09 (m, 1H), 5.08 (ddt, J = 8.9, 6.1, 4.4 Hz, 1H), 4.85-4.71 (m, 2H), 4.20 (t, J = 9.1 Hz, 1H), 3.97 (dd, J = 9.4, 6.1 Hz, 1H), 2.38 (s, 3H), 1.45 (tt, J = 8.1, 5.1 Hz, 1H), 0.91-0.84 (m, 2H), 0.84-0.78 (m, 2H). |
| I-62 | 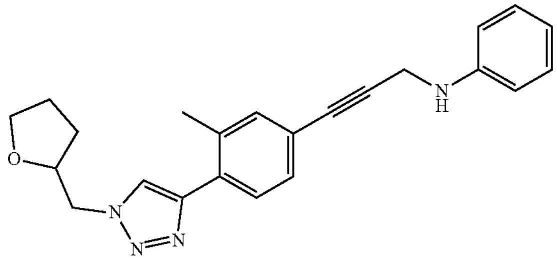 [SMILES: Cc1cc(C#CCNc2ccccc2)ccc1-c1cn(CC2CCCO2)nn1] | 373.2 | $^1$H NMR (400 MHz, $CDCl_3$ δ 7.84 (s, 1H), 7.76 (d, J = 8.6 Hz, 1H), 7.32-7.28 (m, 2H), 7.26-7.21 (m, 2H), 6.79 (t, J = 7.4 Hz, 1H), 6.75 (dd, J = 8.6, 1.1 Hz, 2H), 4.61 (dd, J = 14.1, 3.3 Hz, 1H), 4.45 (dd, J = 14.2, 5.9 Hz, 1H), 4.28 (ddt, J = 10.2, 6.9, 3.2 Hz, 1H), 4.17 (s, 2H), 3.97 (s, 1H), 3.87-3.73 (m, 2H), 2.44 (s, 3H), 2.14-2.02 (m, 1H), 1.96-1.82 (m, 1H), 1.80-1.59 (m, 2H). |
| I-66 | 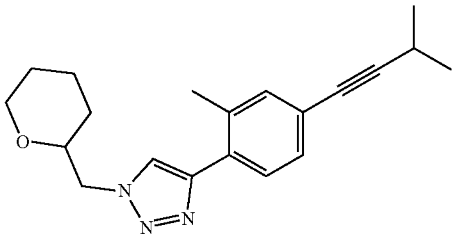 [SMILES: Cc1cc(C#CC(C)C)ccc1-c1cn(CC2CCCCO2)nn1] | 324.2 | $^1$H NMR (400 MHz, $CDCl_3$ δ 7.80 (s, 1H), 7.76 (d, J = 7.8 Hz, 1H), 7.34-7.27 (m, 2H), 4.51 (dd, J = 14.2, 3.0 Hz, 1H), 4.32 (dd, J = 14.2, 7.6 Hz, 1H), 3.98 (dd, J = 10.9, 2.0 Hz, 1H), 3.75-3.65 (m, 1H), 3.44-3.35 (m, 1H), 2.78 (hept, J = 6.8 Hz, 1H), 2.44 (s, 3H), 1.93-1.80 (m, 1H), 1.71-1.64 (m, 1H), 1.59-1.48 (m, 3H), 1.32-1.26 (m, 4H), 1.26 (s, 3H). |
| I-67 | 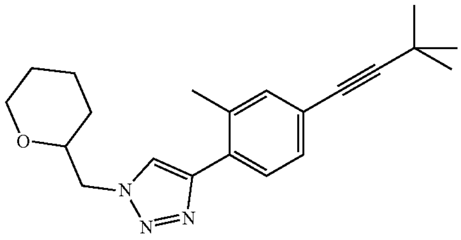 [SMILES: Cc1cc(C#CC(C)(C)C)ccc1-c1cn(CC2CCCCO2)nn1] | 338.2 | $^1$H NMR (400 MHz, $CDCl_3$ δ 7.80 (s, 1H), 7.76 (d, J = 8.0 Hz, 1H), 7.29 (ddd, J = 9.5, 1.7, 0.7 Hz, 2H), 4.51 (dd, J = 14.2, 3.0 Hz, 1H), 4.32 (dd, J = 14.2, 7.6 Hz, 8.2 1H), 4.02-3.95 (m, 1H), 3.74-3.65 (m, 1H), 3.40 (ddd, J = 11.4, 9.1, 4.5 Hz, 1H), 2.44 (s, 3H), 1.93-1.83 (m, 1H), 1.71-1.63 (m, 1H), 1.58-1.49 (m, 3H), 1.32 (s, 9H), 1.29-1.24 (m, 1H). |

TABLE 4-continued

Characterization Data for Additional Exemplary Compounds

| Compound No. | Chemical Structure | [M + H] observed | $^1$H NMR (400 MHz) |
| --- | --- | --- | --- |
| I-68 | 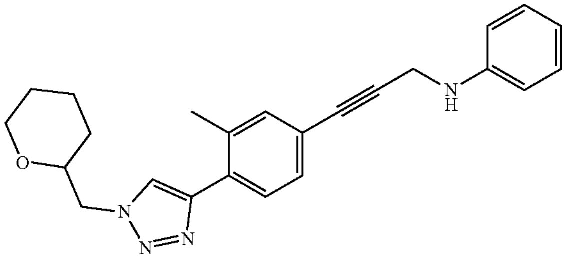 | 387.2 | $^1$H NMR (400 MHz, $CDCl_3$ δ 7.81 (s, 1H), 7.78 (d, J = 8.6 Hz, 1H), 7.32-7.29 (m, 2H), 7.26-7.21 (m, 2H), 6.79 (td, J = 7.4, 1.1 Hz, 1H), 6.77-6.71 (m, 2H), 4.52 (dd, J = 14.2, 3.0 Hz, 1H), 4.33 (dd, J = 14.2, 7.6 Hz, 1H), 4.17 (s, 2H), 3.98 (d, J = 10.4 Hz, 2H), 3.75-3.65 (m, 1H), 3.45-3.35 (m, 1H), 2.44 (s, 3H), 1.93-1.84 (m, 1H), 1.68 (d, J = 12.5 Hz, 1H), 1.56-1.48 (m, 3H), 1.32-1.20 (m, 1H). |
| I-72 | 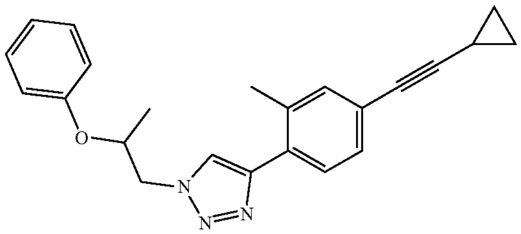 [SMILES: Cc1cc(C#CC2CC2)ccc1-c1cn(CC(C)Oc2ccccc2)nn1] | 358.2 | $^1$H NMR (400 MHz, $CDCl_3$) δ 7.79 (s, 1H), 7.69 (d, J = 8.6 Hz, 1H), 7.30-7.24 (m, 4H), 6.99-6.92 (m, 1H), 6.82 (dd, J = 8.7, 1.0 Hz, 2H), 4.81 (dh, J = 9.5, 3.1 Hz, 1H), 4.72 (dd, J = 14.2, 3.2 Hz, 1H), 4.56 (dd, J = 14.2, 7.3 Hz, 1H), 2.35 (s, 3H), 1.45 (tt, J = 8.2, 5.1 Hz, 1H), 1.38 (d, J = 6.2 Hz, 3H), 0.90-0.84 (m, 2H), 0.84-0.78 (m, 2H). |
| I-73 | 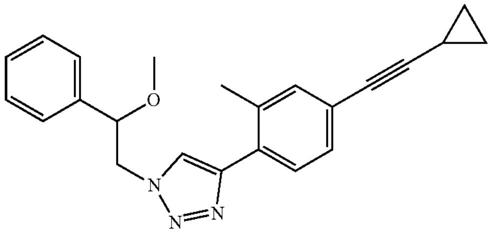 [SMILES: COC(Cn1cc(-c2ccc(C#CC3CC3)cc2C)nn1)c1ccccc1] | 358.2 | $^1$H NMR (400 MHz, $CDCl_3$) δ 7.73 (d, J = 8.7 Hz, 1H), 7.68 (s, 1H), 7.44-7.31 (m, 5H), 7.28 (dd, J = 7.8, 0.9 Hz, 2H), 4.67-4.56 (m, 2H), 4.51 (td, J = 12.0, 5.3 Hz, 1H), 3.23 (s, 3H), 2.39 (s, 3H), 1.50-1.40 (m, 1H), 0.91-0.85 (m, 2H), 0.85-0.79 (m, 2H). |
| I-78 | 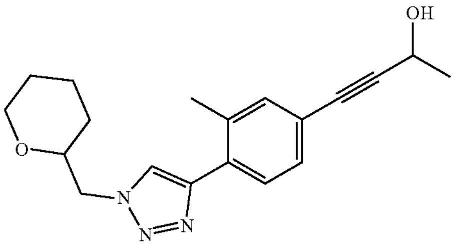 [SMILES: Cc1cc(C#CC(C)O)ccc1-c1cn(CC2CCCCO2)nn1] | 326.2 | $^1$H NMR (400 MHz, $CDCl_3$ δ 7.83 (s, 1H), 7.80 (d, J = 8.0 Hz, 1H), 7.37-7.31 (m, 2H), 4.82-4.73 (m, 1H), 4.53 (dd, J = 14.2, 3.0 Hz, 1H), 4.33 (dd, J = 14.2, 7.6 Hz, 1H), 3.99 (dd, J = 10.8, 2.0 Hz, 1H), 3.76-3.65 (m, 1H), 3.45-3.36 (m, 1H), 2.46 (s, 3H), 1.95-1.81 (m, 2H), 1.69 (d, J = 12.7 Hz, 1H), 1.61-1.47 (m, 6H), 1.34-1.21 (m, 1H). |
| I-79 | 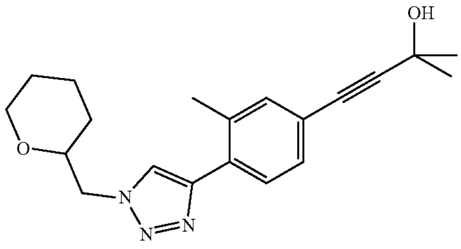 [SMILES: Cc1cc(C#CC(C)(C)O)ccc1-c1cn(CC2CCCCO2)nn1] | 340.2 | $^1$H NMR (400 MHz, $CDCl_3$ δ 7.82 (s, 1H), 7.79 (d, J = 8.0 Hz, 1H), 7.36-7.30 (m, 2H), 4.53 (dd, J = 14.2, 3.0 Hz, 1H), 4.33 (dd, J = 14.2, 7.6 Hz, 1H), 3.99 (dd, J = 10.8, 2.1 Hz, 1H), 3.75-3.65 (m, 1H), 3.45-3.35 (m, 1H), 2.45 (s, 3H), 2.02 (s, 1H), 1.89 (d, J = 5.3 Hz, 1H), 1.69 (d, J = 12.9 Hz, 1H), 1.63 (s, 6H), 1.60-1.46 (m, 4H), 1.35-1.18 (m, 2H). |
| I-83 | 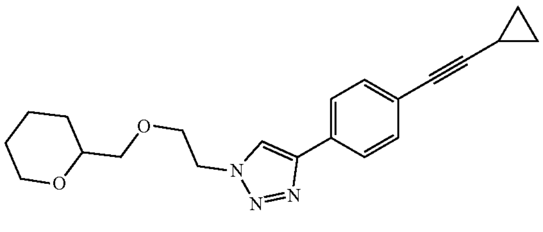 [SMILES: C(#CC1CC1)c1ccc(-c2cn(CCOCC3CCCCO3)nn2)cc1] | 352.2 | $^1$H NMR (400 MHz, $CDCl_3$) δ 8.03 (s, 1H), 7.74 (d, J = 8.6 Hz, 2H), 7.42 (d, J = 8.5 Hz, 2H), 4.62-4.55 (m, 2H), 4.01 (dt, J = 11.3, 2.1 Hz, 1H), 3.88 (ddd, J = 6.1, 5.0, 3.1 Hz, 2H), 3.54-3.37 (m, 4H), 1.87-1.79 (m, 1H), 1.61-1.40 (m, 5H), 1.35-1.23 (m, 1H), 0.96-0.85 (m, 2H), 0.85-0.76 (m, 2H). |

TABLE 4-continued

Characterization Data for Additional Exemplary Compounds

| Compound No. | Chemical Structure | [M + H] observed | $^1$H NMR (400 MHz) |
|---|---|---|---|
| I-84 | 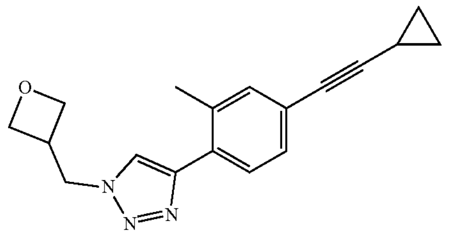 [SMILES: Cc1cc(C#CC2CC2)ccc1-c1cn(CC2COC2)nn1] | 294.1 | $^1$H NMR (400 MHz, $CDCl_3$) δ 7.69 (d, J = 7.9 Hz, 1H), 7.62 (s, 1H), 7.32-7.22 (m, 2H), 4.88 (dd, J = 7.6, 6.6 Hz, 2H), 4.73 (d, J = 7.6 Hz, 2H), 4.60-4.50 (m, 2H), 3.62 (dtd, J = 13.3, 7.6, 1.8 Hz, 1H), 2.42 (s, 3H), 1.45 (tt, J = 8.2, 5.1 Hz, 1H), 0.91-0.78 (m, 4H). |
| I-85 | 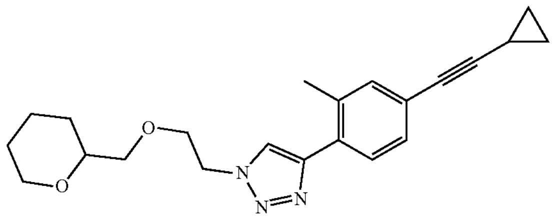 [SMILES: Cc1cc(C#CC2CC2)ccc1-c1cn(CCOCC2CCCCO2)nn1] | 366.2 | $^1$H NMR (400 MHz, $CDCl_3$) δ 7.88 (s, 1H), 7.72 (d, J = 8.1 Hz, 1H), 7.26-7.21 (m, 2H), 4.61-4.54 (m, 2H), 3.95 (dt, J = 11.4, 2.0 Hz, 1H), 3.91-3.79 (m, 2H), 3.48-3.32 (m, 4H), 2.40 (s, 3H), 1.84-1.75 (m, 1H), 1.59-1.36 (m, 5H), 1.32-1.20 (m, 1H), 0.97-0.81 (m, 2H), 0.81-0.73 (m, 2H) |
| I-93 | 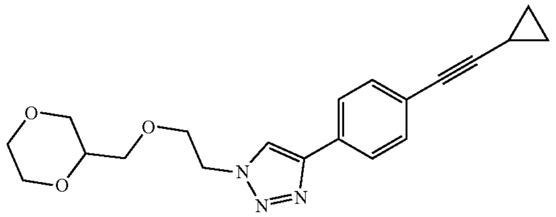 [SMILES: C(#CC1CC1)c1ccc(-c2cn(CCOCC3COCCO3)nn2)cc1] | 354.2 | $^1$H NMR ($CDCl_3$, 400 MHz): δ 7.93 (d, J = 1.2 Hz, 1H), 7.76-7.69 (m, 2H), 4.58-4.53 (m, 2H), 3.91-3.81 (m, 2H), 3.81-3.64 (m, 5H), 3.63-3.50 (m, 1H), 3.48-3.38 (m, 2H), 3.38-3.28 (m, 1H), 1.52-1.37 (m, 1H), 0.95-0.83 (m, 2H), 0.83-0.73 (m, 2H). |
| I-94 | 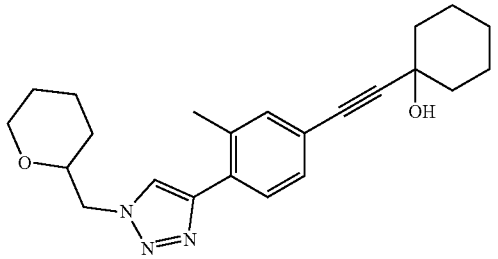 [SMILES: Cc1cc(C#CC2(O)CCCCC2)ccc1-c1cn(CC2CCCCO2)nn1] | 380.2 | $^1$H NMR ($CDCl_3$, 400 MHz) δ 7.82 (s, 1H), 7.78 (d, J = 7.8 Hz, 1H), 7.35-7.30 (m, 2H), 4.51 (dd, J = 14.2, 3.0 Hz, 1H), 4.33 (dd, J = 14.2, 7.6 Hz, 1H), 4.02-3.95 (m, 1H), 3.70 (ddt, J = 10.7, 7.5, 2.5 Hz, 1H), 3.39 (td, J = 11.3, 4.6 Hz, 1H), 2.44 (s, 3H), 2.29 (s, 1H), 2.02-1.96 (m, 1H), 1.90-1.83 (m, 1H), 1.79-1.46 (m, 12H), 1.34-1.23 (m, 2H). |
| I-122 | 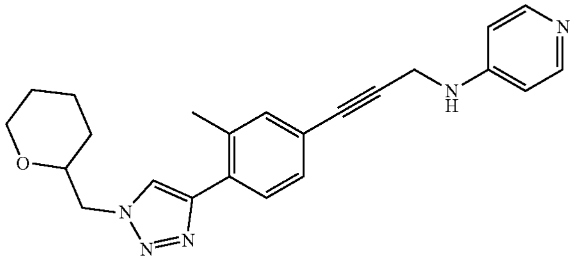 [SMILES: Cc1cc(C#CCNc2ccncc2)ccc1-c1cn(CC2CCCCO2)nn1] | 388.2 | $^1$H NMR (400 MHz, $CDCl_3$) δ 8.22 (br s, 2H), 7.82 (s, 1H), 7.78 (d, J = 8.6 Hz, 1H), 7.33-7.26 (m, 2H), 6.64 (br s, 2H), 5.38 (br s, 1H), 4.52 (dd, J = 14.2, 2.9 Hz, 1H), 4.33 (dd, J = 14.2, 7.6 Hz, 1H), 4.21 (d, J = 5.2 Hz, 2H), 4.10-3.93 (m, 1H), 3.78-3.58 (m, 1H), 3.46-3.29 (m, 1H), 2.43 (s, 3H), 1.94-1.84 (m, 1H), 1.72-1.64 (m, 1H), 1.57-1.44 (m, 3H), 1.38-1.19 (m, 1H). |
| I-131 | 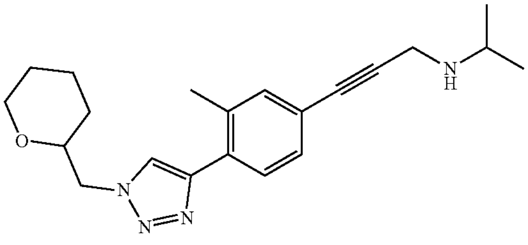 [SMILES: Cc1cc(C#CCNC(C)C)ccc1-c1cn(CC2CCCCO2)nn1] | 353.2 | $^1$H NMR (400 MHz, $CDCl_3$) δ 7.81 (s, 1H), 7.81-7.74 (m, 1H), 7.33 (s, 1H), 7.31 (d, J = 1.4 Hz, 1H), 4.51 (dd, J = 14.2, 3.0 Hz, 1H), 4.33 (dd, J = 14.2, 7.6 Hz, 1H), 4.07-3.92 (m, 2H), 3.73 (s, 2H), 3.68 (dt, J = 7.5, 2.3 Hz, 1H), 3.47-3.33 (m, 1H), 3.32-3.16 (m, J = 6.5 Hz, 1H), 2.44 (s, 3H), 1.93-1.82 (m, 1H), 1.66 (t, J = 13.6 Hz, 1H), 1.41-1.33 (m, 3H), 1.31-1.21 (m, 1H), 1.20 (d, J = 6.3 Hz, 6H). |

TABLE 4-continued

Characterization Data for Additional Exemplary Compounds

| Compound No. | Chemical Structure | [M + H] observed | $^{1}$H NMR (400 MHz) |
|---|---|---|---|
| I-159 | 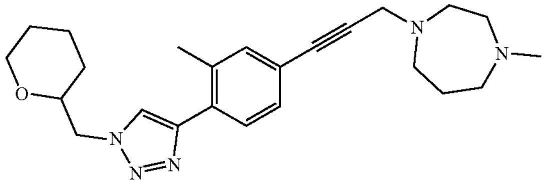 [SMILES: Cc1cc(C#CCN2CCCN(C)CC2)ccc1-c1cn(CC2CCCCO2)nn1] | 408.2 | $^{1}$H NMR (400 MHz, $CDCl_3$) δ 7.81 (s, 1H), 7.77 (d, J = 7.9 Hz, 1H), 7.34-7.26 (m, 2H), 4.50 (dd, J = 14.2, 3.0 Hz, 1H), 4.31 (dd, J = 14.2, 7.6 Hz, 1H), 4.04-3.89 (m, 1H), 3.68 (ddt, J = 10.4, 7.5, 2.5 Hz, 1H), 3.61 (s, 2H), 3.50 (qd, J = 10.7, 10.1, 5.4 Hz, 1H), 3.40-3.29 (m, 1H), 3.27-3.11 (m, 4H), 3.09-2.98 (m, 2H), 2.90 (t, J = 6.3 Hz, 2H), 2.72 (s, 3H), 2.43 (s, 3H), 2.19 (dt, J = 11.9, 6.2 Hz, 2H), 1.86 (d, J = 5.3 Hz, 1H), 1.66 (d, J = 13.0 Hz, 1H), 1.57-1.44 (m, 2H), 1.36-1.18 (m, 1H). |
| I-176 | 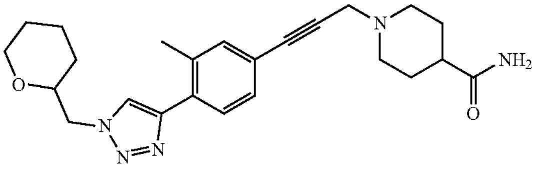 [SMILES: Cc1cc(C#CCN2CCC(C(N)=O)CC2)ccc1-c1cn(CC2CCCCO2)nn1] | 422.2 | $^{1}$H NMR (400 MHz, $CDCl_3$) δ 7.82 (s, 1H), 7.78 (d, J = 8.5 Hz, 1H), 7.33 (d, J = 7.5 Hz, 2H), 5.58 (d, J = 18.1 Hz, 2H), 4.52 (dd, J = 14.2, 2.9 Hz, 1H), 4.33 (dd, J = 14.2, 7.6 Hz, 1H), 4.04-3.88 (m, 1H), 3.69 (dddd, J = 15.4, 10.4, 6.3, 3.0 Hz, 1H), 3.55 (s, 2H), 3.47-3.34 (m, 1H), 3.05 (d, J = 11.4 Hz, 2H), 2.45 (s, 3H), 2.36 (t, J = 10.8 Hz, 2H), 2.29-2.13 (m, 1H), 2.05-1.92 (m, 2H), 1.84 (ddt, J = 20.9, 11.8, 6.7 Hz, 3H), 1.68 (d, J = 12.8 Hz, 1H), 1.60-1.47 (m, 3H), 1.47-1.38 (m, 1H), 1.38-1.17 (m, 2H). |
| I-177 | 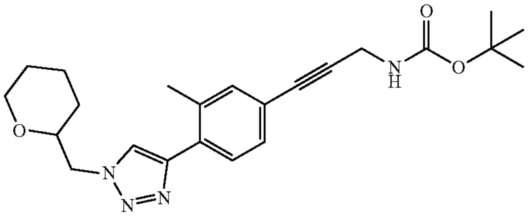 [SMILES: Cc1cc(C#CCNC(=O)OC(C)(C)C)ccc1-c1cn(CC2CCCCO2)nn1] | 411.2 | $^{1}$H NMR (400 MHz, $CDCl_3$) δ 7.82 (s, 1H), 7.79 (d, J = 8.4 Hz, 1H), 7.35-7.28 (m, 2H), 4.77 (s, 1H), 4.52 (dd, J = 14.2, 3.0 Hz, 1H), 4.33 (dd, J = 14.2, 7.6 Hz, 1H), 4.17 (d, J = 4.6 Hz, 2H), 3.99 (dd, J = 10.7, 2.1 Hz, 1H), 3.75-3.66 (m, 1H), 3.44-3.35 (m, 1H), 2.45 (s, 3H), 1.93-1.85 (m, 1H), 1.68 (d, J = 12.6 Hz, 1H), 1.56-1.51 (m, 3H), 1.47 (s, 9H), 1.34-1.20 (m, 1H). |
| I-193 | 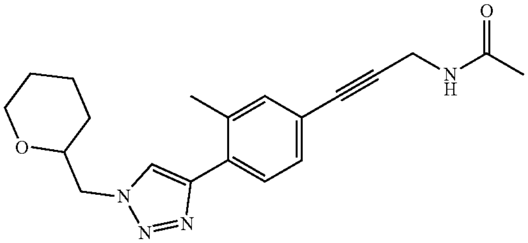 [SMILES: CC(=O)NCC#Cc1ccc(-c2cn(CC3CCCCO3)nn2)c(C)c1] | 352.2 | $^{1}$H NMR (400 MHz, $CDCl_3$) δ 7.82 (s, 1H), 7.79 (d, J = 7.8 Hz, 1H), 7.35-7.28 (m, 2H), 5.85 (s, 1H), 4.52 (dd, J = 14.2, 2.9 Hz, 1H), 4.33 (dd, J = 14.2, 7.6 Hz, 1H), 4.28 (d, J = 5.2 Hz, 2H), 4.02-3.93 (m, 1H), 3.70 (ddt, J = 11.0, 7.5, 2.5 Hz, 1H), 3.44-3.34 (m, 1H), 2.44 (s, 3H), 2.04 (s, 3H), 1.88 (d, J = 4.9 Hz, 1H), 1.66 (s, 1H), 1.59-1.48 (m, 3H), 1.33-1.19 (m, 1H). |
| I-194 | 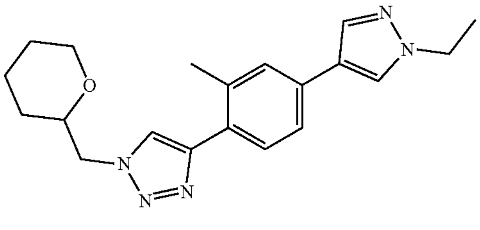 [SMILES: CCn1cc(-c2ccc(-c3cn(CC4CCCCO4)nn3)c(C)c2)cn1] | 352.2 | $^{1}$H NMR (400 MHz, $CD_3CN$) δ 7.96 (s, 1H), 7.90 (s, 1H), 7.80 (s, 1H), 7.76 (d, J = 8.0 Hz, 1H), 7.50-7.48 (m, 1H), 7.43 (dd, J = 8.0, 1.9 Hz, 1H), 4.44 (dd, J = 14.2, 3.7 Hz, 1H), 4.36 (dd, J = 14.2, 7.6 Hz, 1H), 4.17 (q, J = 7.3 Hz, 2H), 3.94-3.86 (m, 1H), 3.79-3.70 (m, 1H), 3.42-3.32 (m, 1H), 2.47 (s, 3H), 1.88-1.80 (m, 1H), 1.71-1.63 (m, 1H), 1.60-1.48 (m, 3H), 1.45 (t, J = 7.3 Hz, 3H), 1.31-1.18 (m, 1H). |
| I-208 | 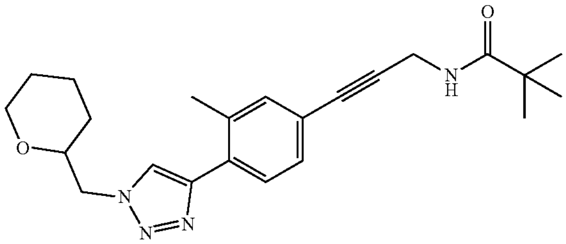 [SMILES: Cc1cc(C#CCNC(=O)C(C)(C)C)ccc1-c1cn(CC2CCCCO2)nn1] | 395.2 | $^{1}$H NMR (400 MHz, DMSO-$d_6$) δ 8.34 (s, 1H), 8.02 (t, J = 5.5 Hz, 1H), 7.76 (d, J = 8.0 Hz, 1H), 7.33 (s, 1H), 7.29 (dd, J = 8.0, 1.7 Hz, 1H), 4.46 (dd, J = 14.1, 3.9 Hz, 1H), 4.38 (dd, J = 14.1, 7.8 Hz, 1H), 4.09 (d, J = 5.5 Hz, 2H), 3.83 (dt, J = 11.0, 1.9 Hz, 1H), 3.77-3.68 (m, 1H), 3.29 (td, J = 11.1, 3.1 Hz, 1H), 2.41 (s, 3H), 1.83-1.73 (m, 1H), 1.62 (d, J = 12.1 Hz, 1H), 1.53-1.35 (m, 3H), 1.27-1.13 (m, 1H), 1.11-1.06 (m, 9H). |

TABLE 4-continued

Characterization Data for Additional Exemplary Compounds

| Compound No. | Chemical Structure | [M + H] observed | $^1$H NMR (400 MHz) |
|---|---|---|---|
| I-209 | 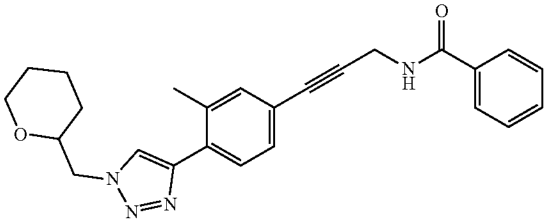 [SMILES: Cc1cc(C#CCNC(=O)c2ccccc2)ccc1-c1cn(CC2CCCCO2)nn1] | 415.2 | $^1$H NMR (400 MHz, DMSO-$d_6$) δ 9.05 (t, J = 5.5 Hz, 1H), 8.34 (s, 1H), 7.94-7.85 (m, 2H), 7.77 (d, J = 8.0 Hz, 1H), 7.58-7.50 (m, 1H), 7.50-7.43 (m, 2H), 7.37 (s, 1H), 7.32 (dd, J = 8.1, 1.6 Hz, 1H), 4.46 (dd, J = 14.1, 3.9 Hz, 1H), 4.42-4.37 (m, 1H), 4.33 (d, J = 5.5 Hz, 2H), 3.86-3.79 (m, 1H), 3.72 (dtd, J = 11.1, 6.0, 4.9, 2.7 Hz, 1H), 3.28 (td, J = 11.0, 3.1 Hz, 1H), 2.41 (s, 3H), 1.82-1.71 (m, 1H), 1.61 (d, J = 12.5 Hz, 1H), 1.53-1.34 (m, 3H), 1.25-1.11 (m, 1H). |
| I-210 | 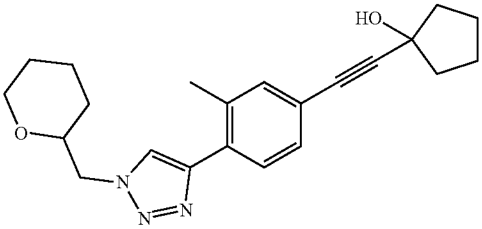 [SMILES: Cc1cc(C#CC2(O)CCCC2)ccc1-c1cn(CC2CCCCO2)nn1] | 366.2 | $^1$H NMR (400 MHz, $CDCl_3$) δ 7.81 (s, 1H), 7.75 (d, J = 7.8 Hz, 1H), 7.27 (d, J = 10.4 Hz, 2H), 4.49 (dd, J = 14.2, 3.0 Hz, 1H), 4.31 (dd, J = 14.2, 7.6 Hz, 1H), 4.00-3.87 (m, 1H), 3.68 (dtd, J = 10.8, 5.0, 2.5 Hz, 1H), 3.37 (td, J = 11.2, 4.4 Hz, 1H), 2.57 (d, J = 8.0 Hz, 1H), 2.41 (s, 3H), 2.12-1.95 (m, 5H), 1.95-1.80 (m, 4H), 1.77 (ddd, J = 13.2, 8.4, 3.2 Hz, 2H), 1.65 (d, J = 14.1 Hz, 2H), 1.30-1.12 (m, 1H). |
| I-215 | 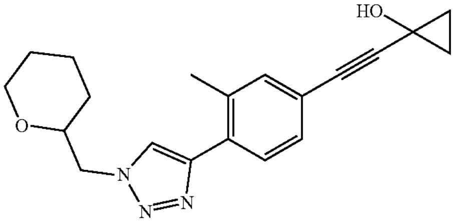 [SMILES: Cc1cc(C#CC2(O)CC2)ccc1-c1cn(CC2CCCCO2)nn1] | 338.2 | $^1$H NMR (400 MHz, $CDCl_3$) δ 7.82 (s, 1H), 7.77 (d, J = 7.9 Hz, 1H), 7.27 (d, J = 9.8 Hz, 2H), 4.51 (dd, J = 14.1, 2.8 Hz, 1H), 4.33 (dd, J = 14.2, 7.6 Hz, 1H), 3.98 (d, J = 10.7 Hz, 1H), 3.76-3.62 (m, 1H), 3.50-3.24 (m, 2H), 2.42 (s, 3H), 1.87 (d, J = 5.7 Hz, 1H), 1.67 (d, J = 12.5 Hz, 1H), 1.57-1.43 (m, 2H), 1.26 (td, J = 14.4, 13.8, 5.3 Hz, 2H), 1.20-1.13 (m, 2H), 1.13-1.02 (m, 2H). |
| I-221 | 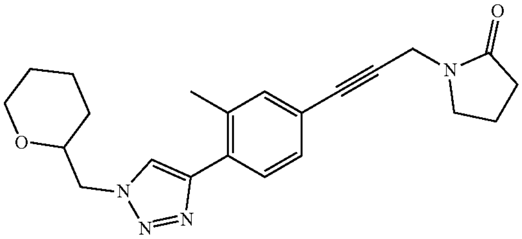 [SMILES: Cc1cc(C#CCN2CCCC2=O)ccc1-c1cn(CC2CCCCO2)nn1] | 379.2 | $^1$H NMR (400 MHz, $CDCl_3$) δ 7.81 (s, 1H), 7.77 (d, J = 8.6 Hz, 1H), 7.30 (d, J = 7.4 Hz, 2H), 4.49 (dd, J = 14.2, 3.0 Hz, 1H), 4.40-4.24 (m, 3H), 4.02-3.90 (m, 1H), 3.68 (ddt, J = 10.9, 7.5, 2.6 Hz, 1H), 3.60-3.49 (m, 2H), 3.37 (td, J = 11.3, 5.0 Hz, 1H), 2.43 (s, 3H), 2.40 (d, J = 8.3 Hz, 2H), 2.12-2.02 (m, 2H), 1.91-1.81 (m, 1H), 1.65 (d, J = 13.1 Hz, 1H), 1.55-1.44 (m, 3H), 1.30-1.17 (m, 1H). |
| I-312 | 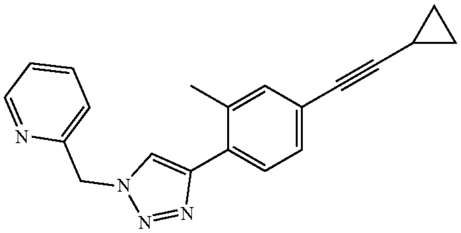 [SMILES: Cc1cc(C#CC2CC2)ccc1-c1cn(Cc2ccccn2)nn1] | 315.1 | $^1$H NMR (400 MHz, $CDCl_3$) δ 8.60 (s, 1H), 7.84 (s, 1H), 7.72 (dd, J = 7.8, 4.9 Hz, 2H), 7.41-7.21 (m, 4H), 5.71 (s, 2H), 2.40 (s, 3H), 1.51-1.37 (m, 1H), 0.92-0.70 (m, 4H). |
| I-224 | 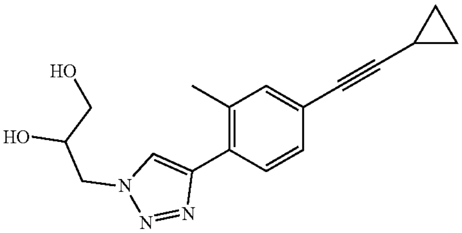 [SMILES: Cc1cc(C#CC2CC2)ccc1-c1cn(CC(O)CO)nn1] | 298.1 | $^1$H NMR (400 MHz, $CD_3CN$) δ 8.01 (s, 1H), 7.74 (d, J = 8.0 Hz, 1H), 7.31-7.28 (m, 1H), 7.25 (ddd, J = 8.0, 1.7, 0.4 Hz, 1H), 4.54 (dd, J = 14.1, 3.7 Hz, 1H), 4.36 (dd, J = 14.1, 7.9 Hz, 1H), 4.05-3.95 (m, 1H), 3.55-3.43 (m, 2H), 3.12 (br s, 2H), 2.43 (s, 3H), 1.75-1.42 (m, 1H), 0.94-0.84 (m, 2H), 0.77-0.70 (m, 2H). |

TABLE 4-continued

Characterization Data for Additional Exemplary Compounds

| Compound No. | Chemical Structure | [M + H] observed | $^1$H NMR (400 MHz) |
|---|---|---|---|
| I-233 | 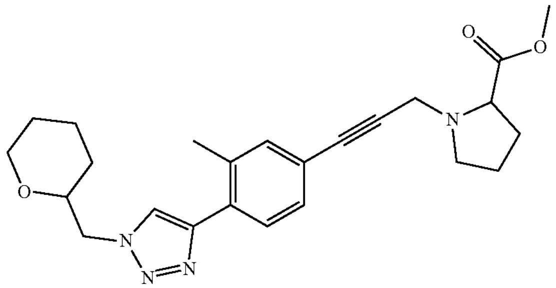 [SMILES: COC(=O)C1CCCN1CC#Cc1ccc(-c2cn(CC3CCCCO3)nn2)c(C)c1] | 423.2 | $^1$H NMR (400 MHz, $CDCl_3$) δ 7.81 (s, 1H), 7.81-7.74 (m, 1H), 7.32 (d, J = 6.8 Hz, 2H), 4.51 (dd, J = 14.2, 3.0 Hz, 1H), 4.32 (dd, J = 14.2, 7.6 Hz, 1H), 4.03-3.95 (m, 1H), 3.80 (d, J = 1.8 Hz, 2H), 3.76-3.74 (m, 3H), 3.69 (ddd, J = 7.9, 5.7, 2.6 Hz, 1H), 3.51 (dd, J = 9.2, 6.6 Hz, 1H), 3.38 (td, J = 11.3, 4.9 Hz, 1H), 3.19-3.09 (m, 1H), 2.79 (td, J = 9.0, 7.6 Hz, 1H), 2.44 (s, 3H), 2.26-2.12 (m, 1H), 2.07-1.94 (m, 2H), 1.94-1.76 (m, 3H), 1.67 (d, J = 13.1 Hz, 1H), 1.59-1.47 (m, 2H), 1.35-1.21 (m, 1H). |
| I-247 | 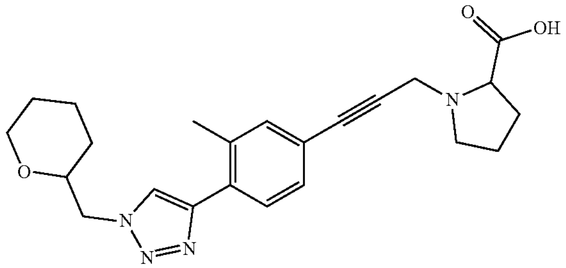 [SMILES: Cc1cc(C#CCN2CCCC2C(=O)O)ccc1-c1cn(CC2CCCCO2)nn1] | 409.2 | $^1$H NMR (400 MHz, $CDCl_3$) δ 7.88-7.76 (m, 2H), 7.32 (d, J = 7.1 Hz, 2H), 4.32 (dd, J = 14.2, 7.6 Hz, 1H), 4.06 (s, 1H), 4.05-3.93 (m, 2H), 3.88 (s, 1H), 3.70 (ddd, J = 11.5, 5.9, 2.5 Hz, 1H), 3.60 (d, J = 29.1 Hz, 1H), 3.46-3.34 (m, 1H), 3.29 (s, 1H), 3.10 (d, J = 7.4 Hz, 1H), 2.44 (s, 4H), 2.41-2.28 (m, 3H), 1.96 (dtdd, J = 4.3, 1.6, 0.8, 0.4 Hz, 1H), 1.95-1.87 (m, 1H), 1.67 (d, J = 12.9 Hz, 1H), 1.62-1.46 (m, 1H), 1.33-1.05 (m, 2H), 0.89 (d, J = 7.5 Hz, 1H). |
| I-259 | 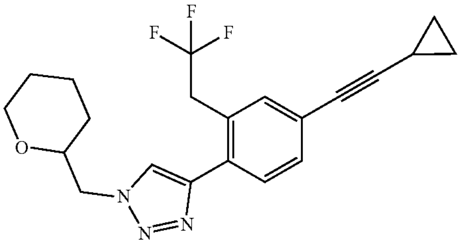 [SMILES: FC(F)(F)Cc1cc(C#CC2CC2)ccc1-c1cn(CC2CCCCO2)nn1] | 390.1 | $^1$H NMR (400 MHz, $CD_3CN$) δ 8.00 (s, 1H), 7.54 (d, J = 8.0 Hz, 1H), 7.44 (s, 1H), 7.40 (dd, J = 8.0, 1.8 Hz, 1H), 4.45 (dd, J = 14.2, 3.6 Hz, 1H), 4.37 (dd, J = 14.2, 7.5 Hz, 1H), 4.01 (qd, J = 11.1, 1.1 Hz, 2H), 3.94-3.85 (m, 1H), 3.72 (dddd, J = 11.1, 7.5, 3.5, 2.2 Hz, 1H), 3.42-3.32 (m, 1H), 1.88-1.80 (m, 1H), 1.70-1.61 (m, 1H), 1.60-1.42 (m, 4H), 1.29-1.15 (m, , 1H), 0.94-0.87 (m, 2H), 0.80-0.73 (m, 2H). |
| I-265 | 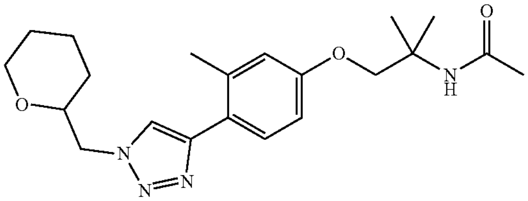 [SMILES: CC(=O)NC(C)(C)COc1ccc(-c2cn(CC3CCCCO3)nn2)c(C)c1] | 387.2 | $^1$H NMR (400 MHz, $CD_3CN$) δ 7.87 (s, 1H), 7.65 (d, J = 8.5 Hz, 1H), 6.87 (d, J = 2.7 Hz, 1H), 6.83 (dd, J = 8.5, 2.7 Hz, 1H), 6.28 (br. s, 1H), 4.42 (dd, J = 14.2, 3.8 Hz, 1H), 4.35 (dd, J = 14.2, 7.5 Hz, 1H), 4.08 (s, 2H), 3.93-3.86 (m, 1H), 3.74 (dddd, J = 11.2, 7.5, 3.7, 2.2 Hz, 1H), 3.41-3.33 (m, 1H), 2.41 (s, 3H), 1.88-1.81 (m, 1H), 1.80 (s, 3H), 1.69-1.62 (m, 1H), 1.60-1.44 (m, 3H), 1.38 (s, 6H), 1.31-1.18 (m, 1H). |
| I-267 | 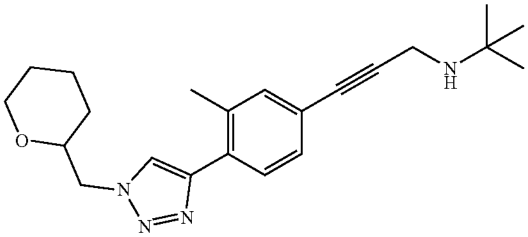 [SMILES: Cc1cc(C#CCNC(C)(C)C)ccc1-c1cn(CC2CCCCO2)nn1] | 367.2 | $^1$H NMR (400 MHz, $CDCl_3$) δ 7.80 (s, 1H), 7.79-7.72 (m, 1H), 7.32 (d, J = 7.4 Hz, 2H), 4.51 (dd, J = 14.2, 3.0 Hz, 1H), 4.32 (dd, J = 14.2, 7.5 Hz, 1H), 4.04-3.93 (m, 1H), 3.70 (dt, J = 8.2, 2.3 Hz, 1H), 3.66 (s, 2H), 3.39 (td, J = 11.3, 4.8 Hz, 1H), 2.43 (s, 3H), 1.92-1.83 (m, 1H), 1.67 (d, J = 13.0 Hz, 1H), 1.65-1.56 (m, 1H), 1.56-1.48 (m, 2H), 1.27 (dd, J = 11.0, 7.6 Hz, 2H), 1.21 (s, 9H). |
| I-287 | 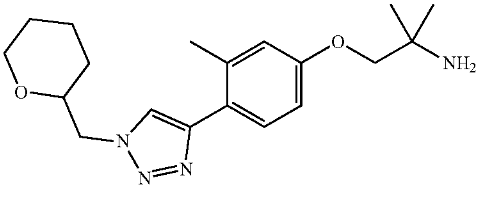 [SMILES: Cc1cc(OCC(C)(C)N)ccc1-c1cn(CC2CCCCO2)nn1] | 345.2 | $^1$H NMR (400 MHz, $CD_3CN$) δ 7.87 (s, 1H), 7.65 (d, J = 8.5 Hz, 1H), 6.87 (d, J = 2.6 Hz, 1H), 6.83 (dd, J = 8.5, 2.6 Hz, 1H), 4.41 (dd, J = 14.2, 3.8 Hz, 1H), 4.34 (dd, J = 14.2, 7.5 Hz, 1H), 3.93-3.85 (m, 1H), 3.77-3.70 (m, 1H), 3.70 (s, 2H), 3.39-3.33 (m, 1H), 2.41 (s, 3H), 1.83 (br. s, 2H), 1.82-1.79 (m, 1H), 1.66-1.62 (m, 1H), 1.57-1.42 (m, 3H), 1.25-1.21 (m, 1H), 1.15 (s, 6H). |

TABLE 4-continued

Characterization Data for Additional Exemplary Compounds

| Compound No. | Chemical Structure | [M + H] observed | $^1$H NMR (400 MHz) |
|---|---|---|---|
| I-288 | 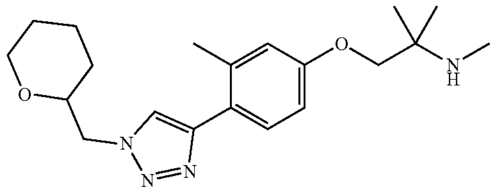 [SMILES: CNC(C)(C)COc1ccc(-c2cn(CC3CCCCO3)nn2)c(C)c1] | 359.2 | $^1$H NMR (400 MHz, $CD_3CN$) δ 7.89 (s, 1H), 7.66 (d, J = 8.5 Hz, 1H), 6.91 (d, J = 2.6 Hz, 1H), 6.87 (dd, J = 8.5, 2.6 Hz, 1H), 4.42 (dd, J = 14.2, 3.7 Hz, 1H), 4.35 (dd, J = 14.2, 7.5 Hz, 1H), 4.02 (s, 2H), 3.90-3.87 (m, 1H), 3.73 (dddd, J = 11.2, 7.5, 3.7, 2.2 Hz, 1H), 3.40-3.32 (m, 1H), 2.50 (s, 3H), 2.41 (s, 3H), 1.87-1.80 (m, 1H), 1.68-1.61 (m, 1H), 1.56-1.46 (m, 3H), 1.37 (s, 6H), 1.29-1.19 (m, 1H). |
| I-289 | 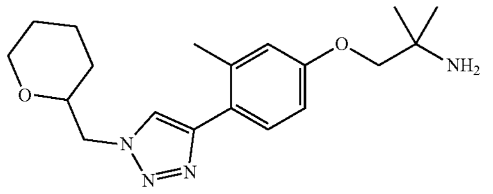 [SMILES: Cc1cc(OCC(C)(C)N)ccc1-c1cn(CC2CCCCO2)nn1] | 373.2 | $^1$H NMR (400 MHz, $CD_3CN$) δ 7.66 (d, J = 8.5 Hz, 1H), 6.90 (d, J = 2.1 Hz, 1H), 6.86 (dd, J = 8.6, 2.4 Hz, 1H), 4.42 (dd, J = 14.2, 3.7 Hz, 1H), 4.35 (dd, J = 14.2, 7.5 Hz, 1H), 3.96 (s, 2H), 3.93-3.86 (m, 1H), 3.77-3.70 (m, 1H), 3.41-3.33 (m, 1H), 2.43 (s, 6H), 2.42 (s, 3H), 1.88-1.81 (m, 1H), 1.68-1.64 (m, 1H), 1.57-1.45 (m, 1H), 1.30-1.22 (m, 7H). |
| I-290 | 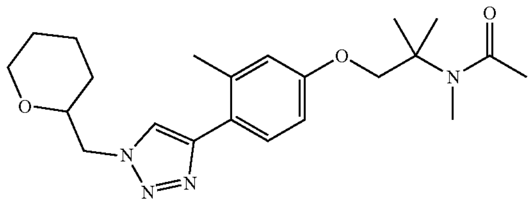 [SMILES: CC(=O)N(C)C(C)(C)COc1ccc(-c2cn(CC3CCCCO3)nn2)c(C)c1] | 401.2 | $^1$H NMR (400 MHz, $CD_3CN$) δ 7.87 (s, 1H), 7.64 (d, J = 8.5 Hz, 1H), 6.85 (d, J = 2.6 Hz, 1H), 6.81 (dd, J = 8.5, 2.6 Hz, 1H), 4.42 (dd, J = 14.2, 3.7 Hz, 1H), 4.35 (dd, J = 14.2, 7.5 Hz, 1H), 4.30 (s, 2H), 3.95-3.85 (m, 1H), 3.73 (dddd, J = 11.2, 7.5, 3.7, 2.2 Hz, 1H), 3.46-3.31 (m, 1H), 2.99 (s, 3H), 2.40 (s, 3H), 1.99 (s, 3H), 1.87-1.79 (m, 1H), 1.70-1.61 (m, 1H), 1.60-1.42 (m, 9H), 1.33-1.18 (m, 1H). |
| I-361 | 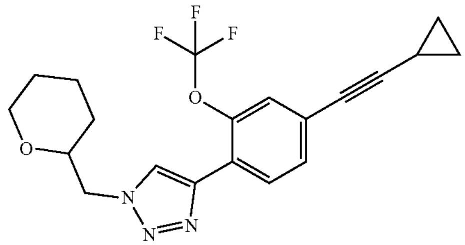 [SMILES: FC(F)(F)Oc1cc(C#CC2CC2)ccc1-c1cn(CC2CCCCO2)nn1] | 392.2 | $^1$H NMR (400 MHz, $CD_3CN$) δ 8.19 (d, J = 8.2 Hz, 1H), 8.12 (s, 1H), 7.42 (dd, J = 8.2, 1.6 Hz, 1H), 7.39-7.36 (m, 1H), 4.47 (dd, J = 14.2, 3.4 Hz, 1H), 4.38 (dd, J = 14.2, 7.6 Hz, 1H), 3.94-3.85 (m, 1H), 3.75-3.66 (m, 1H), 3.42-3.32 (m, 1H), 1.87-1.79 (m, 1H), 1.69-1.60 (m, 1H), 1.59-1.42 (m, 4H), 1.31-1.14 (m, 1H), 0.95-0.88 (m, 2H), 0.82-0.75 (m, 2H). |
| I-362 | 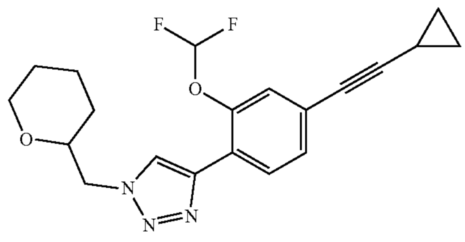 [SMILES: FC(F)Oc1cc(C#CC2CC2)ccc1-c1cn(CC2CCCCO2)nn1] | 374.2 | $^1$H NMR (400 MHz, $CD_3CN$) δ 8.19 (d, J = 8.1 Hz, 1H), 8.17 (s, 1H), 7.31 (dd, J = 8.1, 1.5 Hz, 1H), 7.21 (d, J = 0.9 Hz, 1H), 6.84 (t, J = 73.7 Hz, 1H), 4.45 (dd, J = 14.2, 3.5 Hz, 1H), 4.36 (dd, J = 14.2, 7.7 Hz, 1H), 3.93-3.85 (m, 1H), 3.77-3.67 (m, 1H), 3.41-3.30 (m, 1H), 1.89-1.79 (m, 1H), 1.72-1.62 (m, 1H), 1.61-1.43 (m, 4H), 1.33-1.17 (m, 1H), 0.96-0.86 (m, 2H), 0.82-0.72 (m, 2H). |

Example 4: Synthesis of I-69

Synthetic Scheme of I-69

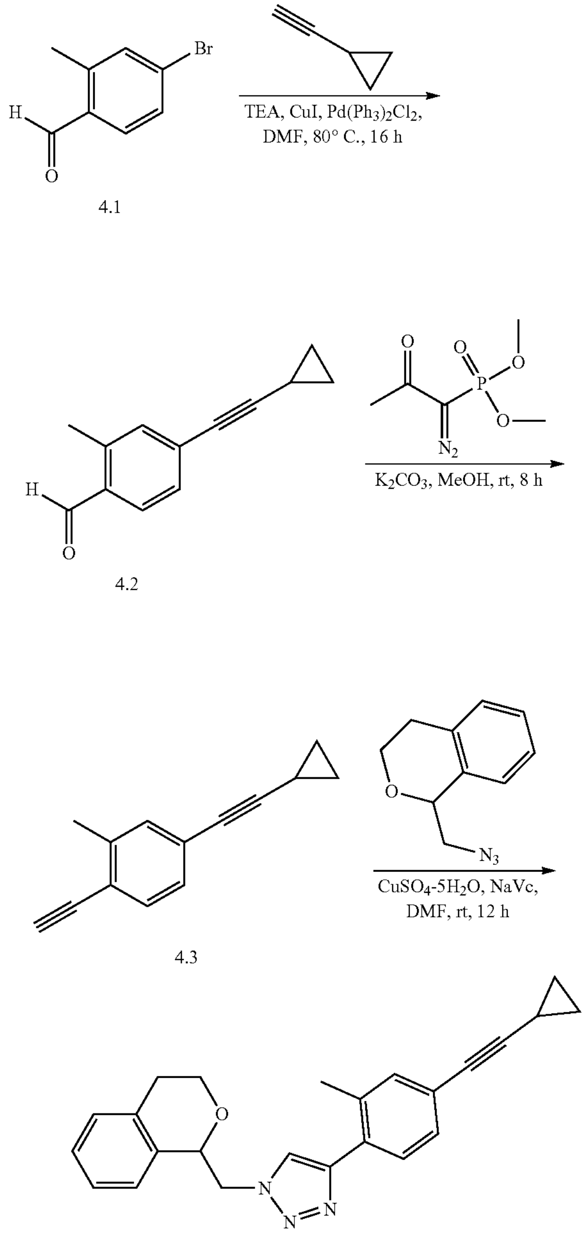

4.1

4.2

4.3

I-69

1. The Synthesis of Intermediate 4.2

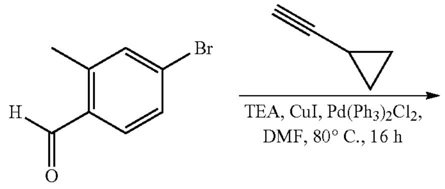

4.1

-continued

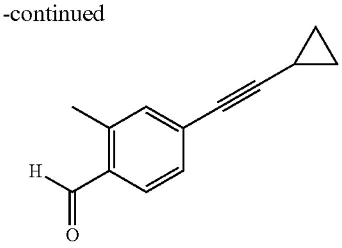

4.2

To a stirred solution of 4.1 (9 g, 45.45 mmol), ethynylcyclopropane (9 g, 136.35 mmol) and TEA (20 mL) in DMF (10 mL) was added $PdCl_2(PPh_3)_2$ (2.9 g) and CuI (455 mg). The reaction mixture was stirred at 80° C. for 16 hours until the reaction was complete. The suspension was diluted with $H_2O$ (20 mL) and extracted with EA (200 mL×2), concentrated. The crude product was purified by prep-HPLC to give 4.2 (7.3 g, yield: 87%) as brown oil. LC-MS m/z: 185.4 $[M+H]^+$.

2. The Synthesis of Intermediate 4.3

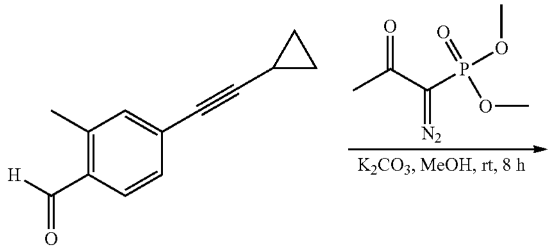

4.2

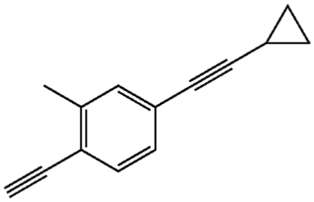

4.3

To a solution of 4.2 (7.3 g, 39.45 mmol) in MeOH (50 mL) was added $K_2CO_3$ (11 g, 79 mol), dimethyl 1-diazo-2-oxopropylphosphonate (7.57 g, 39.45 mmol). The mixture was stirred at RT for 8 h in $N_2$ atmosphere. The solvent was removed under reduced pressure. The residue was partitioned between water and ethyl acetate, and the organic layer was washed with brine and dried. The crude product was purified by flash column chromatography (silica gel, PE/EA=2:1) to give 4.3 (6.5 g, yield: 91.5%) as brown oil. LC-MS m/z: 181.7 $[M+H]^+$.

3. The Synthesis of I-69

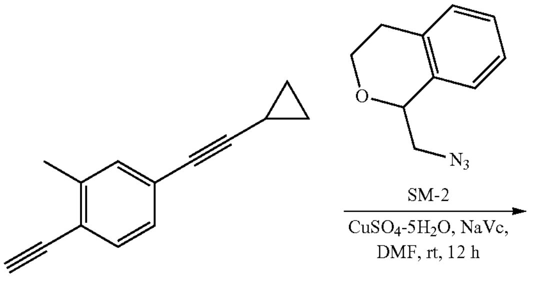

4.3

-continued

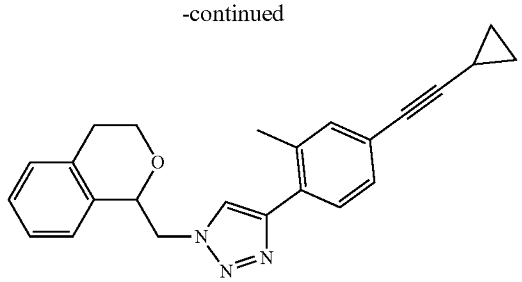

I-69

To a stirred solution of 4.3 (100 mg, 0.7 mmol) in DMF (5 mL) was added SM-2 (123 mg, 0.7 mmol), $CuSO_4.5H_2O$ (50 mg, 0.2 mmol), sodium ascorbate (40 mg, 0.2 mmol) at RT. Stirred at RT for 12 h. After the consumption of starting material (by LCMS), water (10 mL) was added, extracted with ethyl acetate (10 mL×3), washed with water (10 mL×3), dried and concentrated. The crude product was purified by pre-HPLC to give I-69 (55 mg, yield: 23%) as a white solid.

Additional exemplary compounds were prepared following methods substantially similar to the method described above and herein. Data for these compounds are provided below.

TABLE 5

Characterization Data for Additional Exemplary Compounds

| Compound No. | Chemical Structure | [M + H] observed | $^1$H NMR (400 MHz) |
|---|---|---|---|
| I-63 | 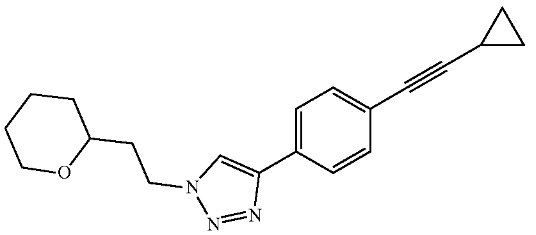 [SMILES: C(#CC1CC1)c1ccc(-c2cn(CCC3CCCCO3)nn2)cc1] | 321.4 | $^1$H NMR (400 MHz, DMSO-$d_6$) δ 8.60 (s, 1H), 7.79 (d, J = 8.4 Hz, 2H), 7.43 (d, J = 8.4 Hz, 2H), 4.45 (d, J = 7.2 Hz, 2H), 3.87-3.91 (m, 1H), 3.16-3.34 (m, 2H), 1.90-2.02 (m, 2H), 1.73-1.75 (m, 1H), 1.52-1.59 (m, 2H), 1.39-1.47 (m, 3H), 1.19-1.25 (m, 1H), 0.87-0.92 (m, 2H), 0.72-0.76 (m, 2H). |
| I-56 | 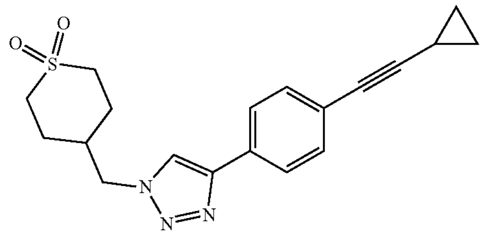 [SMILES: O=S1(=O)CCC(Cn2cc(-c3ccc(C#CC4CC4)cc3)nn2)CC1] | 355.4 | $^1$H NMR (400 MHz, DMSO-$d_6$) δ 8.59 (s, 1H), 7.80 (d, J = 8.4 Hz, 2H), 7.43 (d, J = 8.4 Hz, 2H), 4.41 (d, J = 7.2 Hz, 2H), 3.04-3.18 (m, 4H), 2.21-2.26 (m, 1H), 1.89-1.92 (m, 2H), 1.65-1.75 (m, 2H), 1.52-1.59 (m, 1H), 0.87-0.92 (m, 2H), 0.72-0.76 (m, 2H). |
| I-64 | 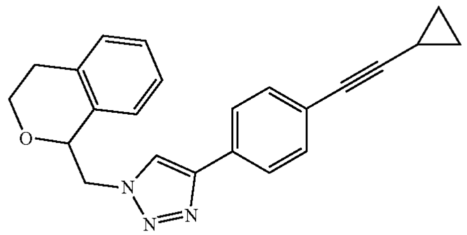 [SMILES: C(#CC1CC1)c1ccc(-c2cn(CC3OCCc4ccccc43)nn2)cc1] | 355.4 | $^1$H NMR (400 MHz, DMSO-$d_6$) δ 8.57 (s, 1H), 7.80 (d, J = 8.4 Hz, 2H), 7.38-7.43 (m, 3H), 7.16-7.27 (m, 3H), 5.18-5.20 (m, 1H), 4.91-4.96 (m, 1H), 4.73-4.79 (m, 1H), 4.07-4.12 (m, 1H), 3.70-3.76 (m, 1H), 2.69-2.82 (m, 2H), 1.52-1.58 (m, 1H), 0.87-0.92 (m, 2H), 0.73-0.76 (m, 2H). |

TABLE 5-continued

Characterization Data for Additional Exemplary Compounds

| Compound No. | Chemical Structure | [M + H] observed | $^1$H NMR (400 MHz) |
|---|---|---|---|
| I-69 | 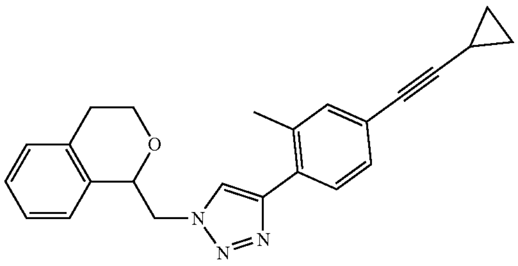 [SMILES: Cc1cc(C#CC2CC2)ccc1-c1cn(CC2OCCc3ccccc32)nn1] | 369.4 | $^1$H NMR (400 MHz, DMSO-$d_6$) δ 8.33 (s, 1H), 7.74 (d, J = 8.0 Hz, 1H), 7.16-7.40 (m, 6H), 5.22-5.24 (m, 1H), 4.91-4.95 (m, 1H), 4.77-4.83 (m, 1H), 4.06-4.12 (m, 1H), 3.70-3.76 (m, 1H), 2.69-2.80 (m, 2H), 2.37 (s, 3H), 1.52-1.57 (m, 1H), 0.87-0.92 (m, 2H), 0.72-0.76 (m, 2H). |
| I-70 | 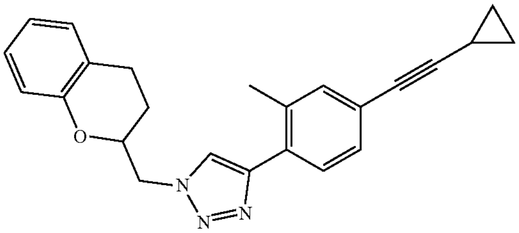 [SMILES: Cc1cc(C#CC2CC2)ccc1-c1cn(CC2CCc3ccccc3O2)nn1] | 369.4 | $^1$H NMR (400 MHz, DMSO-$d_6$) δ 8.46 (s, 1H), 7.76 (d, J = 8.0 Hz, 1H), 7.32 (s, 1H), 7.26-7.28 (m, 1H), 7.03-7.07 (m, 2H), 6.80-6.84 (m, 1H), 6.73 (d, J = 8.0 Hz, 1H), 4.69-4.80 (m, 2H), 4.50-4.53 (m, 1H), 2.76-2.86 (m, 2H), 2.42 (s, 3H), 2.07-2.11 (m, 1H), 1.53-1.63 (m, 2H), 0.87-0.92 (m, 2H), 0.72-0.76 (m, 2H). |
| I-363 | 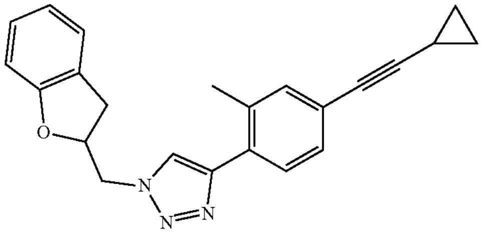 [SMILES: Cc1cc(C#CC2CC2)ccc1-c1cn(CC2Cc3ccccc3O2)nn1] | 355.4 | $^1$H NMR (400 MHz, DMSO-$d_6$): δ 8.42 (s, 1H), 7.70 (d, J = 8.0 Hz, 1H), 7.30 (s, 1H), 7.26 (d, J = 8.4 Hz, 1H), 7.20 (d, J = 7.2 Hz, 1H), 7.08 (t, J = 8.0 Hz, 1H), 6.76-6.83 (m, 2H), 5.26-5.29 (m, 1H), 4.68-4.79 (m, 2H), 3.38-3.42 (m, 1H), 3.03-3.08 (m, 1H), 2.35 (s, 3H), 1.53-1.57 (m, 1H), 0.85-0.92 (m, 2H), 0.72-0.76 (m, 2H). |
| I-100 | 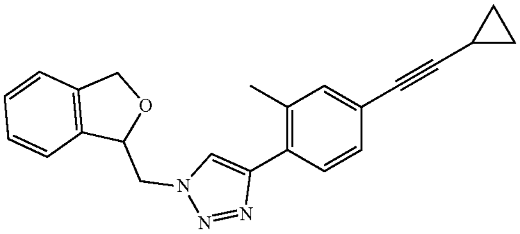 [SMILES: Cc1cc(C#CC2CC2)ccc1-c1cn(CC2OCc3ccccc32)nn1] | 356.0 | $^1$H NMR (400 MHz, DMSO-$d_6$) δ 8.21 (s, 1 H), 7.68 (d, J = 8.0 Hz, 1 H), 7.21-7.41 (m, δ H), 5.64-5.67 (m, 1 H), 4.99 (s, 2 H), 4.87-4.93 (m, 1 H), 4.67-4.75 (m, 1 H), 2.31 (s, 3 H), 1.51-1.59 (m, 1 H), 0.86-0.91 (m, 2 H), 0.71-0.78 (m, 2 H). |
| I-71 | 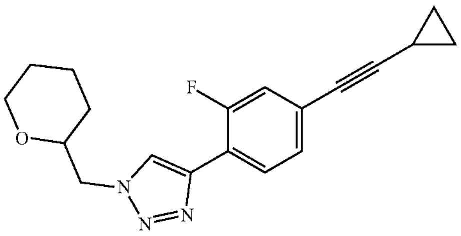 | 326.3 | $^1$H NMR (400 MHz, $CDCl_3$): δ 8.19 (t, J = 8.0 Hz, 1H), 8.04 (d, J = 4.0 Hz, 1H), 7.25 (dd, J = 8.0 Hz, 2.4 Hz, 1H), 7.14 (dd, J = 7.6 Hz, 2.4 Hz, 1H), 4.46-4.53 (m, 1H), 4.30-4.38 (m, 1H), 3.95-4.02 (m, 1H), 3.66-3.74 (m, 1H), 3.34-3.43 (m, 1H), 1.83-1.93 (m, 1H), 1.63-1.71 (m, 1H), 1.42-1.59 (m, 4H), 1.22-1.33 (m, 1H), 0.78-0.93 (m, 4H). |
| I-87 | 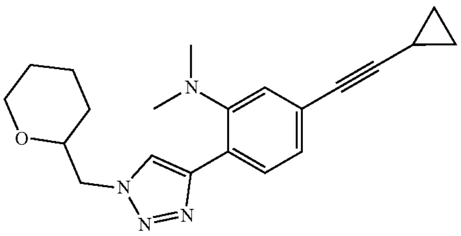 [SMILES: CN(C)c1cc(C#CC2CC2)ccc1-c1cn(CC2CCCCO2)nn1] | 351.3 | $^1$H NMR (400 MHz, DMSO-$d_6$): δ 8.40 (s, 1H), 7.98 (d, J = 8.0 Hz, 1H), 7.13 (s, 1H), 7.09 (d, J = 6.4 Hz, 1H), 4.39-4.51 (m, 2H), 3.85 (d, J = 10.8 Hz, 1H), 3.66-3.71 (m, 1H), 3.30 (s, 1H), 2.57 (s, 6H), 1.78 (d, J = 12.0 Hz, 1H), 1.41-1.64 (m, 5H), 1.12-1.22 (m, 1H), 0.87-0.92 (m, 2H), 0.73-0.76 (m, 2H). |

TABLE 5-continued

| Characterization Data for Additional Exemplary Compounds | | | |
|---|---|---|---|
| Compound No. | Chemical Structure | [M + H] observed | $^1$H NMR (400 MHz) |
| I-90 | 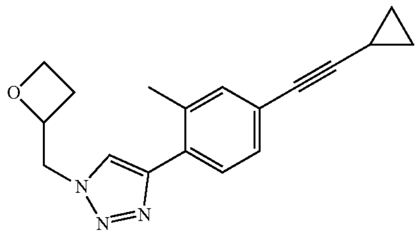 [SMILES: Cc1cc(C#CC2CC2)ccc1-c1cn(CC2CCO2)nn1] | 293.4 | $^1$H NMR (400 MHz, DMSO-$d_6$): δ 8.40 (s, 1H), 7.77 (d, J = 8.0 Hz, 1H), 7.33 (s, 1H), 7. 28 (dd, J = 8.0 Hz, 1.2 Hz, 1H), 5.11-5.14 (m, 1H), 4.64-4.77 (m, 2H), 4.48-4.54 (m, 1H), 4.26-4.31 (m, 1H), 2.68-2.73 (m, 1H), 2.44 (s, 3H), 2.38-2.41 (m, 1H), 1.52-1.58 (m, 1H), 0.87-0.92 (m, 2H), 0.73-0.77 (m, 2H). |
| I-101 | 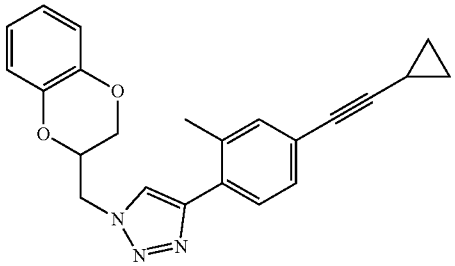 [SMILES: Cc1cc(C#CC2CC2)ccc1-c1cn(CC2COc3ccccc3O2)nn1] | 372.0 | $^1$H NMR (400 MHz, DMSO-$d_6$): δ 8.46 (s, 1H), 7.76 (d, J = 8.0 Hz, 1H), Hz, 1H), 6.89-6.92 (m, 1H), 6.83-6.86 (m, 3H), 4.81-4.86 (m, 1H), 4.71-4.78 (m, 2H), 4.44 (dd, J = 7.6 Hz, 2.0 Hz, 1H), 4.04 (dd, J = 11.6 Hz, 6.0 Hz, 1H), 2.42 (s, 3H), 1.52-1.57 (m, 1H), 0.87-0.92 (m, 2H), 0.72-0.76 (m, 2H). |
| I-133 | 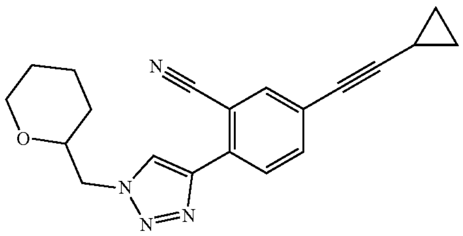 [SMILES: N#Cc1cc(C#CC2CC2)ccc1-c1cn(CC2CCCCO2)nn1] | 332.9 | $^1$H NMR (400 MHz, $CDCl_3$): δ 8.49 (s, 1 H), 8.26 (d, J = 8.4 Hz, 1 H), 7.69 (d, J = 1.2 Hz, 1 H), 7.64 (dd, J = 8.4 Hz, 1.6 Hz, 1 H), 4.50-4.54 (m, 1 H), 4.34-4.40 (m 1 H), 3.97-4.03 (m, 1 H), 3.69-3.73 (m, 1 H), 3.37-3.43 (m, 1 H), 1.89-1.90 (m, 1 H), 1.45-1.70 (m, 5 H), 1.26-1.31 (m, 1 H), 0.81-0.94 (m, 4 H). |
| I-102 | 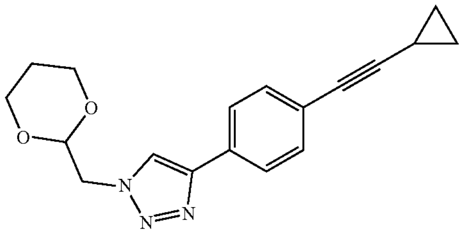 [SMILES: C(#CC1CC1)c1ccc(-c2cn(CC3OCCCO3)nn2)cc1] | 310.0 | $^1$H NMR (400 MHz, DMSO-$d_6$): δ 8.54 (s, 1 H), 7.81 (d, J = 8.4 Hz, 2 H), 7.42 (d, J = 8.4 Hz, 2 H), 4.97 (t, J = 4.8 Hz, 1 H), 4.49 (d, J = 4.4 Hz, 2 H), 3.99-4.06 (m, 2 H), 3.71-3.80 (m, 2 H), 1.81-1.95 (m, 1 H), 1.51-1.60 (m, 1 H), 1.34-1.41 (m, 1 H), 0.86-0.93 (m, 2 H), 0.72-0.77 (m, 2 H). |
| I-91 | 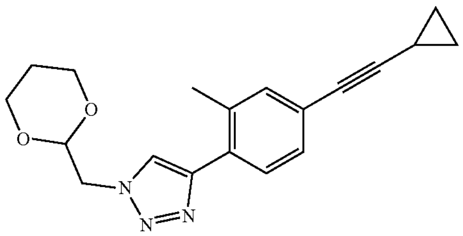 [SMILES: Cc1cc(C#CC2CC2)ccc1-c1cn(CC2OCCCO2)nn1] | 324.0 | $^1$H NMR (400 MHz, DMSO-$d_6$): δ 8.35(s, 1 H), 7.74 (d, J = 7.6Hz, 1H), 7.31 (s, 1 H), 7.24-7.28 (m, 1 H), 5.01 (t, J = 4.8 Hz, 1 H), 4.51 (d, J = 4.8 Hz, 2 H), 4.00-4.06 (m, 2 H), 3.71-3.79 (m, 2 H), 2.41 (s, 3 H), 1.81-1.95 (m, 1 H), 1.50-1.60 (m, 1 H), 1.34-1.41 (m, 1 H), 0.86-0.93 (m, 2 H), 0.71-0.76 (m, 2 H). |
| I-103 | 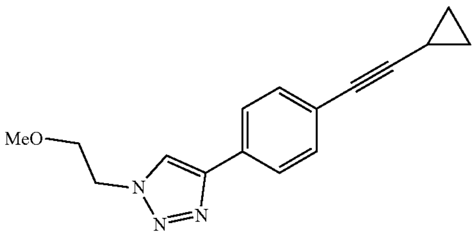 [SMILES: COCCn1cc(-c2ccc(C#CC3CC3)cc2)nn1] | 268.2 | $^1$H NMR (400 MHz, DMSO-$d_6$): δ 8.57 (s, 1H), 7.81 (d, J = 8.4 Hz, 2H), 7.43 (d, J = 8.4 Hz, 2H), 4.57 (t, J = 5.2 Hz, 2H), 3.77 (t, J = 5.2 Hz, 2H), 3.26 (s, 3H), 1.52-1.59 (m, 1H), 0.87-0.92 (m, 2H), 0.72-0.76 (m, 2H). |

TABLE 5-continued

| Compound No. | Chemical Structure | [M + H] observed | $^1$H NMR (400 MHz) |
|---|---|---|---|
| | Characterization Data for Additional Exemplary Compounds | | |
| I-97 | 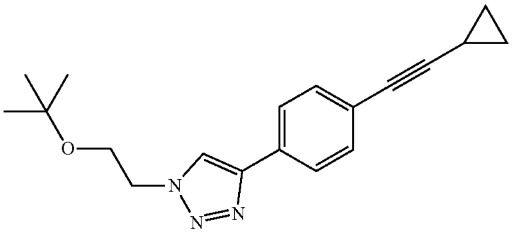 [SMILES: CC(C)(C)OCCn1cc(-c2ccc(C#CC3CC3)cc2)nn1] | 309.4 | $^1$H NMR (400 MHz, DMSO-$d_6$): δ 8.54 (s, 1H), 7.81 (d, J = 8.4 Hz, 2H), 7.43 (d, J = 8.4 Hz, 2H), 4.49 (t, J = 5.2 Hz, 2H), 3.73 (t, J = 5.2 Hz, 2H), 1.55-1.56 (m, 1H), 1.06 (s, 9H), 0.88-0.91 (m, 2H), 0.73-0.77 (m, 2H). |
| I-104 | 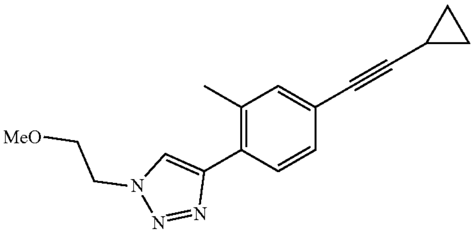 [SMILES: COCCn1cc(-c2ccc(C#CC3CC3)cc2C)nn1] | 282.2 | $^1$H NMR (400 MHz, DMSO-$d_6$): δ 8.39 (s, 1H) , 7.73 (d, J = 8.0 Hz, 1H), 7.31 (s, 1H), 7.26 (d, J = 8.0 Hz, 1H), 4.59 (t, J = 5.2 Hz, 2H), 3.79 (t, J = 5.2 Hz, 2H), 3.26 (s, 3H), 2.41 (s, 3H), 1.52-1.59 (m, 1H), 0.87-0.92 (m, 2H), 0.72-0.76 (m, 2H). |
| I-98 | 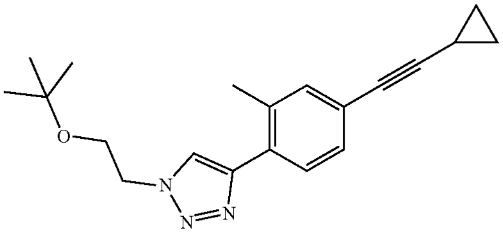 [SMILES: Cc1cc(C#CC2CC2)ccc1-c1cn(CCOC(C)(C)C)nn1] | 323.4 | $^1$H NMR (400 MHz, DMSO-$d_6$): δ 8.34 (s, 1H), 7.73 (d, J = 8.0 Hz, 1H), 7.31 (s, 1H), 7.27 (d, J = 8.0 Hz, 1H), 4.51 (t, J = 5.2 Hz, 2H), 3.74 (t, J = 5.2 Hz, 2H), 2.40 (s, 3H), 1.53-1.57 (m, 1H), 1.06 (s, 9H), 0.87-0.92 (m, 2H), 0.72-0.76 (m, 2H). |
| I-126 | 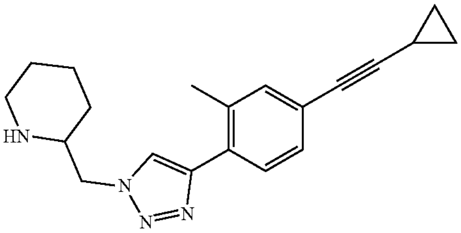 | 321.1 | $^1$H NMR (400 MHz, DMSO-$d_6$): δ 8.38(s, 1 H), 7.74 (d, J = 8.0 Hz, 1H), 7.31 (s, 1 H), 7.26 (dd, J = 8.0 Hz, 1.2 Hz, 1 H), 4.32 (d, J = 6.0 Hz, 2 H), 2.88-2.93 (m, 2 H), 2.45-2.48 (m, 1 H), 2.41 (s, 3 H), 2.06 (s, 1 H), 1.72-1.74 (m, 1 H), 1.48-1.58 (m, 3 H), 1.22-1.31 (m, 2 H), 1.01-1.08 (m, 1 H), 0.87-0.92 (m, 2 H), 0.72-0.76 (m, 2H). |
| I-127 | 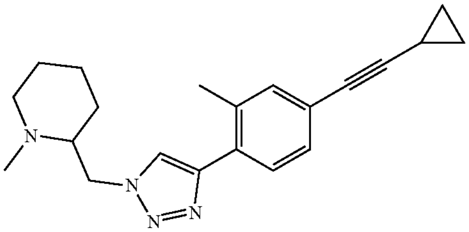 [SMILES: Cc1cc(C#CC2CC2)ccc1-c1cn(CC2CCCCN2C)nn1] | 335.0 | $^1$H NMR (400 MHz, $CDCl_3$): δ 7.76 (s, 1 H), 7.72 (d, J = 8.0 Hz, 1 H), 7.27-7.30 (m, 2 H), 4.68 (dd, J = 14.0 Hz, 4.0 Hz, 1 H), 4.39 (dd, J = 14.0, 6.4 Hz, 1 H), 2.88-2.92 (m, 1 H), 2.45-2.49 (m, 1 H), 2.43-2.44 (m, 6 H), 2.15-2.21 (m, 1 H), 1.43-1.69 (m, 5 H), 1.15-1.30 (m, 2 H), 0.80-0.90 (m, 4H). |
| I-139 | 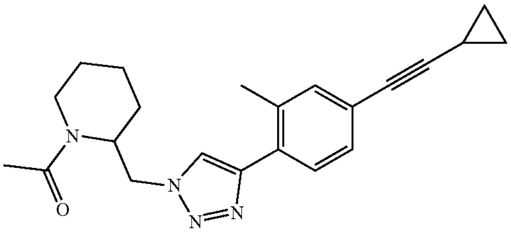 [SMILES: CC(=O)N1CCCCC1Cn1cc(-c2ccc(C#CC3CC3)cc2C)nn1] | 363.3 | $^1$H NMR (400 MHz, DMSO-$d_6$): δ 8.30-8.35 (m, 1 H), 7.67-7.69 (dd, J = 8.0 Hz, 0.8 Hz, 1 H), 7.24-7.31 (m, 2 H), 3.65-5.10 (m, 4 H), 2.83-3.32 (m, 1 H), 2.37 (d, J = 4.8 Hz, 3 H), 1.23-1.86 (m, 10 H), 0.87-0.92 (m, 2 H), 0.72-0.76 (m, 2 H). |

TABLE 5-continued

| Compound No. | Chemical Structure | [M + H] observed | $^1$H NMR (400 MHz) |
|---|---|---|---|
| Characterization Data for Additional Exemplary Compounds | | | |
| I-165 | 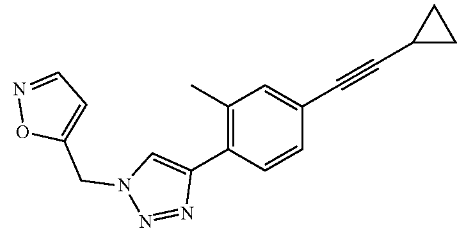 [SMILES: Cc1cc(C#CC2CC2)ccc1-c1cn(Cc2ccno2)nn1] | 305.2 | $^1$H NMR (400 MHz, DMSO-$d_6$): δ 8.54-8.61 (m, 2 H), 7.74 (d, J = 8.0 Hz, 1H),7.31 (s, 1 H), 7.26 (d, J = 8.0 Hz, 1 H), 6.58 (s, 1 H), 5.96 (s, 2 H), 2.40 (s, 3 H), 1.48-1.59 (m, 1H), 0.85-0.93 (m, 2 H), 0.69-0.75 (m, 2 H). |
| I-143 | 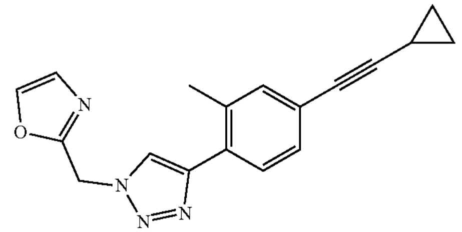 [SMILES: Cc1cc(C#CC2CC2)ccc1-c1cn(Cc2ncco2)nn1] | 305 | $^1$H NMR (400 MHz, DMSO-$d_6$): δ 8.57 (s, 1H), 8.17 (d, J = 0.8 Hz, 1H), 7.74 (d, J = 8.0 Hz, 1H), 7.26-7.32 (m, 3H), 5.92 (s, 2H), 2.41 (s, 3H), 1.52-1.59 (m, 1H), 0.87-0.92 (m, 2H), 0.72-0.76 (m, 2H). |
| I-197 | 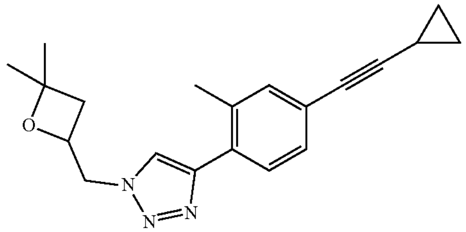 [SMILES: Cc1cc(C#CC2CC2)ccc1-c1cn(CC2CC(C)(C)O2)nn1] | 322.3 | $^1$H NMR (400 MHz, DMSO-$d_6$): δ 8.36(s, 1 H), 7.72 (d, J = 8.0 Hz, 1H), 7.31 (s, 1H), 7.24-7.28 (m, 1H), 4.85-4.95 (m, 1 H), 4.61 (d, J = 4.0 Hz, 2 H), 2.36-2.44 (m, 4 H), 2.18-2.25 (m, 1 H), 1.52-1.59 (m, 1 H), 1.37 (s, 3 H), 1.07(s, 3 H), 0.86-0.93 (m, 2H), 0.71-0.76 (m, 2 H). |
| I-249 | 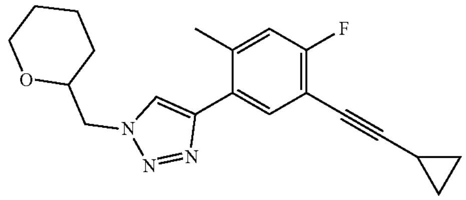 [SMILES: Cc1cc(F)c(C#CC2CC2)cc1-c1cn(CC2CCCCO2)nn1] | 340.0 | $^1$H NMR (400 MHz, DMSO-$d_6$) δ 8.35 (s, 1H), 7.76 (d, J = 7.6 Hz, 1H), 7.24 (d, J = 10.8 Hz, 1H), 4.37-4.49 (m, 2H), 3.84-3.87 (m, 1H), 3.71-3.78 (m, 1H), 3.28-3.35 (m, 1H), 2.44 (s, 3H), 1.78-1.81 (m, 1H), 1.56-1.65 (m, 2H), 1.39-1.54 (m, 3H), 1.16-1.25 (m, 1H), 0.90-0.94 (m, 2H), 0.75-0.79 (m, 2H). |
| I-198 | 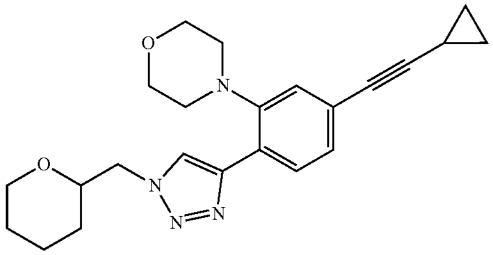 [SMILES: C(#CC1CC1)c1ccc(-c2cn(CC3CCCCO3)nn2)c(N2CCOCC2)c1] | 393.3 | $^1$H NMR (400 MHz, DMSO-$d_6$): δ 8.60 (s, 1 H), 7.92 (d, J = 8.0 Hz, 1 H), 7.12-7.17 (m, 2 H), 4.40-4.54 (m, 2 H), 3.84-3.88 (m, 1 H), 3.66-3.76 (m, 5 H), 3.30-3.37 (m, 1 H), 2.77 (t, J = 4.4 Hz, 4 H), 1.76-1.82 (m, 1 H), 1.42-1.66 (m, 5 H), 1.15-1.22 (m, 1 H) , 0.87-0.92 (m, 2 H), 0.73-0.77 (m, 2 H). |
| I-199 | 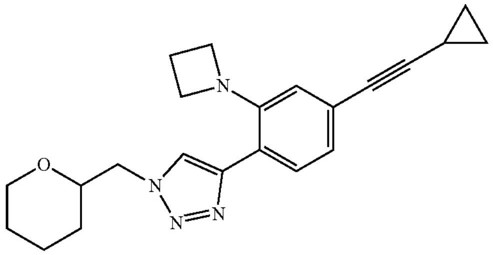 [SMILES: C(#CC1CC1)c1ccc(-c2cn(CC3CCCCO3)nn2)c(N2CCC2)c1] | 363.3 | $^1$H NMR (400 MHz, DMSO-$d_6$): δ 8.04 (s, 1 H), 7.27 (d, J = 8.0 Hz, 1 H), 6.80 (dd, J = 8.0 Hz, 1.6 Hz, 1 H), 6.55 (d, J = 1.2 Hz, 1 H), 4.34-4.50 (m, 2 H), 3.84-3.88 (m, 1 H), 3.65-3.71 (m, 1 H), 3.51 (t, J = 7.2 Hz, 4 H), 3.28-3.37 (m, 1 H), 2.05-2.12 (m, 2 H), 1.76-1.80 (m, 1 H), 1.35-1.66 (m, 5 H), 1.13-1.18 (m, 1 H) , 0.85-0.91 (m, 2 H), 0.71-0.77 (m, 2 H). |

TABLE 5-continued

Characterization Data for Additional Exemplary Compounds

| Compound No. | Chemical Structure | [M + H] observed | $^1$H NMR (400 MHz) |
|---|---|---|---|
| I-187 | 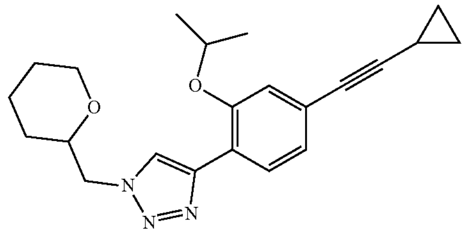 [SMILES: CC(C)Oc1cc(C#CC2CC2)ccc1-c1cn(CC2CCCCO2)nn1] | 366.3 | $^1$H NMR (400 MHz, DMSO-$d_6$) δ 8.28 (s, 1H), 8.07 (d, J = 8.0 Hz, 1H), 7.09 (d, J = 1.2 Hz, 1H), 7.02 (dd, J = 1.6 Hz, 8.0 Hz, 1H), 4.79 (m, 1H), 4.39-4.52 (m, 2H), 3.84-3.88 (m, 1H), 3.68-3.70 (m, 1H), 3.31-3.36 (m, 1H), 1.77-1.81 (m, 1H), 1.43-1.64 (m, 5H), 1.33 (dd, J = 6.4 Hz, 2.0 Hz, 6H), 1.15-1.19 (m, 1H), 0.87-0.92 (m, 2H), 0.73-0.77 (m, 2H). |
| I-211 | 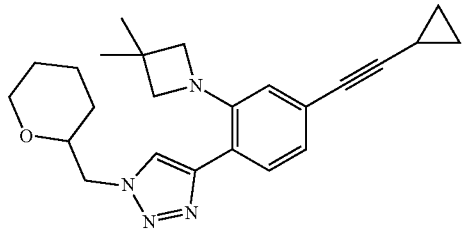 [SMILES: CC1(C)CN(c2cc(C#CC3CC3)ccc2-c2cn(CC3CCCCO3)nn2)C1] | 391.3 | $^1$H NMR (400 MHz, DMSO-$d_6$): δ 7.99 (s, 1H), 7.25 (d, J = 7.6 Hz, 1H), 6.78 (dd, J = 1.6 Hz, 8.0 Hz, 1H), 6.53 (d, J = 1.2 Hz, 1H), 4.47 (dd, J = 3.6 Hz, 14.0 Hz, 1H), 4.38 (dd, J = 7.6, 14.0 Hz, 1H), 3.84-3.87 (m, 1H), 3.67-3.71 (m, 1H), 3.30-3.35 (m, 1H), 3.23 (s, 4H), 1.78-1.81 (m, 1H), 1.62-1.65 (m, 1H), 1.37-1.56 (m, 4H), 1.11-1.21 (m, 7H), 0.86-0.91 (m, 2 H), 0.71-0.75 (m, 2H). |
| I-230 | 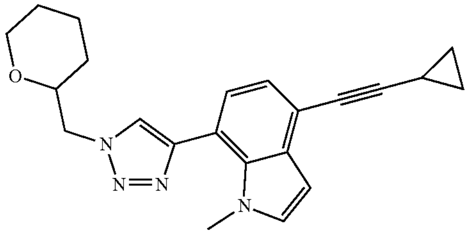 [SMILES: Cn1ccc2c(C#CC3CC3)ccc(-c3cn(CC4CCCCO4)nn3)c21] | 361.2 | $^1$H NMR (400 MHz, DMSO-$d_6$) δ 8.27 (s, 1 H), 7.36 (d, J = 2.8 Hz, 1 H), 7.10 (d, J = 7.6 Hz, 1 H), 6.98 (d, J = 7.6 Hz, 1 H), 6.52 (d, J = 3.2 Hz, 1 H), 4.51 (dd, J = 4.0 Hz, 14.0 Hz, 1 H), 4.43 (dd, J = 7.6 Hz, 14.0 Hz, 1 H), 3.85-3.88 (m, 1 H), 3.73-3.76 (m, 1 H), 3.45 (s, 3 H), 3.36-3.37 (m, 1 H), 1.77-1.82 (m, 1 H), 1.62-1.67 (m, 2H), 1.42-1.51 (m, 2H), 1.18-1.23 (m, 2 H), 0.91-0.96 (m, 2 H), 0.79-0.83 (m, 2H). |
| I-189 | 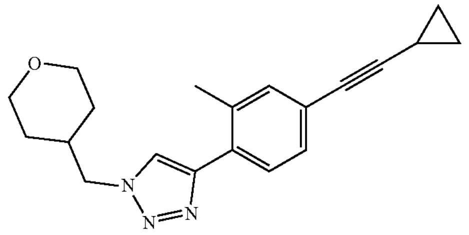 [SMILES: Cc1cc(C#CC2CC2)ccc1-c1cn(CC2CCOCC2)nn1] | 321.4 | $^1$H NMR (400 MHz, DMSO-$d_6$): δ 8.42 (s, 1H), 7.74 (d, J = 8.4 Hz, 1H), 7.31 (s, 1H), 7.26 (dd, J = 8.0 Hz, 1.2 Hz, 1H), 4.33 (d, J = 7.2, 2H), 3.84 (dd, J = 11.2 Hz, 2.8 Hz, 2H), 3.23-3.30 (m, 2H), 2.41 (s, 3H), 2.13-2.14 (m, 1H), 1.53-1.57 (m, 1H), 1.42-1.45 (m, 2H), 1.26-1.33 (m, 2H), 0.87-0.95 (m, 2H), 0.72-0.76 (m, 2H). |
| I-174 | 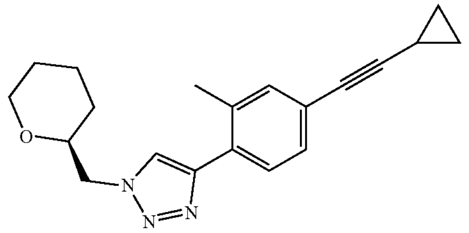 [SMILES: Cc1cc(C#CC2CC2)ccc1-c1cn(C[C@@H]2CCCCO2)nn1] | 322.1 | $^1$H NMR (400 MHz, DMSO-$d_6$): δ 8.33 (s, 1 H), 7.74 (d, J = 8.0 Hz, 1H), 7.31 (s, 1 H), 7.23-7.28 (m, 1 H), 4.37-4.49 (m, 2 H), 3.74-3.86 (m, 2 H), 3.28-3.32 (m, 1 H), 2.41 (s, 3 H), 1.75-1.84 (m, 1 H), 1.35-1.68 (m, 5 H), 1.14-1.27 (m, 1 H), 0.85-0.93 (m, 2 H), 0.70-0.76 (m, 2 H). |
| I-175 | 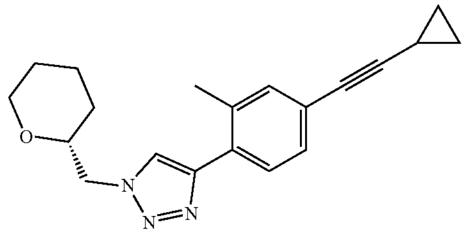 [SMILES: Cc1cc(C#CC2CC2)ccc1-c1cn(C[C@H]2CCCCO2)nn1] | 321.4 | $^1$H NMR (400 MHz, DMSO-$d_6$): δ 8.33 (s, 1H), 7.74 (d, J = 8.0 Hz, 1H), 7.31 (s, 1H), 7.26 (dd, J = 8.0 Hz, 1.6 Hz, 1H), 4.37-4.50 (m, 2H), 3.84-3.87 (m, 1H), 3.74-3.75 (m, 1H), 3.30-3.34 (m, 1H), 2.41 (s, 3H), 1.78-1.81 (m, 1H), 1.62-1.65 (m, 1H), 1.43-1.57 (m, 4H), 1.18-1.22 (m, 1H), 0.87-0.92 (m, 2H), 0.72-0.76 (m, 2H). |

TABLE 5-continued

Characterization Data for Additional Exemplary Compounds

| Compound No. | Chemical Structure | [M + H] observed | $^{1}$H NMR (400 MHz) |
|---|---|---|---|
| I-190 | 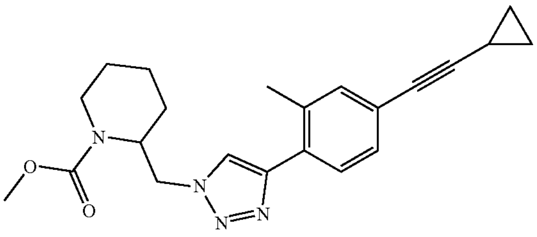 | 379.3 | $^{1}$H NMR (400 MHz, $CDCl_3$) δ 7.69 (d, J = 7.6 Hz, 2H), 7.28 (d, J = 1.6 Hz, 2H), 4.75-4.76 (m, 1H), 4.64-4.69 (m, 1H), 4.50-4.55 (m, 1H), 4.15 (br., 1H), 3.52 (s, 3H), 2.97 (t, J = 13.2 Hz, 1H), 2.41 (s, 3H), 1.62-1.74 (m, 5H), 1.42-1.49 (m, 2H), 0.79-0.90 (m, 4H). |
| I-191 | 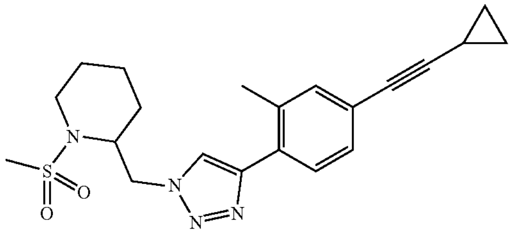 [SMILES: Cc1cc(C#CC2CC2)ccc1-c1cn(CC2CCCCN2S(C)(=O)=O)nn1] | 399.3 | $^{1}$H NMR (400 MHz, $CDCl_3$) δ 7.76 (s, 1H), 7.68 (d, J = 8.0 Hz, 1H), 7.28-7.30 (m, 2H), 4.83 (dd, J = 8.8 Hz, 13.6 Hz, 1H), 4.46-4.57 (m, 2H), 3.72-3.76 (m, 1H), 3.17-3.25 (m, 1H), 2.51 (s, 3H), 2.43 (s, 3H), 1.57-1.81 (m, 6H), 1.42-1.49 (m, 1H), 0.79-0.90 (m, 4H). |
| I-192 | 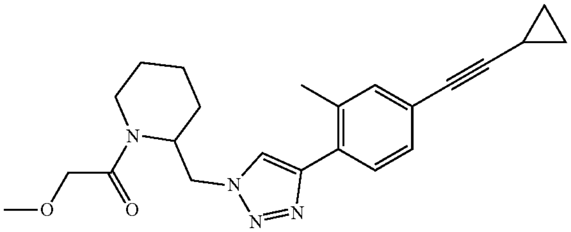 [SMILES: COCC(=O)N1CCCCC1Cn1cc(-c2ccc(C#CC3CC3)cc2C)nn1] | 393.3 | $^{1}$H NMR (400 MHz, DMSO-$d_6$) δ 8.32-8.38 (m, 1H), 7.66-7.69 (m, 1H), 7.30 (d, J = 4.8 Hz, 1H), 7.25 (t, J = 7.6 Hz, 1H), 3.82-5.07 (m, 4H), 3.82-3.87 (m, 1H), 3.56-3.60 (m, 0.5H), 3.16-3.31 (m, 2H), 3.04 (s, 3H), 2.89-2.97 (m, 0.5H), 2.36-2.37 (m, 3H), 1.36-1.74 (m, 5H), 1.26-1.41 (m, 1H), 0.86-0.91 (m, 2H), 0.71-0.75 (m, 2H). |
| I-274 | 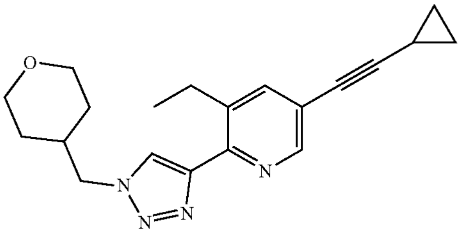 [SMILES: CCc1cc(C#CC2CC2)cnc1-c1cn(CC2CCOCC2)nn1] | 337.2 | $^{1}$H NMR (400 MHz, $CDCl_3$) δ 8.43 (s, 1H), 8.08 (s, 1H), 7.62 (s, 1H), 4.29 (d, J = 7..2 Hz, 2H), 3.98 (dd, J = 3.6 Hz, 11.2 Hz, 2H), 3.34-3.40 (m, 2H), 3.16-3.22 (m, 2H), 2.23-2.25 (m, 1H), 1.60 (s, 2H), 1.40-1.56 (m, 3H), 1.27 (t, J = 6.8 Hz, 3H), 0.83-0.94 (m, 4H). |
| I-239 | 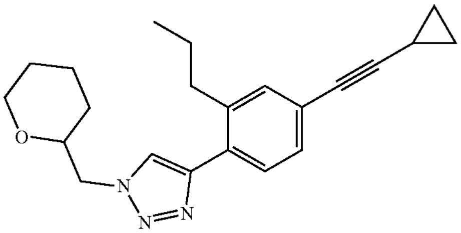 [SMILES: CCCc1cc(C#CC2CC2)ccc1-c1cn(CC2CCCCO2)nn1] | 350.2 | $^{1}$H NMR (400 MHz, DMSO-$d_6$) δ 8.25 (s, 1H), 7.57 (d, J = 8.0 Hz, 1H), 7.28 (d, J = 1.2 Hz, 1H), 7.25 (dd, J = 8.0 Hz, 1.6 Hz, 1H), 4.41-4.47 (m, 2H), 3.83-3.89 (m, 1H), 3.69-3.75 (m, 1H), 3.29-3.35 (m, 1H), 2.74 (t, J = 8.0 Hz, 2H), 1.76-1.82 (m, 1H), 1.40-1.65 (m, 7H), 1.12-1.22 (m, 1H), 0.83-0.90 (m, 5H), 0.72-0.77 (m, 2H). |
| I-245 | 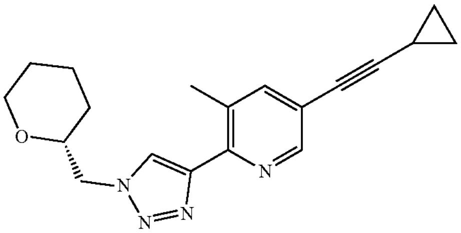 [SMILES: Cc1cc(C#CC2CC2)cnc1-c1cn(C[C@H]2CCCCO2)nn1] | 323.0 | $^{1}$H NMR (400 MHz, DMSO-$d_6$) δ 8.47 (s, 1H), 8.43 (s, 1H), 7.73 (s, 1H), 4.40-4.52 (m, 2H), 3.85-3.87 (m, 1H), 3.72-3.76 (m, 1H), 3.28-3.32 (m, 1H), 2.62 (s, 3H), 1.78-1.81 (m, 1H), 1.57-1.66 (m, 2H), 1.40-1.52 (m, 3H), 1.18-1.24 (m, 1H), 0.90-0.95 (m, 2H), 0.75-0.80 (m, 2H). |

TABLE 5-continued

Characterization Data for Additional Exemplary Compounds

| Compound No. | Chemical Structure | [M + H] observed | $^1$H NMR (400 MHz) |
|---|---|---|---|
| I-364 | 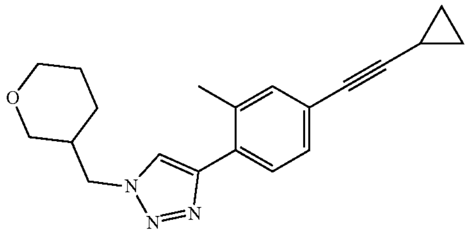 [SMILES: Cc1cc(C#CC2CC2)ccc1-c1cn(CC2CCCOC2)nn1] | 322.0 | $^1$H NMR (400 MHz, DMSO-d$_6$) δ 8.44 (s, 1H), 7.74 (d, J = 8.0 Hz, 1H), 7.31 (s, 1H), 7.26 (d, J = 8.0 Hz, 1H), 4.29-4.40 (m, 2H), 3.65-3.72 (m, 2H), 3.36-3.39 (m, 1H), 3.19-3.24 (m, 1H), 2.41 (s, 3H), 2.13-2.16 (m, 1H), 1.44-1.70 (m, 4H), 1.25-1.31 (m, 1H), 0.87-0.92 (m, 2H), 0.72-0.76 (m, 2H). |
| I-365 | 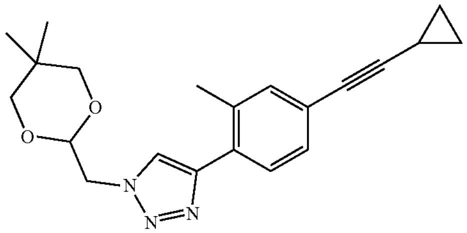 [SMILES: Cc1cc(C#CC2CC2)ccc1-c1cn(CC2OCC(C)(C)CO2)nn1] | 352.0 | $^1$H NMR (400 MHz, DMSO-d$_6$) δ 8.35 (s, 1H), 7.73 (d, J = 8.0 Hz, 1H), 7.31 (s, 1H), 7.26 (dd, J = 1.2 Hz, 8.0 Hz, 1H), 4.92 (t, J = 4.4 Hz, 1H), 4.57 (d, J = 4.4 Hz, 2H), 3.57 (d, J = 11.2 Hz, 2H), 3.46 (d, J = 10.8 Hz, 2H), 2.40 (s, 3H), 1.52-1.59 (m, 1H), 1.04 (s, 3H), 0.87-0.92 (m, 2H), 0.72-0.76 (m, 2H), 0.68 (s, 3H). |
| I-252 | 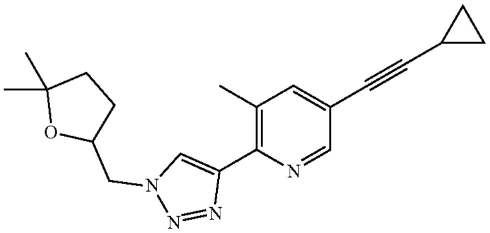 | 337.0 | $^1$H NMR (400 MHz, DMSO-d$_6$) δ 8.48 (s, 1H), 8.43 (s, 1H), 7.72 (d, J = 1.2 Hz, 1H), 4.32-4.56 (m, 3H), 2.63 (s, 3H), 2.05-2.10 (m, 1H), 1.55-1.79 (m, 4H), 1.14 (d, J = 3.6 Hz, 6H), 0.91-0.95 (m, 2H), 0.76-0.80 (m, 2H). |
| I-278 | 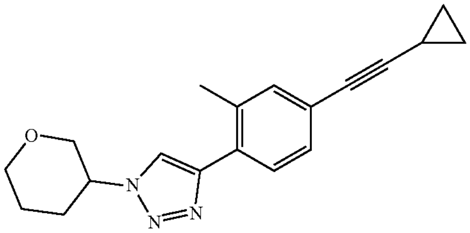 [SMILES: Cc1cc(C#CC2CC2)ccc1-c1cn(C2COCOC2)nn1] | 308.0 | $^1$H NMR (400 MHz, DMSO-d$_6$) δ 8.50 (s, 1H), 7.72 (d, J = 8.0 Hz, 1H), 7.31 (s, 1H), 7.26 (dd, J = 8.0 Hz, 1.6 Hz, 1H), 4.65-4.70 (m, 1H), 4.05-4.09 (m, 1H), 3.74-3.84 (m, 2H), 3.48-3.54 (m, 1H), 2.42 (s, 3H), 2.17-2.26 (m, 2H), 1.68-1.78 (m, 2H), 1.1.53-1.57 (m, 1H), 0.87-0.92 (m, 2H), 0.71-0.76 (m, 2H). |
| I-366 | 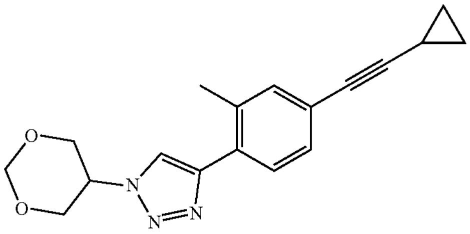 | 310.0 | $^1$H NMR (400 MHz, DMSO-d$_6$) δ 8.41 (s, 1H), 7.73 (d, J = 8.0 Hz, 1H), 7.31 (s, 1H), 7.26 (d, J = 8.0 Hz, 1H), 4.93 (s, 1H), 4.80 (s, 1H), 4.48-4.65 (m, 3H), 3.96-4.00 (m, 1H), 3.72-3.75 (m, 1H), 2.41 (s, 3H), 1.53-1.57 (m, 1H), 0.87-0.91 (m, 2H), 0.71-0.75 (m, 2H). |
| I-367 | 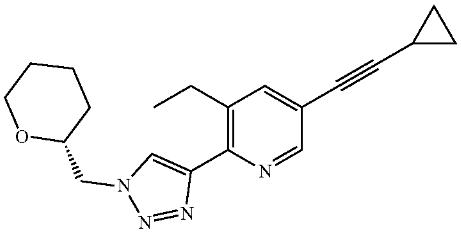 [SMILES: CCc1cc(C#CC2CC2)cnc1-c1cn(C[C@H]2CCCCO2)nn1] | 337.2 | $^1$H NMR (400 MHz, DMSO-d$_6$) δ 8.43-8.45 (m, 2H), 7.73 (d, J = 2.0 Hz, 1H), 4.40-4.52 (m, 2H), 3.85-3.88 (m, 1H), 3.72-3.76 (m, 1H), 3.29-3.32 (m, 1H), 3.10 (q, J = 7.6 Hz, 2H), 1.78-1.81 (m, 1H), 1.58-1.65 (m, 2H), 1.43-1.51 (m, 3H), 1.18-1.24(m, 4H), 0.90-0.95 (m, 2H), 0.77-0.80 (m, 2H). |

TABLE 5-continued

| Characterization Data for Additional Exemplary Compounds | | | |
|---|---|---|---|
| Compound No. | Chemical Structure | [M + H] observed | $^1$H NMR (400 MHz) |
| I-368 | 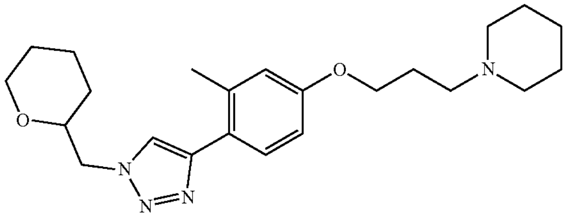 [SMILES: Cc1cc(OCCCN2CCCCC2)ccc1-c1cn(CC2CCCCO2)nn1] | 399.2 | $^1$H NMR (400 MHz, DMSO-$d_6$) δ 8.19 (s, 1H), 7.63 (d, J = 8.4 Hz, 1H), 6.82-6.86 (m, 2H), 4.35-4.47 (m, 2H), 4.01 (t, J = 6.4 Hz, 2H), 3.84-3.87 (m, 1H), 3.71-3.77 (m, 1H), 3.29-3.35 (m, 1H), 2.32-2.39 (m, 9H), 1.78-1.89 (m, 3H), 1.61-1.65 (m, 1H), 1.43-1.55 (m, 7H), 1.37-1.40 (m, 2H), 1.15-1.25 (m, 1H). |
| I-369 | 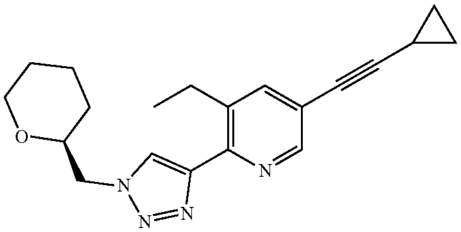 [SMILES: CCc1cc(C#CC2CC2)cnc1-c1cn(C[C@@H]2CCCCO2)nn1] | 337.2 | $^1$H NMR (400 MHz, $CDCl_3$) δ 8.45 (d, J = 2.0 Hz, 1H), 8.19 (s, 1H), 7.60 (d, J = 2.0 Hz, 1H), 4.46-4.52 (m, 1H), 4.32-4.38 (m, 1H), 3.96-4.03 (m, 1H), 3.68-3.77 (m, 1H), 3.36-3.44 (m, 1H), 3.13-3.20 (m, 2H), 1.85-1.92 (m, 1H), 1.64-1.71 (m, 1H), 1.45-1.58 (m, 4H), 1.23-1.35 (m, 4H), 0.81-0.95 (m, 4H). |
| I-370 | 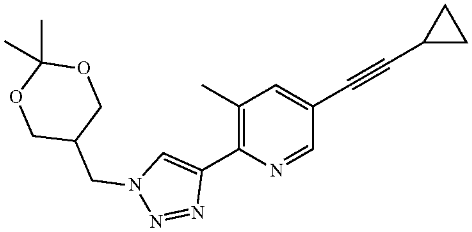 [SMILES: Cc1cc(C#CC2CC2)cnc1-c1cn(CC2COC(C)(C)OC2)nn1] | 353.2 | $^1$H NMR (400 MHz, $CDCl_3$) δ 8.43 (d, J = 1.2 Hz, 1H), 8.17 (s, 1H), 7.57 (s, 1H), 4.66 (d, J = 7.6 Hz, 2H), 4.09 (dd, J = 2.8 Hz, 12.4 Hz, 2H), 3.64 (dd, J = 2.8 Hz, 12.4 Hz, 2H), 2.70 (s, 3H), 2.26-2.28 (m, 1H), 1.44-1.51 (m, 7H), 0.84-0.94 (m, 4H). |
| I-371 | 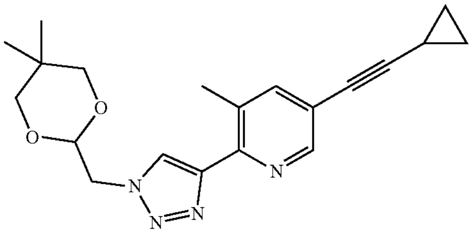 [SMILES: Cc1cc(C#CC2CC2)cnc1-c1cn(CC2OCC(C)(C)CO2)nn1] | 353.0 | $^1$H NMR (400 MHz, DMSO-$d_6$) δ 8.49 (s, 1H), 8.43 (d, J = 2.0 Hz, 1H), 7.73 (d, J = 1.2 Hz, 1H), 4.92 (t, J = 4.4 Hz, 1H), 4.60 (d, J = 4.4 Hz, 2H), 3.57 (d, J = 11.2 Hz, 2H), 3.46 (d, J = 10.8 Hz, 2H), 2.61 (s, 3H), 1.57-1.63 (m, 1H), 1.03 (s, 3H), 0.90-0.95 (m, 2H), 0.76-0.80 (m, 2H), 0.67 (s, 3H). |
| I-92 | 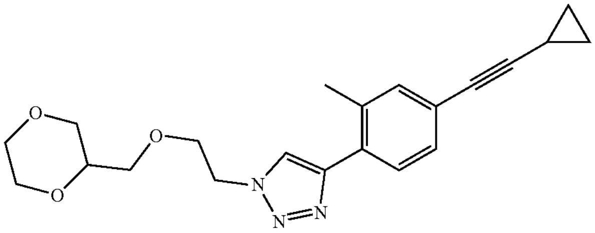 [SMILES: Cc1cc(C#CC2CC2)ccc1-c1cn(CCOCC2COCCO2)nn1] | 368.2 | $^1$H NMR (400 MHz, $CDCl_3$) δ 7.84 (s, 1H), 7.74 (d, J = 8.2 Hz, 1H), 7.28 (d, J = 7.7 Hz, 2H), 4.60 (dd, J = 5.6, 4.4 Hz, 2H), 3.89 (ddd, J = 6.1, 5.0, 3.4 Hz, 2H), 3.82 – 3.63 (m, 5H), 3.64 – 3.55 (m, 1H), 3.52 – 3.40 (m, 2H), 3.36 (dd, J = 11.4, 10.1 Hz, 1H), 2.43 (s, 43H), 1.46 (d, J = 1.1 Hz, 1H), 0.92 – 0.77 (m, 4H) ppm. |
| I-107 | 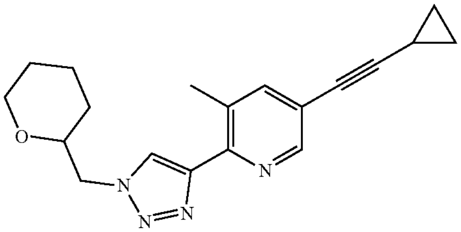 [SMILES: Cc1cc(C#CC2CC2)cnc1-c1cn(CC2CCCCO2)nn1] | 323.1 | $^1$H NMR (400 MHz, $CDCl_3$) δ 8.48 – 8.33 (m, 1H), 8.17 (s, 1H), 7.52 (dd, J = 2.0, 0.7 Hz, 1H), 4.45 (dd, J = 14.1, 3.3 Hz, 1H), 4.31 (dd, J = 14.1, 7.5 Hz, 1H), 3.99 – 3.86 (m, 1H), 3.67 (dddd, J = 11.1, 7.5, 3.2, 2.2 Hz, 1H), 3.34 (td, J = 11.4, 3.2 Hz, 1H), 2.65 (s, 3H), 1.94 – 1.71 (m, 1H), 1.71 – 1.57 (m, 1H), 1.55 – 1.37 (m, 4H), 1.35 – 1.22 (m, 1H), 1.02– 0.71 (m, 4H). |

TABLE 5-continued

Characterization Data for Additional Exemplary Compounds

| Compound No. | Chemical Structure | [M + H] observed | $^1$H NMR (400 MHz) |
|---|---|---|---|
| I-108 | 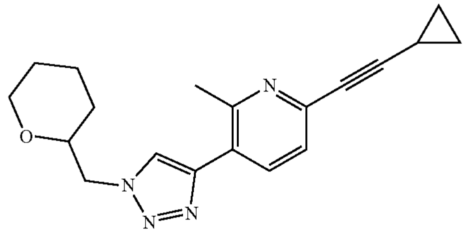 [SMILES: Cc1nc(C#CC2CC2)ccc1-c1cn(CC2CCCCO2)nn1] | 323.1 | $^1$H NMR (400 MHz, $CDCl_3$) δ 8.12 (d, J = 8.0 Hz, 1H), 7.86 (s, 1H), 7.29 (d, J = 8.0 Hz, 1H),4.53 (dd, J = 14.2, 2.9 Hz, 1H), 4.33 (dd, J = 14.2, 7.6 Hz, 1H), 3.99 (dd, J = 10.7, 2.0 Hz, 2H), 3.70 (ddt, J = 10.0, 7.6, 2.5 Hz, 1H), 3.51 – 3.24 (m, 1H), 2.68 (s, 3H), 2.18 – 1.84 (m, 1H), 1.75-1.64 (m, 1H), 1.58 – 1.43 (m, 4H), 1.37 – 1.15 (m, 1H), 1.11 – 0.79 (m, 4H). |
| I-123 | 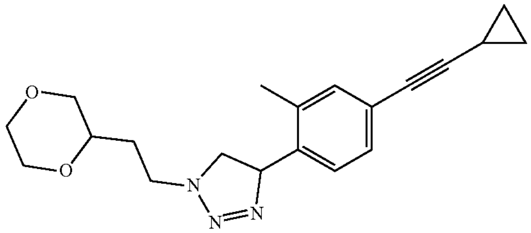 [SMILES: Cc1cc(C#CC2CC2)ccc1C1CN(CCC2COCCO2)N=N1] | 340.1 | $^1$H NMR (400 MHz, $CDCl_3$) δ 7.71 (d, J = 7.7 Hz, 1H), 7.64 (s, 1H), 7.31 – 7.24 (m, 2H), 4.62 – 4.46 (m, 2H), 3.80 (dd, J = 12.2, 4.0 Hz, 1H), 3.75 – 3.65 (m, 3H), 3.65 – 3.55 (m, 1H), 3.50 (tt, J = 9.9, 2.9 Hz, 1H), 3.30 (dd, J = 11.4, 9.9 Hz, 1H), 2.42 (s, 3H), 2.14 – 2.02 (m, 1H), 1.99 – 1.87 (m, 1H), 1.51 – 1.41 (m, 1H), 0.90 – 0.84 (m, 2H), 0.84- 0.78 (m, 2H). |
| I-132 | 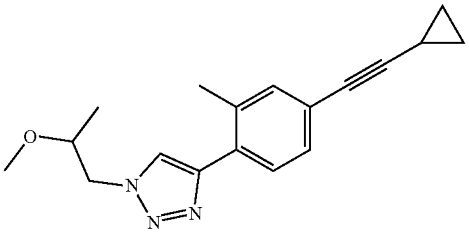 [SMILES: COC(C)Cn1cc(-c2ccc(C#CC3CC3)cc2C)nn1] | 296.1 | $^1$H NMR (400 MHz, $CDCl_3$) δ 7.77 (s, 1H), 7.74 (d, J = 7.7 Hz, 1H), 7.31 – 7.27 (m, 2H), 4.53 (dd, J = 14.1, 3.2 Hz, 1H), 4.30 (dd, J = 14.1, 7.5 Hz, 1H), 3.75 (ddh, J = 12.5, 6.3, 3.3 Hz, 1H), 3.31 (d, J = 0.3 Hz, 3H), 2.43 (s, 3H), 1.50 – 1.41 (m, 1H), 1.21 (d, J = 6.3 Hz, 3H), 0.91 – 0.78 (m, 4H). |
| I-195 | 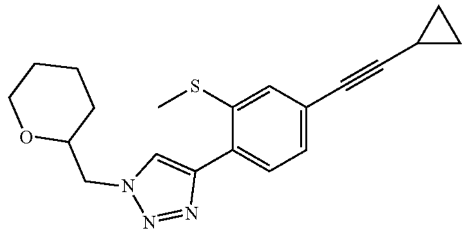 [SMILES: CSc1cc(C#CC2CC2)ccc1-c1cn(CC2CCCCO2)nn1] | 354.2 | $^1$H NMR (400 MHz, $CD_3CN$) δ 8.22 (s, J = 4.7 Hz, 1H), 7.79 (d, J = 8.0 Hz, 1H), 7.31 (d, J = 1.5 Hz, 1H), 7.20 (dd, J = 8.0, 1.6 Hz, 1H), 4.44 (dd, J = 14.2, 3.6 Hz, 1H), 4.36 (dd, J = 14.2, 7.6 Hz, 1H), 3.92 – 3.86 (m, 1H), 3.72 (dddd, J = 11.2, 7.6, 3.5, 2.2 Hz, 1H), 3.40 – 3.30 (m, 1H), 2.46 (s, 3H), 1.87 – 1.79 (m, 1H), 1.68 – 1.61 (m, 1H), 1.56 – 1.42 (m, 4H), 1.29 – 1.17 (m, 1H), 0.94 – 0.87 (m, 2H), 0.79 – 0.73 (m, 2H). |
| I-196 | 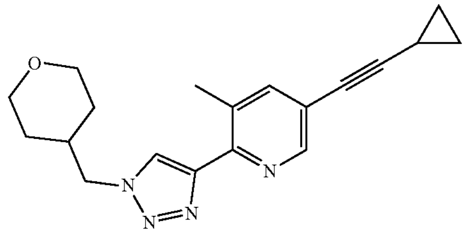 [SMILES: Cc1cc(C#CC2CC2)cnc1-c1cn(CC2CCOCC2)nn1] | 323.2 | $^1$H NMR (400 MHz, $CDCl_3$) δ 8.41 (d, J = 2.0 Hz, 1H), 8.09 (s, 1H), 7.59 – 7.54 (m, 1H), 4.29 (d, J = 7.3 Hz, 2H), 3.98 (dd, J = 11.4, 2.9 Hz, 2H), 3.36 (td, J = 11.8, 2.2 Hz, 2H), 2.70 (s, 3H), 2.30-2.17 (m, 1H), 1.66 – 1.51 (m, 2H), 1.53 – 1.34 (m, 3H), 0.95 – 0.86 (m, 2H), 0.86 – 0.81 (m, 2H). |
| I-204 | 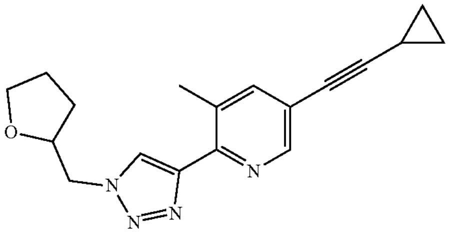 [SMILES: Cc1cc(C#CC2CC2)cnc1-c1cn(CC2CCCO2)nn1] | 309.2 | $^1$H NMR (400 MHz, $CDCl_3$) δ 8.42 (d, J = 1.3 Hz, 1H), 8.24 (s, 1H), 7.61 – 7.50 (m, 1H), 4.57 (dd, J = 14.0, 3.7 Hz, 1H), 4.41 (dd, J = 14.0, 6.3 Hz, 1H), 4.32-4.24 (m, 1H), 3.88-3.81 (m, 1H), 3.80 – 3.72 (m, 1H), 2.67 (s, 3H), 2.13 – 1.95 (m, 1H), 1.95 – 1.71 (m, 2H), 1.70 – 1.58 (m, 1H), 1.50-1.42 (m, 1H), 0.94 – 0.86 (m, 2H), 0.86 – 0.78 (m, 2H). |

TABLE 5-continued

| Characterization Data for Additional Exemplary Compounds | | | |
|---|---|---|---|
| Compound No. | Chemical Structure | [M + H] observed | $^1H$ NMR (400 MHz) |
| I-205 | 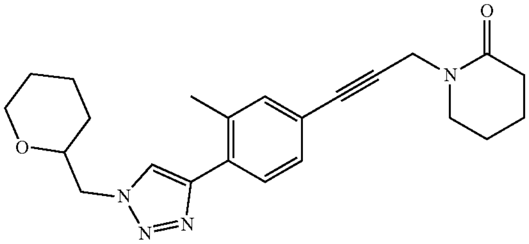 [SMILES: Cc1cc(C#CCN2CCCCC2=O)ccc1-c1cn(CC2CCCCO2)nn1] | 393.2 | $^1H$ NMR (400 MHz, $CDCl_3$) δ 7.82 (s, 1H), 7.78 (d, J = 8.2 Hz, 1H), 7.33 (d, J = 7.7 Hz, 2H), 4.52 (dd, J = 14.2, 3.0 Hz, 1H), 4.48 (s, 1H), 4.33 (dd, J = 14.2, 7.6 Hz, 1H), 4.05 − 3.94 (m, 1H), 3.77 − 3.66 (m, 1H), 3.48 (t, J = 5.9 Hz, 2H), 3.45 − 3.34 (m, 1H), 2.44 (s, 3H), 2.42 (d, J = 6.3 Hz, 1H), 1.97 − 1.78 (m, 5H), 1.68 (d, J = 17.0 Hz, 4H), 1.60 − 1.47 (m, 1H), 1.34 − 1.17 (m, 2H). |
| I-206 | 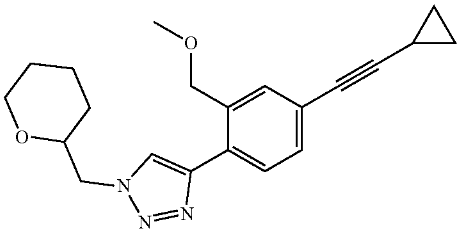 | 352.2 | $^1H$ NMR (400 MHz, $CDCl_3$) δ 7.99 (s, 1H), 7.81 (d, J = 8.0 Hz, 1H), 7.50 (d, J = 1.6 Hz, 1H), 7.39 (dd, J = 8.0, 1.8 Hz, 1H), 4.58-4.42 (m, 3H), 4.33 (dd, J = 14.2, 7.5 Hz, 1H), 4.01-3.94 (m, 1H), 3.73-3.65 (m, 1H), 3.43-3.34 (m, 4H), 1.98 − 1.81 (m, 1H), 1.70-1.63 (m, 1H), 1.57 − 1.40 (m, 4H), 1.37 − 1.18 (m, 1H), 0.94− 0.74 (m, 4H). |
| I-207 | 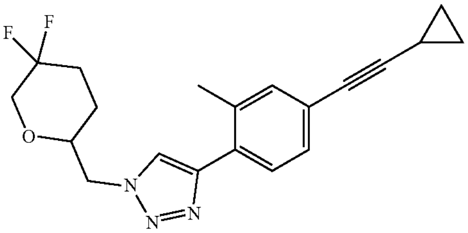 [SMILES: Cc1cc(C#CC2CC2)ccc1-c1cn(CC2CCC(F)(F)CO2)nn1] | 358.1 | $^1H$ NMR (400 MHz, $CDCl_3$) δ 7.78 (s, 1H), 7.73 (d, J = 7.8 Hz, 1H), 7.28 (d, J = 8.1 Hz, 2H), 4.62 (dd, J = 14.3, 2.9 Hz, 1H), 4.40 (dd, J = 14.4, 7.7 Hz, 1H), 4.02 − 3.91 (m, 1H), 3.89 − 3.78 (m, 1H), 3.47 (ddd, J = 26.5, 12.3, 4.3 Hz, 1H), 2.42 (s, 3H), 2.36 − 2.23 (m, 1H), 2.07 − 1.83 (m, 2H), 1.69 (td, J = 12.8, 11.7, 3.8 Hz, 1H), 1.52 − 1.41 (m, 1H), 0.87 (dtd, J = 7.1, 4.9, 1.8Hz, 2H), 0.81 (qd, J = 6.1, 5.2, 2.4 Hz, 2H). |
| I-216 | 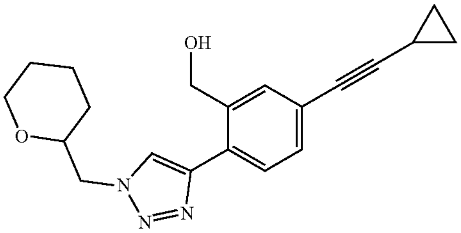 [SMILES: OCc1cc(C#CC2CC2)ccc1-c1cn(CC2CCCCO2)nn1] | 338.1 | $^1H$ NMR (400 MHz, $CDCl_3$) δ 7.94 (s, 1H), 7.46 (d, J = 1.6 Hz, 1H), 7.44 (d, J = 8.0 Hz, 1H), 7.34 (dd, J = 8.0, 1.7 Hz, 1H), 5.50 (t, J = 7.6 Hz, 1H), 4.58 (d, J = 7.6 Hz, 2H), 4.51 (dd, J = 14.1, 2.9 Hz, 1H), 4.33 (dd, J = 14.2, 7.6 Hz, 1H), 4.00 (dd, J = 10.9, 2.0 Hz, 1H), 3.70 (tdd, J = 10.0, 5.0, 2.6 Hz, 1H), 3.51 − 3.33 (m, 1H), 1.97 − 1.80 (m, 1H), 1.68 (d, J = 12.8 Hz, 1H), 1.60 − 1.50 (m, 3H), 1.50 − 1.42 (m, 1H), 1.34 − 1.25 (m, 1H), 0.93 − 0.85 (m, 2H), 0.85 − 0.78 (m, 2H). |
| I-217 | 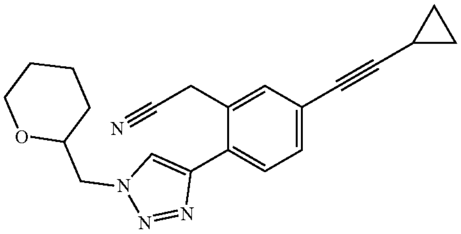 [SMILES: N#CCc1cc(C#CC2CC2)ccc1-c1cn(CC2CCCCO2)nn1] | 347.1 | $^1H$ NMR (400 MHz, $CDCl_3$) δ 7.88 (s, 1H), 7.63 − 7.58 (m, 1H), 7.43 (d, J = 8.0 Hz, 1H), 7.37 (dd, J = 8.0, 1.6 Hz, 1H), 4.52 (dd, J = 14.2, 2.9 Hz, 1H), 4.33 (dd, J =14.2, 7.6 Hz, 1H), 4.22 (s, 2H), 4.04 − 3.95 (m, 1H), 3.75 − 3.65 (m, 1H), 3.52 − 3.35 (m, 1H), 1.93 − 1.85 (m, 1H), 1.73 − 1.64 (m, 1H), 1.56 − 1.40 (m, 4H), 1.37 − 1.21 (m, 1H), 1.04 − 0.81 (m, 4H). |
| I-218 | 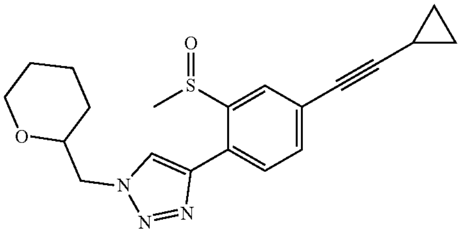 [SMILES: CS(=O)c1cc(C#CC2CC2)ccc1-c1cn(CC2CCCCO2)nn1] | 370.2 | $^1H$ NMR (400 MHz, $CD_3CN$) δ 8.16 (s, 0.5H), 8.16 (s, 0.5H), 8.04 (d, J = 1.7 Hz, 1H), 7.64 (d, J = 8.0 Hz, 1H), 7.48 (dd, J = 8.0, 1.8 Hz, 1H), 4.48 − 4.39 (m, 1H), 4.39 − 4.30 (m, 1H), 3.92 − 3.83 (m, 1H), 3.77 − 3.66 (m, 1H), 3.40 − 3.30 (m, 1H), 2.80 (s, 1.5H), 2.80 (s, 1.5H), 1.86 − 1.78 (m, 1H), 1.70-1.60 (m, 1G), 1.56 − 1.42 (m, 4H), 1.31 − 1.16 (m, 1H), 0.96 − 0.87 (m, 2H), 0.81 − 0.74 (m, 2H). |

TABLE 5-continued

Characterization Data for Additional Exemplary Compounds

| Compound No. | Chemical Structure | [M + H] observed | $^1$H NMR (400 MHz) |
|---|---|---|---|
| I-219 | 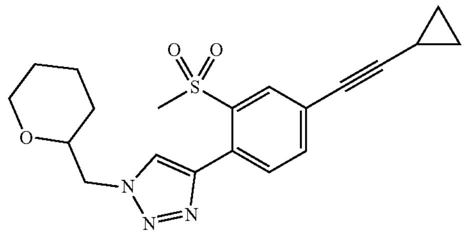 [SMILES: CS(=O)(=O)c1cc(C#CC2CC2)ccc1-c1cn(CC2CCCCO2)nn1] | 386.2 | $^1$H NMR (400 MHz, $CD_3CN$) δ 8.21 (s, 1H), 8.07 (d, J = 1.7 Hz, 1H), 7.72 (d, J = 8.0 Hz, 1H), 7.66 (dd, J = 8.0, 1.7 Hz, 1H), 4.48 (dd, J = 14.2, 3.5 Hz, 1H), 4.38 (dd, J = 14.2, 7.6 Hz, 1H), 3.94 – 3.86 (m, 1H), 3.71 (dddd, J = 9.9, 7.6, 3.4, 2.2 Hz, 1H), 3.42 -3.31 (m, 1H), 3.10 (s, 3H), 1.87 – 1.79 (m, 1H), 1.69 – 1.62 (m, 1H), 1.59 – 1.43 (m, 4H), 1.29 – 1.17 (m, 1H), 0.97 – 0.89 (m, 2H), 0.83 – 0.77 (m, 2H). |
| I-220 | 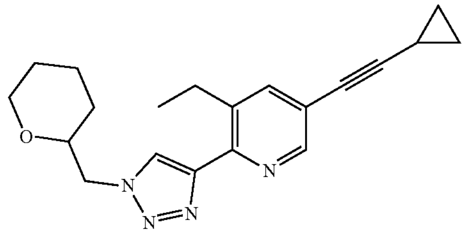 [SMILES: CCc1cc(C#CC2CC2)cnc1-c1cn(CC2CCCCO2)nn1] | 337. 2 | $^1$H NMR (400 MHz, $CD_3CN$) δ 8.40 (br s, 1H), 8.20 (s, 1H), 7.65 (s, 1H), 4.45 (dd, J = 14.2, 3.5 Hz, 1H), 4.37 (dd, J = 14.2, 7.7 Hz, 1H), 3.94-3.85 (m, 1H), 3.79 – 3.69 (m, 1H), 3.42 – 3.31 (m, 1H), 3.13 (q, J = 7.5 Hz, 2H), 1.88 – 1.79 (m, 1H), 1.70 – 1.62 (m, 1H), 1.60 – 1.42 (m, 4H), 1.31 – 1.23 (m, 1H), 1.21 (t, J = 7.5 Hz, 3H), 0.95 – 0.89 (m, 2H), 0.80 – 0.74 (m, 2H). |
| I-225 | 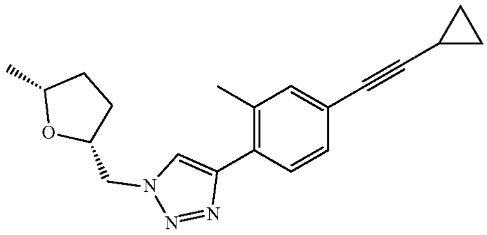 [SMILES: Cc1cc(C#CC2CC2)ccc1-c1cn(C[C@H]2CC[C@@H](C)O2)nn1] | 322.2 | $^1$H NMR (400 MHz, $CD_3CN$) δ 7.99 (s, 1H), 7.72 (d, J = 8.0 Hz, 1H), 7.29 (s, 1H), 7.25 (dd, J = 8.0, 1.5 Hz, 1H), 4.52 (dd, J = 14.1, 4.0 Hz, 1H), 4.42 (dd, J = 14.1, 6.1 Hz, 1H), 4.29 – 4.21 (m, 1H), 3.99 – 3.90 (m, 1H), 2.42 (s, 3H), 2.08 – 1.96 (m, 2H), 1.76 – 1.67 (m, 1H), 1.52 – 1.43 (m, 1H), 1.27 – 1.17 (m, 1H), 1.14 (d, J = 6.1 Hz, 3H), 0.92 – 0.86 (m, 2H), 0.77 – 0.71 (m, 2H). |
| I-226 | 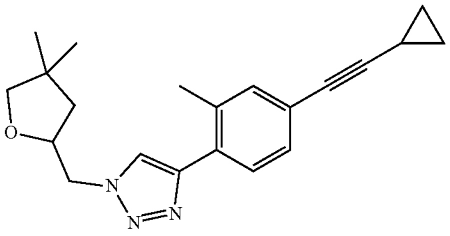 [SMILES: Cc1cc(C#CC2CC2)ccc1-c1cn(CC2CC(C)(C)CO2)nn1] | 336.2 | $^1$H NMR (400 MHz, DMSO-$d_6$) δ 8.36 (s, 1H), 7.71 (d, J = 8.0 Hz, 1H), 7.31 (d, J = 1.4 Hz, 1H), 7.26 (dd, J = 8.0, 1.4 Hz, 1H), 4.54 (dd, J = 13.9, 4.1 Hz, 1H), 4.47 (dd, J = 13.9, 6.7 Hz, 1H), 4.42-4.37 (m, 1H), 3.38 (s, 2H), 2.40 (s, 3H), 1.82 (dd, J = 12.4, 6.9 Hz, 1H), 1.58-1.53 (m, 1H), 1.46 (dd, J = 12.4, 8.5 Hz, 1H), 1.03 (s, 3H), 0.99 (s, 3H), 0.94 – 0.84 (m, 2H), 0.76 – 0.69 (m, 2H). |
| I-262 | 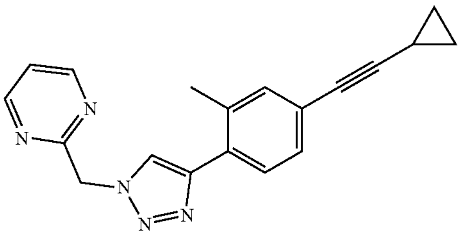 | 316.1 | $^1$H NMR (400 MHz, $CDCl_3$) δ 8.58 (d, J = 4.9 Hz, 2H), 7.86 (s, 1H), 7.72 – 7.63 (m, 1H), 7.23 – 7.04 (m, 3H), 5.75 (s, 2H), 2.32 (s, 3H), 1.37 (tt, J = 8.2, 5.1 Hz, 1H), 0.88 – 0.66 (m, 4H). |
| I-314 | 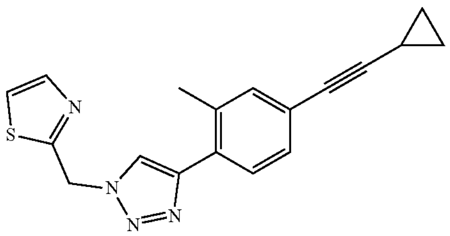 [SMILES: Cc1cc(C#CC2CC2)ccc1-c1cn(Cc2nccs2)nn1] | 321.1 | $^1$H NMR (400 MHz, $CDCl_3$) δ 7.83 (s, 1H), 7.76 (s, 1H), 7.66 (d, J = 7.8 Hz, 1H), 7.35 (s, 1H), 7.20 (d, J = 8.3 Hz, 2H), 5.88 (s, 2H), 2.34 (s, 3H), 1.48 – 1.33 (m, 1H), 0.78 (dddd, J = 21.4, 10.7, 5.4, 2.8 Hz, 4H). |

TABLE 5-continued

Characterization Data for Additional Exemplary Compounds

| Compound No. | Chemical Structure | [M + H] observed | $^1$H NMR (400 MHz) |
|---|---|---|---|
| I-285 | 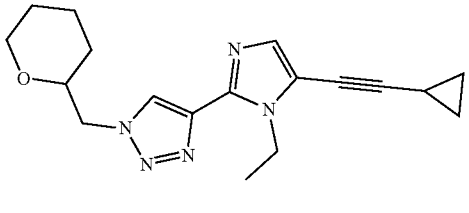 [SMILES: CCn1c(C#CC2CC2)cnc1-c1cn(CC2CCCCO2)nn1] | 326.2 | $^1$H NMR (400 MHz, $CD_3CN$) δ 8.15 (s, 1H), 7.12 (s, 1H), 4.51 (q, J = 7.1 Hz, 2H), 4.45 (dd, J = 14.2, 3.5 Hz, 1H), 4.36 (dd, J = 14.2, 7.8 Hz, 1H), 3.94 – 3.86 (m, 1H), 3.77 – 3.69 (m, 1H), 3.41 -3.31 (m, 1H), 1.88 – 1.80 (m, 1H), 1.72 – 1.62 (m, 1H), 1.60 – 1.44 (m, 4H), 1.36 (t, J = 7.1 Hz, 3H), 1.31 – 1.16 (m, 1H), 0.97 – 0.89 (m, 2H), 0.82 – 0.75 (m, 2H). |
| I-286 | 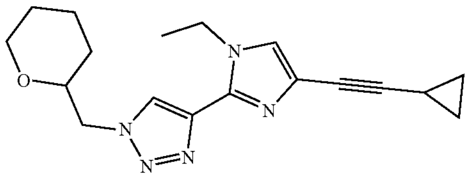 [SMILES: CCn1cc(C#CC2CC2)nc1-c1cn(CC2CCCCO2)nn1] | 326.2 | $^1$H NMR (400 MHz, $CD_3CN$) δ 8.14 (s, 1H), 7.19 (s, 1H), 4.48 – 4.40 (m, 3H), 4.35 (dd, J = 14.2, 7.8 Hz, 1H), 3.94 – 3.87 (m. 1H), 3.77 – 3.69 (m, 1H), 3.41 – 3.32 (m, 1H), 1.89 – 1.78 (m, 1H), 1.71 – 1.62 (m, 1H), 1.59 – 1.41 (m, 4H), 1.38 (t, J = 7.2 Hz, 3H), 1.31 – 1.18 (m, 1H), 0.88 – 0.80 (m, 2H), 0.75 – 0.64 (m, 2H). |
| I-292 | 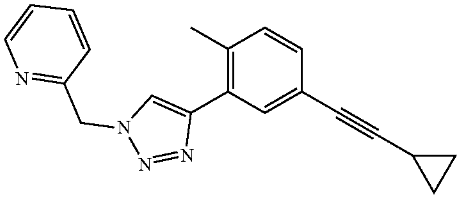 [SMILES: Cc1ccc(C#CC2CC2)cc1-c1cn(Cc2ccccn2)nn1] | 315.1 | $^1$H NMR (400 MHz, $CDCl_3$) δ 8.61 (d, J = 4.8 Hz, 1H), 7.82 (s, 1H), 7.77 (d, J = 1.8 Hz, 1H), 7.70 (td, J = 7.7, 1.8 Hz, 1H), 7.32 – 7.23 (m, 1H), 7.26 – 7.19 (m, 2H), 7.18 – 7.09 (m, 1H), 5.71 (s, 2H), 2.44 (s, 3H), 1.42 (tt, J = 8.2, 5.1 Hz, 1H), 0.98 – 0.61 (m, 4H). |
| I-293 | 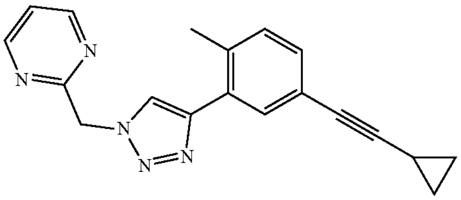 [SMILES: Cc1ccc(C#CC2CC2)cc1-c1cn(Cc2ncccn2)nn1] | 316.1 | $^1$H NMR (400 MHz, $CDCl_3$) δ 8.72 (d, J = 4.9 Hz, 2H), 7.89 (s, 1H), 7.80 (d, J = 1.8 Hz, 1H), 7.36 – 7.21 m, 2H , 7.15 (d, J = 7.9 Hz, 1H), 5.85 (s, 2H), 2.46 (s, 3H), 1.42 (tt, J = 8.2, 5.1 Hz, 1H), 0.92 – 0.73 (m, 4H). |
| I-372 | 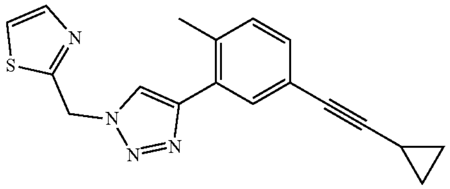 [SMILES: Cc1ccc(C#CC2CC2)cc1-c1cn(Cc2nccs2)nn1] | 321.1 | $^1$H NMR (400 MHz, $CDCl_3$) δ 7.82 (d, J = 3.6 Hz, 2H), 7.76 (d, J = 1.3 Hz, 1H), 7.40 (d, J = 3.2 Hz, 1H), 7.34 – 7.22(m, 1H), 7.15 (d, J = 7.9 Hz, 1H), 5.93 (s, 2H), 2.43 (s, 3H), 1.43 (ddd, J = 13.2, 8.2, 5.1 Hz, 1H), 0.82 (dddd, J = 21.5, 10.7, 5.5, 3.0 Hz, 4H). |
| I-373 | 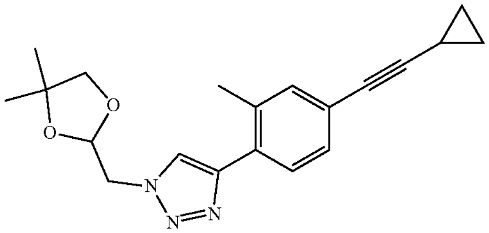 [SMILES: Cc1cc(C#CC2CC2)ccc1-c1cn(CC2OCC(C)(C)O2)nn1] | 338.2 | $^1$H NMR (400 MHz, $CD_3CN$) δ 7.98 (s, 1H), 7.71 (d, J = 8.0 Hz, 1H), 7.31 – 7.29 (m, 1H), 7.26 – 7.23 (m, 1H), 5.36 (t, J = 3.2 Hz, 1H), 4.60 (dd, J = 14.5, 3.0 Hz, 1H), 4.55 (dd, J = 14.5, 3.3 Hz, 1H), 3.62 J = 7.9 Hz, 1H), 3.46 (d, J = 8.0 Hz, 1H), 2.42 (s, 3H), 1.48 (tt, J = 8.2, 5.0 Hz, 1H), 1.25 (s, 3H), 1.09 (s, 3H), 0.92 -0.86 (m, 2H), 0.77 -0.71 (m, 2H). |

Example 5: Synthesis of I-75

Synthetic Scheme of I-75

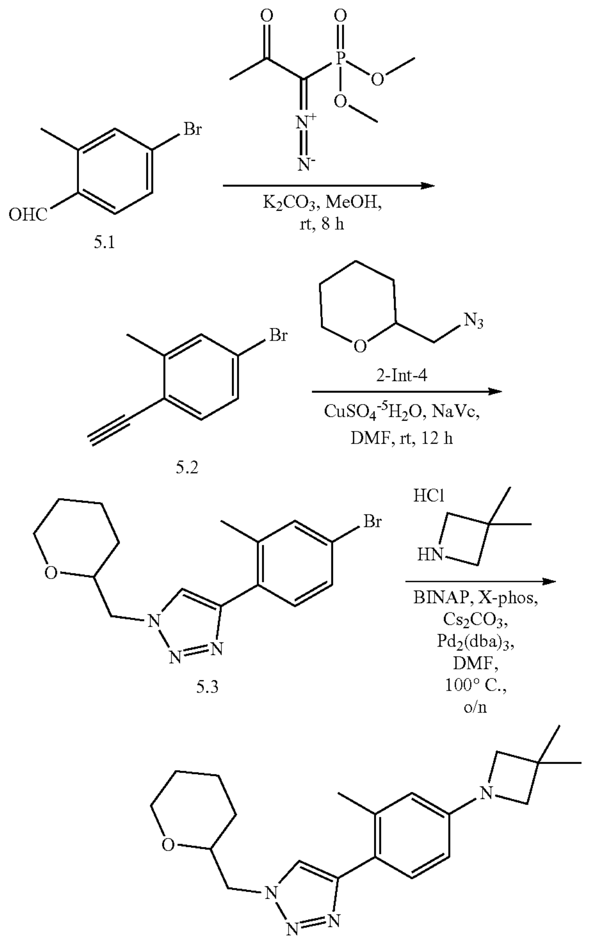

5.1
5.2
5.3
I-75

1. The Synthesis of Intermediate 5.2

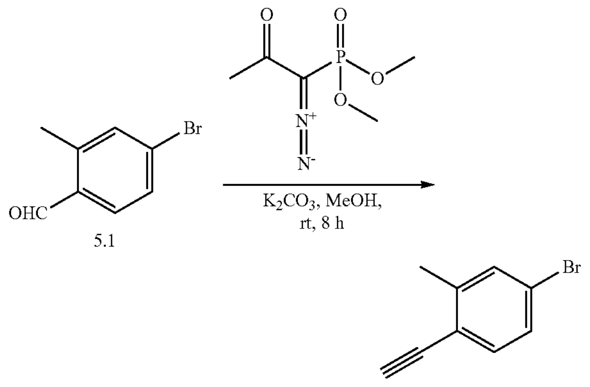

5.1
5.2

To a solution of 5.1 (5.0 g, 25 mmol) in MeOH (50 mL) was added $K_2CO_3$ (6.9 g, 50 mmol) and dimethyl 1-diazo-2-oxopropylphosphonate (5.0 g, 25 mmol). The reaction was stirred at RT for 8 h. After the consumption of starting material (by LCMS), water (30 mL) was added, extracted with ethyl acetate (30 mL×3), washed with water (30 mL×3), dried and concentrated. The crude product was purified by prep-HPLC to get 5.2 (4.5 g, yield: 90%) as a yellow solid. LC-MS m/z: 195.1 $[M+H]^+$.

2. The Synthesis of Intermediate 5.3

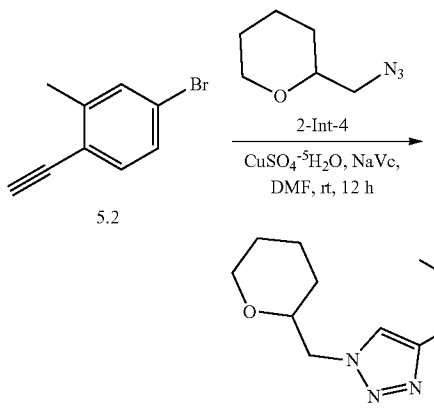

5.2
5.3

To a stirred solution of 5.2 (4.5 g, 23 mmol) in DMF (30 mL) was added 2-Int-4 (3.3 g, 23 mmol), $CuSO_4.5H_2O$ (1.3 g, 5 mmol), sodium ascorbate (1.3 g, 6 mmol) at RT. The reaction mixture was stirred at RT for 12 h. After the consumption of starting material (by LCMS), water (30 mL) was added, extracted with ethyl acetate (30 mL×3), washed with water (30 mL×3), dried and concentrated. The crude product was purified by prep-HPLC to give 5.3 (4.5 g, yield: 60%) as a brown solid.

$^1H$ NMR (400 MHz, DMSO-$d_6$): δ 8.36 (s, 1H), 7.72 (d, J 8.4 Hz, 1H), 7.55 (s, 1H), 7.48 (dd, J 8.4 Hz, 1.6 Hz, 1H), 4.38-4.50 (m, 2H), 3.72-3.87 (m, 2H), 3.29-3.32 (m, 1H), 2.44 (s, 3H), 1.78-1.81 (m, 1H), 1.63-1.66 (m, 1H), 1.40-1.51 (m, 3H), 1.19-1.25 (m, 1H).

3. The Synthesis of I-75

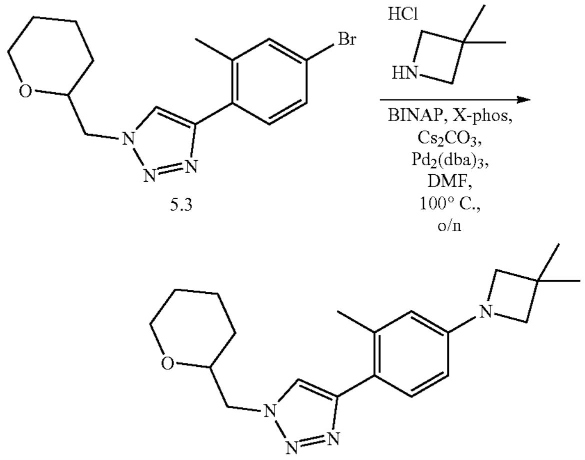

5.3
I-75

Under nitrogen, to a stirred solution of 5.3 (150 mg, 0.45 mmol), 3,3-dimethylazetidine hydrochloride (88 mg, 0.72 mmol) and X-Phos (30 mg) in DMF (10 mL), was added $Pd_2(dba)_3$ (15 mg), $Cs_2CO_3$ (440 mg, 1.35 mmol) and BINAP (30 mg). The reaction mixture was stirred at 100° C. for 16 hours until the reaction was complete (by LCMS). The suspension was diluted with $H_2O$ (20 mL) and extracted with EA (30 mL×3), concentrated. The crude product was purified by prep-HPLC to give I-75 (49.98 mg, yield: 33%) as a white solid.

Additional exemplary compounds were prepared following methods substantially similar to the method described above and herein. Data for these compounds are provided below.

TABLE 6

Characterization Data for Additional Exemplary Compounds

| Compound No. | Chemical Structure | [M + H] observed | $^1$H NMR (400 MHz) |
|---|---|---|---|
| I-36 | 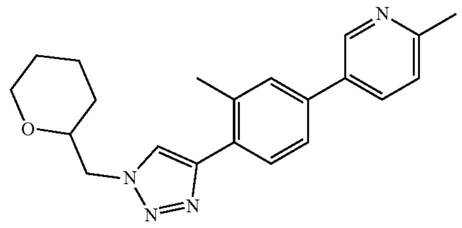 [SMILES: Cc1ccc(-c2ccc(-c3cn(CC4CCCCO4)nn3)c(C)c2)cn1] | 349.4 | $^1$H NMR (400 MHz, DMSO-$d_6$): δ 8.82 (s, 1 H), 8.37 (s, 1 H), 8.00 (d, J = 1.2 Hz, 1 H), 7.88 (d, J = 7.6 Hz, 1 H), 7.67 (s, 1 H), 7.62 (d, J = 8.0 Hz, 1 H), 7.35 (d, J = 8.0 Hz, 1 H), 4.39-4.52 (m, 2 H), 3.77-3.88 (m, 2 H), 3.31-3.35 (m, 1 H), 2.53 (s, 3 H), 2.51 (s, 3 H), 1.64-1.81 (m, 2 H), 1.41-1.51 (m, 3 H), 1.20-1.26 (m, 1 H). |
| I-75 | 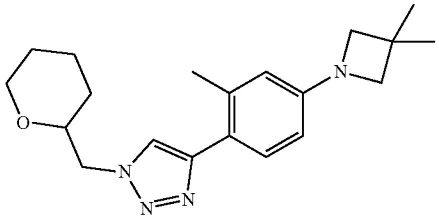 [SMILES: Cc1cc(N2CC(C)(C)C2)ccc1-c1cn(CC2CCCCO2)nn1] | 341.4 | $^1$H NMR (400 MHz, $CDCl_3$): δ 7.68 (s, 1 H), 7.63 (d, J = 8.4 Hz, 1 H), 6.36 (dd, J = 8.4 Hz, 2.4 Hz, 1 H), 6.30 (d, J = 2.0 Hz, 1 H), 4.45-4.50 (m, 1 H), 4.29-4.34 (m, 1 H), 3.96 – 4.00 (m, 1 H), 3.66-3.72 (m, 1 H), 3.59 (s, 4 H), 3.36-3.43 (m, 1 H), 2.41 (s, 3 H), 1.86-1.88 (m, 1 H), 1.64-1.67 (m, 1 H), 1.47-1.57 (m, 3 H), 1.32 (s, δ H), 1.21-1.30 (m, 1 H). |
| I-182 | 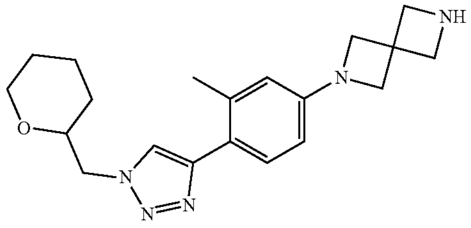 [SMILES: Cc1cc(N2CC3(CNC3)C2)ccc1-c1cn(CC2CCCCO2)nn1] | 354.1 | $^1$H NMR (400 MHz, DMSO-$d_6$): δ 8.10 (s, 1H), 7.53 (d, J = 8.0 Hz, 1H), 6.32-6.35 (m, 2H), 4.33-4.45 (m, 2H), 3.55-3.95 (m, 10H), 3.28 – 3.35 (m, 2H), 2.34 (s, 3H), 1.75 – 1.81 (m, 1H), 1.39-1.53 (m, 4H), 1.14-1.24 (m, 1H). |
| I-145 | 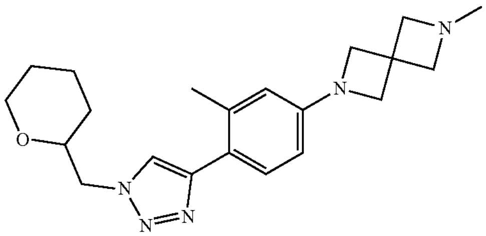 [SMILES: Cc1cc(N2CC3(CN(C)C3)C2)ccc1-c1cn(CC2CCCCO2)nn1] | 368.2 | $^1$H NMR (400 MHz, DMSO-$d_6$): δ 8.10 (s, 1H), 7.52 (d, J = 8.0 Hz, 1H), 6.31-6.34 (m. 2H), 4.33-4.44 (m, 2H), 3.83-3.86 (m, 5H), 3.69-3.75 (m, 1H), 3.28-3.32 (m, 1H), 3.25 (s, 4H), 2.34 (s, 3H), 2.14 (s, 3H), 1.77-1.81 (m. 1H), 1.62 (d, J = 12.4 Hz. IH), 1.38-1.51 (m. 3H), 1.17-1.23 (mr 1H). |
| I-146 | 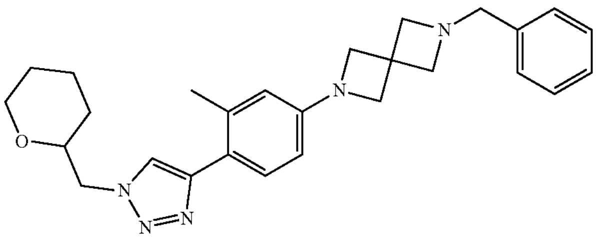 [SMILES: Cc1cc(N2CC3(CN(Cc4ccccc4)C3)C2)ccc1-c1cn(CC2CCCCO2)nn1] | 444.1 | $^1$H NMR (400 MHz, DMSO-$d_6$): δ 8.09 (s, 1H), 7.53 (d, J = 8.0 Hz, 1H), 7.21-7.33 (m, 5H), 6.32-6.34 2H), 4.32-4.44 (m, 2H), 3.83 – 3.88 (m, 5H), 3.69-3.75 (m, 1H), 3.53 (s, 2H), 3.28-3.32 (m, 5H), 2.34 (s, 3H), 1.77-1.80 (m, 1H), 1.62 (d, J = 12.8 Hz, 1H), 1.38-1.52 (m, 3H), 1.14-1.24 (m, 1H). |

TABLE 6-continued

| Characterization Data for Additional Exemplary Compounds | | | |
|---|---|---|---|
| Compound No. | Chemical Structure | [M + H] observed | $^1$H NMR (400 MHz) |
| I-167 | 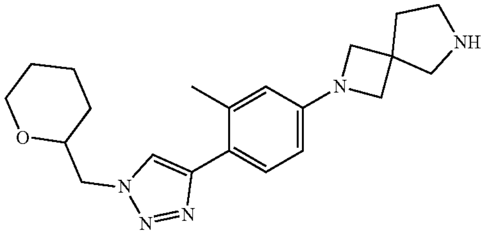 [SMILES: Cc1cc(N2CC3(CCNC3)C2)ccc1-c1cn(CC2CCCCO2)nn1] | 368.2 | $^1$H NMR (400 MHz, MeOD): δ 7.94 (s, 1H), 7.43-7.46 (m, 1H), 6.41 - 6.43 (m, 2H), 4.48 (dd, J = 3.6 Hz, 14.4 Hz, 1H), 4.40 (dd, J = 7.2 Hz, 14.0 Hz, 1H), 3.94-3.97(m, 1H), 3.73-3.85 (m, 5H), 3.39-3.46 (m, 1H), 3.30-3.31 (m, 2H), 3.16 (s, 1H), 3.04 (t, J = 7.2 Hz, 2H), 2.34 (s, 3H), 2.13 (t, J = 7.2 Hz, 2H), 1.87-1.90 (m, 1H), 1.61-1.71 (m, 1H), 1.52-1.62 (m, 3H), 1.22-1.32 (m, 1H). |
| I-168 | 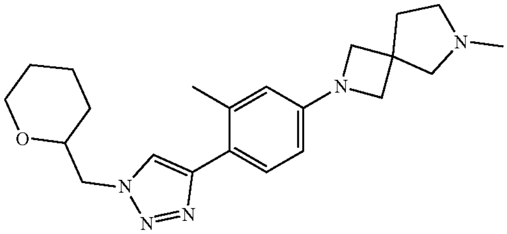 [SMILES: Cc1cc(N2CC3(CCN(C)C3)C2)ccc1-c1cn(CC2CCCCO2)nn1] | 382.1 | $^1$H NMR (400 MHz, DMSO-d$_6$): δ 8.10 (s, 1H), 7.52 (d, J = 8.4 Hz, 1H), 6.32-6.35 (m, 2H), 4.33-4.45 (m, 2H), 3.86-3.87 (m, 1H), 3.70 - 3.79 (m, 5H), 3.28-3.32 (m, 1H), 2.67 (s, 2H), 2.45-2.50 (m, 2H), 2.34 (s, 3H), 2.25 (s, 3H), 2.04 (t, J = 7.2 Hz, 2H), 1.78-1.81 (m, 1H), 1.61-1.64 (m, 1H), 1.39-1.54 (m, 3H), 1.15-1.25 (m, 1H). |
| I-169 | 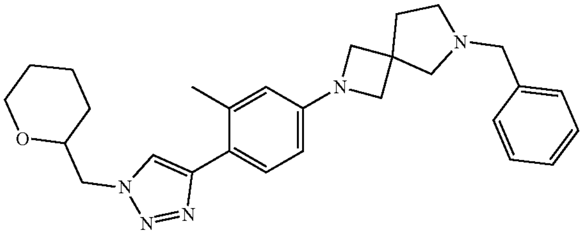 [SMILES: Cc1cc(N2CC3(CCN(Cc4ccccc4)C3)C2)ccc1-c1cn(CC2CCCCO2)nn1] | 458.2 | $^1$H NMR (400 MHz, DMSO-d$_6$): δ 8.09 (s, 1H), 7.52 (d, J = 8.0 Hz, 1H), 7.25-7.33 (m, 5H), 6.32-6.34 (m, 2H), 4.33-4.44 (m, 2H), 3.84 - 3.86 (m, 1H), 3.71-3.80 (m, 5H), 3.59 (s, 2H), 3.28-3.33 (m, 1H), 2.71 (s, 2H), 2.50-2.60 (m, 2H), 2.34 (s, 3H), 2.05 (t, J = 6.8 Hz, 2H), 1.78-1.80 (m, 1H), 1.60-1.63 (m, 1H), 1.36-1.54 (m, 3H), 1.14 - 1.23 (m, 1H). |
| I-147 | 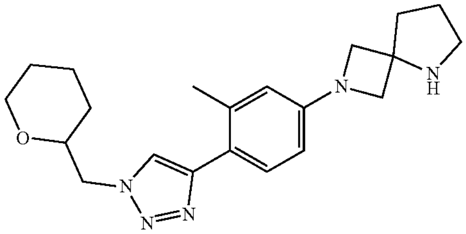 [SMILES: Cc1cc(N2CC3(CCCN3)C2)ccc1-c1cn(CC2CCCCO2)nn1] | 368.1 | $^1$H NMR (400 MHz, DMSO-d$_6$): δ 8.10 (s, 1H), 7.53 (d, J = 8.0 Hz, 1H), 6.34-6.36 (m, 2H), 4.33-4.45 (m, 2H), 3.82-3.87 (m, 3H), 3.60 - 3.76 (m, 3H), 3.29-3.35 (m, 2H), 2.87 (t, J = 7.2 Hz, 2H), 2.35 (s, 3H), 1.97 (t, J = 7.2 Hz, 2H), 1.70 - 1.81 (m, 3H), 1.61-1.64 (m, 1H), 1.39-1.51 (m, 3H), 1.15-1.25 (m, 1H). |
| I-148 | 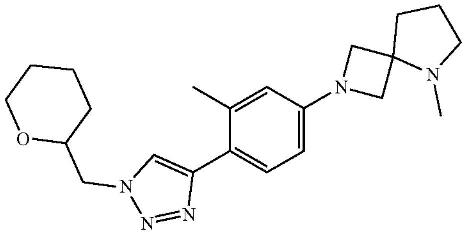 [SMILES: Cc1cc(N2CC3(CCCN3C)C2)ccc1-c1cn(CC2CCCCO2)nn1] | 382.1 | $^1$H NMR (400 MHz, DMSO-d$_6$): δ 8.10 (s, 1H), 7.53 (d, J = 8.0 Hz, 1H), 6.35-6.37 (m, 2H), 4.33-4.45 (m, 2H), 3.90-3.92 (d, J = 7.6 Hz, 2H), 3.84-3.87 (m, 1H), 3.70-3.76 (m, 1H), 3.60 (d, J = 7.6 Hz, 2H), 3.29-3.31 (m, 1H), 2.63 (t, J = 7.2 Hz, 2H), 2.35 (s, 3H), 2.34 (s, 3H), 2.03-2.07 (m, 2H), 1.61-1.81 (m, 4H), 1.39-1.53 (m, 3H), 1.15-1.25 (m, 1H). |
| I-149 | 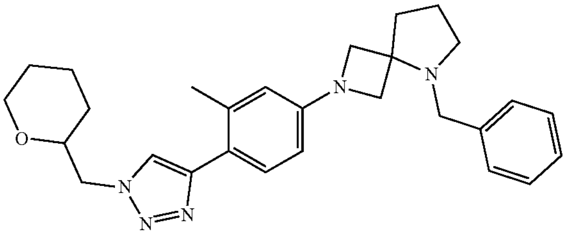 [SMILES: Cc1cc(N2CC3(CCCN3Cc3ccccc3)C2)ccc1-c1cn(CC2CCCCO2)nn1] | 458.2 | $^1$H NMR (400 MHz, DMSO-d$_6$): δ 8.10 (s, 1H), 7.54 (d, J = 8.0 Hz, 7.21-7.34 (m, 5H), 6.38-6.40 (m, 2H), 4.33-4.45 (m, 2H), 4.03 (d, J = 8.0 Hz, 2H), 3.72-3.87 (m, 6H), 3.29-3.33 (m, 1H), 2.55 (t, J = 7.2 Hz, 2H), 2.36 (s, 3H), 2.08-2.13 (m, 2H), 1.61-1.80 (m, 4H), 1.34-1.51 (m, 3H), 1.15-1.24 (m, 1H). |

TABLE 6-continued

Characterization Data for Additional Exemplary Compounds

| Compound No. | Chemical Structure | [M + H] observed | $^1$H NMR (400 MHz) |
|---|---|---|---|
| I-150 | 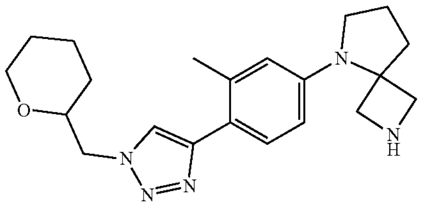 [SMILES: Cc1cc(N2CCCC23CNC3)ccc1-c1cn(CC2CCCCO2)nn1] | 368.2 | $^1$H NMR (400 MHz, $CDCl_3$): δ 7.65-7.71 (m, 2 H), 6.78-7.01 (m, 2 H), 4.62-4.73 (m, 2 H), 4.46 (dd, J = 3.2 Hz, 14.0 Hz, 1 H), 4.31 (dd, J = 7.2 Hz, 14.0 Hz, 1 H), 3.98-3.99 (m, 1 H), 3.64-3.95 (m, 2 H), 3.55 (d, J = 9.2 Hz, 2 H), 3.36-3.42 (m, 3 H), 2.48 (s, 3 H), 2.31-2.45 (m, 2 H), 1.86-1.91 (m, 3 H), 1.64-1.67 (m, 1 H), 1.46-1.57 (m, 3 H), 1.22 - 1.31 (m, 1 H). |
| I-151 | 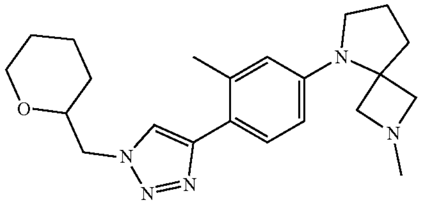 [SMILES: Cc1cc(N2CCCC23CN(C)C3)ccc1-c1cn(CC2CCCCO2)nn1] | 382.1 | $^1$H NMR (400 MHz, $CDCl_3$): δ 7.71 (s, 1 H), 7.68 (d, J = 8.8 Hz, 1 H), 7.17 (dd, J = 2.8 Hz, 8.4 Hz, 1 H), 6.97 (d, J = 2.0 Hz, 1 H), 4.48 (dd, J = 3.2 Hz, 14.4 Hz, 1 H), 4.33 (dd, J = 7.2 Hz, 14.0 Hz, 1 H), 4.22 (d, J = 8.8 Hz, 2 H), 3.97-4.00 (m, 1 H), 3.69-3.73 (m, 1 H), 3.38-3.43 (m, 1 H), 3.35 (t, J = 6.4 Hz, 2 H), 3.19 (d, J = 8.8 Hz, 2 H), 2.58 (s, 3 H), 2.47 (s, 3 H), 2.31 (t, J = 6.4 Hz, 2 H), 1.83-1.89 (m, 3 H), 1.65-1.75 (m, 2 H), 1.50-1.53 (m, 2 H), 1.26 - 1.29 (m, 1 H). |
| I-152 | 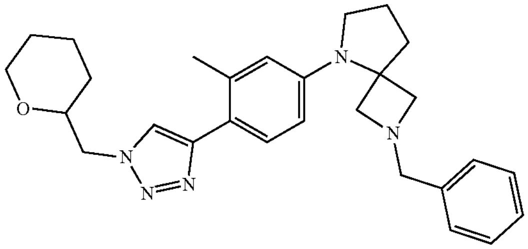 [SMILES: Cc1cc(N2CCCC23CN(Cc2ccccc2)C3)ccc1-c1cn(CC2CCCCO2)nn1] | 458.1 | $^1$H NMR (400 MHz, $CDCl_3$): δ 7.69-7.71 (m, 2 H), 7.30-7.36 (m, 4 H), 7.19-7.26 (m, 3 H), 4.48 (dd, J = 3.2 Hz, 14.4 Hz, 1 H), 4.33 (dd, J = 7.2 Hz, 14.0 Hz, 1 H), 4.22 (d, J = 8.0 Hz, 2 H), 3.98-4.01 (m, 1 H), 3.90 (s, 2 H), 3.68-3.74 (m, 1 H), 3.41-3.44 (m, 1 H), 3.36 (t, J = 6.4 Hz, 2 H), 3.17 (d, J = 8.8 Hz, 2 H), 2.49 (s, 3 H), 2.26 (t, J = 6.8 Hz, 2 H), 1.81-1.89 (m, 3 H), 1.66-1.69 (m, 2 H), 1.51-1.57 (m, 1 H), 1.23 - 1.32 (m, 2 H). |
| I-170 | 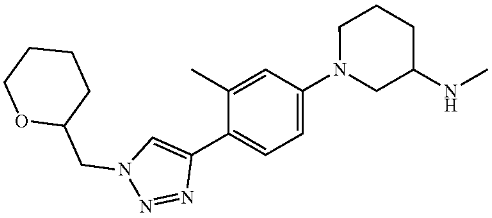 [SMILES: CNC1CCCN(c2ccc(-c3cn(CC4CCCCO4)nn3)c(C)c2)C1] | 370.2 | $^1$H NMR (400 MHz, $CD_3OD$) δ 7.98 (d, J = 4.8 Hz, 1H), 7.49 (d, J = 8.8 Hz, 1H), 6.87-6.90 (m, 2H), 4.39-4.51 (m, 2H), 3.97 (d, J = 10.8 Hz, 1H), 3.68-3.76 (m, 2H), 3.40 - 3.52 (m, 2H), 2.80-2.85 (m, 1H), 2.66-2.67 (m, 2H), 2.52 (s, 3H), 2.37 (s, 3H), 2.02 (d, J = 11.6 Hz, 1H), 1.81-1.86 (m, 2H), 1.67-1.70 (m, 2H) 1.53-1.58 (m, 3H), 1.25 - 1.34 (m, 2H). |
| I-153 | 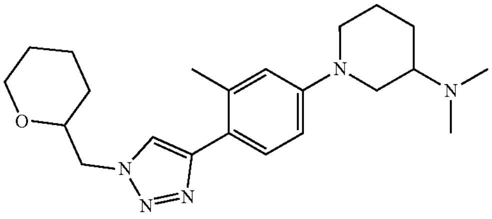 [SMILES: Cc1cc(N2CCCC(N(C)C)C2)ccc1-c1cn(CC2CCCCO2)nn1] | 384.2 | $^1$H NMR (400 MHz, DMSO-$d_6$) δ 8.13 (s, 1H),7.55-7.57 (m, 1H), 6.82-6.84 (m, 2H), 4.34-4.45 (m, 2H), 3.65-3.87 (m, 4H),3.28-3.34 (m, 1H), 2.55-2.64 (m, 2H), 2.30 - 2.37 (m, 4H), 2.25 (s, 6H), 1.89 (m, 1H), 1.73-1.80 (m, 2H), 1.61-1.64 (m, 2H), 1.50-1.54 (m, 1H), 1.43 - 1.49 (m, 2H), 1.18-1.33 (m, 3H). |
| I-171 | 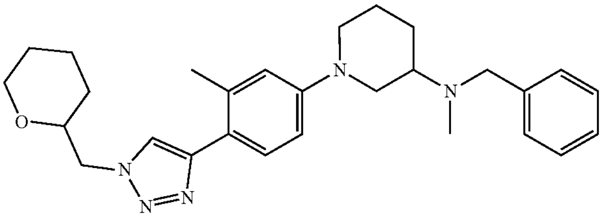 [SMILES: Cc1cc(N2CCCC(N(C)Cc3ccccc3)C2)ccc1-c1cn(CC2CCCCO2)nn1] | 460.2 | $^1$H NMR (400 MHz, DMSO-$d_6$) δ 8.12 (s, 1H), 7.55 (d, J = 9.6 Hz, 1H), 7.29-7.35 (m, 4H), 7.20-7.24 (m, 1H), 6.82 (d, J = 6.8 Hz, 2H), 4.34-4.44 (m, 2H), 3.79-3.87 (m, 2H), 3.66-3.74 (m, 4H), 3.28-3.32 (m, 1H), 2.72 (t, J = 10.8 Hz, 1H), 2.61-2.64 (m, 2H), 2.37 (s, 3H), 2.21 (s, 3H), 1.92 (d, J = 6.4 Hz, 1H), 1.76-1.78 (m, 2H), 1.62 (d, J = 12.4 Hz, 1H), 1.43-1.52 (m, 5H), |

TABLE 6-continued

| Characterization Data for Additional Exemplary Compounds | | | |
|---|---|---|---|
| Compound No. | Chemical Structure | [M + H] observed | $^1$H NMR (400 MHz) |
| | | | 1.18-1.23 (m, 1H). |
| I-183 | 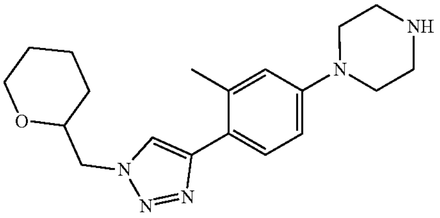 [SMILES: Cc1cc(N2CCNCC2)ccc1-c1cn(CC2CCCCO2)nn1] | 342.2 | $^1$H NMR (400 MHz, DMSO-$d_6$): δ 8.14 (s, 1H) , 7.58 (d, J = 9.2 Hz, 1H), 6.83 (s, 2H), 4.34-4.46 (m, 2H), 3.86 (d, J = 11.6 Hz, 1H), 3.70-3.76 (m, 1H), 3.29-3.35 (m, 2H), 3.08 (s, 4H), 2.84 (s, 4H), 2.38 (s, 3H), 1.78-1.81 (m, 1H), 1.63 (d, J = 12.8 Hz, 1H), 1.39-1.50 (m, 3H), 1.16-1.25 (m, 1H). |
| I-140 | 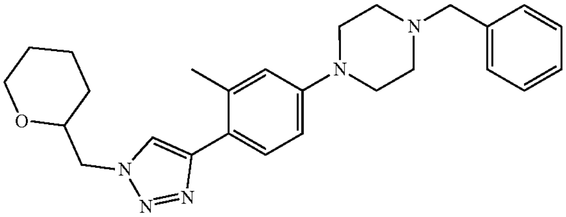 [SMILES: Cc1cc(N2CCN(Cc3ccccc3)CC2)ccc1-c1cn(CC2CCCCO2)nn1] | 432.0 | $^1$H NMR(400 MHz, DMSO-$d_6$): δ 8.14 (s, 1H) , 7.57 (d, J = 9.6 Hz, 1H), 7.34-7.35 (m, 4H), 7.26-7.29 (m, 1H), 6.82-6.84 (m, 2H), 4.34 - 4.46 (m, 2H), 3.84-3.87 (m, 1H), 3.71-3.76 (m, 1H), 3.53 (s, 2H), 3.28-3.32 (m, 1H), 3.17-3.19 (m, 4H), 2.50-2.51 (m, 4H), 2.37 (s, 3H), 1.78-1.81 (m, 1H), 1.61-1.64 (m, 1H), 1.43-1.50 (m, 3H), 1.18 - 1.24 (m, 1H). |
| I-128 | 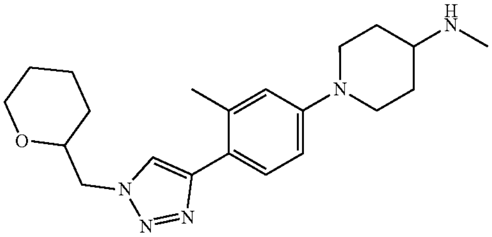 [SMILES: CNC1CCN(c2ccc(-c3cn(CC4CCCCO4)nn3)c(C)c2)CC1] | 370.2 | $^1$H NMR (400 MHz, $CDCl_3$): δ 7.71 (s, 1 H), 7.68 (d, J = 8.4 Hz, 1 H), 6.82-6.86 (m, 2 H), 4.49 (dd, J = 3.2 Hz, 14.0 Hz, 1 H), 4.32 (dd, J = 6.8 Hz, 14.0 Hz, 1 H), 3.96-4.00 (m, 1 H), 3.67-3.73 (m, 3 H), 3.36-3.43 (m, 1 H), 2.76-2.83 (m, 2 H), 2.48 - 2.56 (m, 1 H), 2.47 (s, 3 H), 2.43 (s, 3 H), 1.99-2.02 (m, 2 H), 1.86-1.88 (m, 1 H), 1.53-1.57 (m, 4 H), 1.43 - 1.52 (m, 2 H), 1.22 -1.31 (m, 1 H). |
| I-129 | 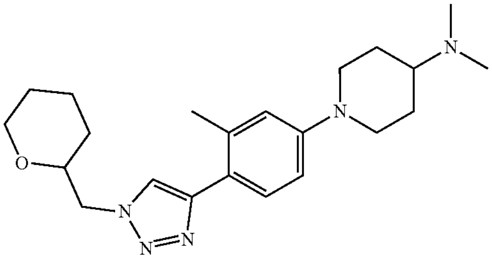 [SMILES: Cc1cc(N2CCC(N(C)C)CC2)ccc1-c1cn(CC2CCCCO2)nn1] | 384.2 | $^1$H NMR (400 MHz, $CDCl_3$): δ 7.71 (s, 1 H), 7.68 (d, J = 8.4 Hz, 1 H), 6.82-6.86 (m, 2 H), 4.49 (dd, J = 3.2 Hz, 14.4 Hz, 1 H), 4.32 (dd, J = 7.2 Hz, 14.4 Hz, 1 H), 3.96-4.00 (m, 1 H), 3.67-3.80 (m, 3 H), 3.36-3.43 (m, 1 H), 2.70-2.77 (m, 2 H), 2.43 (s, 3 H), 2.31 (s, δ H), 2.25-2.29 (m, 1 H), 1.86-1.93 (m, 4 H), 1.50-1.68 (m, 5 H), 1.24-1.28 (m, 1 H). |
| I-141 | 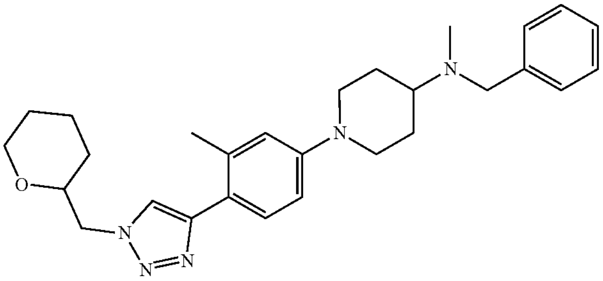 [SMILES: Cc1cc(N2CCC(N(C)Cc3ccccc3)CC2)ccc1-c1cn(CC2CCCCO2)nn1] | 460.3 | $^1$H NMR (400 MHz, $CDCl_3$): δ 7.71 (s, 1 H), 7.69 (d, J = 8.4 Hz, 1 H), 7.29-7.34 (m, 4 H), 7.22-7.26 (m, 1 H), 6.82-6.87 (m, 2 H), 4.49 (dd, J = 3.2 Hz, 14.4 Hz, 1 H), 4.34 (dd, J = 7.2 Hz, 14.0 Hz, 1 H), 3.96-4.00 (m, 1 H), 3.82 (d, J = 12.4 Hz, 2 H), 3.67-3.72 (m, 1 H), 3.61 (s, 2 H), 3.36-3.43 (m, 1 H), 2.71-2.77 (m, 2 H), 2.58-2.64 (m, 1 H), 2.43 (s, 3 H), 2.23 (s, 3 H), 1.65-1.95 (m, 7 H), 1.55-1.56 (m, 2 H), 1.25-1.28 (m, 1 H). |

TABLE 6-continued

| Characterization Data for Additional Exemplary Compounds | | | |
|---|---|---|---|
| Compound No. | Chemical Structure | [M + H] observed | $^1$H NMR (400 MHz) |
| I-184 | 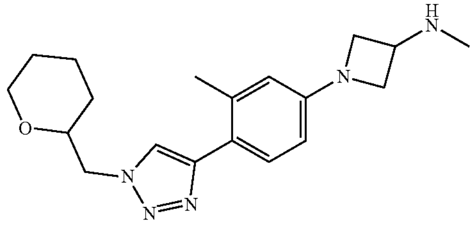 [SMILES: CNC1CN(c2ccc(-c3cn(CC4CCCCO4)nn3)c(C)c2)C1] | 342.1 | $^1$H NMR (400 MHz, $CDCl_3$) δ 7.68 (s, 1H), 7.64 (d, J = 8.4 Hz, 1H), 6.39 (dd, J = 2.0 Hz, 8.0 Hz, 1H), 6.34 (d, J = 2.0 Hz, 1H), 4.48 (dd, J = 2.8 Hz, 14.0 Hz, 1H), 4.32 (dd, J = 7.2 Hz, 14.0 Hz, 1H), 4.12 (t, J = 7.2 Hz, 2H), 3.98 (dd, J = 2.4 Hz, 11.2 Hz, 1H), 3.67-3.72 (m, 2H), 3.55-3.58 (m, 2H), 3.36-3.43 (m, 1H), 2.45 (s, 3H), 2.38 (s, 3H), 1.86 – 1.88 (m, 1H), 1.65-1.68 (m, 1H), 1.46-1.52 (m, 3H), 1.22-1.31 (m, 1H). |
| I-142 | 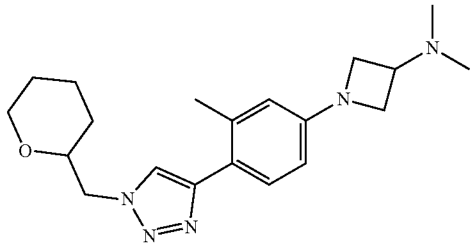 [SMILES: Cc1cc(N2CC(N(C)C)C2)ccc1-c1cn(CC2CCCCO2)nn1] | 336.1 | $^1$H NMR (400 MHz, $CDCl_3$): δ 7.68 (s, 1 H), 7.64 (d, J = 8.4 Hz, 1 H), 6.38 (dd, J = 8.4 Hz, 2.4 Hz, 1 H), 6.33 (d, J = 2.0 Hz, 1 H), 4.48 (dd, J = 14.4 Hz, 3.2 Hz, 1 H), 4.32 (dd, J = 14.0 Hz, 7.2 Hz, 1 H), 3.96-4.00 (m, 1 H), 3.67-3.72 (m, 3 H), 3.37 – 3.42 (m, 1 H), 3.24-3.26 (m, 1 H), 2.41 (s, 3 H), 2.22 (s, δ H), 1.86 (br, 1 H), 1.66 (d, J = 12.8 Hz, 1 H), 1.50-1.53 (m, 3H), 1.25-1.28 (m, 1 H). |
| I-185 | 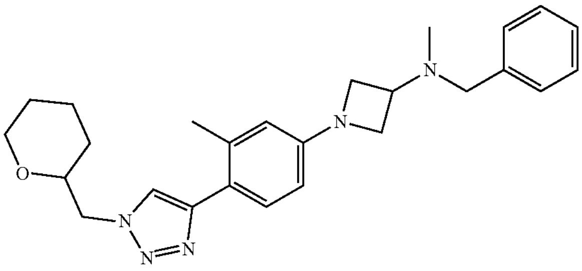 [SMILES: Cc1cc(N2CC(N(C)Cc3ccccc3)C2)ccc1-c1cn(CC2CCCCO2)nn1] | 432.2 | $^1$H NMR (400 MHz, $CDCl_3$) δ 7.68 (s, 1H), 7.65 (d, J = 8.0 Hz, 1H), 7.24-7.34 (m, 5H), 6.40 (dd, J = 2.4 Hz, 8.4 Hz, 1H), 6.35 (d, J = 2.4 Hz, 1H), 4.48 (dd, J = 3.2 Hz, 14.0 Hz, 1H), 4.32 (dd, J = 7.2 Hz, 14.4 Hz, 1H), 3.97-4.02 (m, 3H), 3.67-3.74 (m, 3H), 3.49-3.54 (m, 1H), 3.46 (s, 2H), 3.37-3.43 (m, 1H), 2.41 (s, 3H), 2.12 (s, 3H), 1.86-1.88 (m, 1H), 1.65-1.68 (m, 2H), 1.50-1.57 (m, 2H), 1.22-1.31 (m, 1H). |
| I-154 | 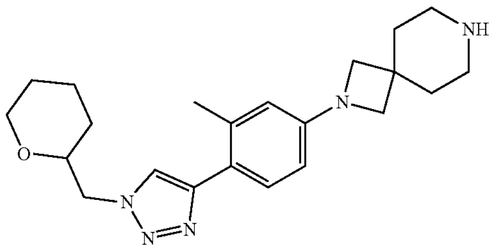 [SMILES: Cc1cc(N2CC3(CCNCC3)C2)ccc1-c1cn(CC2CCCCO2)nn1] | 382.2 | $^1$H NMR (400 MHz, DMSO-$d_6$): δ 8.09 (s, 1H), 7.52 (d, J = 8.0 Hz, 1H), 6.31-6.34 (m, 2H), 4.33-4.44 (m, 2H), 3.84-3.87 (m, 1H), 3.70 – 3.76 (m, 1H), 3.54 (s, 4H), 3.14 – 3.34 (m, 2H), 2.64 (s, 4H), 2.34 (s, 3H), 1.77-1.81 (m, 1H), 1.60-1.65 (m, 5H), 1.37-1.54 (m, 3H), 1.15 – 1.25 (m, 1H). |
| I-155 | 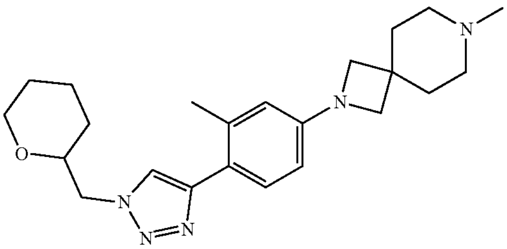 [SMILES: Cc1cc(N2CC3(CCN(C)CC3)C2)ccc1-c1cn(CC2CCCCO2)nn1] | 396.2 | $^1$H NMR (400 MHz, DMSO-$d_6$): δ 8.09 (s, 1H), 7.52 (d, J = 8.0 Hz, 1H), 6.31-6.34 (m, 2H), 4.33-4.44 (m, 2H), 3.84-3.87 (m, 1H), 3.70 – 3.76 (m, 1H), 3.54 (s, 4H), 3.28 – 3.32 (m, 1H), 2.13-2.34 (m, 10H), 1.72-1.81 (m, 5H), 1.62 (d, J = 12.4 Hz, 1H), 1.39-1.53 (m, 3H), 1.15 – 1.25 (m, 1H). |

TABLE 6-continued

| Characterization Data for Additional Exemplary Compounds | | | |
|---|---|---|---|
| Compound No. | Chemical Structure | [M + H] observed | $^1$H NMR (400 MHz) |
| I-156 | 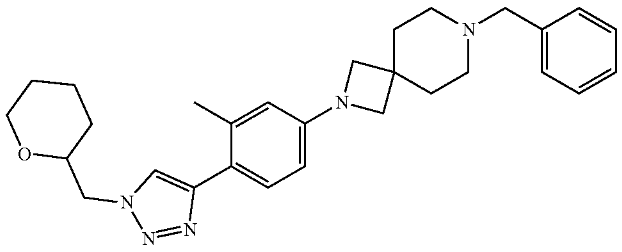 [SMILES: Cc1cc(N2CC3(CCN(Cc4ccccc4)CC3)C2)ccc1-c1cn(CC2CCCCO2)nn1] | 472.2 | $^1$H NMR (400 MHz, DMSO-$d_6$): δ 8.09 (s, 1H), 7.52 (d, J = 8.0 Hz, 1H), 7.23-7.34 (m, 5H), 6.31-6.34 (m, 2H), 4.33-4.44 (m, 2H), 3.84 - 3.87 (m, 1H), 3.70-3.76 (m, 1H), 3.54 (s, 4H), 3.44 (s, 2H), 3.28-3.32 (m, 1H), 2.30-2.40 (m, 7H), 1.73 - 1.80 (m, 5H), 1.62 (d, J = 12.4 Hz, 1H), 1.39-1.53 (m, 3H), 1.14-1.24 (m, 1H). |
| I-186 | 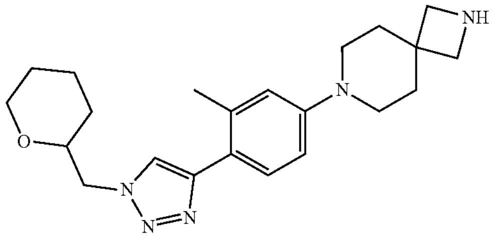 [SMILES: Cc1cc(N2CCC3(CC2)CNC3)ccc1-c1cn(CC2CCCCO2)nn1] | 382.2 | $^1$H NMR (400 MHz, DMSO-$d_6$): δ 8.13 (s, 1 H), 7.56 (d, J = 9.6 Hz, 1 H), 6.82-6.87 (m, 2 H), 4.33-4.46 (m, 2 H), 3.26-3.88 (m, 8 H), 3.14 (br, 4 H), 2.37 (s, 3 H), 1.78 (br, 5 H), 1.60-1.65 (m, 1 H), 1.40-1.49 (m, 3 H), 1.18-1.22 (m, 1 H). |
| I-172 | 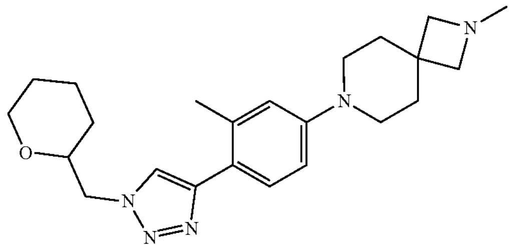 [SMILES: Cc1cc(N2CCC3(CC2)CN(C)C3)ccc1-c1cn(CC2CCCCO2)nn1] | 396.2 | $^1$H NMR (400 MHz, DMSO-$d_6$): δ 8.13 (s, 1 H), 7.54-7.57 (m, 1 H), 6.81-6.84 (m, 2 H), 4.33-4.46 (m, 2 H), 3.83-3.88 (m, 1 H), 3.71-3.75 (m, 1 H), 3.28-3.34 (m, 1 H), 3.12 (t, J = 5.6 Hz, 4 H), 2.94 (s, 4 H), 2.36 (s, 3 H), 2.23 (s, 3 H), 1.72 - 1.81 (m, 5 H), 1.60-1.65 (m, 1 H), 1.42-1.51 (m, 3 H), 1.17-1.22 (m, 1 H). |
| I-173 | 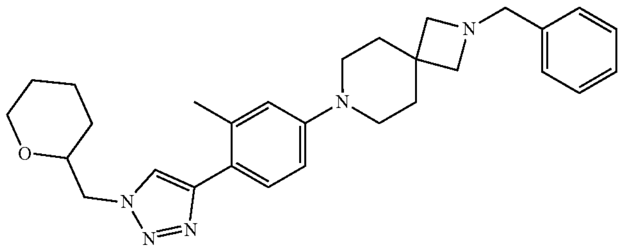 [SMILES: Cc1cc(N2CCC3(CC2)CN(Cc2ccccc2)C3)ccc1-c1cn(CC2CCCCO2)nn1] | 472.2 | $^1$H NMR (400 MHz, DMSO-$d_6$): δ 8.12 (s, 1 H), 7.56 (d, J = 9.2 Hz, 1 H), 7.20-7.33 (m, 5 H), 6.81-6.84 (m, 2 H), 4.37-4.46 (m, 2 H), 3.83 - 3.87 (m, 1 H), 3.70-3.74 (m, 1 H), 3.58 (s, 2 H), 3.28-3.34 (m, 1 H), 3.12 (t, J = 5.2 Hz, 4H), 2.97 (s, 4 H), 2.36 (s, 3 H), 1.75-1.77 (m, 5 H), 1.60-1.65 (m, 1 H), 1.42-1.51 (m, 3 H), 1.17-1.23 (m, 1 H). |
| I-213 | 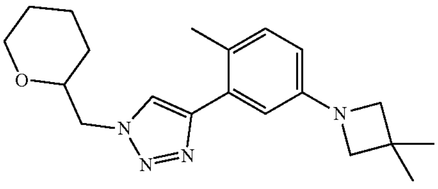 [SMILES: Cc1ccc(N2CC(C)(C)C2)cc1-c1cn(CC2CCCCO2)nn1] | 341.2 | $^1$H NMR (400 MHz, DMSO-$d_6$): δ 8.24 (s, 1H) , 7.07 (d, J = 8.4 Hz, 1H), 6.79 (d, J = 2.4 Hz, 1H), 6.34 (dd, J = 8.0 Hz, 2.4 Hz, 1H), 4.36 - 4.48 (m, 2H), 3.86 (d, J = 2.0 Hz, 1H), 3.72-3.76 (m, 1H), 3.51 (s, 4H), 3.28-3.31 (m, 1H), 2.29 (s, 3H), 1.80 (d, J = 11.2 Hz, 1H), 1.63 (d, J = 12.8 Hz, 1H), 1.39-1.55 (m, 3H), 1.28 (s, 6H), 1.15-1.22 (m, 1H). |
| I-202 | 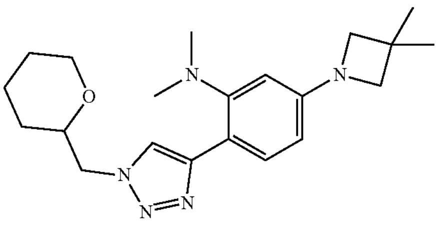 [SMILES: CN(C)c1cc(N2CC(C)(C)C2)ccc1-c1cn(CC2CCCCO2)nn1] | 370.0 | $^1$H NMR (400 MHz, DMSO-$d_6$) δ 8.17 (s, 1H), 7.80 (d, J = 8.0 Hz, 1H), 6.14-6.17 (m, 2H), 4.34-4.46 (m, 2H), 3.84-3.87 (m, 1H), 3.64 - 3.70 (m, 1H), 3.54 (s, 4H), 3.27 - 3.31 (m, 1H), 2.55 (s, 6H), 1.76 - 1.79 (m, 1H), 1.59-1.62 (m, 1H), 1.37-1.50 (m, 3H), 1.28 (s, 6H), 1.11-1.21 (m, 1H). |

TABLE 6-continued

| Characterization Data for Additional Exemplary Compounds | | | |
|---|---|---|---|
| Compound No. | Chemical Structure | [M + H] observed | $^1$H NMR (400 MHz) |
| I-310 | 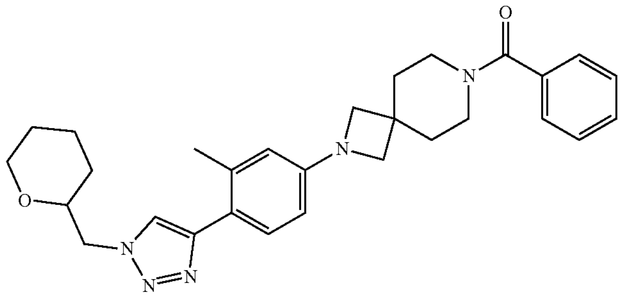 [SMILES: Cc1cc(N2CC3(CCN(C(=O)c4ccccc4)CC3)C2)ccc1-c1cn(CC2CCCCO2)nn1] | 486.1 | $^1$H NMR (400 MHz, DMSO-d6) δ 8.10 (s, 1H), 7.54 (d, J = 8.4 Hz, 1H), 7.37-7.46 (m, 5H), 6.33-6.36 (m, 2H), 4.33-4.45 (m, 2H), 3.84 - 3.87 (m, 1H), 3.62-3.76 (m, 7H), 3.16-3.37 (m, 3H), 2.35 (s, 3H), 1.75-1.80 (m, 5H), 1.60-1.63 (m, 1H), 1.37-1.53 (m, 3H), 1.15-1.24 (m, 1H). |
| I-311 | 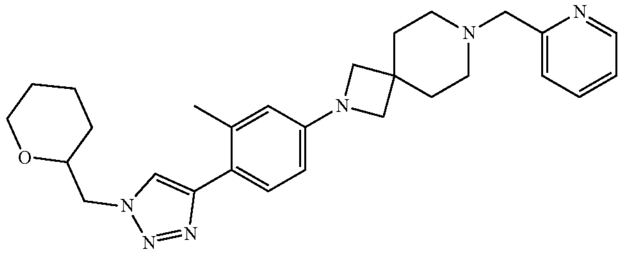 [SMILES: Cc1cc(N2CC3(CCN(Cc4ccccn4)CC3)C2)ccc1-c1cn(CC2CCCCO2)nn1] | 473.0 | $^1$H NMR (400 MHz, DMSO-$d_6$) δ 8.49 (d, J = 4.4 Hz, 1H), 8.09 (s, 1H), 7.74-7.78 (m, 1H), 7.53 (d, J = 8.0 Hz, 1H), 7.44 (d, J = 8.0 Hz, 1H), 7.25 (dd, J = 1.6 Hz, 6.8 Hz, 1H), 6.32-6.35 (m, 2H), 4.33-4.45 (m, 2H), 3.84-3.87 (m, 1H), 3.69 - 3.76 (m, 1H), 3.55-3.57 (m, 6H), 3.28-3.34 (m, 1H), 2.34-2.38 (m 7H), 1.75-1.80 (m, 5H), 1.60-1.64 (m, 1H), 1.39-1.53 (m, 3H), 1.15 - 1.24 (m, 1H). |
| I-236 | 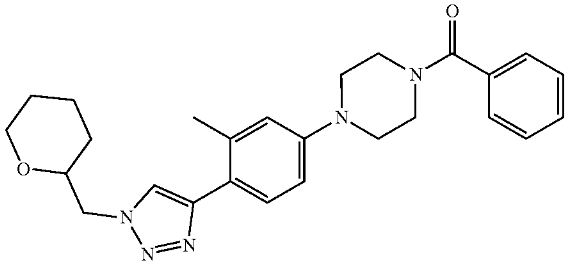 [SMILES: Cc1cc(N2CCN(C(=O)c3ccccc3)CC2)ccc1-c1cn(CC2CCCCO2)nn1] | 446.2 | $^1$H NMR (400 MHz, DMSO-$d_6$) δ 8.16 (s, 1H), 7.61 (d, J = 8.8 Hz, 1H), 7.45-7.47 (s, 5H), 6.87-6.88 (s, 2H), 4.35-4.46 (m, 2H), 3.74-3.87 (m, 4H), 3.48 (br, 2H), 3.20-3.34 (m, 5H), 2.39 (s, 3H), 1.78-1.81 (m, 1H), 1.61-1.64 (m, 1H), 1.40-1.50 (m, 3H), 1.16-1.24 (m, 1H). |
| I-237 | 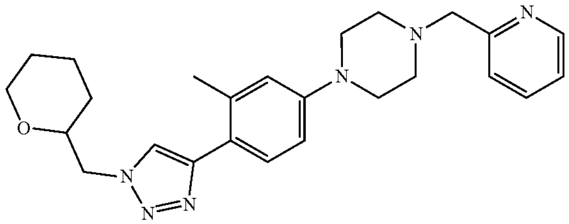 [SMILES: Cc1cc(N2CCN(Cc3ccccn3)CC2)ccc1-c1cn(CC2CCCCO2)nn1] | 433.2 | $^1$H NMR (400 MHz, DMSO-$d_6$) δ 8.51 (d, J = 4.0 Hz, 1H), 8.14 (s, 1H), 7.76-7.81 (m, 1H), 7.57-7.59 (m, 1H), 7.48 (d, J = 7.6 Hz, 1H), 7.27-7.30 (m, 1H), 6.83-6.85 (m, 2H), 4.34-4.46 (m, 2H), 3.84-3.87 (m, 1H), 3.70-3.76 (m, 1H), 3.66 (s, 2H), 3.28-3.32 (m, 1H), 3.18-3.21 (m, 4H), 2.57-2.59 (m, 4H), 2.38 (s, 3H), 1.78-1.81 (m, 1H), 1.61-1.64 (m, 1H), 1.39-1.54 (m, 3H), 1.15 - 1.25 (m, 1H). |
| I-238 | 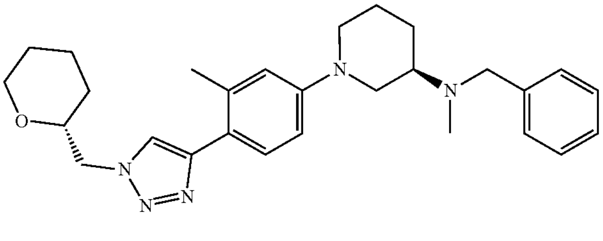 [SMILES: Cc1cc(N2CCC[C@@H](N(C)Cc3ccccc3)C2)ccc1-c1cn(C[C@H]2CCCCO2)nn1] | 460.0 | $^1$H NMR (400 MHz, DMSO-$d_6$) δ 8.13 (s, 1H), 7.56 (d, J = 9.2 Hz, 1H), 7.30-7.35 (m, 4H), 7.21-7.24 (m, 1H), 6.81-6.83 (m, 2H), 4.34 - 4.46 (m, 2H), 3.66-3.87 (m, 6H), 3.29-3.32 (m, 1H), 2.59-2.75 (m, 3H), 2.37 (s, 3H), 2.21 (s, 3H), 1.91 - 1.93 (m, 1H), 1.77-1.80 (m, 2H), 1.61-1.64 (m, 1H), 1.43-1.53 (m, 5H), 1.18-1.23 (m, 1H). |

TABLE 6-continued

| Compound No. | Chemical Structure | [M + H] observed | $^1$H NMR (400 MHz) |
|---|---|---|---|
| Characterization Data for Additional Exemplary Compounds | | | |
| I-240 | 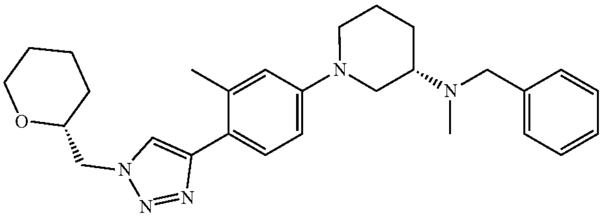 [SMILES: Cc1cc(N2CCC[C@H](N(C)Cc3ccccc3)C2)ccc1-c1cn(C[C@H]2CCCCO2)nn1] | 460.0 | $^1$H NMR (400 MHz, DMSO-$d_6$) δ 8.13 (s, 1H), 7.55 (d, J = 9.2 Hz, 1H), 7.28-7.38 (m, 4H), 7.20-7.26 (m, 1H), 6.80-6.85 (m, 2H), 4.33 - 4.47 (m, 2H), 3.67-3.89 (m, 6H), 3.27-3.31 (m, 1H), 2.60-2.74 (m, 3H), 2.37 (s, 3H), 2.23 (s, 3H), 1.76 - 1.96 (m, 3H), 1.59-1.65 (m, 1H), 1.42-1.55 (m, 5H), 1.17-1.23 (m, 1H). |
| I-253 | 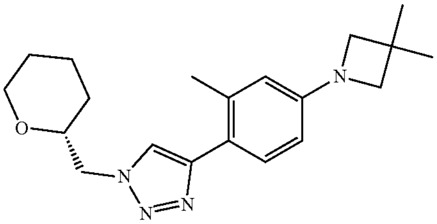 | 341.0 | $^1$H NMR (400 MHz, DMSO-$d_6$) δ 8.09 (s, 1H), 7.52 (d, J = 8.0 Hz, 1H), 6.30-6.33 (m, 2H), 4.33-4.45 (m, 2H), 3.84-3.87 (m, 1H), 3.71 - 3.73 (m, 1H), 3.53 (s, 4H), 3.30 - 3.35 (m, 1H), 2.34 (s, 3H), 1.75 - 1.78 (m, 1H), 1.61-1.64 (m, 1H), 1.43-1.50 (m, 3H), 1.28 (s, 6H), 1.18-1.24 (m, 1H). |
| I-375 | 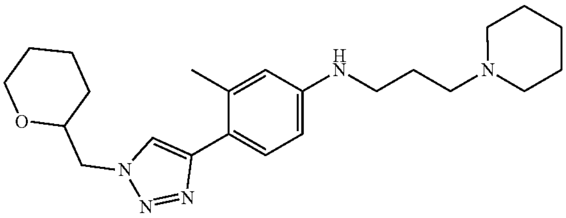 [SMILES: Cc1cc(NCCCN2CCCCC2)ccc1-c1cn(CC2CCCCO2)nn1] | 398.0 | $^1$H NMR (400 MHz, DMSO-$d_6$) δ 8.04 (s, 1H), 7.44 (d, J = 8.4 Hz, 1H), 6.45-6.47 (m, 2H), 5.74 (s, 1H), 4.32-4.36 (m, 2H), 3.84-3.87 (m, 1H), 3.71-3.73 (m, 1H), 3.29 - 3.34 (m, 1H), 3.05 (t, J = 6.0 Hz, 2H), 2.31-2.47 (m, 9H), 1.60-1.80 (m, 4H), 1.39-1.53 (m, 9H), 1.12 - 1.23 (m, 1H). |
| I-376 | 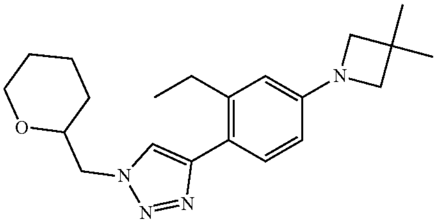 [SMILES: CCc1cc(N2CC(C)(C)C2)ccc1-c1cn(CC2CCCCO2)nn1] | 355.2 | $^1$H NMR (400 MHz, $CDCl_3$) δ 7.67 (s, 1H), 7.51 (d, J = 8.8 Hz, 1H), 6.36-6.40 (m, 2H), 4.48 (dd, J = 3.2 Hz, 14.0 Hz, 1H), 4.32 (dd, J = 7.2 Hz, 14.0 Hz, 1H), 3.97-4.00 (m, 1H), 3.68-3.72 (m, 1H), 3.61 (s, 4H), 3.40-3.42 (m, 1H), 2.76 (q, J = 7.6 Hz, 2H), 1.87-1.89 (m, 1H), 1.65-1.68 (m, 1H), 1.50-1.53 (m, 3H), 1.33 (s, 6H), 1.25-1.31 (m, 1H), 1.19 (t, J = 7.6 Hz, 3H). |
| I-246 | 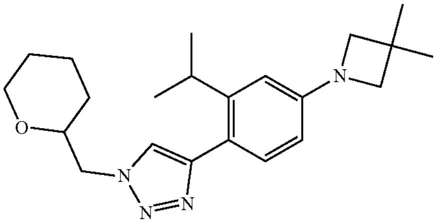 | 369.2 | $^1$H NMR (400 MHz, $CDCl_3$) δ 7.64 (s, 1H), 7.36 (d, J = 8.4 Hz, 1H), 6.42 (d, J = 2.4 Hz, 1H), 6.33 (dd, J 2.8 Hz, 8.4 Hz, 1H), 4.47 (dd, J = 3.2 Hz, 14.0 Hz, 1H), 4.32 (dd, J = 7.2 Hz, 14.0 Hz, 1H), 3.96-4.00 (m, 1H), 3.68-3.74 (m, 1H), 3.62 (s, 4H), 3.31-3.44 (m, 2H), 1.87-1.89 (m, 1H), 1.65-1.68 (m, 1H), 1.49 - 1.53 (m, 3H), 1.33 (s, 6H), 1.24 - 1.31 (m, 1H), 1.21 (d, J = 7.2 Hz, 6H). |
| I-377 | 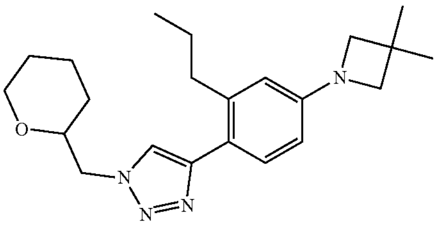 [SMILES: CCCc1cc(N2CC(C)(C)C2)ccc1-c1cn(CC2CCCCO2)nn1] | 369.1 | $^1$H NMR (400 MHz, DMSO-$d_6$) δ 8.01 (s, 1H), 7.36 (d, J = 8.0 Hz, 1H), 6.26-6.34 (m, 2H), 4.34-4.47 (m, 2H), 3.83-3.89 (m, 1H), 3.68 - 3.73 (m, 1H), 3.53 (s, 4H), 3.29 - 3.31 (m, 1H), 2.63-2.66 (m, 2H), 1.76-1.79 (m, 1H), 1.57-1.63 (m, 1H), 1.40-1.51 (m, 5H), 1.28 (s, 6H), 1.12-1.21(m, 1H), 0.87 (t, J = 7.2 Hz, 3H). |

TABLE 6-continued

| Characterization Data for Additional Exemplary Compounds | | | |
|---|---|---|---|
| Compound No. | Chemical Structure | [M + H] observed | $^1$H NMR (400 MHz) |
| I-279 | 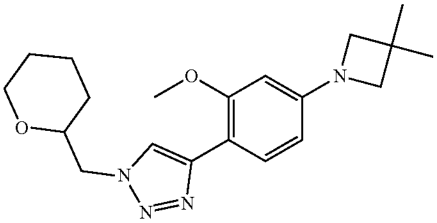 [SMILES: COc1cc(N2CC(C)(C)C2)ccc1-c1cn(CC2CCCCO2)nn1] | 357.3 | $^1$H NMR (400 MHz, DMSO-$d_6$) δ 8.07 (s, 1H), 7.90 (d, J = 8.4 Hz, 1H), 6.06-6.10 (m, 2H), 4.32-4.44 (m, 2H), 3.83-3.86 (m, 4H), 3.67 - 3.72 (m, 1H), 3.57 (s, 4H), 3.27 - 3.30 (m, 1H), 1.77-1.80 (m, 1H), 1.60-1.63 (m, 1H), 1.39-1.51 (m, 2H), 1.29 (s, 6H), 1.17-1.23 (m, 2H). |
| I-378 | 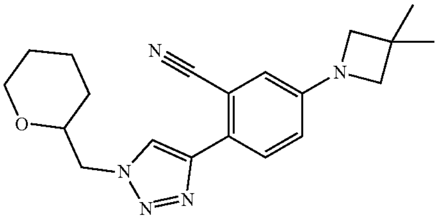 [SMILES: CC1(C)CN(c2ccc(-c3cn(CC4CCCCO4)nn3)c(C#N)c2)C1] | 352.1 | $^1$H NMR (400 MHz, $CDCl_3$) δ 8.31 (s, 1H), 8.09 (d, J = 8.4 Hz, 1H), 6.68 (dd, J = 2.4 Hz, J = 8.4 Hz, 1H), 6.63 (d, J = 2.4 Hz, 1H), 4.48 (dd, J = 3.2 Hz, J = 14.0 Hz, 1H), 4.36 (dd, J = 7.2 Hz, 14.0 Hz, 1H), 3.99-4.02 (m, 1H), 3.69-3.75 (m, 1H), 3.63 (s, 4H), 3.36-3.43 (m, 1H), 1.86-1.89 (m, 1H), 1.64-1.68 (m, 1H), 1.50-1.60 (m, 3H), 1.35 (s, 6H), 1.25-1.31 (m, 1H). |
| I-379 | 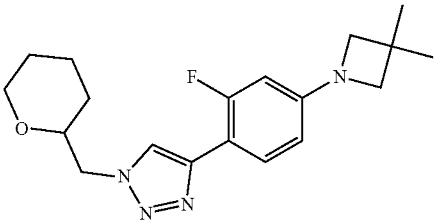 | 345.2 | $^1$H NMR (400 MHz, DMSO-$d_6$) δ 8.09 (d, J = 3.6 Hz, 1H), 7.87 (t, J = 8.4 Hz, 1H), 6.27-6.34 (m, 2H), 4.36-4.47 (m, 2H), 3.83-3.87 (m, 1H), 3.68-3.74 (m, 1H), 3.57 (s, 4H), 3.27-3.33 (m, 1H), 1.77-1.80 (m, 1H), 1.61-1.64 (m, 1H), 1.34 - 1.53 (m, 3H), 1.28 (s, 6H), 1.14 - 1.24 (m, 1H). |
| I-254 | 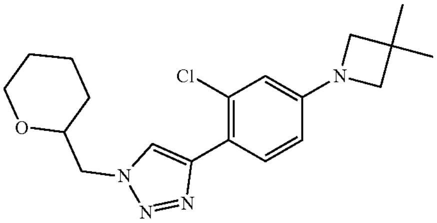 | 361.1 | $^1$H NMR (400 MHz, $CDCl_3$) δ 8.13 (s, 1H), 8.01 (d, J = 8.4 Hz, 1H), 6.44 (d, J = 2.4 Hz, 1H), 6.41 (dd, J = 2.4 Hz, 8.8 Hz, 1H), 4.46 (dd, J = 3.6 Hz, 14.0 Hz, 1H), 4.33 (dd, J = 7.2 Hz, 14.0 Hz, 1H),3.97-4.01 (m, 1H) 3.68-3.74 (m, 1H), 3.61 (s, 4H), 3.36-3.42 (m, 1H), 1.86-1.88 (m, 1H), 1.64-1.67 (m, 1H), 1.46 - 1.58 (m, 3H), 1.33 (s, 6H), 1.17 - 1.29 (m, 1H). |
| I-255 | 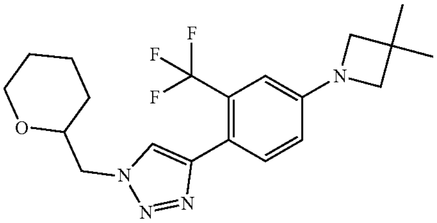 [SMILES: CC1(C)CN(c2ccc(-c3cn(CC4CCCCO4)nn3)c(C(F)(F)F)c2)C1] | 395.0 | $^1$H NMR (400 MHz, $CDCl_3$) δ 7.80 (s, 1H), 7.75 (d, J = 8.4 Hz, 1H), 6.70 (d, J = 2.4 Hz, H), 6.60 (dd, J Hz, 8.4 Hz, 1H, 4.46 (dd, J = 2.0 3.2 Hz, 14.0 Hz, 1H), 4.34 (dd, J = 7.2 Hz, 14.0 Hz, 1H), 3.99 (dd, J = 2.0 Hz, 11.2 Hz, 1H),3.66-3.71 (m, 1H), 3.64 (s, 4H), 3.37-3.42 (m, 1H), 1.86-1.88 (m, 1H), 1.61-1.65 (m, 2H), 1.49-1.54 (m, 2H), 1.34 (s, 6H), 1.23-1.26 (m, 1H). |
| I-271 | 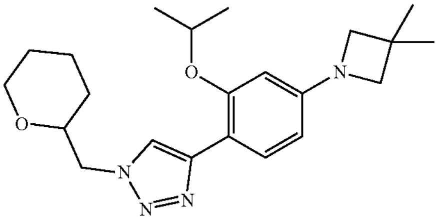 [SMILES: CC(C)Oc1cc(N2CC(C)(C)C2)ccc1-c1cn(CC2CCCCO2)nn1] | 385.3 | $^1$H NMR (400 MHz, DMSO-$d_6$) δ 8.07 (s, 1H), 7.88 (d, J = 8.4 Hz, 1H), 6.06-6.09 (m, 2H), 4.67-4.73 (m, 1H), 4.34-4.47 (m, 2H), 3.85 - 3.88 (m, 1H), 3.65-3.69 (m, 1H), 3.55 (s, 4H), 3.36-3.37 (m, 1H), 1.77-1.80 (m, 1H), 1.60-1.63 (m, 1H), 1.44-1.52 (m, 3H), 1.31-1.33 (m, 6H), 1.29 (s, 6H), 1.15-1.21 (m, 1H). |

TABLE 6-continued

| Characterization Data for Additional Exemplary Compounds | | | |
|---|---|---|---|
| Compound No. | Chemical Structure | [M + H] observed | $^1$H NMR (400 MHz) |
| I-280 | 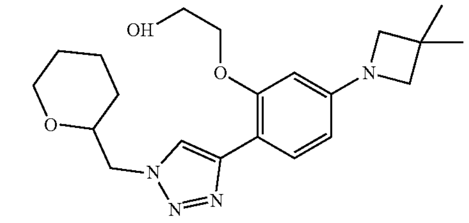 [SMILES: CC1(C)CN(c2ccc(-c3cn(CC4CCCCO4)nn3)c(OCCO)c2)C1] | 387.2 | $^1$H NMR (400 MHz, DMSO-$d_6$) δ 8.19 (s, 1H), 7.89 (d, J = 8.4 Hz, 1H), 6.05-6.10 (m, 2H), 4.96 (t, J = 10.8 Hz, 1H), 4.31-4.43 (m, 2H), 4.06 (t, J = 4.8 Hz, 2H), 3.79-3.87 (m, 3H), 3.66-3.72 (m, 1H), 3.56 (s, 4H), 3.28-3.34 (m, 1H), 1.78-1.80 (m, 1H), 1.60-1.63 (m, 1H), 1.40 – 1.51 (m, 3H), 1.29 (s, 6H), 1.19 – 1.26 (m, 1H). |
| I-380 | 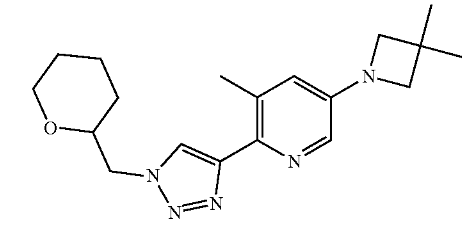 | 342.3 | $^1$H NMR (400 MHz, DMSO-$d_6$) δ 8.22 (s, 1H), 7.68 (d, J = 2.8 Hz, 1H), 6.70 (d, J = 2.8 Hz, 1H), 4.35 – 4.47 (m, 2H), 3.86 (d, J = 11.2 Hz, 1H), 3.70-3.75 (m, 1H), 3.61 (s, 4H), 3.29-3.31 (m, 1H), 2.55 (s, 3H), 1.78-1.81 (m, 1H), 1.61-1.64 (m, 1H), 1.39-1.51 (m, 3H), 1.30 (s, 6H), 1.18-1.25 (m, 1H). |
| I-256 | 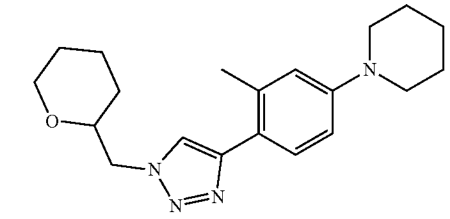 [SMILES: Cc1cc(N2CCCCC2)ccc1-c1cn(CC2CCCCO2)nn1] | 341.0 | $^1$H NMR (400 MHz, DMSO-$d_6$) δ 8.13 (s, 1H), 7.55-7.57 (m, 1H), 6.81-6.83 (m, 2H), 4.37-4.42 (m, 2H), 3.84-3.87 (m, 1H), 3.70-3.78 (m, 1H), 3.28-3.32 (s, 1H), 3.16 – 3.18 (m, 4H), 2.37 (s, 3H), 1.78 – 1.81 (m, 1H), 1.45-1.64 (m, 10H), 1.15-1.25 (m, 1H). |
| I-281 | 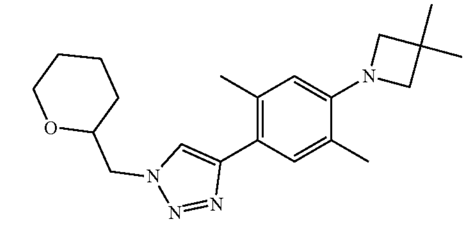 | 355.3 | $^1$H NMR (400 MHz, DMSO-$d_6$) δ 8.10 (s, 1H), 7.35 (s, 1H), 6.28 (s, 1H), 4.33-4.45 (m, 2H), 3.84-3.87 (m, 1H), 3.70-3.76 (m, 1H), 3.60 (s, 4H), 2.28-3.32 (m, 1H), 2.32 (s, 3H), 2.14 (s, 3H), 1.78-1.81 (m, 1H), 1.60-1.63 (m, 1H), 1.40-1.51 (m, 3H), 1.28 (s, 6H), 1.18-1.24 (m, 1H). |
| I-381 | 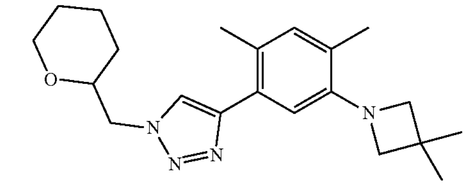 | 355.2 | $^1$HNMR (400 MHz, DMSO-$d_6$) δ 8.21 (s, 1H), 6.89 (s, 1H), 6.82 (s, 1H), 4.35-4.47 (m, 2H), 3.84-3.87 (m, 1H), 3.71-3.77 (m, 1H), 3.56 (s, 4H), 3.28-3.33 (m, 1H), 2.28 (s, 3H), 2.13 (s, 3H), 1.78-1.81 (m, 1H), 1.61-1.65 (m, 1H), 1.40-1.52 (m, 3H), 1.28 (s, 6H), 1.18-1.25 (m, 1H). |
| I-382 | 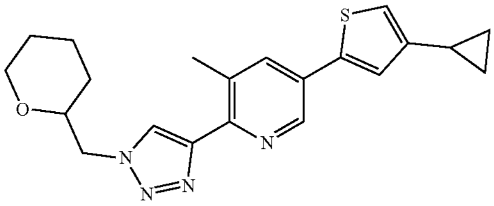 [SMILES: Cc1cc(-c2cc(C3CC3)cs2)cnc1-c1cn(CC2CCCCO2)nn1] | 381.1 | $^1$H NMR (400 MHz, $CDCl_3$) δ 8.69 (d, J = 2.0 Hz, 1H), 8.24 (s, 1H), 7.72 (d, J = 1.6 Hz, 1H), 7.12 (d, J = 1.6 Hz, 1H), 6.89 (d, J = 0.8 Hz, 1H), 4.50 (dd, J = 3.2 Hz, 14.0 Hz, 1H), 4.36 (dd, J = 7.2 Hz, 14.0 Hz, 1H), 3.95-4.03 (m, 1H), 3.69-3.77 (m, 1H), 3.35-3.45 (m, 1H), 2.77 (s, 3H), 1.85-1.97 (m, 2H), 1.65-1.73 (m, 1H), 1.47-1.60 (m, 3H), 1.24 – 1.36 (m, 1H), 0.90-0.97 (m, 2H), 0.67-0.73 (m, 2H). |

TABLE 6-continued

Characterization Data for Additional Exemplary Compounds

| Compound No. | Chemical Structure | [M + H] observed | $^1$H NMR (400 MHz) |
|---|---|---|---|
| I-383 | 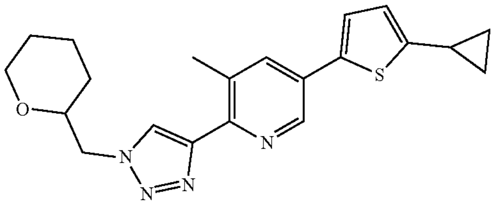 [SMILES: Cc1cc(-c2ccc(C3CC3)s2)cnc1-c1cn(CC2CCCCO2)nn1] | 381.0 | $^1$H NMR (400 MHz, DMSO-$d_6$) δ 8.68 (d, J = 2.0 Hz, 1H), 8.46 (s, 1H), 7.89 (d, J = 1.6 Hz, 1H), 7.47 (d, J = 3.6 Hz, 1H), 6.89 (d, J = 3.6 Hz, 1H), 4.40-4.53 (m, 2H), 3.85 – 3.89 (m, 1H), 3.71-3.79 (m, 1H), 3.29-3.33 (m, 1H), 2.68 (s, 3H), 2.15-2.22 (m, 1H), 1.76-1.85 (m, 1H), 1.61-1.69 (m, 1H), 1.38-1.55 (m, 3H), 1.15-1.28 (m, 1H), 1.01 – 1.08 (m, 2H), 0.70-0.76 (m, 2H). |
| I-384 | 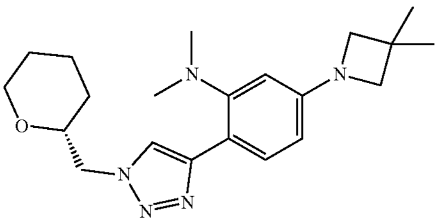 | 370.0 | $^1$H NMR (400 MHz, DMSO-$d_6$) δ 8.17 (s, 1H), 7.80 (d, J = 8.0 Hz, 1H), 6.14-6.17 (m, 2H), 4.34-4.46 (m, 2H), 3.84-3.87 (m, 1H), 3.65 – 3.70 (m, 1H), 3.54 (s, 4H), 3.27 – 3.31 (m, 1H), 2.55 (s, 6H), 1.76 – 1.79 (m, 1H), 1.59-1.62 (m, 1H), 1.37-1.50 (m, 3H), 1.28 (s, 6H), 1.11-1.21 (m, 1H). |
| I-385 | 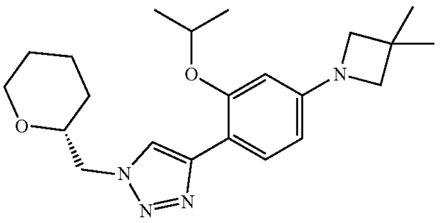 [SMILES: CC(C)Oc1cc(N2CC(C)(C)C2)ccc1-c1cn(C[C@H]2CCCCO2)nn1] | 385.2 | $^1$H NMR (400 MHz, DMSO-$d_6$) δ 8.07 (s, 1H), 7.88 (d, J = 8.0 Hz, 1H), 6.05-6.09 (m, 2H), 4.68-4.73 (m, 1H), 4.36-4.47 (m, 2H), 3.85 – 3.88 (m, 1H), 3.65-3.70 (m, 1H), 3.55 (s, 4H), 3.31-3.32 (m, 1H), 1.77-1.80 (m, 1H), 1.60-1.64 (m, 1H), 1.44-1.50 (m, 3H), 1.32 (dd, J = 6.0 Hz, 2.4 Hz, 6H), 1.29 (s, 6H), 1.15-1.21 (m, 1H). |
| I-386 | 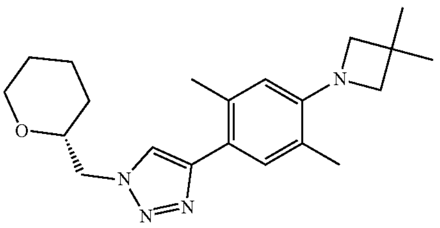 | 355.1 | $^1$H NMR (400 MHz, $CDCl_3$) δ 7.69 (s, 1H), 7.49 (s, 1H), 6.30 (s, 1H), 4.49 (dd, J = 7.2 Hz, J = 14.0 Hz, 1H), 4.32 (dd, J = 7.2 Hz, J = 11.2 Hz, 1H), 3.89 (dd, J = 2.0 Hz, J = 13.2 Hz, 1H), 3.67-3.73 (m, 5H), 3.37-3.43 (m, 1H), 2.39 (s, 3H), 2.23 (s, 3H), 1.87-1.89 (m, 1H), 1.65-1.68 (m, 1H), 1.48-1.57 (m, 3H), 1.32 (s, 6H), 1.22-1.30 (m, 1H). |
| I-387 | 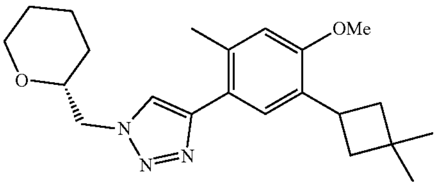 | 371.3 | $^1$HNMR (400 MHz, DMSO-$d_6$) δ 8.15 (s, 1H), 6.75 (s, 1H), 6.73 (s, 1H), 4.34-4.46 (m, 2H), 3.84-3.87 (m, 1H), 3.70-3.76 (m, 4H), 3.53 (s, 4H), 3.28-3.33 (m, 1H), 2.31 (s, 3H), 1.78-1.81 (m, 1H), 1.61-1.64 (m, 1H), 1.39-1.51 (m, 3H), 1.25 (s, 6H), 1.18-1.22 (m, 1H). |
| I-388 | 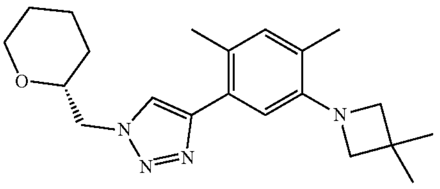 | 355.3 | $^1$HNMR (400 MHz, DMSO-$d_6$) δ 8.21 (s, 1H), 6.89 (s, 1H), 6.82 (s, 1H), 4.35-4.47 (m, 2H), 3.84-3.87 (m, 1H), 3.71-3.77 (m, 1H), 3.56 (s, 4H), 3.28-3.33 (m, 1H), 2.28 (s, 3H), 2.13 (s, 3H), 1.78-1.81 (m, 1H), 1.61-1.65 (m, 1H), 1.37-1.55 (m, 3H), 1.28 (s, 6H), 1.12-1.25 (m, 1H). |

TABLE 6-continued

Characterization Data for Additional Exemplary Compounds

| Compound No. | Chemical Structure | [M + H] observed | $^1$H NMR (400 MHz) |
|---|---|---|---|
| I-389 | 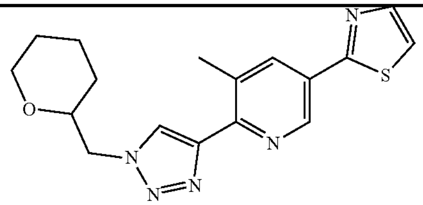 | 342.2 | $^1$H NMR (400 MHz, $CDCl_3$) δ 9.03 (d, J = 2.0 Hz, 1H), 8.30 (s, 1H), 8.16 (d, J = 1.6 Hz, 1H), 7.93 (d, J = 3.2 Hz, 1H), 7.41 (d, J = 3.2 Hz, 1H), 4.53 (dd, J = 3.6 Hz, 14.0 Hz, 1H), 4.38 (dd, J = 7.6 Hz, 14.0 Hz, 1H), 3.99-4.03 (m, 1H), 3.74-3.75 (m, 1H), 3.41-3.44 (m, 1H), 2.84 (s, 3H), 1.89-1.90 (m, 1H), 1.69-1.71 (m, 1H), 1.51-1.57 (m, 3H), 1.31 - 1.33 (m, 1H). |
| I-109 | 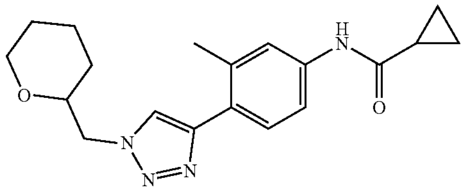 [SMILES: Cc1cc(NC(=O)C2CC2)ccc1-c1cn(CC2CCCCO2)nn1] | 341.2 | $^1$H NMR (400 MHz, $CD_3CN$) δ 8.58 (br. s, 1H), 7.91 (s, 1H), 7.69 (d, J = 8.3 Hz, 1H), 7.53 - 7.46 (m, 2H), 4.43 (dd, J = 14.2, 3.7 Hz, 1H),4.36 (dd, J = 14.2, 7.5 Hz, 1H), 3.93 - 3.87 (m, 1H), 3.74 (dddd, J = 11.2, 7.5, 3.7, 2.2 Hz, 1H), 3.41 - 3.33 (m, 1H), 2.42 (s, 3H), 1.87-1.81 (m, 1H), 1.69-1.64 (m, 2H), 1.53-1.46 (m, 3H), 1.30-1.20 (m, 1H), 0.93 - 0.85 (m, 2H), 0.83-0.78 (m, 2H). |
| I-110 | 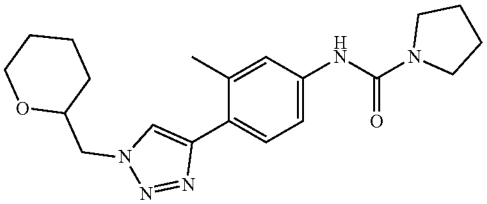 [SMILES: Cc1cc(NC(=O)N2CCCC2)ccc1-c1cn(CC2CCCCO2)nn1] | 370.2 | $^1$H NMR (400 MHz, $CD_3CN$) δ 7.89 (s, 1H), 7.64 (d, J = 8.2 Hz, 1H), 7.44 - 7.38 (m, 2H), 6.90 (br. s, 1H), 4.42 (dd, J = 14.2, 3.8 Hz, 1H), 4.35 (dd, J = 14.2, 7.5 Hz, 1H), 3.95 - 3.86 (m, 1H), 3.74 (dddd, J = 11.2, 7.4, 3.7, 2.2 Hz, 1H), 3.45 - 3.34 (m, 5H), 2.41 (s, 3H), 1.92 - 1.89 (m, 3H), 1.87 - 1.81 (m, 1H), 1.72 - 1.60(m, 1H), 1.54 - 1.45 (m, 3H), 1.32 - 1.20 (m, 2H). |
| I-111 | 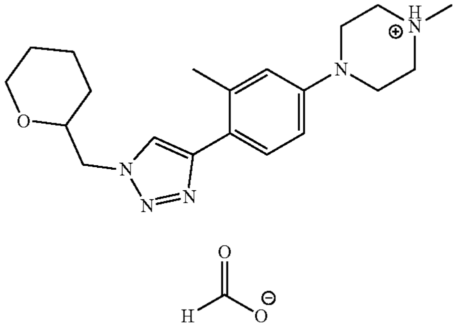 | 356.2 | $^1$H NMR (400 MHz, $CD_3CN$) δ 7.86 (s, 1H), 7.62 (d, J = 8.3 Hz, 1H), 6.89 - 6.82 (m, 2H), 4.41 (dd, J = 14.2, 3.8 Hz, 1H), 4.34 (dd, J = 14.2, 7.5 Hz, 1H), 3.93 - 3.87 (m, 1H), 3.76-3.70 (m, 1H), 3.40-3.34 (m, 1H), 3.32 - 3.27 (m, 4H), 2.81 - 2.74 (m, 4H), 2.44 (s, 3H), 2.40 (s, 3H), 1.86-1.81 (m, 1H), 1.67-1.63 (m, 1H), 1.57 - 1.45 (m, 3H), 1.30 - 1.19 (m, 1H); formate salt @ 8.25 ppm. |
| I-112 | 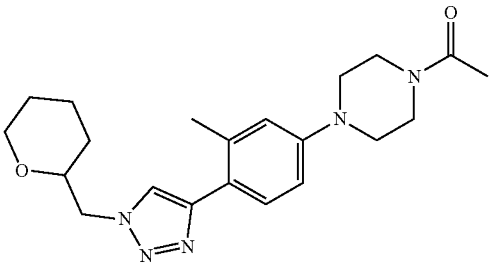 [SMILES: CC(=O)N1CCN(c2ccc(-c3cn(CC4CCCCO4)nn3)c(C)c2)CC1] | 384.2 | $^1$H NMR (400 MHz, $CD_3CN$) δ 8.16 (s, 1H), 7.63 - 7.58 (m, 1H), 6.90 - 6.84 (m, 2H), 4.44 (dd, J = 14.1,4.0 Hz, 1H), 4.37 (dd, J = 14.1, 7.6 Hz, 1H), 3.89 - 3.82 (m, 1H), 3.77 - 3.69 (m, 1H), 3.59-3.56 (m, 4H), 3.31 (td, J = 11.1,3.1 Hz, 1H), 3.23 - 3.16 (m, 2H), 3.16 - 3.10 (m, 2H), 2.39 (s, 3H), 2.04 (s, 3H), 1.85 - 1.75 (m, 1H), 1.64-1.61 (m, 1H), 1.56 - 1.38 (m, 3H), 1.22-1.18 (m, 1H). |
| I-113 | 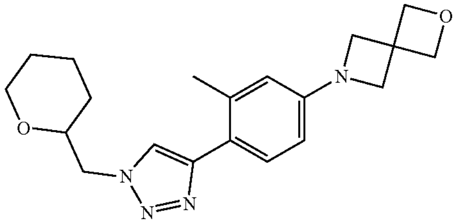 [SMILES: Cc1cc(N2CC3(COC3)C2)ccc1-c1cn(CC2CCCCO2)nn1] | 355.2 | $^1$H NMR (400 MHz, $CD_3CN$) δ 8.10 (s, 1H), 7.53 (d, J = 8.0 Hz, 1H), 6.37 - 6.31 (m, 2H), 4.72 (s, 4H), 4.42 (dd, J = 14.1, 4.1 Hz, 1H),4.36 (dd, J = 14.1, 7.6 Hz, 1H), 3.98 (s, 4H), 3.88 - 3.82 (m, 1H), 3.76 - 3.68 (m, 1H),3.31 (td, J = 11.1, 3.1 Hz, 1H), 2.34 (s, 3H), 1.80-1.77 (m, 1H), 1.66 - 1.57 (m, 1H), 1.52 - 1.37 (m, 3H), 1.25 - 1.13 (m, 1H). |

TABLE 6-continued

Characterization Data for Additional Exemplary Compounds

| Compound No. | Chemical Structure | [M + H] observed | $^1$H NMR (400 MHz) |
|---|---|---|---|
| 1-114 | 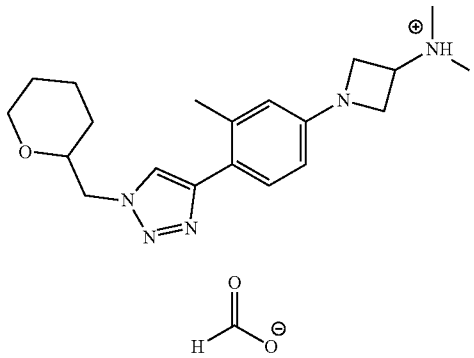 | 356.2 | $^1$H NMR (400 MHz, $CD_3CN$) δ 8.10 (s, 1H), 7.53 (d, J = 8.0 Hz, 1H), 6.39 – 6.29 (m, 2H), 4.42 (dd, J = 14.1, 4.1 Hz, 1H), 4.36 (dd, J = 14.1, 7.6 Hz, 1H), 3.92 (app. t, J = 7.1 Hz, 2H), 3.89 – 3.81 (m, 1H), 3.77 – 3.68 (m, 1H), 3.54 (dd, J = 7.3, 5.8 Hz, 2H), 3.31 (td, J = 11.1, 3.0 Hz, 1H), 3.17 (p, J = 6.2 Hz, 1H), 2.34 (s, 3H), 2.10 (s, 6H), 1.80 – 1.78 (m, 1H), 1.66 – 1.57 (m, 1H), 1.53 – 1.36 (m, 3H), 1.25 – 1.13 (m, 1H); formate salt @ 8.30 ppm. |
| I-130 | 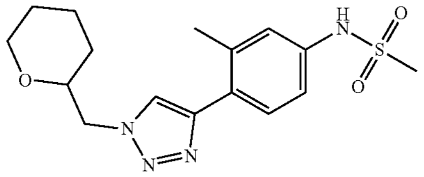 [SMILES: Cc1cc(NS(C)(=O)=O)ccc1-c1cn(CC2CCCCO2)nn1] | 351.1 | $^1$H NMR (400 MHz, DMSO-$d_6$) δ 8.25 (s, 1H), 7.69 (d, J = 9.1 Hz, 1H), 7.14-7.12 (m, 2H), 4.46 (dd, J = 14.1, 4.0 Hz, 1H), 4.39 (dd, J = 14.1, 7.7 Hz, 1H), 3.88 – 3.82 (m, 1H), 3.79 – 3.70 (m, 1H), 3.35 – 3.27(m, 1H under water peak), 3.01 (s, 3H), 2.40 (s, 3H), 1.81-1.78 (m, 1H), 1.67 – 1.58 (m, 1H), 1.54 – 1.37 (m, 3H), 1.20 (qd, J = 12.3, 3.9 Hz, 1H). |
| I-157 | 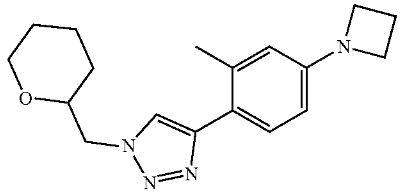 [SMILES: Cc1cc(N2CCC2)ccc1-c1cn(CC2CCCCO2)nn1] | 313.1 | $^1$H NMR (400 MHz, $CD_3CN$) δ 7.80 (s, 1H), 7.58 – 7.51 (m, 1H), 6.37 – 6.32 (m, 2H), 4.40 (dd, J = 14.2, 3.8 Hz, 1H), 4.33 (dd, J = 14.2, 7.5 Hz, 1H), 3.93 – 3.88 (m, 1H), 3.86 (t, J = 7.2 Hz, 4H), 3.73 (dddd, J = 11.2, 7.5, 3.8, 2.1 Hz, 1H), 3.41 – 3.33 (m, 1H), 2.36 (s, 3H), 2.38 – 2.30 (m, 2H), 1.89 – 1.79 (m, 1H), 1.70 – 1.61 (m, 1H), 1.58 – 1.45 (m, 3H), 1.30 – 1.17(m, 1H). |
| I-158 | 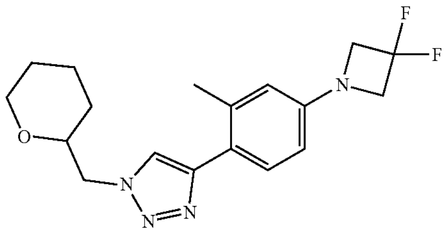 [SMILES: Cc1cc(N2CC(F)(F)C2)ccc1-c1cn(CC2CCCCO2)nn1] | 349.1 | $^1$H NMR (400 MHz, $CD_3CN$) δ 7.85 (s, 1H), 7.62 (d, J = 8.4 Hz, 1H), 6.51 – 6.46 (m, 2H), 4.41 (dd, J = 14.2, 3.8 Hz, 1H), 4.34 (dd, J = 14.2, 7.5 Hz, 1H), 4.24 (t, J = 12.1 Hz, 4H), 3.93 – 3.86 (m, 1H), 3.73 (dddd, J = 11.2, 7.4, 3.7, 2.2 Hz, 1H), 3.42 – 3.33 (m, 1H), 2.40 (s, 3H), 1.89 – 1.80 (m, 1H), 1.70 – 1.61 (m, 1H), 1.57 – 1.44 (m, 3H), 1.31 – 1.18 (m, 1H). |
| I-223 | 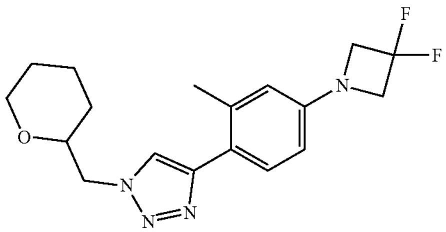 [SMILES: Cc1cc(N2CC(F)(F)C2)ccc1-c1cn(CC2CCCCO2)nn1] | 349.1 | $^1$H NMR (400 MHz, $CD_3CN$) δ 7.78 (s, 1H), 7.55 – 7.50 (m, 1H), 6.38 – 6.32 (m, 2H), 4.37 (dd, J = 14.2,3.8 Hz, 1H), 4.31 (dd, J = 14.2, 7.5 Hz, 1H), 3.91 – 3.83 (m, 1H), 3.76 – 3.64 (m. 5H), 3.39 – 3.30 (m, 1H), 3.21 (s, 3H), 2.34 (s, 3H), 1.85 – 1.77 (m, 1H), 1.66 – 1.58 (m, 1H), 1.56 – 1.40 (m, 6H), 1.28 – 1.16 (m, 1H). |

TABLE 6-continued

| Characterization Data for Additional Exemplary Compounds | | | |
|---|---|---|---|
| Compound No. | Chemical Structure | [M + H] observed | $^{1}$H NMR (400 MHz) |
| I-260 | 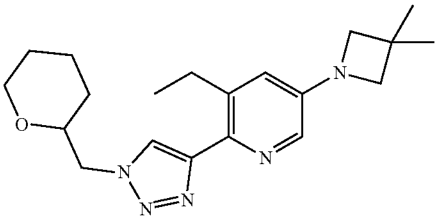 [SMILES: CCc1cc(N2CC(C)(C)C2)cnc1-c1cn(CC2CCCCO2)nn1] | 356.2 | $^{1}$H NMR (400 MHz, $CD_3CN$) δ 8.00 (s, 1H), 7.69 (d, J = 2.7 Hz, 1H), 6.69 (d, J = 2.7 Hz, 1H), 4.42 (dd, J = 14.2, 3.7 Hz, 1H), 4.34 (dd, J = 14.2, 7.5 Hz, 1H), 3.91 (ddd, J = 11.1,4.2, 1.9 Hz, 1H), 3.73 (dddd, J = 11.2, 7.5, 3.7, 2.2 Hz, 1H), 3.64 (s, 4H), 3.43 - 3.32 (m, 1H), 3.03 (q, J = 7.5 Hz, 2H), 1.89 - 1.79 (m, 1H), 1.69 - 1.61 (m, 1H), 1.61 - 1.44 (m, 3H), 1.32 (s, 6H), 1.30 - 1.15 (m 4H). |
| I-261 | 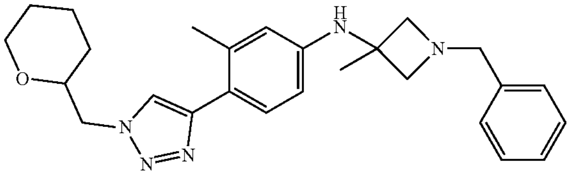 [SMILES: Cc1cc(NC2(C)CN(Cc3ccccc3)C2)ccc1-c1cn(CC2CCCCO2)nn1] | 432.2 | $^{1}$H NMR (400 MHz, $CD_3CN$) δ 8.29 (br. s, 1H), 7.79 (s, 1H), 7.49 - 7.46 (m, 1H), 7.35-7.27 (m, 5H), 6.36 - 6.34 (m, 2H), 4.39 (dd, J = 14.2,3.8 Hz, 1H), 4.33 (dd, J = 14.2, 7.4 Hz, 1H), 3.94 - 3.86 (m, 1H), 3.81 (s, 2H), 3.76-3.70 (m, 2H), 3.55-3.53 (m, 2H), 3.41 - 3.33 (m, 3H), 2.33 (s, 3H), 1.86-1.81 (m, 1H), 1.67 - 1.63 (m, 1 Hz), 1.58 (s, 3H), 1.55 - 1.45 (m, 3H), 1.31 - 1.15 (m, 1H). |
| I-263 | 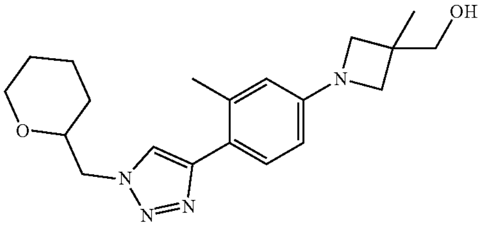 [SMILES: Cc1cc(N2CC(C)(CO)C2)ccc1-c1cn(CC2CCCCO2)nn1] | 357.2 | $^{1}$H NMR (400 MHz, $CD_3CN$) δ 7.80 (s, 1H), 7.57 - 7.51 (m, 1H), 6.38 - 6.31 (m, 2H), 4.40 (dd, J = 14.2,3.9 Hz, 1H), 4.33 (dd, J = 14.2, 7.4 Hz, 1H), 3.94 - 3.86 (m, 1H), 3.77 - 3.72 (m, 1H), 3.70 (d, J = 7.0 Hz, 2H), 3.54 (s, 2H), 3.47 (d, J = 7.0 Hz, 2H), 3.42 - 3.32 (m, 1H), 2.98 (br s, 1H), 2.36 (s, 3H), 1.88 - 1.80 (m, 1H), 1.69 - 1.60 (m, 1H), 1.58 - 1.42 (m, 3H), 1.28 (, 3H), 1.27 - 1.19 (m, 1H). |
| I-264 | 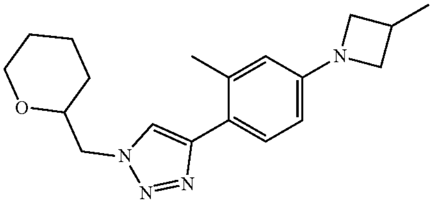 [SMILES: Cc1cc(N2CC(C)C2)ccc1-c1cn(CC2CCCCO2)nn1] | 327.2 | $^{1}$H NMR (400 MHz, $CD_3CN$) δ 7.80 (s, 1H), 7.56 - 7.51 (m, 1H), 6.35 - 6.32 (m, 2H), 4.40 (dd, J = 14.2, 3.8 Hz, 1H), 4.33 (dd, J = 14.2, 7.4 Hz, 1H), 3.99 (t, J = 7.4 Hz, 2H), 3.92 - 3.88 (m, 1H), 3.73 (dddd, J = 11.2, 7.4, 3.8, 2.2 Hz, 1H), 3.41 (dd, J = 6.9, 5.6 Hz, 2H), 3.39 - 3.32 (m, 1H), 2.86 - 2.74 (m, 1H), 2.36 (s, 3H), 1.88 - 1.79 (m, 1H), 1.69 - 1.61 (m, 1H), 1.53 - 1.45 (m, 3H), 1.26 (d, J = 6.9 Hz, 3H), 1.29-1.19 (m, 1H). |
| I-291 | 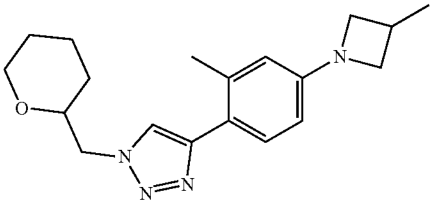 [SMILES: Cc1cc(N2CC(C)C2)ccc1-c1cn(CC2CCCCO2)nn1] | 327.2 | $^{1}$H NMR (400 MHz, $CD_3CN$) δ 7.83 (s, 1H), 7.60-7.57 (m, 1H), 6.43 - 6.38 (m, 2H), 4.40 (dd, J = 14.2, 3.8 Hz, 1H), 4.33 (dd, J = 14.2, 7.5 Hz, 1H), 4.14 (dd, J = 8.3, 7.3 Hz, 2H), 4.02 (dd, J = 7.2, 5.7 Hz, 2H), 3.92 - 3.87 (m, 1H), 3.73 (dddd, J = 11.2, 7.4, 3.8, 2.2 Hz, 1H), 3.64 (tt, J = 8.4, 5.7 Hz, 1H), 3.40-3.34 (m, 1H), 2.38 (s, 3H), 1.86-1.81 (m, 1H), 1.68 - 1.61 (m, 1H), 1.56 - 1.44 (m, 3H), 1.29-1.19 (m, 1H). NMR $^{13}$C (101 MHz, ACN-d3) δ 150.7, 146.3, 136.4, 129.4, 122.7, 121.0, 120.9, 113.8, 109.6, 75.9, 67.9, 55.3, 54.7, 28.6, 25.5, 22.6, 20.8, 18.6. |

TABLE 6-continued
| Characterization Data for Additional Exemplary Compounds | | | |
|---|---|---|---|
| Compound No. | Chemical Structure | [M + H] observed | $^{1}$H NMR (400 MHz) |
| I-390 | 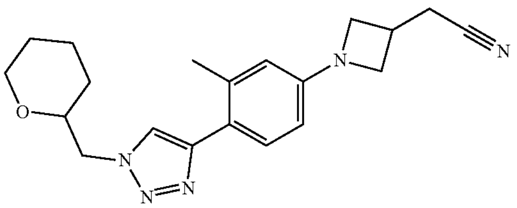 | 352.2 | $^{1}$H NMR (400 MHz, $CD_3CN$) δ 7.81 (s, 1H), 7.59 – 7.53 (m, 1H), 6.41 – 6.34 (m, 2H), 4.40 (dd, J = 14.2, 3.8 Hz, 1H), 4.33 (dd, J = 14.2, 7.5 Hz, 1H), 4.03 (t, J = 7.7 Hz, 2H), 3.94 – 3.86 (m, 1H), 3.77 – 3.69 (m, 1H), 3.63 (dd, J = 7.6, 5.3 Hz, 2H), 3.36 (ddd, J = 11.6, 10.0, 4.4 Hz, 1H), 3.03 (tt, J = 7.8, 4.0 Hz, 1H), 2.77 (d, J = 6.8 Hz, 2H), 2.37 (s, 3H), 1.88 – 1.81 (m, 1H), 1.65 (dd, J = 13.4, 1.6 Hz, 1H), 1.58 – 1.45 (m, 3H), 1.31 – 1.19 (m, 1H). |
Example 6: Synthesis of I-86
Synthetic Scheme of I-86
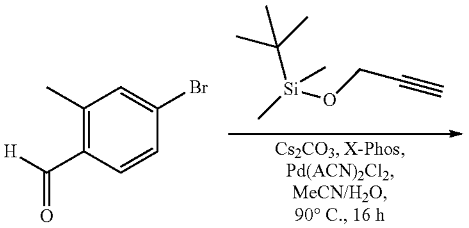
6.1
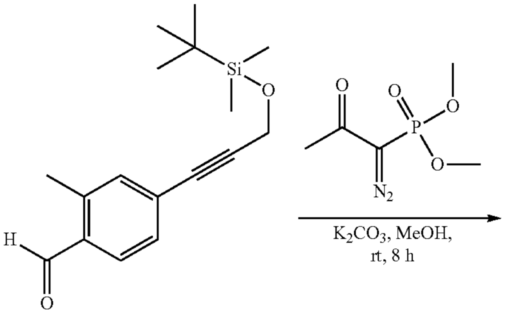
6.2
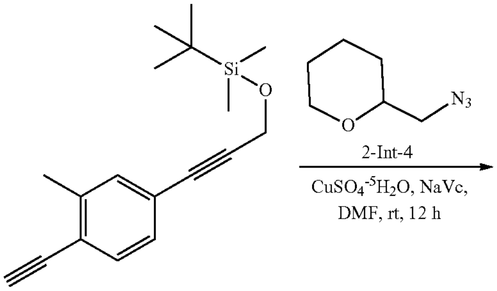
6.3
-continued
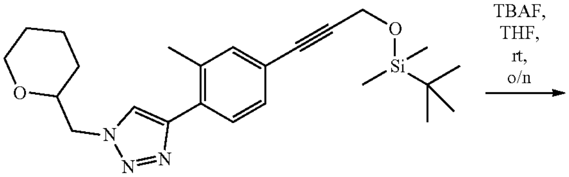
6.4
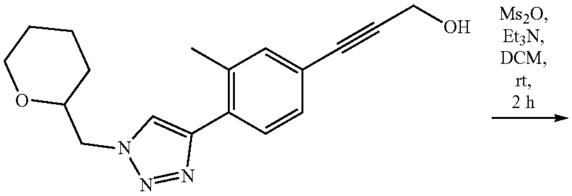
6.5
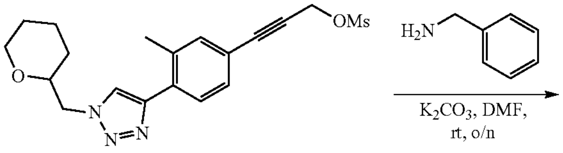
6.6
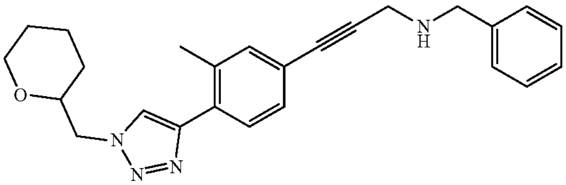
I-86
1. The Synthesis of Intermediate 6.2
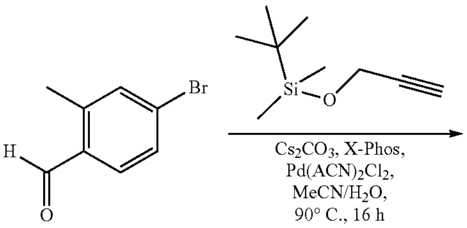
6.1

-continued

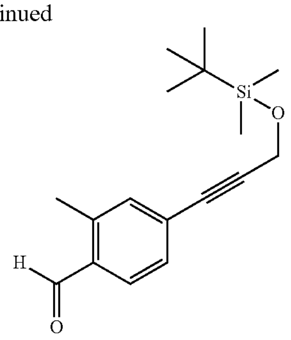

6.2

To a stirred solution of 6.1 (600 mg, 3 mmol), tert-butyldimethyl(prop-2-ynyloxy)silane (1.5 g, 9 mmol) and $Cs_2CO_3$ (2.9 g, 9 mmol) in $CH_3CN$ (10 mL) was added $Pd(ACN)_2Cl_2$ (60 mg), X-Phos (120 mg) and $H_2O$ (5 mL). The reaction mixture was stirred at 90° C. for 16 hours until the reaction was complete (by LCMS). The suspension was diluted with $H_2O$ (20 mL) and extracted with EA (20 mL×2), concentrated. The crude product was purified by flash column chromatography (silica gel, PE/EA=20:1) to give 6.2 (300 mg, yield: 34%) as yellow oil. $^1H$ NMR (400 MHz, $CDCl_3$): δ 10.06 (s, 1H), 7.56 (d, J 8.0 Hz, 1H), 7.22 (d, J 8.0 Hz, 1H), 7.13 (s, 1H), 4.38 (s, 2H), 2.46 (s, 3H), 0.74 (s, 9H), 0.007 (s, 6H).

2. The Synthesis of Intermediate 6.3

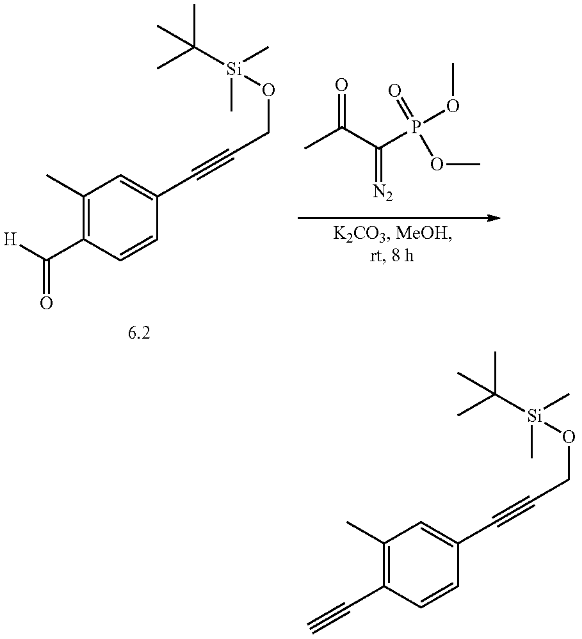

6.2

6.3

To a stirred solution of 6.2 (300 mg, 1.04 mmol) in MeOH (5 mL) was added $K_2CO_3$ (217 mg, 1.56 mmol) and dimethyl 1-diazo-2-oxopropylphosphonate (200 mg, 1.04 mmol). The reaction mixture was stirred at RT for 8 h until the reaction was complete (by LCMS). The reaction was poured into ice water and extracted with DCM (20 mL×2). The reaction mixture was concentrated and the crude product was purified by flash column chromatography (silica gel, PE/EA=50:1) to give 6.3 (280 mg, yield: 94%) as yellow oil.

3. The Synthesis of Intermediate 6.4

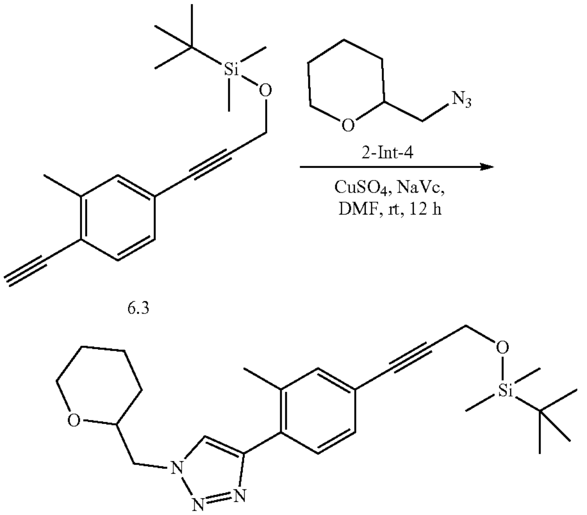

6.3

6.4

To a stirred solution of 6.3 (280 mg, 0.98 mmol) in DMF (5 mL) was added 2-Int-4 (138 mg, 0.98 mmol), $CuSO_4$ (20 mg, 0.098 mmol) and sodium ascorbate (40 mg, 0.196 mmol). The reaction mixture was stirred at RT for 12 h until the reaction was complete (by LCMS). The reaction was poured into ice water and extracted with DCM (20 mL×2). The reaction mixture was concentrated and the crude product was purified by flash column chromatography (silica gel, PE/EA=1:1) to give 6.4 (300 mg, yield: 72%) as yellow oil.

4. The Synthesis of Intermediate 6.5

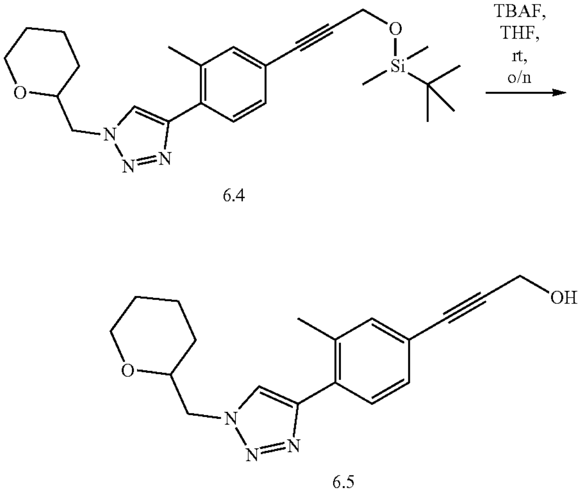

6.4

6.5

To a stirred solution of 6.4 (300 mg, 0.7 mmol) in THF (5 mL) was added TBAF (1.0 N, 5 mL). The reaction mixture was stirred at RT overnight until the reaction was complete (by LCMS). The reaction was poured into water and extracted with DCM (20 mL×2). The reaction mixture was concentrated and the crude product was purified by flash column chromatography (silica gel, PE/EA=1:1) to give 6.5 (200 mg, yield: 91.8%) as yellow oil.

5. The Synthesis of Intermediate 6.6

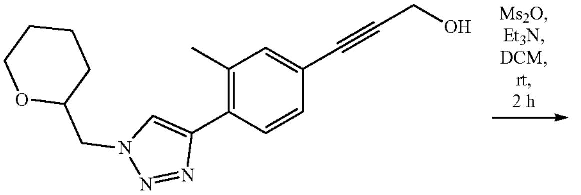

6.5

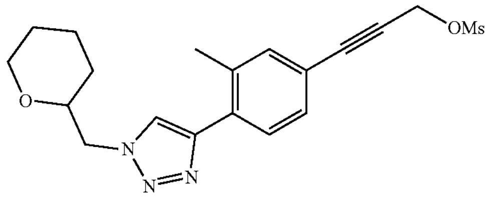

6.6

To a stirred solution of 6.5 (80 mg, 0.26 mmol) in DCM (10 mL) was added TEA (79 mg, 0.78 mmol) and $Ms_2O$ (68 mg, 0.39 mmol). The reaction mixture was stirred at RT for 2 h. $H_2O$ (15 mL) and DCM (10 mL) was added and the organic phases were collected and evaporated under reduced pressure to give 6.6 (90 mg, crude) as yellow oil.

6. The Synthesis of I-86

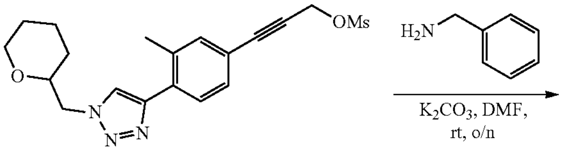

6.6

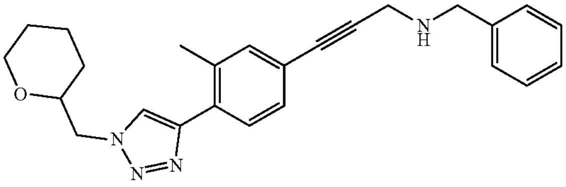

I-86

To a stirred solution of 6.6 (90 mg, 0.23 mmol), phenylmethanamine (25 mg, 0.23 mmol) in DMF (3 mL) was added $K_2CO_3$ (96 mg, 0.69 mmol). The reaction mixture was stirred at RT overnight. $H_2O$ (20 mL) and EA (20 mL) was added and the organic phases were collected and evaporated under reduced pressure. The residue was purified by prep-HPLC to give I-86 (33.52 mg, yield: 36.4%) as a white solid.

Additional exemplary compounds were prepared following methods substantially similar to the method described above and herein. Data for these compounds are provided below.

TABLE 7

Characterization Data for Additional Exemplary Compounds

| Compound No. | Chemical Structure | [M + H] observed | $^1$H NMR (400 MHz) |
|---|---|---|---|
| I-86 | 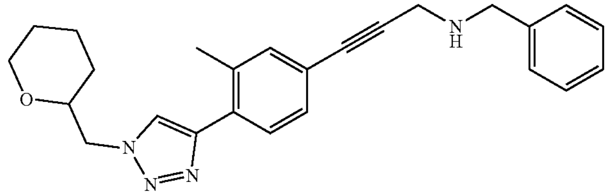 [SMILES: Cc1cc(C#CCNCc2ccccc2)ccc1-c1cn(CC2CCCCO2)nn1] | 401.2 | $^1$H NMR (400 MHz, $CDCl_3$): δ 7.82(s, 1 H), 7.80 (d, J = 8.8 Hz, 1 H), 7.32-7.39 (m, 6 H), 7.26-7.28 (m, 1 H), 4.52 (dd, J = 3.2 Hz, 14.4 Hz, 1 H), 4.33 (dd, J = 7.6 Hz, 14.0 Hz, 1 H), 3.97-4.00 (m, 1 H), 3.96 (s, 2 H), 3.68-3.73 (m, 1 H), 3.66 (s, 2 H), 3.37-3.43 (m, 1 H), 2.47 (s, 3 H), 1.88-1.89 (m, 1 H), 1.57-1.70 (m, 2 H), 1.50-1.53 (m, 3 H), 1.22-1.31 (m, 1 H). |
| I-76 | 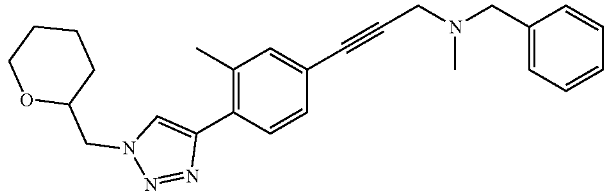 [SMILES: Cc1cc(C#CCN(C)Cc2ccccc2)ccc1-c1cn(CC2CCCCO2)nn1] | 415.3 | $^1$H NMR (400 MHz, $CDCl_3$): δ 7.80-7.83 (m, 2 H), 7.27-7.40 (m, 7 H), 4.53 (dd, J = 3.2 Hz, 14.4 Hz, 1 H), 4.34 (dd, J = 7.6 Hz, 14.0 Hz, 1H), 3.98-4.01 (m, 1 H), 3.66-3.74 (m, 3 H), 3.53 (s, 2 H), 3.37-3.43 (m, 1 H), 2.47 (s, 3 H), 2.42 (s, 3 H), 1.88-1.89 (m, 1 H), 1.50-1.70 (m, 5 H). |
| I-235 | 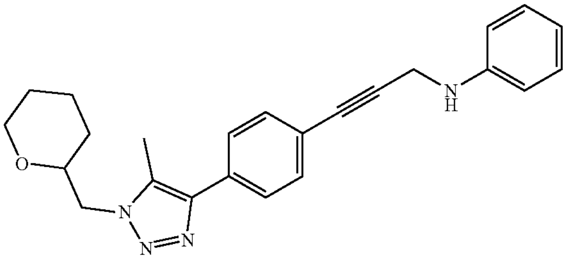 [SMILES: Cc1c(-c2ccc(C#CCNc3ccccc3)cc2)nnn1CC1CCCCO1] | 387.0 | $^1$H NMR (400 MHz, DMSO-$d_6$) δ 7.68 (d, J = 8.4 Hz, 2H), 7.45 (d, J = 8.4 Hz, 2H), 7.13 (dt, J = 1.2 Hz, 8.4 Hz, 2H), 6.71 (d, J = 8.0 Hz, 2H), 6.61 (t, J = 7.2 Hz, 1H), 6.08 (t, J = 6.0 Hz, 1H), 4.28-4.42 (m, 2H), 4.14 (d, J = 6.0 Hz, 2H), 3.80-3.83 (m, 1H), 3.65-3.71 (m, 1H), 3.24-3.30 (m, 1H), 2.45 (s, 3H), 1.78-1.80 (m, 1H), 1.65-1.68 (m, 1H), 1.36-1.54 (m, 3H), 1.20-1.30 (m, |

TABLE 7-continued

Characterization Data for Additional Exemplary Compounds

| Compound No. | Chemical Structure | [M + H] observed | $^1$H NMR (400 MHz) |
|---|---|---|---|
| | | | 1H). |
| I-178 | 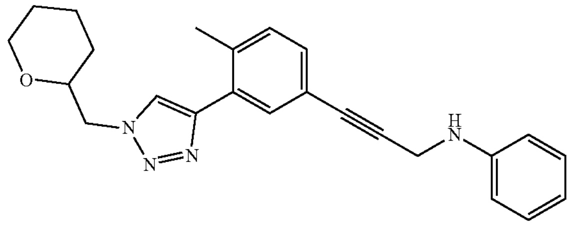 [SMILES: Cc1ccc(C#CCNc2ccccc2)cc1-c1cn(CC2CCCCO2)nn1] | 387.1 | $^1$ H NMR (400 MHz, DMSO-$d_6$) δ 8.36 (s, 1H), 7.76 (d, J = 1.6 Hz, 1H), 7.24-7.30 (m, 2H), 7.11-7.15 (m, 2H), 6.70 (dd, J = 1.2 Hz, 8.4 Hz, 2H), 6.60 (t, J = 7.2 Hz, 1H), 6.07 (t, J = 6.0 Hz, 1H), 4.37-4.49 (m, 2H), 4.12 (d, J = 6.0 Hz, 2H), 3.84-3.87 (m, 1H), 3.72-3.78 (m, 1H), 3.28-3.34 (m, 1H), 2.43 (s, 3H), 1.78-1.81 (m, 1H), 1.62-1.65 (m, 1H), 1.37-1.54 (m, 3H), 1.15-1.25 (m, 1H). |
| I-161 | 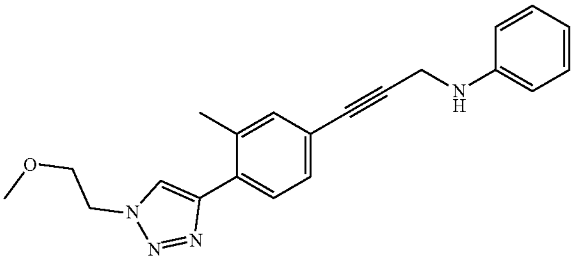 [SMILES: COCCn1cc(-c2ccc(C#CCNc3ccccc3)cc2C)nn1] | 347.3 | $^1$H NMR (400 MHz, DMSO-$d_6$): δ 8.40 (s, 1H), 7.76 (d, J = 8.0 Hz, 1H), 7.27-7.32 (m, 2H), 7.13 (t, J = 7.6 Hz, 2H), 6.70 (d, J = 8.4 Hz, 2H), 6.61 (t, J = 7.6 Hz, 1H), 6.07 (t, J = 6.0 Hz, 1H), 4.58 (t, J = 4.8 Hz, 2H), 4.13 (d, J = 6.0 Hz, 2H), 3.79 (t, J = 5.6 Hz, 2H), 3.25 (s, 3H), 2.41 (s, 3H). |
| I-162 | 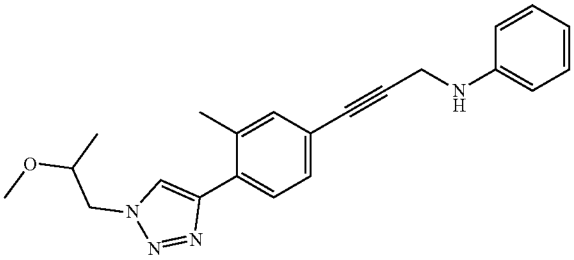 [SMILES: COC(C)Cn1cc(-c2ccc(C#CCNc3ccccc3)cc2C)nn1] | 361.1 | $^1$H NMR (400 MHz, DMSO-$d_6$): δ 8.35 (s, 1H), 7.76 (d, J = 8.0 Hz, 1 H), 7.32 (s, 1H), 7.28 (d, J = 8.0 Hz, 1 H), 7.13 (t, J = 8.0 Hz, 2 H), 6.70 (d, J = 7.6 Hz, 2 H), 6.61 (t, J = 7.6 Hz, 1 H), 6.07 (t, J = 6.0 Hz, 1 H), 4.51 (dd, J ? 4.4 Hz, 14.0 Hz, 1H), 4.40 (dd, J = 6.8 Hz, 14.0 Hz, 1H), 4.13 (d, J = 6.0 Hz, 2 H), 3.76-3.82 (m, 1H), 3.21 (s, 3H), 2.41 (s, 3H), 1.10 (d, J = 6.4 Hz, 3 H). |
| I-163 | 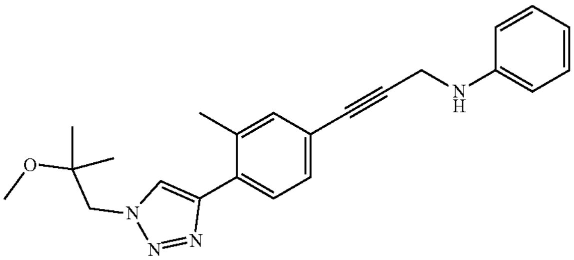 [SMILES: COC(C)(C)Cn1cc(-c2ccc(C#CCNc3ccccc3)cc2C)nn1] | 375.1 | $^1$H NMR (400 MHz, DMSO-$d_6$): δ 8.42 (s, 1H), 7.71 (d, J = 8.0 Hz, 1 H), 7.31 (s, 1H), 7.27 (dd, J = 8.0 Hz, 1.2 Hz, 1 H),7.13 (t, J = 8.0 Hz, 2 H), 6.70 (d, J = 7.6 Hz, 2 H), 6.61 (t, J = 7.6 Hz, 1 H), 6.08 (t, J = 6.0 Hz, 1 H), 4.13 (d, J = 6.0 Hz, 2 H), 3.66 (s, 2H), 3.21 (s, 3H), 2.43 (s, 3H), 1.63 (s, 6H). |
| I-135 | 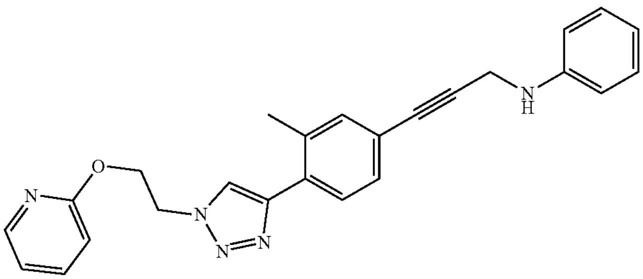 [SMILES: Cc1cc(C#CCNc2ccccc2)ccc1-c1cn(CCOc2ccccn2)nn1] | 410.0 | $^1$H NMR (400 MHz, $CDCl_3$): δ 8.13-8.15 (m, 1H), 7.79 (s, 1H), 7.73 (d, J = 8.4 Hz, 1H), 7.57-7.61 (m, 1H), 7.29-7.31 (m, 2H), 7.21-7.23 (m, 2H), 6.90-6.93 (m, 1H), 6.73-6.81 (m, 4H), 4.76-4.85 (m, 4H), 4.17 (s, 2H), 3.95-3.99 (m., 1H), 2.41 (s, 3H). |

TABLE 7-continued

| Compound No. | Chemical Structure | [M + H] observed | $^1$H NMR (400 MHz) |
|---|---|---|---|
| | Characterization Data for Additional Exemplary Compounds | | |
| I-136 | 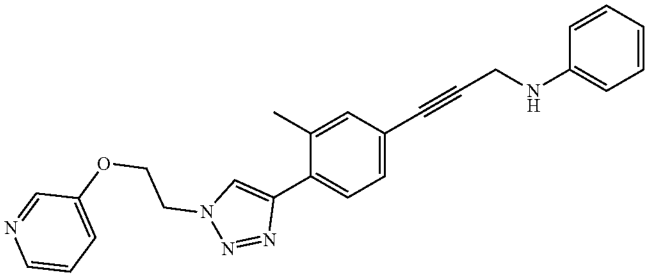 [SMILES: Cc1cc(C#CCNc2ccccc2)ccc1-c1cn(CCOc2cccnc2)nn1] | 410.1 | $^1$H NMR (400 MHz, $CDCl_3$): δ 8.27-8.32 (m, 2H), 7.85 (s, 1H), 7.73 (d, J = 7.6 Hz, 1H), 7.30-7.32 (m, 2H), 7.21-7.26 (m, 3H), 7.14-7.17 (m, 1H), 6.79 (t, J = 7.6 Hz, 1H), 6.74 (d, J = 7.6 Hz, 2H), 4.86 (t, J = 5.0 Hz, 2H), 4.47 (t, J = 4.8 Hz, 2H), 4.17 (s, 2H), 3.99 (br., 1H), 2.43 (s, 3H). |
| I-137 | 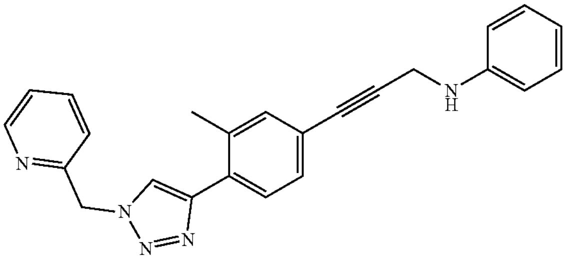 [SMILES: Cc1cc(C#CCNc2ccccc2)ccc1-c1cn(Cc2ccccn2)nn1] | 380.1 | $^1$H NMR (400 MHz, DMSO-$d_6$): δ 8.54-8.56 (m, 2H), 7.60 (dt, J = 8.0 Hz, 1.6 Hz, 1 H), 7.78 (d, J = 8.0 Hz, 1 H), 7.26-7.38 (m, 4H), 7.13 (t, J = 8.4 Hz, 2 H), 6.70 (d, J = 7.6 Hz, 2 H), 6.61 (t, J = 7.6 Hz, 1 H), 6.07 (t, J = 6.0 Hz, 1 H), 5.78 (s, 2H), 4.13 (d, J = 6.4 Hz, 2 H), 2.42 (s, 3H). |
| I-117 | 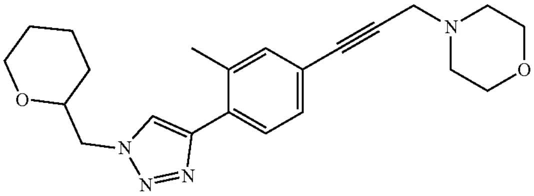 [SMILES: Cc1cc(C#CCN2CCOCC2)ccc1-c1cn(CC2CCCCO2)nn1] | 381.0 | $^1$H NMR (400 MHz, $CDCl_3$): δ 7.82 (d, J = 0.8 Hz, 1 H), 7.79 (d, J = 7.6 Hz, 1 H), 7.33-7.35 (m, 2 H), 4.49-4.54 (m, 1 H), 4.30-4.36 (m, 1 H), 3.98 (d, J = 10.8 Hz, 1 H), 3.78 (t, J = 4.0 Hz, 4 H), 3.68-3.73 (m, 1 H), 3.52 (s, 2 H), 3.37-3.43 (m, 1 H), 2.65-2.66 (m, 4 H), 2.45 (s, 3 H), 1.88-1.89 (m, 1 H), 1.57-1.67 (m, 1 H), 1.52-1.57 (m, 3 H), 1.25-1.28 (m, 1 H). |
| I-118 | 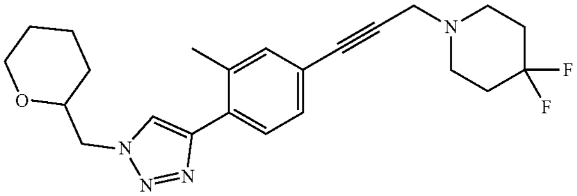 [SMILES: Cc1cc(C#CCN2CCC(F)(F)CC2)ccc1-c1cn(CC2CCCCO2)nn1] | 415.0 | $^1$H NMR (400 MHz, $CDCl_3$): δ 7.82(s, 1 H), 7.79 (d, J = 8.8 Hz, 1 H), 7.33-7.35 (m, 2 H), 4.52 (dd, J = 2.8 Hz, 14.0 Hz, 1 H), 4.33 (dd, J = 7.6 Hz, 14.0 Hz, 1 H), 3.99 (dd, J = 2.4 Hz, 11.2 Hz, 1 H), 3.67-3.73 (m, 1 H), 3.57 (s, 2 H), 3.37-3.43 (m, 1 H), 2.75 (t, J = 5.6 Hz, 4 H), 2.45 (s, 3 H), 2.02-2.12 (m, 4 H), 1.87-1.90 (m, 1 H), 1.67-1.70 (m, 1 H), 1.50-1.54 (m, 3 H), 1.22-1.31 (m, 1 H). |
| I-119 | 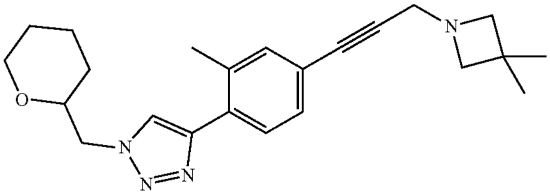 | 379.1 | $^1$H NMR (400 MHz, $CDCl_3$): δ 7.82 (s, 1 H), 7.78-7.80 (m, 1 H), 7.35-7.37 (m, 2 H), 4.52 (dd, J = 3.2 Hz, 14.0 Hz, 1H), 4.33 (dd, J = 7.6 Hz, 14.0 Hz, 1 H), 3.99 (dd, J = 2.4 Hz, 11.2 Hz, 1 H), 3.67-3.73 (m, 1 H), 3.49 (s, 2 H), 3.37-3.43 (m, 1 H), 3.15 (s, 4 H), 2.46 (s, 3 H), 1.88-1.89 (m, 1 H), 1.57-1.67 (m, 1 H), 1.50-1.57 (m, 3 H), 1.27-1.28 (m, 1 H), 1.24 (s, 6 H). |

TABLE 7-continued

| Compound No. | Chemical Structure | [M + H] observed | $^1$H NMR (400 MHz) |
|---|---|---|---|
| Characterization Data for Additional Exemplary Compounds | | | |
| I-120 | 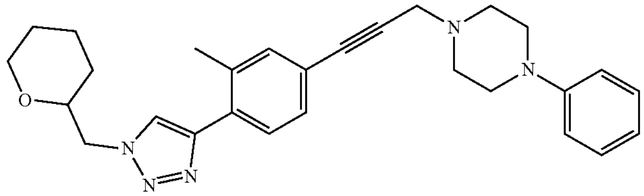 [SMILES: Cc1cc(C#CCN2CCN(c3ccccc3)CC2)ccc1-c1cn(CC2CCCCO2)nn1] | 455.9 | $^1$H NMR (400 MHz, $CDCl_3$): δ 7.82 (s, 1 H), 7.79 (d, J = 7.6 Hz, 1 H), 7.34-7.36 (m, 2 H), 7.27-7.30 (m, 1 H), 7.24-7.26 (m, 1 H), 6.94-6.96 (m, 2 H), 6.86 (t, J = 7.2 Hz, 1 H), 4.52 (dd, J = 2.8 Hz, 14.0 Hz, 1H), 4.33 (dd, J = 7.6 Hz, 14.0 Hz, 1 H), 3.99 (dd, J = 2.4 Hz, 11.2 Hz, 1 H), 3.67-3.73 (m, 1 H), 3.60 (s, 2 H), 3.36-3.43 (m, 1 H), 3.26-3.29 (m, 4 H), 2.82 (t, J = 5.2 Hz, 4 H), 2.45 (s, 3 H), 1.85-1.90 (m, 1 H), 1.56-1.57 (m, 1 H), 1.49-1.53 (m, 3 H), 1.22-1.31 (m, 1 H). |
| I-121 | 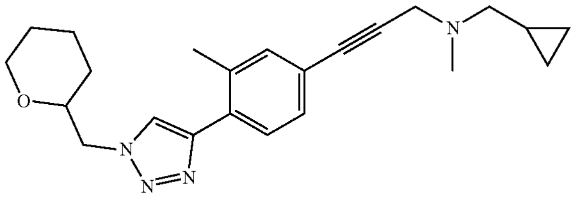 [SMILES: Cc1cc(C#CCN(C)CC2CC2)ccc1-c1cn(CC2CCCCO2)nn1] | 379.0 | $^1$H NMR (400 MHz, $CDCl_3$): δ 7.82(s, 1 H), 7.78 (d, J = 8.8 Hz, 1 H), 7.32-7.34 (m, 1 H), 4.52 (dd, J = 2.8 Hz, 14.0 Hz, 1 H), 4.33 (dd, J = 7.6 Hz, 14.0 Hz, 1 H), 3.97-4.00 (m, 1 H), 3.69-3.73 (m, 1 H), 3.67 (s, 2 H), 3.37-3.43 (m, 1 H), 2.45 (s, 3 H), 2.44 (s, 3 H), 2.39 (d, J = 6.4 Hz, 2 H), 1.88-1.89 (m, 1 H), 1.67-1.70 (m, 1 H), 1.48-1.57 (m, 3 H), 1.22-1.31 (m, 1 H), 0.86-0.93 (m, 1 H), 0.50-0.56 (m, 2 H), 0.18-0.22 (m, 2 H). |
| I-138 | 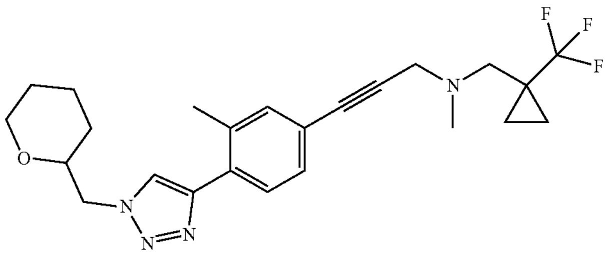 [SMILES: Cc1cc(C#CCN(C)CC2(C(F)(F)F)CC2)ccc1-c1cn(CC2CCCCO2)nn1] | 447.0 | $^1$H NMR (400 MHz, $CDCl_3$): δ 7.82 (s, 1H), 7.79 (d, J = 8.4 Hz, 1H), 7.31-7.33 (m, 2H), 4.52 (dd, J = 3.2 Hz, 14.4 Hz, 1H), 4.33 (dd, J = 7.6 Hz, 14.4 Hz, 1H), 3.98-4.01 (m, 1H), 3.69-3.74 (m, 3H), 3.37-3.44 (m, 1H), 2.69 (s, 2H), 2.46 (s, 3H), 2.42 (s, 3H), 1.86-1.90 (m, 1H), 1.66-1.71 (m, 1H), 1.48-1.55 (m, 3H), 1.22-1.32 (m, 1H), 1.02-1.06 (m, 2H), 0.72-0.78 (m, 2H). |
| I-306 | 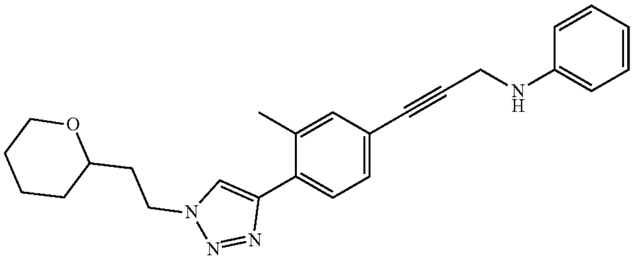 [SMILES: Cc1cc(C#CCNc2ccccc2)ccc1-c1cn(CCC2CCCCO2)nn1] | 401.1 | $^1$H NMR (400 MHz, $CD_3OD$) δ 8.13 (s, 1H), 7.59 (d, J = 8.0 Hz, 1H), 7.24-7.30 (m, 2H), 7.14-7.19 (m, 2H), 6.77 (dd, J = 1.2 Hz, 8.4 Hz, 2H), 6.68-6.72 (m, 1H), 4.53-4.56 (m, 2H), 4.12 (s, 2H), 3.93-3.97 (m, 1H), 3.31-3.43 (m, 1H), 3.21-3.27 (m, 1H), 2.39 (s, 3H), 1.96-2.13 (m, 2H), 1.79-1.83 (m, 1H), 1.44-1.61 (m, 4H), 1.26-1.36 (m, 1H). |

TABLE 7-continued

| Characterization Data for Additional Exemplary Compounds | | | |
|---|---|---|---|
| Compound No. | Chemical Structure | [M + H] observed | $^1$H NMR (400 MHz) |
| I-144 | 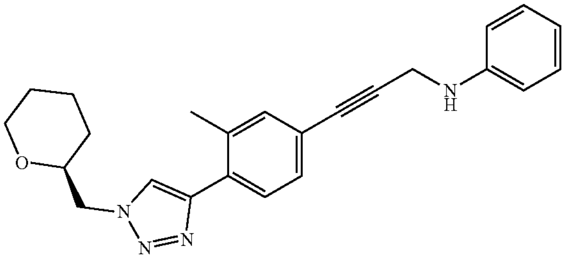 [SMILES: Cc1cc(C#CCNc2ccccc2)ccc1-c1cn(C[C@@H]2CCCCO2)nn1] | 387.1 | $^1$H NMR (400 MHz, $CDCl_3$): δ 7.81(s, 1H), 7.77 (d, J = 8.8 Hz, 1 H), 7.29-7.31 (m, 2 H), 7.21-7.26 (m, 2 H), 6.73-6.81 (m, 3 H), 4.51 (dd, J = 2.8 Hz, 14.0 Hz, 1 H), 4.51 (dd, J = 2.8 Hz, 14.0 Hz, 1 H), 4.32 (dd, J = 7.6 Hz, 14.4 Hz, 1H), 3.96-4.16 (m, 4 H), 3.67-3.72 (m, 1 H), 3.39-3.42 (m, 1 H), 2.43 (s, 3 H), 1.87-1.89 (m, 1 H), 1.65-1.69 (m, 1 H), 1.50-1.56 (m, 3 H), 1.24-1.27 (m, 1 H). |
| I-166 | 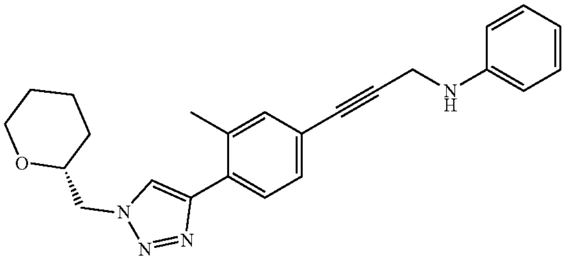 [SMILES: Cc1cc(C#CCNc2ccccc2)ccc1-c1cn(C[C@H]2CCCCO2)nn1] | 387.0 | 1H NMR (400 MHz, DMSO-$d_6$): δ 8.35 (s, 1H), 7.77 (d, J = 8.0 Hz, 1H), 7.32 (s, 1H), 7.27-7.30 (m, 1H), 7.14 (t, J = 8.0 Hz, 2H), 6.71 (d, J = 8.0 Hz, 2H), 6.62 (t, J = 7.2 Hz, 1H), 6.08 (t, J = 6.4 Hz, 1H), 4.37-4.50 (m, 2H), 4.13 (d, = 6.0 Hz, 2H), 3.71-3.86 (m, 2H), 3.27-3.34 (m, 1H), 2.42 (s, 3H), 1.77-1.80 (m, 1H), 1.62-1.65 (m, 1H), 1.38-1.50 (m, 3H), 1.15-1.25 (m, 1H). |
| I-188 | 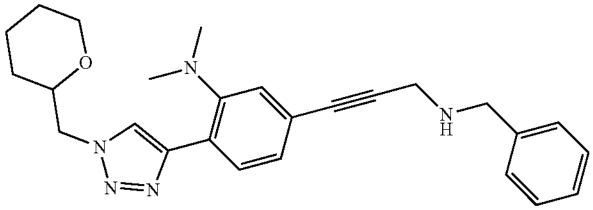 [SMILES: CN(C)c1cc(C#CCNCc2ccccc2)ccc1-c1cn(CC2CCCCO2)nn1] | 430.1 | $^1$H NMR (400 MHz, DMSO-$d_6$) δ 8.42 (s, 1H), 8.02 (d, J = 8.0 Hz, 1H), 7.31-7.38 (m, 4H), 7.16-7.26 (m, 3H), 4.40-4.52 (m, 2H), 3.83-3.88 (m, 3H), 3.67-3.72 (m, 1H), 3.55 (s, 2H), 3.16-3.31 (m, 1H), 2.81 (br, 1H), 2.59 (s, 3H), 1.77-1.80 (m, 1H), 1.62-1.65 (m, 1H), 1.34-1.54 (m, 3H), 1.12-1.22 (m, 1H). |
| I-201 | 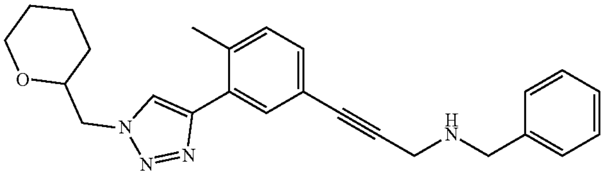 [SMILES: Cc1ccc(C#CCNCc2ccccc2)cc1-c1cn(CC2CCCCO2)nn1] | 401.1 | $^1$H NMR (400 MHz, DMSO-$d_6$) δ 8.38 (s, 1H), 7.81 (s, 1H), 7.30-7.38 (m, 6H), 7.22-7.25 (m, 1H), 4.38-4.50 (m, 2H), 3.83-3.88 (m, 3H), 3.71-3.79 (m, 1H), 3.54 (s, 2H), 3.27-3.35 (m, 1H), 2.70 (br, 1H), 2.45 (s, 3H), 1.78-1.82 (m, 1H), 1.62-1.66 (m, 1H), 1.36-1.55 (m, 3H), 1.16-1.26 (m, 1H). |
| I-203 | 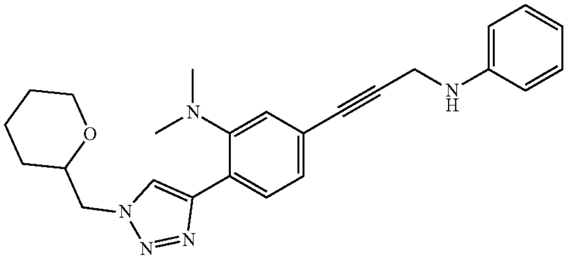 [SMILES: CN(C)c1cc(C#CCNc2ccccc2)ccc1-c1cn(CC2CCCCO2)nn1] | 415.9 | $^1$H NMR (400 MHz, $CD_3OD$-d4) δ 8.41 (s, 1H), 8.00 (d, J = 8.0 Hz, 1H), 7.10-7.15 (m, 4H), 6.70 (d, J = 7.6 Hz, 2H), 6.61 (t, J = 7.2 Hz, 1H), 6.07 (t, J = 6.0 Hz, 1H), 4.39-4.51 (m, 2H), 4.13 (d, J = 6.4 Hz, 2H), 3.83-3.87 (m, 1H), 3.66-3.72 (m, 1H), 3.27-3.34 (m, 1H), 2.57 (s, 6H), 1.76-1.79 (m, 1H), 1.61-1.64 (m, 1H), 1.34-1.53 (m, 3H), 1.11-1.21 (m, 1H). |

TABLE 7-continued

Characterization Data for Additional Exemplary Compounds

| Compound No. | Chemical Structure | [M + H] observed | $^1H$ NMR (400 MHz) |
|---|---|---|---|
| I-391 | 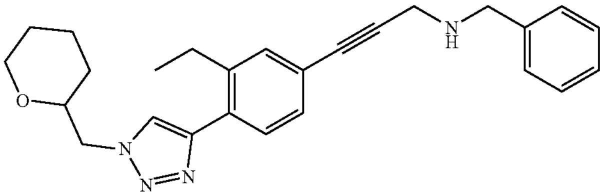 [SMILES: CCc1cc(C#CCNCc2ccccc2)ccc1-c1cn(CC2CCCCO2)nn1] | 415.1 | $^1H$ NMR (400 MHz, $CDCl_3$) δ 7.81 (s, 1H), 7.66 (d, J = 8.0 Hz, 1H), 7.38-7.40 (m, 3H), 7.33-7.36 (m, 3H), 7.25-7.29 (m, 1H), 4.52 (dd, J = 3.2 Hz, 14.4 Hz, 1H), 4.34 (dd, J = 7.6 Hz, 14.0 Hz, 1H), 3.97-4.01 (m, 3H), 3.69-3.74 (m, 1H), 3.67 (s, 2H), 3.37-3.44 (m, 1H), 2.82 (q, J = 7.6 Hz, 2H), 1.88-1.89 (m, 1H), 1.66-1.71 (m, 2H), 1.51-1.57 (m, 3H), 1.27-1.28 (m, 1H), 1.22 (t, J = 7.6 Hz, 3H). |
| I-392 | 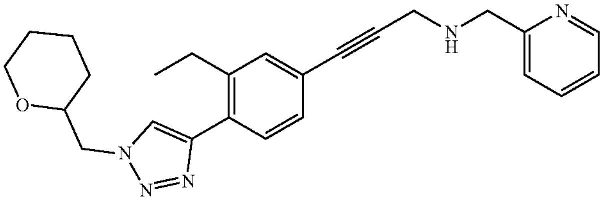 [SMILES: CCc1cc(C#CCNCc2ccccn2)ccc1-c1cn(CC2CCCCO2)nn1] | 416.2 | $^1H$ NMR (400 MHz, $CDCl_3$) δ 8.58 (d, J = 4.8 Hz, 1H), 7.80 (s, 1H), 7.63-7.69 (m, 2H), 7.36-7.38 (m, 2H), 7.30-7.33 (m, 1H), 7.17-7.20 (m, 1H), 4.52 (dd, J = 2.8 Hz, 14.0 Hz, 1H), 4.34 (dd, J = 7.6 Hz, 14.4 Hz, 1H), 4.09 (s, 2H), 3.98-4.01 (m, 1H), 3.69-3.75 (m, 3H), 3.40-3.43 (m, 1H), 2.81 (q, J = 7.6 Hz, 2H), 1.88-1.89 (m, 1H), 1.67-1.70 (m, 2H), 1.53-1.57 (m, 3H), 1.24-1.28 (m, 1H), 1.21 (t, J = 7.6 Hz, 3H). |
| I-393 | 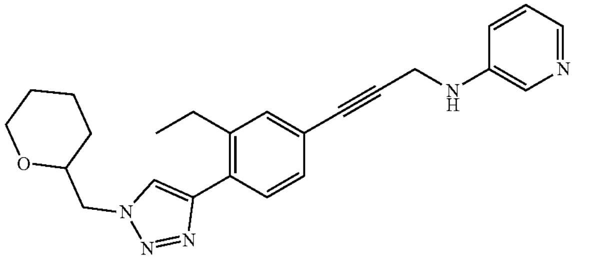 [SMILES: CCc1cc(C#CCNc2cccnc2)ccc1-c1cn(CC2CCCCO2)nn1] | 402.2 | $^1H$ NMR (400 MHz, $CDCl_3$) δ 8.16 (d, J = 2.8 Hz, 1H), 8.05 (dd, J = 1.2 Hz, 4.6 Hz, 1H), 7.80 (s, 1H), 7.64 (d, J = 7.6 Hz, 1H), 7.34 (s, 1H), 7.27-7.30 (m, 1H), 7.14-7.17 (m, 1H), 7.03-7.06 (m, 1H), 4.52 (dd, J = 3.2 Hz, 14.0 Hz, 1H), 4.34 (dd, J = 7.6 Hz, 14.4 Hz, 1H), 4.19-4.21 (m, 2H), 4.11-4.14 (m, 1H), 3.97-4.00 (m, 1H), 3.67-3.73 (m, 1H), 3.37-3.43 (m, 1H),2.81 (q, J = 7.6 Hz, 2H), 1.78-1.89 (m, 1H), 1.66-1.75 (m, 1H), 1.50-1.57 (m, 3H), 1.24-1.31 (m, 1H), 1.20 (t, J = 7.6 Hz, 3H). |
| I-250 | 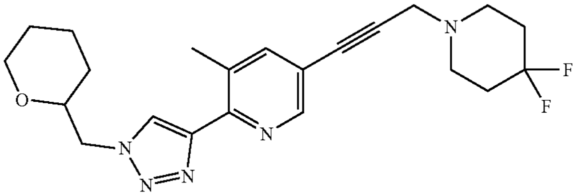 [SMILES: Cc1cc(C#CCN2CCC(F)(F)CC2)cnc1-c1cn(CC2CCCCO2)nn1] | 416.2 | $^1H$ NMR (400 MHz, $CDCl_3$) δ 8.50 (s, 1H), 8.24 (s, 1H), 7.62 (s, 1H), 4.50 (dd, J = 3.2 Hz, J = 14.0 Hz, 1H), 4.36 (q, J = 6.8 Hz, 1H), 3.99 (q, J = 11.6 Hz, 1H), 3.70-3.75 (m, 1H), 3.59 (s, 2H), 3.67-3.43 (m, 1H), 2.73-2.77 (m, 7H), 2.03-2.13 (m, 4H), 1.87-1.89 (m, 1H), 1.67-1.70 (m, 1H), 1.47-1.59 (m, 3H), 1.26-1.35 (m, 1H). |
| I-275 | 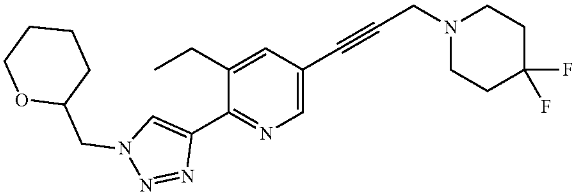 [SMILES: CCc1cc(C#CCN2CCC(F)(F)CC2)cnc1-c1cn(CC2CCCCO2)nn1] | 430.1 | $^1H$ NMR (400 MHz, $CDCl_3$) δ 8.50 (d, J = 2.0 Hz, 1H), 8.22 (s, 1H), 7.66 (d, J = 2.0 Hz, 1H), 4.49 (dd, J = 3.2 Hz, 14.0 Hz, 1H), 4.35 (dd, J = 7.6 Hz, 14.4 Hz, 1H), 3.97-4.01 (m, 1H), 3.71-3.75 (m, 1H), 3.60 (s, 2H), 3.37-3.42 (m, 1H), 3.20 (q, J = 7.6 Hz, 2H), 2.76 (s, 4H), 2.03-2.13 (m, 4H), 1.87-1.89 (m, 1H), |

TABLE 7-continued

| Compound No. | Chemical Structure | [M + H] observed | $^1$H NMR (400 MHz) |
|---|---|---|---|
| Characterization Data for Additional Exemplary Compounds | | | |
| | | | 1.66-1.69 (m, 1H), 1.50-1.61 (m, 3H), 1.28 (t, J = 7.6 Hz, 4H). |
| I-251 | 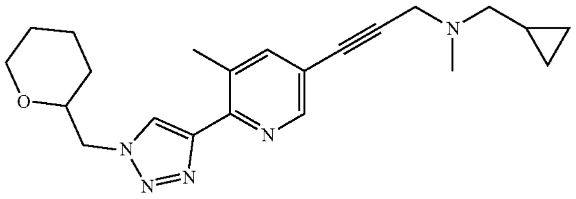 [SMILES: Cc1cc(C#CCN(C)CC2CC2)cnc1-c1cn(CC2CCCCO2)nn1] | 380.0 | $^1$H NMR (400 MHz, $CDCl_3$) δ 8.49 (d, J = 1.2 Hz, 1H), 8.23 (s, 1H), 7.61 (d, J = 0.8 Hz, 1H), 4.50 (dd, J = 3.2 Hz, J = 14.4 Hz, 1H), 4.36 (q, J = 7.2 Hz, 1H), 3.99 (q, J = 11.2 Hz, 1H), 3.71-3.75 (m, 1H), 3.69 (s, 2H), 3.37-3.42 (m, 1H), 2.72 (s, 3H), 2.45 (s, 3H), 2.39 (d, J = 6.4 Hz, 2H), 1.87-1.89 (m, 1H), 1.66-1.70 (m, 1H), 1.50-1.56 (m, 2H), 1.26-1.35 (m, 2H), 0.87-0.92 (m, 1H), 0.53-0.58 (m, 2H), 2.20 (q, J = 5.2 Hz, 2H). |
| I-276 | 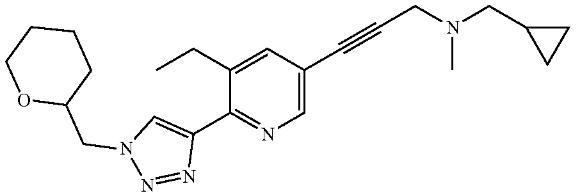 [SMILES: CCc1cc(C#CCN(C)CC2CC2)cnc1-c1cn(CC2CCCCO2)nn1] | 394.1 | $^1$H NMR (400 MHz, $CDCl_3$) δ 8.49 (d, J = 2.0 Hz, 1H), 8.21 (s, 1H), 7.64 (d, J = 2.0 Hz, 1H), 4.49 (dd, J = 3.2 Hz, 14.0 Hz, 1H), 4.35 (q, J = 7.2 Hz, 1H), 3.97-4.01 (m, 1H), 3.71-3.75 (m, 1H), 3.69 (s, 2H), 3.37-3.42 (m, 1H), 3.19 (q, J = 7.6 Hz, 2H), 2.45 (s, 3H), 2.40 (d, J = 6.8 Hz, 2H), 1.86-1.89 (m, 1H), 1.64-1.69 (m, 1H), 1.50-1.59 (m, 3H), 1.28 (t, J = 6.8 Hz, 4H), 0.88-0.92 (m, 1H), 0.53-0.58 (m, 2H), 0.18-0.22 (m, 2H). |
| I-231 | 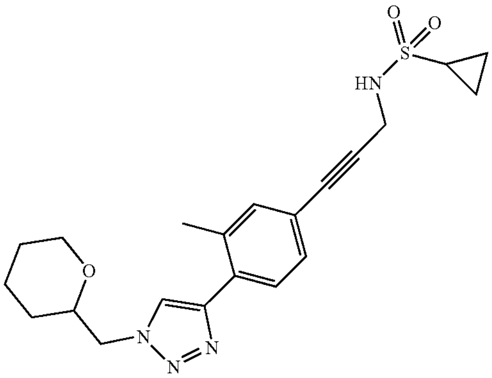 [SMILES: Cc1cc(C#CCNS(=O)(=O)C2CC2)ccc1-c1cn(CC2CCCCO2)nn1] | 415.3 | $^1$H NMR (400 MHz, $CDCl_3$) δ 7.84 (s, 1H), 7.81 (d, J = 8.0 Hz, 1H), 7.29-7.31 (m, 2H), 4.79 (t, J = 6.0 Hz, 1H), 4.53 (dd, J = 2.8 Hz, 14.4 Hz, 1H), 4.34 (q, J = 7.6 Hz, 1H), 4.20 (d, J = 6.4 Hz, 1H), 3.97-4.01 (m, 1H), 3.68-3.74 (m, 1H), 3.37-3.43 (m, 1H), 2.58-2.64 (m, 1H), 2.45 (s, 3H), 1.88-1.89 (m, 1H), 1.67-1.75 (m, 2H), 1.50-1.58 (m, 2H), 1.21-1.31 (m, 3H), 1.02-1.07 (m, 2H). |
| I-277 | 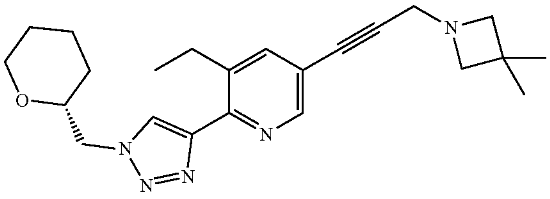 [SMILES: CCc1cc(C#CCN2CC(C)(C)C2)cnc1-c1cn(C[C@H]2CCCCO2)nn1] | 394.2 | $^1$H NMR (400 MHz, $CDCl_3$) δ 8.52 (d, J = 2.0 Hz, 1H), 8.22 (s, 1H), 7.67 (d, J = 2.0 Hz, 1H), 4.49 (dd, J = 3.2 Hz, 14.0 Hz, 1H), 4.35 (q, J = 7.6 Hz, 1H), 3.97-4.01 (m, 1H), 3.71-3.75 (m, 1H), 3.51 (s, 2H), 3.37-3.43 (m, 1H), 3.20 (q, J = 7.6 Hz, 2H), 3.16 (s, 4H), 1.86-1.89 (m, 1H), 1.62-1.69 (m, 2H), 1.51-1.56 (m, 2H), 1.28 (t, J = 7.6 Hz, 4H), 1.25 (s, 6H). |

TABLE 7-continued

| Characterization Data for Additional Exemplary Compounds | | | |
|---|---|---|---|
| Compound No. | Chemical Structure | [M + H] observed | $^1$H NMR (400 MHz) |
| I-232 | 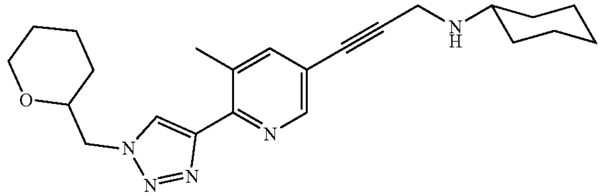 [SMILES: Cc1cc(C#CCNC2CCCCC2)cnc1-c1cn(CC2CCCCO2)nn1] | 393.2 | $^1$H NMR (400 MHz, $CDCl_3$) δ 7.82 (s, 1H), 7.78 (d, J = 8.8 Hz, 1H), 7.32-7.34 (m, 2H), 4.52 (dd, J = 3.2 Hz, 14.0 Hz, 1H), 4.33 (q, J = 7.6 Hz, 1H), 3.98 (dd, J = 3.2 Hz, 11.2 Hz, 1H), 3.70-3.73 (m, 1H), 3.68 (s, 2H), 3.37-3.43 (m, 1H), 2.68-2.75 (m, 1H), 2.45 (s, 3H), 1.89-1.92 (m, 3H), 1.56-1.78 (m, 5H), 1.47-1.53 (m, 2H), 1.07-1.36 (m, 6H). |
| I-394 | 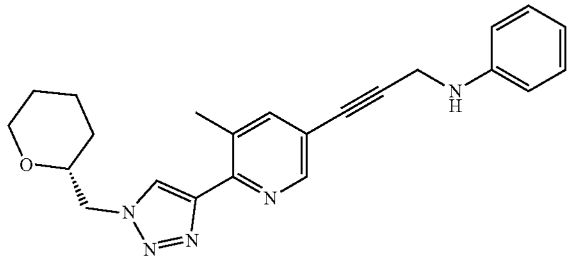 [SMILES: Cc1cc(C#CCNc2ccccc2)cnc1-c1cn(C[C@H]2CCCCO2)nn1] | 327.1 | $^1$H NMR (400 MHz, $CDCl_3$) δ 8.47 (d, J = 1.6 Hz, 1H), 8.22 (s, 1H), 7.58 (d, J = 1.2 Hz, 1H), 7.22-2.24 (m, 2H), 6.81 (t, J = 7.2 Hz, 1H), 6.75 (dd, J = 1.2 Hz, J = 8.8 Hz, 2H), 4.49 (dd, J = 3.2 Hz, J = 14.0 Hz, 1H), 4.34 (q, J = 7.2 Hz, 1H), 4.19 (s, 2H), 3.97-4.00 (m, 2H), 3.68-3.74 (m, 1H), 3.42-3.56 (m, 1H), 2.70 (s, 3H), 1.86-1.88 (m, 1H), 1.65-1.68 (m, 1H), 1.49-1.58 (m, 3H), 1.25-1.34 (m, 1H). |
| I-282 | 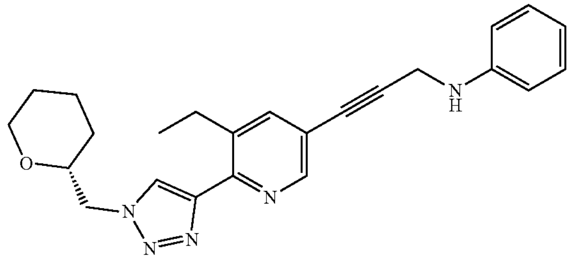 [SMILES: CCc1cc(C#CCNc2ccccc2)cnc1-c1cn(C[C@H]2CCCCO2)nn1] | 402.1 | $^1$H NMR (400 MHz, $CDCl_3$) δ 8.47 (d, J = 2.0 Hz, 1H), 8.20 (s, 1H), 7.62 (d, J = 2.0 Hz, 1H), 7.22-7.26 (m, 2H), 6.74-6.82 (m, 3H), 4.48 (dd, J = 3.6 Hz, 14.0 Hz, 1H), 4.34 (q, J = 7.6 Hz, 1H), 4.20 (s, 2H), 3.97-4.01 (m, 2H), 3.69-3.74 (m, 1H), 3.36-3.43 (m, 1H), 3.17 (q, J = 7.6 Hz, 2H), 1.86-1.88 (m, 1H), 1.65-1.68 (m, 1H), 1.48-1.60 (m, 3H), 1.26 (t, J = 7.6 Hz, 4H). |
| I-283 | 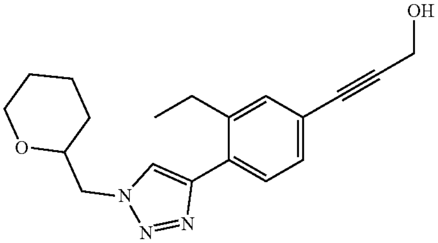 [SMILES: CCc1cc(C#CCO)ccc1-c1cn(CC2CCCCO2)nn1] | 326.1 | $^1$H NMR (400 MHz, $CDCl_3$) δ 7.81 (s, 1H), 7.66 (d, J = 8.0 Hz, 1H), 7.39 (d, J = 1.2 Hz, 1H), 7.31-7.33 (m, 1H), 4.51-4.55 (m, 3H), 4.32-4.37 (m, 1H), 3.99 (dd, J = 1.6 Hz, J = 12.0 Hz, 1H), 3.68-3.74 (m, 1H), 3.38-3.44 (m, 1H), 2.81 (q, J = 7.6 Hz, 2H), 2.05 (br, 1H), 1.88-1.90 (m, 1H), 1.67-170 (m, 2H), 1.50-1.58 (m, 2H), 1.24-1.31 (m, 1H), 1.21 (t, J = 7.6 Hz, 3H). |
| I-395 | 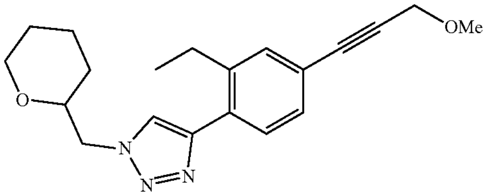 [SMILES: CCc1cc(C#CCOC)ccc1-c1cn(CC2CCCCO2)nn1] | 340.1 | $^1$H NMR (400 MHz, $CDCl_3$) δ 7.82-7.83 (m, 1H), 7.66-7.68 (m, 1H), 7.41-7.44 (m, 1H), 7.34 (dd, J = 1.6 Hz, J = 8.0 Hz, 1H), 4.49-4.53 (m, 1H), 4.31-4.37 (m, 3H), 3.96-3.99 (m, 1H), 3.67-3.73 (m, 1H), 3.46 (s, 3H), 3.36-3.42 (m, 1H), 2.82 (q, J = 7.6 Hz, 2H), 1.87-1.88 (m, 1H), 1.65-1.68 (m, 1H), 1.51-1.55 (m, 3H), 1.26-1.27 (m, 1H), 1.21 (t, J = 7.6 Hz, 3H). |

TABLE 7-continued

| Characterization Data for Additional Exemplary Compounds | | | |
|---|---|---|---|
| Compound No. | Chemical Structure | [M + H] observed | $^1$H NMR (400 MHz) |
| I-272 | 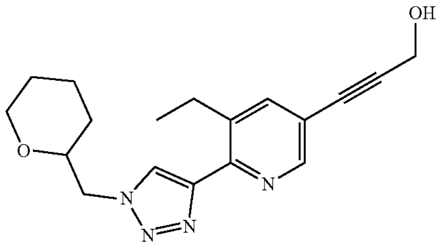 [SMILES: CCc1cc(C#CCO)cnc1-c1cn(CC2CCCCO2)nn1] | 313.1 | $^1$H NMR (400 MHz, $CDCl_3$) δ 8.60 (d, J = 1.6 Hz, 1H), 8.27 (s, 1H), 7.62 (d, J = 1.2 Hz, 1H), 4.49-4.53 (m, 3H), 4.37 (q, J= 7.6 Hz, 1H), 3.98-4.01 (m, 1H), 3.70-3.76 (m, 1H), 3.37-3.43 (m, 1H), 3.28 (s, 1H), 2.73 (s, 3H), 1.87-1.89 (m, 1H), 1.66-1.69 (m, 1H), 1.50-1.59 (m, 3H), 1.26-1.35 (m, 1H). |
| I-273 | 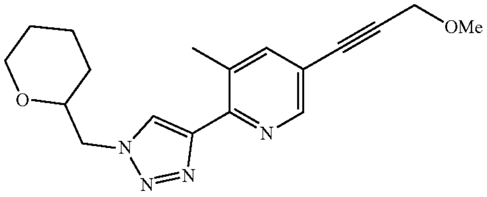 [SMILES: COCC#Cc1cnc(-c2cn(CC3CCCCO3)nn2)c(C)c1] | 327.1 | $^1$H NMR (400 MHz, $CDCl_3$) δ 8.52 (d, J = 1.6 Hz, 1H), 8.24 (s, 1H), 7.64 (d, J = 1.2 Hz, 1H), 4.50 (dd, J = 3.2 Hz, J = 14.2 Hz, 1H), 4.30-4.38 (m, 3H), 3.98-4.01 (m, 1H), 3.69-3.75 (m, 1H), 3.47 (s, 3H), 3.37-3.43 (m, 1H), 2.73 (s, 3H), 1.87-1.89 (m, 1H), 1.66-1.69 (m, 1H), 1.50-1.59 (m, 3H), 1.26-1.35 (m, 1H). |
| I-396 | 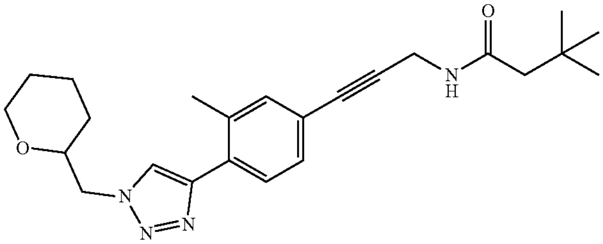 [SMILES: Cc1cc(C#CCNC(=O)CC(C)(C)C)ccc1-c1cn(CC2CCCCO2)nn1] | 409.2 | $^1$H NMR (400 MHz, $CDCl_3$) δ 7.83 (s, 1H), 7.79 (d, J = 8.0 Hz, 1H), 7.31-7.33 (m, 2H), 5.64 (s, 1H), 4.52 (dd, J= 2.8 Hz, 14.0 Hz, 1H), 4.33 (q, J = 7.6 Hz, 1H), 4.28 (d, J = 5.2 Hz, 2H), 3.99 (dd, J = 2.0 Hz, 10.8 Hz, 1H), 3.68-3.73 (m, 1H), 3.39-3.42 (m, 1H), 2.45 (s, 3H), 2.11 (s, 2H), 1.88-1.89 (m, 1H), 1.57-1.70 (m, 1H), 1.51-1.54 (m, 3H), 1.25-1.28 (m, 1 H), 1.07 (s, 9H). |
| I-397 | 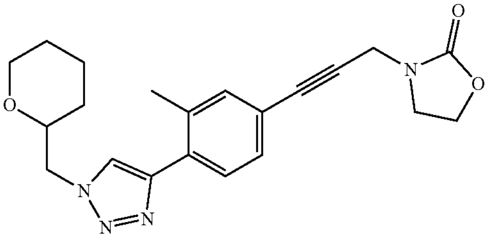 [SMILES: Cc1cc(C#CCN2CCOC2=O)ccc1-c1cn(CC2CCCCO2)nn1] | 381.1 | $^1$H NMR (400 MHz, $CDCl_3$) δ 7.84 (s, 1H), 7.82 (d, J = 8.4 Hz, 1H), 7.33-7.35 (m, 2H), 4.53 (dd, J = 3.2 Hz, 14.4 Hz, 1H), 4.40 (dd, J = 7.6 Hz, 15.6 Hz, 2H), 4.31-4.35 (m, 3H), 3.98-4.01 (m, 1H), 3.68-3.77 (m, 3H), 3.37-3.44 (m, 1H), 2.47 (s, 3H), 1.89-1.90 (m, 1H), 1.68-1.71 (m, 1H), 1.50-1.54 (m, 3H), 1.25-1.29 (m, 1H). |
| I-398 | 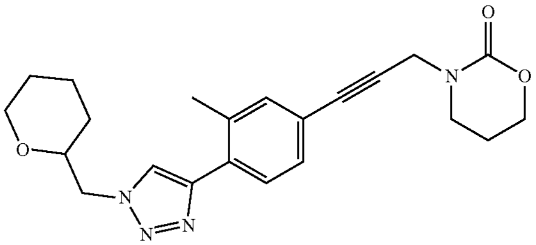 [SMILES: Cc1cc(C#CCN2CCCOC2=O)ccc1-c1cn(CC2CCCCO2)nn1] | 395.0 | $^1$H NMR (400 MHz, $CDCl_3$) δ 7.84 (s, 1H), 7.81 (d, J = 7.6 Hz, 1H), 7.33-7.35 (m, 2H), 4.53 (dd, J = 3.2 Hz, 14.0 Hz, 1H), 4.46 (s, 2H), 4.29-4.37 (m, 3H), 3.98-4.01 (m, 1H), 3.68-3.74 (m, 1H), 3.53 (t, J = 6.0 Hz, 2H), 3.37-3.44 (m, 1H), 2.46 (s, 3H), 2.10-2.16 (m, 2H), 1.88-1.90 (m, 1H), 1.67-1.71 (m,1H), 1.50-1.58 (m, 3H), 1.25-1.29 (m, 1H). |

TABLE 7-continued

Characterization Data for Additional Exemplary Compounds

| Compound No. | Chemical Structure | [M + H] observed | $^1$H NMR (400 MHz) |
|---|---|---|---|
| I-400 | 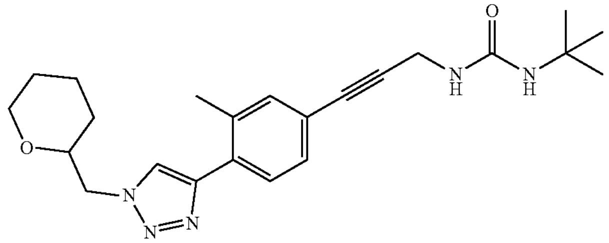 [SMILES: Cc1cc(C#CCNC(=O)NC(C)(C)C)ccc1-c1cn(CC2CCCCO2)nn1] | 410.2 | $^1$H NMR (400 MHz, $CDCl_3$) δ 7.82 (s, 1H), 7.77 (d, J = 8.0 Hz, 1H), 7.27-7.31 (m, 2H), 4.48-4.59 (m, 3H), 4.33 (dd, J = 8.0 Hz, 14.0 Hz, 1H),4.19 (d, J = 5.6 Hz, 2H), 3.98 (dd, J = 2.0 Hz, 11.2 Hz, 1H), 3.67-3.73 (m, 1H), 3.36-3.43 (m, 1H), 2.44 (s, 3H), 1.88-1.89 (m, 1H), 1.66-1.70 (m, 1H), 1.49-1.58 (m, 3H), 1.36 (s, 9H), 1.20-1.31 (m, 1 H). |
| I-401 | 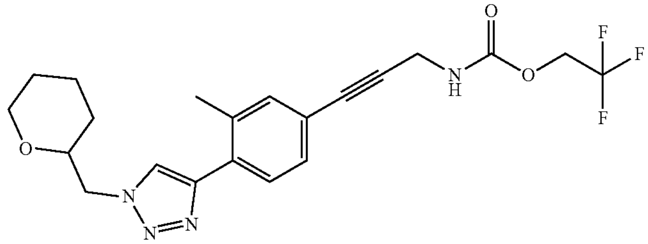 [SMILES: Cc1cc(C#CCNC(=O)OCC(F)(F)F)ccc1-c1cn(CC2CCCCO2)nn1] | 437.0 | $^1$H NMR (400 MHz, $CDCl_3$) δ 7.83 (s, 1H), 7.81 (d, J = 8.0 Hz, 1H), 7.32-7.34 (m, 2H), 5.19 (br, 1H), 4.47-4.55 (m, 3H), 4.34 (dd, J = 7.6 Hz, 14.0 Hz, 1H), 4.26 (d, J = 5.6 Hz, 2H), 3.98-4.01 (m, 1H), 3.70-3.71 (m, 1H), 3.40-3.41 (m, 1H), 2.46 (s, 3H), 1.88-1.90 (m, 1H), 1.67-1.71 (m, 1H), 1.53-1.54 (m, 3H), 1.26-1.29 (m, 1H). |
| I-48 | 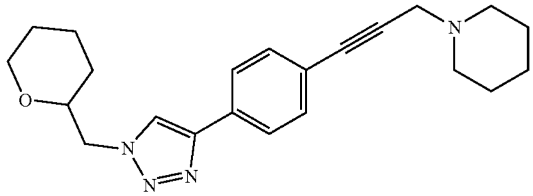 [SMILES: C(#Cc1ccc(-c2cn(CC3CCCCO3)nn2)cc1)CN1CCCCC1] | 365.2 | $^1$H NMR (400 MHz, $CDCl_3$δ 7.90 (s, 1H), 7.78 (d, J = 8.1 Hz, 2H), 7.48 (d, J = 8.2 Hz, 2H), 4.49 (dd, J = 14.2, 2.9 Hz, 1H), 4.30 (dd, J = 14.2, 7.6 Hz, 1H), 4.03-3.95 (m, 1H), 3.73-3.63 (m, 1H), 3.49 (s, 2H), 3.39 (td, J = 11.2, 4.0 Hz, 1H), 2.57 (s, 4H), 1.91-1.81 (m, 1H), 1.64 (p, J = 5.7 Hz, 5H), 1.58-1.38 (m, 5H), 1.32-1.19 (m, 1H). |
| I-266 | 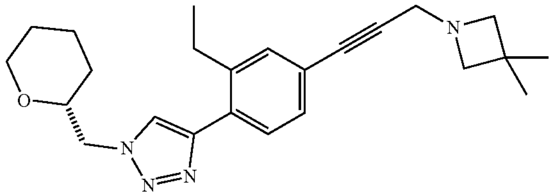 | 393.2 | $^1$H NMR (400 MHz, $CDCl_3$) 7.80 (s, 1H), 7.65 (d, J = 8.0 Hz, 1H), 7.40 (d, J = 1.4 Hz, 1H), 7.34 (dd, J ? 8.0, 1.7 Hz, 1H), 4.52 (dd, J = 14.1, 3.0 Hz, 1H), 4.34 (dd, J = 14.2, 7.5 Hz, 1H), 3.99 (dd, J = 10.7, 2.0 Hz, 1H), 3.78-3.66 (m, 1H), 3.50 (s, 2H), 3.40 (ddd, J = 11.4, 8.2, 5.6 Hz, 1H), 3.17 (s, 4H), 2.81 (q, J = 7.5 Hz, 2H), 1.98-1.84 (m, 1H), 1.72-1.65 (m, 1H), 1.64-1.48 (m, 3H), 1.35-1.17 (m, 10H). |
| I-284 | 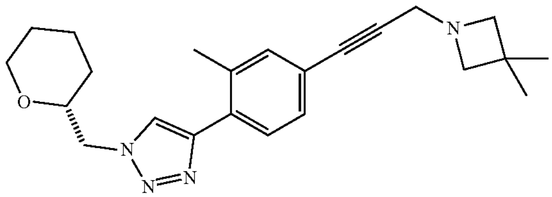 | 380.2 | $^1$H NMR (400 MHz, $CDCl_3$) δ 8.52 (d, J = 1.6 Hz, 1H), 8.22 (s, 1H), 7.62 (dd, J = 2.0, 0.7 Hz, 2H), 4.50 (dd, J = 14.1, 3.3 Hz, 1H), 4.35 (dd, J = 14.1, 7.5 Hz, 1H), 4.06-3.88 (m, 1H), 3.86-3.66 (m, 1H), 3.50 (s, 2H), 3.39 (td, J = 11.4, 3.2 Hz, 1H), 3.15 (s, 4H), 2.72 (s, 3H), 2.00-1.82 (m, 1H), 1.74-1.61 (m, 1H), 1.56-1.46 (m, 3H), 1.33-1.23 (m, 7H). |

Example 7: Synthesis of I-344

Synthetic Scheme of I-344

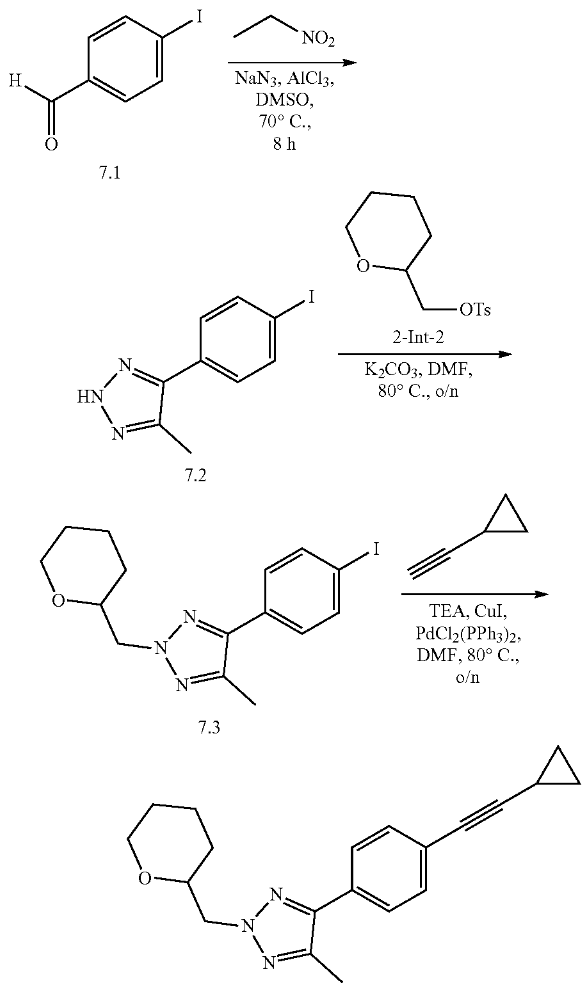

7.1

7.2

7.3

I-344

1. The Synthesis of Intermediate 7.2

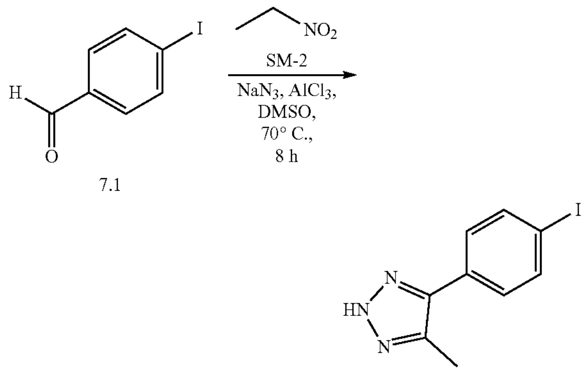

7.1

7.2

To a solution of 7.1 (2.3 g, 10 mmol) in DMSO (10 mL) was added $AlCl_3$ (0.1 g, 1 mmol), $NaN_3$ (0.7 g, 10 mmol) and SM-2 (0.75 g, 10 mmol). The reaction was stirred at 70° C. for 8 h. After the consumption of starting material (by LCMS), water (30 mL) was added, extracted with ethyl acetate (30 mL×3), washed with water (30 mL×3), dried and concentrated. The crude product was purified by pre-HPLC to get 7.2 (1.0 g, 35% yield) as yellow oil. LC-MS m/z: 285.08 $[M+H]^+$.

2. The Synthesis of Intermediate 7.3

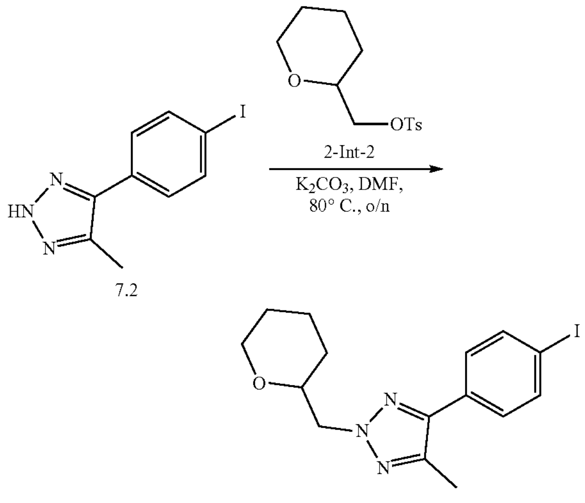

7.2

7.3

To a stirred solution of 7.2 (1.0 g, 3.5 mmol) in DMF (10 mL) was added $K_2CO_3$ (1.0 g, 7.0 mmol), and 2-Int-2 (1.0 mg, 3.5 mmol) at RT. Stirred at 80° C. for overnight. $H_2O$ was added, and the mixture was extracted with EA (10 mL×2). The organic layer was washed with water, dried over $Na_2SO_4$ and evaporated to dryness. The crude product was purified by pre-HPLC to give 7.3 (0.3 g, yield: 22%) as yellow oil. LC-MS m/z: 383.23 $[M+H]^+$.

3. The Synthesis of I-344

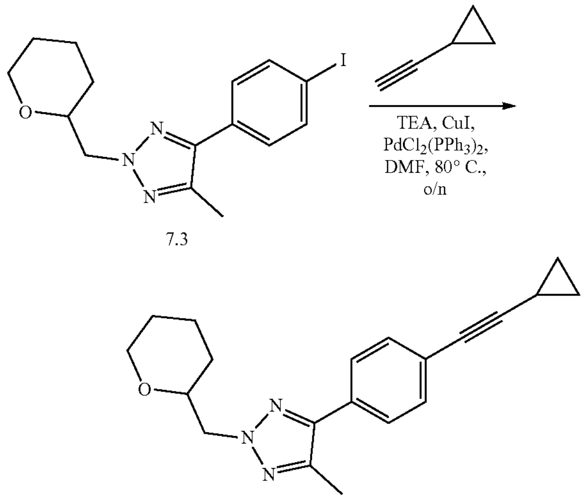

7.3

I-344

To a stirred solution of 7.3 (300 mg, 0.8 mmol), cyclopropyl acetylene (264 mg, 4.0 mmol) and TEA (505 mg, 5.0 mmol) in DMF (5 mL) was added $PdCl_2(PPh_3)_2$ (80 mg) and CuI (80 mg). The reaction mixture was stirred at 80° C. for 16 hours until the reaction was completed. The suspension was diluted with $H_2O$ (20 mL) and extracted with EA (20 mL×2), concentrated. The crude product was purified by pre-HPLC to give I-344 (60 mg, yield: 24%) as yellow oil.

Additional exemplary compounds were prepared following methods substantially similar to the method described above and herein. Data for these compounds are provided below.

TABLE 8

Characterization Data for Additional Exemplary Compounds

| Compound No. | Chemical Structure | [M + H] observed | $^1$H NMR (400 MHz) |
|---|---|---|---|
| I-344 | 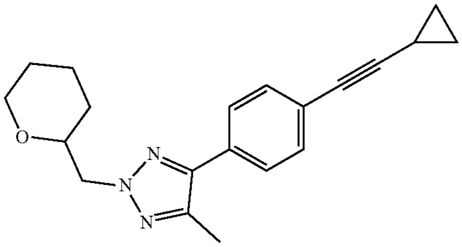 | 321.4 | $^1$H NMR (400 MHz, DMSO-$d_6$) δ 7.65 (d, J = 8.4 Hz, 2H), 7.44 (d, J = 8.4, 2H), 4.35 (d, J = 6 Hz, 2H), 3.78-3.85 (m, 2H), 3.25-3.31 (m, 1H), 2.42 (s, 3H), 1.77-1.80 (m, 1H), 1.23-1.61 (m, 6H), 0.88-0.92 (m, 2H), 0.73-0.77 (m, 2H). |
| I-345 | 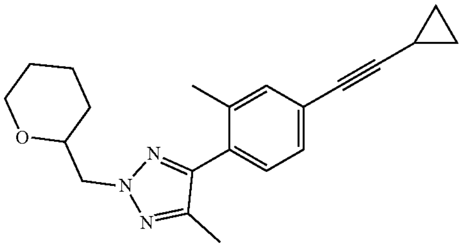 [SMILES: Cc1cc(C#CC2CC2)ccc1-c1nn(CC2CCCCO2)nc1C] | 321.4 | $^1$H NMR (400 MHz, DMSO-$d_6$): δ 7.33 (s, 1H), 7.24-7.25 (m, 2H), 4.30-4.40 (m, 2H), 3.80-3.84 (m, 2H), 3.28-3.30 (m, 1H), 2.20 (s, 3H), 2.18 (s, 3H), 1.77-1.79 (m, 1H), 1.44-1.59 (m, 5H), 1.23-1.29 (m, 1H), 0.87-0.92 (m, 2H), 0.73-0.76 (m, 2H). |

Example 8: Synthesis of I-74

Synthetic Scheme of I-74

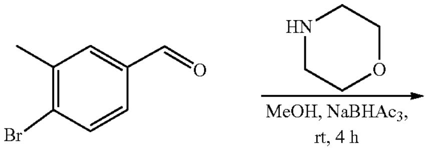

8.1

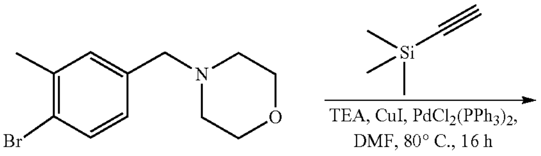

8.2

-continued

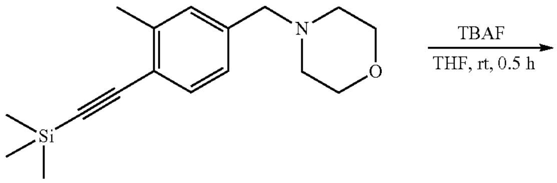

8.3

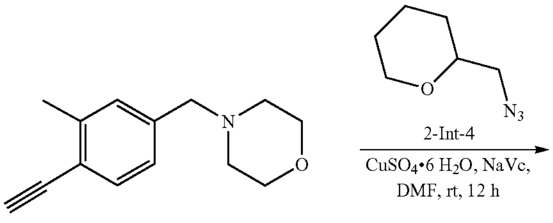

8.4

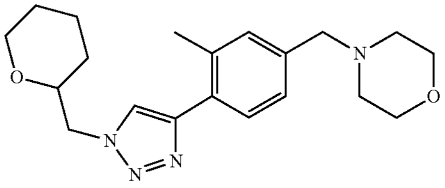

I-74

1. The Synthesis of Intermediate 8.2

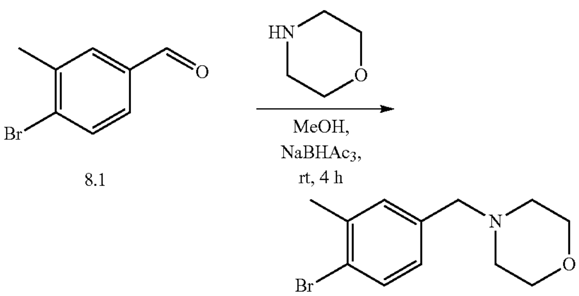

8.1

8.2

To a solution of 8.1 (198 mg, 1.0 mmol) in MeOH (5 mL) was added morpholine (87 mg, 1.0 mmol), $NaBHAc_3$ (820 mg, 5.0 mmol). The reaction was stirred at rt for 4 h. After the consumption of starting material (by LCMS), water (10 mL) was added, extracted with ethyl acetate (10 mL×3), washed with water (10 mL×3), dried and concentrated. The crude product was purified by pre-HPLC to get 8.2 (100 mg, 37% yield) as yellow oil. LC-MS m/z: 270.2 $[M+H]^+$.

2. The Synthesis of Intermediate 8.3

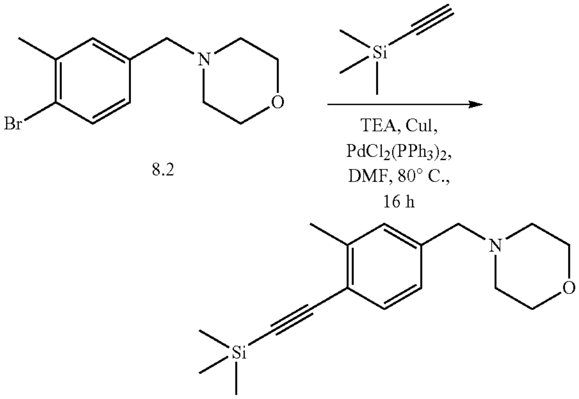

8.2

8.3

To a stirred solution of 8.2 (100 mg, 0.4 mmol), ethynyltrimethylsilane (80 mg, 0.8 mmol) and TEA (200 mg, 2 mmol) in DMF (5 mL) was added $PdCl_2(PPh_3)_2$ (40 mg) and CuI (40 mg). The reaction mixture was stirred at 80° C. for 16 hours until the reaction was completed. The suspension was diluted with $H_2O$ (20 mL) and extracted with EA (20 mL×2), concentrated. The crude product was purified by pre-HPLC to give 8.3 (110 mg, yield: 87%) as yellow oil. LC-MS m/z: 288.4 $[M+H]^+$.

3. The Synthesis of Intermediate 8.4

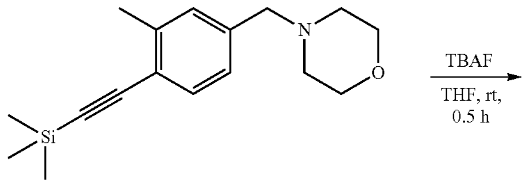

8.3

-continued

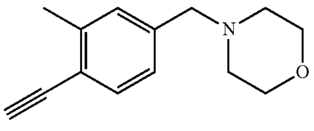

8.4

To a stirred solution of 8.3 (110 mg, 0.3 mmol) in THF (3 mL), TBAF (1 M in THF, 2 mL) was added at RT. Stirred at RT for 0.5 h. After the consumption of starting material (by LCMS), water (5 mL) was added, extracted with ethyl acetate (5 mL×3), washed with water (5 mL×3), dried and concentrated. The crude product was purified by pre-HPLC to give 8.4 (70 mg, yield: 70%) as brown oil. LC-MS m/z: 216.4 $[M+H]^+$.

4. The Synthesis of Intermediate I-74

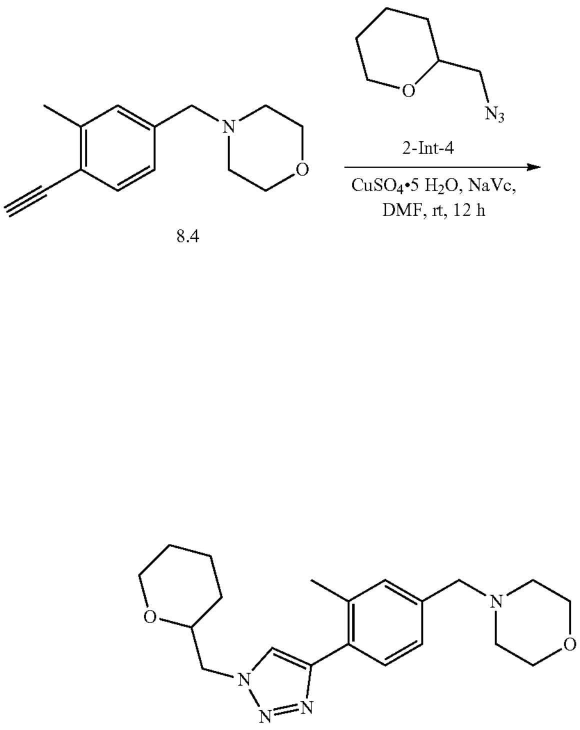

8.4

I-74

To a stirred solution of 8.4 (70 mg, 0.3 mmol) in DMF (5 mL), 2-(azidomethyl)tetrahydro-2H-pyran (2-Int-4, 42 mg, 0.3 mmol), $CuSO_4.5H_2O$ (25 mg, 0.1 mmol), sodium ascorbate (20 mg, 0.1 mmol) were added at RT. The reaction mixture was stirred at RT for 12 h. After the consumption of starting material (by LCMS), water (10 mL) was added, extracted with ethyl acetate (10 mL×3), washed with water (10 mL×3), dried and concentrated. The crude product was purified by pre-HPLC to give I-74 (8 mg, yield: 8%) as yellow oil.

Additional exemplary compounds were prepared following methods substantially similar to the method described above and herein. Data for these compounds are provided below.

TABLE 9

Characterization Data for Additional Exemplary Compounds

| Compound No. | Chemical Structure | [M + H] observed | $^1$H NMR (400 MHz) |
|---|---|---|---|
| I-7 | 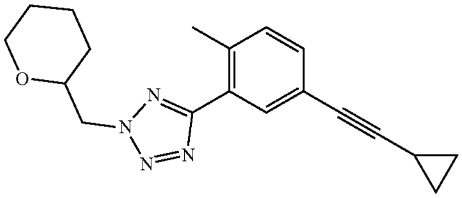 [SMILES: Cc1ccc(C#CC2CC2)cc1-c1nnn(CC2CCCCO2)n1] | 323.3 | $^1$H NMR (400 MHz, DMSO-$d_6$) δ 7.88 (d, J = 1.6 Hz, 1H), 7.36-7.42 (m, 2H), 4.73-4.80 (m, 2H), 3.80-3.95 (m, 2H), 3.26-3.32 (m, 1H), 2.56 (s, 3H), 1.70-1.83 (m, 2H), 1.28-1.59 (m, 5H), 0.87-0.92 (m, 2H), 0.74-0.78 (m, 2H). |
| I-8 | 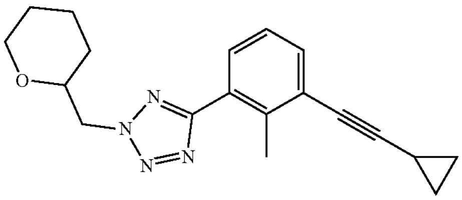 [SMILES: Cc1c(C#CC2CC2)cccc1-c1nnn(CC2CCCCO2)n1] | 323.1 | $^1$H NMR (400 MHz, DMSO-$d_6$) δ 7.79 (d, J = 7.6 Hz, 1H), 7.51 (d, J = 8.0 Hz, 1H), 7.32 (t, J = 7.6 Hz, 1H), 4.76-4.78 (m, 2H), 3.80-3.94 (m, 2H), 3.26-3.30 (m, 1H), 2.58 (s, 3H), 1.70-1.83 (m, 2H), 1.41-1.63 (m, 4H), 1.31-1.37 (m, 1H), 0.91-0.96 (m, 2H), 0.75-0.80 (m, 2H). |
| I-74 | 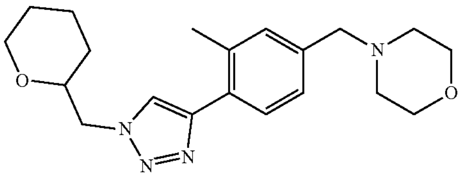 [SMILES: Cc1cc(CN2CCOCC2)ccc1-c1cn(CC2CCCCO2)nn1] | 357.3 | $^1$H NMR (400 MHz, DMSO-$d_6$): δ 8.28 (s, 1H), 7.70 (d, J = 8.0, 1H), 7.20-7.22 (m, 2H), 4.37-4.50 (m, 2H), 3.72-3.87 (m, 2H), 3.57-3.59 (m, 4H), 3.45 (s, 2H), 3.29-3.35 (s, 1H), 2.42 (s, 3H), 2.36 (s, 4H), 1.78-1.81 (m, 1H), 1.62-1.65 (m, 1H), 1.40-1.51 (m, 3H), 1.18-1.24 (m, 1H). |
| I-9 | 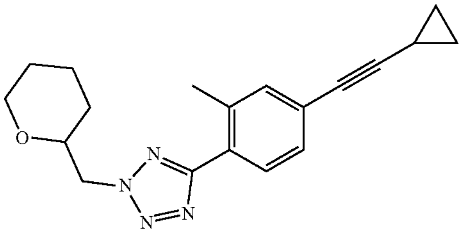 [SMILES: Cc1cc(C#CC2CC2)ccc1-c1nnn(CC2CCCCO2)n1] | 323.2 | $^1$H NMR (400 MHz, DMSO-$d_6$) δ 7.90 (d, J = 8.0 Hz, 1H), 7.40 (s, 1H), 7.34 (dd, J = 1.2, 8.0 Hz, 1H), 4.76-4.78 (m, 2H), 3.88-3.94 (m, 1H), 3.79-3.83 (m, 1H), 3.25-3.32 (m, 1H), 2.54 (s, 3H), 1.80-1.83 (m, 1H), 1.70-1.73 (m, 1H), 1.40-1.61 (m, 4H), 1.28-1.38 (m, 1H), 0.89-0.94 (m, 2H), 0.74-0.78 (m, 2H). |

Example 9: Synthesis of I-269

Synthetic Scheme of I-269

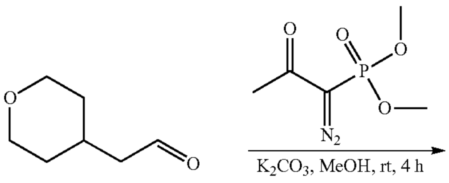

9.1

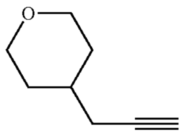

9.2

-continued

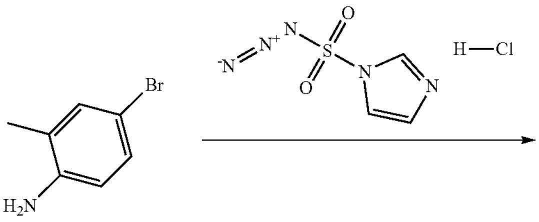

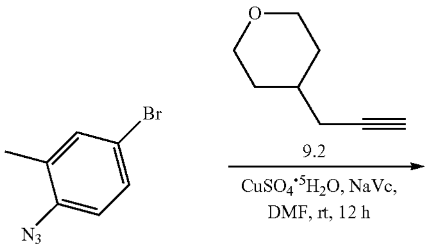

-continued

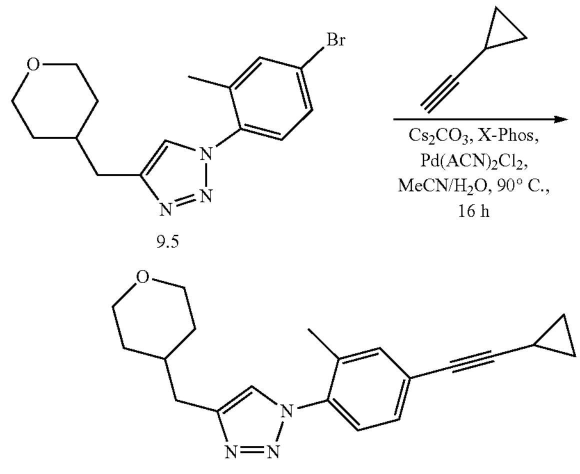

9.5

I-269

1. The Synthesis of Intermediate 9.2

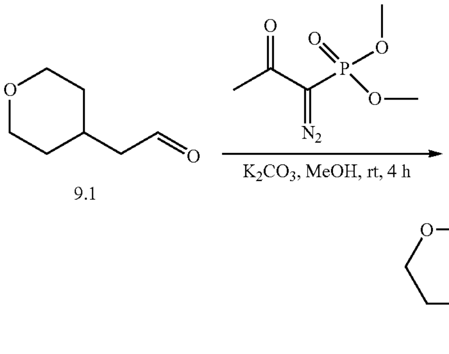

9.1

9.2

To a stirred solution of 9.1 (384 mg, 3.0 mmol) and $K_2CO_3$ (828 Mg, 6.0 mmol) in MeOH (15 mL) was added dimethyl 1-diazo-2-oxopropylphosphonate (576 mg, 3.0 mmol). The reaction mixture was stirred at RT for 4 hours until the reaction was complete. The suspension was concentrated and then diluted with $H_2O$ (20 mL) and extracted with EA (20 mL×2), the combined organic phases were washed with brine (20 ml), dried over anhydrous $Na_2SO_4$ and concentrated to dryness. The crude product was purified by Prep-HPLC to give 9.2 (200 mg, yield: 54%) as yellow oil.

2. The Synthesis of Intermediate 9.4

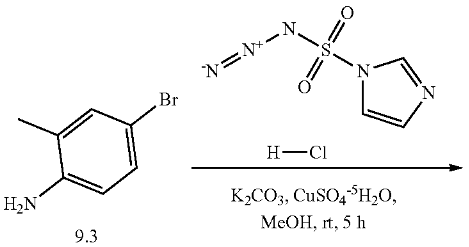

9.3

-continued

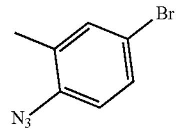

9.4

To a solution of 9.3 (185 mg, 1.0 mmol) in MeOH (10 mL) was added $K_2CO_3$ (276 mg, 2.0 mmol), $CuSO_4.5H_2O$ (50 mg, 0.2 mmol) and imidazole-1-sulfonyl azide hydrochloride (208 mg, 1 mmol). The reaction was stirred at room temperature for 5 h. After the consumption of starting material (by LCMS), water (10 mL) was added, extracted with ethyl acetate (10 mL×3), the combined organic phases were washed with brine (20 ml), dried over anhydrous $Na_2SO_4$ and concentrated to dryness. The crude product was purified by Prep-HPLC to get 9.4 (100 mg, 47% yield) as colorless oil.

3. The Synthesis of Intermediate 9.5

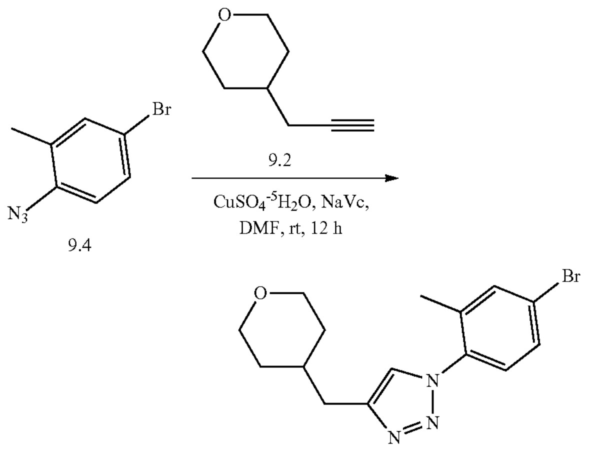

9.4

9.5

To a stirred solution of 9.4 (100 mg, 0.47 mmol) in DMF (5 mL) was added 9.2 (124 mg, 1.0 mmol), $CuSO_4.5H_2O$ (50 mg, 0.20 mmol), sodium ascorbate (40 mg, 0.20 mmol) at RT. Stirred at RT for 12 h. After the consumption of starting material (by LCMS), water (10 mL) was added, extracted with ethyl acetate (10 mL×3), washed with water (10 mL×3), dried and concentrated. The crude product was purified by Prep-HPLC to give 9.5 (70 mg, yield: 45%) as yellow oil. LC-MS m/z: 336.0 $[M+H]^+$.

4. The Synthesis of Target I-269

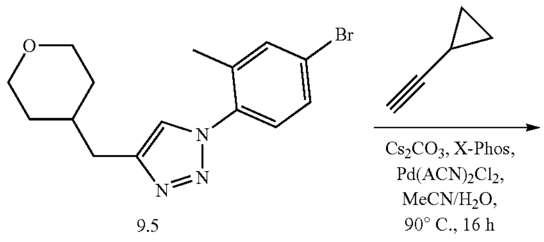

9.5

-continued

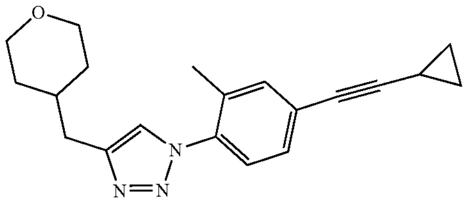

I-269

To a stirred solution of 9.5 (70 mg, 0.21 mmol), ethynylcyclopropane (40 mg, 0.60 mmol), X-Phos (10 mg) and $Cs_2CO_3$ (324 mg, 1.0 mmol) in CAN/$H_2O$ (10 mL/1 mL) was added $PdCl_2(ACN)_2$ (10 mg). The reaction mixture was stirred at 90° C. for 16 hours until the reaction was complete. The suspension was diluted with $H_2O$ (10 mL) and extracted with EA (10 mL×2) and concentrated. The crude product was purified by Prep-HPLC to give I-269 (28 mg, yield: 42%) as an off-white solid.

Additional exemplary compounds were prepared following methods substantially similar to the method described above and herein. Data for these compounds are provided below.

TABLE 10

Characterization Data for Additional Exemplary Compounds

| Compound No. | Chemical Structure | [M + H] observed | $^1H$ NMR (400 MHz) |
|---|---|---|---|
| I-402 | 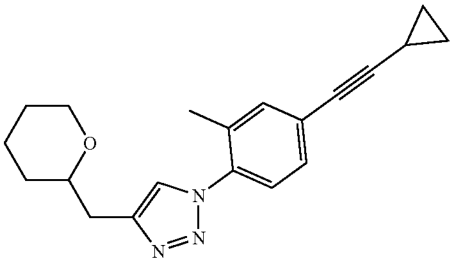 [SMILES: Cc1cc(C#CC2CC2)ccc1-n1cc(CC2CCCCO2)nn1] | 322.1 | $^1H$ NMR (400 MHz, DMSO-$d_6$) δ 8.20 (s, 1H), 7.46 (s, 1H), 7.34-7.38 (m, 2H), 3.85 (dd, J = 14.4 Hz, 1.6 Hz, 1H), 3.52-3.58 (m, 1H), 3.31-3.33 (m, 1H), 2.75-2.87 (m, 2H), 2.12 (s, 3H), 1.75-1.77 (m, 1H), 1.54-1.61 (m, 2H), 1.40-1.47 (m, 3H), 1.20-1.26 (m, 1H), 0.89-0.94 (m, 2H), 0.74-0.78 (m, 2H). |
| I-269 | 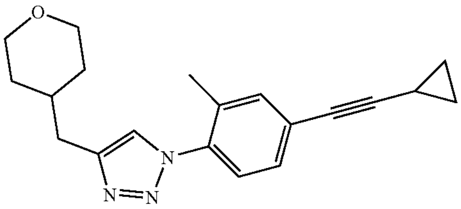 [SMILES: Cc1cc(C#CC2CC2)ccc1-n1cc(CC2CCOCC2)nn1] | 322.3 | $^1H$ NMR (400 MHz, DMSO-$d_6$) δ 8.24 (s, 1H), 7.47 (s, 1H), 7.35-7.39 (m, 2H), 3.82-3.85 (m, 2H), 3.27 (t, J = 11.2 Hz, 2H), 2.65 (d, J ? 6.8 Hz, 2H), 2.12 (s, 3H), 1.84-1.89 (m, 1H), 1.57-1.60 (m, 3H), 1.19-1.29 (m, 2H), 0.90-0.94 (m, 2H), 0.75-0.78 (m, 2H). |
| I-294 | 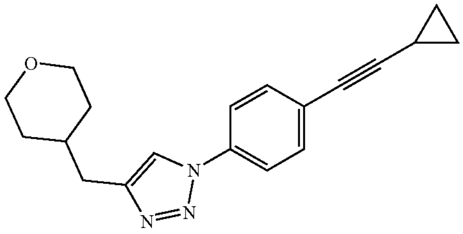 | 308.2 | $^1H$ NMR (400 MHz, $CDCl_3$) δ 7.71 (s, 1H), 7.63 (d, J = 8.8 Hz, 2H), 7.49 (d, J = 8.8 Hz, 2H), 3.99-3.91 (m, 2H), 3.37 (td, J = 11.9, 2.1 Hz, 2H), 2.72 (d, J = 7.1 Hz, 2H), 1.96 (ttt, J = 10.9, 7.1, 3.8 Hz, 1H), 1.68-1.61 (m, 2H), 1.51-1.31 (m, 3H), 0.93-0.86 (m, 2H), 0.85-0.80 (m, 2H). |
| I-295 | 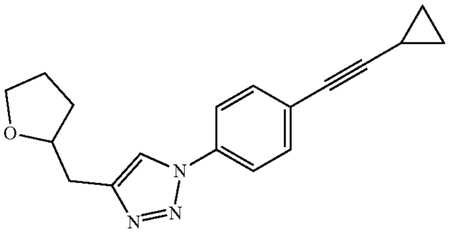 [SMILES: C(#CC1CC1)c1ccc(-n2cc(CC3CCCO3)nn2)cc1] | 294.2 | $^1H$ NMR (400 MHz, $CDCl_3$) δ 7.86 (s, 1H), 7.65 (d, J = 8.8 Hz, 2H), 7.49 (d, J = 8.8 Hz, 2H), 4.18 (qd, J = 7.3, 5.0 Hz, 1H), 3.89 (dt, J = 8.3, 6.8 Hz, 1H), 3.76 (dt, J = 8.3, 6.9 Hz, 1H), 3.06 (dd, J = 14.9, 4.9 Hz, 2H), 2.98 (ddd, J = 15.0, 7.2, 0.6 Hz, 2H), 2.12-2.00 (m, 1H), 1.96-1.84 (m, 2H), 1.71-1.57 (m, 1H), 1.46 (tt, J = 8.2, 5.1 Hz, 1H), 0.93-0.85 (m, 2H), 0.85-0.80 (m, 2H). |

Example 10: Synthesis of I-333

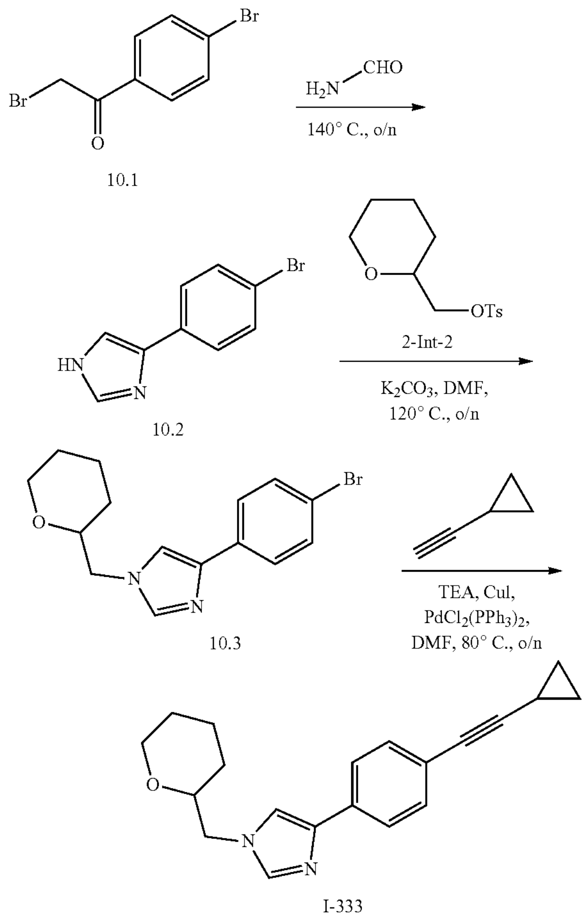

10.1

10.2

10.3

I-333

1. The Synthesis of Intermediate 10.2

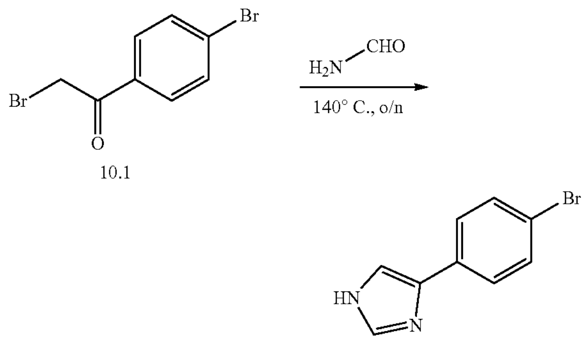

10.1

10.2

A solution of 10.1 (5.00 g, 18.11 mmol) in formamide (30 mL) was stirred at 140° C. for 8 hours until the reaction was complete (by LCMS). The suspension was diluted with $NaHCO_3$ (aq.), extracted with EtOAc (30 mL×3), washed with NaCl (aq.) and concentrated, the crude product was purified by flash column chromatography (silica gel, PE/EA=1:1) to give 10.2 (3.5 g, 87% yield) as a yellow solid. LC-MS m/z: 223.1 $[M+H]^+$.

2. The Synthesis of Intermediate 10.3

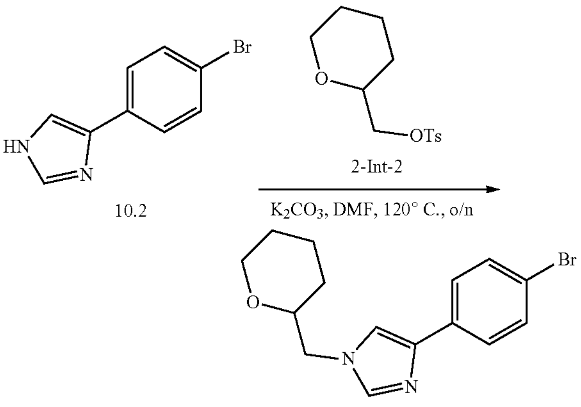

10.2

10.3

To a stirred solution of 10.2 (500 mg, 2.25 mmol) and 2-Int-2 (730 mg, 2.71 mmol) in DMF (6 mL) was added $K_2CO_3$ (466 mg, 3.37 mmol). The reaction mixture was stirred at 120° C. overnight until the reaction was complete. The suspension was diluted with $H_2O$ (10 mL), extracted with EtOAc (15 mL×3). The organic layers were washed by NaCl (aq.) and concentrated. The residue was purified flash column chromatography (silica gel, PE/EA=1:2) to give 10.3 (600 mg, 69% yield) as yellow oil. $^1H$ NMR (400 MHz, $CDCl_3$) δ 7.54 (d, J 8.4 Hz, 2H), 7.42 (s, 1H), 7.37 (d, J 8.4 Hz, 2H), 7.14 (s, 1H), 3.86-3.89 (m, 1H), 3.79-3.81 (m, 2H), 3.38-3.44 (m, 1H), 3.24-3.30 (m, 1H), 1.73-1.77 (m, 1H), 1.33-1.46 (m, 4H), 1.09-1.18 (m, 1H).

3. The Synthesis of I-333

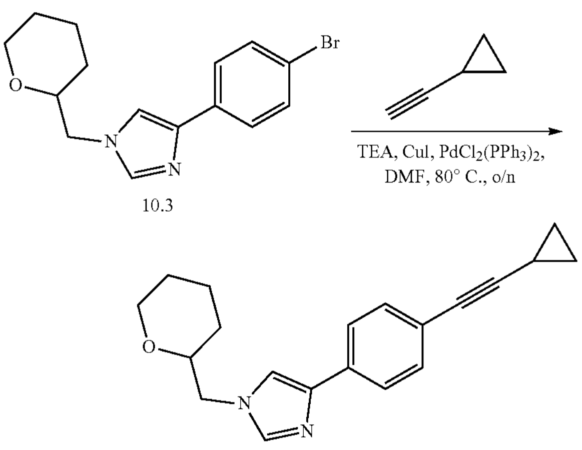

10.3

I-333

To a stirred solution of 10.3 (300 mg, 0.94 mmol), ethynylcyclopropane (186 mg, 2.81 mmol), CuI (18 mg, 0.09 mmol) and TEA (0.39 mL, 2.81 mmol) in DMF (10 mL) was added $Pd(PPh_3)_2Cl_2$ (66 mg, 0.09 mmol). The reaction mixture was stirred at 80° C. overnight under $N_2$ until the reaction was complete. The suspension was diluted with $H_2O$ (25 mL), extracted with EtOAc (25 mL×3). The organic layers were washed by NaC (aq.) and concentrated. The residue was purified by Prep-HPLC to give I-333 (60 mg, 210 yield) as pink oil.

Additional exemplary compounds were prepared following methods substantially similar to the method described above and herein. Data for these compounds are provided below.

TABLE 11

Characterization Data for Additional Exemplary Compounds

| Compound No. | Chemical Structure | [M + H] observed | $^1$H NMR (400 MHz) |
| --- | --- | --- | --- |
| I-333 | 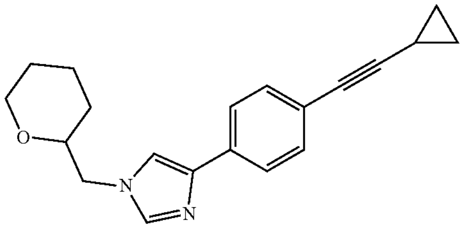 [SMILES: C(#CC1CC1)c1ccc(-c2cn(CC3CCCCO3)cn2)cc1] | 307.1 | $^1$H NMR (400 MHz, DMSO-$d_6$) δ 7.68 (d, J = 8.4 Hz, 2H), 7.63 (s, 2H), 7.31 (d, J = 8.0 Hz, 2H), 3.85-4.05 (m 3H), 3.52-3.56 (m, 1H), 3.28-3.31 (m, 1H), 1.77-1.79 (m, 1H), 1.38-1.58 (m, 5H), 1.12-1.18 (m, 1H), 0.85-0.90 (m, 2H), 0.70-0.74 (m, 2H). |
| I-334 | 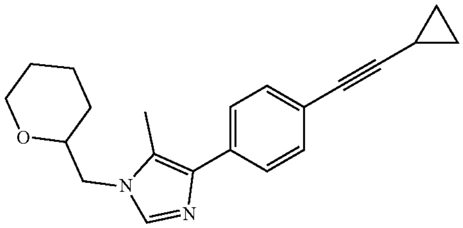 | 321.4 | $^1$H NMR (400 MHz, $CDCl_3$): δ 7.58 (d, J = 8.4 Hz, 2H), 7.51 (s, 1H), 7.40 (d, J = 8.4 Hz, 2H), 3.94-4.00 (m, 1H), 3.81-3.92 (m, 2H), 3.47-3.52 (m, 1H), 3.33-3.40 (m, 1H), 2.38 (s, 3H), 1.83-1.91 (m, 1H), 1.42-1.62 (m, 5H), 1.22-1.35 (m, 1H), 0.78-0.90 (m, 4H). |
| I-335 | 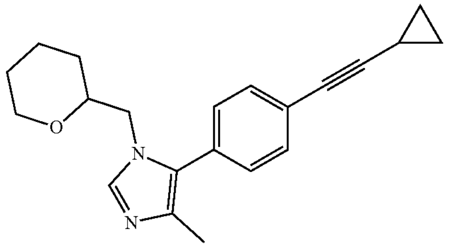 [SMILES: Cc1ncn(CC2CCCCO2)c1-c1ccc(C#CC2CC2)cc1] | 321.4 | $^1$H NMR (400 MHz, $CDCl_3$): δ 7.57 (s, 1H), 7.44 (d, J = 8.0 Hz, 2H), 7.18 (d, J = 8.0 Hz, 2H), 3.89-3.96 (m, 1H), 3.73-3.86 (m, 2H), 3.25-3.32 (m, 2H), 2.18 (s, 3H), 1.75-1.79 (m, 1H), 1.27-1.54 (m, 5H), 1.02-1.12 (m, 1H), 0.80-0.93 (m, 4H). |
| I-339 | 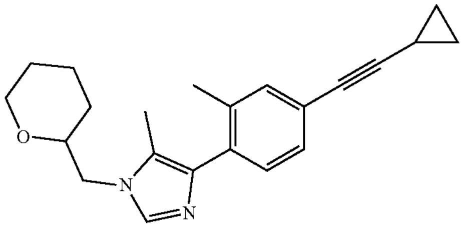 | 335.2 | $^1$H NMR (400 MHz, DMSO-$d_6$) δ 7.57 (s, 1H), 7.23 (s, 1H), 7.16 (d, J = 8.0 Hz, 1H), 7.10 (d, J = 8.0 Hz, 1H), 3.86-3.98 (m, 3H), 3.49-3.56 (m, 1H), 3.29-3.37 (m, 1H), 2.22 (s, 3H), 2.10 (s, 3H), 1.78-1.80 (m, 1H), 1.40-1.61 (m, 5H), 1.16-1.23 (m, 1H), 0.85-0.91 (m, 2H), 0.69-0.75 (m, 2H). |
| I-341 | 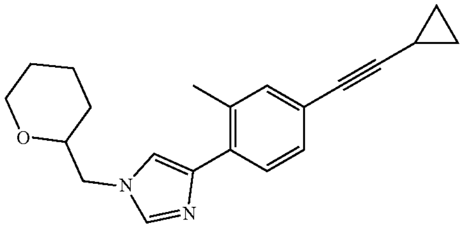 [SMILES: Cc1cc(C#CC2CC2)ccc1-c1cn(CC2CCCCO2)cn1] | 321.3 | $^1$H NMR (400 MHz, DMSO-$d_6$): δ 7.79 (d, J = 8.4 Hz, 1H), 7.66 (s, 1H), 7.43 (s, 1H), 7.22 (s, 1H), 7.18 (dd, J = 8.4 Hz, 1.2 Hz, 1H), 4.05 (dd, J = 14.4 Hz, 4.0 Hz, 1H), 3.97 (dd, J = 14.4 Hz, 7.6 Hz, 1H), 3.84-3.90 (m, 1H), 3.54-3.58 (m, 1H), 3.28-3.34 (m, 1H), 2.40 (s, 3H), 1.77-1.79 (m, 1H), 1.37-1.58 (m, 5H), 1.13-1.19 (m, 1H), 0.85-0.90 (m, 2H), 0.70-0.74 (m, 2H). |
| I-340 | 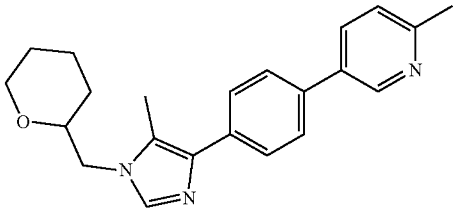 [SMILES: Cc1ccc(-c2ccc(-c3ncn(CC4CCCCO4)c3C)cc2)cn1] | 348.3 | $^1$H NMR (400 MHz, $CDCl_3$) δ 8.78 (d, J = 2.0 Hz, 1H), 7.82 (dd, J = 8.0 Hz, 2.4 Hz, 1H), 7.77 (d, J = 8.4 Hz, 2H), 7.61 (d, J = 8.4 Hz, 2H), 7.56 (s, 1H), 7.22 (d, J = 8.0 Hz, 1H), 3.84-4.02 (m, 3H), 3.49-3.56 (m, 1H), 3.36-3.42 (m, 1H), 2.60 (s, 3H), 2.43 (s, 3H), 1.85-1.93 (m, 1H), 1.45-1.65 (m, 4H), 1.24-1.36 (m, 1H). |

Example 11: Synthesis of I-338

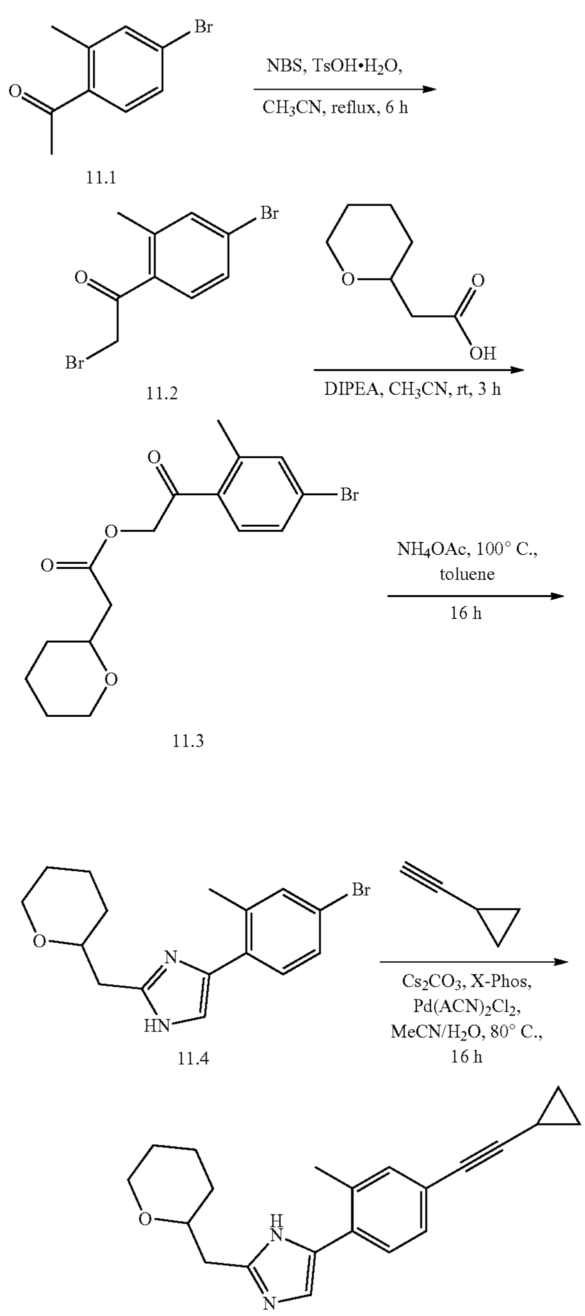

11.1

11.2

11.3

11.4

I-338

1. The Synthesis of Intermediate 11.2

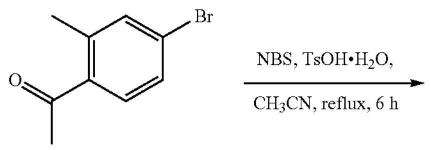

11.1

-continued

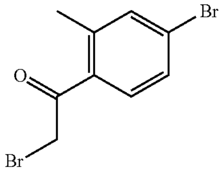

11.2

To a mixture of compound 11.1 (636 mg, 3.0 mmol) and NBS (587 mg, 3.3 mmol) in $CH_3CN$ (20 mL) was added $TsOH.H_2O$ (570 mg, 3.0 mmol) and heated to reflux for 6 h. The reaction mixture was cooled down to RT and then diluted with $H_2O$ (40 mL) and extracted with EtOAc (25 mL×3). The combined organic phases were washed with brine (20 ml), dried over anhydrous $Na_2SO_4$ and concentrated to dryness. The crude product was purified by column chromatography (petroleum/ethyl acetate=10/1) to give 11.2 (770 mg, yield: 88%) as a white solid. $^1H$ NMR (400 MHz, DMSO-$d_6$) δ 7.81 (d, J 8.4 Hz, 1H), 7.62 (s, 1H), 7.57 (dd, J 1.6 Hz, 8.4 Hz, 1H), 4.86 (s, 2H), 2.39 (s, 3H).

2. The Synthesis of Intermediate 11.3

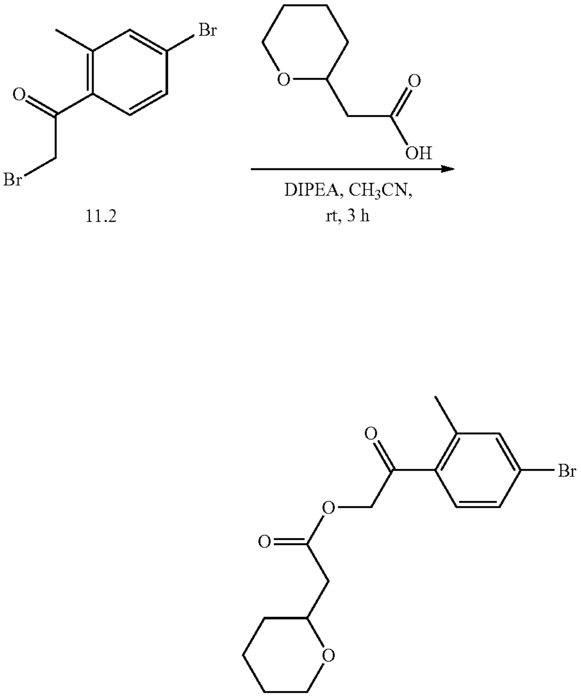

11.2

11.3

To a mixture of compound 11.2 (580 mg, 2.0 mmol) and 2-(tetrahydro-2H-pyran-2-yl)acetic acid (288 mg, 2.0 mmol) in $CH_3CN$ (20 mL) was added DIPEA (774 mg, 6.0 mmol) and the reaction mixture was stirred at room temperature for 3 h. The reaction mixture was diluted with $H_2O$ (40 mL) and extracted with EtOAc (25 mL×3). The combined organic phases were washed with brine (20 ml), dried over anhydrous $Na_2SO_4$ and concentrated to dryness. The crude product was purified by column chromatography (petroleum/ethyl acetate=6/1) to give 11.3 (600 mg, yield: 85%) as yellow oil. LC-MS m/z: 355.1 $[M+H]^+$.

3. The Synthesis of Intermediate 11.4

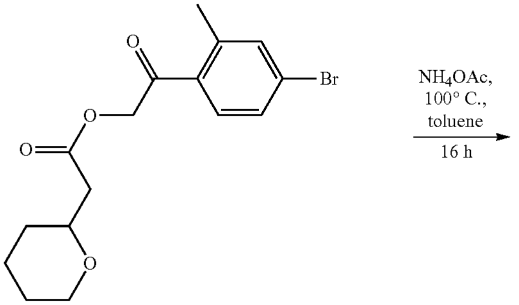

11.3

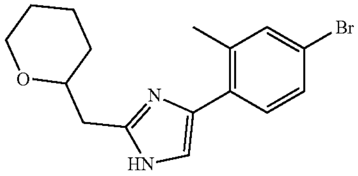

11.4

A mixture of 11.3 (300 mg, 0.9 mmol) and $NH_4OAc$ (776 mg, 12.7 mmol) in toluene (15 mL) was heated to 100° C. for 16 h. The mixture was concentrated and purified by column chromatography (petroleum/ethyl acetate=5/1, 3/1) to give 11.4 (110 mg, yield: 39%) as a yellow solid. LC-MS m/z: 335.0 $[M+H]^+$.

4. The Synthesis of I-338

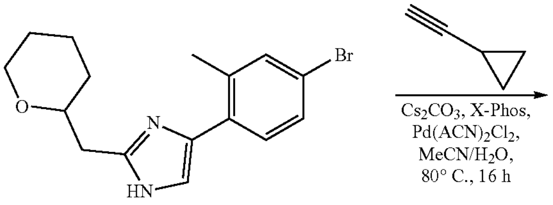

11.4

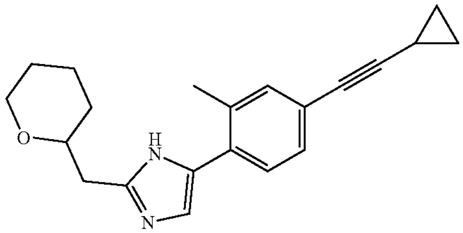

I-338

A solution of 11.4 (110 mg, 0.3 mmol), ethynylcyclopropane (119 mg, 2.0 mmol), X-phos (15 mg, 0.03 mmol), Bis(acetonitrile)dichloropalladium(II) (8 mg, 0.03 mmol) and cesium carbonate (213 mg, 0.7 mmol) in MeCN (6 mL) and $H_2O$ (2 mL), the reaction mixture was heated to 80° C. for 16 h and cooled down to room temperature, extracted with EtOAc (10 mL×3). The organic phase was concentrated and purified by column chromatography (petroleum/ethyl acetate=3/1) then Prep-HPLC to give I-338 (15 mg, yield: 14%) as a gray solid.

Additional exemplary compounds were prepared following methods substantially similar to the method described above and herein. Data for these compounds are provided below.

TABLE 12

Characterization Data for Additional Exemplary Compounds

| Compound No. | Chemical Structure | [M + H] observed | $^1H$ NMR (400 MHz) |
|---|---|---|---|
| I-336 | 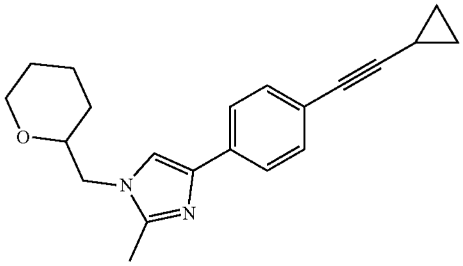 [SMILES: Cc1nc(-c2ccc(C#CC3CC3)cc2)cn1CC1CCCCO1] | 321.3 | $^1H$ NMR (400 MHz, DMSO-$d_6$) δ 7.64 (d, J = 8.0 Hz, 2H), 7.51 (s, 1H), 7.30 (d, J = 8.0 Hz, 2H), 3.84-3.95 (m, 3H), 3.49-3.57 (m, 1H), 3.27-3.33 (m, 1H), 3.23 (s, 3H), 1.74-1.83 (m, 1H), 1.50-1.61 (m, 2H), 1.45 (s 3H), 1.23-1.77 (m, 1H), 0.88 (d, J = 5.2 Hz, 2H), 0.72 (d, J = 2.0 Hz, 2H). |

TABLE 12-continued
| Compound No. | Chemical Structure | [M + H] observed | $^1$H NMR (400 MHz) |
|---|---|---|---|
| I-337 | 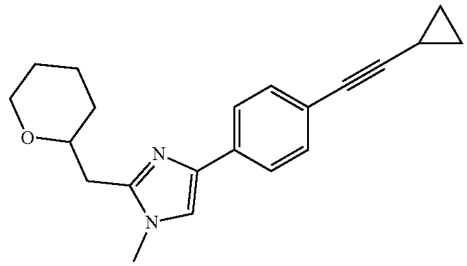 [SMILES: Cn1cc(-c2ccc(C#CC3CC3)cc2)nc1CC1CCCCO1] | 321.4 | $^1$H NMR (400 MHz, DMSO-$d_6$) δ 7.63 (d, J = 8.4 Hz, 2H), 7.51 (s, 1H), 7.29 (d, J = 8.4 Hz, 2H), 3.81-3.84 (m, 1H), 3.61-3.62 (m, 1H), 3.59 (s, 3H), 3.28-3.21 (m, 1H), 3.75-3.79 (m, 2H), 1.73-1.78 (m, 1H), 1.65-1.68 (m, 1H), 1.51-1.54 (m, 1H), 1.43-1.44 (m, 3H), 1.24-1.31 (m, 1H), 0.85-0.90 (m, 2H) , 0.70-0.74 (m, 2H). |
| I-338 | 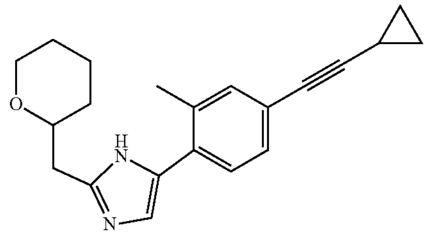 [SMILES: Cc1cc(C#CC2CC2)ccc1-c1cnc(CC2CCCCO2)[nH]1] | 321.0 | $^1$H NMR (400 MHz, DMSO-$d_6$) δ 11.95 (br, 1H), 7.73 (d, J = 5.2 Hz, 1H), 7.21 (s, 1H), 7.16-7.19 (m, 2H), 3.82-3.86 (m, 1H), 3.59-3.65 (m, 1H), 3.29-3.33 (m, 1H), 2.69-2.82 (m, 2H), 2.38 (m, 3H), 1.71-1.81 (m, 1H), 1.59-1.62 (m, 1H), 1.50-1.56 (m, 1H), 1.40-1.46 (m, 3H) , 1.21-1.26 (m, 1H), 0.85-0.90 (m, 2H), 0.70-0.73 (m, 2H). |
Characterization Data for Additional Exemplary Compounds
Example 12: Synthesis of I-316
Synthetic Sechme of I-316
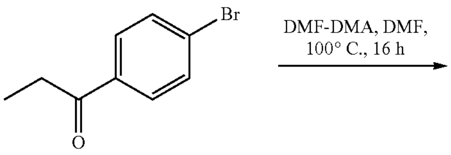
12.1
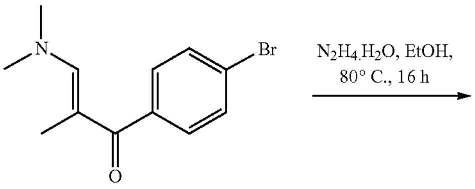
12.2
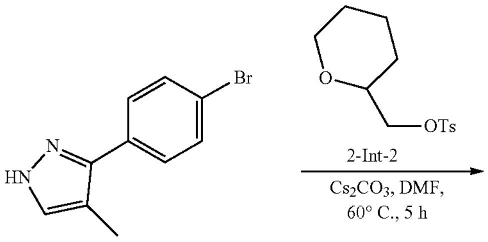
12.3
-continued
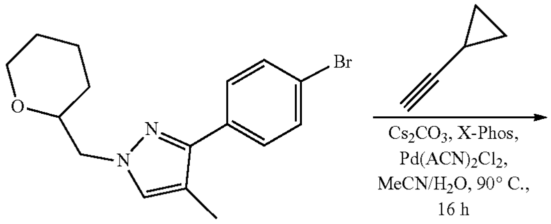
12.4
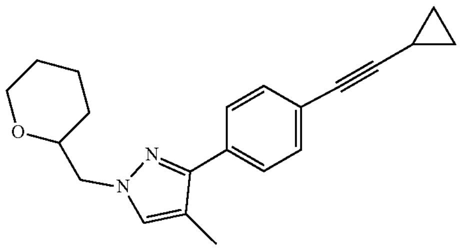
I-316
1. The Synthesis of Intermediate 12.2
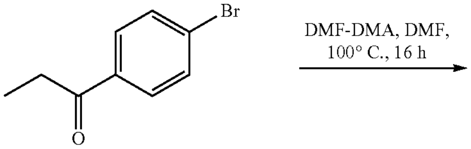
12.1

-continued

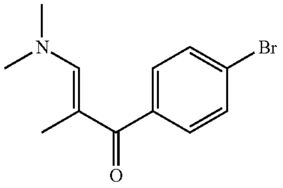

12.2

To a solution of 12.1 (852 mg, 4.0 mmol) in DMF (10 mL) was added DMF-DMA (952 mg, 8.0 mmol) and stirred at 100° C. for 16 h. The reaction mixture was diluted with $H_2O$ (40 mL) and extracted with EtOAc (25 mL×3). The combined organics phase was washed with brine (20 ml), dried over anhydrous $Na_2SO_4$ and concentrated to dryness to give 12.2 (800 mg, yield: 75%) as a yellow solid. LC-MS m/z: 267.8 $[M+H]^+$ 2. The Synthesis of Intermediate 12.3

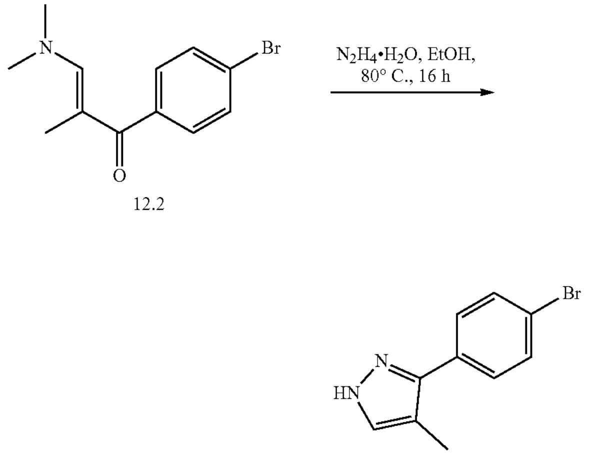

12.2

12.3

To a solution of 12.2 (800 mg, 2.99 mmol) in EtOH (10 mL) was added $N_2H4.H_2O$ (746 mg, 14.93 mmol) and stirred at 80° C. for 16 h. The reaction mixture was diluted with $H_2O$ (30 mL) and extracted with EtOAc (25 mL×3). The combined organics phase were washed with brine (20 ml), dried over $Na_2SO_4$ and concentrated to dryness. The residue was purified by column chromatography (ethyl acetate/petroleum ether=1/1) to give 12.3 (660 mg, 94% yield) as a yellow solid. LC-MS m/z: 236.9 $[M+H]^+$ 3. The Synthesis of Intermediate 12.4

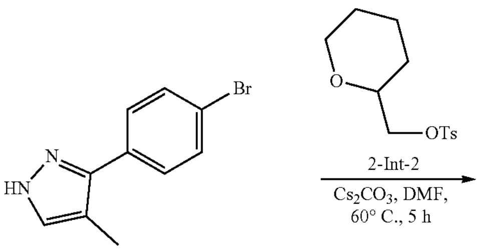

12.3

-continued

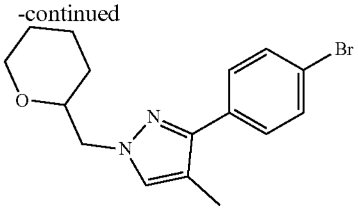

12.4

To a mixture of 12.3 (501 mg, 2.1 mmol) and $Cs_2CO_3$ (1374 mg, 4.2 mmol) in DMF (15 mL) was added 2-Int-2 (573 mg, 2.1 mmol). The reaction mixture was stirred at 60° C. for 5 h then diluted with $H_2O$ (30 mL) and extracted with EtOAc (25 mL×3). The combined organic phases were washed with brine (20 ml), dried over $Na_2SO_4$ and concentrated to dryness. The residue was purified by column chromatography (ethyl acetate/petroleum ether=1/3) to give 12.4 (500 mg, 71% yield) as colorless oil. LC-MS m/z: 334.9 $[M+H]^+$.

4. The Synthesis of I-316

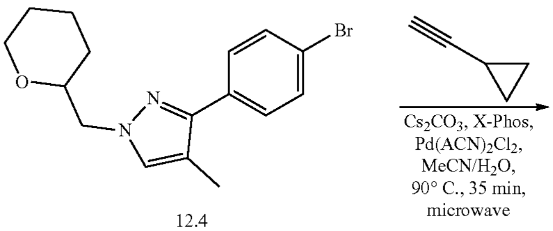

12.4

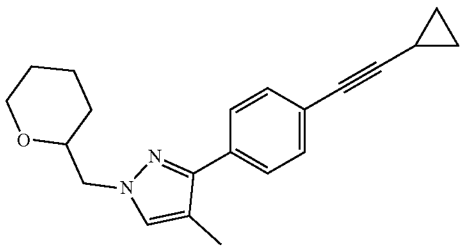

I-316

To a mixture of 12.4 (200 mg, 0.6 mmol), $Cs_2CO_3$ (585 mg, 1.8 mmol), X-phos (28 mg, 0.06 mmol) and $Pd(ACN)_2Cl_2$ (15 mg, 0.06 mmol) in $MeCN/H_2O$ (3/1, 4 mL) was added ethynylcyclopropane (237 mg, 3.6 mmol). The reaction mixture was stirred at 90° C. for 35 min under microwave irradiation conditions. The reaction mixture was diluted with $H_2O$ (10 mL) and extracted with EtOAc (10 mL×3). The combined organic phases were washed with brine (10 ml), dried over $Na_2SO_4$ and concentrated to dryness. The residue was purified by Prep-HPLC to give I-316 (70 mg, 36% yield) as a grey solid.

Additional exemplary compounds were prepared following methods substantially similar to the method described above and herein. Data for these compounds are provided below.

TABLE 13

Characterization Data for Additional Exemplary Compounds

| Compound No. | Chemical Structure | [M + 1] observed | $^1$H NMR (400 MHz) |
|---|---|---|---|
| I-321 | 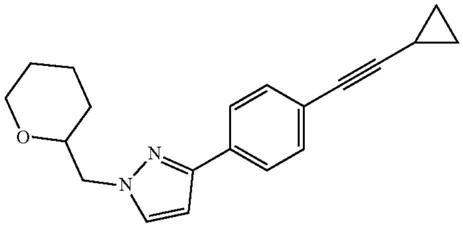 [SMILES: C(#CC1CC1)c1ccc(-c2ccn(CC3CCCCO3)n2)cc1] | 307.1 | $^1$H NMR (400 MHz, DMSO-$d_6$) δ 7.71-7.7.74 (m, 3H), 7.37 (d, J = 8.4Hz, 2H), 6.69 (d, J = 2.0 Hz, 1H), 4.13 (d, J = 6.0 Hz, 2H), 3.83-3.85 (m, 1H), 3.64-3.70 (m, 1H), 3.26-3.32 (m, 1H), 1.76-1.78 (m, 1H), 1.51-1.58 (m, 2H), 1.38-1.49 (m, 3H), 1.15-1.24 (m, 1H), 0.86-0.91 (m, 2H) , 0.72-0.76 (m, 2H). |
| I-316 | 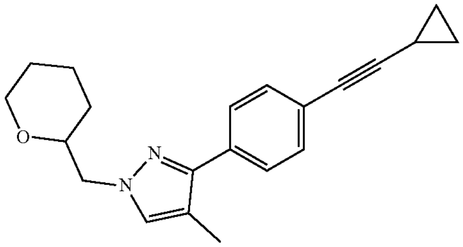 [SMILES: Cc1cn(CC2CCCCO2)nc1-c1ccc(C#CC2CC2)cc1] | 321.1 | $^1$H NMR (400 MHz, DMSO-$d_6$) δ 7.61 (d, J = 8.4 Hz, 2H), 7.52 (s, 1H), 7.38 (d, J = 8.4 Hz, 2H), 4.05 (d, J = 5.6 Hz, 2H), 3.84 (d, J = 10.8 Hz, 1H), 3.62-3.65 (m, 1H), 3.26-3.32 (m, 1H), 2.17 (s, 3H), 1.76-1.78 (m, 1H), 1.52-1.57 (m, 2H), 1.42-1.47 (m, 3H), 1.16-1.19 (m, 1H), 0.87-0.97 (m, 2H) , 0.72-0.76 (m, 2H). |
| I-324 | 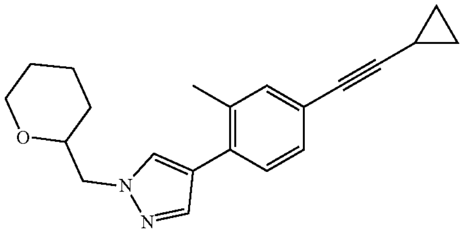 [SMILES: Cc1cc(C#CC2CC2)ccc1-c1cnn(CC2CCCCO2)c1] | 321.3 | $^1$H NMR (400 MHz, DMSO-$d_6$) δ 7.95 (s, 1H), 7.70 (s, 1H), 7.34 (d, J = 8.4 Hz, 1H), 7.25 (s, 1H), 7.17 (d, J = 9.6 Hz, 1H), 4.13 (d, J = 6.0 Hz, 2H), 3.85 (d, J = 11.2 Hz, 1H), 3.65-3.71 (m, 1H), 3.28-3.31 (m, 1H), 2.33 (s, 3H), 1.77 (s, 1H), 1.39-1.57 (m, 5H) , 1.17-1.23 (m, 1H), 0.85-0.90 (m, 2H), 0.70-0.74 (m, 2H). |
| I-325 | 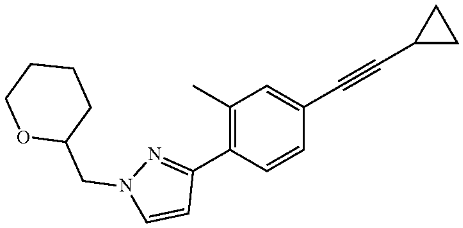 [SMILES: Cc1cc(C#CC2CC2)ccc1-c1ccn(CC2CCCCO2)n1] | 321.4 | $^1$H NMR (400 MHz, DMSO-$d_6$): δ 7.72 (d, J = 2.4 Hz, 1H), 7.52 (d, J = 8.0 Hz, 1H), 7.25 (s, 1H), 7.20 (d, J = 8.0 Hz, 1H), 6.50 (d, J = 2.4 Hz, 1H), 4.14 (d, J = 2.0 Hz, 2H), 3.85 (d, J = 11.2 Hz, 1H), 3.65-3.71 (m, 1H), 3.28-3.31 (m, 1H), 2.42 (s, 3H), 1.76-1.78 (m, 1H), 1.39-1.56 (m, 5H), 1.14-1.23 (m, 1H), 0.82-0.91 (m, 2H), 0.71-0.75 (m, 2H). |
| I-326 | 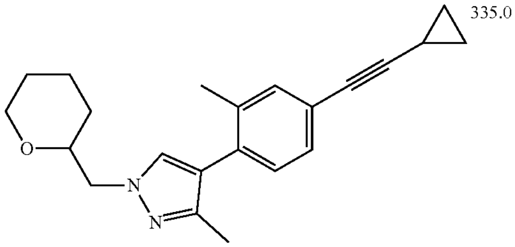 | 335.0 | $^1$H NMR (400 MHz, DMSO-$d_6$) δ 7.65 (s, 1H), 7.26 (s, 1H), 7.17 (dd, J = 1.2 Hz, 8.0 Hz, 1H), 7.10 (d, J = 8.0 Hz, 1H), 4.01-4.04 (m, 2H), 3.85 (d, J = 11.2 Hz, 1H), 3.63-3.66 (m, 1H), 3.28-3.32 (m, 1H), 2.16 (s, 3H), 2.06 (s, 3H), 1.76-1.78 (m, 1H), 1.42-1.55 (m, 5H), 1.15-1.18 (m, 1H), 0.85-0.90 (m, 2H), 0.70-0.73 (m, 2H). |
| I-327 | 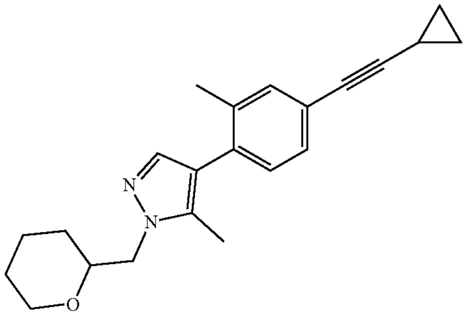 [SMILES: Cc1cc(C#CC2CC2)ccc1-c1cnn(CC2CCCCO2)c1C] | 335.0 | $^1$H NMR (400 MHz, DMSO-$d_6$) δ 7.41 (s, 1H), 7.27 (s, 1H), 7.18 (d, J = 7.2 Hz, 1H), 7.06 (d, J = 8.0 Hz, 1H), 4.00-4.11 (m, 2H), 3.84 (d, J = 10.4 Hz, 1H), 3.68 (br, 1H), 3.22 (m, 1H), 2.14 (s, 3H), 2.13 (s, 3H), 1.77-1.78 (m, 1H), 1.45-1.57 (m, 5H), 1.18-1.19 (m, 1H), 0.87-0.89 (m, 2H), 0.72-0.73 (m, 2H). |

TABLE 13-continued

Characterization Data for Additional Exemplary Compounds

| Compound No. | Chemical Structure | [M + 1] observed | $^1$H NMR (400 MHz) |
|---|---|---|---|
| I-317 | 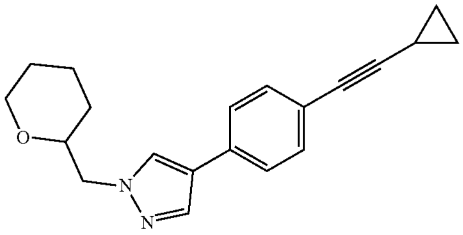 [SMILES: C(#CC1CC1)c1ccc(-c2cnn(CC3CCCCO3)c2)cc1] | 307.1 | $^1$H NMR ($CDCl_3$, 400 MHz) δ 7.75 (d, J = 0.7 Hz, 1H), 7.71 (d, J = 0.7 Hz, 1H), 7.39 (d, J = 8.6 Hz, 2H), 7.35 (d, J = 8.6 Hz, 2H), 4.23-4.14 (m, 1H), 4.14-4.07 (m, 1H), 4.03-3.91 (m, 1H), 3.70 (dddd, J = 11.2, 6.6, 4.4, 2.1 Hz, 1H), 3.40 (td, J = 11.4, 3.1 Hz, 1H), 1.90-1.82 (m, 1H), 1.60-1.41 (m, 5H), 1.34-1.19 (m, 1H), 0.94-0.94 (m, 2H), 0.84-0.77 (m, 2H) |
| I-318 | 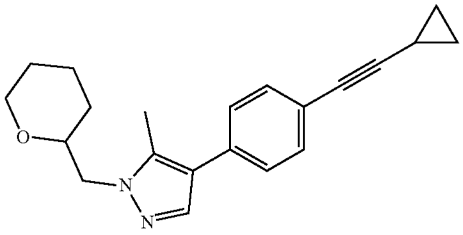 | 321.2 | $^1$H NMR ($CDCl_3$, 400 MHz) δ 7.56 (s, 1H), 7.37 (d, J = 8.5 Hz, 2H), 7.26 (d, J = 8.6 Hz, 2H), 4.12 (dd, J = 14.2, 7.3 Hz, 1H), 4.03 (dd, J = 14.2, 4.4 Hz, 1H), 3.98-3.86 (m, 1H), 3.73 (dddd, J = 11.6, 7.0, 4.4, 2.1 Hz, 1H), 3.36 (td, J = 11.6, 2.7, 1H), 2.38 (s, 3H), 1.94-1.80 (m, 1H), 1.66-1.40 (m, 5H), 1.38-1.22 (m, 1H), 0.93-0.83 (m, 2H), 0.83-0.75 (m, 2H) |
| I-319 | 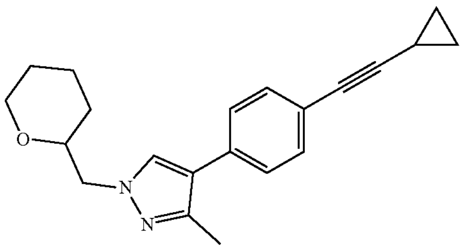 [SMILES: Cc1nn(CC2CCCCO2)cc1-c1ccc(C#CC2CC2)cc1] | 321.2 | $^1$H NMR ($CDCl_3$, 400 MHz) δ 7.53 (s, 1H), 7.37 (d, J = 8.5 Hz, 2H), 7.30 (d, J = 8.5 Hz, 2H), 4.08-4.04 (m, 2H), 3.99-3.92 (m, 1H), 3.69 (dddd, J = 11.3, 6.8, 5.0, 2.1 Hz, 2H), 3.40 (td, J = 11.4, 3.0 Hz, 1H), 2.39 (s, 3H), 1.95-1.79 (m, 1H), 1.77-1.40 (m, 5H), 1.37-1.19 (m, 1H), 0.96-0.84 (m, 2H), 0.84-0.77 (m, 2H) |
| I-320 | 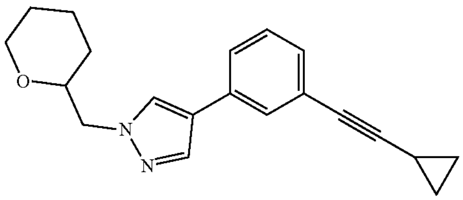 [SMILES: C(#CC1CC1)c1cccc(-c2cnn(CC3CCCCO3)c2)c1] | 307.1 | %). $^1$H NMR ($CDCl_3$, 400 MHz) δ 7.75 (s, 1H), 7.71 (s, 1H), 7.51 (t, J = 1.3 Hz, 1H), 7.37 (dt, J = 7.4, 1.7 Hz, 1H), 7.28-7.13 (m, 2H), 4.14 (dd, J = 5.5, 2.6 Hz, 2H), 4.06-3.91 (m, 1H), 3.69 (dtt, J = 8.4, 4.6, 2.0 Hz, 1H), 3.40 (td, J = 11.3, 3.0 Hz, 1H), 1.89-1.81 (m, 1H), 1.66-1.40 (m, 5H), 1.38-1.16 (m, 1H), 0.92-0.84 (m, 2H), 0.84-0.75 (m, 2H) |
| I-322 | 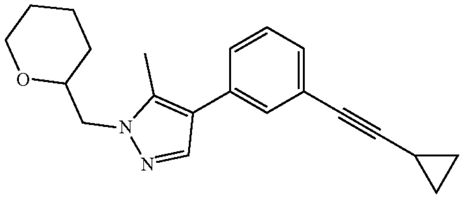 [SMILES: Cc1c(-c2cccc(C#CC3CC3)c2)cnn1CC1CCCCO1] | 321.2 | $^1$H NMR ($CDCl_3$, 400 MHz) δ 7.55 (s, 1H), 7.37 (dt, J = 2.3, 1.0 Hz, 1H), 7.30-7.21 (m, 3H), 4.12 (dd, J = 14.2, 7.3 Hz, 1H), 4.03 (dd, J = 14.2, 4.5 Hz, 1H), 3.93 (ddd, 11.5, 4.0, 2.0 Hz, 1H), 3.73 (dddd, 11.5, 7.0, 4.5, 2.1 Hz, 1H), 3.36 (td, J = 11.6, 2.7 Hz, 1H), 2.37 (s, 3H), 1.92-1.77 (m, 1H), 1.64-1.39 (m, 5H), 1.37-1.23 (m, 1H), 0.90-0.83 (m, 2H), 0.83-0.76 (m, 2H) |
| I-323 | 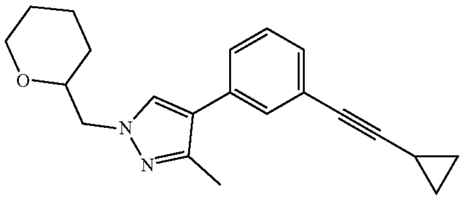 [SMILES: Cc1nn(CC2CCCCO2)cc1-c1cccc(C#CC2CC2)c1] | 321.2 | $^1$H NMR ($CDCl_3$, 400 MHz) δ 7.52 (s, 1H), 7.47-7.39 (m, 1H), 7.33-7.20 (m, 3H), 4.05 (d, J = 5.5 Hz, 2H), 3.97 (dt, J = 11.6, 2.1 Hz, 1H), 3.69 (dtd, J = 11.3, 5.8, 2.0 Hz, 1H), 3.40 (td, J = 11.3, 2.9 Hz, 1H), 2.39 (s, 3H), 1.95-1.81 (m, 1H), 1.66-1.39 (m, 5H), 1.33-1.20 (m, 1H), 0.98-0.82 (m, 2H), 0.82-0.78 (m, 2H) |

Example 13: Synthesis of I-299

Synthetic Scheme of I-299

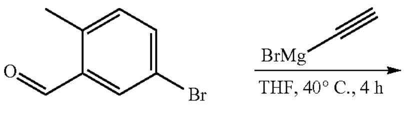

13.1

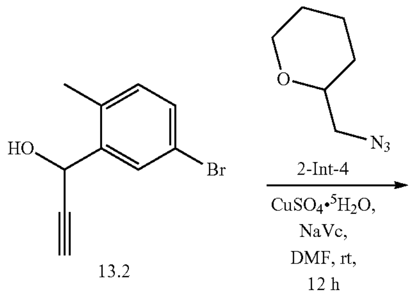

13.2

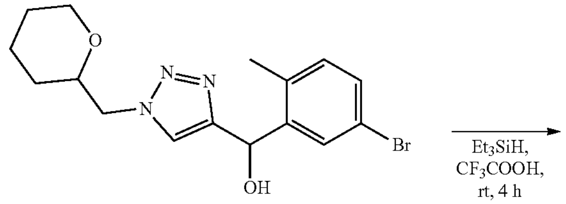

13.3

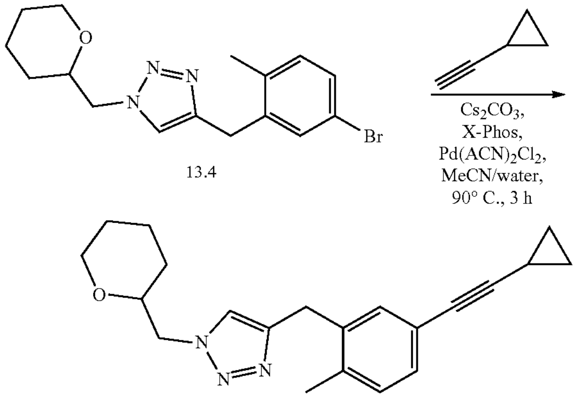

13.4

I-299

1. The Synthesis of Intermediate 13.2

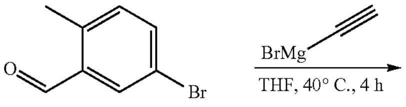

13.1

-continued

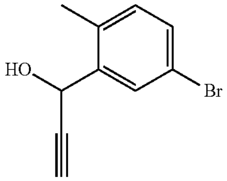

13.2

To a stirred solution of 13.1 (1.20 g, 6.03 mmol) in THF (15 mL) was added ethynylmagnesium bromide (15 mL, 7.50 mmol) at 0° C. The reaction mixture was stirred at 40° C. for 4 hours until the reaction was complete, $NH_4Cl$ (10 mL) was added and the mixture stirred at room temperature for 30 min. The reaction mixture was diluted with $H_2O$ (20 mL) and extracted with DCM (20 mL×2). The combined organic phases were washed with brine (10 ml), dried over anhydrous $Na_2SO_4$ and concentrated to dryness. The crude product was purified by Prep-HPLC to give 13.2 (1.0 g, yield: 74%) as brown oil.

2. The Synthesis of Intermediate 13.3

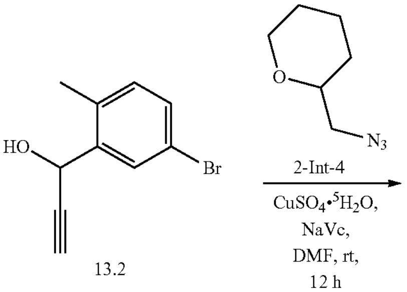

13.2

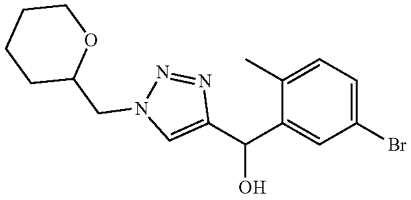

13.3

To a stirred solution of 13.2 (500 mg, 2.22 mmol) and 2-Int-4 (313 mg, 2.22 mmol) in DMF (15 mL), a solution of $CuSO_4$. $H_2O$ (111 mg, 0.44 mmol) in water (1 mL) and sodium ascorbate (176 mg, 0.88 mmol) in water (1 mL) was added. The reaction mixture was stirred at room temperature for 12 hours until the reaction was complete. The reaction mixture was diluted with $H_2O$ (20 mL) and extracted with DCM (20 mL×2). The combined organics phase were washed with brine (10 ml), dried over anhydrous $Na_2SO_4$ and concentrated to dryness. The crude product was purified by Prep-HPLC to give 13.3 (600 mg, yield: 73%) as a yellow solid.

3. The Synthesis of Intermediate 13.4

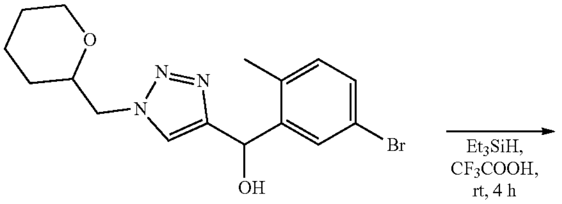

13.3

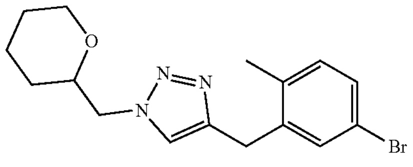

13.4

To a stirred solution of 13.3 (400 mg, 1.09 mmol) in $CF_3COOH$ (5 mL) was added triethylsilane (380 mg, 3.27 mmol). The reaction mixture was stirred at RT for 4 hours until the reaction was complete. The reaction mixture was diluted with $H_2O$ (10 mL) and extracted with DCM (20 mL×2). The combined organics phase were washed with brine (10 ml), dried over $Na_2SO_4$ and concentrated to dryness. The crude product was purified by Prep-HPLC to give 13.4 (300 mg, yield: 78%) as yellow oil.

4. The Synthesis of Target I-299

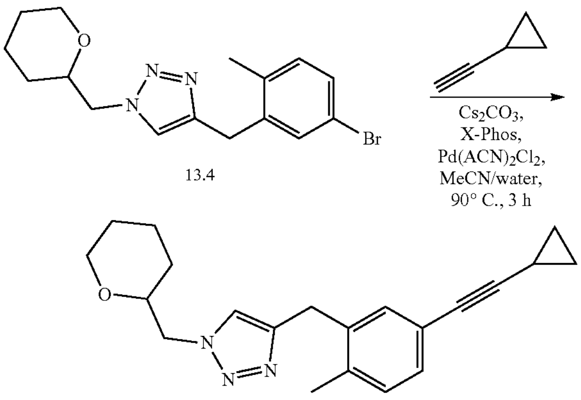

13.4

I-299

To a stirred solution of 13.4 (200 mg, 0.57 mmol) in $CH_3CN$ (10 mL) and $H_2O$ (1 mL) was added $Cs_2CO_3$ (371 mg, 1.14 mmol), $PdCl_2(CH_3CN)_2$ (20 mg) and X-phos (40 mg), and then backfill with argon (three times). Add ethynylcyclopropane (75 mg, 1.14 mmol) to the resulting suspension and the reaction mixture was stirred at 90° C. for 3 hours until the reaction was complete. The reaction mixture was diluted with $H_2O$ (10 mL) and extracted with DCM (10 mL×2). The combined organic phases were washed with brine (10 ml), dried over $Na_2SO_4$ and concentrated to dryness. The crude product was purified by Prep-HPLC to give 1-299 (75 mg, yield: 39%) as a white solid.

Additional exemplary compounds were prepared following methods substantially similar to the method described above and herein. Data for these compounds are provided below.

TABLE 14

Characterization Data for Additional Exemplary Compounds

| Compound No. | Chemical Structure | [M + H] observed | $^1$H NMR (400 MHz) |
|---|---|---|---|
| I-299 | 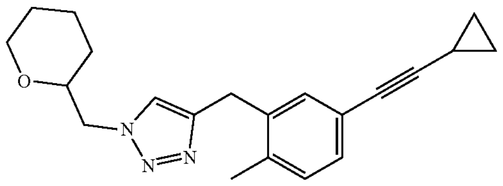 [SMILES: Cc1ccc(C#CC2CC2)cc1Cc1cn(CC2CCCCO2)nn1] | 336.3 | $^1$H NMR (400 MHz, DMSO-$d_6$) δ 7.71 (s, 1H), 7.03-7.18 (m, 3H), 4.26-4.37 (m, 2H), 3.92 (s, 2H), 3.81-3.84 (m, 1H), 3.62-3.65 (m, 1H), 3.25-3.31 (m, 1H), 2.26 (s, 3H), 1.75-1.78 (m, 1H), 1.40-1.58 (m, 5H), 1.10-1.14 (m, 1H), 0.82-0.87 (m, 2H), 0.66-0.70 (m, 2H). |
| I-300 | 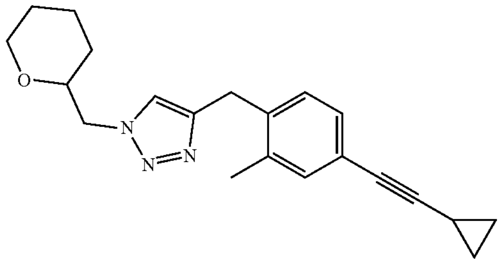 [SMILES: Cc1cc(C#CC2CC2)ccc1Cc1cn(CC2CCCCO2)nn1] | 336.1 | $^1$H NMR (400 MHz, DMSO-$d_6$) δ 7.67 (s, 1H), 7.16 (s, 1H), 7.06-7.12 (m, 2H), 4.24-4.36 (m, 2H), 3.94 (s, 2H), 3.80-3.83 (m, 1H), 3.60-3.64 (m, 1H), 3.24-3.30 (m, 1H), 2.23 (s, 3H), 1.75-1.77 (m, 1H), 1.38-1.57 (m, 5H), 1.10-1.13 (m, 1H), 0.84-0.88 (m, 2H), 0.67-0.71 (m, 1H). |

TABLE 14-continued

Characterization Data for Additional Exemplary Compounds

| Compound No. | Chemical Structure | [M + H] observed | $^1$H NMR (400 MHz) |
|---|---|---|---|
| I-298 | 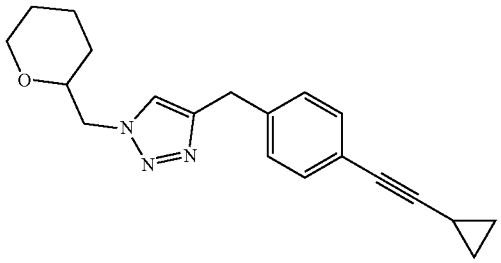 [SMILES: C(#CC1CC1)c1ccc(Cc2cn(CC3CCCCO3)nn2)cc1] | 322.2 | $^1$H NMR (400 MHz, $CDCl_3$) δ 7.30 (d, J = 8.5 Hz, 3H), 7.16 (d, J = 8.3 Hz, 2H), 4.37 (dd, J = 14.1, 3.2 Hz, 1H), 4.20 (dd, J = 14.2, 7.5 Hz, 1H), 4.05 (s, 2H), 3.94 (dd, J = 10.3, 2.2 Hz, 1H), 3.68-3.58 (m, 1H), 3.35 (ddd, J = 11.5, 8.6, 6.7 Hz, 1H), 1.90- 1.80 (m, 1H), 1.65-1.56 (m, 1H), 1.53-1.47 (m, 3H), 1.43 (tt, J = 8.2, 5.1 Hz, 1H), 1.28-1.13 (m, 1H), 0.89-0.82 (m, 2H), 0.81-0.76 (m, 2H). |
| I-313 | 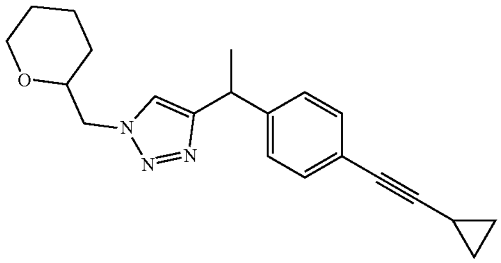 [SMILES: CC(c1ccc(C#CC2CC2)cc1)c1cn(CC2CCCCO2)nn1] | 336.1 | $^1$H NMR (400 MHz, $CDCl_3$) δ 7.30 (d, J = 8.3 Hz, 2H), 7.25 (d, J = 5.0 Hz, 1H), 7.17 (d, J = 8.2 Hz, 2H), 4.36 (dt, J = 14.1, 3.3 Hz, 1H), 4.29- 4.13 (m, 2H), 4.01-3.89 (m, 1H), 3.70-3.57 (m, 1H), 3.42-3.29 (m, 1H), 1.87-1.81 (m, 1H), 1.65 (dd, J = 7.2, 3.2 Hz, 3H), 1.63-1.56 (m, 1H), 1.53-1.47 (m, 3H), 1.47-1.38 (m, 1H), 1.26-1.12 (m, 1H), 0.88-0.82 (m, 2H), 0.82 -0.74 (m, 2H) |
| I-301 | 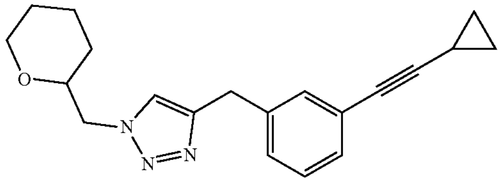 [SMILES: C(#CC1CC1)c1cccc(Cc2cn(CC3CCCCO3)nn2)c1] | 322.2 | $^1$H NMR (400 MHz, $CDCl_3$) δ 7.30 (s, 1H), 7.27 (d, J = 1.5 Hz, 1H), 7.22 (dt, J = 7.2, 1.8 Hz, 1H), 7.21-7.13 (m, 2H), 4.37 (dd, J = 14.1, 3.2 Hz, 1H), 4.20 (dd, J = 14.1, 7.5 Hz, 1H), 4.03 (d, J = 1.3 Hz, 2H), 3.97-3.90 (m, 1H), 3.68-3.58 (m, 1H), 3.36 (ddd, J = 14.4, 7.6, 4.4 Hz, 1H), 1.89-1.79 (m, 1H), 1.65-1.57 (m, 1H), 1.54-1.46 (m, 3H), 1.46-1.37 (m, 1H), 1.25-1.14 (m, 1H), 0.88-0.81 (m, 2H), 0.80 -0.75 (m, 2H). |
| I-302 | 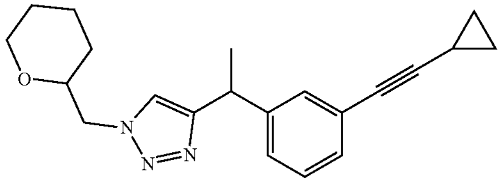 [SMILES: CC(c1cccc(C#CC2CC2)c1)c1cn(CC2CCCCO2)nn1] | 336.2 | :$^1$H NMR ($CDCl_3$, 400 MHz) δ 7.31-7.25 (m, 2H), 7.23-7.15 (m, 3H), 4.41-4.33 (m, 1H), 4.25-4.15 (m, 2H), 3.98-3.90 (m, 1H), 3.68-3.59 (m, 1H), 3.40-3.31 (m, 1H), 1.87-1.80 (m, 1H), 1.68-1.64 (2 X d, J = 4.0 Hz, 3H), 1.63-1.56 (m, 1H), 1.55-1.38 (m, 4H), 1.26-1.12 (m, 1H), 0.88-0.80 (m, 2H), 0.80-0.75 (m, 2H). |

Example 14: Synthesis of I-10

Synthetic Scheme I-10

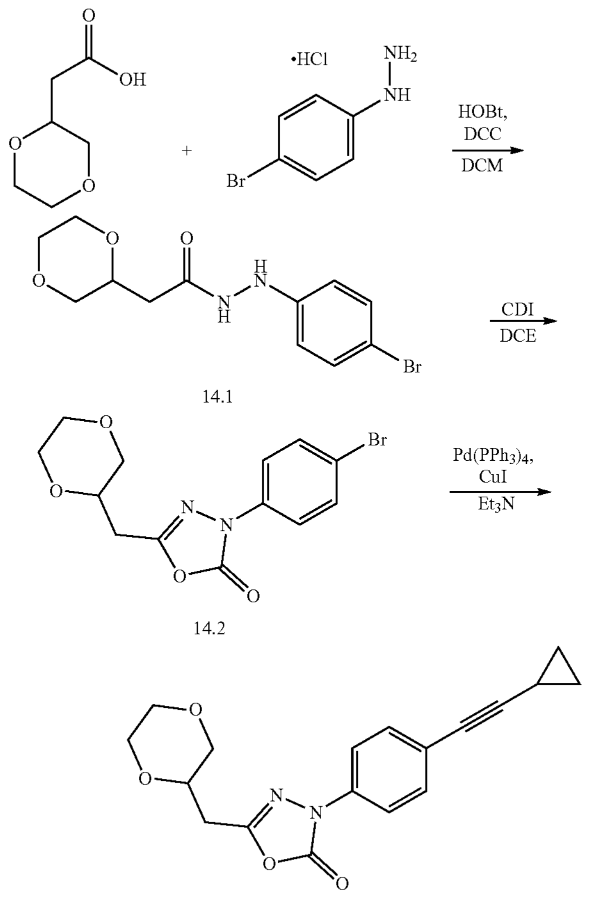

14.1

14.2

I-10

1. The Synthesis of Intermediate N'-(4-bromophenyl)-2-(1,4-dioxan-2-yl)acetohydrazide (14.1)

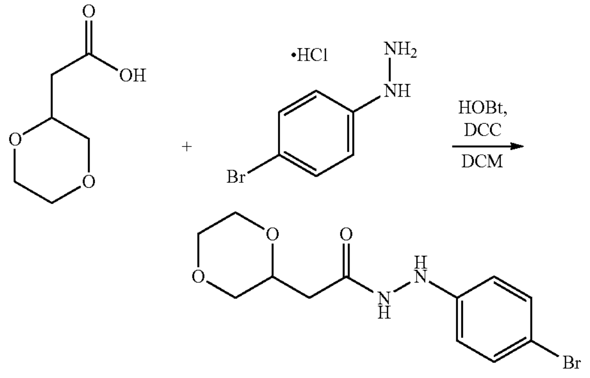

14.1

At 0° C., (4-bromophenyl)hydrazine hydrochloride (224 mg, 1.0 mmol, 1.0 eq.) was added to a mixture of 2-(1,4-dioxan-2-yl)acetic acid (146 mg, 1.0 mmol, 1.0 eq.), hydroxybenzotriazole (189 mg, 1.4 mmol, 1.4 eq.) and N,N'-dicyclohexylcarbodiimide (248 mg, 1.2 mmol, 1.2 eq.) in DCM (5 mL). The mixture was allowed to warm up to RT and stirred for 48 hours at RT. DCM and 1N HCl were added and the organic layer was separated, washed twice with 1N HCl then brine, dried over $Na_2SO_4$, filtered and concentrated. The residue was purified on silica gel chromatography (30-100% EtOAc in hexanes) to afford N-(4-bromophenyl)-2-(1,4-dioxan-2-yl)acetohydrazide (14.1) as a beige solid (84 mg, 27%).

2. The Synthesis of Intermediate 5-((1,4-dioxan-2-yl)methyl)-3-(4-bromophenyl)-1,3,4-oxadiazol-2(3H)-one (14.2)

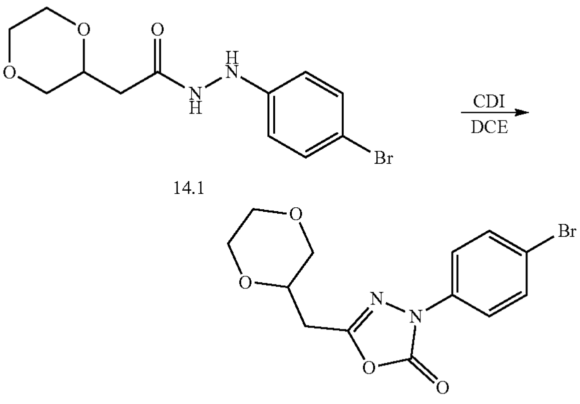

14.1

14.2

1,1'-Carbonyldiimidazole (65 mg, 0.40 mmol, 1.5 eq.) was added to a solution of N-(4-bromophenyl)-2-(1,4-dioxan-2-yl)acetohydrazide (14.1, 84 mg, 0.267 mmol, 1.0 eq.) in DCE (3 mL). The mixture was stirred at 80° C. for 18 hours. Once at RT, the mixture was purified on silica gel chromatography (30-100% EtOAc in hexanes) to afford 5-((1,4-dioxan-2-yl)methyl)-3-(4-bromophenyl)-1,3,4-oxadiazol-2(3H)-one (14.2) as a yellow solid (29 mg, 32%).

3. The Synthesis of 5-((1,4-dioxan-2-yl)methyl)-3-(4-(cyclopropylethynyl)phenyl)-1,3,4-oxadiazol-2(3H)-one (I-10)

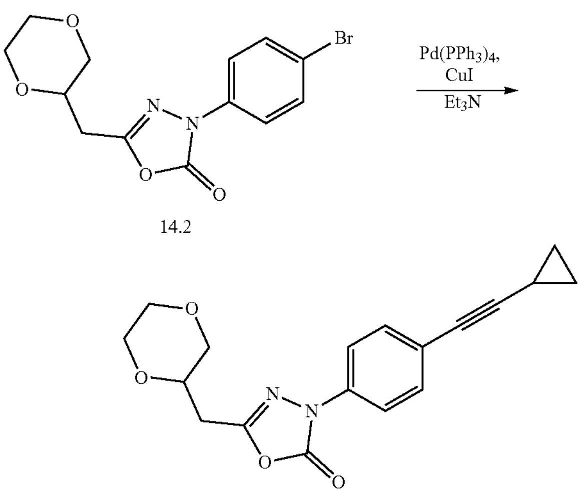

14.2

I-10

Cyclopropylacetylene (104 μL, 1.23 mmol, 10 eq.) was added to a $N_2$ bubbled solution of 5-((1,4-dioxan-2-yl)methyl)-3-(4-bromophenyl)-1,3,4-oxadiazol-2(3H)-one, 14.2 (42 mg, 0.12 mmol, 1.00 eq.), $Pd(PPh_3)_4$ (14 mg, 0.012 mmol, 0.1 eq.) and CuI (5 mg, 0.012 mmol, 0.1 eq.) in $Et_3N$ (1.2 mL). After 5 minutes of $N_2$ bubbling, the reaction was stirred at 90° C. for 24 hours. Once at RT, the mixture was poured in aq. sat. $NH_4Cl$ and MTBE was added. The organic layer was separated, dried over $Na_2SO_4$, filtered and concentrated. The residue was purified on silica gel chromatography (2-10 EtOAc in hexanes) to afford 5-((1,4-dioxan-2-yl)methyl)-3-(4-(cyclopropylethynyl)phenyl)-1,3,4-oxadiazol-2(3N)-one (I-10) as a yellow solid (34 mg, 85% ). Mp 64-70° C.

Additional exemplary compounds were prepared following methods substantially similar to the method described above and herein. Data for these compounds are provided below.

TABLE 15

Characterization Data for Additional Exemplary Compounds

| Compound No. | Chemical Structure | [M + H] observed | $^1$H NMR (400 MHz) |
|---|---|---|---|
| I-10 | 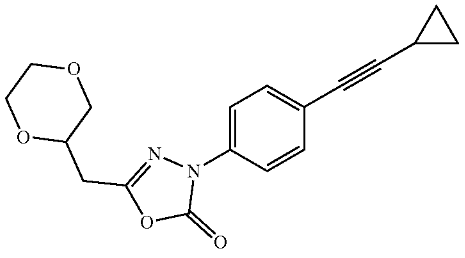 [SMILES: O=c1oc(CC2COCCO2)nn1-c1ccc(C#CC2CC2)cc1] | 327.2 | $^1$H NMR (400 MHz, $CDCl_3$) δ 7.76 (d, J = 8.9 Hz, 2H), 7.42 (d, J = 8.9 Hz, 2H), 4.02 (dtd, J = 10.5, 5.2, 2.6 Hz, 1H), 3.89-3.81 (m, 1H), 3.81-3.76 (m, 1H), 3.75 (d, J = 2.5 Hz, 1H), 3.72 (d, J = 2.3 Hz, 1H), 3.63 (ddd, J = 11.4, 10.4, 3.3 Hz, 1H), 3.41 (dd, J = 11.5, 9.8 Hz, 1H), 2.79 (dd, J = 15.4, 8.0 Hz, 1H), 2.70 (dd, J-15.4, 5.1 Hz, 1H), 1.45 (tt, J = 8.2, 5.1 Hz, 1H), 0.87 (dtd, J = 8.5, 5.6, 2.7 Hz, 2H), 0.81 (tt, J = 5.2, 2.6 Hz, 2H). |
| I-11 | 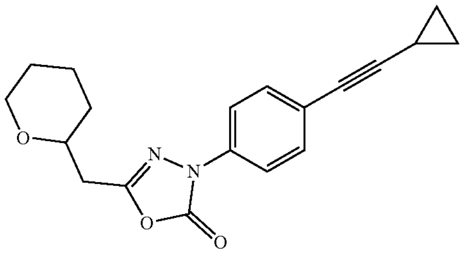 [SMILES: O=c1oc(CC2CCCCO2)nn1-c1ccc(C#CC2CC2)cc1] | 325.2 | $^1$H NMR (400 MHz, $CDCl_3$) δ 7.77 (d, J = 8.9 Hz, 2H), 7.41 (d, J = 8.9 Hz, 2H), 4.01-3.93 (m, 1H), 3.72 (dddd, J = 10.4, 7.9, 4.9, 2.1 Hz, 1H), 3.51-3.36 (m, 1H), 2.81 (dd, J = 15.2, 8.1 Hz, 1H), 2.72 (dd, J = 15.1, 4.9 Hz, 1H), 1.91-1.83 (m, 1H), 1.75-1.67 (m, 1H), 1.62-1.33 (m, 5H), 0.90-0.83 (m, 2H), 0.80 (tt, J = 5.2, 2.4 Hz, 2H). |
| I-12 | 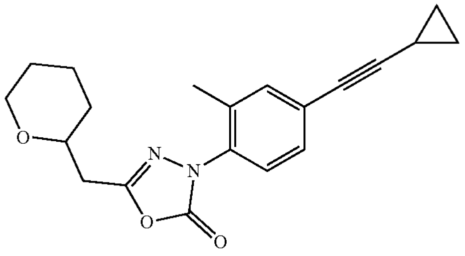 [SMILES: Cc1cc(C#CC2CC2)ccc1-n1nc(CC2CCCCO2)oc1=O] | 339.2 | $^1$H NMR (400 MHz, $CDCl_3$) δ 7.31 (s, 1H), 7.27 (s, 2H), 4.04-3.93 (m, 1H), 3.73 (dddd, J = 10.4, 7.5, 5.2, 2.0 Hz, 1H), 3.55-3.38 (m, 1H), 2.81 (dd, J = 15.1, 7.8 Hz, 1H), 2.72 (dd, J = 15.2, 5.2 Hz, 1H), 2.27 (s, 3H), 1.95-1.80 (m, 1H), 1.71 (d, J = 12.4 Hz, 1H), 1.55 (td, J = 13.2, 12.6, 3.5 Hz, 3H), 1.52-1.32 (m, 2H), 0.88 (dtd, J = 9.2, 6.7, 5.8, 3.1 Hz, 2H), 0.81 (tt, J = 5.4, 2.7 Hz, 2H). |
| I-13 | 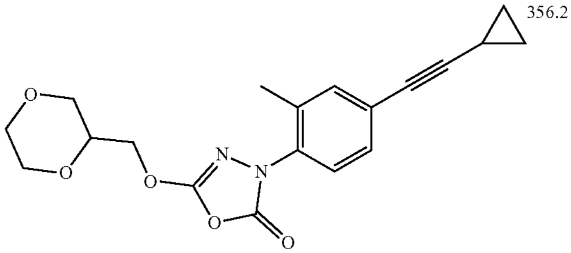 | 356.2 | $^1$H NMR (400 MHz, $CDCl_3$) δ 7.30 (s, 1H), 7.28-7.23 (m, 2H), 4.35-4.25 (m, 2H), 4.05-3.95 (m, 1H), 3.89-3.71 (m, 4H), 3.66 (td, J = 11.2, 3.1 Hz, 1H), 3.50 (dd, J = 11.4, 10.1 Hz, 1H), 2.28 (s, 3H), 1.45 (tt, J = 8.1, 5.1 Hz, 1H), 0.89 (ddt, J = 8.2, 5.7, 3.0 Hz, 2H), 0.81 (tt, J = 5.3, 3.1 Hz, 2H). |

TABLE 15-continued

| Compound No. | Chemical Structure | [M + H] observed | $^1$H NMR (400 MHz) |
|---|---|---|---|
| I-14 | 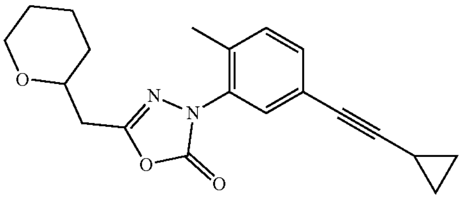 [SMILES: Cc1ccc(C#CC2CC2)cc1-n1nc(CC2CCCCO2)oc1=O] | 339.2 | $^1$H NMR (400 MHz, $CDCl_3$) δ 7.38 (d, J = 1.6 Hz, 1H), 7.29 (dd, J = 7.9, 1.7 Hz, 1H), 7.18 (d, J = 7.9 Hz, 1H), 4.02 -3.95 (m, 1H), 3.72 (dtd, J = 10.0, 5.3, 2.7 Hz, 1H), 3.51-3.41 (m, 1H), 2.80 (dd, J = 15.2, 7.8 Hz, 1H), 2.71 (dd, J = 15.2, 5.3 Hz, 1H), 2.29 (s, 3H), 1.88 (dd, J = 9.1, 3.5 Hz, 1H), 1.71 (d, J = 12.6 Hz, 1H), 1.64-1.47 (m, 3H), 1.46-1.33 (m, 2H), 0.89-0.83 (m, 2H), 0.83-0.75 (m, 2H). |
| I-15 | 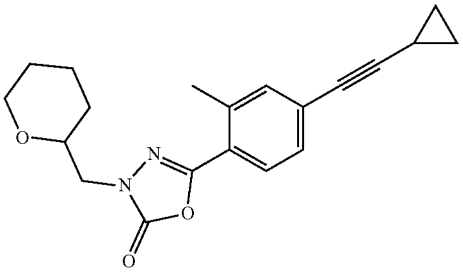 [SMILES: Cc1cc(C#CC2CC2)ccc1-c1nn(CC2CCCCO2)c(=O)o1] | 339.2 | $^1$H NMR (400 MHz, $CDCl_3$) δ 7.69 (d, J = 8.0 Hz, 1H), 7.30-7.24 (m, 2H), 4.03-3.94 (m, 1H), 3.94-3.84 (m, 1H), 3.72 (tdd, J = 11.2, 5.4, 3.1 Hz, 2H), 3.39 (td, J = 11.6, 2.3 Hz, 1H), 2.54 (s, 3H), 1.92-1.83 (m, 1H), 1.66 (d, J = 13.0 Hz, 1H), 1.60-1.43 (m, 4H), 1.43-1.31 (m, 1H), 0.93-0.87 (m, 2H), 0.86-0.79 (m, 2H). |
| I-16 | 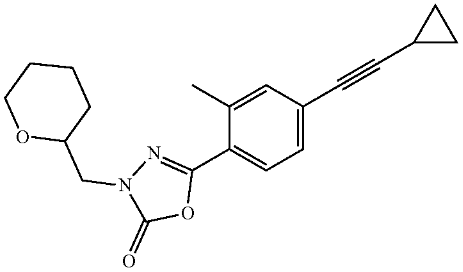 [SMILES: Cc1cc(C#CC2CC2)ccc1-c1nn(CC2CCCCO2)c(=O)o1] | 339.2 | $^1$H NMR (400 MHz, $CDCl_3$) δ 7.82 (d, J = 1.8 Hz, 1H), 7.35 (dd, J = 7.9, 1.8 Hz, 1H), 7.17 (d, J-7.9 Hz, 1H), 4.04 -3.95 (m, 1H), 3.95-3.85 (m, 1H), 3.72 (dddd, J = 12.6, 8.0, 4.2, 2.0 Hz, 2H), 3.39 (td, J = 11.6, 2.3 Hz, 1H), 2.56 (s, 3H), 1.93-1.83 (m, 1H), 1.70 -1.64 (m, 1H), 1.63-1.47 (m, 3H), 1.48-1.30 (m, 2H), 0.91-0.85 (m, 2H), 0.84-0.78 (m, 2H). |
| I-17 | 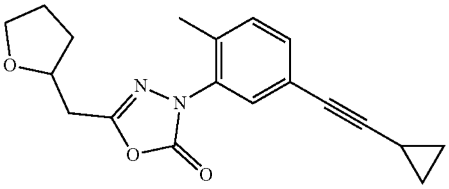 [SMILES: Cc1ccc(C#CC2CC2)cc1-n1nc(CC2CCCO2)oc1=O] | 325.2 | $^1$H NMR (400 MHz, $CDCl_3$) δ 7.37 (d, J = 1.6 Hz, 1H), 7.29 (dd, J = 7.9, 1.7 Hz, 1H), 7.18 (d, J = 7.9 Hz, 1H), 4.32 -4.23 (m, 1H), 3.92 (dt, J = 8.4, 6.8 Hz, 1H), 3.79 (dt, J = 8.4, 7.0 Hz, 1H), 2.86 (dd, J = 15.3, 7.0 Hz, 1H), 2.78 (dd, J = 15.3, 5.9 Hz, 1H), 2.28 (s, 3H), 2.14 (ddd, J = 12.3, 7.8, 6.4 Hz, 1H), 2.01-1.89 (m, 2H), 1.73-1.63 (m, 1H), 1.42 (tt, J = 8.2, 5.1 Hz, 1H), 0.91-0.82 (m, 2H), 0.82-0.72 (m, 2H). |
| I-20 | 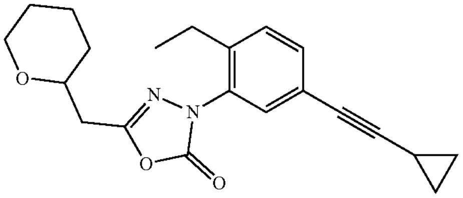 [SMILES: CCc1ccc(C#CC2CC2)cc1-n1nc(CC2CCCCO2)oc1=O] | 353.2 | $^1$H NMR (400 MHz, $CDCl_3$) δ 7.41-7.31 (m, 2H), 7.22 (d, J = 8.5 Hz, 1H), 4.02-3.94 (m, 1H), 3.77-3.66 (m, 1H), 3.45 (td, J = 11.5, 2.8 Hz, 1H), 2.79 (dd, J = 15.2, 7.7 Hz, 1H), 2.71 (dd, J-15.2, 5.3 Hz, 1H), 2.62 (q, J = 7.6 Hz, 2H), 1.94-1.81 (m, 1H), 1.75 -1.66 (m, 1H), 1.65-1.47 (m, 3H), 1.45-1.32 (m, 2H), 1.17 (t, J = 7.6 Hz, 3H), 0.89-0.81 (m, 2H), 0.77 (qd, J = 4.9, 2.1 Hz, 2H). |

TABLE 15-continued

| Characterization Data for Additional Exemplary Compounds | | | |
|---|---|---|---|
| Compound No. | Chemical Structure | [M + H] observed | $^1$H NMR (400 MHz) |
| I-403 | 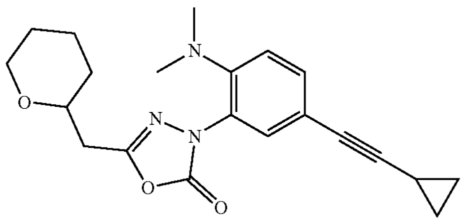 [SMILES: CN(C)c1ccc(C#CC2CC2)cc1-n1nc(CC2CCCCO2)oc1=O] | 368.2 | $^1$H NMR (400 MHz, $CDCl_3$) δ 7.34-7.28 (m, 2H), 6.87 (d, J-9.1 Hz, 1H), 4.04-3.88 (m, 1H), 3.79-3.64 (m, 1H), 3.43 (td, J = 11.5, 2.8 Hz, 1H), 2.80 (dd, J = 15.1, 7.8 Hz, 1H), 2.75-2.69 (m, 7H), 1.94-1.80 (m, 1H), 1.75 -1.64 (m, 1H), 1.62-1.48 (m, 3H), 1.47-1.32 (m, 2H), 0.92-0.79 (m, 2H), 0.79-0.70 (m, 2H) |

Example 15: Synthesis of I-18

Synthetic Scheme of I-18

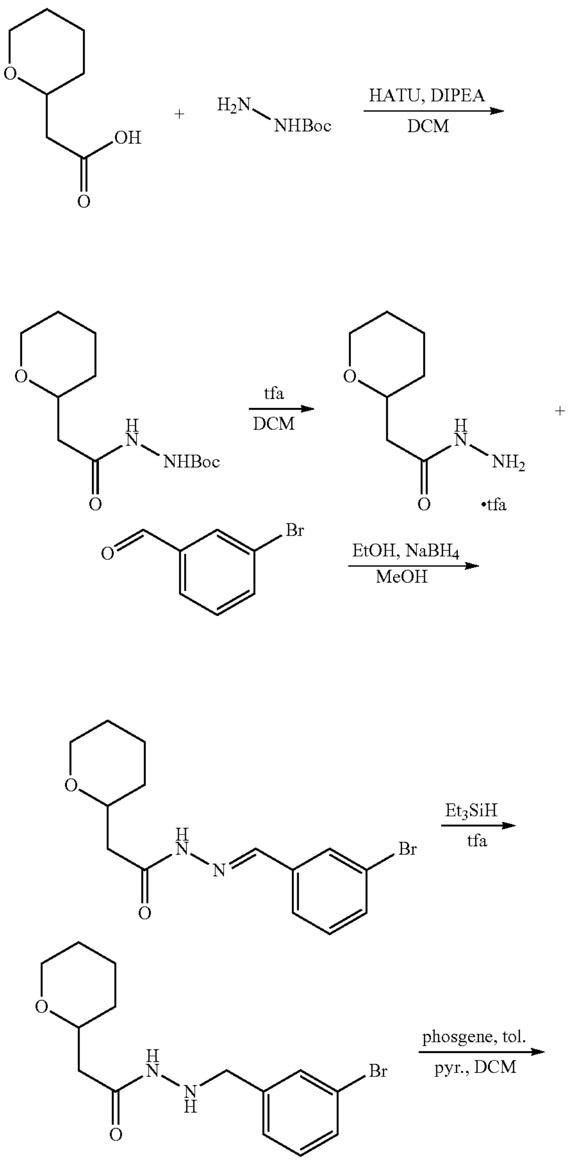

-continued

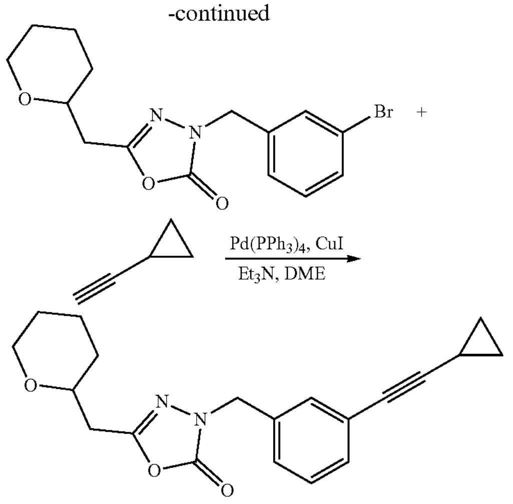

1. the Synthesis of Intermediate tert-butyl 2-(2-(tetrahydro-2H-pyran-2-yl)acetyl)-hydrazine-1-carboxylate

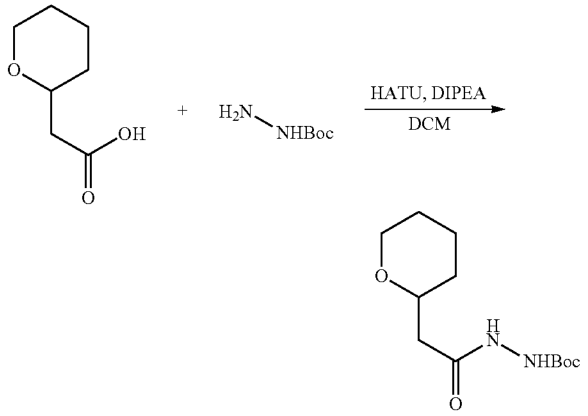

At 0° C., DIPEA (1.81 mL, 10.4 mmol, 3.0 eq.) was added to a mixture of 2-(tetrahydro-2H-pyran-2-yl)acetic acid (500 mg, 3.47 mmol, 1.0 eq.), tert-butyl hydrazinecarboxylate (687 mg, 5.20 mmol, 1.5 eq.) and HATU (1.58 g, 10.4 mmol, 3.0 eq.) in dichloromethane (14 mL). The mixture was stirred at 0° C. for 1 hour, then $H_2O$ and dichloromethane were added. The organic layer was separated, washed with $H_2O$ and brine, dried over $Na_2SO_4$, filtered and concentrated. The residue was purified on silica gel (10-80% EtOAc in hexanes) to afford impure material that was used as is to the next step.

2. The Synthesis of Intermediate 2-(tetrahydro-2H-pyran-2-yl)acetohydrazide, trifluoro-acetic acid salt

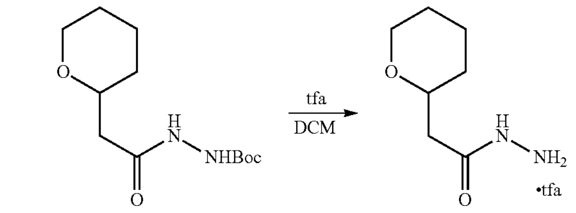 [SMILES: CC(C)(C)OC(=O)NNC(=O)CC1CCCCO1 ; NNC(=O)CC1CCCCO1]

Trifluoroacetic acid (4 mL) was added to a mixture of tert-butyl 2-(2-(tetrahydro-2H-pyran-2-yl)acetyl)hydrazine-1-carboxylate (896 mg, 3.47 mmol, 1.0 eq.) in dichloromethane (10 mL). After 2 hours of stirring at RT, the mixture was concentrated and used as is to the next step.

3. the Synthesis of Intermediate (E,Z)-N'-(3-bromobenzylidene)-2-(tetrahydro-2H-pyran-2-yl)acetohydrazide

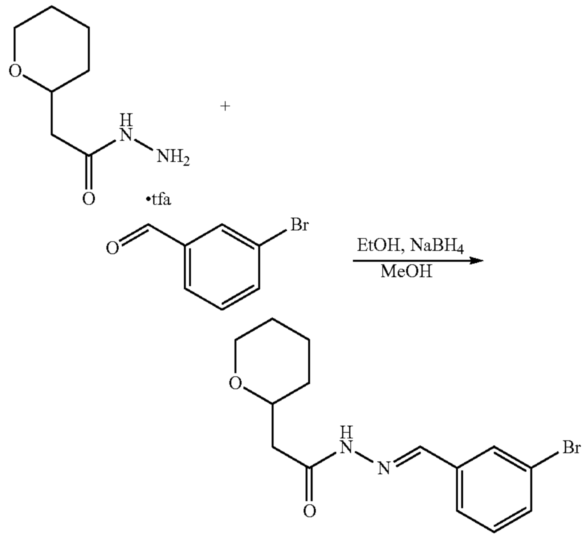

3-Bromobenzaldehyde (0.80 mL, 6.94 mmol, 2.0 eq.) was added to a mixture of 2-(tetrahydro-2H-pyran-2-yl)acetohydrazide trifluoroacetic acid salt (944 mg, 3.47 mmol, 1.0 eq.) in ethanol (7 mL). The mixture was stirred at RT for 4 hours. Methanol was added (7 mL) and the mixture was cooled down to 0° C. Sodium borohydride (394 mg, 10.4 mmol, 3.0 eq.) was added portionwise and the mixture was stirred at RT for 1 hour. The mixture was cooled down to 0° C. and again sodium borohydride (394 mg, 10.4 mmol, 3.0 eq.) was added portionwise. The mixture was allowed to warm up to RT and stirred for 18 hours at RT. The mixture was concentrated and dissolved in dichloromethane, $H_2O$ was added. The organic layer was separated, washed with $H_2O$ and brine, dried over $Na_2SO_4$, filtered and concentrated. The residue was purified on silica gel (10-80% EtOAc in hexanes) to afford (E,Z)-N'-(3-bromobenzylidene)-2-(tetrahydro-2H-pyran-2-yl)acetohydrazide as a white solid (729 mg, 65%).

4. the Synthesis of Intermediate N'-(3-bromobenzyl)-2-(tetrahydro-2H-pyran-2-yl)-acetohydrazide

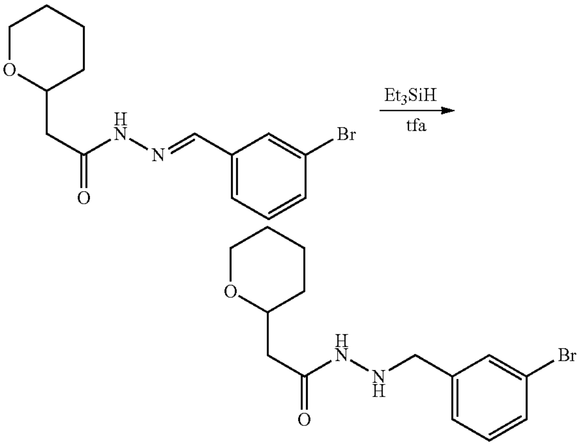

Triethylsilane (0.72 mL, 4.48 mL, 2 eq.) was added dropwise to a mixture of (E,Z)-N'-(3-bromobenzylidene)-2-(tetrahydro-2H-pyran-2-yl)acetohydrazide (729 mg, 2.24 mmol, 1.0 eq.) in trifluoroacetic acid (3.4 mL). After 20 minutes of stirring, the reaction was poured slowly in aqueous saturated $NaHCO_3$ and dichloromethane and MTBE were added. The organic layer was separated, washed with brine, dried over $Na_2SO_4$, filtered and concentrated. The residue was purified on silica gel (30-90% EtOAc in hexanes) to afford N-(3-bromobenzyl)-2-(tetrahydro-2H-pyran-2-yl)acetohydrazide as an off-white solid (325 mg, 44%).

5. The Synthesis of Intermediate 3-(3-bromobenzyl)-5-((tetrahydro-2H-pyran-2-yl)methyl)-1,3,4-oxadiazol-2(3H)-one

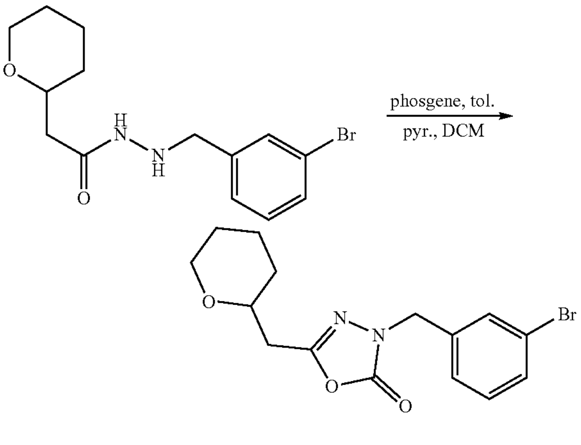

At 0° C., a solution of phosgene (20% in toluene, 2.62 mL, 4.97 mmol, 5.0 eq.) was added dropwise to a mixture of N'-(3-bromobenzyl)-2-(tetrahydro-2H-pyran-2-yl)acetohydrazide (325 mg, 0.99 mmol, 1.0 eq.) in DCM (7.5 mL). The mixture was allowed to warm up to RT and stirred at RT for 1 hour. The mixture was concentrated and the residue was dissolved in MTBE and water. The organic layer was separated, washed with brine, dried over $Na_2SO_4$, filtered and concentrated. The residue was purified on silica gel chromatography (0-40% EtOAc in hexanes) to afford 3-(3- bromobenzyl)-5-((tetrahydro-2H-pyran-2-yl)methyl)-1,3,4-oxadiazol-2(3H)-one as a colorless oil (327 mg, 94%).

6. The Synthesis of 3-(3-(cyclopropylethynyl)benzyl)-5-((tetrahydro-2H-pyran-2-yl)methyl)-1,3,4-oxadiazol-2(3H)-one (I-18)

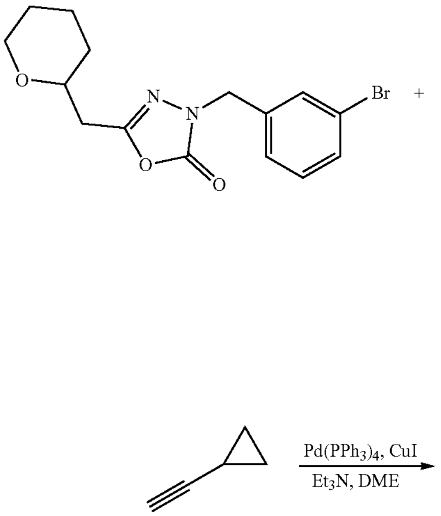

-continued

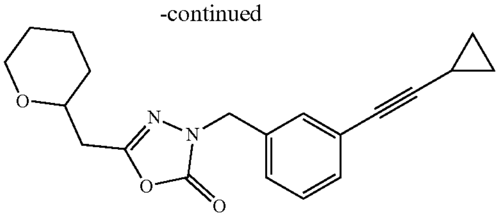

I-18

Cyclopropylacetylene (391 μL, 4.61 mmol, 10 eq.) was added to a $N_2$ bubbled solution of 3-(3-bromobenzyl)-5-((tetrahydro-2H-pyran-2-yl)methyl)-1,3,4-oxadiazol-2(3H)-one (163 mg, 0.461 mmol, 1.0 eq.), $Pd(PPh_3)_4$ (53 mg, 0.046 mmol, 0.1 eq.) and CuI (9 mg, 0.046 mmol, 0.1 eq.) in $Et_3N$ (2.3 mL) and DME (2.3 mL). After 1 minutes of $N_2$ bubbling, the reaction was stirred at 90° C. for 18 hours. Once at RT, the mixture was poured in aq. sat. $NH_4Cl$ and MTBE was added. The organic layer was separated, dried over $Na_2SO_4$, filtered and concentrated. The residue was purified on silica gel chromatography (0-40% EtOAc in hexanes) to afford 3-(3-(cyclopropylethynyl)benzyl)-5-((tetrahydro-2H-pyran-2-yl)methyl)-1,3,4-oxadiazol-2(3H)-one (I-18) as an orange oil (132 mg, 85%).

Additional exemplary compounds were prepared following methods substantially similar to the method described above and herein. Data for these compounds are provided below.

TABLE 16

Characterization Data for Additional Exemplary Compounds

| Compound No. | Chemical Structure | [M + H] observed | $^1H$ NMR (400 MHz) |
|---|---|---|---|
| I-18 | 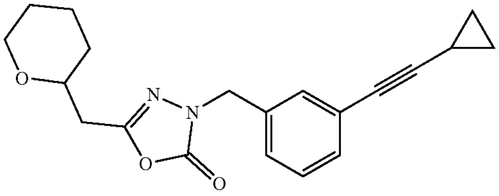 [SMILES: O=c1oc(CC2CCCCO2)nn1Cc1cccc(C#CC2CC2)c1] | 339.2 | $^1H$ NMR (400 MHz, $CDCl_3$) δ 7.34 (s, 1H), 7.31 (dt, J = 6.9, 1.9 Hz, 1H), 7.30-7.18 (m, 2H), 4.77 (d, J = 4.8 Hz, 2H), 4.02-3.88(m, 1H), 3.64 (dddd, J = 10.2, 7.6, 5.1, 2.2 Hz, 1H), 3.41 (td, J- 11.5, 2.9 Hz, 1H), 2.69 (dd, J = 15.1, 7.9 Hz, 1H), 2.60 (dd, J = 15.1, 5.1 Hz, 1H), 1.91-1.76 (m, 1H), 1.68-1.60 (m, 1H), 1.60-1.38 (m, 4H), 1.38-1.23 (m, 1H), 0.91-0.82 (m, 2H), 0.82-0.75 (m, 2H). |
| I-19 | 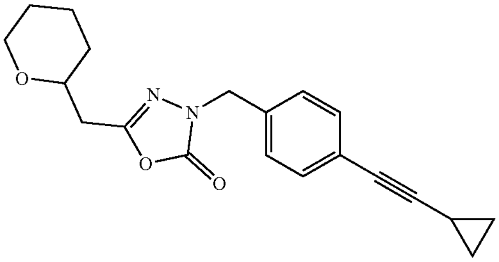 [SMILES: O=c1oc(CC2CCCCO2)nn1Cc1ccc(C#CC2CC2)cc1] | 339.2 | 1H NMR (400 MHz, $CDCl_3$) δ 7.34 (d, J = 8.2 Hz, 2H), 7.23 (d, J = 8.1 Hz, 2H), 4.79 (d, J = 5.2 Hz, 2H), 3.99-3.89 (m, 1H), 3.63 (dddd, J = 10.5, 7.7, 5.2, 2.2 Hz, 1H), 3.40 (td, J = 11.4, 2.8 Hz, 1H), 2.69 (dd, J -15.1, 7.9 Hz, 1H), 2.60 (dd, J = 15.1, 5.1 Hz, 1H), 1.90-1.76 (m, 1H), 1.68-1.58 (m, 1H), 1.59-1.23 (m, 5H), 0.90-0.82 (m, 2H), 0.79 (tt, J = 5.1, 2.8 Hz, 2H). 0.91 -0.82 (m, 2H), 0.82-0.75 (m, 2H). |
| I-404 | 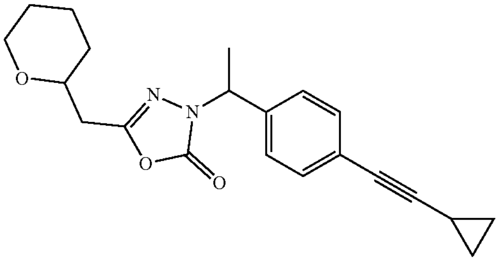 [SMILES: CC(c1ccc(C#CC2CC2)cc1)n1nc(CC2CCCCO2)oc1=O] | 353.1 | $^1H$ NMR (400 MHz, DMSO-$d_6$) δ 7.35 (d, J = 8.4 Hz, 2H), 7.27 (d, J = 8.4 Hz, 2H), 5.21-5.26 (m, 1H), 3.81-3.85 (m, 1H), 3.54-3.60 (m, 1H), 3.30-3.33 (m, 1H), 2.73-2.78 (m, 1H), 2.62-2.69 (m, 1H), 1.74-1.77 (m, 1H), 1.61-1.68 (m, 4H), 1.43-1.57 (m, 4H), 1.20-1.27 (m, 1H), 0.85-0.90 (m, 2H), 0.70-0.74 (m, 2H). |

TABLE 16-continued

| Characterization Data for Additional Exemplary Compounds | | | |
|---|---|---|---|
| Compound No. | Chemical Structure | [M + H] observed | $^1$H NMR (400 MHz) |
| I-405 | 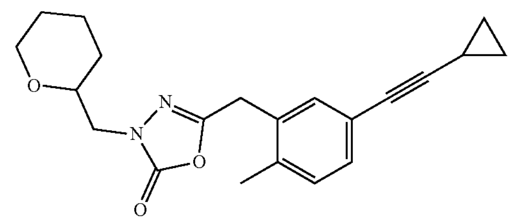 [SMILES: Cc1ccc(C#CC2CC2)cc1Cc1nn(CC2CCCCO2)c(=O)o1] | 353.0 | $^1$H NMR (400 MHz, DMSO-$d_6$) δ 7.15-7.23 (m, 3H), 3.95 (s, 2H), 3.82-3.84 (m, 1H), 3.50-3 65 (m, 3H) 3.24-3.30 (m, 1H), 2.25 (s, 3H), 1.76-1.77 (m, 1H), 1.39-1.58 (m, 5H), 1.16-1.22 (m, 1H), 0.85-0.89 (m, 2H), 0.69-0.72 (m, 2H). |

Example 16: Synthesis of I-406 and I-407

Synthetic Scheme of I-406 and I-407

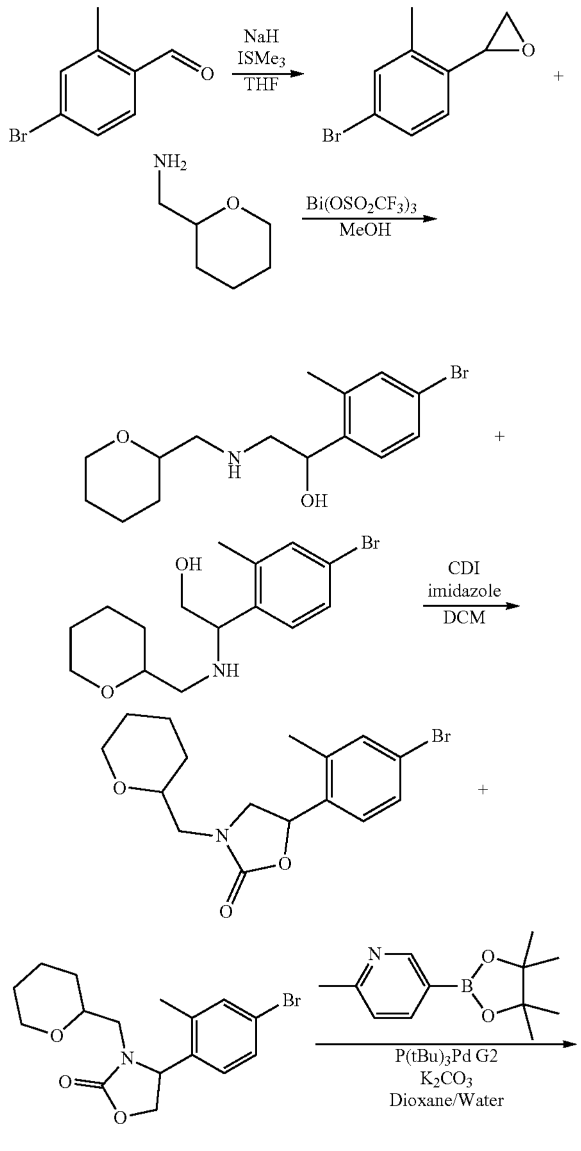

-continued

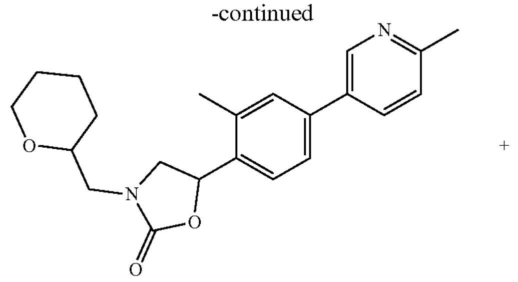

I-406

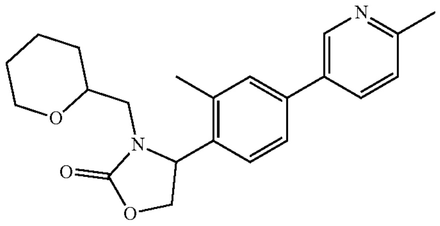

I-407

1. The Synthesis of Intermediate 2-(4-bromo-2-methylphenyl)oxirane

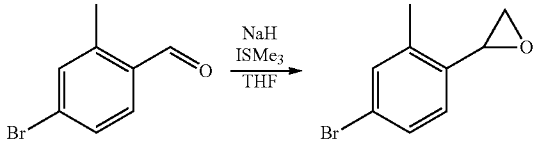

To a solution of 4-Bromo-2-methylbenzaldehyde (500 mg, 2.46 mmol) in THF (2 mL) were added Sodium hydride (118 mg, 4.92 mmol) and Trimethylsulfonium Iodide (1.03 g, 4.92 mmol). The reaction mixture was stirred at RT for 2h30, and partitioned between ethyl acetate and water. The layers were separated and the organic one was washed, dried over MgSO4 and concentrated to afford the crude 2-(4-bromo-2-methylphenyl)oxirane (500 mg) used as is in the next step. HPLC (Method C): 1.04 min 2. The Synthesis of Intermediates 1-(4-bromo-2-methylphenyl)-2-(((tetrahydro-2H-pyran-2-yl)methyl)amino)ethanol and 2-(4-bromo-2-methylphenyl)-2-(((tetrahydro-2H-pyran-2-yl)methyl)amino)ethanol

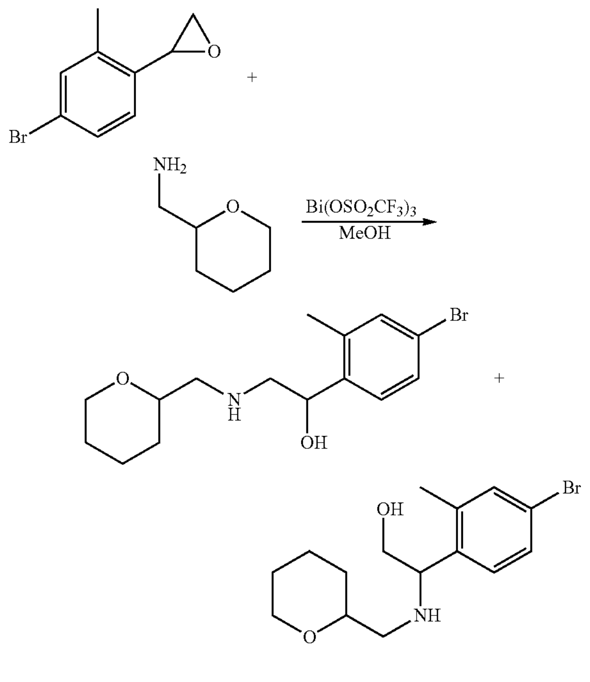

To a solution of 2-(4-bromo-2-methylphenyl)oxirane (500 mg, 2.35 mmol) in MeOH (4 mL) were added Bismuth(III) trifluoromethanesulfonate (77.0 mg, 117 umol) and (Tetrahydro-2H-pyran-2-yl)methanamine (284 mg, 2.35 mmol). The reaction mixture was stirred at 60° C. overnight, cooled to RT and partitioned between ethyl acetate and water. The layers were separated and the organic one was washed, dried over $MgSO_4$, concentrated and purified by reverse phase FCC (30 g C18 cartridge, 5 to 40% ACN in 10 mM AmF) to afford the desired mixture of compound 1-(4-bromo-2-methylphenyl)-2-(((tetrahydro-2H-pyran-2-yl)methyl)amino)ethanol (58 mg) and 2-(4-bromo-2-methylphenyl)-2-(((tetrahydro-2H-pyran-2-yl)methyl)amino)ethanol (58 mg). HPLC (Method C): 0.85 and 0.90 min 3. The Synthesis of Intermediates 5-(4-bromo-2-methylphenyl)-3-((tetrahydro-2H-pyran-2-yl)methyl)oxazolidin-2-one, 4-(4-bromo-2-methylphenyl)-3-((tetrahydro-2H-pyran-2-yl)methyl)oxazolidin-2-one

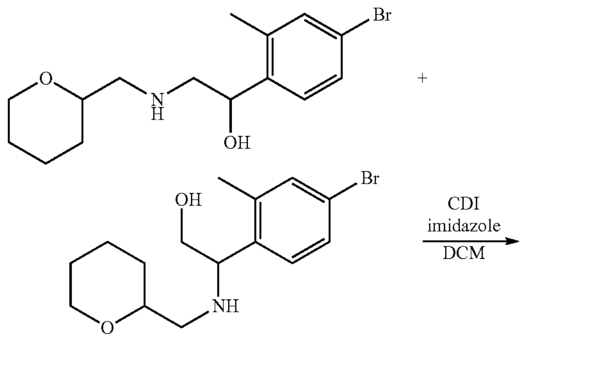

-continued

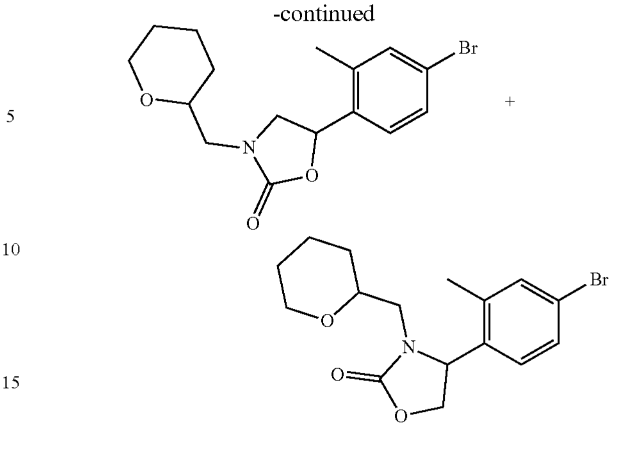

To a solution of 1-(4-bromo-2-methylphenyl)-2-(((tetrahydro-2H-pyran-2-yl)methyl)amino)-ethanol (58.0 mg, 177 umol) and 2-(4-bromo-2-methylphenyl)-2-(((tetrahydro-2H-pyran-2-yl)-methyl)amino)ethanol (58.0 mg, 177 umol) in DCM (504 uL) were added at 0° C. 1,1-carbonylimidazole (32.2 mg, 194 umol) and Imidazole (6.08 mg, 88.3 umol). The reaction mixture was stirred at RT for 2h30 and diluted with methyene chloride. The reaction mixture was washed, dried over $MgSO_4$, concentrated and purified by reverse phase FCC (30 g C18 cartridge, 5 to 70% ACN in 10 mM ammonium formate gradient) to afford a mixture of isomers 5-(4-bromo-2-methylphenyl)-3-((tetrahydro-2H-pyran-2-yl)methyl)oxazolidin-2-one (53 mg), 4-(4-bromo-2-methylphenyl)-3-((tetrahydro-2H-pyran-2-yl)methyl)oxazolidin-2-one (53 mg). HPLC (Method C): 1.32 and 1.34 min.

4. The Synthesis of 5-(2-methyl-4-(6-methylpyridin-3-yl)phenyl)-3-((tetrahydro-2H-pyran-2-yl)methyl)oxazolidin-2-one (I-406) and 4-(2-methyl-4-(6-methylpyridin-3-yl)phenyl)-3-((tetrahydro-2H-pyran-2-yl)methyl)oxazolidin-2-one (I-407)

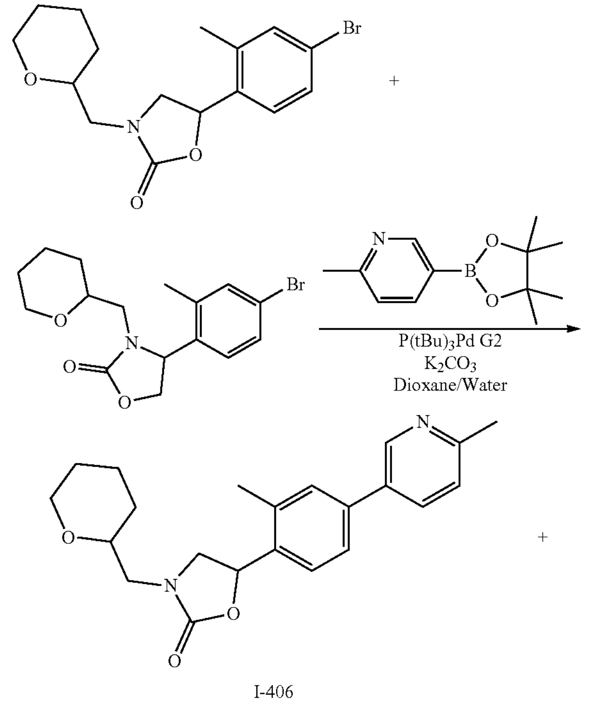

I-406

-continued

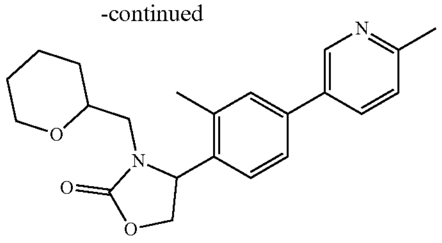

I-407

A microwave vial was charged with 5-(4-bromo-2-methylphenyl)-3-((tetrahydro-2H-pyran-2-yl)methyl)oxazolidin-2-one (53.0 mg, 150 umol), 4-(4-bromo-2-methylphenyl)-3-((tetrahydro-2H-pyran-2-yl)methyl)oxazolidin-2-one (53.0 mg, 150 umol), $K_2CO_3$ (62.0 mg, 449 umol) and 2-methylpyridine-5-boronic acid, pinacol ester (51.2 mg, 224 umol). A degassed mixture of Dioxane (389 uL) and Water (43.2 uL) was then added and the mixture was degassed with nitrogen. The reaction mixture was stirred at 100° C. for 16 h and partitioned between ethyl acetate and an aqueous solution of ammonium chloride. The layers were separated and the organic one was washed, dried over $MgSO_4$ and concentrated. The crude product was purified by reverse phase FCC (30 g C18 cartridge, 5 to 70% ACN in 10 mM ammonium formate gradient) and by reverse Prep LC-MS (C18 OBD cartridge, 20 to 100% ACN in 10 mM ammonium formate gradient) to afford 5-(2-methyl-4-(6-methylpyridin-3-yl)phenyl)-3-((tetrahydro-2H-pyran-2-yl)methyl)oxazolidin-2-one, I-406 (4.5 mg) and 4-(2-methyl-4-(6-methylpyridin-3-yl)phenyl)-3-((tetrahydro-2H-pyran-2-yl)methyl)oxazolidin-2-one, I-407 (7.1 mg).

Additional exemplary compounds were prepared following methods substantially similar to the method described above and herein. Data for these compounds are provided below.

TABLE 17

Characterization Data for Additional Exemplary Compounds

| Compound No. | Chemical Structure | [M + H] observed | $^1$H NMR (400 MHz) |
| --- | --- | --- | --- |
| I-406 | 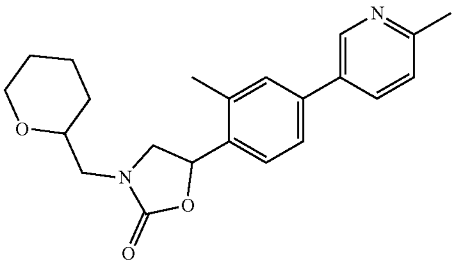 [SMILES: Cc1ccc(-c2ccc(C3CN(CC4CCCCO4)C(=O)O3)c(C)c2)cn1] | 442 5 | $^1$H NMR (400 MHz, $CD_3CN$) δ 8.73 (s, 1H), 7.88 (dd, J = 8.1, 2.4 Hz, 1H), 7.57-7.50 (m, 2H), 7.32 (d, J = 7.9 Hz, 1H), 7.28 (d, J = 8.0 Hz, 1H), 5.45 (dd, J = 8.9, 7.0 Hz, 1H), 4.64 (t, J = 8.7 Hz, 1H), 3.93 (dd, J = 8.5, 6.9 Hz, 1H), 3.90-3.83 (m, 1H), 3.50-3.41 (m, 1H), 3.41-3.32 (m, 2H), 2.67 (dd, J = 14.6, 8.8 Hz, 1H), 2.53 (s, 3H), 2.37 (s, 3H), 1.77-1.73 (m, 1H), 1.56-1.37 (m, 4H), 1.15-1.02 (m, 1H). |
| I-407 | 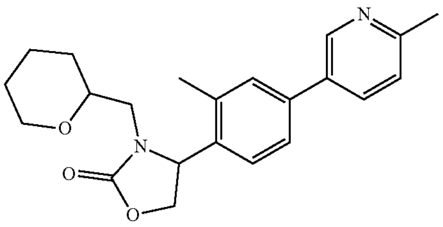 [SMILES: Cc1ccc(-c2ccc(C3COC(=O)N3CC3CCCCO3)c(C)c2)cn1] | 325.2 | $^1$H NMR (400 MHz, $CD_3CN$) δ 8.73 (s, 1H), 7.87 (ddd, J = 8.1, 2.3, 1.2 Hz, 1H), 7.56-7.47 (m, 2.5H), 7.32 (d, J = 8.0, 0.5H), 7.28 (d, J = 8.0, 1H), 5.73 (dd, J = 8.6, 7.4 Hz, 0.5H), 5.32 (dd, J = 8.9, 6.7 Hz, 0.5H), 4.68 (t, J = 8.7 Hz, 0.5H), 4.08 (td, J = 9.0, 2.2 Hz, 0.5H), 3.94 (dd, J = 8.5, 6.7 Hz, 0.5H), 3.89 -3.83 (m, 1H), 3.56-3.45 (m, 1.5H), 3.42-3.26 (m, 1.5H), 3.25-3.22 (m, 1H), 2.78 (dd, J = 14.5, 3.0 Hz, 0.5H), 2.53 (s, 3H), 2.39 (s, 1.5H), 2.38 (s, 1.5H), 1.83-1.76 (m, 1H), 1.60 -1.41 (m, 4H), 1.32-1.21 (m, 1H). |

Example 17: Synthesis of I-7

Synthetic Scheme of I-7

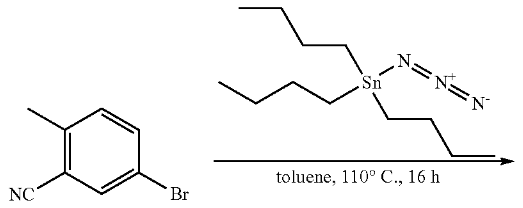

17.1

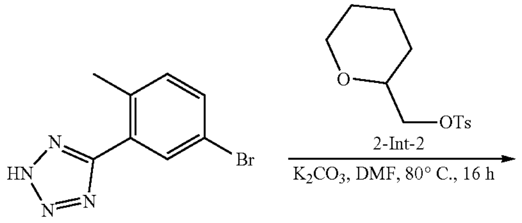

17.2

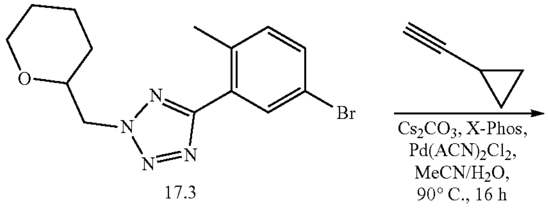

17.3

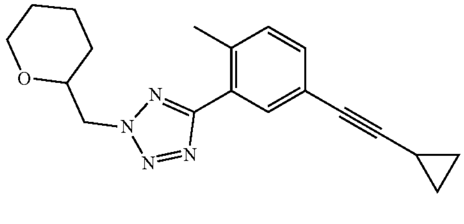 [SMILES: Cc1ccc(C#CC2CC2)cc1-c1nnn(CC2CCCCO2)n1]

I-7

1. The Synthesis of Intermediate 17.2

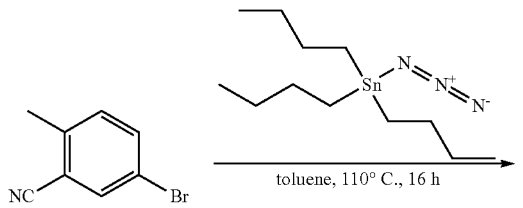

17.1

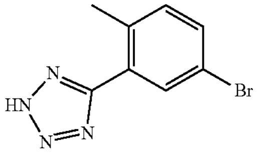

17.2

To a stirred solution of 17.1 (2.2 g, 11.2 mmol) in toluene (30 mL) was added tributyltin azide (4.1 g, 12.3 mmol). The reaction mixture was heated to 110° C. for 16 h and concentrated to give 17.2 (2.5 g, crude) as brown oil. LC-MS m/z: 239.0 $[M+H]^+$.

2. The Synthesis of Intermediate 17.3

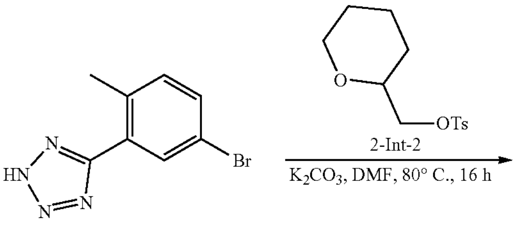

17.2

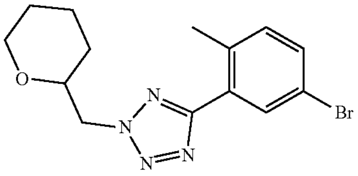

17.3

To a stirred solution of 17.2 (1.0 g, 4.2 mmol, crude) and $K_2CO_3$ (1.2 g, 8.4 mmol) in anhydrous DMF (30 mL), was added 2-Int-2 (1.7 g, 6.3 mmol). The reaction mixture was stirred for 16 h at 80° C. The reaction mixture was diluted with $H_2O$ (20 mL) and extracted with EA (50 mL×2), concentrated to dryness. The crude product was purified by Prep-HPLC to give 17.3 (250 mg, yield: 6.6% for two steps) as yellow oil. LC-MS m/z: 337.0 $[M+H]^+$.

3. The Synthesis of I-7

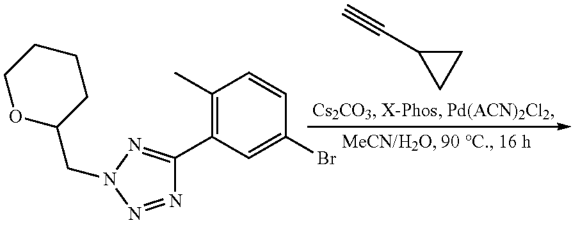

17.3

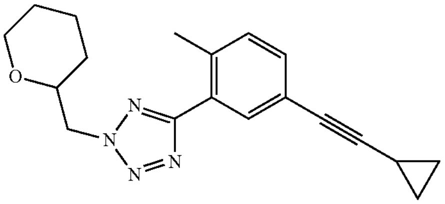

I-7

To a stirred solution of 17.3 (200 mg, 0.59 mmol), $K_2CO_3$ (163 mg, 1.18 mmol), ethynylcyclopropane (103 mg, 1.53 mmol) in MeCN (30 mL) was added X-Phos (48 mg, 0.10 mmol), $Pd(ACN)_2Cl_2$ (13 mg, 0.05 mmol). The reaction mixture was stirred at 90° C. for 16 hours. The suspension was concentrated and purified by Prep-HPLC to give I-7 (45 mg, yield: 23%) as yellow oil.

Additional exemplary compounds were prepared following methods substantially similar to the method described above and herein. Data for these compounds are provided below.

TABLE 18

Characterization Data for Additional Exemplary Compounds

| Compound No. | Chemical Structure | [M + 1H] observed | $^1H$ NMR (400 MHz) |
|---|---|---|---|
| I-7 | 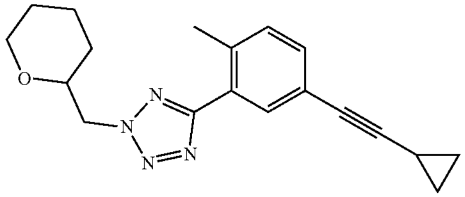 | 323.3 | $^1H$ NMR (400 MHz, DMSO-$d_6$): δ 7.88 (d, J = 1.6 Hz, 1H), 7.36-7.42 (m, 2H), 4.73-4.80 (m, 2H), 3.80-3.95 (m, 2H), 3.26-3.32 (m, 1H), 1.28-1.59 (m, 5H), 0.87-0.92 (m, 2H), 0.74-0.78 (m, 2H). |
| I-8 | 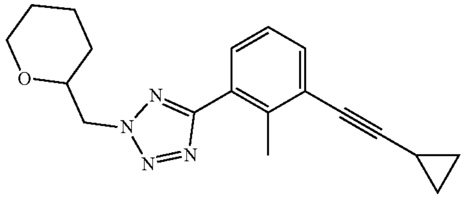 [SMILES: Cc1c(C#CC2CC2)cccc1-c1nnn(CC2CCCCO2)n1] | 323.1 | $^1H$ NMR (400 MHz, DMSO-$d_6$): δ 7.79 (d, J = 7.6 Hz, 1H), 7.51 (d, J = 8.0 Hz, 1H), 7.32 (t, J = 7.6 Hz, 1H), 4.76-4.78 (m, 2H), 3.80-3.94 (m, 2H), 3.26-3.30 (m, 1H), 2.58 (s, 3H), 1.70-1.83 (m, 2H), 1.41-1.63 (m, 4H), 1.31-1.37 (m, 1H), 0.91-0.96 (m, 2H), 0.75-0.80 (m, 2H). |
| I-9 | 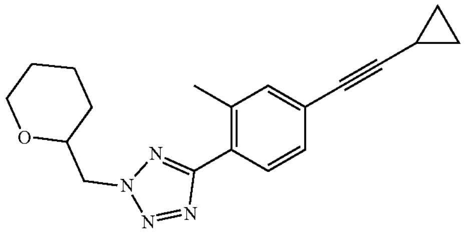 | 323.2 | $^1H$ NMR (400 MHz, DMSO-$d_6$) δ 7.90 (d, J = 8.0 Hz, 1H), 7.40 (s, 1H), 7.34 (dd, J = 1.2, 8.0 Hz, 1H), 4.76-4.78 (m, 2H), 3.88-3.94 (m, 1H), 3.79-3.83 (m, 1H), 3.25-3.32 (m, 1H), 2.54 (s, 3H), 1.80-1.83 (m, 1H), 1.70-1.73 (m, 1H), 1.40-1.61 (m, 4H), 1.28-1.38 (m, 1H), 0.89-0.94 (m, 2H), 0.74-0.78 (m, 2H). |
| I-1 | 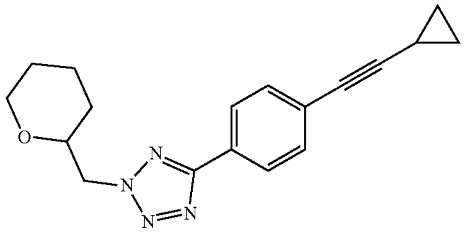 [SMILES: C(#CC1CC1)c1ccc(-c2nnn(CC3CCCCO3)n2)cc1] | 309.2 | $^1H$ NMR ($CDCl_3$, 400 MHz) δ 8.04 (d, J = 8.6 Hz, 2H), 7.45 (d, J = 8.6 Hz, 2H), 4.68 (dd, J = 13.7, 7.9 Hz, 1H), 4.54 (dd, J = 13.7, 4.3 Hz, 1H), 3.95-3.85 (m, 2H), 3.33 (td, J = 11.6, 2.5 Hz, 1H), 1.85 (ddd, J = 8.9, 4.9, 2.4 Hz, 1H), 1.67-1.59 (m, 1H), 1.58-1.28 (m, 5H), 0.90-0.82 (m, 2H), 0.82-0.77 (m, 2H). |
| I-2 | 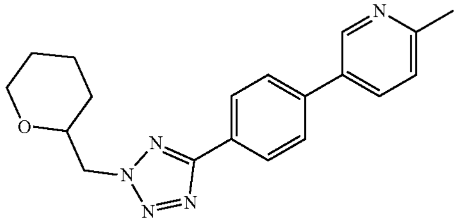 [SMILES: Cc1ccc(-c2ccc(-c3nnn(CC4CCCCO4)n3)cc2)cn1] | 336.2 | $^1H$ NMR ($CDCl_3$, 400 MHz) δ 8.79 (d, J = 1.9 Hz, 1H), 8.26 (d, J = 8.4 Hz, 2H), 7.83 (dd, J = 8.0, 2.4 Hz, 1H), 7.69 (d, J = 8.4 Hz, 2H), 7.25 (d, J = 7.9 Hz, 1H), 4.75 (dd, J13.7, 7.9 Hz, 1H), 4.61 (dd, J = 13.7, 4.3 Hz, 1H), 4.03-3.92 (m, 2H), 3.40 (td, J = 11.6, 2.5 Hz, 1H), 2.62 (s, 3H), 1.95-1.87 (m, 1H), 1.74-1.36 (m, 5H). |
| I-346 | 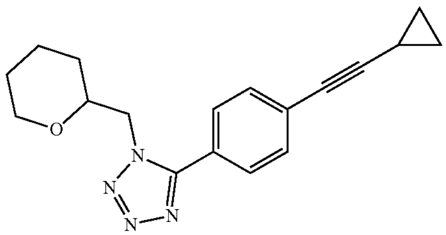 [SMILES: C(#CC1CC1)c1ccc(-c2nnnn2CC2CCCCO2)cc1] | 309.2 | $^1H$ NMR ($CDCl_3$, 400 MHz) δ 7.75 (d, J = 8.6 Hz, 2H), 7.50 (d, J = 8.6 Hz, 2H), 4.38-4.25 (m, 2H), 3.95-3.85 (m, 2H), 3.31 (td, J = 11.4, 2.5 Hz, 1H), 1.95-1.82 (m, 1H), 1.75-1.65 (m, 1H), 1.60-1.40 (m, 4H), 1.40-1.27 (m, 1H), 1.01-0.86 (m, 2H), 0.86-0.79 (m, 2H) |

TABLE 18-continued

Characterization Data for Additional Exemplary Compounds

| Compound No. | Chemical Structure | [M + 1H] observed | $^1$H NMR (400 MHz) |
|---|---|---|---|
| I-3 | 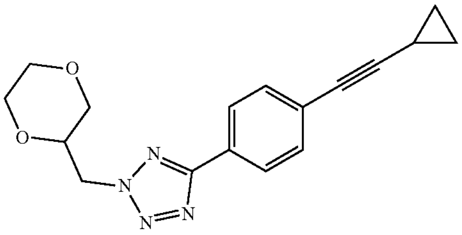 [SMILES: C(#CC1CC1)c1ccc(-c2nnn(CC3COCCO3)n2)cc1] | 311.2 | $^1$H NMR ($CDCl_3$, 400 MHz) δ 8.17-7.98 (m, 2H), 7.59-7.42 (m, 2H), 4.78 (dd, J = 14.0, 7.3 Hz, 1H), 4.62 (dd, J = 14.0, 4.9 Hz, 1H), 4.21 (dddd, J = 9.9, 7.5, 5.1, 2.8 Hz, 1H), 3.98-3.79 (m, 2H), 3.76-3.59 (m, 3H), 3.49 (dd, J = 11.6, 9.5 Hz, 1H), 1.50-1.41 (m, 1H), 0.98-0.86 (m, 2H), 0.86-0.79 (m, 2H). |
| I-4 | 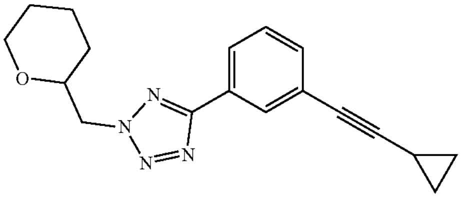 [SMILES: C(#CC1CC1)c1cccc(-c2nnn(CC3CCCCO3)n2)c1] | 309.2 | $^1$H NMR ($CDCl_3$, 400 MHz) δ 8.28-8.13 (m, 1H), 8.05 (dt, J = 7.7, 1.5 Hz, 1H), 7.45 (dt, J = 7.7, 1.4 Hz, 1H), 7.38 (td, J = 7.7, 0.5 Hz, 1H), 4.73 (dd, J = 13.7, 7.9 Hz, 1H), 4.58 (dd, J = 13.7, 4.4 Hz, 1H), 4.11-3.82 (m, 2H), 3.38 (td, J = 11.7, 2.5 Hz, 1H), 2.10-1.83 (m, 1H), 1.75-1.64 (m, 1H), 1.60-1.31 (m, 4H), 1.04-0.85 (m, 2H), 0.82 (tt, J = 5.1, 2.5 Hz, 2H) |
| I-6 | 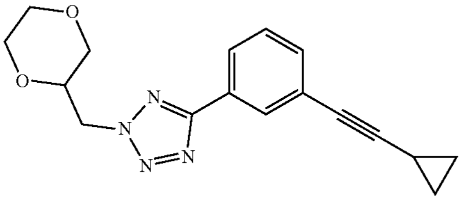 [SMILES: C(#CC1CC1)c1cccc(-c2nnn(CC3COCCO3)n2)c1] | 311.2 | $^1$H NMR ($CDCl_3$, 400 MHz) δ 8.18 (dt, J = 1.7, 0.8 Hz, 1H), 8.04 (dt, J = 7.5, 1.5 Hz, 1H), 7.46 (dt, J = 7.7, 1.4 Hz, 1H), 7.39 (td, J = 7.7, 0.5 Hz, 1H), 4.78 (dd, J = 14.0, 7.3 Hz, 1H), 4.62 (dd, J = 14.0, 4.9 Hz, 1H), 4.21 (dddd, J = 9.8, 7.4, 4.9, 2.7 Hz, 1H), 3.93-3.79 (m, 2H), 3.76-3.57 (m, 3H), 3.49 (dd, J = 11.6, 9.6 Hz, 1H), 1.52-1.41 (m, 1H), 0.96-0.87 (m, 2H), 0.87-0.76 (m, 2H) |

Example 18: Synthesis of I-342

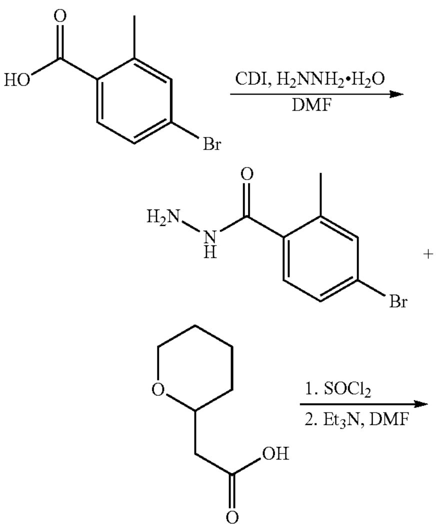

-continued

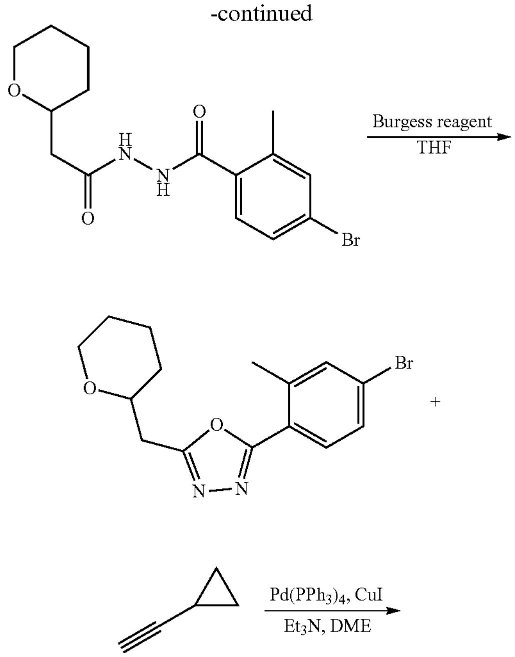

-continued

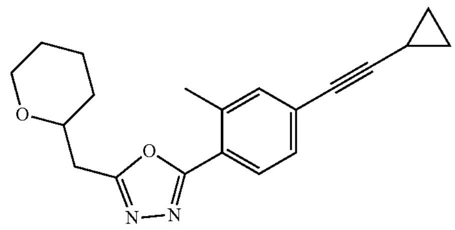

I-342

1. The Synthesis of Intermediate 4-bromo-2-methylbenzohydrazide

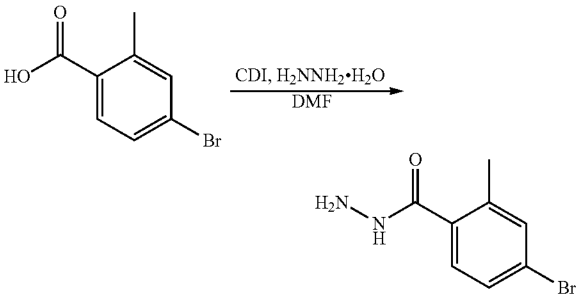

1,1'-Carbonyldiimidazole (5.66 g, 34.9 mmol, 1.5 eq.) was added to a mixture of 4-bromo-2-methylbenzoic acid (5.0 g, 23.3 mmol, 1.0 eq.) in DMF (50 mL). After 2 hours of stirring at RT, hydrazine hydrate (5.7 mL, 116 mmol, 5.0 eq.) was slowly added. The mixture was stirred at RT for 2 hours then it was poured in saturated aqueous ammonium chloride and the precipitate was filtered to afford 4-bromo-2-methylbenzohydrazide (4.01 g, 75%).

2. The Synthesis of Intermediate 4-Bromo-2-methyl-N'-(2-(tetrahydro-2H-pyran-2-yl)-acetyl)benzohydrazide

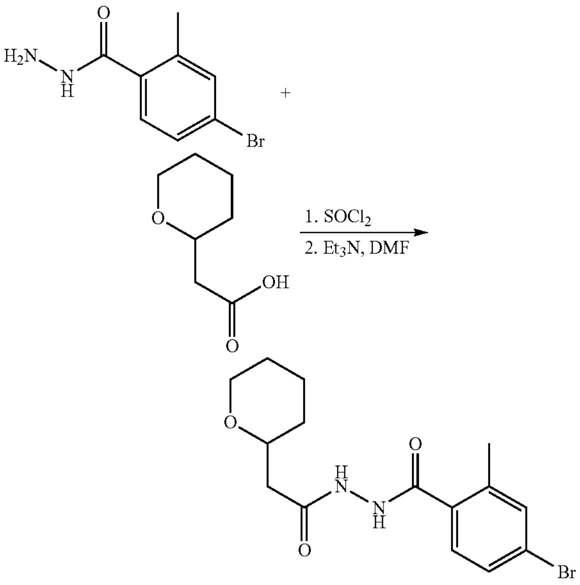

A mixture of 2-(tetrahydro-2H-pyran-2-yl)acetic acid (755 mg, 5.24 mmol, 1.2 eq.) and $SOCl_2$ (1.4 mL, 21.8 mmol, 5.0 eq.) was stirred at reflux for 1 hour. Once at RT, the mixture was concentrated and dissolved in DMF (1 mL). At 0° C., the resulting solution was added to a mixture of 4-bromo-2-methylbenzohydrazide (1.0 g, 4.37 mmol, 1.0 eq.) and $Et_3N$ (3.04 mL, 21.8 mmol, 5.0 eq.) in DMF (12 mL). The mixture was allowed to warm up to RT and stirred for 4 hours at RT. The mixture was poured in aq. sat. $NH_4Cl$ and the precipitate was filtered to afford 4-bromo-2-methyl-N-(2-(tetrahydro-2H-pyran-2-yl)acetyl)benzohydrazide as an off-white solid (1.25 g, 81%).

3. The Synthesis of Intermediate 2-(4-Bromo-2-methylphenyl)-5-((tetrahydro-2H-pyran-2-yl)-methyl)-1,3,4-oxadiazole

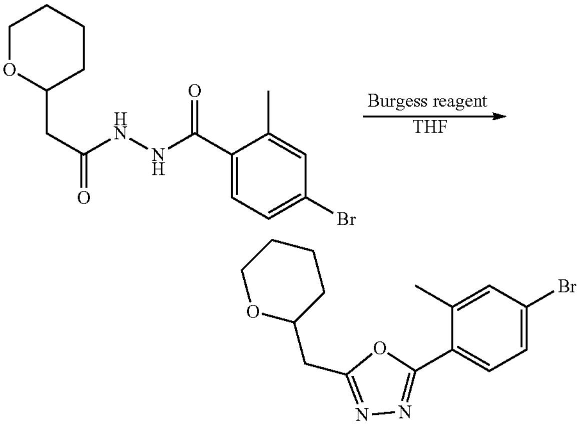

Methyl N-(triethylammoniumsulfonyl)carbamate [Burgess reagent] (101 mg, 0.422 mmol, 1.5 eq.) was added to a mixture of 4-bromo-2-methyl-N'-(2-(tetrahydro-2H-pyran-2-yl)acetyl)benzohydrazide (100 mg, 0.282 mmol, 1.0 eq.) in THF (3 mL). The mixture was stirred at reflux for 18 hours. Once at RT, the mixture was concentrated and the residue was dissolved in MTBE and $H_2O$. The organic layer was separated, washed with brine, dried over $Na_2SO_4$, filtered and concentrated. The residue was purified on silica gel chromatography (0-40% EtOAc in hexanes) to afford 2-(4-bromo-2-methylphenyl)-5-((tetrahydro-2H-pyran-2-yl)methyl)-1,3,4-oxadiazole as a pale yellow oil (56 mg, 59%).

4. The Synthesis of I-342

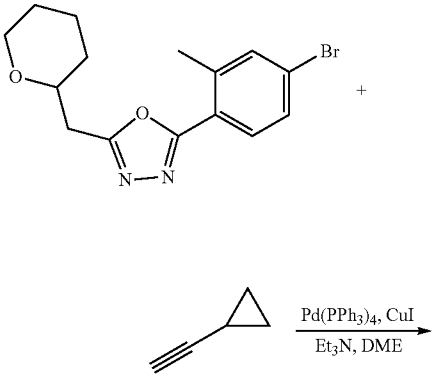

-continued

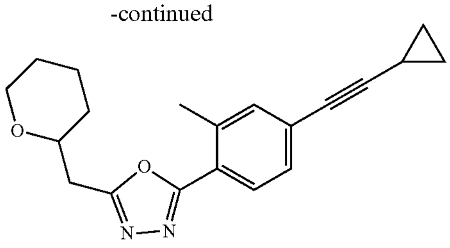

I-342

Cyclopropylacetylene (138 μL, 1.63 mmol, 10 eq.) was added to a $N_2$ bubbled solution of 2-(4-bromo-2-methylphenyl)-5-((tetrahydro-2H-pyran-2-yl)methyl)-1,3,4-oxadiazole (55 mg, 0.163 mmol, 1.0 eq.), $Pd(PPh_3)_4$ (19 mg, 0.016 mmol, 0.1 eq.) and Cul (3 mg, 0.016 mmol, 0.1 eq.) in $Et_3N$ (0.8 mL) and DME (0.8 mL). After 1 minutes of $N_2$ bubbling, the reaction was stirred at 90° C. for 3 hours. Once at (RT, the mixture was poured in aq. sat. $NH_4Cl$ and MTBE was added. The organic layer was separated, dried over $Na_2SO_4$, filtered and concentrated. The residue was purified on silica gel chromatography (040 EtOAc in hexanes) to afford 2-(4-(cyclopropylethynyl)-2-methylphenyl)-5-((tetrahydro-2H-pyran-2-yl)methyl)-1,3,4-oxadiazole, I-342 an orange oil (47 mg, 8955).

Additional exemplary compounds were prepared following methods substantially similar to the method described above and herein. Data for these compounds are provided below.

TABLE 19

Characterization Data for Additional Exemplary Compounds

| Compound No. | Chemical Structure | [M + H] observed | ¹H NMR (400 MHz) |
|---|---|---|---|
| I-342 | 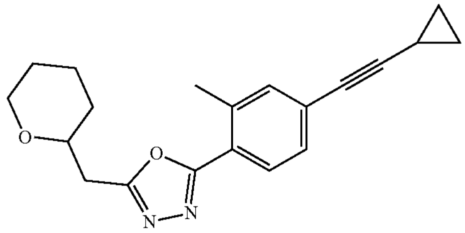 [SMILES: Cc1cc(C#CC2CC2)ccc1-c1nnc(CC2CCCCO2)o1] | 323.2 | ¹H NMR (400 MHz, $CDCl_3$) δ 7.83 (d, J = 8.1 Hz, 1H), 7.33 (s, 1H), 7.29 (dd, J = 8.1, 1.6 Hz, 1H), 4.01-3.91 (m, 1H), 3.86-3.76 (m, 1H), 3.49-3.39 (m, 1H), 3.12 (dd, J = 15.1, 7.4 Hz, 1H), 3.02 (dd, J = 15.1, 5.5 Hz, 1H), 2.65 (s, 3H), 1.87 (dq, J = 8.7, 2.7 Hz, 1H), 1.78-1.71 (m, 1H), 1.61 -1.36 (m, 5H), 0.90 (ddt, J = 8.3, 5.7, 2.9 Hz, 2H), 0.87-0.80 (m, 2H).. |
| I-343 | 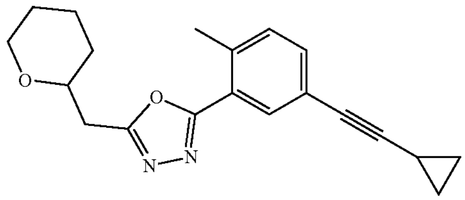 [SMILES: Cc1ccc(C#CC2CC2)cc1-c1nnc(CC2CCCCO2)o1] | 323.2 | ¹H NMR (400 MHz, $CDCl_3$) δ 7.93 (d, J = 1.8 Hz, 1H), 7.38 (dd, J = 7.9, 1.8 Hz, 1H), 7.23 (dt, J = 7.9, 0.6 Hz, 1H), 4.01 -3.93 (m, 1H), 3.81 (dddd, J = 10.6, 7.5, 5.5, 2 1 Hz, 1H) 3.49-3.38 (m, 1H), 3.12 (dd, J = 15.1, 7.4 Hz, 1H), 3.02 (dd, J = 15.1, 5.5 Hz, 1H), 2.67 (s, 3H), 1.87 (dq, J = 8.5, 2.8 Hz, 1H), 1.78-1.70 (m, 1H), 1.64-1.35 (m, 5H), 0.91-0.85 (m, 2H), 0.85-0.78 (m, 2H). |
| I-408 | 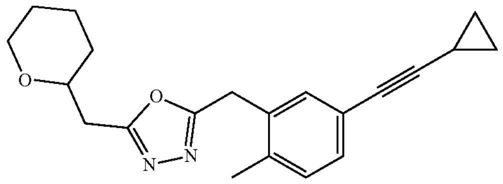 [SMILES: Cc1ccc(C#CC2CC2)cc1Cc1nnc(CC2CCCCO2)o1] | 337.2 | ¹H NMR (400 MHz, $CDCl_3$) δ 7.14 (s, 1H), 7.12 (d, J = 1.2 Hz, 1H), 7.01 (d, J = 7.6 Hz, 1H), 4.03 (s, 2H), 3.86-3.90 (m, 1H), 3.61-3.68 (m, 1H), 3.31-3.37 (m, 1H), 2.91 (dd, J = 7.2 Hz, 14.8 Hz, 1H), 2.82 (dd, J = 5.6 Hz, 15.2 Hz, 1H), 2.26 (s, 3 H), 1.75-1.79 (m, 1H), 1.58-1.61 (m, 1H), 1.23-1.52 (m, 5H), 0.74-0.80 (m, 2H), 0.68-0.72 (m, 2H). |

Example 19: Synthesis of I-330, I-331, and I-328

Synthetic Scheme of I-330, I-331, and I-328

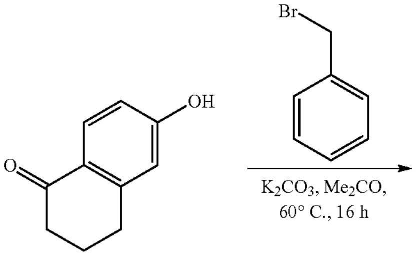

19.1

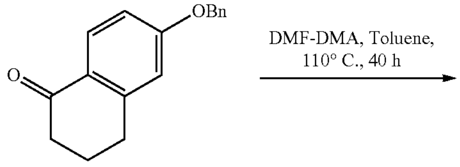

19.2

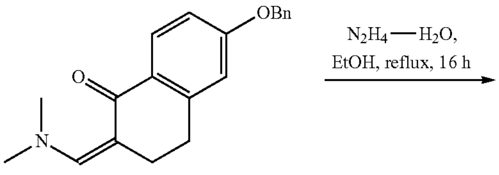

19.3

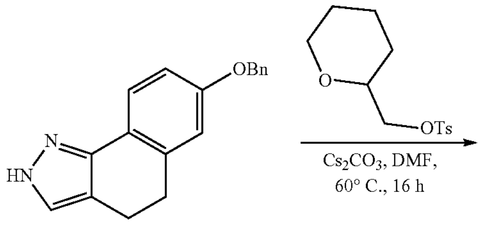

19.4

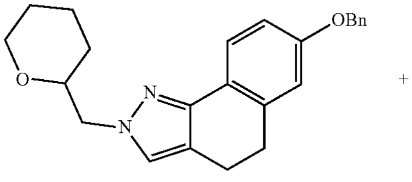

I-330

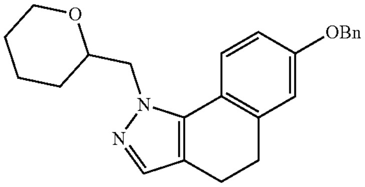

I-331

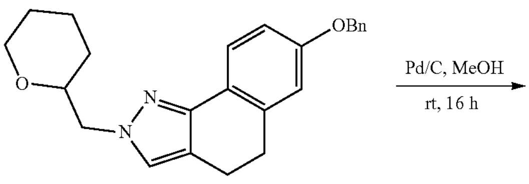

I-330

-continued

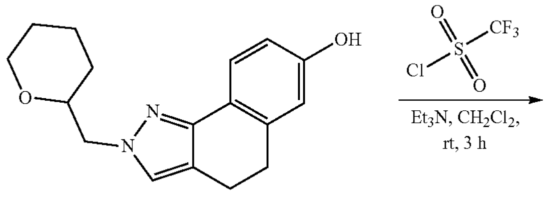

19.5

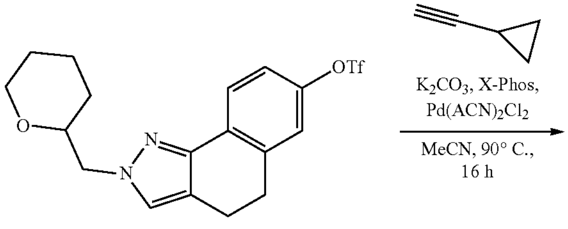

19.6

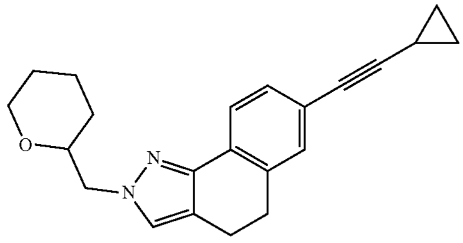

I-328

1. The Synthesis of Intermediate 19.2

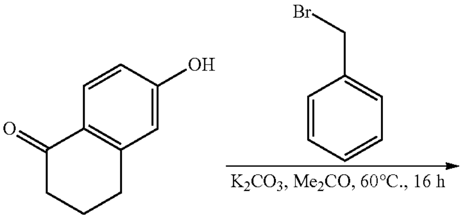

19.1

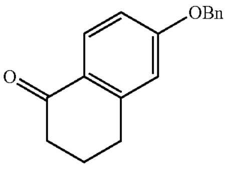

19.2

To a stirred solution of 19.1 (1.5 g, 9.2 mmol) and $K_2CO_3$ (3.8 g, 27.7 mmol) in acetone (100 mL) was added (bromomethyl)benzene (2.4 g, 13.8 mmol). The reaction mixture was heated to 60° C. for 16 h. The reaction mixture was diluted with $H_2O$ (50 mL) and extracted with EA (200 mL×2), the combined organic layer was concentrated to give 19.2 (2.0 g, crude) as brown oil.

2. The Synthesis of Intermediate 19.3

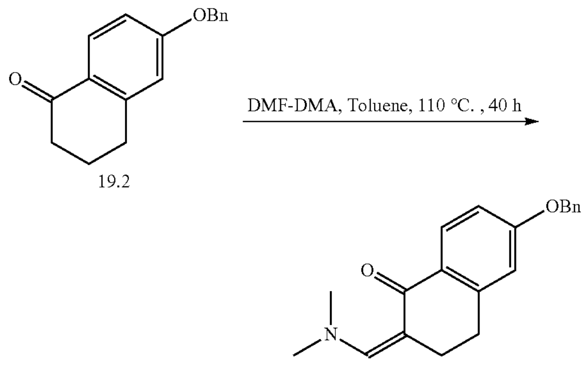

19.2

19.3

To a stirred solution of 19.2 (2.0 g, 7.9 mmol) in toluene (30 mL) was added DMF-DMA (19.0 g, 15.8 mmol). The reaction mixture was heated to 110° C. for 40 h until the reaction was complete (by LCMS). The reaction mixture was concentrated to give 19.3 (2.0 g, crude) as a brown solid.

3. The Synthesis of Intermediate 19.4

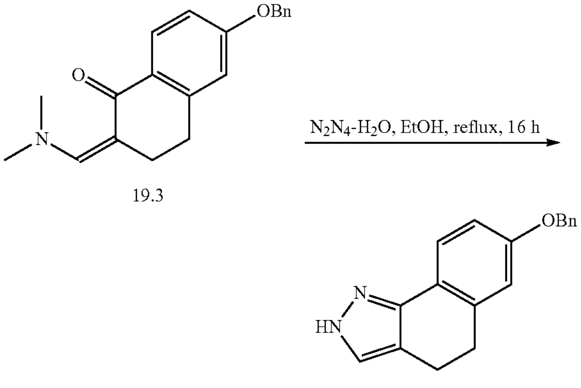

19.3

19.4

To a stirred solution of 19.3 (2.0 g, 6.5 mmol) in EtOH (30 mL) was added $N_2H4$-$H_2O$ (4.0 g, 65.0 mmol, 80%). The reaction mixture was stirred at 80° C. for 16 hours until the reaction was complete (by LCMS). The suspension was concentrated and diluted with $H_2O$ (50 mL) and extracted with EA (100 mL×2), the combined organic layer was concentrated to give 19.4 (1.6 g, crude) as a yellow solid.

4. The Synthesis of Intermediates/Targets I-330 and I-331

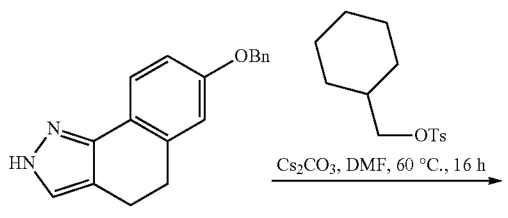

19.4

-continued

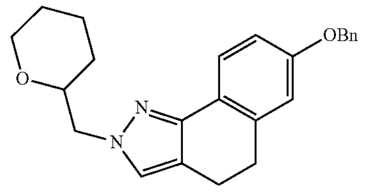

I-330

+

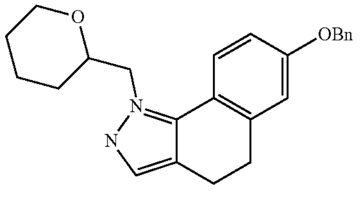

I-331

To a stirred solution of 19.4 (1.6 g, 5.8 mmol), $Cs_2CO_3$ (4.7 g, 14.5 mmol) in DMF (50 mL) was added (tetrahydro-2H-pyran-2-yl)methyl 4-methylbenzenesulfonate (1.9 g, 6.9 mmol). The reaction mixture was stirred at 60° C. for 16 hours. The suspension was diluted with $H_2O$ (100 mL) and extracted with EA (200 mL×2), the combined organic layer was concentrated. The crude product was purified by CC (silica gel, PE/EA=2:1) and chiral-HPLC to give I-330 (1.5 g, yield: 69%) and I-331 (450 mg, yield: 21%) as yellow oil.

5. The Synthesis of Intermediate 19.5

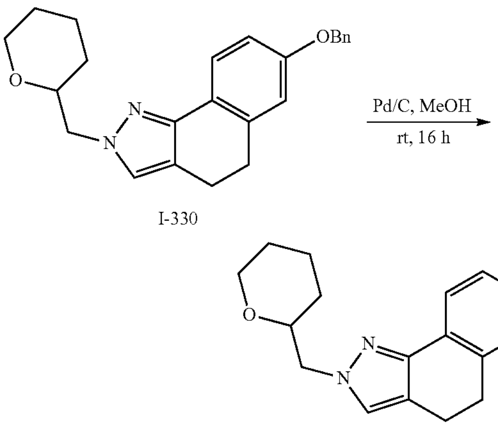

I-330

19.5

To a stirred solution of I-330 (1.0 g, 2.67 mmol), Pd/C (10% palladium on activated carbon, 400 mg) in MeOH (20 mL) was stirred at room temperature for 16 h under $H_2$ atmosphere (1.0 atm) until the reaction was complete (by LCMS). The hydrogen gas was removed in vacuo and Ar was filled. The reaction mixture was filtered via a pad of Celite and the filtrate was concentrated to give 19.5 (650 mg, crude) as yellow oil.

6. The Synthesis of Intermediate 19.6

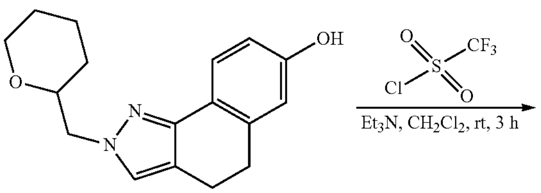

19.5

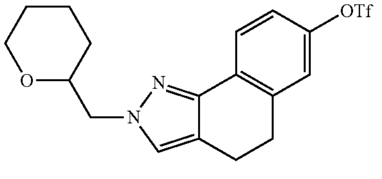

19.6

To a solution of 19.5 (300 mg, 1.06 mmol), trifluoromethanesulfonyl chloride (214 mg, 1.27 mmol) and $Et_3N$ (268 mg, 2.65 mmol) in $CH_2Cl_2$ (15 mL) was stirred at room temperature for 3 h. The solvent was removed in vacuum to give 19.6 (450 mg, crude) as yellow oil.

7. The Synthesis of Target I-328

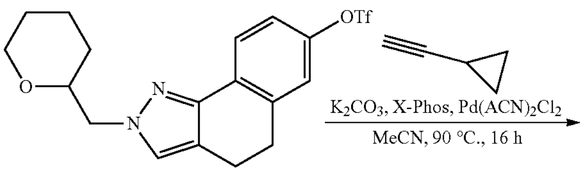

19.6

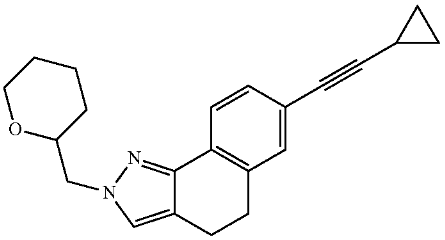

I-328

To a stirred solution of 19.6 (200 mg, 0.7 mmol) in MeCN (20 mL) was added ethynylcyclopropane (140 mg, 2.1 mmol), $K_2CO_3$ (194 mg, 1.4 mmol), X-Phos (67 mg, 0.14 mmol) and $PdCl_2(ACN)_2$ (19 mg, 0.07 mmol). The reaction mixture was stirred at 90° C. for 16 h until the reaction was complete (by LCMS). $H_2O$ (10 mL) and EA (20 mL) were added and the organic phase was collected and evaporated under reduced pressure. The residue was purified by Prep-HPLC to give H-328 (39.5 mg, yield: 17%) as yellow oil.

Additional exemplary compounds were prepared following methods substantially similar to the method described above and herein. Data for these compounds are provided below.

TABLE 20

Characterization Data for Additional Exemplary Compounds

| Compound No. | Chemical Structure | [M + H] observed | $^1$H NMR (400 MHz) |
|---|---|---|---|
| I-330 | 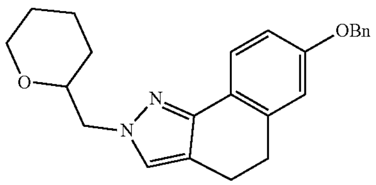 [SMILES: c1ccc(COc2ccc3c(c2)CCc2cn(CC4CCCCO4)nc2-3)cc1] | 375.2 | $^1$H NMR (400 MHz, DMSO-$d_6$): δ 7.55 (d, J = 8.4 Hz, 1H), 7.32-7.47 (m, 6H), 6.95 (d, J = 2.4 Hz, 1H), 6.88 (dd, J = 2.4 Hz, 8.4 Hz, 1H), 5.10 (s, 2H), 4.05 (d, J = 6.0 Hz, 2H), 3.85 (d, J = 11.2 Hz, 1H), 3.61-3.67 (m, 1H), 3.26-3.30 (m, 1H), 2.80-2.84 (m, 2H), 2.63-2.67 (m, 2H), 1.76-1.78 (m, 1H), 1.39-1.57 (m, 4H), 1.14-1.23 (m, 1H). |
| I-331 | 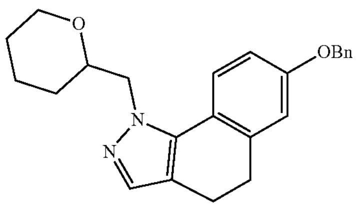 [SMILES: c1ccc(COc2ccc3c(c2)CCc2cnn(CC4CCCCO4)c2-3)cc1] | 375.3 | $^1$H NMR (400 MHz, DMSO-$d_6$): δ 7.71 (d, J = 8.8 Hz, 1H), 7.31-7.47 (m, 6H), 7.05 (d, J = 2.0 Hz, 1H), 6.96 (dd, J = 2.4 Hz, 8.4 Hz, 1H), 5.13 (s, 2H), 4.35-4.40 (m, 1H), 4.19-4.24 (m, 1H), 3.74-3.84 (m, 2H), 3.24-3.30 (m, 1H), 2.53-2.82 (m, 4H), 1.78 (s, 1H), 1.58 (d, J = 12.0 Hz, 1H), 1.23-1.45 (m, 4H). |

TABLE 20-continued
| Characterization Data for Additional Exemplary Compounds | | | |
|---|---|---|---|
| Compound No. | Chemical Structure | [M + H] observed | $^1$H NMR (400 MHz) |
| I-328 | 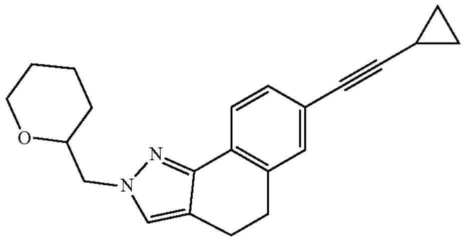 [SMILES: C(#CC1CC1)c1ccc2c(c1)CCc1cn(CC3CCCCO3)nc1-2] | 333.0 | $^1$H NMR (400 MHz, DMSO-$d_6$): δ 7.55 (d, J = 7.6 Hz, 1H), 7.48 (s, 1H), 7.25 (s, 1H), 7.20 (dd, J = 1.6 Hz, 8.0 Hz, 1H), 4.08 (d, J = 6.0 Hz, 2H), 3.85 (d, J = 11.2 Hz, 1H), 3.62-3.68 (m, 1H), 3.26-3.31 (m, 1H), 2.80-2.83 (m, 2H), 2.64-2.68 (m, 2H), 1.76-1.78 (m, 1H), 1.39-1.58 (m, 5H), 1.15-1.25 (m, 1H), 0.86-0.91 (m, 2H), 0.70-0.74 (m, 2H). |
| I-329 | 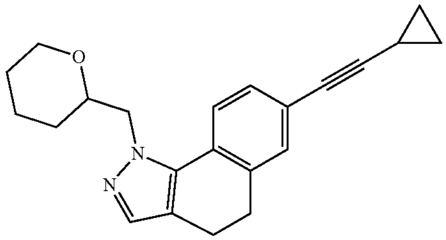 [SMILES: C(#CC1CC1)c1ccc2c(c1)CCc1cnn(CC3CCCCO3)c1-2] | 333.4 | $^1$H NMR (400 MHz, DMSO-$d_6$): δ 7.72 (d, J = 8.0 Hz, 1H), 7.36 (s, 1H), 7.34 (s, 1H), 7.29 (d, J = 7.6 Hz, 1H), 4.40 (dd, J = 7.2 Hz, 14.4 Hz, 1H), 4.25 (dd, J = 4.8 Hz, 14.4 Hz, 1H), 3.74-3.83 (m, 2H), 3.23-3.29 (m, 1H), 2.70-2.82 (m, 2H), 2.53-2.66 (m, 2H), 1.78 (s, 1H), 1.44-1.58 (m, 5H), 1.22-1.34 (m, 1H), 0.87-0.92 (m, 2H), 0.71-0.75 (m, 2H). |
Example 20: Synthesis of I-332
Synthetic Scheme of I-332
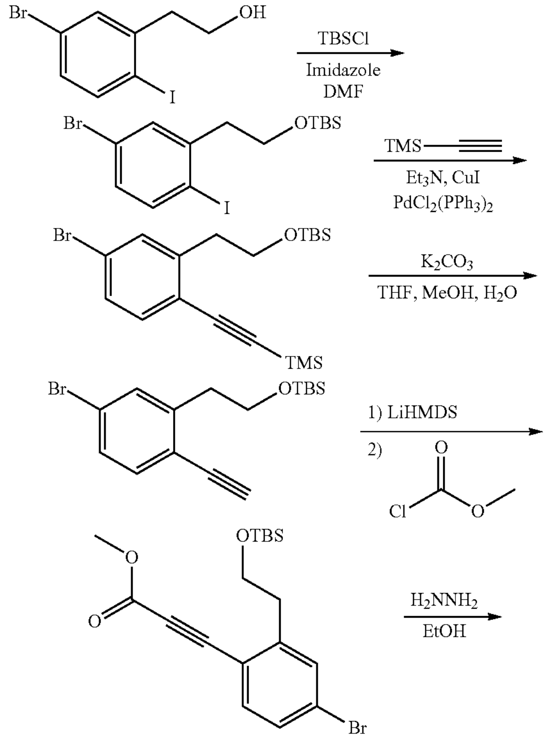
-continued
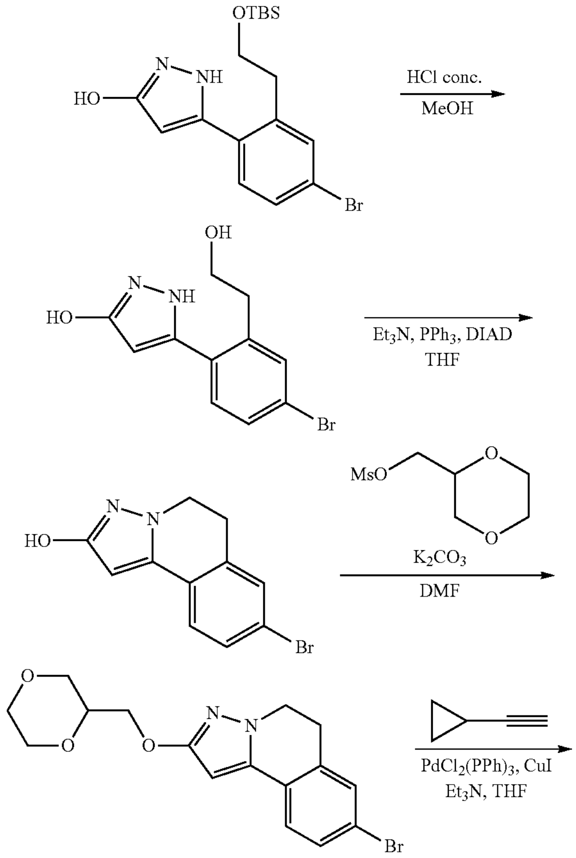

-continued

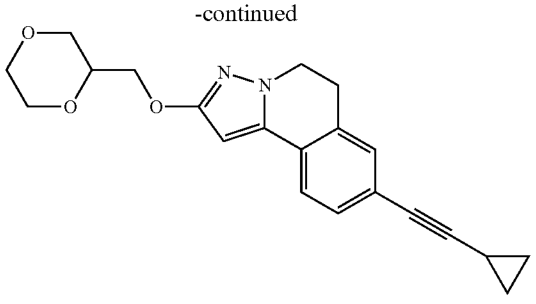

I-332

1. The Synthesis of Intermediate (5-bromo-2-iodophenethoxy)(tert-butyl)dimethylsilane

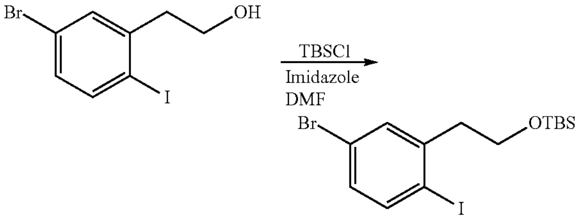

A reaction vial was charged with 2-(5-bromo-2-iodophenyl)ethanol (1.40 g, 4.28 mmol) and anh. DMF (4.28 mL), Imidazole (471 mg, 6.85 mmol) followed by tert-butyldimethylsilyl chloride (1.05 g, 6.85 mmol), the reaction was stirred at RT for 1 hour. The reaction mixture was diluted with EtOAc (15 ml) and heptanes (15 ml), washed with half-sat. $NH_4Cl$ (2×15 ml) and water (2×15 ml), dried over sodium sulfate and concentrated to dryness. Co-evaporation with heptanes (1×30 ml) afforded (5-bromo-2-iodophenethoxy)(tert-butyl)dimethylsilane (1.80 g, 95%) as a colorless oil.

$^1H$ NMR (400 MHz, $CDCl_3$) δ 7.63 (d, J 8.4 Hz, 1H), 7.39 (d, J 2.4 Hz, 1H), 7.02 (dd, J 8.4, 2.45 Hz, 1H), 3.78 (t, J 6.6 Hz, 2H), 2.90 (t, J 6.6 Hz, 2H), 0.85 (s, J 2.9 Hz, 9H), −0.05 (s, J 3.1 Hz, 6H).

2. The Synthesis of Intermediate (5-bromo-2-((trimethylsilyl)ethynyl)phenethoxy)(tert-butyl)dimethylsilane

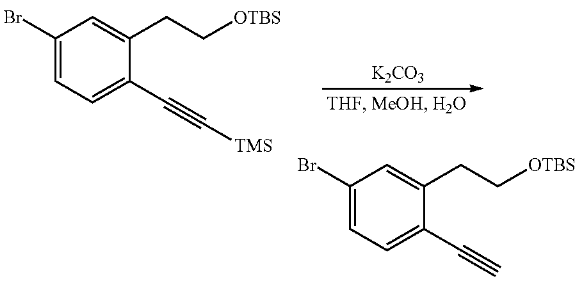

A reaction vial was charged with (5-bromo-2-iodophenethoxy)(tert-butyl)dimethylsilane (1.75 g, 3.97 mmol), $PdCl_2(PPh_3)_2$ (84.4 mg, 119 umol), Copper(I) iodide (22.8 mg, 119 umol) and flushed with nitrogen. Anh. THF (7.93 mL) was added and further degassed with nitrogen for 2 minutes, cooled to 0° C. in an ice bath and Triethylamine (1.68 mL, 11.9 mmol) and (Trimethylsilyl)acetylene (623 uL, 4.36 mmol) were added and degassed for 1 minute and capped with septum and nitrogen balloon. The reaction mixture was warmed to RT over 18h. The reaction mixture was diluted with EtOAc (40 ml) and washed with half-saturated $NH_4Cl$ (2×30 ml), dried over sodium sulfate and concentrated. Purification by normal phase FCC (50 g cartridge, 0 to 5% DCM in hexanes gradient) afforded (5-bromo-2-((trimethylsilyl)ethynyl)phenethoxy)(tert-butyl)dimethylsilane (1.23 g, 57%) as a light yellow oil. LCMS (C): Rt=2.65 min; 97% purity, no ionisation.

3. The Synthesis of Intermediate (5-bromo-2-ethynylphenethoxy)(tert-butyl)dim ethylsilane

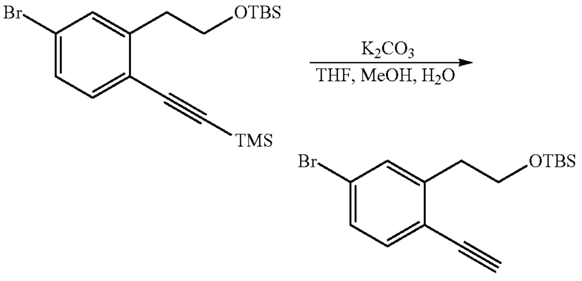

A reaction vial was charged with (5-bromo-2-((trimethylsilyl)ethynyl)phenethoxy)(tert-butyl)dimethylsilane (1.23 g, 2.99 mmol), THF (7.40 mL), $H_2O$ (148 uL), MeOH (7.40 mL) and Potassium carbonate (413 mg, 2.99 mmol) and the reaction mixture was stirred for 30 min at RT. The reaction mixture was diluted with half-saturated $NH_4Cl$ (20 ml) and extracted with 1:1 EtOAc:heptanes (2×25 ml), dried over sodium sulfate and concentrated to dryness to afford (5-bromo-2-ethynylphenethoxy)(tert-butyl)dimethylsilane (0.970 g, 96%) as a colorless oil used directly in the next step.

4. The Synthesis of Intermediate 3-(4-bromo-2-(2-((tert-butyldimethylsilyl)oxy)ethyl)-phenyl)propiolate

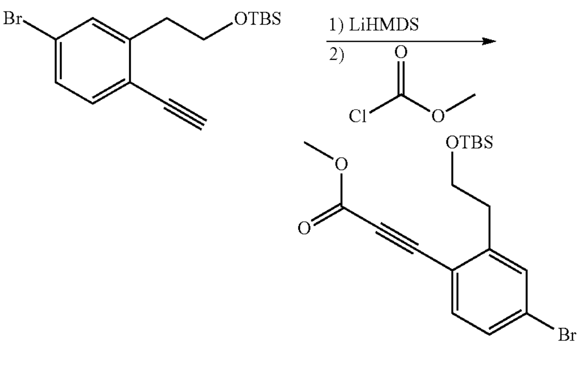

A flame dried flask was charged with (5-bromo-2-ethynylphenethoxy)(tert-butyl)dimethylsilane (970 mg, 2.86 mmol), anh. THE (9.53 mL) and cooled to −78° C. Lithium bis(trimethylsilyl)amide solution (4.29 mL, 4.29 mmol) (1 M in THF) was added dropwise and the reaction mixture was stirred at that temperature for 35 minutes. Methyl chloroformate (339 uL, 4.34 mmol) was added and stirred for 30 minutes at −78° C. and quenched by addition of sat. $NH_4Cl$ (5 ml). Once warmed to RT, the reaction mixture was extracted with EtOAc (30 ml), dried over sodium sulfate and concentrated to afford methyl 3-(4-bromo-2-(2-((tert-butyldimethylsilyl)oxy)ethyl)phenyl)-propiolate (1.29 g, crude) as a crude mixture used directly in the next step.

5. The Synthesis of Intermediate 5-(4-bromo-2-(2-((tert-butyldimethylsilyl)oxy)ethyl)-phenyl)-1H-pyrazol-3-ol

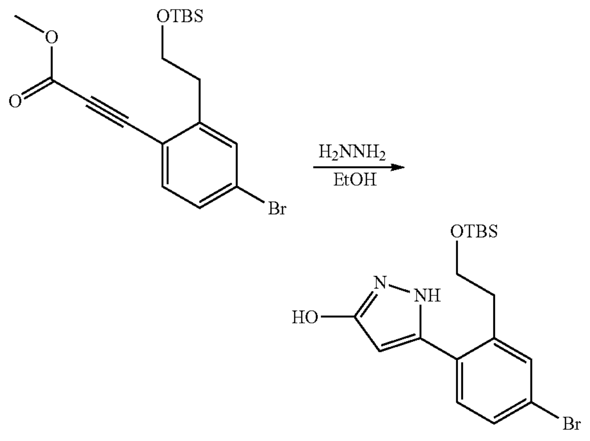

A reaction vial under nitrogen was charged with methyl 3-(4-bromo-2-(2-((tert-butyldimethylsilyl)oxy)ethyl)phenyl)propiolate (1.18 g, 2.86 mmol), anh. EtOH (14.3 mL) and hydrazine hydrate solution (302 uL, 5.72 mmol) (60 wt %) was added and the reaction mixture was heated at 80° C. for 2h. The reaction mixture was concentrated to dryness, co-evaporated with heptanes (4 ml) and purification by reverse phase FCC (30 g C18 cartridge, 10 to 70% ACN in 10 mM ammonium formate gradient) afforded 5-(4-bromo-2-(2-((tert-butyldimethylsilyl)oxy)-ethyl)phenyl)-1H-pyrazol-3-ol (580 mg, 48%) as a tan solid. LCMS (C): Rt=1.96 min (M+H)+: 399.2; >98% purity.

6. The Synthesis of Intermediate 5-(4-bromo-2-(2-hydroxyethyl)phenyl)-1H-pyrazol-3-ol

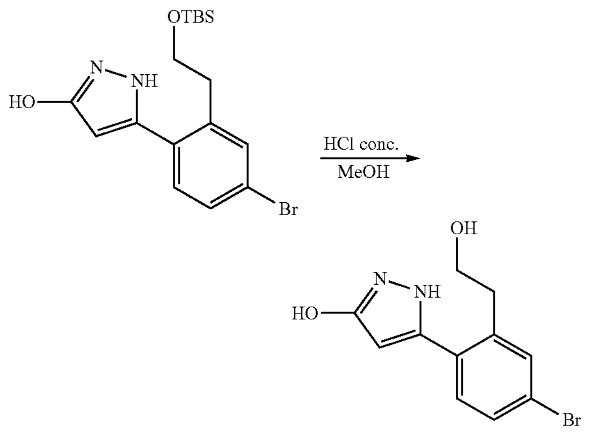

A flask was charged with 5-(4-bromo-2-(2-((tert-butyldimethylsilyl)oxy)ethyl)phenyl)-1H-pyrazol-3-ol (580 mg, 1.46 mmol), anh. MeOH (14.6 mL) and Hydrochloric acid (120 uL, 1.46 mmol) (concentrated) was added and the reaction mixture was stirred at RT for 30 minutes. The reaction mixture was concentrated to dryness, co-evaporated with MeOH and heptanes. The residue was triturated with DCM (15 ml) and filtered to afford 5-(4-bromo-2-(2-hydroxyethyl)phenyl)-1H-pyrazol-3-ol (445 mg, crude) (HCl salt) as a link pink solid used directly in the next step.

7. The Synthesis of Intermediate 8-bromo-5,6-dihydropyrazolo[5,1-a]isoquinolin-2-ol

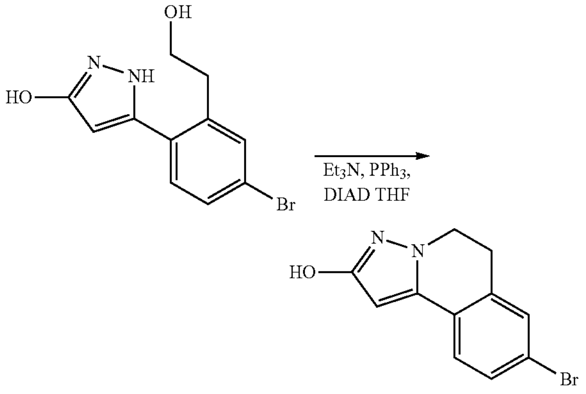

A reaction vial was charged with 5-(4-bromo-2-(2-hydroxyethyl)phenyl)-1H-pyrazol-3-ol (400 mg, 1.41 mmol) (HCl salt), triphenylphosphine (561 mg, 2.12 mmol), anh. THE (10.6 mL) and Triethylamine (197 uL, 1.40 mmol) was added and cooled to 0° C. using an ice bath and Diisopropylazodicarboxylat (426 uL, 2.12 mmol) was added. After 5 minutes the ice bath was removed and the reaction mixture was stirred for 1h. The reaction mixture was diluted with half-saturated $NH_4Cl$ (30 ml) and extracted with EtOAc (3×15 mL) and ($CHCl_3$:IPA(4:1), 25 ml), dried over sodium sulfate and concentrated to dryness. The residue was triturated with MeOH (8 ml) at 4° C. and the supernatant was pipetted off and the residue was dried under vacuum to afford 8-bromo-5,6-dihydropyrazolo[5,1-a]isoquinolin-2-ol (257 mg, 62%) as a white solid. $^1$NMR (400 MHz, DMSO-$d_6$) δ 9.81 (s, 1H), 7.56 (d, J 1.4 Hz, 1H), 7.51 (d, J 8.2 Hz, 1H), 7.47 (dd, J 8.3, 1.9 Hz, 1H), 5.97 (s, 1H), 4.00 (t, J 7.0 Hz, 2H), 3.13 (t, J 7.0 Hz, 2H). LCMS (C): Rt=1.43 min (M+H)+H: 267.0, 90% purity at 220 nm.

8. The Synthesis of Intermediate 8-bromo-5,6-dihydropyrazolo[5,1-a]isoquinolin-2-ol

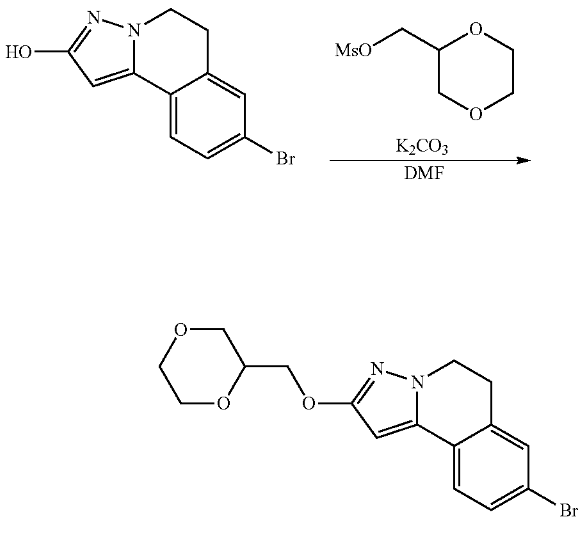

A reaction vial was charged with 8-bromo-5,6-dihydropyrazolo[5,1-a]isoquinolin-2-ol (80.0 mg, 302 umol), (1,4-dioxan-2-yl)methyl methanesulfonate (118 mg, 604 umol), Potassium carbonate (125 mg, 905 umol), flushed with nitrogen and anh. DMF (1.00 mL) was added and the reaction mixture was stirred at 60° C. overnight a second portion of (1,4-dioxan-2-yl)methyl methanesulfonate (118 mg, 604 umol) and Potassium carbonate (125 mg, 905 umol) were added and the reaction mixture was heated at 80° C. for 6h. The reaction mixture was diluted with EtOAc (25 ml) and washed with water (4×15 ml), dried over sodium sulfate and concentrated to dryness. Trituration with MeOH (2×3 ml) afforded 2-((1,4-dioxan-2-yl)methoxy)-8-bromo-5,6-dihydropyrazolo[5,1-a]isoquinoline (67.0 mg, 61%) as a white solid. LCMS (C): Rt=1.63 min, >95% purity; (M+H+): 367.1

9. The Synthesis of I-332

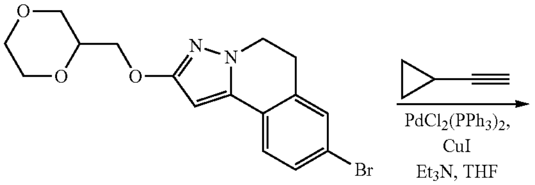

-continued

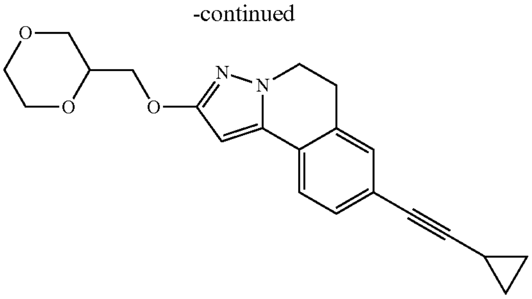

A reaction vial was charged with 2-((1,4-dioxan-2-yl)methoxy)-8-bromo-5,6-dihydropyrazolo[5,1-a]isoquinoline (30.0 mg, 82.1 umol), Copper(I) iodide (1.56 mg, 8.21 umol), PdCl2(PPh3)2 (5.88 mg, 8.21 umol), and flushed with nitrogen. THE (479 uL) and Triethylamine (92.5 uL, 657 umol) were added and the reaction mixture was further degassed with nitrogen for 2 minutes and then Cyclopropylacetylene (57.3 uL, 657 umol) was added and the reaction mixture was heated to 60° C. for 18h. The reaction mixture concentrated overnight. It was directly purified by reverse phase FCC (30 g C18 cartridge, 5 to 50% ACN in 10 mM ammonium formate gradient) to afford 2-((1,4-dioxan-2-yl)methoxy)-8-(cyclopropylethynyl)-5,6-dihydropyrazolo[5,1-a]isoquinoline, I-332 (15.0 mg, 52%) as a light tan powder after lyophilisation.

Additional exemplary compounds were prepared following methods substantially similar to the method described above and herein. Data for these compounds are provided below.

TABLE 21

Characterization Data for Additional Exemplary Compounds

| Compound No. | Chemical Structure | [M + H] observed | $^1$H NMR (400 MHz) |
|---|---|---|---|
| I-332 | 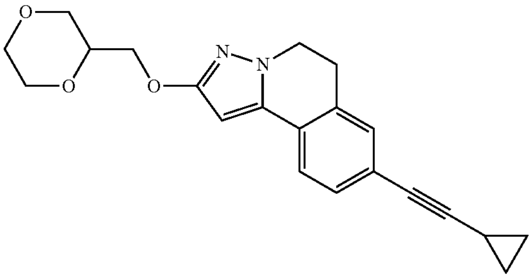 [SMILES: C(#CC1CC1)c1ccc2c(c1)CCn1nc(OCC3COCCO3)cc1-2] | 351.2 | $^1$H NMR (400 MHz, DMSO-d$_6$): δ 7.52 (d, J = 8.0 Hz, 1H), 7.33 (d, J = 0.89 Hz, 1H), 7.28 (dd, J = 8.0, 1.6 Hz, 1H), 6.21 (s, 1H), 4.11-3.99 (m, 4H), 3.88-3.81 (m, 1H), 3.81-3.72 (m, 2H), 3.69-3.56 (m, 2H), 3.53-3.45 (m, 1H), 3.41-3.33 (m, 1H), 3.11 (t, J = 7.0 Hz, 2H), 1.55 (tt, J = 8.2, 5.0 Hz, 1H), 0.93-0.86 (m, 2H), 0.76-0.70 (m, 2H). |

Example 21: Synthesis of I-303

Synthetic Scheme of I-303

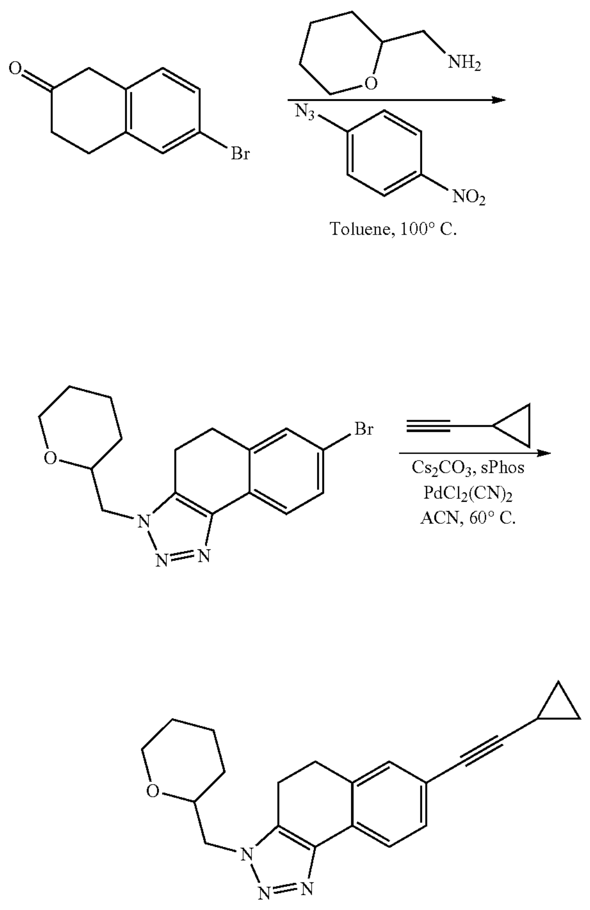

I-303

1. The Synthesis of Intermediate 7-bromo-3-((tetrahydro-2H-pyran-2-yl)methyl)-4,5-dihydro-3H-naphtho[1,2-d][1,2,3]triazole

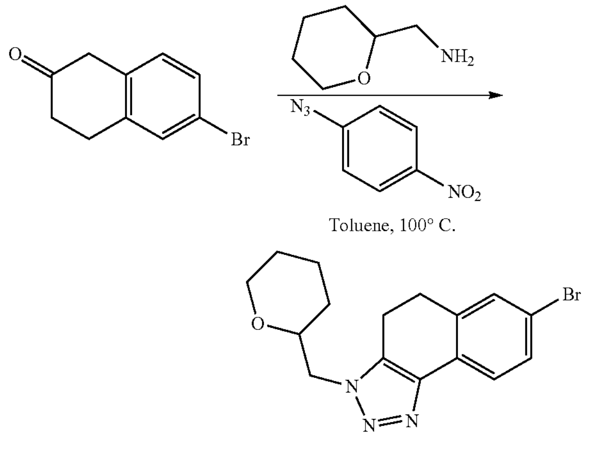

A flame dried reaction vial was charged with 6-bromo-3,4-dihydro-2(1H)-naphthalenone (80.0 mg, 355 umol), (tetrahydro-2H-pyran-2-yl)methanamine (60.3 mg, 498 umol), 1-azido-4-nitrobenzene (58.3 mg, 355 umol) and 80 mg of 4A molecular sieves (briefly flame dried under vacuum), and purged with nitrogen. Anh. Toluene (800 uL) was added and the reaction mixture was heated at 100° C. for 90 minutes. Once cooled, the reaction mixture was diluted with DCM (20 ml), washed with 1 M HCl (20 ml), dried over sodium sulfate and concentrated. Purification by reverse phase FCC (30 g C18 cartridge, 10 to 60% ACN in 10 mM ammonium formate gradient) afforded 7-bromo-3-((tetrahydro-2H-pyran-2-yl)methyl)-4,5-dihydro-3H-naphtho[1,2-d][1,2,3]triazole (71.0 mg, 57%) as a tan powder after lyophilisation. $^1$H NMR (400 MHz, CDCl3) δ 7.86-7.78 (m, 1H), 7.42 (dd, J 8.1, 1.9 Hz, 1H), 7.38 (d, J 1.9 Hz, 1H), 4.40 (dd, J 14.2, 3.3 Hz, 1H), 4.20 (dd, J 14.2, 7.7 Hz, 1H), 3.93-3.84 (m, 1H), 3.75-3.66 (m, 1H), 3.39-3.27 (m, 1H), 3.09-2.88 (m, 4H), 1.90-1.83 (m, 1H), 1.73-1.64 (m, 1H), 1.59-1.43 (m, 3H), 1.35-1.19 (m, 1H). LCMS (C): Rt=1.76 min (M+H)+: 350.1. 95% purity.

2. The Synthesis of I-303

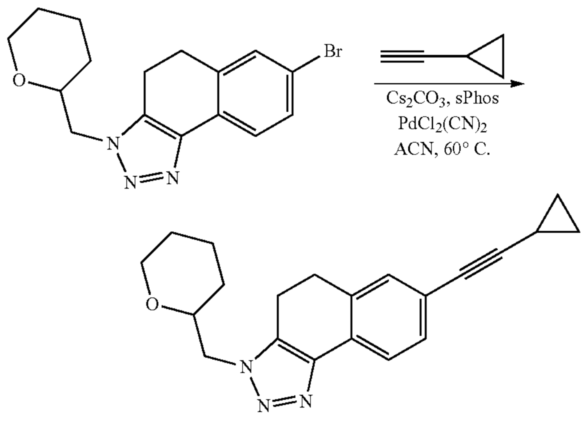

I-303

A reaction vial was charged with 7-bromo-3-((tetrahydro-2H-pyran-2-yl)methyl)-4,5-dihydro-3H-naphtho[1,2-d][1,2,3]triazole (30.0 mg, 86.1 umol), bis(acetonitrile)dichloropalladium(II) (2.26 mg, 8.61 umol), 2-dicyclohexylphosphino-2',6'-dimethoxybiphenyl (10.8 mg, 25.8 umol), cesium carbonate (56.7 mg, 172 umol) and flushed with nitrogen. ACN (137 uL) was added and the reaction mixture was further degassed with nitrogen for 2 minutes and then cyclopropylacetylene (60.1 uL, 689 umol) was added and the reaction mixture was heated to 60° C. overnight. Half-saturated $NH_4Cl$ (4 ml) was added and extracted with EtOAc (2×5 ml). The organic layer was dried over sodium sulfate, concentrated and purified by reverse chromatography (30 g C18 cartridge; 5 to 50% ACN in 10 mM ammonium formate gradient) and then and purified by normal chromatography (10 g SiO2 cartridge, 0 to 5% MeOH in DCM gradient) to afford 7-(cyclopropylethynyl)-3-((tetrahydro-2H-pyran-2-yl)methyl)-4,5-dihydro-3H-naphtho[1,2-d][1,2,3]triazole, I-303 (5 mg, 17%) as a white powder.

Additional exemplary compounds were prepared following methods substantially similar to the method described above and herein. Data for these compounds are provided below.

TABLE 22

Characterization Data for Additional Exemplary Compounds

| Compound No. | Chemical Structure | [M + H] observed | $^{1}H$ NMR (400 MHz) |
|---|---|---|---|
| I-303 | 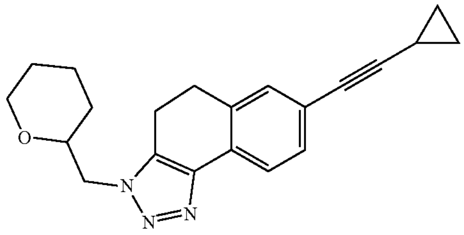 [SMILES: C(#CC1CC1)c1ccc2c(c1)CCc1c-2nnn1CC1CCCCO1] | 334.2 | $^{1}H$ NMR (400 MHz, $CD_3CN$): δ 7.70 (d, J = 8.4 Hz, 1H), 7.27-7.25 (m, 2H), 4.34 (dd, J = 14.4, 3.7 Hz, 1H), 4.25 (dd, J = 14.4, 7.7 Hz, 1H), 3.86-3.82 (m, 1H), 3.71-3.65 (m, 1H), 3.35-3.25 (m, 1H), 3.04-2.97 (m, 2H), 2.97-2.90 (m, 2H), 1.86-1.79 (m, 1H), 1.69-1.65 (m, 1H), 1.50-1.41 (m, 3H), 1.30-1.20 (m, 1H), 0.92-0.85 (m, 2H), 0.76-0.69 (m, 2H). |
| I-304 | 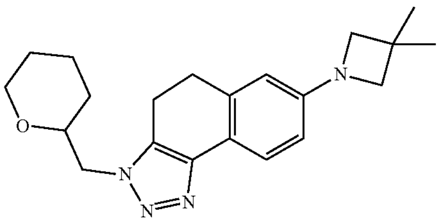 [SMILES: CC1(C)CN(c2ccc3c(c2)CCc2c-3nnn2CC2CCCCO2)C1] | 353.2 | $^{1}H$ NMR (400 MHz, $CD_3CN$): δ 7.58 (d, J = 8.1 Hz, 1H), 6.36 (d, J = 2.0 Hz, 1H), 6.33 (dd, J = 8.1, 2.4 Hz, 1H), 4.29 (dd, J = 14.3, 3.9 Hz, 1H), 4.22 (dd, J = 14.3, 7.6 Hz, 1H), 3.87-3.80 (m, 1H), 3.67 (dddd, J = 11.3, 7.5, 3.9, 2.1 Hz, 1H), 3.55 (s, 4H), 3.35-3.25 (m, 1H), 2.97-2.91 (m, 2H), 2.90-2.84 (m, 2H), 1.86-1.78 (m, 1H), 1.68-1.61 (m, 1H), 1.56-1.40 (m, 3H), 1.30(s, 6H), 1.29-1.18 (m, 1H). |
| I-305 | 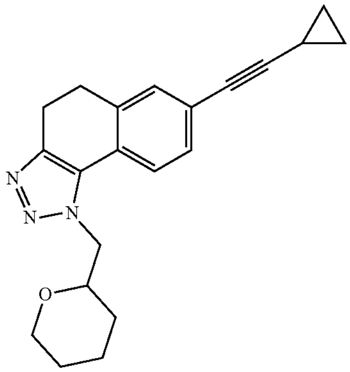 [SMILES: C(#CC1CC1)c1ccc2c(c1)CCc1nnn(CC3CCCCO3)c1-2] (from isomeric SM: 6-bromo-3, 4-dihydronaphthalen-1(2H)-one) | 334.2 | $^{1}H$ NMR (400 MHz, $CD_3CN$): δ 7.72 (d, J = 8.1 Hz, 1H), 7.33 (d, J = 1.0 Hz, 1H), 7.29 (dd, J = 8.1, 1.7 Hz, 1H), 4.59-4.55 (m, 2H), 3.86-3.77 (m, 2H), 3.33-3.23 (m, 1H), 3.00-2.92 (m, 2H), 2.92-2.79 (m, 2H), 1.88-1.80 (m, 1H), 1.75-1.68 (m, 1H), 1.56-1.45 (m, 4H), 1.44-1.32 (m, 1H), 0.94-0.86 (m, 2H), 0.78-0.72 (m, 2H). |

Example 22: Synthesis of I-447

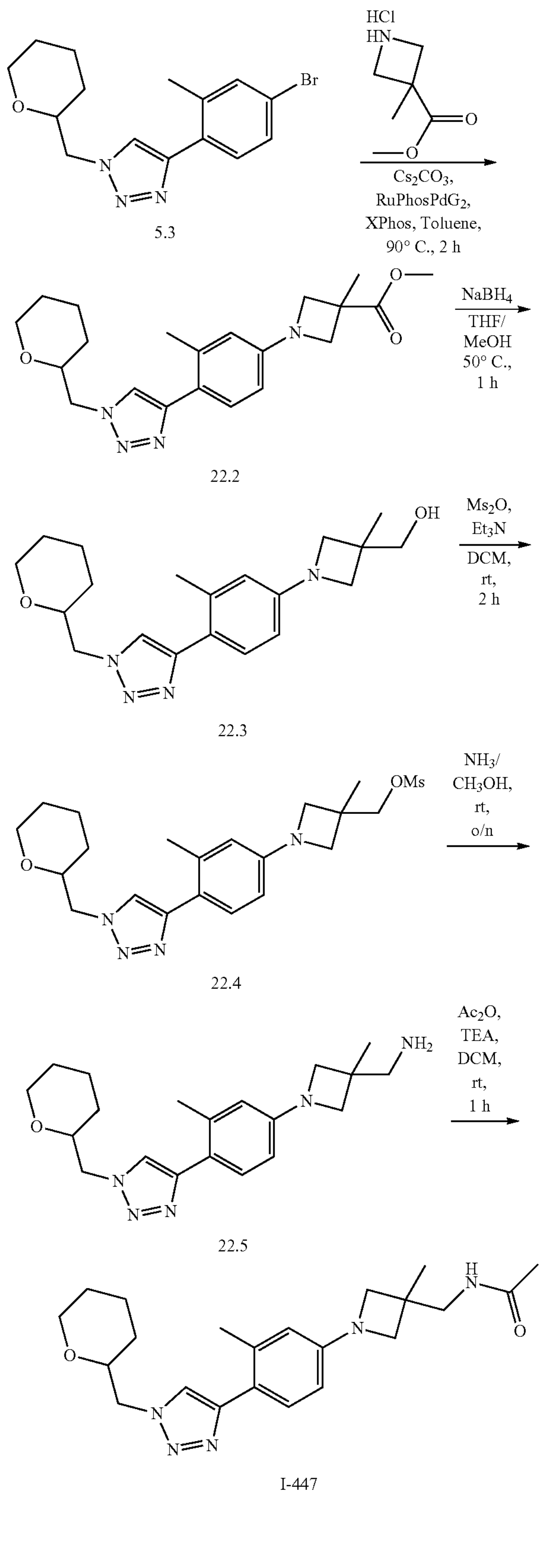

5.3

22.2

22.3

22.4

22.5

I-447

1. The Synthesis of Intermediate 22.2

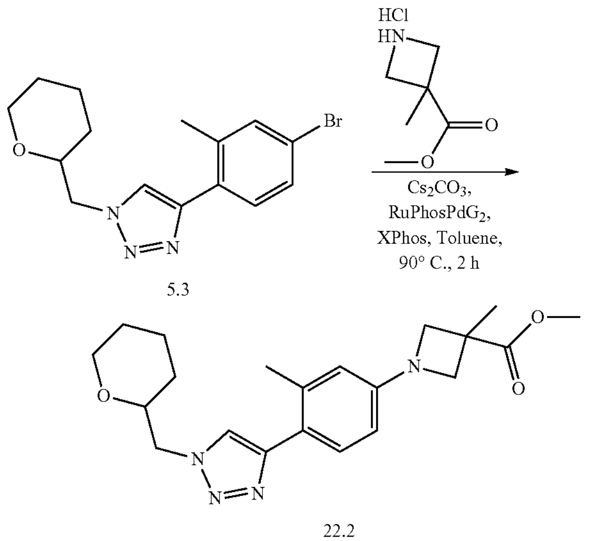

5.3

22.2

To a stirred solution of 5.3 (1 g, 3 mmol), methyl 3-methylazetidine-3-carboxylate hydrochloride (742 mg, 4.5 mmol) and $Cs_2CO_3$ (2.9 g, 9 mmol) in toluene (20 mL) was added $RuPhosPdG_2$ (100 mg), X-Phos (200 mg). The reaction mixture was stirred at 90° C. for 2 hours until the reaction was complete (by LCMS). The suspension was diluted with $H_2O$ (40 mL), extracted with EA (40 mL×2) and concentrated. The crude product was purified by flash column chromatography (silica gel, PE/EA=1:1) to give 22.2 (1.1 g, yield: 95%) as yellow oil.

2. The Synthesis of Intermediate 22.3

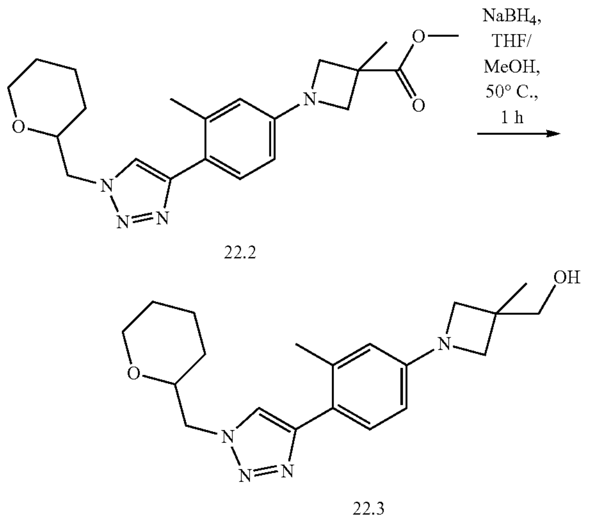

22.2

22.3

To a stirred solution of 22.2 (1.1 g, 2.8 mmol) in anhydrous THF (20 mL), was added $NaBH_4$ (319 mg, 8.4 mmol) and MeOH (10 mL). The reaction mixture was stirred for 1 h at 50° C. The reaction mixture was diluted with $H_2O$ (40 mL), extracted with EA (50 mL×2) and concentrated to dryness. The crude product was purified by flash column chromatography (silica gel, PE/EA=1:1) to give 22.3 (800 mg, yield: 80%) as yellow oil.

3. The Synthesis of Intermediate 22.4

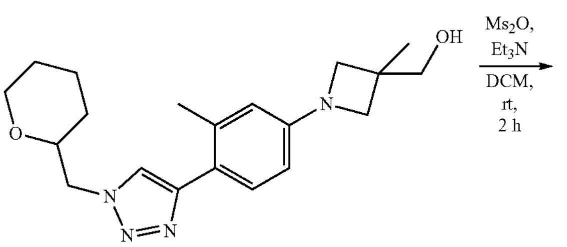

22.3

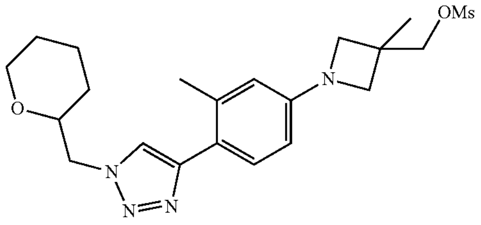

22.4

To a stirred solution of 22.3 (800 mg, 2.2 mmol) in DCM (20 mL) was added $Et_3N$ (667 mg, 6.6 mmol) and $Ms_2O$ (766 mg, 4.4 mmol). The reaction mixture was stirred at room temperature for 2 h until the reaction was complete. The suspension was diluted with $H_2O$ (30 mL), extracted with DCM (30 mL×2) and concentrated. The crude product was used to the next step directly.

4. The Synthesis of Intermediate 22.5

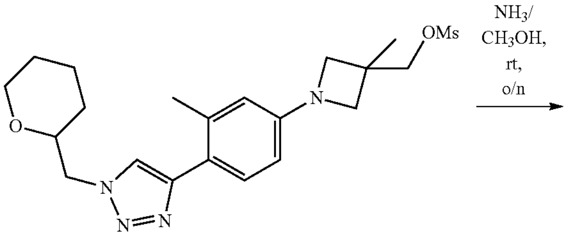

22.4

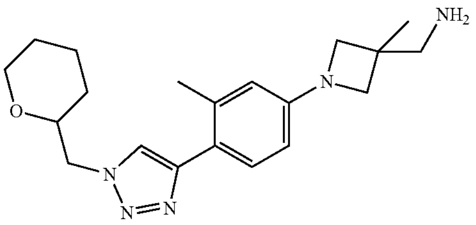

22.5

To a stirred solution of 22.4 (900 mg, 2.1 mmol) in $NH_3$ (20 mL, 7 N in $CH_3OH$) was stirred at room temperature overnight until the reaction was complete. The suspension was concentrated to give 22.5 (400 mg, yield: 54%) as yellow oil. LC-MS m/z: 356.2 $[M+H]^+$.

5. The Synthesis of I-447

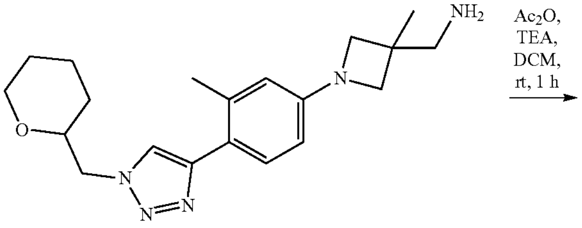

22.5

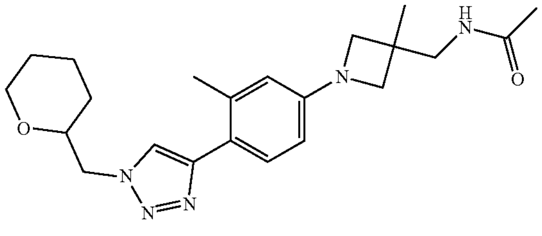

I-447

To a stirred solution of 22.5 (100 mg, 0.28 mmol) in DCM (5 mL) was added $Et_3N$ (85 mg, 0.84 mmol) and $Ac_2O$ (57 mg, 0.56 mmol). The reaction mixture was stirred at room temperature for 1 h until the reaction was complete. The suspension was diluted with $H_2O$ (30 mL), extracted with DCM (30 mL×2) and concentrated. The crude product was purified by Prep-HPLC to give I-447 (54.44 mg, yield: 49%) as a white solid.

Additional exemplary compounds were prepared following methods substantially similar to the method described above and herein. Data for these compounds are provided in Table 23, Following Example 34.

Example 23: Synthesis of I-609

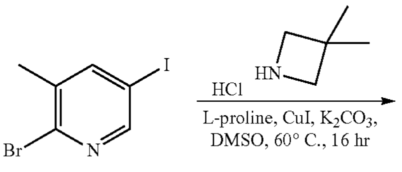

23.1

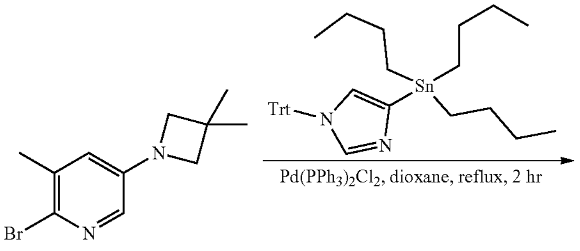

23.2

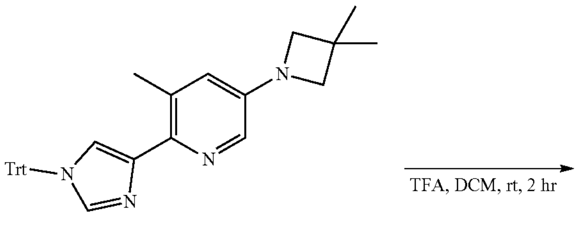

23.3

-continued

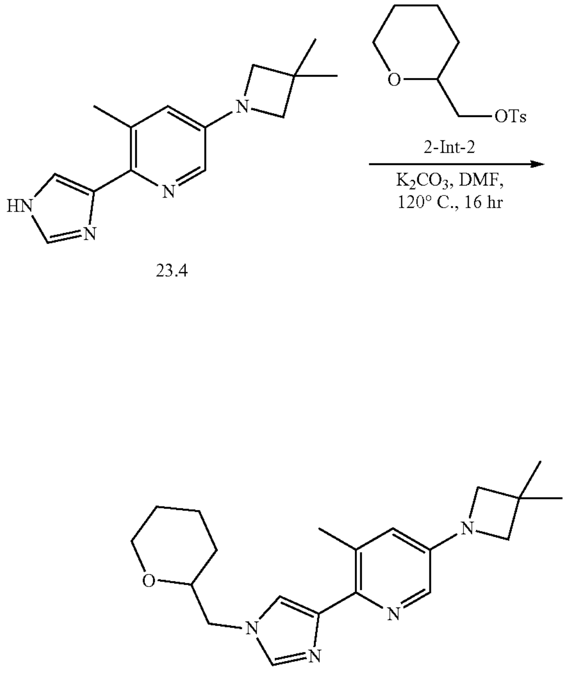

23.4

I-609

1. The Synthesis of Intermediate 23.2

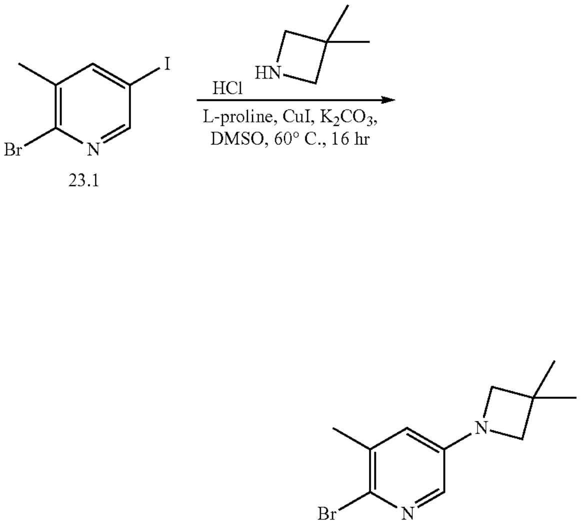

23.1

23.2

To a stirred solution of 23.1 (6.0 g, 20.1 mmol), 3,3-dimethylazetidine hydrochloride (2.4 g, 20.1 mmol) and $K_2CO_3$ (5.5 g, 40.2 mmol) in DMSO (150 mL) was added L-proline (483 mg) and CuI (382 mg). The reaction mixture was stirred at 60° C. for 16 hours until the reaction was complete (by LCMS). The suspension was diluted with $H_2O$ (100 mL) and extracted with EA (50 mL×2), the combined organic layer was concentrated. The crude product was purified by flash column 464hromatography (silica gel, PE/EA=2:1) to give 23.2 (900 mg, yield: 17%) as yellow oil.

2. The Synthesis of Intermediate 23.3

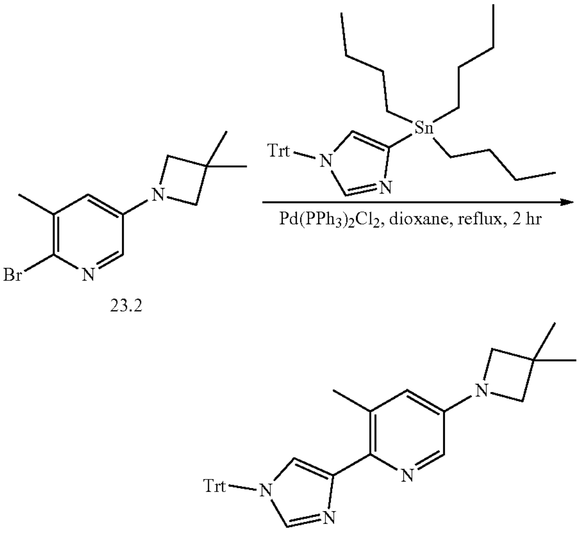

23.2

23.3

To a stirred solution of 23.2 (900 mg, 3.5 mmol), 4-(tributylstannyl)-1-trityl-1H-imidazole (2.3 g, 3.85 mmol) in dioxane (60 mL) was added $Pd(PPh_3)_2Cl_2$ (382 mg). The reaction mixture was stirred at reflux for 2 hours until the reaction was complete (by LCMS). The suspension was diluted with $H_2O$ (100 mL) and extracted with EA (50 mL×2), the combined organic layer was concentrated. The crude product was purified by flash column chromatography (silica gel, DCM/MeOH=10:1) to give 23.3 (592 mg, yield: 35%) as yellow solid. LC-MS m/z: 485.0 $[M+H]^+$.

2. The Synthesis of Intermediate 23.4

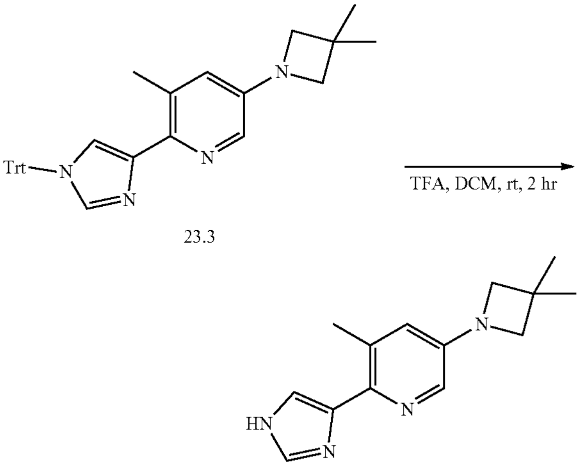

23.3

23.4

To a stirred solution of 23.3 (592 mg, 1.2 mmol) in DCM (40 mL) was added TFA (8 mL). The reaction mixture was stirred at rt for 2 hours until the reaction was complete (by LCMS). The suspension was diluted with $H_2O$ (100 mL) and extracted with DCM (50 mL×2), the combined organic layer was concentrated. The crude product was purified by flash column chromatography (silica gel, DCM/MeOH=10:1) to give 23.4 (261 mg, yield: 90%) as a yellow solid. LC-MS m/z: 243.1 $[M+H]^+$.

3. The Synthesis of Target I-609

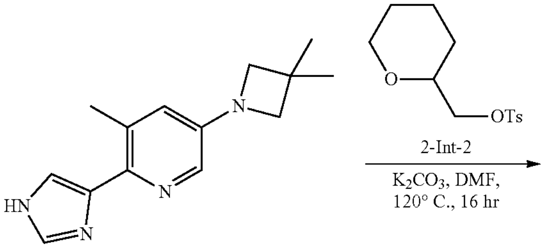

23.4

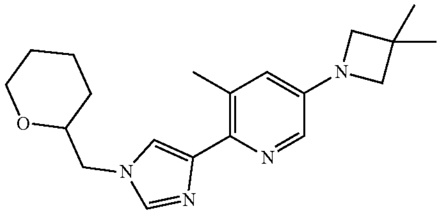

I-609

To a stirred solution of 23.4 (261 mg, 1.1 mmol), (tetrahydro-2H-pyran-2-yl)methyl 4-methylbenzenesulfonate (2-Int-2, 297 mg, 1.1 mmol) in DMF (20 mL) was added $K_2CO_3$ (303 mg, 2.2 mmol). The reaction mixture was stirred at 120° C. for 16 hours until the reaction was complete (by LCMS). The suspension was diluted with $H_2O$ (100 mL) and extracted with EA (100 mL×2), the combined organic layer was concentrated. The crude product was purified by Prep-HPLC to give I-609 (295 mg, yield: 79%) as a white solid.

Additional exemplary compounds were prepared following methods substantially similar to the method described above and herein. Data for these compounds are provided in Table 23, Following Example 34.

Example 24: Synthesis of I-425

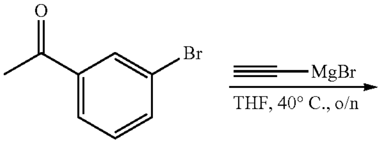

24.1

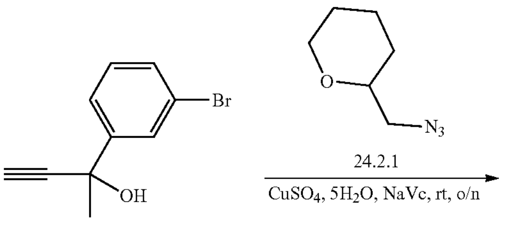

24.2

-continued

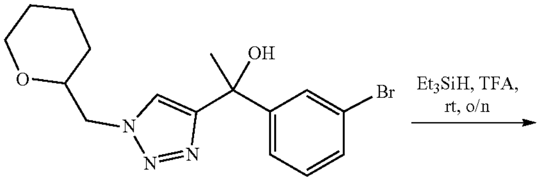

24.3

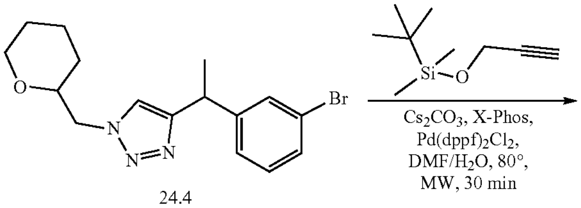

24.4

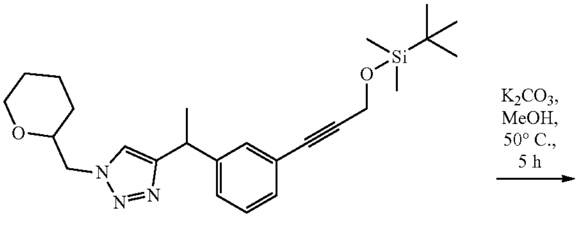

24.5

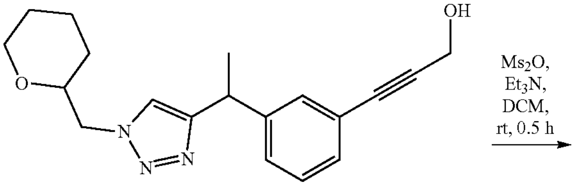

24.6

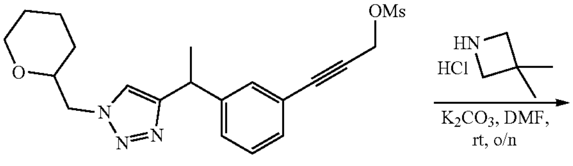

24.7

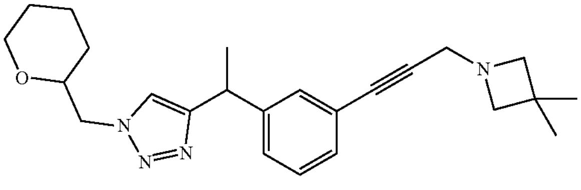

I-425

1. The Synthesis of Intermediate 24.2

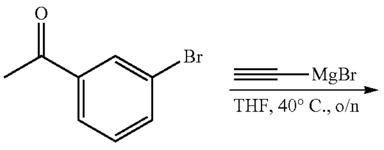

24.1

-continued

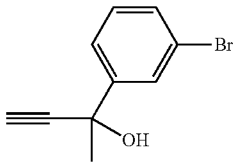

24.2

To a stirred solution of 24.1 (400 mg, 2.02 mmol) in THF (5 mL) was added ethynylmagnesium bromide (2.4 mL, 2.4 mmol) at 0° C. The reaction mixture was stirred at 40° C. overnight until the reaction was complete (by LCMS), aqueous $NH_4Cl$ (5 mL) was added and the mixture was stirred at room temperature for another 30 min. The reaction mixture was diluted with $H_2O$ (10 mL) and extracted with DCM (10 mL×2). The combined organic phase was dried over anhydrous $Na_2SO_4$ and concentrated to dryness. The crude product was used to the next step directly without further purification.

2. The Synthesis of Intermediate 24.3

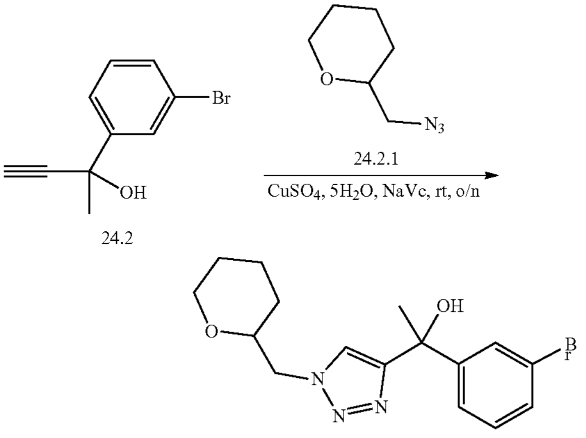

24.2 24.2.1 24.3

To a stirred solution of 24.2 (450 mg, 2.0 mmol) and 24.2.1 (283 mg, 2.02 mmol) in DMF (5 mL), a solution of $CuSO_4.5H_2O$ (50 mg, 0.20 mmol) in water (0.5 mL) and sodium ascorbate (80 mg, 0.40 mmol) in water (0.5 mL) was added. The reaction mixture was stirred at room temperature overnight until the reaction was complete (by LCMS). The reaction mixture was diluted with $H_2O$ (10 mL) and extracted with EA (15 mL×3). The combined organic layer was washed with brine (15 mL×3), dried over anhydrous $Na_2SO_4$ and concentrated to dryness. The crude product was purified by Prep-HPLC to give 24.3 (450 mg, yield: 61%, over two steps) as a yellow solid. LC-MS m/z: 366.0 $[M+H]^+$.

3. The Synthesis of Intermediate 24.4

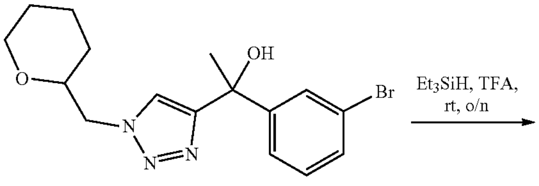

24.3

-continued

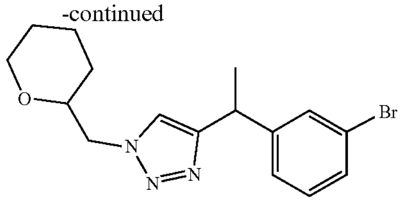

24.4

To a stirred solution of 24.3 (450 mg, 1.23 mmol) in $CF_3COOH$ (2 mL) was added triethylsilane (429 mg, 3.70 mmol). The reaction mixture was stirred at room temperature overnight until the reaction was complete (by LCMS). The reaction mixture was diluted with $H_2O$ (10 mL) and neutralized by $NaHCO_3$ to pH 7-8, then extracted with EA (15 mL×3). The combined organics phase was dried over anhydrous $Na_2SO_4$ and concentrated to dryness. The crude product was purified by Prep-HPLC to give 24.4 (300 mg, yield: 70%) as yellow oil. LC-MS m/z: 350.0 $[M+H]^+$.

4. The Synthesis of Intermediate 24.5

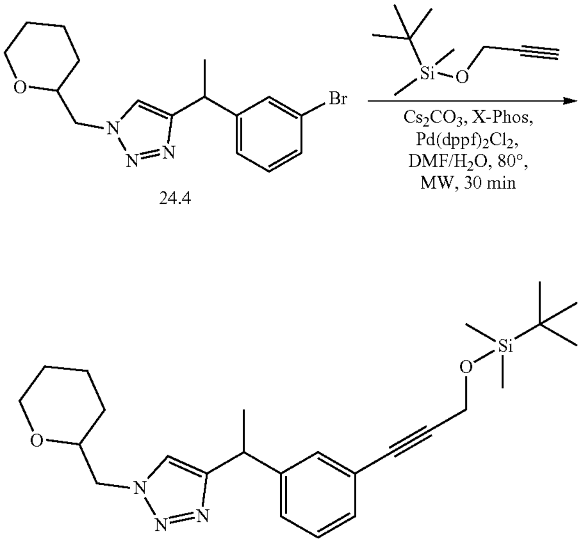

24.4 24.5

To a stirred solution of 24.4 (300 mg, 0.86 mmol) in DMF (5 mL) and $H_2O$ (0.5 mL) was added $Cs_2CO_3$ (40 mg, 1.29 mmol), $Pd(dppf)Cl_2$ (30 mg) and X-phos (30 mg), then backfill with argon (three times). Add tert-butyldimethyl (prop-2-ynyloxy)silane (438 mg, 2.58 mmol) to the resulting suspension and the reaction mixture was stirred at 80° C. under Microwave for 30 min. until the reaction was complete (by LCMS). The reaction mixture was diluted with $H_2O$ (10 mL) and extracted with EA (15 mL×3). The combined organic phase was washed with brine (10 mL×3), dried over anhydrous $Na_2SO_4$ and concentrated to dryness. The crude product was purified by Prep-HPLC to give 24.5 (340 mg, yield: 90%) as a white solid. LC-MS m/z: 440.2 $[M+H]^+$; $^1H$ NMR (400 MHz, $CDCl_3$): δ 7.32 (s, 1H), 7.21-7.29 (m, 4H), 4.51 (s, 2H), 4.34-4.39 (m, 1H), 4.16-4.25 (m, 2H), 3.92-3.95 (m, 1H), 3.60-3.65 (m, 1H), 3.34-3.37 (m, 1H), 1.82-1.86 (m, 1H), 1.48-1.67 (m, 4H), 1.45-1.48 (m, 3H), 1.22-1.25 (m, 1H), 0.92 (s, 9H), 0.12 (s, 6H).

5. The Synthesis of Intermediate 24.6

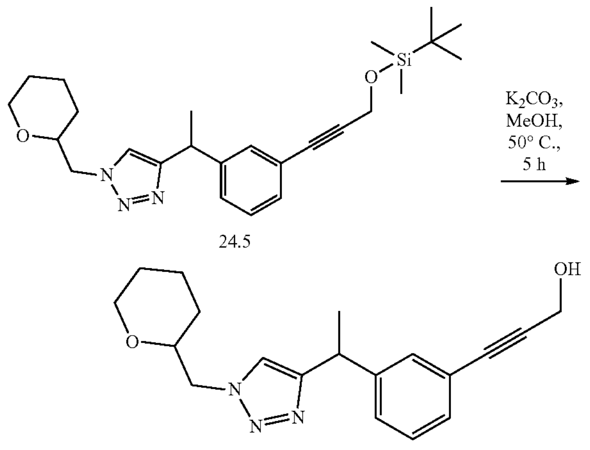

24.5

24.6

To a stirred solution of 24.5 (340 mg, 0.77 mmol) in MeOH (3 mL) was added $K_2CO_3$ (534 mg, 3.87 mmol). The reaction mixture was stirred at 50° C. for 5 hours until the reaction was complete (by LCMS). The reaction mixture was concentrated to dryness. The crude product was diluted with $H_2O$ (10 mL) and extracted with EA (15 mL×3). The combined organic phase was dried over anhydrous $Na_2SO_4$ and concentrated to dryness, then used to the next step directly without further purification.

6. The Synthesis of Intermediate 24.7

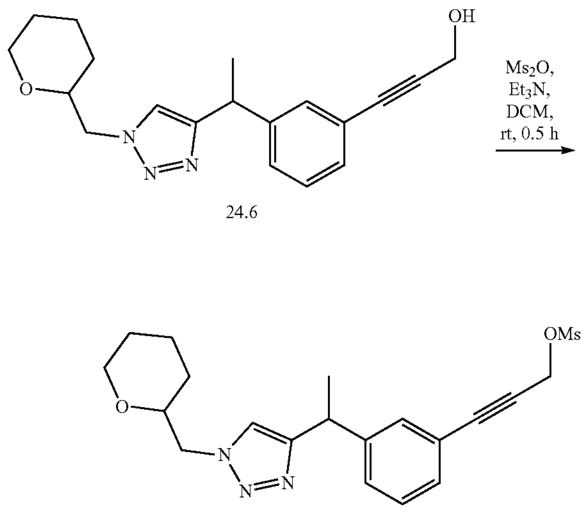

24.6

24.7

To a stirred solution of 24.6 (252 mg, 0.77 mmol) and TEA (235 mg, 2.32 mmol) in DCM (3 mL) was added $Ms_2O$ (270 mg, 1.55 mmol). The reaction mixture was stirred at room temperature for 0.5 h until the reaction was complete (by LCMS). The reaction mixture was diluted with $H_2O$ (10 mL) and extracted with DCM (15 mL×3). The combined organic phase was dried over anhydrous $Na_2SO_4$ and concentrated to dryness, then used to the next step directly without further purification.

7. The Synthesis of Target I-425

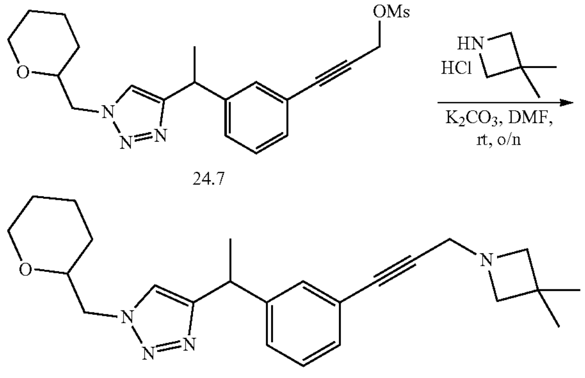

24.7

I-425

To a stirred solution of 24.7 (312 mg, 0.77 mmol) and $K_2CO_3$ (321 mg, 2.32 mmol) in DMF (3 mL) was added 3,3-dimethylazetidine hydrochloride (141 mg, 1.16 mmol). The reaction mixture was stirred at room temperature overnight until the reaction was complete (by LCMS). The reaction mixture was diluted with $H_2O$ (10 mL) and extracted with EA (10 mL×3). The combined organic phase was washed with brine (10 mL×3), dried over anhydrous $Na_2SO_4$ and concentrated to dryness. The crude product was purified by Prep-HPLC to give I-425 (32.1 mg, yield: 11%, over three steps) as yellow oil.

Additional exemplary compounds were prepared following methods substantially similar to the method described above and herein. Data for these compounds are provided in Table 23, Following Example 34.

Example 25: Synthesis of I-443

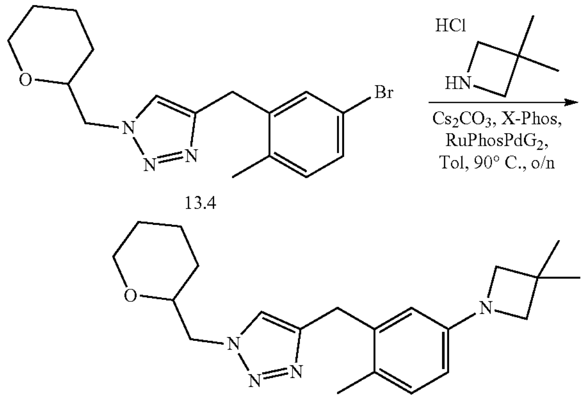

13.4

I-443

1. The Synthesis of Target I-443

To a stirred solution of 13.4 (300 mg, 0.86 mmol) in toluene (10 mL) was added 3,3-dimethylazetidine hydrochloride (104 mg, 0.86 mmol), $Cs_2CO_3$ (836 mg, 2.57 mmol), X-Phos (82 mg, 0.17 mmol) and $RuPhosPdG_2$ (130 mg). The reaction mixture was stirred at 90° C. overnight. After the consumption of starting material (by LCMS), the reaction mixture was concentrated to oil, then water (10 mL) was added and extracted with ethyl acetate (10 mL×3), the organic layer was washed with water (10 mL×3), dried and concentrated. The crude was purified by Prep-HPLC to get I-443 (69 mg, 23% yield) as a white solid.

Additional exemplary compounds were prepared following methods substantially similar to the method described above and herein. Data for these compounds are provided in Table 23, Following Example 34.

Example 26: Synthesis of I-469

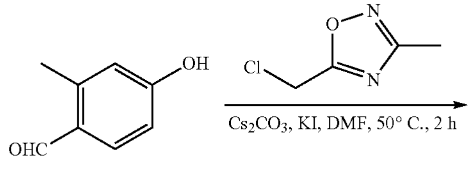

26.1

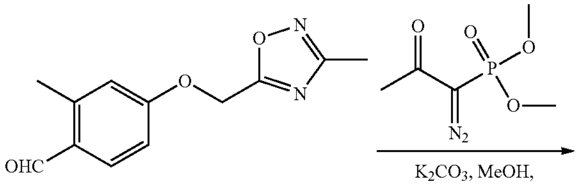

26.2

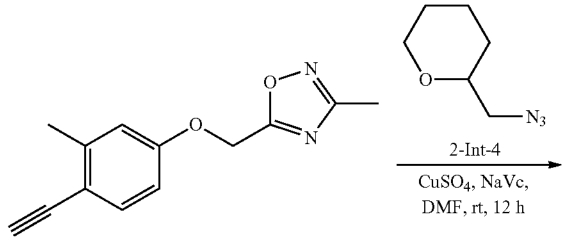

26.3

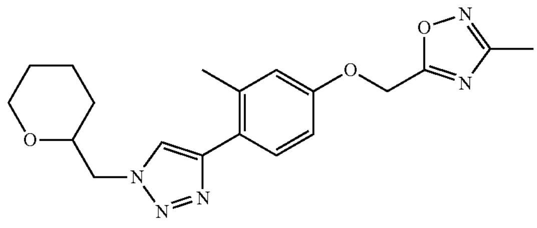

I-469

1. The Synthesis of Intermediate 26.2

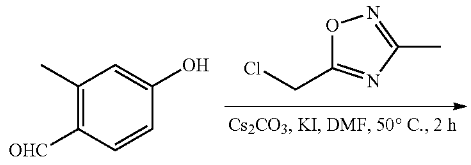

26.1

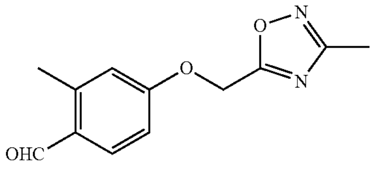

26.2

To a stirred solution of 26.1 (500 mg, 3.7 mmol), 5-(chloromethyl)-3-methyl-1,2,4-oxadiazole (528 mg, 4 mmol) and $Cs_2CO_3$ (3.6 g, 11 mmol) in DMF (10 mL) was added KI (50 mg). The reaction mixture was stirred at 50° C. for 2 hours until the reaction was complete (by LCMS). The suspension was diluted with $H_2O$ (20 mL), extracted with EA (20 mL×2) and concentrated. The crude product was purified by Prep-HPLC to give 26.2 (150 mg, yield: 18%) as yellow oil.

2. The Synthesis of Intermediate 26.3

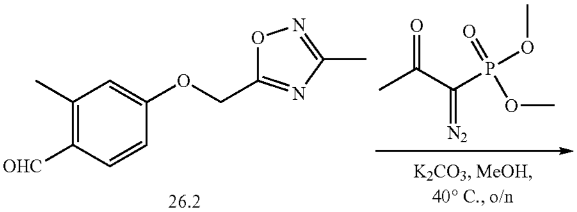

26.2

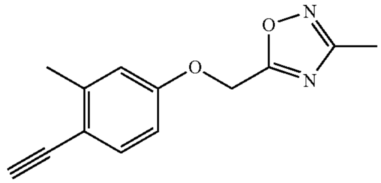

26.3

A mixture of 26.2 (150 mg, 0.7 mmol), dimethyl 1-diazo-2-oxopropylphosphonate (192 mg, 1.0 mmol) and potassium carbonate (276 mg, 2 mmol) in methanol (5 mL) was stirred at 40° C. for 16 h. The mixture was concentrated and used for the next step directly. 3. The synthesis of Target I-469

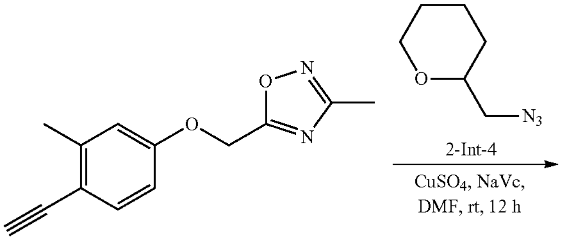

26.3

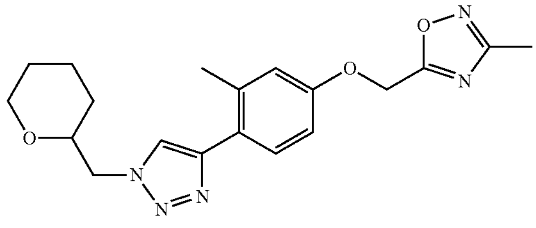

I-469

To a solution of $CuSO_4.5H_2O$ (50 mg, 0.2 mmol) was dissolved in water (1 ml) and added sodium ascorbate (60 mg, 0.3 mmol). The resulting mixture was added into a solution of compound 26.3 (150 mg, 0.7 mmol) and 2-Int-4 (141 mg, 1.0 mmol) in DMF (4 ml). The reaction mixture was stirred at room temperature overnight then diluted with water (8 mL) and extracted with ethyl acetate (3×10 ml). The combined organic phases were washed with brine (10 ml), dried over $Na_2SO_4$ and concentrated to dryness. The crude product was purified by prep-HPLC to afford I-469 (40 mg, yield: 17%) as yellow oil.

Additional exemplary compounds were prepared following methods substantially similar to the method described above and herein. Data for these compounds are provided in Table 23, Following Example 34.

Example 27: Synthesis of I-461

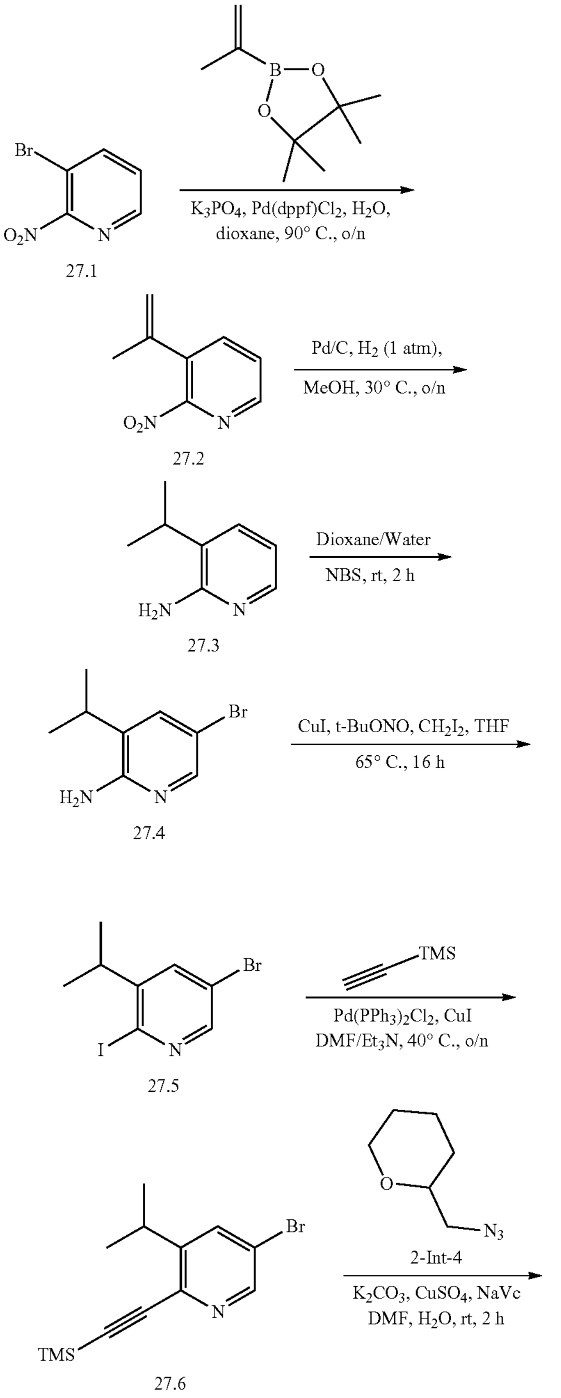

-continued

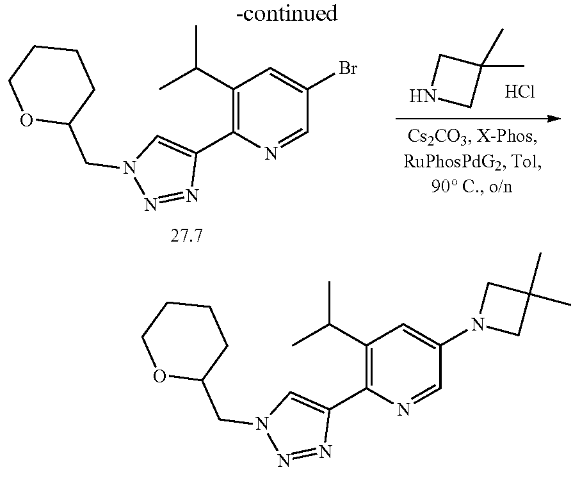

I-661

1. The Synthesis of Intermediate 27.2

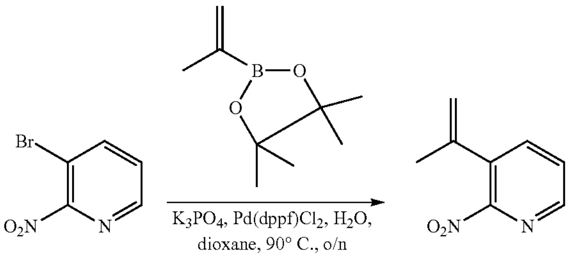

27.1 27.2

To a solution of 27.1 (10.0 g, 49.2 mmol), 4,4,5,5-tetramethyl-2-(prop-1-en-2-yl)-1,3,2-dioxaborolane (10.0 g, 59.1 mmol) in dioxane (500 mL) and Water (50 mL), was added $K_3PO_4$ (31.3 g, 147.6 mmol) and Pd(dppf)Cl2 (1.8 g, 2.46 mmol). The mixture was stirred at 90° C. overnight under nitrogen. The suspension was diluted with $H_2O$ (300 mL), extracted with EA (500 mL×2) and concentrated. The crude product was purified by flash column chromatography (silica gel, PE/EA=3:1) to give 27.2 (7.5 g, yield: 93%) as yellow oil.

2. The Synthesis of Intermediate 27.3

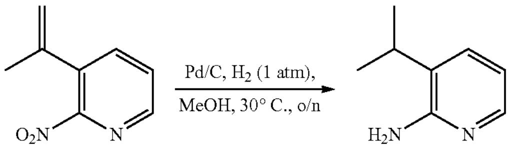

27.2 27.3

To a stirred solution of 27.2 (7.5 g, 45.7 mmol), Pd/C (10% palladium on activated carbon, 3.0 g) in MeOH (200 mL) was stirred at 30° C. overnight under $H_2$ atmosphere (1.0 atm) until the reaction was complete (by LCMS). The hydrogen gas was removed in vacuo and Ar was filled. The reaction mixture was filtered via a pad of Celite and the filtrate was concentrated to give 27.3 (5.5 g, 88%) as an off-white solid.

3. The Synthesis of Intermediate 27.4

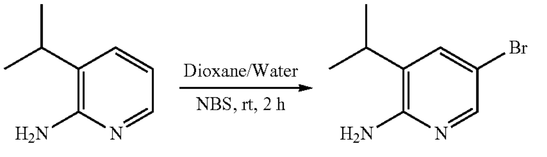

27.3

27.4

To a solution of 27.3 (5.5 g, 40.4 mmol) in dioxane (150 mL) and $H_2O$ (50 mL), was added NBS (8.0 g, 44.4 mmol) at 0° C. The reaction mixture was allowed to warm to room temperature and stirred for 2 h. After the consumption of starting material (by LCMS), the reaction was quenched with a solution of sodium thiosulfate, extracted with EA (200 mL×2) and concentrated. The crude product was purified by flash column chromatography (silica gel, PE/EA=3:1) to give 27.4 (5.5 g, yield: 63%) as a brown solid.

4. The Synthesis of Intermediate 27.5

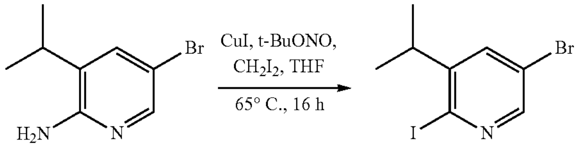

27.4

27.5

To a solution of 27.4 (5.5 g, 25.5 mmol) in THF (100 mL), was added tert-butyl nitrite (7.9 g, 76.5 mmol), CuI (7.3 g, 38.3 mmol) and $CH_2I_2$(13.7 g, 51.0 mmol). The reaction mixture was stirred at 65° C. for 16 h and quenched with a solution of sodium thiosulfate, extracted with EA (200 mL×2) and concentrated. The crude product was purified by flash column chromatography (silica gel, PE) to give 27.5 (5.0 g, purity: ~60%) as yellow oil.

5. The Synthesis of Intermediate 27.6

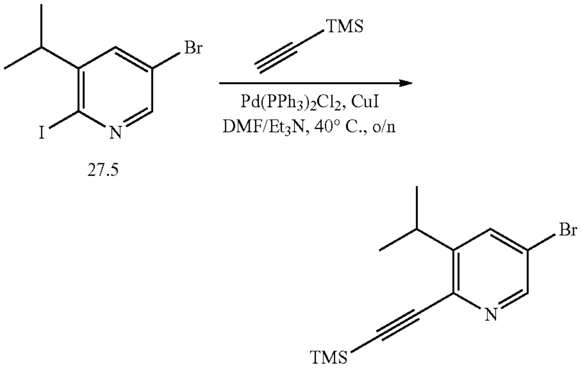

27.5

27.6

To a nitrogen bubbled solution of 27.5 (4.5 g, 13.8 mmol), $Pd(PPh_3)_2Cl_2$ (9.67 mg, 1.38 mmol), CuI (526 mg, 2.76 mmol) and $Et_3N$ (4.2 g, 41.4 mmol) in DMF (50 mL), was added ethynyltrimethylsilane (1.4 g, 13.8 mmol). The reaction was stirred at 40° C. overnight under nitrogen atmosphere, the mixture was quenched with $H_2O$ (100 mL), extracted with EA (100 mL×2) and concentrated. The crude product was purified by flash column chromatography (silica gel, PE) to give 27.6 (3.0 g, purity: ~50%) as brown oil.

6. The Synthesis of Intermediate 27.7

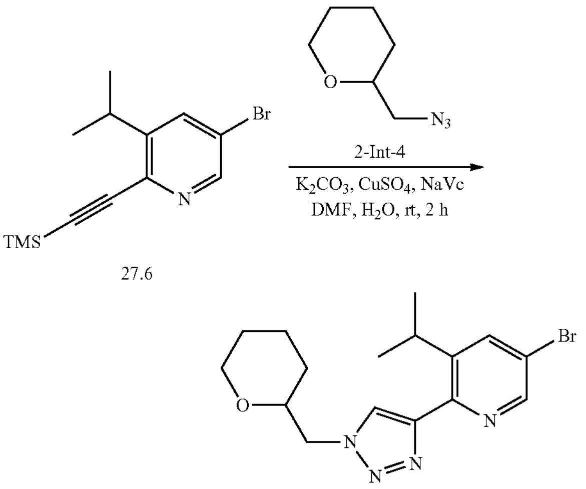

27.6

27.7

To a stirred solution of 27.6 (2.0 g, purity: ~50%, 3.4 mmol), $K_2CO_3$ (940 mg, 6.8 mmol), 2-Int-4 (480 mg, 3.4 mmol) in DMF (20 mL) and $H_2O$ (2 mL), was added $CuSO_4$ (170 mg, 0.68 mmol) and sodium ascorbate (270 mg, 1.36 mmol). The reaction mixture was stirred at room temperature for 2 h until the reaction was complete (by LCMS). The mixture was quenched with $H_2O$ (50 mL), extracted with EA (100 mL×3) and concentrated. The crude product was purified by flash column chromatography (silica gel, PE/EA=1:2) to give 27.7 (1.1 g, yield: 89%) as a yellow solid.

7. The synthesis of target 1-461

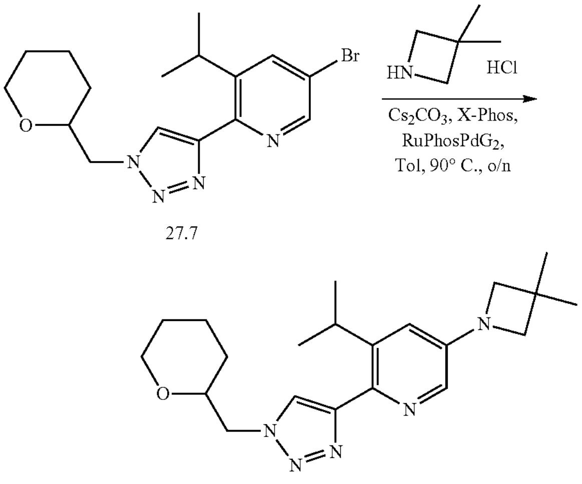

27.7

I-461

To a stirred solution of 27.7 (300 mg, 0.82 mmol), 3,3-dimethylazetidine hydrochloride (120 mg, 0.98 mmol), $Cs_2CO_3$ (802 mg, 2.46 mmol) in toluene (30 mL), was added X-Phos (80 mg, 0.164 mmol) and $RuPhosPdG_2$ (64 mg, 0.082 mmol). The reaction mixture was stirred at 90° C. overnight under nitrogen until the reaction was complete (by LCMS). The suspension was diluted with $H_2O$ (50 mL), extracted with EA (100 mL×2) and concentrated. The crude product was purified by prep-HPLC to give I-461 (65 mg, yield: 21%) as a white solid.

Additional exemplary compounds were prepared following methods substantially similar to the method described above and herein. Data for these compounds are provided in Table 23, Following Example 34.

Example 28: Synthesis of I-462

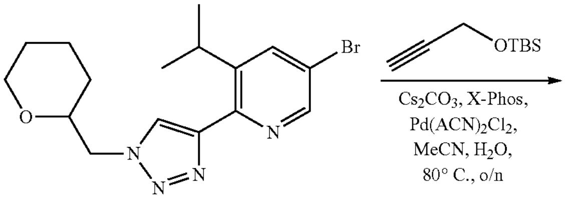

27.7

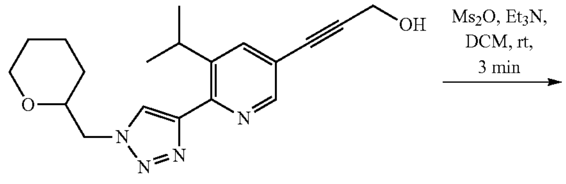

28.2

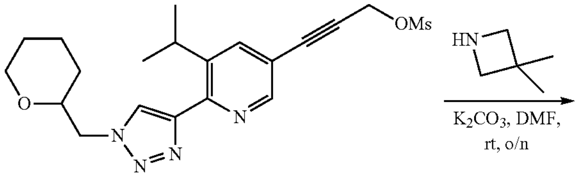

28.3

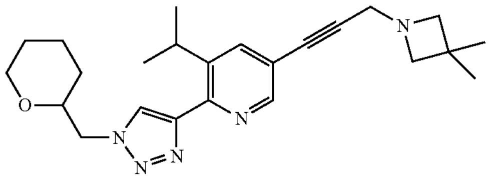

I-462

1. The Synthesis of Intermediate 28.2

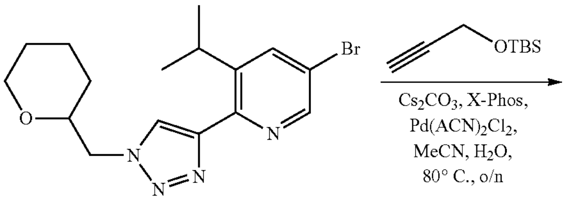

27.7

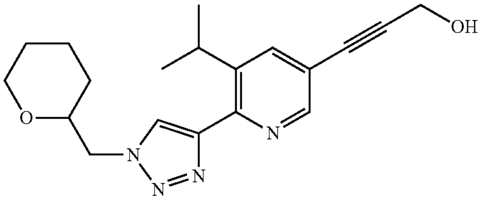

28.2

To a stirred solution of 27.7 (600 mg, 1.64 mmol), tert-butyldimethyl(prop-2-ynyloxy)silane (336 mg, 1.97 mmol) and $Cs_2CO_3$ (1.6 g, 4.92 mmol) in $CH_3CN$ (40 mL) and $H_2O$ (5 mL), was added $Pd(ACN)_2Cl_2$ (43 mg, 0.164 mmol), X-Phos (157 mg, 0.328). The reaction mixture was stirred at 80° C. overnight until the reaction was complete (by LCMS). The suspension was diluted with $H_2O$ (50 mL), extracted with EA (100 mL×2) and concentrated. The crude product was purified by flash column chromatography (silica gel, PE/EA=1:4) to give 28.2 (300 mg, yield: 54%) as yellow oil.

2. The Synthesis of Intermediate 28.3

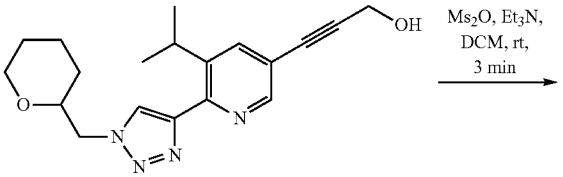

28.2

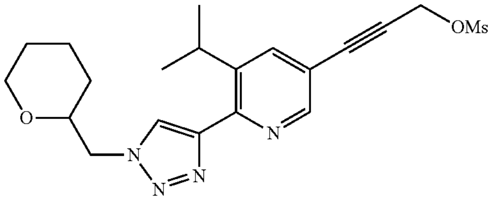

28.3

To a stirred solution of 28.2 (300 mg, 0.88 mmol) in DCM (10 mL) was added TEA (270 mg, 2.64 mmol) and $Ms_2O$ (300 mg, 1.76 mmol). The reaction mixture was stirred at room temperature for 3 min. then $H_2O$ (15 mL) and DCM (10 mL) was added and the organic phase was collected and evaporated under reduced pressure to give 28.3 (350 mg, crude) as yellow oil, which was used for the next step directly.

3. The Synthesis of Target I-462

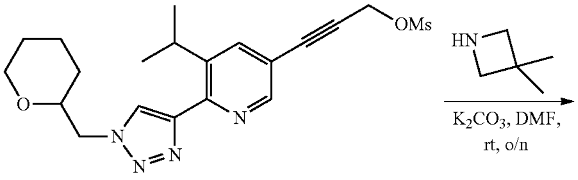

28.3

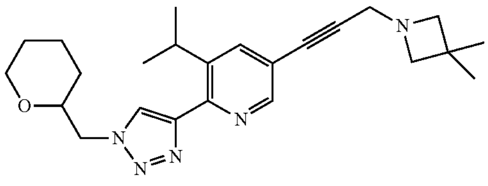

I-462

To a stirred solution of 28.3 (350 mg, 0.836 mmol), 3,3-dimethylazetidine (122 mg, 1.0 mmol) in DMF (10 mL) was added $K_2CO_3$ (350 mg, 2.51 mmol). The reaction mixture was stirred at room temperature overnight. The suspension was diluted with $H_2O$ (30 mL), extracted with EA (100 mL×2) and concentrated. The residue was purified by prep-HPLC to give I-462 (64 mg, yield: 19%) as a white solid.

Additional exemplary compounds were prepared following methods substantially similar to the method described above and herein. Data for these compounds are provided in Table 23, Following Example 34.

Example 29: Synthesis of I-483

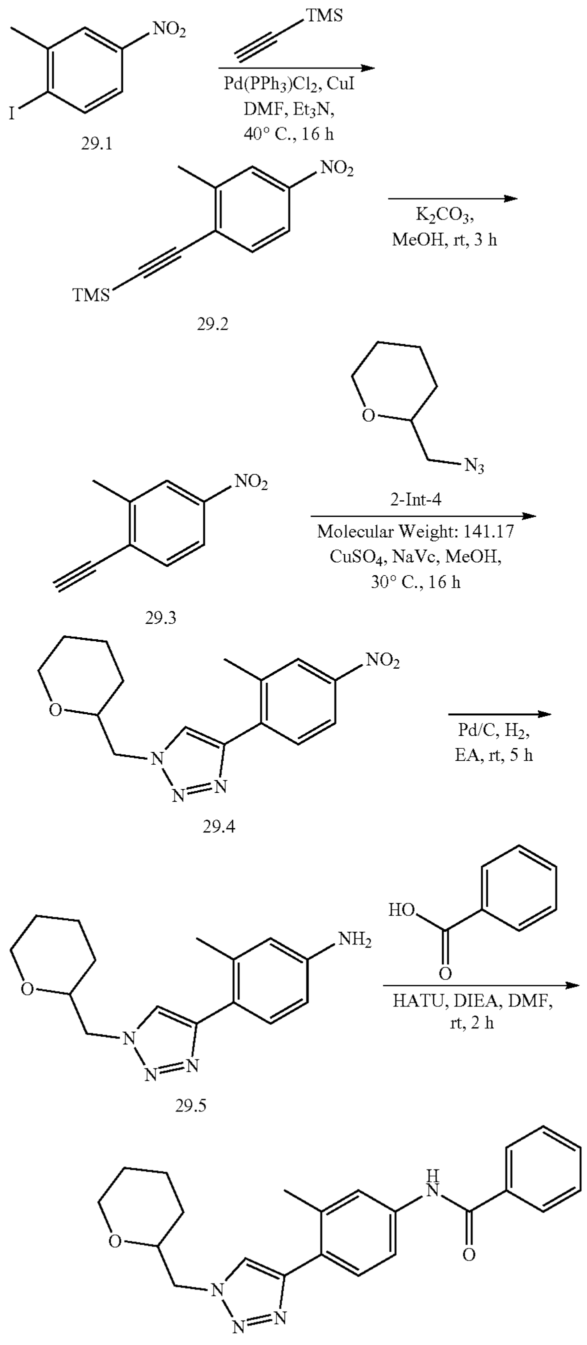

29.1

29.2

29.3

29.4

29.5

I-483

1. The Synthesis of Iintermediate 29.2

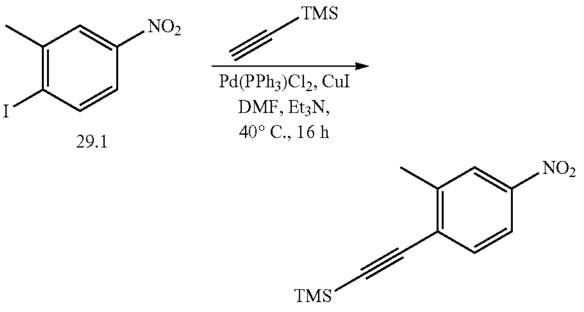

29.1

29.2

To a stirred solution of 29.1 (1.3 g, 4.7 mmol) in DMF (20 mL) was added $Et_3N$ (1.4 g, 14.1 mmol), $PdCl_2(PPh_3)_2$(180 mg), CuI (89 mg, 0.47 mmol) and ethynyltrimethylsilane (921 mg, 9.4 mmol). The reaction mixture was stirred at 40° C. for 16 hours until the reaction was complete (by LCMS), then it was cooled down to room temperature, diluted with water and extracted with dichloromethane. The combined organic phase was washed with water and brine, dried over anhydrous $Na_2SO_4$ and concentrated to dryness. The crude product was purified by purified by column chromatography (silica gel, PE/EA=5:1) to give 29.2 (750 mg, yield: 68%) as a white solid. LC-MS m/z: 234.1[M+H]$^+$.

2. The Synthesis of Intermediate 29.3

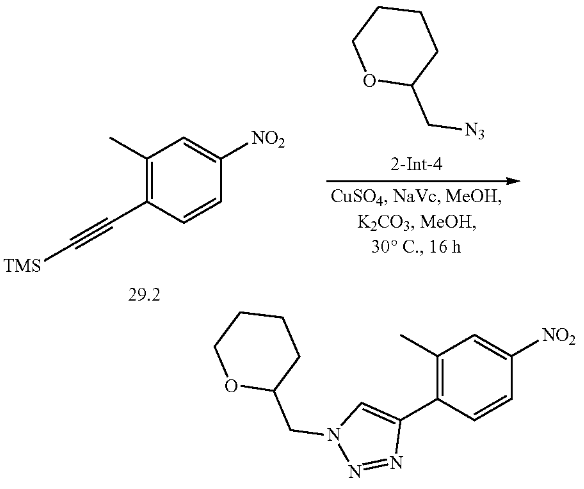

29.2

29.3

To a stirred solution of 29.2 (0.7 g, 3.0 mmol) in MeOH (5 mL) and water (3 mL) was added $CuSO_4.5H_2O$ (75 mg, 0.3 mmol) and sodium ascorbate (119 mg, 0.9 mmol). The resulting mixture was added to a solution of 2-Int-4 (0.42 g, 3.0 mmol) and $K_2CO_3$ (621 mg, 4.5 mmol) in DMF (5 mL). The reaction mixture was stirred at room temperature overnight then diluted with water, extracted with ethyl acetate and the combined organic phase was washed with brine, dried over anhydrous $Na_2SO_4$ and concentrated to dryness. The crude product was purified by Prep-TLC to afford the 29.3 (450 mg, yield: 49%) as brown oil. LC-MS m/z: 303.2 [M+H]$^+$.

3. The Synthesis of Intermediate 29.4

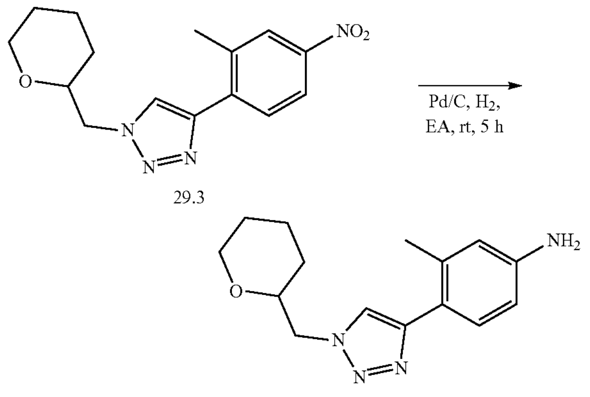

29.3

29.4

To a stirred solution of 29.3 (450 mg, 1.49 mmol) in EA (10 mL) was added Pd/C (10% w/w, 45 mg). The reaction mixture was stirred at room temperature under $H_2$ atmosphere (1.0 atm) for 5 h until the reaction was complete (by LCMS). The suspension was filtered and concentrated. The crude product was purified by Prep-HPLC to give 29.4 (146 mg, yield: 23%) as brown oil. LC-MS m/z: 273.2 $[M+H]^+$.

Additional exemplary compounds were prepared following methods substantially similar to the method described above and herein. Data for these compounds are provided in Table 23, Following Example 34.

4. The Synthesis of I-483

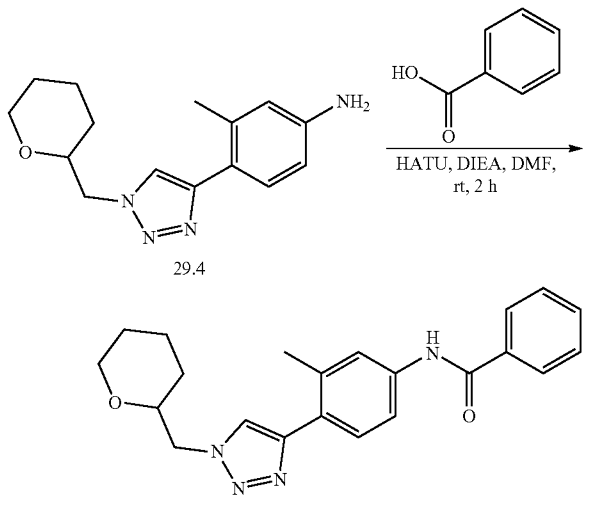

29.4

I-483

To a solution of 29.4 (146 mg, 0.54 mmol) in DMF (5 mL) was added DIPEA (279 mg, 2.16 mmol) and HATU (205 mg, 0.54 mmol). The reaction was stirred at room temperature for 15 min, then benzoic acid (62 mg, 0.54 mmol) was added and the mixture was stirred at room temperature for 2 h. After the consumption of starting material (by LCMS), water (30 mL) was added, the reaction mixture was extracted with ethyl acetate (30 mL×3), washed with water (30 mL×3), dried over anhydrous $Na_2SO_4$ and concentrated. The crude product was purified by prep-HPLC to get I-483 (34.78 mg, 17% yield) as white solid.

Example 30: Synthesis of I-558

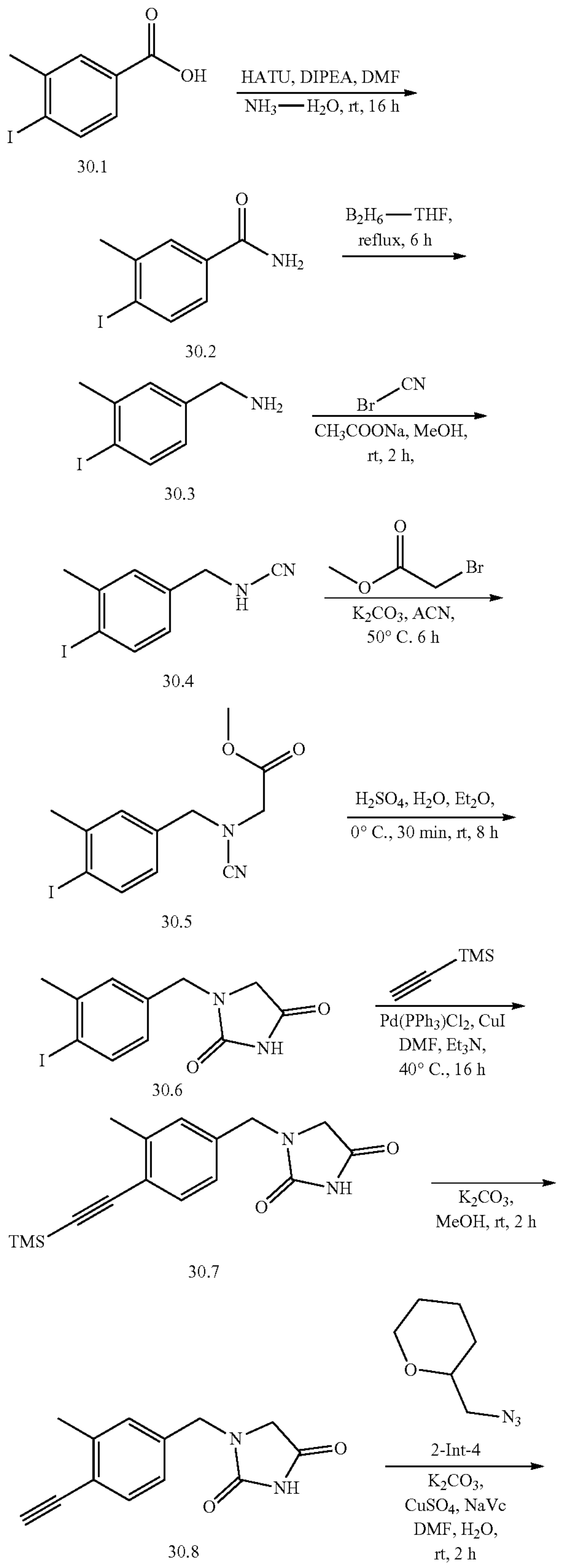

30.1

30.2

30.3

30.4

30.5

30.6

30.7

30.8

2-Int-4

-continued

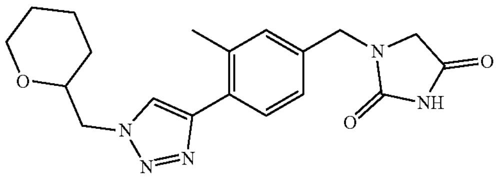

I-558

1. The Synthesis of Intermediate 30.2

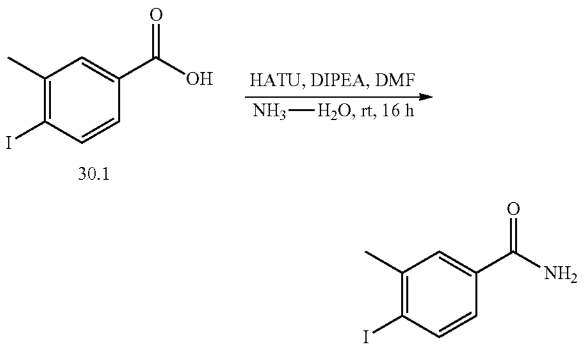

30.1

30.2

To a solution of 30.1 (1.0 g, 4.0 mmol) in DMF (10 mL) was added DIPEA (2.6 g, 20 mmol) and HATU (1.7 g, 4.4 mmol). The reaction was stirred at room temperature for 15 min, then $NH_3$—$H_2O$ (4 mL) was added and the mixture was stirred at room temperature for 16 h. After the consumption of starting material (by LCMS), water (30 mL) was added, the mixture was extracted with ethyl acetate (30 mL×3), washed with water (30 mL×3), dried over anhydrous $Na_2SO_4$ and concentrated. The crude product was purified by prep-HPLC to get 30.2 (0.4 g, 38% yield) as a yellow solid. LC-MS m/z: 262.0 $[M+H]^+$.

2. The Synthesis of Intermediate 30.3

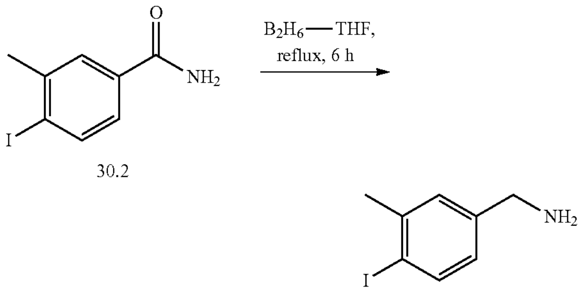

30.2

30.3

To a solution of 30.2 (0.4 g, 1.5 mmol) in THF (10 mL) was added $B_2H6$-THF (6 mL). The reaction was refluxed for 16 h. After the consumption of starting material (by LCMS), MeOH (20 mL) was added, the mixture was concentrated to dryness. The crude product was purified by prep-HPLC to get 30.3 (340 mg, 92% yield) as yellow oil. LC-MS m/z: 248.2 $[M+H]^+$.

3. The Synthesis of Intermediate 30.4

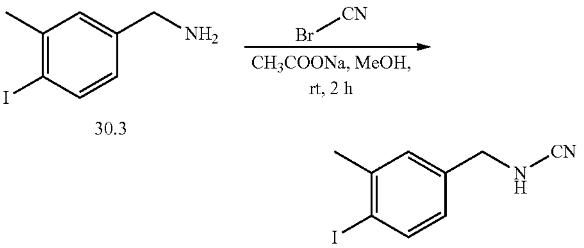

30.3

30.4

To a solution of 30.3 (340 mg, 1.4 mmol) in MeOH (20 mL) was added $CH_3COONa$ (1148 mg, 14 mmol) and BrCN (147 mg, 1.4 mmol). The reaction was stirred at room temperature for 2 h. After the consumption of starting material (by LCMS), concentrated the mixture to oil. The crude product was purified by prep-HPLC to get 30.4 (300 mg, 79% yield) as yellow oil. LC-MS m/z: 273.1 $[M+H]^+$.

4. The Synthesis of Intermediate 30.5

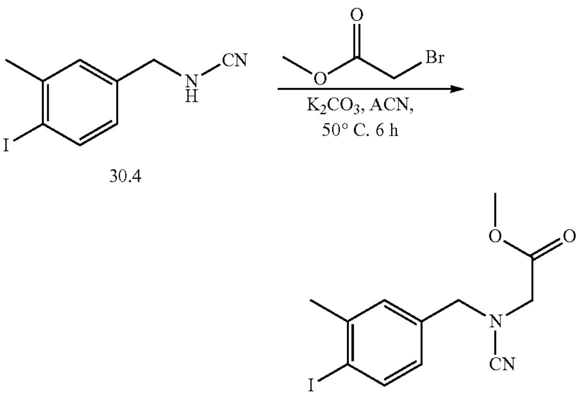

30.4

30.5

To a solution of 30.4 (300 mg, 1.1 mmol) in ACN (10 mL) was added $K_2CO_3$ (455 mg, 3.3 mmol) and methyl 2-bromoacetate (167 mg, 1.1 mmol). The reaction was stirred at 50° C. for 6 h. After the consumption of starting material (by LCMS), concentrated the mixture to dryness. The crude product was purified by prep-HPLC to get 30.5 (250 mg, 66% yield) as yellow oil. LC-MS m/z: 345.0 $[M+H]^+$.

5. The Synthesis of Intermediate 30.6

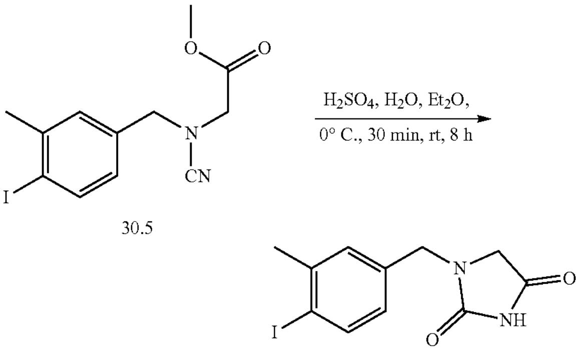

30.5

30.6

To a solution of 30.5 (250 mg, 0.7 mmol) in $Et_2O$ (5 mL) was added $H_2O$ (5 mL) and $H_2SO_4$ (3 mL) at 0° C. The reaction was stirred at 0° C. for 30 min then allowed to warm to room temperature and stirred for 8 h. After the consumption of starting material (by LCMS), concentrated the mixture and the crude product was purified by prep-HPLC to get 30.6 (200 mg, 84% yield) as yellow oil. LC-MS m/z: 331.0 $[M+H]^+$.

6. The Synthesis of Intermediate 30.7

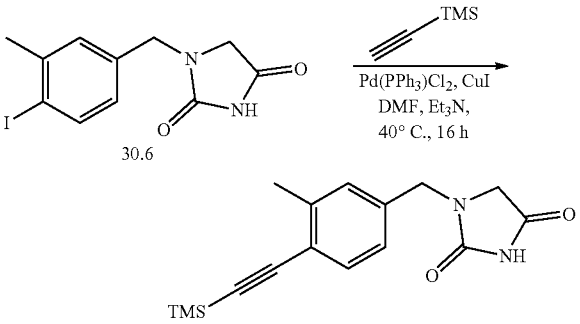

30.6

30.7

To a stirred solution of 30.6 (200 mg, 0.6 mmol), ethynyltrimethylsilane (176 mg, 1.8 mmol) and TEA (3 mL) in DMF (3 mL) was added $PdCl_2(PPh_3)_2$ (30 mg) and CuI (30 mg). The reaction mixture was stirred at 40° C. for 16 hours until the reaction was complete. The suspension was diluted with $H_2O$ (20 mL), extracted with EA (20 mL×2) and concentrated. The crude product was purified by flash column chromatography (silica gel, PE/EA=100:1) to give 30.7 (150 mg, yield: 93%) as a yellow solid.

7. The Synthesis of Intermediate 30.8

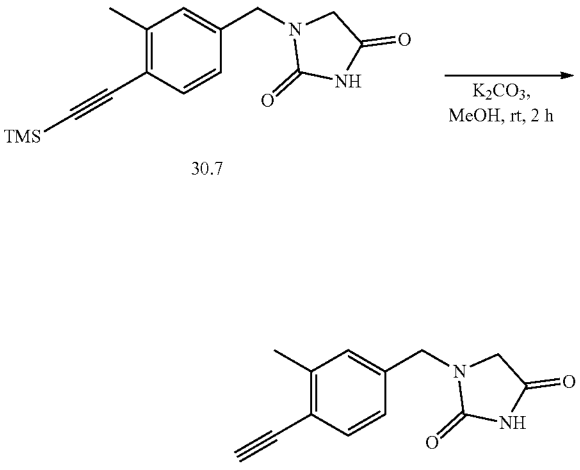

30.7

30.8

To a stirred solution of 30.7 (150 mg, 0.5 mmol) in MeOH (5 mL) was added $K_2CO_3$ (276 mg, 2.0 mmol). The reaction mixture was stirred at room temperature for 2 h until the reaction was complete. The reaction mixture was concentrated and the crude product was purified by prep-HPLC to give 30.8 (70 mg, yield: 61%) as yellow oil.

8. The Synthesis of Target I-558

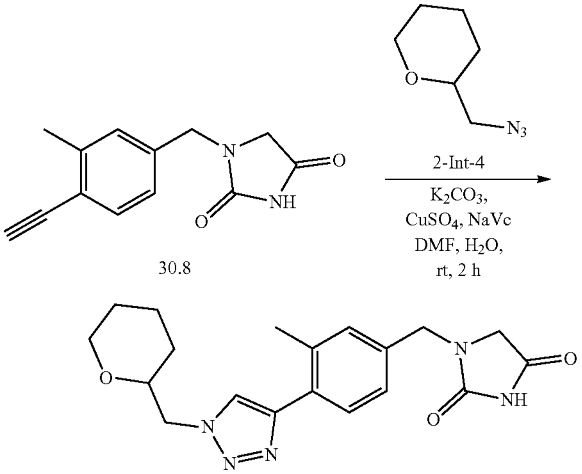

30.8

I-558

To a solution of $CuSO_4.5H_2O$ (25 mg, 0.1 mmol) in water (0.5 mL) was added sodium ascorbate (60 mg, 0.3 mmol). The resulting mixture was added to a solution of compound 30.8 (70 mg, 0.3 mmol) and 2-Int-4 (70 mg, 0.5 mmol) in DMF (4 ml). The reaction mixture was stirred at room temperature for 2 h then diluted with water (8 mL) and extracted with ethyl acetate (3×10 ml). The combined organic phase was washed with brine (10 ml), dried over $Na_2SO_4$ and concentrated to dryness. The crude product was purified by prep-HPLC to afford I-558 (21 mg, yield: 19%) as a light-yellow solid.

Additional exemplary compounds were prepared following methods substantially similar to the method described above and herein. Data for these compounds are provided in Table 23, Following Example 34.

Example 31: Synthesis of I-625

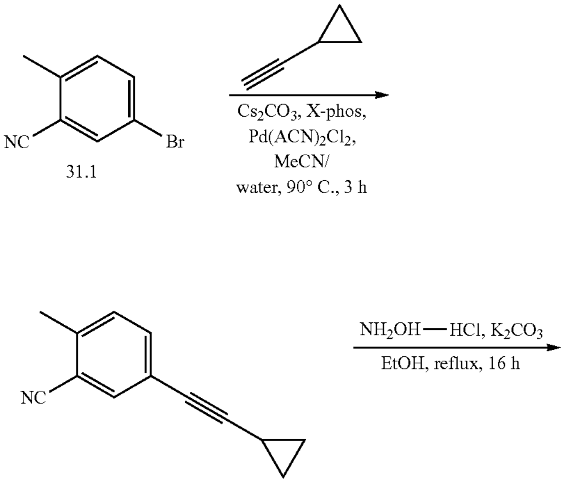

31.1

31.2

-continued

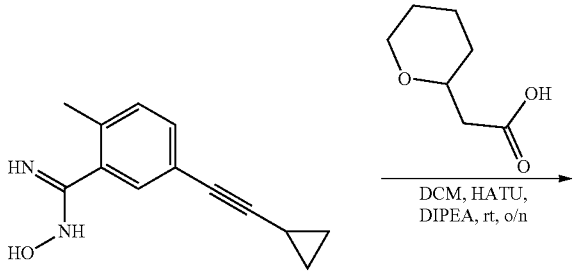

31.3

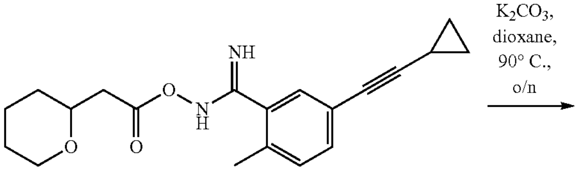

31.4

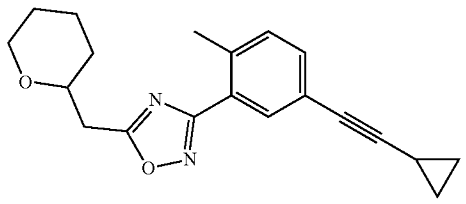

I-625

1. The Synthesis of Intermediate 31.2

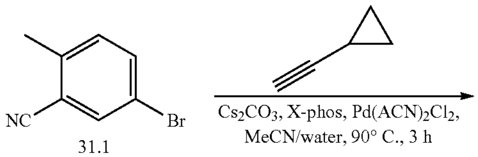

31.1

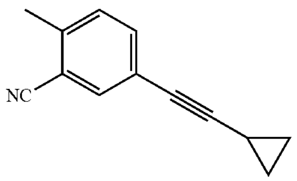

31.1

To a stirred solution of 31.1 (2.0 g, 10.2 mmol), ethynylcyclopropane (1.35 g, 20.5 mmol) and $Cs_2CO_3$ (10.0 g, 30.7 mmol) in $CH_3CN$ (100 mL) and $H_2O$ (5 mL), was added $Pd(ACN)_2Cl_2$ (265 mg, 1.0 mmol) and X-Phos (972 mg, 2.0 mmol). The reaction mixture was stirred at 90° C. for 3 h until the reaction was complete (by LCMS). The suspension was diluted with $H_2O$ (100 mL), extracted with EA (200 mL×2) and concentrated. The crude product was purified by flash column chromatography (silica gel, PE/EA=100:1) to give 31.2 (890 mg, yield: 48%) as a yellow solid.

2. The Synthesis of Intermediate 31.3

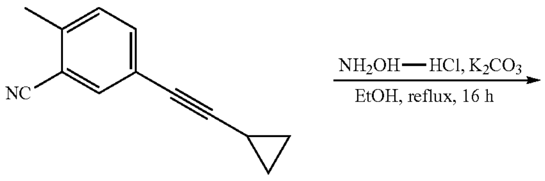

31.2

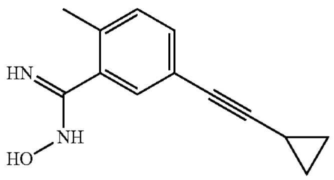

31.3

To a stirred solution of 31.2 (870 mg, 4.8 mmol), hydroxylamine hydrochloride (672 mg, 9.6 mmol) in EtOH (50 mL), was added $K_2CO_3$ (1.9 g, 14.4 mmol). The reaction mixture was stirred at reflux for 16 hours. The suspension was concentrated, diluted with $H_2O$ (50 mL), extracted with EA (100 mL×2) and concentrated. The crude product was purified by flash column chromatography (silica gel, EA) to give 31.3 (350 mg, yield: 34%) as a yellow solid.

3. The Synthesis of Intermediate 31.4

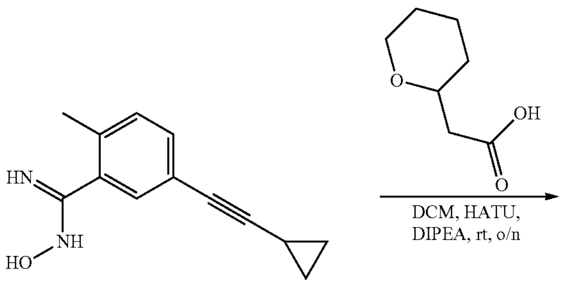

31.3

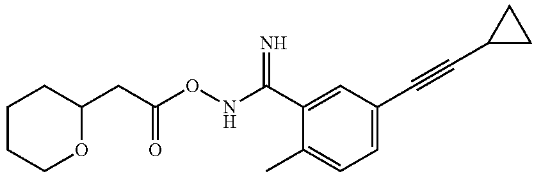

31.4

To a stirred solution of 31.3 (250 mg, 1.17 mmol), 2-(tetrahydro-2H-pyran-2-yl)acetic acid (185 mg, 1.28 mmol) and HATU (533 mg, 1.40 mmol) in DCM (20 mL), was added DIPEA (303 mg, 2.34 mmol). The reaction mixture was stirred at room temperature overnight. The suspension was concentrated and diluted with $H_2O$ (50 mL), extracted with EA (100 mL×2) and concentrated. The crude product was purified by flash column chromatography (silica gel, PE/EA=1:2) to give 31.4 (220 mg, yield: 41%, purity: ~74%) as a yellow solid.

4. The Synthesis of Target I-625

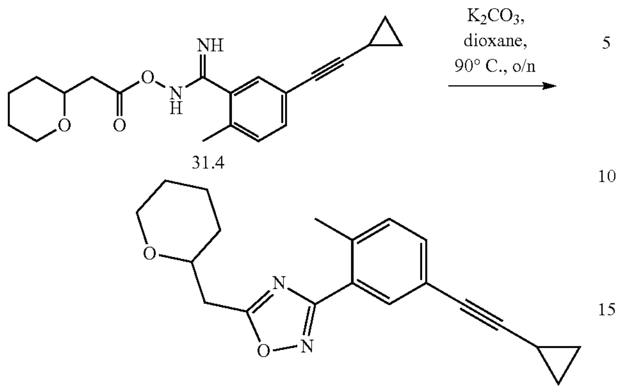

31.4

I-625

To a stirred solution of 31.4 (220 mg, 0.646 mmol) in dioxane (10 mL), was added $K_2CO_3$ (270 mg, 1.98 mmol). The reaction mixture was stirred at 90° C. overnight. The suspension was concentrated and diluted with $H_2O$ (20 mL), extracted with EA (50 mL×2) and concentrated. The crude product was purified by prep-HPLC to give I-625 (86.4 mg, yield: 41%) as a white solid.

Additional exemplary compounds were prepared following methods substantially similar to the method described above and herein. Data for these compounds are provided in Table 23, Following Example 34.

Example 32: Synthesis of I-646

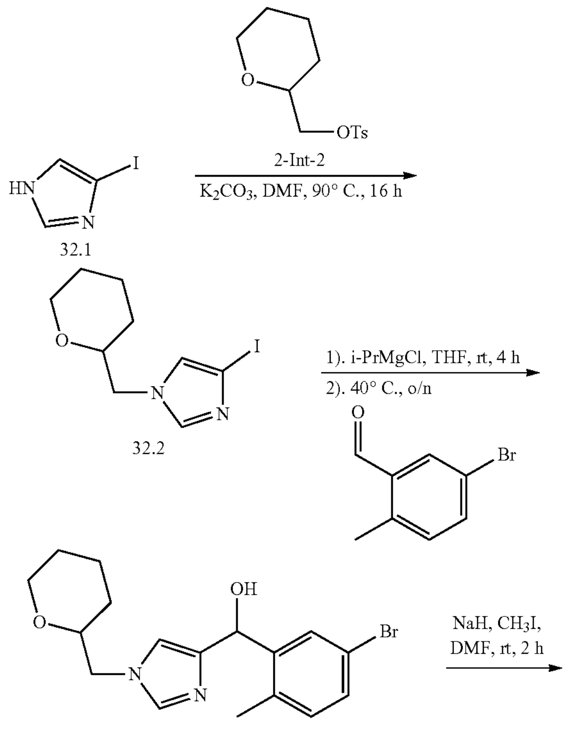

32.1

32.2

32.3

-continued

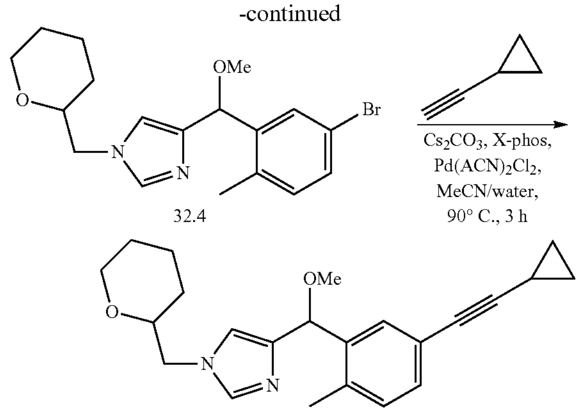

32.4

I-646

1. The Synthesis of Intermediate 32.2

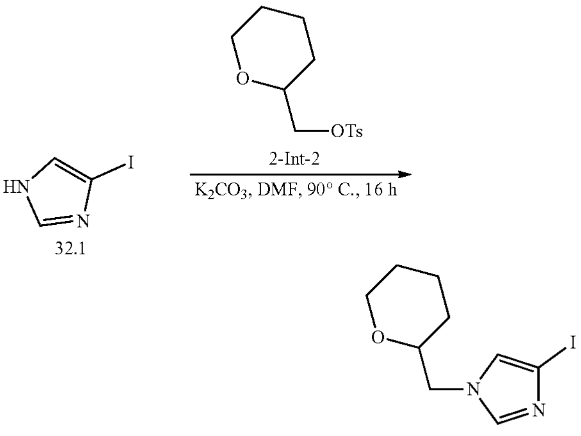

32.1

32.2

To a stirred solution of 32.1 (2.0 g, 10.3 mmol) in DMF (25 mL) was added (tetrahydro-2H-pyran-2-yl)methyl 4-methylbenzenesulfonate (2-Int-2, 2.92 g, 10.8 mmol) and $K_2CO_3$ (4.26 g, 30.9 mmol). The mixture was stirred at 90° C. for 16 h. After the consumption of starting material (by LCMS), concentrated the mixture to oil, then water (25 mL) was added, extracted with ethyl acetate (25 mL×3), washed with water (25 mL×3), dried over anhydrous $Na_2SO_4$ and concentrated. The crude was purified by pre-HPLC to get 32.2 (2.1 g, 70% yield) as a white solid.

2. The Synthesis of Intermediate 32.3

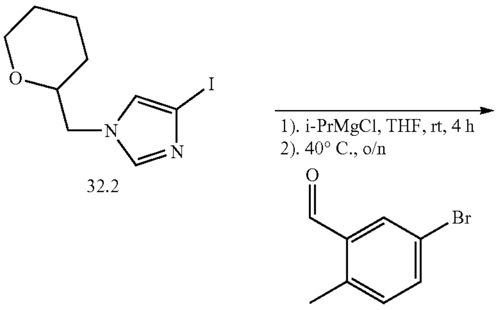

32.2

-continued

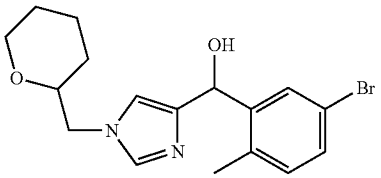

32.3

To a stirred solution of 32.2 (1.0 g, 3.42 mmol) in THF (25 mL) was added isopropylmagnesium chloride (5 mL, 5 mmol). The mixture was stirred at room temperature for 4 h. Then 5-bromo-2-methylbenzaldehyde (1.0 g, 3.42 mmol) was added into the mixture. The mixture was stirred at 40° C. overnight. After the consumption of starting material (by LCMS), concentrated the mixture to oil, then water (25 mL) was added, extracted with ethyl acetate (25 mL×3), washed with water (25 mL×3), dried over anhydrous $Na_2SO_4$ and concentrated. The crude was purified by pre-HPLC to get 32.3 (600 mg, 48% yield) as yellow oil.

3. The Synthesis of Intermediate 32.4

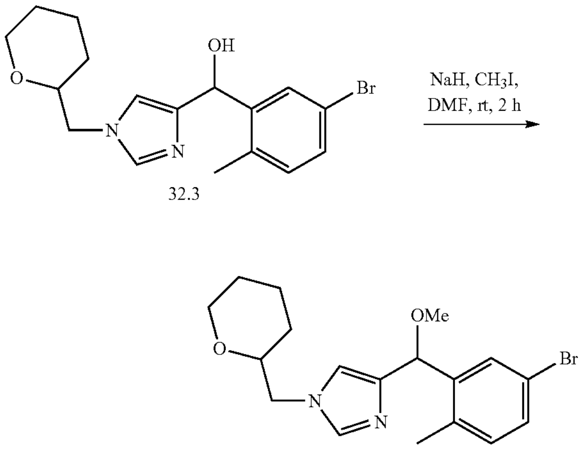

32.3

32.4

To a stirred solution of 32.3 (600 mg, 1.64 mmol) in DMF (15 mL) was added NaH (180 mg, 60% w/w, 4.92 mmol) and $CH_3I$ (694 mg, 4.92 mmol). The mixture was stirred at room temperature for 2 h. After the consumption of starting material (by LCMS), water (15 mL) was added, extracted with ethyl acetate (15 mL×3), washed with water (15 mL×3), dried over anhydrous $Na_2SO_4$ and concentrated. The crude was purified by pre-HPLC to get 32.4 (500 mg, 80% yield) as yellow oil.

4. The Synthesis of Target 1-646

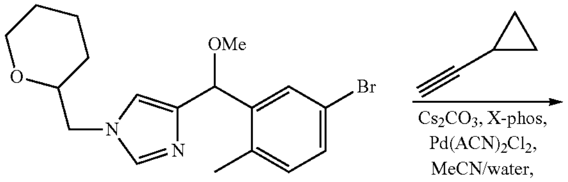

32.4

-continued

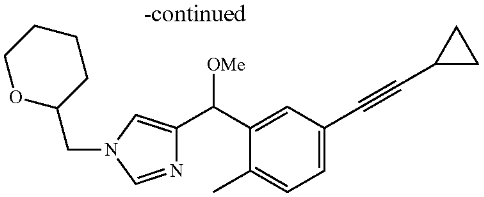

I-646

To a stirred solution of 32.4 (500 mg, 1.32 mmol) in MeCN (15 mL) was added ethynylcyclopropane (261 mg, 3.96 mmol), $Cs_2CO_3$ (1.29 g, 3.96 mmol), X-Phos (126 mg, 0.26 mmol) and $Pd(ACN)_2Cl_2$ (35 mg). The mixture was stirred at 90° C. for 3 h. After the consumption of starting material (by LCMS), concentrated the mixture to oil, then water (15 mL) was added, extracted with ethyl acetate (15 mL×3), washed with water (15 mL×3), dried over anhydrous $Na_2SO_4$ and concentrated. The crude was purified by prep-HPLC to get I-646 (111 mg, 23% yield) as yellow oil.

Example 33: Synthesis of I-671 and I-672

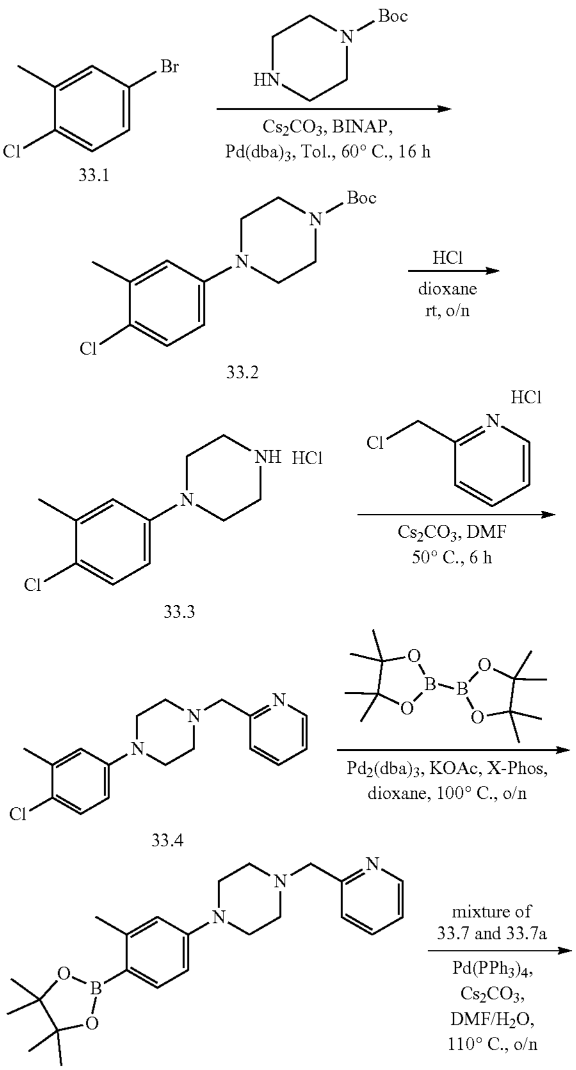

33.1

33.2

33.3

33.4

33.5

-continued

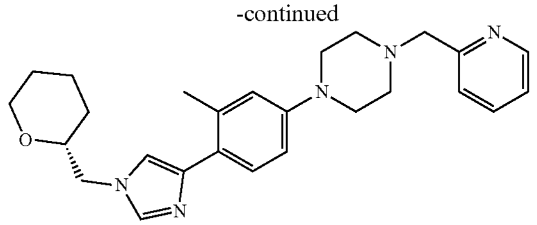

+

I-671

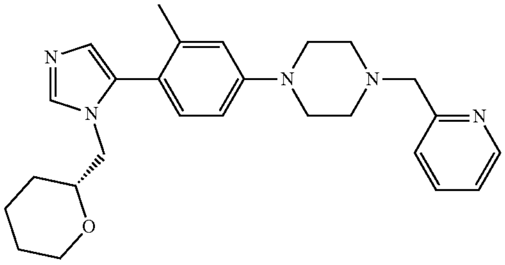

I-672

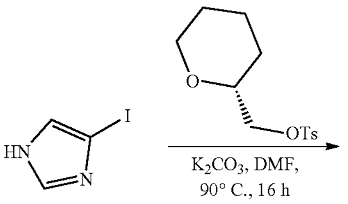

33.6

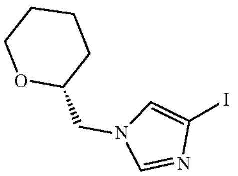

+

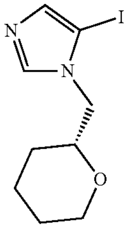

33.7 33.7a

1. The Synthesis of Intermediate 33.2

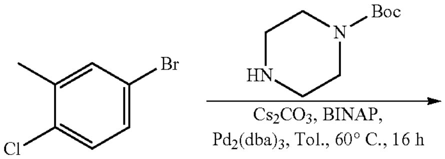

33.1

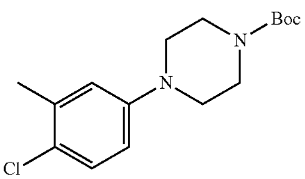

33.2

To a stirred solution of 33.1 (10.0 g, 48.66 mmol), tert-butyl piperazine-1-carboxylate (9.97 g, 53.53 mmol) and $Cs_2CO_3$ (31.7 g, 97.32 mmol) in toluene (300 mL), was added BINAP (6.0 g, 9.73 mmol) and $Pd_2(dba)_3$ (4.4 g, 4.86 mmol). The reaction mixture was stirred at 60° C. for 16 h under nitrogen until the reaction was complete (by LCMS). The suspension was diluted with $H_2O$ (500 mL), extracted with EA (500 mL×3) and concentrated. The crude product was purified by flash column chromatography (silica gel, PE/EA=5:1) to give 33.2 (12.0 g, yield: 79%) as a yellow solid.

2. The Synthesis of Intermediate 33.3

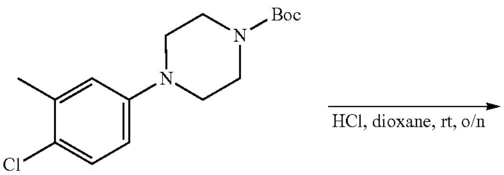

33.2

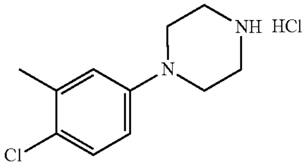

33.3

To a solution of 33.2 (5.0 g, 16.08 mmol) was dissolved in HCl in dioxane (2M) (100 mL). The reaction mixture was stirred at room temperature overnight until the reaction was complete (by LCMS) then concentrated to give 33.3 (3.5 g, yield: 88%) as a yellow solid.

3. The Synthesis of Intermediate 33.4

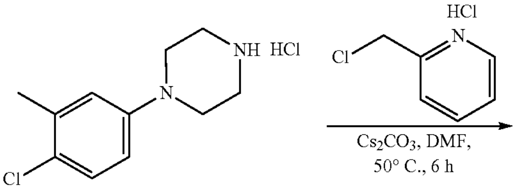

33.3

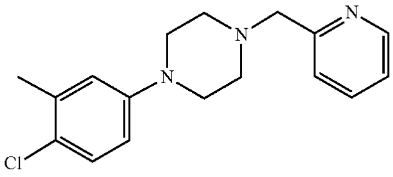

33.4

To a stirred solution of 33.3 (3.0 g, 12.13 mmol) and 2-(chloromethyl)pyridine hydrochloride (2.4 g, 1.4.56 mmol) in DMF (30 mL) was added $Cs_2CO_3$ (11.8 g, 36.39 mmol). The reaction mixture was stirred at 50° C. for 6 h. The suspension was diluted with $H_2O$ (50 mL), extracted with EA (100 mL×3) and concentrated. The crude product was purified by flash column chromatography (silica gel, PE/EA=3:1) to give 33.4 (3.2 g, yield: 87%) as a light brown solid 4. The Synthesis of Intermediate 33.5

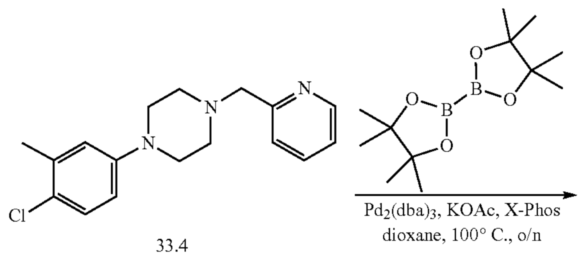

33.4

33.5

To a solution of 33.4 (3.2 g, 10.60 mmol), 4,4,4',4',5,5,5',5'-octamethyl-2,2'-bi(1,3,2-dioxaborolane) (3.2 g, 12.72 mmol), KOAc (2.1 g, 21.2 mmol) in dioxane (100 mL), was added X-Phos (1.0 g, 2.12 mmol) and $Pd_2(dba)_3$ (970 mg, 1.06 mmol). The mixture was stirred at 100° C. overnight under nitrogen atmosphere. The suspension was diluted with $H_2O$ (100 mL), extracted with EA (100 mL×3) and concentrated. The crude product was purified by flash column chromatography (silica gel, PE/EA=3:1) to give 33.5 (2.5 g, purity: ~69%) as light brown oil.

5. The Synthesis of Intermediate 33.7 and 33.7a

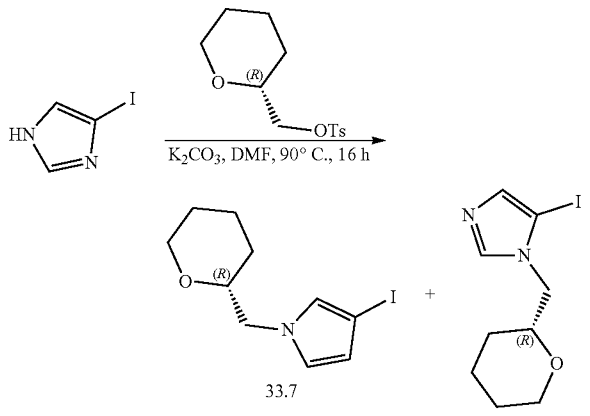

33.7

33.7a

To a stirred solution of 33.6 (600 mg, 3.09 mmol), (R)-(tetrahydro-2H-pyran-2-yl)methyl 4-methylbenzenesulfonate (1.0 g, 3.71 mmol) in DMF (10 mL), was added $K_2CO_3$ (854 mg, 6.18 mmol). The reaction mixture was stirred at 90° C. for 16 h. The suspension was diluted with $H_2O$ (20 mL), extracted with EA (50 mL×2) and concentrated to afford a mixture of 33.7 and 33.7a (900 mg, yield: crude) as a yellow semi-solid.

6. The Synthesis of Target I-672 and I-671

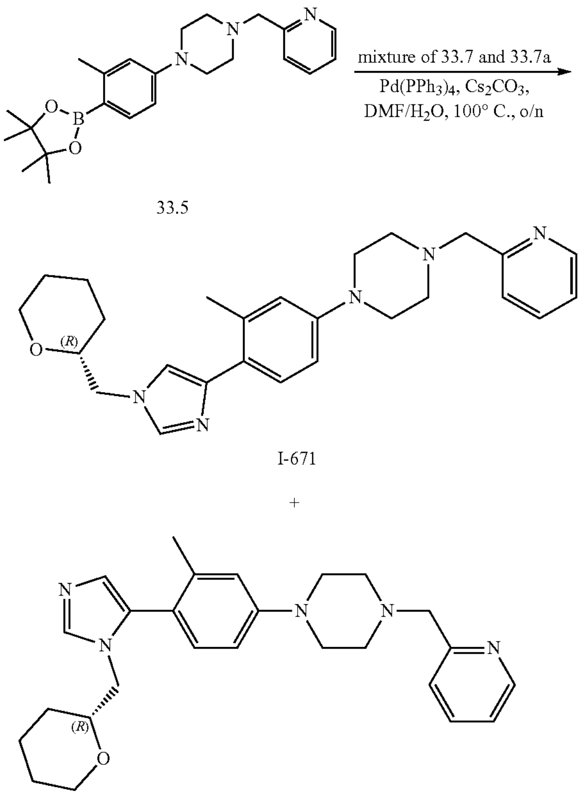

33.5

I-671

+

I-672

To a solution of 33.5 (450 mg, 1.14 mmol), a mixture of 33.7 and 33.7a (401 mg, 1.37 mmol), $Cs_2CO_3$ (1.14 g, 3.42 mmol) in DMF (30 mL) and $H_2O$ (3 mL), was added $Pd(PPh_3)_4$ (132 mg, 0.114 mmol). The mixture was stirred at 110° C. overnight under nitrogen atmosphere. The suspension was diluted with $H_2O$ (50 mL), extracted with EA (50 mL×3) and concentrated. The crude was purified by flash column chromatography (silica gel, EA) to give a crude product, then further purified by prep-HPLC then Chiral HPLC to afford I-671 (47.71 mg, yield: 9.1%) as brown oil and I-672 (37.83 mg, yield: 7.6%) as brown oil.

Additional exemplary compounds were prepared following methods substantially similar to the method described above and herein. Data for these compounds are provided in Table 23, Following Example 34.

Example 34: Synthesis of I-417

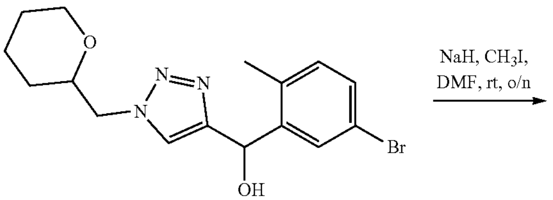

13.3

-continued

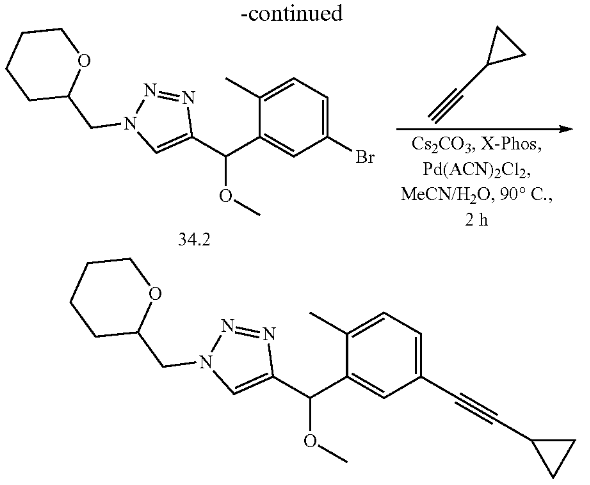

34.2

I-417

1. The Synthesis of Intermediate 34.2

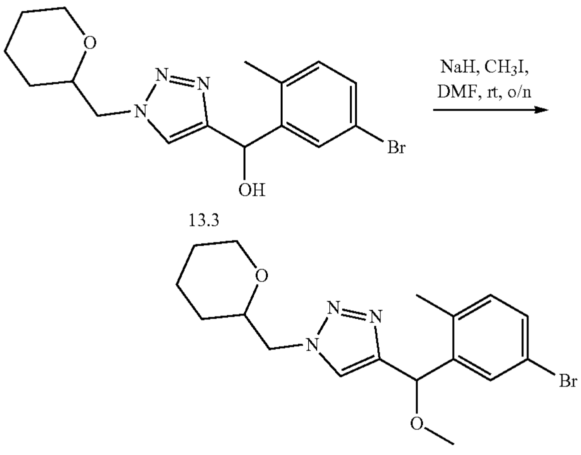

13.3

34.2

To a stirred solution of 13.3 (400 mg, 1.09 mmol) in DMF (15 mL) was added NaH (120 mg, 60% w/w, 3.28 mmol) and $CH_3I$ (464 mg, 3.28 mmol). The mixture was stirred at room temperature overnight. After the consumption of starting material (by LCMS), water (15 mL) was added, extracted with ethyl acetate (15 mL×3), washed with water (15 mL×3), dried over anhydrous $Na_2SO_4$ and concentrated. The crude was purified by pre-HPLC to get 34.2 (320 mg, 77% yield) as yellow oil.

2. The Synthesis of Target 1-417

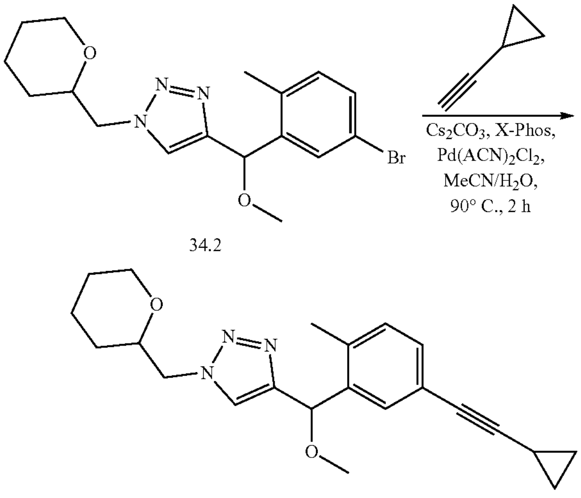

34.2

I-417

To a stirred solution of 34.2 (300 mg, 0.79 mmol) in MeCN (15 mL) was added ethynylcyclopropane (156 mg, 2.37 mmol), $Cs_2CO_3$ (770 mg, 2.37 mmol), X-Phos (75 mg, 0.16 mmol) and $Pd(ACN)_2Cl_2$ (21 mg). The mixture was stirred at 90° C. for 2 h. After the consumption of starting material (by LCMS), concentrated the mixture to oil, then water (15 mL) was added, extracted with ethyl acetate (15 mL×3), washed with water (15 mL×3), dried over anhydrous $Na_2SO_4$ and concentrated. The crude was purified by pre-HPLC to get I-417 (90 mg, 3100 yield) as a white solid.

Additional exemplary compounds were prepared following methods substantially similar to the method described above and herein. Data for these compounds are provided in Table 23, below.

TABLE 23

Characterization data for exemplary compounds

| Compound No. | Chemical Structure | M + 1 | $^1$H NMR (400 MHz) | Example of Synthesis |
|---|---|---|---|---|
| I-574 | 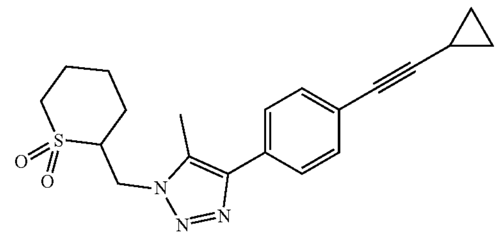 [SMILES: Cc1c(-c2ccc(C#CC3CC3)cc2)nnn1CC1CCCCS1(=O)=O] | 370.0 | $^1$HNMR (400 MHz, $CDCl_3$) δ 7.62 (d, J = 8.0 Hz, 2H), 7.45 (d, J = 8.4 Hz, 2H), 4.88 (dd, J = 4.8 Hz, 14.4 Hz, 1H), 4.47 (dd, J = 8.0 Hz, 14 4 Hz, 1H) 3.50-3.55 (m, 1H), 3.14-3.18 (m, 1H), 2.95-3.03 (m, 1H), 2.52 (s, 3H), 2.08-2.15 (m, 3H), 1.89-1.96 (m, 2H), 1.44-1.50 (m, 2H), 0.80-0.91 (m, 4 H). | 1 |

TABLE 23-continued

| Characterization data for exemplary compounds | | | | |
|---|---|---|---|---|
| Compound No. | Chemical Structure | M + 1 | $^1$H NMR (400 MHz) | Example of Synthesis |
| I-539 | 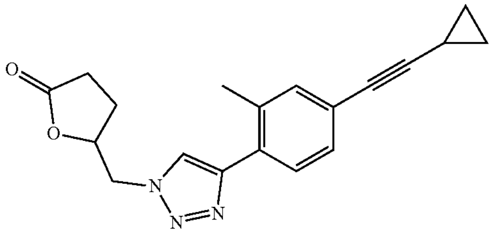 [SMILES: Cc1cc(C#CC2CC2)ccc1-c1cn(CC2CCC(=O)O2)nn1] | 322.1 | $^1$HNMR (400 MHz, DMSO-$d_6$) δ 8.43 (s, 1H), 7.74 (d, J = 8.0 Hz, 1H), 7.32 (s, 1H), 7.27 (dd, J = 1.6 Hz, 8.0 Hz, 1H), 4.97-5.03 (m, 1H), 4.69-4.80 (m, 2H), 2.50-2.59 (m, 1H), 2.41 (s, 3H), 2.30-2.39 (m, 2H), 1.96-2.05 (m, 1H), 1.52-1.59 (m, 1H), 0.87-0.92 (m, 2H), 0.72-0.76 (m, 2H). | 4 |
| I-525 | 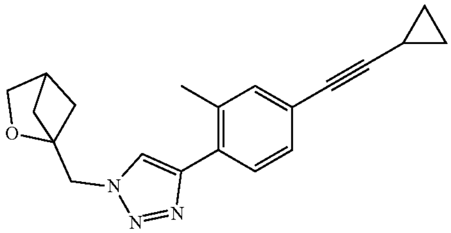 [SMILES: Cc1cc(C#CC2CC2)ccc1-c1cn(CC23CC(CO2)C3)nn1] | 320.0 | $^1$HNMR (400 MHz, DMSO-$d_6$) δ 8.33 (s, 1H), 7.74 (d, J = 8.0 Hz, 1H), 7.31 (s, 1H), 7.26 (d, J = 8.0 Hz, 1H), 4.79 (s, 2H), 3.66 (s, 2H), 2.90 (t, J = 3.2 Hz, 1H), 2.41 (s, 3H), 1.82 (t, J = 4.8 Hz, 2H), 1.53-1.57 (m, 1H), 1.34-1.36 (m, 2H), 0.87-0.92 (m, 2H), 0.72-0.76 (m, 2H). | 4 |
| I-556 | 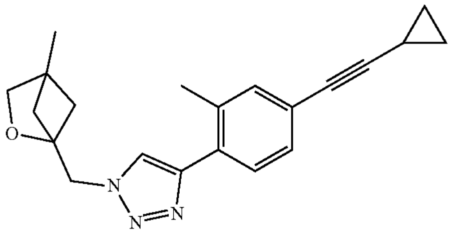 [SMILES: Cc1cc(C#CC2CC2)ccc1-c1cn(CC23CC(C)(CO2)C3)nn1] | 334.2 | $^1$HNMR (400 MHz, DMSO-$d_6$) δ 8.31 (s, 1H), 7.74 (d, J = 8.0 Hz, 1H), 7.31 (s, 1H), 7.26 (dd, J = 1.2 Hz, 8.0 Hz, 1H), 4.75 (s, 2H), 3.46 (s, 2H), 2.40 (s, 3H), 1.61-1.63 (m, 2H), 1.52-1.57 (m, 1H), 1.42-1.43 (m, 2H), 1.27 (s, 3H), 0.87-0.92 (m, 2H), 0.72-0.76 (m, 2H). | 4 |
| I-557 | 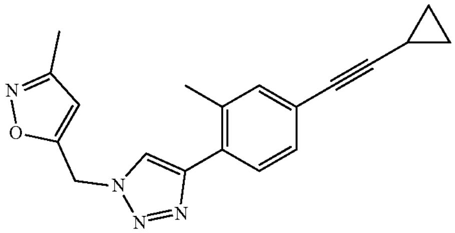 [SMILES: Cc1cc(Cn2cc(-c3ccc(C#CC4CC4)cc3C)nn2)on1] | 319.0 | $^1$HNMR (400 MHz, DMSO-$d_6$) δ 8.55 (s, 1H), 7.74 (d, J = 8.0 Hz, 1H), 7.32 (s, 1H), 7.27 (dd, J = 1.6 Hz, 8.0 Hz, 1H), 6.42 (s, 1H), 5.89 (s, 2H), 2.41 (s, 3H), 2.22 (s, 3H), 1.52-1.57 (m, 1H), 0.87-0.92 (m, 2H), 0.72-0.76 (m, 2H). | 4 |
| I-497 | 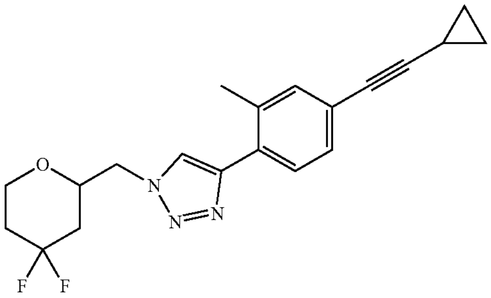 [SMILES: Cc1cc(C#CC2CC2)ccc1-c1cn(CC2CC(F)(F)CCO2)nn1] | 358.2 | $^1$HNMR (400 MHz, DMSO-$d_6$) δ 8.40 (s, 1H), 7.75 (d, J = 8.0 Hz, 1H), 7.32 (s, 1H), 6.69 (dd, J = 8.0 Hz, 1.2 Hz, 1H), 4.52-4.65 (m, 2H), 3.96-4.02 (m, 2H), 3.42-3.49 (m, 1H), 2.42 (s, 3H), 2.20-2.33 (m, 1H), 1.71-2.02 (m, 3H), 1.52-1.59 (m, 1H), 0.84-0.92 (m, 2H), 0.72-0.78 (m, 2H). | 4 |

TABLE 23-continued

Characterization data for exemplary compounds

| Compound No. | Chemical Structure | M + 1 | $^1$H NMR (400 MHz) | Example of Synthesis |
|---|---|---|---|---|
| I-599 | 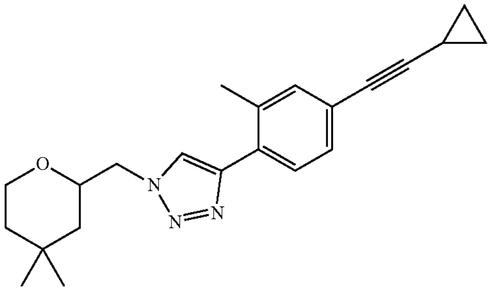 [SMILES: Cc1cc(C#CC2CC2)ccc1-c1cn(CC2CC(C)(C)CCO2)nn1] | 350.1 | $^1$HNMR (400 MHz, DMSO-$d_6$) δ 8.35 (s, 1H), 7.74 (d, J = 8.0 Hz, 1H), 7.31 (s, 1H), 7.26 (d, J = 9.2 Hz, 1H), 4.46 (dd, J = 3.6 Hz, 14.0 Hz, 1H), 4.36 (dd, J = 7.6 Hz, 14.0 Hz, 1H), 3.89-3.93 (m, 1H), 3.71 (dd, J = 4.0 Hz, 11.6 Hz, 1H), 3.45-3.51 (m, 1H), 2.41 (s, 3H), 1.52-1.57 (m, 1H), 1.31-1.39 (m, 2H), 1.19-1.22 (m, 1H), 1.06-1.12 (m, 1H), 1.00 (s, 3H), 0.98 (s, 3H), 0.87-0.97 (m, 2H), 0.72-0.76 (m, 2H). | 4 |
| I-424 | 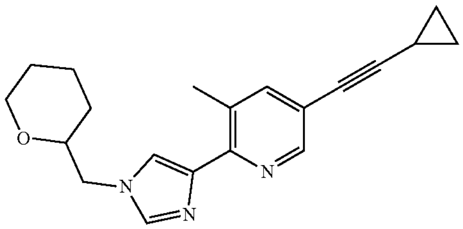 [SMILES: Cc1cc(C#CC2CC2)cnc1-c1cn(CC2CCCCO2)cn1] | 322.0 | $^1$HNMR (400 MHz, $CDCl_3$) δ 8.41 (s, 1H), 7.60-7.63 (m, 2H), 7.52 (s, 1H), 3.96-3.98 (m, 3H), 3.55-3.58 (m, 1H), 3.34-3.40 (m, 1H), 2.61 (s, 3H), 1.85-1.87 (m, 1H), 1.44-1.61 (m, 5H), 1.24-1.27 (m, 1H), 0.80-0.91 (m, 4H). | 23 |
| I-609 | 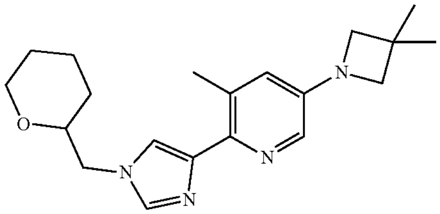 [SMILES: Cc1cc(N2CC(C)(C)C2)cnc1-c1cn(CC2CCCCO2)cn1] | 341.4 | $^1$HNMR (400 MHz, DMSO-$d_6$) δ 7.60 (d, J = 2.4 Hz, 1H), 7.56 (d, J = 1.2 Hz, 1H), 7.41 (d, J = 1.6 Hz, 1H), 6.60 (d, J = 2.4 Hz, 1H), 4.01-4.05 (m, 1H), 3.86-3.97 (m, 2H), 3.54-3.57 (m, 5H), 3.30 (s, 1H), 2.53 (s, 3H), 1.77-1.80 (m, 1H), 1.54-1.57 (m, 1H), 1.42-1.48 (m, 3H), 1.29 (s, 6H), 1.13-1.16 (m, 1H). | 23 |
| I-433 | 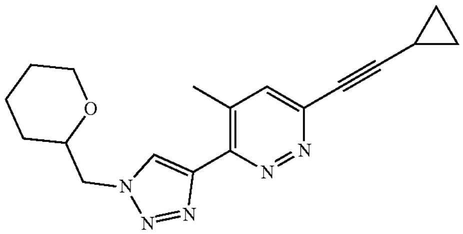 [SMILES: Cc1cc(C#CC2CC2)nnc1-c1cn(CC2CCCCO2)nn1] | 324.1 | $^1$HNMR (400 MHz, DMSO-$d_6$) δ 8.69 (s, 1H), 7.68 (s, 1H), 4.41-4.54 (m, 2H), 3.83 (d, J = 11.2 Hz, 1H), 3.72-3.77 (m, 1H), 3.26-3.29 (m, 1H), 2.60 (s, 3H), 1.69-1.79 (m, 1H), 1.62-1.68 (m, 2H), 1.39-1.52 (m, 3H), 1.18-1.25 (m, 1H), 0.94-0.99 (m, 2H), 0.81-0.85 (m, 2H). | 4 |
| I-434 | 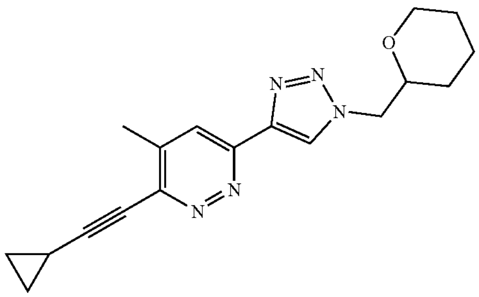 [SMILES: Cc1cc(-c2cn(CC3CCCCO3)nn2)nnc1C#CC1CC1] | 324.2 | $^1$HNMR (400 MHz, DMSO-$d_6$) δ 8.72 (s, 1H), 8.11 (s, 1H), 4.40-4.53 (m, 2H), 3.83 (d, J = 11.2 Hz, 1H), 3.73-3.76 (m, 1H), 3.26-3.29 (m, 1H), 2.38 (s, 3H), 1.61-1.78 (m, 3H), 1.43-1.48 (m, 3H), 1.17-1.23 (m, 1H), 0.96-1.01 (m, 2H), 0.84-0.88 (m, 2H). | 4 |

TABLE 23-continued

| Characterization data for exemplary compounds | | | | |
|---|---|---|---|---|
| Compound No. | Chemical Structure | M + 1 | $^1$H NMR (400 MHz) | Example of Synthesis |
| I-610 | 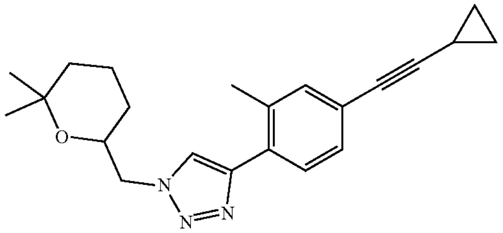 [SMILES: Cc1cc(C#CC2CC2)ccc1-c1cn(CC2CCCC(C)(C)O2)nn1] | 350.2 | $^1$HNMR (400 MHz, DMSO-$d_6$) δ 8.27 (s, 1H), 7.75 (d, J = 8.0 Hz, 1H), 7.31 (s, 1H), 7.27 (dd, J = 1.2 Hz, 8.0 Hz, 1H), 4.33-4.45 (m, 2H), 3.95-3.98 (m, 1H), 2.40 (s, 3H), 1.52-1.63 (m, 4H), 1.43-1.47 (m, 1H), 1.24-1.29 (m, 1H), 1.13 (s, 3H), 1.10 (s, 3H), 0.99-1.03 (m, 1H), 0.87-0.92 (m, 2H), 0.72-0.76 (m, 2 H). | 4 |
| I-498 | 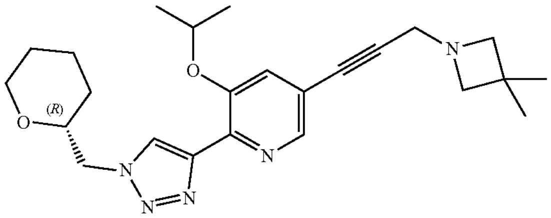 | 424.0 | $^1$HNMR (400 MHz, DMSO-$d_6$) δ 8.43 (s, 1H), 8.30 (d, J = 1.6 Hz, 1H), 7.62 (d, J = 1.6 Hz, 1H), 4.84-4.90 (m, 1H), 4.42-4.55 (m, 2H), 3.85-3.89 (m, 1H), 3.68-3.74 (m, 1H), 3.49 (s, 2H), 3.32-3.34 (m, 1H), 3.04 (s, 4H), 1.78-1.81 (m, 1H), 1.64 (d, J = 12.4 Hz, 1H), 1.40-1.53 (m, 3H), 1.34-1.36 (m, 6H), 1.15-1.27 (m, 7H). | 28 |
| I-418 | 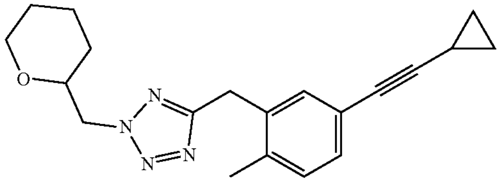 [SMILES: Cc1ccc(C#CC2CC2)cc1Cc1nnn(CC2CCCCO2)n1] | 337.2 | $^1$HNMR (400 MHz, DMSO-$d_6$) δ 7.09-7.13 (m, 1H), 4.56-4.65 (m, 2H), 4.15 (s, 2H), 3.74-3.81 (m, 2H), 3.19-3.26 (m, 1H), 2.21 (s, 3H), 1.76-1.80 (m, 1H), 1.62-1.66 (m, 1H), 1.37-1.54 (m, 4H), 1.20-1.30 (m, 1H), 0.83-0.87 (m, 2H), 0.67-0.71 (m, 2H). | 17 |
| I-419 | 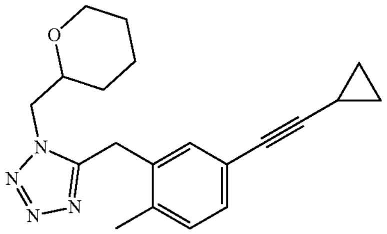 [SMILES: Cc1ccc(C#CC2CC2)cc1Cc1nnnn1CC1CCCCO1] | 337.2 | $^1$HNMR (400 MHz, DMSO-$d_6$) δ 7.15-7.20 (m, 2H), 7.07 (s, 1H), 4.52 (dd, J = 3.2 Hz, 14.4 Hz, 1H), 4.34 (dd, J = 8.4 Hz, 14.4 Hz, 1H), 4.25 (s, 2H), 3.75-3.78 (m, 1H), 3.55-3.61 (m, 1H), 3.17-3.23 (m, 1H), 2.23 (s, 3H), 1.76-1.79 (m, 1H), 1.65-1.68 (m, 1H), 1.35-1.53 (m, 4H), 1.15-1.25 (m, 1H), 0.81-0.87 (m, 2H), 0.65-0.69 (m, 2H). | 17 |
| I-622 | 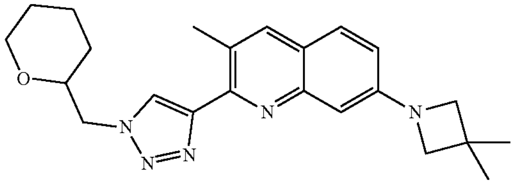 [SMILES: Cc1cc2ccc(N3CC(C)(C)C3)cc2nc1-c1cn(CC2CCCCO2)nn1] | 392.1 | $^1$HNMR (400 MHz, $CDCl_3$) δ 8.32 (s, 1H), 7.85 (s, 1H), 7.57 (d, J = 8.8 Hz, 1H), 6.88 (s, 1H), 6.78 (dd, J = 2.0 Hz, 8.8 Hz, 1H), 4.52 (dd, J = 3.6 Hz, 14.0 Hz, 1H), 4.38 (dd, J = 7.6 Hz, 14.0 Hz, 1H), 3.99-4.01 (m, 1H), 3.71-3.78 (m, 5H), 3.41-3.44 (m, 1H), 2.77 (s, 3H), 1.88-1.90 (m, 1H), 1.68-1.71 (m, 1H), 1.51-1.57 (m, 2H), 1.32-1.36 (m, 8H). | 5 |
| I-420 | 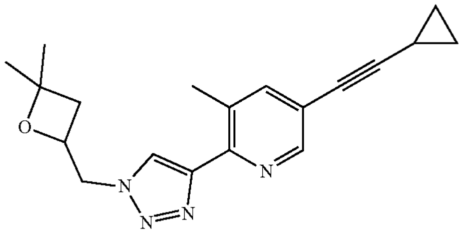 [SMILES: Cc1cc(C#CC2CC2)cnc1-c1cn(CC2CC(C)(C)O2)nn1] | 323.0 | $^1$HNMR (400 MHz, $CDCl_3$) δ 8.44 (d, J = 1.6 Hz, 1H), 8.25 (s, 1H), 7.56 (d, J = 1.2 Hz, 1H), 4.97-4.98 (m, 1H), 4.60 (d, J = 4.8 Hz, 2H), 2.69 (s, 3H), 2.47 (dd, J = 7.6 Hz, 11.6 Hz, 1H), 2.28 (dd, J = 7.2 Hz, 11.2 Hz, 1H), 1.47-1.48 (m, 4H), 1.20 (s, 3H), 0.89-0.92 (m, 2H), 0.84-0.86 (m, 2H). | 4 |

TABLE 23-continued

| Characterization data for exemplary compounds | | | | |
|---|---|---|---|---|
| Compound No. | Chemical Structure | M + 1 | $^1$H NMR (400 MHz) | Example of Synthesis |
| I-425 | 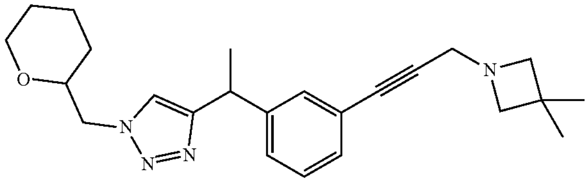 [SMILES: CC(c1cccc(C#CCN2CC(C)(C)C2)c1)c1cn(CC2CCCCO2)nn1] | 393.2 | $^1$HNMR (400 MHz, $CDCl_3$) δ 7.35 (s, 1H), 7.28-7.30 (m, 2H), 7.22-7.23 (m, 2H), 4.35-4.40 (m, 1H), 4.16-4.27 (m, 2H), 3.92-3.95 (m, 1H), 3.61-3.66 (m, 1H), 3.46 (s, 2H), 3.32-3.38 (m, 1H), 3.14 (s, 4H), 1.83-1.85 (m, 1H), 1.65-1.68 (m, 3H), 1.59-1.62 (m, 1H), 1.45-1.53 (m, 3H), 1.20-1.27 (m, 7H). | 24 |
| I-426 | 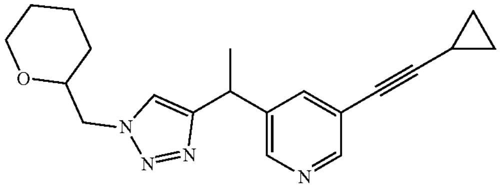 [SMILES: CC(c1cncc(C#CC2CC2)c1)c1cn(CC2CCCCO2)nn1] | 337.2 | $^1$HNMR (400 MHz, DMSO-$d_6$) δ 8.41 (d, J = 2.0 Hz, 1H), 8.37 (d, J = 2.0 Hz, 1H), 7.85 (d, J = 2.8 Hz, 1H), 7.59 (t, J = 2.0 Hz, 1H), 4.23-4.35 (m, 3H), 3.79-3.82 (m, 1H), 3.60-3.66 (m, 1H), 3.23-3.31 (m, 1H), 1.73-1.76 (m, 1H), 1.50-1.57 (m, 5H), 1.35-1.46 (m, 3H), 1.09-1.12 (m, 1H), 0.85-0.90 (m, 2H), 0.70-0.74 (m, 2H). | 24 |
| I-435 | 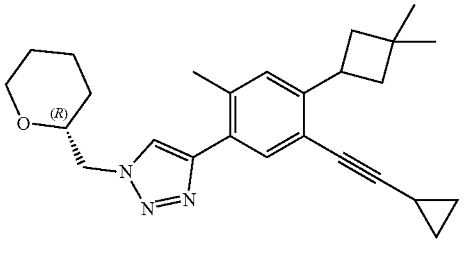 | 405.2 | $^1$HNMR (400 MHz, DMSO-$d_6$) δ 8.12 (s, 1H), 7.45 (s, 1H), 6.25 (s, 1H), 4.30-4.41 (m, 2H), 3.81-3.84 (m, 1H), 3.69-3.71 (m, 5H), 3.26-3.29 (m, 1H), 2.31 (s, 3H), 1.75-1.78 (m, 1H), 1.57-1.60 (m, 1H), 1.37-1.53 (m, 4H), 1.25 (s, 6H), 1.15-1.21 (m, 1H), 0.80-0.85 (m. 2H), 0.64-0.68 (m, 2H). | 4 |
| I-421 | 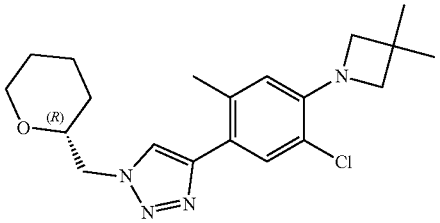 | 375.0 | $^1$HNMR (400 MHz, DMSO-$d_6$) δ 8.19 (s, 1H), 7.56 (s, 1H), 6.44 (s, 1H), 4.31-4.43 (m, 2H), 3.81-3.84 (m, 1H), 3.69-3.73 (m, 5H), 3.26-3.29 (m, 1H), 2.33 (s, 3H), 1.75-1.78 (m, 1H), 1.58-1.61 (m, 1H) , 1.40-1.47 (m, 3H) , 1.25 (s, 6H), 1.15-1.21 (m, 1H). | 5 |
| I-422 | 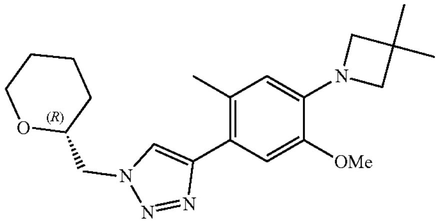 | 371.0 | $^1$HNMR (400 MHz, $CDCl_3$) δ 7.70 (s, 1H), 7.37 (s, 1H), 6.25 (s, 1H), 4.48 (dd, J = 3.2 Hz, 14.0 Hz, 1H), 4.31 (dd, J = 7.2 Hz, 14.0 Hz, 1H), 3.96-3.99 (m, 1H), 3.82 (s, 3H), 3.66-3.72 (m, 5H), 3.35-3.41 (m, 1H), 2.34 (s, 3H), 1.86-1.88 (m, 1H), 1.64-1.67 (m, 1H), 1.49-1.52 (m, 3H), 1.30 (s, 6H), 1.24-1.27 (m, 1H). | 5 |
| I-431 | 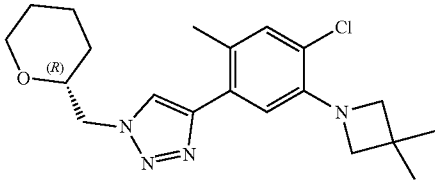 | 375.0 | $^1$HNMR (400 MHz, $CDCl_3$) δ 7.77 (s, 1H), 7.10 (s, 1H), 7.05 (s, 1H), 4.50 (dd, J = 3.2 Hz, 14.0 Hz, 1H), 4.32 (dd, J = 7.6 Hz, 14.4 Hz, 1H), 3.96-3.99 (m, 1H), 3.75-3.78 (m, 4H), 3.66-3.72 (m, 1H), 3.35-3.42 (m, 1H), 2.31 (s, 3H), 1.86-1.88 (m, 1H), 1.65-1.68 (m, 1H), 1.48-1.56 (m, 3H), 1.30 (s, 6H), 1.23-1.27 (m, 1H). | 5 |

TABLE 23-continued

Characterization data for exemplary compounds

| Compound No. | Chemical Structure | M + 1 | $^1$H NMR (400 MHz) | Example of Synthesis |
|---|---|---|---|---|
| I-417 | 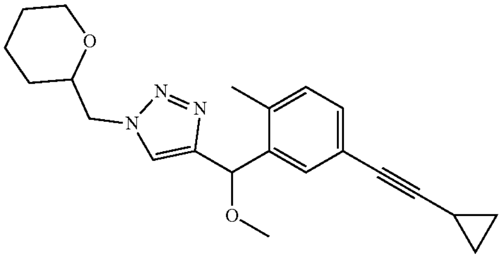 [SMILES: COC(c1cn(CC2CCCCO2)nn1)c1cc(C#CC2CC2)ccc1C] | 366.2 | $^1$HNMR (400 MHz, DMSO-$d_6$) δ 7.83 (d, J = 12.0 Hz, 1H), 7.39 (d, J = 4.8 Hz, 1H), 7.10-7.19 (m, 2H), 5.58 (s, 1H), 4.27-4.35 (m, 2H), 3.80-3.83 (m, 1H), 3.64-3.67 (m, 1H), 3.24-3.31 (m, 4H), 2.20 (s, 3H), 1.75-1.77 (m, 1H), 1.38-1.56 (m, 5H), 1.08-1.12 (m, 1H), 0.84-0.89 (m, 2H), 0.70-0.73 (m, 2H). | 34 |
| I-423 | 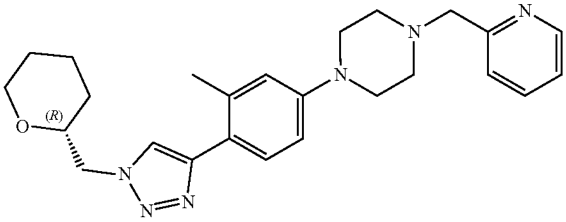 | 433.2 | $^1$HNMR (400 MHz, DMSO-$d_6$) δ 8.51 (d, J = 4.8 Hz, 1H), 8.15 (s, 1H), 7.78 (t, J = 7.6 Hz, 1H), 7.58 (d, J = 9.2 Hz, 1H), 7.48 (d, J = 8.0 Hz, 1H), 7.28 (t, J = 6.0 Hz, 1H), 6.83-6.85 (m, 2H), 4.34-4.46 (m, 2H), 3.84-3.87 (m, 1H), 3.72-3.73 (m, 1H), 3.66 (s, 2H), 3.29-3.32 (m, 1H), 3.19 (s, 4H), 2.57 (s, 4H), 2.38 (s, 3H), 1.78-1.80 (m, 1H), 1.61-1.64 (m, 1H), 1.40-1.53 (m, 3H), 1.15-1.24 (m, 1H). | 5 |
| I-459 | 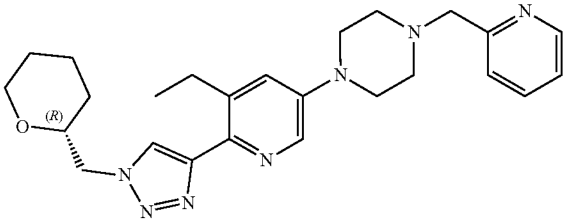 | 448.0 | $^1$HNMR (400 MHz, DMSO-$d_6$) δ 8.52 (d, J = 4.0 Hz, 1H), 8.25 (s, 1H), 8.18 (d, J = 2.8 Hz, 1H), 7.77-7.81 (m, 1H), 7.49 (d, J = 8.0 Hz, 1H), 7.27-7.30 (m, 1H), 7.22 (d, J = 2.4 Hz, 1H), 4.37-4.48 (m, 2H), 3.85-3.88 (m, 1H), 3.71-3.75 (m, 1H), 3.67 (s, 2H), 3.26-3.32 (m, 5H), 3.03 (q, J = 7.2 Hz, 2H), 2.58-2.61 (m, 4H), 1.78-1.81 (m, 1H), 1.61-1.64 (m, 1H), 1.40-1.51 (m, 3H), 1.21-1.23 (m, 1H), 1.17 (t, J = 7.2 Hz, 3H). | 27 |
| I-460 | 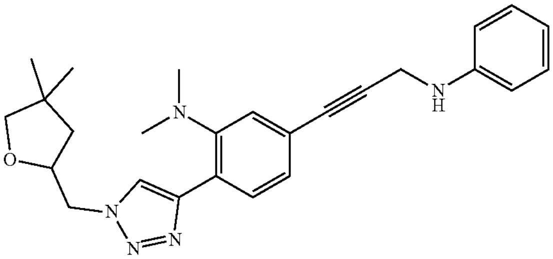 [SMILES: CN(C)c1cc(C#CCNc2ccccc2)ccc1-c1cn(CC2CC(C)(C)CO2)nn1] | 430.2 | $^1$HNMR (400 MHz, DMSO-$d_6$) δ 8.44 (s, 1H), 8.00 (d, J = 7.6 Hz, 1H), 7.10-7.16 (m, 4H), 6.70 (d, J = 7.6 Hz, 2H), 6.61 (t, J = 7.2 Hz, 1H), 6.08 (t, J = 6.0 Hz, 1H), 4.46-4.55 (m, 2H), 4.36-4.38 (m, 1H), 4.13 (d, J = 6.0 Hz, 2H), 3.37 (s, 2H), 2.57 (s, 6H), 1.77-1.82 (m, 1H), 1.42-1.47 (m, 1H), 1.02 (s, 3H), 0.98 (s, 3H). | 6 |
| I-499 | 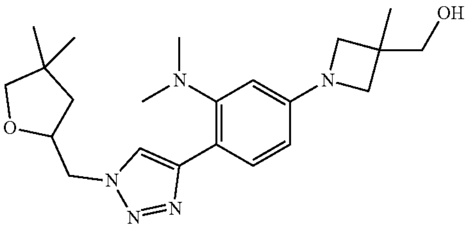 [SMILES: CN(C)c1cc(N2CC(C)(CO)C2)ccc1-c1cn(CC2CC(C)(C)CO2)nn1] | 400.0 | $^1$HNMR (400 MHz, DMSO-$d_6$) δ 8.19 (s, 1H), 7.79 (d, J = 8.4 Hz, 1H), 6.14-6.17 (m, 1H), 4.90 (t, J = 5.2 Hz, 1H), 4.42-4.53 (m, 2H), 4.32-4.38 (m, 1H), 3.68 (d, J = 6.8 Hz, 2H), 3.41-3.44 (m, 4H), 3.37 (s, 2H), 2.55 (s, 6H), 1.78 (dd, J = 12.4 Hz, 6.8 Hz, 1H), 1.43 (dd, J = 12.4 Hz, 8.8 Hz, 1H), 1.25 (s, 3H), 1.03 (s, 3H), 0.98 (s, 3H). | 22 |

TABLE 23-continued

Characterization data for exemplary compounds

| Compound No. | Chemical Structure | M + 1 | $^1$H NMR (400 MHz) | Example of Synthesis |
|---|---|---|---|---|
| I-588 | 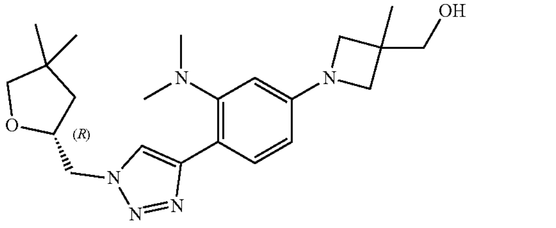 | 400.0 | $^1$HNMR (400 MHz, DMSO-$d_6$) δ 8.19 (s, 1H), 7.79 (d, J = 8.4 Hz, 1H), 6.14-6.17 (m, 1H), 4.89 (t, J = 5.2 Hz, 1H), 4.42-4.53 (m, 2H), 4.32-4.38 (m, 1H), 3.68 (d, J = 6.8 Hz, 2H), 3.41-3.44 (m, 4H), 3.37 (s, 2H), 2.55 (s, 6H), 1.78 (dd, J = 12.4 Hz, 6.8 Hz, 1H), 1.43 (dd, J = 12.4 Hz, 8.4 Hz, 1H), 1.25 (s, 3H), 1.03 (s, 3H), 0.98 (s, 3H). | 22 |
| I-589 | 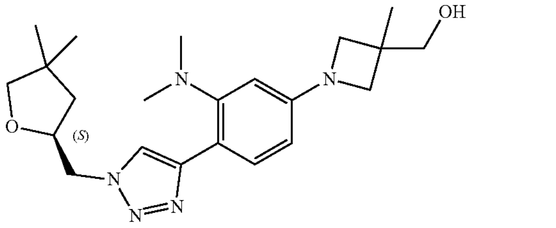 | 400.0 | $^1$HNMR (400 MHz, DMSO-$d_6$) δ 8.19 (s, 1H), 7.79 (d, J = 8.0 Hz, 1H), 6.14-6.17 (m, 1H), 4.89 (t, J = 5.2 Hz, 1H), 4.44-4.53 (m, 2H), 4.33-4.37 (m, 1H), 3.68 (d, J = 6.8 Hz, 2H), 3.41-3.44 (m, 4H), 3.37 (s, 2H), 2.55 (s, 6H), 1.78 (dd, J = 12.4 Hz, 6.8 Hz, 1H), 1.43 (dd, J = 12.4 Hz, 8.0 Hz, 1H), 1.25 (s, 3H), 1.03 (s, 3H), 0.98 (s, 3H). | 22 |
| I-474 | 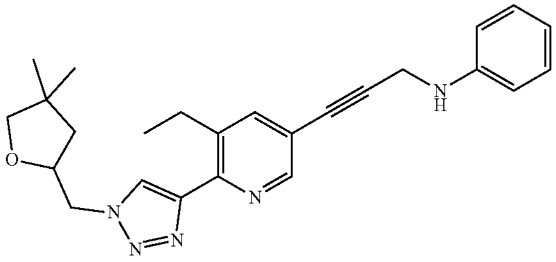 [SMILES: CCc1cc(C#CCNc2ccccc2)cnc1-c1cn(CC2CC(C)(C)CO2)nn1] | 416.1 | $^1$HNMR (400 MHz, $CDCl_3$) δ 8.46 (d, J = 2.0 Hz, 1H), 8.27 (s, 1H), 7.62 (d, J = 2.0 Hz, 1H), 7.23-7.26 (m, 2H), 6.79-6.83 (m, 1H), 6.76 (dd, , I = 1.2 Hz, 8.8 Hz, 2H), 4.56-4.62 (m, 1H), 4.40-4.48 (m, 2H), 4.20 (s, 2H), 4.01 (s, 1H), 3.49 (q, J = 8.0 Hz, 2H), 3.14-3.23 (m, 2H), 1.87 (dd, J = 6.4 Hz, 12.4 Hz, 1H), 1.47-1.53 (m, 1H), 1.26 (t, J = 7.6 Hz, 3H), 1.10 (s, 3H), 1.04 (s, 3H). | 28 |
| I-500 | 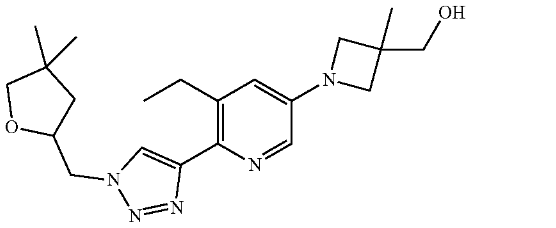 [SMILES: CCc1cc(N2CC(C)(CO)C2)cnc1-c1cn(CC2CC(C)(C)CO2)nn1] | 386.1 | $^1$HNMR (400 MHz, DMSO-$d_6$) δ 8.23 (s, 1H), 7.68 (d, J = 1.6 Hz, 1H), 6.69 (d, J = 2.4 Hz, 1H), 4.92 (t, J = 5.2 Hz, 1H), 4.44-4.55 (m, 2H), 4.35-4.42 (m, 1H), 3.75 (d, J = 7.2 Hz, 2H), 3.50 (d, J = 7.2 Hz, 2H), 3.44 (d, J = 5.6 Hz, 2H), 3.38 (t, J = 8.4 Hz, 2H), 2.96-3.05 (m, 2H), 1.81 (dd, J = 12.4 Hz, 6.4 Hz, 1H), 1.46 (dd, J = 12.4 Hz, 8.8 Hz, 1H), 1.26 (s, 3H), 1.15 (t, J = 7.6 Hz, 3H), 1.03 (s, 3H), 1.00 (s, 3H). | 22 |
| I-526 | 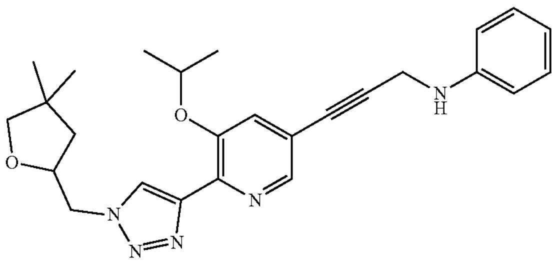 [SMILES: CC(C)Oc1cc(C#CCNc2ccccc2)cnc1-c1cn(CC2CC(C)(C)CO2)nn1] | 446.0 | $^1$HNMR (400 MHz, DMSO-$d_6$) δ 8.44 (s, 1H), 8.23 (d, J = 1.6 Hz, 1H), 7.55 (d, J = 1.2 Hz, 1H), 7.14 (t, J = 7.6 Hz, 2H), 6.71 (d, J = 8.0 Hz, 2H), 6.62 (t, J = 7.2 Hz, 1H), 6.11 (t, J = 6.0 Hz, 1H), 4.82-4.88 (m, 1H), 4.49-4.62 (m, 2H), 4.35-4.40 (m, 1H), 4.18 (d, J = 6.0 Hz, 2H), 3.38 (s, 2H), 1.81 (dd, J = 7.2 Hz, 12.8 Hz, 1H), 1.38-1.44 (m, 1H), 1.33 (t, J = 5.6 Hz, 6H), 1.03 (s, 3H), 0.97 (s, 3H). | 28 |

TABLE 23-continued

| Compound No. | Chemical Structure | M + 1 | $^1$H NMR (400 MHz) | Example of Synthesis |
|---|---|---|---|---|
| Characterization data for exemplary compounds | | | | |
| I-501 | 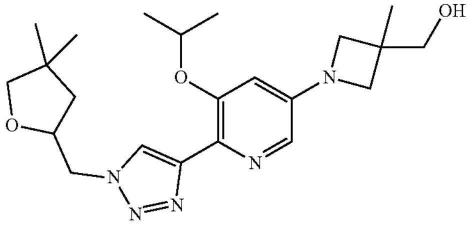 [SMILES: CC(C)Oc1cc(N2CC(C)(CO)C2)cnc1-c1cn(CC2CC(C)(C)CO2)nn1] | 416.1 | $^1$HNMR (400 MHz, DMSO-$d_6$) δ 8.19 (s, 1H), 7.47 (d, J = 2.0 Hz, 1H), 6.48 (d, J = 2.0 Hz, 1H), 4.93 (t, J = 5.2 Hz, 1H), 4.73-4.79 (m, 1H), 4.44-4.56 (m, 2H), 4.32-4.39 (m, 1H), 3.76 (d, J = 7.2 Hz, 2H), 3.51 (d, J = 7.2 Hz, 2H), 3.44 (d, J = 5.2 Hz, 2H), 3.38 (s, 2H), 1.77-1.82 (m, 1H), 1.38-1.43 (m, 1H), 1.32 (t, J = 5.6 Hz, 6H ), 1.27 (s, 3H), 1.03 (s, 3H), 0.97 (s, 3H). | 22 |
| I-475 | 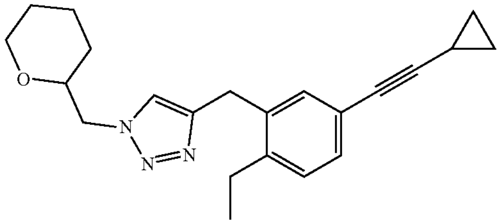 [SMILES: CCc1ccc(C#CC2CC2)cc1Cc1cn(CC2CCCCO2)nn1] | 350.2 | $^1$HNMR (400 MHz, DMSO-$d_6$) δ 7.70 (s, 1H), 7.12-7.17 (m, 3H), 4.25-4.37 (m, 2H), 3.95 (s, 2H), 3.78-3.84 (m, 1H), 3.60-3.64 (m, 1H), 3.23-3.30 (m, 1H), 2.63 (q, J = 7.6 Hz, 2H), 1.75-1.78 (m, 1H), 1.36-1.54 (m, 5H), 1.10-1.13 (m, 1H), 1.08 (t, J = 7.6 Hz, 3H), 0.83-0.88 (m, 2H), 0.66-0.70 (m, 2H). | 13 |
| I-476 | 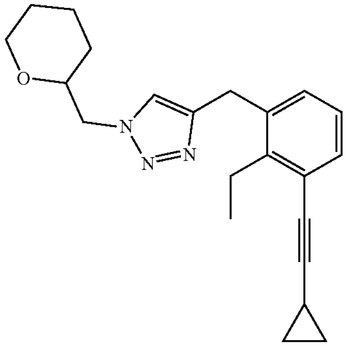 [SMILES: CCc1c(C#CC2CC2)cccc1Cc1cn(CC2CCCCO2)nn1] | 350.2 | $^1$HNMR (400 MHz, DMSO-$d_6$) δ 7.65 (s, 1H), 7.20 (dd, J = 7.6 Hz, 1.2 Hz, 1H), 7.13 (dd, J = 7.6 Hz, 1.2 Hz, 1H), 7.07 (t, J = 7.6 Hz, 1H), 4.23-4.35 (m, 2H), 3.98 (s, 2H), 3.78-3.82 (m, 1H), 3.59-3.62 (m, 1H), 3.22-3.29 (m, 1H), 2.77 (q, J = 7.6 Hz, 2H), 1.74-1.77 (m, 1H), 1.52-1.58 (m, 2H), 1.37-1.48 (m, 3H), 1.10-1.13 (m, 1H), 1.01 (t, J = 7.6 Hz, 3H), 0.87-0.92 (m, 2H), 0.68-0.72 (m, 2H). | 13 |
| I-443 | 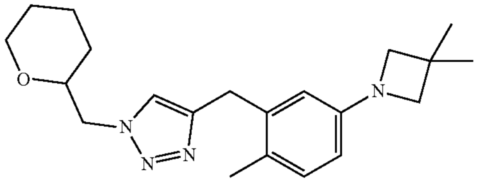 [SMILES: Cc1ccc(N2CC(C)(C)C2)cc1Cc1cn(CC2CCCCO2)nn1] | 355.2 | $^1$HNMR (400 MHz, DMSO-$d_6$) δ 7.61 (s, 1H), 6.89 (d, J = 7.6 Hz, 1H), 6.14-6.16 (m, 2H), 4.23-4.33 (m, 2H), 3.77-3.82 (m, 3H), 3.58-3.63 (m, 1H), 3.38 (s, 4H), 3.21-3.28 (m, 1H), 2.10 (s, 3H), 1.71-1.74 (m, 1H), 1.50-1.54 (m, 1H), 1.33-1.44 (m, 3H), 1.22 (s, 6H), 1.05-1.10 (m, 1H). | 25 |
| I-444 | 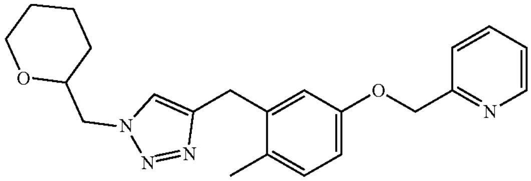 [SMILES: Cc1ccc(OCc2ccccn2)cc1Cc1cn(CC2CCCCO2)nn1] | 379.2 | $^1$HNMR (400 MHz, DMSO-$d_6$) δ 8.53 (d, J = 4.8 Hz, 1H), 7.76-7.80 (m, 1H), 7.64 (s, 1H), 7.45 (d, J = 8.0 Hz, 1H), 7.29-7.32 (m, 1H), 7.03 (d, J = 8.0 Hz, 1H), 6.73-6.79 (m, 2H), 5.06 (s, 2H), 4.22-4.34 (m, 2H), 3.88 (s, 2H), 3.77-3.80 (m, 1H), 3.58-3.63 (m, 1H), 3.21-3.27 (m, 1H), 2.16 (s, 3H), 1.73 (d, J = 10.8 Hz, 1H), 1.53 (d, J = 12.4 Hz, 1H), 1.31-1.46 (m, 3H), 1.05-1.13 (m, 1H). | 13 |

TABLE 23-continued

| Characterization data for exemplary compounds | | | | |
|---|---|---|---|---|
| Compound No. | Chemical Structure | M + 1 | $^1$H NMR (400 MHz) | Example of Synthesis |
| I-461 | 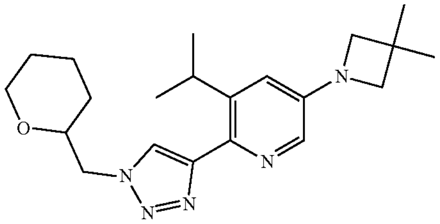 [SMILES: CC(C)c1cc(N2CC(C)(C)C2)cnc1-c1cn(CC2CCCCO2)nn1] | 370.2 | $^1$HNMR (400 MHz, DMSO-$d_6$) δ 8.17 (s, 1H), 7.68 (d, J = 2.8 Hz, 1H), 6.76 (d, J = 2.4 Hz, 1H), 4.36-4.47 (m, 2H), 3.93-4.00 (m, 1H), 3.85-3.88 (m, 1H), 3.70-3.76 (m, 1H), 3.62 (s, 4H), 3.29-3.34 (m, 1H), 1.78-1.81 (m, 1H), 1.61-1.64 (m, 1H), 1.40-1.52 (m, 3H), 1.30 (s, 6H), 1.15-1.25 (m, 7H). | 27 |
| I-462 | 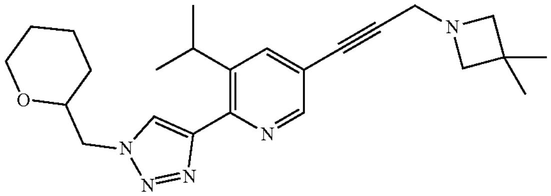 [SMILES: CC(C)c1cc(C#CCN2CC(C)(C)C2)cnc1-c1cn(CC2CCCCO2)nn1] | 408.2 | $^1$HNMR (400 MHz, DMSO-$d_6$) δ 8.52 (d, J = 1.6 Hz, 1H), 8.44 (s, 1H), 7.91 (d, J = 1.6 Hz, 1H), 4.41-4.53 (m, 2H), 4.13-4.20 (m, 1H), 3.85-3.88 (m, 1H), 3.72-3.77 (m, 1H), 3.48 (s, 2H), 3.29-3.33 (m, 1H), 3.03 (s, 4H), 1.78-1.81 (m, 1H), 1.63-1.66 (m, 1H), 1.40-1.52 (m, 3H), 1.15-1.25 (m, 6H), 1.19 (s, 7H). | 28 |
| I-600 | 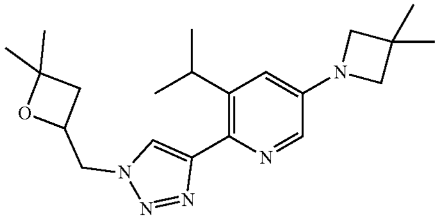 | 370.2 | $^1$HNMR (400 MHz, DMSO-$d_6$) δ 8.19 (s, 1H), 7.68 (d, J = 2.4 Hz, 1H), 6.76 (d, J = 2.8 Hz, 1H), 4.86-4.90 (m, 1H), 4.60 (d, J = 4.8 Hz, 2H), 3.94-3.99 (m, 1H), 3.63 (s, 4H), 2.40 (dd, J = 8.0 Hz, 11.2 Hz, 1H), 2.21 (dd, J = 7.2 Hz, 11.2 Hz, 1H), 1.37 (s, 3H), 1.30 (s, 6H), 1.18 (dd, J = 4.4 Hz, 6.8 Hz, 6H), 1.11 (s, 3H). | 27 |
| I-477 | 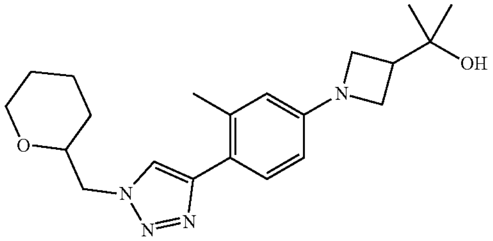 [SMILES: Cc1cc(N2CC(C(C)(C)O)C2)ccc1-c1cn(CC2CCCCO2)nn1] | 371.1 | $^1$HNMR (400 MHz, DMSO-$d_6$) δ 8.09 (s, 1H), 7.52 (d, J = 8.0 Hz, 1H), 6.30-6.33 (m, 2H), 4.33-4.45 (m, 3H), 3.68-3.87 (m, 6H), 3.28-3.35 (m, 1H), 2.70-2.74 (m, 1H), 2.34 (s, 3H), 1.78-1.81 (m, 1H), 1.61-1.64 (m, 1H), 1.43-1.50 (m, 3H), 1.18-1.22 (m, 1H), 1.06 (s, 6H). | 22 |
| I-436 | 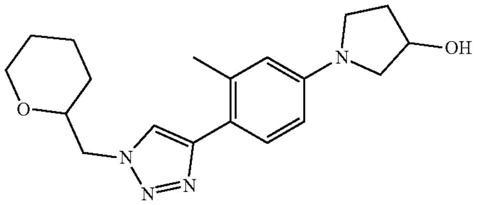 [SMILES: Cc1cc(N2CCC(O)C2)ccc1-c1cn(CC2CCCCO2)nn1] | 343.2 | $^1$HNMR (400 MHz, DMSO-$d_6$) δ 8.07 (s, 1H), 7.54 (d, J = 8.0, 1H), 6.41-6.44 (m, 2H), 4.96 (d, J = 3.6, 1H), 4.33-4.44 (m, 3H), 3.84-3.87 (m, 1H), 3.70-3.76 (m, 1H), 3.37-3.44 (m, 1H), 3.26-3.31 (m, 3H), 3.08-3.11 (m, 1H), 2.36 (s, 3H), 2.00-2.06 (m, 1H), 1.87-1.91 (m, 1H), 1.78-1.81 (m, 1H), 1.61-1.64 (m. 1H), 1.40-1.50 (m, 3H), 1.18-1.24 (m, 1H). | 5 |
| I-463 | 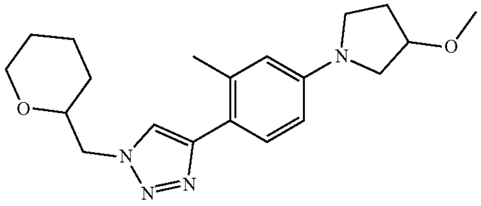 [SMILES: COC1CCN(c2ccc(-c3cn(CC4CCCCO4)nn3)c(C)c2)C1] | 357.2 | $^1$HNMR (400 MHz, DMSO-$d_6$) δ 8.08 (s, 1H), 7.55 (d, J = 8.4 Hz, 1H), 6.44-6.47 (m, 2H), 4.33-4.44 (m, 2H), 4.08-4.09 (m, 1H), 3.84-3.88 (m, 1H), 3.70-3.78 (m, 1H), 3.43 (dd, J = 4.8 Hz, 10.4 Hz, 1H), 3.24-3.34 (m, 7H), 2.37 (s, 3H), 2.04-2.09 (m, 2H), 1.78-1.79 (m, 1H), 1.61-1.64 (m, 1H), 1.43-1.50 (m, 3H), 1.18-1.21 (m, 1H). | 5 |

TABLE 23-continued

| Characterization data for exemplary compounds | | | | |
|---|---|---|---|---|
| Compound No. | Chemical Structure | M + 1 | $^1$H NMR (400 MHz) | Example of Synthesis |
| I-445 | 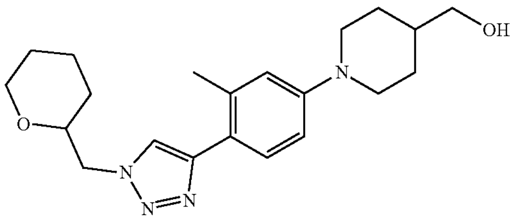 [SMILES: Cc1cc(N2CCC(CO)CC2)ccc1-c1cn(CC2CCCCO2)nn1] | 371.2 | $^1$HNMR (400 MHz, DMSO-$d_6$) δ 8.10 (s, 1H), 7.52-7.54 (m, 1H), 6.80-6.81 (m, 2H), 4.46 (t, J = 5.2 Hz, 1H), 4.31-4.43 (m, 2H), 3.81-3.84 (m, 1H), 3.69-3.75 (m, 3H), 3.24-3.31 (m, 3H), 2.60-2.66 (m, 2H), 2.34 (s, 3H), 1.69-1.78 (m, 3H), 1.58-1.61 (m, 1H), 1.40-1.50 (m, 4H), 1.15-1.24 (m, 3H). | 22 |
| I-446 | 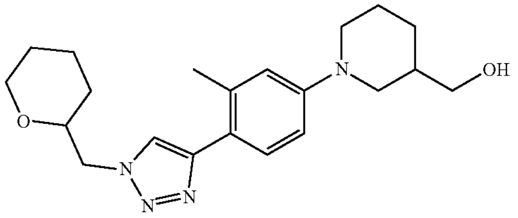 [SMILES: Cc1cc(N2CCCC(CO)C2)ccc1-c1cn(CC2CCCCO2)nn1] | 371.2 | $^1$HNMR (400 MHz, DMSO-$d_6$) δ 8.10 (s, 1H), 7.52-7.55 (m, 1H), 6.79-6.80 (m, 2H), 4.54 (t, J = 5.2, 1H), 4.31-4.43 (m, 2H), 3.84-3.91 (m, 1H), 3.70-3.73 (m, 2H), 3.61-3.64 (m, 1H), 3.32-3.35 (m, 1H), 3.24-3.29 (m, 2H), 2.61-2.66 (m, 1H), 2.38-2.43 (m, 1H), 2.34 (s, 3H), 1.75-1.78 (m, 1H), 1.40-1.53 (m, 8H), 1.15-1.21 (m. 1H), 1.04-1.07 (m, 1H). | 22 |
| I-447 | 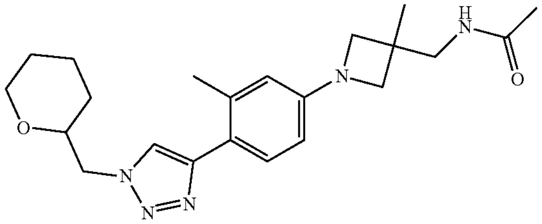 [SMILES: CC(=O)NCC1(C)CN(c2ccc(-c3cn(CC4CCCCO4)nn3)c(C)c2)C1] | 398.0 | $^1$HNMR (400 MHz, $CDCl_3$) δ 7.68 (s, 1H), 7.63 (d, J = 8.4 Hz, 1H), 6.32-6.36 (m, 2H), 6.22 (s, 1H), 4.47 (dd, J = 2.8 Hz, 14.0 Hz, 1H), 4.30 (dd, J = 7.6 Hz, 14.0 Hz, 1H), 3.97 (dd, J = 2.0 Hz, 11.2 Hz, 1H), 3.73 (d, J = 7.6 Hz, 2H), 3.66-3.72 (m, 1H), 3.54 (d, J = 7.2 Hz, 2H), 3.45 (d, J = 10.8 Hz, 2H), 3.35-3.42 (m, 1H), 2.39 (s, 3H), 2.01 (s, 3H), 1.86-1.88 (m, 1H), 1.64-1.67 (m, 1H), 1.49-1.55 (m, 3H), 1.31 (s, 3H), 1.23-1.27 (m, 1H). | 22 |
| I-448 | 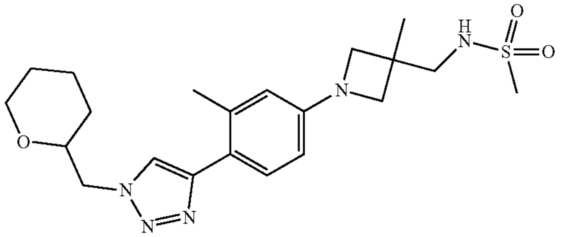 [SMILES: Cc1cc(N2CC(C)(CNS(C)(=O)=O)C2)ccc1-c1cn(CC2CCCCO2)nn1] | 434.0 | $^1$HNMR (400 MHz, $CDCl_3$) δ 7.69 (s, 1H), 7.64 (d, J = 8.4 Hz, 1H), 6.38 (br., 2H), 5.10 (br, 1H), 4.48 (dd, J = 2.8 Hz, 14.0 Hz, 1H), 4.31 (dd, J = 7.6 Hz, 14.0 Hz, 1H), 3.97 (dd, J = 2.0 Hz, 10.8 Hz, 1H), 3.80 (d, J = 7.6 Hz, 2H), 3.66-3.72 (m, 1H), 3.58 (d, J = 7.2 Hz, 2H), 3.36-3.42 (m, 1H), 3.32 (d, , / = 6.0 Hz, 2H), 2.99 (s, 3H), 2.40 (s, 3H), 1.86-1.87 (m, 1H), 1.65-1.68 (m, 1H), 1.46-1.57 (m, 3H), 1.34 (s, 3H), 1.21-1.30 (m, 1H). | 22 |
| I-449 | 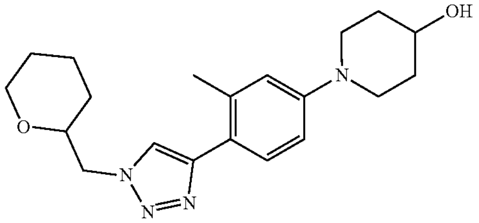 [SMILES: Cc1cc(N2CCC(O)CC2)ccc1-c1cn(CC2CCCCO2)nn1] | 357.2 | $^1$HNMR (400 MHz, DMSO-$d_6$) δ 8.10 (s, 1H), 7.53 (d, J = 9.2, 1H), 6.79-6.81 (m, 2H), 4.71 (br, 1H), 4.31-4.43 (m, 2H), 3.81-3.84 (m, 1H), 3.67-3.72 (m, 1H), 3.54-3.64 (m, 3H), 3.25-3.29 (m, 1H), 2.80-2.86 (m, 2H), 2.34 (s, 3H), 1.76-1.79 (m, 3H), 1.58-1.61 (m, 1H), 1.36-1.50 (m, 5H), 1.15-1.21 (m, 1H). | 5 |

TABLE 23-continued

| Characterization data for exemplary compounds | | | | |
|---|---|---|---|---|
| Compound No. | Chemical Structure | M + 1 | $^1$H NMR (400 MHz) | Example of Synthesis |
| I-437 | 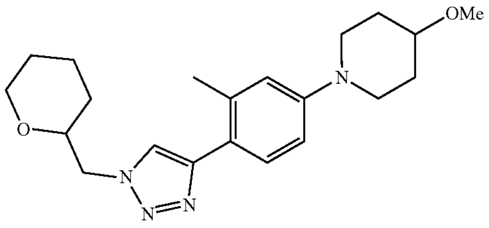 [SMILES: COC1CCN(c2ccc(-c3cn(CC4CCCCO4)nn3)c(C)c2)CC1] | 371.2 | $^1$HNMR (400 MHz, DMSO-$d_6$) δ 8.11 (s, 1H), 7.53-7.55 (m, 1H), 6.80-6.83 (m, 2H), 4.31-4.43 (m, 2H), 3.81-3.84 (m, 1H), 3.67-3.73 (m, 1H), 3.49-3.54 (m, 2H), 3.32-3.35 (m, 1H), 3.24-3.30 (m, 4H), 2.85-2.92 (m, 2H), 2.34 (s, 3H), 1.88-1.92 (m, 2H), 1.75-1.78 (m, 1H), 1.58-1.61 (m, 1H), 1.36-1.51 (m, 5H), 1.12-1.22 (m, 1H). | 5 |
| I-450 | 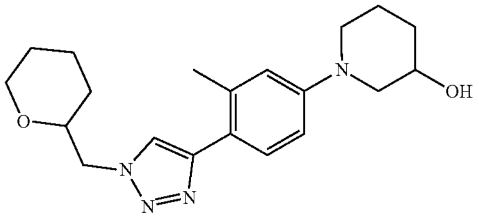 [SMILES: Cc1cc(N2CCCC(O)C2)ccc1-c1cn(CC2CCCCO2)nn1] | 357.2 | $^1$HNMR (400 MHz, DMSO-$d_6$) δ 8.10 (s, 1H), 7.52-7.54 (m, 1H), 6.77-6.79 (m, 2H), 4.81 (d, J = 4.4 Hz, 1H), 4.31-4.43 (m, 2H), 3.81-3.85 (m, 1H), 3.67-3.71 (m, 1H), 3.50-3.64 (m, 3H), 3.26-3.29 (m, 1H), 2.61-2.68 (m, 1H), 2.50-2.53 (m, 1H), 2.34 (s, 3H), 1.85-1.89 (m, 1H), 1.69-1.78 (m, 2H), 1.60 (d, J = 12.8 Hz, 1H), 1.40-1.48 (m, 3H), 1.13-1.30 (m, 3H). | 5 |
| I-428 | 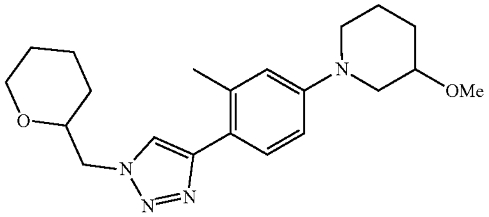 [SMILES: COC1CCCN(c2ccc(-c3cn(CC4CCCCO4)nn3)c(C)c2)C1] | 371.2 | $^1$HNMR (400 MHz, DMSO-$d_6$) δ 8.11 (s, 1H), 7.53-7.55 (m, 1H), 6.82-6.83 (m, 2H), 4.31-4.43 (m, 2H), 3.81-3.84 (m, 1H), 3.65-3.72 (m, 2H), 3.42-3.46 (m, 1H), 3.25-3.31 (m, 5H), 2.74-2.81 (m, 1H), 2.64-2.70 (m, 1H), 2.35 (s, 3H), 1.93-1.98 (m, 1H), 1.72-1.75 (m, 2H), 1.58-1.61 (m, 1H), 1.29-1.50 (m, 5H), 1.15-1.21 (m, 1H). | 5 |
| I-558 | 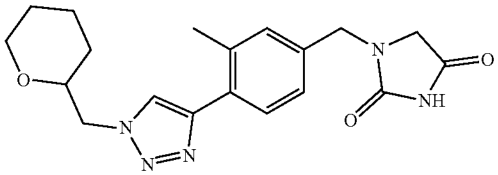 [SMILES: Cc1cc(CN2CC(=O)NC2=O)ccc1-c1cn(CC2CCCCO2)nn1] | 370.0 | $^1$HNMR (400 MHz, DMSO-$d_6$) δ 10.88 (s, 1H), 8.30 (s, 1H), 7.73 (d, J = 7.6 Hz, 1H), 7.17-7.20 (m, 2H), 4.37-4.50 (m, 4H), 3.84-3.86 (m, 3H), 3.72-3.78 (m, 1H), 3.29-3.34 (m, 1H), 2.43 (s, 3H), 1.78-1.81 (m, 1H), 1.62-1.65 (m, 1H), 1.40-1.52 (m, 3H), 1.19-1.25 (m, 1H). | 30 |
| I-559 | 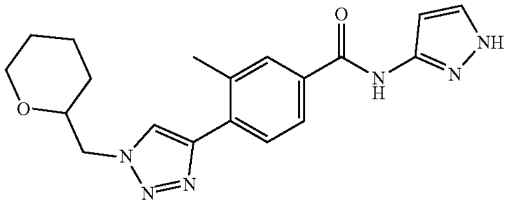 [SMILES: Cc1cc(C(=O)Nc2cc[nH]n2)ccc1-c1cn(CC2CCCCO2)nn1] | 367.1 | $^1$HNMR (400 MHz, DMSO-$d_6$) δ 12.48 (br., 1H), 10.90 (br., 1H), 8.48 (s, 1H), 8.03 (s, 1H), 7.93-7.98 (m, 2H), 7.70 (d, J = 2.4 Hz, 1H), 6.68 (d, J = 1.2 Hz, 1H), 4.45-4.57 (m, 2H), 3.90-3.93 (m, 1H), 3.81-3.82 (m, 1H), 3.35-3.41 (m, 1H), 2.57 (s, 3H), 1.82-1.84 (m, 1H), 1.69-1.72 (m, 1H), 1.49-1.56 (m, 3H), 1.28-1.29 (m, 1H). | 29 |
| I-438 | 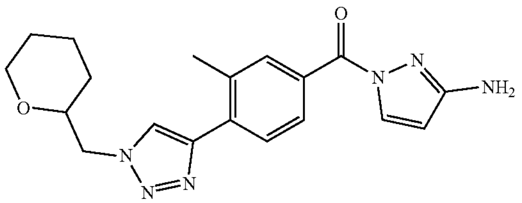 [SMILES: Cc1cc(C(=O)n2ccc(N)n2)ccc1-c1cn(CC2CCCCO2)nn1] | 367.1 | $^1$HNMR (400 MHz, DMSO-$d_6$) δ 8.44 (s, 1H), 8.17 (d, J = 2.8 Hz, 1H), 7.89 (s, 3H), 6.00 (d, J = 3.2 Hz, 1H), 5.70 (s, 2H), 4.38-4.50 (m, 2H), 3.82-3.85 (m, 1H), 3.72-3.76 (m, 1H), 3.29-3.31 (m, 1H), 2.49 (s, 3H), 1.76-1.79 (m, 1H), 1.62-1.65 (m, 1H), 1.41-1.46 (m, 3H), 1.13-1.21 (m, 1H). | 29 |

TABLE 23-continued

| Characterization data for exemplary compounds | | | | |
|---|---|---|---|---|
| Compound No. | Chemical Structure | M + 1 | $^1$H NMR (400 MHz) | Example of Synthesis |
| I-439 | 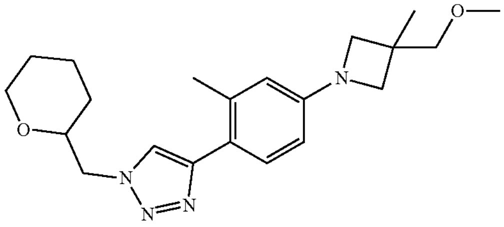 [SMILES: COCC1(C)CN(c2ccc(-c3cn(CC4CCCCO4)nn3)c(C)c2)C1] | 371.1 | $^1$HNMR (400 MHz, $CDCl_3$) δ 7.67 (s, 1H), 7.63 (d, J = 8.0 Hz, 1H), 6.35 (d, J = 8.4 Hz, 1H), 6.30 (s, 1H), 4.47 (dd, J = 2.8 Hz, 14.0 Hz, 1H), 4.31 (dd, J = 7.6 Hz, 14.0 Hz, 1H), 3.97 (d, J = 10.8 Hz, 1H), 3.74 (d, J = 7.2 Hz, 2H), 3.67-3.71 (m, 1H), 3.52 (d, J = 7.2 Hz, 2H), 3.41 (s, 2H), 3.36-3.39 (m, 4H), 2.40 (s, 3H), 1.86-1.87 (m, 1H), 1.64-1.67 (m, 1H), 1.51-1.55 (m, 3H), 1.34 (s, 3H), 1.24-1.27 (m, 1H). | 5 |
| I-440 | 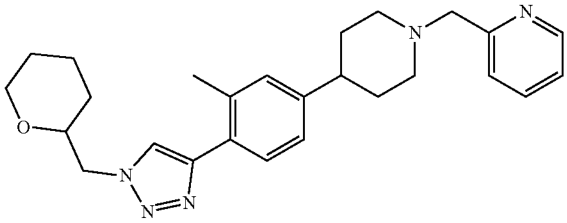 [SMILES: Cc1cc(C2CCN(Cc3ccccn3)CC2)ccc1-c1cn(CC2CCCCO2)nn1] | 432.1 | $^1$HNMR (400 MHz, $CDCl_3$) δ 8.56 (dd, J = 0.8 Hz, 4.8 Hz, 1H), 7.76 (s, 1H), 7.71 (d, J = 8.4 Hz, 1H), 7.64-7.68 (m, 1H), 7.47 (d, J = 7.6 Hz, 1H), 7.12-7.18 (m, 3H), 4.49 (dd, J = 2.8 Hz, 14.0 Hz, 1H), 4.31 (dd, J = 7.6 Hz, 14.0 Hz, 1H), 3.96 (dd, J = 2.0 Hz, 10.4 Hz, 1H), 3.65-3.71 (m, 3H), 3.34-3.41 (m, 1H), 3.04 (d, J = 11.2 Hz, 2H), 2.48-2.56 (m, 1H), 2.44 (s, 3H), 2.22 (t, J = 10.4 Hz, 2H), 1.80-1.92 (m, 5H), 1.64-1.67 (m, 1H), 1.45-1.55 (m, 3H), 1.19-1.28 (m, 1H). | 5 |
| I-441 | 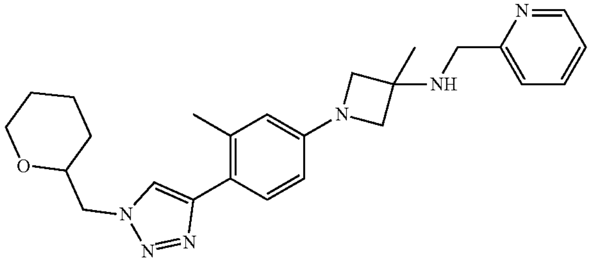 [SMILES: Cc1cc(N2CC(C)(NCc3ccccn3)C2)ccc1-c1cn(CC2CCCCO2)nn1] | 433.1 | $^1$HNMR (400 MHz, $CDCl_3$) δ 8.54 (dd, J = 0.8 Hz, 5.2 Hz, 1H), 7.68 (s, 1H), 7.61-7.66 (m, 2H), 7.30 (d, J = 8.0 Hz, 1H), 7.15-7.18 (m, 1H), 6.38 (dd, J = 2.4 Hz, 8.4 Hz, 1H), 6.33 (d, J = 2.4 Hz, 1H), 4.47 (dd, J = 3.2 Hz, 14.0 Hz, 1H), 4.31 (dd, J = 7.2 Hz, 14.0 Hz, 1H), 3.94-3.99 (m, 3H), 3.74-3.79 (m, 4H), 3.66-3.72 (m, 1H), 3.36-3.42 (m, 1 H), 2.40 (s, 3H), 1.85-1.88 (m, 1H), 1.64-1.67 (m, 1H), 1.58 (s, 3H), 1.49-1.56 (m, 3H), 1.21-1.30 (m, 1H). | 5 |
| I-464 | 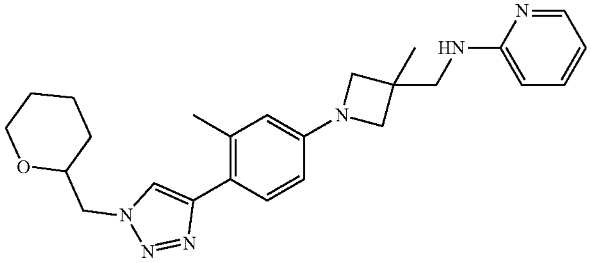 [SMILES: Cc1cc(N2CC(C)(CNc3ccccn3)C2)ccc1-c1cn(CC2CCCCO2)nn1] | 433.1 | $^1$HNMR (400 MHz, $CDCl_3$) δ 8.02 (d, J = 5.2 Hz, 1H), 7.69 (s, 1H), 7.66 (d, J = 8.4 Hz, 1H), 7.48-7.52 (m, 1H), 6.62 (t, J = 6.0 Hz, 1H), 6.40 (d, J = 8.4 Hz, 1H), 6.39 (dd, , I = 2.0 Hz, 8.0 Hz, 1H), 6.34 (d, J = 2.4 Hz, 1H), 4.49 (dd, J = 3.2 Hz, 14.0 Hz, 1H), 4.32 (dd, J = 7.6 Hz, 14.0 Hz, 1H), 3.97-4.00 (m, 1H), 3.84 (d, J = 7.2 Hz, 2H), 3.68-3.73 (m, 1H), 3.61 (d, J = 7.2 Hz, 2H), 3.54 (d, J = 5.6 Hz, 2H), 3.40-3.42 (m, 1H), 2.42 (s, 3H), 1.87-1.89 (m, 1H), 1.66-1.69 (m, 1H), 1.51-1.53 (m, 3H), 1.42 (s, 3H), 1.26-1.31 (m, 1H). | 22 |

TABLE 23-continued

| Compound No. | Chemical Structure | M + 1 | $^1$H NMR (400 MHz) | Example of Synthesis |
|---|---|---|---|---|
| | Characterization data for exemplary compounds | | | |
| I-451 | 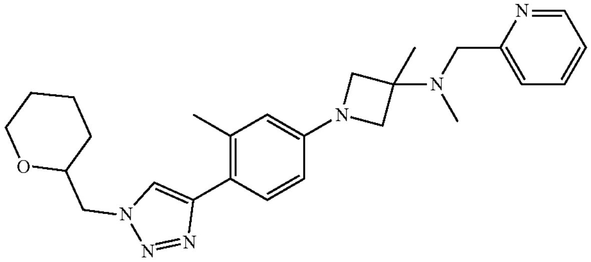 [SMILES: Cc1cc(N2CC(C)(N(C)Cc3ccccn3)C2)ccc1-c1cn(CC2CCCCO2)nn1] | 447.1 | $^1$HNMR (400 MHz, $CDCl_3$) δ 8.51 (d, J = 4.0 Hz, 1H), 7.68 (s, 1H), 7.62-7.66 (m, 2H), 7.51-7.53 (m, 1H), 7.13-7.16 (m, 1H), 6.40 (dd, J = 2.4 Hz, 8.4 Hz, 1H), 6.35 (d, J = 2.0 Hz, 1H), 4.48 (dd, J = 3.2 Hz, 14.0 Hz, 1H), 4.31 (dd, J = 7.6 Hz, 14.0 Hz, 1H), 3.96-3.99 (m, 1H), 3.69-3.76 (m, 4H), 3.66-3.68 (m, 1H), 3.63 (s, 2H), 3.39-3.41 (m, 1H), 2.40 (s, 3H), 2.14 (s, 3H), 1.86-1.88 (m, 1H), 1.64-1.67 (m, 1H), 1.49-1.56 (m, 6H), 1.24-1.27 (m, 1H). | 5 |
| I-452 | 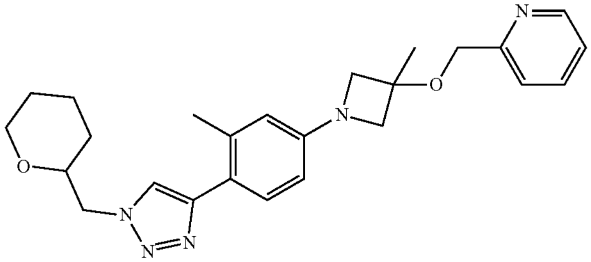 [SMILES: Cc1cc(N2CC(C)(OCc3ccccn3)C2)ccc1-c1cn(CC2CCCCO2)nn1] | 434.1 | $^1$HNMR (400 MHz, $CDCl_3$) δ 8.53 (d, J = 4.0 Hz, 1H), 7.64-7.70 (m, 3H), 7.46 (d, J = 8.0 Hz, 1H), 7.16-7.19 (m, 1H), 6.40 (dd, J = 2.4 Hz, 8.4 Hz, 1H), 6.35 (d, J = 2.4 Hz, 1H), 4.63 (s, 2H), 4.47 (dd, J = 3.2 Hz, 14.0 Hz, 1H), 4.31 (dd, J = 7.6 Hz, 14.4 Hz, 1H), 3.92-3.99 (m, 3H), 3.82 (d, J = 7.6 Hz, 2H), 3.67-3.71 (m, 1H), 3.38-3.41 (m, 1H), 2.41 (s, 3H), 1.86-1.88 (m, 1H), 1.64-1.73 (m, 4H), 1.49-1.52 (m, 3H), 1.24-1.27 (m, 1H). | 5 |
| I-514 | 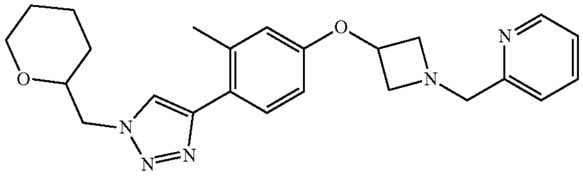 [SMILES: Cc1cc(OC2CN(Cc3ccccn3)C2)ccc1-c1cn(CC2CCCCO2)nn1] | 420.1 | $^1$HNMR (400 MHz, $CDCl_3$) δ 8.56-8.57 (m, 1H), 7.73 (s, 1H), 7.64-7.69 (m, 2H), 7.33 (d, J = 8.0 Hz, 1H), 7.16-7.19 (m, 1H), 6.66-6.69 (m, 2H), 4.85-4.90 (m, 1H), 4.50 (dd, J = 2.8 Hz, 14.0 Hz, 1H), 4.32 (dd, J = 7.6 Hz, 14.4 Hz, 1H), 3.97-4.00 (m, 1H), 3.91-3.95 (m, 2H), 3.87 (s, 2H), 3.67-3.73 (m, 1H), 3.37-3.43 (m, 1H), 3.28-3.32 (m, 2H), 2.42 (s, 3H), 1.88-1.89 (m, 1H), 1.66-1.69 (m, 1H), 1.49-1.58 (m, 3H), 1.22-1.31 (m, 1H). | 26 |
| I-442 | 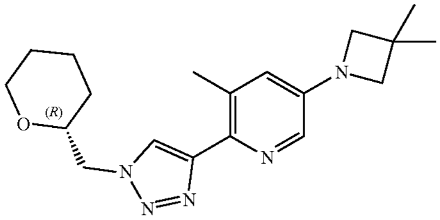 | 342.2 | $^1$HNMR (400 MHz, $CDCl_3$) δ 8.03 (s, 1H), 7.71 (d, J = 2.4 Hz, 1H), 6.57 (d, J = 2.4 Hz, 1H), 4.46 (dd, J = 3.6 Hz, 14.0 Hz, 1H), 4.33 (dd, J = 7.2 Hz, 14.0 Hz, 1H), 3.95-3.98 (m, 1H), 3.68-3.74 (m, 1H), 3.63 (s, 4H), 3.35-3.42 (m, 1H), 2.62 (s, 3H), 1.82-1.87 (m, 1H), 1.63-1.66 (m, 1H), 1.45-1.58 (m, 3H), 1.33 (s, 6H), 1.24-1.30 (m, 1H). | 5 |
| I-429 | 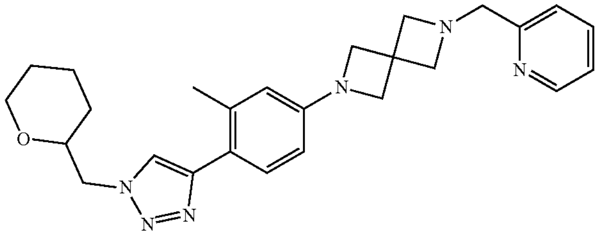 [SMILES: Cc1cc(N2CC3(CN(Cc4ccccn4)C3)C2)ccc1-c1cn(CC2CCCCO2)nn1] | 445.0 | $^1$HNMR (400 MHz, DMSO-$d_6$) δ 8.45 (d, J = 4.0 Hz, 1H), 8.07 (s, 1H), 7.71 (t, J = 7.2 Hz, 1H), 7.50 (d, J = 8.0 Hz, 1H), 7.31 (d, J = 7.6 Hz, 1H), 7.20-7.23 (m, 1H), 6.29-6.31 (m, 2H), 4.30-4.41 (m, 2H), 3.80-3.86 (m, 5H), 3.63-3.69 (m, 3H), 3.25-3.34 (m, 5H), 2.31 (s, 3H), 1.74-1.76 (m, 1H), 1.57-1.60 (m, 1H), 1.36-1.49 (m, 3H), 1.11-1.20 (m, 1H). | 5 |

TABLE 23-continued

Characterization data for exemplary compounds

| Compound No. | Chemical Structure | M + 1 | ¹H NMR (400 MHz) | Example of Synthesis |
|---|---|---|---|---|
| I-465 | 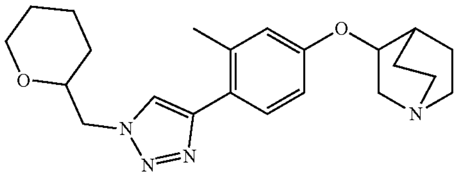 [SMILES: Cc1cc(OC2CN3CCC2CC3)ccc1-c1cn(CC2CCCCO2)nn1] | 383.1 | ¹HNMR (400 MHz, $CDCl_3$) δ 7.69-7.74 (m, 2H), 6.76-6.77 (m, 2H), 4.30-4.52 (m, 3H), 3.97-4.00 (m, 1H), 3.63-3.79 (m, 1H), 3.26-3.40 (m, 2H), 2.79-2.98 (m, 5H), 2.43 (s, 3H), 2.11-2.23 (m, 1H), 1.89-2.00 (m, 2H), 1.53-1.75 (m, 6H), 1.25-1.39 (m, 2H). | 26 |
| I-430 | 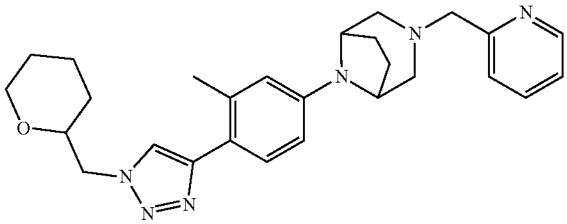 [SMILES: Cc1cc(N2C3CCC2CN(Cc2ccccn2)C3)ccc1-c1cn(CC2CCCCO2)nn1] | 459.0 | ¹HNMR (400 MHz, $CDCl_3$) δ 8.49 (d, J = 2.8 Hz, 1H), 7.70 (s, 1H), 7.65-7.68 (m, 2H), 7.49-7.51 (m, 1H), 7.12-7.20 (m, 1H), 6.65-6.69 (m, 2H), 4.49 (dd, J = 3.2 Hz, 14.0 Hz, 1H), 4.32 (dd, J = 7.2 Hz, 14.0 Hz, 1H), 4.21 (s, 2H), 3.96-4.00 (m, 1H), 3.66-3.72 (m, 1H), 3.58 (s, 2H), 3.36-3.43 (m, 1H), 2.51-2.66 (m, 4H), 2.41 (s, 3H), 1.93-2.09 (m, 4H), 1.84-1.88 (m, 1H), 1.62-1.68 (m, 1H), 1.49-1.57 (m, 3H), 1.21-1.31 (m, 1H). | 5 |
| I-466 | 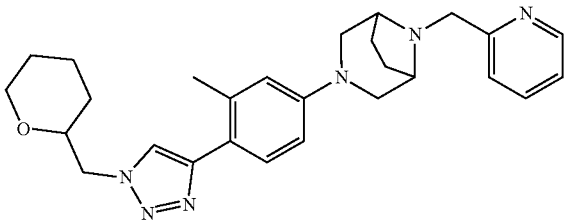 [SMILES: Cc1cc(N2CC3CCC(C2)N3Cc2ccccn2)ccc1-c1cn(CC2CCCCO2)nn1] | 459.1 | ¹HNMR (400 MHz, $CDCl_3$) δ 8.55 (d, J = 4.8 Hz, 1H), 7.67-7.74 (m, 4H), 7.14-7.24 (m, 1H), 6.72 (dd, J = 2.8 Hz, 8.8 Hz, 1H), 6.68 (d, J = 2.4 Hz, 1H), 4.49 (dd, J = 2.8 Hz, 14.0 Hz, 1H), 4.32 (dd, J = 7.6 Hz, 14.4 Hz, 1H), 3.97-4.00 (m, 1H), 3.79 (s, 2H), 3.68-3.74 (m, 1H), 3.37-3.45 (m, 4H), 3.04-3.20 (m, 1H), 2.43 (s, 3H), 2.04-2.21 (m, 2H), 1.86-1.88 (m, 3H), 1.61-1.79 (m, 2H), 1.50-1.58 (m, 4H), 1.24-1.28 (m, 1H). | 5 |
| I-502 | 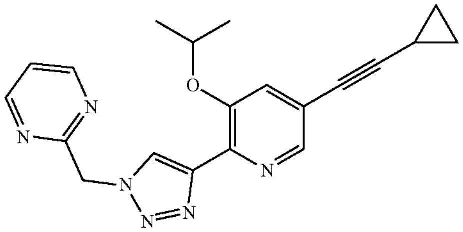 [SMILES: CC(C)Oc1cc(C#CC2CC2)cnc1-c1cn(Cc2ncccn2)nn1] | 361.2 | ¹HNMR (400 MHz, DMSO-$d_6$) δ 8.81 (d, J = 4.8 Hz, 2H), 8.60 (s, 1H), 8.23 (d, J = 1.2 Hz, 1H), 7.56 (d, J = 0.6 Hz, 1H), 7.49 (t, J = 4.8 Hz, 1H), 5.98 (s, 2H), 4.82-4.88 (m, 1H), 1.58-1.65 (m, 1H), 1.33 (d, J = 6.0 Hz, 6H), 0.91-0.96 (m, 2H), 0.79-0.83 (m, 2H). | 3 |
| I-478 | 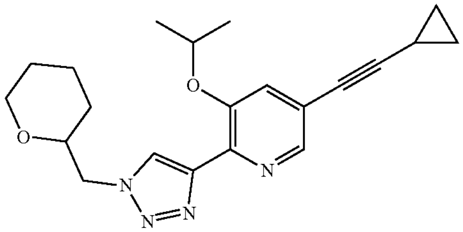 [SMILES: CC(C)Oc1cc(C#CC2CC2)cnc1-c1cn(CC2CCCCO2)nn1] | 367.1 | ¹HNMR (400 MHz, DMSO-$d_6$) δ 8.41 (s, 1H), 8.21 (s, 1H), 7.55 (s, 1H), 4.81-4.87 (m, 1H), 4.42-4.54 (m, 2H), 3.86 (d, J = 11.2 Hz, 1H), 3.70-3.72 (m, 1H), 3.31-3.37 (m, 1H), 1.79 (d, J = 10.0 Hz, 1H), 1.58-1.65 (m, 2H), 1.40-1.54 (m, 3H), 1.33 (dd, J = 1.6 Hz, 6.0 Hz, 6H), 1.13-1.23 (m, 1H), 0.89-0.96 (m, 2H), 0.78-0.82 (m, 2H). | 3 |
| I-479 | 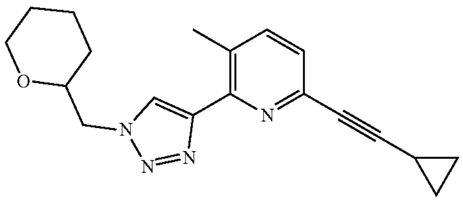 [SMILES: Cc1ccc(C#CC2CC2)nc1-c1cn(CC2CCCCO2)nn1] | 323.0 | ¹HNMR (400 MHz, DMSO-$d_6$) δ 8.48 (s, 1H), 7.70 (d, J = 8.0 Hz, 1H), 7.32 (d, J = 7.6 Hz, 1H), 4.42-4.54 (m, 2H), 3.88-3.91 (m, 1H), 3.75-3.79 (m, 1H), 3.31-3.35 (m, 1H), 2.64 (s, 3H), 1.80-1.83 (m, 1H), 1.58-1.68 (m, 2H), 1.46-1.53 (m, 3H), 1.21-1.27 (m, 1H), 0.92-0.97 (m, 2H), 0.79-0.83 (m, 2H). | 2 |

TABLE 23-continued

Characterization data for exemplary compounds

| Compound No. | Chemical Structure | M + 1 | $^1$H NMR (400 MHz) | Example of Synthesis |
|---|---|---|---|---|
| I-480 | 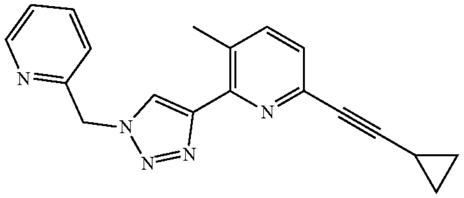 [SMILES: Cc1ccc(C#CC2CC2)nc1-c1cn(Cc2ccccn2)nn1] | 316.0 | $^1$HNMR (400 MHz, DMSO-$d_6$) δ 8.66 (s, 1H), 8.55-8.57 (m, 1H), 7.84 (dt, J = 7.6 Hz, 2.0 Hz, 1H), 7.68 (d, J = 8.0 Hz, 1H), 7.34-7.38 (m, 2H), 7.30 (d, J = 8.0 Hz, 1H), 5.80 (s, 2H), 2.62 (s, 3H), 1.56-1.60 (m, 1H), 0.89-0.93 (m, 2H), 0.76-0.80 (m, 2H). | 2 |
| I-481 | 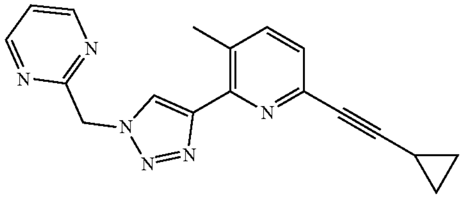 [SMILES: Cc1ccc(C#CC2CC2)nc1-c1cn(Cc2ncccn2)nn1] | 317.0 | $^1$HNMR (400 MHz, DMSO-$d_6$) δ 8.84 (d, J = 4.8 Hz, 2H), 8.70 (s, 1H), 7.71 (d, J = 8.4 Hz, 1H), 7.52 (t, J = 4.8 Hz, 1H), 7.33 (d, J = 7.6 Hz, 1H), 5.98 (s, 2H), 2.66 (s, 3H), 1.58-1.60 (m, 1H), 0.92-0.95 (m, 2H), 0.78-0.82 (m, 2H). | 2 |
| I-482 | 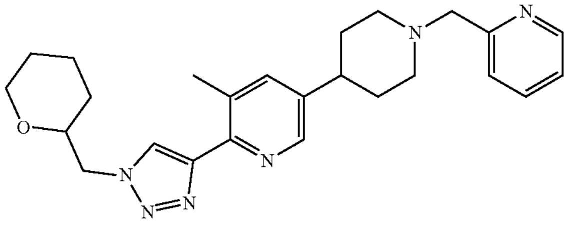 [SMILES: Cc1cc(C2CCN(Cc3ccccn3)CC2)cnc1-c1cn(CC2CCCCO2)nn1] | 433.1 | $^1$HNMR (400 MHz, DMSO-$d_6$) δ 8.48-8.50 (m, 1H), 8.39 (s, 1H), 8.35 (d, J = 2.0 Hz, 1H), 7.77 (dt, J = 7.6 Hz, 2.0 Hz, 1H), 7.60 (d, J = 2.0 Hz, 1H), 7.47 (d, J = 8.0 Hz, 1H), 7.24-7.28 (m, 1H), 4.39-4.51 (m, 2H), 3.84-3.87 (m, 1H), 3.71-3.76 (m, 1H), 3.63 (s, 2H), 3.28-3.31 (m, 1H), 2.94 (d, J = 11.6 Hz, 2H), 2.62 (s, 3H), 2.54-2.57 (m, 1H), 2.11-2.17 (m, 2H), 1.71-1.79 (m, 5H), 1.61-1.64 (m, 1H), 1.42-1.50 (m, 3H), 1.15-1.24 (m, 1H). | 5 |
| I-503 | 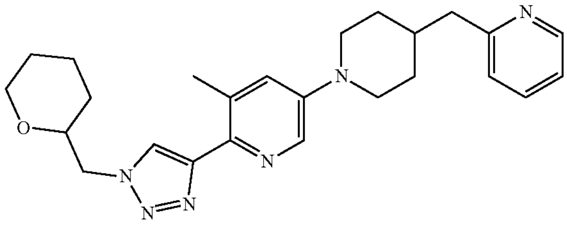 [SMILES: Cc1cc(N2CCC(Cc3ccccn3)CC2)cnc1-c1cn(CC2CCCCO2)nn1] | 433.1 | $^1$HNMR (400 MHz, DMSO-$d_6$) δ 8.49 (d, J = 4.4 Hz, 1H), 8.25 (s, 1H), 8.15 (d, J = 2.4 Hz, 1H), 7.69 (dt, J = 7.6 Hz, 1.6 Hz, 1H), 7.19-7.25 (m, 3H), 4.36-4.47 (m, 2H), 3.69-3.87 (m, 4H), 3.28-3.34 (m, 1H), 2.67-2.72 (m, 4H), 2.56 (s, 3H), 1.92-1.95 (m, 1H), 1.77-1.79 (m, 1H), 1.62-1.65 (m, 3H), 1.44-1.49 (m, 3H), 1.28-1.38 (m, 2H), 1.17-1.20 (m, 1H). | 5 |
| I-504 | 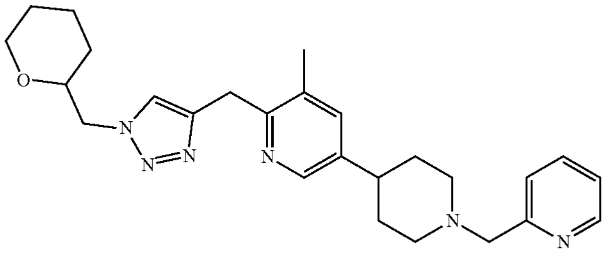 [SMILES: Cc1cc(C2CCN(Cc3ccccn3)CC2)cnc1Cc1cn(CC2CCCCO2)nn1] | 447.1 | $^1$HNMR (400 MHz, DMSO-$d_6$) δ 8.49 (dd, J = 4.8, 0.8 Hz, 1H), 8.19 (d, J = 2.0 Hz, 1H), 7.77 (dt, J = 7.6, 1.6 Hz, 1H), 7.69 (s, 1H), 7.46-7.48 (m, 2H), 7.24-7.27 (m, 1H), 4.23-4.35 (m, 2H), 4.08 (s, 2H), 3.80-3.83 (m, 1H), 3.62-3.66 (m, 3H), 3.23-3.32 (m, 1H), 2.91-2.94 (m, 2H), 2.47-2.54 (m, 1H), 2.29 (s, 3H), 2.08-2.18 (m, 2H), 1.63-1.77 (m, 5H), 1.54-1.57 (m, 1H), 1.35-1.50 (m, 3H), 1.08-1.18 (m, 1H). | 13 |
| I-505 | 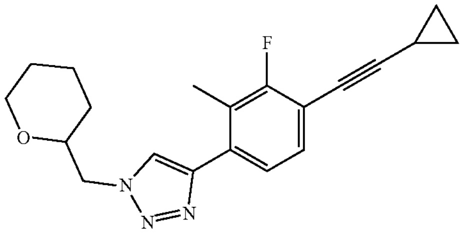 [SMILES: Cc1c(-c2cn(CC3CCCCO3)nn2)ccc(C#CC2CC2)c1F] | 340.1 | $^1$HNMR (400 MHz, DMSO-$d_6$) δ 8.40 (s, 1H), 7.53 (d, J = 8.0 Hz, 1H), 7.33 (t, J = 7.8 Hz, 1H), 4.38-4.51 (m, 2H), 3.85 (d, J = 10.8 Hz, 1H), 3.72-3.77 (m, 1H), 3.28-3.31 (m, 1H), 2.34 (d, J = 2.0 Hz, 3H), 1.78-1.81 (m, 1H), 1.58-1.66 (m, 2H), 1.39-1.54(m, 3H), 1.15-1.24 (m, 1H), 0.89-0.95 (m, 2H), 0.75-0.79 (m, 2H). | 3 |

TABLE 23-continued

| Compound No. | Chemical Structure | M + 1 | $^1$H NMR (400 MHz) | Example of Synthesis |
|---|---|---|---|---|
| Characterization data for exemplary compounds | | | | |
| I-575 | 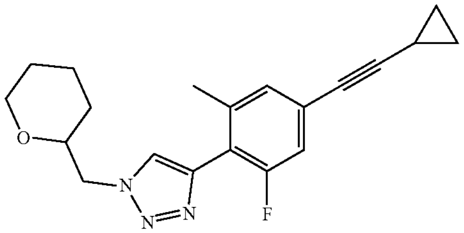 [SMILES: Cc1cc(C#CC2CC2)cc(F)c1-c1cn(CC2CCCCO2)nn1] | 340.1 | $^1$HNMR (400 MHz, DMSO-$d_6$) δ 8.25 (d, J = 2.8 Hz, 1H), 7.19 (s, 1H), 7.15 (d, J = 10.8 Hz, 1H), 4.40-4.52 (m, 2H), 3.84-3.88 (m, 1H), 3.71-3.77 (m, 1H), 3.29-3.32 (m, 1H), 2.35 (s, 3H), 1.78-1.81 (m, 1H), 1.53-1.64 (m, 2H), 1.38-1.52 (m, 3H), 1.14-1.24 (m, 1H), 0.89-0.94 (m, 2H), 0.74-0.78 (m, 2H). | 27 |
| I-467 | 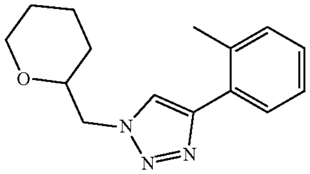 [SMILES: Cc1ccccc1-c1cn(CC2CCCCO2)nn1] | 258.1 | $^1$HNMR (400 MHz, DMSO-$d_6$) δ 8.28 (s, 1H), 7.70-7.72 (m, 1H), 7.23-7.27 (m, 3H), 4.35-4.46 (m, 2H), 3.82-3.85 (m, 1H), 3.69-3.75 (m, 1H), 3.27-3.31 (m, 1H), 2.40 (s, 3H), 1.73-1.81 (m, 1H), 1.59 (d, J = 2.0 Hz, 1H), 1.37-1.52 (m, 3H), 1.12-1.24 (m, 1H). | 2 |
| I-468 | 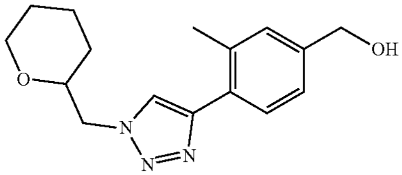 [SMILES: Cc1cc(CO)ccc1-c1cn(CC2CCCCO2)nn1] | 288.1 | $^1$HNMR (400 MHz, DMSO-$d_6$) δ 8.28 (s, 1H), 7.70 (d, J = 7.6 Hz, 1H), 7.20-7.23 (m, 2H), 5.20 (t, J = 6.0 Hz, 1H), 4.50 (d, J = 5.6 Hz, 2H), 4.37-4.49 (m, 2H), 3.84-3.88 (m, 1H), 3.70-3.78 (m, 1H), 3.30-3.35 (m, 1H), 2.43 (s, 3H), 1.78-1.79 (m, 1H), 1.63-1.66 (m, 1H), 1.44-1.51 (m, 3H), 1.19-1.22 (m, 1H). | 3 |
| I-469 | 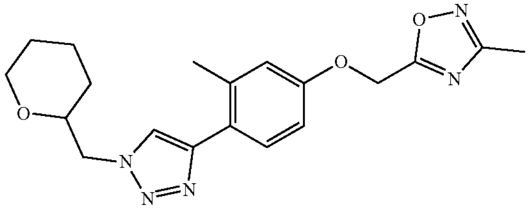 [SMILES: Cc1noc(COc2ccc(-c3cn(CC4CCCCO4)nn3)c(C)c2)n1] | 370.0 | $^1$HNMR (400 MHz, DMSO-$d_6$) δ 8.24 (s, 1H), 7.67 (d, J = 7.6, 1H), 6.95-7.01 (m, 2H), 5.51 (s, 2H), 4.36-4.48 (m, 2H), 3.84-3.87 (m, 1H), 3.72-3.76 (m, 1H), 3.29-3.32 (m, 1H), 2.41 (s, 3H), 2.37 (s, 3H), 1.78-1.81 (m, 1H), 1.62-1.65 (m, 1H), 1.43-1.51 (m, 3H), 1.18-1.24 (m, 1H). | 26 |
| I-483 | 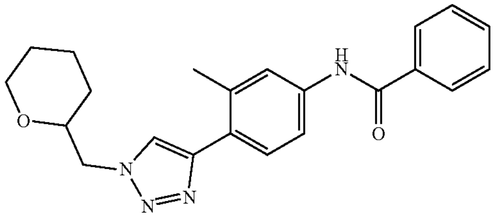 [SMILES: Cc1cc(NC(=O)c2ccccc2)ccc1-c1cn(CC2CCCCO2)nn1] | 377.1 | $^1$HNMR (400 MHz, $CDCl_3$) δ 7.88-7.92 (m, 3H), 7.80-7.83 (m, 2H), 7.68 (s, 1H), 7.48-7.58 (m, 4H), 4.52 (dd, J = 3.2 Hz, 14.0 Hz, 1H), 4.34 (dd, J = 7.6 Hz, 14.0 Hz, 1H), 3.99-4.02 (m, 1H), 3.69-3.75 (m, 1H), 3.38-3.43 (m, 1H), 2.49 (s, 3H), 1.85-1.93 (m, 1H), 1.65-1.73 (m, 1H), 1.52-1.58 (m, 3H), 1.27-1.30 (m, 1H). | 29 |
| I-484 | 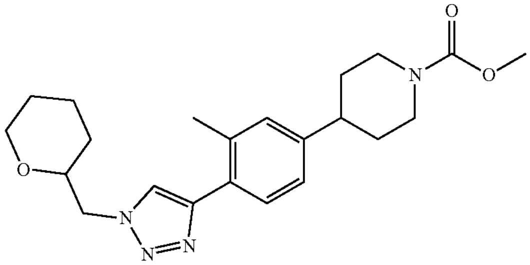 [SMILES: COC(=O)N1CCC(c2ccc(-c3cn(CC4CCCCO4)nn3)c(C)c2)CC1] | 399.1 | $^1$HNMR (400 MHz, $CDCl_3$) δ 7.79 (s, 1H), 7.75 (d, J = 8.0 Hz, 1H), 7.10-7.12 (m, 2H), 4.52 (dd, J = 3.2 Hz, 14.4 Hz, 1H), 4.26-4.36 (m, 3H), 3.97-4.00 (m, 1H), 3.67-3.73 (m, 4H), 3.37-3.43 (m, 1H), 2.85-2.90 (m, 2H), 2.64-2.70 (m, 1H), 2.46 (s, 3H), 1.84-1.87 (m, 3H), 1.67-1.69 (m, 2H), 1.50-1.57 (m, 3H), 1.24-1.30 (m, 1H). | 5 |

TABLE 23-continued

Characterization data for exemplary compounds

| Compound No. | Chemical Structure | M + 1 | $^1$H NMR (400 MHz) | Example of Synthesis |
|---|---|---|---|---|
| I-485 | 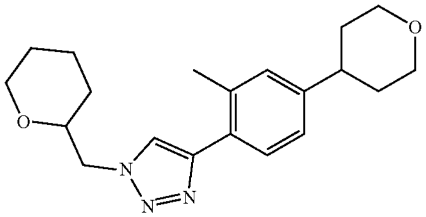 [SMILES: Cc1cc(C2CCOCC2)ccc1-c1cn(CC2CCCCO2)nn1] | 342.2 | $^1$HNMR (400 MHz, DMSO-$d_6$) δ 8.26 (s, 1H), 7.67 (d, J = 8.0 Hz, 1H), 7.15-7.18 (m, 2H), 4.37-4.49 (m, 2H), 3.93-3.97 (m, 2H), 3.84-3.87 (m, 1H), 3.71-3.77 (m, 1H), 3.40-3.47 (m, 2H), 3.29-3.32 (m, 1H), 2.72-2.79 (m, 1H), 2.42 (s, 3H), 1.78-1.81 (m, 1H), 1.62-1.71 (m, 5H), 1.39-1.54 (m, 3H), 1.15-1.25 (m, 1H). | 5 |
| I-576 | 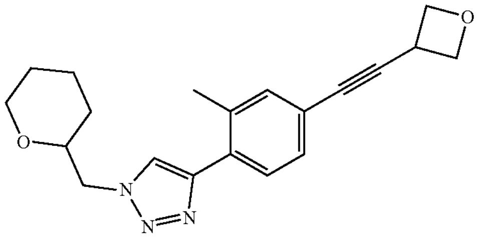 [SMILES: Cc1cc(C#CC2COC2)ccc1-c1cn(CC2CCCCO2)nn1] | 338.0 | $^1$HNMR (400 MHz, DMSO-$d_6$) δ 8.36 (s, 1H), 7.79 (d, J = 8.0 Hz, 1H), 7.40 (s, 1H), 7.35 (dd, J = 1.2 Hz, 8.0 Hz, 1H), 4.80-4.83 (m, 2H), 4.61-4.64 (m, 2H), 4.38-4.51 (m, 2H), 4.14-4.18 (m, 1H), 3.84-3.87 (m, 1H), 3.73-3.76 (m, 1H), 3.29-3.32 (m, 1H), 2.44 (s, 3H), 1.78-1.81 (m, 1H), 1.63-1.66 (m, 1H), 1.43-1.51 (m, 3H), 1.19-1.23 (m, 1H). | 2 |
| I-540 | 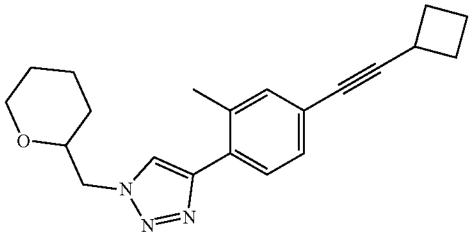 [SMILES: Cc1cc(C#CC2CCC2)ccc1-c1cn(CC2CCCCO2)nn1] | 336.1 | $^1$HNMR (400 MHz, DMSO-$d_6$) δ 8.35 (s, 1H), 7.75 (d, J = 8.0 Hz, 1H), 7.34 (s, 1H), 7.28 (dd, J = 1.6 Hz, 8.0 Hz, 1H), 4.37-4.50 (m, 2H), 3.84-3.87 (m, 1H), 3.71-3.78 (m, 1H), 3.25-3.32 (m, 2H), 2.42 (s, 3H), 2.27-2.35 (m, 2H), 2.09-2.18 (m, 2H), 1.78-2.00 (m, 3H), 1.62-1.65 (m, 1H), 1.39-1.52 (m, 3H), 1.19-1.25 (m, 1H). | 2 |
| I-515 | 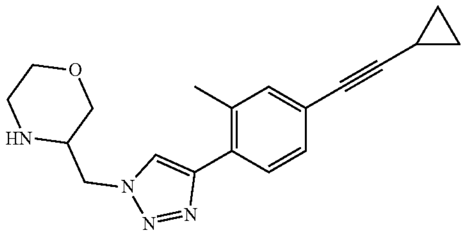 [SMILES: Cc1cc(C#CC2CC2)ccc1-c1cn(CC2COCCN2)nn1] | 323.1 | $^1$HNMR (400 MHz, $CDCl_3$) δ 7.74 (d, J = 7.6 Hz, 1H), 7.71 (s, 1H), 7.28-7.30 (m, 2H), 4.38 (d, J = 5.6 Hz, 2H), 3.87-3.89 (m, 1H), 3.78-3.82 (m, 1H), 3.55-3.61 (m, 1H), 3.31-3.43 (m, 2H), 2.88-2.98 (m, 2H), 2.44 (s, 3H), 1.43-1.50 (m, 1H), 0.87-0.91 (m, 2H), 0.80-0.85 (m, 2H). | 1 |
| I-527 | 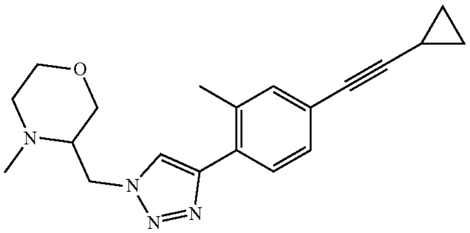 [SMILES: Cc1cc(C#CC2CC2)ccc1-c1cn(CC2COCCN2C)nn1] | 337.1 | $^1$HNMR (400 MHz, DMSO-$d_6$) δ 8.42 (s, 1H), 7.74 (d, J = 8.0 Hz, 1H), 7.31 (s, 1H), 7.26 (d, J = 7.6 Hz, 1H), 4.64 (dd, J = 3.6 Hz, 14.4 Hz, 1H), 4.48 (dd, J = 6.8 Hz, 14.4 Hz, 1H), 3.63-3.66 (m, 1H), 3.55-3.59 (m, 1H), 3.40-3.46 (m, 1H), 3.16-3.21 (m, 1H), 2.68-2.71 (m, 1H), 2.54-2.60 (m, 1H), 2.41 (s, 3H), 2.35 (s, 3H), 2.21-2.27 (m, 1H), 1.52-1.57 (m, 1H), 0.87-0.92 (m, 2H), 0.72-0.76 (m, 2H). | 1 |
| I-541 | 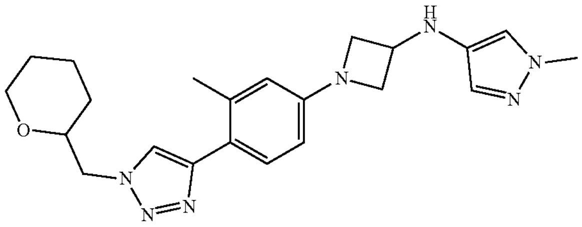 [SMILES: Cc1cc(N2CC(Nc3cnn(C)c3)C2)ccc1-c1cn(CC2CCCCO2)nn1] | 408.1 | $^1$HNMR (400 MHz, DMSO-$d_6$) δ 8.10 (s, 1H), 7.54 (d, J = 8.0 Hz, 1H), 7.10 (d, J = 0.8 Hz, 1H), 6.96 (d, J = 0.8 Hz, 1H), 6.34-6.37 (m, 2H), 5.00-5.02 (m, 1H), 4.33-4.45 (m, 2H), 4.15 (t, J = 6.8 Hz, 2H), 4.01-4.08 (m, 1H), 3.84-3.87 (m, 1H), 3.72-3.75 (m, 1H), 3.70 (s, 3H), 3.50-3.53 (m, 2H), 3.29-3.32 (m, 1H), 2.35 (s, 3H), 1.78-1.81 (m, 1H), 1.60-1.64 (m, 1H), 1.43-1.50 (m, 3H), 1.16-1.25 (m, 1H). | 5 |

TABLE 23-continued

| Characterization data for exemplary compounds | | | | |
|---|---|---|---|---|
| Compound No. | Chemical Structure | M + 1 | $^1$H NMR (400 MHz) | Example of Synthesis |
| I-486 | 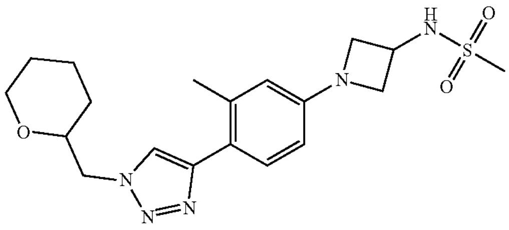 [SMILES: Cc1cc(N2CC(NS(C)(=O)=O)C2)ccc1-c1cn(CC2CCCCO2)nn1] | 406.1 | $^1$HNMR (400 MHz, $CDCl_3$) δ 7.70 (s, 1H), 7.65 (d, J = 8.4 Hz, 1H), 6.35 (dd, J = 2.4 Hz, 8.4 Hz, 1H), 6.31 (d, J = 2.0 Hz, 1H), 5.30 (d, J = 9.6 Hz, 1H), 4.48 (dd, J = 2.8 Hz, 14.0 Hz, 1H), 4.39-4.45 (m, 1H), 4.24-4.33 (m, 3H), 3.96-4.00 (m, 1H), 3.66-3.73 (m, 3H), 3.36-3.43 (m, 1H), 3.00 (s, 3H), 2.40 (s, 3H), 1.87-1.88 (m, 1H), 1.63-1.68 (m, 1H), 1.50-1.56 (m, 3H), 1.21-1.30 (m, 1H). | 5 |
| I-487 | 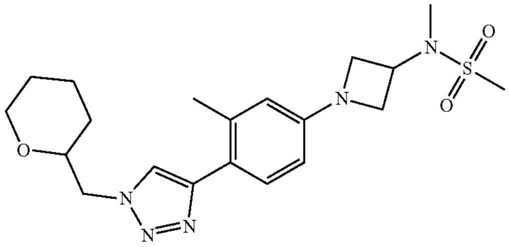 [SMILES: Cc1cc(N2CC(N(C)S(C)(=O)=O)C2)ccc1-c1cn(CC2CCCCO2)nn1] | 420.0 | $^1$HNMR (400 MHz, $CDCl_3$) 6 7.71 (s, 1H), 7.68 (d, J = 8.4 Hz, 1H), 6.40 (dd, J = 2.0 Hz, 8.4 Hz, 1H), 6.35 (d, J = 2.4 Hz, 1H), 4.73-4.80 (m, 1H), 4.50 (dd, J = 3.2 Hz, 14.0 Hz, 1H), 4.32 (dd, J = 7.2 Hz, 14.0 Hz, 1H), 4.15 (t, J = 8.0 Hz, 2H), 3.93-4.00 (m, 3H), 3.67-3.73 (m, 1H), 3.37-3.43 (m, 1H), 3.00 (s, 3H), 2.84 (s, 3H), 2.42 (s, 3H), 1.87-1.89 (m, 1H), 1.66-1.69 (m, 1H), 1.47-1.58 (m, 3H), 1.22-1.31 (m, 1H). | 5 |
| I-516 | 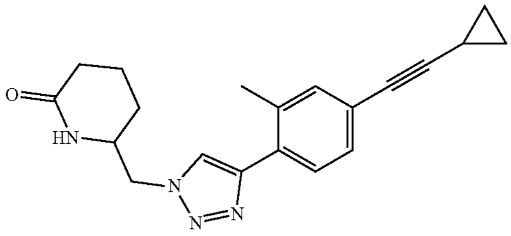 [SMILES: Cc1cc(C#CC2CC2)ccc1-c1cn(CC2CCCC(=O)N2)nn1] | 335.0 | $^1$HNMR (400 MHz, DMSO-$d_6$) δ 8.39 (s, 1H), 7.76 (d, J = 8.0 Hz, 1H), 7.66 (s, 1H), 7.32 (s, 1H), 7.27 (d, J = 8.0 Hz, 1H), 4.55 (dd, J = 4.4 Hz, 13.6 Hz, 1H), 4.44 (dd, J = 6.4 Hz, 13.6 Hz, 1H), 3.78-3.86 (m, 1H), 2.41 (s, 3H), 1.99-2.15 (m, 2H), 1.67-1.73 (m, 2H), 1.52-1.62 (m, 2H), 1.27-1.35 (m, 1H), 0.84-0.92 (m, 2H), 0.72-0.80 (m, 2H). | 4 |
| I-542 | 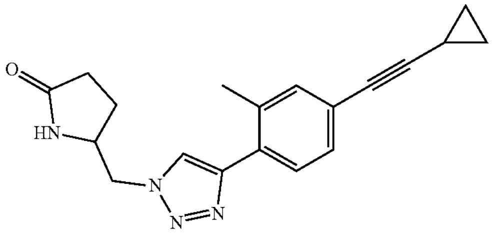 [SMILES: Cc1cc(C#CC2CC2)ccc1-c1cn(CC2CCC(=O)N2)nn1] | 321.1 | $^1$HNMR (400 MHz, DMSO-$d_6$) δ 8.39 (s, 1H), 7.87 (s, 1H), 7.75 (d, J = 8.0 Hz, 1H), 7.32 (s, 1H), 7.27 (d, J = 8.0 Hz, 1H), 4.43-4.53 (m, 2H), 4.02-4.06 (m, 1H), 2.41 (s, 3H), 2.01-2.16 (m, 2H), 1.79-1.95 (m, 2H), 1.52-1.59 (m, 1H), 0.87-0.92 (m, 2H), 0.72-0.76 (m, 2H). | 4 |
| I-543 | 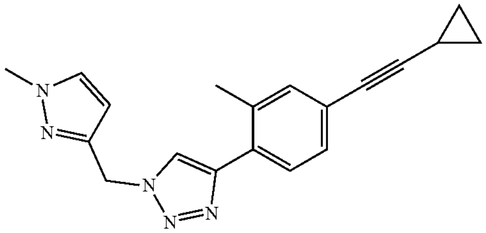 [SMILES: Cc1cc(C#CC2CC2)ccc1-c1cn(Cc2ccn(C)n2)nn1] | 318.1 | $^1$HNMR (400 MHz, DMSO-$d_6$) δ 8.43 (s, 1H), 7.71 (d, J = 8.0 Hz, 1H), 7.66 (d, J = 2.0 Hz, 1H), 7.30 (m, 1H), 7.25 (dd, J = 1.2 Hz, 8.0 Hz, 1H), 6.26 (d, J = 2.4 Hz, 1H), 5.57 (s, 2H), 3.80 (s, 3H), 2.39 (s, 3H), 1.52-1.55 (m, 1H), 0.86-0.90 (m, 2H), 0.72-0.75 (m, 2H). | 4 |

TABLE 23-continued

| Characterization data for exemplary compounds | | | | |
|---|---|---|---|---|
| Compound No. | Chemical Structure | M + 1 | $^1$H NMR (400 MHz) | Example of Synthesis |
| I-517 | 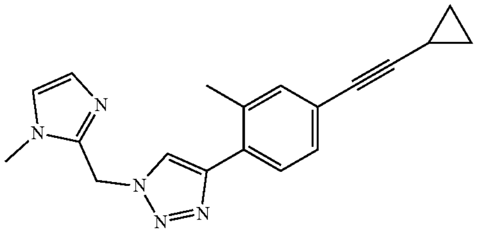 [SMILES: Cc1cc(C#CC2CC2)ccc1-c1cn(Cc2nccn2C)nn1] | 318.1 | $^1$HNMR (400 MHz, DMSO-$d_6$) δ 8.43 (s, 1H), 7.71 (d, J = 8.0 Hz, 1H), 7.31 (s, 1H), 7.25 (dd, J = 1.2 Hz, 8.0 Hz, 1H), 7.18 (s, 1H), 6.87 (s, 1H), 5.77 (s, 2H), 3.73 (s, 3H), 2.40 (s, 3H), 1.53-1.57(m, 1H), 0.87-0.92 (m, 2H), 0.72-0.76 (m, 2H). | 4 |
| I-528 | 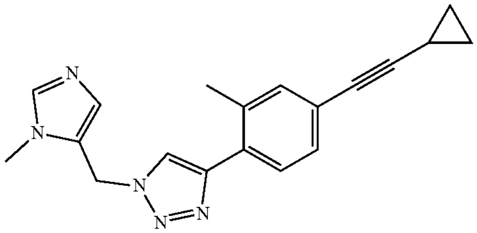 [SMILES: Cc1cc(C#CC2CC2)ccc1-c1cn(Cc2cncn2C)nn1] | 318.1 | $^1$HNMR (400 MHz, DMSO-$d_6$) δ 8.41 (s, 1H), 7.70 (d, J = 8.0 Hz, 1H), 7.64 (s, 1H), 7.30 (s, 1H), 7.25 (dd, J = 1.2 Hz, 8.0 Hz, 1H), 7.06 (s, 1H), 5.71 (s, 2H), 3.63 (s, 3H), 2.39 (s, 3H), 1.53-1.55 (m, 1H), 0.87-0.90 (m, 2H), 0.71-0.75 (m, 2H). | 4 |
| I-506 | 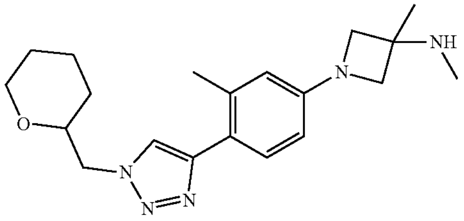 [SMILES: CNC1(C)CN(c2ccc(-c3cn(CC4CCCCO4)nn3)c(C)c2)C1] | 356.2 | $^1$HNMR (400 MHz, $CDCl_3$) δ 7.70 (s, 1H), 7.65 (d, J = 8.4 Hz, 1H), 6.39 (dd, , I = 2.4 Hz, 8.4 Hz, 1H), 6.34 (d, J = 2.0 Hz, 1H), 4.49 (dd, J = 3.2 Hz, 14.0 Hz, 1H), 4.32 (dd, J = 7.2 Hz, 14.0 Hz, 1H), 3.97-4.00 (m, 1H), 3.68-3.74 (m, 5H), 3.37-3.43 (m, 1H), 2.43 (s, 3H), 2.42 (s, 3H), 1.87-1.88 (m, 1H), 1.66-1.68 (m, 1H), 1.52-1.57 (m, 3H), 1.48 (s, 3H), 1.22-1.31 (m, 1H). | 5 |
| I-470 | 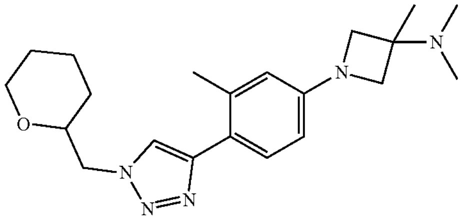 [SMILES: Cc1cc(N2CC(C)(N(C)C)C2)ccc1-c1cn(CC2CCCCO2)nn1] | 370.1 | $^1$HNMR (400 MHz, $CDCl_3$) δ 7.68 (s, 1H), 7.64 (d, J = 8.4 Hz, 1H), 6.38 (dd, J = 2.4 Hz, 8.4 Hz, 1H), 6.33 (d, J = 2.0 Hz, 1H), 4.48 (dd, J = 3.2 Hz, 14.0 Hz, 1H), 4.32 (dd, J = 7.2 Hz, 14.0 Hz, 1H), 3.97-4.00 (m, 1H), 3.62-3.77 (m, 5H), 3.37-3.43 (m, 1H), 2.41 (s, 3H), 2.25 (s, 6H), 1.87-1.89 (m, 1H), 1.65-1.68 (m, 1H), 1.50-1.58 (m, 3H), 1.39 (s, 3H), 1.22-1.31 (m, 1H). | 5 |
| I-518 | 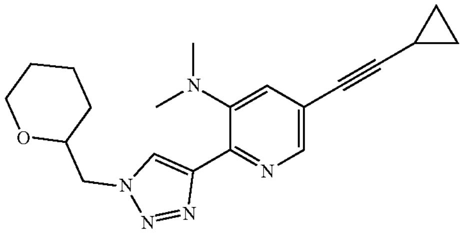 [SMILES: CN(C)c1cc(C#CC2CC2)cnc1-c1cn(CC2CCCCO2)nn1] | 352.0 | $^1$HNMR (400 MHz, DMSO-$d_6$) δ 8.43 (s, 1H), 8.21 (d, J = 1.6 Hz, 1H), 7.46 (d, J = 1.6 Hz, 1H), 4.39-4.52 (m, 2H), 3.84-3.88 (m, 1H) 3.68-3.74 (m, 1H), 3.28-3.31 (m, 1H), 2.60 (s, 6H), 1.77-1.80 (m, 1H), 1.56-1.64 (m, 2H), 1.37-1.51 (m, 3H), 1.13-1.23 (m, 1H), 0.90-0.95 (m, 2H), 0.77-0.81 (m, 2H). | 2 |
| I-507 | 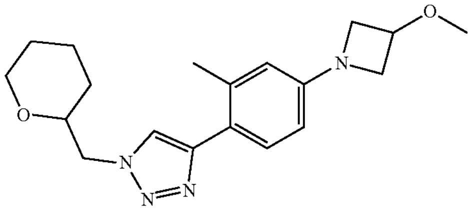 [SMILES: COC1CN(c2ccc(-c3cn(CC4CCCCO4)nn3)c(C)c2)C1] | 343.1 | $^1$HNMR (400 MHz, $CDCl_3$) δ 7.69 (s, 1H), 7.65 (d, J = 8.4 Hz, 1H), 6.40 (dd, , I = 2.4 Hz, 8.4 Hz, 1H), 6.35 (d, J = 2.4 Hz, 1H), 4.49 (dd, J = 2.8 Hz, 14.0 Hz, 1H), 4.29-4.36 (m, 2H), 4.10-4.14 (m, 2H), 3.97-4.00 (m, 1H), 3.70-3.75 (m, 3H), 3.37-3.43 (m, 1H), 3.34 (s, 3H), 2.42 (s, 3H), 1.83-1.93 (m, 1H), 1.65-1.68 (m, 1H), 1.50-1.53 (m, 3H), 1.22-1.31 (m, 1H). | 5 |

TABLE 23-continued

Characterization data for exemplary compounds

| Compound No. | Chemical Structure | M + 1 | $^1$H NMR (400 MHz) | Example of Synthesis |
|---|---|---|---|---|
| I-519 | 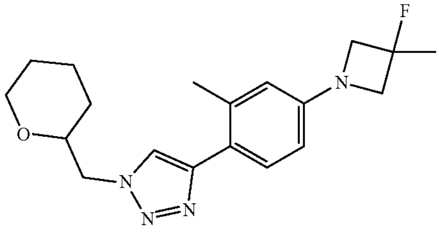 [SMILES: Cc1cc(N2CC(C)(F)C2)ccc1-c1cn(CC2CCCCO2)nn1] | 345.2 | $^1$HNMR (400 MHz, $CDCl_3$) δ 7.70 (s, 1H), 7.67 (d, J = 8.4 Hz, 1H), 6.41 (dd, J = 2.4 Hz, 8.4 Hz, 1H), 6.36 (d, J = 2.0 Hz, 1H), 4.49 (dd, J = 3.2 Hz, 14.0 Hz, 1H), 4.32 (dd, J = 7.6 Hz, 14.0 Hz, 1H), 3.88-4.05 (m, 5H), 3.67-3.73 (m, 1H), 3.37-3.43 (m, 1H), 2.42 (s, 3H), 1.84-1.91 (m, 1H), 1.67-1.73 (m, 4H), 1.50-1.53 (m, 3H), 1.19-1.31 (m, 1H). | 5 |
| I-520 | 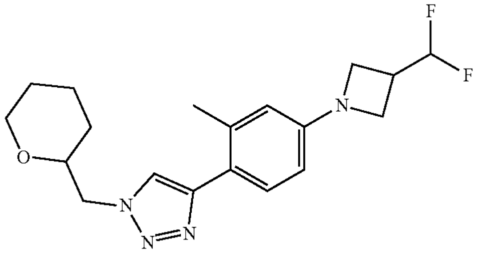 [SMILES: Cc1cc(N2CC(C(F)F)C2)ccc1-c1cn(CC2CCCCO2)nn1] | 363.1 | $^1$HNMR (400 MHz, DMSO-$d_6$) δ 8.12 (s, 1H), 7.56 (d, J = 8.4 Hz, 1H), 6.23-6.52 (m, 3H), 4.34-4.45 (m, 2H), 3.95 (t, J = 8.0 Hz, 2H), 3.84-3.87 (m, 1H), 3.70-3.79 (m, 3H), 3.18-3.34 (m, 2H), 2.36 (s, 3H), 1.78-1.81 (m, 1H), 1.61-1.64 (m, 1H), 1.39-1.51 (m, 3H), 1.18-1.25 (m, 1H). | 5 |
| I-529 | 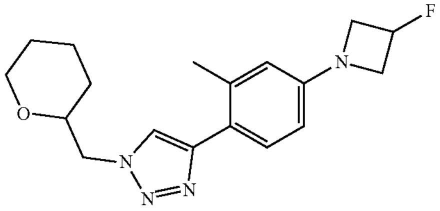 [SMILES: Cc1cc(N2CC(F)C2)ccc1-c1cn(CC2CCCCO2)nn1] | 331.1 | $^1$HNMR (400 MHz, $CDCl_3$) δ 7.70 (s, 1H), 7.67 (d, J = 8.4 Hz, 1H), 6.42 (dd, J = 2.0 Hz, 8.0 Hz, 1H), 6.37 (d, J = 2.0 Hz, 1H), 5.33-5.52 (m, 1H), 4.49 (dd, J = 3.2 Hz, 14.0 Hz, 1H), 4.32 (dd, J = 7.6 Hz, 14.0 Hz, 1H), 4.18-4.26 (m, 2H), 3.93-4.03 (m, 3H), 3.67-3.73 (m, 1H), 3.36-3.44 (m, 1H), 2.43 (s, 3H), 1.81-1.93 (m, 1H), 1.62-1.71 (m, 2H), 1.52-1.53 (m, 2H), 1.22-1.33 (m, 1H). | 5 |
| I-471 | 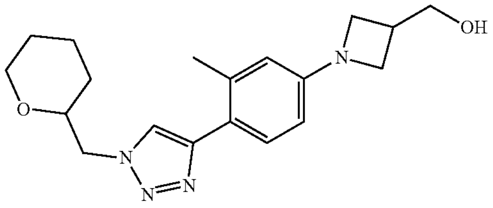 [SMILES: Cc1cc(N2CC(CO)C2)ccc1-c1cn(CC2CCCCO2)nn1] | 343.3 | $^1$HNMR (400 MHz, DMSO-$d_6$) δ 8.09 (s, 1H), 7.53 (d, J = 8.0 Hz, 1H), 6.30-6.33 (m, 2H), 4.77 (t, J = 4.8 Hz, 1H), 4.33-4.45 (m, 2H), 3.82-3.87 (m, 3H), 3.70-3.76 (m, 1H), 3.54-3.60 (m, 4H), 3.28-3.35 (m, 1H), 2.76-2.81 (m, 1H), 2.34 (s, 3H), 1.78-1.81 (m, 1H), 1.62 (d, J = 12.4 Hz, 1H), 1.40-1.51 (m, 3H), 1.18-1.24 (m, 1H). | 22 |
| I-544 | 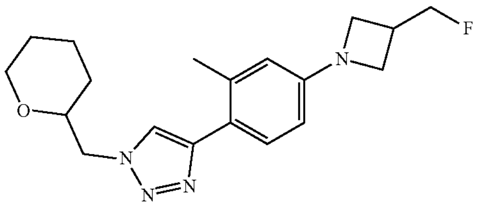 [SMILES: Cc1cc(N2CC(CF)C2)ccc1-c1cn(CC2CCCCO2)nn1] | 345.1 | $^1$HNMR (400 MHz, $CDCl_3$) δ 7.69 (m, 1H), 7.65 (d, J = 8.0 Hz, 1H), 6.39 (dd, J = 2.0 Hz, 8.0 Hz, 1H), 6.33 (d, J = 2.0 Hz, 1H), 4.69 (d, J = 6.4 Hz, 1H), 4.57 (d, J = 6.0 Hz, 1H), 4.49 (dd, J = 3.2 Hz, 14.4 Hz, 1H), 4.32 (dd, J = 7.2 Hz, 14.0 Hz, 1H), 3.98-4.01 (m, 3H), 3.68-3.74 (m, 3H), 3.37-3.43 (m, 1H), 3.04-3.11 (m, 1H), 2.42 (s, 3H), 1.87-1.88 (m, 1H), 1.65-1.68 (m, 2H), 1.50-1.58 (m, 2H), 1.20-1.31 (m, 1H). | 22 |

TABLE 23-continued

| Compound No. | Chemical Structure | M + 1 | $^1$H NMR (400 MHz) | Example of Synthesis |
|---|---|---|---|---|
| Characterization data for exemplary compounds | | | | |
| I-508 | 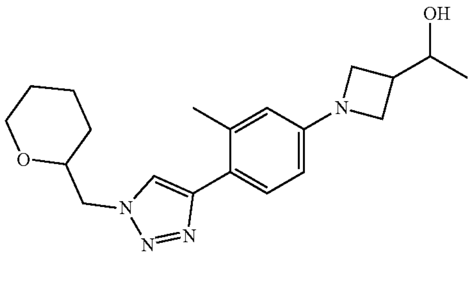 [SMILES: Cc1cc(N2CC(C(C)O)C2)ccc1-c1cn(CC2CCCCO2)nn1] | 357.2 | $^1$HNMR (400 MHz, $CDCl_3$) δ 7.69 (s, 1H), 7.65 (d, , I = 8.4 Hz, 1H), 6.39 (dd, , I = 2.4 Hz, 8.0 Hz, 1H), 6.34 (d, J = 2.4 Hz, 1H), 4.49 (dd, J = 2.8 Hz, 14.0 Hz, 1H), 4.32 (dd, J = 7.6 Hz, 14.0 Hz, 1H), 3.93-4.05 (m, 4H), 3.78-3.81 (m, 1H), 3.68-3.72 (m, 1H), 3.60-3.63 (m, 1H), 3.37-3.43 (m, 1H), 2.67-2.73 (m, 1H), 2.42 (s, 3H), 1.87-1.89 (m, 1H), 1.56-1.68 (m, 2H), 1.50-1.53 (m, 3H), 1.24-1.28 (m, 1H), 1.22 (d, J = 6.0 Hz, 3H). | 5 |
| I-560 | 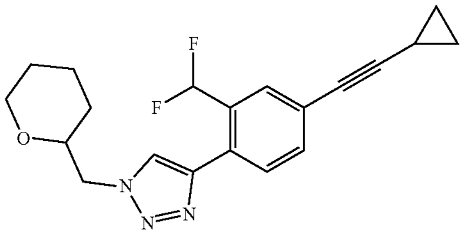 [SMILES: FC(F)c1cc(C#CC2CC2)ccc1-c1cn(CC2CCCCO2)nn1] | 358.2 | $^1$HNMR (400 MHz, $CDCl_3$) δ 7.90 (s, 1H), 7.79 (s, 1H), 7.67 (d, J = 8.0 Hz, 1H), 7.51 (d, J = 7.2 Hz, 1H), 7.11 (t, , I = 54.8 Hz, 1H), 4.52 (dd, J = 2.8 Hz, 14.0 Hz, 1H), 4.33 (dd, J = 7.6 Hz, 14.0 Hz, 1H), 3.98-4.01 (m, 1H), 3.68-3.73 (m, 1H), 3.37-3.43 (m, 1H), 1.88-1.91 (m, 1H), 1.67-1.70 (m, 1H), 1.51-1.54 (m, 3H), 1.44-1.46 (m, 1H), 1.26-1.29 (m, 1H), 0.88-0.93 (m, 2H), 0.82-0.87 (m, 2H). | 3 |
| I-561 | 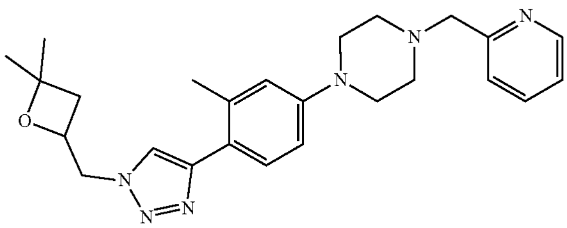 [SMILES: Cc1cc(N2CCN(Cc3ccccn3)CC2)ccc1-c1cn(CC2CC(C)(C)O2)nn1] | 433.2 | $^1$HNMR (400 MHz, DMSO-$d_6$) δ 8.51 (d, J = 4.0 Hz, 1H), 8.16 (s, 1H), 7.77-7.81 (m, 1H), 7.56 (d, J = 9.2 Hz, 1H), 7.48 (d, J = 8.0 Hz, 1H), 7.26-7.29 (m, 1H), 6.83-6.85 (m, 2H), 4.87-4.91 (m, 1H), 4.58 (d, J = 4.4 Hz, 2H), 3.66 (s, 2H), 3.20 (t, J = 4.4 Hz, 4H), 2.58 (t, J = 4.4 Hz, 4H), 2.37-2.42 (m, 4H), 2.19-2.34 (m, 1H), 1.37 (s, 3H), 1.08 (s, 3H). | 5 |
| I-530 | 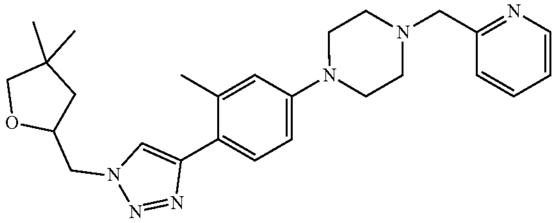 [SMILES: Cc1cc(N2CCN(Cc3ccccn3)CC2)ccc1-c1cn(CC2CC(C)(C)CO2)nn1] | 447.1 | $^1$HNMR (400 MHz, $CDCl_3$) δ 8.60 (d, J = 4.8 Hz, 1H), 7.76 (s, 1H), 7.67-7.72 (m, 2H), 7.52 (s, 1H), 7.22-7.26 (m, 1H), 6.81-6.84 (m, 2H), 4.56-4.62 (m, 1H), 4.40-4.47 (m, 2H), 3.81 (br., 2H), 3.50 (d, J = 8.0 Hz, 1H), 3.43 (d, J = 8.0 Hz, 1H), 3.33 (br., 4H), 2.68-2.77 (m, 4H), 2.44 (s, 3H), 1.84 (dd, J = 6.4 Hz, 12.8 Hz, 1H), 1.45 (dd, J = 9.2 Hz, 12.8 Hz, 1H), 1.10 (s, 3H), 1.01 (s, 3H). | 5 |
| I-562 | 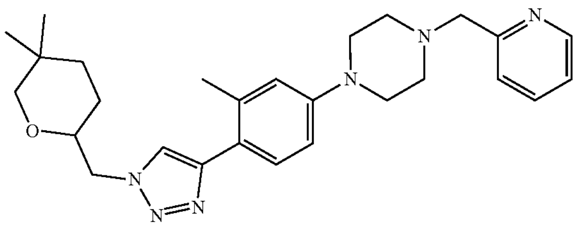 [SMILES: Cc1cc(N2CCN(Cc3ccccn3)CC2)ccc1-c1cn(CC2CCC(C)(C)CO2)nn1] | 461.2 | $^1$HNMR (400 MHz, DMSO-$d_6$) δ 8.51 (d, J = 4.0 Hz, 1H), 8.14 (s, 1H), 7.76-7.81 (m, 1H), 7.57 (d, J = 9.2 Hz, 1H), 7.48 (d, J = 8.0 Hz, 1H), 7.26-7.29 (m, 1H), 6.83-6.85 (m, 2H), 4.44-4.46 (m, 2H), 3.60-3.69 (m, 3H), 3.33-3.38 (m, 1H), 3.20 (t, J = 4.4 Hz, 4H), 3.07-3.09 (m, 1H), 2.58 (t, J = 4.4 Hz, 4H), 2.37 (s, 3H), 1.35-1.48 (m, 4H), 0.92 (s, 3H), 0.77 (s, 3H). | 5 |

TABLE 23-continued

Characterization data for exemplary compounds

| Compound No. | Chemical Structure | M + 1 | $^1$H NMR (400 MHz) | Example of Synthesis |
|---|---|---|---|---|
| I-531 | 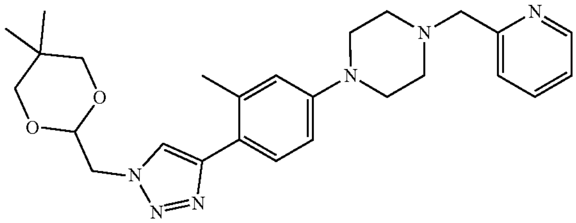 [SMILES: Cc1cc(N2CCN(Cc3ccccn3)CC2)ccc1-c1cn(CC2OCC(C)(C)CO2)nn1] | 463.1 | $^1$HNMR (400 MHz, DMSO-$d_6$) δ 8.51 (d, J = 4.0 Hz, 1H), 8.15 (s, 1H), 7.76-7.81 (m, 1H), 7.55-7.58(m, 1H), 7.48 (d, J = 7.6Hz, 1H), 7.26-7.29 (m, 1H), 6.83-6.85 (m, 2H), 4.91 (t, J = 4.4 Hz, 1H), 4.54 (d, J = 4.4 Hz, 2H), 3.66 (s, 2H), 3.57 (d, J = 10.8 Hz, 2H), 3.46 (d, J = 10.8 Hz, 2H), 3.20 (t, J = 4.4 Hz, 4H), 2.58 (t, J = 4.4 Hz, 4H), 2.37 (s, 3H), 1.04 (s, 3H), 0.68 (s, 3H). | 5 |
| I-532 | 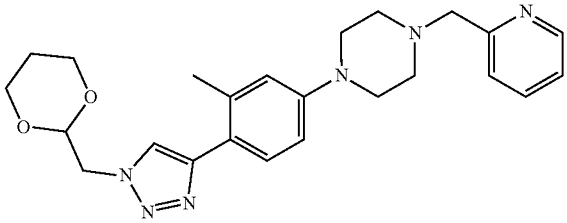 [SMILES: Cc1cc(N2CCN(Cc3ccccn3)CC2)ccc1-c1cn(CC2OCCCO2)nn1] | 435.1 | $^1$HNMR (400 MHz, DMSO-$d_6$) δ 8.51 (d, J = 4.0 Hz, 1H), 8.16 (s, 1H), 7.76-7.81 (m, 1H), 7.56-7.59 (m, 1H), 7.48 (d, J = 7.6 Hz, 1H), 7.26-7.29 (m, 1H), 6.83-6.85 (m, 2H), 5.00 (t, J = 4.8 Hz, 1H), 4.48 (d, J = 4.8 Hz, 2H), 4.03 (dd, J = 5.2 Hz, 11.2 Hz, 2H), 3.72-3.79 (m, 2H), 3.66 (s, 2H), 3.20 (t, J = 4.8 Hz, 4H), 2.58 (t, J = 4.8 Hz, 4H), 2.37 (s, 3H), 1.87-1.90 (m, 1H), 1.36-1.39 (m, 1H). | 5 |
| I-533 | 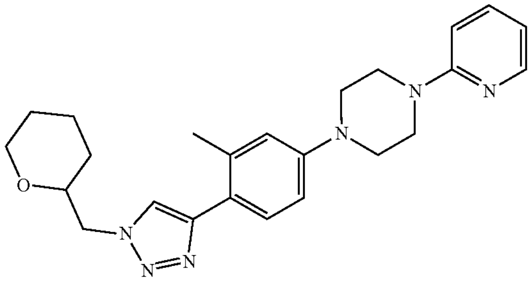 [SMILES: Cc1cc(N2CCN(c3ccccn3)CC2)ccc1-c1cn(CC2CCCCO2)nn1] | 419.0 | $^1$HNMR (400 MHz, DMSO-$d_6$) δ 8.14-8.16 (m, 2H), 7.54-7.63 (m, 2H), 6.89-6.93 (m, 3H), 6.67 (dd, J = 6.8 Hz, 5.2 Hz, 1H), 4.35-4.46 (m, 2H), 3.85-3.88 (m, 1H), 3.71-3.77 (m, 1H), 3.63-3.65 (m, 4H), 3.28-3.33 (m, 5H), 2.40 (s, 3H), 1.78-1.81 (m, 1H), 1.61-1.65 (m, 1H), 1.39-1.52 (m, 3H), 1.15-1.25 ( m, 1H). | 5 |
| I-545 | 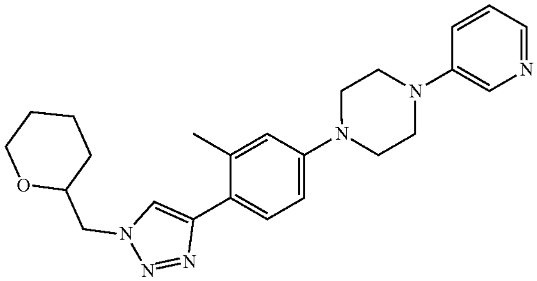 [SMILES: Cc1cc(N2CCN(c3cccnc3)CC2)ccc1-c1cn(CC2CCCCO2)nn1] | 419.1 | $^1$HNMR (400 MHz, DMSO-$d_6$) δ 8.38 (d, J = 2.8 Hz, 1H), 8.17 (s, 1H), 8.03 (dd, J = 1.2 Hz, 4.4 Hz, 1H), 7.61-7.64 (m, 1H), 7.39-7.42 (m, 1H), 7.25 (dd, J = 4.4 Hz, 8.4 Hz, 1H), 6.92-6.94 (m, 2H), 4.35-4.47 (m, 2H), 3.85-3.87 (m, 1H), 3.71-3.77 (m, 1H), 3.29-3.35 (m, 9H), 2.41 (s, 3H), 1.79-1.81 (m, 1H), 1.62-1.65 ( m, 1H), 1.39-1.52 (m, 3H), 1.19-1.25 ( m, 1H). | 5 |
| I-563 | 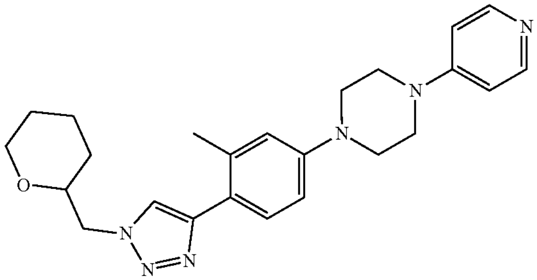 [SMILES: Cc1cc(N2CCN(c3ccncc3)CC2)ccc1-c1cn(CC2CCCCO2)nn1] | 419.2 | $^1$HNMR (400 MHz, DMSO-$d_6$) δ 8.19 (d, J = 6.0 Hz, 1H), 8.17 (s, 2H), 7.61-7.63 (m, 1H), 6.88-6.92 (m, 4H), 4.35-4.47 (m, 2H), 3.84-3.87 (m, 1H), 3.71-3.77 (m, 1H), 3.47-3.49 (m, 4H), 3.30-3.33 (m, 5H), 2.40 (s, 3H), 1.78-1.81 (m, 1H), 1.62-1.65 (m, 1H), 1.39-1.52 (m, 3H), 1.19-1.25 (m, 1H). | 5 |

TABLE 23-continued

Characterization data for exemplary compounds

| Compound No. | Chemical Structure | M + 1 | $^1$H NMR (400 MHz) | Example of Synthesis |
|---|---|---|---|---|
| I-546 | 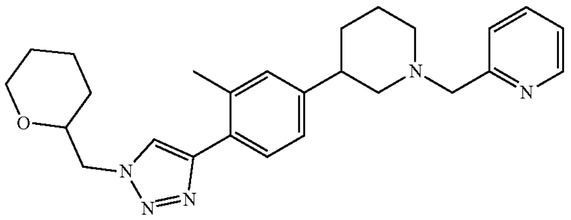 [SMILES: Cc1cc(C2CCCN(Cc3ccccn3)C2)ccc1-c1cn(CC2CCCCO2)nn1] | 432.1 | $^1$HNMR (400 MHz, DMSO-$d_6$) δ 8.47 (dd, J = 0.8 Hz, 4.8 Hz, 1H), 8.24 (s, 1H), 7.73-7.78 (m, 1H), 7.63 (d, J = 8.0 Hz, 1H), 7.46 (d, J = 7.6 Hz, 1H), 7.22-7.25 (m, 1H), 7.12-7.16 (m, 2H), 4.36-4.48 (m, 2H), 3.83-3.86 (m, 1H), 3.73-3.75 (m, 1H), 3.62 (s, 2H), 3.28-3.31 (m, 1H), 2.84-2.87 (m, 2H), 2.74-2.77 (m, 1H), 2.39 (s, 3H), 2.05-2.14 (m, 2H), 1.77-1.84 (m, 2H), 1.60-1.71 (m, 1H), 1.60-1.63 (m, 2H), 1.41-1.50 (m, 4H), 1.17-1.21 (m, 1H). | 5 |
| I-564 | 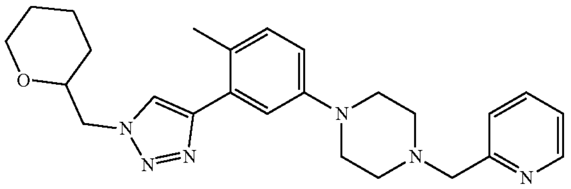 [SMILES: Cc1ccc(N2CCN(Cc3ccccn3)CC2)cc1-c1cn(CC2CCCCO2)nn1] | 433.0 | $^1$HNMR (400 MHz, DMSO-$d_6$) δ 8.50-8.52 (m, 1H), 8.28 (s, 1H), 7.76-7.80 (m, 1H), 7.48 (d, J = 8.0 Hz, 1H), 7.26-7.30 (m, 2H), 7.13 (d, J = 8.4 Hz, 1H), 6.86 (dd, J = 2.8 Hz, 8.4 Hz, 1H), 4.36-4.48 (m, 2H), 3.84-3.87 (m, 1H), 3.71-3.77 (m, 1H), 3.66 (s, 2H), 3.28-3.32 (m, 1H), 3.14-3.16 (m, 4H), 2.58 (t, J = 4.8 Hz, 4H), 2.32 (s, 3H), 1.78-1.81 (m, 1H), 1.62-1.65 (m, 1H), 1.40-1.51 (m, 3H), 1.18-1.24 (m, 1H). | 5 |
| I-534 | 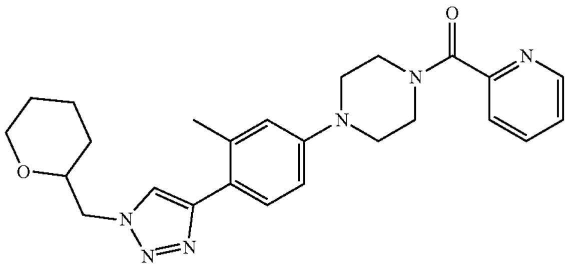 [SMILES: Cc1cc(N2CCN(C(=O)c3ccccn3)CC2)ccc1-c1cn(CC2CCCCO2)nn1] | 447.1 | $^1$HNMR (400 MHz, DMSO-$d_6$) δ 8.61-8.63 (m, 1H), 8.16 (s, 1H), 7.93-7.98 (m, 1H), 7.59-7.64 (m, 2H), 7.49-7.53 (m, 1H), 6.87-6.89 (m, 2H), 4.35-4.46 (m, 2H), 3.80-3.87 (m, 3H), 3.70-3.76(m, 1H), 3.56-3.59 (m, 2H), 3.29-3.31 (m, 3H), 3.17-3.19 (m, 2H), 2.39 (s, 3H), 1.78-1.81 (m, 1H), 1.61-1.64 (m, 1H), 1.41-1.51 (m, 3H), 1.18-1.24 (m, 1H). | 5 |
| I-657 | 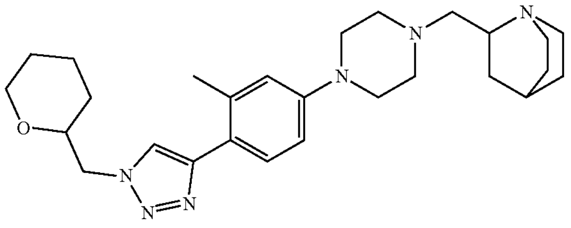 [SMILES: Cc1cc(N2CCN(CC3CC4CCN3CC4)CC2)ccc1-c1cn(CC2CCCCO2)nn1] | 465.2 | $^1$HNMR (400 MHz, DMSO-$d_6$) δ 8.13 (s, 1H), 7.57 (dd, J = 6.0, 3.2 Hz, 1H), 6.82-6.83 (m, 2H), 4.34-4.36 (m, 2H), 3.84-3.87 (m, 1H), 3.70-3.76 (m, 1H), 3.28-3.34 (m, 1H), 3.11-3.18 (m, 4H), 2.84-3.00 (m, 2H), 2.75-2.82 (m, 2H), 2.54-2.66 (m, 3H), 2.31-2.50 (m, 7H), 1.78-1.81 (m, 1H), 1.61-1.70 (m, 3H), 1.39-1.52 (m, 7H), 1.15-1.25 (m, 1H), 1.05-1.10 (m, 1H). | 5 |
| I-565 | 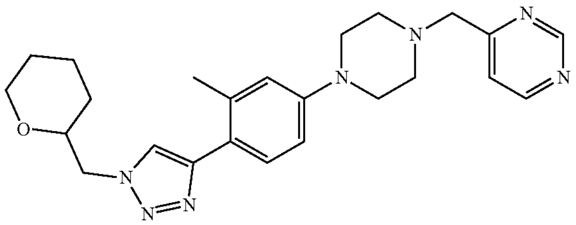 [SMILES: Cc1cc(N2CCN(Cc3ccncn3)CC2)ccc1-c1cn(CC2CCCCO2)nn1] | 434.0 | $^1$HNMR (400 MHz, DMSO-$d_6$) δ 9.12 (d, J = 1.2 Hz, 1H), 8.78 (d, J = 5.2 Hz, 1H), 8.15 (s, 1H), 7.57-7.62 (m, 2H), 6.84-6.86 (m, 2H), 4.38-4.42 (m, 2H), 3.84-3.87 (m, 1H), 3.70-3.76 (m, 1H), 3.68 (s, 2H), 3.31-3.34 (m, 1H), 3.22 (t, J = 4.4 Hz, 4H), 2.61 (t, J = 4.4 Hz, 4H), 2.38 (s, 3H), 1.78 (m, 1H), 1.61-1.64 (m, 1H), 1.43-1.48 (m, 3H), 1.18-1.24 (m, 1H). | 5 |

TABLE 23-continued

| Compound No. | Chemical Structure | M + 1 | $^1$H NMR (400 MHz) | Example of Synthesis |
|---|---|---|---|---|
| Characterization data for exemplary compounds | | | | |
| I-566 | 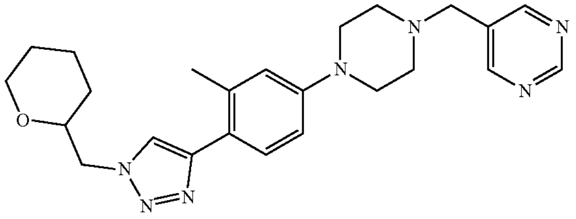 [SMILES: Cc1cc(N2CCN(Cc3cncnc3)CC2)ccc1-c1cn(CC2CCCCO2)nn1] | 434.0 | $^1$HNMR (400 MHz, DMSO-$d_6$) δ 9.12 (s, 1H), 8.77 (s, 2H), 8.14 (s, 1H), 7.58 (d, J = 9.6 Hz, 1H), 6.83-6.84 (m, 2H), 4.38-4.42 (m, 2H), 3.84-3.87 (m, 1H), 3.70-3.76 (m, 1H), 3.60 (s, 2H), 3.29-3.32 (m, 1H), 3.19 (t, J = 4.4 Hz, 4H), 2.54 (t, J = 4.8 Hz, 4H), 2.37 (s, 3H), 1.78-1.81 (m, 1H), 1.61-1.64 (m, 1H), 1.46-1.48 (m, 3H), 1.15-1.25 (m, 1H). | 5 |
| I-547 | 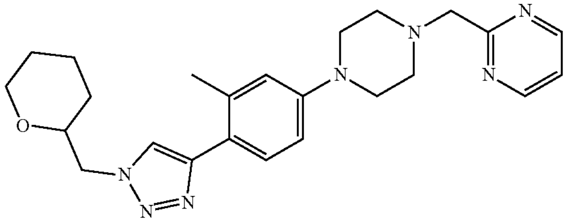 [SMILES: Cc1cc(N2CCN(Cc3ncccn3)CC2)ccc1-c1cn(CC2CCCCO2)nn1] | 434.0 | $^1$HNMR (400 MHz, DMSO-$d_6$) δ 8.80 (d, J = 4.8 Hz, 2H), 8.14 (s, 1H), 7.56-7.59 (m, 1H), 7.43 (t, J = 4.8 Hz, 1H), 6.84 (s, 2H), 4.34-4.46 (m, 2H), 3.84-3.87 (m, 1H), 3.77 (s, 2H), 3.71-3.75 (m, 1H), 3.29-3.32 (m, 1H), 3.16-3.17 (m, 4H), 2.66 (t, J = 4.4 Hz, 4H), 2.37 (s, 3H), 1.78-1.81 (m, 1H), 1.61-1.64 (m, 1H), 1.40-1.50 (m, 3H), 1.18-1.24 (m, 1H). | 5 |
| I-548 | 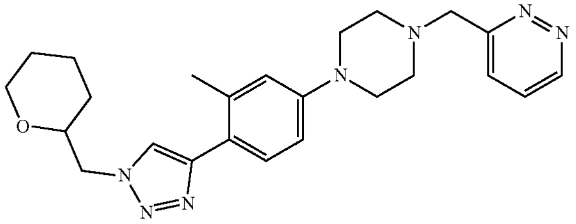 [SMILES: Cc1cc(N2CCN(Cc3cccnn3)CC2)ccc1-c1cn(CC2CCCCO2)nn1] | 434.1 | $^1$HNMR (400 MHz, DMSO-$d_6$) δ 9.16 (dd, J = 2.0 Hz, 4.8 Hz, 1H), 8.15 (s, 1H), 7.76 (dd, J = 1.6 Hz, 8.4 Hz, 1H), 7.70 (dd, J = 4.2 Hz, 8.4 Hz, 1H), 7.57 (d, J = 9.2 Hz, 1H), 6.83-6.85 (m, 2H), 4.34-4.46 (m, 2H), 3.84-3.86 (m, 3H), 3.70-3.76 (m, 1H), 3.28-3.32 (m, 1H), 3.18-3.20 (m, 4H), 2.58-2.60 (m, 4H), 2.37 (s, 3H), 1.78-1.81 (m, 1H), 1.61-1.64 (m, 1H), 1.39-1.53 (m, 3H), 1.15-1.25 (m, 1H). | 5 |
| I-577 | 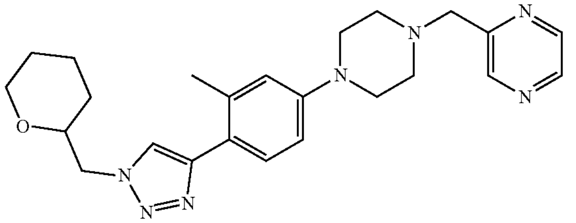 [SMILES: Cc1cc(N2CCN(Cc3cnccn3)CC2)ccc1-c1cn(CC2CCCCO2)nn1] | 434.0 | $^1$HNMR (400 MHz, DMSO-$d_6$) δ 8.73 (d, J = 1.2 Hz, 1H), 8.61 (dd, J = 1.6 Hz, 2.4 Hz, 1H), 8.56 (d, ,J = 2.4 Hz, 1H), 8.14(s, 1H), 7.58 (d, J = 9.2 Hz, 1H), 6.83-6.85 (m, 2H), 4.34-4.45 (m, 2H), 3.84-3.87 (m, 1H), 3.70-3.80 (m, 3H), 3.29-3.32 (m, 1H), 3.20 (t, J = 4.4 Hz, 4H), 2.60 (d, J = 4.8 Hz, 4H), 2.38 (s, 3H), 1.70-1.90 (m, 1H), 1.58-1.69 (m, 1H), 1.43-1.48 (m, 3H), 1.15-1.30 (m, 1H). | 5 |
| I-578 | 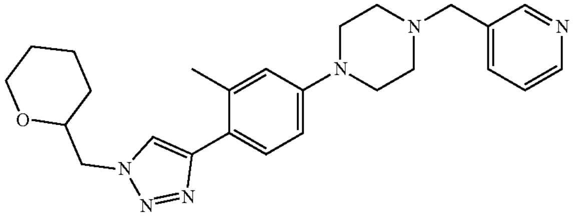 [SMILES: Cc1cc(N2CCN(Cc3cccnc3)CC2)ccc1-c1cn(CC2CCCCO2)nn1] | 433.0 | $^1$HNMR (400 MHz, DMSO-$d_6$) δ 8.53 (d, J = 1.6 Hz, 1H), 8.49 (dd, J = 1.6 Hz, 4.8 Hz, 1H), 8.14 (s, 1H), 7.74-7.77 (m, 1H), 7.56-7.59 (m, 1H), 7.38 (dd, J = 4.8 Hz, 7.6 Hz, 1H), 6.83-6.84 (m, 2H), 4.30-4.46 (m, 2H), 3.84-3.87 (m, 1H), 3.70-3.76 (m, 1H), 3.57 (s, 2H), 3.28-3.34 (m, 1H), 3.18 (t, J = 4.4 Hz, 4H), 2.50-2.53 (m, 4H), 2.37 (s, 3H), 1.78-1.81 (m, 1H), 1.61-1.64 (m, 1H), 1.40-1.51 (m, 3H), 1.18-1.24 (m, 1H). | 5 |

TABLE 23-continued

| Characterization data for exemplary compounds | | | | |
|---|---|---|---|---|
| Compound No. | Chemical Structure | M + 1 | $^1$H NMR (400 MHz) | Example of Synthesis |
| I-549 | 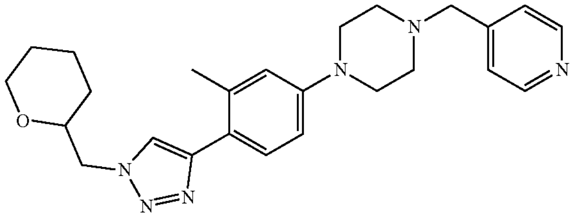 [SMILES: Cc1cc(N2CCN(Cc3ccncc3)CC2)ccc1-c1cn(CC2CCCCO2)nn1] | 433.2 | $^1$HNMR (400 MHz, DMSO-$d_6$) δ 8.53 (dd, J = 1.6 Hz, 4.4 Hz, 2H), 8.15 (s, 1H), 7.57-7.59 (m, 1H), 7.37 ( d, J = 5.6 Hz, 2H), 6.83-6.85 (m, 2H), 4.34-4.46 (m, 2H), 3.84-3.87 (m, 1H), 3.70-3.76 (m, 1H), 3.57 (s, 2H), 3.28-3.32 (m, 1H), 3.19-3.21 (m, 4H), 2.52-2.54 (m, 4H), 2.38 (s, 3H), 1.78-1.81 (m, 1H), 1.61-1.64 (m, 1H), 1.39-1.51 (m, 3H), 1.15-1.25 (m, 1H). | 5 |
| I-611 | 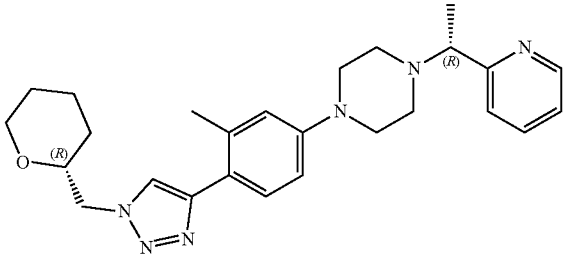 | 447.1 | $^1$HNMR (400 MHz, DMSO-$d_6$) δ 8.52 (d, J = 4.4 Hz, 1H), 8.13 (s, 1H), 7.75-7.80 (m, 1H), 7.55-7.57(m, 1H), 7.45 (d, J = 7.6 Hz, 1H), 7.25-7.28 (m, 1H), 6.81 (d, J = 2.4 Hz, 2H), 4.34-4.45 (m, 2H), 3.85 (d, J = 11.2 Hz, 1H), 3.63-3.74 (m, 2H), 3.28-3.32 (m, 2H), 3.16 (t, J = 4.8 Hz, 4H), 2.58-2.63 (m, 2H), 2.46-2.50 (m, 1H), 2.36 (m, 3H), 1.78-1.81 (m, 1H), 1.61-1.64 (m, 1H), 1.43-1.51 (m, 3H), 1.35-1.41 (m, 3H), 1.18-1.24 (m, 1H). | 5 |
| I-612 | 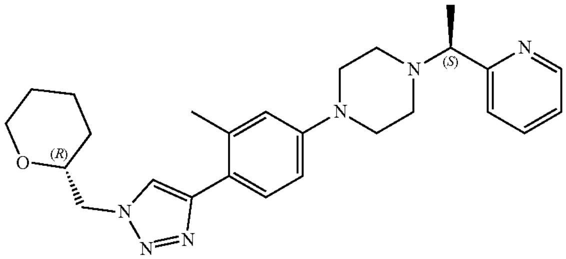 | 447.1 | $^1$HNMR (400 MHz, DMSO-$d_6$) δ 8.52 (d, J = 4.0 Hz, 1H), 8.13 (s, 1H), 7.75-7.80 (m, 1H), 7.55-7.57 (m, 1H), 7.45 (d, J = 7.6 Hz, 1H), 7.25-7.28 (m, 1H), 6.80-6.81 (m, 2H), 4.34-4.45 (m, 2H), 3.84-3.87 (m, 1H), 3.70-3.75 (m, 1H), 3.66 (q, J = 6.8 Hz, 1H), 3.28-3.35 (m, 2H), 3.16 (t, J = 5.2 Hz, 4H), 2.57-2.67 (m, 2H), 2.50-2.51 (m, 1H), 2.36 (s, 3H), 1.78-1.81 (m, 1H), 1.60-1.64 (m, 1H), 1.40-1.50 (m, 3H), 1.35 (d, J = 6.8 Hz, 3H), 1.18-1.24 (m, 1H). | 5 |
| I-613 | 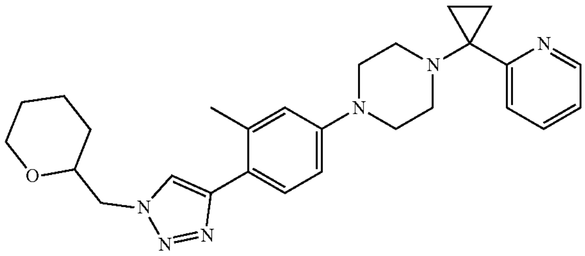 [SMILES: Cc1cc(N2CCN(C3(c4ccccn4)CC3)CC2)ccc1-c1cn(CC2CCCCO2)nn1] | 459.1 | $^1$HNMR (400 MHz, DMSO-$d_6$) δ 8.51 (d, J = 4.0 Hz, 1H), 8.13 (s, 1H), 7.74 (dt, J = 1.6 Hz, 7.6 Hz, 1H), 7.51-7.57 (m, 2H), 7.21 (dd, J = 4.8 Hz, 6.4 Hz, 1H), 6.81 (d, J = 2.4 Hz, 2H), 4.34-4.45 (m, 2H), 3.84-3.86 (m, 1H), 3.71-3.75 (m, 1H), 3.28-3.34 (m, 1H), 3.16 (t, J = 4.4 Hz, 4H), 2.71 (t, J = 4.4 Hz, 4H), 2.36 (s, 3H), 1.78-1.81 (m, 1H), 1.60-1.64 (m, 1H), 1.39-1.51 (m, 3H), 1.17-1.23 (m, 1H), 1.01-1.09 (m, 4H). | 5 |
| I-579 | 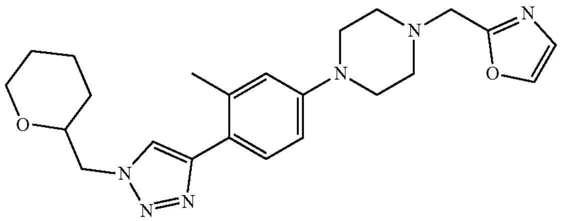 [SMILES: Cc1cc(N2CCN(Cc3ncco3)CC2)ccc1-c1cn(CC2CCCCO2)nn1] | 423.0 | $^1$HNMR (400 MHz, DMSO-$d_6$) δ 8.14 (s, 1H), 8.10 (d, J = 0.4 Hz, 1H), 7.56-7.58 (m, 1H), 7.19 (d, J = 0.4 Hz, 1H), 6.82-6.84 (m, 2H), 4.34-4.45 (m, 2H), 3.84-3.87 (m, 1H), 3.72-3.76 (m, 3H), 3.28-3.29 (m, 1H), 3.18 (t, J = 4.8 Hz, 4H), 2.59 (t, J = 4.8 Hz, 4H), 2.37 (s, 3H), 1.78-1.81 (m, 1H), 1.61-1.64 (m, 1H), 1.43-1.50 (m, 3H), 1.18-1.24 (m, 1H). | 5 |

TABLE 23-continued

| Compound No. | Chemical Structure | M + 1 | $^1$H NMR (400 MHz) | Example of Synthesis |
|---|---|---|---|---|
| Characterization data for exemplary compounds | | | | |
| I-580 | 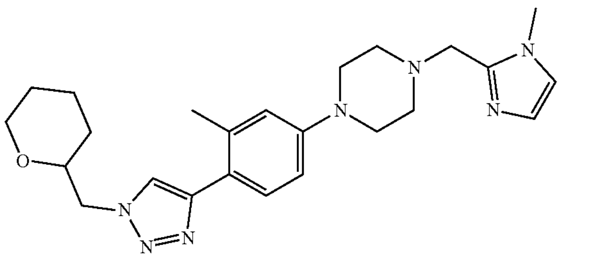 [SMILES: Cc1cc(N2CCN(Cc3nccn3C)CC2)ccc1-c1cn(CC2CCCCO2)nn1] | 436.2 | $^1$HNMR (400 MHz, DMSO-$d_6$) δ 8.14 (s, 1H), 7.57 (d, J = 9.2 Hz, 1H), 7.09 (d, J = 0.8 Hz, 1H), 6.81-6.87 (m, 2H), 6.77 (d, J = 0.8 Hz, 1H), 4.30-4.46 (m, 2H), 3.84-3.87 (m, 1H), 3.70-3.76 (m, 1H), 3.67-3.68 (m, 3H), 3.50-3.57 (m, 2H), 3.28-3.33 (m, 1H), 3.14-3.16 (m, 4H), 2.50-2.52 (m, 4H), 2.37-2.38 (m, 3H), 1.78-1.81 (m, 1H), 1.61-1.64 (m, 1H), 1.39-1.51 (m, 3H), 1.18-1.24 (m, 1H). | 5 |
| I-581 | 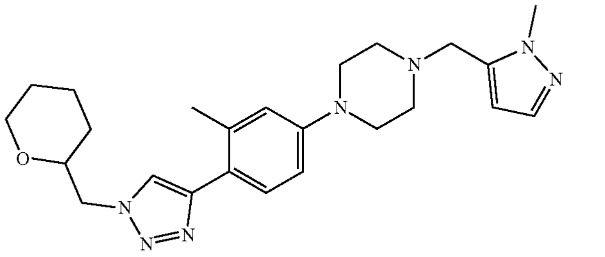 [SMILES: Cc1cc(N2CCN(Cc3ccnn3C)CC2)ccc1-c1cn(CC2CCCCO2)nn1] | 436.0 | $^1$HNMR (400 MHz, DMSO-$d_6$) δ 8.14 (s, 1H), 7.57 (d, J = 9.2 Hz, 1H), 7.32 (d, J = 2.0 Hz, 1H), 6.82-6.84 (m, 2H), 6.17 (d, J = 1.6 Hz, 1H), 4.34-4.46 (m, 2H), 3.82-3.87 (m, 4H), 3.70-3.76 (m, 1H), 3.57 (s, 2H), 3.28-3.32 (m, 1H), 3.17 (t, J = 4.8 Hz, 4H), 2.49-2.53 (m, 4H), 2, 37 (s, 3H), 1.78-1.81 (m, 1H), 1.60-1.64 (m, 1H), 1.39-1.51 (m, 3H), 1.17-1.25 (m, 1H). | 5 |
| I-582 | 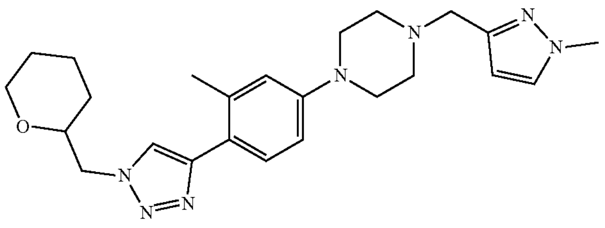 [SMILES: Cc1cc(N2CCN(Cc3ccn(C)n3)CC2)ccc1-c1cn(CC2CCCCO2)nn1] | 436.0 | $^1$HNMR (400 MHz, DMSO-$d_6$) δ 8.13 (s, 1H), 7.60 (d, J = 2.4 Hz, 1H), 7.56-7.58 (m, 1H), 6.80-6.83 (m, 2H), 6.14 (d, J = 2.4 Hz, 1H), 4.34-4.45 (m, 2H), 3.84-3.95 (m, 1H), 3.79 (s, 3H), 3.70-3.79 (m, 1H), 3.46 (s, 2H), 3.29-3.35 (m, 1H), 3.10-3.17 (m, 4H), 2.49-2.53 (m, 4H), 2.37 (s, 3H), 1, 78-1.81 (m, 1H), 1.61-1.64 (m, 1H), 1.37-1.54 (m, 3H), 1.15-1.25 (m, 1H). | 5 |
| I-550 | 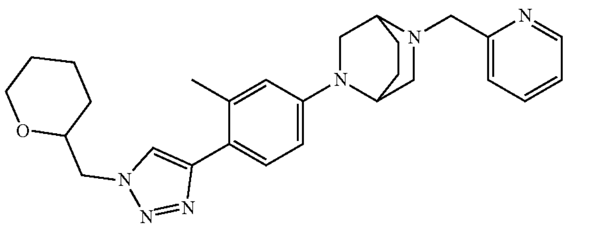 [SMILES: Cc1cc(N2CC3CCC2CN3Cc2ccccn2)ccc1-c1cn(CC2CCCCO2)nn1] | 459.0 | $^1$HNMR (400 MHz, $CDCl_3$) δ 8.55 (d, J = 4.8 Hz, 1H), 7.66-7.74 (m, 3H), 7.47-7.58 (m, 1H), 7.14-7.21 (m, 1H), 6.58 (dd, J = 2.4 Hz, 8.8 Hz, 1H), 6.53 (d, J = 2.4 Hz, 1H), 4.49 (dd, J = 3.2 Hz, 14.0 Hz, 1H), 4.32 (dd, J = 7.2 Hz, 14.0 Hz, 1H), 3.88-4.00 (m, 4H), 3.68-3.74 (m, 1H), 3.37-3.46 (m, 1H), 3.29 (dd, J = 1.6 Hz, 10.0 Hz, 1H), 3.03-3.14 (m, 2H), 2.94-3.02 (m, 1H), 2.44 (s, 3H), 2.13-2.32 (m, 1H), 1.97-2.09 (m, 1H), 1.81-1.89 (m, 2H), 1.65-1.74 (m, 3H), 1.50-1.53 (m, 3H), 1.21-1.31 (m, 1H). | 5 |
| I-583 | 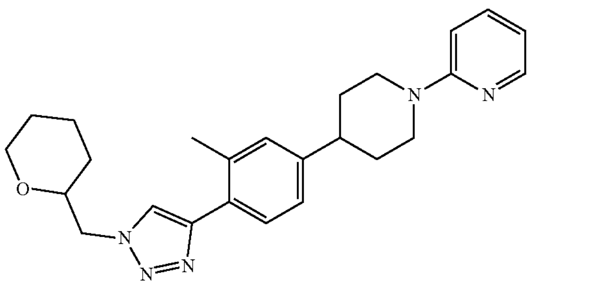 [SMILES: Cc1cc(C2CCN(c3ccccn3)CC2)ccc1-c1cn(CC2CCCCO2)nn1] | 418.1 | $^1$HNMR (400 MHz, DMSO-$d_6$) δ 8.25 (s, 1H), 8.11 (d, J = 3.6 Hz, 1H), 7.66 (d, J = 7.6 Hz, 1H), 7.50-7.54 (m, 1H), 7.14-7.17 (m, 2H), 6.86 (d, J = 8.8 Hz, 1H), 6.59-6.62 (m, 1H), 4.37-4.47 (m, 4H), 3.84-3.87 (m, 1H), 3.73-3.75 (m, 1H), 3.29-3.33 (m, 1H), 2.75-2.90 (m, 3H), 2.41 (s, 3H), 1.78-1.86 (m, 3H), 1.58-1.68 (m, 3H), 1.40-1.50 (m, 3H), 1.18-1.24 (m, 1H). | 5 |

TABLE 23-continued

| Characterization data for exemplary compounds | | | | |
|---|---|---|---|---|
| Compound No. | Chemical Structure | M + 1 | $^1$H NMR (400 MHz) | Example of Synthesis |
| I-521 | 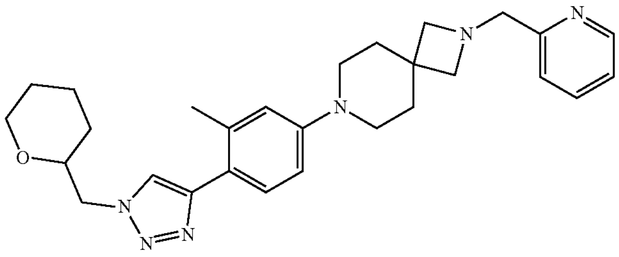 [SMILES: Cc1cc(N2CCC3(CC2)CN(Cc2ccccn2)C3)ccc1-c1cn(CC2CCCCO2)nn1] | 473.2 | $^1$HNMR (400 MHz, DMSO-$d_6$) δ 8.47-8.48 (m, 1H), 8.13 (s, 1H), 7.75 (dt, J = 1.6 Hz, 7.6 Hz, 1H), 7.54-7.57 (m, 1H), 7.35 (d, J = 7.6 Hz, 1H), 7.24 (dd, J = 5.2 Hz, 6.8 Hz, 1H), 6.83-6.84 (m, 2H), 4.34-4.44 (m, 2H), 3.84-3.87 (m, 1H), 3.71-3.73 (m, 3H), 3.28-3.29 (m, 1H), 3.13-3.16 (m, 4H), 3.06 (s, 4H), 2.33 (s, 3H), 1.77-1.80 (m, 5H), 1.60-1.64 (m, 1H), 1.43-1.48 (m, 3H), 1.18-1.21 (m, 1H). | 5 |
| I-590 | 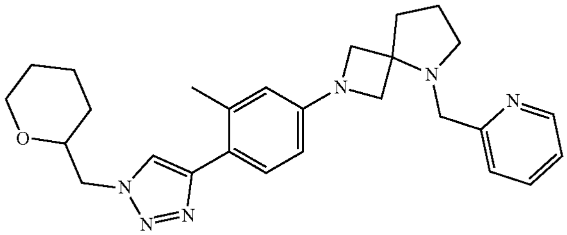 [SMILES: Cc1cc(N2CC3(CCCN3Cc3ccccn3)C2)ccc1-c1cn(CC2CCCCO2)nn1] | 459.1 | $^1$HNMR (400 MHz, DMSO-$d_6$) δ 8.47 (d, J = 4.4 Hz, 1H), 8.10 (s, 1H), 7.73-7.78 (m, 1H), 7.54 (d, J = 7.6 Hz, 1H), 7.44 (d, J = 7.6 Hz, 1H), 7.23-7.26 (m, 1H), 6.38-6.40 (m, 2H), 4.33-4.45 (m, 2H), 4.01 (d, J = 8.0 Hz, 2H), 3.93 (s, 2H), 3.84-3.87 (m, 1H), 3.71-3.76 (m, 3H), 3.29-3.34 (m, 1H), 2.65 (t, J = 7.2 Hz, 2H), 2.35 (s, 3H), 2.12 (t, J = 7.6 Hz, 2H), 1.70-1.81 (m, 3H), 1.61-1.64 (m, 1H), 1.42-1.50 (m, 3H), 1.18-1.24 (m, 1H). | 5 |
| I-567 | 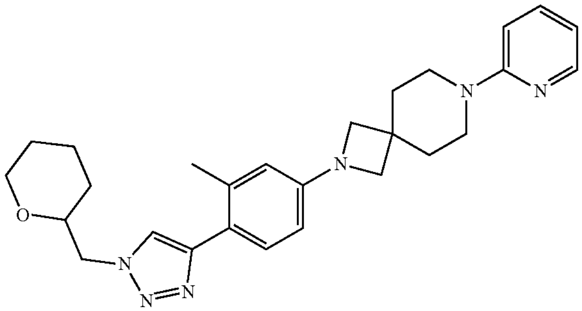 [SMILES: Cc1cc(N2CC3(CCN(c4ccccn4)CC3)C2)ccc1-c1cn(CC2CCCCO2)nn1] | 459.0 | $^1$HNMR (400 MHz, DMSO-$d_6$) δ 8.10 (t, J = 2.8 Hz, 2H), 7.49-7.55 (m, 2H), 6.86 (d, J = 8.8Hz, 1H), 6.60 (dd, J = 5.2 Hz, 6.8 Hz, 1H), 6.34-6.37 (m, 2H), 4.34-4.45 (m, 2H), 3.84-3.88 (m, 1H), 3.70-3.76 (m, 1H), 3.63 (s, 4H), 3.53 (t, J = 5.2 Hz, 4H), 3.29-3.32 (m, 1H), 2.35 (s, 3H), 1.77-1.79 (m, 5H), 1.61-1.64 (m, 1H), 1.39-1.53 (m, 3H), 1.15-1.25 (m, 1H). | 5 |
| I-623 | 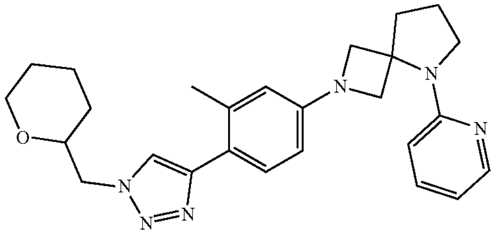 [SMILES: Cc1cc(N2CC3(CCCN3c3ccccn3)C2)ccc1-c1cn(CC2CCCCO2)nn1] | 459.1 | $^1$HNMR (400 MHz, DMSO-$d_6$) δ 8.11 (s, 1H), 7.91 (d, J = 3.6 Hz, 1H), 7.55 (d, J = 8.4 Hz, 1H), 7.47-7.51 (m, 1H), 6.68 (d, J = 8.4 Hz, 1H), 6.53-6.56 (m, 1H), 6.36-6.38 (m, 2H), 4.75 (d, J = 6.8 Hz, 2H), 4.35-4.46 (m, 2H), 3.85-3.88 (m, 1H), 3.72-3.74 (m, 3H), 3.45 (t, , I = 6.4 Hz, 2H), 3.28-3.33 (m, 1H), 2.35-2.38 (m, 5H), 1.86-1.92 (m, 2H), 1.79-1.81 (m, 1H), 1.61-1.65 (m, 1H), 1.46-1.51 (m, 3H), 1.19-1.25 (m, 1H). | 5 |
| I-658 | 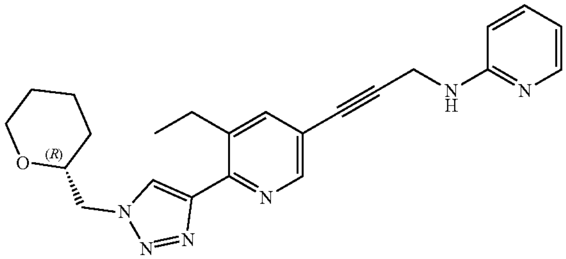 | 403.1 | $^1$HNMR (400 MHz, $CDCl_3$) δ 8.45 (d, J = 1.6 Hz, 1H), 8.20 (s, 1H), 8.05 (d, J = 6.4 Hz, 1H), 7.63-7.66 (m, 2H), 7.22-7.24 (m, 2H), 6.83 (t, J = 6.8 Hz, 1H), 4.49 (dd, J = 3.6 Hz, 14.0 Hz, 1H), 4.36 (dd, J = 7.2 Hz, 14.0 Hz, 1H), 4.21 (s, 2H), 3.99 (d, J = 11.2 Hz, 1H), 3.36-3.43 (m, 1H), 3.16 (q, J = 7.6 Hz, 2H), 1.87-1.89 (m, 1H), 1.66-1.69 (m, 1H), 1.50-1.55 (m, 2H), 1.24-1.31 (m, 5H). | 28 |

TABLE 23-continued

Characterization data for exemplary compounds

| Compound No. | Chemical Structure | M + 1 | $^{1}$H NMR (400 MHz) | Example of Synthesis |
|---|---|---|---|---|
| I-535 | 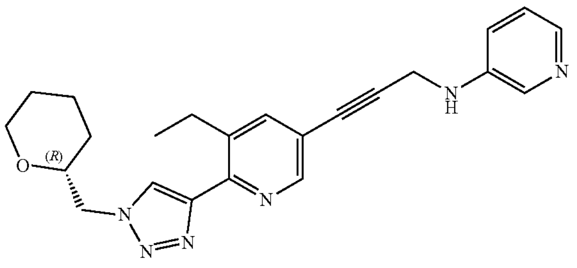 | 403.0 | $^{1}$HNMR (400 MHz, DMSO-$d_6$) δ 8.45 (s, 2H), 8.09 (d, J = 2.8 Hz, 1H), 7.86 (dd, J = 2.0 Hz, 4.4 Hz, 1H), 7.75 (d, J = 2.0 Hz, 1H), 7.14-7.18 (m, 1H), 7.06-7.09 (m, 1H), 6.39 (t, , I = 6.4 Hz, 1H), 4.40-4.52 (m, 2H), 4.24 (d, J = 6.4 Hz, 2H), 3.84-3.87 (m, 1H), 3.72-3.76 (m, 1H), 3.29-3.35 (m, 1H), 3.11 (q, J = 7.6 Hz, 2H), 1.78-1.80 (m, 1H), 1.62-1.65 (m, 1H), 1.43-1.50 (m, 3H), 1.15-1.24 (m, 4H). | 28 |
| I-624 | 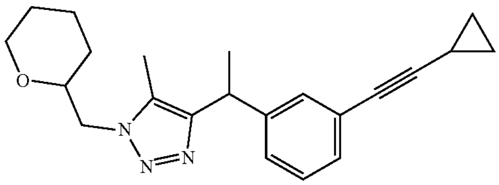 [SMILES: Cc1c(C(C)c2cccc(C#CC3CC3)c2)nnn1CC1CCCCO1] | 350.2 | $^{1}$HNMR (400 MHz, DMSO-$d_6$) δ 7.22-7.26 (m, 3H), 7.14-7.16 (m, 1H), 4.11-4.28 (m, 3H), 3.78-3.81 (m, 1H), 3.60-3.64 (m, 1H), 3.22-3.28 (m, 1H), 2.09 ( d, J = 6.8 Hz, 3H), 1.75-1.78 (m, 1H), 1.47-1.57 (m, 4H), 1.37-1.45 (m, 3H), 1.14-1.23 (m, 2H), 0.85-0.89 (m, 2H), 0.70-0.72 (m, 2H). | 24 |
| I-551 | 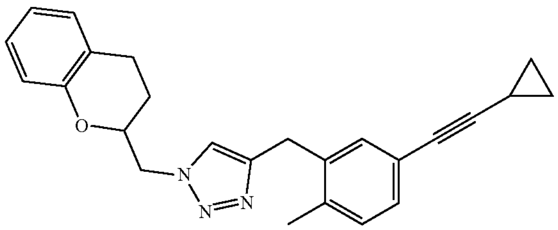 [SMILES: Cc1ccc(C#CC2CC2)cc1Cc1cn(CC2CCc3ccccc3O2)nn1] | 384.1 | $^{1}$HNMR (400 MHz, DMSO-$d_6$) δ 7.82 (s, 1H), 7.11-7.13 (m, 3H), 7.03-7.07 (m, 2H), 6.80-6.84 (m, 1H), 6.65-6.68 (m, 1H), 4.56-4.67 (m, 2H), 4.39-4.44 (m, 1H), 3.95 (s, 2H), 2.70-2.82 (m, 2H), 2.26 (s, 3H), 1.99-2.05 (m, 1H), 1.46-1.60 (m, 2H), 0.83-0.87 (m, 2H), 0.66-0.70 (m, 2H). | 13 |
| I-552 | 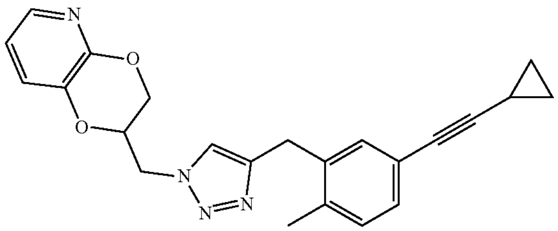 [SMILES: Cc1ccc(C#CC2CC2)cc1Cc1cn(CC2COc3ncccc3O2)nn1] | 387.1 | $^{1}$HNMR (400 MHz, DMSO-$d_6$) δ 7.83 (s, 1H), 7.77 (dd, J = 1.2 Hz, 4.4 Hz, 1H), 7.24 (dd, J = 1.6 Hz, 8.0 Hz, 1H), 7.12-7.13 (m, 3H), 6.96 (dd, , I = 4.8 Hz, 7.6 Hz, 1H), 4.62-4.76 (m, 3H), 4.52 (dd, J = 2.0 Hz, 11.6 Hz, 1H), 4.16 (dd, J = 6.0 Hz, 11.6 Hz, 1H), 3.95 (s, 2H), 2.26 (s 3H), 1.48-1.52 (m, 1H), 0.83-0.87 (m, 2H), 0.66-0.70 (m, 2H). | 13 |
| I-625 | 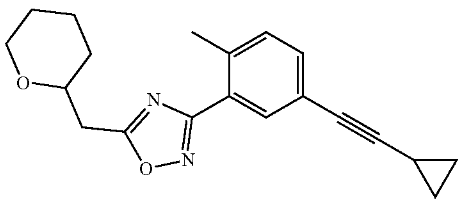 [SMILES: Cc1ccc(C#CC2CC2)cc1-c1noc(CC2CCCCO2)n1] | 323.0 | $^{1}$HNMR (400 MHz, DMSO-$d_6$) δ 7.88 (d, J = 1.6 Hz, 1H), 7.44 (dd, J = 8.0 Hz, 1.6 Hz, 1H), 7.37 (d, J = 7.6 Hz, 1H), 3.78-3.84 (m, 2H), 3.35-3.38 (m, 1H), 3.07-3.20 (m, 2H), 2.54 (s, 3H), 1.72-1.81 (m, 2H), 1.38-1.59 (m, 4H), 1.29-1.36 (m, 1H), 0.87-0.92 (m, 2H), 0.74-0.78 (m, 2H). | 31 |
| I-591 | 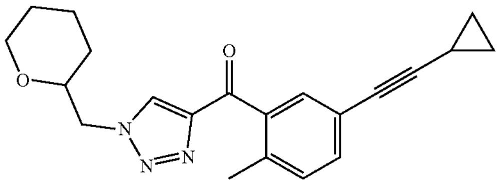 [SMILES: Cc1ccc(C#CC2CC2)cc1C(=O)c1cn(CC2CCCCO2)nn1] | 350.1 | $^{1}$HNMR (400 MHz, $CDCl_3$) δ 8.29 (s, 1H), 7.74 (d, J = 1.6 Hz, 1H), 7.40 (dd, J = 1.6 Hz, 8.0 Hz, 1H), 7.20 (d, J = 8.0 Hz, 1H), 4.55 (dd, J = 2.8 Hz, 14.4 Hz, 1H), 4.33 (dd, J = 8.0 Hz, 14.4 Hz, 1H), 3.99-4.02 (m, 1H), 3.66-3.72 (m, 1H), 3.37-3.43 (m, 1H), 2.43 (s, 3H), 1.89-2.01 (m, 1H), 1.69 (d, J = 13.6 Hz, 1H), 1.58-1.62 (m, 1H), 1.51-1.55 (m, 2H), 1.39-1.46 (m, 1H), 1.25-1.29 (m, 1H), 0.81-0.87 (m, 2H), 0.76-0.80 (m, 2H). | 34 |

TABLE 23-continued

Characterization data for exemplary compounds

| Compound No. | Chemical Structure | M + 1 | $^1$H NMR (400 MHz) | Example of Synthesis |
|---|---|---|---|---|
| I-646 | 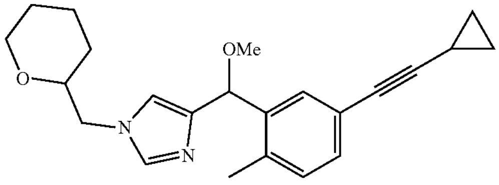 [SMILES: COC(c1cn(CC2CCCCO2)cn1)c1cc(C#CC2CC2)ccc1C] | 365.1 | $^1$HNMR (400 MHz, DMSO-$d_6$) δ 7.45 (d, J = 2.4 Hz, 1H) 7.38 (t, J = 2.0 Hz, 1H), 7.13 (dd, J = 2.0 Hz, 8.0 Hz, 1H), 7.06 (d, J = 8.0 Hz, 1H), 6.85 (s, 1H), 5.29 (s, 1H), 3.83-3.95 (m, 3H), 3.43-3.48 (m, 1H), 3.26-3.34 (m, 1H), 3.22 (s, 3H), 2.20 (s, 3H), 1.74-1.75 (m, 1H), 1.39-1.53 (m, 5H), 1.02-1.06 (m, 1H), 0.84-0.88 (m, 2H), 0.69-0.73 (m, 2H). | 32 |
| I-671 | 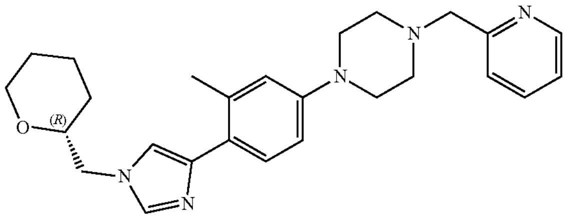 | 432.1 | $^1$HNMR (400 MHz, DMSO-$d_6$) δ 8.51 (d, J = 4.0 Hz, 1H), 7.78 (dt, J = 7.6 Hz, 1.6 Hz, 1H), 7.63 (d, J = 8.8 Hz, 1H), 7.57 (d, J = 0.8 Hz, 1H), 7.48 (d, J = 8.0 Hz, 1H), 7.26-7.29 (m, 1H), 7.21 (d, J = 0.8 Hz, 1H), 6.77-6.79 (m, 2H), 3.92-4.04 (m, 2H), 3.86-3.89 (m, 1H), 3.65 (s, 2H), 3.52-3.58 (m, 1H), 3.29-3.32 (m, 1H), 3.15 (t, J = 4.8 Hz, 4H), 2.57 (t, J = 4.8 Hz, 4H), 2.37 (s, 3H), 1.77-1.79 (m, 1H), 1.54-1.57 (m, 1H), 1.38-1.48 (m, 3H), 1.13-1.19 (m, 1H). | 33 |
| I-672 | 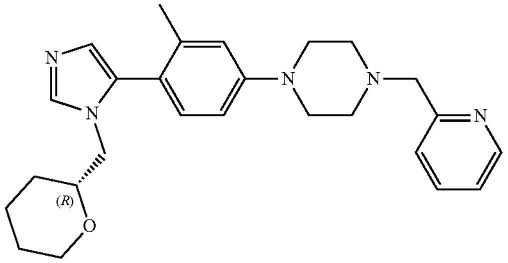 | 432.0 | $^1$HNMR (400 MHz, DMSO-$d_6$) δ 8.51 (d, J = 4.0 Hz, 1H), 7.78 (dt, J = 7.6 Hz, 2.0 Hz, 1H), 7.66 (s, 1H), 7.48 (d, J = 7.6 Hz, 1H), 7.26-7.30 (m, 1H), 7.02 (d, J = 8.4 Hz, 1H), 6.88 (d, J = 2.0 Hz, 1H), 6.80 (dd, , I = 8.4 Hz, 2.4 Hz, 1H), 6.73 (s, 1H), 3.79-3.81 (m, 1H), 3.66-3.75 (m, 4H), 3.16-3.29 (m, 6H), 2.57 (t, J = 4.8 Hz, 4H), 2.05 (s, 3H), 1.67-1.69 (m, 1H), 1.28-1.38 (m, 3H), 1.21-1.24 (m, 1H), 0.93-1.02 (m, 1H). | 33 |
| I-601 | 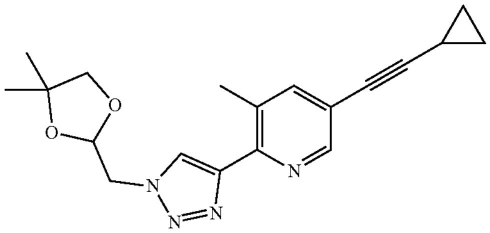 [SMILES: Cc1cc(C#CC2CC2)cnc1-c1cn(CC2OCC(C)(C)O2)nn1] | 339.0 | $^1$HNMR (400 MHz, DMSO-$d_6$) δ 8.54 (s, 1H), 8.43 (d, J = 1.6 Hz, 1H), 7.73 (s, 1H), 4.61-4.65 (m, 1H), 4.51-4.55 (m, 2H), 4.07-4.10 (m, 1H), 3.79-3.83 (m, 1H), 2.62 (s, 3H), 1.58-1.61 (m, 1H), 1.31 (s, 3H), 1.26 (s, 3H), 0.90-0.95 (m, 2H), 0.76-0.80 (m, 2H). | 4 |
| I-602 | 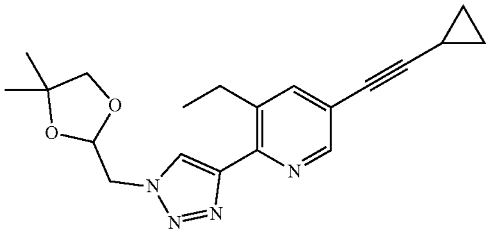 [SMILES: CCc1cc(C#CC2CC2)cnc1-c1cn(CC2OCC(C)(C)O2)nn1] | 353.0 | $^1$HNMR (400 MHz, DMSO-$d_6$) δ 8.52 (s, 1H), 8.44 (d, J = 2.0 Hz, 1H), 7.73 (d, J = 2.0 Hz, 1H), 4.61-4.65 (m, 1H), 4.49-4.55 (m, 2H), 4.09 (dd, J = 5.6 Hz, 8.4 Hz, 1H), 3.81 (dd, J = 4.8 Hz, 8.4 Hz, 1H), 3.10 (q, J = 7.2 Hz, 2H), 1.58-1.62 (m, 1H), 1.30 (s, 3H), 1.26 (s, 3H), 1.17 (t, J = 7.6 Hz, 3H), 0.91-0.95 (m, 2H), 0.77-0.80 (m, 2H). | 4 |

TABLE 23-continued

| Characterization data for exemplary compounds | | | | |
|---|---|---|---|---|
| Compound No. | Chemical Structure | M + 1 | $^1$H NMR (400 MHz) | Example of Synthesis |
| I-603 | 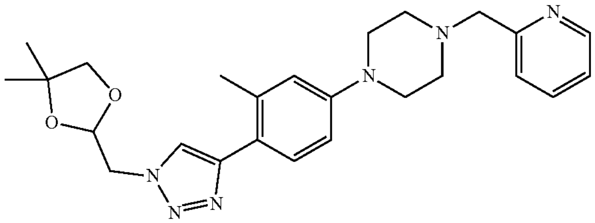 [SMILES: Cc1cc(N2CCN(Cc3ccccn3)CC2)ccc1-c1cn(CC2OCC(C)(C)O2)nn1] | 449.0 | $^1$HNMR (400 MHz, DMSO-$d_6$) δ 8.51 (d, J = 4.0 Hz, 1H), 8.19 (s, 1H), 7.76-7.81 (m, 1H), 7.57 (d, J = 9.2 Hz, 1H), 7.48 (d, J = 8.0 Hz, 1H), 7.26-7.29 (m, 1H), 6.84-6.85 (m, 2H), 4.46-4.59 (m, 3H), 4.05-4.09 (m, 1H), 3.77-3.80 (m, 1H), 3.66 (s, 2H), 3.20 (t, J = 4.4 Hz, 4H), 2.58 (t, J = 4.8 Hz, 4H), 2.38 (s, 3H), 1.29 (s, 3H), 1.26 (s, 3H). | 5 |
| I-626 | 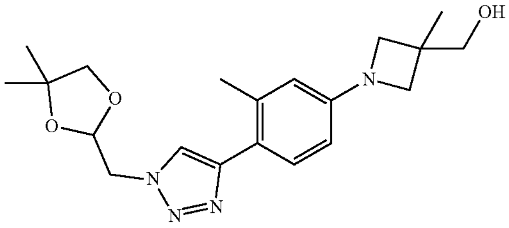 [SMILES: Cc1cc(N2CC(C)(CO)C2)ccc1-c1cn(CC2OCC(C)(C)O2)nn1] | 373.2 | $^1$HNMR (400 MHz, DMSO-$d_6$) δ 8.14 (s, 1H), 7.51 (d, J = 8.4 Hz, 1H), 6.30-6.32 (m, 2H), 4.46-4.58 (m, 3H), 4.06-4.08 (m, 1H), 3.78-3.80 (m, 1H), 3.67 (d, J = 7.2 Hz, 2H), 3.39-3.43 (m, 4H), 2.34 (s, 3H), 1.29 (s, 3H), 1.26 (d, J = 4.8 Hz, 6H). | 22 |
| I-592 | 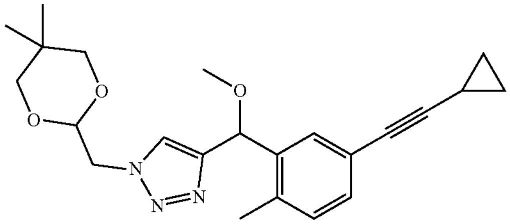 [SMILES: COC(c1cn(CC2OCC(C)(C)CO2)nn1)c1cc(C#CC2CC2)ccc1C] | 396.1 | $^1$HNMR (400 MHz, $CDCl_3$) δ 7.57 (d, J = 1.6 Hz, 1H), 7.22-7.24 (m, 2H), 7.05 (d, J = 8.0 Hz, 1H), 5.63 (s, 1H), 4.51 (d, J = 7.6 Hz, 2H), 4.01-4.05 (m, 2H), 3.56 (dd, J = 3.2 Hz, 12.4 Hz, 2H), 3.40 (s, 3H), 2.24 (s, 3H), 2.17-2.19 (m, 1H), 1.57 (s, 1H), 1.44-1.47 (m, 4H), 1.41-1.43 (s, 3H), 0.80-0.88 (m, 4H). | 34 |
| I-593 | 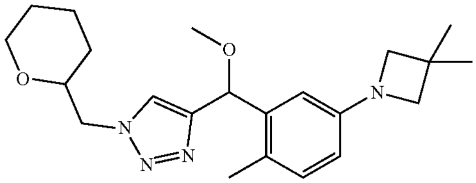 [SMILES: COC(c1cn(CC2CCCCO2)nn1)c1cc(N2CC(C)(C)C2)ccc1C] | 385.1 | $^1$HNMR (400 MHz, DMSO-$d_6$) δ 7.75 (d, J = 10.4 Hz, 1H), 6.92 (d, J = 8.0 Hz, 1H), 6.49 (s, 1H), 6.24-6.26 (m, 1H), 5.51 (s, 1H), 4.27-4.36 (m, 2H), 3.80-3.83 (m, 1H), 3.62-3.64 (m, 1H), 3.46 (s, 4H), 3.24-3.30 (m, 1H), 3.26 (s, 3H), 2.10 (s, 3H), 1.72-1.75 (m, 1H), 1.52-1.56 (m, 1H), 1.35-1.46 (m, 3H), 1.27 (s, 6H), 1.09-1.15 (m, 1H). | 34 |
| I-594 | 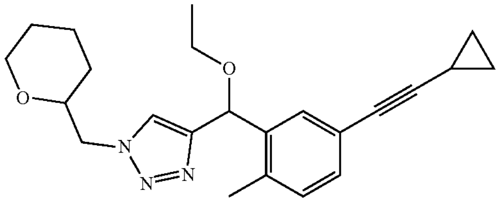 [SMILES: CCOC(c1cn(CC2CCCCO2)nn1)c1cc(C#CC2CC2)ccc1C] | 380.0 | $^1$HNMR (400 MHz, DMSO-$d_6$) δ 7.82 (d, J = 12.4 Hz, 1H), 7.40 (dd, J = 1.6 Hz, 6.4 Hz, 1H), 7.17 (dd, J = 1.6 Hz, 8.0 Hz, 1H), 7.10 (d, J = 8.0 Hz, 1H), 5.68 (s, 1H), 4.27-4.35 (m, 2H), 3.80-3.83 (m, 1H), 3.63-3.67 (m, 1H), 3.41-3.48 (m, 2H), 3.24-3.31 (m, 1H), 2.20 (s, 3H), 1.75-1.78 (m, 1H), 1.39-1.57 (m, 5H), 1.10-1.16 (m, 4H), 0.84-0.89 (m, 2H), 0.70-0.74 (m, 2H). | 34 |
| I-584 | 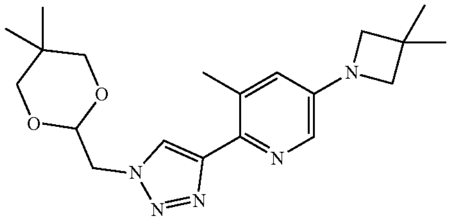 | 372.2 | $^1$HNMR (400 MHz, DMSO-$d_6$) δ 8.25 (s, 1H), 7.68 (d, J = 2.4 Hz, 1H), 6.70 (d, J = 2.0 Hz, 1H), 4.91 (t, J = 4.4 Hz, 1H), 4.55 (d, J = 4.8 Hz, 2H), 3.56-3.61 (m, 6H), 3.46 (d, J = 10.8 Hz, 2H), 2.54 (s, 3H), 1.29 (s, 6H), 1.05 (s, 3H), 0.68 (s, 3H). | 5 |

TABLE 23-continued

| Characterization data for exemplary compounds | | | | |
|---|---|---|---|---|
| Compound No. | Chemical Structure | M + 1 | $^1$H NMR (400 MHz) | Example of Synthesis |
| I-614 | 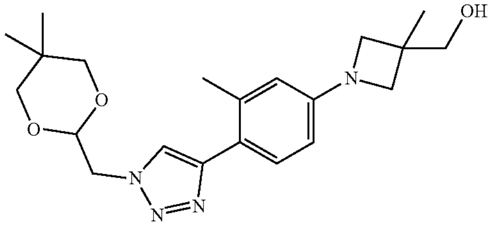 [SMILES: Cc1cc(N2CC(C)(CO)C2)ccc1-c1cn(CC2OCC(C)(C)CO2)nn1] | 387.1 | $^1$HNMR (400 MHz, DMSO-$d_6$) 8.19 (s, 1H), 7.52 (d, J = 8.0 Hz, 1H), 6.30-6.32 (m, 2H), 4.88 (t, J = 5.2 Hz, 1H), 4.49 (d, J = 7.2 Hz, 2H), 3.89 (dd, J = 4.0 Hz, 12.0 Hz, 2H), 3.67 (d, J = 6.8 Hz, 2H), 3.61 (dd, J = 5.6 Hz, 12.0 Hz, 2H), 3.42 (t, J = 6.8 Hz, 3H), 3.40 (s, 1H), 2.34 (s, 3H), 2.20-2.22 (m, 1H), 1.35 (s, 6H), 1.25 (s, 3H). | 22 |
| I-595 | 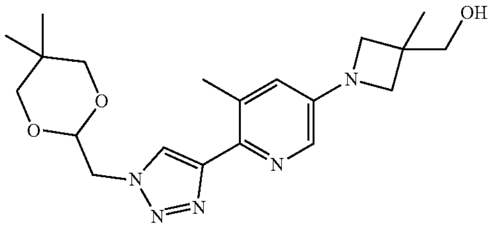 | 388.0 | $^1$HNMR (400 MHz, DMSO-$d_6$) δ 8.24 (s, 1H), 7.68 (d, J = 2.4 Hz, 1H), 6.69 (d, J = 2.4 Hz, 1H), 4.89-4.93 (m, 2H), 4.55 (d, J = 4.4 Hz, 2H), 3.75 (d, J = 7.2 Hz, 2H), 3.57 (d, J = 11.2 Hz, 2H), 3.43-3.50 (m, 6H), 2.54 (s, 3H), 1.26 (s, 3H), 1.05 (s, 3H), 0.68 (s, 3H). | 22 |
| I-634 | 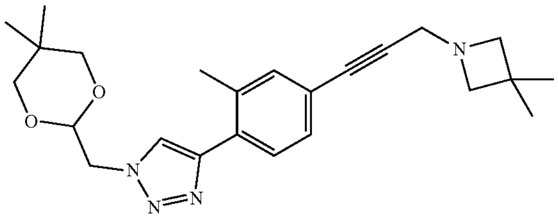 | 409.2 | $^1$HNMR (400 MHz, DMSO-$d_6$) δ 8.37 (s, 1H), 7.78 (d, J = 8.0 Hz, 1H), 7.40 (s, 1H), 7.35 (d, J = 8.0 Hz, 1H), 4.93 (t, J = 4.4 Hz, 1H), 4.58 (d, J = 4.4 Hz, 2H), 3.57 (d, J = 11.2 Hz, 2H), 3.47 (d, J = 8.8 Hz, 4H), 3.03 (s, 4H), 2.43 (s, 3H), 1.19 (s, 6H), 1.04 (s, 3H), 0.68 (s, 3H). | 6 |
| I-596 | 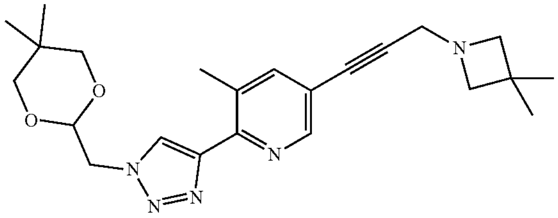 | 410.2 | $^1$HNMR (400 MHz, DMSO-$d_6$) δ 8.52 (s, 2H), 7.81 (d, J = 1.2 Hz, 1H), 4.93 (t, J = 4.4 Hz, 1H), 4.62 (d, J = 4.4 Hz, 2H), 3.58 (d, J = 11.2 Hz, 2H), 3.45-3.48 (m, 4H), 3.02 (s, 4H), 2.65 (s, 3H), 1.18 (s, 6H), 1.04 (s, 3H), 0.68 (s, 3H). | 28 |
| I-615 | 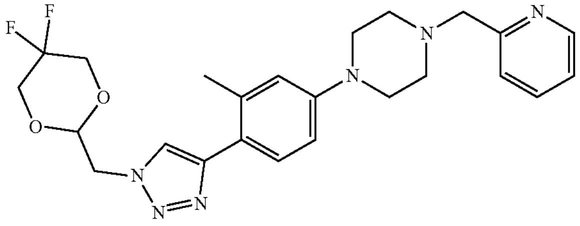 [SMILES: Cc1cc(N2CCN(Cc3ccccn3)CC2)ccc1-c1cn(CC2OCC(F)(F)CO2)nn1] | 471.1 | $^1$HNMR (400 MHz, $CDCl_3$) δ 8.59 (d, J = 4.4 Hz, 1H), 7.67-7.69 (m, 3H), 7.47 (d, J = 7.6 Hz, 1H), 7.20 (t, J = 6.4 Hz, 1H), 6.81-6.85 (m, 2H), 4.98 (t, J = 4.8 Hz, 1H), 4.61 (d, J = 4.8 Hz, 2H), 4.18 (t, J = 11.6 Hz, 2H), 3.76-3.86 (m, 4H), 3.28-3.29 (m, 4H), 2.71 (s, 4H), 2.43 (s, 3H). | 5 |
| I-635 | 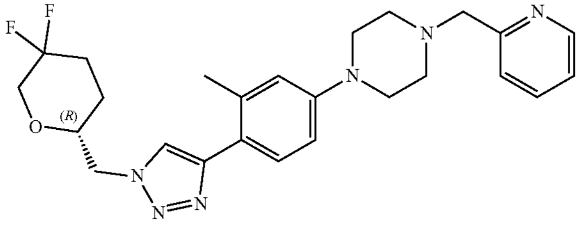 | 469.0 | $^1$HNMR (400 MHz, DMSO-$d_6$) δ: 8.51 (d, J = 4.0 Hz, 1H), 8.16 (s, 1H), 7.79 (dt, J = 1.6 Hz, 7.6 Hz, 1H), 7.57-7.59 (m, 1H), 7.48 (d, J = 8.0 Hz, 1H), 7.27-7.29 (m, 1H), 6.83-6.85 (m, 2H), 4.45-4.59 (m, 2H), 3.96-4.01 (m, 1H), 3.85-3.90 (m, 1H), 3.55-3.66 (m, 3H), 3.19-3.21 (m, 4H), 2.56-2.59 (m, 4H), 2.38 (s, 3H), 2.17-2.19 (m, 2H), 1.88-1.92 (m, 1H), 1.50-1.54 (m, 1H). | 5 |

TABLE 23-continued

Characterization data for exemplary compounds

| Compound No. | Chemical Structure | M + 1 | $^1$H NMR (400 MHz) | Example of Synthesis |
|---|---|---|---|---|
| I-636 | 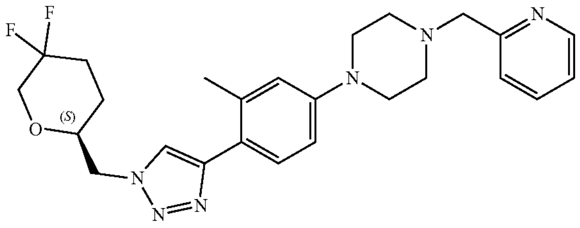 | 469.0 | $^1$HNMR (400 MHz, DMSO-$d_6$) δ 8.51 (s, 1H), 8.16 (s, 1H), 7.79 (t, J = 7.6 Hz, 1H), 7.57-7.59 (m, 1H), 7.48 (d, J = 7.2 Hz, 1H), 7.27-7.29 (m, 1H), 6.83-6.85 (m, 2H), 4.45-4.59 (m, 2H), 3.97-4.01 (m, 1H), 3.85-3.91 (m, 1H), 3.55-3.66 (m, 3H), 3.16-3.19 (m, 4H), 2.56-2.59 (m, 4H), 2.38 (s, 3H), 2.02-2.19 (m, 2H), 1.88-1.92 (m, 1H), 1.51-1.55 (m, 1H). | 5 |
| I-637 | 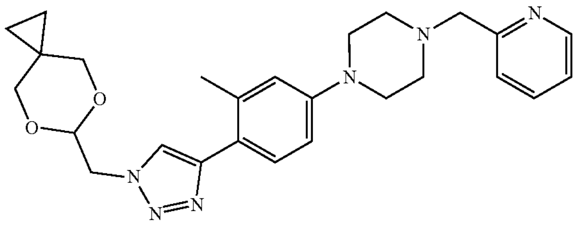 [SMILES: Cc1cc(N2CCN(Cc3ccccn3)CC2)ccc1-c1cn(CC2OCC3(CC3)CO2)nn1] | 461.2 | $^1$HNMR (400 MHz, DMSO-$d_6$) δ 8.51 (d, J = 4.0 Hz, 1H), 8.20 (s, 1H), 7.76-7.81 (m, 1H), 7.57-7.59 (m, 1H), 7.48 (d, J = 7.6 Hz, 1H), 7.26-7.29 (m, 1H), 6.83-6.85 (m, 2H), 5.09 (t, J = 4.8 Hz, 1H), 4.55 (d, J = 4.8 Hz, 2H), 4.08 (d, J = 11.2 Hz, 2H), 3.66 (s, 2H), 3.18-3.27 (m, 7H), 2.58 (t, , I = 4.8 Hz, 3H), 2.37 (s, 3H), 0.56-0.60 (m, 2H), 0.31-0.35 (m, 2H). | 5 |
| I-597 | 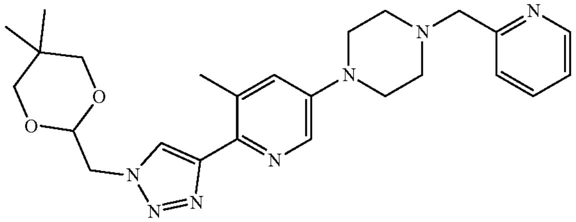 [SMILES: Cc1cc(N2CCN(Cc3ccccn3)CC2)cnc1-c1cn(CC2OCC(C)(C)CO2)nn1] | 464.1 | $^1$HNMR (400 MHz, DMSO-$d_6$) δ 8.51 (dd, J = 4.8 Hz, 0.8 Hz, 1H), 8.29 (s, 1H), 8.17 (d, J = 2.4 Hz, 1H), 7.93 (dt, J = 7.6 Hz, 2.0 Hz, 1H), 7.48 (d, J = 7.6 Hz, 1H), 7.27-7.30 (m, 1H), 7.22 (d, J = 2.4 Hz, 1H), 4.91 (t, J = 4.4 Hz, 1H), 4.56 (d, J = 4.4 Hz, 2H), 3.67 (s, 2H), 3.57 (d, J = 10.8 Hz, 2H), 3.46 (d, J = 10.8 Hz, 2H), 3.26 (t, J = 4.8 Hz, 4H), 2.57-2.60 (m, 7H), 1.05 (s, 3H), 0.68 (s, 3H). | 5 |
| I-585 | 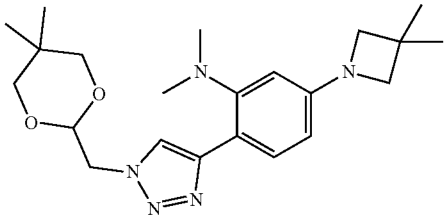 | 400.1 | $^1$HNMR (400 MHz, DMSO-$d_6$) δ 8.24 (s, 1H), 7.79 (d, J = 8.0 Hz, 1H), 6.14-6.17 (m, 2H), 4.48 (d, J = 7.6 Hz, 2H), 3.87 (dd, J = 3.6 Hz, 11.6 Hz, 2H), 3.58 (dd, J = 6.0 Hz, 12.0 Hz, 2H), 3.55 (s, 4H), 2.55 (s, 6H), 2.16-2.19 (m, 1H), 1.35 (d, J = 4.8 Hz, 6H), 1.29 (s, 6H). | 5 |
| I-604 | 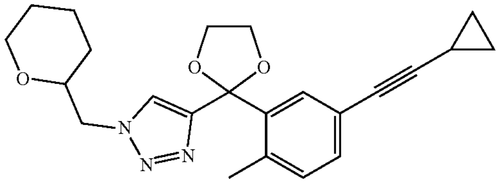 [SMILES: Cc1ccc(C#CC2CC2)cc1C1(c2cn(CC3CCCCO3)nn2)OCCO1] | 394.1 | 1HNMR (400 MHz, $CDCl_3$) δ 7.81 (d, J = 1.2 Hz, 1H), 7.36 (s, 1H), 7.25 (d, J = 1.6 Hz, 1H), 7.06 (d, J = 7.6 Hz, 1H), 4.39 (dd, J = 3.2 Hz, 14.4 Hz, 1H), 4.25-4.30 (m, 2H), 4.19 (dd, J = 7.6 Hz, 14.0 Hz, 1H), 3.98-4.04 (m, 2H), 3.90-3.93 (m, 1H), 3.57-3.63 (m, 1H), 3.30-3.36 (m, 1H), 2.24 (s, 3H), 1.83-1.85 (m, 1H), 1.58-1.65 (m, 1H), 1.41-1.49 (m, 4H), 1.13-1.27 (m, 1H), 0.78-0.88 (m, 4H). | 13 |

TABLE 23-continued

| Characterization data for exemplary compounds | | | | |
|---|---|---|---|---|
| Compound No. | Chemical Structure | M + 1 | $^1$H NMR (400 MHz) | Example of Synthesis |
| I-647 | 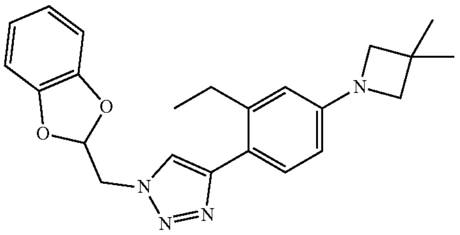 [SMILES: CCc1cc(N2CC(C)(C)C2)ccc1-c1cn(CC2Oc3ccccc3O2)nn1] | 391.0 | $^1$HNMR (400 MHz, DMSO-$d_6$) δ 8.07 (s, 1H), 7.28 (d, J = 8.0 Hz, 1H), 6.85-6.88 (m, 2H), 6.77-6.80 (m, 2H), 6.71 (t, J = 3.2 Hz, 1H), 6.27-6.30 (m, 2H), 4.95 (d, J = 3.2 Hz, 2H), 3.53 (s, 4H), 2.53-2.58 (m, 2H), 1.28 (s, 6H), 1.00 (t, J = 7.6 Hz, 3H). | 5 |
| I-627 | 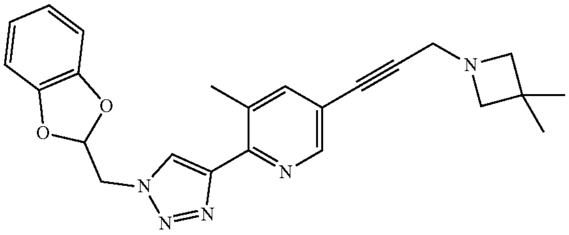 [SMILES: Cc1cc(C#CCN2CC(C)(C)C2)cnc1-c1cn(CC2Oc3ccccc3O2)nn1] | 416.0 | $^1$HNMR (400 MHz, DMSO-$d_6$) δ 8.59 (s, 1H), 8.51 (d, J = 2.0 Hz, 1H), 7.81 (d, J = 1.2 Hz, 1H), 6.89-6.93 (m, 2H), 6.79-1H), (m, 2H), 6.72 (t, J = 3.6 Hz, 1H), 5.03 (d, J = 3.6 Hz, 2H), 3.48 (s, 2H), 3.02 (s, 4H), 2.59 (s, 3H), 1.18 (s, 6H). | 3 |
| I-628 | 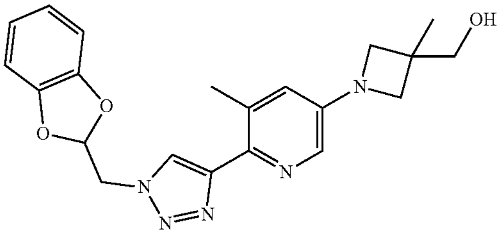 [SMILES: Cc1cc(N2CC(C)(CO)C2)cnc1-c1cn(CC2Oc3ccccc3O2)nn1] | 394.1 | $^1$HNMR (400 MHz, $CDCl_3$) δ 8.13 (s, 1H), 7.71 (d, J = 2.8 Hz, 1H), 6.84 (s, 4H), 6.60 (d, J = 2.4 Hz, 1H), 6.47 (t, J = 4.4 Hz, 1H), 4.81 (d, J = 4.0 Hz, 2H), 3.85 (d, J = 7.2 Hz, 2H), 3.70 (s, 2H), 3.58 (d, J = 7.2 Hz, 2H), 2.60 (s, 3H), 1.90-1.95 (m, 1H), 1.35 (s, 3H). | 22 |
| I-605 | 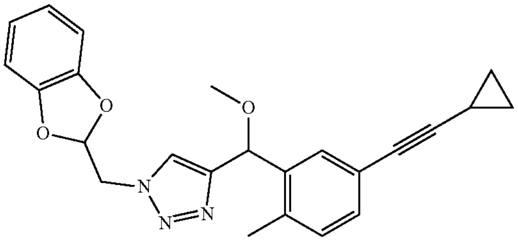 [SMILES: COC(c1cn(CC2Oc3ccccc3O2)nn1)c1cc(C#CC2CC2)ccc1C] | 402.1 | $^1$HNMR (400 MHz, $CDCl_3$) δ 7.54 (d, J = 1.2 Hz, 1H), 7.34 (s, 1H), 7.22 (dd, J = 1.6 Hz, 8.0 Hz, 1H), 7.01 (d, J = 8.0 Hz, 1H), 6.75-6.82 (m, 3H), 6.70-6.73 (m, 1H), 6.41 (t, J = 3.6 Hz, 1H), 5.57 (s, 1H), 4.71 (d, J = 3.6 Hz, 2H), 3.35 (s, 3H), 2.11 (s, 3H), 1.42-1.49 (m, 1H), 0.79-0.89 (m, 4H). | 34 |
| I-638 | 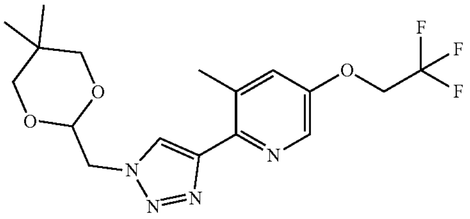 [SMILES: Cc1cc(OCC(F)(F)F)cnc1-c1cn(CC2OCC(C)(C)CO2)nn1] | 387.0 | $^1$HNMR (400 MHz, DMSO-$d_6$) δ 8.39 (s, 1H), 8.29 (d, J = 2.8 Hz, 1H), 7.51 (d, J = 2.8 Hz, 1H), 4.89-4.92 (m, 3H), 4.59 (d, J = 4.4 Hz, 2H), 3.58 (d, J = 11.2 Hz, 2H), 3.46 (d, J = 10.8 Hz, 2H), 2.63(s, 3H), 1.04 (s, 3H), 0.68 (s, 3H). | 26 |
| I-639 | 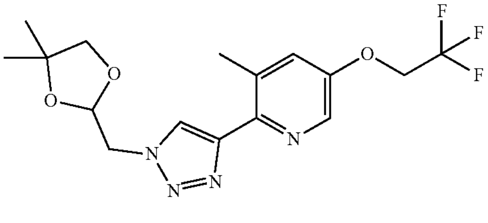 [SMILES: Cc1cc(OCC(F)(F)F)cnc1-c1cn(CC2OCC(C)(C)O2)nn1] | 373.0 | $^1$HNMR (400 MHz, DMSO-$d_6$) δ 8.43 (s, 1H), 8.29 (d, J = 2.4 Hz, 1H), 7.52 (d, J = 2.8 Hz, 1H), 4.91 (q, J = 8.8 Hz, 2H), 4.59-4.64 (m, 1H), 4.50-4.53 (m, 2H), 4.07-4.11 (m, 1H), 3.79-3.82 (m, 1H), 2.64 (s, 3H), 1.31 (s, 3H), 1.26 (s, 3H). | 26 |

TABLE 23-continued

Characterization data for exemplary compounds

| Compound No. | Chemical Structure | M + 1 | $^1$H NMR (400 MHz) | Example of Synthesis |
|---|---|---|---|---|
| I-749 | 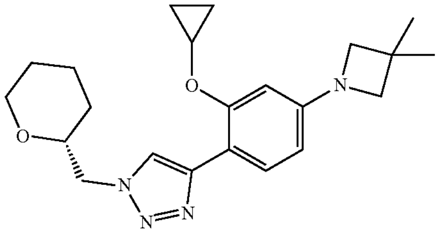 [SMILES: CC1(C)CN(c2ccc(-c3cn(C[C@H]4CCCCO4)nn3)c(OC3CC3)c2)C1] | 383.2 | $^1$HNMR (400 MHz, DMSO-$d_6$) δ 7.96 (s, 1H), 7.89 (d, J = 8.4 Hz, 1H), 6.38 (d, J = 2.0 Hz, 1H), 6.11 (dd, = 2.4 Hz, 8.4 Hz, 1H), 4.33-4.43 (m, 2H), 3.84-3.94 (m, 2H), 3.65-3.71 (m, 1H), 3.56 (s, 4H), 3.28-3.34 (m, 1H), 1.76-1.79 (m, 1H), 1.59-1.62 (m, 1H), 1.40-1.50 (m, 3H), 1.29 (s, 6H), 1.13-1.23 (m, 1H), 0.72-0.84 (m, 4H). | 5 |
| I-606 | 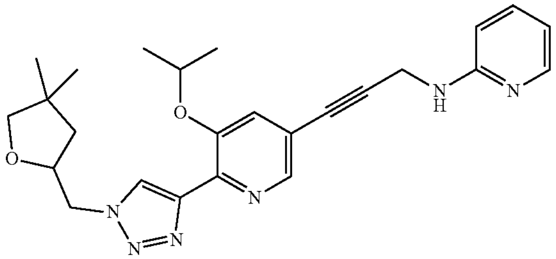 [SMILES: CC(C)Oc1cc(C#CCNc2ccccn2)cnc1-c1cn(CC2CC(C)(C)CO2)nn1] | 447.0 | $^1$HNMR (400 MHz, DMSO-$d_6$) δ 8.35-8.37 (m, 2H), 8.18 (s, 1H), 7.57 (d, J = 8.8 Hz, 1H), 7.49 (d, J = 1.2 Hz, 1H), 7.45 (s, 1H), 7.21-7.25 (m, 1H), 6.91-6.94 (m, 1H), 4.70-4.73 (m, 1H), 4.48-4.60 (m, 2H), 4.36 (s, 3H), 3.37-3.39 (m, 2H), 1.80 (dd, J = 12.0 Hz, 6.8 Hz, 1H), 1.40 (dd, J = 12.4 Hz, 8.4 Hz, 1H), 1.30 (t, J = 6.0 Hz, 6H), 1.03 (s, 3H), 0.96 (s, 3H). | 3 |
| I-674 | 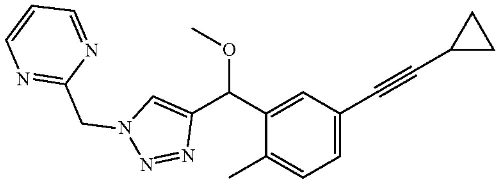 [SMILES: COC(c1cn(Cc2ncccn2)nn1)c1cc(C#CC2CC2)ccc1C] | 360.1 | $^1$HNMR (400 MHz, DMSO-$d_6$) δ 8.78 (d, J = 4.8 Hz, 2H), 8.02 (s, 1H), 7.43-7.48 (m, 2H), 7.19 (dd, J = 1.2 Hz, 8.0 Hz, 1H), 7.12 (d, J = 8.0 Hz, 1H), 5.81 (s, 2H), 5.63 (s, 1H), 3.29 (s, 3H), 2.23 (s, 3H), 1.50-1.55 (m, 1H), 0.84-0.89 (m, 2H), 0.70-0.74 (m, 2H). | 34 |
| I-640 | 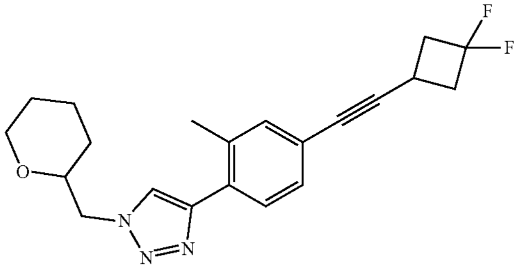 [SMILES: Cc1cc(C#CC2CC(F)(F)C2)ccc1-c1cn(CC2CCCCO2)nn1] | 372.0 | $^1$HNMR (400 MHz, DMSO-$d_6$) δ 8.36 (s, 1H), 7.78 (d, J = 8.0 Hz, 1H), 7.38 (s, 1H), 7.32 (dd, J = 1.6 Hz, 8.0 Hz, 1H), 4.38-4.50 (m, 2H), 3.84-3.87 (m, 1H), 3.74-3.75 (m, 1H), 3.25-3.35 (m, 2H), 3.02-3.08 (m, 2H), 2.67-2.76 (m, 2H), 2.43 (s, 3H), 1.77-1.79 (m, 1H) , 1.63-1.66 (m, 1H), 1.43-1.51 (m, 3H) , 1.19-1.23 (m, 1H). | 2 |
| I-648 | 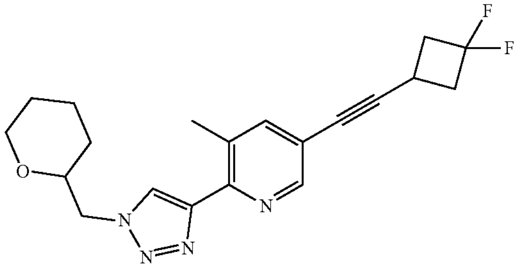 [SMILES: Cc1cc(C#CC2CC(F)(F)C2)cnc1-c1cn(CC2CCCCO2)nn1] | 373.0 | $^1$HNMR (400 MHz, DMSO-$d_6$) δ 8.49 (s, 2H), 7.80 (d, J = 1.2 Hz, 1H), 4.40-4.53 (m, 2H), 3.72-3.87 (m, 2H), 3.29-3.32 (m, 2H), 3.01-3.13 (m, 2H), 2.70-2.83 (m, 2H), 2.64 (s, 3H), 1.78-1.81 (m, 1H), 1.63-1.66 (m, 1H), 1.40-1.51 (m, 3H), 1.19-1.26 (m, 1H). | 4 |
| I-649 | 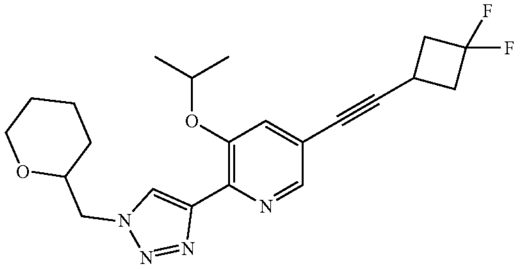 [SMILES: CC(C)Oc1cc(C#CC2CC(F)(F)C2)cnc1-c1cn(CC2CCCCO2)nn1] | 417.0 | $^1$HNMR (400 MHz, DMSO-$d_6$) δ 8.42 (s, 1H), 8.27 (d, J = 1.6 Hz, 1H), 7.62 (d, J = 1.6 Hz, 1H), 4.82-4.88 (m, 1H), 4.42-4.55 (m, 2H), 3.85-3.88 (m, 1H), 3.68-3.73 (m, 1H), 3.29-3.34 (m, 2H), 3.01-3.13 (m, 2H), 2.73-2.86 (m, 2H), 1.78-1.80 (m, 1H), 1.64 (d, J = 13.2 Hz, 1H), 1.39-1.52 (m, 3H), 1.34 (dd, J = 2.0 Hz, 6.0 Hz 6H), 1.16-1.25 (m, 1H). | 3 |

TABLE 23-continued

| Compound No. | Chemical Structure | M + 1 | $^1$H NMR (400 MHz) | Example of Synthesis |
|---|---|---|---|---|
| I-650 | 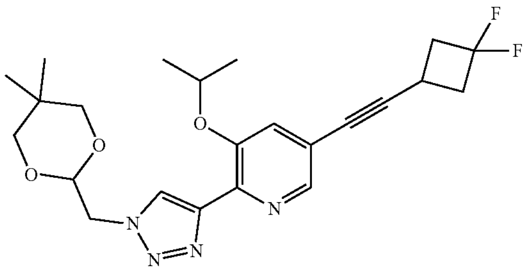 [SMILES: CC(C)Oc1cc(C#CC2CC(F)(F)C2)cnc1-c1cn(CC2OCC(C)(C)CO2)nn1] | 447.0 | $^1$HNMR (400 MHz, DMSO-$d_6$) δ 8.47 (s, 1H), 8.27 (d, J = 1.2 Hz, 1H), 7.62 (d, J = 1.2 Hz, 1H), 4.84-4.91 (m, 2H), 4.63 (d, J = 4.0 Hz, 2H), 3.56 (d, J = 10.8 Hz, 2H), 3.48 (d, J = 10.4 Hz, 2H), 3.29-3.33 (m, 1H), 3.01-3.13 (m, 2H), 2.73-2.86 (m, 2H), 1.34 (d, J = 6.0 Hz, 6H), 1.02 (s, 3H), 0.68 (s, 3H). | 3 |
| I-659 | 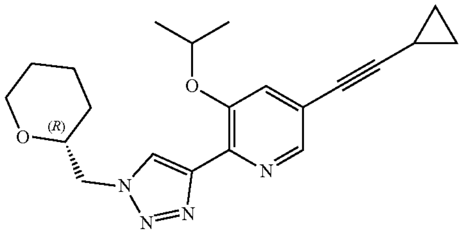 | 367.1 | $^1$HNMR (400 MHz, DMSO-$d_6$) δ 8.40 (s, 1H), 8.21 (s, 1H), 7.55 (s, 1H), 4.81-4.87 (m, 1H), 4.42-4.54 (m, 2H), 3.85-3.88 (m, 1H), 3.68-3.73 (m, 1H), 3.31-3.35 (m, 1H), 1.77-1.80 (m, 1H), 1.58-1.65 (m, 2H), 1.39-1.52 (m, 3H), 1.32-1.34 (m, 6H), 1.14-1.23 (m, 1H), 0.91-0.96 (m, 2H), 0.78-0.82 (m, 2H). | 3 |
| I-651 | 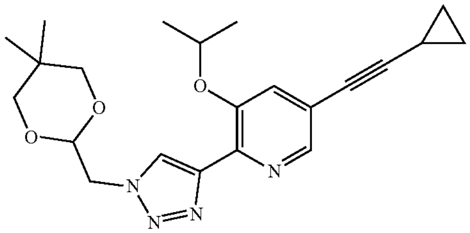 [SMILES: CC(C)Oc1cc(C#CC2CC2)cnc1-c1cn(CC2OCC(C)(C)CO2)nn1] | 397.1 | $^1$HNMR (400 MHz, DMSO-$d_6$) δ 8.45 (s, 1H), 8.21 (d, J = 1.6 Hz, 1H), 7.55 (d, J = 1.6 Hz, 1H), 4.82-4.91 (m, 2H), 4.62 (d, J = 4.0 Hz, 2H), 3.56 (d, , I = 10.8 Hz, 2H), 3.48 (d, J = 10.8 Hz, 2H), 1.57-1.63 (m, 1H), 1.33 (d, J = 6.0 Hz, 6H), 1.02 (s, 3H), 0.91-0.96 (m, 2H), 0.78-0.82 (m, 2H), 0.68 (s, 3H). | 3 |
| I-701 | 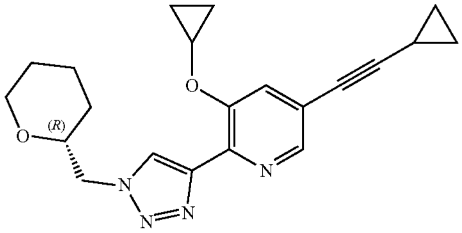 | 365.2 | $^1$HNMR (400 MHz, DMSO-$d_6$) δ: 8.32 (s, 1H), 8.27 (d, J = 1.6 Hz, 1H), 7.75 (d, J = 1.6 Hz, 1H), 4.40-4.52 (m, 2H), 4.08-4.11 (m, 1H), 3.84-3.87 (m, 1H), 3.68-3.73 (m, 1H), 3.28-3.32 (m, 1H), 1.77-1.80 (m, 1H), 1.59-1 .66 (m, 2H), 1.42-1.51 (m, 3H), 1.17-1.23 (m, 1H) , 0.76-0.96 (m, 8H). | 2 |
| I-660 | 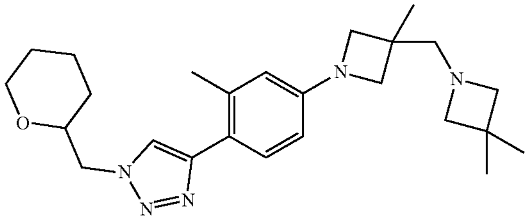 [SMILES: Cc1cc(N2CC(C)(CN3CC(C)(C)C3)C2)ccc1-c1cn(CC2CCCCO2)nn1] | 424.3 | $^1$HNMR (400 MHz, DMSO-$d_6$) δ 8.09 (s, 1H), 7.51 (d, J = 8.0 Hz, 1H), 6.29-6.32 (m, 2H), 4.33-4.44 (m, 2H), 3.84-3.87 (m, 1H), 3.71-3.75 (m, 1H), 3.56 (d, J = 6.8 Hz, 2H), 4.43 (d, J = 7.2 Hz, 2H), 3.28-3.33 (m, 1H), 2.94 (s, 4H), 2.54 (s, 2H), 2.33 (s, 3H), 1.78-1.81 (m, 1H), 1.60-1.64 (m, 1H), 1.43-1.50 (m, 3H), 1.25 (s, 3H), 1.18-1.21 (m, 1H), 1.15 (s, 6H). | 22 |
| I-739 | 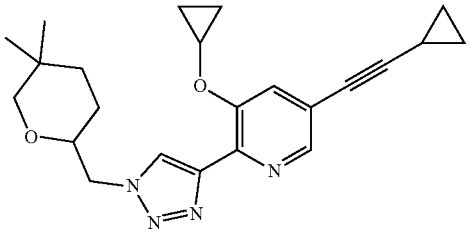 [SMILES: CC1(C)CCC(Cn2cc(-c3ncc(C#CC4CC4)cc3OC3CC3)nn2)OC1] | 393.3 | $^1$HNMR (400 MHz, DMSO-$d_6$) δ 8.34 (s, 1H), 8.26 (s, 1H), 7.75 (s, 1H), 4.50-4.52 (m, 2H), 4.09-4.11 (m, 1H), 3.65 (s, 1H), 3.34-3.38 (m, 1H), 3.08 (d, J = 11.2 Hz, 1H), 1.61-1.62 (m, 1H), 1.46-1.48 (m, 2H), 1.34-1.41 (m, 2H), 0.77-0.95 (m, 14H). | 4 |

TABLE 23-continued

Characterization data for exemplary compounds

| Compound No. | Chemical Structure | M + 1 | $^1$H NMR (400 MHz) | Example of Synthesis |
|---|---|---|---|---|
| I-673 | 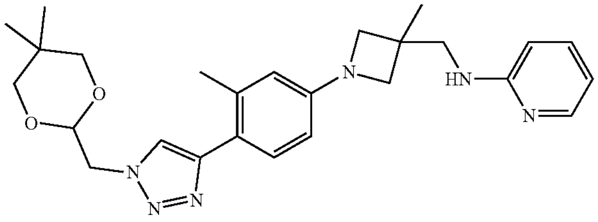 [SMILES: Cc1cc(N2CC(C)(CNc3ccccn3)C2)ccc1-c1cn(CC2OCC(C)(C)CO2)nn1] | 463.1 | $^1$HNMR (400 MHz, $CDCl_3$) δ 8.06 (d, J = 4.4 Hz, 1H), 7.68 (s, 1H), 7.63 (d, J = 8.0 Hz, 1H), 7.41-7.45 (m, 1H), 6.56-6.59 (m, 1H), 6.46 (d, J = 8.4 Hz, 1H), 6.37 (dd, J = 2.4 Hz, 8.4 Hz, 1H), 6.32 (d, J = 2.0 Hz, 1H), 5.04-5.12(m, 1H), 4.79 (t, J = 4.8 Hz, 1H), 4.54 (d, J = 4.4 Hz, 2H), 3.83 (d, J = 6.8 Hz, 2H), 3.58-3.64 (m, 4H), 3.52 (d, J = 5.6 Hz, 2H), 3.43 (d, J = 10.8 Hz, 2H), 2.40 (s, 3H), 1.39 (s, 3H), 1.15 (s, 3H), 0.72 (s, 3H). | 22 |
| I-675 | 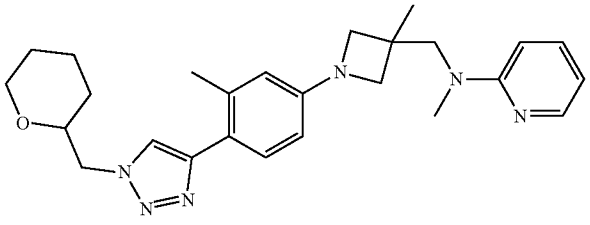 [SMILES: Cc1cc(N2CC(C)(CN(C)c3ccccn3)C2)ccc1-c1cn(CC2CCCCO2)nn1] | 447.3 | $^1$HNMR (400 MHz, $CDCl_3$) δ 8.13-8.14 (m, 1H), 7.68 (s, 1H), 7.63-7.66 (m, 1H), 7.42-7.46 (m, 1H), 6.50-6.56 (m, 2H), 6.37 (dd, , I = 2.0 Hz, 8.0 Hz, 1H), 6.32 (d, J = 2.0 Hz, 1H), 4.48 (dd, J = 3.2 Hz, 14.0 Hz, 1H), 4.32 (dd, J = 7.2 Hz, 14.0 Hz, 1H), 3.97-4.00 (m, 1H), 3.82-3.83 (m, 3H), 3.67-3.73 (m, 1H), 3.60 (d, J = 6.8 Hz, 2H), 3.37-3.43 (m, 1H), 3.16-3.27 (m, 1H), 3.06 (s, 3H), 2.41 (s, 3H), 1.87-1.88 (m, 2H), 1.65-1.68 (m, 1H), 1.50-1.56 (m, 2H), 1.37 (s, 3H), 1.24-1.28 (m, 1H). | 22 |
| I-652 | 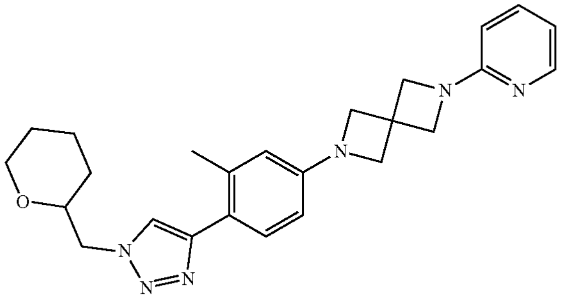 [SMILES: Cc1cc(N2CC3(C2)CN(c2ccccn2)C3)ccc1-c1cn(CC2CCCCO2)nn1] | 431.2 | $^1$HNMR (400 MHz, DMSO-$d_6$) δ 8.11 (s, 1H), 8.07 (d, J = 4.0 Hz, 1H), 7.49-7.57 (m, 2H), 6.65 (dd, J = 5.2 Hz, 6.4 Hz, 1H), 6.36-6.41 (m, 3H), 4.34-4.45 (m, 2H), 4.11 (s, 4H), 4.01 (s, 4H), 3.84-3.87 (m, 1H), 3.71-3.76 (m, 1H), 3.29-3.32 (m, 1H), 2.36 (s, 3H), 1.78-1.81 (m, 1H), 1.62 (d, J = 12.4 Hz, 1H), 1.39-1.54 (m, 3H), 1.15-1.24 (m, 1H). | 5 |
| I-629 | 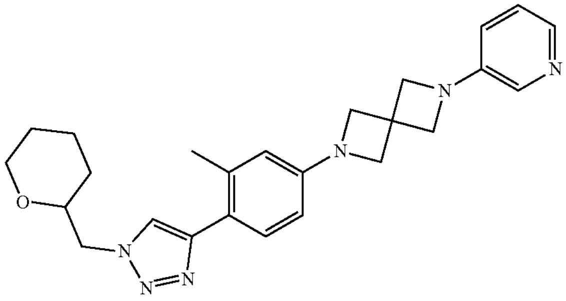 [SMILES: Cc1cc(N2CC3(CN(c4cccnc4)C3)C2)ccc1-c1cn(CC2CCCCO2)nn1] | 431.2 | $^1$HNMR (400 MHz, DMSO-$d_6$) δ 8.11 (s, 1H), 7.94 (d, J = 4.0 Hz, 1H), 7.85 (d, J = 2.4 Hz, 1H), 7.55 (d, J = 8.0 Hz, 1H), 7.18 (dd, J = 8.0 Hz, 4.8 Hz, 1H), 6.85 (dd, J = 8.0 Hz, 1.2 Hz, 1H), 6.37-6.39 (m, 2H), 4.34-4.45 (m, 2H), 4.07 (s, 4H), 4.02 (s, 4H), 3.84-3.87 (m, 1H), 3.72-3.74 (m, 1H), 3.29-3.32 (m, 1H), 2.36 (s, 3H), 1.78-1.81 (m, 1H), 1.63 (d, J = 12.4 Hz, 1H), 1.40-1.53 (m, 3H), 1.15-1.24 (m, 1H). | 5 |
| I-630 | 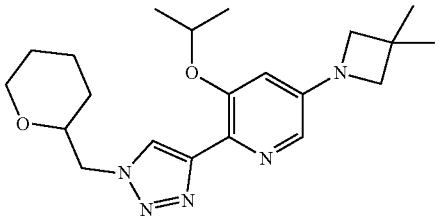 [SMILES: CC(C)Oc1cc(N2CC(C)(C)C2)cnc1-c1cn(CC2CCCCO2)nn1] | 386.1 | $^1$HNMR (400 MHz, DMSO-$d_6$) δ 8.17 (s, 1H), 7.47 (d, J = 2.4 Hz, 1H), 6.48 (d, J = 2.0 Hz, 1H), 4.71-4.77 (m, 1H), 4.36-4.49 (m, 2H), 3.85-3.88 (m, 1H), 3.67-3.72 (m, 1H), 3.63 (s, 4H), 3.31-3.33 (m, 1H), 1.77-1.80 (m, 1H), 1.61-1.64 (m, 1H), 1.41-1.54 (m, 3H), 1.31-1.32 (m, 12H), 1.16-1.20 (m, 1H). | 5 |

TABLE 23-continued

Characterization data for exemplary compounds

| Compound No. | Chemical Structure | M + 1 | $^1$H NMR (400 MHz) | Example of Synthesis |
|---|---|---|---|---|
| I-726 | 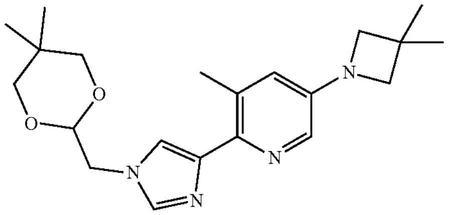 | 371.3 | $^1$HNMR (400 MHz, DMSO-$d_6$) δ 7.60 (d, J = 2.8 Hz, 1H), 7.58 (d, J = 1.2 Hz, 1H), 7.43 (d, J = 1.2 Hz, 1H), 6.60 (d, J = 2.0 Hz, 1H), 4.73 (t, J = 4.4 Hz, 1H), 4.12 (d, J = 4.4 Hz, 2H), 3.55-3.58 (m, 6H), 3.44 (d, J = 10.8 Hz, 2H), 2.52 (s, 3H), 1.29 (s, 6H), 1.05 (s, 3H), 0.67 (s, 3H). | 23 |
| I-661 | 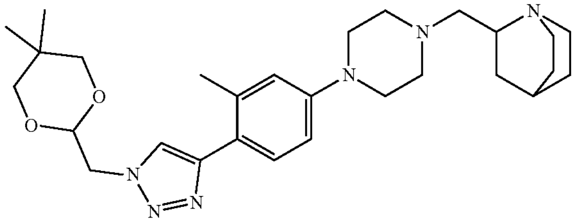 [SMILES: Cc1cc(N2CCN(CC3CC4CCN3CC4)CC2)ccc1-c1cn(CC2OCC(C)(C)CO2)nn1] | 495.2 | $^1$HNMR (400 MHz, DMSO-$d_6$) δ 8.15 (s, 1H), 7.56 (dd, J = 6.0 Hz, 3.2 Hz, 1H), 6.82-6.84 (m, 2H), 4.91 (t, J = 4.4 Hz, 1H), 4.53 (d, J = 4.4 Hz, 2H), 3.57(d, J = 10.8 Hz, 2H), 3.46 (d, J = 10.8 Hz, 2H), 3.11-3.18 (m, 4H), 2.85-3.01 (m, 2H), 2.76-2.83 (m, 2H), 2.55-2.66 (m, 3H), 2.31-2.50 (m, 7H), 1.62-1.71 (m, 2H), 1.39-1.47 (m, 4H), 1.04-1.11 (m, 4H), 0.68 (s, 3H). | 5 |
| I-715 | 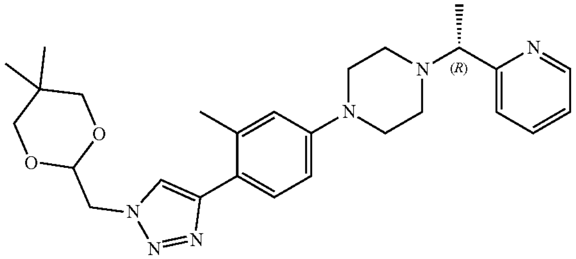 | 477.2 | $^1$HNMR (400 MHz, DMSO-$d_6$) δ 8.52 (dd, J = 0.8 Hz, 4.8 Hz, 1H), 8.15 (s, 1H), 7.77 (dt, J = 2.0 Hz, 7.6 Hz, 1H), 7.54-7.56 (m, 1H), 7.45 (d, J = 7.6 Hz, 1H), 7.25-7.28 (m, 1H), 6.80-6.82 (m, 2H), 4.91 (t, J = 4.0 Hz, 1H), 4.53 (d, J = 4.4 Hz, 2H), 3.66 (q, J = 6.8 Hz, 1H), 3.56 (d, J = 10.8 Hz, 2H), 3.46 (d, J = 10.4 Hz, 2H), 3.16 (t, J = 4.8 Hz, 4H), 2.57-2.63 (m, 2H), 2.46-2.50 (m, 2H), 2.36 (s, 3H), 1.36 (d, J = 6.8 Hz, 3H), 1.04 (s, 3H), 0.68 (s, 3H). | 5 |
| I-716 | 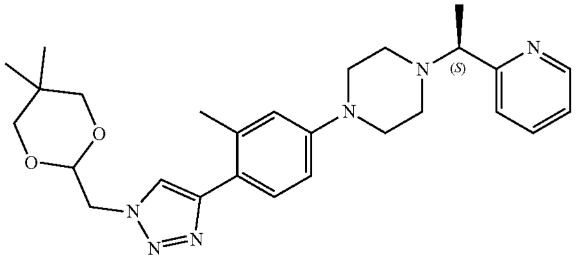 | 477.2 | $^1$HNMR (400 MHz, DMSO-$d_6$) δ 8.52 (d, J = 4.0 Hz, 1H), 8.15 (s, 1H), 7.75-7.79 (m, 1H), 7.54-7.57 (m, 1H), 7.45 (d, J = 7.6 Hz, 1H), 7.26 (dd, J = 5.2 Hz, 6.8 Hz, 1H), 6.81 (d, J = 2.4 Hz, 0 2H), 4.91 (t, J = 4.4 Hz, 1H), 4.54 (d, J = 4.0 Hz, 2H), 3.65 (q, J = 6.8 Hz, 1H), 3.57 (d, J = 11.2 Hz, 2H), 3.46 (d, J = 10.8 Hz, 2H), 3.15-3.17 (m, 4H), 2.58-2.62 (m, 2H), 2.47-2.50 (m, 2H), 2.36 (s, 3H), 1.36 (d, J = 6.8 Hz, 3H), 1.04 (s, 3H), 0.68 (s, 3H). | 5 |
| I-689 | 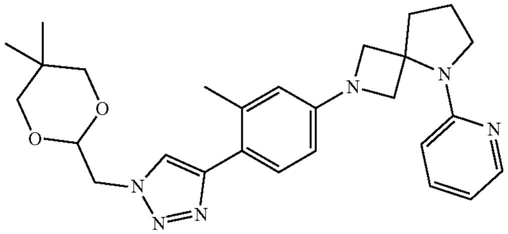 [SMILES: Cc1cc(N2CC3(CCCN3c3ccccn3)C2)ccc1-c1cn(CC2OCC(C)(C)CO2)nn1] | 475.1 | $^1$HNMR (400 MHz, DMSO-$d_6$) δ 8.13 (s, 1H), 7.91 (dd, J = 1.2 Hz, 4.8 Hz, 1H), 7.55 (d, J = 8.4 Hz, 1H), 7.47-7.51 (m, 1H), 6.68 (d, J = 8.8 Hz, 1H), 6.53-6.56 (m, 1H), 6.36-6.39 (m, 2H), 4.91 (t, J = 4.4 Hz, 1H), 4.75 (d, J = 7.2 Hz, 2H), 4.54 (d, J = 4.0 Hz, 2H), 3.73 (d, J = 6.8 Hz, 2H), 3.58 (d, J = 10.8 Hz, 2H), 3.41-3.48 (m, 4H), 2.35-2.38 (m, 5H), 1.85-1.92 (m, 2H), 1.06 (s, 3H), 0.69 (s, 3H). | 5 |

TABLE 23-continued

Characterization data for exemplary compounds

| Compound No. | Chemical Structure | M + 1 | $^1$H NMR (400 MHz) | Example of Synthesis |
|---|---|---|---|---|
| I-682 | 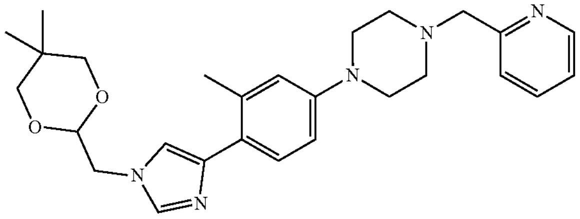 [SMILES: Cc1cc(N2CCN(Cc3ccccn3)CC2)ccc1-c1cn(CC2OCC(C)(C)CO2)cn1] | 462.0 | $^1$HNMR (400 MHz, DMSO-$d_6$) δ 8.51 (dd, J = 0.8 Hz, 4.8 Hz, 1H), 7.77 (dt, J = 1.6 Hz, 7.6 Hz, 1H), 7.63 (d, J = 9.2 Hz, 1H), 7.60 (d, J = 0.8 Hz, 1H), 7.47 (d, J = 7.6 Hz, 1H), 7.23-7.28 (m, 2H), 6.77-6.78 (m, 2H), 4.73 (t, J = 4.4 Hz, 1H), 4.12 (d, J = 4.4 Hz, 2H), 3.65 (s, 2H), 3.56 (d, J = 10.8 Hz, 2H), 3.43 (d, J = 10.8 Hz, 2H), 3.13-3.19 (m, 4H), 2.57 (t, J = 4.8 Hz, 4H), 2.37 (s, 3H), 1.05 (s, 3H), 0.67 (s, 3H). | 33 |
| I-683 | 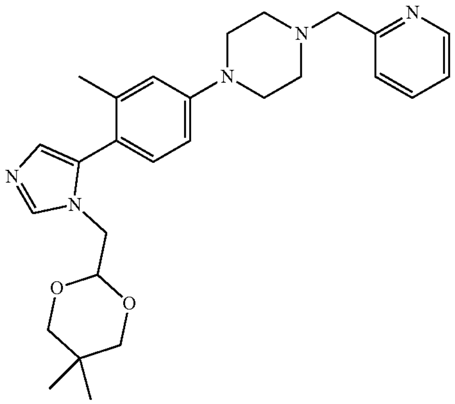 [SMILES: Cc1cc(N2CCN(Cc3ccccn3)CC2)ccc1-c1cncn1CC1OCC(C)(C)CO1] | 462.0 | $^1$HNMR (400 MHz, DMSO-$d_6$) δ 8.51 (d, J = 4.0 Hz, 1H), 7.78 (dt, J1.6 Hz, 7.6 Hz, 1H), 7.65 (s, 1H), 7.48 (d, J = 7.6 Hz, 1H), 7.28 (dd, J = 5.2 Hz, 6.8 Hz, 1H), 7.03 (d, J = 8.4 Hz, 1H), 6.88 (d, J = 2.0 Hz, 1H), 6.80 (dd, J = 2.4 Hz, 8.8 Hz, 1H), 6.74 (s, 1H), 4.41 (t, J = 4.4 Hz, 1H), 3.82 (d, J = 4.4 Hz, 2H), 3.66 (s, 2H), 3.48 (d, J = 11.2 Hz, 2H), 3.29 (d, J = 11.8 Hz, 2H), 3.17-3.21 (m, 4H), 2.57 (t, J = 4.4 Hz, 4H), 2.05 (s, 3H), 1.00 (s, 3H), 0.63 (s, 3H). | 33 |
| I-662 | 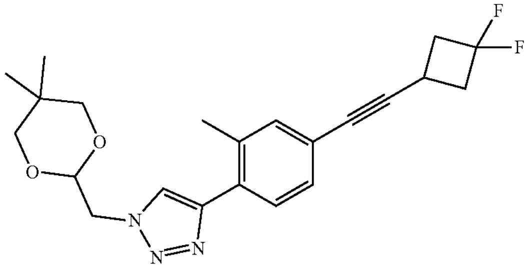 | 402.0 | $^1$HNMR (400 MHz, DMSO-$d_6$) δ 8.38 (s, 1H), 7.77 (d, J = 7.6 Hz, 1H), 7.38 (s, 1H), 7.33 (d, J = 8.0 Hz, 1H), 4.92 (t, J = 4.0 Hz, 1H), 4.58 (d, J = 4.4 Hz, 2H), 3.57 (d, J = 11.2 Hz, 2H), 3.46 (d, J = 10.8 Hz, 2H), 3.25-3.30(m, 1H), 3.02-3.08 (m, 2H), 2.70-2.75 (m, 2H), 2.42 (s, 3H), 1.04 (s, 3H), 0.68 (s, 3H). | 2 |
| I-653 | 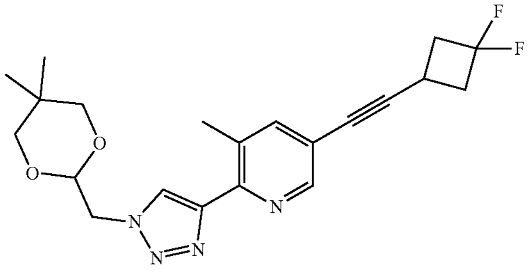 [SMILES: Cc1cc(C#CC2CC(F)(F)C2)ccc1-c1cn(CC2OCC(C)(C)CO2)nn1] | 403.2 | $^1$HNMR (400 MHz, DMSO-$d_6$) δ: 8.49-8.51 (m, 2H), 7.80 (s, 1H), 4.92 (t, J = 4.4 Hz, 1H), 4.60 (d, J = 4.4 Hz, 2H), 3.57(d, J = 11.2 Hz, 2H), 3.46 (d, J = 10.8 Hz, 2H), 3.30-3.33 (m, 1H), 3.03-3.10 (m, 2H), 2.73-2.79 (m, 2H), 2.64 (s, 3H), 1.03 (s, 3H), 0.68 (s, 3H). | 4 |
| I-693 | 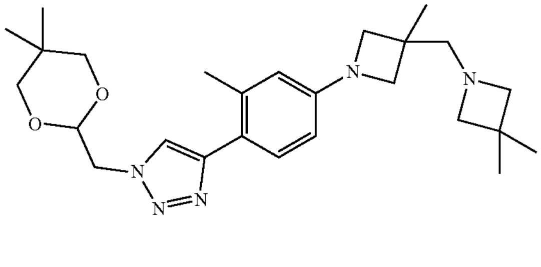 | 454.3 | $^1$HNMR (400 MHz, DMSO-$d_6$) δ 8.20 (s, 1H), 8.10 (s, 1H), 7.51 (d, J = 8.0 Hz, 1H), 6.29-6.32 (m, 2H), 4.90 (t, J = 4.4 Hz, 1H), 4.53 (d, J = 4.4 Hz, 2H), 3.57 (t, J = 6.0 Hz, 4H), 3.42-3.47 (m, 4H), 3.01 (s, 4H), 2.61 (s, 2H), 2.33(s, 3H), 1.26 (s, 3H), 1.16 (s, 6H), 1.05 (s, 3H), 0.68 (s, 3H). | 22 |

TABLE 23-continued

Characterization data for exemplary compounds

| Compound No. | Chemical Structure | M + 1 | $^1$H NMR (400 MHz) | Example of Synthesis |
|---|---|---|---|---|
| I-702 | 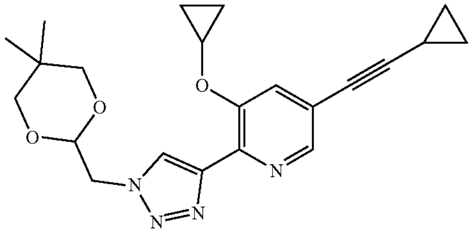 [SMILES: CC1(C)COC(Cn2cc(-c3ncc(C#CC4CC4)cc3OC3CC3)nn2)OC1] | 395.0 | $^1$HNMR (400 MHz, DMSO-$d_6$) δ 8.37 (s, 1H), 8.26 (d, J = 1.2 Hz, 1H), 7.75 (d, J = 1.6 Hz, 1H), 4.90 (t, J = 4.0 Hz, 1H), 4.60 (d, J = 4.0 Hz, 2H), 4.09-4.12 (m, 1H), 3.56 (d, J = 10.8 Hz, 2H), 3.47 (d, J = 11.2 Hz, 2H), 1.60-1.64 (m, 1H), 1.03 (s, 3H), 0.90-0.96 (m, 2H), 0.77-0.88 (m, 6H) , 0.68 (s, 3H). | 28 |
| I-663 | 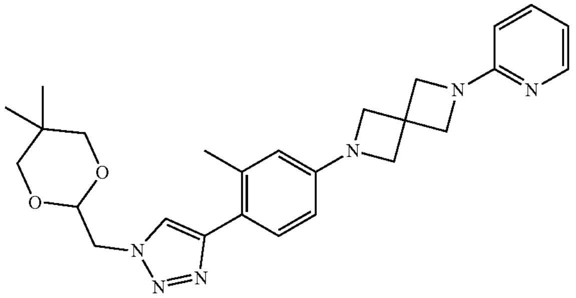 [SMILES: Cc1cc(N2CC3(C2)CN(c2ccccn2)C3)ccc1-c1cn(CC2OCC(C)(C)CO2)nn1] | 461.2 | $^1$HNMR (400 MHz, DMSO-$d_6$) δ 8.13 (s, 1H), 8.07 (dd, J = 5.2 Hz, 1.2 Hz, 1H), 7.49-7.56 (m, 2H), 6.64 (dd, , I = 7.2 Hz, 5.6 Hz, 1H), 6.36-6.41 (m, 3H), 4.91 (t, J = 4.4 Hz, 1H), 4.53 (d, J = 4.0 Hz, 2H), 4.11 (s, 4H), 4.02 (s, 4H), 3.57 (d, J = 10.8 Hz, 2H), 3.46 (d, J = 10.8 Hz, 2H), 2.35 (s, 3H), 1.05 (s, 3H), 0.68 (s, 3H). | 5 |
| I-684 | 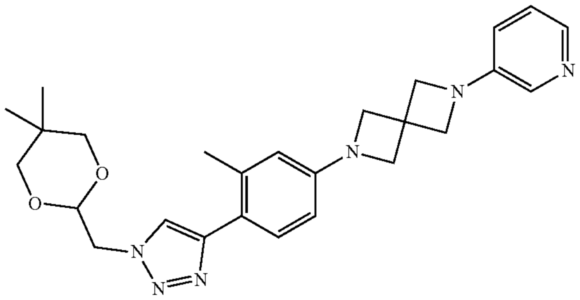 [SMILES: Cc1cc(N2CC3(CN(c4cccnc4)C3)C2)ccc1-c1cn(CC2OCC(C)(C)CO2)nn1] | 461.2 | $^1$HNMR (400 MHz, DMSO-$d_6$) δ 8.13 (s, 1H), 7.93-7.94 (m, 1H), 7.85 (d, J = 2.4 Hz, 1H), 7.55 (d, J = 8.0 Hz, 1H), 7.17 (dd, J = 4.8 Hz, 8.0 Hz, 1H), 6.84-6.87 (m, 1H), 6.37-6.39 (m, 2H), 4.91 (t, J = 4.4 Hz, 1H), 4.53 (d, J = 4.4 Hz, 2H), 4.06 (s, 4H), 4.02 (s, 4H), 3.57 (d, J = 11.2 Hz, 2H), 3.46 (d, J = 10.8 Hz, 2H), 2.35 (s, 3H), 1.05 (s, 3H), 0.68 (s, 3H). | 5 |
| I-664 | 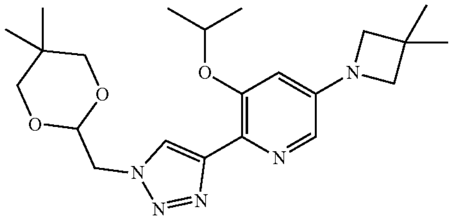 | 416.2 | $^1$HNMR (400 MHz, DMSO-$d_6$) δ 8.22 (s, 1H), 7.47 (s, 1H), 6.48 (d, J = 2.0 Hz, 1H), 4.88 (t, J = 4.0 Hz, 1H), 4.73-4.79 (m, 1H), 4.56 (d, J = 4.0 Hz, 2H), 3.63 (s, 4H), 3.56 (d, J 10.8 Hz, 2H), 3.47 (d, J = 10.8 Hz, 2H), 1.30-1.32 (m, 12H), 1.04 (s, 3H), 0.68 (s, 3H). | 5 |
| I-685 | 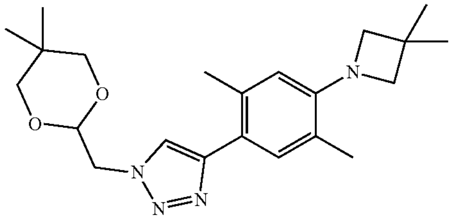 | 385.2 | $^1$HNMR (400 MHz, $CDCl_3$) δ 7.62 (s, 1H), 7.41 (s, 1H), 6.22 (s, 1H), 4.72 (t, J = 4.4 Hz, 1H), 4.47 (d, J = 4.4 Hz, 2H), 3.55-3.59 (m, 6H), 3.37 (d, J = 11.2 Hz, 2H), 2.32 (s, 3H), 2.15 (s, 3H), 1.25 (s, 6H), 1.09 (s, 3H), 0.65 (s, 3H). | 27 |

TABLE 23-continued

| Characterization data for exemplary compounds | | | | |
|---|---|---|---|---|
| Compound No. | Chemical Structure | M + 1 | $^1$H NMR (400 MHz) | Example of Synthesis |
| I-654 | 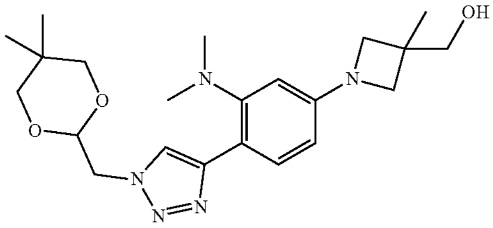 [SMILES: CN(C)c1cc(N2CC(C)(CO)C2)ccc1-c1cn(CC2OCC(C)(C)CO2)nn1] | 416.1 | $^1$HNMR (400 MHz, DMSO-$d_6$) δ 8.20 (s, 1H), 7.81 (d, J = 8.0 Hz, 1H), 6.15 (d, J = 8.8 Hz, 2H), 4.85-4.89 (m, 2H), 4.53 (d, J = 4.0 Hz, 2H), 3.68 (d, J = 6.8 Hz, 2H), 3.56 (d, J = 10.8 Hz, 2H), 3.41-3.47 (m, 6H), 2.55 (s, 6H), 1.25 (s, 3H), 1.04 (s, 3H), 0.67 (s, 3H). | 22 |
| I-665 | 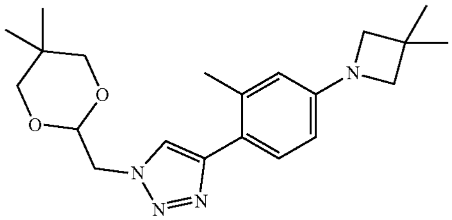 | 357.1 | $^1$HNMR (400 MHz, DMSO-$d_6$) δ 8.10 (s, 1H), 7.51 (d, J = 8.0 Hz, 1H), 6.30-6.33 (m, 2H), 4.90 (t, J = 4.4 Hz, 1H), 4.53 (d, J = 4.4 Hz, 2H), 3.57 (d, J = 11.2 Hz, 2H), 3.53 (s, 4H), 3.46 (d, J = 10.8 Hz, 2H), 2.34 (s, 3H), 1.28 (s, 6H), 1.05 (s, 3H), 0.68 (s, 3H). | 5 |
| I-676 | 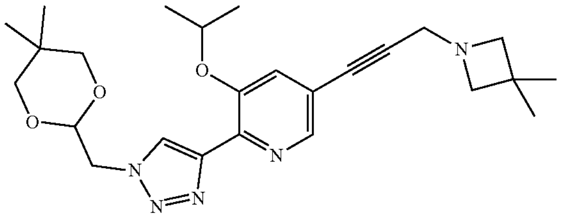 | 454.1 | $^1$HNMR (400 MHz, DMSO-$d_6$) δ 8.48 (s, 1H), 8.30 (d, J = 1.6 Hz, 1H), 7.62 (d, J = 1.2 Hz, 1H), 4.87-4.92 (m, 2H), 4.63 (d, J = 4.0 Hz, 2H), 3.55-3.58 (m, 2H), 3.47-3.50 (m, 4H), 3.03 (s, 4H), 1.35 (d, J = 6.0 Hz, 6H), 1.19 (s, 6H), 1.02 (s, 3H), 0.68 (s, 3H). | 28 |
| I-666 | 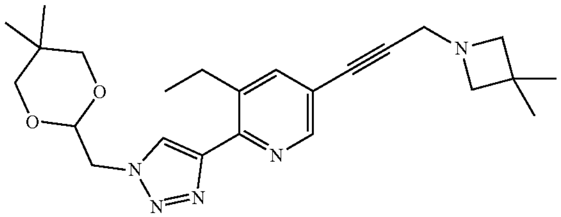 | 424.0 | $^1$HNMR (400 MHz, DMSO-$d_6$) δ 8.52 (d, J = 2.0 Hz, 1H), 8.48 (s, 1H), 7.82 (d, J = 2.0 Hz, 1H), 4.93 (t, J = 4.4 Hz, 1H), 4.61 (d, J = 4.4 Hz, 2H), 3.57 (d, J = 10.8 Hz, 2H), 3.45-3.48 (m, 4H), 3.10-3.15 (m, 2H), 3.02 (s, 4H), 1.16-1.20 (m, 9H), 1.03 (s, 3H), 0.68 (s, 3H). | 28 |
| I-727 | 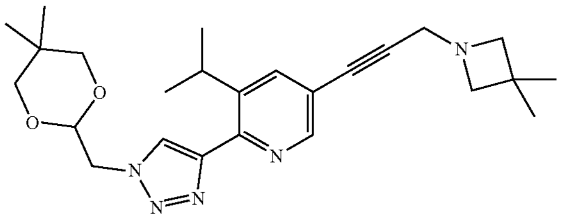 | 438.1 | $^1$HNMR (400 MHz, DMSO-$d_6$) δ 8.51 (d, J = 2.0 Hz, 1H), 8.44 (s, 1H), 7.91 (d, J = 2.0 Hz, 1H), 4.93 (t, J = 4.4 Hz, 1H), 4.61 (d, J = 4.4 Hz, 2H), 4.09-4.14 (m, 1H), 3.57 (d, J = 10.8 Hz, 2H), 3.45-3.48 (m, 4H), 3.03 (s, 4H), 1.25 (d, J = 10.4 Hz, 6H), 1.19 (s, 6H), 1.03 (s, 3H), 0.68 (s, 3H). | 28 |
| I-667 | 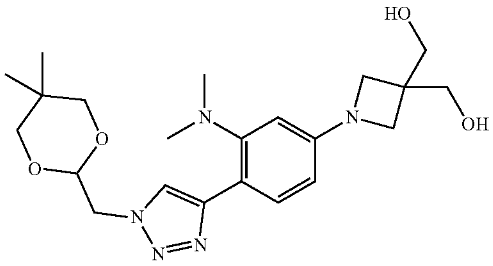 [SMILES: CN(C)c1cc(N2CC(CO)(CO)C2)ccc1-c1cn(CC2OCC(C)(C)CO2)nn1] | 432.1 | $^1$HNMR (400 MHz, DMSO-$d_6$) δ 8.20 (s, 1H), 7.80 (d, J = 8.4 Hz, 1H), 6.15-6.17 (m, 2H), 4.86 (t, J = 4.4 Hz, 1H), 4.78 (t, J = 5.2 Hz, 2H), 4.53 (d, J = 4.0 Hz, 2H), 3.56-3.57 (m, 10H), 3.45 (d, J = 10.8 Hz, 2H), 2.55 (s, 6H), 1.04 (s, 3H), 0.67 (s, 3H). | 22 |

TABLE 23-continued

Characterization data for exemplary compounds

| Compound No. | Chemical Structure | M + 1 | $^1H$ NMR (400 MHz) | Example of Synthesis |
|---|---|---|---|---|
| I-744 | 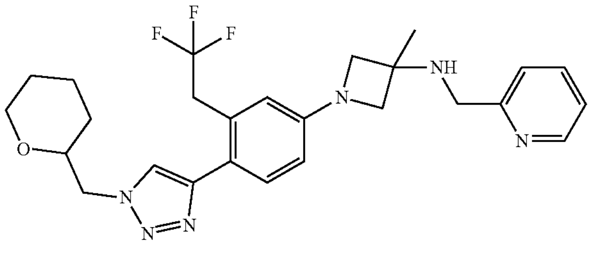 [SMILES: CC1(NCc2ccccn2)CN(c2ccc(-c3cn(CC4CCCCO4)nn3)c(CC(F)(F)F)c2)C1] | 501.0 | $^1HNMR$ (400 MHz, DMSO-$d_6$) δ 8.48 (d, J = 4.0 Hz, 1H), 8.15 (s, 1H), 7.73-7.76 (m, 1H), 7.45 (d, J = 6.4 Hz, 1H), 7.38 (d, J = 8.0 Hz, 1H), 7.23-7.26 (m, 1H), 6.46-6.49 (m, 2H), 4.35-4.46 (m, 2H), 3.94-4.02 (m, 2H), 3.83-3.87 (m, 3H), 3.66-3.78 (m, 5H), 3.24-3.30 (m, 1H), 2.89 (br., 1H), 1.77-1.80 (m, 1H), 1.59-1.62 (m, 1H), 1.29-1.53 (m, 6H), 1.15-1.21 (m, 1H). | 5 |
| I-745 | 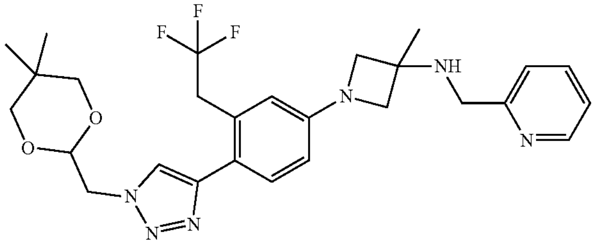 [SMILES: CC1(C)COC(Cn2cc(-c3ccc(N4CC(C)(NCc5ccccn5)C4)cc3CC(F)(F)F)nn2)OC1] | 531.0 | $^1HNMR$ (400 MHz, DMSO-$d_6$) δ 8.48 (d, J = 4.4 Hz, 1H), 8.15 (s, 1H), 7.72-7.76 (m, 1H), 7.47 (d, J = 7.6 Hz, 1H), 7.36 (d, J = 8.4 Hz, 1H), 7.22-7.26 (m, 1H), 6.46-6.50 (m, 2H), 4.89 (t, J = 4.0 Hz, 1H), 4.54 (d, J = 4.0 Hz, 2H), 4.01 (q, J = 11.6 Hz, 2H), 3.83 (s, 2H), 3.64-3.68 (m, 4H), 3.56 (d, J = 10.8 Hz, 2H), 3.46 (d, J = 10.8 Hz, 2H), 2.88 (s, 1H), 1.48 (s, 3H), 1.02 (s, 3H), 0.67 (s, 3H). | 5 |
| I-740 | 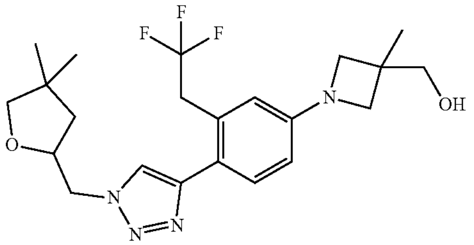 [SMILES: CC1(C)COC(Cn2cc(-c3ccc(N4CC(C)(CO)C4)cc3CC(F)(F)F)nn2)C1] | 439.0 | $^1HNMR$ (400 MHz, DMSO-$d_6$) δ 8.17 (s, 1H), 7.35 (d, J = 8.0 Hz, 1H), 6.44-6.47 (m, 2H), 4.91 (s, 1H), 4.37-4.55 (m, 3H), 3.96-4.11 (m, 2H), 3.70 (d, J = 7.2 Hz, 2H), 3.44 (d, J = 6.4 Hz, 4H), 3.32-3.39 (m, 2H), 1.79 (dd, J = 6.8 Hz, 12.4 Hz, 1H), 1.42 (dd, J = 8.8 Hz, 12.4 Hz, 1H), 1.26 (s, 3H), 1.03 (s, 3H), 0.97 (s, 3H). | 22 |
| I-735 | 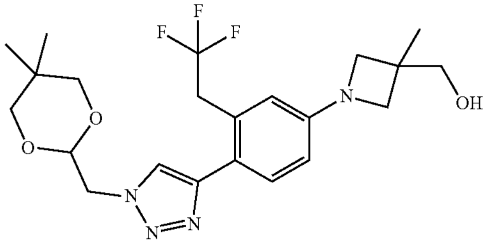 [SMILES: CC1(C)COC(Cn2cc(-c3ccc(N4CC(C)(CO)C4)cc3CC(F)(F)F)nn2)OC1] | 455.0 | $^1HNMR$ (400 MHz, DMSO-$d_6$) δ 8.15 (s, 1H), 7.35 (d, J = 8.4 Hz, 1H), 6.43-6.48 (m, 2H), 4.88-4.92 (m, 2H), 4.54 (d, J = 4.0 Hz, 2H), 4.00 (q, J = 11.6 Hz, 2H), 3.70 (d, J = 7.2 Hz, 2H), 3.56 (d, J = 10.8 Hz, 2H), 3.43-3.48 (m, 6H), 1.26 (s, 3H), 1.02 (s, 3H), 0.67 (s, 3H). | 22 |
| I-677 | 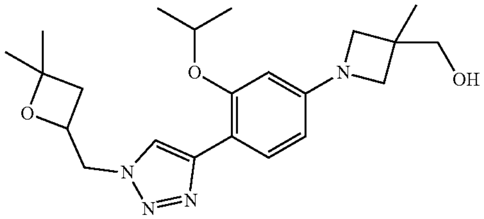 [SMILES: CC(C)Oc1cc(N2CC(C)(CO)C2)ccc1-c1cn(CC2CC(C)(C)O2)nn1] | 401.4 | $^1HNMR$ (400 MHz, DMSO-$d_6$) δ 8.10 (s, 1H), 7.91 (dd, J = 1.6 Hz, 8.0 Hz, 1H), 6.05-6.09 (m, 2H), 4.82-4.90 (m, 2H), 4.69-4.75(m, 1H), 4.58 (d, J = 4.8Hz, 2H), 3.69 (d, J = 6.8 Hz, 2H), 3.42-3.44 (m, 4H), 2.34-2.39 (m, 1H), 2.36 (dd, J = 7.6 Hz, 11.2 Hz, 1H), 2.12 (dd, J = 7.6 Hz, 10.8 Hz, 1H), 1.36 (s, 3H), 1.33 (t, J = 5.6 Hz, 6H), 1.25 (s, 3H), 1.09 (s, 3H). | 22 |

TABLE 23-continued

Characterization data for exemplary compounds

| Compound No. | Chemical Structure | M + 1 | $^1$H NMR (400 MHz) | Example of Synthesis |
|---|---|---|---|---|
| I-678 | 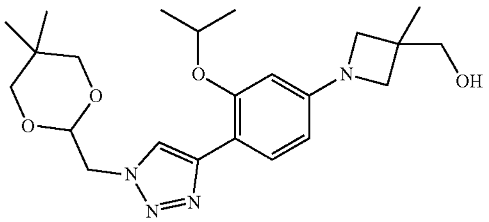 [SMILES: CC(C)Oc1cc(N2CC(C)(CO)C2)ccc1-c1cn(CC2OCC(C)(C)CO2)nn1] | 431.1 | $^1$HNMR (400 MHz, DMSO-$d_6$) δ 8.12 (s, 1H), 7.89 (d, J = 8.4 Hz, 1H), 6.05-6.08 (m, 2H), 4.86-4.90 (m, 2H), 4.68-4.74 (m, 1H), 4.54 (d, J = 4.0 Hz, 2H), 3.68 (d, J = 6.8 Hz, 2H), 3.54-3.57 (m, 2H), 3.42-3.49 (m, 6H), 1.33 (d, J = 6.0 Hz, 6H), 1.25 (s, 3H), 1.04 (s, 3H) , 0.68 (s, 3H). | 22 |
| I-746 | 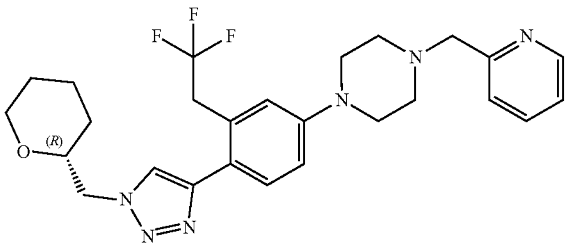 | 501.0 | $^1$HNMR (400 MHz, DMSO-$d_6$) δ 8.51 (d, J = 4.4 Hz, 1H), 8.21 (s, 1H), 7.78 (dt, J = 7.6 Hz, 2.0 Hz, 1H), 7.49 (d, J = 7.6 Hz, 1H), 7.43-7.45 (m, 1H), 7.26-4.36-4.47 (m, 2H), 4.00-4.10 (m, 2H), 3.84-3.87 (m, 1H), 3.69-3.74 (m, 1H), 3.67 (s, 2H), 3.29-3.32 (m, 1H), 3.22 (t, J = 4.8 Hz, 4H), 2.59 (t, J = 4.8 Hz, 4H), 1.77-1.80 (m, 1H), 1.59-1.63 (m, 1H), 1.38-1.51 (m, 3H), 1.15-1.21 (m, 1H). | 5 |
| I-747 | 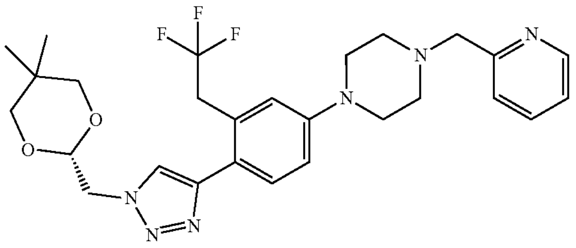 | 531.0 | $^1$HNMR (400 MHz, DMSO-$d_6$) δ 8.51 (d, J = 4.0 Hz, 1H), 8.21 (s, 1H), 7.78 (dt, J = 7.6 Hz, 2.0 Hz, 1H), 7.49 (d, J = 7.6 Hz, 1H), 7.40-7.43 (m, 1H), 7.27-7.29 (m, 1H), 6.99-7.00 (m, 2H), 4.89 (t, J = 4.4 Hz, 1H), 4.55 (d, J = 4.4 Hz, 2H), 4.04 (q, J = 11.6 Hz, 2H), 3.66 (s, 2H), 3.56 (d, J = 11.2 Hz, 2H), 3.46 (d, J = 11.2 Hz, 2H), 3.22 (t, J = 4.8 Hz, 4H), 2.59 (t, J = 4.8 Hz, 4H), 1.01 (s, 3H), 0.67 (s, 3H). | 5 |
| I-686 | 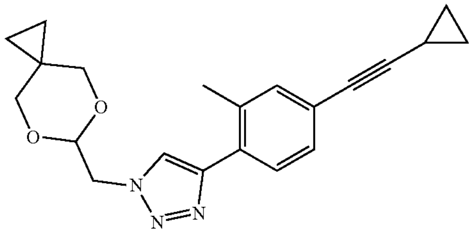 [SMILES: Cc1cc(C#CC2CC2)ccc1-c1cn(CC2OCC3(CC3)CO2)nn1] | 350.2 | $^1$HNMR (400 MHz, DMSO-$d_6$) δ 8.39 (s, 1H), 7.74 (d, J = 8.0 Hz, 1H), 7.31 (s, 1H), 7.26 (d, J = 8.0 Hz, 1H), 5.10 ( t, J = 4.8 Hz, 1H ), 4.59 (d, J = 4.8 Hz, 2H), 4.07 (d, J = 11.2 Hz, 2H), 3.25 (d, J = 11.2 Hz, 2H), 2.40 (s, 3H), 1.53-1.56 (m, 1H), 0.88-0.89 (m, 2H), 0.73-0.74 (m, 2H), 0.56-0.59 (m, 2H), 0.30-0.34 (m, 2H). | 4 |
| I-868 | 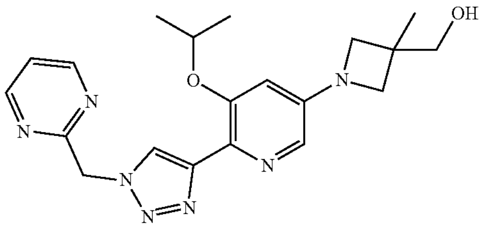 [SMILES: CC(C)Oc1cc(N2CC(C)(CO)C2)cnc1-c1cn(Cc2ncccn2)nn1] | 396.4 | $^1$HNMR (400 MHz, DMSO-$d_6$) δ 8.81 (d, J = 4.8 Hz, 2H), 8.34 (s, 1H), 7.47-7.50 (m, 2H), 6.49 (d, J = 2.0 Hz, 1H), 5.91 (s, 2H), 4.73-4.79 (m, 1H), 3.77 (d, J = 7.2 Hz, 2H), 3.52 (d, J = 7.2 Hz, 4H), 1.31 (d, J = 6.0 Hz, 6H), 1.27 (s, 3H). | 22 |
| I-694 | 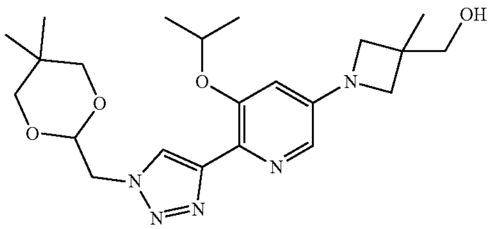 [SMILES: CC(C)Oc1cc(N2CC(C)(CO)C2)cnc1-c1cn(CC2OCC(C)(C)CO2)nn1] | 432.1 | $^1$HNMR (400 MHz, DMSO-$d_6$) δ 8.21 (s, 1H), 7.47 (d, J = 2.0 Hz, 1H), 6.47 (d, J = 2.0 Hz, 1H), 4.92 (t, J = 5.2 Hz, 1H), 4.88 (t, J = 4.0 Hz, 1H), 4.74-4.77(m, 1H), 4.56 (d, J = 4.0 Hz, 2H), 3.77 (d, J = 7.2 Hz, 2H), 3.44-3.57 (m, 8H), 1.32 (d, J = 6.0 Hz, 6H), 1.27 (s, 3H), 1.04 (s, 3H), 0.68 (s, 3H). | 22 |

TABLE 23-continued

Characterization data for exemplary compounds

| Compound No. | Chemical Structure | M + 1 | $^1$H NMR (400 MHz) | Example of Synthesis |
|---|---|---|---|---|
| I-703 | 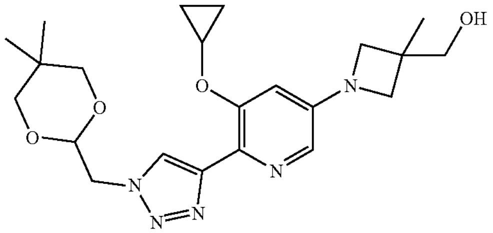 [SMILES: CC1(C)COC(Cn2cc(-c3ncc(N4CC(C)(CO)C4)cc3OC3CC3)nn2)OC1] | 430.1 | $^1$HNMR (400 MHz, DMSO-$d_6$) δ 8.11 (s, 1H), 7.50 (d, J = 2.0 Hz, 1H), 6.74 (d, J = 2.0 Hz, 1H), 4.94 (t, J = 5.2 Hz, 1H), 4.88 (t, J = 4.4 Hz, 1H), 4.54 (d, J = 4.4 Hz, 2H), 3.99-4.01 (m, 1H), 3.79 (d, J = 7.2 Hz, 2H), 3.53-3.58 (m, 4H), 3.33-3.48 (m, 4H), 1.28 (s, 3H), 1.05 (s, 3H), 0.81-0.84 (m, 2H), 0.75-0.76 (m, 2H), 0.68 (s, 3H). | 22 |
| I-748 | 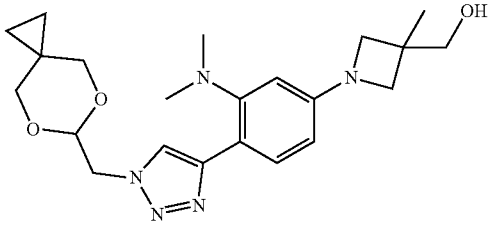 [SMILES: CN(C)c1cc(N2CC(C)(CO)C2)ccc1-c1cn(CC2OCC3(CC3)CO2)nn1] | 414.2 | $^1$HNMR (400 MHz, DMSO-$d_6$) δ 8.22 (s, 1H), 7.80 (d, J = 8.4 Hz, 1H), 6.13-6.16 (m, 2H), 5.02-5.03 (m, 1H), 4.87 (s, 1H), 4.55 (d, J = 4.4 Hz, 2H), 4.06(d, J = 11.2 Hz, 2H), 3.67 (d, J = 6.8 Hz, 2H), 3.41-3.43 (m, 4H), 3.24 (d, J = 11.2 Hz, 2H), 2.54 (s, 6H), 1.25 (s, 3H), 0.54-0.58 (m, 2H), 0.29-0.33 (m, 2H). | 22 |
| I-728 | 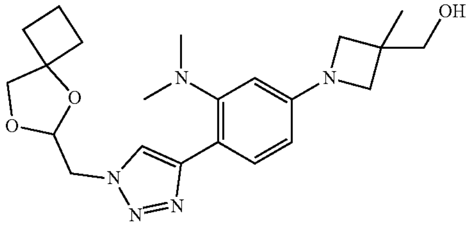 [SMILES: CN(C)c1cc(N2CC(C)(CO)C2)ccc1-c1cn(CC2OCC3(CCC3)O2)nn1] | 414.1 | $^1$HNMR (400 MHz, DMSO-$d_6$) δ 8.17 (s, 1H), 7.80 (d, J = 8.8 Hz, 1H), 6.15-6.17 (m, 2H), 5.29 (d, J = 3.6 Hz, 1H), 4.88 (d, J = 5.2 Hz, 1H), 4.54 (d, J = 3.6 Hz, 2H), 3.81-3.86 (m, 2H), 3.68(d, J = 7.2 Hz, 2H), 3.41-3.44 (m, 4H), 2.55 (s, 6H), 2.17-2.25 (m, 1H), 2.02-2.14 (m, 2H), 1.89-1.95 (m, 1H), 1.59-1.67 (m, 1H), 1.41-1.48 (m, 1H), 1.25 (s, 3H). | 22 |
| I-729 | 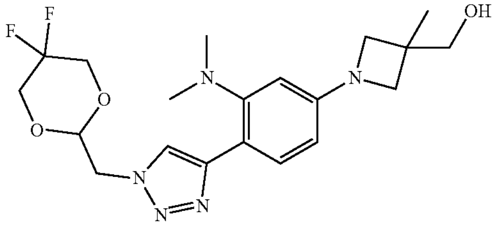 [SMILES: CN(C)c1cc(N2CC(C)(CO)C2)ccc1-c1cn(CC2OCC(F)(F)CO2)nn1] | 424.1 | $^1$HNMR (400 MHz, DMSO-$d_6$) δ 8.22 (s, 1H), 7.81 (d, J = 8.0 Hz, 1H), 6.14-6.17 (m, 2H), 5.20 (t, J = 4.8 Hz, 1H), 4.88 (t, J = 5.2 Hz, 1H), 4.63 (d, J = 4.4 Hz, 2H), 4.19 (t, J = 12.0 Hz, 2H), 4.07 (d, J = 11.6 Hz, 1H), 3.99 (d, J = 11.6 Hz, 1H), 3.68 (d, J = 6.8 Hz, 2H), 3.42-3.44 (m, 4H), 2.55 (s, 6H), 1.25 (s, 3H). | 22 |
| I-707 | 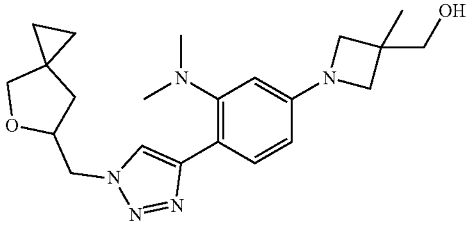 [SMILES: CN(C)c1cc(N2CC(C)(CO)C2)ccc1-c1cn(CC2CC3(CC3)CO2)nn1] | 398.3 | $^1$HNMR (400 MHz, DMSO-$d_6$) δ 8.22 (s, 1H), 7.80 (d, J = 8.0 Hz, 1H), 6.14-6.17 (m, 2H), 4.88 (t, J = 5.2 Hz, 1H), 4.52-4.54 (m, 2H), 4.42-4.44 (m, 1H), 3.68 (d, J = 6.8 Hz, 2H), 3.63 (d, J = 8.0 Hz, 1H), 3.53 (d, J = 8.0 Hz, 1H), 3.42-3.44 (m, 4H), 2.55 (s, 6H), 1.90 (dd, J = 7.2 Hz, 12.4 Hz, 1H), 1.69 (dd, J = 7.2 Hz, 12.4 Hz, 1H), 1.25 (s, 3H), 0.53-0.59 (m, 4H). | 22 |
| I-869 | 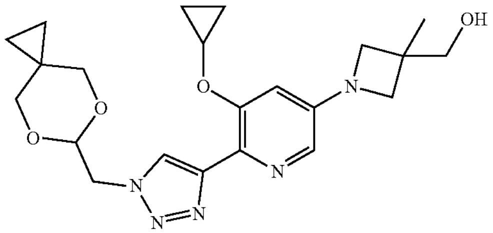 [SMILES: CC1(CO)CN(c2cnc(-c3cn(CC4OCC5(CC5)CO4)nn3)c(OC3CC3)c2)C1] | 428.4 | $^1$HNMR (400 MHz, DMSO-$d_6$) δ 8.13 (s, 1H), 7.50 (d, J = 1.6 Hz, 1H), 6.74 (s, 1H), 5.05 (s, 1H), 4.93 (s, 1H), 4.56 (d, , I = 4.8 Hz, 2H), 4.07 (d, J = 10.8 Hz, 2H), 4.00 (s, 1H), 3.79 (d, J = 6.8 Hz, 2H), 3.54 (d, J = 7.2 Hz, 2H), 3.45 (d, J = 4.8 Hz, 2H), 3.24 (d, J = 11.6 Hz, 2H), 1.28 (s, 3H), 0.76-0.84 (m, 4H), 0.57-0.60 (m, 2H), 0.31-0.35 (m, 2H). | 22 |

TABLE 23-continued

| Characterization data for exemplary compounds | | | | |
|---|---|---|---|---|
| Compound No. | Chemical Structure | M + 1 | $^1$H NMR (400 MHz) | Example of Synthesis |
| I-767 | 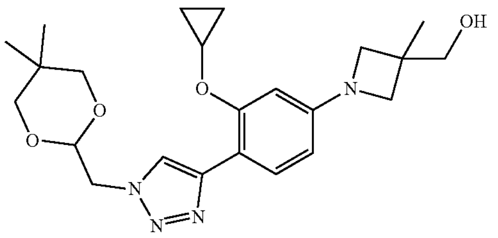 [SMILES: CC1(C)COC(Cn2cc(-c3ccc(N4CC(C)(CO)C4)cc3OC3CC3)nn2)OC1] | 429.3 | $^1$HNMR (400 MHz, DMSO-$d_6$) δ 8.00 (s, 1H), 7.88 (d, J = 8.0 Hz, 1H), 6.37 (d, J = 2.0 Hz, 1H), 6.11 (dd, J = 2.0 Hz, 8.4 Hz, 1H), 4.97 (s, 1H), 4.86-4.88 (m, 7.2 Hz, 2H), 3.56 (d, J = 11.2 Hz, 1H), 4.52 (d, J = 4.0 Hz, 2H), 3.91-3.95 (m, 1H), 3.71 (d, J = 2H), 3.44-3.51 (m, 6H), 1.26 (s, 3H), 1.05 (s, 3H), 0.78-0.85 (m, 2H), 0.71-0.76 (m, 2H) , 0.68 (s, 3H). | 22 |
| I-721 | 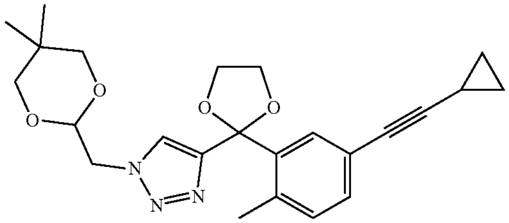 [SMILES: Cc1ccc(C#CC2CC2)cc1C1(c2cn(CC3OCC(C)(C)CO3)nn2)OCCO1] | 424.0 | $^1$HNMR (400 MHz, $CDCl_3$) δ 7.73 (d, J = 1.6 Hz, 1H), 7.31 (s, 1H), 7.17 (d, J = 1.6 Hz, 1H), 6.98 (d, J = 7.6 Hz, 1H), 4.64 (t, J = 4.4 Hz, 1H), 4.37 (d, J = 4.4 Hz, 2H), 4.18-4.21 (m, 2H), 3.92-3.95 (m, 2H), 3.51 (d, J = 11.2 Hz, 2H), 3.31 (d, J = 10.8 Hz, 2H), 2.17 (s, 3H), 1.28-1.42 (m, 1H), 1.01 (s, 3H), 0.72-0.80 (m, 4H), 0.63 (s, 3H). | 13 |
| I-695 | 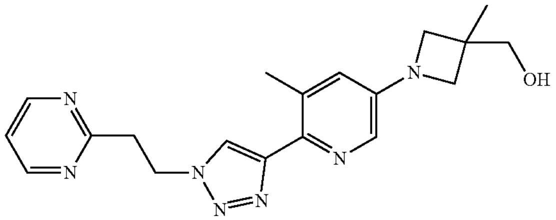 [SMILES: Cc1cc(N2CC(C)(CO)C2)cnc1-c1cn(CCc2ncccn2)nn1] | 366.0 | $^1$HNMR (400 MHz, DMSO-$d_6$) δ 8.76 (d, J = 4.8 Hz, 2H), 8.29 (s, 1H), 7.66 (d, J = 2.4 Hz, 1H), 7.39 (t, J = 4.8 Hz, 1H), 6.68 (d, J = 2.4 Hz, 1H), 4.90 (t, J = 7.2 Hz, 3H), 3.74 (d, J = 7.2 Hz, 2H), 3.54 (t, J = 7.2 Hz, 2H), 3.48 (d, J = 7.2 Hz, 2H), 3.43 (s, 2H), 2.50 (s, 3H), 1.26 (s, 3H). | 22 |
| I-717 | 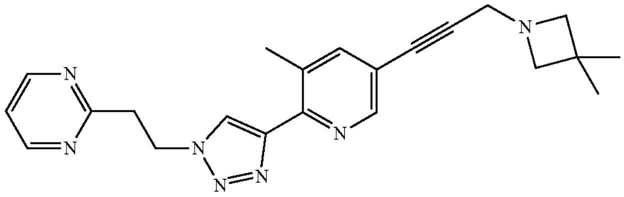 [SMILES: Cc1cc(C#CCN2CC(C)(C)C2)cnc1-c1cn(CCc2ncccn2)nn1] | 388.0 | $^1$HNMR (400 MHz, $CD_3OD$-$d_4$) δ 8.72 (d, J = 4.8 Hz, 2H), 8.45 (s, 1H), 8.35 (s, 1H), 7.76 (s, 1H), 7.34 (t, J = 4.8 Hz, 1H), 5.04 (t, J = 6.8 Hz, 2H), 3.62 (t, J = 6.8 Hz, 2H), 3.54 (s, 2H), 3.20 (s, 4H), 2.55 (s, 3H), 1.24 (s, 6H). | 6 |
| I-708 | 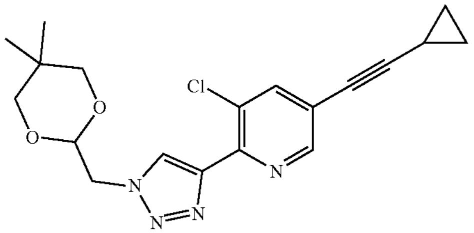 [SMILES: CC1(C)COC(Cn2cc(-c3ncc(C#CC4CC4)cc3Cl)nn2)OC1] | 373.0 | $^1$HNMR (400 MHz, DMSO) 8.68 (br., 1H), 8.08 (s, 1H), 5.76 (s, 1H), 4.94 (s, 1H), 4.64 (s, 2H), 3.57 (d, J = 10.8 Hz, 2H), 3.46 (d, J = 10.8 Hz, 2H), 1.57-1.72 (m, 1H), 1.03 (s, 3H), 0.90-0.99 (m, 2H), 0.81-0.87 (m, 2H), 0.68 (s, 3H). | 2 |
| I-750 | 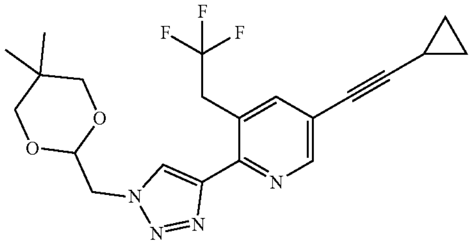 [SMILES: CC1(C)COC(Cn2cc(-c3ncc(C#CC4CC4)cc3CC(F)(F)F)nn2)OC1] | 421.3 | $^1$HNMR (400 MHz, DMSO-$d_6$) δ 8.60 (d, J = 1.6 Hz, 1H), 8.55 (s, 1H), 7.89 (s, 1H), 4.92 (t, J = 4.0 Hz, 1H), 4.62 (d, J = 4.4 Hz, 2H), 4.51 (q, J = 11.2 Hz, 2H), 3.57 (d, J = 10.8 Hz, 2H), 3.46 (d, J = 10.8 Hz, 2H), 1.60-1.64 (m, 1H), 1.01 (s, 3H), 0.93-0.96 (m, 2H), 079-0.82 (m, 2H), 0.67 (s, 3H). | 4 |

TABLE 23-continued

Characterization data for exemplary compounds

| Compound No. | Chemical Structure | M + 1 | $^1$H NMR (400 MHz) | Example of Synthesis |
|---|---|---|---|---|
| I-762 | 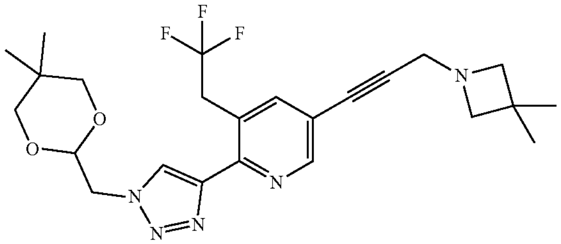 | 478.4 | $^1$HNMR (400 MHz, DMSO-$d_6$) δ 8.69 (d, J = 2.0 Hz, 1H), 8.57 (s, 1H), 7.99 (s, 1H), 4.93 (t, J = 4.4 Hz, 1H), 4.63 (d, J = 4.4 Hz, 2H), 4.51-4.59 (m, 2H), 3.57 (d, J = 11.2 Hz, 2H), 3.49 (s, 2H), 3.47 (d, J = 10.8 Hz, 2H), 3.03 (s, 4H), 1.19 (s, 6H), 1.00 (s, 3H), 0.67 (s, 3H). | 6 |
| I-709 | 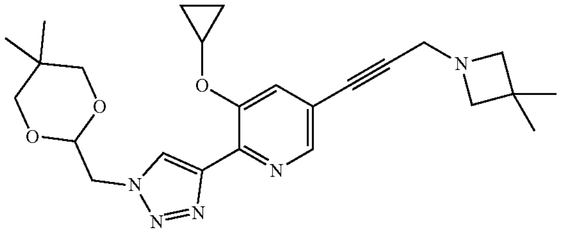 | 452.0 | $^1$HNMR (400 MHz, DMSO-$d_6$) δ 8.40 (s, 1H), 8.35 (d, J = 1.6 Hz, 1H), 7.83 (d, J = 1.6 Hz, 1H), 4.91 (t, J = 4.0 Hz, 1H), 4.61 (d, J = 4.0 Hz, 2H), 4.14 (t, J = 2.8 Hz, 1H), 3.55-3.58 (m, 2H), 3.46-3.50 (m, 4H), 3.04 (s, 4H), 1.19 (s, 6H), 1.04 (s, 3H), 0.79-0.89 (m, 4H), 0.68 (s, 3H). | 28 |
| I-722 | 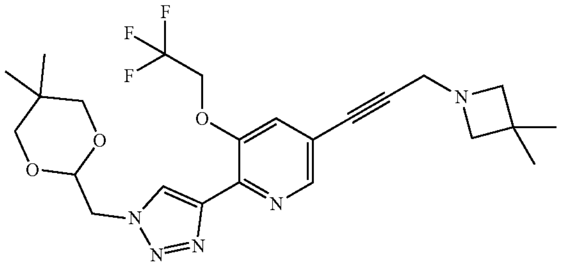 | 494.0 | $^1$HNMR (400 MHz, DMSO-$d_6$) δ 8.42 (d, J = 1.2 Hz, 1H), 8.36 (s, 1H), 7.78 (d, J = 1.2 Hz, 1H), 5.03 (q, J = 8.8 Hz, 2H), 4.88 (t, J = 4.0 Hz, 1H), 4.63 (d, J = 4.0 Hz, 2H), 3.46-3.56 (m, 6H), 3.04 (s, 4H), 1.19 (s, 6H), 0.99 (s, 3H), 0.67 (s, 3H). | 28 |
| I-696 | 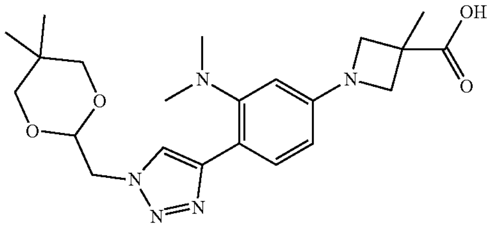 [SMILES: CN(C)c1cc(N2CC(C)(C(=O)O)C2)ccc1-c1cn(CC2OCC(C)(C)CO2)nn1] | 430.3 | $^1$HNMR (400 MHz, DMSO-$d_6$) δ 8.21 (s, 1H), 7.81 (d, J = 8.8 Hz, 1H), 6.16-6.19 (m, 2H), 4.86 (t, J = 4.4 Hz, 1H), 4.53 (d, J = 4.4 Hz, 2H), 4.00 (d, J = 7.2 Hz, 2H), 3.55-3.58 (m, 4H), 3.45 (d, J = 10.8 Hz, 2H), 2.55 (s, 6H), 1.48 (s, 3H), 1.04 (s, 3H), 0.67 (s, 3H). | 22 |
| I-704 | 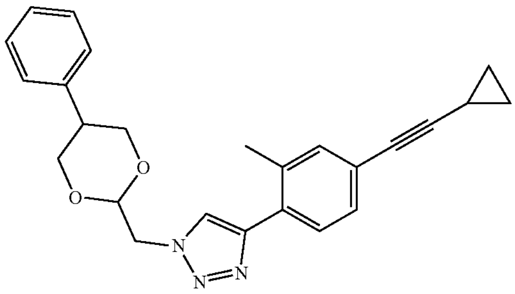 [SMILES: Cc1cc(C#CC2CC2)ccc1-c1cn(CC2OCC(c3ccccc3)CO2)nn1] | 400.0 | $^1$HNMR (400 MHz, DMSO-$d_6$) δ 8.40 (s, 1H), 7.76 (d, J = 8.0 Hz, 1H), 7.23-7.34 (m, 7H), 5.18 (t, J = 4.4 Hz, 1H), 4.63 (d, J = 4.4 Hz, 2H), 4.11 (dd, J = 4.4 Hz, 11.2 Hz, 2H), 3.89 (t, J = 11.2 Hz, 2H), 3.11-3.18 (m, 1H), 2.43 (s, 3H), 1.52-1.59 (m, 1H), 0.85-0.92 (m, 2H), 0.72-0.76 (m, 2H). | 4 |

TABLE 23-continued

Characterization data for exemplary compounds

| Compound No. | Chemical Structure | M + 1 | $^{1}$H NMR (400 MHz) | Example of Synthesis |
|---|---|---|---|---|
| I-705 | 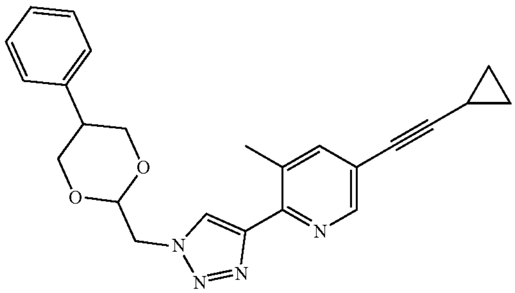 [SMILES: Cc1cc(C#CC2CC2)cnc1-c1cn(CC2OCC(c3ccccc3)CO2)nn1] | 401.0 | $^{1}$HNMR (400 MHz, DMSO-$d_6$) δ 8.53 (s, 1H), 8.44 (d, J = 2.0 Hz, 1H), 7.73 (d, J = 1.6 Hz, 1H), 7.23-7.34 (m, 5H), 5.18 (t, J = 4.8 Hz, 1H), 4.66 (d, J = 4.8 Hz, 2H), 4.12 (dd, J = 4.8 Hz, 11.2 Hz, 2H), 3.89 (t, J = 11.2 Hz, 2H), 3.10-3.18 (m, 1H), 2.64 (s, 3H), 1.57-1.63 (m, 1H), 0.89-0.95 (m, 2H), 0.76-0.79 (m, 2H). | 4 |
| I-763 | 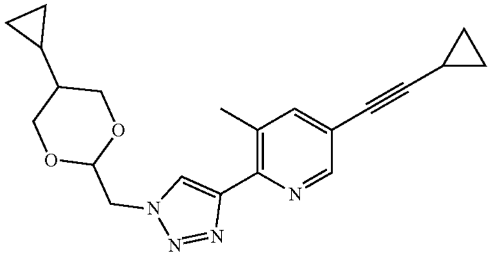 [SMILES: Cc1cc(C#CC2CC2)cnc1-c1cn(CC2OCC(C3CC3)CO2)nn1] | 365.4 | $^{1}$HNMR (400 MHz, DMSO-$d_6$) δ 8.47 (s, 1H), 8.43 (d, J = 1.6 Hz, 1H), 7.73 (d, J = 1.6 Hz, 1H), 4.96 (t, J = 4.8 Hz, 1H), 4.57 (d, J = 4.8 Hz, 2H), 4.04 (dd, J = 4.8 Hz, 11.6 H, 2H), 3.52 (t, J = 11.6 Hz, 2H), 2.62 (s, 3H), 1.58-1.62 (m, 1H), 1.10-1.12(m, 1H), 0.90-0.95 (m, 2H), 0.76-0.80 (m, 2H), 0.25-0.34 (m, 3H), 0.09-0.12 (m, 2H). | 4 |
| I-706 | 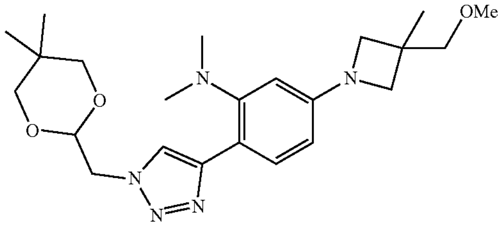 [SMILES: COCC1(C)CN(c2ccc(-c3cn(CC4OCC(C)(C)CO4)nn3)c(N(C)C)c2)C1] | 430.4 | $^{1}$HNMR (400 MHz, $CDCl_3$) δ 8.12 (s, 1H), 7.98 (d, , I = 8.0 Hz, 1H), 6.22 (d, J = 8.4 Hz, 1H), 6.16 (s, 1H), 4.78 (t, J = 4.4 Hz, 1H), 4.54 (s, 1H), 4.54 (d, J = 0.8 Hz, 1H), 3.77 (d, J = 6.8 Hz, 2H), 3.63 (d, J = 11.2 Hz, 2H), 3.55 (d, J = 6.8 Hz, 2H), 3.44-3.46 (m, 3H), 3.40-3.41 (m, 4H), 2.61 (s, 6H), 1.35 (s, 3H), 1.17 (s, 3H), 0.72 (s, 3H). | 22 |
| I-736 | 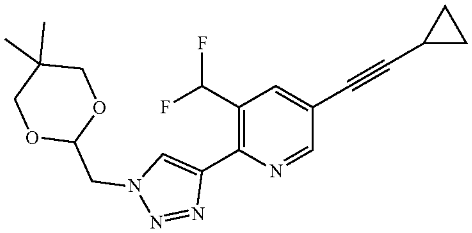 [SMILES: CC1(C)COC(Cn2cc(-c3ncc(C#CC4CC4)cc3C(F)F)nn2)OC1] | 389.0 | $^{1}$HNMR (400 MHz, $CDCl_3$) 8.56 (s, 1H), 8.27 (s, 1H), 8.02 (s, 1H), 7.97 (d, J = 54.8 Hz, 1H), 4.75 (t, J = 4.4 Hz, 1H), 4.50 (d, J = 4.4 Hz, 2H), 3.58 (d, J = 11.2 Hz, 2H), 3.36 (d, J = 10.8 Hz, 2H), 1.41-1.45 (m, 2H), 1.07 (s, 3H), 0.84-0.88 (m, 2H), 0.79-0.82 (m, 2H), 0.66 (s, 3H). | 4 |
| I-730 | 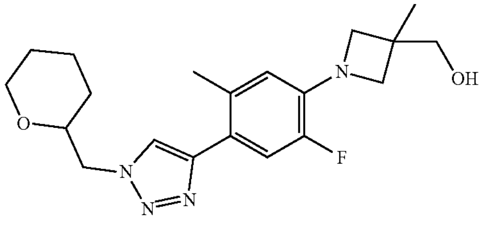 [SMILES: Cc1cc(N2CC(C)(CO)C2)c(F)cc1-c1cn(CC2CCCCO2)nn1] | 375.3 | $^{1}$HNMR (400 MHz, DMSO-$d_6$) δ 8.18 (s, 1H), 7.39 (d, J = 14.0 Hz, 1H), 6.40 (d, J = 9.6 Hz, 1H), 4.88-4.92 (m, 1H), 4.34-4.46 (m, 2H), 3.71-3.87 (m, 4H), 3.51-3.53 (m, 2H), 3.44 (s, 2H), 3.29-3.33 (m, 1H), 2.33 (s, 3H), 1.78-1.81 (m, 1H), 1.61-1.64 (m, 1H), 1.39-1.54 (m, 3H), 1.15-1.25 (m, 4H). | 22 |
| I-804 | 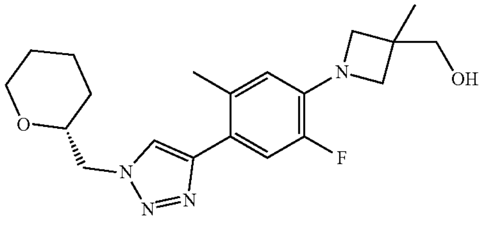 [SMILES: Cc1cc(N2CC(C)(CO)C2)c(F)cc1-c1cn(C[C@H]2CCCCO2)nn1] | 375.2 | $^{1}$HNMR (400 MHz, DMSO-$d_6$) δ 8.18 (s, 1H), 7.39 (d, J = 14.0 Hz, 1H), 6.40 (d, J = 9.2 Hz, 1H), 4.89 (t, J = 5.6 Hz, 1H), 4.34-4.46 (m, 2H), 3.70-3.87 (m, 4H), 3.51-3.53 (m, 2H), 3.44 (d, J = 5.2 Hz, 2H), 3.28-3.33 (m, 1H), 2.33 (s, 3H), 1.78-1.81 (m, 1H), 1.61-1.64 (m, 1H), 1.43-1.50 (m, 3H), 1.18-1.25 (m, 4H). | 22 |

TABLE 23-continued

| Characterization data for exemplary compounds | | | | |
|---|---|---|---|---|
| Compound No. | Chemical Structure | M + 1 | $^1$H NMR (400 MHz) | Example of Synthesis |
| I-805 | 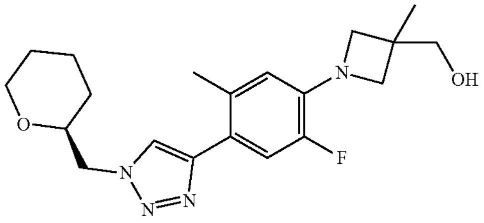 [SMILES: Cc1cc(N2CC(C)(CO)C2)c(F)cc1-c1cn(C[C@@H]2CCCCO2)nn1] | 375.3 | $^1$HNMR (400 MHz, DMSO-$d_6$) δ 8.18 (s, 1H), 7.39 (d, J = 14.0 Hz, 1H), 6.40 (d, J = 9.2 Hz, 1H), 4.89 (t, J = 5.6 Hz, 1H), 4.34-4.46 (m, 2H), 3.71-3.87 (m, 4H), 3.52 (dd, J = 2.0 Hz, 7.2 Hz, 2H), 3.44 (d, J = 5.2 Hz, 2H), 3.28-3.33 (m, 1H), 2.33 (s, 3H), 1.78-1.81 (m, 1H), 1.61-1.64 (m, 1H), 1.40-1.50 (m, 3H), 1.18-1.25 (m, 4H). | 22 |
| I-710 | 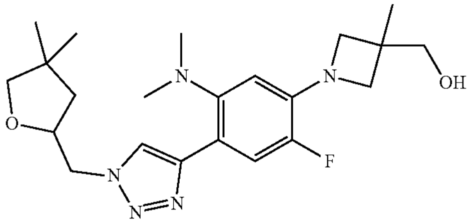 [SMILES: CN(C)c1cc(N2CC(C)(CO)C2)c(F)cc1-c1cn(CC2CC(C)(C)CO2)nn1] | 418.4 | $^1$HNMR (400 MHz, $CDCl_3$) δ 8.26 (br., 1H), 7.80 (br., 1H), 6.23 (s, 1H), 4.55-4.57 (m, 1H), 4.40-4.47 (m, 3H), 3.89-3.93 (m, 2H), 3.73 (s, 3H), 3.67-3.69 (m, 1H), 3.49 (d, J = 8.0 Hz, 1H), 3.44 (d, J = 8.4 Hz, 1H), 2.50-2.68 (m, 6H), 1.77-1.90 (m, 1H), 1.44-1.50 (m, 1H), 1.34 (s, 3H), 1.10 (s, 3H), 1.01 (s, 3H). | 22 |
| I-711 | 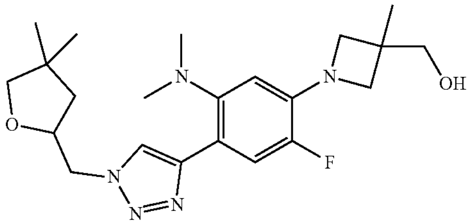 [SMILES: CN(C)c1cc(N2CC(C)(CO)C2)c(F)cc1-c1cn(CC2CC(C)(C)CO2)nn1] | 434.0 | $^1$HNMR (400 MHz, DMSO-$d_6$) δ 8.30 (s, 1H), 7.65 (d, J = 14.4 Hz, 1H), 6.27 (d, J = 8.8 Hz, 1H), 4.86-4.91 (m, 2H), 4.55 (d, J = 4.0 Hz, 2H), 3.81 (dd, J = 1.6 Hz, 7.2 Hz, 2H), 3.54-3.57 (m, 4H), 3.44-3.47 (m, 4H), 2.55 (s, 6H), 1.25 (s, 3H), 1.03 (s, 3H), 0.67 (s, 3H). | 22 |
| I-737 | 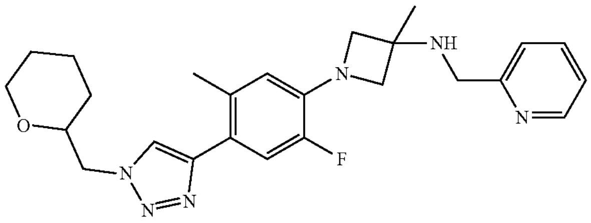 [SMILES: Cc1cc(N2CC(C)(NCc3ccccn3)C2)c(F)cc1-c1cn(CC2CCCCO2)nn1] | 451.0 | $^1$HNMR (400 MHz, DMSO-$d_6$) δ 8.48 (d, J = 4.0 Hz, 1H), 8.19 (s, 1H), 7.75 (dt, J = 1.6 Hz, 7.6 Hz, 1H), 7.47 (d, J = 8.4 Hz, 1H), 7.42 (d, J = 14.0 Hz, 1H), 7.23-7.26 (m, 1H), 6.43 (d, J = 9.6 Hz, 1H), 4.34-4.46 (m, 2H), 3.71-3.87 (m, 8H), 3.28-3.34 (m, 1H), 2.84 (s, 1H), 2.34 (s, 3H), 1.78-1.81 (m, 1H), 1.61-1.64 (m, 1H), 1.40-1.51 (m, 6H), 1.18-1.24 (m, 1H). | 5 |
| I-731 | 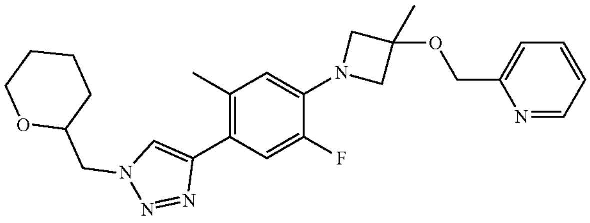 | 452.1 | $^1$HNMR (400 MHz, DMSO-$d_6$) δ 8.51 (d, J = 4.4 Hz, 1H), 8.20 (s, 1H), 7.78-7.82 (m, 1H), 7.48 (d, J = 7.6 Hz, 1H), 7.43 (d, J = 12.8 Hz, 1H), 7.28-7.31 (m, 1H), 6.49 (d, J = 9.6 Hz, 1H), 4.57 (s, 2H), 4.34-4.46 (m, 2H), 3.93-3.95 (m, 2H), 3.84-3.89 (m, 3H), 3.71-3.75 (m, 1H), 3.28-3.29 (m, 1H), 2.35 (s, 3H), 1.78-1.81 (m, 1H), 1.61-1.64 (m, 4H), 1.40-1.50 (m, 3H), 1.18-1.24 (m, 1H). | 5 |
| I-690 | 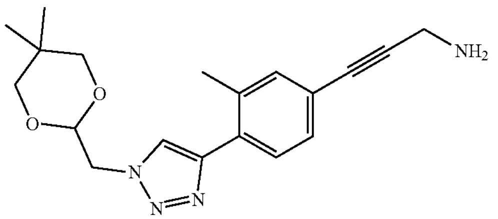 [SMILES: Cc1cc(C#CCN)ccc1-c1cn(CC2OCC(C)(C)CO2)nn1] | 341.1 | $^1$HNMR (400 MHz, DMSO-$d_6$) δ 8.37 (s, 1H), 7.76 (d, J = 8.0 Hz, 1H), 7.35 (s, 1H), 7.31 (d, J = 8.4 Hz, 1H), 4.92 (t, J = 4.4 Hz, 1H), 4.58 (d, J = 4.4 Hz, 2H), 3.57 (d, J = 11.2 Hz, 2H), 3.47 (d, J = 10.8 Hz, 2H), 3.31 (s, 2H), 2.42 (s, 3H), 1.04 (s, 3H), 0.68 (s, 3H). | 6 |

TABLE 23-continued

| Characterization data for exemplary compounds | | | | |
|---|---|---|---|---|
| Compound No. | Chemical Structure | M + 1 | $^1$H NMR (400 MHz) | Example of Synthesis |
| I-697 | 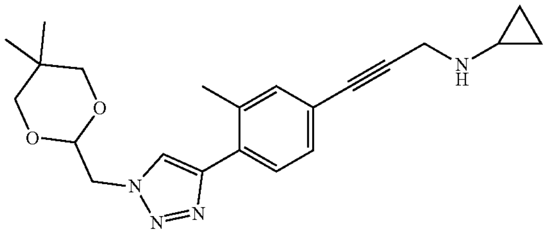 [SMILES: Cc1cc(C#CCNC2CC2)ccc1-c1cn(CC2OCC(C)(C)CO2)nn1] | 381.3 | $^1$HNMR (400 MHz, DMSO-$d_6$) δ 8.37 (s, 1H), 7.76 (d, J = 8.0 Hz, 1H), 7.37 (s, 1H), 7.32 (dd, J = 1.6 Hz, 8.0 Hz, 1H), 4.92 (t, J = 4.0 Hz, 1H), 5.88 (d, J = 4.4 Hz, 2H), 3.56-3.58 (m, 4H), 3.45-3.48 (m, 2H), 2.71 (s, 1H), 2.42 (s, 3H), 2.28-2.33 (m, 1H), 1.04 (s, 3H), 0.68 (s, 3H), 0.39-0.43 (m, 2H), 0.26-0.30 (m, 2H). | 6 |
| I-698 | 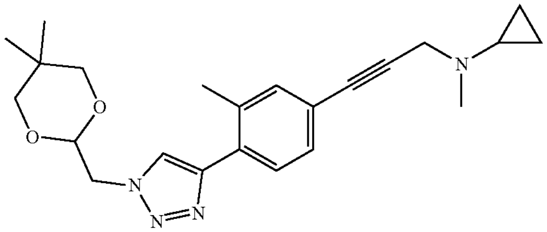 [SMILES: Cc1cc(C#CCN(C)C2CC2)ccc1-c1cn(CC2OCC(C)(C)CO2)nn1] | 395.3 | $^1$HNMR (400 MHz, DMSO-$d_6$) δ 8.37 (s, 1H), 7.77 (d, J = 7.6 Hz, 1H), 7.40 (s, 1H), 7.35 (d, J = 8.0 Hz, 1H), 4.93 (t, J = 4.4 Hz, 1H), 4.58 (d, J = 4.4 Hz, 2H), 3.56-3.61 (m, 4H), 3.45-3.48 (m, 2H), 2.43 (s, 3H), 2.39 (s, 3H), 1.91-1.93 (m, 1H), 1.04 (s, 3H), 0.68 (s, 3H), 0.45-0.48 (m, 2H), 0.35-0.37 (m, 2H). | 6 |
| I-741 | 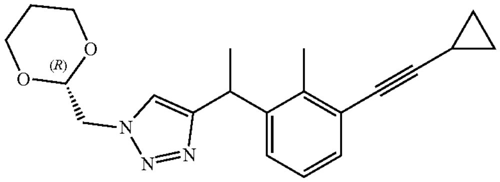 | 350.1 | $^1$HNMR (400 MHz, DMSO-$d_6$) δ 7.71 (s, 1H), 7.18 (dd, J = 2.4 Hz, 6.4 Hz, 1H), 7.05-7.11 (m, 2H), 4.44 (q, J = 7.2 Hz, 1H), 4.24-4.35 (m, 2H), 3.81-3.83 (m, 1H), 3.62-3.66 (m, 1H), 3.25-3.33 (m, 1H), 2.39 (s, 3H), 1.75-1.78 (m, 1H), 1.36-1.60 (m, 8H), 1.10-1.13 (m, 1H), 0.88-0.92 (m, 2H), 0.70-0.74 (m, 2H). | 13 |
| I-752 | 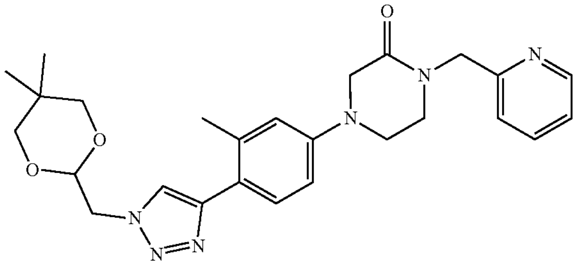 [SMILES: Cc1cc(N2CCN(Cc3ccccn3)C(=O)C2)ccc1-c1cn(CC2OCC(C)(C)CO2)nn1] | 477.3 | $^1$HNMR (400 MHz, $CDCl_3$) δ 8.55 (d, J = 4.4 Hz, 1H), 7.66-7.74 (m, 3H), 7.34 (d, J = 8.0 Hz, 1H), 7.20-7.23 (m, 1H), 6.76-6.81 (m, 2H), 4.79-4.82 (m, 3H), 4.56 (d, J = 4.4 Hz, 2H), 4.01 (s, 2H), 3.57-3.66 (m, 4H), 3.43-3.54 (m, 4H), 2.45 (s, 3H), 1.15 (s, 3H), 0.73 (s, 3H). | 5 |
| I-751 | 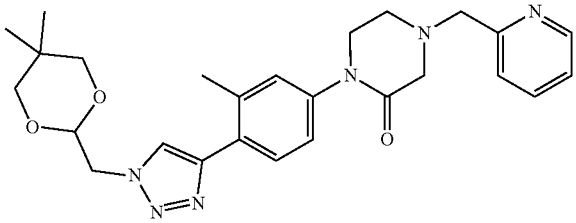 [SMILES: Cc1cc(N2CCN(Cc3ccccn3)CC2=O)ccc1-c1cn(CC2OCC(C)(C)CO2)nn1] | 477.1 | $^1$HNMR (400 MHz, $CDCl_3$) δ 8.52 (d, J = 4.4 Hz, 1H), 7.73 (d, J = 6.4 Hz, 2H), 7.60-7.64 (m, 1H), 7.36 (d, J = 8.0 Hz, 1H), 7.11-7.15 (m, 3H), 4.74 (t, J = 4.4 Hz, 1H), 4.47-4.50 (m, 2H), 3.72 (s, 2H), 3.66 (t, J = 5.2 Hz, 2H), 3.56 (d, J = 11.2 Hz, 2H), 3.36 (d, J = 11.2 Hz, 2H), 3.32 (s, 2H), 2.84 (t, J = 5.2 Hz, 2H), 2.38 (s, 3H), 1.06 (d, , I = 6.8 Hz, 3H), 0.65 (s, 3H). | 5 |
| I-753 | 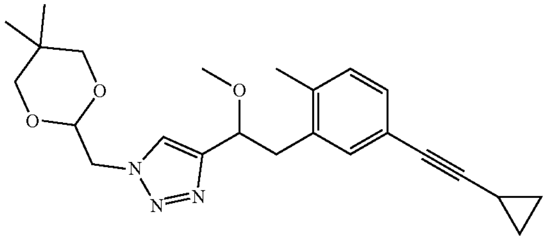 [SMILES: COC(Cc1cc(C#CC2CC2)ccc1C)c1cn(CC2OCC(C)(C)CO2)nn1] | 410.4 | $^1$HNMR (400 MHz, DMSO-$d_6$) δ 7.98 (s, 1H), 7.09 (s, 1H), 7.06 (s, 2H), 4.82 (t, J = 4.0 Hz, 1H), 4.56 (t, J = 6.4 Hz, 1H), 4.49 (d, J = 4.0 Hz, 2H), 3.53-3.58 (m, 2H), 3.42-3.46 (m, 2H), 3.10-3.14 (m, 1H), 3.08 (s, 1H), 2.99 (dd, J = 6.0 Hz, 14.0 Hz, 1H), 2.21 (s, 3H), 1.47-1.53 (m, 1H), 1.01 (s, 3H), 0.84-0.88 (m, 2H), 0.68-0.71 (m, 5H). | 34 |

TABLE 23-continued

| Compound No. | Chemical Structure | M + 1 | $^1$H NMR (400 MHz) | Example of Synthesis |
|---|---|---|---|---|
| Characterization data for exemplary compounds | | | | |
| I-768 | 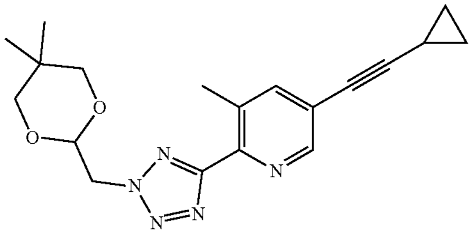 [SMILES: Cc1cc(C#CC2CC2)cnc1-c1nnn(CC2OCC(C)(C)CO2)n1] | 354.3 | $^1$HNMR (400 MHz, DMSO-$d_6$) δ 8.55 (d, J = 1.6 Hz, 1H), 7.86 (d, J = 1.2 Hz, 1H), 5.07 (t, J = 4.8 Hz, 1H), 4.92 (d, J = 4.8 Hz, 2H), 3.56 (d, J = 10.8 Hz, 2H), 3.48 (d, J = 10.8 Hz, 2H), 2.51-2.62 (m, 3H), 1.61-1.65 (m, 1H), 1.04 (s, 3H), 0.93-0.98 (m, 2H), 0.79-0.83 (m, 2H), 0.68 (s, 3H). | 17 |
| I-769 | 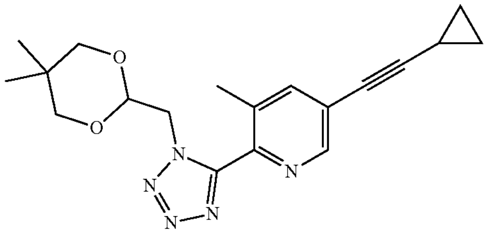 [SMILES: Cc1cc(C#CC2CC2)cnc1-c1nnnn1CC1OCC(C)(C)CO1] | 354.3 | $^1$HNMR (400 MHz, DMSO-$d_6$) 8.54 (s, 1H), 7.90 (s, 1H), 4.81 (s, 2H), 4.74 (s, 1H), 3.31 (s, 4H), 2.36 (s, 3H), 1.58-1.67 (m, 1H), 0.98 (d, J = 6.4 Hz, 2H), 0.78-0.85 (m, 2H), 0.72 (s, 3H), 0.58 (s, 3H). | 17 |
| I-835 | 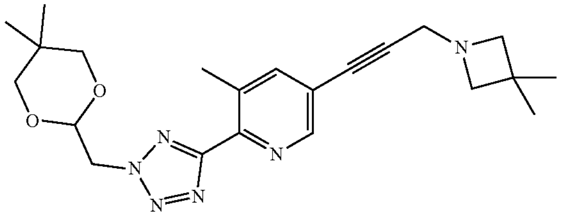 | 411.4 | $^1$HNMR (400 MHz, DMSO-$d_6$) 8.64 (d, J = 1.6 Hz, 1H), 7.96 (s, 1H), 5.08 (t, J = 4.8 Hz, 1H), 4.93 (d, J = 4.4 Hz, 2H), 3.56(d, J = 10.8 Hz, 2H), 3.47-3.51 (m, 4H), 3.03 (s, 4H), 2.53 (s, 3H), 1.19 (s, 6H), 1.04 (s, 3H), 0.68 (s, 3H). | 28 |
| I-870 | 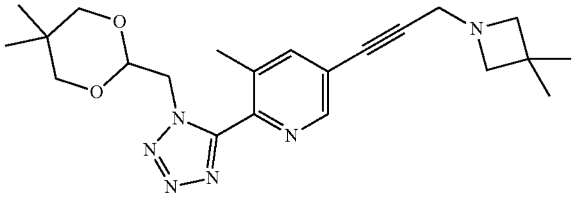 | 411.4 | $^1$HNMR (400 MHz, DMSO-$d_6$) 8.57 (s, 1H), 7.94 (s, 1H), 4.77 (d, J = 3.6 Hz, 2H), 4.70 (t, J = 3.6 Hz, 1H), 3.43 (s, 2H), 3.22-3.28 (m, 4H), 2.95 (s, 4H), 2.34 (s, 3H), 1.10 (s, 6H), 0.69 (s, 3H), 0.50 (s, 3H). | 28 |
| I-871 | 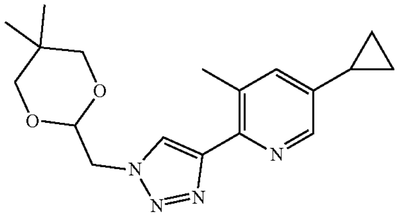 [SMILES: Cc1cc(C2CC2)cnc1-c1cn(CC2OCC(C)(C)CO2)nn1] | 329.4 | $^1$HNMR (400 MHz, $CDCl_3$) δ 8.19 (d, J = 1.6 Hz, 1H), 8.12 (s, 1H), 7.10 (d, J = 1.6 Hz, 1H), 4.74 (t, J = 4.4 Hz, 1H), 4.49 (d, J = 4.8 Hz, 2H), 3.56 (d, J = 11.2 Hz, 2H), 3.36 (d, J = 10.8 Hz, 2H), 2.60 (s, 3H), 1.80-1.83 (m, 1H), 1.08 (s, 3H), 0.94-0.97 (m, 2H), 0.65-0.69 (m, 5H). | 5 |
| I-738 | 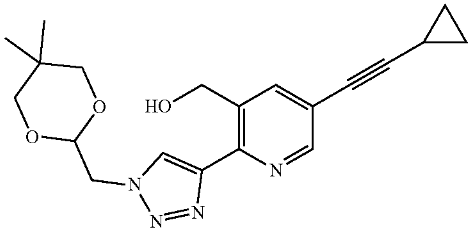 [SMILES: CC1(C)COC(Cn2cc(-c3ncc(C#CC4CC4)cc3CO)nn2)OC1] | 369.3 | $^1$HNMR (400 MHz, $CDCl_3$) δ 8.62 (s, 1H), 8.53-8.58 (m, 1H), 7.85 (s, 1H), 5.68-5.95 (m, 1H), 4.84 (t, J = 4.4 Hz, 1H), 4.78 (s, 2H), 4.61 (d, J = 4.0 Hz, 2 H), 3.66 (d, J = 11.2 Hz, 2H), 3.45 (d, J = 11.2 Hz, 2H), 1.46-1.52 (m, 1H), 1.12 (s, 3H), 0.91-0.97 (m, 2H), 0.85-0.88 (m, 2H), 0.73 (s, 3H). | 4 |

TABLE 23-continued

| Characterization data for exemplary compounds | | | | |
|---|---|---|---|---|
| Compound No. | Chemical Structure | M + 1 | $^1$H NMR (400 MHz) | Example of Synthesis |
| I-754 | 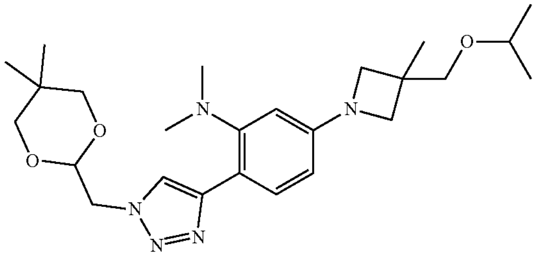 [SMILES: CC(C)OCC1(C)CN(c2ccc(-c3cn(CC4OCC(C)(C)CO4)nn3)c(N(C)C)c2)C1] | 458.4 | $^1$HNMR (400 MHz, DMSO-$d_6$) δ 8.20 (s, 1H), 7.81 (d, J = 8.0 Hz, 1H), 6.15-6.17 (m, 2H), 4.86 (t, J = 4.0 Hz, 1H), 4.54 (d, J = 4.4 Hz, 2H), 3.65 (d, J = 6.8 Hz, 2H), 3.55-3.61 (m, 3H), 3.43-3.47 (m, 6H), 2.55 (s, 6H), 1.28 (s, 3H), 1.10 (d, J = 6.0 Hz, 6H), 1.04 (s, 3H), 0.67 (s, 3H). | 5 |
| I-755 | 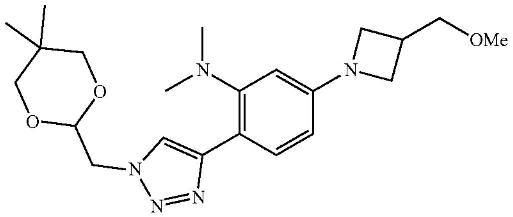 [SMILES: COCC1CN(c2ccc(-c3cn(CC4OCC(C)(C)CO4)nn3)c(N(C)C)c2)C1] | 416.5 | $^1$HNMR (400 MHz, DMSO-$d_6$) δ 8.20 (s, 1H), 7.81 (d, J = 8.0 Hz, 1H), 6.16-6.18 (m, 2H), 4.86 (t, J = 4.0 Hz, 1H), 4.53 (d, J = 4.0 Hz, 2H), 3.90 (t, J = 7.2 Hz, 2H), 3.52-3.57 (m, 6H), 3.44-3.47 (m, 2H), 3.28 (s, 3H), 2.88-2.95 (m, 1H), 2.55 (s, 6H), 1.04 (s, 3H), 0.67 (s, 3H). | 5 |
| I-756 | 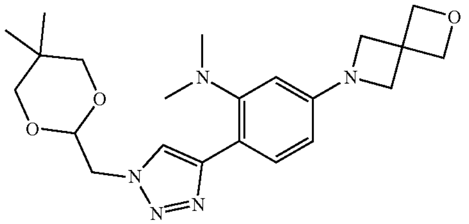 [SMILES: CN(C)c1cc(N2CC3(COC3)C2)ccc1-c1cn(CC2OCC(C)(C)CO2)nn1] | 414.4 | $^1$HNMR (400 MHz, DMSO-$d_6$) δ 8.21 (s, 1H), 7.82 (d, J = 8.0 Hz, 1H), 6.18-6.21 (m, 2H), 4.86 (t, J = 4.4 Hz, 1H), 4.72 (s, 4H), 4.53 (d, J = 4.4 Hz, 2H), 4.00 (s, 4H), 3.56 (d, J = 10.8 Hz, 2H), 3.45 (d, J = 10.8 Hz, 2H), 2.55 (s, 6H), 1.03 (s, 3H), 0.67 (s, 3H). | 5 |
| I-764 | 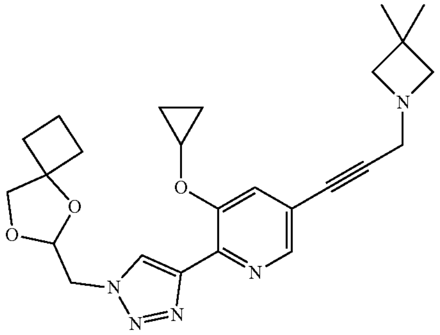 [SMILES: CC1(C)CN(CC#Cc2cnc(-c3cn(CC4OCC5(CCC5)O4)nn3)c(OC3CC3)c2)C1] | 450.4 | $^1$HNMR (400 MHz, $CDCl_3$) δ 8.50 (d, J = 1.6 Hz, 1H), 8.22 (s, 1H), 7.71 (d, J = 1.6 Hz, 1H), 5.33 (t, J = 3.2 Hz, 1H), 4.59 (d, J = 3.6 Hz, 2H), 3.87-3.91 (m, 1H), 3.85 (s, 2H), 3.67 (s, 2H), 3.39 (s, 4H), 2.32-2.40 (m, 1H), 2.18-2.26 (m, 1H), 2.06-2.13 (m, 1H), 1.90-1.97 (m, 1H), 1.70-1.79 (m, 1H), 1.41-1.53 (m, 1H), 1.32 (s, 6H), 0.86-0.98 (m, 4H). | 28 |
| I-794 | 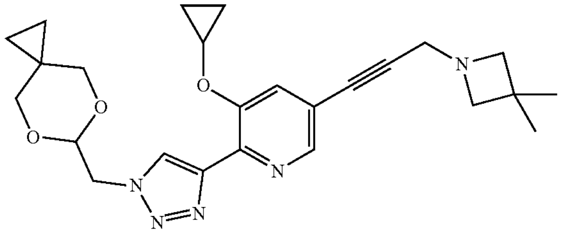 [SMILES: CC1(C)CN(CC#Cc2cnc(-c3cn(CC4OCC5(CC5)CO4)nn3)c(OC3CC3)c2)C1] | 450.4 | $^1$HNMR (400 MHz, $CDCl_3$) δ 8.49 (s, 1H), 8.20 (s, 1H), 7.69 (s, 1H), 5.00 (t, J = 4.8 Hz, 1H), 4.61 (d, J = 5.2 Hz, 2H), 4.11 (d, J = 11.2 Hz, 2H), 3.85-3.88 (m, 1H), 3.60 (s, 2H), 3.25-3.30 (m, 6H), 1.29 (s, 6H), 0.83-0.94 (m, 4H), 0.69-0.73 (m, 2H), 0.35-0.38 (m, 2H). | 28 |

TABLE 23-continued

| Compound No. | Chemical Structure | M + 1 | $^1$H NMR (400 MHz) | Example of Synthesis |
|---|---|---|---|---|
| Characterization data for exemplary compounds | | | | |
| I-788 | 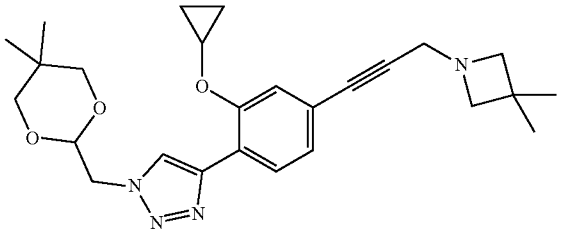 | 451.2 | $^1$HNMR (400 MHz, DMSO-$d_6$) δ 8.26 (s, 1H), 8.12 (d, J = 8.0 Hz, 1H), 7.45 (d, J = 1.6 Hz, 1H), 7.16 (dd, , I = 1.2 Hz, 8.0 Hz, 1H), 4.90 (t, J = 4.4 Hz, 1H), 4.59 (d, J = 4.4 Hz, 2H), 4.06-4.07 (m, 1H), 3.57 (d, J = 10.8 Hz, 2H), 3.46-3.48 (m, 4H), 3.03 (s, 4H), 1.19 (s, 6H), 1.04 (s, 3H), 0.78-0.87 (m, 4H), 0.68 (s, 3H). | 6 |
| I-784 | 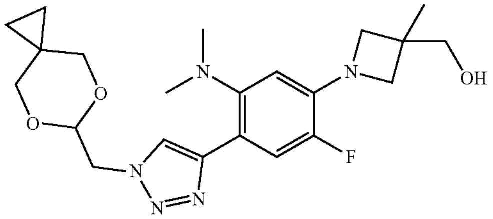 [SMILES: CN(C)c1cc(N2CC(C)(CO)C2)c(F)cc1-c1cn(CC2OCC3(CC3)CO2)nn1] | 432.3 | $^1$HNMR (400 MHz, DMSO-$d_6$) δ 8.32 (s, 1H), 7.64 (d, J = 14.0 Hz, 1H), 6.26 (d, J = 8.8 Hz, 1H), 5.05 (t, J = 4.8 Hz, 1H), 4.88 (t, J = 5.6 Hz, 1H), 4.57 (d, J = 4.8 Hz, 2H), 4.07 (d, J = 11.2 Hz, 2H), 3.80 (d, J = 7.2 Hz, 2H), 3.54 (d, J = 7.2 Hz, 2H), 3.44 (d, J = 5.6 Hz, 2H), 3.24 (d, J = 11.6 Hz, 2H), 2.55 (s, 6H), 1.25 (s, 3H), 0.51-0.58 (m, 2H), 0.24-0.33 (m, 2H). | 22 |
| I-765 | 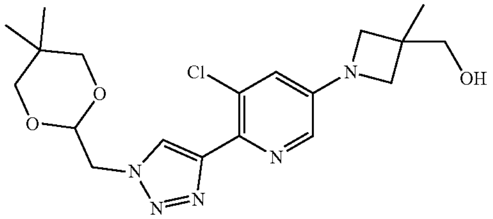 [SMILES: CC1(C)COC(Cn2cc(-c3ncc(N4CC(C)(CO)C4)cc3Cl)nn2)OC1] | 408.3 | $^1$HNMR (400 MHz, $CDCl_3$) δ 8.20 (s, 1H), 7.85 (s, 1H), 6.75 (d, J = 2.4 Hz, 1H), 4.81 (t, J = 4.8 Hz, 1H), 4.57 (d, J = 4.4 Hz, 2H), 3.89 (d, J = 7.2 Hz, 2H), 3.70 (s, 2H), 3.59-3.65 (m, 4H), 3.43 (d, J = 11.2 Hz, 2H), 1.36 (s, 3H), 1.16 (s, 3H), 0.72 (s, 3H). | 22 |
| I-776 | 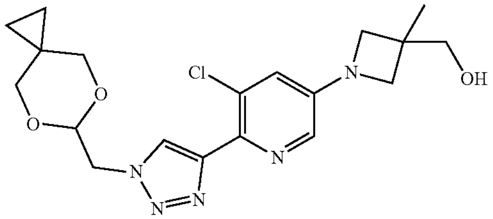 [SMILES: CC1(CO)CN(c2cnc(-c3cn(CC4OCC5(CC5)CO4)nn3)c(Cl)c2)C1] | 403.2 | $^1$HNMR (400 MHz, DMSO-$d_6$) δ 8.36 (s, 1H), 7.83 (d, J = 2.4 Hz, 1H), 6.96 (d, J = 2.4 Hz, 1H), 5.09 (t, J = 5.2 Hz, 1H), 4.95 (t, J = 5.6 Hz, 1H), 4.59 (d, J = 4.8 Hz, 2H), 4.08 (d, J = 12.4 Hz, 2H), 3.79 (d, J = 7.2 Hz, 2H), 3.55 (d, J = 7.6 Hz, 2H), 3.43 (d, J = 5.2 Hz, 2H), 3.25 (d, J = 11.6 Hz, 2H), 1.26 (s, 3H), 0.53-0.65 (m, 2H), 0.31-0.38 (m, 2H). | 22 |
| I-777 | 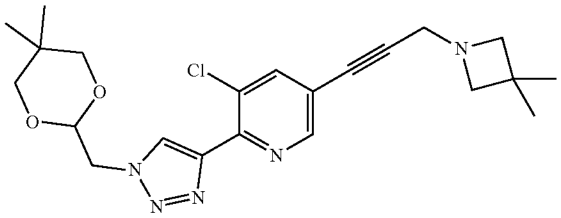 | 430.3 | $^1$HNMR (400 MHz, DMSO-$d_6$) δ 8.68 (d, J = 1.6 Hz, 1H), 8.64 (s, 1H), 8.15 (d, J = 1.6 Hz, 1H), 4.94 (t, J = 4.4 Hz, 1H), 4.63 (d, J = 4.4 Hz, 2H), 3.57 (d, J = 10.8 Hz, 2H), 3.50 (s, 2H), 3.47 (d, J = 10.8 Hz, 2H), 3.03 (s, 4H), 1.19 (s, 6H), 1.03 (s, 3H), 0.68 (s, 3H). | 28 |
| I-778 | 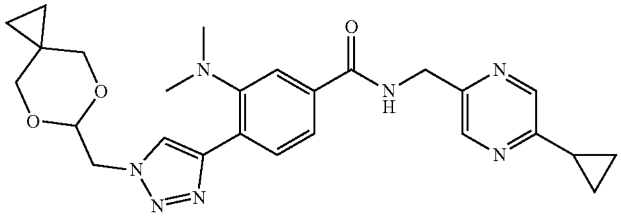 [SMILES: CN(C)c1cc(C(=O)NCc2cnc(C3CC3)cn2)ccc1-c1cn(CC2OCC3(CC3)CO2)nn1] | 490.4 | $^1$HNMR (400 MHz, $CDCl_3$) δ 8.48 (s, 1H), 8.44 (d, J = 1.2 Hz, 1H), 8.38 (s, 1H), 8.25 (d, , I = 8.0 Hz, 1H), 7.74 (s, 1H), 7.48-7.52 (m, 1H), 7.19-7.21 (m, 1H), 4.99 (t, J = 4.8 Hz, 1H), 4.75 (d, J = 5.2 Hz, 2H), 4.61 (d, J = 4.8 Hz, 2H), 4.13 (d, J = 11.2, 2H), 3.27 (d, J = 11.6, 2H), 2.68 (s, 6H), 2.05-2.08 (m, 1H), 1.06 (d, J = 6.8, 4H), 0.68-0.72 (m, 2H), 0.35-0.38 (m, 2H). | 29 |

TABLE 23-continued

Characterization data for exemplary compounds

| Compound No. | Chemical Structure | M + 1 | $^1$H NMR (400 MHz) | Example of Synthesis |
|---|---|---|---|---|
| I-779 | 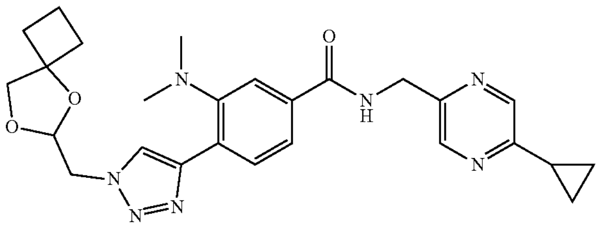 [SMILES: CN(C)c1cc(C(=O)NCc2cnc(C3CC3)cn2)ccc1-c1cn(CC2OCC3(CCC3)O2)nn1] | 400.3 | $^1$HNMR (400 MHz, $CDCl_3$) δ 8.48 (s, 1H), 8.44 (d, J = 1.6 Hz, 1H), 8.35 (s, 1H), 8.23-8.25 (m, 1H), 7.73-7.79 (m, 1H), 7.48-7.52 (m, 1H), 7.29-7.35 (m, 1H), 5.33 (t, J = 4.0 Hz, 1H), 4.75 (d, J = 5.2 Hz, 2H), 4.58 (d, J = 2.8 Hz, 2H), 3.86 (s, 2H), 2.80 (s, 6H), 2.32-2.39 (m, 1H), 2.19-2.27 (m, 1H), 2.04-2.13 (m, 2H), 1.91-1.98 (m, 1H), 1.70-1.80 (m, 1H), 1.44-1.54 (m, 1H), 1.05-1.07 (m, 4H). | 29 |
| I-872 | 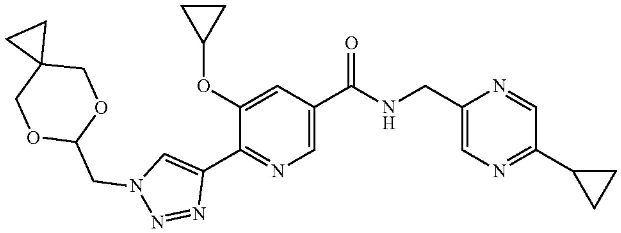 [SMILES: O=C(NCc1cnc(C2CC2)cn1)c1cnc(-c2cn(CC3OCC4(CC4)CO3)nn2)c(OC2CC2)c1] | 504.3 | $^1$HNMR (400 MHz, DMSO-$d_6$) δ 9.42 ( t, J = 5.6 Hz, 1H), 8.79 (d, J = 2.0 Hz, 1H), 8.58 (d, J = 1.2 Hz, 1H), 8.49 (d, J = 1.2 Hz, 1H), 8.48 (s, 1H), 8.20 (d, J = 1.6 Hz, 1H), 5.09 (t, J = 4.8 Hz, 1H), 4.65 (d, J = 4.8 Hz, 2H), 4.60 (d, J = 5.6 Hz, 2H), 4.07-4.15 (m, 3H), 3.25 (d, J = 11.6 Hz, 2H), 2.18-2.22 (m, 1H), 1.01-1.05 (m, 2H), 0.84-0.95 (m, 6H), 0.57-0.60 (m, 2H), 0.31-0.35 (m, 2H). | 27 |
| I-770 | 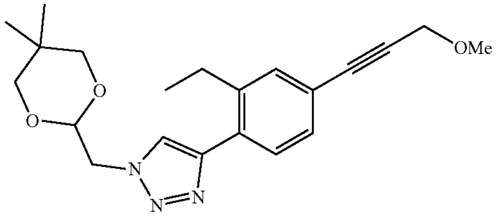 [SMILES: CCc1cc(C#CCOC)ccc1-c1cn(CC2OCC(C)(C)CO2)nn1] | 370.4 | $^1$HNMR (400 MHz, DMSO-$d_6$) δ 8.33 (s, 1H), 7.64 (d, J = 8.0 Hz, 1H), 7.72 (d, J = 1.2 Hz, 1H), 7.36 (dd, J = 1.6 Hz, 8.0 Hz, 1H), 4.92 (t, J = 4.0 Hz, 1H), 4.59 (d, J = 4.0 Hz, 2H), 4.34 (s, 2H), 3.57 (d, J = 11.2 Hz, 2H), 3.47 (d, J = 10.8 Hz, 2H), 3.35 (s, 3H), 2.81 (q, J = 7.2 Hz, 2H), 1.13 (t, J = 7.6 Hz, 3H), 1.02 (s, 3H), 0.68 (s, 3H). | 6 |
| I-780 | 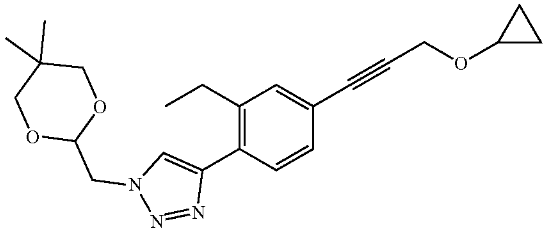 [SMILES: CCc1cc(C#CCOC2CC2)ccc1-c1cn(CC2OCC(C)(C)CO2)nn1] | 396.4 | $^1$HNMR (400 MHz, DMSO-$d_6$) δ 8.33 (s, 1H), 7.64 (d, J = 8.0 Hz, 1H), 7.42 (d, J = 1.6 Hz, 1H), 7.36 (dd, J = 8.0 Hz, 1.6 Hz, 1H), 4.92 (t, J = 4.0 Hz, 1H), 4.59 (d, J = 4.4 Hz, 2H), 4.39 (s, 2H), 3.46-3.58 (m, 5H), 2.81 (q, J = 7.6 Hz, 2H), 1.13 (t, J = 7.6 Hz, 3H), 1.02 (s, 3H), 0.68 (s, 3H), 0.57-0.61 (m, 2H), 0.47-0.56 (m, 2H). | 6 |
| I-757 | 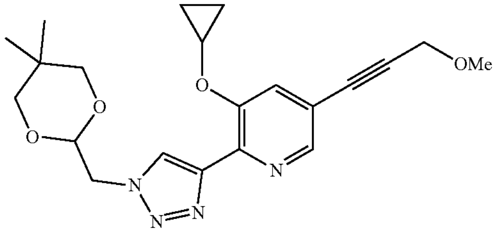 [SMILES: COCC#Cc1cnc(-c2cn(CC3OCC(C)(C)CO3)nn2)c(OC2CC2)c1] | 399.3 | $^1$HNMR (400 MHz, $CDCl_3$) δ 8.49 (s, 1H), 8.22 (s, 1H), 7.70 (s, 1H), 4.81 (t, J = 4.4 Hz, 1H), 4.58 (d, J = 4.4 Hz, 2H), 4.37 (s, 2H), 3.86-3.88 (m, 1H), 3.64 (d, J = 11.2 Hz, 2H), 3.49 (s, 3H), 3.44 (d, J = 11.2 Hz, 2H), 1.17 (s, 3H), 0.86-0.93 (m, 4H), 0.73 (s, 3H). | 28 |
| I-758 | 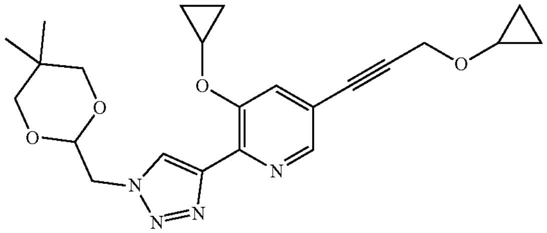 [SMILES: CC1(C)COC(Cn2cc(-c3ncc(C#CCOC4CC4)cc3OC3CC3)nn2)OC1] | 425.4 | $^1$HNMR (400 MHz, $CDCl_3$) δ 8.49 (d, J = 1.6 Hz, 1H), 8.24 (s, 1H), 7.71 (d, J = 1.2 Hz, 1H), 4.81 (t, J = 4.8 Hz, 1H), 4.58 (d, J = 4.4 Hz, 2H), 4.42 (s, 2H), 3.86-3.89 (m, 1H), 3.64 (d, J = 11.2 Hz, 2H), 3.55-3.59 (m, 1H), 3.44 (d, J = 11.2 Hz, 2H), 1.17 (s, 3H), 0.84-0.95 (m, 4H), 0.73 (s, 3H), 0.69-0.72 (m, 2H), 0.54-0.57 (m, 2H). | 28 |

TABLE 23-continued

| Characterization data for exemplary compounds | | | | |
|---|---|---|---|---|
| Compound No. | Chemical Structure | M + 1 | $^1$H NMR (400 MHz) | Example of Synthesis |
| I-828 | 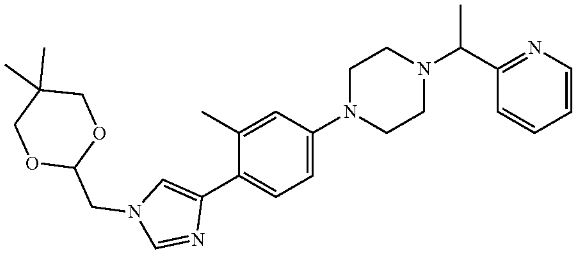 [SMILES: Cc1cc(N2CCN(C(C)c3ccccn3)CC2)ccc1-c1cn(CC2OCC(C)(C)CO2)cn1] | 476.4 | $^1$HNMR (400 MHz, DMSO-$d_6$) δ 8.51-8.52 (m, 1H), 7.75-7.79 (m, 1H), 7.59-7.61 (m, 2H), 7.45 (d, J = 8.0 Hz, 1H), 7.22-7.28 (m, 2H), 6.74-6.76 (m, 2H), 4.73 (t, J = 4.0 Hz, 1H), 4.12 (d, J = 4.0 Hz, 2H), 3.65 (q, J = 6.8 Hz, 1H), 3.56 (d, J = 10.8 Hz, 2H), 3.44 (d, J = 10.8 Hz, 2H), 3.11 (t, J = 4.8 Hz, 4H), 2.58-2.61 (m, 2H), 2.47-2.50 (m, 2H), 2.36 (s, 3H), 1.35 (d, J = 6.8 Hz, 3H), 1.04 (s, 3H), 0.67 (s, 3H). | 33 |
| I-795 | 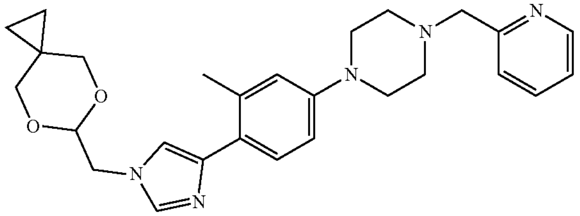 [SMILES: Cc1cc(N2CCN(Cc3ccccn3)CC2)ccc1-c1cn(CC2OCC3(CC3)CO2)cn1] | 460.3 | $^1$HNMR (400 MHz, DMSO-$d_6$) δ 8.50-8.52 (m, 1H), 7.76-7.80 (m, 1H), 7.61-7.64 (m, 2H), 7.48 (d, J = 7.6 Hz, 1H), 7.26-7.29 (m, 2H), 6.77-6.79 (m, 2H), 4.91 (t, J = 4.8 Hz, 1H), 4.14 (d, J = 5.2 Hz, 2H), 4.06 (d, J = 11.6 Hz, 2H), 3.65 (s, 2H), 3.25 (d, J = 11.6 Hz, 2H), 3.15 (t, J = 4.8 Hz, 4H), 2.57 (t, J = 4.8 Hz, 4H), 2.37 (s, 3H), 0.56-0.60 (m, 2H), 0.30-0.34 (m, 2H). | 33 |
| I-831 | 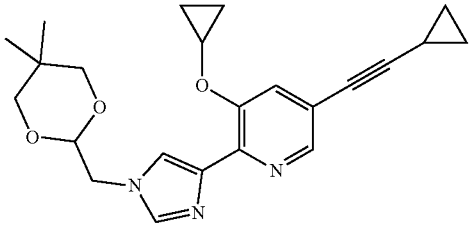 [SMILES: CC1(C)COC(Cn2cnc(-c3ncc(C#CC4CC4)cc3OC3CC3)c2)OC1] | 394.3 | $^1$HNMR (400 MHz, $CDCl_3$) δ 8.35 (s, 1H), 7.59-7.66 (m, 2H), 7.55 (s, 1H), 4.63 (t, J = 4.0 Hz, 1H), 4.10 (d, J = 4.0 Hz, 2H), 3.80-3.88 (m, 1H), 3.62 (d, J = 10.8 Hz, 2H), 3.42 (d, J = 11.2 Hz, 2H), 1.47-1.50 (m, 1H), 1.13 (s, 3H), 0.85-0.93 (m, 8H), 0.72 (s, 3H). | 23 |
| I-832 | 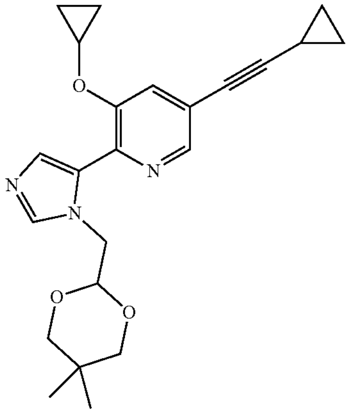 [SMILES: CC1(C)COC(Cn2cncc2-c2ncc(C#CC3CC3)cc2OC2CC2)OC1] | 394.4 | $^1$HNMR (400 MHz, $CDCl_3$) δ 8.22 (d, J = 1.6 Hz, 1H), 7.66(d, J = 6.0 Hz, 2H), 7.57 (d, J = 1.6 Hz, 1H), 4.69 (t, J = 4.8 Hz, 1H), 4.57 (d, J = 4.4 Hz, 2H), 3.78-3.81 (m, 1H), 3.56 (d, J = 11.2 Hz, 2H), 3.33 ( d, J = 11.2 Hz, 2H), 1.48-1.52 (m, 1H), 1.17 (s, 3H), 0.85-0.95 (m, 8H), 0.68 (s, 3H). | 23 |
| I-820 | 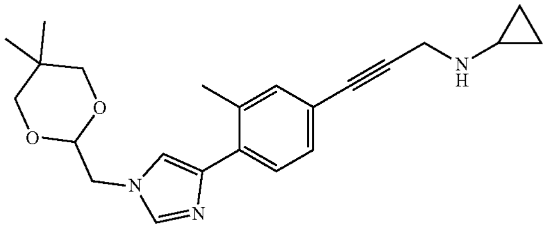 [SMILES: Cc1cc(C#CCNC2CC2)ccc1-c1cn(CC2OCC(C)(C)CO2)cn1] | 380.2 | $^1$HNMR (400 MHz, DMSO-$d_6$) δ 7.82 (d, J = 8.0 Hz, 1H), 7.69 (d, J = 0.8 Hz, 1H), 7.46 (d, J = 0.8 Hz, 1H), 7.27 (s, 1H), 7.24 (d, J = 8.0 Hz, 1H), 4.75 (t, J = 4.0 Hz, 1H), 4.16 (d, J = 4.0 Hz, 2H), 3.58 (s, 1H), 3.55 (d, J = 5.2 Hz, 2H), 3.43-3.46 (m, 3H), 2.41 (s, 3H), 2.27-2.32 (m, 1H), 1.23 (br, 1H), 1.04 (s, 3H), 0.67 (s, 3H), 0.38-0.42 (m, 2H), 0.26-0.29 (m, 2H). | 33 |

TABLE 23-continued

| Characterization data for exemplary compounds | | | | |
|---|---|---|---|---|
| Compound No. | Chemical Structure | M + 1 | $^1$H NMR (400 MHz) | Example of Synthesis |
| I-845 | 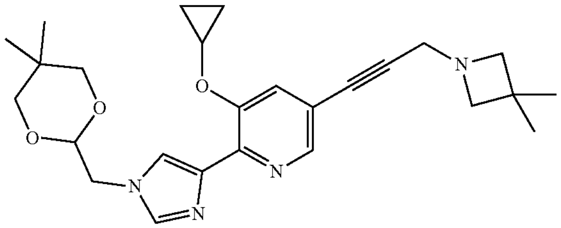 | 451.3 | $^1$HNMR (400 MHz, $CDCl_3$) δ 8.43 (d, J = 1.2 Hz, 1H), 7.64 (d, J = 0.8 Hz, 1H), 7.60-7.62 (m, 2H), 4.64 (t, J = 4.2 Hz, 1H), 4.09 (d, J = 4.0 Hz, 2H), 3.83-3.86 (m, 1H), 3.63 (d, J = 11.2 Hz, 2H), 3.54 (s, 2H), 3.42 (d, J = 11.2 Hz, 2H), 3.22 (s, 4H), 1.26 (s, 6H), 1.13 (s, 3H), 0.86-0.90 (m, 4H), 0.72 (s, 3H). | 23 |
| I-785 | 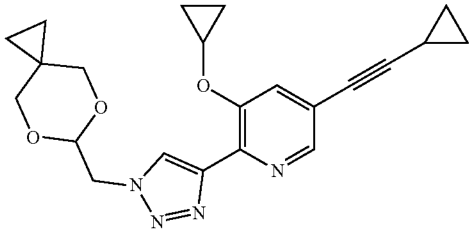 [SMILES: C(#CC1CC1)c1cnc(-c2cn(CC3OCC4(CC4)CO3)nn2)c(OC2CC2)c1] | 393.4 | $^1$HNMR (400 MHz, DMSO-$d_6$) δ 8.40 (s, 1H), 8.26 (s, 1H), 7.76 (d, J = 1.2 Hz, 1H), 5.08 (t, J = 4.8 Hz, 1H), 4.63 (d, J = 4.8 Hz, 2H), 4.06-4.12 (m, 3H), 3.25 (d, J = 12.0 Hz, 2H), 1.60-1.64 (m, 1H), 0.79-0.96 (m, 8H), 0.56-0.60 (m, 2H), 0.31-0.34 (m, 2H). | 4 |
| I-771 | 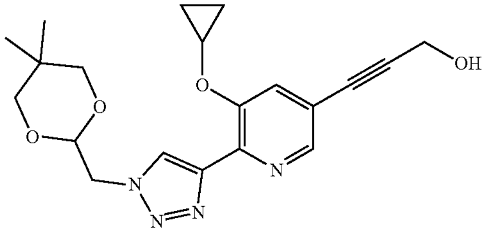 [SMILES: CC1(C)COC(Cn2cc(-c3ncc(C#CCO)cc3OC3CC3)nn2)OC1] | 385.5 | $^1$HNMR (400 MHz, DMSO-$d_6$) δ 8.40 (s, 1H), 8.34 (s, 1H), 7.82 (d, J 1.2 Hz, 1H), 5.45 (t, J = 6.0 Hz, 1H), 4.91 (t, J = 4.0 Hz, 1H), 4.61 (d, J = 4.4 Hz, 2H), 4.37 (d, J = 6.0 Hz, 2H), 4.12-4.14 (m, 1H), 3.57 (d, J = 11.2 Hz, 2H), 3.47 (d, J = 10.4 Hz, 2H), 1.04 (s, 3H), 0.79-0.89 (m, 4H), 0.68 (s, 3H). | 28 |
| I-772 | 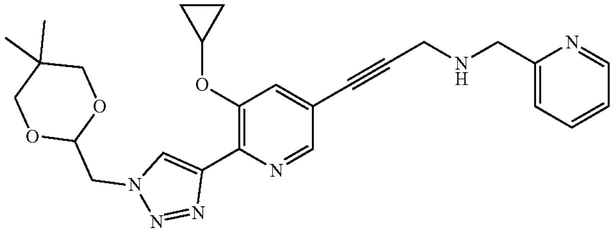 [SMILES: CC1(C)COC(Cn2cc(-c3ncc(C#CCNCc4ccccn4)cc3OC3CC3)nn2)OC1] | 475.3 | $^1$HNMR (400 MHz, $CDCl_3$) δ 8.59 (d, J = 5.2 Hz, 1H), 8.42 (d, J = 2.0 Hz, 1H), 8.20 (s, 1H), 7.67-7.71 (m, 2H), 7.40 (d, J = 8.0 Hz, 1H), 7.20-7.23 (m, 1H), 4.81 (t, J = 4.4 Hz, 1H), 4.58 (d, J = 4.4 Hz, 3H), 4.16 (s, 2H), 3.85-3.88 (m, 3H), 3.64 (d, J = 11.2 Hz, 2H), 3.44 (d, J = 10.8 Hz, 2H), 1.17 (s, 3H), 0.83-0.93 (m, 4H), 0.73 (s, 3H). | 28 |
| I-806 | 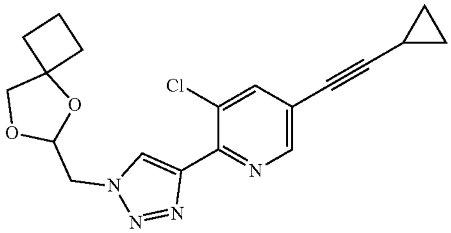 [SMILES: Clc1cc(C#CC2CC2)cnc1-c1cn(CC2OCC3(CCC3)O2)nn1] | 371.1 | $^1$HNMR (400 MHz, DMSO-$d_6$) 8.59-8.60 (m, 2H), 8.05 (d, J = 1.6 Hz, 1H), 5.36 (d, J = 3.2 Hz, 1H), 4.65 (d, J = 3.2 Hz, 2H), 3.90 (d, J = 8.0 Hz, 1H), 3.82 (d, J = 8.0 Hz, 1H), 2.24 (q, J = 10.0 Hz, 1H), 2.01-2.09 (m, 2H), 1.85-1.90 (m, 1H), 1.57-1.66 (m, 2H), 1.40-1.47 (m, 1H), 0.94-0.98 (m, 2H), 0.80-0.84 (m, 2H). | 2 |
| I-807 | 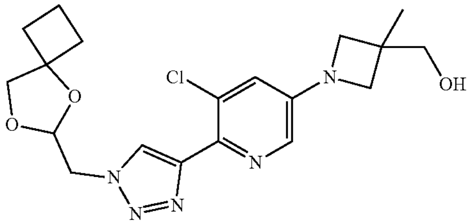 [SMILES: CC1(CO)CN(c2cnc(-c3cn(CC4OCC5(CCC5)O4)nn3)c(Cl)c2)C1] | 406.1 | $^1$HNMR (400 MHz, DMSO-$d_6$) 8.29 (s, 1H), 7.83 (d, J = 2.0 Hz, 1H), 6.96 (d, J = 2.0 Hz, 1H), 5.33 (t, J = 3.2 Hz, 1H), 4.96 (t, J = 5.2 Hz, 1H), 4.58 (d, J = 3.6 Hz, 2H), 3.89 (d, J = 8.0 Hz, 1H), 3.82 (t, J = 8.0 Hz, 3H), 3.56 (d, J = 7.2 Hz, 2H), 3.43 (d, J = 5.2 Hz, 2H), 2.19-2.28 (m, 1H), 2.02-2.07 (m, 2H), 1.87-1.92 (m, 1H), 1.57-1.65 (m, 1H), 1.40-1.57 (m, 1H), 1.26 (s, 3H). | 22 |

TABLE 23-continued

Characterization data for exemplary compounds

| Compound No. | Chemical Structure | M + 1 | $^1$H NMR (400 MHz) | Example of Synthesis |
|---|---|---|---|---|
| I-815 | 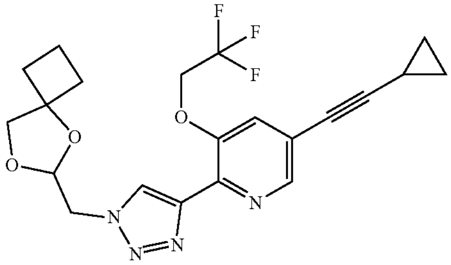 [SMILES: FC(F)(F)COc1cc(C#CC2CC2)cnc1-c1cn(CC2OCC3(CCC3)O2)nn1] | 435.1 | $^1$HNMR (400 MHz, DMSO-$d_6$) δ 8.34 (d, J = 1.6 Hz, 1H), 8.28 (s, 1H), 7.70 (d, J = 1.2 Hz, 1H), 5.29 (t, J = 3.2 Hz, 1H), 5.01 (q, J = 8.8 Hz, 2H), 4.58-4.69 (m, 2H), 3.86 (d, J = 8.0 Hz, 1H), 3.80 (d, J = 8.0 Hz, 1H), 2.18-2.26 (m, 1H), 1.92-2.07 (m, 2H), 1.77-1.83 (m, 1H), 1.54-1.66 (m, 2H), 1.38-1.45 (m, 1H), 0.93-0.98 (m, 2H), 0.78-0.82 (m, 2H). | 3 |
| I-816 | 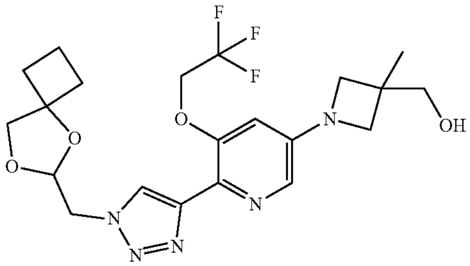 [SMILES: CC1(CO)CN(c2cnc(-c3cn(CC4OCC5(CCC5)O4)nn3)c(OCC(F)(F)F)c2)C1] | 470.2 | $^1$HNMR (400 MHz, DMSO-$d_6$) δ 8.05 (s, 1H), 7.57 (d, J = 2.4 Hz, 1H), 6.63 (d, J = 2.0 Hz, 1H), 5.27 (t, J = 7.2 Hz, 1H), 4.88-4.96 (m, 3H), 4.51-4.63 (m, 2H), 3.79-3.87 (m, 4H), 3.54 (d, J = 7.2 Hz, 2H), 3.44 (d, J = 5.2 Hz, 2H), 2.21-2.26 (m, 1H), 1.98-2.07 (m, 2H), 1.81-1.86(m, 1H), 1.58-1.63 (m, 1H), 1.38-1.46 (m, 1H), 1.27 (s, 3H). | 22 |
| I-796 | 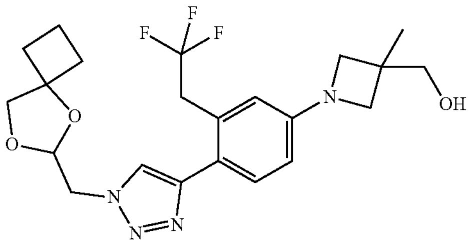 [SMILES: CC1(CO)CN(c2ccc(-c3cn(CC4OCC5(CCC5)O4)nn3)c(CC(F)(F)F)c2)C1] | 453.2 | $^1$HNMR (400 MHz, DMSO-$d_6$) δ 8.12 (s, 1H), 7.35 (d, J = 8.4 Hz, 1H), 6.43-6.48 (m, 2H), 5.32 (t, J = 3.2 Hz, 1H), 4.90 (s, 1H), 4.55 (d, J = 3.2 Hz, 2H), 4.02 (q, J = 11.6 Hz, 2H), 3.80-3.85 (m, 2H), 3.70 (d, J = 7.2 Hz, 2H), 3.42-3.44 (m, 4H), 2.23 (q, J = 10.4 Hz, 2H), 2.01-2.08 (m, 1H), 1.82-1.88 (m, 1H), 1.57-1.65 (m, 1H), 1.37-1.47 (m, 1H), 1.26 (s, 3H). | 22 |
| I-808 | 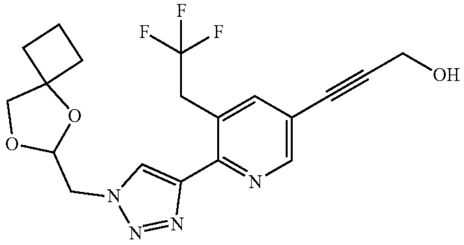 [SMILES: OCC#Cc1cnc(-c2cn(CC3OCC4(CCC4)O3)nn2)c(CC(F)(F)F)c1] | 408.2 | $^1$HNMR (400 MHz, DMSO-$d_6$) δ 8.41 (s, 1H), 7.64 (d, J = 8.0 Hz, 1H), 7.55 (s, 1H), 7.50 (d, J = 8.0 Hz, 1H), 5.40 (t, J = 5.6 Hz, 1H), 5.34 (s, 1H), 4.62 (d, J = 2.8 Hz, 2H), 4.34 (d, J = 5.6 Hz, 2H), 4.20 (q, J = 11.2 Hz, 2H), 3.83 (q, J = 8.0 Hz, 2H), 2.23 (q, J = 10.0 Hz, 1H), 1.98-2.06 (m, 2H), 1.79-1.83 (m, 1H), 1.56-1.64 (m, 1H), 1.39-1.48 (m, 1H). | 6 |
| I-797 | 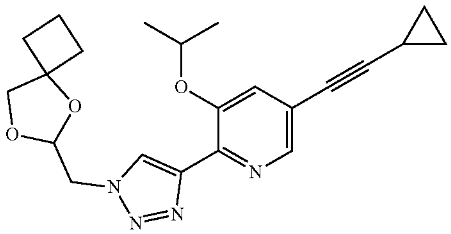 [SMILES: CC(C)Oc1cc(C#CC2CC2)cnc1-c1cn(CC2OCC3(CCC3)O2)nn1] | 395.3 | $^1$HNMR (400 MHz, DMSO-$d_6$) δ 8.40 (s, 1H), 8.21 (d, J = 1.2 Hz, 1H), 7.55 (d, J = 1.6 Hz, 1H), 5.32 (t, J = 3.2 Hz, 1H), 4.85-4.88 (m, 1H), 4.62-4.64 (m, 2H), 3.84 (q, J = 8.0 Hz, 2H), 2.18-2.23 (m, 1H), 1.98-2.08 (m, 2H), 1.84-1.87 (m, 1H), 1.58-1.64 (m, 2H), 1.42-1.47 (m, 1H), 1.35 (d, J = 6.0 Hz, 6H), 0.91-0.96 (m, 2H), 0.78-0.82 (m, 2H). | 3 |

TABLE 23-continued

| Characterization data for exemplary compounds | | | | |
|---|---|---|---|---|
| Compound No. | Chemical Structure | M + 1 | $^1$H NMR (400 MHz) | Example of Synthesis |
| I-809 | 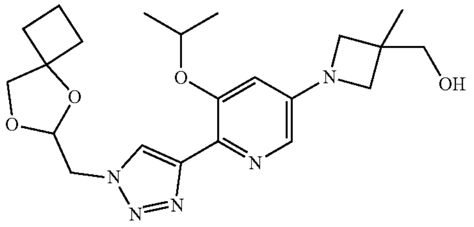 [SMILES: CC(C)Oc1cc(N2CC(C)(CO)C2)cnc1-c1cn(CC2OCC3(CCC3)O2)nn1] | 430.3 | $^1$HNMR (400 MHz, DMSO-$d_6$) δ 8.17 (s, 1H), 7.47 (d, J = 2.0 Hz, 1H), 6.48 (d, J = 2.0 Hz, 1H), 5.30 (t, J = 3.2 Hz, 1H), 4.93 (t, J = 4.8 Hz, 1H), 4.75-4.82 (m, 1H), 4.53-4.62 (m, 2H), 3.87 (d, J = 8.4 Hz, 1H), 3.82 (d, J = 8.4 Hz, 1H), 3.76 (d, J = 7.2 Hz, 2H), 3.51 (d, J = 7.2 Hz, 2H), 3.44 (d, J = 4.8 Hz, 2H), 2.22 (q, J = 10.0 Hz, 1H), 2.00-2.08 (m, 2H), 1.85-1.91 (m, 1H), 1.58-1.64 (m, 1H), 1.43-1.47 (m, 1H), 1.32-1.34 (m, 6H), 1.27 (s, 3H). | 22 |
| I-821 | 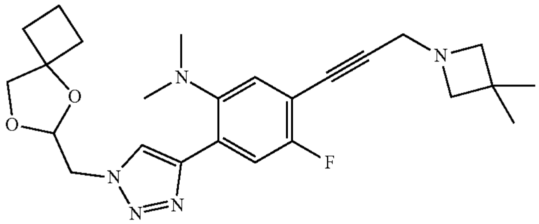 [SMILES: CN(C)c1cc(C#CCN2CC(C)(C)C2)c(F)cc1-c1cn(CC2OCC3(CCC3)O2)nn1] | 454.4 | $^1$HNMR (400 MHz, DMSO-$d_6$) 8.52 (s, 1H), 7.89 (d, J = 10.8 Hz, 1H), 7.33 (d, J = 6.8 Hz, 1H), 5.32 (t, J = 3.2 Hz, 1H), 4.63 (d, J = 3.2 Hz, 2H), 3.83 (s, 2H), 3.49 (s, 2H), 3.03 (s, 4H), 2.59 (s, 6H), 2.19-2.26 (m, 1H), 2.03-2.08 (m, 2H), 1.84-1.89(m, 1H), 1.60-1.65 (m, 1H), 1.40-1.47 (m, 1H), 1.18 (s, 6H). | 6 |
| I-786 | 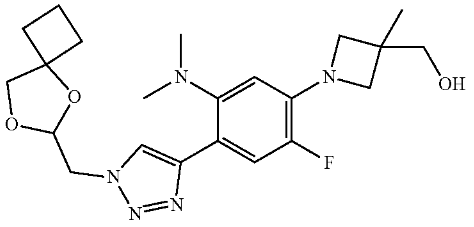 [SMILES: CN(C)c1cc(N2CC(C)(CO)C2)c(F)cc1-c1cn(CC2OCC3(CCC3)O2)nn1] | 432.3 | $^1$HNMR (400 MHz, DMSO-$d_6$) 8.26 (s, 1H), 7.64 (d, J = 14.0 Hz, 1H), 6.28 (d, J = 8.8 Hz, 1H), 5.30 (t, J = 3.6 Hz, 1H), 4.89 (t, J = 5.2 Hz, 1H), 4.57 (d, J = 3.2 Hz, 2H), 3.83 (s, 2H), 3.79-3.82 (m, 2H), 3.54 (dd, J = 1.6 Hz, 7.2 Hz, 2H), 3.44 (d, J = 5.2 Hz, 2H), 2.55 (s, 6H), 2.18-2.26 (m, 1H), 2.02-2.09 (m, 2H), 1.86-1.93 (m, 1H), 1.58-1.66 (m, 1H), 1.41-1.48 (m, 1H), 1.25 (s, 3H). | 22 |
| I-798 | 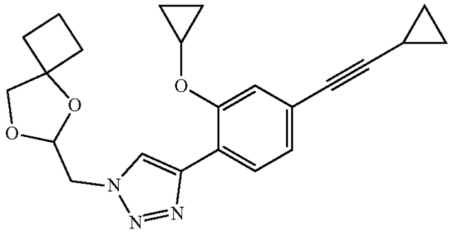 [SMILES: C(#CC1CC1)c1ccc(-c2cn(CC3OCC4(CCC4)O3)nn2)c(OC2CC2)c1] | 392.2 | $^1$HNMR (400 MHz, DMSO-$d_6$) δ 8.18 (s, 1H), 8.06 (d, J = 7.6 Hz, 1H), 7.36 (d, J = 1.2 Hz, 1H), 7.07 (dd, J = 1.6 Hz? 8.0 Hz, 1H), 5.31 (t, J = 3.6 Hz, 1H), 4.59 (d, J = 3.6 Hz, 2H), 4.03-4.06 (m, 1H), 3.83 (q, J = 8.0 Hz, 2H), 2.18-2.23 (m, 1H), 2.01-2.09 (m, 2H), 1.86-1.90 (m, 1H), 1.55-1.63 (m, 2H), 1.42-1.47 (m, 1H), 0.73-0.93 (m, 8H). | 2 |
| I-810 | 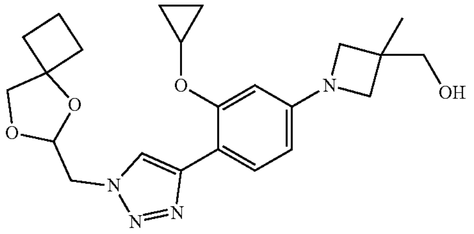 [SMILES: CC1(CO)CN(c2ccc(-c3cn(CC4OCC5(CCC5)O4)nn3)c(OC3CC3)c2)C1] | 427.3 | $^1$HNMR (400 MHz, DMSO-$d_6$) δ 7.96 (s, 1H), 7.88 (d, J = 8.4 Hz, 1H), 6.38 (d, J = 2.0 Hz, 1H), 6.11 (dd, , I = 2.4 Hz, 8.4 Hz, 1H), 5.29 (t, J = 3.6 Hz, 1H), 4.91 (t, J = 5.2 Hz, 1H), 4.53 (d, J = 3.6 Hz, 2H), 3.92-3.96 (m, 1H), 3.81-3.87 (m, 2H), 3.66-3.72 (m, 2H), 3.44-3.46 (m, 4H), 2.18-2.26 (m, 1H), 2.04-2.11 (m, 2H), 1.83-1.93 (m, 1H), 1.58-1.64 (m, 1H), 1.41-1.48 (m, 1H), 1.26 (s, 3H), 0.72-0.86 (m, 4H). | 22 |

TABLE 23-continued

| Compound No. | Chemical Structure | M + 1 | $^1$H NMR (400 MHz) | Example of Synthesis |
|---|---|---|---|---|
| Characterization data for exemplary compounds | | | | |
| I-799 | 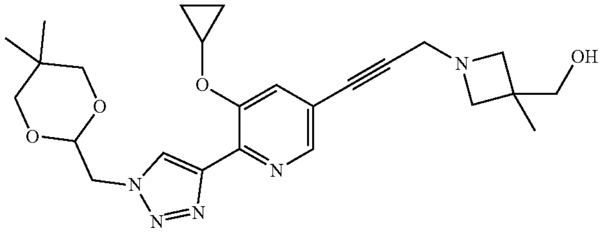 [SMILES: CC1(C)COC(Cn2cc(-c3ncc(C#CCN4CC(C)(CO)C4)cc3OC3CC3)nn2)OC1] | 468.4 | $^1$HNMR (400 MHz, $CDCl_3$) δ 8.46-8.48 (m, 1H), 8.21 (s, 1H), 7.69 (s, 1H), 4.81 (t, J = 4.4 Hz, 1H), 4.57-4.59 (m, 2H), 3.86-3.89 (m, 1H), 3.62-3.66 (m, 4H), 3.55 (d, J = 1.6 Hz, 2H), 3.40-3.45 (m, 4H), 3.19 (d, J = 5.6 Hz, 2H), 1.22 (s, 3H), 1.17 (s, 3H), 0.86-0.97 (m, 4H), 0.73 (s, 3H). | 28 |
| I-789 | 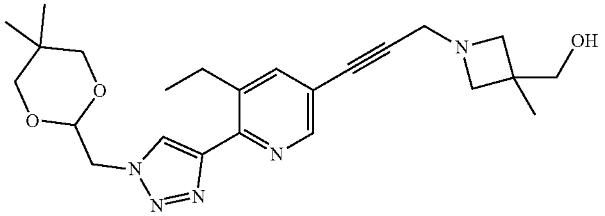 [SMILES: CCc1cc(C#CCN2CC(C)(CO)C2)cnc1-c1cn(CC2OCC(C)(C)CO2)nn1] | 440.4 | $^1$HNMR (400 MHz, $CDCl_3$) δ 8.52 (d, J = 2.0 Hz, 1H), 8.24 (s, 1H), 7.68 (d, J = 2.0 Hz, 1H), 4.83 (t, J = 4.8 Hz, 1H), 4.57 (d, J = 4.4 Hz, 2H), 3.63-3.66 (m, 4H), 3.55 (s, 2H), 3.41-3.45 (m, 4H), 3.18-3.23 (m, 4H), 1.28 (t, J = 7.6 Hz, 3H), 1.22 (s, 3H), 1.16 (s, 3H), 0.73 (s, 3H). | 28 |
| I-800 | 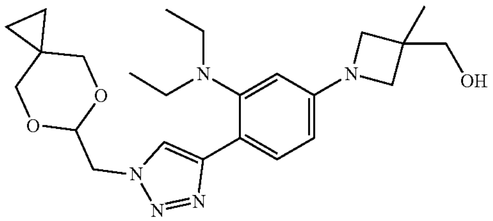 [SMILES: CCN(CC)c1cc(N2CC(C)(CO)C2)ccc1-c1cn(CC2OCC3(CC3)CO2)nn1] | 442.2 | $^1$HNMR (400 MHz, DMSO-$d_6$) δ 8.37 (s, 1H), 7.86 (d, J = 8.4 Hz, 1H), 6.19-6.24 (m, 2H), 5.02 (t, J = 4.8 Hz, 1H), 4.86-4.89 (m, 1H), 4.55 (d, J = 4.8 Hz, 2H), 4.08 (d, J = 11.6 Hz, 2H), 3.66 (d, J = 6.8 Hz, 2H), 3.40-3.44 (m, 4H), 3.24 (d, J = 11.6 Hz, 2H), 2.89 (q, J = 6.8 Hz, 4H), 1.25 (s, 3H), 0.91 (t, J = 7.2 Hz, 6H), 0.55-0.58 (m, 2H), 0.30-0.34 (m, 2H). | 22 |
| I-801 | 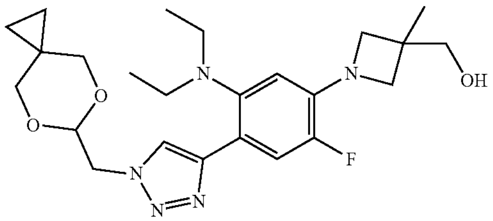 [SMILES: CCN(CC)c1cc(N2CC(C)(CO)C2)c(F)cc1-c1cn(CC2OCC3(CC3)CO2)nn1] | 460.3 | $^1$HNMR (400 MHz, DMSO-$d_6$) 8.48 (s, 1H), 7.67 (d, J = 14.0 Hz, 1H), 6.30 (d, J = 9.2 Hz, 1H), 5.02 (t, J = 4.8 Hz, 1H), 4.89 (t, J = 5.6 Hz, 1H), 4.57 (d, J = 4.4 Hz, 2H), 4.08 (d, J = 11.6 Hz, 2H), 3.79 (dd, J = 1.6 Hz, 7.2 Hz, 2H), 3.53 (dd, J = 1.6 Hz, 6.8 Hz, 2H), 3.44 (d, J = 5.6 Hz, 2H), 3.24 (d, J = 11.6 Hz, 2H), 2.88 (q, J = 6.8 Hz, 4H), 1.25 (s, 3H), 0.89 (t, J = 7.2 Hz, 6H), 0.54-0.58 (m, 2H), 0.30-0.34 (m, 2H). | 22 |
| I-817 | 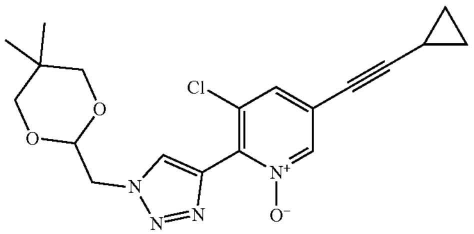 [SMILES: CC1(C)COC(Cn2cc(-c3c(Cl)cc(C#CC4CC4)c[n+]3[O-])nn2)OC1] | 389.3 | $^1$HNMR (400 MHz, DMSO-$d_6$) 8.72 (s, 1H), 8.45 (d, J = 1.6 Hz, 1H), 7.66 (d, J = 1.2 Hz, 1H), 4.93 (t, J = 4.0 Hz, 1H), 4.65 (d, J = 4.0 Hz, 2H), 3.56 (d, J = 11.2 Hz, 2H), 3.47 (d, J = 10.8 Hz, 2H), 1.59-1.65 (m, 1H), 1.03 (s, 3H), 0.95-0.98 (m, 2H), 0.82-0.85 (m, 2H), 0.67 (s, 3H). | 2 |
| I-822 | 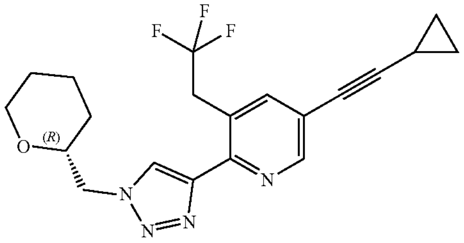 | 391.3 | $^1$HNMR (400 MHz, DMSO-$d_6$) δ 8.60 (d, J = 2.0 Hz, 1H), 8.54 (s, 1H), 7.89 (s, 1H), 4.41-4.55 (m, 4H), 3.84-3.87 (m, 1H), 3.72-3.77 (m, 1H), 3.28-3.29 (m, 1H), 1.78-1.80 (m, 1H), 1.60-1.65 (m, 2H), 1.42-1.50 (m, 3H), 1.17-1.23 (m, 1H), 0.92-0.97 (m, 2H), 0.79-0.83 (m, 2H). | 4 |

TABLE 23-continued

| Compound No. | Chemical Structure | M + 1 | $^1$H NMR (400 MHz) | Example of Synthesis |
|---|---|---|---|---|
| Characterization data for exemplary compounds | | | | |
| I-818 | 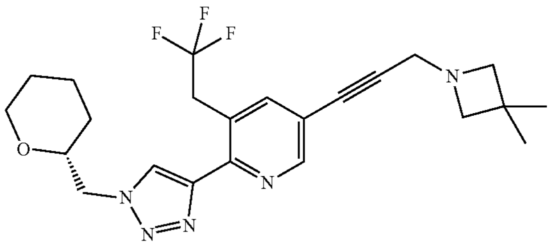 [SMILES: CC1(C)CN(CC#Cc2cnc(-c3cn(C[C@H]4CCCCO4)nn3)c(CC(F)(F)F)c2)C1] | 448.3 | $^1$HNMR (400 MHz, $CDCl_3$) δ 8.63 (d, J = 2.0 Hz, 1H), 8.29 (s, 1H), 7.79 (s, 1H), 4.334.52 (m, 4H), 3.99-4.02 (m, 1H), 3.69-3.75 (m, 1H), 3.58 (s, 2H), 3.38-3.44 (m, 1H), 3.25 (s, 4H), 1.86-1.90 (m, 1H), 1.68 (d, J = 12.8 Hz, 1H), 1.51-1.59 (m, 3H), 1.28-1.34 (m, 7H). | 28 |
| I-823 | 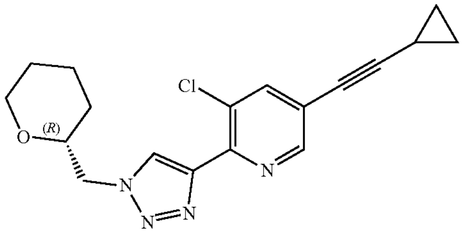 | 343.2 | $^1$HNMR (400 MHz, DMSO-$d_6$) 8.59 (s, 2H), 8.06 (d, J = 2.0 Hz, 1H), 4.45-4.51 (m, 2H), 3.83-3.88 (m, 1H), 3.72-3.77 (m, 1H), 3.41-3.48 (m, 1H), 1.78-1.83 (m, 1H), 1.58-1.66 (m, 2H), 1.39-1.48 (m, 3H), 1.16-1.24 (m, 1H), 0.94-0.97 (m, 2H), 0.79-0.84 (m, 2H). | 2 |
| I-833 | 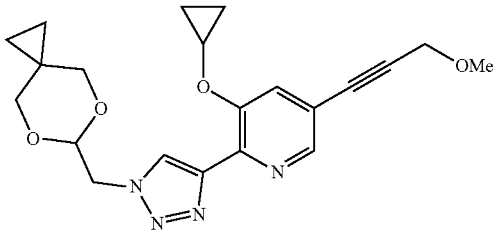 [SMILES: COCC#Cc1cnc(-c2cn(CC3OCC4(CC4)CO3)nn2)c(OC2CC2)c1] | 397.3 | $^1$HNMR (400 MHz, $CDCl_3$) δ 8.49 (d, J = 1.6 Hz, 1H), 8.21 (s, 1H), 7.70 (d, J = 1.2 Hz, 1H), 4.99 (t, J = 4.8 Hz, 1H), 4.61 (d, J = 5.2 Hz, 2H), 4.37 (s, 2H), 4.11 (d, J = 11.6 Hz, 2H), 3.85-3.88 (m, 1H), 3.49 (s, 3H), 3.26 (d, J = 11.6 Hz, 2H), 0.83-0.95 (m, 4H), 0.69-0.73 (m, 2H), 0.35-0.39 (m, 2H). | 3 |
| I-834 | 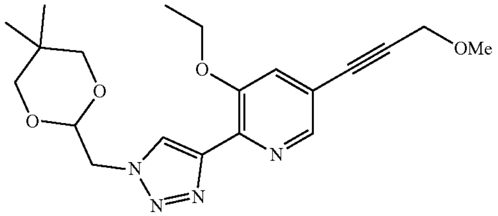 [SMILES: CCOc1cc(C#CCOC)cnc1-c1cn(CC2OCC(C)(C)CO2)nn1] | 387.3 | $^1$HNMR (400 MHz, DMSO-$d_6$) δ 8.50 (s, 1H), 8.33 (d, J = 1.6 Hz, 1H), 7.63 (d, J = 1.2 Hz, 1H), 4.91 (t, J = 4.4 Hz, 1H), 4.63 (d, J = 4.0 Hz, 2H), 4.39 (s, 2H), 4.24 (q, J = 7.2 Hz, 2H), 3.57 (d, J = 11.2 Hz, 2H), 3.48 (d, J = 10.8 Hz, 2H), 3.36 (s, 3H), 1.43 (t, J = 7.2 Hz 3H), 1.03 (s, 3H), 0.68 (s, 3H). | 3 |
| I-837 | 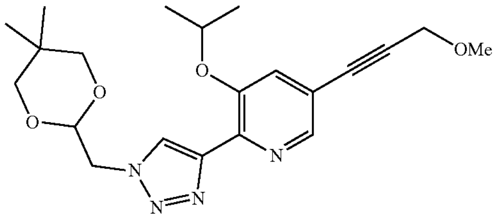 [SMILES: COCC#Cc1cnc(-c2cn(CC3OCC(C)(C)CO3)nn2)c(OC(C)C)c1] | 401.4 | $^1$HNMR (400 MHz, DMSO-$d_6$) δ 8.49 (s, 1H), 8.32 (d, J = 1.6 Hz, 1H), 7.67 (d, J = 1.6 Hz, 1H), 4.88-4.92 (m, 2H), 4.64 (d, J = 4.0 Hz, 2H), 4.39 (s, 2H), 3.56 (d, J = 11.2 Hz, 2H), 3.49 (d, J = 10.8 Hz, 2H), 3.37 (s, 3H), 1.35 (d, J = 6.0 Hz, 6H), 1.02 (s, 3H), 0.68 (s, 3H). | 3 |
| I-819 | 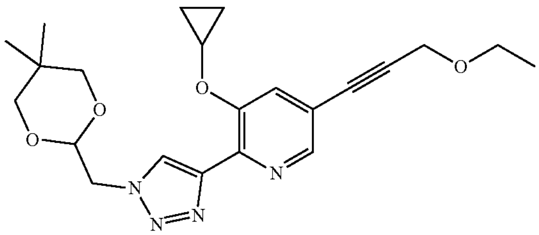 [SMILES: CCOCC#Cc1cnc(-c2cn(CC3OCC(C)(C)CO3)nn2)c(OC2CC2)c1] | 413.3 | $^1$HNMR (400 MHz, $CDCl_3$) δ 8.50 (s, 1H), 8.28 (s, 1H), 7.74 (s, 1H), 4.82 (s, 1H), 4.59 (d, J = 4.0 Hz, 2H), 4.41 (s, 2H), 3.88-3.89 (m, 1H), 3.62-3.70 (m, 4H), 3.44 (d, J = 11.2 Hz, 2H), 1.29 (t, J = 6.8 Hz, 3H), 1.17 (s, 3H), 0.87-0.94 (m, 4H), 0.73 (s, 3H). | 3 |

TABLE 23-continued

| Characterization data for exemplary compounds | | | | |
|---|---|---|---|---|
| Compound No. | Chemical Structure | M + 1 | $^1$H NMR (400 MHz) | Example of Synthesis |
| I-873 | 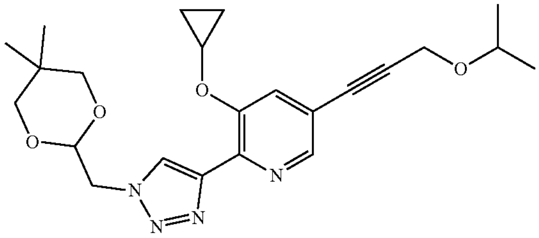 [SMILES: CC(C)OCC#Cc1cnc(-c2cn(CC3OCC(C)(C)CO3)nn2)c(OC2CC2)c1] | 427.2 | $^1$HNMR (400 MHz, DMSO-$d_6$) δ 8.35-8.47 (m, 2H), 7.87 (s, 1H), 4.90 (s, 1H), 4.63 (s, 2H), 4.44 (s, 2H), 4.14 (s, 1H), 3.77-3.83 (m, 1H), 3.56 (d, J = 10.8 Hz, 2H), 3.47 (d, J = 11.2 Hz, 2H), 1.15 (d, J = 6.0 Hz, 6H), 1.03 (s, 3H), 0.81-0.90 (m, 4H), 0.68 (s, 3H). | 28 |
| I-829 | 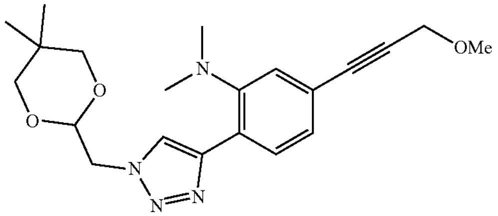 [SMILES: COCC#Cc1ccc(-c2cn(CC3OCC(C)(C)CO3)nn2)c(N(C)C)c1] | 385.3 | $^1$HNMR (400 MHz, DMSO-$d_6$) δ 8.47 (s, 1H), 8.05 (d, J = 8.0 Hz, 1H), 7.19-7.24 (m, 2H), 4.89 (t, J = 4.4 Hz, 1H), 4.60 (d, J = 4.4 Hz, 2H), 4.34 (s, 2H), 3.57 (d, J = 10.8 Hz, 2H), 3.46 (d, J = 11.2 Hz, 2H), 3.35 (s, 3H), 2.59 (s, 6H), 1.02 (s, 3H), 0.67 (s, 3H). | 3 |
| I-874 | 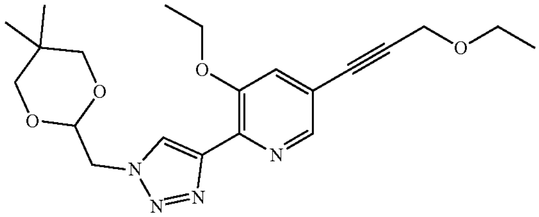 [SMILES: CCOCC#Cc1cnc(-c2cn(CC3OCC(C)(C)CO3)nn2)c(OCC)c1] | 401.4 | $^1$HNMR (400 MHz, DMSO-$d_6$) δ 8.49 (s, 1H), 8.32 (d, J = 1.2 Hz, 1H), 7.62 (d, J = 1.2 Hz, 1H), 4.91 (t, J = 4.0 Hz, 1H), 4.62 (d, J = 4.0 Hz, 2H), 4.41 (s, 2H), 4.23 (q, J = 6.8 Hz, 2H), 3.55-3.61 (m, 4H), 3.48 (d, J = 11.2 Hz, 2H), 1.43 (t, J = 6.8 Hz, 3H), 1.17 (t, J = 6.8 Hz, 3H), 1.03 (s, 3H), 0.68 (s, 3H). | 3 |
| I-875 | 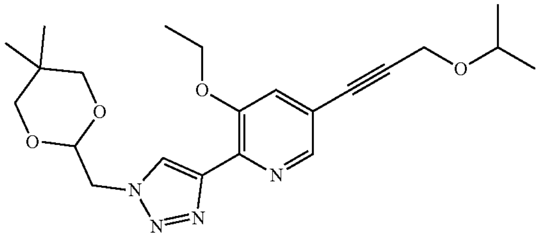 | 415.4 | $^1$HNMR (400 MHz, DMSO-$d_6$) δ 8.49 (s, 1H), 8.31 (s, 1H), 7.61 (s, 1H), 4.91 (t, J = 4.0 Hz, 1H), 4.62 (d, J = 4.0 Hz, 2H), 4.41 (s, 2H), 4.23 (q J = 6.8 Hz, 2H), 3.79-3.82 (m, 1H), 3.56 (d, J = 10.8 Hz, 2H), 3.48 (d, J = 10.8 Hz, 2H), 1.43 (t, J = 6.8 Hz, 3H), 1.15 (d, J = 6.4 Hz, 6H), 1.03 (s, 3H), 0.68 (s, 3H). | 3 |
| I-838 | 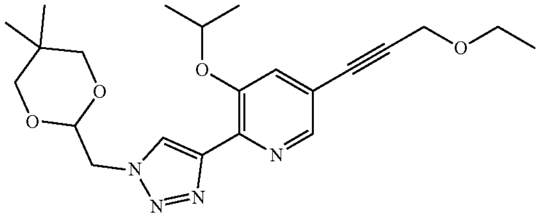 [SMILES: CCOCC#Cc1cnc(-c2cn(CC3OCC(C)(C)CO3)nn2)c(OC(C)C)c1] | 415.3 | $^1$HNMR (400 MHz, DMSO-$d_6$) δ 8.49 (s, 1H), 8.31 (d, J = 2.0 Hz, 1H), 7.66 (d, J = 1.6 Hz, 1H), 4.88-4.92 (m, 2H), 4.63 (d, J = 4.0 Hz, 2H), 4.41 (s, 2H), 3.55-3.61 (m, 4H), 3.48 (d, J = 10.8 Hz, 2H), 1.34 (d, J = 5.6Hz, 6H), 1.17 (t, J = 6.8 Hz, 3H), 1.02 (s, 3H), 0.68 (s, 3H). | 3 |
| I-846 | 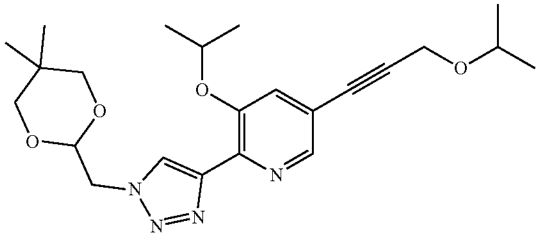 [SMILES: CC(C)OCC#Cc1cnc(-c2cn(CC3OCC(C)(C)CO3)nn2)c(OC(C)C)c1] | 429.3 | $^1$HNMR (400 MHz, DMSO-$d_6$) δ 8.49 (s, 1H), 8.30 (d, J = 1.6 Hz, 1H), 7.65 (d, J = 1.6 Hz, 1H), 4.88-4.92 (m, 2H), 4.63 (d, J = 4.0 Hz, 2H), 4.41 (s, 2H), 3.77-3.83 (m, 1H), 3.56 (d, J = 11.2 Hz, 2H), 3.49 (d, J = 10.4 Hz, 2H), 1.35 (d, J = 6.0 Hz, 6H), 1.15 (d, J = 6.0 Hz, 6H), 1.02 (s, 3H), 0.68 (s, 3H). | 3 |

TABLE 23-continued

Characterization data for exemplary compounds

| Compound No. | Chemical Structure | M + 1 | $^1$H NMR (400 MHz) | Example of Synthesis |
|---|---|---|---|---|
| I-847 | 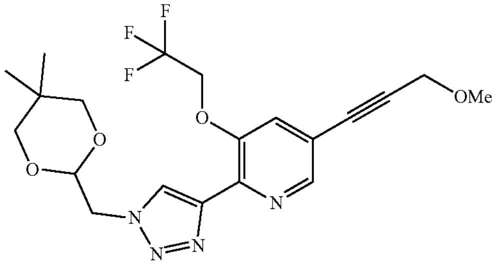 [SMILES: COCC#Cc1cnc(-c2cn(CC3OCC(C)(C)CO3)nn2)c(OCC(F)(F)F)c1] | 441.3 | $^1$HNMR (400 MHz, DMSO-$d_6$) δ 8.45 (d, J = 1.6 Hz, 1H), 8.37 (s, 1H), 7.83 (d, J = 1.6 Hz, 1H), 5.03 (q, J = 8.4 Hz, 2H), 4.88 (t, J = 4.4 Hz, 1H), 4.63 (d, J = 4.0 Hz, 2H), 4.40 (s, 2H), 3.55 (d, J = 10.8 Hz, 2H), 3.47 (d, J = 10.8 Hz, 2H), 3.37 (s, 3H), 0.99 (s, 3H), 0.67 (s, 3 H). | 3 |
| I-848 | 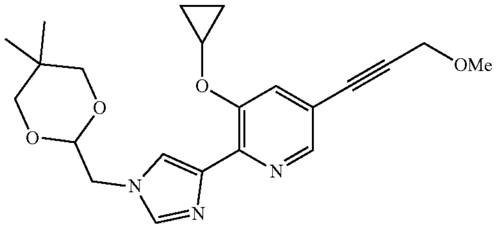 [SMILES: COCC#Cc1cnc(-c2cn(CC3OCC(C)(C)CO3)cn2)c(OC2CC2)c1] | 398.3 | $^1$HNMR (400 MHz, DMSO-$d_6$) δ 8.28 (d, J = 1.6 Hz, 1H), 7.73-7.74 (m, 2H), 7.67 (s, 1H), 4.73 (t, J = 4.0 Hz, 1H), 4.38 (s, 2H), 4.18 (d, J = 4.0 Hz, 2H), 4.08-4.11 (m, 1H), 3.56 (d, J = 10.8 Hz, 2H), 3.45 (d, J = 10.8 Hz, 2H), 3.36 (s, 3H), 1.03 (s, 3H), 0.76-0.89 (m, 4H), 0.67 (s, 3H). | 23 |
| I-851 | 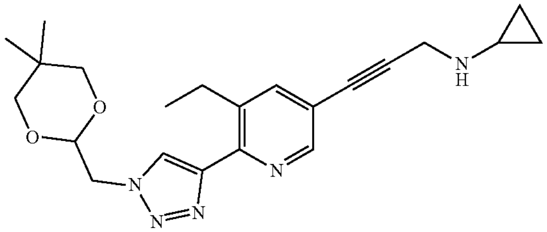 [SMILES: CCc1cc(C#CCNC2CC2)cnc1-c1cn(CC2OCC(C)(C)CO2)nn1] | 395.4 | $^1$HNMR (400 MHz, DMSO-$d_6$) δ 8.31 (s, 1H), 8.23 (s, 1H), 7.61 (d, J = 8.0 Hz, 1H), 7.37 (d, J = 1.6 Hz, 1H), 7.31 (dd, J = 1.6 Hz, 8.0 Hz, 1H), 4.92 (t, J = 4.0 Hz, 1H), 4.58 (d, J = 4.4 Hz, 2H), 3.58 (s, 2H), 3.47 (d, J = 10.8 Hz, 4H), 2.80 (q, J = 7.6 Hz, 2H), 2.29-2.32 (m, 1H), 1.12 (t, J = 7.6 Hz, 3H), 1.02 (s, 3H), 0.68 (s, 3H), 0.39-0.42 (m, 2H), 0.26-0.30 (m, 2H). | 28 |
| I-856 | 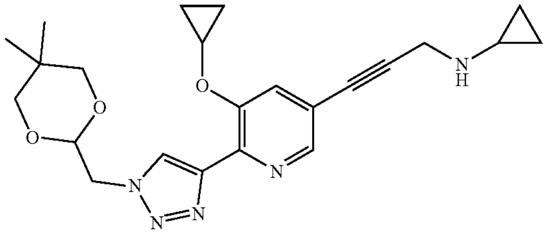 | 424.3 | $^1$HNMR (400 MHz, DMSO-$d_6$) δ 8.39 (s, 1H), 8.32 (d, J = 1.6 Hz, 1H), 7.80 (d, J = 2.0 Hz, 1H), 4.90 (t, J = 4.4 Hz, 1H), 4.61 (d, J = 4.0 Hz, 2H), 4.11-4.15 (m, 1H), 3.61 (s, 2H), 3.56 (d, J = 11.2 Hz, 2H), 3.47 (d, , I = 10.8 Hz, 2H), 2.82-2.89 (br, 1H), 2.29-2.34 (m, 1H), 1.04 (s, 3H), 0.77-0.91 (m, 4H), 0.64 (s, 3H), 0.38-0.44 (m, 2H), 0.24-0.31 (m, 2H). | 28 |
| I-857 | 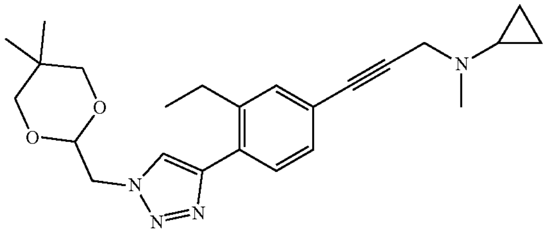 [SMILES: CCc1cc(C#CCN(C)C2CC2)ccc1-c1cn(CC2OCC(C)(C)CO2)nn1] | 409.4 | $^1$HNMR (400 MHz, DMSO-$d_6$) δ 8.32 (s, 1H), 7.63 (d, J = 7.6 Hz, 1H), 7.40 (d, J = 1.6 Hz, 1H), 7.34 (dd, J = 1.6 Hz, 8.0 Hz, 1H), 4.92 (t, J = 4.4 Hz, 1H), 4.59 (d, J = 4.0 Hz, 2H), 3.61 (s, 2H), 3.57 (d, J = 11.2 Hz, 2H), 3.47 (d, J = 10.8 Hz, 2H), 2.81 (q, J = 7.2 Hz, 2H), 2.39 (s, 3H), 1.91-1.94(m, 1H), 1.13 (t, J = 7.6 Hz, 3H), 1.03 (s, 3H), 0.68 (s, 3H), 0.46-0.49 (m, 2H), 0.36-0.38 (m, 2H). | 28 |

TABLE 23-continued

| Compound No. | Chemical Structure | M + 1 | $^1$H NMR (400 MHz) | Example of Synthesis |
|---|---|---|---|---|
| I-858 | 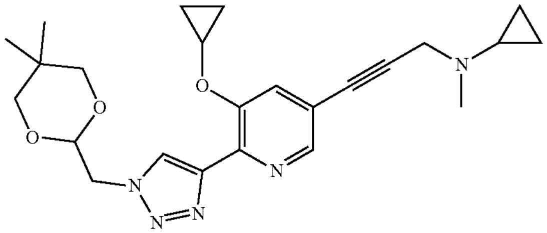 [SMILES: CN(CC#Cc1cnc(-c2cn(CC3OCC(C)(C)CO3)nn2)c(OC2CC2)c1)C1CC1] | 438.3 | $^1$HNMR (400 MHz, DMSO-$d_6$) δ 8.40 (s, 1H), 8.36 (d, J = 1.6 Hz, 1H), 7.83 (d, J = 1.6 Hz, 1H), 4.91 (t, J = 4.4 Hz, 1H), 4.62 ( d, J = 4.0 Hz, 2H), 4.14-4.16 (m, 1H), 3.67 (s, 2H), 3.57 (d, J = 11.2 Hz, 2H), 3.47 (d, J = 10.8 Hz, 2H), 2.42 (s, 3H), 1.93-1.96 (m, 1H), 1.04 (s, 3H), 0.80-0.89 (m, 4H), 0.68 (s, 3H), 0.47-0.50 (m, 2H), 0.37-0.39 (m, 2H). | 28 |
| I-876 | 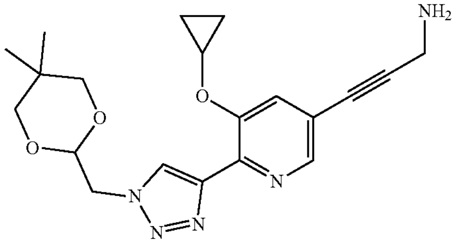 [SMILES: CC1(C)COC(Cn2cc(-c3ncc(C#CCN)cc3OC3CC3)nn2)OC1] | 384.3 | $^1$HNMR (400 MHz, DMSO-$d_6$) δ 8.39 (s, 1H), 8.31 (d, J = 1.6 Hz, 1H), 7.79 (d, J = 1.6 Hz, 1H), 4.90 (t, J = 4.4 Hz, 1H), 4.61 (d, J = 4.4 Hz, 2H ), 4.10-4.14 (m, 1H), 3.63 (s, 2H), 3.56 (d, J = 10.8 Hz, 2H), 3.47 (d, J = 11.2 Hz, 2H), 3.24-3.41 (m, 2H), 1.03 (s, 3H), 0.79-0.91 (m, 4H), 0.68 (s, 3H). | 28 |
| I-859 | 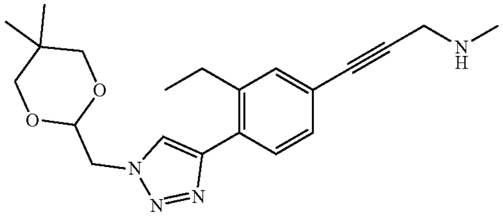 | 369.3 | $^1$HNMR (400 MHz, DMSO-$d_6$) δ 8.31 (s, 1H), 7.61 (d, J = 8.0 Hz, 1H), 7.37 (d, J = 1.6 Hz, 1H), 7.31 (dd, J = 2.0 Hz, 8.0 Hz, 1H), 4.92 (t, J = 4.4 Hz, 1H), 4.58 (d, J = 4.4 Hz, 2H), 3.57 (d, J = 11.2 Hz, 2H), 3.52 (s, 2H), 3.47 (d, J = 10.8 Hz, 2H), 2.80 (q, J = 7.6 Hz, 2H), 2.35 (s, 3H), 1.12 (t, J = 7.6 Hz, 3H), 1.02 (s, 3H), 0.68 (s, 3H). | 28 |
| I-877 | 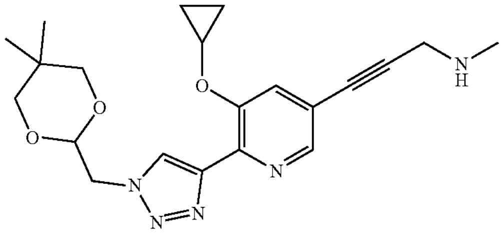 | 398.2 | $^1$HNMR (400 MHz, DMSO-$d_6$) δ 8.39-8.41 (m, 1H), 8.30-8.34 (m, 1H), 7.79-7.81 (m, 1H), 4.91 (t, J = 4.4 Hz, 1H), 4.62 (d, J = 4.0 Hz, 2H), 4.12-4.35 (m, 2H), 3.56 (d, J = 10.4 Hz, 3H), 3.47 (d, J = 10.8 Hz, 2H), 3.16-3.17 (m, 1H), 2.73 (s, 1H), 2.38 (s, 2H), 1.03 (s, 3H), 0.81-0.92 (m, 4H) , 0.68 (s, 3H). | 28 |
| I-852 | 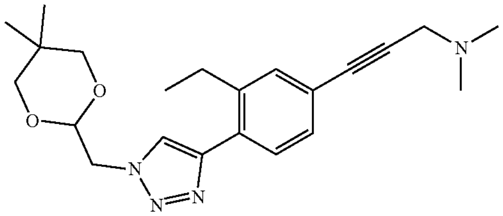 | 383.2 | $^1$HNMR (400 MHz, DMSO-$d_6$) δ 8.32 (s, 1H), 7.62 (d, J = 8.0 Hz, 1H), 7.39 (d, J = 1.6 Hz, 1H), 7.34 (dd, J = 1.6 Hz, 8.0 Hz, 1H), 4.92 (t, J = 4.0 Hz, 1H), 4.59 (d, J = 4.4 Hz, 2H), 3.57(d, J = 10.8 Hz, 2H), 3.47-3.52 (m, 4H), 2.80 (q, J = 7.6 Hz, 2H), 2.25 (s, 6H), 1.13 (t, J = 7.2 Hz, 3H), 1.02 (s, 3H), 0.68 (s, 3H). | 28 |
| I-878 | 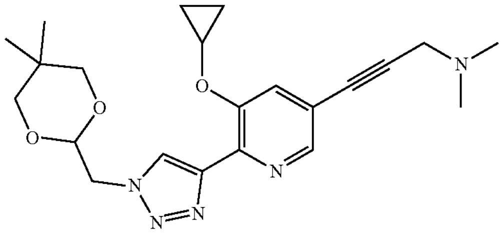 | 412.3 | $^1$HNMR (400 MHz, DMSO-$d_6$) δ 8.40 (s, 1H), 8.35 (d, J = 1.6 Hz, 1H), 7.82 (d, J = 2.0 Hz, 1H), 4.91 (t, J = 4.4 Hz, 1H), 4.61 (d, J = 4.0 Hz, 2H), 4.14-4.15 (m, 1H), 3.56 (d, J = 10.8 Hz, 2H), 3.53 (s, 2H), 3.47 (d, J = 10.8 Hz, 2H), 2.28 (s, 6H), 1.04 (s, 3H), 0.81-0.89 (m, 4H), 0.68 (s, 3H). | 28 |

TABLE 23-continued

| Compound No. | Chemical Structure | M + 1 | $^1$H NMR (400 MHz) | Example of Synthesis |
|---|---|---|---|---|
| I-879 | 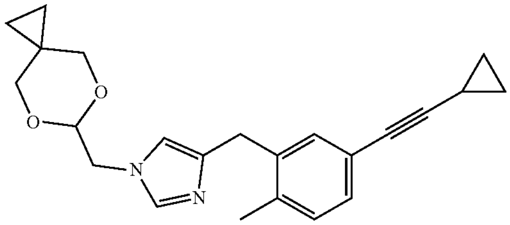 [SMILES: Cc1ccc(C#CC2CC2)cc1Cc1cn(CC2OCC3(CC3)CO2)cn1] | 363.3 | $^1$HNMR (400 MHz, DMSO-$d_6$) δ 7.48 (d, J = 0.8 Hz, 1H), 7.10 (s, 1H), 7.07 (d, J = 0.8 Hz, 2H), 6.76 (s, 1H), 4.80 (t, J = 4.8 Hz, 1H), 4.03 (d, J = 4.4 Hz, 3H), 4.05 (s, 1H), 3.70 (s, 2H), 3.21 (d, J = 11.6 Hz, 2H), 2.26 (s, 3H), 1.46-1.53 (m, 1H), 0.82-0.87 (m, 2H), 0.66-0.70 (m, 2H), 0.54-0.57 (m, 2H), 0.28-0.32 (m, 2H). | 32 |
| I-880 | 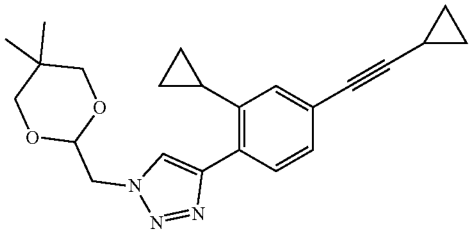 [SMILES: CC1(C)COC(Cn2cc(-c3ccc(C#CC4CC4)cc3C3CC3)nn2)OC1] | 378.4 | $^1$HNMR (400 MHz, $CDCl_3$) δ 8.06 (s, 1H), 7.85 (d, J = 7.6 Hz, 1H), 7.28 (d, J = 8.0 Hz, 1H), 7.14 (s, 1H), 4.82 (s, 1H), 4.59 (s, 2H), 3.64 (d, J = 10.8 Hz, 2H), 3.46 (d, J = 10.8 Hz, 2H), 2.06 (s, 1H), 1.43-1.48 (m, 1H), 1.14 (s, 3H), 0.80-0.94 (m, 6H), 0.73 (s, 5H). | 4 |
| I-860 | 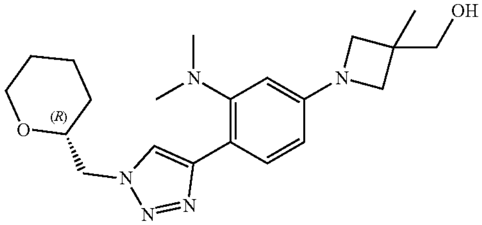 | 386.4 | $^1$HNMR (400 MHz, DMSO-$d_6$) δ 8.17 (s, 1H), 7.80 (d, J = 8.4 Hz, 1H), 6.13-6.17 (m, 2H), 4.89 (br, 1H), 4.34-4.46 (m, 2H), 3.84-3.87 (m, 1H), 3.67-3.69 (m, 3H), 3.41-3.43 (m, 4H), 3.27-3.31 (m, 1H), 2.55 (s, 6H), 1.76-1.79 (m, 1H), 1.61 (d, J = 12.8 Hz, 1H), 1.41-1.51 (m, 3H), 1.25 (s, 3H), 1.14-1.21 (m, 1H). | 22 |
| I-881 | 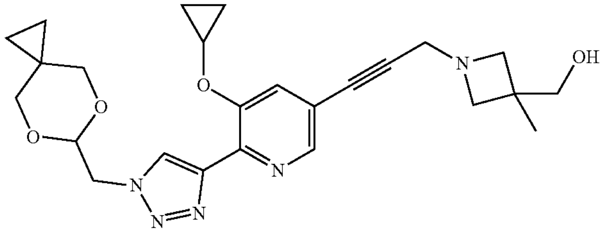 [SMILES: CC1(CO)CN(CC#Cc2cnc(-c3cn(CC4OCC5(CC5)CO4)nn3)c(OC3CC3)c2)C1] | 466.3 | $^1$HNMR (400 MHz, DMSO-$d_6$) δ 8.43 (s, 1H), 8.36 (d, J = 1.2 Hz, 1H), 7.83 (d, J = 1.6 Hz, 1H), 5.08 (t, J = 4.8 Hz, 1H), 4.73 (t, J = 5.6 Hz, 1H), 4.64 (d, J = 4.8 Hz, 2H), 4.11-4.15 (m, 1H), 4.08 ( d, J = 11.2 Hz, 2H), 3.49 (s, 2H), 3.41 (d, J = 5.6 Hz, 2H), 3.25 (d, J = 11.6 Hz, 2H), 3.17 (d, J = 6.8 Hz, 2H), 2.92(d, J = 6.8 Hz, 2H), 1.17 (s, 3H), 0.81-0.91 (m, 4H), 0.57-0.60 (m, 2H), 0.31-0.35 (m, 2H). | 28 |
| I-861 | 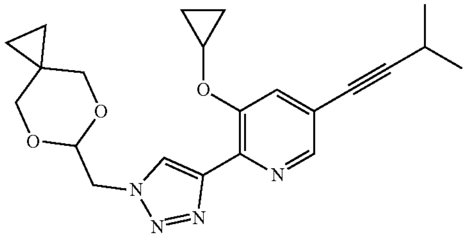 [SMILES: CC(C)C#Cc1cnc(-c2cn(CC3OCC4(CC4)CO3)nn2)c(OC2CC2)c1] | 395.3 | $^1$HNMR (400 MHz, DMSO-$d_6$) δ 8.40 (s, 1H), 8.28 (d, J = 1.6 Hz, 1H), 7.75 (d, J = 1.6 Hz, 1H), 5.08 (t, J = 4.8 Hz, 1H), 4.63 (d, J = 4.8 Hz, 2H), 4.11-4.15 (m, 1H), 4.08 (d, J = 11.2 Hz, 2H), 3.25 (d, J = 11.6 Hz, 2H), 2.85-2.92 (m, 1H), 1.26 (d, J = 6.8 Hz, 6H), 0.80-0.90 (m, 4H), 0.56-0.60 (m, 2H), 0.31-0.34 (m, 2H). | 2 |
| I-862 | 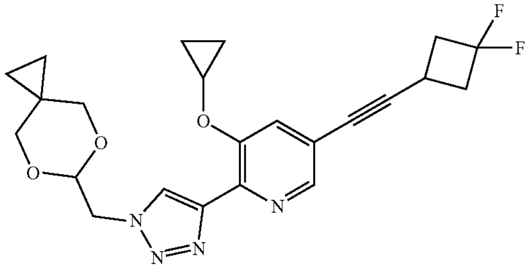 [SMILES: FC1(F)CC(C#Cc2cnc(-c3cn(CC4OCC5(CC5)CO4)nn3)c(OC3CC3)c2)C1] | 443.3 | $^1$HNMR (400 MHz, DMSO-$d_6$) δ 8.42 (s, 1H), 8.33 (d, J = 1.6 Hz, 1H), 7.82 (d, J = 1.6 Hz, 1H), 5.08 (t, J = 4.8 Hz, 1H), 4.63 (d, J = 4.8 Hz, 2H), 4.11-4.14 (m, 1H), 4.08 (d, J = 11.6 Hz, 2H), 3.32-3.37 (m, 1H), 3.25 (d, J = 11.6 Hz, 2H), 3.02-3.13 (m, 2H), 2.74-2.87 (m, 2H), 0.80-0.91 (m, 4H), 0.56-0.60 (m, 2H), 0.31-0.34 (m, 2H). | 2 |

TABLE 23-continued

Characterization data for exemplary compounds

| Compound No. | Chemical Structure | M + 1 | $^1$H NMR (400 MHz) | Example of Synthesis |
|---|---|---|---|---|
| I-853 | 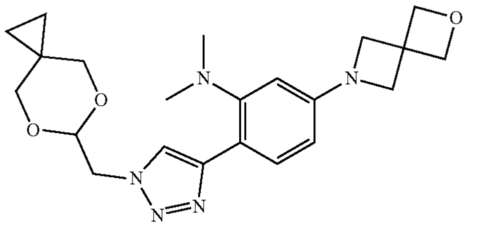 [SMILES: CN(C)c1cc(N2CC3(COC3)C2)ccc1-c1cn(CC2OCC3(CC3)CO2)nn1] | 412.4 | $^1$HNMR (400 MHz, DMSO-$d_6$) δ 8.24 (s, 1H), 7.82 (d, J = 8.0 Hz, 1H), 6.17-6.21 (m, 2H), 5.03 (t, J = 4.8 Hz, 1H), 4.72 (s, 4H), 4.56 (d, J = 4.8 Hz, 2H), 4.06 (d, J = 11.6 Hz, 2H), 4.00 (s, 4H), 3.24 (d, J = 12.0 Hz, 2H), 2.55 (s, 6H), 0.54-0.58 (m, 2H), 0.29-0.33 (m, 2H). | 5 |
| I-854 | 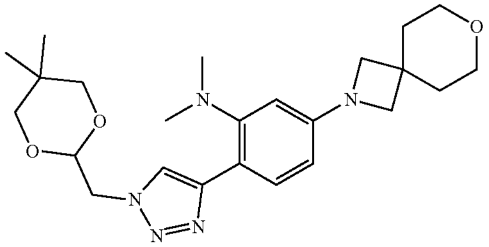 [SMILES: CN(C)c1cc(N2CC3(CCOCC3)C2)ccc1-c1cn(CC2OCC(C)(C)CO2)nn1] | 442.3 | $^1$HNMR (400 MHz, DMSO-$d_6$) δ 8.21 (s, 1H), 7.81-7.83 (m, 1H), 6.18-6.20 (m, 2H), 4.86 (t, J = 4.0 Hz, 1H), 4.53 (d, J = 4.4 Hz, 2H), 3.62 (s, 4H), 3.55-3.57 (m, 6H), 3.45 (d, J = 10.8 Hz, 2H), 2.55 (s, 6H), 1.74 (t, J = 4.8 Hz, 4H), 1.03 (s, 3H), 0.67 (s, 3 H). | 5 |
| I-863 | 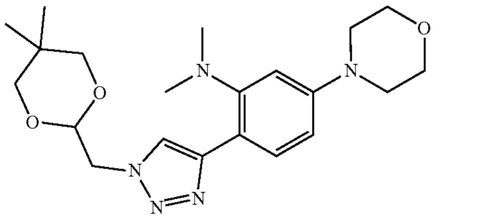 [SMILES: CN(C)c1cc(N2CCOCC2)ccc1-c1cn(CC2OCC(C)(C)CO2)nn1] | 402.3 | $^1$HNMR (400 MHz, DMSO-$d_6$) δ 8.26 (s, 1H), 7.87-7.89 (m, 1H), 6.68-6.71 (m, 2H), 4.87 (t, J = 4.4 Hz, 1H), 4.55 (d, J = 4.0 Hz, 2H), 3.74 (t, J = 4.8 Hz, 4H), 3.56 (d, J = 11.2 Hz, 2H), 3.46 (d, J = 10.8 Hz, 2H), 3.15 (t, J = 5.2 Hz, 4H), 2.58 (s, 6H), 1.03 (s, 3H), 0.67 (s, 3H). | 5 |
| I-849 | 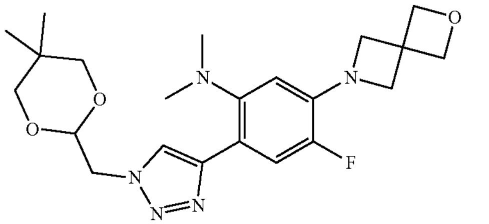 [SMILES: CN(C)c1cc(N2CC3(COC3)C2)c(F)cc1-c1cn(CC2OCC(C)(C)CO2)nn1] | 432.3 | $^1$HNMR (400 MHz, DMSO-$d_6$) δ 8.31 (s, 1H), 7.66 (d, J = 14.0 Hz, 1H), 6.31 (d, J = 8.8 Hz, 1H), 4.87 (t, J = 4.0 Hz, 1H), 4.72 (s, 4H), 4.55 (d, J = 4.4 Hz, 2H), 4.12 (d, J = 1.6 Hz, 4H), 3.56 (d, J = 11.2 Hz, 2H), 3.45 (d, J = 10.4 Hz, 2H), 2.55 (s, 6H), 1.02 (s, 3H), 0.67 (s, 3H). | 5 |
| I-839 | 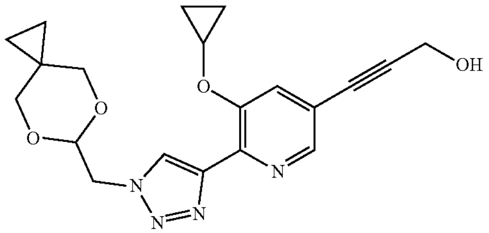 [SMILES: OCC#Cc1cnc(-c2cn(CC3OCC4(CC4)CO3)nn2)c(OC2CC2)c1] | 383.3 | $^1$HNMR (400 MHz, $CDCl_3$) 8.49 (s, 1H), 8.20 (s, 1H), 7.69 (s, 1H), 4.99 (t, J = 4.8 Hz, 1H), 4.61 (d, J = 5.2 Hz, 2H), 4.56 (s, 2H), 4.11 (d, J = 11.6 Hz, 2H), 3.85-3.88 (m, 1H), 3.26 (d, J = 12.0 Hz, 2H), 0.83-0.95 (m, 4H), 0.69-0.73 (m, 2H), 0.35-0.38 (m, 2H). | 28 |
| I-855 | 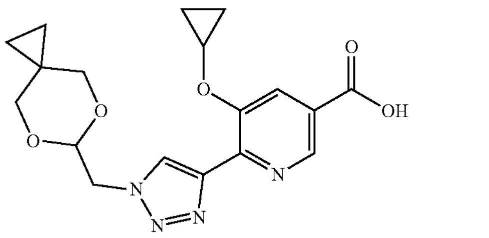 [SMILES: O=C(O)c1cnc(-c2cn(CC3OCC4(CC4)CO3)nn2)c(OC2CC2)c1] | 373.2 | $^1$HNMR (400 MHz, DMSO-$d_6$) δ 8.76 (s, 1H), 8.45 (s, 1H), 8.18 (d, J = 1.6 Hz, 1H), 5.09 (t, J = 4.8 Hz, 1H), 4.64 (d, J = 4.8 Hz, 2H ), 4.07-4.13 (m, 3H), 3.25 (d, J = 11.6 Hz, 2H), 0.84-0.89 (m, 4H), 0.57-0.61 (m, 2H), 0.31-0.35 (m, 2H). | 27 |

TABLE 23-continued

| Compound No. | Chemical Structure | M + 1 | $^1$H NMR (400 MHz) | Example of Synthesis |
|---|---|---|---|---|
| I-882 | 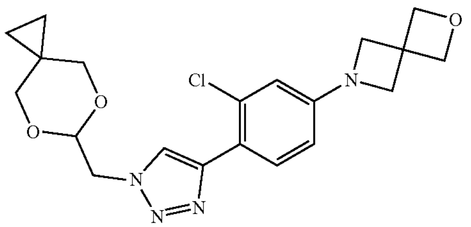 [SMILES: Clc1cc(N2CC3(COC3)C2)ccc1-c1cn(CC2OCC3(CC3)CO2)nn1] | 403.2 | $^1$HNMR (400 MHz, DMSO-$d_6$) δ 8.42 (s, 1H), 7.86 (d, J = 8.4 Hz, 1H), 6.50-6.54 (m, 2H), 5.09 (t, J = 5.2 Hz, 1H), 4.72 (s, 4H), 4.59 (d, J = 4.8 Hz, 2H), 4.09 (s, 1H), 4.04-4.06 (m, 5H), 3.25 (d, J = 11.6 Hz, 2H), 0.56-0.59 (m, 2H), 0.30-0.34 (m, 2H). | 5 |
| I-883 | 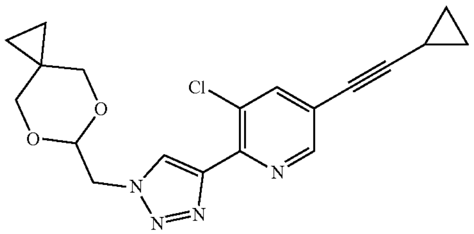 | 371.2 | $^1$HNMR (400 MHz, DMSO-$d_6$) δ 8.66 (s, 1H), 8.59 (d, J = 1.6 Hz, 1H), 8.07 (d, J = 1.6 Hz, 1H), 5.11 (t, J = 4.8 Hz, 1H), 4.64 (d, J = 4.8 Hz, 2H), 4.08 (d, J = 11.6 Hz, 2H), 3.25 (d, J = 11.6 Hz, 2H), 1.58-1.66(m, 1H), 0.92-1.01 (m, 2H), 0.79-0.84 (m, 2H), 0.56-0.59 (m, 2H), 0.30-0.34 (m, 2H). | 2 |

Characterization data for exemplary compounds

Example 35: Synthesis of I-432

I-432

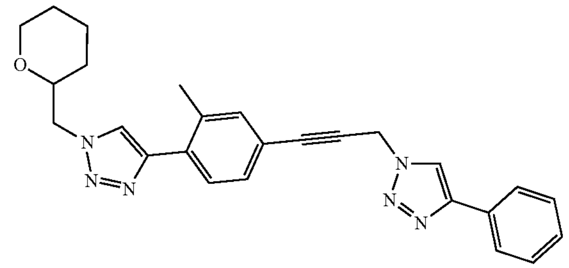

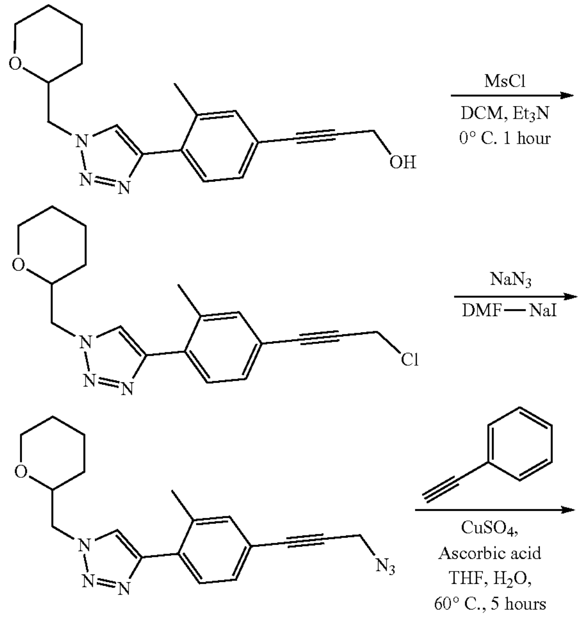

-continued

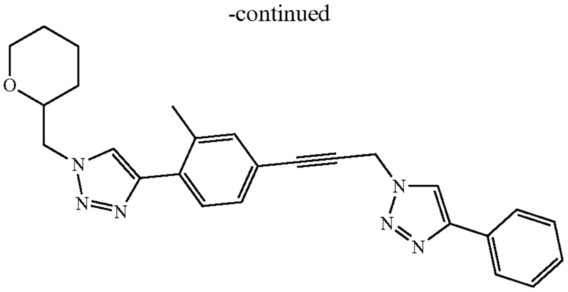

Step1

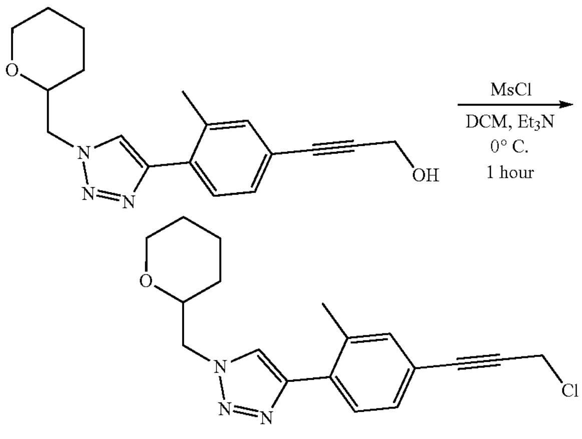

A solution of 3-(3-methyl-4-(1-((tetrahydro-2H-pyran-2-yl)methyl)-1H-1,2,3-triazol-4-yl)phenyl)prop-2-yn-1-ol (238.3 mg, 0.76 mmol) and triethylamine (0.13 ml, 0.912 mmol) in dichloromethane anhydrous (3.3 ml) is cooled to 0° C. and treated with methanesulfonyl chloride (59 ul, 0.76 mmol). The reaction is stirred at 0° C. for 1 hour then poured into 4 ml water. The organic layer is separated. The aqueous phase is re-extracted with dichloromethane. The combined organic extracts are washed with brine, dried over anhydrous sodium sulfate, filtered and concentrated in vacuum. The crude is purified on silica gel column chromatography (0-50% EtOAc in hexane) to provide 4-(4-(3-chloroprop-1-ynyl)-2-methylphenyl)-1-((tetrahydro-2H-pyran-2-yl) methyl)-1H-1,2,3-triazole (39 mg, 15%).

Step 2:

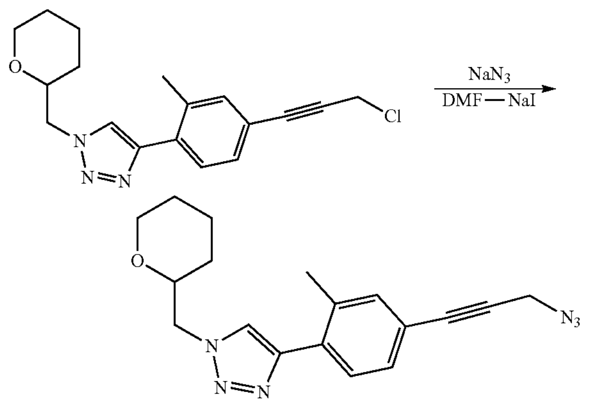

A solution of 4-(4-(3-chloroprop-1-ynyl)-2-methylphenyl)-1-((tetrahydro-2H-pyran-2-yl)methyl)-1H-1,2,3-triazole (38.5 mg, 0.12 mmol) in DMF (80 ul) is treated with sodium azide (15.6 mg, 0.24 mmol) and sodium iodide (3.6 mg, 0.024 mmol). The reaction is stirred at room temperature overnight to provide 4-(4-(3-azidoprop-1-ynyl)-2-methylphenyl)-1-((tetrahydro-2H-pyran-2-yl)methyl)-1H-1,2,3-triazole. This one will be used directly in the next step.

Step 3:

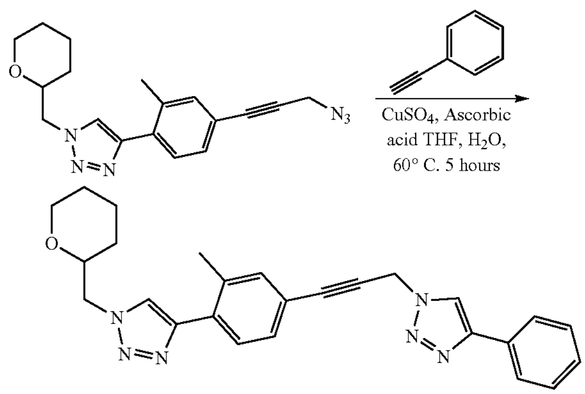

Under inert atmosphere, a solution of ethynylbenzene (13.8 mg, 0.132 mmol) in THF (0.78 ml) is added to 4-(4-(3-azidoprop-1-ynyl)-2-methylphenyl)-1-((tetrahydro-2H-pyran-2-yl)methyl)-1H-1,2,3-triazole (40 mg, 0.12 mmol). A solution of copper sulfate (3.1 mg, 0.012 mmol) in water (0.26 ml) is then added. The reaction is stirred at room temperature for 10 minutes then ascorbic acid (10.7 mg, 0.06 mmol) is added. The reaction is stirred and heated to 60° C. for 5 hours. The reaction is poured into saturated aqueous ammonium chloride solution. The organic layer is separated, and the aqueous phase is re-extracted twice with ethyl acetate. The combined organic layers are washed with brine, dried over anhydrous sodium sulfate, filtered and concentrated in vacuum to get the crude compound. Purification on silica gel chromatography column (0-2% MeOH/DCM) provides 1-(3-(3-methyl-4-(1-((tetrahydro-2H-pyran-2-yl) methyl)-1H-1,2,3-triazol-4-yl)phenyl)prop-2-ynyl)-4-phenyl-1H-1,2,3-triazole (11 mg, 21%) as white solid.

$^1$H NMR (400 MHz, Chloroform-d) δ 8.07 (s, 1H), 7.91-7.83 (m, 1H), 7.84 (d, J=1.4 Hz, 3H), 7.49-7.36 (m, 3H), 7.39-7.29 (m, 1H), 5.47 (s, 2H), 4.53 (dd, J=14.2, 2.9 Hz, 1H), 4.33 (dd, J=14.2, 7.6 Hz, 1H), 3.99 (dd, J=10.7, 2.0 Hz, 1H), 3.71 (ddt, J=10.1, 7.6, 2.6 Hz, 1H), 3.57-3.26 (m, 1H), 2.47 (s, 3H), 1.97-1.83 (m, 1H), 1.67 (t, J=13.7 Hz, 2H), 1.41-1.12 (m, 3H), 1.01-0.74 (m, 1H).

Additional exemplary compounds were prepared following methods substantially similar to the method described above and herein. Data for these compounds are provided in Table 24, Following Example 53.

Example 36: Synthesis of I-494

I-494

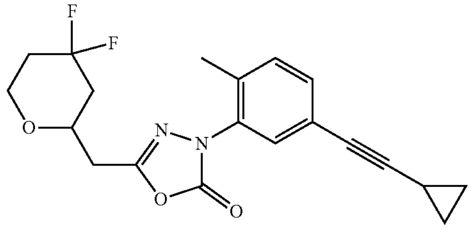

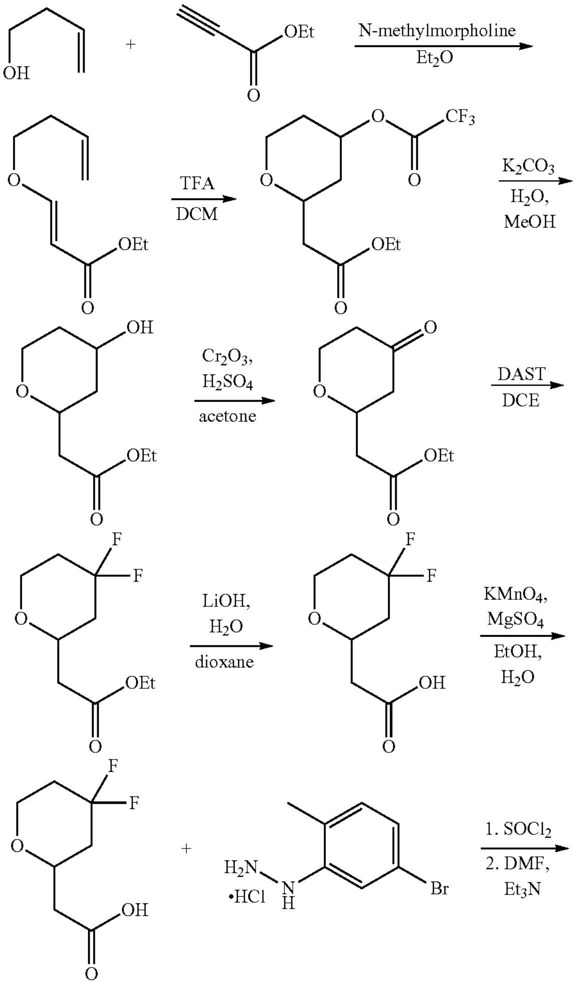

-continued

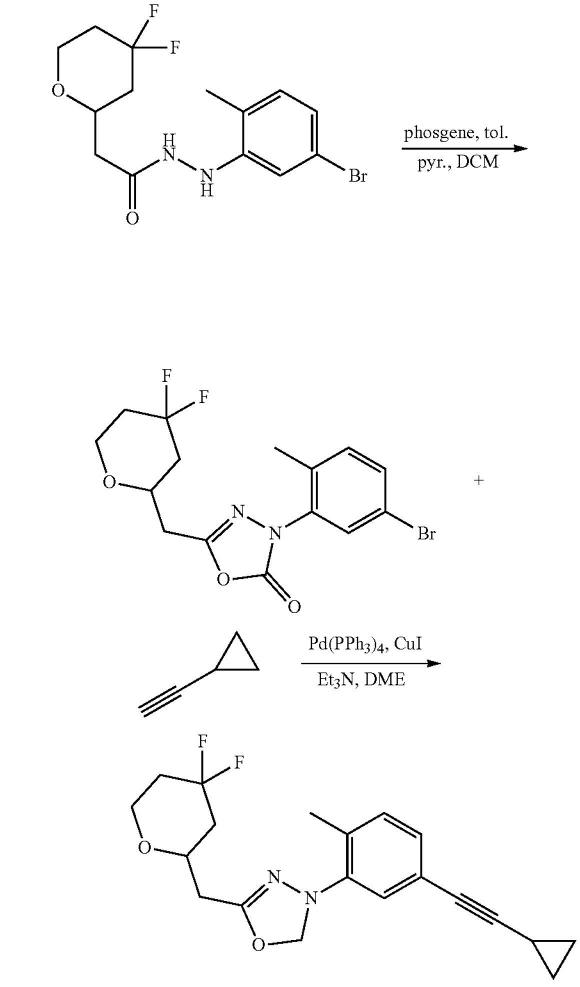

Step 1

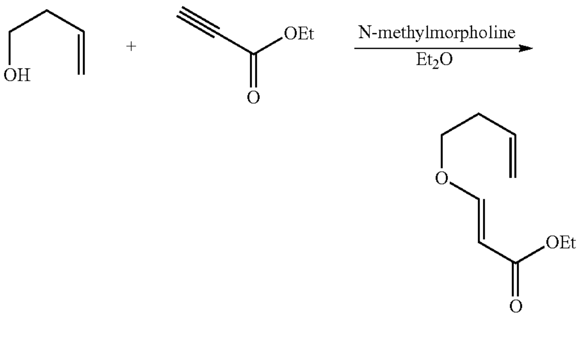

But-3-en-1-ol (5.0 mL, 58.1 mmol, 1.0 eq.) was added to a mixture of ethyl propiolate (6.4 mL, 63.2 mmol, 1.09 eq.) and N-methylmorpholine (6.8 mL, 61.6 mmol, 1.06 eq.) in $Et_2O$ (80 mL). The mixture was stirred at room temperature for 18 hours. The mixture was poured in 0.5 M aqueous AcOH and the organic layer was separated, washed with brine, dried over $Na_2SO_4$, filtered and concentrated to afford ethyl (E,Z)-3-(but-3-en-1-yloxy)acrylate as a yellow oil (9.1 g, 92%).

Step 2

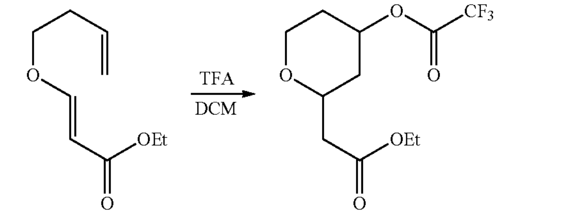 [SMILES: C=CCCO/C=C/C(=O)OCC ; CCOC(=O)CC1CC(OC(=O)C(F)(F)F)CCO1]

At 0° C., TFA was added slowly over 30 min to a mixture of ethyl (E,Z)-3-(but-3-en-1-yloxy)acrylate (9.1 g, 53.5 mmol, 1.0 eq.) in DCM (150 mL). The mixture was stirred at 0° C. for 2.5 hours then it was at 4° C. for 3 days. The mixture was concentrated and diluted in EtOAc. The organic layer was washed with cold aqueous saturated $NaHCO_3$ and brine, dried over $Na_2SO_4$, filtered and concentrated. The residue was purified on silica gel (0-20% EtOAc in hexanes) to afford 2-(2-ethoxy-2-oxoethyl)tetrahydro-2H-pyran-4-yl 2,2,2-trifluoroacetate as a colorless oil (11.72 g, 77%).

Step 3

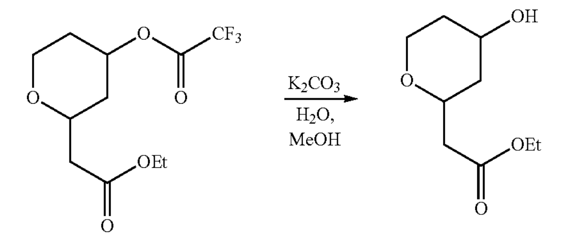

A solution of $K_2CO_3$ (5.83 g, 42.2 mmol, 1.2 eq.) in $H_2O$ (140 mL) was added to a mixture of 2-(2-ethoxy-2-oxoethyl) tetrahydro-2H-pyran-4-yl 2,2,2-trifluoroacetate (9.99 g, 35.1 mmol, 1.0 eq.) in MeOH (56 mL). After 20 min of stirring at room temperature, acetic acid was added until pH 7 was reached. DCM was added and the organic layer was separated. The aqueous layer was extracted twice with DCM. The combined organic layers were washed with brine, dried over $Na_2SO_4$, filtered and concentrated to afford ethyl 2-(4-hydroxytetrahydro-2H-pyran-2-yl)acetate as a colorless oil (6.4 g, 97%).

Step 4

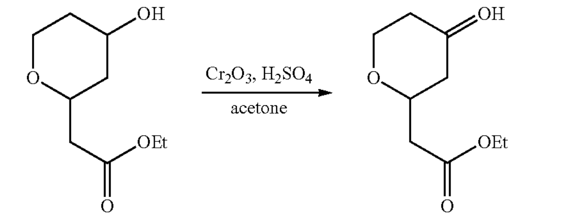 [SMILES: CCOC(=O)CC1CC(O)CCO1 ; CCOC(=O)CC1CC(=O)CCO1]

At 0° C., $Cr_2O_3$ (2Mv in H2SO4, 1/mL, 34.0 mmol, 1.0 eq.) was added dropwise to a mixture of ethyl 2-(4-hydroxytetrahydro-2H-pyran-2-yl)acetate (6.4 g, 34.0 mmol, 1.0 eq.) in acetone (136 mL). After 30 min of stirring at 0° C., an aqueous saturated solution of $NaHSO_3$ was added and EtOAc was added. The organic layer was separated and the aqueous layer was extracted with EtOAc. The combined organic layers were washed with brine, dried over $Na_2SO_4$, filtered and concentrated. The residue was purified on silica gel (0-30% EtOAc in hexanes) to afford ethyl 2-(4-oxotetrahydro-2H-pyran-2-yl)acetate as a colorless oil (3.27 g, 52%).

Step 5

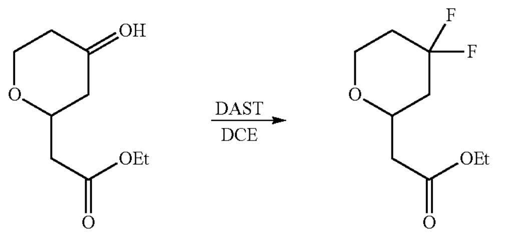 [SMILES: CCOC(=O)CC1CC(=O)CCO1 ; "DAST" ; CCOC(=O)CC1CC(F)(F)CCO1]

At 0° C., DAST (2.84 mL, 21.5 mmol, 4.0 eq.) was added dropwise to a mixture of ethyl 2-(4-oxotetrahydro-2H-pyran-2-yl)acetate (1.0 g, 5.37 mmol, 1.0 eq.) in DCE (21 mL). The mixture was stirred at 70° C. for 45 min then cooled down to 0° C. Aqueous saturated $NaHCO_3$ was carefully added dropwise and the mixture was allowed to warm up to room temperature. DCM was added and the organic layer was separated, washed with brine, dried over $Na_2SO_4$, filtered and concentrated. The residue was purified on silica gel (0-20% EtOAc/hexanes) to afford ethyl 2-(4,4-difluorotetrahydro-2H-pyran-2-yl)acetate as a colorless oil (846 mg, 76%).

Step 6

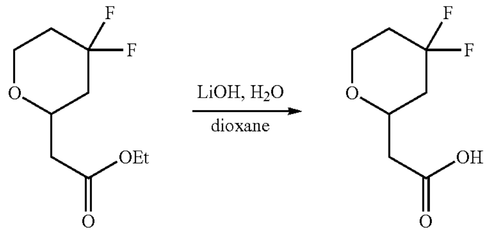 [SMILES: CCOC(=O)CC1CC(F)(F)CCO1 ; O=C(O)CC1CC(F)(F)CCO1]

A solution of LiOH (554 mg, 13.2 mmol, 3.0 eq.) in $H_2O$ (12 mL) was added to a mixture of ethyl 2-(4,4-difluorotetrahydro-2H-pyran-2-yl)acetate (916 mg, 4.4 mmol, 1.0 eq.) in dioxane (24 mL). The mixture was stirred at room temperature for 18 hours. 1N HCl was added until pH 2 was reached and EtOAc was added. The organic layer was separated and the aqueous layer was extracted with EtOAc. The combined organic layers were washed with brine, dried over $Na_2SO_4$, filtered and concentrated to afford 2-(4,4-difluorotetrahydro-2H-pyran-2-yl)acetic acid as a yellow solid (793 mg, quant.).

Step 7 (Clean-Up)

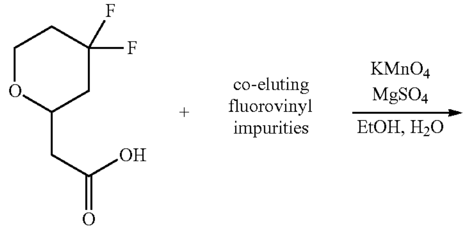

-continued

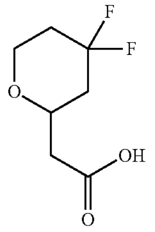

At −40° C., a solution of $KMnO_4$ (73 mg, 0.46 mmol, 0.25 eq.) in $H_2O$ (1.0 mL) was added dropwise to a mixture of 2-(4,4-difluorotetrahydro-2H-pyran-2-yl)acetic acid (278 mg, 1.54 mmol, 1.0 eq.) and $MgSO_4$ (46 mg, 0.46 mmol, 0.3 eq.) in EtOH (5.0 mL). The mixture was stirred at −40° C. for 1 hour, then an aqueous saturated solution of $NaHSO_3$ was added. The mixture was allowed to warm up to room temperature then it was filtered on celite. The filtrate was concentrated and the residue was acidified to pH 2 with 1N HCl. The resulting mixture was extracted twice with EtOAc. The combined organic layers were washed with brine, dried over $Na_2SO_4$, filtered and concentrated to afford 2-(4,4-difluorotetrahydro-2H-pyran-2-yl)acetic acid as a yellow solid (250 mg, 90%).

Step 8

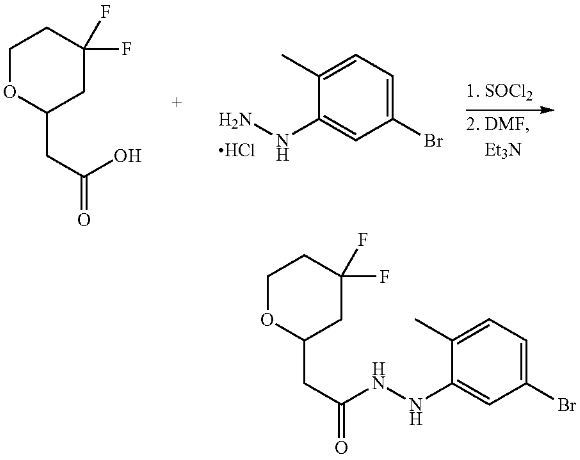

A mixture of 2-(4,4-difluorotetrahydro-2H-pyran-2-yl) acetic acid (242 mg, 1.34 mmol, 1.2 eq.) and sulfonyl chloride (0.72 mL, 11.2 mmol, 10 eq.) was stirred at reflux for 1 hour. Once at room temperature, the mixture was concentrated and dissolved in DMF (1 mL). The resulting solution was added dropwise to a mixture of (5-bromo-2-methylphenyl)hydrazine hydrochloride (266 g, 1.12 mmol, 1.0 eq.) and $Et_3N$ (0.94 mL, 6.72 mmol, 6.0 eq.) in DMF (1.8 mL) at 0° C. The mixture was allowed to warm up to room temperature and stirred for 3 hours at room temperature. The mixture was poured in aq. sat. $NH_4Cl$ and EtOAc was added. The organic layer was separated and the aqueous layer was extracted with EtOAc. The combined organic layers were dried over $Na_2SO_4$, filtered and concentrated. The residue was purified on silica gel (20-70% EtOAc/hexanes) to afford N'-(5-bromo-2-methylphenyl)-2-(4,4-difluorotetrahydro-2H-pyran-2-yl)acetohydrazide as a beige solid (227 mg, 56%).

Step 9

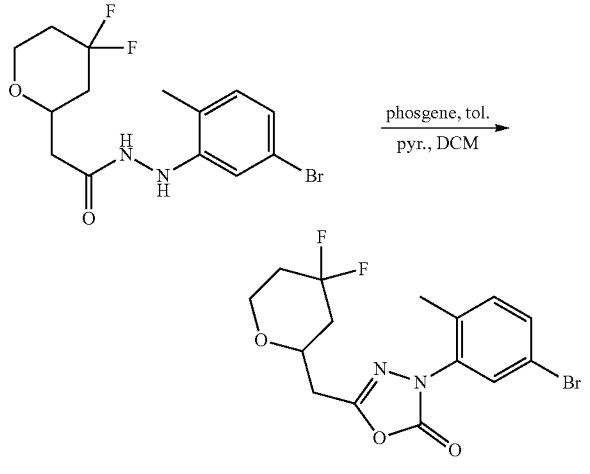

At 0° C., a solution of phosgene (20% in toluene, 1.64 mL, 3.11 mmol, 5.0 eq.) was added dropwise to a mixture of N'-(5-bromo-2-methylphenyl)-2-(4,4-difluorotetrahydro-2H-pyran-2-yl)acetohydrazide (226 mg, 0.622 mmol, 1.0 eq.) in DCM (4.6 mL). The mixture was allowed to warm up to room temperature and stirred at room temperature for 75 min. The mixture was concentrated and the residue was purified on silica gel chromatography (0-30% EtOAc in hexanes) to afford 3-(5-bromo-2-methylphenyl)-5-((4,4-difluorotetrahydro-2H-pyran-2-yl)methyl)-1,3,4-oxadiazol-2(3H)-one as a pale yellow oil (192 mg, 79%).

Step 10

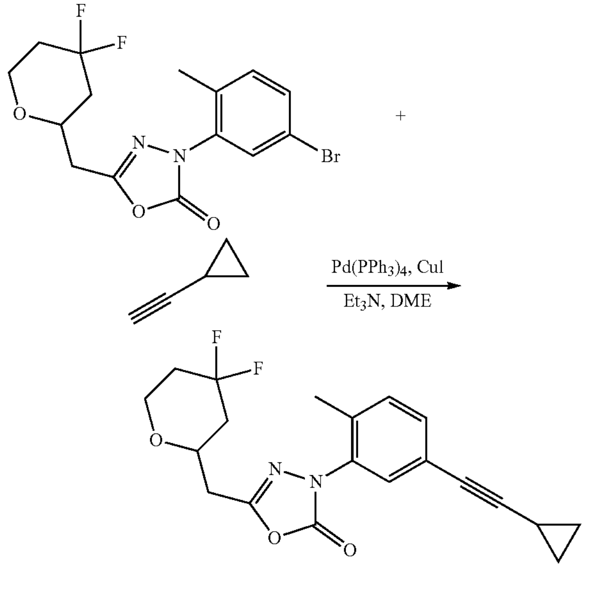

Cyclopropylacetylene (415 μL, 4.91 mmol, 10 eq.) was added to a $N_2$ bubbled solution of 3-(5-bromo-2-methylphenyl)-5-((4,4-difluorotetrahydro-2H-pyran-2-yl)methyl)-1,3,4-oxadiazol-2(3H)-one (191 mg, 0.491 mmol, 1.0 eq.), $Pd(PPh_3)_4$ (57 mg, 0.049 mmol, 0.1 eq.) and CuI (9 mg, 0.049 mmol, 0.1 eq.) in $Et_3N$ (2.5 mL) and DME (2.5 mL). After 1 minutes of $N_2$ bubbling, the reaction was stirred at 90° C. for 18 hours. Once at room temperature, the mixture was poured in aq. sat. $NH_4Cl$ and MTBE was added. The organic layer was separated, dried over $Na_2SO_4$, filtered and concentrated. The residue was purified on silica gel chromatography (0-30% EtOAc in hexanes) to afford 3-(5-(cyclopropylethynyl)-2-methylphenyl)-5-((4,4-difluorotetrahydro-2H-pyran-2-yl)methyl)-1,3,4-oxadiazol-2(3H)-one as a yellow oil (163 mg, 89%). $^1H$ NMR (400 MHz, $CDCl_3$) δ 7.38 (d, J=1.6 Hz, 1H), 7.31 (dd, J=7.9, 1.7 Hz, 1H), 7.19 (d, J=8.0 Hz, 1H), 4.07 (ddd, J=11.5, 6.1, 2.8 Hz, 1H), 4.02-3.91 (m, 1H), 3.64 (td, J=11.9, 2.8 Hz, 1H), 2.92-2.78 (m, 2H), 2.29 (s, 3H), 2.21 (tdt, J=10.6, 5.1, 2.6 Hz, 1H), 2.10-1.90 (m, 2H), 1.81 (dddd, J=32.8, 13.3, 11.7, 3.8 Hz, 1H), 1.42 (tt, J=8.2, 5.1 Hz, 1H), 0.89-0.82 (m, 2H), 0.81-0.75 (m, 2H). $^{13}C$ NMR (101 MHz, $CDCl_3$) δ 153.71, 152.05, 134.19, 133.46, 132.24, 131.31, 129.35, 123.16, 122.76, 120.78, 118.33, 94.25, 74.38, 70.92, 70.82, 64.39, 64.30, 39.97, 39.76, 39.73, 39.52, 34.48, 34.27, 34.24, 34.03, 32.83, 32.82, 18.02, 8.59, 0.09.

Additional exemplary compounds were prepared following methods substantially similar to the method described above and herein. Data for these compounds are provided in Table 24, Following Example 53.

Example 37: Synthesis of I-522

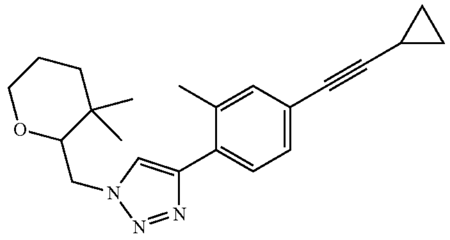

I-522

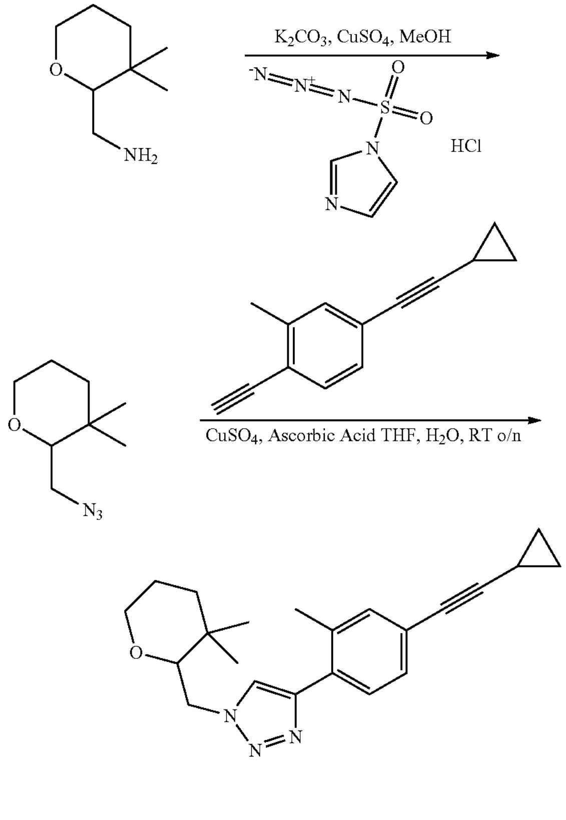

Step 1:

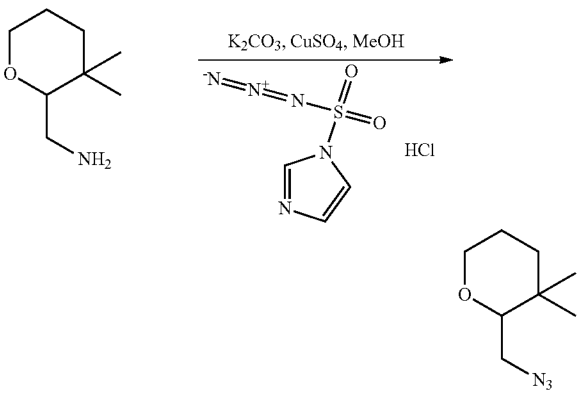

A solution of (3,3-dimethyloxan-2yl) methanamine hydrochloride (189 mg, 1 mmol) in methanol (10 ml) was treated with potassium carbonate (276.4 mg, 2 mmol), Copper sulphate hydrate (50.9 mg, 0.2 mmol) and imidazole 1-sulfonyl azide hydrochloride (220.6 mg, 1 mmol). The reaction was stirred at room temperature overnight. The blue color of the reaction changed into purple. The solvent was evaporated without heating, the reaction was dissolved into 3.5 ml methanol and 2 ml ethyl acetate then filtered. The solvent was then evaporated, and the crude was dissolved in the minimum amount of water. The PH was adjusted to 3 by adding 3M aqueous HCl. The reaction was then extracted 3 times with ethyl acetate.

The combined organic layers were dried over anhydrous sodium sulphate, filtered and concentrated without heating giving the crude 2-(azidomethyl)-3,3-dimethyltetrahydro-2H-pyran which was used directly in the next step.

Step 2:

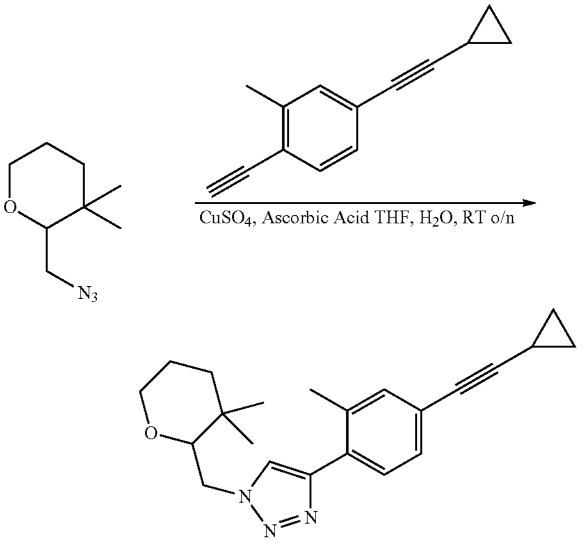

Under inert atmosphere, a solution of 4-(cyclopropyl ethynyl)-1-ethynyl-2-methylbenzene (198.3 mg, 1.1 mmol) in THF (6.5 ml) was added to 2-(azidomethyl)-3,3-dimethyltetrahydro-2H-pyran (169 mg, 1.00 mmol). A solution of copper sulfate (25.5 mg, 0.1 mmol) in water (2.2 ml) was then added. The reaction was stirred at room temperature for 10 minutes then ascorbic acid (88.9 mg, 0.50 mmol) was added. The reaction was stirred at room temperature over night. The reaction was poured into saturated aqueous ammonium chloride solution. The organic layer was separated, and the aqueous phase was re-extracted twice with ethyl acetate. The combined organic layers were washed with brine, dried over anhydrous sodium sulfate, filtered and concentrated in vacuum to get the crude compound. Purification on silica gel chromatography column (0-40% Ethyl acetate in hexanes) provided 4-(4-(cyclopropylethynyl)-2-methylphenyl)-1-((3,3-dimethyltetrahydro-2H-pyran-2-yl)methyl)-1H-1,2,3-triazole (223 mg, 64%) as white solid.

$^1H$ NMR (400 MHz, Chloroform-I) δ 7.80 (s, 1H), 7.75 (d, J=8.3 Hz, 1H), 7.28 (d, J=7.3 Hz, 2H), 4.70 (d, J=14.1 Hz, 1H), 4.10 (dd, J=14.0, 9.8 Hz, 1H), 3.97 (dd, J=11.2, 4.9 Hz, 1H), 3.38 (d, J=9.6 Hz, 1H), 3.34-3.17 (m, 1H), 2.42 (s, 3H), 1.97-1.73 (m, 1H), 1.62-1.48 (m, 1H), 1.48-1.35 (m, 3H), 1.04 (s, 6H), 0.95-0.75 (m, 4H).

$^{13}C$ NMR (101 MHz, Chloroform-d) δ 146.27, 135.16, 133.97, 129.48, 129.26, 128.53, 123.41, 123.26, 93.87, 84.30, 77.43, 77.12, 76.80, 75.77, 68.72, 51.04, 38.91, 32.35, 27.50, 22.72, 21.34, 19.15, 8.68, 0.27.

Additional exemplary compounds were prepared following methods substantially similar to the method described above and herein. Data for these compounds are provided in Table 24, Following Example 53.

Example 38: Synthesis of I-537

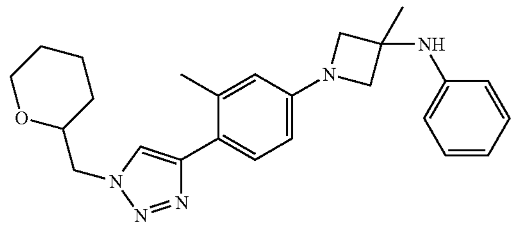

I-537

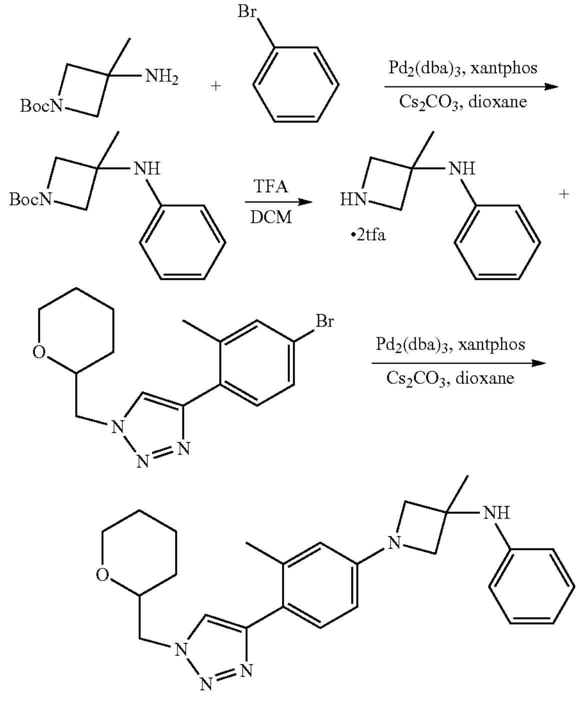

Step 1:

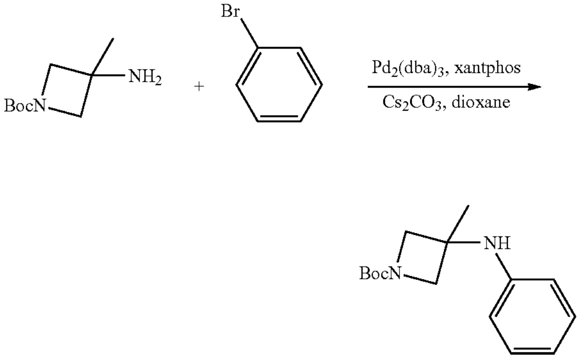

$Cs_2CO_3$ (1.75 g, 5.37 mmol, 2.0 eq.) was added to a $N_2$ bubbled mixture of bromobenzene (282 μg, 2.68 mmol, 1.0 eq.), tert-butyl 3-amino-3-methylazetidine-1-carboxylate (500 mg, 2.68 mmol, 1.0 eq.), $Pd_2(dba)_3$ (246 mg, 0.27 mmol, 0.1 eq.) and 4,5-Bis(diphenylphosphino)-9,9-dimethylxanthene (233 mg, 0.40 mmol, 0.15 eq.) in dioxane (13.4 mL). After 1 minute of $N_2$ bubbling, the mixture was stirred at 100° C. for 18 hours. Once at room temperature, the mixture was poured in aqueous saturated $NH_4Cl$ and EtOAc was added. The organic layer was separated, dried over $Na_2SO_4$, filtered and concentrated. The residue was purified on silica gel chromatography (0-30% EtOAc in hexanes) to afford tert-butyl 3-methyl-3-(phenylamino)azetidine-1-carboxylate as a yellow oil (489 mg, 70%).

Step 2

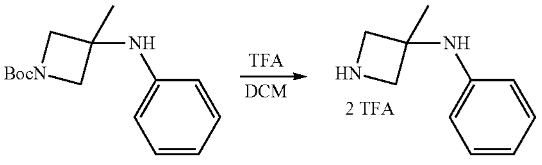 [SMILES: CC1(Nc2ccccc2)CN(C(=O)OC(C)(C)C)C1 ; CC1(Nc2ccccc2)CNC1]

TFA (2.5 mL) was added to a mixture of tert-butyl 3-methyl-3-(phenylamino)azetidine-1-carboxylate (488 mg, 1.86 mmol, 1.0 eq.) in DCM (5.0 mL). The mixture was stirred at room temperature for 3 hours. The mixture was concentrated and the residue was used as is to next step.

Step 3

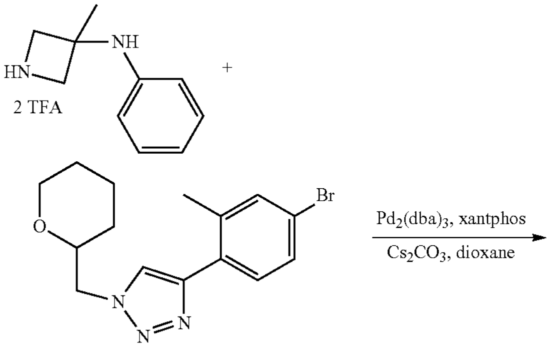

-continued

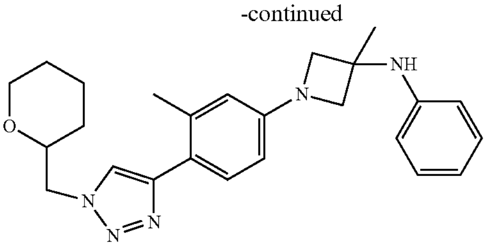

$Cs_2CO_3$ (485 mg, 1.49 mmol, 5.0 eq.) was added to a $N_2$ bubbled mixture of 4-(4-bromo-2-methylphenyl)-1-((tetrahydro-2H-pyran-2-yl)methyl)-1H-1,2,3-triazole (100 mg, 0.297 mmol, 1.0 eq.), 3-methyl-N-phenylazetidin-3-amine bistrifluoroacetic acid (116 mg, 0.297 mmol, 1.0 eq.), $Pd_2(dba)_3$ (27 mg, 0.030 mmol, 0.1 eq.) and 4,5-Bis(diphenylphosphino)-9,9-dimethylxanthene (26 mg, 0.045 mmol, 0.15 eq.) in dioxane (3.0 mL). After 1 minute of $N_2$ bubbling, the mixture was stirred at 100° C. for 18 hours. Once at room temperature, the mixture was poured in aqueous saturated $NH_4Cl$ and EtOAc was added. The organic layer was separated, dried over $Na_2SO_4$, filtered and concentrated. The residue was purified on silica gel chromatography (10-60% EtOAc in hexanes) to afford 3-methyl-1-(3-methyl-4-(1-((tetrahydro-2H-pyran-2-yl)methyl)-1H-1,2,3-triazol-4-yl)phenyl)-N-phenylazetidin-3-amine as a yellow solid (55 mg, 44%). $^1H$ NMR (400 MHz, $CDCl_3$) 7.70 (s, 1H), 7.67 (d, J=8.3 Hz, 1H), 7.20 (dd, J=8.4, 7.4 Hz, 2H), 6.75 (t, J=7.3 Hz, 1H), 6.60-6.52 (m, 2H), 6.41 (dd, J=8.3, 2.5 Hz, 1H), 6.36 (d, J=2.2 Hz, 1H), 4.50 (dd, J=14.1, 3.2 Hz, 1H), 4.33 (dd, J=14.2, 7.5 Hz, 1H), 4.07-3.92 (m, 6H), 3.71 (dtd, J=11.1, 5.3, 2.8 Hz, 1H), 3.41 (td, J=11.3, 4.3 Hz, 1H), 2.42 (s, 3H), 1.93-1.83 (m, 1H), 1.73 (s, 3H), 1.68 (d, J=12.4 Hz, 1H), 1.59-1.45 (m, 3H), 1.34-1.20 (m, 1H). $^{13}C$ NMR (101 MHz, $CDCl_3$) δ 150.77, 147.15, 145.17, 136.37, 129.76, 129.34, 122.40, 119.76, 117.85, 114.06, 113.34, 109.27, 76.23, 68.45, 63.77, 55.01, 51.11, 28.77, 25.61, 24.83, 22.87, 21.65.

Additional exemplary compounds were prepared following methods substantially similar to the method described above and herein. Data for these compounds are provided in Table 24, Following Example 53.

Example 39: Synthesis of I-570

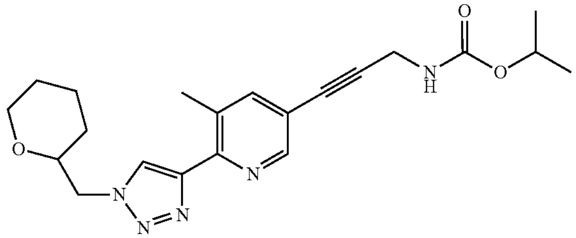

I-570

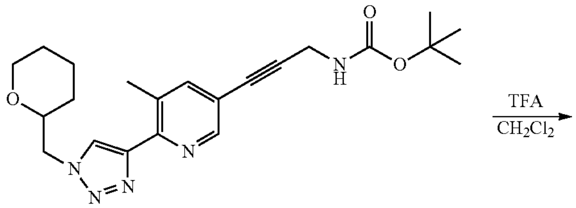

-continued

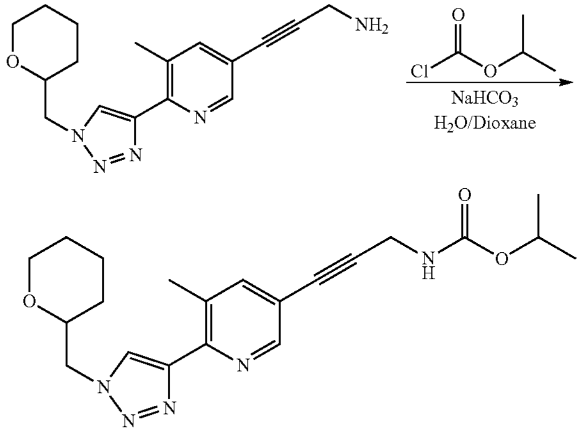

Step 1:

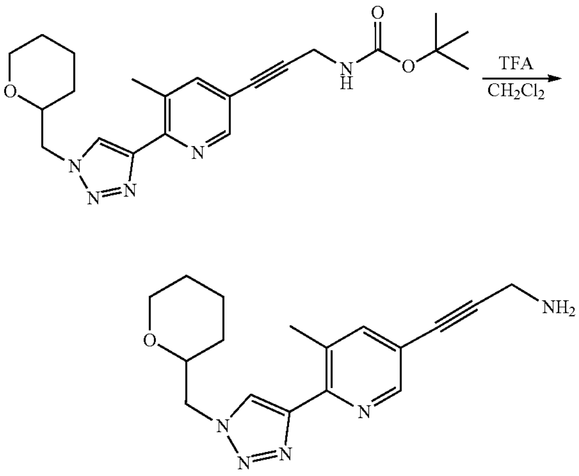

Trifluoroacetic acid (1.26 mL, 16.5 mmol, 20.0 eq.) was slowly added to an ice-cold solution of tert-butyl (3-(5-methyl-6-(1-((tetrahydro-2H-pyran-2-yl)methyl)-1H-1,2,3-triazol-4-yl)pyridin-3-yl)prop-2-yn-1-yl)carbamate (340 mg, 0.827 mmol, 1.00 eq.) in $CH_2Cl_2$ (4 mL). The mixture was stirred at room temperature for 2 hours. A saturated $NaHCO_3$ solution was added, and the mixture was extracted twice with EtOAc. The combined organic layers were washed with brine, dried over $Na_2SO_4$, filtered and concentrated under reduced pressure to provide 3-(5-methyl-6-(1-((tetrahydro-2H-pyran-2-yl)methyl)-1H-1,2,3-triazol-4-yl)pyridin-3-yl)prop-2-yn-1-amine as an amber semi-solid (237 mg, 92%).

Step 2

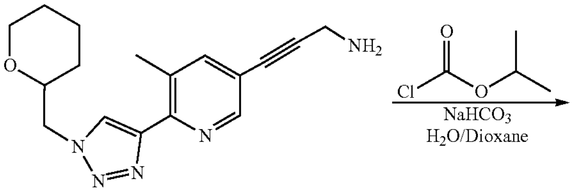

-continued

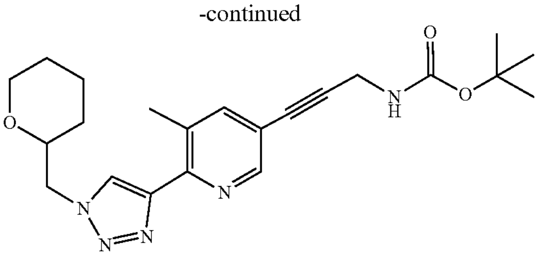

A saturated $NaHCO_3$ solution (0.32 mL) was added to a solution of 3-(5-methyl-6-(1-((tetrahydro-2H-pyran-2-yl)methyl)-1H-1,2,3-triazol-4-yl)pyridin-3-yl)prop-2-yn-1-amine (100 mg, 0.322 mmol, 1.00 eq.) in dioxane (0.32 mL). The mixture was stirred for 30 minutes then isopropyl chloroformate (0.40 mL, 0.402 mmol, 1.25 eq., 1.0 M in PhMe) was added. The mixture was vigorously stirred for 20 hours, then diluted with water and extracted twice with EtOAc. The combined organic layers were washed with brine, dried over $Na_2SO_4$, filtered, and concentrated under reduced pressure. The residue was purified by silica gel (15-100%) to provide isopropyl (3-(5-methyl-6-(1-((tetrahydro-2H-pyran-2-yl)methyl)-1H-1,2,3-triazol-4-yl)pyridin-3-yl)prop-2-yn-1-yl)carbamate as a pale yellow solid (24 mg, 19%).

$^1H$ NMR (400 MHz, $CDCl_3$) δ 8.47 (d, J=1.5 Hz, 1H), 8.22 (s, 1H), 7.59 (s, 1H), 5.05-4.90 (m, 2H), 4.49 (dd, J=14.1, 3.3 Hz, 1H), 4.34 (dd, J=14.1, 7.5 Hz, 1H), 4.22 (d, J=4.8 Hz, 2H), 3.97 (d, J=11.1 Hz, 1H), 3.70 (dtd, J=10.9, 5.3, 2.7 Hz, 1H), 3.38 (td, J=11.3, 3.0 Hz, 1H), 2.70 (s, 3H), 1.95-1.79 (m, 1H), 1.66 (d, J=12.7 Hz, 1H), 1.58-1.44 (m, 3H), 1.35-1.20 (m, 7H) ppm. $^{13}C$ NMR (101 MHz, $CDCl_3$) δ 149.06, 148.67, 147.80, 141.74, 131.10, 125.48, 117.97, 88.62, 80.09, 75.87, 68.70, 68.39, 55.06, 31.42, 28.77, 25.46, 22.78, 22.10, 20.64 ppm.

Additional exemplary compounds were prepared following methods substantially similar to the method described above and herein. Data for these compounds are provided in Table 24, Following Example 53.

Example 40: Synthesis of I-617

I-617

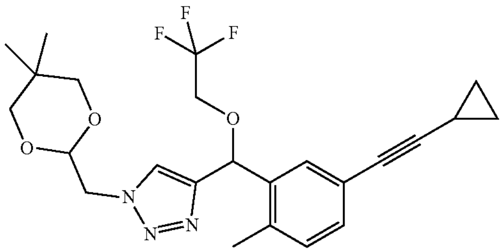

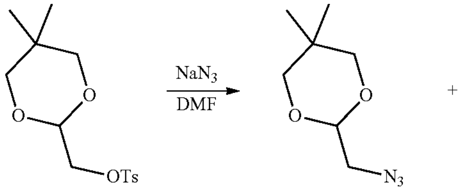

-continued

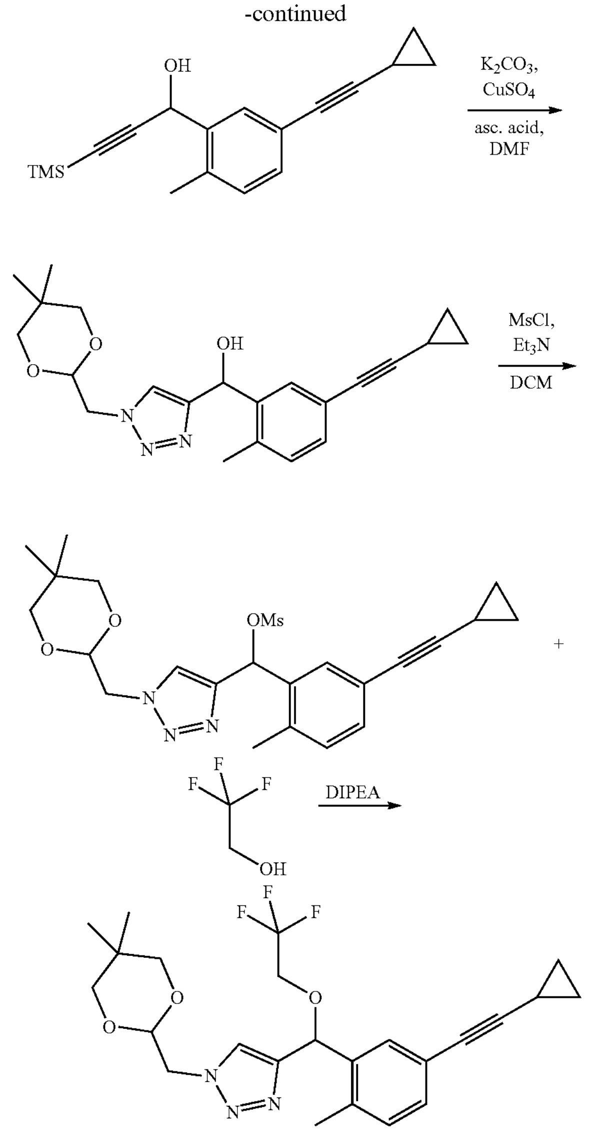

Step 1

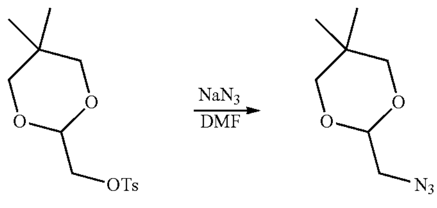

Sodium azide (0.5 g, 7.72 mmol, 2.0 eq.) was added to a solution of (5,5-dimethyl-1,3-dioxan-2-yl)methyl 4-methylbenzenesulfonate (1.16 g, 3.86 mmol, 1.0 eq.) in DMF (7.7 mL). The mixture was stirred at 90° C. for 18 hours. Once at room temperature, $H_2O$ and MTBE were added. The organic layer was separated and the aqueous layer was extracted with MTBE. The combined organic layers were washed with 1N NaOH and brine, dried over $Na_2SO_4$, filtered and concentrated to afford 2-(azidomethyl)-5,5-dimethyl-1,3-dioxane as a pale yellow solid (661 mg, quant.).

Step 2

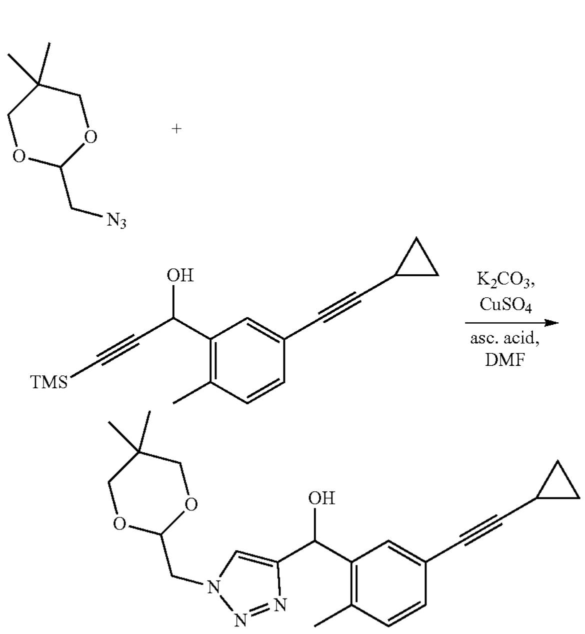

$K_2CO_3$ (646 mg, 4.67 mmol, 5.0 eq.) was added to a mixture of 2-(azidomethyl)-5,5-dimethyl-1,3-dioxane (160 mg, 0.935 mmol, 1.0 eq.), 1-(5-(cyclopropylethynyl)-2-methylphenyl)-3-(trimethylsilyl)prop-2-yn-1-ol (264 mg, 0.935 mmol, 1.0 eq.), CuSO4-5$H_2O$ (117 mg, 0.47 mmol, 0.5 eq.) and ascorbic acid (165 mg, 0.935 mmol, 1.0 eq.) in DMF (6.0 mL). After 2 hours of stirring at room temperature, the mixture was poured in aq. sat. $NH_4Cl$ and EtOAc was added. The organic layer was separated, dried over $Na_2SO_4$, filtered and concentrated. The residue was purified on silica gel chromatography (10-70% EtOAc in hexanes) to afford (5-(cyclopropylethynyl)-2-methylphenyl)(1-((5,5-dimethyl-1,3-dioxan-2-yl)methyl)-1H-1,2,3-triazol-4-yl) methanol as a white foam (298 mg, 84%).

Step 3

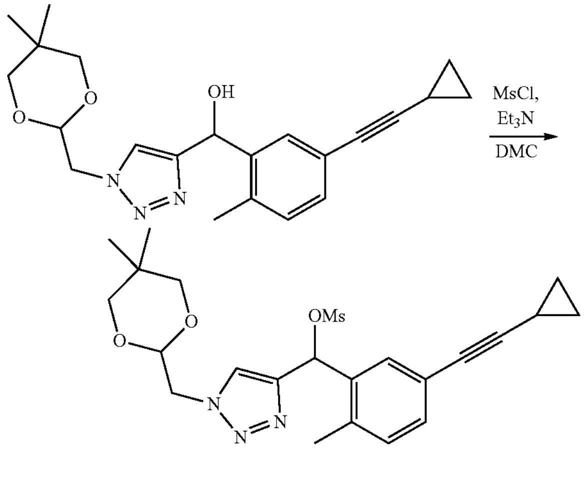

At 0° C., methanesulfonyl chloride (47 μL, 0.610 mmol, 1.2 eq.) was added to a solution of (5-(cyclopropylethynyl)-2-methylphenyl) (1-((5,5-dimethyl-1,3-dioxan-2-yl) methyl)-1H-1,2,3-triazol-4-yl) methanol (194 mg, 0.509 mmol, 1.0 eq.) and $Et_3N$ (106 μL, 0.763 mmol, 1.5 eq.) in DCM (2.5 mL). The reaction was allowed to warm up to room temperature and stirred for 4 hours at room temperature. Water and DCM were added to the mixture and the organic layer was separated, dried over $Na_2SO_4$, filtered and concentrated to afford (5-(cyclopropylethynyl)-2-methylphenyl)(1-((5,5-dimethyl-1,3-dioxan-2-yl)methyl)-1H-1,2,3-triazol-4-yl)methyl methanesulfonate as a yellow solid (209 mg, 89%).

Step 4

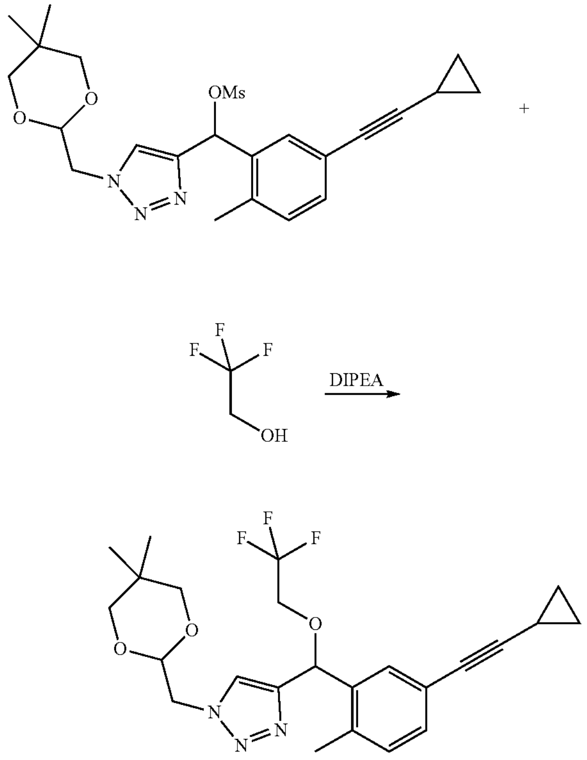 [SMILES: Cc1ccc(C#CC2CC2)cc1C(OS(C)(=O)=O)c1cn(CC2OCC(C)(C)CO2)nn1 ; OCC(F)(F)F ; Cc1ccc(C#CC2CC2)cc1C(OCC(F)(F)F)c1cn(CC2OCC(C)(C)CO2)nn1]

DIPEA (158 μL, 0.907 mmol, 4.0 eq.) was added to a mixture of (5-(cyclopropylethynyl)-2-methylphenyl)(1-((5,5-dimethyl-1,3-dioxan-2-yl)methyl)-1H-1,2,3-triazol-4-yl) methyl methanesulfonate (104 mg, 0.226 mmol, 1.0 eq.) in 2,2,2-trifluoroethan-1-ol (1.0 mL). The mixture was stirred at 80° C. for 100 min. Once at room temperature, the mixture was concentrated and the residue was purified on silica gel chromatography (0-40% EtOAc in hexanes) to afford 4-((5-(cyclopropylethynyl)-2-methylphenyl)(2,2,2-trifluoroethoxy)methyl)-1-((5,5-dimethyl-1,3-dioxan-2-yl) methyl)-1H-1,2,3-triazole as a colorless oil (86 mg, 82%).

$^1H$ NMR (400 MHz, $CDCl_3$) δ 7.58 (d, J=1.5 Hz, 1H), 7.45 (s, 1H), 7.23 (dd, J=7.8, 1.7 Hz, 1H), 7.04 (d, J=7.8 Hz, 1H), 5.88 (s, 1H), 4.74 (t, J=4.1 Hz, 1H), 4.53-4.38 (m, 2H), 4.04-3.78 (m, 2H), 3.59 (d, J=11.2 Hz, 2H), 3.40 (d, J=11.3 Hz, 2H), 2.21 (s, 3H), 1.50-1.41 (m, 1H), 1.02 (s, 3H), 0.87 (ddd, J=11.3, 5.4, 2.2 Hz, 2H), 0.82 (td, J=5.5, 2.6 Hz, 2H), 0.70 (s, 3H). $^{13}C$ NMR (101 MHz, $CDCl_3$) δ 147.30, 137.12, 135.13, 131.27, 130.66, 128.99, 127.98, 125.22, 124.13, 122.45, 121.85, 97.96, 93.10, 76.95, 76.93, 75.67, 74.46, 66.54, 66.19, 65.85, 65.51, 53.13, 30.11, 22.66, 21.60, 19.12, 8.55, 0.14.

Additional exemplary compounds were prepared following methods substantially similar to the method described above and herein. Data for these compounds are provided in Table 24, Following Example 53.

Example 41: Synthesis of I-669

I-669

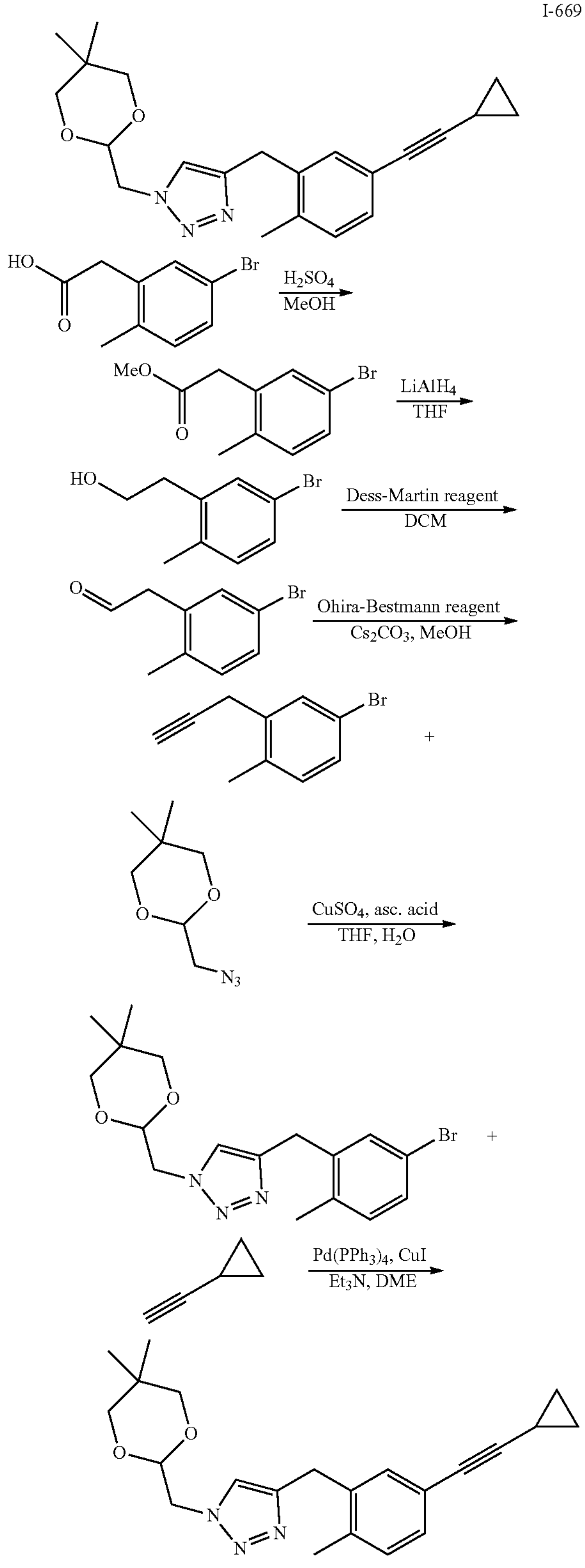

Step 1

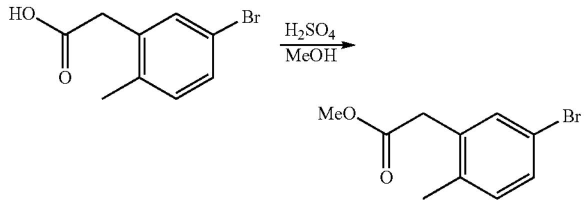

Conc. $H_2SO_4$ (149 μL, 2.79 mmol, 0.4 eq.) was added to a mixture of 2-(5-bromo-2-methylphenyl)acetic acid (1.6 g, 6.98 mmol, 1.0 eq.) in MeOH (35 mL). The mixture was stirred at room temperature for 18 hours. The mixture was concentrated and dissolved in MTBE. Water was added and the organic layer was separated, washed twice with water and brine, dried over $Na_2SO_4$, filtered and concentrated to afford methyl 2-(5-bromo-2-methylphenyl)acetate as a colorless oil (1.68 g, 99%).

Step 2

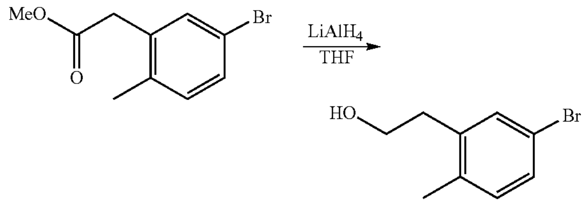

At 0° C., a solution of methyl 2-(5-bromo-2-methylphenyl)acetate (1.68 g, 6.91 mmol, 1.0 eq.) in THE (4.0 mL) was added dropwise in a mixture of $LiAlH_4$ (312 mg, 8.29 mmol, 1.2 eq.) in THE (10 mL). After 2.5 hours of stirring at 0° C., aq. Sat. $Na_2SO_4$ was slowly added dropwise. The mixture was filtered and the filtrate was extracted twice with MTBE. The combined organic layers were washed with brine, dried over $Na_2SO_4$, filtered and concentrated to afford 2-(5-bromo-2-methylphenyl)ethan-1-ol as a colorless oil (955 mg, 64%).

Step 3

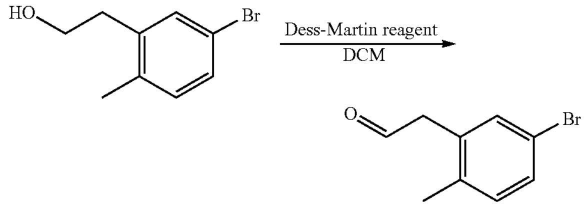

Dess-Martin reagent (3.77 g, 8.88 mmol, 2.0 eq.) was added to a mixture of 2-(5-bromo-2-methylphenyl)ethan-1-ol (955 mg, 4.44 mmol, 1.0 eq.) in DCM (22 mL). The mixture was stirred at room temperature for 2 hours. Aq. Sat. sodium metabisulfite and DCM were added. The organic layer was separated, washed with brine, dried over $Na_2SO_4$, filtered and concentrated. The residue was purified on silica gel (0-15% EtOAc in hexanes) to afford 2-(5-bromo-2-methylphenyl)acetaldehyde as a colorless oil (403 mg, 45%).

Step 4

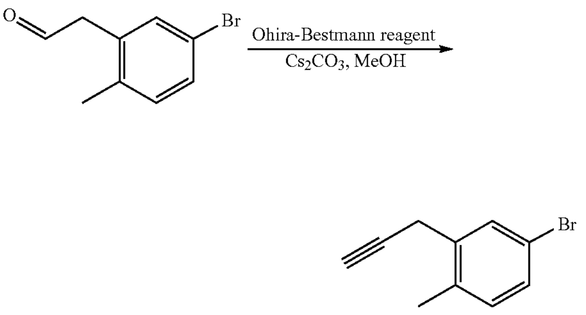

Ohira-Bestmann reagent (0.40 mL, 2.64 mmol, 1.4 eq.) was added to a mixture of 2-(5-bromo-2-methylphenyl) acetaldehyde (402 mg, 1.89 mmol, 1.0 eq.) and $Cs_2CO_3$ (1.84 g, 5.66 mmol, 3.0 eq.) in MeOH (19 mL). After 1 hour of stirring at room temperature, hexanes and $H_2O$ were added. The organic layer was separated and the aqueous layer was extracted with hexanes. The combined organic layers were washed with brine, dried over $Na_2SO_4$, filtered and concentrated to afford 4-bromo-1-methyl-2-(prop-2-yn-1-yl)benzene as a yellow oil (356 mg, 90%).

Step 5

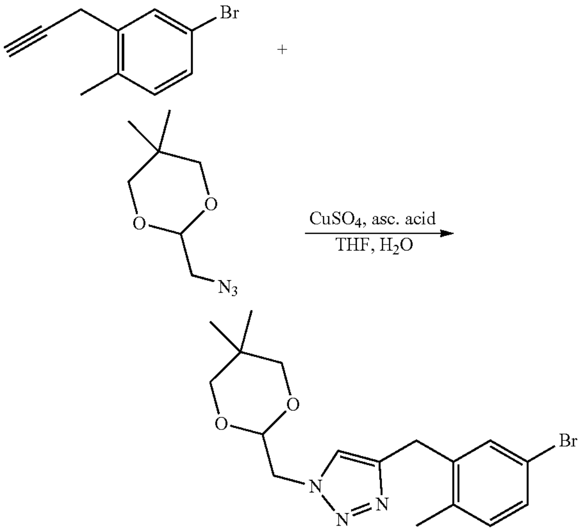

A solution of $CuSO_4$ (42 mg, 0.17 mmol, 0.1 eq.) in $H_2O$ (4.0 mL) was added to a solution of 2-(azidomethyl)-5,5-dimethyl-1,3-dioxane (291 mg, 1.70 mmol, 1.0 eq.) and 4-bromo-1-methyl-2-(prop-2-yn-1-yl)benzene (355 mg, 1.70 mmol, 1.0 eq.) in THE (12 mL). After 1 minute of stirring at room temperature, ascorbic acid (150 mg, 0.85 mmol, 0.5 eq.) was added. The mixture was stirred at room temperature for 2.5 hours. The mixture was poured in aq. Sat. $NH_4Cl$ and EtOAc was added. The organic layer was separated, dried over $Na_2SO_4$, filtered and concentrated. The residue was purified on silica gel chromatography (0-50% EtOAc in hexanes) to afford 4-(5-bromo-2-methylbenzyl)-1-((5,5-dimethyl-1,3-dioxan-2-yl)methyl)-1H-1,2,3-triazole as a yellow oil (334 mg, 52%).

Step 6

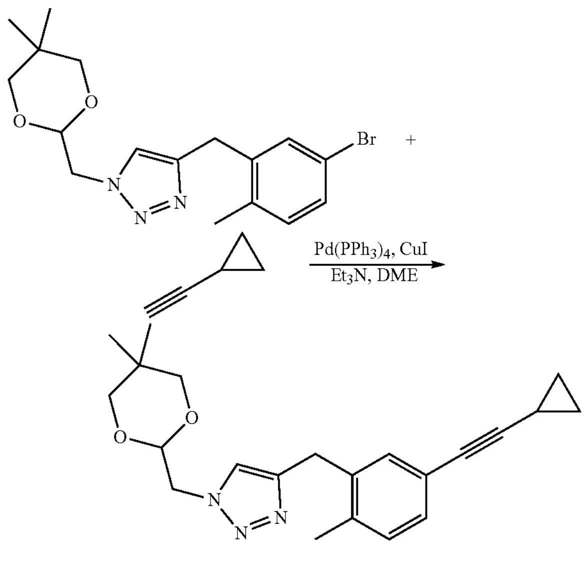

Cyclopropylacetylene (0.25 mL, 2.92 mmol, 10 eq.) was added to a $N_2$ bubbled mixture of 4-(5-bromo-2-methylbenzyl)-1-((5,5-dimethyl-1,3-dioxan-2-yl)methyl)-1H-1,2,3-triazole (111 mg, 0.292 mmol, 1.0 eq.), $Pd(PPh_3)_4$ (34 mg, 0.029 mmol, 0.1 eq.) and CuI (6 mg, 0.029 mmol, 0.1 eq.) in $Et_3N$ (1.5 mL) and DME (1.5 mL). After 1 minutes of $N_2$ bubbling, the reaction was stirred at 90° C. for 18 hours. Once at room temperature, the mixture was poured in aq. Sat. $NH_4Cl$ and MTBE was added. The organic layer was separated, dried over $Na_2SO_4$, filtered and concentrated. The residue was purified on silica gel chromatography (0-50% EtOAc in hexanes) to afford 4-(5-(cyclopropylethynyl)-2-methylbenzyl)-1-((5,5-dimethyl-1,3-dioxan-2-yl)methyl)-1H-1,2,3-triazole as a yellow oil (80 mg, 75%).

$^1H$ NMR (400 MHz, $CDCl_3$) δ 7.19 (s, 2H), 7.16 (dd, J=7.7, 1.7 Hz, 1H), 7.05 (d, J=7.8 Hz, 1H), 4.73 (t, J=4.4 Hz, 1H), 4.42 (d, J=4.4 Hz, 2H), 4.01 (s, 2H), 3.64-3.55 (m, 2H), 3.39 (d, J=10.6 Hz, 2H), 2.24 (s, 3H), 1.42 (tt, J=8.2, 5.1 Hz, 1H), 1.08 (s, 3H), 0.84 (ddt, J=8.3, 5.6, 2.8 Hz, 2H), 0.81-0.74 (m, 2H), 0.70 (s, 3H). $^{13}C$ NMR (101 MHz, $CDCl_3$) δ 146.61, 137.29, 136.11, 132.54, 130.30, 129.94, 123.16, 121.49, 98.38, 92.69, 76.97, 75.71, 53.02, 30.16, 29.95, 22.79, 21.65, 19.45, 8.52, 0.13.

Additional exemplary compounds were prepared following methods substantially similar to the method described above and herein. Data for these compounds are provided in Table 24, Following Example 53.

Example 42: Synthesis of I-679

I-679

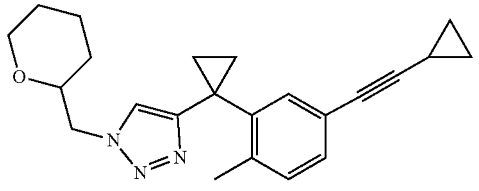

-continued

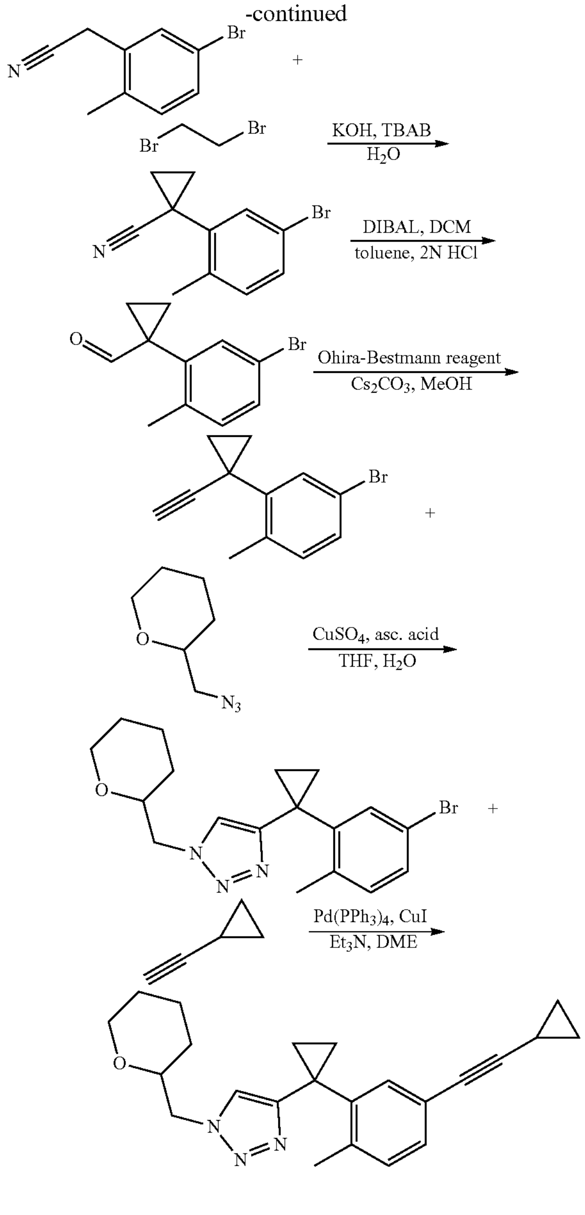

Step 1

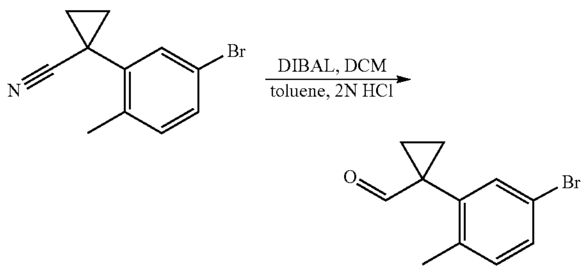

A mixture of KOH (574 mg, 10.2 mmol, 4.3 eq.) in H2O (0.57 mL) was added to a mixture of 2-(5-bromo-2-methylphenyl)acetonitrile, tetramethylammonium bromide (115 mg, 0.357 mmol, 0.15 eq.) and 1,2-dibromoethane (0.31 mL, 3.57 mmol, 1.5 eq.). The mixture was stirred at 50° C. for 18 hours. Once at room temperature, 1N HCl and MTBE were added. The organic layer was separated, washed with brine, dried over $Na_2SO_4$, filtered and concentrated. The residue was purified on silica gel (0-10% EtOAc in hexanes) to afford 1-(5-bromo-2-methylphenyl)cyclopropane-1-carbonitrile as an off-white solid (443 mg, 79%).

Step 2

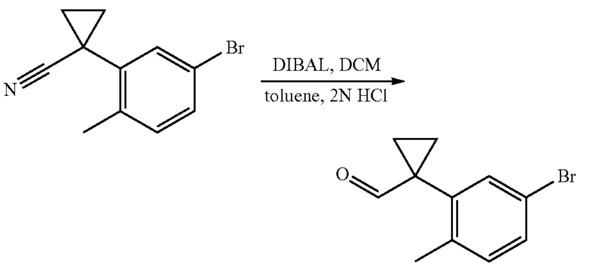

At 0° C., diisobutylaluminum hydride (1M/DCM, 2.48 mL, 2.48 mmol, 1.5 eq.) was added dropwise to a mixture of 1-(5-bromo-2-methylphenyl)cyclopropane-1-carbonitrile (390 mg, 1.65 mmol, 1.0 eq.) in toluene (8.0 mL). The mixture was allowed to warm up to room temperature and stirred at room temperature for 30 min. 2N HCl was added and the mixture was stirred at room temperature for 30 min. MTBE was added and the organic layer was separated, washed with water and brine, dried over $Na_2SO_4$, filtered and concentrated. The residue was purified on silica gel (0-7% EtOAc in hexanes) to afford 1-(5-bromo-2-methylphenyl)cyclopropane-1-carbaldehyde as a colorless oil (311 mg, 79%).

Step 3

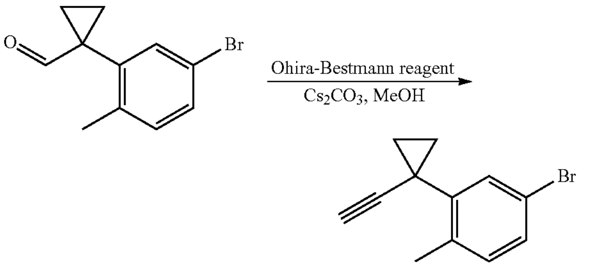

Ohira-Bestmann reagent (0.30 mL, 1.97 mmol, 1.4 eq. was added to a mixture of 1-(5-bromo-2-methylphenyl) cyclopropane-1-carbaldehyde (337 mg, 1.41 mmol, 1.0 eq.) and $Cs_2CO_3$ (1.38 g, 4.23 mmol, 3.0 eq.) in MeOH (7.0 mL). After 2 hour of stirring at room temperature, hexanes and $H_2O$ were added. The organic layer was separated and the aqueous layer was extracted with hexanes. The combined organic layers were washed with brine, dried over $Na_2SO_4$, filtered and concentrated to afford 4-bromo-2-(1-ethynylcyclopropyl)-1-methylbenzene as a colorless oil (277 mg, 84%).

Step 4

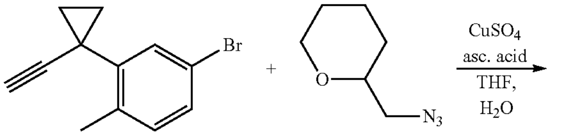

-continued

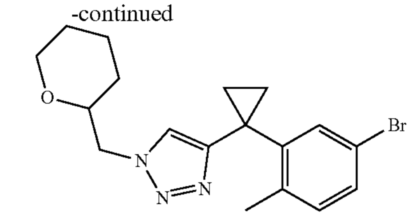

A solution of $CuSO_4$ (29 mg, 0.12 mmol, 0.1 eq.) in $H_2O$ (3.0 mL) was added to a solution of 2-(azidomethyl)tetrahydro-2H-pyran (182 mg, 1.29 mmol, 1.1 eq.) and 4-bromo-2-(1-ethynylcyclopropyl)-1-methylbenzene (276 mg, 1.17 mmol, 1.0 eq.) in THF (9.0 mL). Ascorbic acid (103 mg, 0.59 mmol, 0.5 eq.) was added the mixture was stirred at 60° C. for 48 hours. Once at room temperature, the mixture was poured in aq. sat. $NH_4Cl$ and MTBE was added. The organic layer was separated, dried over $Na_2SO_4$, filtered and concentrated. The residue was purified on silica gel chromatography (0-40% EtOAc in hexanes) to afford 4-(1-(5-bromo-2-methylphenyl)cyclopropyl)-1-((tetrahydro-2H-pyran-2-yl)methyl)-1H-pyrazole as a colorless oil (407 mg, 92%).

Step 5

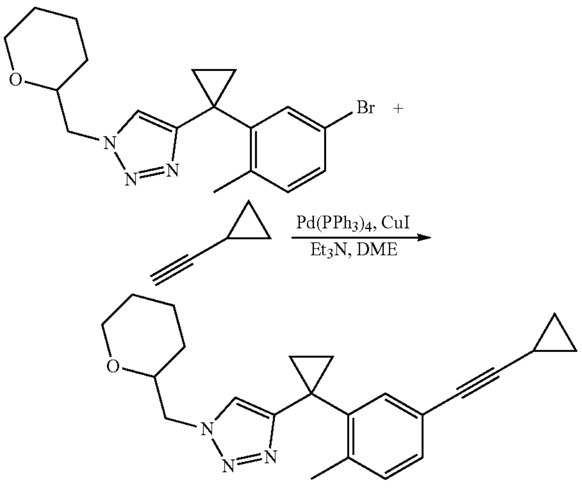

Cyclopropylacetylene (180 μL, 2.13 mmol, 10 eq.) was added to a $N_2$ bubbled mixture of 4-(1-(5-bromo-2-methylphenyl)cyclopropyl)-1-((tetrahydro-2H-pyran-2-yl) methyl)-1H-pyrazole (80 mg, 0.213 mmol, 1.0 eq.), $Pd(PPh_3)_4$ (25 mg, 0.021 mmol, 0.1 eq.) and CuI (4 mg, 0.021 mmol, 0.1 eq.) in $Et_3N$ (1.1 mL) and DME (1.1 mL). After 1 minutes of $N_2$ bubbling, the reaction was stirred at 90° C. for 4 hours. Once at room temperature, the mixture was poured in aq. sat. $NH_4Cl$ and MTBE was added. The organic layer was separated, dried over $Na_2SO_4$, filtered and concentrated. The residue was purified on silica gel chromatography (0-40% EtOAc in hexanes) to afford 4-(1-(5-(cyclopropylethynyl)-2-methylphenyl)cyclopropyl)-1-((tetrahydro-2H-pyran-2-yl)methyl)-1H-1,2,3-triazole as an orange oil (63 mg, 82%). $^1H$ NMR (400 MHz, $CDCl_3$) δ 7.42 (d, J=1.7 Hz, 1H), 7.21 (dd, J=7.8, 1.8 Hz, 1H), 7.06 (d, J=7.8 Hz, 1H), 6.87 (s, 1H), 4.26 (dd, J=14.1, 3.5 Hz, 1H), 4.11 (dd, J=14.1, 7.4 Hz, 1H), 3.94-3.85 (m, 1H), 3.63-3.51 (m, 1H), 3.37-3.26 (m, 1H), 2.23 (s, 3H), 1.86-1.78 (m, 1H), 1.73-1.60 (m, 2H), 1.56 (d, J=12.8 Hz, 1H), 1.52-1.40 (m, 4H), 1.25-1.09 (m, 3H), 0.89-0.83 (m, 2H), 0.83-0.76 (m, 2H). $^{13}C$ NMR (101 MHz, $CDCl_3$) δ 151.60, 141.14, 138.64, 133.75, 130.44, 130.29, 122.48, 121.27, 92.76, 75.99, 75.67, 68.30, 54.89, 28.76, 25.56, 22.80, 21.76, 19.41, 16.67, 16.54, 8.56, 0.13.

Additional exemplary compounds were prepared following methods substantially similar to the method described above and herein. Data for these compounds are provided in Table 24, Following Example 53.

Example 43: Synthesis of I-733

I-733

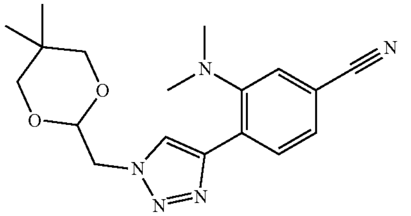

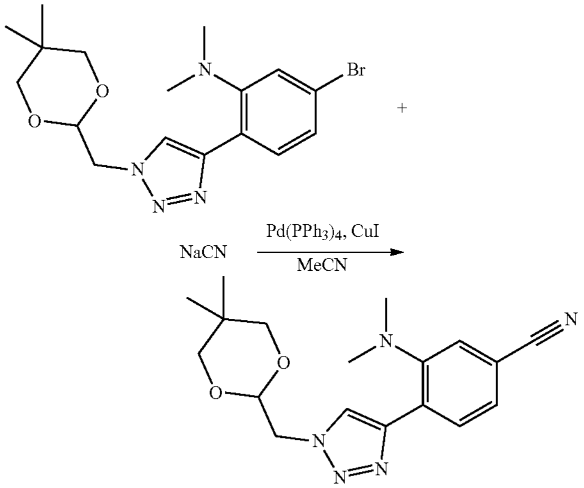

Step 1

Sodium cyanide (22 mg, 0.455 mmol, 2.0 eq.) was added to a $N_2$ bubbled mixture of 5-bromo-2-(1-((5,5-dimethyl-1,3-dioxan-2-yl)methyl)-1H-1,2,3-triazol-4-yl)-N,N-dimethylaniline (90 mg, 0.228 mmol, 1.0 eq.), $Pd(PPh_3)_4$ (26 mg, 0.023 mmol, 0.1 eq.) and copper iodide (9 mg, 0.046 mmol, 0,2 eq.) in acetonitrile (0.5 mL). After 1 min of $N_2$ bubbling, the mixture was stirred at 85° C. for 18 hours. Once at room temperature, the mixture was filtered on celite using EtOAc. The filtrate was washed with aq. sat. $NH_4Cl$, dried over $Na_2SO_4$, filtered and concentrated. The residue was purified on silica gel (0-50% EtOAc/hexanes) to afford 4-(1-((5,5-dimethyl-1,3-dioxan-2-yl)methyl)-1H-1,2,3-triazol-4-yl)-3-(dimethylamino)benzonitrile as a yellow oil (60 mg, 77%).

$^1H$ NMR (400 MHz, $CDCl_3$) δ 8.34 (s, 1H), 8.27 (dd, J=7.9, 0.5 Hz, 1H), 7.42-7.35 (m, 2H), 4.80 (t, J=4.5 Hz, 1H), 4.58 (d, J=4.5 Hz, 2H), 3.64 (d, J=11.3 Hz, 2H), 3.44 (d, J=11.2 Hz, 2H), 2.65 (s, 6H), 1.14 (s, 3H), 0.72 (s, 3H). $^{13}C$ NMR (101 MHz, $CDCl_3$) δ 151.43, 143.57, 129.82, 129.63, 126.62, 125.23, 122.77, 119.13, 111.63, 98.50, 77.10, 53.11, 44.00, 30.23, 22.93, 21.68.

Additional exemplary compounds were prepared following methods substantially similar to the method described above and herein. Data for these compounds are provided in Table 24, Following Example 53.

Example 44: Synthesis of I-743

I-743

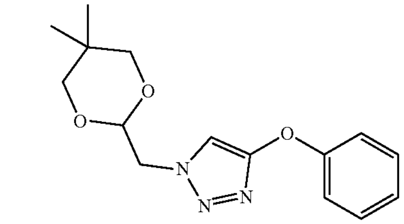

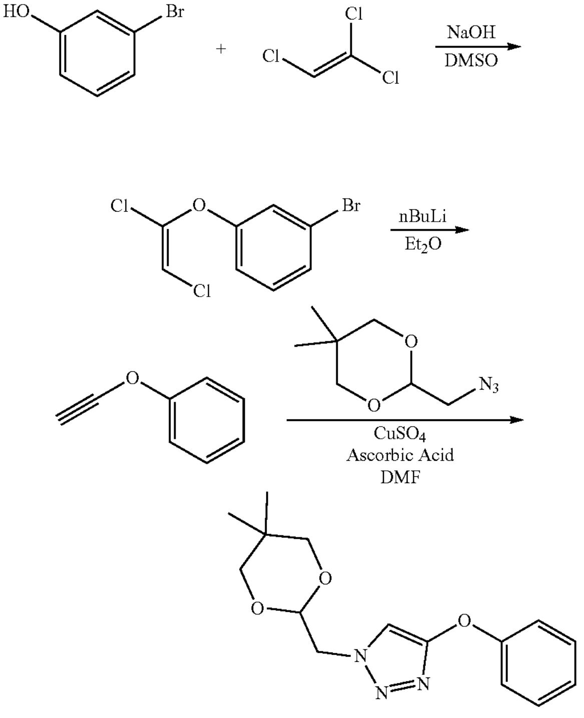

Step 1

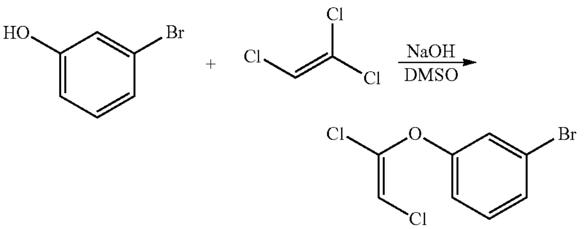

NaOH (116 mg, 2.89 mmol, 1.00 eq.) was added to a solution of 3-bromophenol (500 mg, 2.89 mmol, 1.00 eq.) in DMSO (5.0 mL). The mixture was stirred at room temperature for 2 hours, then 1,1,2-trichloroethylene (253 μL, 2.89 mmol, 1.00 eq.) was added. The mixture was stirred at room temperature for 1 hour. Water was added and the mixture was extracted twice with $CH_2Cl_2$. The combined organic layers were washed with brine, dried over $Na_2SO_4$, filtered, and concentrated under reduced pressure. The residue was purified by silica gel chromatography (0-15% EtOAc in hexanes) to provide (E)-1-bromo-3-((1,2-dichlorovinyl)oxy)benzene as a colorless oil (520 mg, 67%).

Step 2

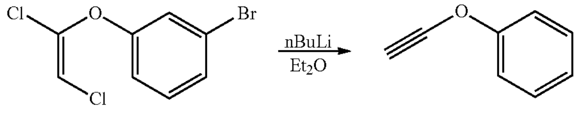

A solution of (E)-1-bromo-3-((1,2-dichlorovinyl)oxy) benzene (250 mg, 0.936 mmol, 1.00 eq.) in $Et_2O$ (5.0 mL) was cooled to −40° C. nBuLi (1.50 mL, 3.75 mmol, 4.00 eq., 2.5M in hexane) was added dropwise and the mixture was warmed to 0° C. and stirred for 1 hour. Water was added and the mixture was extracted twice with $CH_2Cl_2$. The combined organic layers were washed with brine, dried over $Na_2SO_4$, filtered, and concentrated under reduced pressure. The crude mixture (150 mg) was used directly in the next step.

Step 3

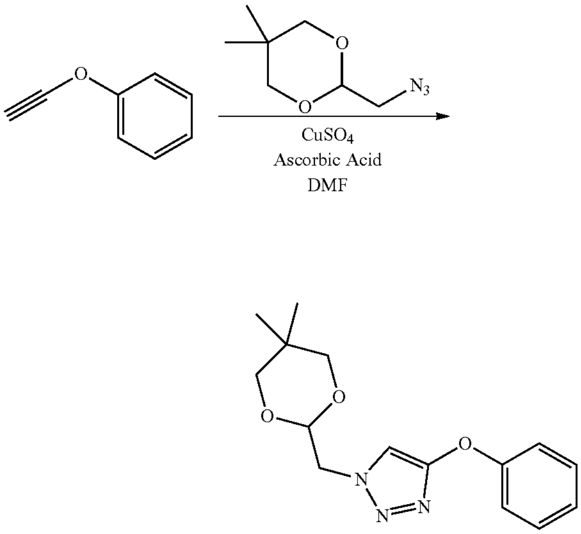

A mixture of the previous crude mixture (150 mg), 2-(azidomethyl)-5,5-dimethyl-1,3-dioxane (173 mg, 0.877 mmol, 1.00 eq.), $CuSO_4$ (55 mg, 0.219 mmol, 0.25 eq.) and ascorbic acid (77 mg, 0.439 mmol, 0.50 eq.) in DMF (5.0 mL) was stirred at room temperature for 75 minutes. A saturated $NH_4Cl$ solution was added, and the mixture was extracted twice with EtOAc. The combined organic layers were washed with brine, dried over $Na_2SO_4$, filtered, and concentrated under reduced pressure. The residue was purified by silica gel chromatography (0-50% EtOAc in hexanes) to provide 1-((5,5-dimethyl-1,3-dioxan-2-yl)methyl)-4-phenoxy-1H-1,2,3-triazole as an amber oil (45 mg, 18%).

$^1H$ NMR (400 MHz, $CDCl_3$) δ 7.37 (s, 1H), 7.35-7.28 (m, 2H), 7.13-7.04 (m, 3H), 4.77 (t, J=4.3 Hz, 1H), 4.47 (d, J=4.3 Hz, 2H), 3.63 (d, J=11.3 Hz, 2H), 3.53-3.33 (m, 2H), 1.13 (s, 3H), 0.72 (s, 3H) ppm. $^{13}C$ NMR (101 MHz, $CDCl_3$) δ 157.73, 157.06, 129.61, 123.62, 117.37, 112.14, 98.18, 77.00, 53.95, 30.16, 22.81, 21.62 ppm.

Additional exemplary compounds were prepared following methods substantially similar to the method described above and herein. Data for these compounds are provided in Table 24, Following Example 53.

Example 45: Synthesis of I-759

I-759

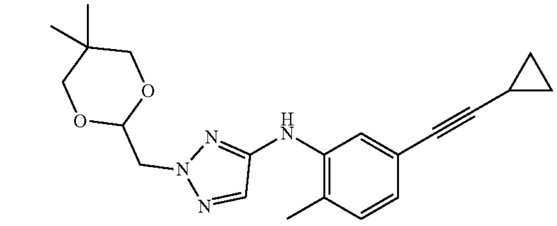

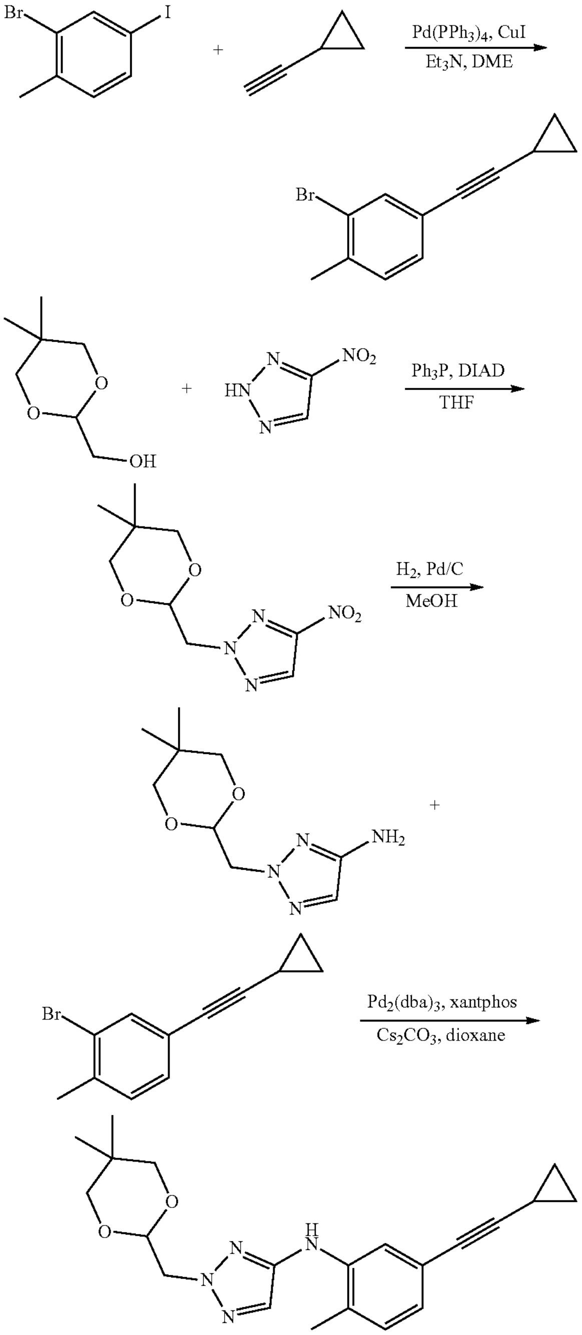

Step 1

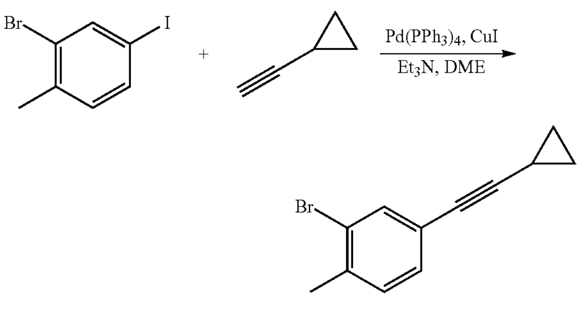

Cyclopropylacetylene (5.7 mL, 67.4 mmol, 10 eq.) was added to a $N_2$ bubbled mixture of 2-bromo-4-iodo-1-methylbenzene (2.0 g, 6.74 mmol, 1.0 eq.), $Pd(PPh_3)_4$ (779 mg, 0.674 mmol, 0.1 eq.) and CuI (128 mg, 0.674 mmol, 0.1 eq.) in $Et_3N$ (33 mL) and DME (33 mL). After 2 minutes of $N_2$ bubbling, the reaction was stirred at 50° C. for 3 hours. Once at room temperature, the mixture was poured in aq. sat. $NH_4Cl$ and hexanes and MTBE were added. The organic layer was separated, dried over $Na_2SO_4$, filtered and concentrated. The residue was purified on silica gel chromatography (100% hexanes) to afford 2-bromo-4-(cyclopropylethynyl)-1-methylbenzene as an orange oil (1.57 g, 99%).

Step 2

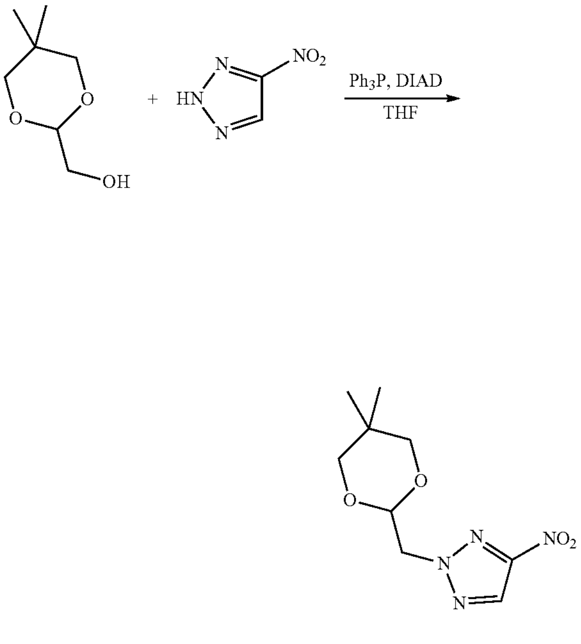

Diisopropyl azodicarboxylate (295 µL, 1.5 mmol, 1.5 eq.) was added to a mixture of (5,5-dimethyl-1,3-dioxan-2-yl) methanol (219 mg, 1.5 mmol, 1.5 eq.), 4-nitro-2H-1,2,3-triazole (114 mg, 1.0 mmol, 1.0 eq.) and triphenylphosphine (393 mg, 1.5 mmol, 1.5 eq.) in THF (2.5 mL). The mixture was stirred at room temperature for 66 hours. The mixture was concentrated and the residue was purified on silica gel (0-50% EtOAc/hexanes) to afford 2-((5,5-dimethyl-1,3-dioxan-2-yl)methyl)-4-nitro-2H-1,2,3-triazole as a white solid (159 mg, 66%).

Step 3

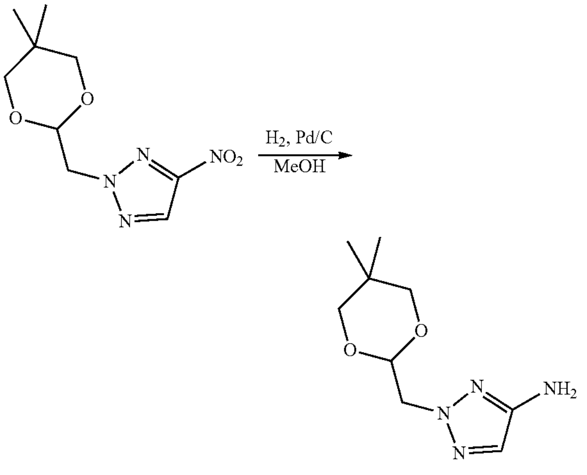

2-((5,5-Dimethyl-1,3-dioxan-2-yl)methyl)-4-nitro-2H-1,2,3-triazole (158 mg, 0.652 mmol, 1.0 eq.) was added to a $N_2$ bubbled mixture of palladium on carbon (10% w/w, 69 mg, 0.065 mmol, 0.1 eq.) in methanol (7 mL). $N_2$ was removed and $H_2$ was bubbled in the mixture for 5 minutes. The mixture was stirred under $H_2$ atmosphere for 2 hours. $H_2$ was removed and $N_2$ was bubbled in the mixture. Celite was added and the mixture was filtered on celite. The filtrate was concentrated to afford 2-((5,5-dimethyl-1,3-dioxan-2-yl) methyl)-2H-1,2,3-triazol-4-amine as a pale yellow solid (138 mg, quant.).

Step 4

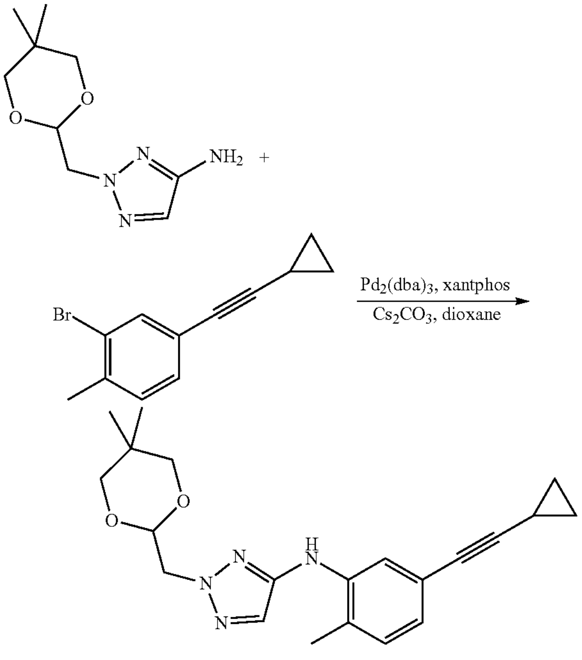

$Cs_2CO_3$ (322 mg, 0.989 mmol, 3.0 eq.) was added to a $N_2$ bubbled mixture of 2-bromo-4-(cyclopropylethynyl)-1-methylbenzene (78 mg, 0.330 mmol, 1.0 eq.), 2-((5,5-dimethyl-1,3-dioxan-2-yl)methyl)-2H-1,2,3-triazol-4-amine (70 mg, 0.330 mmol, 1.0 eq.), $Pd_2(dba)_3$ (30 mg, 0.033 mmol, 0.1 eq.) and 4,5-Bis(diphenylphosphino)-9,9-dimethylxanthene (28 mg, 0.049 mmol, 0.15 eq.) in dioxane (3.3 mL). After 1 minute of $N_2$ bubbling, the mixture was stirred at 100° C. for 18 hours. Once at room temperature, the mixture was poured in aqueous saturated $NH_4Cl$ and MTBE was added. The organic layer was separated, dried over $Na_2SO_4$, filtered and concentrated. The residue was purified on silica gel chromatography (0-30% EtOAc/hexanes) to afford N-(5-(cyclopropylethynyl)-2-methylphenyl)-2-((5,5-dimethyl-1,3-dioxan-2-yl)methyl)-2H-1,2,3-triazol-4-amine as an orange gum (74 mg, 61%).

$^1$H NMR (400 MHz, $CDCl_3$) δ 7.42 (s, 1H), 7.24 (d, J=1.3 Hz, 1H), 7.03 (d, J=7.8 Hz, 1H), 6.87 (dd, J=7.7, 1.5 Hz, 1H), 5.77 (s, 1H), 4.91 (t, J=4.9 Hz, 1H), 4.49 (d, J=4.9 Hz, 2H), 3.67 (d, J=11.3 Hz, 2H), 3.44 (d, J=10.7 Hz, 3H), 2.22 (s, 3H), 1.49-1.37 (m, 1H), 1.19 (s, 4H), 0.87-0.81 (m, 2H), 0.81-0.76 (m, 2H), 0.72 (s, 3H). $^{13}$C NMR (101 MHz, $CDCl_3$) δ 148.33, 140.52, 130.57, 124.05, 124.03, 123.87, 122.43, 116.98, 98.91, 92.55, 77.14, 75.91, 57.57, 30.31, 22.90, 21.75, 17.58, 8.53, 0.15.

Additional exemplary compounds were prepared following methods substantially similar to the method described above and herein. Data for these compounds are provided in Table 24, Following Example 53.

Example 46: Synthesis of I-760

I-760

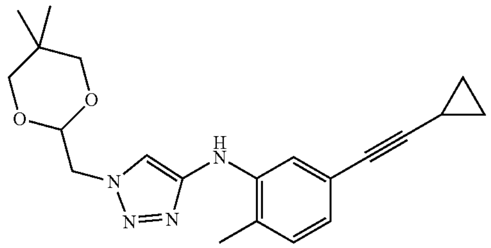

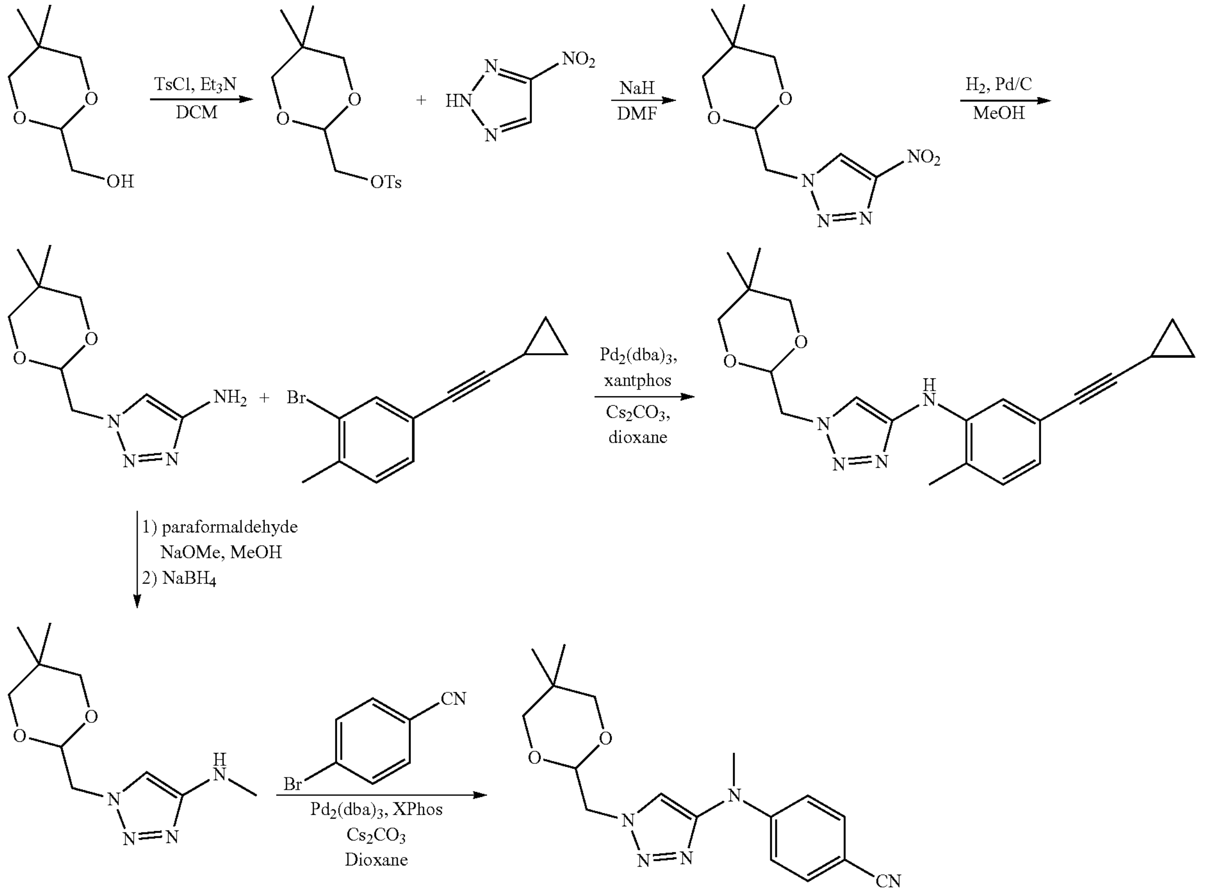

Step 1

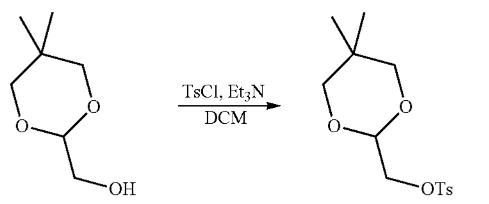

At 0° C., $Et_3N$ (3.1 mL, 22.1 mmol, 2.5 eq.) was added to a mixture of (5,5-dimethyl-1,3-dioxan-2-yl)methanol (1.29 g, 8.82 mmol, 1.0 eq.) and tosyl chloride (1.85 g, 9.71 mmol, 1.1 eq.) in DCM (22 mL). The mixture was allowed to warm up to room temperature and stirred at room temperature for 18 hours. Another portion of tosyl chloride (841 mg, 4.41 mmol, 0.5 eq.) and $Et_3N$ (1.23 mL, 8.82 mmol, 1.0 eq.) were added and the mixture was stirred at room temperature for 4 hours. Aq. sat. $NaHCO_3$ and DCM were added, the org. layer was separated, washed with brine, dried over $Na_2SO_4$, filtered and concentrated. The residue was purified on silica gel (0-30% EtOAc/hexanes) to afford (5,5-dimethyl-1,3-dioxan-2-yl)methyl 4-methylbenzenesulfonate as a white solid (2.45 g, 92%).

Step 2

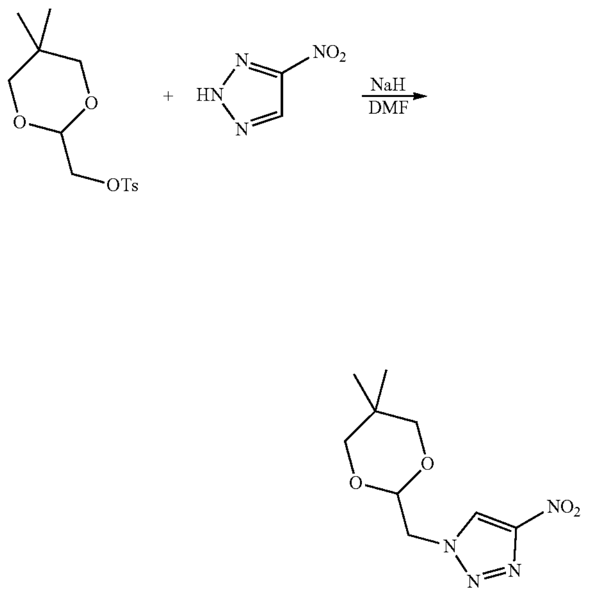

At 0° C., 4-nitro-2H-1,2,3-triazole (228 mg, 2.0 mmol, 1.0 eq.) was added to a mixture of sodium hydride (60% $^{W}$/w oil dispersion, 84 mg, 2.1 mmol, 1.05 eq.) in DMF (10 mL). After 10 minutes of stirring at 0° C., (5,5-dimethyl-1,3-dioxan-2-yl)methyl 4-methylbenzenesulfonate was added. The mixture was stirred at 100° C. for 66 hours. Once at room temperature, the mixture was poured in aq. sat. $NH_4Cl$ and MTBE was added. The org. layer was separated, dried over $Na_2SO_4$, filtered and concentrated. The residue was purified on silica gel (0-40% EtOAc/hexanes) to afford 1-((5,5-dimethyl-1,3-dioxan-2-yl)methyl)-4-nitro-1H-1,2,3-triazole as a white solid (210 mg, 43%).

Step 3

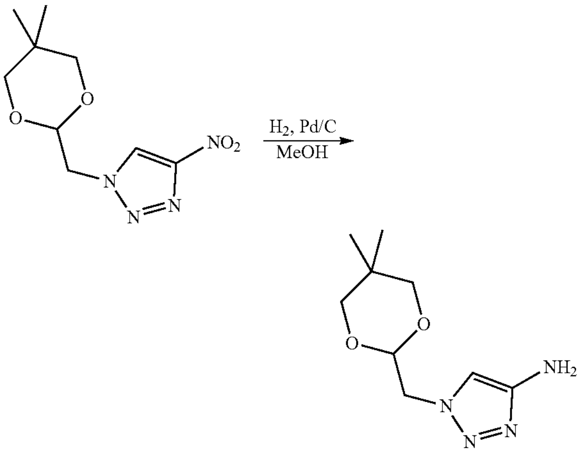

1-((5,5-Dimethyl-1,3-dioxan-2-yl)methyl)-4-nitro-1H-1,2,3-triazole (209 mg, 0.863 mmol, 1.0 eq.) was added to a $N_2$ bubbled mixture of palladium on carbon (10% w/w, 92 mg, 0.086 mmol, 0.1 eq.) in methanol (9 mL). $N_2$ was removed and $H_2$ was bubbled in the mixture for 5 minutes. The mixture was stirred under $H_2$ atmosphere for 2 hours. $H_2$ was removed and $N_2$ was bubbled in the mixture. Celite was added and the mixture was filtered on celite. The filtrate was concentrated to afford 1-((5,5-dimethyl-1,3-dioxan-2-yl)methyl)-1H-1,2,3-triazol-4-amine as a pale yellow solid (177 mg, 97%).

Step 4

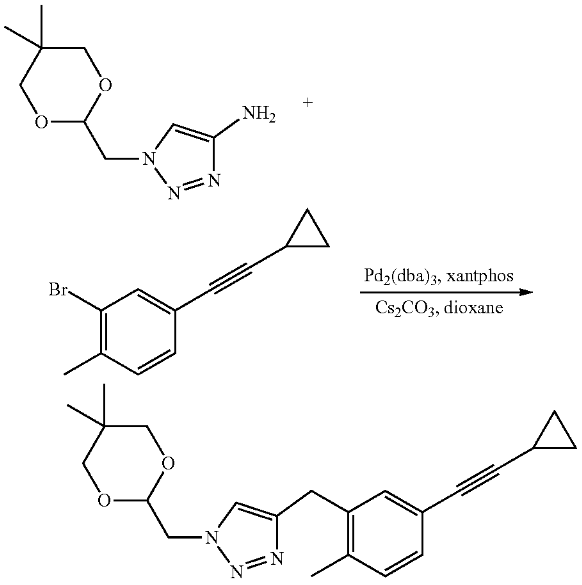

$Cs_2CO_3$ (926 mg, 2.84 mmol, 3.0 eq.) was added to a $N_2$ bubbled mixture of 2-bromo-4-(cyclopropylethynyl)-1-methylbenzene (223 mg, 0.947 mmol, 1.0 eq.), 1-((5,5-dimethyl-1,3-dioxan-2-yl)methyl)-1H-1,2,3-triazol-4-amine (201 mg, 0.947 mmol, 1.0 eq.), $Pd_2(dba)_3$ (87 mg, 0.095 mmol, 0.1 eq.) and 4,5-Bis(diphenylphosphino)-9,9-dimethylxanthene (82 mg, 0.142 mmol, 0.15 eq.) in dioxane (9.5 mL). After 1 minute of $N_2$ bubbling, the mixture was stirred at 100° C. for 18 hours. Once at room temperature, the mixture was poured in aqueous saturated $NH_4Cl$ and EtOAc was added. The organic layer was separated, dried over $Na_2SO_4$, filtered and concentrated. The residue was purified on silica gel chromatography (0-50% EtOAc/hexanes) to afford N-(5-(cyclopropylethynyl)-2-methylphenyl)-1-((5,5-dimethyl-1,3-dioxan-2-yl)methyl)-1H-1,2,3-triazol-4-amine as a yellow solid (174 mg, 50%).

$^1$H NMR (400 MHz, $CDCl_3$) δ 7.53 (s, 1H), 7.06-7.00 (m, 2H), 6.84 (dd, J=7.6, 1.5 Hz, 1H), 5.88 (s, 1H), 4.79 (t, J=4.3 Hz, 1H), 4.50 (d, J=4.3 Hz, 2H), 3.65 (d, J=11.3 Hz, 2H), 3.45 (d, J=10.8 Hz, 2H), 2.24 (s, 3H), 1.42 (tt, J=8.2, 5.1 Hz, 1H), 1.17 (s, 3H), 0.87-0.80 (m, 2H), 0.78 (tt, J=5.1, 2.3 Hz, 2H), 0.73 (s, 3H). $^{13}$C NMR (101 MHz, $CDCl_3$) δ 147.44, 141.10, 130.60, 123.76, 123.55, 122.29, 115.76, 112.71, 98.43, 92.34, 77.06, 76.07, 53.63, 30.23, 22.95, 21.68, 17.58, 8.50, 0.15.

Additional exemplary compounds were prepared following methods substantially similar to the method described above and herein. Data for these compounds are provided in Table 24, Following Example 53.

Synthesis of I-793

I-793

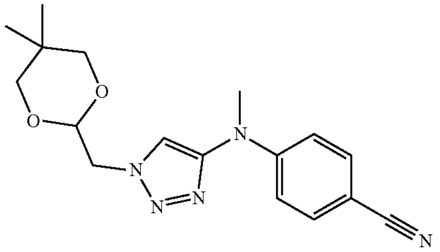

Step 1

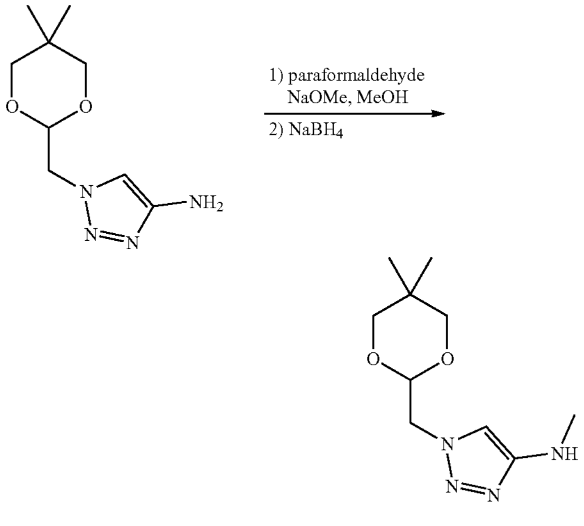

Paraformaldehyde (373 mg, 12.4 mmol, 6.00 eq.) and NaOMe (1.04 mL, 6.24 mmol, 3.00 eq., 25% w/w) were added to a solution of 1-((5,5-dimethyl-1,3-dioxan-2-yl)methyl)-4-nitro-1H-1,2,3-triazole (440 mg, 2.08 mmol, 1.00 eq.) in MeOH (7.0 mL). The mixture was stirred at 65° C. for three hours and then cooled to room temperature. $NaBH_4$ (196 mg, 5.20 mmol, 2.50 eq.) was added and the mixture was stirred at room temperature for 1 hour. A saturated $NaHCO_3$ was added dropwise, and the mixture was concentrated under reduced pressure to remove MeOH. The aqueous residue was diluted with brine and extracted twice with $CH_2Cl_2$. The combined organic layers were dried over $Na_2SO_4$, filtered, and concentrated under reduced pressure. The residue was purified by silica gel chromatography (20-100% EtOAc in hexanes) to provide 1-((5,5-dimethyl-1,3-dioxan-2-yl)methyl)-N-methyl-1H-1,2,3-triazol-4-amine as a white solid (253 mg, 54%).

Step 2

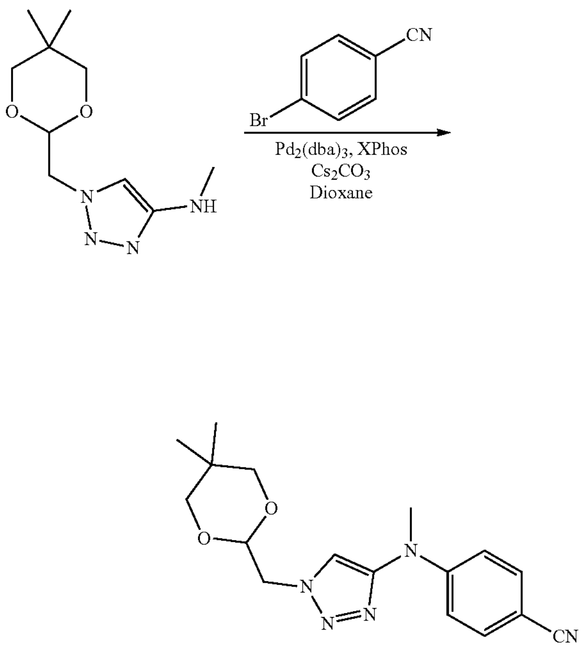

A mixture of 1-((5,5-dimethyl-1,3-dioxan-2-yl)methyl)-N-methyl-1H-1,2,3-triazol-4-amine (40 mg, 0.177 mmol, 1.00 eq.), 4-bromobenzonitrile (32 mg, 0.177 mmol, 1.00 eq.), $Cs_2CO_3$ (144 mg, 0.443 mmol, 2.50 eq.), XPhos (17 mg, 0.0354 mmol, 0.20 eq.) and $Pd_2(dba)_3$ (16 mg, 0.0177 mmol, 0.10 eq.) in dioxane (1.0 mL) was degassed with $N_2$ for 10 minutes and stirred at 100° C. for 4 hours. The mixture was cooled to room temperature, diluted with water, and extracted twice with EtOAc. The combined organic layers were washed with brine, dried over $Na_2SO_4$, filtered, and concentrated under reduced pressure. The residue was purified by silica gel chromatography (20-70% EtOAc in hexanes) to provide 4-((1-((5,5-dimethyl-1,3-dioxan-2-yl)methyl)-1H-1,2,3-triazol-4-yl)(methyl)amino)benzonitrile as an orange oil (46 mg, 79%).

$^1$H NMR (400 MHz, $CDCl_3$) δ 7.59 (s, 1H), 7.47 (d, J=9.0 Hz, 2H), 6.92 (d, J=9.0 Hz, 2H), 4.80 (t, J=4.1 Hz, 1H), 4.52 (d, J=4.1 Hz, 2H), 3.64 (d, J=11.3 Hz, 2H), 3.45 (d, J=10.8 Hz, 2H), 3.40 (s, 3H), 1.12 (s, 3H), 0.73 (s, 3H) ppm. $^{13}$C NMR (101 MHz, $CDCl_3$) δ 150.63, 150.28, 133.25, 119.89, 117.71, 114.23, 101.01, 97.99, 77.00, 53.61, 39.03, 30.14, 22.76, 21.58 ppm.

Additional exemplary compounds were prepared following methods substantially similar to the method described above and herein. Data for these compounds are provided in Table 24, Following Example 53.

Example 47: Synthesis of I-761

I-761

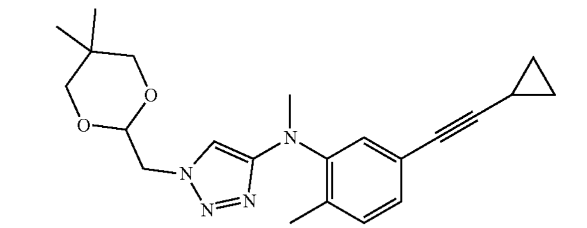

Step 1

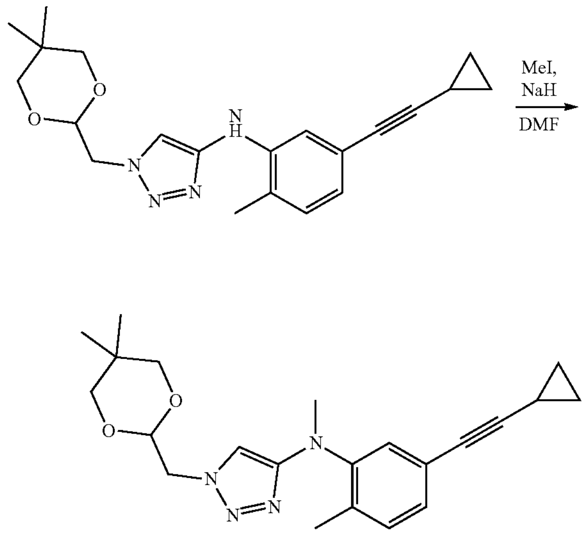

Sodium hydride (60% $^{w}$/w oil dispersion, 7 mg, 0.164 mmol, 1.2 eq.) was added to a mixture of N-(5-(cyclopropylethynyl)-2-methylphenyl)-1-((5,5-dimethyl-1,3-dioxan-2-yl)methyl)-1H-1,2,3-triazol-4-amine (50 mg, 0.136 mmol, 1.0 eq.) in DMF (1.4 mL). The mixture was stirred at room temperature for 5 hours. The mixture was poured in aq. sat. $NH_4Cl$ and MTBE was added. The org. layer was separated, dried over $Na_2SO_4$, filtered and concentrated. The residue was dissolved in acetonitrile. The resulting solution was washed with heptane and concentrated to afford N-(5-(cyclopropylethynyl)-2-methylphenyl)-1-((5,5-dimethyl-1,3-dioxan-2-yl)methyl)-N-methyl-1H-1,2,3-triazol-4-amine as an orange gum (37 mg, 72%).

$^1$H NMR (400 MHz, $CDCl_3$) δ 7.21 (s, 1H), 7.17-7.10 (m, 2H), 6.62 (s, 1H), 4.72 (t, J=4.5 Hz, 1H), 4.34 (d, J=4.5 Hz, 2H), 3.59 (d, J=11.4 Hz, 2H), 3.40 (d, J=11.3 Hz, 2H), 3.31 (s, 3H), 2.15 (s, 3H), 1.47-1.38 (m, 1H), 1.12 (s, 3H), 0.85 (ddt, J=8.3, 5.7, 3.2 Hz, 2H), 0.77 (tt, J=5.0, 2.8 Hz, 2H), 0.71 (s, 3H). $^{13}$C NMR (101 MHz, $CDCl_3$) δ 155.55, 146.54, 135.04, 131.33, 128.95, 128.60, 122.58, 108.90, 98.70, 93.04, 76.98, 75.29, 53.45, 39.26, 30.19, 22.86, 21.68, 17.91, 8.55, 0.10.

Additional exemplary compounds were prepared following methods substantially similar to the method described above and herein. Data for these compounds are provided in Table 24, Following Example 53.

Example 48: Synthesis of I-774

I-774

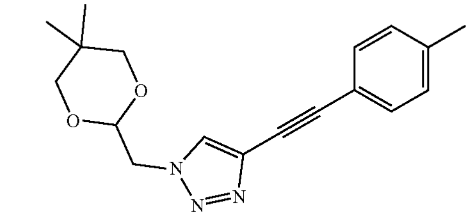

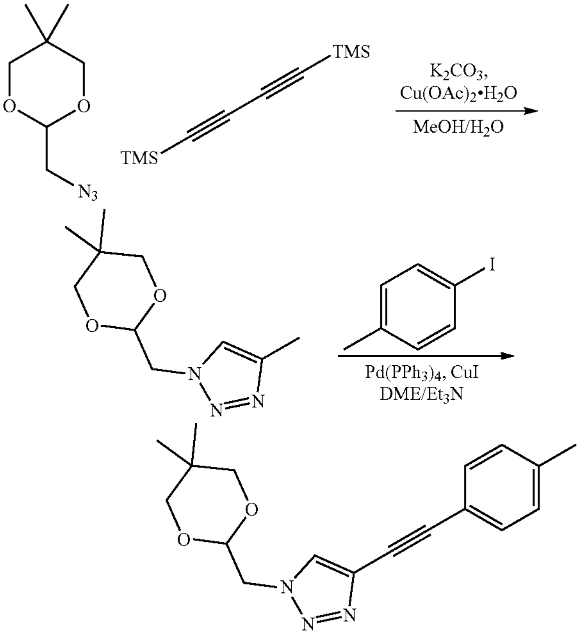

Step 1

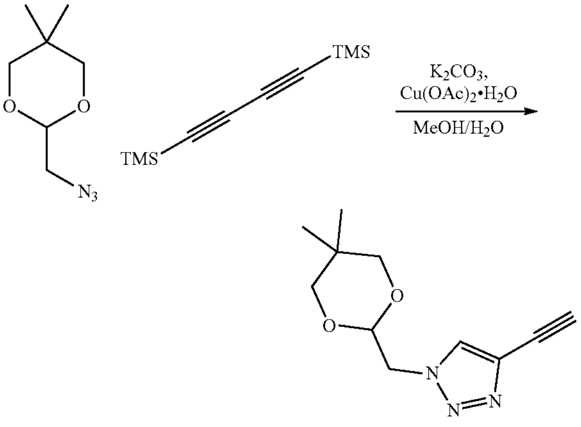

2-(azidomethyl)-5,5-dimethyl-1,3-dioxane (300 mg, 1.75 mmol, 1.00 eq.), 1,4-bis(trimethylsilyl)buta-1,3-diyne (880 mg, 4.53 mmol, 2.5 eq.) and $K_2CO_3$ (1.2 g, 8.70 mmol, 5.0 eq.) were added to a solution of $Cu(OAc)_2$. $H_2O$ (64 mg, 0.35 mmol, 0.20 eq.) in MeOH (3.5 mL) and water (3.5 mL). The mixture was stirred at room temperature for 3 hours. A saturated $NH_4Cl$ solution was added, and the mixture was extracted with twice with EtOAc. The combined organic layers were washed with brine, dried over $Na_2SO_4$, filtered, and concentrated under reduced pressure. The residue was purified by silica gel chromatography (0-100% EtOAc in hexanes) to provide 1-((5,5-dimethyl-1,3-dioxan-2-yl)methyl)-4-ethynyl-1H-1,2,3-triazole as a white solid (55 mg, 14%).

Step 2

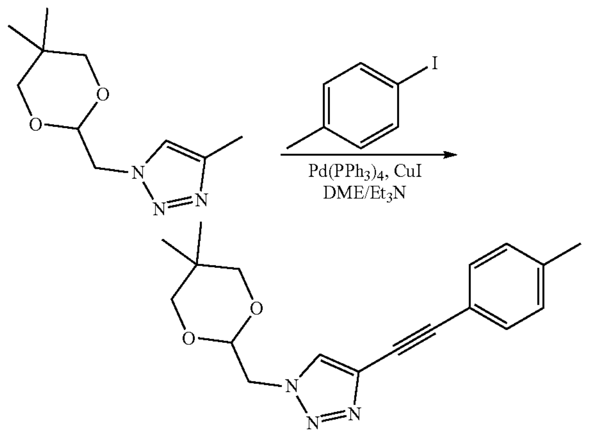

A mixture of 4-iodotoluene (45 mg, 0.207 mmol, 1.00 eq.), 1-((5,5-dimethyl-1,3-dioxan-2-yl)methyl)-4-ethynyl-1H-1,2,3-triazole (55 mg, 0.249 mmol, 1.20 eq.), $Pd(PPh_3)_4$ (24 mg, 0.021 mmol, 0.10 eq.) and CuI (4 mg, 0.021 mmol, 0.10 eq.) in DME (0.8 mL) and $Et_3N$ (0.2 mL) was degassed with $N_2$ for 10 minutes and then stirred at 50° C. for 4 hours. The mixture was cooled to room temperature, poured into a saturated $NH_4Cl$ solution was added, and the mixture was extracted with twice with EtOAc. The combined organic layers were washed with brine, dried overNa2$SO_4$, filtered, and concentrated under reduced pressure. The residue was purified by silica gel chromatography (0-50% EtOAc in hexanes) to provide 1-((5,5-dimethyl-1,3-dioxan-2-yl)methyl)-4-(p-tolylethynyl)-1H-1,2,3-triazole as yellow solid (47 mg, 73%).

$^1$H NMR (400 MHz, $CDCl_3$) δ 7.84 (s, 1H), 7.43 (d, J=8.0 Hz, 2H), 7.15 (d, J=8.0 Hz, 2H), 4.75 (t, J=4.4 Hz, 1H), 4.52 (d, J=4.4 Hz, 2H), 3.62 (d, J=11.3 Hz, 2H), 3.42 (d, J=10.9 Hz, 2H), 2.35 (s, 3H), 1.13 (s, 3H), 0.72 (s, 3H) ppm. $^{13}$C NMR (101 MHz, $CDCl_3$) δ 138.88, 131.46, 131.03, 129.09, 127.35, 119.26, 98.08, 92.49, 76.97, 53.07, 30.14, 22.83, 21.60, 21.49 ppm.

Additional exemplary compounds were prepared following methods substantially similar to the method described above and herein. Data for these compounds are provided in Table 24, Following Example 53.

Example 49: Synthesis of I-781, I-782, and I-783

I-781

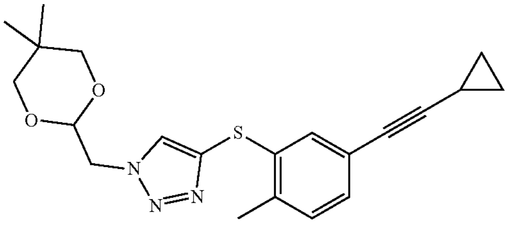

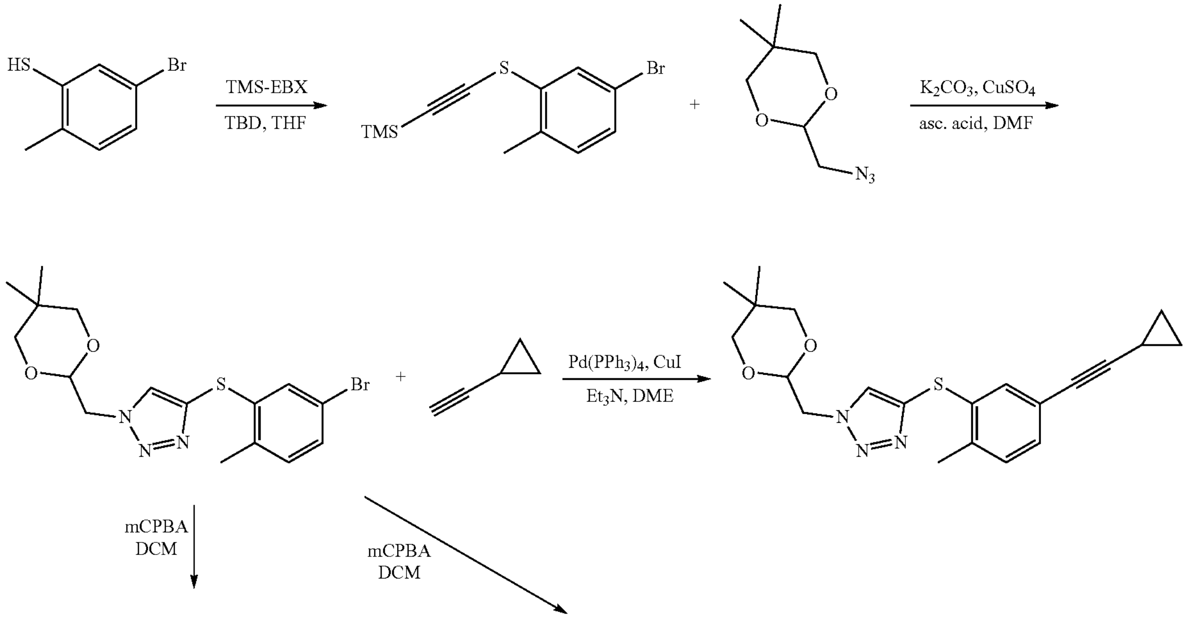

-continued

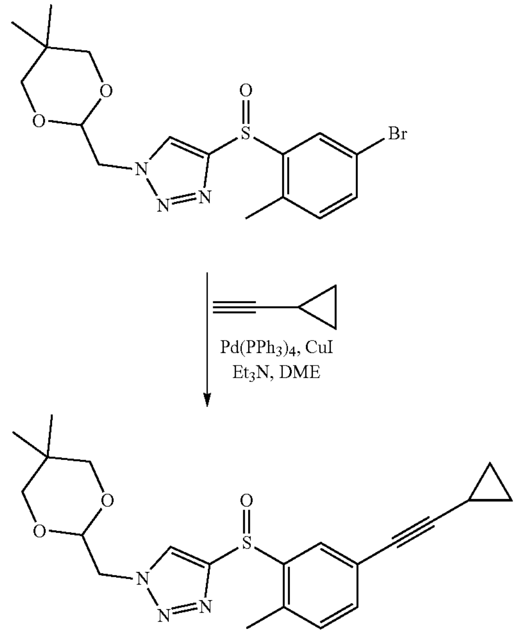

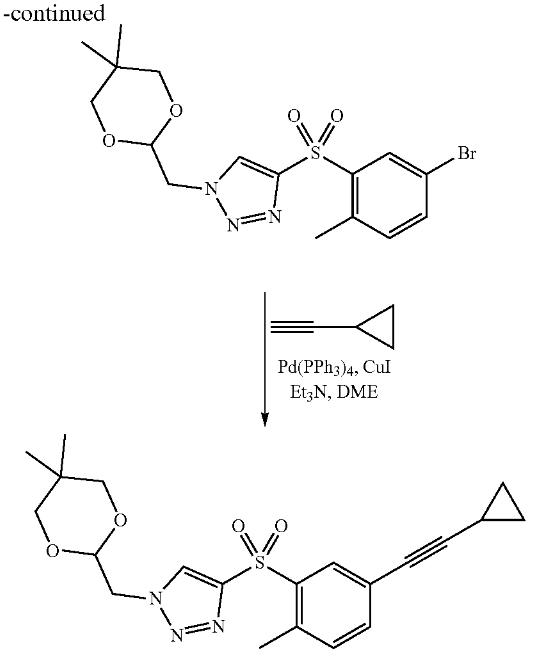

Step 1

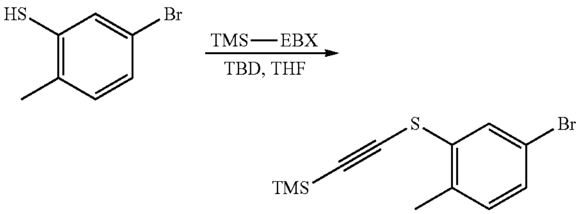

1-[(Trimethylsilyl)ethynyl]-1,2-benziodoxol-3(1H)-one (559 mg, 1.62 mmol, 1.1 eq.) was added to a mixture of 5-bromo-2-methylbenzenethiol (300 mg, 1.48 mmol, 1.0 eq.) and triazabicyclodecene (205 mg, 1.48 mmol, 1.0 eq.) in THE (18 mL). After 10 minutes of stirring at room temperature, the mixture was concentrated and the residue was purified on silica gel (0-10% EtOAc/hexanes) to afford (((5-bromo-2-methylphenyl)thio)ethynyl)trimethylsilane as a colorless oil (421 mg, 95%).

Step 2

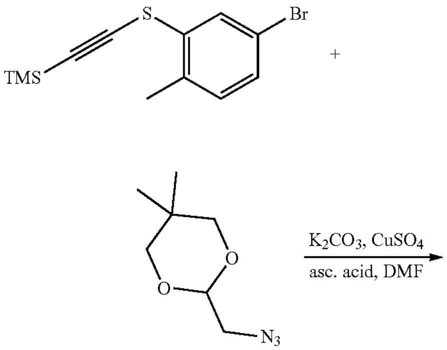

-continued

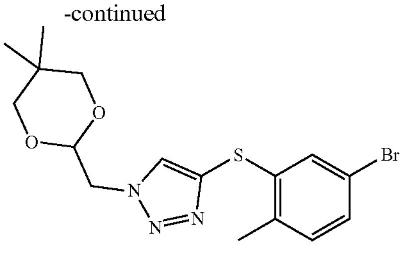

$K_2CO_3$ (970 mg, 7.02 mmol, 5.0 eq.) was added to a mixture of 2-(azidomethyl)-5,5-dimethyl-1,3-dioxane (240 mg, 1.40 mmol, 1.0 eq.), (((5-bromo-2-methylphenyl)thio)ethynyl)trimethylsilane (420 mg, 1.40 mmol, 1.0 eq.), $CuSO_4$ $5H_2O$ (175 mg, 0.70 mmol, 0.5 eq.) and ascorbic acid (247 mg, 1.40 mmol, 1.0 eq.) in DMF (7.0 mL). After 2 hours of stirring at room temperature, the mixture was poured in aq. sat. $NH_4Cl$ and MTBE was added. The org. layer was separated, dried over $Na_2SO_4$, filtered and concentrated. The residue was purified on silica gel (0-40% EtOAc/hexanes) to afford 4-((5-bromo-2-methylphenyl)thio)-1-((5,5-dimethyl-1,3-dioxan-2-yl)methyl)-1H-1,2,3-triazole as a colorless oil (393 mg, 70%).

Step 3

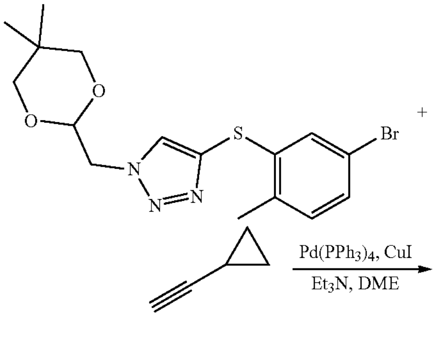

-continued

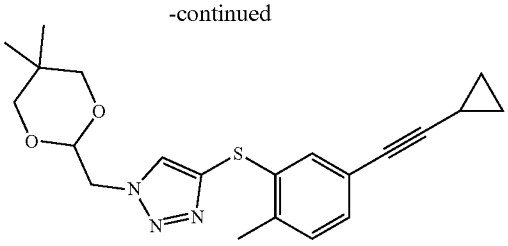

Cyclopropylacetylene (149 μL, 1.76 mmol, 10 eq.) was added to a $N_2$ bubbled mixture of 4-((5-bromo-2-methylphenyl)thio)-1-((5,5-dimethyl-1,3-dioxan-2-yl)methyl)-1H-1,2,3-triazole (70 g, 0.176 mmol, 1.0 eq.), $Pd(PPh_3)_4$ (21 mg, 0.018 mmol, 0.1 eq.) and CuI (3 mg, 0.018 mmol, 0.1 eq.) in $Et_3N$ (0.9 mL) and DME (0.9 mL). After 1 minute of $N_2$ bubbling, the reaction was stirred at 90° C. for 5 hours. Once at room temperature, the mixture was poured in aq. sat. $NH_4Cl$ and MTBE was added. The organic layer was separated, dried over $Na_2SO_4$, filtered and concentrated. The residue was purified on silica gel chromatography (0-40% EtOAc/hexanes) to 4-((5-(cyclopropylethynyl)-2-methylphenyl)thio)-1-((5,5-dimethyl-1,3-dioxan-2-yl)methyl)-1H-1,2,3-triazole as a pale yellow oil (46 mg, 68%). $^1H$ NMR (400 MHz, $CDCl_3$) δ 7.80 (s, 1H), 7.12-6.98 (m, 3H), 4.79 (t, J=4.2 Hz, 1H), 4.55 (d, J=4.2 Hz, 2H), 3.64 (d, J=11.3 Hz, 2H), 3.44 (d, J=10.7 Hz, 2H), 2.41 (s, 3H), 1.42-1.33 (m, 1H), 1.10 (s, 3H), 0.85-0.78 (m, 2H), 0.77-0.71 (m, 5H). $^{13}C$ NMR (101 MHz, $CDCl_3$) δ 137.11, 136.26, 135.01, 131.43, 130.07, 129.79, 129.68, 122.25, 97.97, 93.16, 77.02, 53.34, 30.18, 22.84, 21.65, 20.20, 8.49, 0.11.

I-782

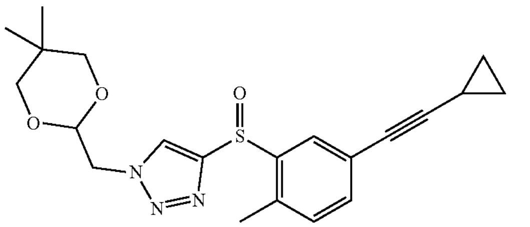

Step 1

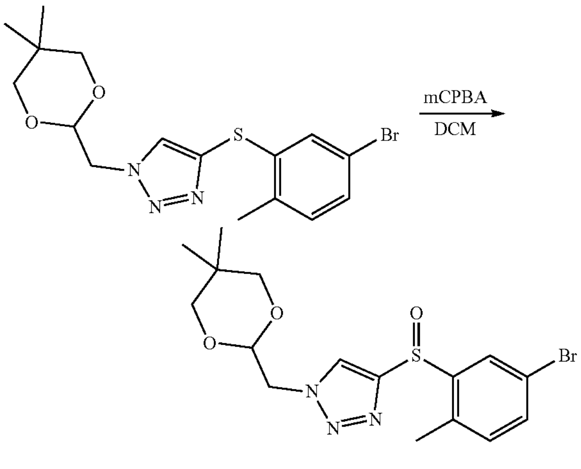

At 0° C., mCPBA (~70%, 62 mg, 0.251 mmol, 1.0 eq.) was added to a mixture of 4-((5-bromo-2-methylphenyl)thio)-1-((5,5-dimethyl-1,3-dioxan-2-yl)methyl)-1H-1,2,3-triazole (100 mg, 0.251 mmol, 1.0 eq.) in DCM (2.5 mL). After 15 minutes of stirring at 0° C., aq. sat. $NaHCO_3$ was added. DCM was added and the org. layer was separated, dried over $Na_2SO_4$, filtered and concentrated. The residue was purified on silica gel (10-60% EtOAc/hexanes) to afford (RS)-4-((5-bromo-2-methylphenyl)sulfinyl)-1-((5,5-dimethyl-1,3-dioxan-2-yl)methyl)-1H-1,2,3-triazole as a white foam (94 mg, 90%).

Step 2

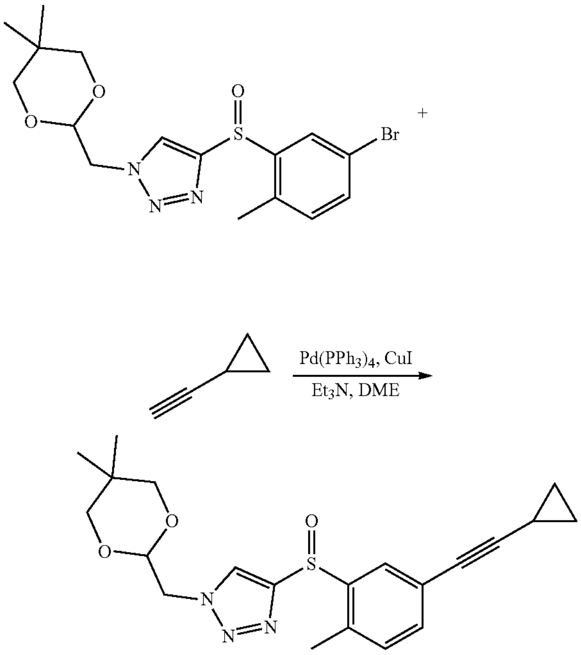

Cyclopropylacetylene (192 μL, 2.27 mmol, 10 eq.) was added to a $N_2$ bubbled mixture of (RS)-4-((5-bromo-2-methylphenyl)sulfinyl)-1-((5,5-dimethyl-1,3-dioxan-2-yl)methyl)-1H-1,2,3-triazole (94 g, 0.227 mmol, 1.0 eq.), $Pd(PPh_3)_4$ (27 mg, 0.023 mmol, 0.1 eq.) and CuI (4 mg, 0.023 mmol, 0.1 eq.) in $Et_3N$ (1.15 mL) and DME (1.15 mL). After 1 minute of $N_2$ bubbling, the reaction was stirred at 90° C. for 3 hours. Once at room temperature, the mixture was poured in aq. sat. $NH_4Cl$ and EtOAc was added. The organic layer was separated, washed with brine, dried over $Na_2SO_4$, filtered and concentrated. The residue was purified on silica gel chromatography (10-60% EtOAc/hexanes) to afford (RS)-4-((5-(cyclopropylethynyl)-2-methylphenyl)sulfinyl)-1-((5,5-dimethyl-1,3-dioxan-2-yl)methyl)-1H-1,2,3-triazole as a yellow gum (88 mg, 97%).

$^1H$ NMR (400 MHz, $CDCl_3$) δ 8.04 (d, J=1.6 Hz, 1H), 7.85 (s, 1H), 7.37 (dd, J=7.8, 1.8 Hz, 1H), 7.09 (d, J=7.9 Hz, 1H), 4.73 (t, J=4.1 Hz, 1H), 4.57-4.42 (m, 2H), 3.63-3.54 (m, 2H), 3.39 (dd, J=11.2, 3.0 Hz, 2H), 2.33 (s, 3H), 1.48-1.40 (m, 1H), 1.00 (s, 3H), 0.92-0.84 (m, 2H), 0.84-0.77 (m, 2H), 0.71 (s, 3H). $^{13}C$ NMR (101 MHz, $CDCl_3$) δ 151.91, 141.46, 134.63, 133.86, 130.84, 126.68, 125.84, 123.20, 97.52, 94.78, 76.96, 76.93, 74.65, 53.42, 30.10, 22.74, 21.58, 18.26, 8.64, 0.1;

I-782

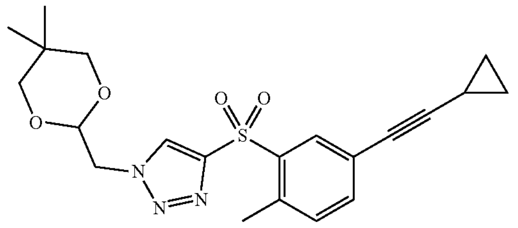

Step 1

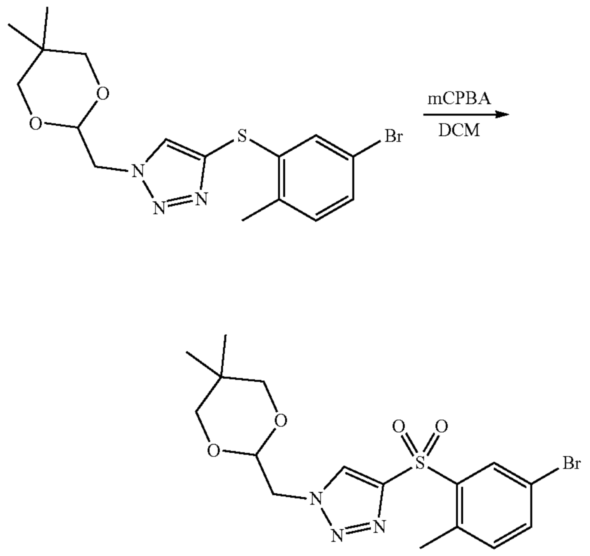 [SMILES: Cc1ccc(Br)cc1Sc1cn(CC2OCC(C)(C)CO2)nn1 ; Cc1ccc(Br)cc1S(=O)(=O)c1cn(CC2OCC(C)(C)CO2)nn1]

At 0° C., mCPBA (~70%, 124 mg, 0.502 mmol, 2.0 eq.) was added to a mixture of 4-((5-bromo-2-methylphenyl)thio)-1-((5,5-dimethyl-1,3-dioxan-2-yl)methyl)-1H-1,2,3-triazole (100 mg, 0.251 mmol, 1.0 eq.) in DCM (2.5 mL). The mixture was allowed to warm up to room temperature and stirred at room temperature for 66 hours. Aq. sat. $NaHCO_3$ and DCM were added. The org. layer was separated, washed with brine, dried over $Na_2SO_4$, filtered and concentrated to afford 4-((5-bromo-2-methylphenyl)sulfonyl)-1-((5,5-dimethyl-1,3-dioxan-2-yl)methyl)-1H-1,2,3-triazole as a white foam (108 mg, quant.).

Step 2

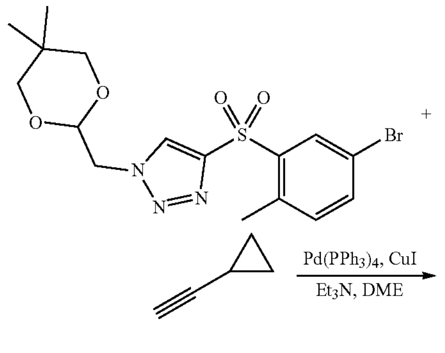

-continued

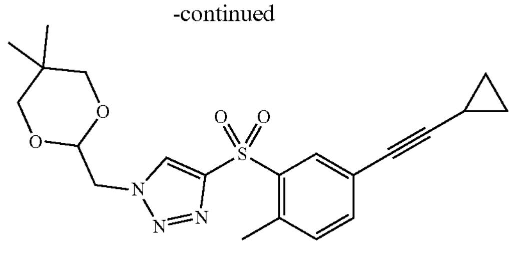

Cyclopropylacetylene (210 μL, 2.49 mmol, 10 eq.) was added to a $N_2$ bubbled mixture of 4-((5-bromo-2-methylphenyl)sulfonyl)-1-((5,5-dimethyl-1,3-dioxan-2-yl)methyl)-1H-1,2,3-triazole (107 g, 0.249 mmol, 1.0 eq.), $Pd(PPh_3)_4$ (29 mg, 0.025 mmol, 0.1 eq.) and CuI (5 mg, 0.025 mmol, 0.1 eq.) in $Et_3N$ (1.25 mL) and DME (1.25 mL). After 1 minute of $N_2$ bubbling, the reaction was stirred at 90° C. for 18 hours. Once at room temperature, the mixture was poured in aq. sat. $NH_4Cl$ and EtOAc was added. The organic layer was separated, dried over $Na_2SO_4$, filtered and concentrated. The residue was purified on silica gel chromatography (10-60% EtOAc/hexanes) to afford 4-((5-(cyclopropylethynyl)-2-methylphenyl)sulfonyl)-1-((5,5-dimethyl-1,3-dioxan-2-yl)methyl)-1H-1,2,3-triazole as a yellow gum (98 mg, 95%).

$^1$H NMR (400 MHz, $CDCl_3$) δ 8.30 (s, 1H), 8.19 (d, J=1.7 Hz, 1H), 7.45 (dd, J=7.8, 1.8 Hz, 1H), 7.17 (d, J=8.0 Hz, 1H), 4.75 (t, J=4.1 Hz, 1H), 4.55 (d, J=4.1 Hz, 2H), 3.62 (d, J=11.4 Hz, 2H), 3.42 (d, J=11.1 Hz, 2H), 2.65 (s, 3H), 1.48-1.39 (m, 1H), 1.04 (s, 3H), 0.94-0.84 (m, 2H), 0.84-0.77 (m, 2H), 0.72 (s, 3H). $^{13}$C NMR (101 MHz, $CDCl_3$) δ 148.73, 138.19, 137.66, 136.47, 132.82, 132.64, 128.08, 122.90, 97.33, 95.34, 76.99, 74.01, 53.41, 30.13, 22.73, 21.59, 20.39, 8.67, 0.09.

Additional exemplary compounds were prepared following methods substantially similar to the method described above and herein. Data for these compounds are provided in Table 24, Following Example 53.

Example 50: Synthesis of I-790

I-790

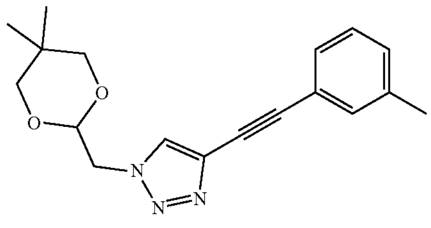

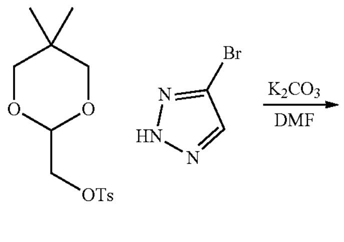

-continued

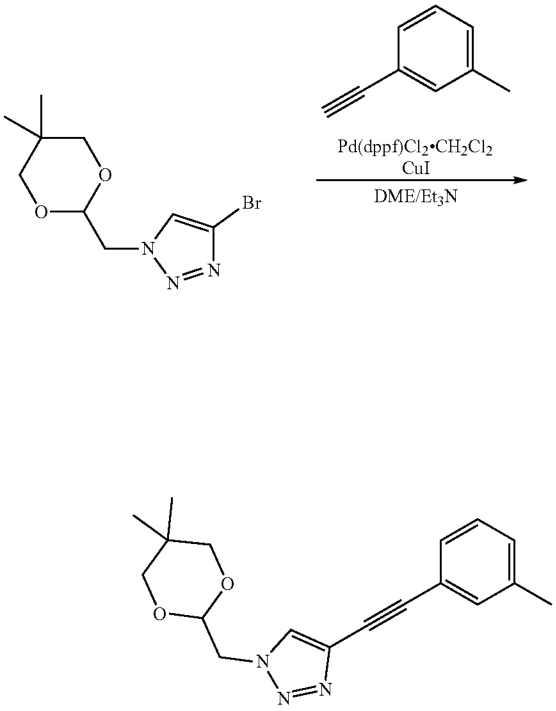

Step 1

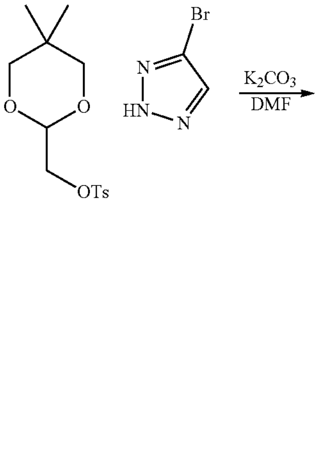

Potassium carbonate (275 mg, 2.00 mmol, 1.50 eq.) was added to a solution of 4-bromo-2H-1,2,3-triazole (197 mg, 1.33 mmol, 1.00 eq.) in DMF (7.0 mL). (5,5-dimethyl-1,3-dioxan-2-yl)methyl 4-methylbenzene sulfonate (480 mg, 1.60 mmol, 1.20 eq.) was added and the mixture was stirred at 50° C. for 3 days. The mixture was cooled to room temperature, poured into a saturated $NH_4Cl$ solution, and extracted twice with EtOAc. The combined organic layers were washed with brine, dried over $Na_2SO_4$, filtered, and concentrated under reduced pressure. The residue was purified by silica gel chromatography (0-40% EtOAc in hexanes) to provide 4-bromo-1-((5,5-dimethyl-1,3-dioxan-2-yl)methyl)-1H-1,2,3-triazole as a white solid (110 mg, 30%).

Step 2

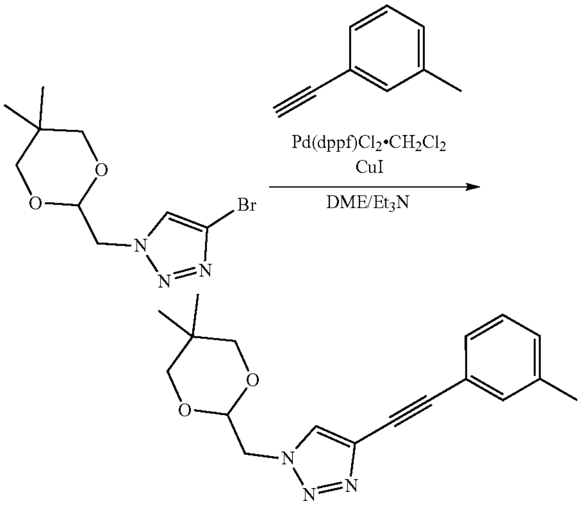

A mixture of 4-bromo-1-((5,5-dimethyl-1,3-dioxan-2-yl)methyl)-1H-1,2,3-triazole (50 mg, 0.181 mmol, 1.00 eq.), $Pd(dppf)Cl_2$. $CH_2Cl_2$ (15 mg, 0.0181 mmol, 0.10 eq.) and CuI (3.4 mg, 0.0181 mmol, 0.10 eq.) in DME (0.8 mL) and $Et_3N$ (0.2 mL) was degassed with $N_2$ for 10 minutes. 3-Ethynyltoluene (35 μL, 0.272 mmol, 1.50 eq.) was added and the mixture was stirred at 90° C. for 18 hours. The mixture was cooled to room temperature, poured into a saturated $NH_4Cl$ solution, and extracted twice with EtOAc. The combined organic layers were washed with brine, dried over $Na_2SO_4$, filtered, and concentrated under reduced pressure. The residue was purified by silica gel chromatography (0-40% EtOAc in hexanes) to provide a yellow oil 1-((5,5-dimethyl-1,3-dioxan-2-yl)methyl)-4-(m-tolylethynyl)-1H-1,2,3-triazole (15 mg, 27%).

$^1H$ NMR (400 MHz, $CDCl_3$) δ 7.85 (s, 1H), 7.40-7.33 (m, 2H), 7.24 (t, J=7.5 Hz, 1H), 7.19-7.12 (m, 1H), 4.76 (d, J=4.4 Hz, 1H), 4.53 (d, J=4.4 Hz, 2H), 3.73-3.56 (m, 2H), 3.43 (d, J=10.7 Hz, 2H), 2.35 (s, 3H), 1.14 (s, 3H), 0.73 (s, 3H) ppm. $^{13}C$ NMR (101 MHz, $CDCl_3$) δ 138.04, 132.15, 131.00, 129.61, 128.68, 128.25, 127.47, 122.18, 98.13, 92.54, 78.24, 77.03, 53.12, 30.20, 22.87, 21.65, 21.23 ppm.

Additional exemplary compounds were prepared following methods substantially similar to the method described above and herein. Data for these compounds are provided in Table 24, Following Example 53.

Example 51: Synthesis of I-792

I-792

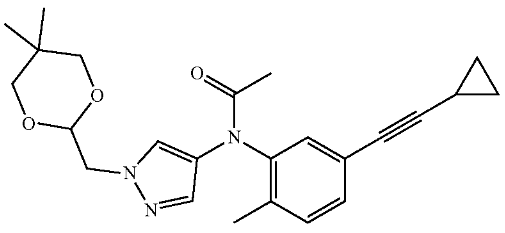

-continued

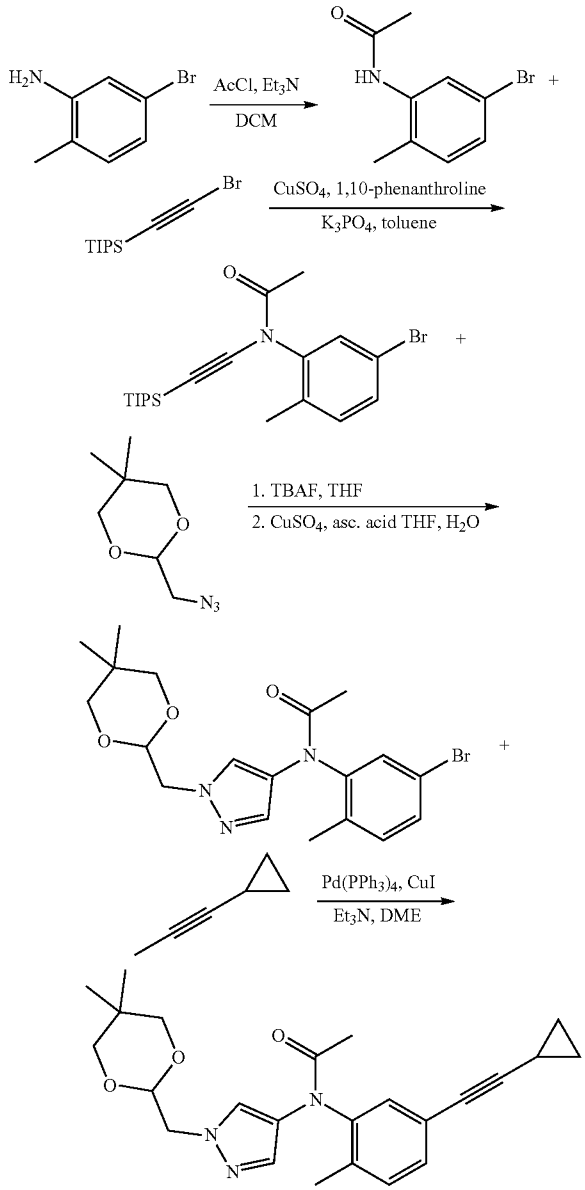

Step 1

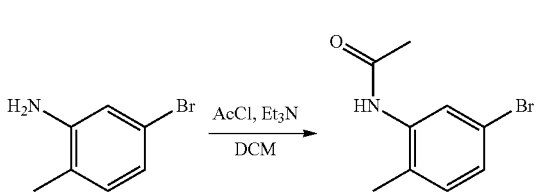

At 0° C., $Et_3N$ (1.5 mL, 10.7 mmol, 2.0 eq.) was added to a mixture of 5-bromo-2-methylaniline (1.0 g, 5.37 mmol, 1.0 eq.) and acetyl chloride (0.5 mL, 6.99 mmol, 1.3 eq.) in DCM (8.0 mL). After 2 hours of stirring at 0° C., the mixture was poured in $H_2O$ and DCM was added. The organic layer was separated, washed with brine, dried over $Na_2SO_4$, filtered and concentrated to afford N-(5-bromo-2-methylphenyl)acetamide as a brown solid (1.23 g, quant.).

Step 2

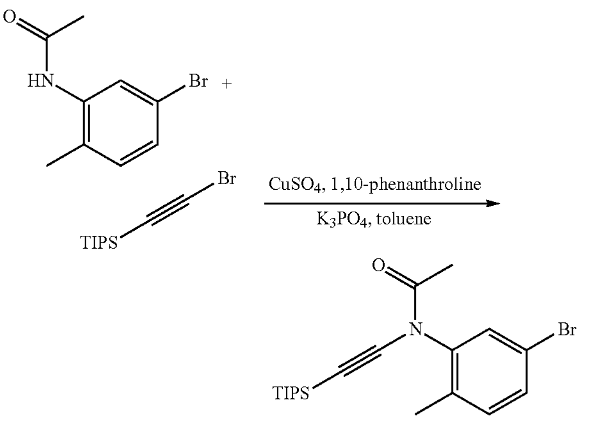

(Bromoethynyl) triisopropylsilane 0.52 mL, 1.97 mmol, 1.5 eq. was added to a $N_2$ bubbled mixture of N-(5-bromo-2-methylphenyl)acetamide (300 mg, 1.32 mmol, 1.0 eq.), $CuSO_4.5H_2O$ (66 mg, 0.263 mmol, 0.2 eq.), 1,10-phenanthroline (95 mg, 0.526 mmol, 0.4 eq.) and $K_3PO_4$ (558 mg, 2.63 mmol, 2.0 eq.) in toluene (5 mL). After 1 minute of $N_2$ bubbling, the reaction was stirred at 110° C. for 18 hours. Once at room temperature, the mixture was filtered on celite using DCM. The filtrate was concentrated and the residue was purified on silica gel chromatography (0-6% EtOAc/hexanes) to afford N-(5-bromo-2-methylphenyl)-N-((triisopropylsilyl)ethynyl)acetamide as an orange oil (330 mg, 61%).

Step 3

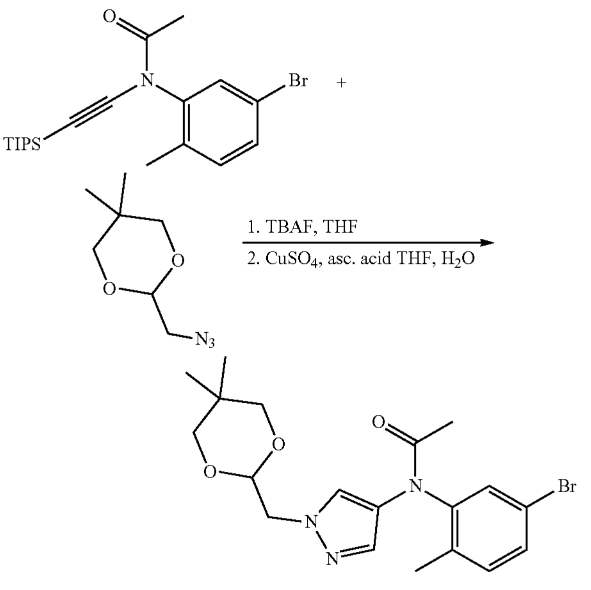

At 0° C., TBAF (1M in THF, 0.96 mL, 0.964 mmol, 1.2 eq.) was added dropwise to a mixture of N-(5-bromo-2-methylphenyl)-N-((triisopropylsilyl)ethynyl)acetamide (328 mg, 0.803 mmol, 1.0 eq.) in THF (10 mL). After 20 minutes of stirring at 0° C., the mixture was poured in aq. sat. $NH_4Cl$ and MTBE was added. The organic layer was separated, dried over $Na_2SO_4$, filtered and concentrated. The residue was dissolved in THF (6 mL) then 2-(azidomethyl)-5,5-dimethyl-1,3-dioxane (137 mg, 0.803 mmol, 1.0 eq.), a solution of $CuSO_4$ $5H_2O$ (20 mg, 0.080 mmol, 0.1 eq.) in $H_2O$ (2 mL) and ascorbic acid (71 mg, 0.402 mmol, 0.5 eq.) were added. The mixture was stirred at 60° C. for 18 hours. Once at room temperature, the mixture was poured in aq. sat. $NH_4Cl$ and EtOAc was added. The organic layer was separated, dried over $Na_2SO_4$, filtered and concentrated. The residue was purified on silica gel chromatography (10-60% EtOAc/hexanes) to afford N-(5-bromo-2-methylphenyl)-N-(1-((5,5-dimethyl-1,3-dioxan-2-yl)methyl)-1H-1,2,3-triazol-4-yl)acetamide as a colorless oil (52 mg, 15%).

Step 4

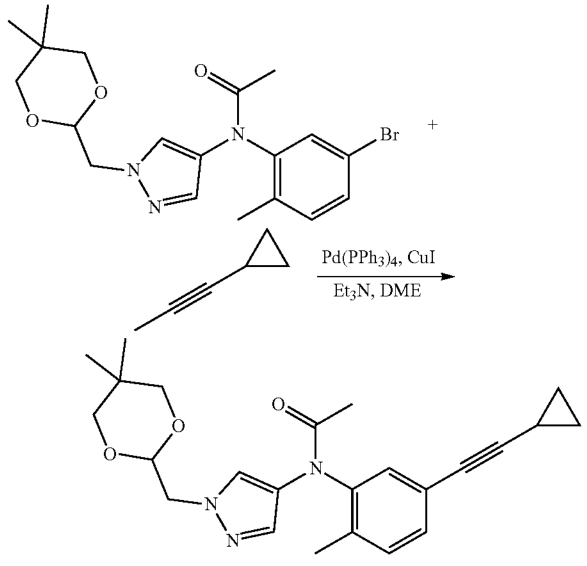

Cyclopropylacetylene (104 μL, 1.23 mmol, 10 eq.) was added to a $N_2$ bubbled mixture of N-(5-bromo-2-methylphenyl)-N-(1-((5,5-dimethyl-1,3-dioxan-2-yl)methyl)-1H-1,2,3-triazol-4-yl)acetamide (52 mg, 0.123 mmol, 1.0 eq.), $Pd(PPh_3)_4$ (14 mg, 0.012 mmol, 0.1 eq.) and CuI (2 mg, 0.012 mmol, 0.1 eq.) in $Et_3N$ (0.6 mL) and DME (0.6 mL). After 1 minute of $N_2$ bubbling, the reaction was stirred at 90° C. for 3 hours. Once at room temperature, the mixture was poured in aq. sat. $NH_4Cl$ and EtOAc was added. The organic layer was separated, dried over $Na_2SO_4$, filtered and concentrated. The residue was purified on silica gel chromatography (10-60% EtOAc/hexanes) to afford N-(5-(cyclopropylethynyl)-2-methylphenyl)-N-(1-((5,5-dimethyl-1,3-dioxan-2-yl)methyl)-1H-1,2,3-triazol-4-yl)acetamide as a white solid (36 mg, 72%).

$^1H$ NMR (400 MHz, $CDCl_3$) δ 8.31 (s, 1H), 7.36 (d, J=7.7 Hz, 1H), 7.30-7.22 (m, 2H), 4.77 (t, J=4.6 Hz, 1H), 4.53-4.41 (m, 2H), 3.63 (d, J=11.2 Hz, 2H), 3.42 (dd, J=10.4, 4.9 Hz, 2H), 2.14 (s, 3H), 1.92 (s, 3H), 1.42 (ddd, J=13.1, 8.3, 5.2 Hz, 1H), 1.16 (s, 3H), 0.89-0.81 (m, 2H), 0.81-0.74 (m, 2H), 0.72 (s, 3H). $^{13}C$ NMR (101 MHz, $CDCl_3$) δ 168.93, 145.70, 138.95, 136.21, 132.34, 131.46, 123.38, 116.55, 98.46, 94.14, 76.97, 74.70, 53.52, 30.21, 23.15, 22.86, 21.71, 17.55, 8.58, 0.09.

Additional exemplary compounds were prepared following methods substantially similar to the method described above and herein. Data for these compounds are provided in Table 24, Following Example 53.

Example 52: Synthesis of I-826 and I-841

I-826

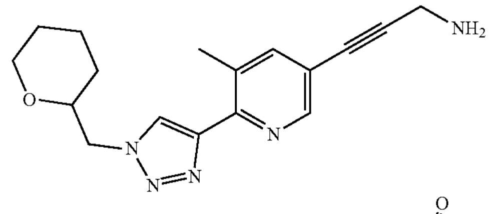

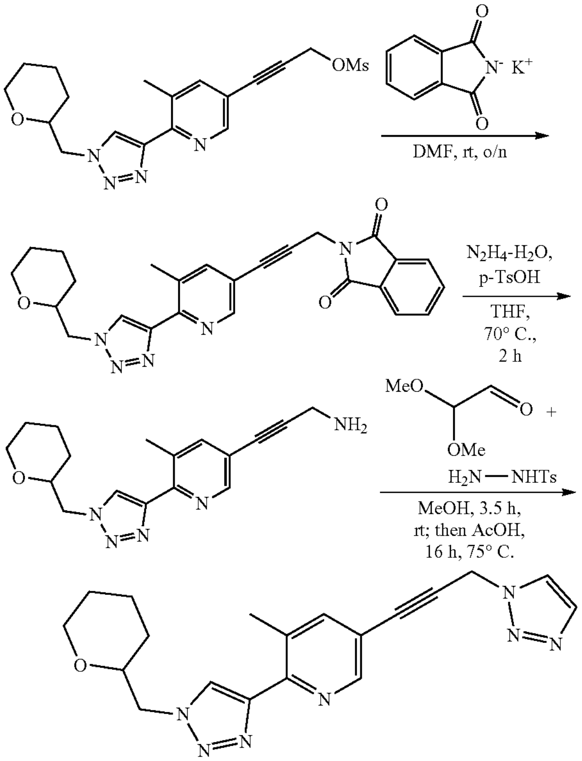

Step 1:

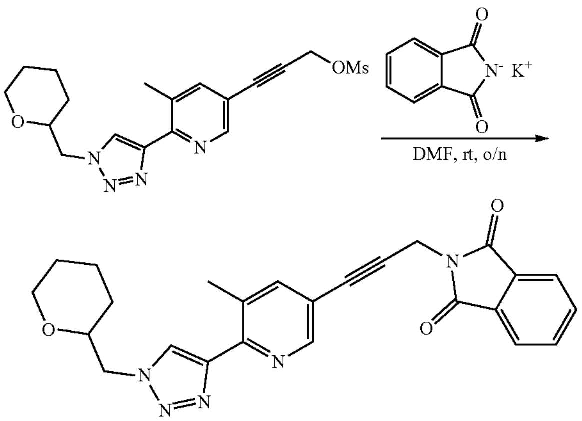

A solution of 3-(5-methyl-6-(1-((tetrahydro-2H-pyran-2-yl)methyl)-1H-1,2,3-triazol-4-yl)pyridin-3-yl)prop-2-yn-1-yl methanesulfonate (1.36 g, 3.48 mmol, 1 eq) in DMF (10 ml) was treated with phthalimide potassium salt (790 mg, 4.18 mmol, 1.2 eq) and stirred at room temperature overnight for 19 hours then poured into saturated aqueous $NH_4Cl$ and extracted 3 times with ethyl acetate. The combined organic layers were washed with brine, dried over anhydrous sodium sulfate, filtered and concentrated in vacuum to provide the crude. Purification on Combi-Flash chromatography using 0-100% EtOAc in hexane provided 2-(3-(5-methyl-6-(1-((tetrahydro-2H-pyran-2-yl) methyl)-1H-1,2,3-triazol-4-yl)pyridin-3-yl)prop-2-yn-1-yl)isoindoline-1,3-dione (810 mg, 53%)

Step 2:

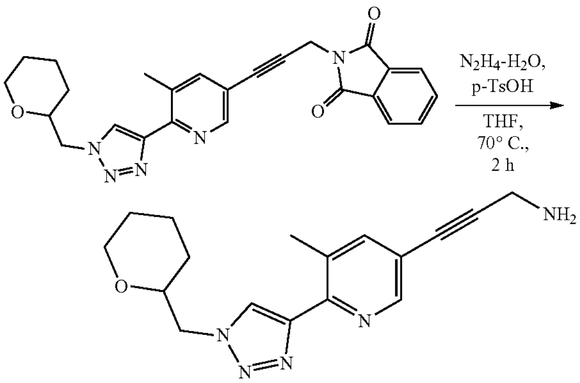

A solution of 2-(3-(5-methyl-6-(1-((tetrahydro-2H-pyran-2-yl)methyl)-1H-1,2,3-triazol-4-yl)pyridin-3-yl)prop-2-yn-1-yl)isoindoline-1,3-dione (397 mg, 0.90 mmol, 1 eq) in THF (3.9 ml) was treated with hydrazine monohydrate (0.17 ml, 3.60 mmol, 4 eq) and p-toluene sulfonic acid (12 mg, 0.064 mmol). The reaction was refluxed at 70° C. for 2 hours then poured into saturated aqueous $NH_4Cl$ and extracted 3 times with ethyl acetate. The combined organic layers were washed with brine, dried over anhydrous sodium sulfate, filtered and concentrated in vacuum to provide the crude. Purification on Combi-Flash chromatography using 0-20% MeOH in DCM provided 3-(5-methyl-6-(1-((tetrahydro-2H-pyran-2-yl)methyl)-1H-1,2,3-triazol-4-yl)pyridin-3-yl) prop-2-yn-1-amine (162 mg, 58%) as orange solid.

1H NMR (400 MHz, Chloroform-d) δ 8.36 (s, 1H), 8.20-8.08 (m, 1H), 7.52 (s, 1H), 4.50-4.34 (m, 1H), 4.27 (dd, J=14.2, 7.5 Hz, 1H), 3.89 (d, J=11.5 Hz, 1H), 3.61 (d, J=18.1 Hz, 3H), 3.31 (q, J=11.4, 10.2 Hz, 3H), 2.59 (s, 3H), 1.78 (d, J=9.2 Hz, 1H), 1.59 (d, J=13.0 Hz, 1H), 1.43 (s, 3H), 1.20 (q, J=12.9, 12.2 Hz, 1H).

13C NMR (101 MHz, cdcl3) δ 148.77, 148.05, 147.31, 141.75, 131.34, 125.50, 118.61, 92.64, 79.59, 77.46, 77.14, 76.82, 75.81, 68.34, 55.00, 49.43, 49.22, 49.00, 48.79, 48.58, 31.54, 28.67, 25.38, 22.69, 20.41.

I-841

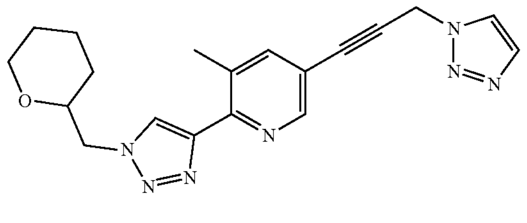

Step 1:

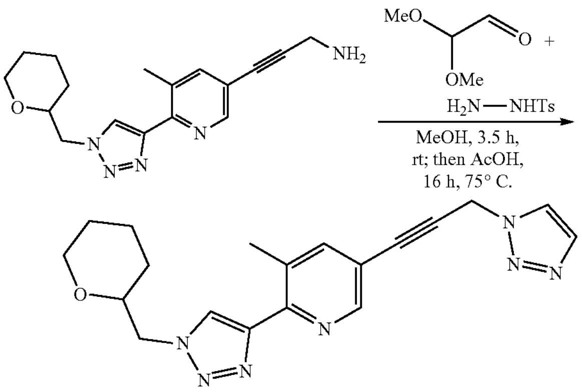

To a solution of 4-methyl benzenesulfonohydrazide (45 mg, 0.24 mmol, 1 eq) in MeOH (0.51 ml) was added 2,2-dimethoxyacetaldehyde (40 ul, 0.26 mmol, 1.10 eq). The reaction is stirred at RT for 3.5 hours. 3-(5-methyl-6-(1-((tetrahydro-2H-pyran-2-yl)methyl)-1H-1,2,3-triazol-4-yl) pyridin-3-yl)prop-2-yn-1-amine (80 mg, 0.26 mmol, 1.1 eq) in 0.5 ml MeOH was then added followed by glacial acetic acid (13.7 ul, 0.24 mmol, 1.0 eq) The reaction is heated at 75° C. for 16 hours then cooled to room temperature, concentrated in vacuo and partitioned with DCM/water (2 ml/2 ml). The combined organic layers are washed with 10 ml (5% aq.$K_2CO_3$), then brine, dried over anhydrous $Na_2SO_4$ and concentrated in vacuo. Purification on silica gel chromatography using 0-100% EtOAc in hexanes provided 5-(3-(1H-1,2,3-triazol-1-yl)prop-1-yn-1-yl)-3-methyl-2-(1-((tetrahydro-2H-pyran-2-yl)methyl)-1H-1,2,3-triazol-4-yl) pyridine (35 mg, 37%) as yellow oil.

$^1$H NMR (400 MHz, Chloroform-d) δ 8.49 (d, J=2.0 Hz, 1H), 8.23 (s, 1H), 7.85 (d, J=1.1 Hz, 1H), 7.75 (d, J=1.1 Hz, 1H), 7.65-7.61 (m, 1H), 5.45 (s, 2H), 4.48 (dd, J=14.1, 3.2 Hz, 1H), 4.33 (dd, J=14.1, 7.6 Hz, 1H), 3.95 (dt, J=11.9, 2.3 Hz, 1H), 3.69 (ddt, J=10.4, 7.6, 2.8 Hz, 1H), 3.36 (td, J=11.2, 3.3 Hz, 1H), 2.70 (s, 3H), 2.01 (s, 1H), 1.87-1.82 (m, 1H), 1.65 (d, J=12.9 Hz, 1H), 1.54-1.45 (m, 2H), 1.39-1.33 (m, 1H).

$^{13}$C NMR (101 MHz, $CDCl_3$) δ 171.26, 149.10, 148.57, 148.35, 142.03, 134.18, 131.40, 125.79, 123.33, 116.82, 83.91, 83.59, 77.38, 77.06, 76.74, 75.87, 68.41, 60.41, 55.10, 53.43, 50.60, 40.45, 29.66, 28.77, 25.47, 22.78, 21.19, 21.01, 20.66, 17.37, 14.14.

Additional exemplary compounds were prepared following methods substantially similar to the method described above and herein. Data for these compounds are provided in Table 24, Following Example 53.

Example 53: Synthesis of I-843

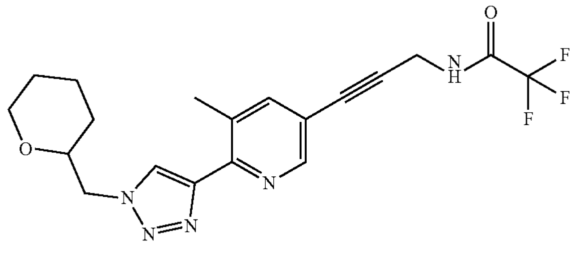

-continued

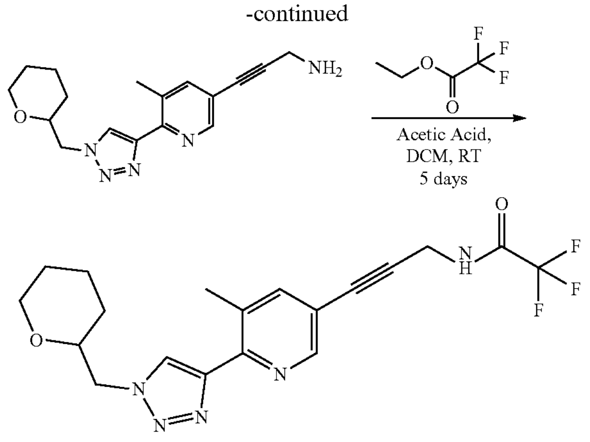

Step 1:

Ethyl trifluoroacetate (31 ul, 0.26 mmol, 1 eq) was added to 3-(5-methyl-6-(1-((tetrahydro-2H-pyran-2-yl)methyl)-1H-1,2,3-triazol-4-yl)pyridin-3-yl)prop-2-yn-1-amine (81 mg, 0.26 mmol, 1 eq) in 0.5 ml DCM followed by acetic acid (1.4 ul, 0.026 mmol, 0.1 eq). After 5 days at room temperature, the solvent is evaporated, and the crude is purified on Combi-Flash chromatography using 0-80% EtOAc in hexane to provide 2,2,2-trifluoro-N-(3-(5-methyl-6-(1-((tetrahydro-2H-pyran-2-yl)methyl)-1H-1,2,3-triazol-4-yl)pyridin-3-yl)prop-2-yn-1-yl)acetamide (22 mg, 21%) as off white solid.

$^1$H NMR (400 MHz, CDCl3) δ 8.50 (s, 1H), 8.22 (s, 1H), 7.60 (s, 1H), 7.17 (s, 1H), 4.51 (dd, J=14.1, 3.2 Hz, 1H), 4.45-4.27 (m, 3H), 4.07-3.91 (m, 1H), 3.71 (ddt, J=11.0, 7.8, 2.7 Hz, 1H), 3.38 (td, J=11.2, 3.4 Hz, 1H), 2.70 (s, 3H), 1.87 (dq, J=9.9, 2.7 Hz, 1H), 1.79-1.62 (m, 1H), 1.41-1.16 (m, 4H).

$^{13}$C NMR (101 MHz, cdcl3) δ 157.09, 156.71, 149.13, 148.41, 141.91, 131.31, 125.63, 117.35, 117.09, 114.23, 85.83, 81.63, 77.33, 77.01, 76.69, 75.88, 68.44, 55.17, 30.42, 29.69, 28.81, 25.50, 22.82, 20.65.

$^{19}$F NMR (377 MHz, CDCl3) δ-75.44, −75.66, −75.69, −75.76, −76.20, −189.55.

Additional exemplary compounds were prepared following methods substantially similar to the method described above and herein. Data for these compounds are provided in Table 24, below.

TABLE 24

Characterization for exemplary compounds of the invention

| Compound No. | Chemical Structure | M + 1 | $^1$H NMR (400 M Hz) | Example of Synthesis |
|---|---|---|---|---|
| I-432 | 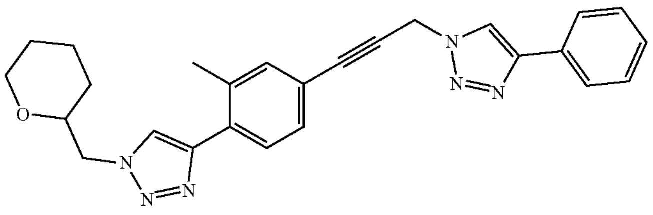 [SMILES: Cc1cc(C#CCn2cc(-c3ccccc3)nn2)ccc1-c1cn(CC2CCCCO2)nn1] | 438.54 | $^1$H NMR (400 M Hz, $CDCl_3$) δ 8.07 (s, 1H), 7.91-7.83 (m, 1H), 7.84 (d, J = 1.4 Hz, 3H), 7.49-7.36 (m, 3H), 7.39-7.29 (m, 1H), 5.47 (s, 2H), 4.53 (dd, J = 14.2, 2.9 Hz, 1H), 4.33 (dd, J = 14.2, 7.6 Hz, 1H), 3.99 (dd, J = 10.7, 2.0 Hz, 1H), 3.71 (ddt, J = 10.1, 7.6, 2.6 Hz, 1H), 3.57-3.26 (m, 1H), 2.47 (s, 3H), 1.97-1.83 (m, 1H), 1.67 (t, J = 13.7 Hz, 2H), 1.41-1.12 (m, 3H), 1.01-0.74 (m, 1H). | 35 |
| I-453 | 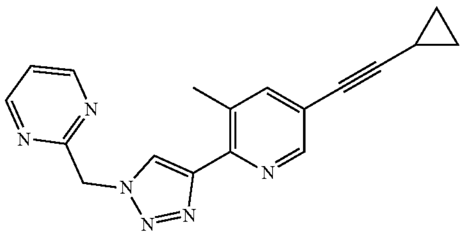 [SMILES: Cc1cc(C#CC2CC2)cnc1-c1cn(Cc2ncccn2)nn1] | 316.37 | $^1$H NMR (400 M Hz, $CDCl_3$) δ 8.73 (d, J = 4.9 Hz, 2H), 8.44-8.39 (m, 1H), 8.33 (s, 1H), 7.56 (dd, J = 2.0, 0.7 Hz, 1H), 7.26 (t, J = 4.9 Hz, 1H), 5.86 (s, 2H), 2.72 (s, 3H), 1.53-1.42 (m, 1H), 1.11-0.86 (m, 2H), 0.88-0.77 (m, 2H) ppm. | 3 |
| I-454 | 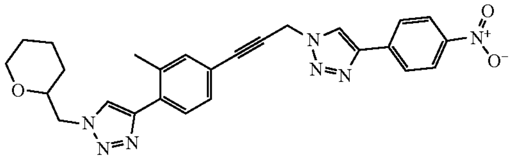 [SMILES: Cc1cc(C#CCn2cc(-c3ccc([N+](=O)[O-])cc3)nn2)ccc1-c1cn(CC2CCCCO2)nn1] | 483.53 | $^1$H NMR (400 M Hz, $CDCl_3$) δ 8.34-8.26 (m, 2H), 8.23 (s, 1H), 8.09-8.01 (m, 2H), 7.87 (d, J = 5.2 Hz, 1H), 7.86 (d, J = 1.5 Hz, 1H), 7.40 (d, J = 5.5 Hz, 2H), 5.50 (s, 2H), 4.54 (dd, J = 14.2, 2.9 Hz, 1H), 4.34 (dd, J = 14.2, 7.6 Hz, 1H), 3.99 (dd, J = 10.5, 1.9 Hz, 1H), 3.71 (ddt, J = 10.7, 7.8, 2.7 Hz, 1H), 3.58-3.28 (m, 1H), 2.48 (s, 3H), 1.89 (d, J = 3.8 Hz, 1H), 1.70 (d, J = 13.1 Hz, 1H), 1.34-1.08 (m, 3H), 0.95-0.68 (m, 1H). | 35 |

TABLE 24-continued

| Characterization for exemplary compounds of the invention | | | | |
|---|---|---|---|---|
| Compound No. | Chemical Structure | M + 1 | $^1$H NMR (400 M Hz) | Example of Synthesis |
| I-455 | 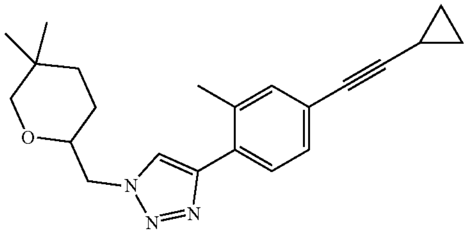 [SMILES: Cc1cc(C#CC2CC2)ccc1-c1cn(CC2CCC(C)(C)CO2)nn1] | 349.48 | $^1$H NMR (400 M Hz, $CDCl_3$) δ 7.84 (s, 1H), 7.74 (d, J = 8.1 Hz, 1H), 7.28 (d, J = 7.7 Hz, 2H), 4.55 (dd, J = 14.2, 3.0 Hz, 1H), 4.40 (dd, J = 14.2, 7.1 Hz, 1H), 3.61 (ddd, J = 10.1, 6.9, 2.9 Hz, 1H), 3.47 (dd, J = 11.2, 2.5 Hz, 1H), 3.13 (d, J = 11.2 Hz, 1H), 2.43 (s, 3H), 1.64-1.35 (m, 5H), 0.96 (s, 3H), 0.90-0.85 (m, 2H), 0.84-0.79 (m, 5H). | 3 |
| I-456 | 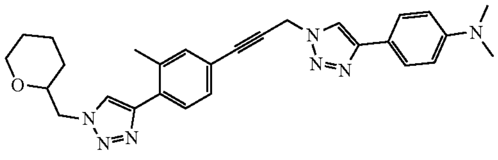 [SMILES: Cc1cc(C#CCn2cc(-c3ccc(N(C)C)cc3)nn2)ccc1-c1cn(CC2CCCCO2)nn1] | 481.60 | $^1$H NMR (400 M Hz, $CDCl_3$) δ 7.93 (s, 1H), 7.88-7.82 (m, 2H), 7.79-7.70 (m, 2H), 7.38 (d, J = 6.3 Hz, 2H), 6.85-6.70 (m, 2H), 5.43 (s, 2H), 4.53 (dd, J = 14.2, 2.9 Hz, 1H), 4.33 (dd, J = 14.2, 7.6 Hz, 1H), 3.99 (dd, J = 10.8, 2.0 Hz, 1H), 3.70 (ddt, J = 10.1, 7.6, 2.6 Hz, 1H), 3.49-3.36 (m, 1H), 2.99 (s, 6H), 2.47 (s, 3H), 1.93-1.84 (m, 1H), 1.69 (d, J = 12.9 Hz, 1H), 1.61-1.50 (m, 3H), 1.38-1.21 (m, 1H). | 35 |
| I-457 | 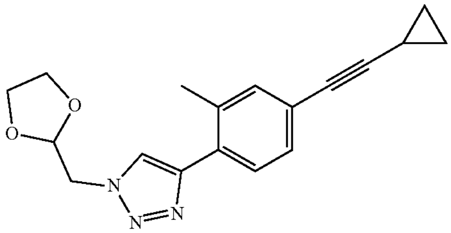 [SMILES: Cc1cc(C#CC2CC2)ccc1-c1cn(CC2OCCO2)nn1] | 309.37 | $^1$H NMR (400 M Hz, $CDCl_3$) δ 7.80 (s, 1H), 7.73 (d, J = 7.1 Hz, 1H), 7.28 (d, J = 10.6 Hz, 2H), 5.26 (s, 1H), 4.61 (s, 2H), 3.90 (s, 4H), 2.43 (s, 3H), 1.53-1.39 (m, 1H), 0.92-0.83 (m, 2H), 0.84-0.76 (m, 2H). | 3 |
| I-458 | 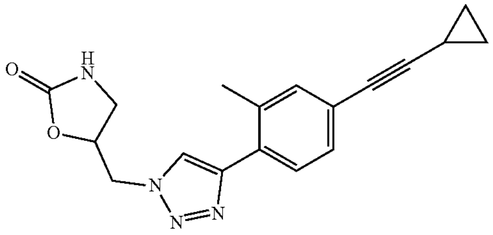 [SMILES: Cc1cc(C#CC2CC2)ccc1-c1cn(CC2CNC(=O)O2)nn1] | 322.37 | $^1$H NMR (400 M Hz, $CDCl_3$) δ 7.85 (s, 1H), 7.70 (d, J = 7.8 Hz, 1H), 7.31-7.25 (m, 2H), 5.56 (s, 1H), 5.03 (ddt, J = 8.9, 6.0, 4.4 Hz, 1H), 4.77-4.61 (m, 2H), 3.75 (t, J = 9.0 Hz, 1H), 3.49 (dd, J = 8.6, 6.1 Hz, 1H), 2.41 (s, 3H), 1.45 (tt, J = 8.1, 5.1 Hz, 1H), 0.90-0.84 (m, 2H), 0.84-0.78 (m, 2H). | 3 |
| I-472 | 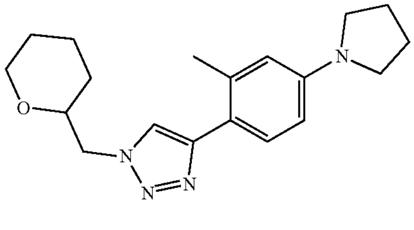 [SMILES: Cc1cc(N2CCCC2)ccc1-c1cn(CC2CCCCO2)nn1] | 326.44 | $^1$H NMR (400 M Hz, $CDCl_3$) δ 7.71-7.64 (m, 2H), 6.49 (dd, J = 8.5, 2.6 Hz, 1H), 6.44 (d, J = 2.4 Hz, 1H), 4.48 (dd, J =14.1, 3.2 Hz, 1H), 4.32 (dd, J =14.1, 7.4 Hz, 1H), 3.99 (dd, J =11.1, 2.0 Hz, Hz, 1H), 3.40 (td, J = 11.3, 4.3 Hz, 1H), 3.70 (dtd, J = 10.9, 5.4, 2.6 1H), 3.35-3.26 (m, 4H), 2.44 (s, 3H), 2.07-1.94 (m, 4H), 1.92-1.81 (m, 1H), 1.66 (d, J = 12.1 Hz, 1H), 1.60-1.43 (m, 3H), 1.33-1.20 (m, 1H). | 5 |

TABLE 24-continued

Characterization for exemplary compounds of the invention

| Compound No. | Chemical Structure | M + 1 | $^1$H NMR (400 M Hz) | Example of Synthesis |
|---|---|---|---|---|
| I-473 | 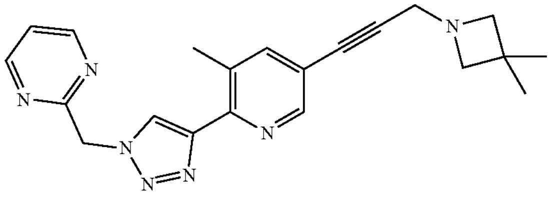 [SMILES: Cc1cc(C#CCN2CC(C)(C)C2)cnc1-c1cn(Cc2ncccn2)nn1] | 373.46 | $^1$H NMR (400 M Hz, $CDCl_3$) δ 8.73 (d, J = 4.9 Hz, 2H), 8.49 (d, J = 1.7 Hz, 1H), 8.35 (s, 1H), 7.65-7.60 (m, 1H), 7.34-7.19 (m, 1H), 5.86 (s, 2H), 3.51 (s, 2H), 3.17 (s, 4H), 2.75 (s, 3H), 1.23 (s, 6H) ppm. | 6 |
| I-488 | 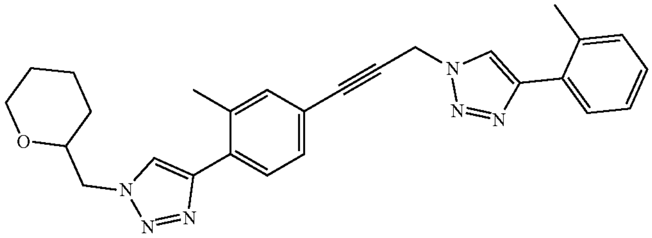 [SMILES: Cc1ccccc1-c1cn(CC#Cc2ccc(-c3cn(CC4CCCCO4)nn3)c(C)c2)nn1] | 452.56 | $^1$H NMR (400 M Hz, $CDCl_3$) δ 7.95 (s, 1H), 7.84 (t, J = 4.2 Hz, 2H), 7.76 (dd, J = 6.4, 3.2 Hz, 1H), 7.37 (d, J = 6.3 Hz, 2H), 7.27 (d, J = 3.0 Hz, 3H), 5.48 (s, 2H), 4.52 (dd, J = 14.2, 2.9 Hz, 1H), 4.33 (dd, J = 14.2, 7.6 Hz, 1H), 3.98 (d, J = 10.6 Hz, 1H), 3.79-3.62 (m, 1H), 3.47-3.32 (m, 1H), 2.49 (s, 3H), 2.46 (s, 3H), 1.88 (s, 1H), 1.68 (d, J = 12.8 Hz, 1H), 1.60-1.46 (m, 3H), 1.36-1.17 (m, 1H). | 35 |
| I-489 | 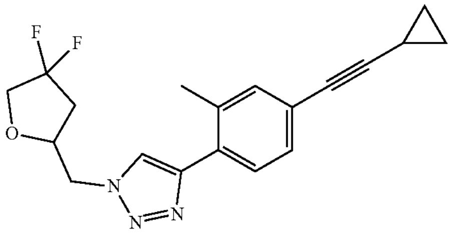 [SMILES: Cc1cc(C#CC2CC2)ccc1-c1cn(CC2CC(F)(F)CO2)nn1] | 343.38 | $^1$H NMR (400 M Hz, $CDCl_3$) δ 7.79 (s, 1H), 7.71 (d, J = 7.8 Hz, 1H), 7.32-7.26 (m, 2H), 4.73-4.64 (m, 1H), 4.61-4.51 (m, 2H), 4.11-4.00 (m, 1H), 3.88 (ddd, J = 15.3, 12.7, 10.7 Hz, 1H), 2.55 (tdd, J = 14.5, 8.4, 6.4 Hz, 1H), 2.42 (s, 3H), 2.22-2.05 (m, 1H), 1.51-1.40 (m, 1H), 0.90-0.84 (m, 2H), 0.84-0.78 (m, 2H). | 3 |
| I-490 | 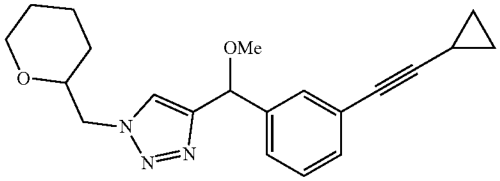 [SMILES: COC(c1cccc(C#CC2CC2)c1)c1cn(CC2CCCCO2)nn1] | 351.45 | $^1$H NMR (400 M Hz, $CDCl_3$) δ 7.46-7.43 (m, 1H), 7.42 (m, 1H), 7.37-7.27 (m, 3H), 5.45 (d, J = 2.2 Hz, 1H), 4.38 (td, J = 14.1, 3.3 Hz, 1H), 4.21 (ddd, J = 26.8, 14.1, 7.5 Hz, 1H), 3.98-3.87 (m, 1H), 3.63 (dtd, J = 10.4, 5.4, 2.4 Hz, 1H), 3.39 (d, J = 2.2 Hz, 3H), 3.37-3.31 (m, 1H), 1.90-1.80 (m, 1H), 1.69-1.55 (m, 2H), 1.53-1.39 (m, 3H), 1.25-1.10 (m, 1H), 0.86 (ddt, J = 8.3, 5.7, 2.9 Hz, 2H), 0.83-0.75 (m, 2H) | 34 |
| I-491 | 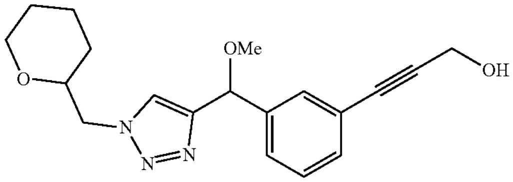 [SMILES: COC(c1cccc(C#CCO)c1)c1cn(CC2CCCCO2)nn1] | 341.41 | $^1$H NMR (400 M Hz, $CDCl_3$) δ 7.51-7.46 (m, 1H), 7.43 (d, J = 3.3 Hz, 1H), 7.38-7.34 (m, 1H), 7.34-7.30 (m, 1H), 7.30-7.21 (m, 1H), 5.44 (d, J = 1.8 Hz, 1H), 4.44 (d, J = 6.0 Hz, 2H), 4.35 (td, J = 14.2, 3.2 Hz, 1H), 4.18 (ddd, J = 27.3, 14.2, 7.6 Hz, 1H), 3.90 (ddt, J = 8.8, 3.9, 2.2 Hz, 1H), 3.71-3.55 (m, 1H), 3.35 (d, J = 1.8 Hz, 3H), 3.33-3.26 (m, 1H), 2.46 (td, J = 6.0, 2.1 Hz, 1H), 1.86-1.77 (m, 1H), 1.57 (d, J = 12.2 Hz, 1H), 1.46 (dt, J = 7.0, 2.1 Hz, 3H), 1.29-1.10 (m, 1H) | 34 |

TABLE 24-continued

| Characterization for exemplary compounds of the invention | | | | |
|---|---|---|---|---|
| Compound No. | Chemical Structure | M + 1 | $^1$H NMR (400 M Hz) | Example of Synthesis |
| I-492 | 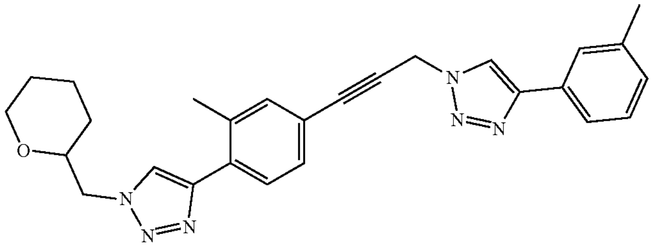 [SMILES: Cc1cccc(-c2cn(CC#Cc3ccc(-c4cn(CC5CCCCO5)nn4)c(C)c3)nn2)c1] | 452.56 | $^1$H NMR (400 M Hz, $CDCl_3$) δ 8.05 (s, 1H), 7.85 (d, J = 5.8 Hz, 2H), 7.71 (s, 1H), 7.63 (d, J = 7.6 Hz, 1H), 7.39 (s, 2H), 7.31 (t, J = 7.6 Hz, 1H), 7.15 (d, J = 7.3 Hz, 1H), 5.45 (s, 2H), 4.61-4.46 (m, 1H), 4.33 (dd, J = 14.1, 7.6 Hz, 1H), 3.98 (d, J = 11.1 Hz, 1H), 3.70 (t, J = 9.2 Hz, 1H), 3.47-3.28 (m, 1H), 2.47 (s, 3H), 2.40 (s, 3H), 1.88 (s, 1H), 1.68 (d, J = 12.5 Hz, 1H), 1.52 (s, 3H), 1.26 (d, J = 7.6 Hz, 1H). | 35 |
| I-493 | 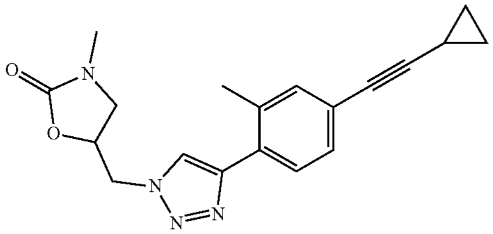 [SMILES: Cc1cc(C#CC2CC2)ccc1-c1cn(CC2CN(C)C(=O)O2)nn1] | 336.40 | $^1$H NMR (400 M Hz, $CDCl_3$) δ 7.83 (s, 1H), 7.68 (d, J = 7.9 Hz, 1H), 7.30-7.24 (m, 2H), 4.96-4.87 (m, 1H), 4.72 (dd, J = 14.7, 3.7 Hz, 1H), 4.66 (dd, J = 14.7, 4.8 Hz, 1H), 3.71 (t, J = 9.1 Hz, 1H), 3.47 (dd, J = 9.2, 5.9 Hz, 1H), 2.74 (s, 3H), 2.40 (s, 3H), 1.50-1.40 (m, 1H), 0.90-0.84 (m, 2H), 0.84-0.78 (m, 2H). | 3 |
| I-494 | 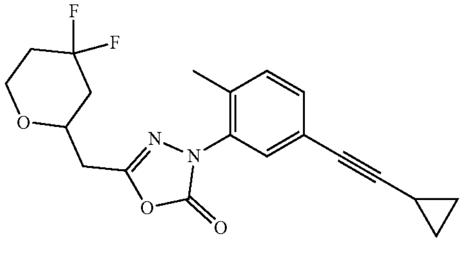 [SMILES: Cc1ccc(C#CC2CC2)cc1-n1nc(CC2CC(F)(F)CCO2)oc1=O] | 374.39 | $^1$H NMR (400 M Hz, $CDCl_3$) δ 7.38 (d, J = 1.6 Hz, 1H), 7.31 (dd, J = 7.9, 1.7 Hz, 1H), 7.19 (d, J = 8.0 Hz, 1H), 4.07 (ddd, J = 11.5, 6.1, 2.8 Hz, 1H), 4.02-3.91 (m, 1H), 3.64 (td, J = 11.9, 2.8 Hz, 1H), 2.92-2.78 (m, 2H), 2.29 (s, 3H), 2.21 (tdt, J = 10.6, 5.1, 2.6 Hz, 1H), 2.10-1.90 (m, 2H), 1.81 (dddd, J = 32.8, 13.3, 11.7, 3.8 Hz, 1H), 1.42 (tt, J = 8.2, 5.1 Hz, 1H), 0.89-0.82 (m, 2H), 0.81-0.75 (m, 2H). | 36 |
| I-495 | 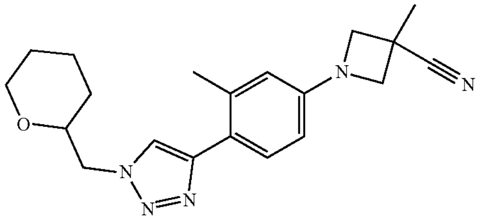 [SMILES: Cc1cc(N2CC(C)(C#N)C2)ccc1-c1cn(CC2CCCCO2)nn1] | 351.45 | $^1$H NMR (400 M Hz, $CDCl_3$) δ 7.71 (s, 1H), 7.68 (d, J = 8.3 Hz, 1H), 6.37 (dd, J = 8.3, 2.5 Hz, 1H), 6.32 (d, J = 2.4 Hz, 1H), 4.49 (dd, J = 14.2, 3.1 Hz, 1H), 4.32 (dd, J = 14.2, 7.5 Hz, 1H), 4.22 (d, J = 7.1 Hz, 2H), 3.98 (dd, J = 10.9, 2.0 Hz, 1H), 3.83 (d, J = 7.1 Hz, 2H), 3.70 (dtd, J = 11.0, 5.2, 2.7 Hz, 1H), 3.44-3.34 (m, 1H), 2.42 (s, 3H), 1.93-1.81 (m, 1H), 1.76 (s, 3H), 1.67 (d, J = 12.8 Hz, 1H), 1.58-1.44 (m, 3H), 1.32-1.20 (m, 1H). | 5 |
| I-496 | 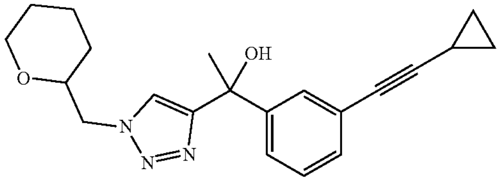 [SMILES: CC(O)(c1cccc(C#CC2CC2)c1)c1cn(CC2CCCCO2)nn1] | 351.45 | $^1$H NMR (400 M Hz, $CDCl_3$) δ 7.48-7.44 (m, 2H), 7.40 (dq, J = 7.3, 1.7 Hz, 1H), 7.28-7.15 (m, 2H), 4.40 (ddd, J = 14.1, 3.1, 1.5 Hz, 1H), 4.30-4.15 (m, 1H), 4.00-3.88 (m, 1H), 3.74-3.54 (m, 1H), 3.42-3.30 (m, 1H), 3.23-3.14 (m, 1H), 1.93 (m, 3H), 1.89-1.82 (m, 1H), 1.67-1.55 (m, 1H), 1.56-1.47 (m, 3H), 1.42 (tt, J = 8.2, 5.1 Hz, 1H), 1.27-1.15 (m, 1H), 0.90-0.81 (m, 2H), 0.81-0.74 (m, 2H) | 24 |

TABLE 24-continued

Characterization for exemplary compounds of the invention

| Compound No. | Chemical Structure | M + 1 | $^1$H NMR (400 M Hz) | Example of Synthesis |
|---|---|---|---|---|
| I-509 | 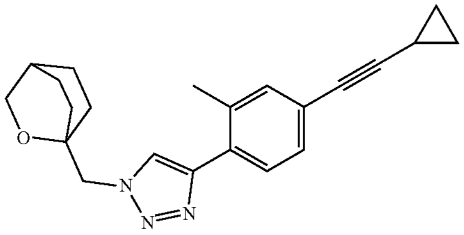 [SMILES: Cc1cc(C#CC2CC2)ccc1-c1cn(CC23CCC(CC2)CO3)nn1] | 347.46 | $^1$H NMR (400 M Hz, $CDCl_3$) δ 7.83 (s, 1H), 7.80-7.74 (m, 1H), 7.32-7.27 (m, 2H), 4.29 (s, 2H), 3.87 (s, 2H), 2.44 (s, 3H), 1.81-1.60 (m, 9H), 1.46 (tt, J = 8.1, 5.1 Hz, 1H), 0.91-0.84 (m, 2H), 0.84-0.79 (m, 2H). | 3 |
| I-522 | 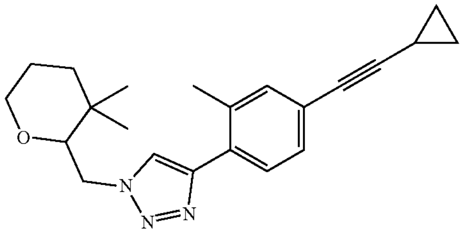 [SMILES: Cc1cc(C#CC2CC2)ccc1-c1cn(CC2OCCCC2(C)C)nn1] | 349.48 | $^1$H NMR (400 M Hz, $CDCl_3$) δ 7.80 (s, 1H), 7.75 (d, J = 8.3 Hz, 1H), 7.28 (d, J = 7.3 Hz, 2H), 4.70 (d, J = 14.1 Hz, 1H), 4.10 (dd, J = 14.0, 9.8 Hz, 1H), 3.97 (dd, J = 11.2, 4.9 Hz, 1H), 3.38 (d, J = 9.6 Hz, 1H), 3.34-3.17 (m, 1H), 2.42 (s, 3H), 1.97-1.73 (m, 1H), 1.62-1.48 (m, 1H), 1.48-1.35 (m, 3H), 1.04 (s, 6H), 0.95-0.75 (m, 4H). | 37 |
| I-523 | 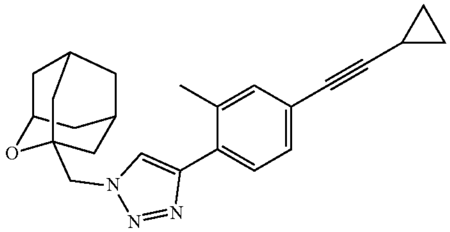 [SMILES: Cc1cc(C#CC2CC2)ccc1-c1cn(CC23CC4CC(CC(C4)O2)C3)nn1] | 373.50 | $^1$H NMR (400 M Hz, $CDCl_3$) δ 7.87 (s, 1H), 7.78 (d, J = 8.6 Hz, 1H), 7.29 (d, J = 6.9 Hz, 2H), 4.29 (s, 2H), 4.12 (s, 1H), 2.44 (s, 3H), 2.18 (s, 2H), 1.93-1.76 (m, 4H), 1.68-1.51 (m, 6H), 1.47 (ddd, J = 13.2, 8.3, 5.0 Hz, 1H), 0.88 (ddt, J = 8.3, 5.6, 2.5 Hz, 2H), 0.85-0.79 (m, 2H). | 3 |
| I-524 | 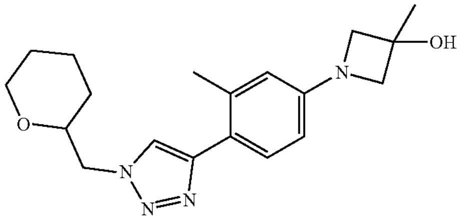 [SMILES: Cc1cc(N2CC(C)(O)C2)ccc1-c1cn(CC2CCCCO2)nn1] | 342.44 | $^1$H NMR (400 M Hz, $CDCl_3$) δ 7.71 (s, 1H), 7.67 (d, J = 8.2 Hz, 1H), 6.41 (d, J = 8.3 Hz, 1H), 6.37 (s, 1H), 4.50 (dd, J = 14.2, 3.2 Hz, 1H), 4.33 (dd, J = 14.1, 7.5 Hz, 1H), 3.99 (d, J = 10.2 Hz, 1H), 3.90 (d, J = 7.8 Hz, 2H), 3.78 (d, J = 7.6 Hz, 2H), 3.76-3.67 (m, 1H), 3.48-3.35 (m, 1H), 2.43 (s, 3H), 1.95-1.81 (m, 1H), 1.68 (d, J = 12.8 Hz, 1H), 1.63 (s, 3H), 1.53 (s, 3H), 1.28 (d, J = 10.3 Hz, 2H). | 5 |
| I-536 | 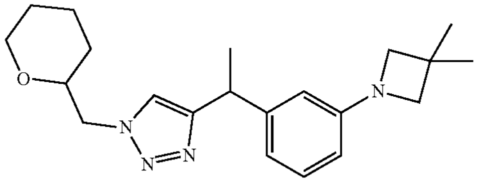 [SMILES: CC(c1cccc(N2CC(C)(C)C2)c1)c1cn(CC2CCCCO2)nn1] | 354.50 | $^1$H NMR (400 M Hz, $CDCl_3$) δ 7.25 (d, J = 4.6 Hz, 1H), 7.12 (t, J = 7.8 Hz, 1H), 6.62 (d, J = 7.6 Hz, 1H), 6.35-6.31 (m, 2H), 6.28 (dd, J = 8.0, 2.1 Hz, 1H), 4.46-4.27 (m, 1H), 4.23-4.13 (m, 2H), 3.96-3.89 (m, 1H), 3.66-3.58 (m, 1H), 3.53 (s, 4H), 3.40-3.27 (m, 1H), 1.89-1.76 (m, 1H), 1.69-1.64 (m, 3H), 1.59 (d, J =12.8 Hz, 1H), 1.54-1.43 (m, 3H), 1.28 (s, 6H), 1.25-1.10 (m, 1H) | 25 |

TABLE 24-continued

Characterization for exemplary compounds of the invention

| Compound No. | Chemical Structure | M + 1 | $^1$H NMR (400 M Hz) | Example of Synthesis |
|---|---|---|---|---|
| I-537 | 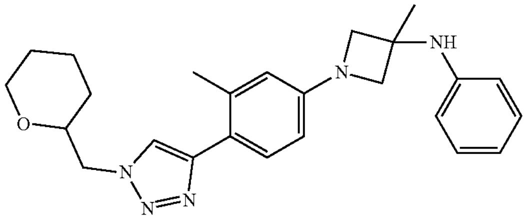 [SMILES: Cc1cc(N2CC(C)(Nc3ccccc3)C2)ccc1-c1cn(CC2CCCCO2)nn1] | 417.56 | $^1$H NMR (400 M Hz, $CDCl_3$) δ 7.70 (s, 1H), 7.67 (d, J = 8.3 Hz, 1H), 7.20 (dd, J = 8.4, 7.4 Hz, 2H), 6.75 (t, J = 7.3 Hz, 1H), 6.60-6.52 (m, 2H), 6.41 (dd, J = 8.3, 2.5 Hz, 1H), 6.36 (d, J = 2.2 Hz, 1H), 4.50 (dd, J = 14.1, 3.2 Hz, 1H), 4.33 (dd, J = 14.2, 7.5 Hz, 1H), 4.07-3.92 (m, 6H), 3.71 (dtd, J = 11.1, 5.3, 2.8 Hz, 1H), 3.41 (td, J = 11.3, 4.3 Hz, 1H), 2.42 (s, 3H), 1.93-1.83 (m, 1H), 1.73 (s, 3H), 1.68 (d, J = 12.4 Hz, 1H), 1.59-1.45 (m, 3H), 1.34-1.20 (m, 1H). | 38 |
| I-538 | 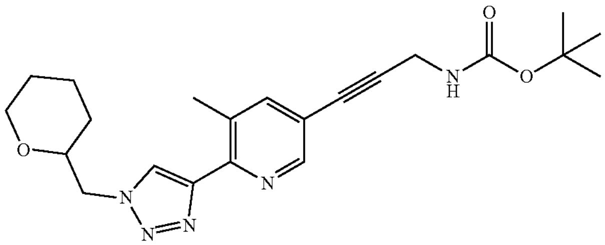 [SMILES: Cc1cc(C#CCNC(=O)OC(C)(C)C)cnc1-c1cn(CC2CCCCO2)nn1] | 411.51 | $^1$H NMR (400 M Hz, $CDCl_3$) δ 8.46 (s, 1H), 8.21 (s, 1H), 7.57 (s, 1H), 4.96 (s, 1H), 4.48 (dd, J = 14.1, 3.3 Hz, 1H), 4.33 (dd, J = 14.1, 7.5 Hz, 1H), 4.17 (d, J = 4.7 Hz, 2H), 4.01-3.92 (m, 1H), 3.69 (dtd, J = 10.9, 5.3, 2.7 Hz, 1H), 3.42-3.30 (m, 1H), 2.69 (s, 3H), 1.86-1.82 (m, 1H), 1.65 (d, J =12.5 Hz, 1H), 1.55-1.40 (m, 12H), 1.34-1.19 (m, 1H) | 3 |
| I-553 | 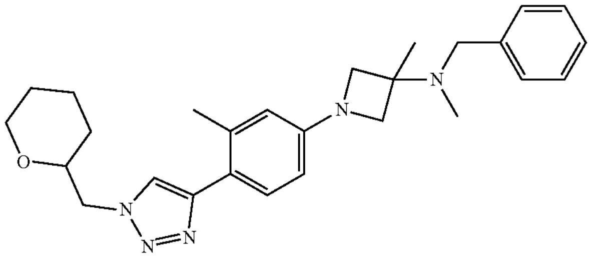 [SMILES: Cc1cc(N2CC(C)(N(C)Cc3ccccc3)C2)ccc1-c1cn(CC2CCCCO2)nn1] | 445.61 | $^1$H NMR (400 M Hz, $CDCl_3$) δ 7.69 (s, 1H), 7.67 (d, J = 8.3 Hz, 1H), 7.31 (dt, J = 12.8, 7.3 Hz, 4H), 7.26-7.20 (m, 1H), 6.42 (dd, J = 8.3, 2.4 Hz, 1H), 6.37 (d, J = 2.2 Hz, 1H), 4.49 (dd, J = 14.1, 3.1 Hz, 1H), 4.32 (dd, J = 14.1, 7.4 Hz, 1H), 4.03-3.95 (m, 1H), 3.77-3.65 (m, 5H), 3.46-3.36 (m, 3H), 2.43 (s, 3H), 2.03 (s, 3H), 1.88 (d, J = 6.2 Hz, 1H), 1.67 (d, J = 12.4 Hz, 1H), 1.59-1.50 (m, 3H), 1.49 (s, 3H), 1.34-1.20 (m, 1H). | 5 |
| I-554 | 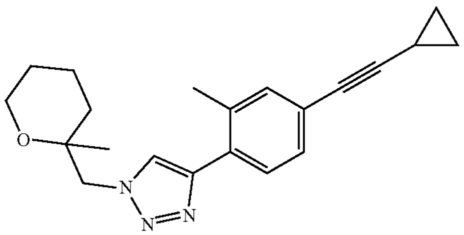 [SMILES: Cc1cc(C#CC2CC2)ccc1-c1cn(CC2(C)CCCCO2)nn1] | 335.45 | $^1$H NMR (400 M Hz, $CDCl_3$) δ 7.83 (s, 1H), 7.79-7.71 (m, 1H), 7.29 (d, J = 0.8 Hz, 1H), 7.28-7.20 (m, 1H), 4.51-4.28 (m, 2H), 3.80-3.70 (m, 1H), 3.65 (ddd, J = 11.8, 10.7, 3.1 Hz, 1H), 2.42 (s, 3H), 1.68 (td, J = 8.8, 8.1, 4.6 Hz, 2H), 1.59-1.42 (m, 4H), 1.42-1.32 (m, 1H), 1.16 (s, 3H), 0.94-0.72 (m, 4H). | 37 |
| I-555 | 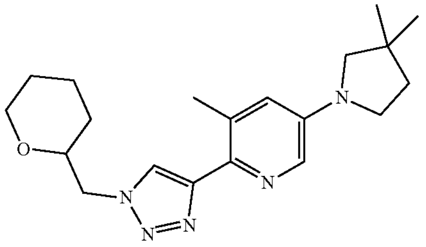 [SMILES: Cc1cc(N2CCC(C)(C)C2)cnc1-c1cn(CC2CCCCO2)nn1] | 355.49 | $^1$H NMR (400 M Hz, $CDCl_3$) δ 8.03 (s, 1H), 7.82 (d, J = 2.7 Hz, 1H), 6.65 (d, J = 2.6 Hz, 1H), 4.46 (dd, J = 14.1, 3.6 Hz, 1H), 4.34 (dd, J = 14.1, 7.3 Hz, 1H), 3.98 (d, J 11.4 Hz, 1H), 3.77-3.66 (m, 1H), 3.47-3.34 (m, 3H), 3.09 (s, 2H), 2.64 (s, 3H), 1.92-1.83 (m, 1H), 1.81 (t, J = 6.9 Hz, 2H), 1.65 (d, J = 12.8 Hz, 1H), 1.60-1.43 (m, 3H), 1.37-1.23 (m, 1H), 1.15 (s, 6H) | 5 |

TABLE 24-continued

| Characterization for exemplary compounds of the invention | | | | |
|---|---|---|---|---|
| Compound No. | Chemical Structure | M + 1 | $^1$H NMR (400 M Hz) | Example of Synthesis |
| I-568 | 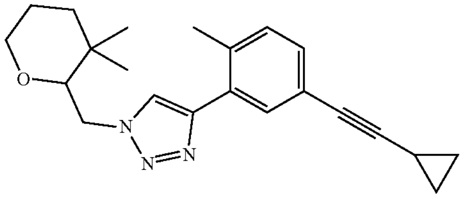 [SMILES: Cc1ccc(C#CC2CC2)cc1-c1cn(CC2OCCCC2(C)C)nn1] | 349.48 | $^1$H NMR (400 M Hz, $CDCl_3$) δ 7.83-7.75 (m, 1H), 7.25 (d, J = 5.8 Hz, 1H), 7.16 (dt, J = 7.9, 0.7 Hz, 1H), 4.71 (dd, J = 14.1, 1.8 Hz, 1H), 4.19-4.07 (m, 1H), 4.07-3.89 (m, 1H), 3.44-3.19 (m, 2H), 2.45 (s, 3H), 1.94-1.73 (m, 1H), 1.65-1.46 (m, 2H), 1.46-1.33 (m, 3H), 1.04 (d, , I= 3.0 Hz, 6H), 0.92-0.72 (m, 4H). | 37 |
| I-569 | 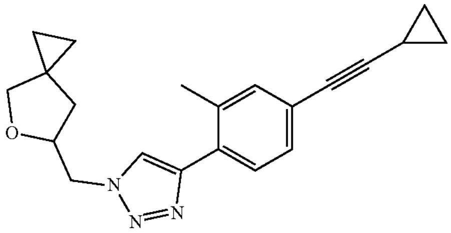 [SMILES: Cc1cc(C#CC2CC2)ccc1-c1cn(CC2CC3(CC3)CO2)nn1] | 333.44 | $^1$H NMR (400 M Hz, $CDCl_3$) δ 7.86 (s, 1H), 7.73 (d, J = 7.8 Hz, 1H), 7.31-7.26 (m, 2H), 4.67-4.58 (m, 1H), 4.57-4.46 (m, 2H), 3.72-3.61 (m, 2H), 2.44 (s, 3H), 2.01-1.90 (m, 1H), 1.78-1.67 (m, 1H), 1.49-1.41 (m, 1H), 0.92-0.84 (m, 2H), 0.86-0.76 (m, 2H), 0.63 (ddd, J = 8.4, 5.9, 3.4 Hz, 1H), 0.58-0.47 (m, 3H). | 3 |
| I-570 | 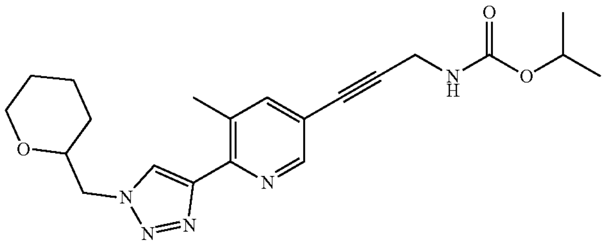 [SMILES: Cc1cc(C#CCNC(=O)OC(C)C)cnc1-c1cn(CC2CCCCO2)nn1] | 397.48 | $^1$H NMR (400 M Hz, $CDCl_3$) δ 8.47 (d, J = 1.5 Hz, 1H), 8.22 (s, 1H), 7.59 (s, 1H), 5.05-4.90 (m, 2H), 4.49 (dd, J = 14.1, 3.3 Hz, 1H), 4.34 (dd, J = 14.1, 7.5 Hz, 1H), 4.22 (d, J = 4.8 Hz, 2H), 3.97 (d, J = 11.1 Hz, 1H), 3.70 (dtd, J = 10.9, 5.3, 2.7 Hz, 1H), 3.38 (td, J = 11.3, 3.0 Hz, 1H), 2.70 (s, 3H), 1.95-1.79 (m, 1H), 1.66 (d, J = 12.7 Hz, 1H), 1.58-1.44 (m, 3H), 1.35-1.20 (m, 7H) | 39 |
| I-571 | 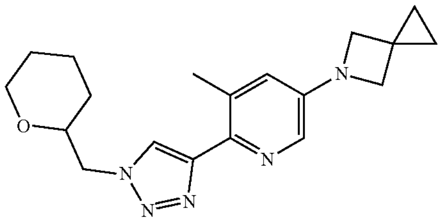 [SMILES: Cc1cc(N2CC3(CC3)C2)cnc1-c1cn(CC2CCCCO2)nn1] | 339.44 | $^1$H NMR (400 M Hz, $CDCl_3$) 8.05 (s, 1H), 7.75 (d, J = 2.7 Hz, 1H), 6.62 (d, J 2.6 Hz, 1H), 4.47 (dd, J = 14.1, 3.5 Hz, 1H), 4.34 (dd, J = 14.1, 7.3 Hz, 1H), 4.04 (s, 4H), 4.01-3.94 (m, 1H), 3.71 (dddd, J = 9.7, 5.8, 3.7, 2.2 Hz, 1H), 3.39 (td, J = 11.4, 3.0 Hz, 1H), 2.65 (s, 3H), 1.91-1.81 (m, 1H), 1.71-1.61 (m, 1H), 1.59-1.43 (m, 3H), 1.35-1.26 (m, 1H), 0.69 (s, 4H). | 5 |
| I-572 | 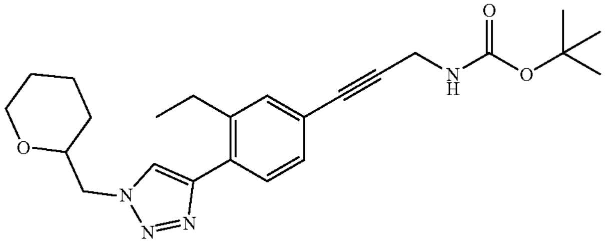 [SMILES: CCc1cc(C#CCNC(=O)OC(C)(C)C)ccc1-c1cn(CC2CCCCO2)nn1] | 424.55 | $^1$H NMR (400 M Hz, $CDCl_3$) δ 7.78 (s, 1H), 7.62 (d, J = 8.0 Hz, 1H), 7.34 (s, 1H), 7.28 (d, J = 8.0 Hz, 1H), 4.90 (s, 1H), 4.49 (dd, J = 14.1, 2.9 Hz, 1H), 4.32 (dd, J = 14.2, 7.5 Hz, 1H), 4.15 (d, J = 4.5 Hz, 2H), 4.00-3.92 (m, 2H), 3.72-3.64 (m, 1H), 3.45-3.32 (m, 1H), 2.78 (q, J = 7.5 Hz, 2H), 1.85 (d, J = 4.8 Hz, 1H), 1.65 (d, J = 12.6 Hz, 1H), 1.1.55-1.40 (m, 12H), 1.36-1.09 (m, 4H) | 3 |

TABLE 24-continued

| Characterization for exemplary compounds of the invention | | | | |
|---|---|---|---|---|
| Compound No. | Chemical Structure | M + 1 | $^1$H NMR (400 M Hz) | Example of Synthesis |
| I-573 | 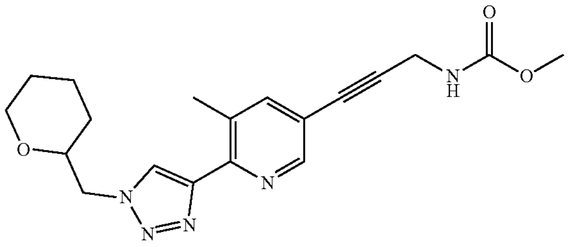 [SMILES: COC(=O)NCC#Cc1cnc(-c2cn(CC3CCCCO3)nn2)c(C)c1] | 369.43 | $^1$H NMR (400 M Hz, $CDCl_3$) δ 8.48 (d, J = 1.9 Hz, 1H), 8.23 (s, 1H), 7.60 (d, J = 1.1 Hz, 1H), 5.03 (s, 1H), 4.50 (dd, J = 14.1, 3.3 Hz, 1H), 4.35 (dd, J = 14.1, 7.5 Hz, 1H), 4.24 (d, , I= 5.4 Hz, 2H), 4.12-3.90 (m, 1H), 3.80-3.65 (m, 4H), 3.39 (td, J = 11.3, 3.2 Hz, 1H), 2.71 (s, 3H), 1.91-1.83 (m, 1H), 1.67 (d, J = 12.2 Hz, 2H), 1.58-1.44 (m, 3H), 1.39-1.21 (m, 1H) | 39 |
| I-586 | 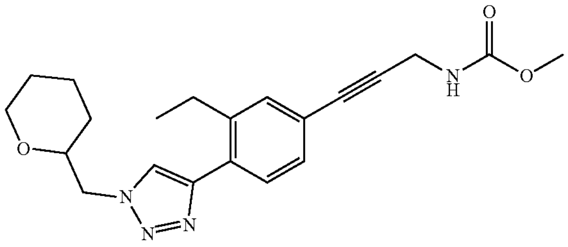 [SMILES: CCc1cc(C#CCNC(=O)OC)ccc1-c1cn(CC2CCCCO2)nn1] | 382.46 | $^1$H NMR (400 M Hz, $CDCl_3$) δ 7.80 (s, 1H), 7.65 (d, J = 8.0 Hz, 1H), 7.37 (s, 1H), 7.30 (dd, J = 8.0, 1.6 Hz, 1H), 4.99 (s, 1H), 4.52 (dd, J = 14.2, 3.0 Hz, 1H), 4.33 (dd, J = 14.2, 7.5 Hz, 1H), 4.23 (d, J = 5.4 Hz, 2H), 3.98 (dd, J = 10.3, 2.4 Hz, 1H), 3.80-3.65 (m, 4H), 3.49-3.33 (m, 1H), 2.80 (q, J = 7.5 Hz, 2H), 1.88 (d, J = 3.8 Hz, 1H), 1.72-1.64 (m, 1H), 1.59-1.46 (m, 2H), 1.35-1.13 (m, 4H) | 39 |
| I-587 | 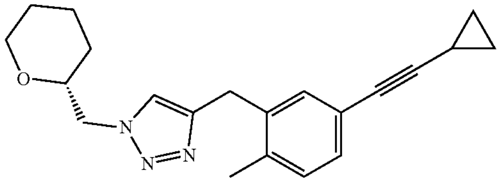 | 335.45 | $^1$H NMR (400 M Hz, $CDCl_3$) δ 7.20 (d, J = 2.3 Hz, 2H), 7.17 (dd, J = 7.8, 1.8 Hz, 1H), 7.06 (d, J = 7.8 Hz, 1H), 4.36 (dd, J = 14.1, 3.3 Hz, 1H), 4.22 (q, J = 7.0 Hz, 1H), 4.08-3.95 (m, 2H), 3.98-3.84 (m, 1H), 3.63 (dddd, J = 11.1, 7.5, 3.3, 2.2 Hz, 1H), 3.44-3.23 (m, 1H), 2.26 (s, 3H), 1.85 (tt, J = 6.5, 4.6, 2.2 Hz, 1H), 1.71-1.57 (m, 1H), 1.57-1.48 (m, 3H), 1.42 (tt, J = 8.2, 5.1 Hz, 1H), 1.24-1.09 (m, 1H), 0.96-0.69 (m, 4H). | 13 |
| I-598 | 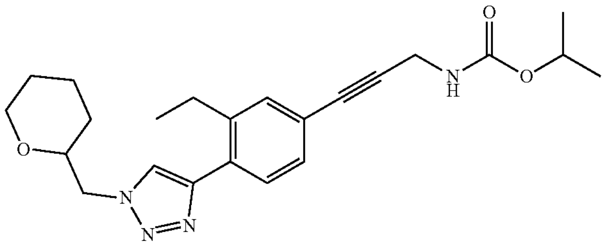 [SMILES: CCc1cc(C#CCNC(=O)OC(C)C)ccc1-c1cn(CC2CCCCO2)nn1] | 410.52 | $^1$H NMR (400 M Hz, $CDCl_3$) δ 7.80 (s, 1H), 7.65 (d, J = 8.0 Hz, 1H), 7.37 (s, 1H), 7.31 (dd, J = 7.9, 1.6 Hz, 1H), 5.06-4.91 (m, 1H), 4.85 (s, 1H), 4.52 (dd, J = 14.2, 3.0 Hz, 1H), 4.34 (dd, J = 14.2, 7.5 Hz, 1H), 4.22 (d, J = 5.0 Hz, 2H), 4.04-3.90 (m, 1H), 3.70 (ddd, J = 12.5, 5.0, 2.5 Hz, 1H), 3.54-3.34 (m, 1H), 2.81 (q, J = 7.6 Hz, 2H), 1.89 (d, J = 5.5 Hz, 1H), 1.68 (d, J = 12.1 Hz, 1H), 1.57-1.46 (m, 3H), 1.37-1.14 (m, 10H). | 39 |
| I-607 | 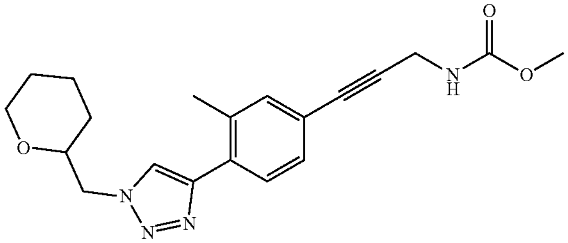 [SMILES: COC(=O)NCC#Cc1ccc(-c2cn(CC3CCCCO3)nn2)c(C)c1] | 368.44 | $^1$H NMR (400 M Hz, $CDCl_3$) δ 7.82 (s, 1H), 7.78 (d, J = 7.8 Hz, 1H), 7.34-7.28 (m, 2H), 5.02 (s, 1H), 4.51 (dd, J = 14.2, 3.0 Hz, 1H), 4.33 (dd, J = 14.2, 7.6 Hz, 1H), 4.22 (d, J = 5.1 Hz, 3H), 4.02-3.94 (m, 1H), 3.78-3.64 (m, 4H), 3.53-3.33 (m, 1H), 2.44 (s, 3H), 1.96-1.81 (m, 1H), 1.67 (d, J = 13.1 Hz, 1H), 1.59-1.44 (m, 3H), 1.40-1.17 (m, 1H). | 39 |

TABLE 24-continued

Characterization for exemplary compounds of the invention

| Compound No. | Chemical Structure | M + 1 | $^1$H NMR (400 M Hz) | Example of Synthesis |
|---|---|---|---|---|
| I-608 | 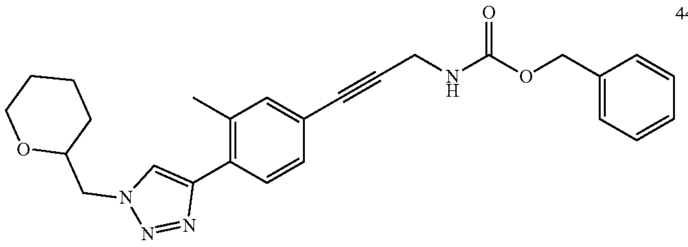 | 444.54 | $^1$H NMR (400 M Hz, $CDCl_3$) δ 7.81 (s, 1H), 7.78 (d, J = 7.9 Hz, 1H), 7.59-7.14 (m, 7H), 5.22 (s, 1H), 5.13 (s, 2H), 4.50 (dd, J = 14.2, 3.0 Hz, 1H), 4.32 (dd, J = 14.2, 7.5 Hz, 1H), 4.23 (d, J = 5.3 Hz, 2H), 4.04-3.91 (m, 1H), 3.68 (dtd, J = 10.9, 5.0, 2.5 Hz, 1H), 3.38 (ddd, J = 14.1, 9.8, 4.5 Hz, 1H), 2.43 (s, 3H), 1.89-1.82 (m, 1H), 1.66 (d, J = 13.0 Hz, 1H), 1.59-1.41 (m, 3H), 1.40-1.18 (m, 1H). | 39 |
| I-616 | 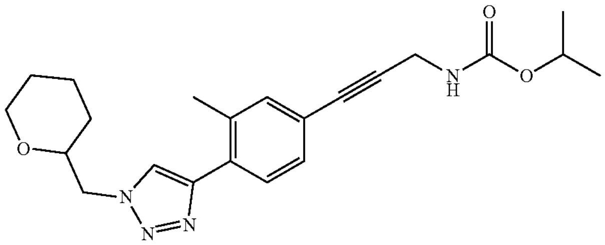 [SMILES: Cc1cc(C#CCNC(=O)OC(C)C)ccc1-c1cn(CC2CCCCO2)nn1] | 396.49 | $^1$H NMR (400 M Hz, $CDCl_3$) δ 7.81 (s, 1H), 7.77 (d, J = 8.2 Hz, 1H), 7.33-7.28 (m, 2H), 5.09-4.86 (m, 2H), 4.51 (dd, J = 14.2, 3.0 Hz, 1H), 4.32 (dd, J = 14.2, 7.6 Hz, 1H), 4.20 (d, J = 5.1 Hz, 2H), 4.01-3.89 (m, 1H), 3.69 (ddt, J = 10.6, 7.5, 2.6 Hz, 1H), 3.38 (ddd, J = 14.2, 9.8, 4.8 Hz, 1H), 2.43 (s, 3H), 1.99-1.78 (m, 1H), 1.67 (d, J = 13.0 Hz, 1H), 1.60-1.44 (m, 3H), 1.34-1.16 (m, 7H) | 39 |
| I-617 | 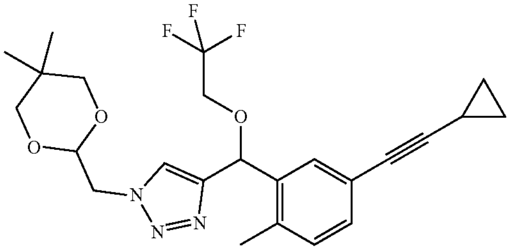 [SMILES: Cc1ccc(C#CC2CC2)cc1C(OCC(F)(F)F)c1cn(CC2OCC(C)(C)CO2)nn1] | 463.50 | $^1$H NMR (400 M Hz, $CDCl_3$) δ 7.58 (d, J = 1.5 Hz, 1H), 7.45 (s, 1H), 7.23 (dd, J = 7.8, 1.7 Hz, 1H), 7.04 (d, J = 7.8 Hz, 1H), 5.88 (s, 1H), 4.74 (t, J = 4.1 Hz, 1H), 4.53-4.38 (m, 2H), 4.04-3.78 (m, 2H), 3.59 (d, J = 11.2 Hz, 2H), 3.40 (d, J = 11.3 Hz, 2H), 2.21 (s, 3H), 1.50-1.41 (m, 1H), 1.02 (s, 3H), 0.87 (ddd, J = 11.3, 5.4, 2.2 Hz, 2H), 0.82 (td, J = 5.5, 2.6 Hz, 2H), 0.70 (s, 3H). | 40 |
| I-618 | 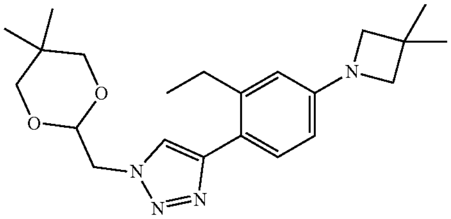 | 384.52 | $^1$H NMR (400 M Hz, $CDCl_3$) δ 7.67 (s, 1H), 7.54-7.45 (m, 1H), 6.39-6.27 (m, 2H), 4.80 (t, J = 4.4 Hz, 1H), 4.55 (d, J = 4.4 Hz, 2H), 3.69-3.57 (m, 6H), 3.54-3.36 (m, 2H), 2.76 (q, J = 7.5 Hz, 2H), 1.33 (s, 6H), 1.25 (d, J = 3.4 Hz, 1H), 1.23-1.11 (m, 5H), 0.72 (s, 3H). | 5 |
| I-619 | 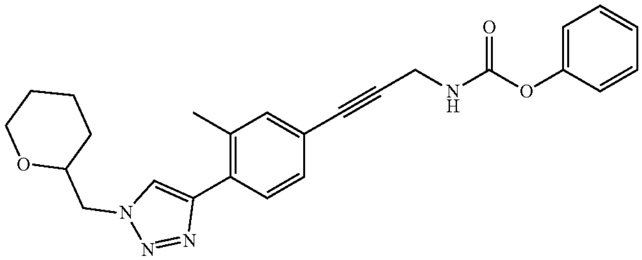 [SMILES: Cc1cc(C#CCNC(=O)Oc2ccccc2)ccc1-c1cn(CC2CCCCO2)nn1] | 430.51 | .83 (s, 1H), 7.81 (d, J = 8.0 Hz, 1H), 7.42-7.29 (m, 4H), 7.24-7.08 (m, 3H), 5.37 (s, 1H), 4.53 (dd, J = 14.2, 3.0 Hz, 1H), 4.36-4.28 (m, 3H), 4.05-3.84 (m, 1H), 3.71 (dtd, J = 10.8, 4.9, 2.5 Hz, 1H), 3.40 (td, J = 11.3, 4.8 Hz, 1H), 2.46 (s, 3H), 1.93-1.84 (m, 1H), 1.80-1.63 (m, 1H), 1.58-1.49 (m, 3H), 1.37-1.24 (m, 1H). | 39 |

TABLE 24-continued

Characterization for exemplary compounds of the invention

| Compound No. | Chemical Structure | M + 1 | $^1$H NMR (400 M Hz) | Example of Synthesis |
|---|---|---|---|---|
| I-620 | 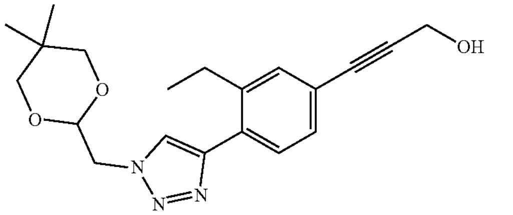 [SMILES: CCc1cc(C#CCO)ccc1-c1cn(CC2OCC(C)(C)CO2)nn1] | 355.44 | $^1$H NMR (400 M Hz, $CDCl_3$) δ 7.80 (s, 1H), 7.62 (d, J = 8.0 Hz, 1H), 7.37 (d, J = 1.7 Hz, 1H), 7.29 (dd, J = 8.0, 1.7 Hz, 1H), 4.81 (t, J = 4.3 Hz, 1H), 4.57 (d, J = 4.3 Hz, 2H), 4.50 (d, , I= 5.9 Hz, 2H), 3.63 (dt, J = 11.2, 1.3 Hz, 2H), 3.50-3.32 (m, 2H), 2.79 (q, J = 7.5 Hz, 2H), 2.29 (t, J = 6.1 Hz, 1H), 1.19 (t, J = 7.5 Hz, 3H), 1.13 (s, 3H), 0.72 (s, 3H). | 6 |
| I-621 | 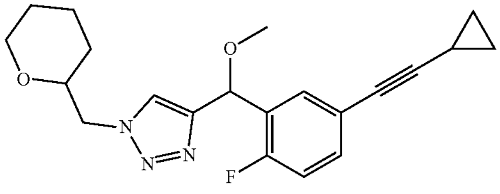 [SMILES: COC(c1cn(CC2CCCCO2)nn1)c1cc(C#CC2CC2)ccc1F] | 369.44 | $^1$H NMR ($CDCl_3$, 400 M Hz) δ 7.53 (dt, J = 6.9, 2.2 Hz, 1H), 7.50 (s, 1H), 7.35-7.24 (m, 1H), 6.93 (dd, J = 9.7, 8.6 Hz, 1H), 5.74 (d, J = 1.9 Hz, 1H), 4.38 (ddd, J = 14.4, 11.3, 3.2 Hz, 1H), 4.21 (ddd, J = 19.8, 14.1, 7.5 Hz, 1H), 4.01-3.87 (m, 1H), 3.62 (dddd, J = 9.8, 7.6, 5.2, 2.6 Hz, 1H), 3.39 (d, J = 2.3 Hz, 3H), 3.38-3.27 (m, 1H), 1.83 (d, J = 7.0 Hz, 1H), 1.59 (d, J = 12.7 Hz, 1H), 1.57-1.45 (m, 3H), 1.40 (tt, J = 8.2, 5.1 Hz, 1H), 1.26-1.11 (m, 1H), 0.94-0.81 (m, 2H), 0.81-0.70 (m, 2H) | 34 |
| I-631 | 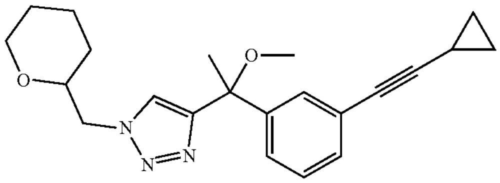 [SMILES: COC(C)(c1cccc(C#CC2CC2)c1)c1cn(CC2CCCCO2)nn1] | 365.48 | $^1$H NMR (400 M Hz, $CDCl_3$) δ 7.47-7.41 (m, 2H), 7.33 (dd, J = 7.4, 1.6 Hz, 1H), 7.27-7.13 (m, 2H), 4.40 (ddd, J = 14.0, 9.4, 3.3 Hz, 1H), 4.24 (ddd, J = 18.8, 14.1, 7.4 Hz, 1H), 4.06-3.87 (m, 1H), 3.64 (ddt, J = 10.7, 5.2, 2.9 Hz, 1H), 3.40-3.28 (m, 1H), 3.18 (d, J = 1.2 Hz, 3H), 1.95 (d, J = 3.2 Hz, 3H), 1.91-1.75 (m, 1H), 1.61 (d, J = 11.8 Hz, 1H), 1.53-1.47 (m, 3H), 1.46-1.34 (m, 1H), 1.20 (ddt, J = 16.2, 8.7, 4.4 Hz, 1H), 0.87-0.81 (m, 2H), 0.81-0.73 (m, 2H) | 24 & 34 |
| I-632 | 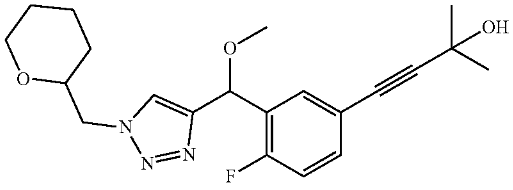 [SMILES: COC(c1cn(CC2CCCCO2)nn1)c1cc(C#CC(C)(C)O)ccc1F] | 387.46 | $^1$H NMR (400 M Hz, $CDCl_3$) δ 7.59 (dt, J = 6.8, 1.8 Hz, 1H), 7.52 (s, 1H), 7.30 (ddd, J = 8.4, 5.0, 2.2 Hz, 1H), 6.95 (dd, J = 9.7, 8.6 Hz, 1H), 5.74 (s, 1H), 4.38 (ddd, J = 13.9, 10.6, 3.2 Hz, 1H), 4.21 (ddd, J = 20.4, 14.2, 7.6 Hz, 1H), 3.97-3.88 (m, 1H), 3.61 (dtd, J =10.1, 5.2, 2.8 Hz, 1H), 3.39 (d, J = 1.9 Hz, 3H), 3.37-3.28 (m, 1H), 2.48 (s, 1H), 1.85-1.79 (m, 1H), 1.63-1.55 (m, 7H), 1.52-1.44 (m, 3H), 1.28-1.09 (m, 1H) | 34 |

TABLE 24-continued

| Compound No. | Chemical Structure | M + 1 | $^1$H NMR (400 M Hz) | Example of Synthesis |
|---|---|---|---|---|
| Characterization for exemplary compounds of the invention | | | | |
| I-633 | 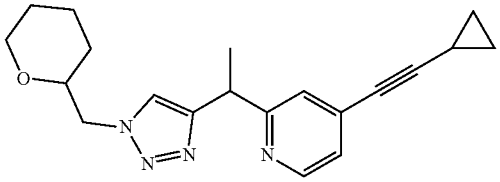 [SMILES: CC(c1cc(C#CC2CC2)ccn1)c1cn(CC2CCCCO2)nn1] | 336.44 | $^1$H NMR (400 M Hz, $CDCl_3$) δ 8.42 (s, 1H), 7.46 (d, J = 7.1 Hz, 1H), 7.20 (s, 1H), 7.05 (d, J = 5.0 Hz, 1H), 4.38 (dd, J = 13.3, 3.2 Hz, 2H), 4.21 (dd, J = 14.2, 7.5 Hz, 1H), 3.94 (dq, J = 11.7, 2.1 Hz, 1H), 3.70-3.59 (m, 1H), 3.36 (tdd, J = 11.3, 3.9, 1.9 Hz, 1H), 1.88-1.79 (m, 1H), 1.70 (dd, J = 7.2, 4.1 Hz, 3H), 1.64-1.57 (m, 1H), 1.57-1.37 (m, 4H), 1.29-1.15 (m, 1H), 0.94-0.75 (m, 4H). | 24 |
| I-641 | 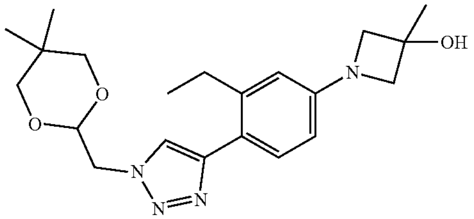 [SMILES: CCc1cc(N2CC(C)(O)C2)ccc1-c1cn(CC2OCC(C)(C)CO2)nn1] | 386.50 | $^1$H NMR (400 M Hz, $CDCl_3$) δ 7.67 (s, 1H), 7.51-7.39 (m, 1H), 6.40-6.29 (m, 2H), 4.78 (t, J = 4.3 Hz, 1H), 4.52 (d, J = 4.3 Hz, 2H), 3.85 (d, J = 7.8 Hz, 2H), 3.76 (d, J = 7.5 Hz, 2H), 3.66-3.58 (m, 2H), 3.43 (dd, J = 11.2, 1.5 Hz, 2H), 2.73 (q, J = 7.5 Hz, 2H), 1.58 (s, 3H), 1.19-1.08 (m, 6H), 0.71 (s, 3H). | 5 |
| I-642 | 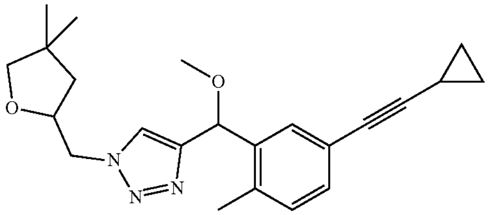 [SMILES: COC(c1cn(CC2CC(C)(C)CO2)nn1)c1cc(C#CC2CC2)ccc1C] | 379.50 | $^1$H NMR (400 M Hz, $CDCl_3$) δ 7.57 (dd, J = 4.5, 1.6 Hz, 1H), 7.39 (d, J = 8.8 Hz, 1H), 7.20 (ddd, J = 7.8, 4.0, 1.8 Hz, 1H), 7.03 (t, J = 7.3 Hz, 1H), 5.62 (d, J = 3.3 Hz, 1H), 4.51-4.39 (m, 1H), 4.39-4.24 (m, 2H), 3.47-3.21 (m, 5H), 2.23 (d, J = 9.9 Hz, 3H), 1.76 (ddd, J = 12.9, 9.4, 6.3 Hz, 1H), 1.49-1.21 (m, 2H), 1.06 (d, J = 7.6 Hz, 3H), 0.95 (d, J = 29.3 Hz, 3H), 0.88-0.82 (m, 2H), 0.82-0.76 (m, 2H). | 34 |
| I-643 | 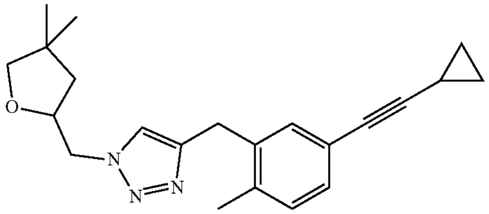 [SMILES: Cc1ccc(C#CC2CC2)cc1Cc1cn(CC2CC(C)(C)CO2)nn1] | 349.48 | $^1$H NMR (400 M Hz, $CDCl_3$) δ 7.23 (s, 1H), 7.18 (s, 1H), 7.15 (dd, J = 7.7, 1.6 Hz, 1H), 7.04 (d, J = 7.8 Hz, 1H), 4.50-4.42 (m, 1H), 4.38-4.25 (m, 2H), 4.06-3.93 (m, 2H), 3.43 (d, J = 8.1 Hz, 1H), 3.32 (d, J = 8.1 Hz, 1H), 2.24 (s, 3H), 1.77 (dd, J = 12.5, 6.5 Hz, 1H), 1.45-1.30 (m, 2H), 1.06 (s, 3H), 0.97 (s, 3H), 0.83 (ddt, J = 8.2, 5.6, 2.8 Hz, 2H), 0.80-0.73 (m, 2H). | 13 |
| I-644 | 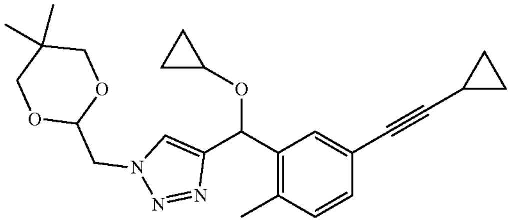 | 421.54 | $^1$H NMR (400 M Hz, $CDCl_3$) δ 7.61 (d, J = 1.7 Hz, 1H), 7.36 (s, 1H), 7.20 (dd, J = 7.8, 1.8 Hz, 1H), 7.02 (d, J = 7.8 Hz, 1H), 5.85 (s, 1H), 4.72 (t, J = 4.3 Hz, 1H), 4.50-4.35 (m, 2H), 3.58 (d, J = 11.2 Hz, 2H), 3.41-3.34 (m, 3H), 2.24 (s, 3H), 1.50-1.38 (m, 1H), 1.05 (s, 3H), 0.89-0.83 (m, 2H), 0.80 (td, J = 5.8, 5.2, 2.8 Hz, 2H), 0.72-0.68 (m, 5H), 0.53-0.41 (m, 2H). | 40 |

TABLE 24-continued

| Compound No. | Chemical Structure | M + 1 | $^1H$ NMR (400 M Hz) | Example of Synthesis |
|---|---|---|---|---|
| | Characterization for exemplary compounds of the invention | | | |
| I-645 | 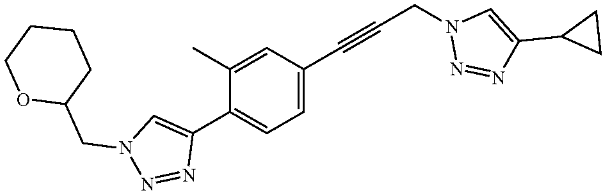 [SMILES: Cc1cc(C#CCn2cc(C3CC3)nn2)ccc1-c1cn(CC2CCCCO2)nn1] | 402.50 | $^1H$ NMR (400 M Hz, $CDCl_3$) δ 7.83 (d, J = 8.3 Hz, 2H), 7.53 (s, 1H), 7.35 (d, J = 6.5 Hz, 2H), 5.33 (s, 2H), 4.52 (dd, J = 14.2, 2.9 Hz, 1H), 4.32 (dd, J = 14.2, 7.6 Hz, 1H), 4.04-3.92 (m, 1H), 3.69 (ddt, J = 12.8, 7.5, 2.6 Hz, 1H), 3.39 (ddd, J = 11.3, 8.6, 5.0 Hz, 1H), 2.45 (s, 3H), 1.96 (tt, J = 8.4, 5.1 Hz, 1H), 1.89-1.82 (m, 1H), 1.72-1.62 (m, 1H), 1.59-1.44 (m, 3H), 1.34-1.18 (m, 1H), 1.02-0.80 (m, 4H). | 35 |
| I-655 | 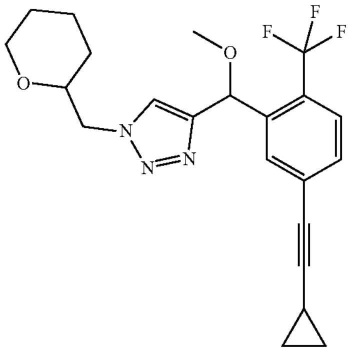 [SMILES: COC(c1cn(CC2CCCCO2)nn1)c1cc(C#CC2CC2)ccc1C(F)(F)F] | 419.45 | $^1H$ NMR (400 M Hz, $CDCl_3$) δ 7.86 (d, J = 7.3 Hz, 1H), 7.53 (dd, J = 8.2, 1.3 Hz, 1H), 7.41-7.34 (m, 2H), 5.81 (d, J = 4.5 Hz, 1H), 4.37 (dt, J = 14.1, 3.2 Hz, 1H), 4.18 (ddd, J = 14.2, 9.3, 7.6 Hz, 1H), 4.03-3.84 (m, 1H), 3.64-3.56 (m, 1H), 3.45-3.26 (m, 4H), 1.88-1.77 (m, 1H), 1.58 (d, J = 12.7 Hz, 1H), 1.53-1.38 (m, 4H), 1.22-1.10 (m, 1H), 0.98-0.75 (m, 4H) ppm. $^{19}F$ NMR (377M Hz, $CDCl_3$) δ-57.97 (d, J = 21.4 Hz) | 34 |
| I-656 | 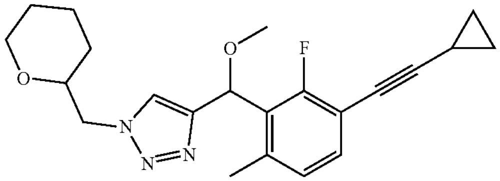 [SMILES: COC(c1cn(CC2CCCCO2)nn1)c1c(C)ccc(C#CC2CC2)c1F] | 383.47 | $^1H$ NMR (400 M Hz, $CDCl_3$) δ 7.58 (d, J = 14.7 Hz, 1H), 7.20 (t, J = 7.5 Hz, 1H), 6.85 (d, J = 7.9 Hz, 1H), 5.96 (s, 1H), 4.38 (ddd, J = 14.1, 12.2, 3.3 Hz, 1H), 4.31-4.09 (m, 1H), 3.99-3.89 (m, 1H), 3.67-3.57 (m, 1H), 3.40-3.30 (m, 4H), 2.33 (s, 3H), 1.93-1.77 (m, 1H), 1.59 (d, J = 13.0 Hz, 1H), 1.54-1.37 (m, 4H), 1.26-1.14 (m, 1H), 0.94-0.72 (m, 4H) | 34 |
| I-668 | 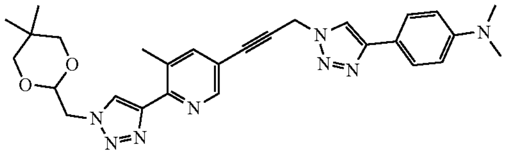 | 512.62 | $^1H$ NMR (400 M Hz, $CDCl_3$) δ 8.53 (d, J = 2.0 Hz, 1H), 8.28 (s, 1H), 7.90 (s, 1H), 7.79-7.69 (m, 2H), 7.69-7.62 (m, 1H), 6.83-6.59 (m, 2H), 5.45 (s, 2H), 4.82 (t, J = 4.5 Hz, 1H), 4.57 (d, J = 4.5 Hz, 2H), 3.64 (dt, J = 11.2, 1.3 Hz, 2H), 3.51-3.35 (m, 2H), 2.99 (s, 6H), 2.74 (s, 3H), 1.15 (s, 3H), 0.72 (s, 3H). | 35 |
| I-669 | 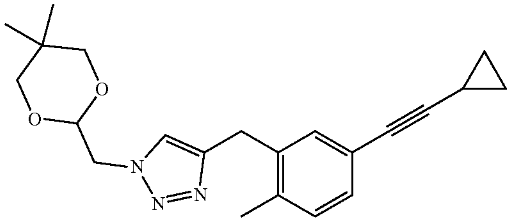 [SMILES: Cc1ccc(C#CC2CC2)cc1Cc1cn(CC2OCC(C)(C)CO2)nn1] | 365.48 | $^1H$ NMR (400 M Hz, $CDCl_3$) δ 7.19 (s, 2H), 7.16 (dd, J = 7.7, 1.7 Hz, 1H), 7.05 (d, J = 7.8 Hz, 1H), 4.73 (t, J = 4.4 Hz, 1H), 4.42 (d, J = 4.4 Hz, 2H), 4.01 (s, 2H), 3.64-3.55 (m, 2H), 3.39 (d, J = 10.6 Hz, 2H), 2.24 (s, 3H), 1.42 (tt, J = 8.2, 5.1 Hz, 1H), 1.08 (s, 3H), 0.84 (ddt, J = 8.3, 5.6, 2.8 Hz, 2H), 0.81-0.74 (m, 2H), 0.70 (s, 3H). | 41 |

TABLE 24-continued

| Characterization for exemplary compounds of the invention | | | | |
|---|---|---|---|---|
| Compound No. | Chemical Structure | M + 1 | $^1$H NMR (400 M Hz) | Example of Synthesis |
| I-670 | 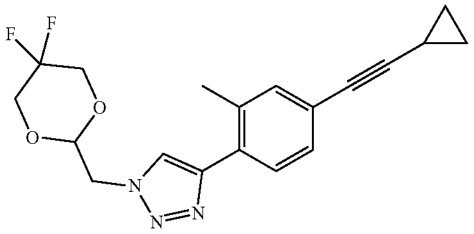 [SMILES: Cc1cc(C#CC2CC2)ccc1-c1cn(CC2OCC(F)(F)CO2)nn1] | 359.38 | $^1$H NMR (400 M Hz, $CDCl_3$) δ 7.76 (s, 1H), 7.73 (d, J = 7.8 Hz, 1H), 7.37-7.27 (m, 2H), 4.98 (t, J = 4.8 Hz, 1H), 4.63 (d, J = 4.8 Hz, 2H), 4.38-3.98 (m, 2H), 3.85 (dd, J = 12.3, 1.3 Hz, 1H), 3.78 (dd, J = 12.3, 1.4 Hz, 1H), 2.42 (s, 3H), 1.46 (tt, J = 8.2, 5.1 Hz, 1H), 0.99-0.74 (m, 4H) | 3 |
| I-679 | 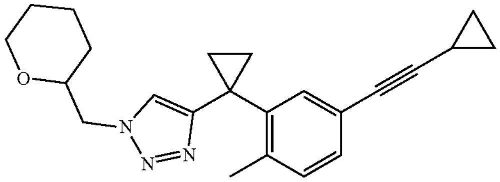 [SMILES: Cc1ccc(C#CC2CC2)cc1C1(c2cn(CC3CCCCO3)nn2)CC1] | 361.49 | $^1$H NMR (400 M Hz, $CDCl_3$) δ 7.42 (d, J = 1.7 Hz, 1H), 7.21 (dd, J = 7.8, 1.8 Hz, 1H), 7.06 (d, J = 7.8 Hz, 1H), 6.87 (s, 1H), 4.26 (dd, J = 14.1, 3.5 Hz, 1H), 4.11 (dd, J = 14.1, 7.4 Hz, 1H), 3.94-3.85 (m, 1H), 3.63-3.51 (m, 1H), 3.37-3.26 (m, 1H), 2.23 (s, 3H), 1.86-1.78 (m, 1H), 1.73-1.60 (m, 2H), 1.56 (d, J = 12.8 Hz, 1H), 1.52-1.40 (m, 4H), 1.25-1.09 (m, 3H), 0.89-0.83 (m, 2H), 0.83-0.76 (m, 2H). | 42 |
| I-680 | 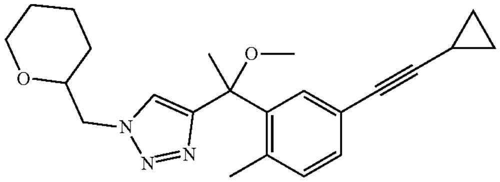 [SMILES: COC(C)(c1cn(CC2CCCCO2)nn1)c1cc(C#CC2CC2)ccc1C] | 379.50 | $^1$H NMR (400 M Hz, $CDCl_3$) δ 7.58 (dd, J = 5.9, 1.6 Hz, 1H), 7.37 (d, J = 11.5 Hz, 1H), 7.20 (dd, J = 7.8, 1.7 Hz, 1H), 7.02-6.95 (m, 1H), 4.39 (dt, J = 14.1, 3.0 Hz, 1H), 4.23 (ddd, J = 14.1, 9.3, 7.3 Hz, 1H), 3.92 (dq, J = 7.8, 2.3 Hz, 1H), 3.61 (dddq, J = 10.9, 7.6, 5.4, 2.9 Hz, 1H), 3.40-3.27 (m, 1H), 3.12-3.08 (m, 3H), 2.03 (d, J = 9.2 Hz, 3H), 1.95 (s, 3H), 1.84 (d, J = 4.2 Hz, 1H), 1.59 (d, J = 12.8 Hz, 1H), 1.53-1.39 (m, 4H), 1.27-1.08 (m, 1H), 0.99-0.68 (m, 4H) | 24 & 34 |
| I-681 | 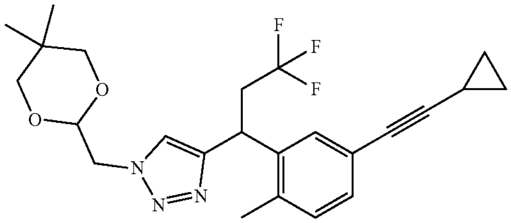 [SMILES: Cc1ccc(C#CC2CC2)cc1C(CC(F)(F)F)c1cn(CC2OCC(C)(C)CO2)nn1] | 447.50 | $^1$H NMR (400 M Hz, $CDCl_3$) δ 7.29 (d, J = 1.6 Hz, 1H), 7.27 (s, 1H), 7.15 (dd, J = 7.8, 1.7 Hz, 1H), 7.06 (d, J = 7.9 Hz, 1H), 4.73 (t, J = 4.2 Hz, 1H), 4.70-4.62 (m, 1H), 4.51-4.37 (m, 2H), 3.59 (d, J = 11.2 Hz, 2H), 3.40 (dd, J = 11.2, 3.2 Hz, 2H), 3.37-3.19 (m, 1H), 2.74 (dqd, J = 15.1, 10.4, 8.0 Hz, 1H), 2.35 (s, 3H), 1.41 (tt, J = 8.2, 5.1 Hz, 1H), 1.06 (s, 3H), 0.87-0.82 (m, 2H), 0.82-0.75 (m, 2H), 0.70 (s, 3H). | 42 |
| I-687 | 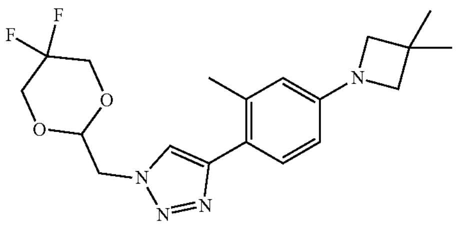 [SMILES: Cc1cc(N2CC(C)(C)C2)ccc1-c1cn(CC2OCC(F)(F)CO2)nn1] | 378.42 | $^1$H NMR (400 M Hz, $CDCl_3$) δ 7.64-7.60 (m, 2H), 6.35 (dd, J = 8.3, 2.4 Hz, 1H), 6.30 (d, J = 2.3 Hz, 1H), 4.97 (t, J = 4.9 Hz, 1H), 4.60 (d, J = 4.9 Hz, 2H), 4.31-4.10 (m, 2H), 3.85 (dd, J = 12.3, 1.3 Hz, 1H), 3.77 (dd, J = 12.3, 1.4 Hz, 1H), 3.60 (s, 3H), 2.40 (s, 3H), 1.32 (s, 4H) | 5 |

TABLE 24-continued

| Characterization for exemplary compounds of the invention | | | | |
|---|---|---|---|---|
| Compound No. | Chemical Structure | M + 1 | $^1$H NMR (400 M Hz) | Example of Synthesis |
| I-688 | 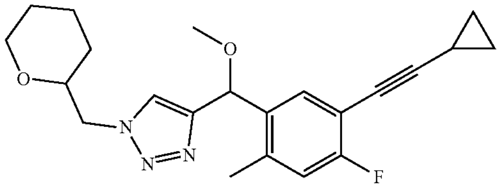 [SMILES: COC(c1cn(CC2CCCCO2)nn1)c1cc(C#CC2CC2)c(F)cc1C] | 383.47 | $^1$H NMR (400 M Hz, $CDCl_3$) δ 7.50 (dd, J = 7.5, 2.1 Hz, 1H), 7.35 (d, J = 2.5 Hz, 1H), 6.81 (d, J = 10.1 Hz, 1H), 5.56 (d, J = 2.0 Hz, 1H), 4.51-4.30 (m, 1H), 4.26-4.12 (m, 1H), 3.92 (ddd, J = 9.9, 3.9, 2.0 Hz, 1H), 3.71-3.56 (m, 1H), 3.43-3.24 (m, 4H), 2.22 (d, J = 3.7 Hz, 3H), 1.88-1.80 (m, 1H), 1.59 (d, J = 12.4 Hz, 1H), 1.52-1.39 (m, 4H), 1.19 (ddt, J = 20.7, 12.8, 6.7 Hz, 1H), 0.97-0.73 (m, 4H) | 24 & 34 |
| I-691 | 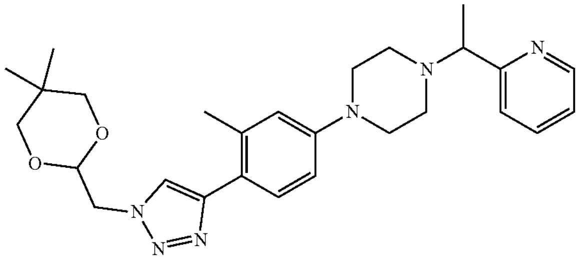 [SMILES: Cc1cc(N2CCN(C(C)c3ccccn3)CC2)ccc1-c1cn(CC2OCC(C)(C)CO2)nn1] | 476.63 | $^1$H NMR (400 M Hz, $CDCl_3$) δ 8.57 (dd, J = 5.1, 1.8 Hz, 1H), 7.71 (s, 1H), 7.66 (td, , I= 7.8, 1.7 Hz, 2H), 7.41 (dt, J = 7.9, 1.2 Hz, 1H), 7.16 (ddd, J = 7.5, 4.9, 1.2 Hz, 1H), 6.88- 6.72 (m, 2H), 4.79 (t, J = 4.4 Hz, 1H), 4.54 (d, J = 4.4 Hz, 2H), 3.69-3.54 (m, 3H), 3.43 (d, J = 11.0 Hz, 2H), 3.23 (t, J = 5.2 Hz, 4H), 2.74 (dt, , I= 10.5, 5.0 Hz, 2H), 2.57 (dt, J = 10.9, 5.0 Hz, 2H), 2.42 (s, 3H), 1.44 (d, , I= 6.8 Hz, 3H), 1.14 (s, 3H), 0.71 (s, 3H). | 5 |
| I-692 | 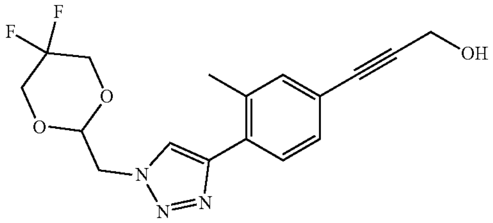 [SMILES: Cc1cc(C#CCO)ccc1-c1cn(CC2OCC(F)(F)CO2)nn1] | 349.34 | $^1$H NMR (400 M Hz, $CDCl_3$) δ 7.79 (s, 1H), 7.77 (d, J = 7.9 Hz, 1H), 7.36-7.30 (m, 2H), 4.99 (t, J = 4.8 Hz, 1H), 4.64 (d, J = 4.8 Hz, 2H), 4.51 (d, J = 6.1 Hz, 2H), 4.35-4.09 (m, 2H), 3.85 (dd, J = 12.3, 1.3 Hz, 2H), 3.78 (dd, J = 12.3, 1.3 Hz, 2H), 2.44 (s, 3H) | 6 |
| I-699 | 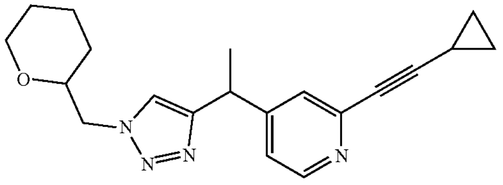 [SMILES: CC(c1ccnc(C#CC2CC2)c1)c1cn(CC2CCCCO2)nn1] | 336.44 | $^1$H NMR (400 M Hz, $CDCl_3$) δ 8.40 (d, J = 5.2 Hz, 1H), 7.35 (d, J = 5.5 Hz, 1H), 7.25 (d, J = 4.7 Hz, 1H), 7.07 (dd, J = 5.2, 1.7 Hz, 1H), 4.39 (dt, J = 14.2, 2.9 Hz, 1H), 4.31-4.15 (m, 2H), 4.01-3.82 (m, 1H), 3.75-3.52 (m, 1H), 3.35 (dddt, J = 11.5, 7.4, 4.9, 2.0 Hz, 1H), 1.92-1.79 (m, 1H), 1.70-1.58 (m, 4H), 1.56-1.44 (m, 2H), 1.44-1.33 (m, 2H), 1.23-1.11 (m, 1H), 0.97-0.71 (m, 4H). | 24 |
| I-700 | 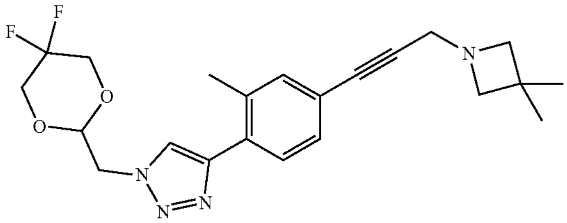 [SMILES: Cc1cc(C#CCN2CC(C)(C)C2)ccc1-c1cn(CC2OCC(F)(F)CO2)nn1] | 416.47 | $^1$H NMR (400 M Hz, $CDCl_3$) δ 7.80-7.75 (m, 2H), 7.40-1.32 (m, 2H), 4.99 (t, J = 4.7 Hz, 1H), 4.64 (d, J = 4.8 Hz, 2H), 4.19 (t, J = 11.7 Hz, 2H), 3.86 (d, J = 11.2 Hz, 1H), 3.78 (d, J = 11.1 Hz, 1H), 3.50 (s, 2H), 3.17 (s, 4H), 2.45 (s, 4H), 1.25 (s, 6H) | 6 |

TABLE 24-continued

Characterization for exemplary compounds of the invention

| Compound No. | Chemical Structure | M + 1 | $^1$H NMR (400 M Hz) | Example of Synthesis |
|---|---|---|---|---|
| I-712 | 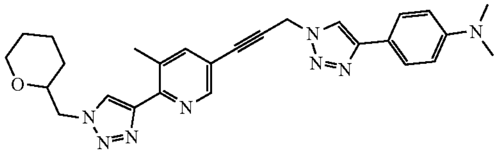 [SMILES: Cc1cc(C#CCn2cc(-c3ccc(N(C)C)cc3)nn2)cnc1-c1cn(CC2CCCCO2)nn1] | 482.59 | $^1$H NMR (400 M Hz, $CDCl_3$) δ 8.51 (d, J = 2.0 Hz, 1H), 8.23 (s, 1H), 7.88 (s, 1H), 7.76-7.65 (m, 2H), 7.65-7.57 (m, 1H), 6.82-6.68 (m, 2H), 5.41 (s, 2H), 4.47 (dd, J = 14.1, 3.3 Hz, 1H), 4.32 (dd, J = 14.1, 7.5 Hz, 1H), 3.95 (dt, J = 11.7, 2.5 Hz, 1H), 3.78-3.62 (m, 1H), 3.35 (td, J = 11.2, 3.3 Hz, 1H), 2.95 (s, 6H), 2.70 (s, 3H), 1.92-1.78 (m, 1H), 1.73-1.59 (m, 1H), 1.50 (dtd, J = 12.2, 9.2, 5.1 Hz, 3H), 1.35-1.15 (m, 1H). | 35 |
| I-713 | 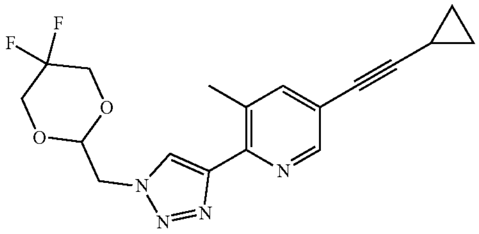 [SMILES: Cc1cc(C#CC2CC2)cnc1-c1cn(CC2OCC(F)(F)CO2)nn1] | 360.36 | $^1$H NMR (400 M Hz, $CDCl_3$) δ 8.42 (d, J = 1.6 Hz, 1H), 8.17 (s, 1H), 7.71-7.43 (m, 1H), 4.96 (t, J = 4.8 Hz, 1H), 4.61 (d, J = 4.9 Hz, 2H), 4.44-4.05 (m, 2H), 3.95-3.79 (m, 1H), 3.79-3.70 (m, 1H), 2.67 (s, 3H), 1.46 (tt, J = 8.2, 5.1 Hz, 1H), 0.97-0.76 (m, 4H) | 3 |
| I-714 | 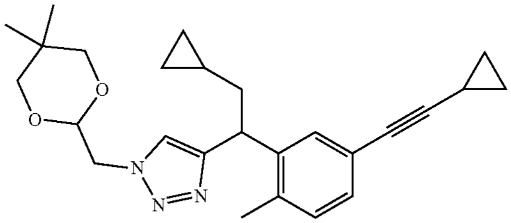 | 419.57 | $^1$H NMR (400 M Hz, $CDCl_3$) δ 7.29 (d, J = 1.5 Hz, 1H), 7.26 (s, 1H), 7.12 (dd, J = 7.8, 1.6 Hz, 1H), 7.03 (d, J = 7.8 Hz, 1H), 4.73 (t, J = 4.3 Hz, 1H), 4.47-4.40 (m, 3H), 3.60 (d, J = 11.2 Hz, 2H), 3.40 (d, J = 11.1 Hz, 2H), 2.35 (s, 3H), 1.96 (td, J = 7.5, 2.7 Hz, 2H), 1.48-1.37 (m, 1H), 1.09 (s, 3H), 0.84 (ddt, J = 8.1, 5.4, 2.4 Hz, 2H), 0.79 (td, J = 5.9, 5.3, 2.9 Hz, 2H), 0.71 (s, 3H), 0.69-0.56 (m, 1H), 0.42-0.31 (m, 2H), 0.13--0.01 (m, 2H). | 42 |
| I-718 | 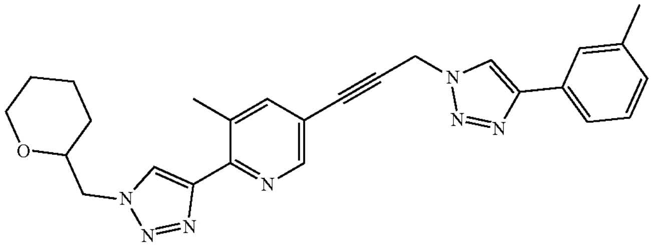 [SMILES: Cc1cccc(-c2cn(CC#Cc3cnc(-c4cn(CC5CCCCO5)nn4)c(C)c3)nn2)c1] | 453.55 | $^1$H NMR (400 M Hz, $CDCl_3$) δ 8.52 (d, J = 2.0 Hz, 1H), 8.23 (s, 1H), 7.98 (s, 1H), 7.69 (d, J = 1.9 Hz, 1H), 7.66-7.55 (m, 2H), 7.36-7.24 (m, 1H), 7.20-7.07 (m, 1H), 5.46 (s, 2H), 4.48 (dd, J = 14.1, 3.2 Hz, 1H), 4.33 (dd, J = 14.1, 7.6 Hz, 1H), 3.96 (ddt, J = 11.4, 3.7, 1.7 Hz, 1H), 3.69 (dddd, J = 11.1, 7.6, 3.2, 2.2 Hz, 1H), 3.36 (td, J = 11.2, 3.2 Hz, 1H), 2.71 (s, 3H), 2.38 (s, 3H), 1.85 (d, , I= 9.7 Hz, 1H), 1.65 (dt, J = 12.7, 3.5 Hz, 1H), 1.61-1.40 (m, 3H), 1.36-1.18 (m, 1H). | 35 |
| I-719 | 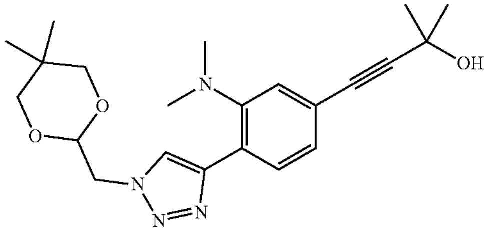 [SMILES: CN(C)c1cc(C#CC(C)(C)O)ccc1-c1cn(CC2OCC(C)(C)CO2)nn1] | 398.51 | $^1$H NMR (400 M Hz, $CDCl_3$) δ 8.30 (s, 1H), 8.12 (d, J = 8.4 Hz, 1H), 7.20-7.15 (m, 2H), 4.79 (t, J = 4.5 Hz, 1H), 4.55 (d, J = 4.5 Hz, 2H), 3.63 (d, J = 11.3 Hz, 2H), 3.43 (d, J = 10.8 Hz, 2H), 2.62 (s, 6H), 2.17 (s, 1H), 1.63 (s, 6H), 1.16 (s, 3H), 0.72 (s, 3H). | 4 |

TABLE 24-continued

Characterization for exemplary compounds of the invention

| Compound No. | Chemical Structure | M + 1 | $^1$H NMR (400 M Hz) | Example of Synthesis |
|---|---|---|---|---|
| I-720 | 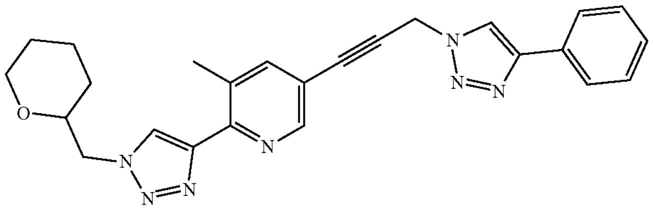 [SMILES: Cc1cc(C#CCn2cc(-c3ccccc3)nn2)cnc1-c1cn(CC2CCCCO2)nn1] | 439.52 | $^1$H NMR (400 M Hz, $CDCl_3$) δ 8.53 (d, J = 1.7 Hz, 1H), 8.24 (s, 1H), 8.04 (s, 1H), 7.90-7.78 (m, 2H), 7.71-7.58 (m, 1H), 7.42 (t, J = 7.5 Hz, 2H), 7.39-7.30 (m, 1H), 5.47 (s, 2H), 4.49 (dd, J = 14.1, 3.2 Hz, 1H), 4.33 (dd, J = 14.1, 7.5 Hz, 1H), 4.06-3.91 (m, 1H), 3.70 (dtd, J = 10.9, 5.3, 2.7 Hz, 1H), 3.37 (td, , I= 11.3, 3.2 Hz, 1H), 2.72 (s, 3H), 1.98-1.80 (m, 1H), 1.66 (d, J = 12.5 Hz, 1H), 1.51 (td, J = 12.3, 11.8, 6.3 Hz, 3H), 1.42-1.20 (m, 1H). | 35 |
| I-723 | 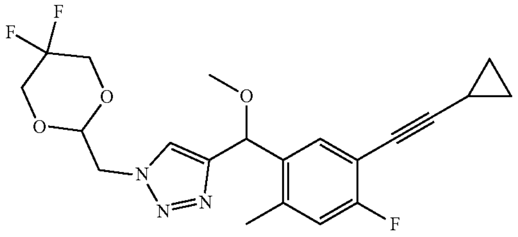 [SMILES: COC(c1cn(CC2OCC(F)(F)CO2)nn1)c1cc(C#CC2CC2)c(F)cc1C] | 421.42 | $^1$H NMR (400 M Hz, $CDCl_3$) δ 7.49 (d, J = 7.5 Hz, 1H), 7.35 (s, 1H), 6.83 (d, J = 10.1 Hz, 1H), 5.57 (s, 1H), 4.90 (t, J = 4.7 Hz, 1H), 4.50 (qd, J = 14.3, 4.7 Hz, 2H), 4.20-4.07 (m, 2H), 3.91-3.68 (m, 2H), 3.38 (s, 3H), 2.23 (s, 3H), 1.59-1.40 (m, 1H), 0.98-0.74 (m, 4H) | 24 & 34 |
| I-724 | 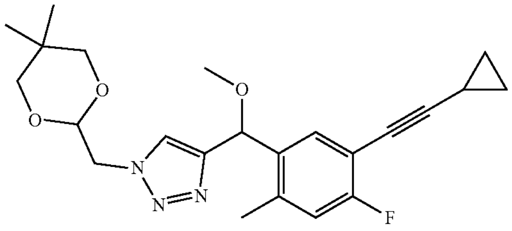 [SMILES: COC(c1cn(CC2OCC(C)(C)CO2)nn1)c1cc(C#CC2CC2)c(F)cc1C] | 413.49 | $^1$H NMR (400 M Hz, $CDCl_3$) δ 7.52 (d, J = 7.5 Hz, 1H), 7.38 (s, 1δH), 6.81 (d, J = 10.2 Hz, 1H), 5.58 (s, 1H), 4.73 (t, J = 4.2 Hz, 1H), 4.45 (dd, J = 4.1, 3.5 Hz, 2H), 3.63-3.55 (m, 2H), 3.49-3.30 (m, 5H), 2.22 (s, 3H), 1.53-1.42 (m, 1H), 1.04 (s, 3H), 0.93-0.78 (m, 4H), 0.70 (s, 3H) | 24 & 34 |
| I-725 | 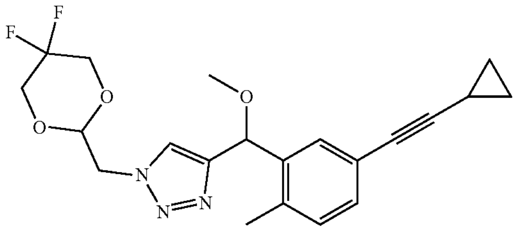 [SMILES: COC(c1cn(CC2OCC(F)(F)CO2)nn1)c1cc(C#CC2CC2)ccc1C] | 403.43 | $^1$H NMR (400 M Hz, $CDCl_3$) δ 7.54 (d, J = 1.7 Hz, 1H), 7.31 (s, 1H), 7.22 (dd, J = 7.8, 1.8 Hz, 1H), 7.04 (d, J = 7.8 Hz, 1H), 5.62 (s, 1H), 4.89 (t, J = 4.8 Hz, 1H), 4.53 (dd, J = 14.3, 4.5 Hz, 1H), 4.44 (dd, J = 14.3, 5.2 Hz, 1H), 4.14 (t, J = 11.7 Hz, 2H), 3.91-3.76 (m, 1H), 3.76-3.66 (m, 1H), 3.40 (s, 3H), 2.24 (s, 3H), 1.44 (tt, J = 8.3, 5.1 Hz, 1H), 0.99-0.73 (m, 4H) | 24 & 34 |
| I-732 | 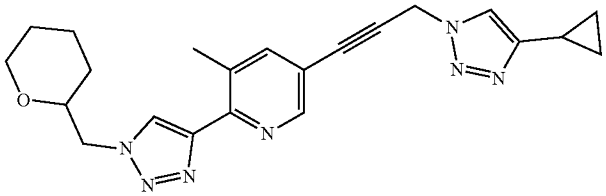 [SMILES: Cc1cc(C#CCn2cc(C3CC3)nn2)cnc1-c1cn(CC2CCCCO2)nn1] | 403.49 | $^1$H NMR (400 M Hz, $CDCl_3$) δ 8.50 (d, J = 1.6 Hz, 1H), 8.23 (s, 1H), 7.71-7.58 (m, 1H), 7.51 (s, 1H), 5.35 (s, 2H), 4.49 (dd, J = 14.1, 3.2 Hz, 1H), 4.33 (dd, J = 14.1, 7.6 Hz, 1H), 4.06-3.92 (m, 1H), 3.70 (dtd, J = 10.9, 5.3, 2.7 Hz, 1H), 3.37 (td, J = 11.3, 3.3 Hz, 1H), 2.71 (s, 3H), 1.96 (tt, J = 8.5, 5.1 Hz, 1H), 1.92-1.81 (m, 1H), 1.66 (d, J = 12.5 Hz, 1H), 1.51 (td, J = 11.9, 10.9, 6.3 Hz, 3H), 1.40-1.21 (m, 1H), 0.94 (dtd, J = 9.8, 6.6, 6.2, 3.3 Hz, 2H), 0.86 (ddd, J = 7.2, 5.3, 3.6 Hz, 2H). | 35 |

TABLE 24-continued

Characterization for exemplary compounds of the invention

| Compound No. | Chemical Structure | M + 1 | $^1$H NMR (400 M Hz) | Example of Synthesis |
|---|---|---|---|---|
| I-733 | 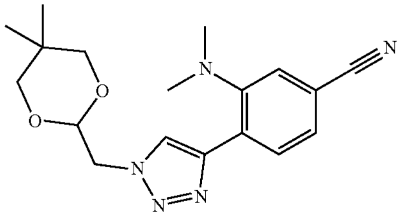 [SMILES: CN(C)c1cc(C#N)ccc1-c1cn(CC2OCC(C)(C)CO2)nn1] | 341.42 | $^1$H NMR (400 M Hz, $CDCl_3$) δ 8.34 (s, 1H), 8.27 (dd, J = 7.9, 0.5 Hz, 1H), 7.42-7.35 (m, 2H), 4.80 (t, J = 4.5 Hz, 1H), 4.58 (d, J = 4.5 Hz, 2H), 3.64 (d, J = 11.3 Hz, 2H), 3.44 (d, J = 11.2 Hz, 2H), 2.65 (s, 6H), 1.14 (s, 3H), 0.72 (s, 3H). | 43 |
| I-734 | 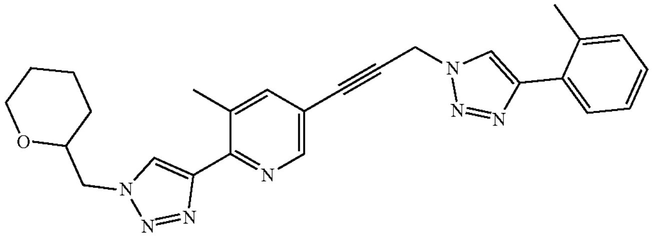 [SMILES: Cc1ccccc1-c1cn(CC#Cc2cnc(-c3cn(CC4CCCCO4)nn3)c(C)c2)nn1] | 453.55 | $^1$H NMR (400 M Hz, $CDCl_3$) δ 8.54 (d, J = 1.9 Hz, 1H), 8.25 (s, 1H), 7.93 (s, 1H), 7.77 (dd, J = 6.2, 3.2 Hz, 1H), 7.66 (d, J = 1.9 Hz, 1H), 7.42-7.16 (m, 3H), 5.51 (s, 2H), 4.51 (dd, J = 14.1, 3.2 Hz, 1H), 4.35 (dd, J = 14.1, 7.6 Hz, 1H), 4.10-3.89 (m, 1H), 3.72 (ddt, J = 11.0, 5.4, 2.7 Hz, 1H), 3.39 (td, J = 11.3, 3.2 Hz, 1H), 2.74 (s, 3H), 2.50 (s, 3H), 2.05-1.83 (m, 1H), 1.81-1.42 (m, 3H), 1.42-1.21 (m, 2H). | 35 |
| I-743 | 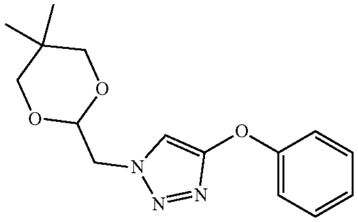 [SMILES: CC1(C)COC(Cn2cc(Oc3ccccc3)nn2)OC1] | 289.34 | $^1$H NMR (400 M Hz, $CDCl_3$) δ 7.37 (s, 1H), 7.35-7.28 (m, 2H), 7.13-7.04 (m, 3H), 4.77 (t, J = 4.3 Hz, 1H), 4.47 (d, J = 4.3 Hz, 2H), 3.63 (d, J = 11.3 Hz, 2H), 3.53-3.33 (m, 2H), 1.13 (s, 3H), 0.72 (s, 3H) | 44 |
| I-759 | 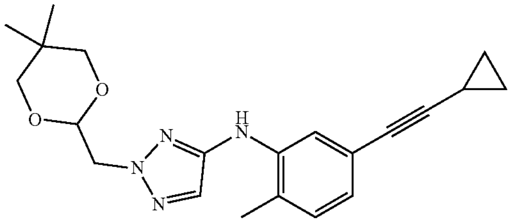 [SMILES: Cc1ccc(C#CC2CC2)cc1Nc1cnn(CC2OCC(C)(C)CO2)n1] | 366.47 | $^1$H NMR (400 M Hz, $CDCl_3$) δ 7.42 (s, 1H), 7.24 (d, J = 1.3 Hz, 1H), 7.03 (d, J = 7.8 Hz, 1H), 6.87 (dd, J = 7.7, 1.5 Hz, 1H), 5.77 (s, 1H), 4.91 (t, J = 4.9 Hz, 1H), 4.49 (d, J = 4.9 Hz, 2H), 3.67 (d, J = 11.3 Hz, 2H), 3.44 (d, J = 10.7 Hz, 3H), 2.22 (s, 3H), 1.49-1.37 (m, 1H), 1.19 (s, 4H), 0.87-0.81 (m, 2H), 0.81-0.76 (m, 2H), 0.72 (s, 3H). | 45 |
| I-760 | 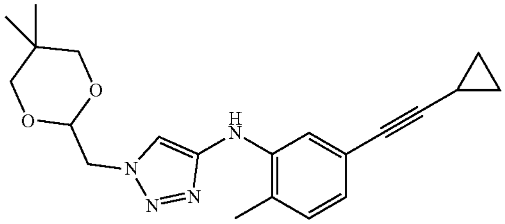 [SMILES: Cc1ccc(C#CC2CC2)cc1Nc1cn(CC2OCC(C)(C)CO2)nn1] | 366.47 | $^1$H NMR (400 M Hz, $CDCl_3$) δ 7.53 (s, 1H), 7.06-7.00 (m, 2H), 6.84 (dd, J = 7.6, 1.5 Hz, 1H), 5.88 (s, 1H), 4.79 (t, J = 4.3 Hz, 1H), 4.50 (d, J = 4.3 Hz, 2H), 3.65 (d, J = 11.3 Hz, 2H), 3.45 (d, J = 10.8 Hz, 2H), 2.24 (s, 3H), 1.42 (tt, J = 8.2, 5.1 Hz, 1H), 1.17 (s, 3H), 0.87-0.80 (m, 2H), 0.78 (tt, J = 5.1, 2.3 Hz, 2H), 0.73 (s, 3H). | 46 |

TABLE 24-continued

| Characterization for exemplary compounds of the invention | | | | |
|---|---|---|---|---|
| Compound No. | Chemical Structure | M + 1 | $^1$H NMR (400 M Hz) | Example of Synthesis |
| I-761 | 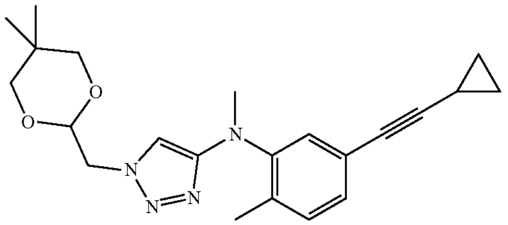 [SMILES: Cc1ccc(C#CC2CC2)cc1N(C)c1cn(CC2OCC(C)(C)CO2)nn1] | 380.49 | $^1$H NMR (400 M Hz, $CDCl_3$) δ 7.21 (s, 1H), 7.17-7.10 (m, 2H), 6.62 (s, 1H), 4.72 (t, J = 4.5 Hz, 1H), 4.34 (d, J = 4.5 Hz, 2H), 3.59 (d, J = 11.4 Hz, 2H), 3.40 (d, J = 11.3 Hz, 2H), 3.31 (s, 3H), 2.15 (s, 3H), 1.47-1.38 (m, 1H), 1.12 (s, 3H), 0.85 (ddt, J = 8.3, 5.7, 3.2 Hz, 2H), 0.77 (tt, J = 5.0, 2.8 Hz, 2H), 0.71 (s, 3H). | 47 |
| I-766 | 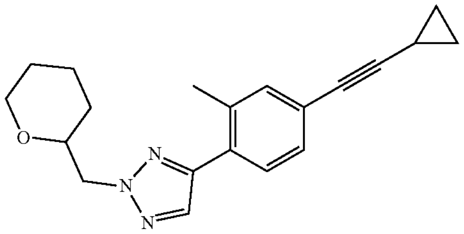 | 321.42 | $^1$H NMR (400 M Hz, $CDCl_3$) δ 7.72 (s, 1H), 7.53 (d, J = 8.0 Hz, 1H), 7.29 (s, 1H), 7.27-7.21 (m, 1H), 4.55 (dd, J = 13.7, 7.4 Hz, 1H), 4.41 (dd, J = 13.7, 4.9 Hz, 1H), 4.09-3.95 (m, 1H), 3.95-3.83 (m, 1H), 3.40 (td, J = 11.5, 2.3 Hz, 1H), 2.44 (s, 3H), 1.98-1.79 (m, 1H), 1.72-1.30 (m, 6H), 1.00-0.84 (m, 2H), 0.84-0.77 (m, 2H) | 7 |
| I-773 | 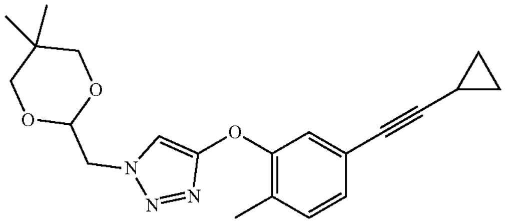 [SMILES: Cc1ccc(C#CC2CC2)cc1Oc1cn(CC2OCC(C)(C)CO2)nn1] | 367.45 | $^1$H NMR (400 M Hz, $CDCl_3$) δ 7.28 (s, 1H), 7.13-7.08 (m, 1H), 7.03 (dd, J = 7.8, 1.5 Hz, 1H), 6.93 (d, J = 1.4 Hz, 1H), 4.77 (t, J = 4.2 Hz, 1H), 4.46 (d, J = 4.2 Hz, 2H), 3.67-3.55 (m, 2H), 3.44 (d, J = 10.6 Hz, 2H), 2.29 (s, 3H), 1.38 (tt, J = 8.2, 5.1 Hz, 1H), 1.13 (s, 3H), 0.91-0.79 (m, 2H), 0.79-0.69 (m, 5H) | 44 |
| I-774 | 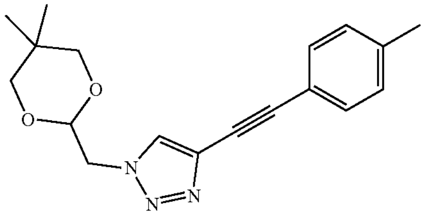 | 311.39 | $^1$H NMR (400 M Hz, $CDCl_3$) δ 7.84 (s, 1H), 7.43 (d, J = 8.0 Hz, 2H), 7.15 (d, J = 8.0 Hz, 2H), 4.75 (t, J = 4.4 Hz, 1H), 4.52 (d, J = 4.4 Hz, 2H), 3.62 (d, J = 11.3 Hz, 2H), 3.42 (d, J = 10.9 Hz, 2H), 2.35 (s, 3H), 1.13 (s, 3H), 0.72 (s, 3H) | 48 |
| I-781 | 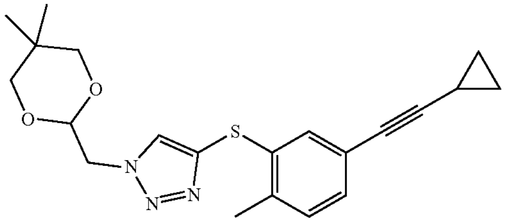 | 383.51 | $^1$H NMR (400 M Hz, $CDCl_3$) δ 7.80 (s, 1H), 7.12-6.98 (m, 3H), 4.79 (t, J = 4.2 Hz, 1H), 4.55 (d, J = 4.2 Hz, 2H), 3.64 (d, J = 11.3 Hz, 2H), 3.44 (d, J = 10.7 Hz, 2H), 2.41 (s, 3H), 1.42-1.33 (m, 1H), 1.10 (s, 3H), 0.85-0.78 (m, 2H), 0.77-0.71 (m, 5H). | 49 |
| I-782 | 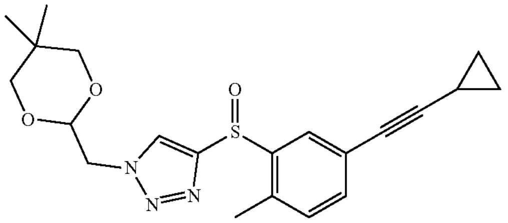 [SMILES: Cc1ccc(C#CC2CC2)cc1S(=O)c1cn(CC2OCC(C)(C)CO2)nn1] | 399.51 | %). 1HNMR (400 M Hz, $CDCl_3$) δ 8.04 (d, J = 1.6 Hz, 1H), 7.85 (s, 1H), 7.37 (dd, J = 7.8, 1.8 Hz, 1H), 7.09 (d, J = 7.9 Hz, 1H), 4.73 (t, J = 4.1 Hz, 1H), 4.57-4.42 (m, 2H), 3.63-3.54 (m, 2H), 3.39 (dd, J = 11.2, 3.0 Hz, 2H), 2.33 (s, 3H), 1.48-1.40 (m, 1H), 1.00 (s, 3H), 0.92-0.84 (m, 2H), 0.84-0.77 (m, 2H), 0.71 (s, 3H). | 49 |

TABLE 24-continued

| Characterization for exemplary compounds of the invention | | | | |
|---|---|---|---|---|
| Compound No. | Chemical Structure | M + 1 | $^1$H NMR (400 M Hz) | Example of Synthesis |
| I-783 | 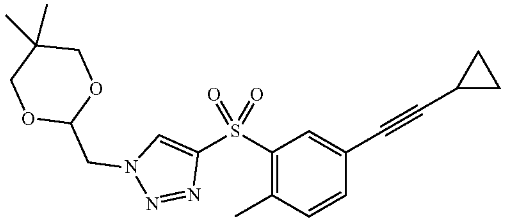 [SMILES: Cc1ccc(C#CC2CC2)cc1S(=O)(=O)c1cn(CC2OCC(C)(C)CO2)nn1] | 415.51 | $^1$H NMR (400 M Hz, $CDCl_3$) δ 8.30 (s, 1H), 8.19 (d, J = 1.7 Hz, 1H), 7.45 (dd, J = 7.8, 1.8 Hz, 1H), 7.17 (d, J = 8.0 Hz, 1H), 4.75 (t, J = 4.1 Hz, 1H), 4.55 (d, J = 4.1 Hz, 2H), 3.62 (d, J = 11.4 Hz, 2H), 3.42 (d, J =11.1 Hz, 2H), 2.65 (s, 3H), 1.48-1.39 (m, 1H), 1.04 (s, 3H), 0.94-0.84 (m, 2H), 0.84-0.77 (m, 2H), 0.72 (s, 3H). | 49 |
| I-790 | 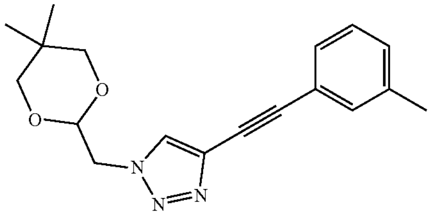 | 311.39 | $^1$H NMR (400 M Hz, $CDCl_3$) δ 7.85 (s, 1H), 7.40-7.33 (m, 2H), 7.24 (t, J = 7.5 Hz, 1H), 7.19-7.12 (m, 1H), 4.76 (d, J = 4.4 Hz, 1H), 4.53 (d, J = 4.4 Hz, 2H), 3.73-3.56 (m, 2H), 3.43 (d, J = 10.7 Hz, 2H), 2.35 (s, 3H), 1.14 (s, 3H), 0.73 (s, 3H) | 50 |
| I-791 | 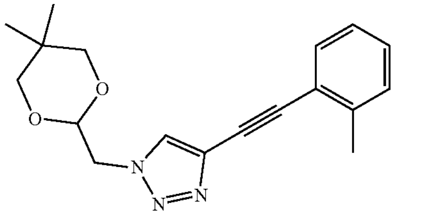 [SMILES: Cc1ccccc1C#Cc1cn(CC2OCC(C)(C)CO2)nn1] | 311.39 | $^1$H NMR (400 M Hz, $CDCl_3$) δ 7.86 (s, 1H), 7.51 (d, J = 7.5 Hz, 1H), 7.29-7.20 (m, 2H), 7.19-7.13 (m, 1H), 4.77 (t, J = 4.5 Hz, 1H), 4.53 (d, J = 4.5 Hz, 2H), 3.64 (d, J = 11.3 Hz, 2H), 3.43 (d, J = 10.7 Hz, 2H), 2.51 (s, 3H), 1.15 (s, 3H), 0.73 (s, 3H) | 50 |
| I-792 | 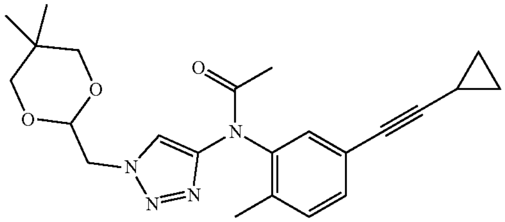 [SMILES: CC(=O)N(c1cn(CC2OCC(C)(C)CO2)nn1)c1cc(C#CC2CC2)ccc1C] | 408.50 | $^1$H NMR (400 M Hz, $CDCl_3$) δ 8.31 (s, 1H), 7.36 (d, J = 7.7 Hz, 1H), 7.30-7.22 (m, 2H), 4.77 (t, J = 4.6 Hz, 1H), 4.53-4.41 (m, 2H), 3.63 (d, J = 11.2 Hz, 2H), 3.42 (dd, J = 10.4, 4.9 Hz, 2H), 2.14 (s, 3H), 1.92 (s, 3H), 1.42 (ddd, J = 13.1, 8.3, 5.2 Hz, 1H), 1.16 (s, 3H), 0.89-0.81 (m, 2H), 0.81-0.74 (m, 2H), 0.72 (s, 3H). | 51 |
| I-793 | 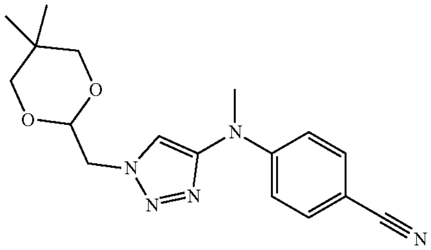 [SMILES: CN(c1ccc(C#N)cc1)c1cn(CC2OCC(C)(C)CO2)nn1] | 327.39 | $^1$H NMR (400 M Hz, $CDCl_3$) δ 7.59 (s, 1H), 7.47 (d, J = 9.0 Hz, 2H), 6.92 (d, J = 9.0 Hz, 2H), 4.80 (t, J = 4.1 Hz, 1H), 4.52 (d, J = 4.1 Hz, 2H), 3.64 (d, J = 11.3 Hz, 2H), 3.45 (d, J = 10.8 Hz, 2H), 3.40 (s, 3H), 1.12 (s, 3H), 0.73 (s, 3H) | 46 |
| I-802 | 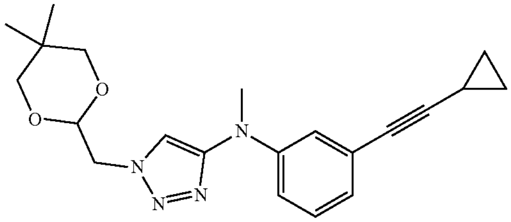 [SMILES: CN(c1cccc(C#CC2CC2)c1)c1cn(CC2OCC(C)(C)CO2)nn1] | 327.39 | $^1$H NMR (400 M Hz, $CDCl_3$) δ 7.51 (s, 1H), 7.34-7.28 (m, 1H), 7.20 (ddd, J = 5.8, 2.4, 1.1 Hz, 2H), 7.11 (dt, J = 7.5, 1.2 Hz, 1H), 4.80 (t, J = 4.2 Hz, 1H), 4.51 (d, J = 4.2 Hz, 2H), 3.65 (d, J = 11.3 Hz, 2H), 3.46 (d, J = 10.7 Hz, 2H), 3.39 (s, 3H), 1.14 (s, 3H), 0.73 (s, 3H). | 46 |

TABLE 24-continued

| Characterization for exemplary compounds of the invention | | | | |
|---|---|---|---|---|
| Compound No. | Chemical Structure | M + 1 | $^1$H NMR (400 M Hz) | Example of Synthesis |
| I-803 | 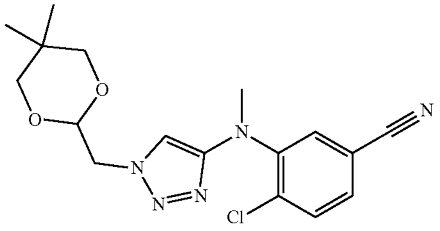 [SMILES: CN(c1cn(CC2OCC(C)(C)CO2)nn1)c1cc(C#N)ccc1Cl] | 361.83 | $^1$H NMR (400 M Hz, $CDCl_3$) δ 7.57 (d, J = 1.9 Hz, 1H), 7.52 (d, J = 8.3 Hz, 1H), 7.38 (ddd, J = 8.3, 1.9, 0.5 Hz, 1H), 7.01 (s, 1H), 4.75 (t, J = 4.4 Hz, 1H), 4.42 (d, J = 4.4 Hz, 2H), 3.62 (d, J = 11.3 Hz, 2H), 3.43 (d, J = 10.9 Hz, 2H), 3.34 (s, 3H), 1.14 (s, 3H), 0.72 (s, 3H) | 46 |
| I-811 | 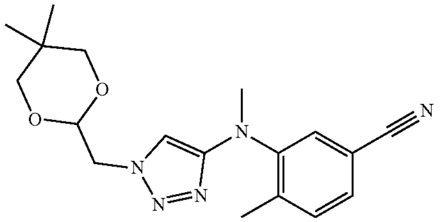 [SMILES: Cc1ccc(C#N)cc1N(C)c1cn(CC2OCC(C)(C)CO2)nn1] | 341.42 | $^1$H NMR (400 M Hz, $CDCl_3$) δ 7.45 (d, J = 1.5 Hz, 1H), 7.38 (dd, J = 7.9, 1.6 Hz, 1H), 7.31 (d, J = 7.9 Hz, 1H), 6.80 (s, 1H), 4.73 (t, J = 4.4 Hz, 1H), 4.38 (d, J = 4.4 Hz, 2H), 3.60 (d, J = 11.3 Hz, 2H), 3.41 (d, J = 10.8 Hz, 2H), 3.29 (s, 3H), 2.23 (s, 3H), 1.11 (s, 3H), 0.71 (s, 3H). | 46 |
| I-812 | 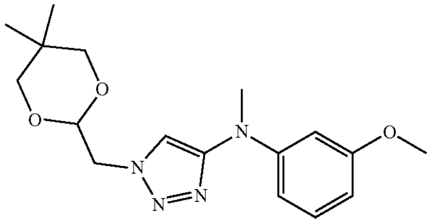 | 332.40 | $^1$H NMR (400 M Hz, $CDCl_3$) δ 7.41 (s, 1H), 7.16 (t, J = 8.2 Hz, 1H), 6.68-6.61 (m, 2H), 6.46 (dd, J = 8.1, 2.0 Hz, 1H), 4.77 (t, J = 4.4 Hz, 1H), 4.45 (d, J = 4.4 Hz, 2H), 3.77 (s, 3H), 3.62 (d, J = 11.3 Hz, 2H), 3.46-3.40 (m, 5H), 1.14 (s, 3H), 0.72 (s, 3H). | 46 |
| I-813 | 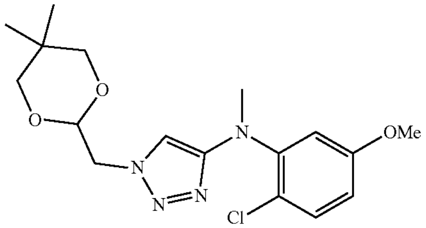 [SMILES: COc1ccc(Cl)c(N(C)c2cn(CC3OCC(C)(C)CO3)nn2)c1] | 366.85 | $^1$H NMR (400 M Hz, $CDCl_3$) δ 7.30 (d, J = 8.8 Hz, 1H), 6.87-6.81 (m, 2H), 6.70 (dd, J = 8.8, 3.0 Hz, 1H), 4.73 (t, J = 4.6 Hz, 1H), 4.38 (d, J = 4.6 Hz, 2H), 3.76 (s, 3H), 3.60 (d, J = 11.3 Hz, 2H), 3.40 (d, J = 10.8 Hz, 2H), 3.36 (s, 3H), 1.13 (s, 3H), 0.71 (s, 3H) | 46 |
| I-814 | 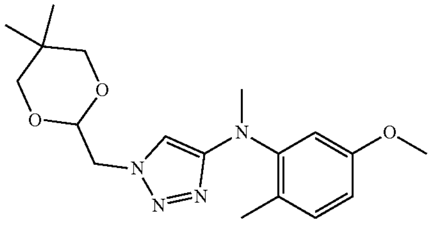 | 346.43 | $^1$H NMR (400 M Hz, $CDCl_3$) δ 7.13 (d, J = 8.4 Hz, 1H), 6.75 (d, J = 2.7 Hz, 1H), 6.70 (dd, J = 8.4, 2.7 Hz, 1H), 6.65 (s, 1H), 4.72 (t, J = 4.6 Hz, 1H), 4.34 (d, J = 4.6 Hz, 2H), 3.76 (s, 3H), 3.59 (d, J = 11.3 Hz, 2H), 3.39 (d, J = 10.8 Hz, 2H), 3.33 (s, 3H), 2.10 (s, 3H), 1.12 (s, 3H), 0.71 (s, 3H). | 46 |
| I-824 | 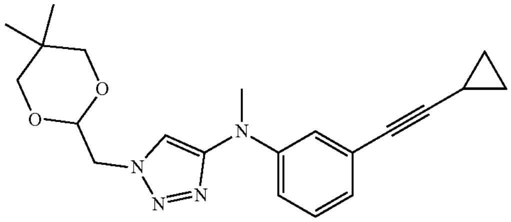 [SMILES: CN(c1cccc(C#CC2CC2)c1)c1cn(CC2OCC(C)(C)CO2)nn1] | 366.47 | $^1$H NMR (400 M Hz, $CDCl_3$) δ 7.39 (s, 1H), 7.18-7.11 (m, 1H), 7.06-7.02 (m, 1H), 6.96 (ddd, J = 8.3, 2.5, 0.9 Hz, 1H), 6.94-6.88 (m, 1H), 4.77 (t, J = 4.4 Hz, 1H), 4.46 (d, J = 4.4 Hz, 2H), 3.63 (d, J = 11.3 Hz, 2H), 3.43 (d, J = 10.7 Hz, 2H), 3.39 (s, 3H), 1.43 (tt, J = 8.2, 5.1 Hz, 1H), 1.14 (s, 3H), 0.88-0.81 (m, 2H), 0.78 (tt, J = 5.1, 2.2 Hz, 2H), 0.72 (s, 3H). | 46 |

TABLE 24-continued

| Characterization for exemplary compounds of the invention | | | | |
|---|---|---|---|---|
| Compound No. | Chemical Structure | M + 1 | $^1$H NMR (400 M Hz) | Example of Synthesis |
| I-825 | 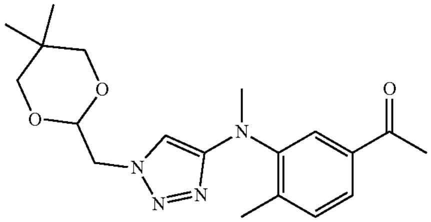 [SMILES: CC(=O)c1ccc(C)c(N(C)c2cn(CC3OCC(C)(C)CO3)nn2)c1] | 358.44 | $^1$H NMR (400 M Hz, $CDCl_3$) δ 7.80 (d, J = 1.8 Hz, 1H), 7.70 (dd, J = 7.9, 1.8 Hz, 1H), 7.32 (d, J = 7.9 Hz, 1H), 6.69 (s, 1H), 4.72 (t, J = 4.5 Hz, 1H), 4.36 (d, J = 4.5 Hz, 2H), 3.59 (d, J = 11.3 Hz, 2H), 3.40 (d, J = 10.7 Hz, 2H), 3.34 (s, 3H), 2.55 (s, 3H), 2.24 (s, 3H), 1.11 (s, 3H), 0.70 (s, 3H). | 46 |
| I-826 | 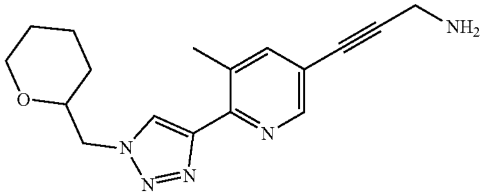 [SMILES: Cc1cc(C#CCN)cnc1-c1cn(CC2CCCCO2)nn1] | 311.39 | $^1$H NMR (400 M Hz, $CDCl_3$) δ 8.36 (s, 1H), 8.20-8.08 (m, 1H), 7.52 (s, 1H), 4.50-4.34 (m, 1H), 4.27 (dd, J = 14.2, 7.5 Hz, 1H), 3.89 (d, J = 11.5 Hz, 1H), 3.61 (d, J = 18.1 Hz, 3H), 3.31 (q, J = 11.4, 10.2 Hz, 3H), 2.59 (s, 3H), 1.78 (d, J = 9.2 Hz, 1H), 1.59 (d, J = 13.0 Hz, 1H), 1.43 (s, 3H), 1.20 (q, J = 12.9, 12.2 Hz, 1H). | 52 |
| I-830 | 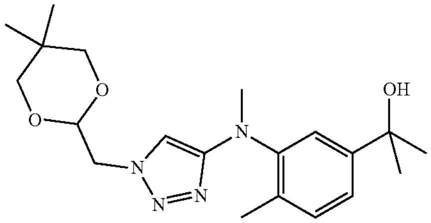 [SMILES: Cc1ccc(C(C)(C)O)cc1N(C)c1cn(CC2OCC(C)(C)CO2)nn1] | 374.49 | $^1$H NMR (400 M Hz, $CDCl_3$) δ 7.34 (d, J = 1.7 Hz, 1H), 7.25-7.17 (m, 2H), 6.64 (s, 1H), 4.72 (t, J = 4.6 Hz, 1H), 4.34 (d, J = 4.6 Hz, 2H), 3.59 (d, J = 11.3 Hz, 2H), 3.40 (d, J = 11.0 Hz, 2H), 3.34 (s, 3H), 2.16 (s, 3H), 1.75 (s, 1H), 1.55 (s, 6H), 1.12 (s, 3H), 0.71 (s, 3H). | 46 |
| I-840 | 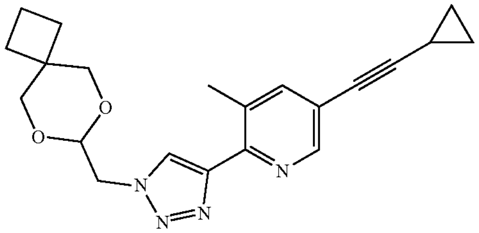 [SMILES: Cc1cc(C#CC2CC2)cnc1-c1cn(CC2OCC3(CCC3)CO2)nn1] | 364.45 | $^1$H NMR (400 M Hz, $CDCl_3$) δ 8.38 (d, J = 2.0 Hz, 1H), 8.16 (s, 1H), 7.49 (d, J = 2.1 Hz, 1H), 4.77 (t, J = 4.7 Hz, 1H), 4.46 (d, J = 4.7 Hz, 2H), 4.02-3.86 (m, 2H), 3.43 (d, J = 11.1 Hz, 2H), 2.62 (s, 3H), 2.00 (t, J = 8.0 Hz, 2H), 1.93-1.76 (m, 2H), 1.56-1.40 (m, 3H), 0.94-0.69 (m, 4H). | 3 |
| I-841 | 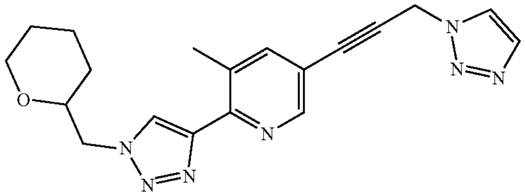 [SMILES: Cc1cc(C#CCn2ccnn2)cnc1-c1cn(CC2CCCCO2)nn1] | 363.43 | $^1$H NMR (400 M Hz, $CDCl_3$) δ 8.49 (d, J = 2.0 Hz, 1H), 8.23 (s, 1H), 7.85 (d, J = 1.1 Hz, 1H), 7.75 (d, J = 1.1 Hz, 1H), 7.65-7.61 (m, 1H), 5.45 (s, 2H), 4.48 (dd, J = 14.1, 3.2 Hz, 1H), 4.33 (dd, J = 14.1, 7.6 Hz, 1H), 3.95 (dt, J = 11.9, 2.3 Hz, 1H), 3.69 (ddt, J = 10.4, 7.6, 2.8 Hz, 1H), 3.36 (td, J = 11.2, 3.3 Hz, 1H), 2.70 (s, 3H), 2.01 (s, 1H), 1.87-1.82 (m, 1H), 1.65 (d, J = 12.9 Hz, 1H), 1.54-1.45 (m, 2H), 1.39-1.33 (m, 1H). | 52 |

TABLE 24-continued

| Characterization for exemplary compounds of the invention | | | | |
|---|---|---|---|---|
| Compound No. | Chemical Structure | M + 1 | $^1$H NMR (400 M Hz) | Example of Synthesis |
| I-842 | 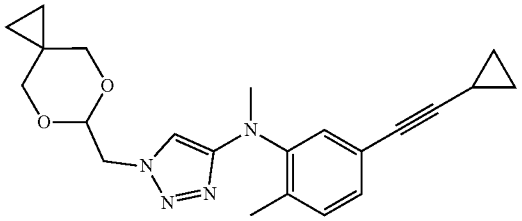 [SMILES: Cc1ccc(C#CC2CC2)cc1N(C)c1cn(CC2OCC3(CC3)CO2)nn1] | 378.48 | $^1$H NMR (400 M Hz, $CDCl_3$) δ 7.22 (s, 1H), 7.16-7.11 (m, 2H), 6.61 (s, 1H), 4.90 (t, J = 4.8 Hz, 1H), 4.37 (d, J = 4.8 Hz, 2H), 4.08 (d, J = 11.5 Hz, 2H), 3.31 (s, 3H), 3.22 (d, J =11.9 Hz, 2H), 2.15 (s, 3H), 1.42 (tt, J = 8.3, 5.0 Hz, 1H), 0.97-0.81 (m, 2H), 0.78 (dt, J = 5.4, 2.9 Hz, 2H), 0.71-0.58 (m, 2H), 0.34 (dd, J = 8.5, 6.5 Hz, 2H) ppm. | 46 |
| I-843 | 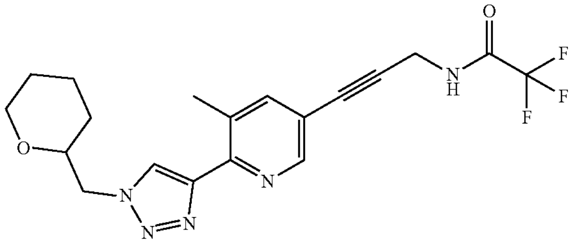 [SMILES: Cc1cc(C#CCNC(=O)C(F)(F)F)cnc1-c1cn(CC2CCCCO2)nn1] | 407.40 | $^1$H NMR (400 M Hz, $CDCl_3$) δ 8.50 (s, 1H), 8.22 (s, 1H), 7.60 (s, 1H), 7.17 (s, 1H), 4.51 (dd, J = 14.1, 3.2 Hz, 1H), 4.45-4.27 (m, 3H), 4.07-3.91 (m, 1H), 3.71 (ddt, J = 11.0, 7.8, 2.7 Hz, 1H), 3.38 (td, J = 11.2, 3.4 Hz, 1H), 2.70 (s, 3H), 1.87 (dq, J = 9.9, 2.7 Hz, 1H), 1.79-1.62 (m, 1H), 1.41-1.16 (m, 4H). | 53 |
| I-844 | 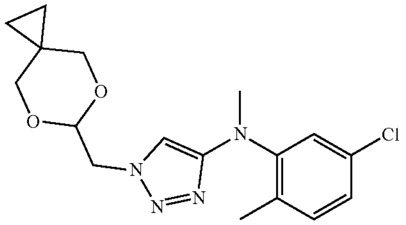 [SMILES: Cc1ccc(Cl)cc1N(C)c1cn(CC2OCC3(CC3)CO2)nn1] | 348.83 | $^1$H NMR (400 M Hz, $CDCl_3$) 7.17 (d, J = 2.1 Hz, 1H), 7.15 (d, J = 8.2 Hz, 1H), 7.09 (dd, J = 8.2, 2.1 Hz, 1H), 6.70 (s, 1H), 4.91 (t, J = 4.8 Hz, 1H), 4.39 (d, J = 4.8 Hz, 2H), 4.09 (d, J = 11.5 Hz, 2H), 3.32 (s, 3H), 3.22 (d, J = 11.9 Hz, 2H), 2.14 (s, 3H), 0.69-0.61 (m, 2H), 0.34 (dd, J = 8.5, 6.6 Hz, 2H). | 46 |
| I-850 | 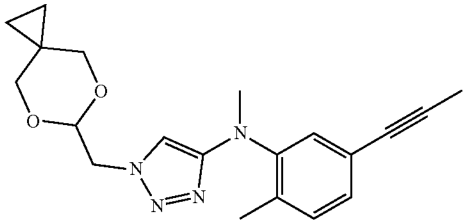 [SMILES: CC#Cc1ccc(C)c(N(C)c2cn(CC3OCC4(CC4)CO3)nn2)c1] | 352.44 | $^1$H NMR (400 M Hz, $CDCl_3$) δ 7.23 (s, 1H), 7.14 (d, J = 1.3 Hz, 2H), 6.62 (s, 1H), 4.90 (t, J = 4.8 Hz, 1H), 4.37 (d, J = 4.8 Hz, 2H), 4.07 (d, J = 11.5 Hz, 2H), 3.32 (s, 3H), 3.21 (d, J = 11.9 Hz, 2H), 2.15 (s, 3H), 2.02 (s, 3H), 0.69-0.61 (m, 2H), 0.33 (dd, J = 8.5, 6.6 Hz, 2H) | 46 |

Example 54: Preparation of Salts of Compounds of Table 1

TABLE 25

| Salts prepared of compounds in Table 1 | |
|---|---|
| Compound | Structure |
| I-884 | 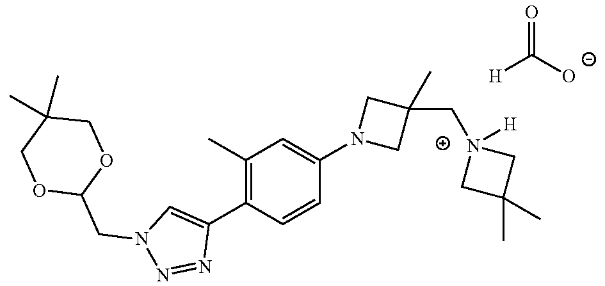 |

Example 55: BRET assays

Background—The following assays can be used for determination of GPR84 activation in living HEK293 cells. The Gai BRET biosensor (Gagnon et al., 2018; Gales et al., 2006. *Nat StructMol Biol.* 13, 778-86; Saulieres et al., 2012. *Nat Chem Biol.* 8, 622-30) allows to directly monitor GPR84-mediated activation of Gai. The Gai biosensor consists of a Rluc8-tagged $G\alpha_{i2}$ subunit, a GFP10-tagged $G\gamma_2$ subunit, and an untagged $G\beta_1$. Agonist stimulation and GPR84 activation triggers a physical separation between the RLuc8-$G\alpha_i$ donor and the GFP10-Gγ2 acceptor, resulting in a decrease in BRET signal whose amplitude is correlated to ligand efficacy (Gales et al., 2006). Moreover, signaling functions of GPCRs are tightly regulated by endocytosis, the targeting of receptors to endosomes and their sorting to lysosomes or recycling to the plasma membrane. The early endosomes (EEs) trafficking assay (Namkung et al., 2016. *Nat Commun.* 7, 12178) uses Rluc8-tagged GPR84 and *Renilla* GFP (rGFP) attached to the FYVE domain from human endofin/zinc finger FYVE domain-containing protein 16, which binds phosphatidylinositol 3-phosphate in EEs. Agonist stimulation of GPR84-Rluc8 leads to trafficking of the receptor to EEs, and ensuing increase of the donor concentration relative to the rGFP-FYVE acceptor anchored in the same cellular compartment, and thus results in an increase in BRET signal.

Plasmids—The cDNA clones for human GPR84 receptor, human $Gai_2$, $Gp_1$, and $Gy_2$ were obtained from the cDNA Resource Center (www.cdna.org). GFP10 (F64L, S147P, S202F and H231L variant of *Aequorea victoria* Green Fluorescent Protein) gBlocks gene fragments (Integrated DNA Technologies, IA) and linker were inserted in frame at the N-terminus of human $G\gamma_2$. Rluc8 (A55T, $C_{124}A$, S130A, K136R, A143M, M185V, M253L, and S287L variant of the *Renilla* renformis luciferase) gBlocks gene fragment was inserted with linkers in frame in between residues 91 and 92 of $Gai_2$ or at the C-terminus of GPR84. The FYVE domain from human endofin (residues Q739 to K806) attached in frame at the C terminus of a humanized *Renilla* GFP (rGFP), were synthesized as gBlocks gene fragments.

Bioluminescence Resonance Energy Transfer (BRET) Measurement—HEK293 cells were transfected with GPR84-Rluc8 and rGFP-FYVE for the EEs trafficking biosensor or with GPR84, $G\alpha_{i2}$-Rluc8, GFP10-$G\gamma_2$, and $G\beta_1$ for the $G\alpha_i$ biosensor. The following day, transiently transfected cells were seeded in 96-well white clear bottom microplates coated with poly-D-lysine and left in culture for 24 hours. Cells were washed once with Tyrode's buffer (140 mmol/L NaCl, 1 mmol/L $CaCl_2$, 2.7 mmol/L KCl, 0.49 mmol/L $MgCl_2$, 0.37 mmol/L $NaH_2PO_4$, 5.6 mmol/L glucose, 12 mmol/L $NaHCO_3$, and 25 mmol/L HEPES, pH 7.5) before performing assays in Tyrode's buffer. Test compounds were incubated with cells for 5 ($G\alpha_i$) or 15 (EEs) minutes at 37° C. before addition of 200 nmol/L of the GPR84 agonist ZQ-16 (2-(Hexylthio)-6-hydroxy-4(3H)-pyrimidinone) for 5 minutes at room temperature ($G\alpha_i$) or 30 minutes at 37° C. (EEs). The Rluc8 substrate coelenterazine 400A (Prolume, Lakeside, AZ) was added at a final concentration of 5 μmol/L and BRET readings were collected using an Infinite M1000 microplate reader (Tecan, Morrisville, NC). $BRET^2$ readings between Rluc8 and GFP10 or rGFP were collected by sequential integration of the signals detected in the 370 to 450 nm (Rluc8) and 510 to 540 nm (GFP10, rGFP) windows. The BRET signal was calculated as the ratio of light emitted by acceptor (GFP10, rGFP) over the light emitted by donor (Rluc8). The values were corrected to net BRET by subtracting the background BRET signal obtained in cells transfected with Rluc8 constructs alone. Ligand-promoted net BRET values were calculated by subtracting vehicle-induced net BRET from ligand-induced net BRET.

Table 26 shows the activity of selected compounds of this invention in the Gαi biosensor BRET assay when tested at a single concentration. The compound numbers correspond to the compound numbers in Table 1. Compounds tested at a concentration less than 1 μM are designated "A*"; compounds tested at a concentration of 1 μM are designated "A°"; compounds tested at a concentration of 2 μM are designated "A"; compounds tested at a concentration of 3 μM are designated "B"; compounds tested at a concentration of 3.3 μM are designated "C"; compounds tested at a concentration of 5 μM are designated "D"; compounds tested at a concentration of 6.00 μM are designated "D°"; compounds tested at a concentration of 6.25 μM are designated "E"; compounds tested at a concentration of 10 μM are designated "F"; compounds tested at a concentration of 12.5 μM are designated "G"; compounds tested at a concentration of 15 µM are designated “H”; and compounds tested at a concentration of 25 µM are designated “I”. Compounds having an activity designated as “*” provided a percent inhibition of ≤25; compounds having an activity designated as “*” provided a percent inhibition of >25-≤50; compounds having an activity designated as “*” provided a percent inhibition of >50-≤75; and compounds having an activity designated as “” provided a percent inhibition of >75.

TABLE 26

| BRET Assay (% inhibition) | | |
|---|---|---|
| Compound | Concentration | % Inhibition |
| I-1 | I | * |
| I-2 | I | * |
| I-3 | I | * |
| I-4 | I | ** |
| I-5 | I | ** |
| I-6 | I | * |
| I-7 | I | **** |
| I-8 | I | * |
| I-9 | F | * |
| I-10 | I | * |
| I-11 | I | ** |
| I-12 | F | ** |
| I-13 | F | ** |
| I-14 | F | **** |
| I-15 | F | * |
| I-16 | F | ** |
| I-17 | F | **** |
| I-18 | F | *** |
| I-19 | F | **** |
| I-20 | F | **** |
| I-22 | I | * |
| I-23 | I | * |
| I-24 | I | **** |
| I-25 | G | * |
| I-26 | I | * |
| I-27 | I | ** |
| I-28 | I | ** |
| I-29 | I | *** |
| I-31 | I | * |
| I-32 | F | * |
| I-33 | I | ** |
| I-34 | E | *** |
| I-35 | I | * |
| I-36 | I | ** |
| I-37 | I | *** |
| I-38 | I | *** |
| I-39 | I | **** |
| I-40 | I | ** |
| I-41 | I | * |
| I-42 | I | * |
| I-43 | I | * |
| I-44 | F | * |
| I-45 | G | ** |
| I-46 | D | * |
| I-47 | I | * |
| I-48 | H | * |
| I-50 | I | ** |
| I-51 | I | * |
| I-52 | I | * |
| I-53 | I | * |
| I-54 | I | *** |
| I-56 | I | * |
| I-57 | I | * |
| I-58 | I | * |
| I-62 | F | **** |
| I-63 | I | * |
| I-65 | I | **** |
| I-68 | D | *** |
| I-69 | I | * |
| I-72 | I | * |
| I-73 | I | * |
| I-74 | I | ** |
| I-75 | I | **** |
| I-76 | D | **** |

TABLE 26-continued

| BRET Assay (% inhibition) | | |
|---|---|---|
| Compound | Concentration | % Inhibition |
| I-77 | D | **** |
| I-79 | H | **** |
| I-80 | I | * |
| I-81 | F | *** |
| I-82 | F | ** |
| I-83 | I | ** |
| I-85 | I | ** |
| I-90 | I | *** |
| I-92 | I | ** |
| I-93 | F | * |
| I-94 | F | **** |
| I-95 | F | * |
| I-96 | F | * |
| I-97 | F | * |
| I-98 | F | * |
| I-99 | F | * |
| I-100 | F | * |
| I-101 | F | ** |
| I-102 | F | ** |
| I-103 | F | * |
| I-104 | F | * |
| I-105 | F | * |
| I-106 | F | * |
| I-107 | F | **** |
| I-109 | F | ** |
| I-110 | F | * |
| I-111 | F | * |
| I-112 | F | * |
| I-113 | F | ** |
| I-114 | F | * |
| I-115 | F | * |
| I-116 | F | ** |
| I-118 | F | **** |
| I-121 | F | **** |
| I-122 | F | ** |
| I-123 | F | * |
| I-124 | F | ** |
| I-125 | F | * |
| I-126 | F | * |
| I-128 | F | * |
| I-129 | F | * |
| I-130 | F | * |
| I-131 | F | * |
| I-132 | F | ** |
| I-133 | F | *** |
| I-134 | F | * |
| I-135 | F | * |
| I-136 | F | * |
| I-137 | F | * |
| I-138 | F | *** |
| I-139 | F | * |
| I-140 | F | ** |
| I-141 | F | * |
| I-142 | F | * |
| I-143 | F | * |
| I-144 | F | * |
| I-145 | F | * |
| I-146 | F | ** |
| I-147 | F | * |
| I-148 | F | *** |
| I-149 | A | ** |
| I-150 | F | * |
| I-151 | F | * |
| I-153 | F | * |
| I-154 | F | ** |
| I-155 | F | * |
| I-156 | F | *** |
| I-157 | F | *** |
| I-158 | F | * |
| I-159 | F | * |
| I-160 | F | **** |
| I-161 | F | * |
| I-162 | F | ** |
| I-163 | F | * |
| I-164 | F | **** |

TABLE 26-continued

BRET Assay (% inhibition)

| Compound | Concentration | % Inhibition |
|---|---|---|
| I-166 | F | **** |
| I-167 | F | * |
| I-168 | F | * |
| I-169 | F | * |
| I-170 | F | * |
| I-171 | F | **** |
| I-172 | F | * |
| I-173 | F | * |
| I-174 | D | * |
| I-175 | D | *** |
| I-177 | F | *** |
| I-178 | F | * |
| I-179 | F | ** |
| I-180 | F | * |
| I-181 | F | * |
| I-182 | F | * |
| I-183 | F | * |
| I-184 | F | * |
| I-185 | F | * |
| I-186 | D | * |
| I-190 | F | * |
| I-191 | F | * |
| I-192 | F | * |
| I-193 | F | ** |
| I-194 | F | * |
| I-196 | F | * |
| I-197 | F | *** |
| I-198 | F | ** |
| I-199 | F | * |
| I-200 | F | ** |
| I-201 | F | * |
| I-202 | F | **** |
| I-203 | A | **** |
| I-204 | F | ** |
| I-205 | F | ** |
| I-206 | F | *** |
| I-207 | F | *** |
| I-208 | F | ** |
| I-212 | F | * |
| I-213 | F | * |
| I-214 | F | * |
| I-215 | F | *** |
| I-216 | F | * |
| I-217 | F | ** |
| I-218 | F | * |
| I-219 | F | * |
| I-220 | F | **** |
| I-222 | F | *** |
| I-223 | F | * |
| I-224 | F | ** |
| I-225 | F | ** |
| I-226 | F | **** |
| I-227 | F | ** |
| I-229 | F | * |
| I-230 | F | * |
| I-233 | F | *** |
| I-234 | F | * |
| I-235 | F | ** |
| I-236 | F | *** |
| I-237 | F | **** |
| I-238 | F | *** |
| I-240 | F | **** |
| I-241 | F | * |
| I-242 | F | * |
| I-243 | F | ** |
| I-244 | F | ** |
| I-245 | F | **** |
| I-246 | F | **** |
| I-247 | F | * |
| I-248 | F | * |
| I-249 | F | *** |
| I-250 | F | *** |
| I-251 | F | **** |
| I-252 | F | ** |
| I-253 | C | **** |

TABLE 26-continued

BRET Assay (% inhibition)

| Compound | Concentration | % Inhibition |
|---|---|---|
| I-254 | F | ** |
| I-255 | F | ** |
| I-256 | F | * |
| I-257 | F | * |
| I-258 | F | *** |
| I-260 | F | *** |
| I-261 | F | * |
| I-262 | F | *** |
| I-263 | F | **** |
| I-264 | F | *** |
| I-265 | F | ** |
| I-266 | A | **** |
| I-267 | F | ** |
| I-268 | F | * |
| I-269 | F | * |
| I-270 | F | * |
| I-271 | A | **** |
| I-272 | F | *** |
| I-273 | F | *** |
| I-274 | F | *** |
| I-275 | F | **** |
| I-276 | F | **** |
| I-277 | F | **** |
| I-279 | F | **** |
| I-280 | F | **** |
| I-281 | F | *** |
| I-282 | F | **** |
| I-283 | A | **** |
| I-284 | F | **** |
| I-285 | F | **** |
| I-287 | F | * |
| I-288 | F | ** |
| I-289 | F | ** |
| I-290 | F | ** |
| I-291 | F | *** |
| I-293 | A | **** |
| I-294 | I | * |
| I-295 | I | * |
| I-296 | I | * |
| I-297 | I | * |
| I-298 | F | ** |
| I-300 | F | ** |
| I-301 | F | *** |
| I-302 | F | **** |
| I-303 | F | * |
| I-305 | F | * |
| I-306 | F | ** |
| I-309 | F | * |
| I-310 | F | *** |
| I-311 | F | *** |
| I-312 | F | ** |
| I-313 | F | *** |
| I-314 | F | ** |
| I-315 | I | **** |
| I-316 | I | * |
| I-317 | I | * |
| I-318 | I | * |
| I-319 | I | * |
| I-320 | I | * |
| I-321 | I | ** |
| I-322 | I | * |
| I-323 | I | * |
| I-324 | I | * |
| I-325 | F | * |
| I-326 | F | * |
| I-327 | F | * |
| I-328 | F | * |
| I-329 | F | ** |
| I-330 | F | * |
| I-331 | F | * |
| I-332 | F | * |
| I-333 | H | * |
| I-334 | I | **** |
| I-335 | I | ** |
| I-336 | I | * |

TABLE 26-continued

| BRET Assay (% inhibition) | | |
|---|---|---|
| Compound | Concentration | % Inhibition |
| I-337 | D | * |
| I-339 | F | ** |
| I-340 | F | ** |
| I-341 | F | *** |
| I-342 | F | * |
| I-343 | F | *** |
| I-344 | I | * |
| I-345 | F | * |
| I-346 | I | ** |
| I-355 | F | *** |
| I-356 | F | ** |
| I-357 | F | *** |
| I-358 | A | * |
| I-363 | B | ** |
| I-364 | F | ** |
| I-379 | F | **** |
| I-380 | F | **** |
| I-394 | F | **** |
| I-406 | F | * |
| I-407 | F | * |
| I-409 | F | ** |
| I-410 | A | ** |
| I-411 | F | **** |
| I-412 | F | * |
| I-413 | A | **** |
| I-414 | F | *** |
| I-415 | F | ** |
| I-416 | F | ** |
| I-417 | A | **** |
| I-418 | A | **** |
| I-419 | F | ** |
| I-420 | F | *** |
| I-421 | F | **** |
| I-422 | F | * |
| I-423 | D° | **** |
| I-424 | F | **** |
| I-425 | F | ** |
| I-426 | F | ** |
| I-427 | F | ** |
| I-428 | F | ** |
| I-429 | F | ** |
| I-430 | F | ** |
| I-431 | F | * |
| I-432 | F | **** |
| I-433 | F | * |
| I-434 | F | * |
| I-435 | F | * |
| I-436 | F | * |
| I-437 | F | ** |
| I-438 | F | ** |
| I-439 | F | ** |
| I-440 | F | * |
| I-441 | F | *** |
| I-443 | F | * |
| I-444 | F | * |
| I-445 | F | *** |
| I-446 | F | ** |
| I-447 | F | ** |
| I-448 | F | *** |
| I-449 | F | ** |
| I-450 | F | ** |
| I-451 | F | **** |
| I-452 | F | **** |
| I-453 | F | * |
| I-454 | F | **** |
| I-455 | F | **** |
| I-456 | A | **** |
| I-457 | F | * |
| I-458 | F | * |
| I-459 | F | **** |
| I-460 | F | **** |
| I-461 | F | **** |
| I-462 | F | **** |
| I-463 | A | * |
| I-464 | A | **** |

TABLE 26-continued

| BRET Assay (% inhibition) | | |
|---|---|---|
| Compound | Concentration | % Inhibition |
| I-465 | F | * |
| I-466 | F | * |
| I-467 | F | * |
| I-468 | F | ** |
| I-469 | F | * |
| I-470 | F | * |
| I-471 | F | **** |
| I-472 | F | ** |
| I-473 | F | * |
| I-474 | A | **** |
| I-475 | A | ** |
| I-476 | A | * |
| I-477 | F | *** |
| I-478 | F | **** |
| I-479 | F | * |
| I-480 | A | * |
| I-481 | A | * |
| I-482 | F | * |
| I-483 | F | * |
| I-484 | F | * |
| I-485 | F | * |
| I-486 | F | * |
| I-487 | F | * |
| I-488 | F | *** |
| I-489 | A | * |
| I-490 | F | **** |
| I-491 | F | * |
| I-492 | F | **** |
| I-493 | F | * |
| I-494 | F | **** |
| I-495 | F | ** |
| I-496 | F | ** |
| I-497 | F | ** |
| I-498 | A | *** |
| I-499 | F | **** |
| I-500 | F | **** |
| I-501 | F | **** |
| I-502 | F | **** |
| I-503 | F | **** |
| I-504 | F | * |
| I-505 | A | * |
| I-506 | F | *** |
| I-507 | F | ** |
| I-508 | F | *** |
| I-509 | A | * |
| I-510 | A | *** |
| I-511 | A | **** |
| I-512 | A | **** |
| I-513 | A | ** |
| I-514 | A | * |
| I-515 | F | * |
| I-516 | F | * |
| I-517 | F | * |
| I-518 | F | **** |
| I-519 | F | ** |
| I-520 | F | *** |
| I-521 | F | * |
| I-522 | F | *** |
| I-523 | A | * |
| I-524 | F | * |
| I-525 | F | * |
| I-526 | F | *** |
| I-527 | F | * |
| I-528 | F | * |
| I-529 | F | * |
| I-530 | F | **** |
| I-531 | F | **** |
| I-532 | F | ** |
| I-533 | F | * |
| I-534 | F | * |
| I-535 | F | **** |
| I-536 | F | * |
| I-537 | F | **** |
| I-538 | F | **** |
| I-539 | F | * |

TABLE 26-continued

BRET Assay (% inhibition)

| Compound | Concentration | % Inhibition |
|---|---|---|
| I-540 | F | **** |
| I-541 | F | ** |
| I-542 | A | * |
| I-543 | A | * |
| I-544 | F | ** |
| I-545 | F | * |
| I-546 | F | *** |
| I-547 | F | ** |
| I-548 | F | *** |
| I-549 | F | *** |
| I-550 | F | *** |
| I-551 | F | ** |
| I-552 | A | ** |
| I-553 | F | ** |
| I-554 | A | **** |
| I-555 | F | * |
| I-556 | A | * |
| I-557 | A | * |
| I-558 | F | * |
| I-559 | F | * |
| I-560 | F | ** |
| I-561 | F | **** |
| I-562 | F | **** |
| I-563 | F | * |
| I-564 | F | * |
| I-565 | F | *** |
| I-566 | F | ** |
| I-567 | F | *** |
| I-568 | F | * |
| I-569 | F | **** |
| I-570 | F | **** |
| I-571 | F | * |
| I-572 | F | **** |
| I-573 | F | **** |
| I-574 | F | * |
| I-575 | F | **** |
| I-576 | F | *** |
| I-577 | F | ** |
| I-578 | F | *** |
| I-579 | F | **** |
| I-580 | F | ** |
| I-581 | F | * |
| I-582 | F | **** |
| I-583 | F | * |
| I-584 | F | **** |
| I-585 | F | **** |
| I-586 | F | **** |
| I-587 | F | *** |
| I-588 | A° | **** |
| I-589 | A° | **** |
| I-590 | F | * |
| I-591 | F | **** |
| I-592 | F | *** |
| I-593 | F | * |
| I-594 | F | **** |
| I-595 | F | **** |
| I-596 | F | **** |
| I-597 | F | *** |
| I-598 | F | **** |
| I-599 | F | * |
| I-600 | F | **** |
| I-601 | F | * |
| I-602 | F | * |
| I-603 | F | *** |
| I-604 | F | **** |
| I-605 | F | **** |
| I-606 | F | *** |
| I-607 | F | ** |
| I-608 | F | **** |
| I-609 | F | *** |
| I-610 | A | * |
| I-611 | F | ** |
| I-612 | F | **** |
| I-613 | F | * |
| I-614 | F | *** |

TABLE 26-continued

BRET Assay (% inhibition)

| Compound | Concentration | % Inhibition |
|---|---|---|
| I-615 | F | *** |
| I-616 | F | **** |
| I-617 | F | **** |
| I-618 | F | **** |
| I-619 | F | **** |
| I-620 | F | **** |
| I-621 | F | *** |
| I-622 | A | * |
| I-623 | F | *** |
| I-624 | F | * |
| I-625 | F | *** |
| I-626 | F | ** |
| I-627 | F | **** |
| I-628 | F | **** |
| I-629 | F | * |
| I-630 | F | **** |
| I-631 | F | **** |
| I-632 | F | * |
| I-633 | F | *** |
| I-634 | F | **** |
| I-635 | F | *** |
| I-636 | F | **** |
| I-637 | A | **** |
| I-638 | F | * |
| I-639 | F | * |
| I-640 | F | **** |
| I-641 | F | **** |
| I-642 | F | **** |
| I-643 | A | *** |
| I-644 | A | **** |
| I-645 | F | **** |
| I-646 | A | **** |
| I-647 | A | **** |
| I-648 | F | **** |
| I-649 | A | **** |
| I-650 | A | **** |
| I-651 | A | **** |
| I-652 | F | * |
| I-653 | F | **** |
| I-654 | F | **** |
| I-655 | F | *** |
| I-656 | F | **** |
| I-657 | F | * |
| I-658 | F | **** |
| I-659 | F | **** |
| I-660 | F | * |
| I-661 | F | * |
| I-662 | F | **** |
| I-663 | F | **** |
| I-664 | F | **** |
| I-665 | F | **** |
| I-666 | A | **** |
| I-667 | F | **** |
| I-668 | A | **** |
| I-669 | A | **** |
| I-670 | F | *** |
| I-671 | F | **** |
| I-672 | F | * |
| I-673 | A | **** |
| I-674 | A | **** |
| I-675 | F | **** |
| I-676 | A | **** |
| I-677 | A | **** |
| I-678 | A | **** |
| I-679 | F | **** |
| I-680 | F | *** |
| I-681 | A | **** |
| I-682 | F | **** |
| I-683 | F | * |
| I-684 | F | **** |
| I-685 | F | **** |
| I-686 | F | **** |
| I-687 | F | *** |
| I-688 | F | **** |
| I-689 | F | **** |

TABLE 26-continued

| BRET Assay (% inhibition) | | |
|---|---|---|
| Compound | Concentration | % Inhibition |
| I-690 | F | ** |
| I-691 | F | **** |
| I-692 | F | *** |
| I-749 | F | *** |
| I-694 | F | **** |
| I-695 | F | * |
| I-696 | F | ** |
| I-697 | F | **** |
| I-698 | F | **** |
| I-699 | F | * |
| I-700 | A | *** |
| I-701 | A | **** |
| I-702 | A | **** |
| I-703 | F | **** |
| I-704 | F | * |
| I-705 | F | * |
| I-706 | F | **** |
| I-707 | F | **** |
| I-708 | F | **** |
| I-709 | A | **** |
| I-710 | A | **** |
| I-711 | A | **** |
| I-712 | A | **** |
| I-713 | F | *** |
| I-714 | A | **** |
| I-715 | F | **** |
| I-716 | F | **** |
| I-717 | F | * |
| I-718 | A | **** |
| I-719 | F | **** |
| I-720 | F | **** |
| I-721 | A | **** |
| I-722 | A | **** |
| I-723 | F | **** |
| I-724 | A | **** |
| I-725 | F | **** |
| I-726 | F | **** |
| I-727 | A | **** |
| I-728 | F | **** |
| I-729 | F | **** |
| I-730 | F | **** |
| I-731 | F | **** |
| I-732 | F | * |
| I-733 | F | *** |
| I-734 | F | **** |
| I-735 | A | **** |
| I-736 | F | * |
| I-737 | F | **** |
| I-738 | A | * |
| I-739 | A | **** |
| I-740 | A | **** |
| I-741 | F | **** |
| I-742 | F | **** |
| I-743 | F | * |
| I-744 | F | **** |
| I-745 | A | **** |
| I-746 | A | **** |
| I-747 | A | **** |
| I-748 | A | **** |
| I-749 | A | **** |
| I-750 | F | **** |
| I-751 | F | ** |
| I-752 | F | ** |
| I-753 | F | **** |
| I-754 | F | **** |
| I-755 | F | **** |
| I-756 | F | **** |
| I-757 | A | **** |
| I-758 | A | **** |
| I-759 | F | * |
| I-780 | F | **** |
| I-781 | F | **** |
| I-782 | F | **** |
| I-783 | F | * |
| I-871 | F | ** |

TABLE 26-continued

| BRET Assay (% inhibition) | | |
|---|---|---|
| Compound | Concentration | % Inhibition |
| I-785 | A | **** |
| I-786 | F | **** |
| I-787 | F | * |
| I-788 | F | **** |
| I-789 | F | *** |
| I-790 | F | * |
| I-791 | A | **** |
| I-792 | A | **** |
| I-793 | A | **** |
| I-794 | A | **** |
| I-795 | F | ** |
| I-796 | A* | **** |
| I-797 | F | **** |
| I-798 | F | **** |
| I-799 | F | **** |
| I-800 | F | *** |
| I-801 | A | **** |
| I-802 | F | **** |
| I-803 | F | **** |
| I-804 | A° | ** |
| I-805 | A | **** |
| I-806 | A | **** |
| I-807 | F | **** |
| I-808 | A | **** |
| I-809 | A | **** |
| I-810 | F | **** |
| I-811 | F | * |
| I-812 | F | * |
| I-813 | F | **** |
| I-814 | F | * |
| I-815 | A | **** |
| I-816 | F | **** |
| I-817 | F | **** |
| I-818 | F | **** |
| I-819 | F | **** |
| I-820 | A | **** |
| I-821 | F | **** |
| I-822 | A | **** |
| I-823 | F | * |
| I-824 | F | * |
| I-825 | A | **** |
| I-826 | F | **** |
| I-827 | F | *** |
| I-828 | F | *** |
| I-829 | F | **** |
| I-830 | F | *** |
| I-831 | A | **** |
| I-832 | F | * |
| I-833 | F | * |
| I-834 | F | * |
| I-835 | F | * |
| I-836 | F | *** |
| I-837 | F | * |
| I-838 | F | *** |
| I-839 | F | **** |
| I-840 | A | **** |
| I-841 | A | **** |
| I-842 | A | *** |
| I-843 | F | **** |
| I-844 | F | *** |
| I-845 | F | **** |
| I-846 | F | * |
| I-847 | F | * |
| I-848 | F | * |
| I-849 | F | **** |
| I-850 | F | **** |
| I-851 | F | * |
| I-852 | A | **** |
| I-853 | F | * |
| I-854 | A | **** |
| I-855 | A | **** |
| I-856 | F | **** |
| I-857 | F | * |
| I-858 | A | **** |
| I-859 | A | **** |

TABLE 26-continued

| BRET Assay (% inhibition) | | |
|---|---|---|
| Compound | Concentration | % Inhibition |
| I-860 | A* | **** |
| I-861 | F | **** |
| I-862 | F | *** |
| I-863 | A | **** |
| I-864 | F | ** |
| I-865 | F | * |

Table 27 shows the activity of selected compounds of this invention in the Gαi biosensor BRET assay. The compound numbers correspond to the compound numbers in Table 1. Compounds having an activity designated as "A" provided an $IC_{50}$≤0.3 μM; compounds having an activity designated as "B" provided an $IC_{50}$ of 0.3-1 μM; compounds having an activity designated as "C" provided an $IC_{50}$ of 1--3 μM; compounds having an activity designated as "D*" provided an $IC_{50}$ of ">2 μM" but an exact quantity was not measured; compounds having an activity designated as "D" provided an $IC_{50}$ of >3 μM.

TABLE 27

| BRET Assay ($IC_{50}$) | |
|---|---|
| Compound | BRET $IC_{50}$ (μM) |
| I-4 | A |
| I-7 | D |
| I-14 | C |
| I-17 | B |
| I-24 | D |
| I-27 | D |
| I-34 | D |
| I-36 | D |
| I-37 | D |
| I-39 | D |
| I-54 | B |
| I-60 | D |
| I-62 | D |
| I-65 | C |
| I-66 | D |
| I-67 | C |
| I-68 | C |
| I-75 | B |
| I-76 | B |
| I-77 | B |
| I-78 | C |
| I-79 | D |
| I-81 | D |
| I-82 | D |
| I-86 | B |
| I-87 | C |
| I-88 | C |
| I-90 | D |
| I-91 | C |
| I-94 | C |
| I-107 | C |
| I-118 | D |
| I-119 | C |
| I-120 | A |
| I-121 | B |
| I-138 | C |
| I-144 | C |
| I-160 | D |
| I-164 | C |
| I-166 | B |
| I-171 | C |
| I-174 | D |
| I-175 | C |
| I-177 | C |
| I-187 | D |
| I-188 | D |

TABLE 27-continued

| BRET Assay ($IC_{50}$) | |
|---|---|
| Compound | BRET $IC_{50}$ (μM) |
| I-202 | C |
| I-203 | C |
| I-209 | D* |
| I-210 | B |
| I-220 | B |
| I-226 | C |
| I-236 | C |
| I-237 | C |
| I-238 | C |
| I-245 | C |
| I-246 | B |
| I-253 | A |
| I-299 | D |
| I-310 | C |
| I-315 | D |
| I-329 | B |
| I-330 | B |
| I-346 | D |
| I-411 | A |
| I-413 | B |
| I-417 | B |
| I-418 | B |
| I-423 | B |
| I-424 | C |
| I-427 | D |
| I-430 | B |
| I-432 | B |
| I-441 | C |
| I-451 | B |
| I-452 | B |
| I-454 | A |
| I-455 | C |
| I-456 | A |
| I-459 | C |
| I-460 | B |
| I-462 | C |
| I-464 | B |
| I-474 | B |
| I-478 | A |
| I-488 | A |
| I-490 | B |
| I-492 | A |
| I-498 | B |
| I-499 | B |
| I-500 | C |
| I-501 | C |
| I-502 | C |
| I-510 | B |
| I-511 | A |
| I-512 | B |
| I-513 | D* |
| I-518 | C |
| I-526 | A |
| I-530 | A |
| I-531 | A |
| I-535 | A |
| I-537 | B |
| I-538 | B |
| I-548 | D |
| I-549 | C |
| I-553 | B |
| I-561 | D |
| I-562 | A |
| I-567 | C |
| I-569 | C |
| I-570 | D |
| I-572 | B |
| I-578 | D |
| I-585 | A |
| I-586 | C |
| I-587 | B |
| I-588 | A |
| I-589 | A |
| I-591 | B |
| I-594 | A |
| I-596 | B |

TABLE 27-continued

| BRET Assay ($IC_{50}$) | |
|---|---|
| Compound | BRET $IC_{50}$ (μM) |
| I-598 | C |
| I-600 | C |
| I-603 | D |
| I-604 | C |
| I-605 | B |
| I-608 | B |
| I-609 | D |
| I-612 | B |
| I-616 | D |
| I-617 | A |
| I-618 | A |
| I-619 | A |
| I-620 | A |
| I-634 | A |
| I-635 | A |
| I-636 | A |
| I-637 | B |
| I-641 | B |
| I-642 | C |
| I-644 | B |
| I-646 | B |
| I-647 | B |
| I-649 | C |
| I-650 | B |
| I-651 | A |
| I-654 | A |
| I-656 | B |
| I-658 | D |
| I-659 | A |
| I-662 | D |
| I-663 | D |
| I-664 | A |
| I-665 | A |
| I-666 | A |
| I-667 | B |
| I-668 | A |
| I-669 | A |
| I-671 | C |
| I-673 | A |
| I-674 | B |
| I-676 | A |
| I-677 | A |
| I-678 | B |
| I-681 | B |
| I-682 | B |
| I-685 | C |
| I-686 | B |
| I-688 | B |
| I-689 | C |
| I-691 | B |
| I-697 | B |
| I-698 | B |
| I-701 | A |
| I-702 | A |
| I-703 | B |
| I-706 | B |
| I-707 | A |
| I-708 | A |
| I-709 | A |
| I-710 | A |
| I-711 | A |
| I-712 | A |
| I-713 | B |
| I-714 | C |
| I-716 | B |
| I-718 | B |
| I-719 | C |
| I-720 | B |
| I-721 | B |
| I-722 | A |
| I-724 | A |
| I-725 | B |
| I-727 | B |
| I-730 | B |
| I-731 | B |
| I-734 | B |

TABLE 27-continued

| BRET Assay ($IC_{50}$) | |
|---|---|
| Compound | BRET $IC_{50}$ (μM) |
| I-735 | A |
| I-737 | B |
| I-739 | A |
| I-740 | A |
| I-744 | B |
| I-745 | B |
| I-746 | A |
| I-747 | A |
| I-748 | A |
| I-749 | A |
| I-750 | A |
| I-754 | B |
| I-756 | B |
| I-757 | A |
| I-758 | A |
| I-761 | B |
| I-762 | A |
| I-764 | B |
| I-765 | C |
| I-767 | B |
| I-770 | A |
| I-771 | A |
| I-772 | A |
| I-773 | B |
| I-775 | A |
| I-777 | C |
| I-780 | B |
| I-784 | A |
| I-785 | A |
| I-786 | B |
| I-787 | B |
| I-788 | A |
| I-789 | B |
| I-792 | B |
| I-794 | A |
| I-795 | A |
| I-796 | A |
| I-797 | A |
| I-799 | A |
| I-800 | B |
| I-801 | A |
| I-804 | B |
| I-808 | B |
| I-810 | B |
| I-819 | A |
| I-820 | B |
| I-822 | A |
| I-828 | B |
| I-829 | A |
| I-831 | A |
| I-833 | A |
| I-834 | A |
| I-864 | B |
| I-865 | B |
| I-866 | C |
| I-867 | A |

Example 56: Neutrophil Migration Assay

Neutrophil migration assay. After isolation, neutrophils were resuspended in chemotaxis buffer (DMEM supplemented with 10 mM HEPES) at a concentration of 8.9×106 cells/ml. In a 96-well plate, 20 μl of compound solution in chemotaxis buffer is added to 180 μl of cell suspension. After incubation at 37° C. for 30 minutes, 75 μl of cell suspension is transferred in the upper chamber of a 5 μm pore size Corning HTS transwell. 235 μl of chemotaxis buffer containing the chemotactic agent (embelin) is added to the lower chamber of the transwell. After a 60-minute incubation time at 37° C. in 5%0 $C_{02}$, the upper chamber of the transwell is removed and the plate is centrifuged at 1500 rpm for 6 minutes. Supermatant is removed and cells resuspended in 100 ul of PBS. ATP content was assessed using ATPlite Luminescence Assay System® according to manufacturer instructions (Perkin Elmer, Buckinghamshire, UK). Briefly, 50 μl of ATPlite buffer and 50 μl of lysis solution is added to the lower chamber of the Transwells. After incubation at room temperature, in the dark with constant agitation for 5 minutes, 150 μl of cell lysate is transferred in a 96 wells white plate and incubated for 10 minutes in the dark. Luminescence is read on a TECAN plate reader, Infinite M1000 (Tecan, Morrisville, NC).

Table 27 shows the activity of selected compounds of this invention in the neutrophil migration assay. The compound numbers correspond to the compound numbers in Table 1. Neutrophil migration results are normalized to a GPR84 antagonist Control Compound which provided an average $IC_{50}$ value of 131 nM and an $IC_{50}$ range of 15 nM to 553 nM in the neutrophil migration assay (n=26). Normalization of the results takes the donor's variation into account. Compounds having an activity designated as "A" provided an $IC_{50}$≤300 nM; compounds having an activity designated as "B" provided an $IC_{50}$ of >300-≤1,000 nM; compounds having an activity designated as "C" provided an $IC_{50}$ of >1,000-3,000 nM; and compounds having an activity designated as "D" provided an $IC_{50}$ of >3,000 nM. Compounds having a migration inhibition potency relative to Control Compound designated as "C" provided an $IC_{50}$≤0.5-fold relative to Control Compound; compounds having an activity designated as "B" provided an $IC_{50}$ of >0.5-≤1.0-fold relative to Control Compound; and compounds having an activity designated as "A" provided an $IC_{50}$ of >1.0-fold relative to Control Compound.

TABLE 27

Neutrophil Migration Assay

| Compound | Human Neutrophil migration inhibition $IC_{50}$ | Human Neutrophil migration inhibition - fold potency to Control Compound |
|---|---|---|
| I-7 | D | C |
| I-14 | A | A |
| I-17 | A | B |
| I-34 | C | C |
| I-65 | C | C |
| I-66 | C | C |
| I-67 | B | B |
| I-68 | B | B |
| I-75 | A | B |
| I-76 | A | B |
| I-77 | A | A |
| I-79 | B | C |
| I-81 | B | C |
| I-86 | B | C |
| I-87 | C | C |
| I-88 | C | C |
| I-94 | C | C |
| I-107 | A | A |
| I-118 | A | C |
| I-119 | B | C |
| I-120 | A | B |
| I-121 | B | C |
| I-138 | C | C |
| I-144 | C | C |
| I-149 | C | C |
| I-166 | A | A |
| I-177 | A | A |
| I-187 | A | B |
| I-188 | A | A |
| I-245 | B | C |

TABLE 27-continued

Neutrophil Migration Assay

| Compound | Human Neutrophil migration inhibition $IC_{50}$ | Human Neutrophil migration inhibition - fold potency to Control Compound |
|---|---|---|
| I-315 | B | C |
| I-411 | B | B |
| I-413 | A | B |
| I-417 | A | A |
| I-418 | C | C |
| I-423 | A | A |
| I-424 | A | A |
| I-441 | A | A |
| I-451 | A | A |
| I-452 | A | A |
| I-454 | A | A |
| I-455 | A | B |
| I-456 | A | A |
| I-459 | A | C |
| I-460 | A | A |
| I-462 | A | C |
| I-464 | A | C |
| I-474 | A | A |
| I-478 | A | B |
| I-499 | A | A |
| I-510 | A | B |
| I-511 | A | A |
| I-512 | A | C |
| I-530 | A | A |
| I-531 | A | A |
| I-535 | A | B |
| I-553 | A | B |
| I-562 | A | A |
| I-572 | A | A |
| I-585 | A | A |
| I-588 | A | A |
| I-589 | A | A |
| I-596 | A | A |
| I-612 | A | A |
| I-618 | A | A |
| I-620 | A | A |
| I-634 | A | A |
| I-635 | B | C |
| I-636 | A | A |
| I-637 | A | A |
| I-644 | A | A |
| I-650 | A | A |
| I-651 | A | A |

While we have described a number of embodiments of this invention, it is apparent that our examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A compound of formula I:

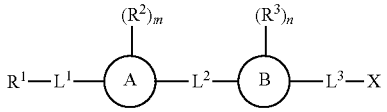

I or a pharmaceutically acceptable salt thereof, wherein:
Ring A is phenyl or pyridyl;
Ring B together with $(R^3)_n$ is one of the following:

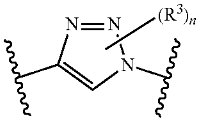

or

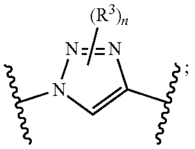

;

$R^1$ is a 4-8 membered saturated or partially unsaturated monocyclic heterocyclic ring having 1-2 heteroatoms independently selected from nitrogen, oxygen, and sulfur substituted with p instances of $R^4$;

each instance of $R^2$, $R^4$, and $R^5$ is independently hydrogen, deuterium, $R^z$, halogen, —CN, —$NO_2$, —OR, —SR, —$NR_2$, —$S(O)_2R$, —$S(O)_2NR_2$, —S(O)R, —$S(O)NR_2$, —$CF_2R$, —$CF_3$, —$CR_2(CN)$, —$CR_2(OR)$, —$CR_2(NR_2)$, —C(O)R, —C(O)OR, —$C(O)NR_2$, —C(O)N(R)OR, —OC(O)R, —$OC(O)NR_2$, —$C(S)NR_2$, —N(R)C(O)OR, —N(R)C(O)R, —$N(R)C(O)NR_2$, —$N(R)C(NR)NR_2$, —$N(R)NR_2$, —$N(R)S(O)_2NR_2$, —$N(R)S(O)_2R$, —N═$S(O)R_2$, —S(NR)(O)R, —N(R)S(O)R, —N(R)CN, —$Si(OR)R_2$, —$SiR_3$, —$P(O)(R)NR_2$, —P(O)(R)OR, or —$P(O)R_2$;

each instance of $R^z$ is independently a $C_{1-3}$ aliphatic;

$R^3$ is hydrogen;

$L^1$ is a covalent bond;

$L^2$ is a covalent bond;

$L^3$ is

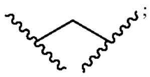 [SMILES: *C*]

;

X is a 4-8 membered saturated or partially unsaturated monocyclic heterocyclic ring having 1-2 heteroatoms independently selected from nitrogen, oxygen, and sulfur; or a 6-11 membered saturated or partially unsaturated bridged or spiro cyclic, bicyclic heterocyclic ring having 1-2 heteroatoms independently selected from nitrogen, oxygen, and sulfur; each of which is substituted with q instances of $R^5$;

each instance of R is independently hydrogen or $C_{1-3}$ aliphatic;

m is 0, 1, or 2;

n is 0, 1, 2, 3, or 4;

p is 0, 1, 2, or 3; and q is 0, 1, 2, or 3.

2. The compound of claim 1, wherein the compound is any one of formulae I-a, I-b-1, I-b-2, or I-b-3:

I-a

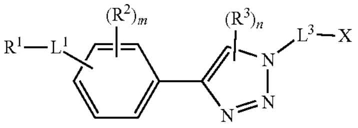

I-b-1

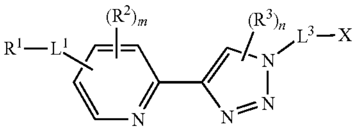

-continued

I-b-2

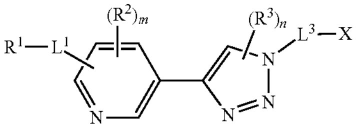

I-b-3

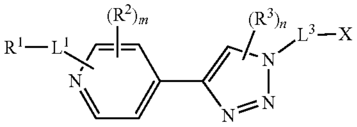

I-c

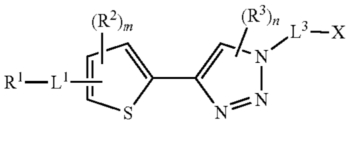

or a pharmaceutically acceptable salt thereof.

3. The compound of claim 1, wherein the Ring A is phenyl.

4. The compound of claim 1, wherein Ring A and its $R^2$ substituents is

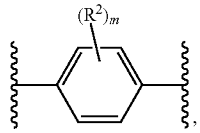

,

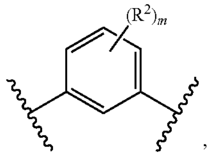

,

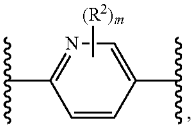

, or

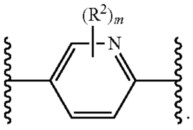

.

5. The compound of claim 1, wherein Ring B and its $R^3$ substituents is

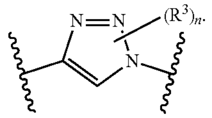

6. The compound of claim 1, wherein Ring B and its $R^3$ substituents is

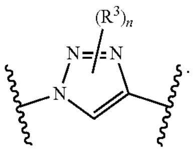

7. The compound of claim 1, wherein $R^1$ is a 4 membered saturated or partially unsaturated monocyclic heterocyclic ring having 1-2 heteroatoms independently selected from nitrogen, oxygen, and sulfur which is substituted with p instances of $R^4$.

8. The compound of claim 1, wherein $R^1$ and its $R^4$ substituents is

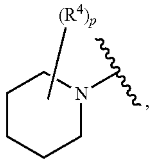, 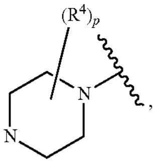, 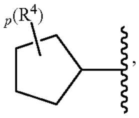,

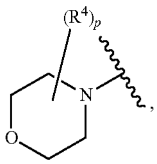, 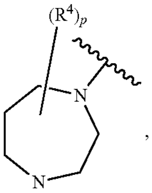, 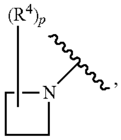,

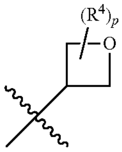, 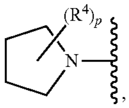, 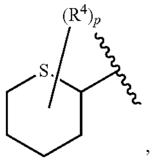,

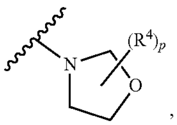, or 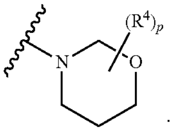.

9. The compound of claim 1, wherein Ring A is pyridyl; Ring B together with $(R^3)_n$ is

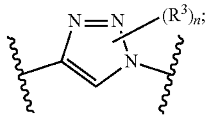

each instance of $R^2$, $R^4$, and $R^5$ is independently hydrogen, deuterium, $R^z$, halogen, —CN, —$NO_2$, —OR, —SR, or —$NR_2$; X is a 4-8 membered saturated monocyclic heterocyclic ring having 1-2 heteroatoms independently selected from nitrogen, oxygen, and sulfur wherein said ring is substituted with q instances of $R^5$; n is 0 or 1; p is 0, 1, or 2; and q is 0, 1, or 2.

10. The compound of claim 9, wherein X is a 5-7 membered saturated monocyclic heterocyclic ring having 1 or 2 oxygen atoms, wherein said ring is substituted with q instances of $R^5$.

11. The compound of claim 1, wherein each instance of $R^2$ and $R^5$ is independently hydrogen, deuterium, $R^z$, halogen, —CN, —$NO_2$, —OR, —SR, or —$NR_2$; m is 0, 1, or 2; n is 0 or 1; p is 0, 1, or 2; and q is 0, 1, or 2.

12. The compound of claim 1, wherein X is a 5-7 membered saturated monocyclic heterocyclic ring having 1 or 2 oxygen atoms, wherein said ring is substituted with q instances of $R^5$.

13. The compound of claim 1, wherein the compound is of either one of formulae I-ii-1 or I-ii-2:

I-ii-1

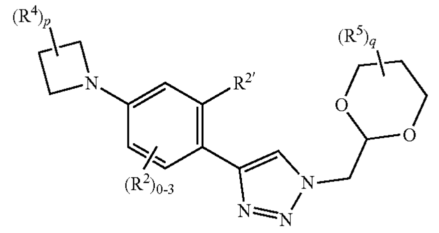

I-ii-2

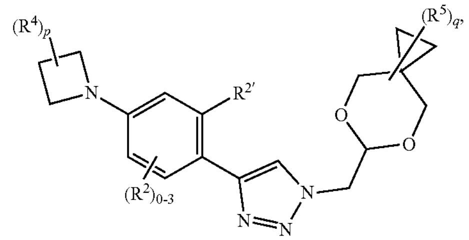

or a pharmaceutically acceptable salt thereof, wherein $R^{2'}$ is an $R^2$.

14. The compound of claim 1, wherein the compound is of either one of formulae I-jj-1 or I-jj-2:

I-jj-1

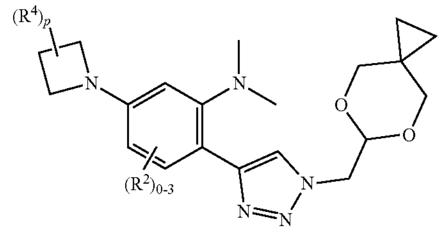

I-jj-2

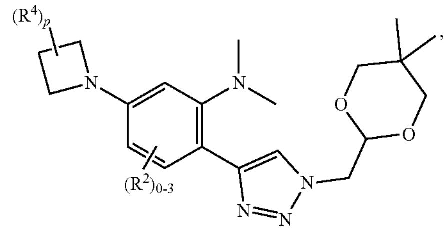, or a pharmaceutically acceptable salt thereof.

15. The compound of claim 1, wherein the compound is of either one of formulae I-kk-1 or I-kk-2:

I-kk-1

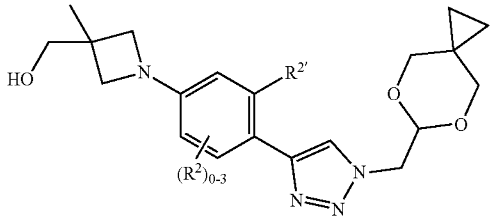

-continued

I-kk-2

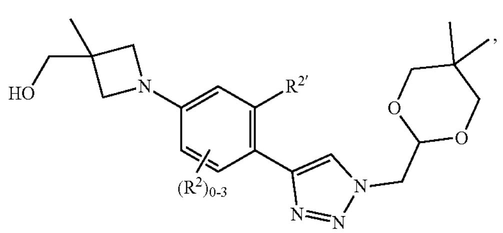

or a pharmaceutically acceptable salt thereof, wherein $R^{2'}$ is an $R^2$.

16. The compound of claim 1, wherein the compound is of either one of formulae I-II-1 or I-11-2:

I-II-1

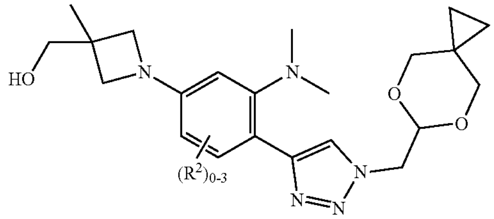

I-II-2

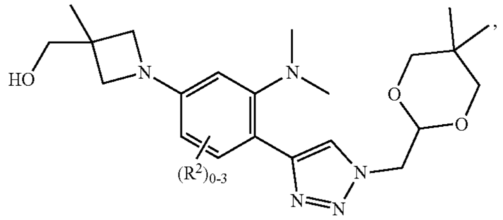

or a pharmaceutically acceptable salt thereof.

17. A compound selected from the following or a pharmaceutically acceptable salt thereof:

| Compound | Structure |
|---|---|
| I-75 | 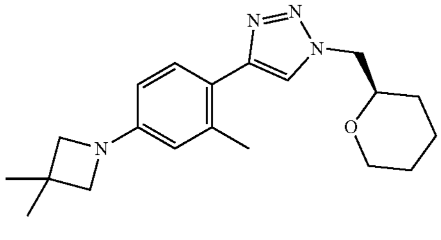 [SMILES: Cc1cc(N2CC(C)(C)C2)ccc1-c1cn(C[C@H]2CCCCO2)nn1] |
| I-111 | 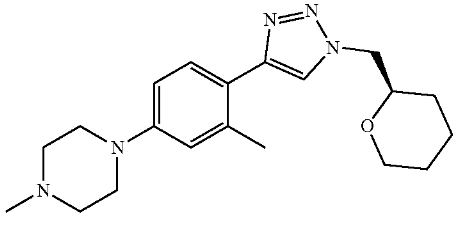 [SMILES: Cc1cc(N2CCN(C)CC2)ccc1-c1cn(C[C@H]2CCCCO2)nn1] |

-continued

| Compound | Structure |
|---|---|
| I-112 | 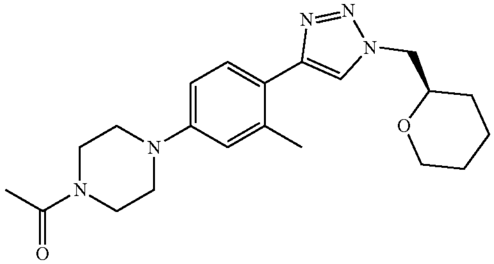 [SMILES: CC(=O)N1CCN(c2ccc(-c3cn(C[C@H]4CCCCO4)nn3)c(C)c2)CC1] |
| I-114 | 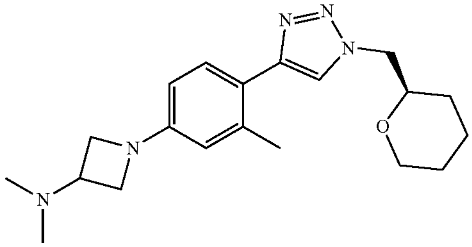 [SMILES: Cc1cc(N2CC(N(C)C)C2)ccc1-c1cn(C[C@H]2CCCCO2)nn1] |
| I-128 | 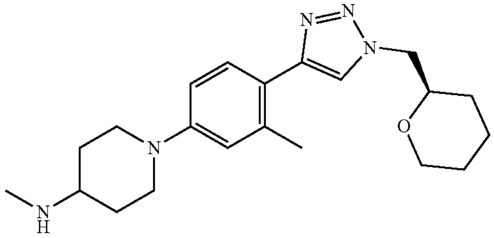 [SMILES: CNC1CCN(c2ccc(-c3cn(C[C@H]4CCCCO4)nn3)c(C)c2)CC1] |
| I-129 | 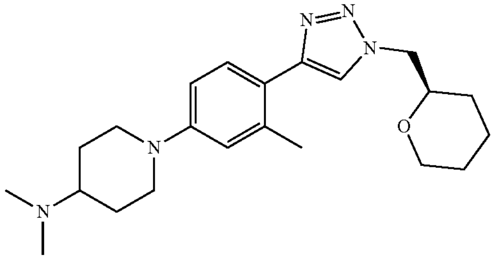 [SMILES: Cc1cc(N2CCC(N(C)C)CC2)ccc1-c1cn(C[C@H]2CCCCO2)nn1] |
| I-142 | 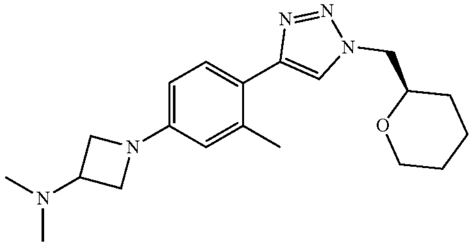 [SMILES: Cc1cc(N2CC(N(C)C)C2)ccc1-c1cn(C[C@H]2CCCCO2)nn1] |
| I-153 | 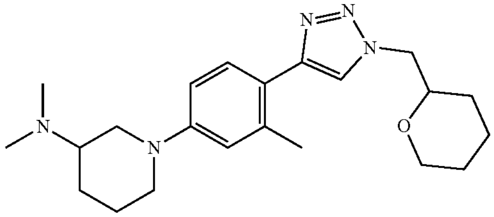 [SMILES: Cc1cc(N2CCCC(N(C)C)C2)ccc1-c1cn(CC2CCCCO2)nn1] |

-continued
| Compound | Structure |
|---|---|
| I-157 | 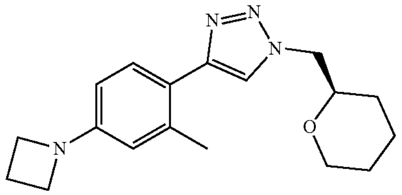 [SMILES: Cc1cc(N2CCC2)ccc1-c1cn(C[C@H]2CCCCO2)nn1] |
| I-158 | 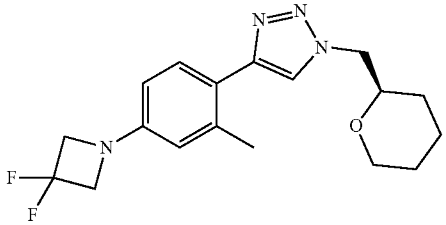 [SMILES: Cc1cc(N2CC(F)(F)C2)ccc1-c1cn(C[C@H]2CCCCO2)nn1] |
| I-170 | 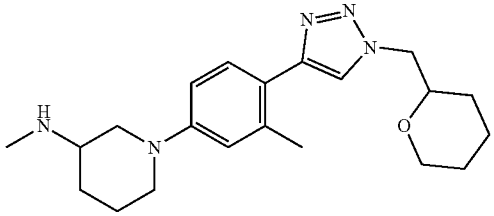 [SMILES: CNC1CCCN(c2ccc(-c3cn(CC4CCCCO4)nn3)c(C)c2)C1] |
| I-183 | 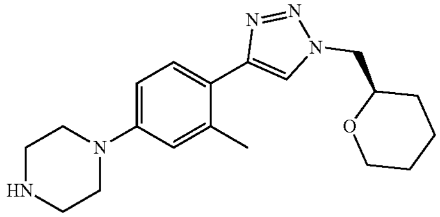 [SMILES: Cc1cc(N2CCNCC2)ccc1-c1cn(C[C@H]2CCCCO2)nn1] |
| I-184 | 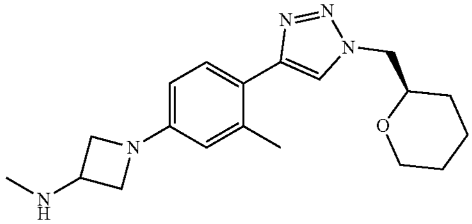 [SMILES: CNC1CN(c2ccc(-c3cn(C[C@H]4CCCCO4)nn3)c(C)c2)C1] |
| I-202 | 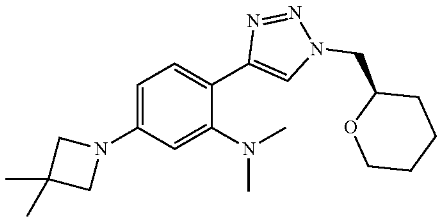 [SMILES: CN(C)c1cc(N2CC(C)(C)C2)ccc1-c1cn(C[C@H]2CCCCO2)nn1] |
| I-213 | 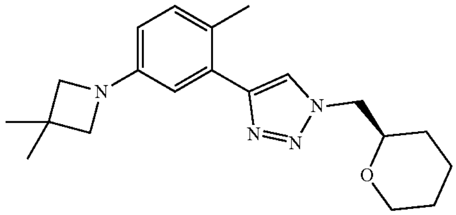 [SMILES: Cc1ccc(N2CC(C)(C)C2)cc1-c1cn(C[C@H]2CCCCO2)nn1] |
-continued
| Compound | Structure |
|---|---|
| I-223 | 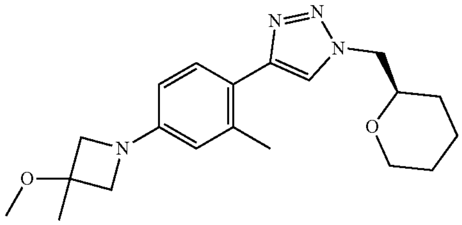 [SMILES: COC1(C)CN(c2ccc(-c3cn(C[C@H]4CCCCO4)nn3)c(C)c2)C1] |
| I-253 | 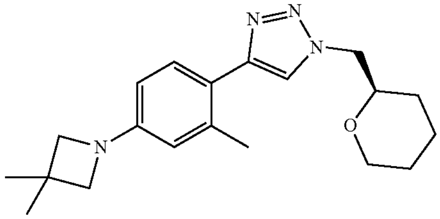 [SMILES: Cc1cc(N2CC(C)(C)C2)ccc1-c1cn(C[C@H]2CCCCO2)nn1] |
| I-254 | 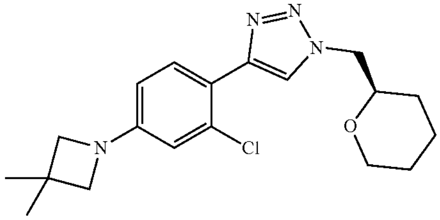 [SMILES: CC1(C)CN(c2ccc(-c3cn(C[C@H]4CCCCO4)nn3)c(Cl)c2)C1] |
| I-255 | 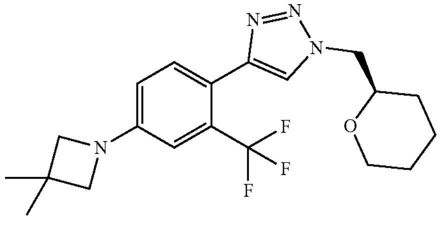 [SMILES: CC1(C)CN(c2ccc(-c3cn(C[C@H]4CCCCO4)nn3)c(C(F)(F)F)c2)C1] |
| I-256 | 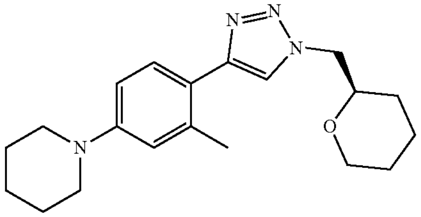 [SMILES: Cc1cc(N2CCCCC2)ccc1-c1cn(C[C@H]2CCCCO2)nn1] |
| I-260 | 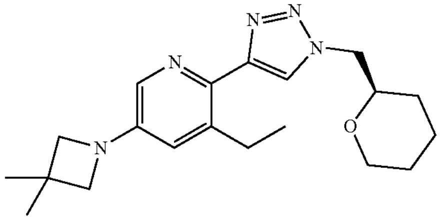 [SMILES: CCc1cc(N2CC(C)(C)C2)cnc1-c1cn(C[C@H]2CCCCO2)nn1] |

| Compound | Structure |
|---|---|
| I-263 | 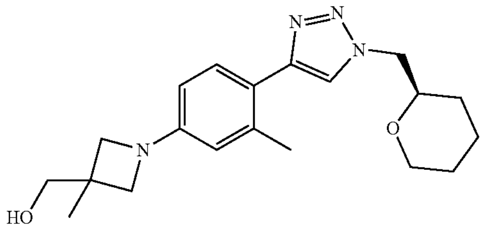 [SMILES: Cc1cc(N2CC(C)(CO)C2)ccc1-c1cn(C[C@H]2CCCCO2)nn1] |
| I-264 | 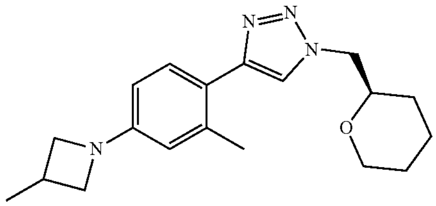 [SMILES: Cc1cc(N2CC(C)C2)ccc1-c1cn(C[C@H]2CCCCO2)nn1] |
| I-271 | 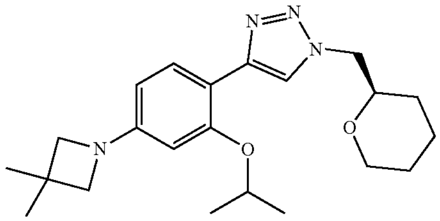 [SMILES: CC(C)Oc1cc(N2CC(C)(C)C2)ccc1-c1cn(C[C@H]2CCCCO2)nn1] |
| I-279 | 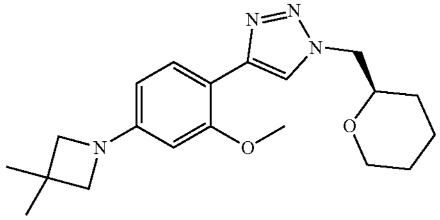 [SMILES: COc1cc(N2CC(C)(C)C2)ccc1-c1cn(C[C@H]2CCCCO2)nn1] |
| I-280 | 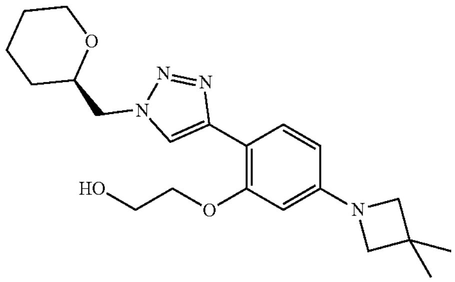 [SMILES: CC1(C)CN(c2ccc(-c3cn(C[C@H]4CCCCO4)nn3)c(OCCO)c2)C1] |
| I-376 | 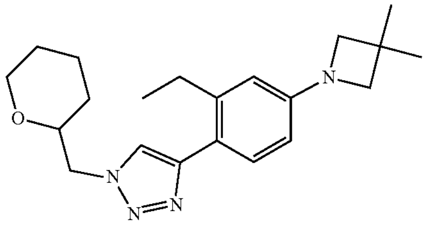 [SMILES: CCc1cc(N2CC(C)(C)C2)ccc1-c1cn(CC2CCCCO2)nn1] |
| Compound | Structure |
|---|---|
| I-377 | 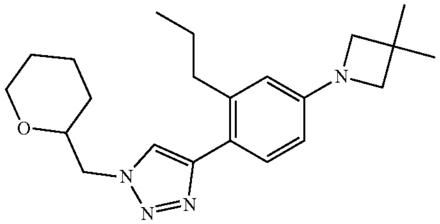 [SMILES: CCCc1cc(N2CC(C)(C)C2)ccc1-c1cn(CC2CCCCO2)nn1] |
| I-378 | 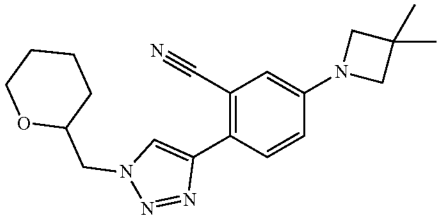 [SMILES: CC1(C)CN(c2ccc(-c3cn(CC4CCCCO4)nn3)c(C#N)c2)C1] |
| I-379 | 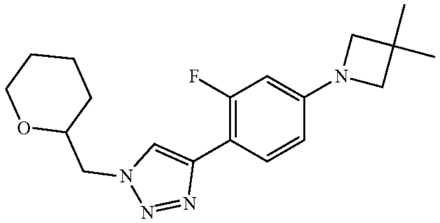 [SMILES: CC1(C)CN(c2ccc(-c3cn(CC4CCCCO4)nn3)c(F)c2)C1] |
| I-380 | 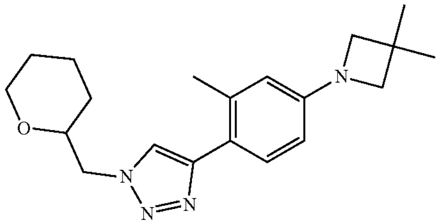 [SMILES: Cc1cc(N2CC(C)(C)C2)ccc1-c1cn(CC2CCCCO2)nn1] |
| I-381 | 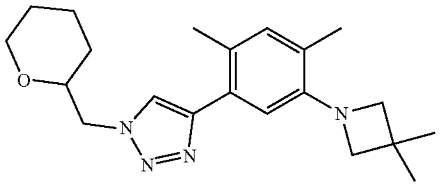 |
| I-384 | 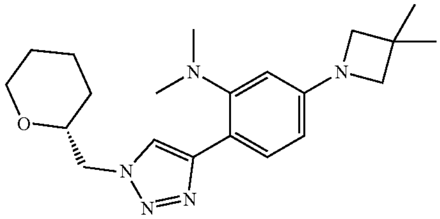 |
| I-385 | 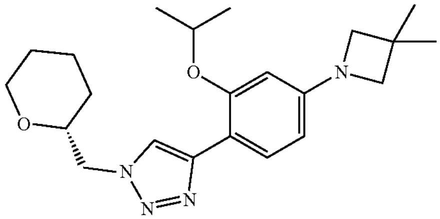 |

-continued
| Compound | Structure |
|---|---|
| I-386 | 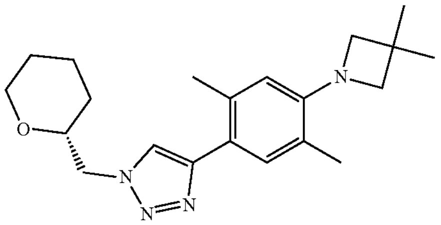 |
| I-387 | 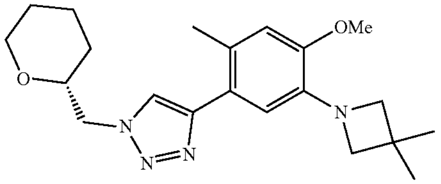 |
| I-388 | 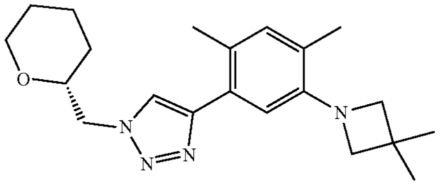 |
| I-390 | 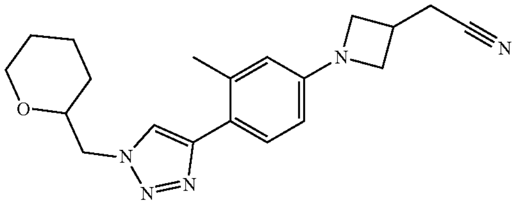 |
| I-409 | 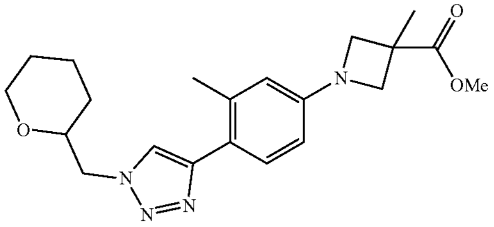 [SMILES: COC(=O)C1(C)CN(c2ccc(-c3cn(CC4CCCCO4)nn3)c(C)c2)C1] |
| I-421 | 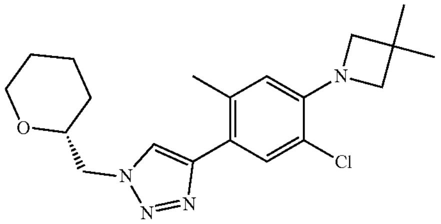 |
| I-422 | 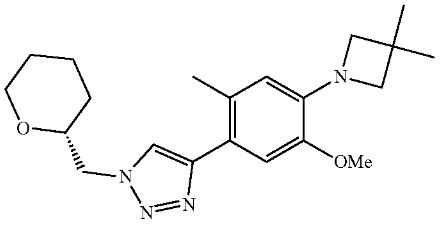 [SMILES: COc1cc(-c2cn(C[C@H]3CCCCO3)nn2)c(C)cc1N1CC(C)(C)C1] |
-continued
| Compound | Structure |
|---|---|
| I-428 | 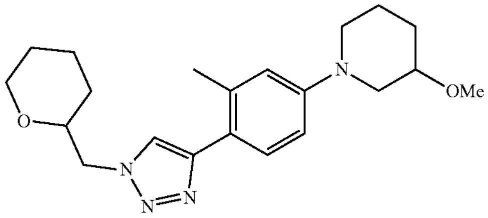 [SMILES: COC1CCCN(c2ccc(-c3cn(CC4CCCCO4)nn3)c(C)c2)C1] |
| I-431 | 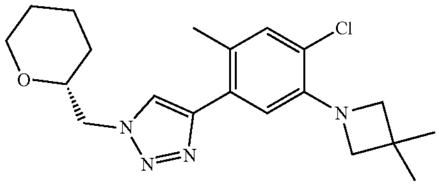 |
| I-436 | 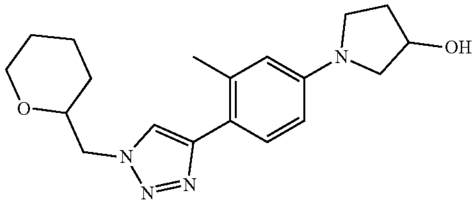 [SMILES: Cc1cc(N2CCC(O)C2)ccc1-c1cn(CC2CCCCO2)nn1] |
| I-437 | 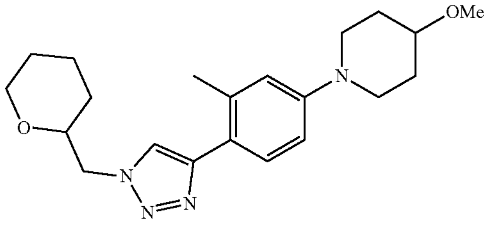 [SMILES: COC1CCN(c2ccc(-c3cn(CC4CCCCO4)nn3)c(C)c2)CC1] |
| I-439 | 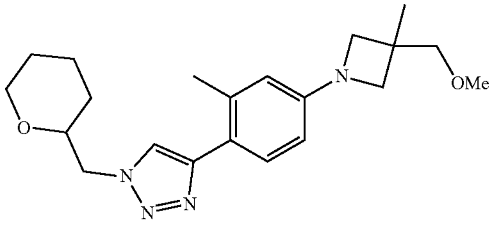 [SMILES: COCC1(C)CN(c2ccc(-c3cn(CC4CCCCO4)nn3)c(C)c2)C1] |
| I-442 | 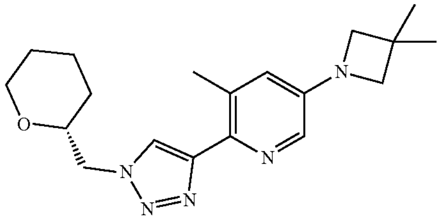 [SMILES: Cc1cc(N2CC(C)(C)C2)cnc1-c1cn(C[C@H]2CCCCO2)nn1] |
| I-445 | 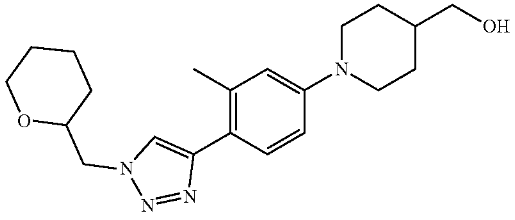 [SMILES: Cc1cc(N2CCC(CO)CC2)ccc1-c1cn(CC2CCCCO2)nn1] |

-continued
| Compound | Structure |
|---|---|
| I-446 | 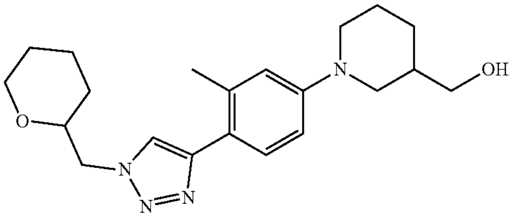 [SMILES: Cc1cc(N2CCCC(CO)C2)ccc1-c1cn(CC2CCCCO2)nn1] |
| I-447 | 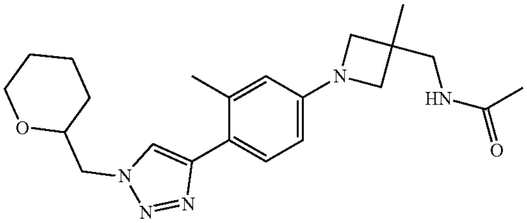 [SMILES: CC(=O)NCC1(C)CN(c2ccc(-c3cn(CC4CCCCO4)nn3)c(C)c2)C1] |
| I-448 | 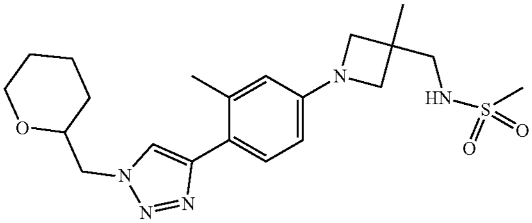 [SMILES: Cc1cc(N2CC(C)(CNS(C)(=O)=O)C2)ccc1-c1cn(CC2CCCCO2)nn1] |
| I-449 | 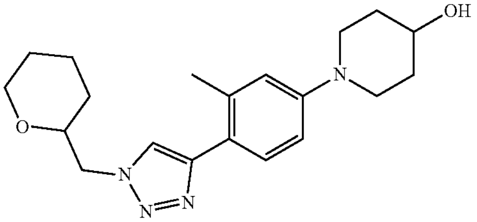 [SMILES: Cc1cc(N2CCC(O)CC2)ccc1-c1cn(CC2CCCCO2)nn1] |
| I-450 | 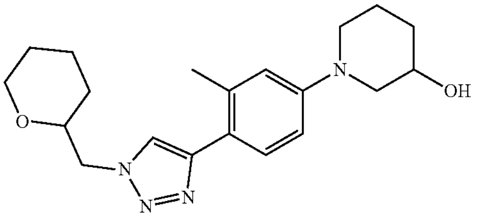 [SMILES: Cc1cc(N2CCCC(O)C2)ccc1-c1cn(CC2CCCCO2)nn1] |
| I-461 | 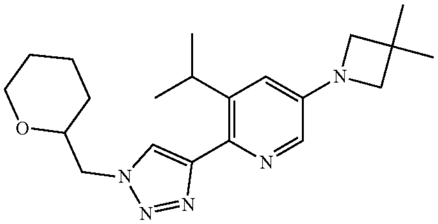 [SMILES: CC(C)c1cc(N2CC(C)(C)C2)cnc1-c1cn(CC2CCCCO2)nn1] |
| I-463 | 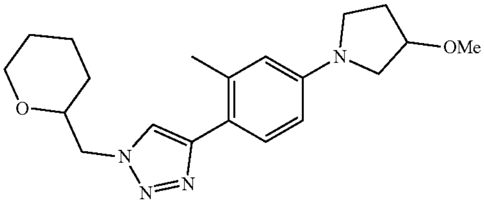 [SMILES: COC1CCN(c2ccc(-c3cn(CC4CCCCO4)nn3)c(C)c2)C1] |
| I-470 | 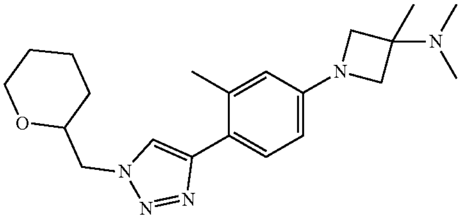 [SMILES: Cc1cc(N2CC(C)(N(C)C)C2)ccc1-c1cn(CC2CCCCO2)nn1] |
| I-471 | 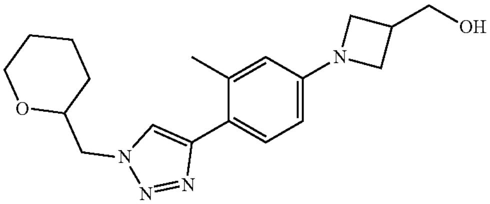 [SMILES: Cc1cc(N2CC(CO)C2)ccc1-c1cn(CC2CCCCO2)nn1] |
| I-472 | 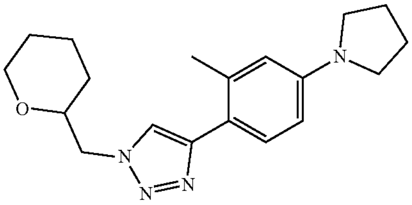 [SMILES: Cc1cc(N2CCCC2)ccc1-c1cn(CC2CCCCO2)nn1] |
| I-477 | 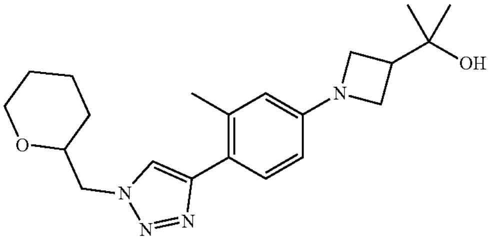 [SMILES: Cc1cc(N2CC(C(C)(C)O)C2)ccc1-c1cn(CC2CCCCO2)nn1] |
| I-484 | 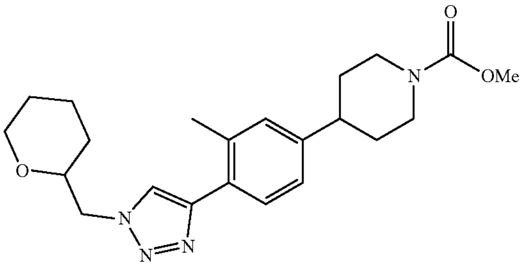 [SMILES: COC(=O)N1CCC(c2ccc(-c3cn(CC4CCCCO4)nn3)c(C)c2)CC1] |

-continued
| Compound | Structure |
|---|---|
| I-485 | 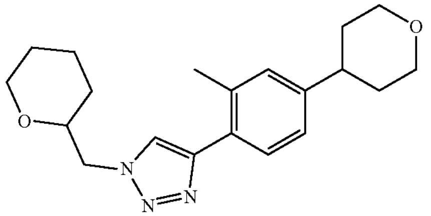 [SMILES: Cc1cc(C2CCOCC2)ccc1-c1cn(CC2CCCCO2)nn1] |
| I-486 | 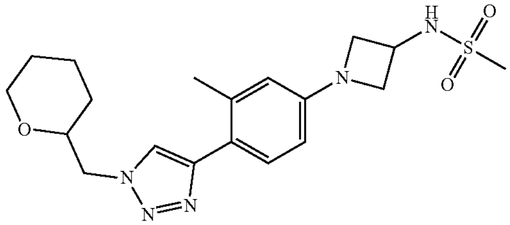 [SMILES: Cc1cc(N2CC(NS(C)(=O)=O)C2)ccc1-c1cn(CC2CCCCO2)nn1] |
| I-487 | 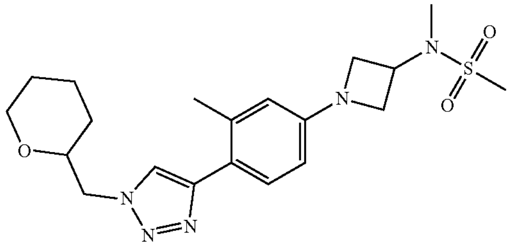 [SMILES: Cc1cc(N2CC(N(C)S(C)(=O)=O)C2)ccc1-c1cn(CC2CCCCO2)nn1] |
| I-495 | 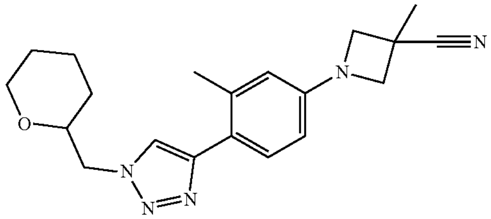 [SMILES: Cc1cc(N2CC(C)(C#N)C2)ccc1-c1cn(CC2CCCCO2)nn1] |
| I-499 | 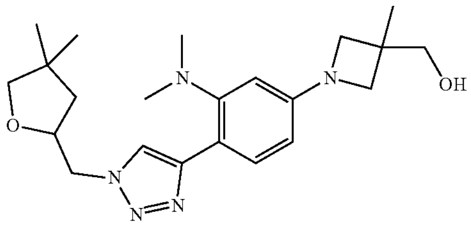 [SMILES: CN(C)c1cc(N2CC(C)(CO)C2)ccc1-c1cn(CC2CC(C)(C)CO2)nn1] |
| I-500 | 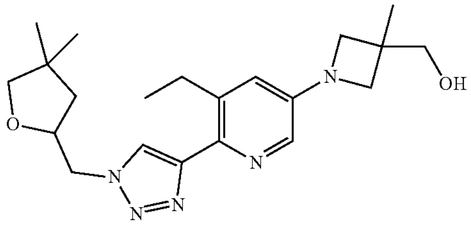 [SMILES: CCc1cc(N2CC(C)(CO)C2)cnc1-c1cn(CC2CC(C)(C)CO2)nn1] |
-continued
| Compound | Structure |
|---|---|
| I-501 | 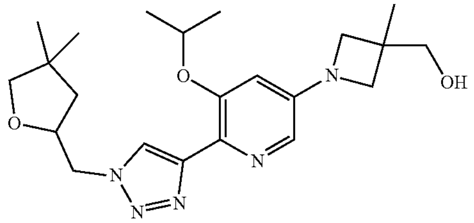 [SMILES: CC(C)Oc1cc(N2CC(C)(CO)C2)cnc1-c1cn(CC2CC(C)(C)CO2)nn1] |
| I-506 | 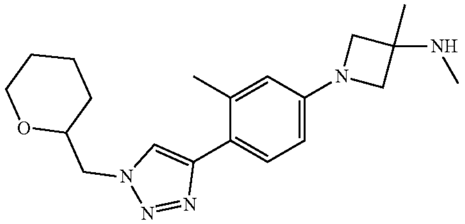 [SMILES: CNC1(C)CN(c2ccc(-c3cn(CC4CCCCO4)nn3)c(C)c2)C1] |
| I-507 | 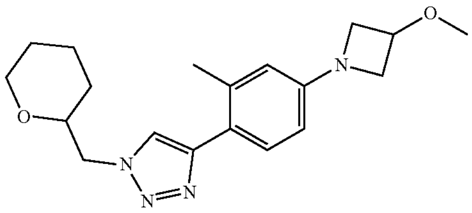 [SMILES: COC1CN(c2ccc(-c3cn(CC4CCCCO4)nn3)c(C)c2)C1] |
| I-508 | 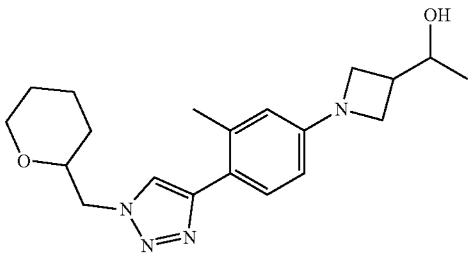 [SMILES: Cc1cc(N2CC(C(C)O)C2)ccc1-c1cn(CC2CCCCO2)nn1] |
| I-519 | 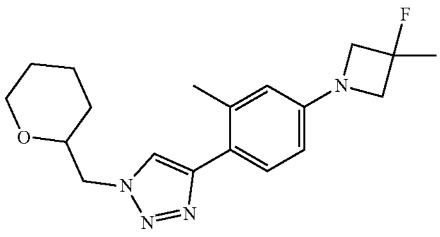 [SMILES: Cc1cc(N2CC(C)(F)C2)ccc1-c1cn(CC2CCCCO2)nn1] |
| I-520 | 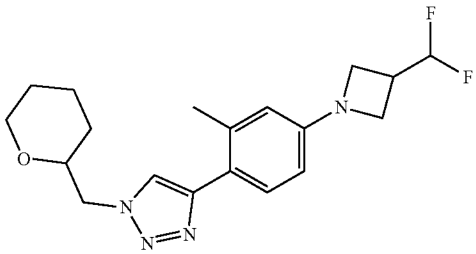 [SMILES: Cc1cc(N2CC(C(F)F)C2)ccc1-c1cn(CC2CCCCO2)nn1] |

-continued
| Compound | Structure |
|---|---|
| I-524 | 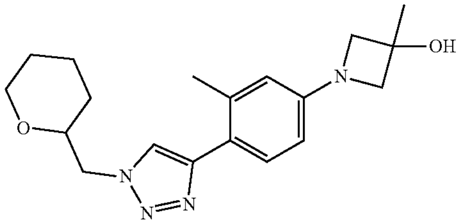 [SMILES: Cc1cc(N2CC(C)(O)C2)ccc1-c1cn(CC2CCCCO2)nn1] |
| I-529 | 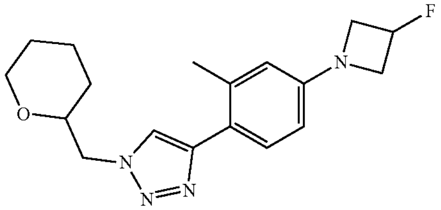 [SMILES: Cc1cc(N2CC(F)C2)ccc1-c1cn(CC2CCCCO2)nn1] |
| I-544 | 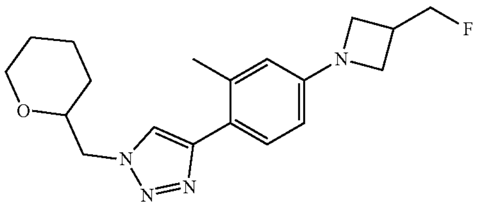 [SMILES: Cc1cc(N2CC(CF)C2)ccc1-c1cn(CC2CCCCO2)nn1] |
| I-555 | 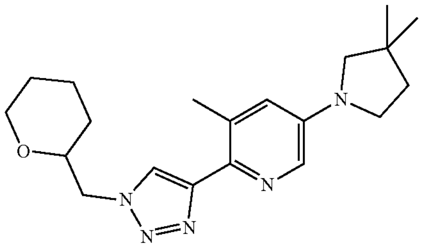 [SMILES: Cc1cc(N2CCC(C)(C)C2)cnc1-c1cn(CC2CCCCO2)nn1] |
| I-584 | 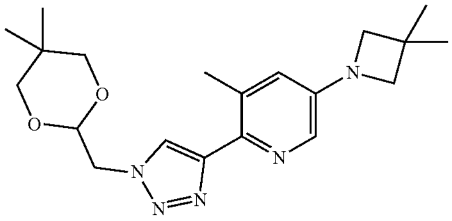 |
| I-585 | 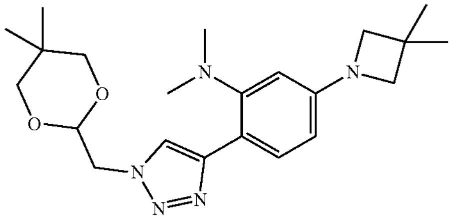 |
-continued
| Compound | Structure |
|---|---|
| I-588 | 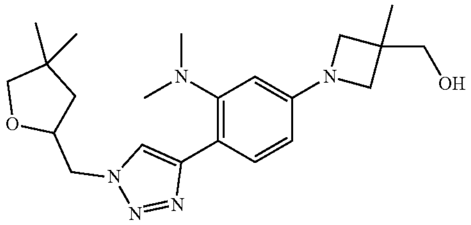 Enantiomer I |
| I-589 | 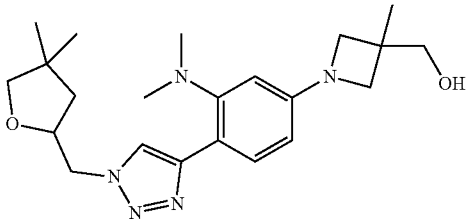 Enantiomer II |
| I-595 | 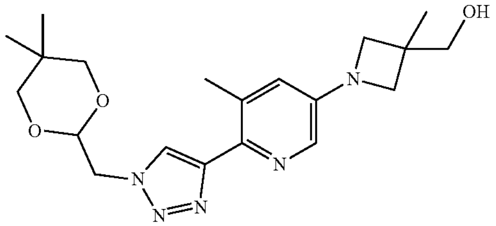 [SMILES: Cc1cc(N2CC(C)(CO)C2)cnc1-c1cn(CC2OCC(C)(C)CO2)nn1] |
| I-600 | 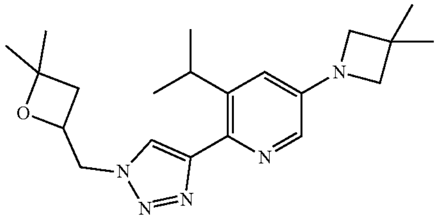 |
| I-609 | 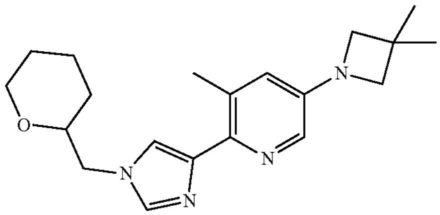 [SMILES: Cc1cc(N2CC(C)(C)C2)cnc1-c1cn(CC2CCCCO2)cn1] |
| I-614 | 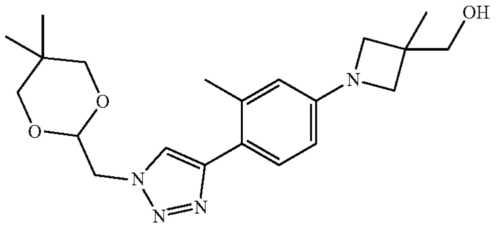 [SMILES: Cc1cc(N2CC(C)(CO)C2)ccc1-c1cn(CC2OCC(C)(C)CO2)nn1] |

-continued
| Compound | Structure |
|---|---|
| I-618 | 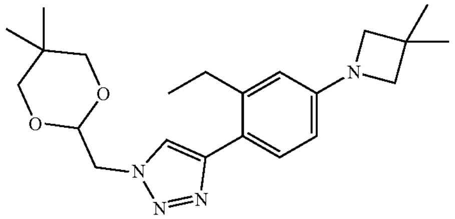 |
| I-626 | 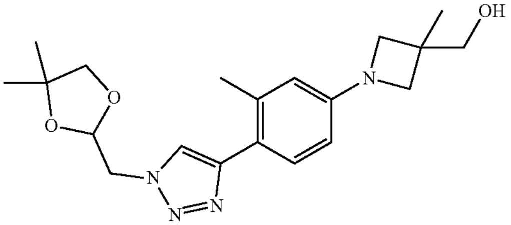 [SMILES: Cc1cc(N2CC(C)(CO)C2)ccc1-c1cn(CC2OCC(C)(C)O2)nn1] |
| I-630 | 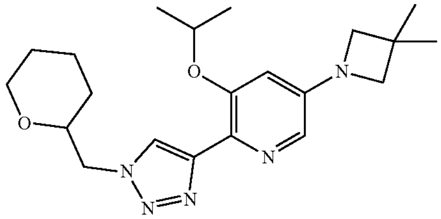 [SMILES: CC(C)Oc1cc(N2CC(C)(C)C2)cnc1-c1cn(CC2CCCCO2)nn1] |
| I-641 | 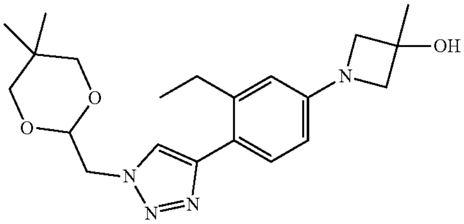 [SMILES: CCc1cc(N2CC(C)(O)C2)ccc1-c1cn(CC2OCC(C)(C)CO2)nn1] |
| I-654 | 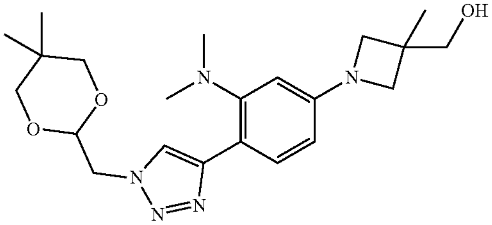 [SMILES: CN(C)c1cc(N2CC(C)(CO)C2)ccc1-c1cn(CC2OCC(C)(C)CO2)nn1] |
| I-664 | 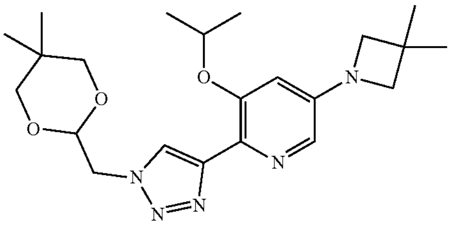 |
-continued
| Compound | Structure |
|---|---|
| I-665 | 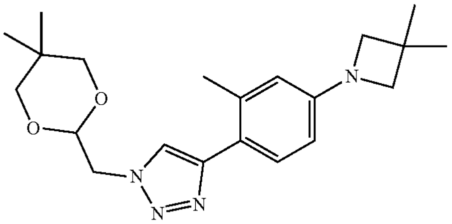 |
| I-667 | 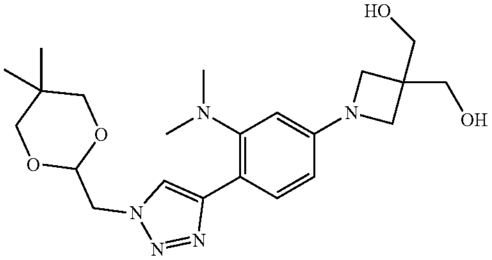 [SMILES: CN(C)c1cc(N2CC(CO)(CO)C2)ccc1-c1cn(CC2OCC(C)(C)CO2)nn1] |
| I-677 | 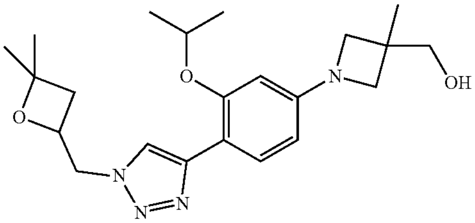 [SMILES: CC(C)Oc1cc(N2CC(C)(CO)C2)ccc1-c1cn(CC2CC(C)(C)O2)nn1] |
| I-678 | 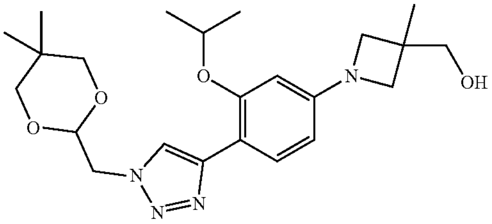 [SMILES: CC(C)Oc1cc(N2CC(C)(CO)C2)ccc1-c1cn(CC2OCC(C)(C)CO2)nn1] |
| I-685 | 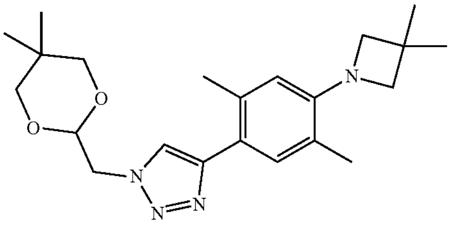 |
| I-687 | 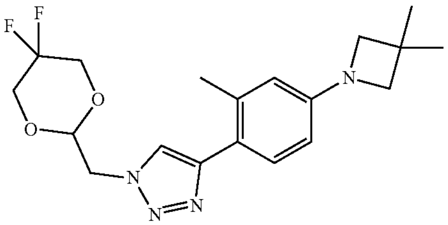 [SMILES: Cc1cc(N2CC(C)(C)C2)ccc1-c1cn(CC2OCC(F)(F)CO2)nn1] |

-continued
| Compound | Structure |
|---|---|
| I-694 | 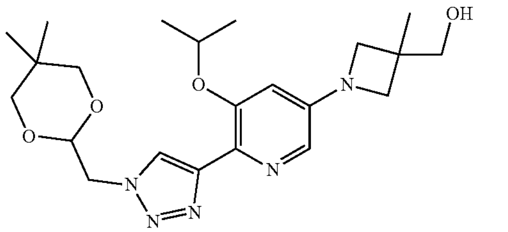 [SMILES: CC(C)Oc1cc(N2CC(C)(CO)C2)cnc1-c1cn(CC2OCC(C)(C)CO2)nn1] |
| I-696 | 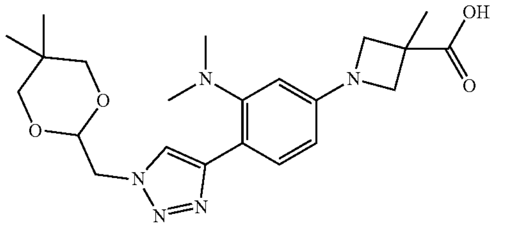 [SMILES: CN(C)c1cc(N2CC(C)(C(=O)O)C2)ccc1-c1cn(CC2OCC(C)(C)CO2)nn1] |
| I-706 | 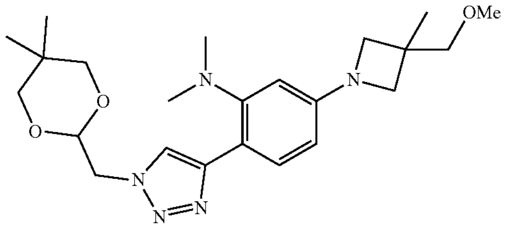 [SMILES: COCC1(C)CN(c2ccc(-c3cn(CC4OCC(C)(C)CO4)nn3)c(N(C)C)c2)C1] |
| I-707 | 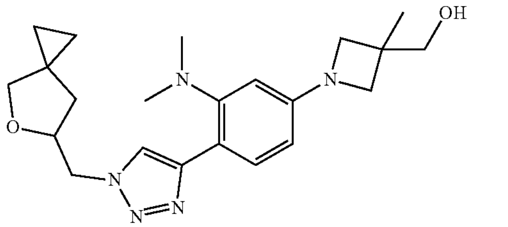 [SMILES: CN(C)c1cc(N2CC(C)(CO)C2)ccc1-c1cn(CC2CC3(CC3)CO2)nn1] |
| I-710 | 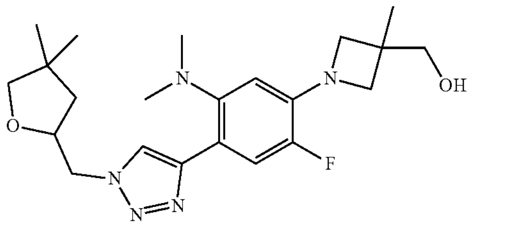 [SMILES: CN(C)c1cc(N2CC(C)(CO)C2)c(F)cc1-c1cn(CC2CC(C)(C)CO2)nn1] |
| I-711 | 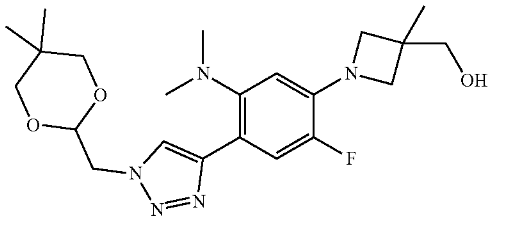 [SMILES: CN(C)c1cc(N2CC(C)(CO)C2)c(F)cc1-c1cn(CC2OCC(C)(C)CO2)nn1] |
-continued
| Compound | Structure |
|---|---|
| I-726 | 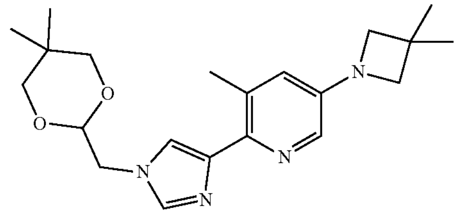 |
| I-728 | 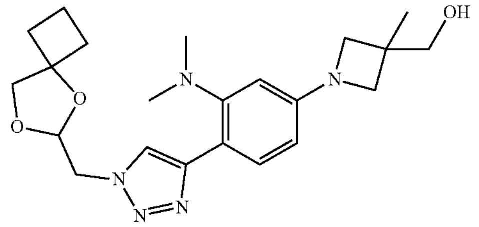 [SMILES: CN(C)c1cc(N2CC(C)(CO)C2)ccc1-c1cn(CC2OCC3(CCC3)O2)nn1] |
| I-729 | 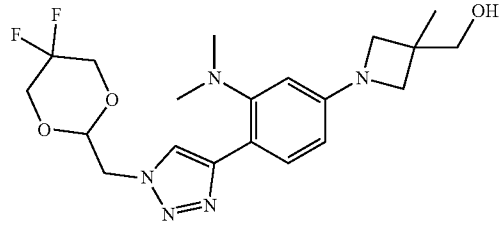 [SMILES: CN(C)c1cc(N2CC(C)(CO)C2)ccc1-c1cn(CC2OCC(F)(F)CO2)nn1] |
| I-730 | 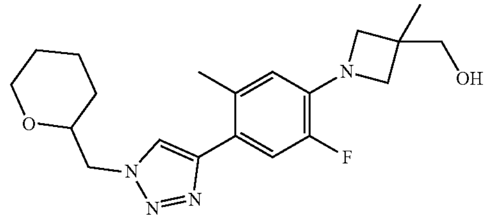 [SMILES: Cc1cc(N2CC(C)(CO)C2)c(F)cc1-c1cn(CC2CCCCO2)nn1] |
| I-735 | 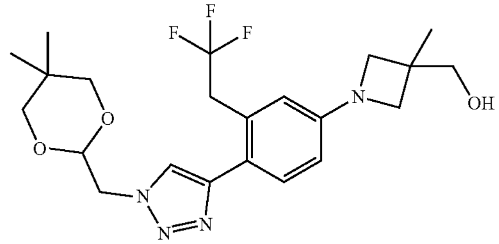 [SMILES: CC1(C)COC(Cn2cc(-c3ccc(N4CC(C)(CO)C4)cc3CC(F)(F)F)nn2)OC1] |
| I-740 | 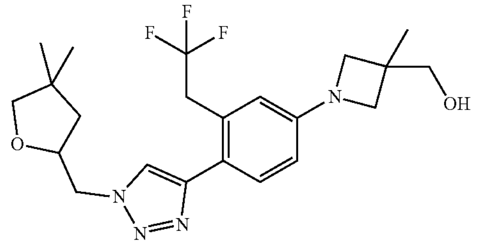 [SMILES: CC1(C)COC(Cn2cc(-c3ccc(N4CC(C)(CO)C4)cc3CC(F)(F)F)nn2)C1] |

-continued
| Compound | Structure |
|---|---|
| I-748 | 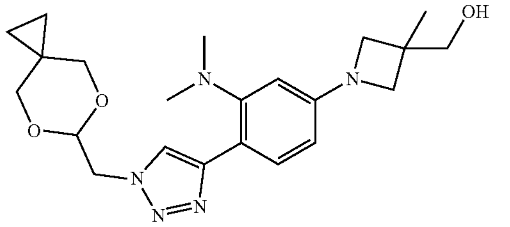 [SMILES: CN(C)c1cc(N2CC(C)(CO)C2)ccc1-c1cn(CC2OCC3(CC3)CO2)nn1] |
| I-754 | 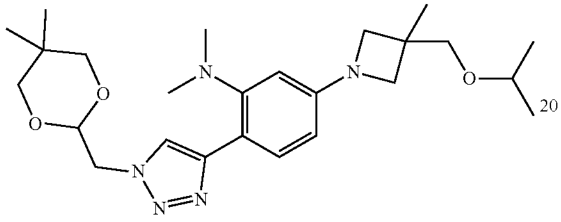 |
| I-755 | 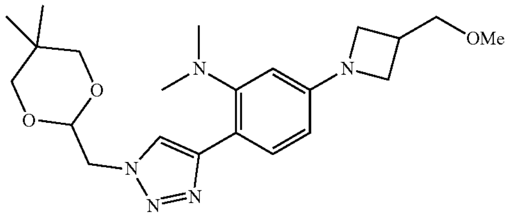 [SMILES: COCC1CN(c2ccc(-c3cn(CC4OCC(C)(C)CO4)nn3)c(N(C)C)c2)C1] |
| I-765 | 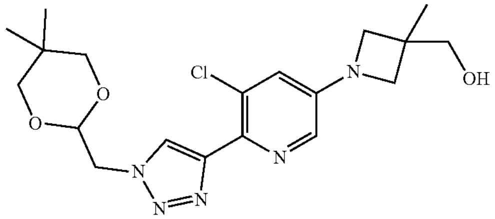 [SMILES: CC1(C)COC(Cn2cc(-c3ncc(N4CC(C)(CO)C4)cc3Cl)nn2)OC1] |
| I-776 | 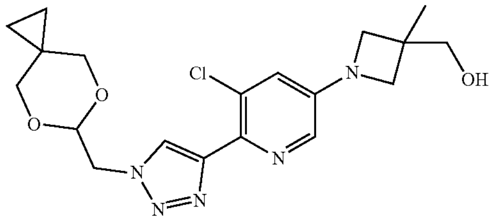 [SMILES: CC1(CO)CN(c2cnc(-c3cn(CC4OCC5(CC5)CO4)nn3)c(Cl)c2)C1] |
| I-784 | 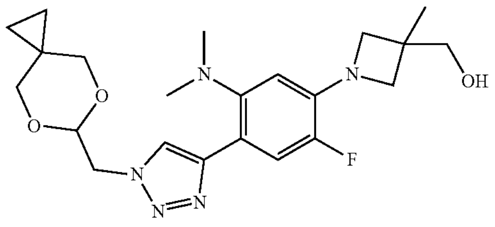 [SMILES: CN(C)c1cc(N2CC(C)(CO)C2)c(F)cc1-c1cn(CC2OCC3(CC3)CO2)nn1] |
-continued
| Compound | Structure |
|---|---|
| I-786 | 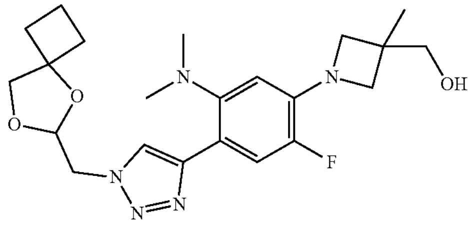 [SMILES: CN(C)c1cc(N2CC(C)(CO)C2)c(F)cc1-c1cn(CC2OCC3(CCC3)O2)nn1] |
| I-796 | 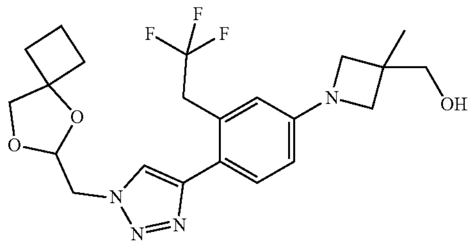 [SMILES: CC1(CO)CN(c2ccc(-c3cn(CC4OCC5(CCC5)O4)nn3)c(CC(F)(F)F)c2)C1] |
| I-800 | 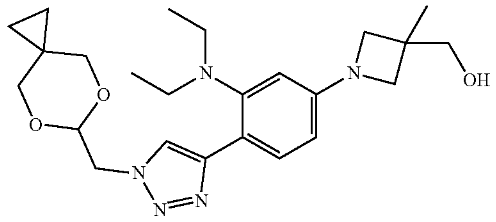 [SMILES: CCN(CC)c1cc(N2CC(C)(CO)C2)ccc1-c1cn(CC2OCC3(CC3)CO2)nn1] |
| I-801 | 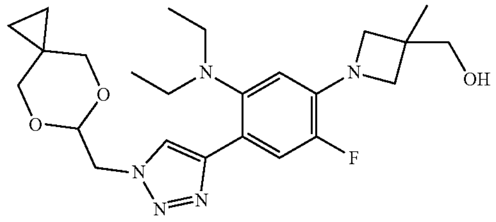 [SMILES: CCN(CC)c1cc(N2CC(C)(CO)C2)c(F)cc1-c1cn(CC2OCC3(CC3)CO2)nn1] |
| I-804 | 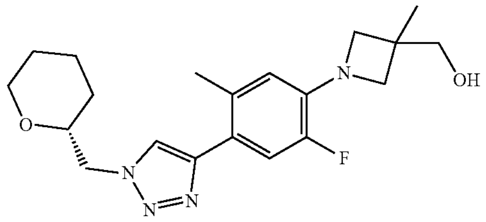 |
| I-805 | 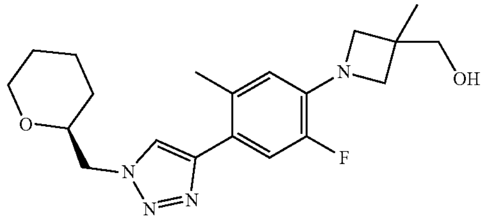 [SMILES: Cc1cc(N2CC(C)(CO)C2)c(F)cc1-c1cn(C[C@@H]2CCCCO2)nn1] |

-continued

| Compound | Structure |
|---|---|
| I-807 | 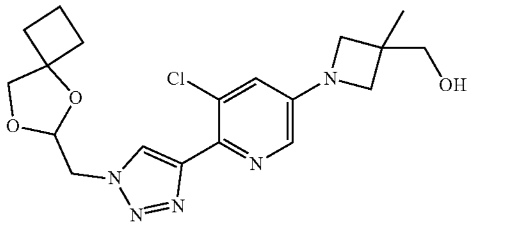 [SMILES: CC1(CO)CN(c2cnc(-c3cn(CC4OCC5(CCC5)O4)nn3)c(Cl)c2)C1] |
| I-809 | 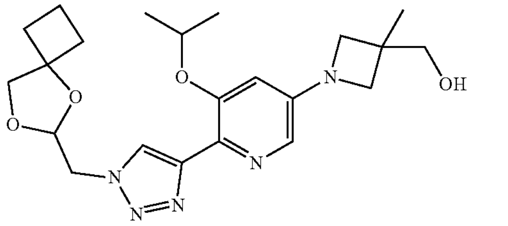 [SMILES: CC(C)Oc1cc(N2CC(C)(CO)C2)cnc1-c1cn(CC2OCC3(CCC3)O2)nn1] |
| I-816 | 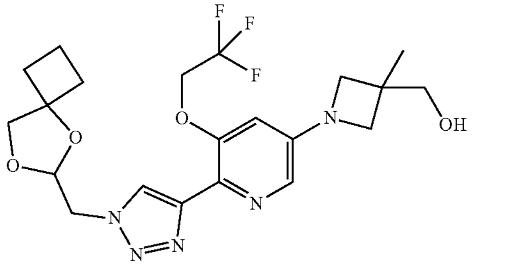 [SMILES: CC1(CO)CN(c2cnc(-c3cn(CC4OCC5(CCC5)O4)nn3)c(OCC(F)(F)F)c2)C1] |
| I-860 | 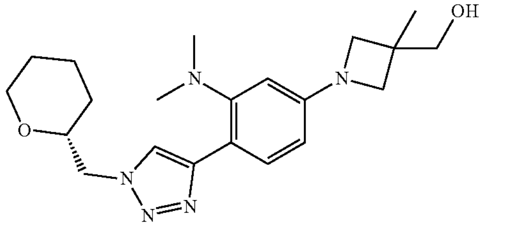 [SMILES: CN(C)c1cc(N2CC(C)(CO)C2)ccc1-c1cn(C[C@H]2CCCCO2)nn1] |
| I-863 | 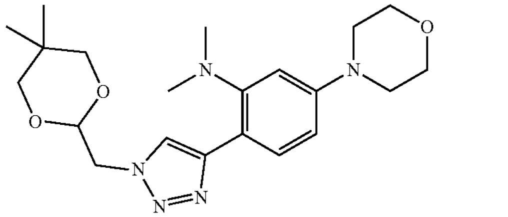 [SMILES: CN(C)c1cc(N2CCOCC2)ccc1-c1cn(CC2OCC(C)(C)CO2)nn1] |
| I-864 | 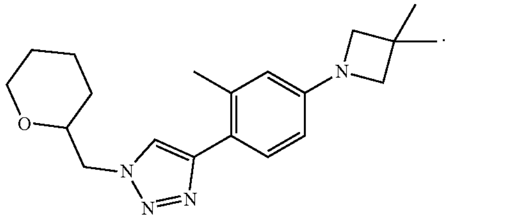 [SMILES: Cc1cc(N2CC(C)(C)C2)ccc1-c1cn(CC2CCCCO2)nn1] |

18. A pharmaceutical composition comprising a compound according to claim 1 or a pharmaceutically acceptable salt thereof, and a pharmaceutically acceptable carrier, adjuvant, or vehicle.

19. A method of inhibiting GPR84 in a biological sample comprising contacting the sample with the compound of claim 1 or a pharmaceutically acceptable salt thereof.

20. A method of treating a GPR84-mediated disorder, disease, or condition in a patient comprising administering to said patient in need thereof the compound of claim 1.

21. The method of claim 20, wherein the disorder, disease, or condition is a proliferative disorder, a fibrotic disease, an infectious disease, an autoimmune disease, an endocrine and/or metabolic disease, a cardiovascular disease, a disease involving impairment of immune cell function, a neuroinflammatory condition, a neurodegenerative condition, an inflammatory condition, multiple sclerosis, or pain.

22. The method of claim 21, wherein the disorder, disease, or condition is an inflammatory condition selected from rheumatoid arthritis, chronic obstructive pulmonary disease, asthma, idiopathic pulmonary fibrosis (IPF), psoriasis, Crohn's disease, ulcerative colitis, uveitis, periodontitis, esophagitis, gastroesophageal reflux disease (GERD), inflammatory bowel disease, and pyoderma gangrenosum.

23. The method of claim 20, wherein the disorder, disease, or condition is idiopathic pulmonary fibrosis (IPF).

24. A method of increasing the efficacy of vaccination in a patient comprising administering to said patient the compound of claim 1 or a pharmaceutically acceptable salt thereof as an adjuvant.

25. A compound of formula I *:

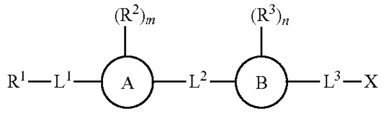

or a pharmaceutically acceptable salt thereof, wherein:

Ring A together with $(R^2)_m$ is selected from

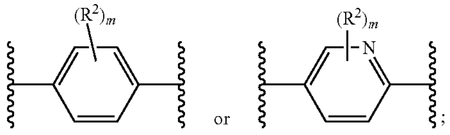

Ring B together with $(R^3)_n$ is selected from

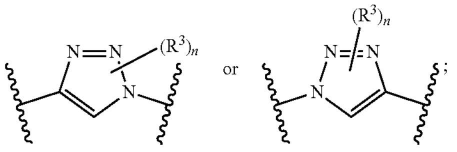

$R^1$ is selected from cyclopropyl; a 6 membered monocyclic heteroaryl ring having 1-4 heteroatoms independently selected from nitrogen, oxygen, and sulfur; a 4 membered saturated or partially unsaturated monocyclic heterocyclic ring having 1-2 heteroatoms independently selected from nitrogen, oxygen, and sulfur; phenyl; and a $C_{1-3}$ aliphatic; each of which is substituted with p instances of $R^4$;

each instance of $R^2$ is independently hydrogen, deuterium, halogen, —CN, —$NO_2$, —OR, —SR, —$NR_2$, —$S(O)_2R$, —$S(O)_2NR_2$, —S(O)R, —$S(O)NR_2$, —$CF_2R$, —$CF_3$, —$CR_2$ (CN), —$CR_2$ (OR), —$CR_2$ ($NR_2$), —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, —N(R)C(NR)$NR_2$, —N(R)$NR_2$, —N(R)CN, —$CH_3$, —$CH_2CH_3$, —OH $CH(CH_3)(CH_3)$, —$CH_2CF_3$, —$OCF_3$, —$OCHF_2$, —$OCH_2CF_3$, or, each instance of $R^4$ and $R^5$ is independently hydrogen, deuterium, halogen, —$CH_3$, —CN, —$NO_2$, —OR, —$NR_2$, —$S(O)_2R$, —$S(O)_2NR_2$, —S(O)R, —S(O)$NR_2$, —$CF_2R$, —$CF_3$, —$CR_2$(CN), —$CR_2$(OR), —$CR_2$($NR_2$), —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, —N(R)C(NR)$NR_2$, —N(R)$NR_2$, or —N(R)CN;

$R^3$ is hydrogen;

$L^1$ is

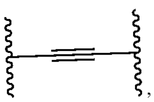,
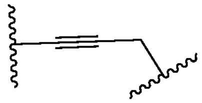,
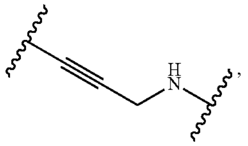, or
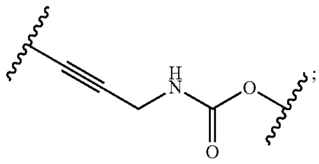;

$L^2$ is a covalent bond;

$L^3$ is

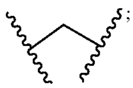 [SMILES: *C*];

X is selected from

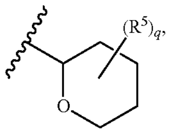,
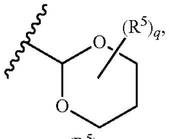,
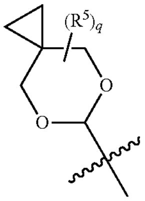, or
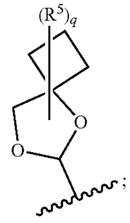;

each instance of R is independently hydrogen or $C_{1-3}$ aliphatic;

m is 0, 1, or 2;

n is 0, 1, 2, 3, or 4;

p is 0, 1, or 2; and q is 0, 1, or 2.

26. A compound selected from the following or a pharmaceutically acceptable salt thereof:

| Compound No. | Structure |
|---|---|
| I-24 | 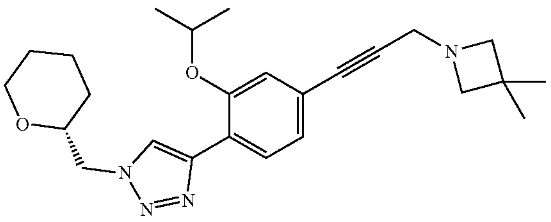 [SMILES: CC(C)Oc1cc(C#CCN2CC(C)(C)C2)ccc1-c1cn(C[C@H]2CCCCO2)nn1] |
| I-28 | 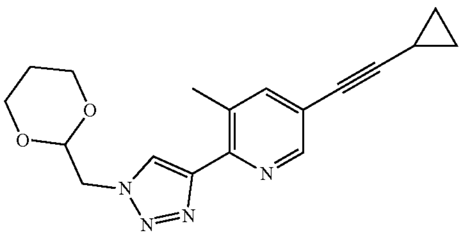 [SMILES: Cc1cc(C#CC2CC2)cnc1-c1cn(CC2OCCCO2)nn1] |

-continued
| Compound No. | Structure |
|---|---|
| I-29 | 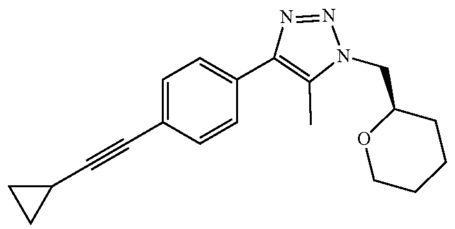 [SMILES: Cc1c(-c2ccc(C#CC3CC3)cc2)nnn1C[C@H]1CCCCO1] |
| I-34 | 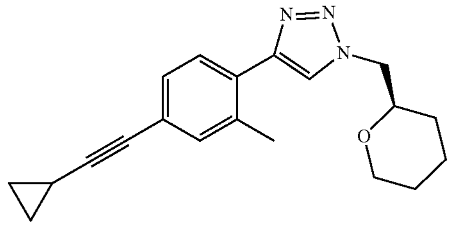 [SMILES: Cc1cc(C#CC2CC2)ccc1-c1cn(C[C@H]2CCCCO2)nn1] |
| I-35 | 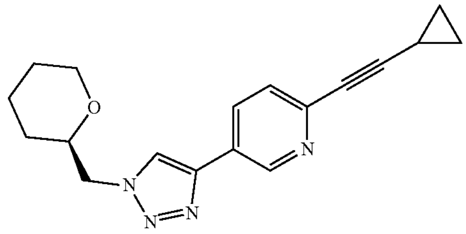 [SMILES: C(#CC1CC1)c1ccc(-c2cn(C[C@H]3CCCCO3)nn2)cn1] |
| I-40 | 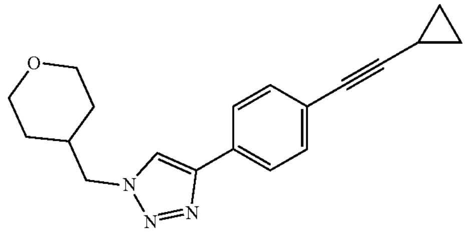 [SMILES: C(#CC1CC1)c1ccc(-c2cn(CC3CCOCC3)nn2)cc1] |
| I-42 | 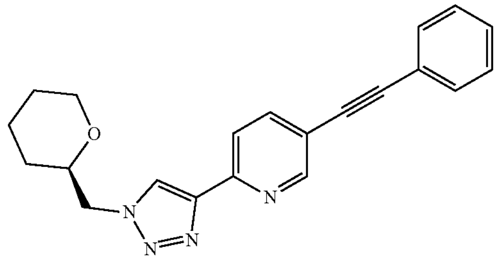 [SMILES: C(#Cc1ccc(-c2cn(C[C@H]3CCCCO3)nn2)nc1)c1ccccc1] |
| I-43 | 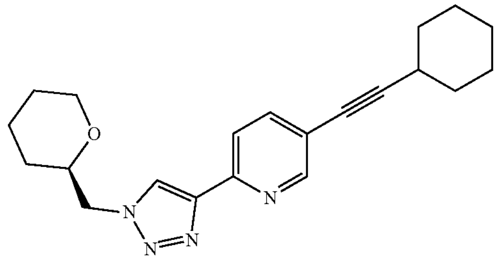 [SMILES: C(#CC1CCCCC1)c1ccc(-c2cn(C[C@H]3CCCCO3)nn2)nc1] |

-continued
| Compound No. | Structure |
|---|---|
| I-44 | 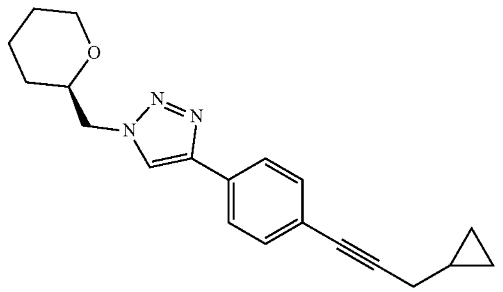 [SMILES: C(#Cc1ccc(-c2cn(C[C@H]3CCCCO3)nn2)cc1)CC1CC1] |
| I-45 | 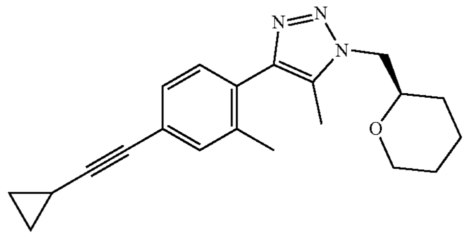 [SMILES: Cc1cc(C#CC2CC2)ccc1-c1nnn(C[C@H]2CCCCO2)c1C] |
| I-65 | 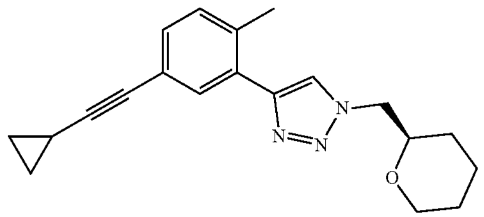 [SMILES: Cc1ccc(C#CC2CC2)cc1-c1cn(C[C@H]2CCCCO2)nn1] |
| I-68 | 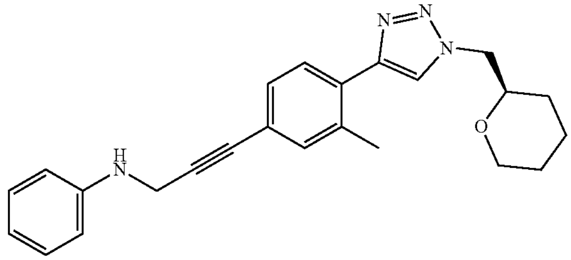 [SMILES: Cc1cc(C#CCNc2ccccc2)ccc1-c1cn(C[C@H]2CCCCO2)nn1] |
| I-71 | 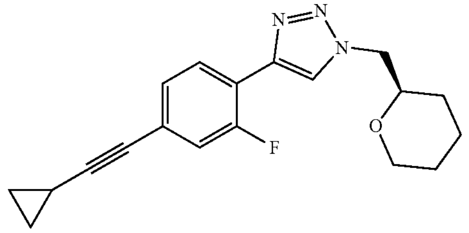 [SMILES: Fc1cc(C#CC2CC2)ccc1-c1cn(C[C@H]2CCCCO2)nn1] |
| I-77 | 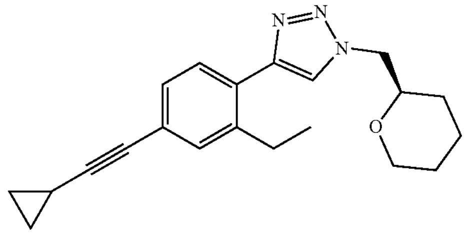 [SMILES: CCc1cc(C#CC2CC2)ccc1-c1cn(C[C@H]2CCCCO2)nn1] |

-continued
| Compound No. | Structure |
|---|---|
| I-80 | 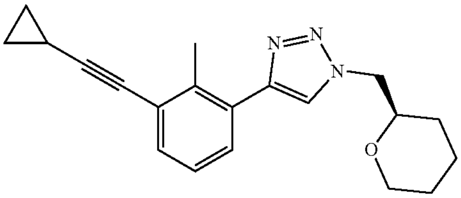 [SMILES: Cc1c(C#CC2CC2)cccc1-c1cn(C[C@H]2CCCCO2)nn1] |
| I-81 | 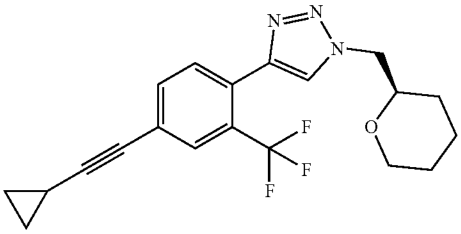 [SMILES: FC(F)(F)c1cc(C#CC2CC2)ccc1-c1cn(C[C@H]2CCCCO2)nn1] |
| I-82 | 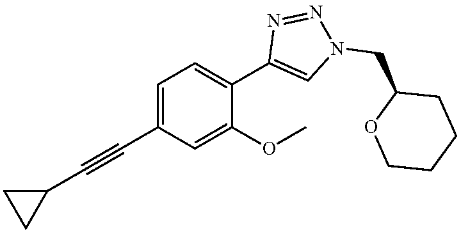 [SMILES: COc1cc(C#CC2CC2)ccc1-c1cn(C[C@H]2CCCCO2)nn1] |
| I-87 | 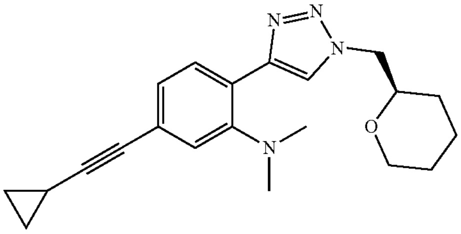 [SMILES: CN(C)c1cc(C#CC2CC2)ccc1-c1cn(C[C@H]2CCCCO2)nn1] |
| I-88 | 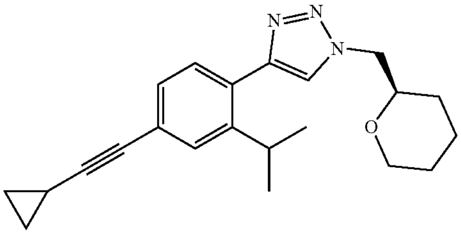 [SMILES: CC(C)c1cc(C#CC2CC2)ccc1-c1cn(C[C@H]2CCCCO2)nn1] |
| I-89 | 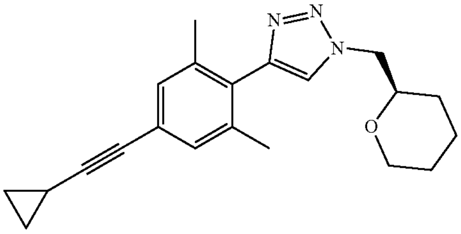 [SMILES: Cc1cc(C#CC2CC2)cc(C)c1-c1cn(C[C@H]2CCCCO2)nn1] |

-continued
| Compound No. | Structure |
|---|---|
| I-91 | 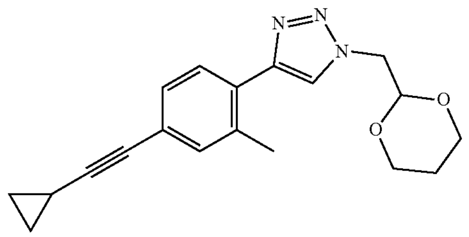 [SMILES: Cc1cc(C#CC2CC2)ccc1-c1cn(CC2OCCCO2)nn1] |
| I-102 | 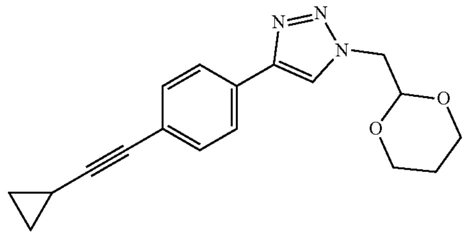 [SMILES: C(#CC1CC1)c1ccc(-c2cn(CC3OCCCO3)nn2)cc1] |
| I-107 | 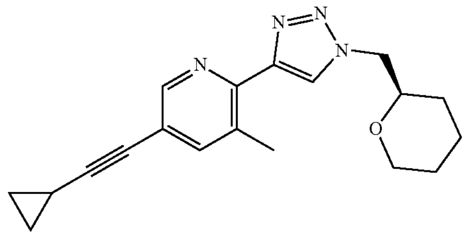 [SMILES: Cc1cc(C#CC2CC2)cnc1-c1cn(C[C@H]2CCCCO2)nn1] |
| I-108 | 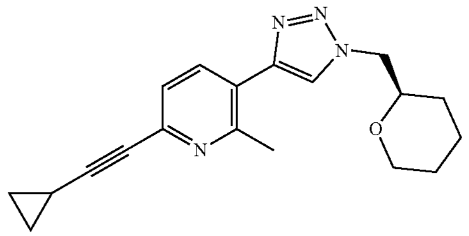 [SMILES: Cc1nc(C#CC2CC2)ccc1-c1cn(C[C@H]2CCCCO2)nn1] |
| I-117 | 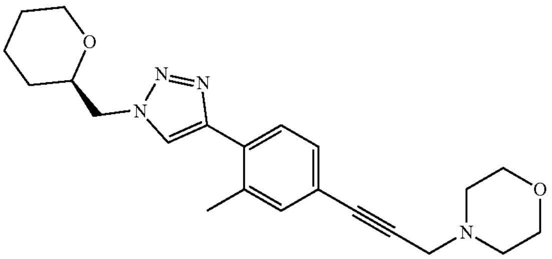 [SMILES: Cc1cc(C#CCN2CCOCC2)ccc1-c1cn(C[C@H]2CCCCO2)nn1] |
| I-118 | 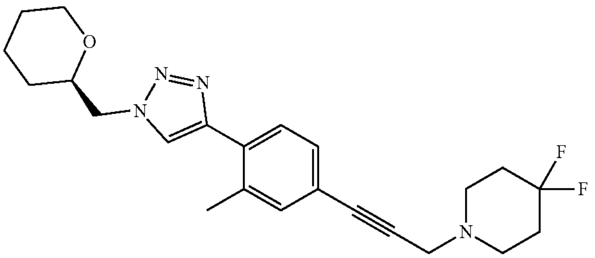 [SMILES: Cc1cc(C#CCN2CCC(F)(F)CC2)ccc1-c1cn(C[C@H]2CCCCO2)nn1] |

-continued
| Compound No. | Structure |
| --- | --- |
| I-119 | 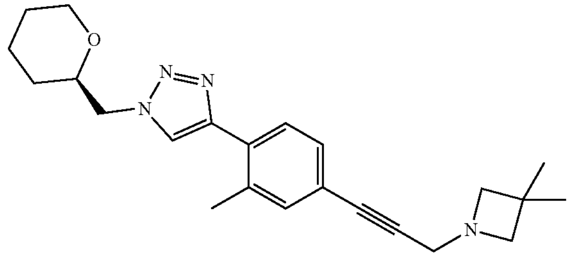 [SMILES: Cc1cc(C#CCN2CC(C)(C)C2)ccc1-c1cn(C[C@H]2CCCCO2)nn1] |
| I-122 | 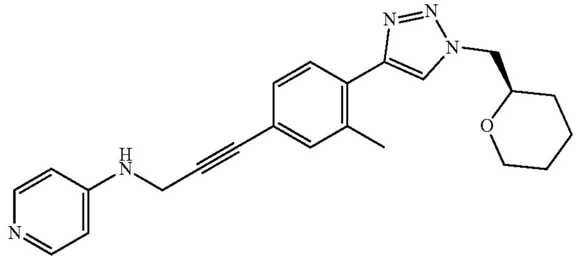 [SMILES: Cc1cc(C#CCNc2ccncc2)ccc1-c1cn(C[C@H]2CCCCO2)nn1] |
| I-124 | 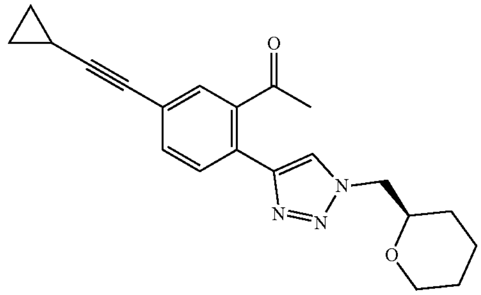 [SMILES: CC(=O)c1cc(C#CC2CC2)ccc1-c1cn(C[C@H]2CCCCO2)nn1] |
| I-125 | 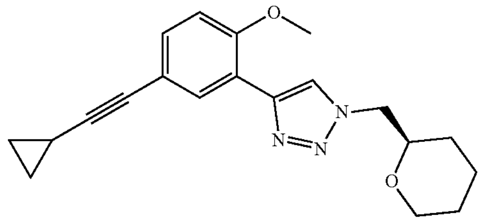 [SMILES: COc1ccc(C#CC2CC2)cc1-c1cn(C[C@H]2CCCCO2)nn1] |
| I-133 | 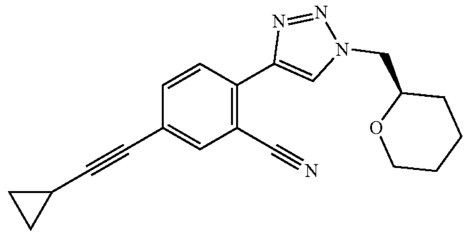 [SMILES: N#Cc1cc(C#CC2CC2)ccc1-c1cn(C[C@H]2CCCCO2)nn1] |
| I-134 | 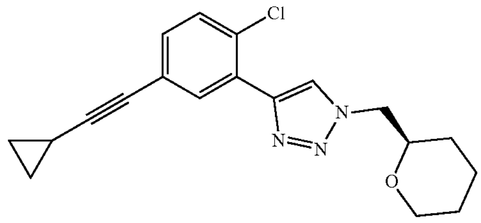 [SMILES: Clc1ccc(C#CC2CC2)cc1-c1cn(C[C@H]2CCCCO2)nn1] |

-continued
| Compound No. | Structure |
|---|---|
| I-144 | 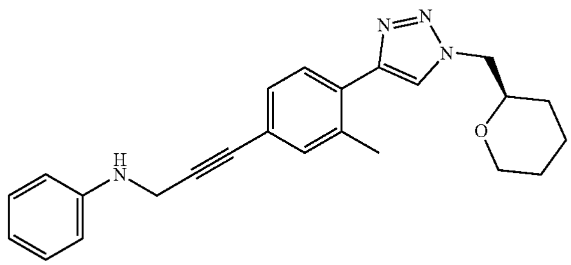 [SMILES: Cc1cc(C#CCNc2ccccc2)ccc1-c1cn(C[C@H]2CCCCO2)nn1] |
| I-160 | 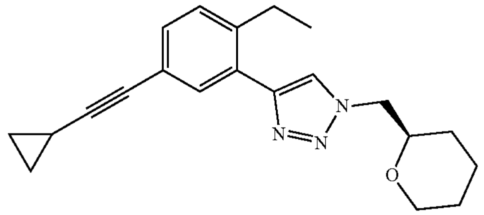 [SMILES: CCc1ccc(C#CC2CC2)cc1-c1cn(C[C@H]2CCCCO2)nn1] |
| I-166 | 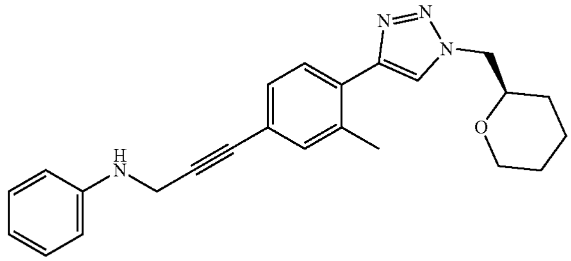 [SMILES: Cc1cc(C#CCNc2ccccc2)ccc1-c1cn(C[C@H]2CCCCO2)nn1] |
| I-174 | 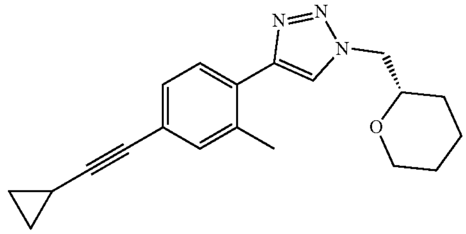 [SMILES: Cc1cc(C#CC2CC2)ccc1-c1cn(C[C@@H]2CCCCO2)nn1] |
| I-175 | 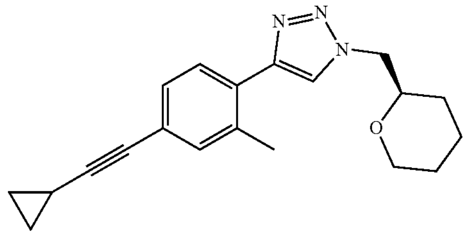 [SMILES: Cc1cc(C#CC2CC2)ccc1-c1cn(C[C@H]2CCCCO2)nn1] |
| I-178 | 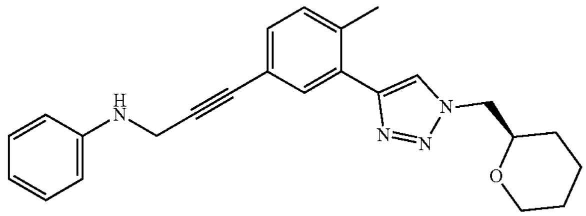 [SMILES: Cc1ccc(C#CCNc2ccccc2)cc1-c1cn(C[C@H]2CCCCO2)nn1] |

-continued
| Compound No. | Structure |
|---|---|
| I-179 | 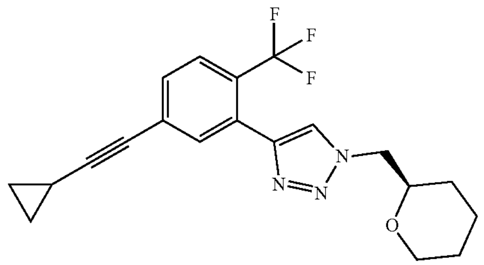 [SMILES: FC(F)(F)c1ccc(C#CC2CC2)cc1-c1cn(C[C@H]2CCCCO2)nn1] |
| I-187 | 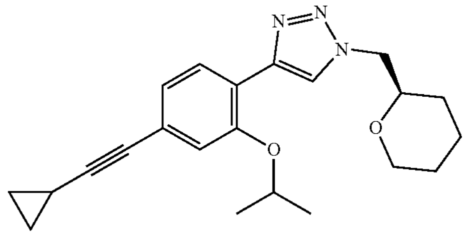 [SMILES: CC(C)Oc1cc(C#CC2CC2)ccc1-c1cn(C[C@H]2CCCCO2)nn1] |
| I-195 | 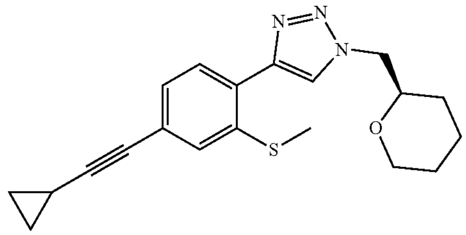 [SMILES: CSc1cc(C#CC2CC2)ccc1-c1cn(C[C@H]2CCCCO2)nn1] |
| I-203 | 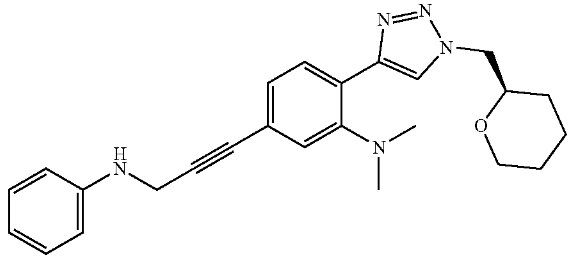 [SMILES: CN(C)c1cc(C#CCNc2ccccc2)ccc1-c1cn(C[C@H]2CCCCO2)nn1] |
| I-206 | 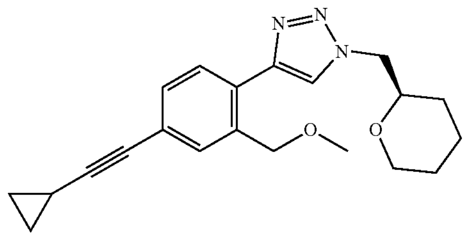 [SMILES: COCc1cc(C#CC2CC2)ccc1-c1cn(C[C@H]2CCCCO2)nn1] |
| I-207 | 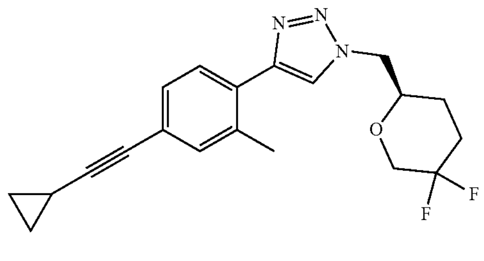 [SMILES: Cc1cc(C#CC2CC2)ccc1-c1cn(C[C@H]2CCC(F)(F)CO2)nn1] |

-continued
| Compound No. | Structure |
| --- | --- |
| I-214 | 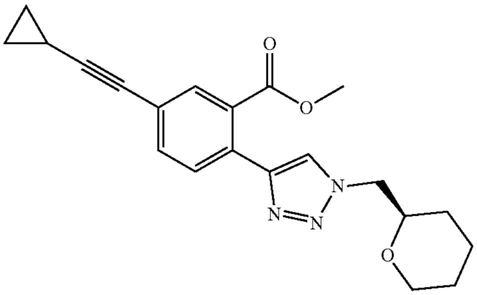 [SMILES: COC(=O)c1cc(C#CC2CC2)ccc1-c1cn(C[C@H]2CCCCO2)nn1] |
| I-215 | 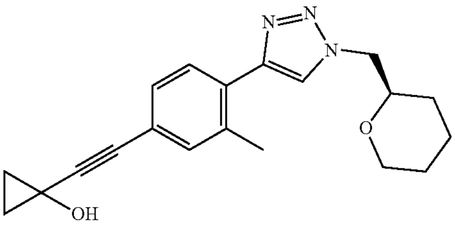 [SMILES: Cc1cc(C#CC2(O)CC2)ccc1-c1cn(C[C@H]2CCCCO2)nn1] |
| I-216 | 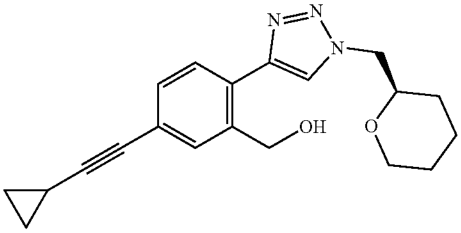 [SMILES: OCc1cc(C#CC2CC2)ccc1-c1cn(C[C@H]2CCCCO2)nn1] |
| I-217 | 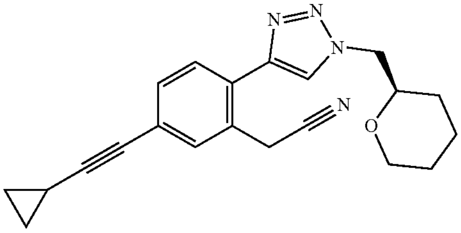 [SMILES: N#CCc1cc(C#CC2CC2)ccc1-c1cn(C[C@H]2CCCCO2)nn1] |
| I-218 | 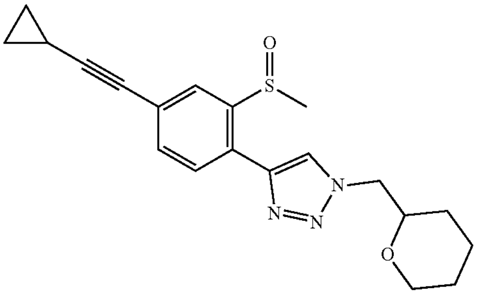 [SMILES: CS(=O)c1cc(C#CC2CC2)ccc1-c1cn(CC2CCCCO2)nn1] |

-continued
| Compound No. | Structure |
|---|---|
| I-219 | 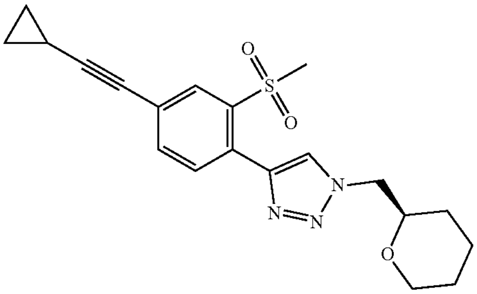 [SMILES: CS(=O)(=O)c1cc(C#CC2CC2)ccc1-c1cn(C[C@H]2CCCCO2)nn1] |
| I-220 | 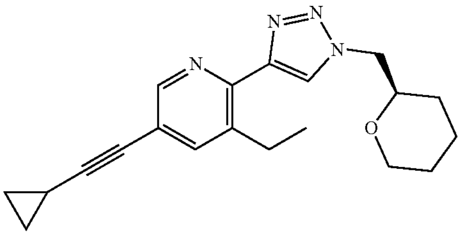 [SMILES: CCc1cc(C#CC2CC2)cnc1-c1cn(C[C@H]2CCCCO2)nn1] |
| I-228 | 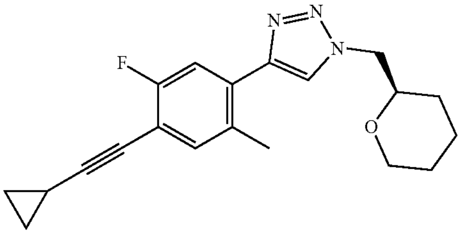 [SMILES: Cc1cc(C#CC2CC2)c(F)cc1-c1cn(C[C@H]2CCCCO2)nn1] |
| I-229 | 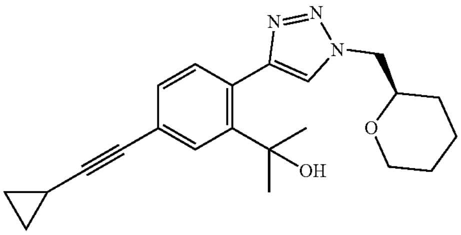 [SMILES: CC(C)(O)c1cc(C#CC2CC2)ccc1-c1cn(C[C@H]2CCCCO2)nn1] |
| I-234 | 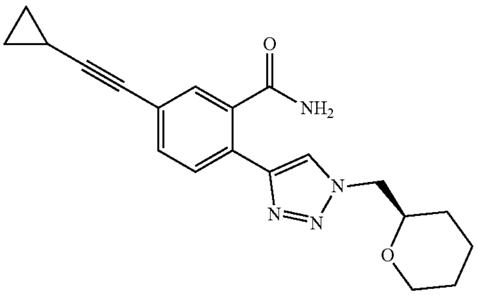 [SMILES: NC(=O)c1cc(C#CC2CC2)ccc1-c1cn(C[C@H]2CCCCO2)nn1] |
| I-245 | 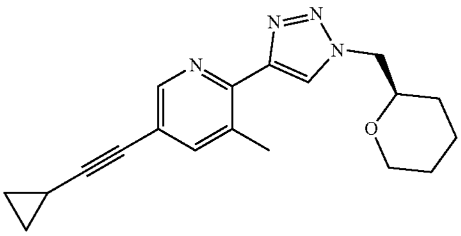 [SMILES: Cc1cc(C#CC2CC2)cnc1-c1cn(C[C@H]2CCCCO2)nn1] |

-continued
| Compound No. | Structure |
|---|---|
| I-249 | 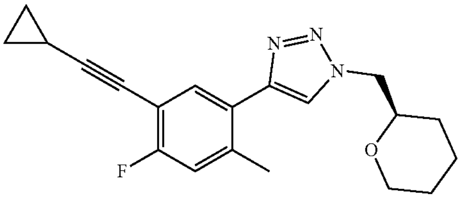 [SMILES: Cc1cc(F)c(C#CC2CC2)cc1-c1cn(C[C@H]2CCCCO2)nn1] |
| I-259 | 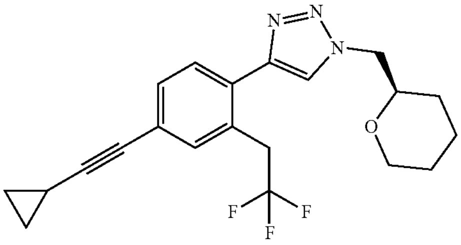 [SMILES: FC(F)(F)Cc1cc(C#CC2CC2)ccc1-c1cn(C[C@H]2CCCCO2)nn1] |
| I-266 | 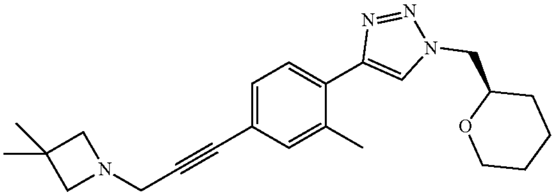 [SMILES: Cc1cc(C#CCN2CC(C)(C)C2)ccc1-c1cn(C[C@H]2CCCCO2)nn1] |
| I-277 | 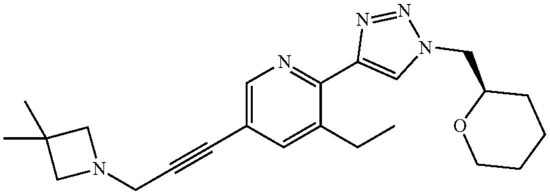 [SMILES: CCc1cc(C#CCN2CC(C)(C)C2)cnc1-c1cn(C[C@H]2CCCCO2)nn1] |
| I-284 | 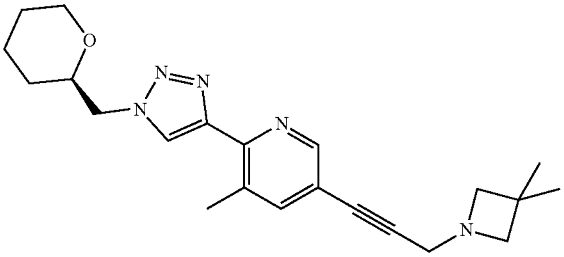 [SMILES: Cc1cc(C#CCN2CC(C)(C)C2)cnc1-c1cn(C[C@H]2CCCCO2)nn1] |
| I-294 | 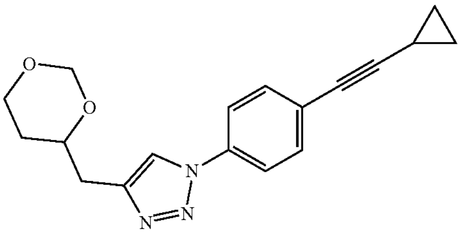 [SMILES: C(#CC1CC1)c1ccc(-n2cc(CC3CCOCO3)nn2)cc1] |

-continued
| Compound No. | Structure |
|---|---|
| I-307 | 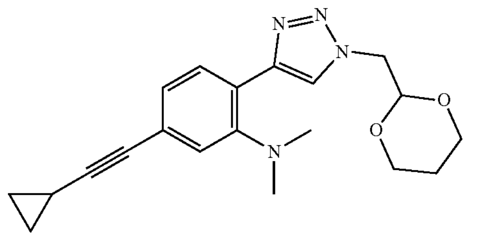 [SMILES: CN(C)c1cc(C#CC2CC2)ccc1-c1cn(CC2OCCCO2)nn1] |
| I-308 | 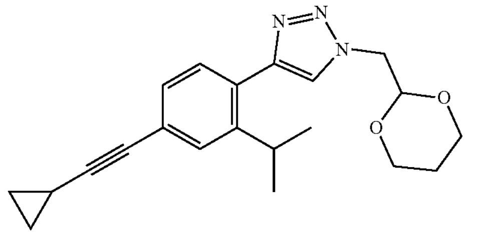 [SMILES: CC(C)c1cc(C#CC2CC2)ccc1-c1cn(CC2OCCCO2)nn1] |
| I-309 | 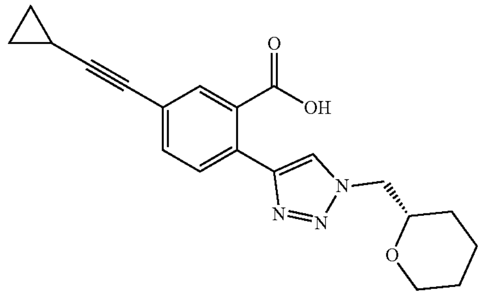 [SMILES: O=C(O)c1cc(C#CC2CC2)ccc1-c1cn(C[C@@H]2CCCCO2)nn1] |
| I-355 | 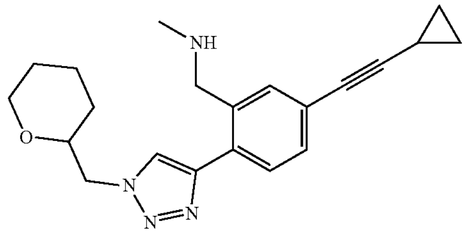 [SMILES: CNCc1cc(C#CC2CC2)ccc1-c1cn(CC2CCCCO2)nn1] |
| I-356 | 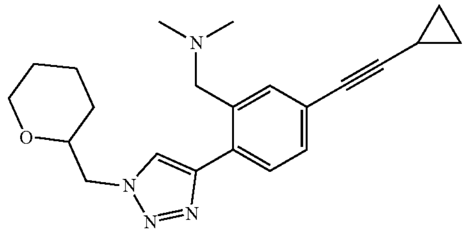 [SMILES: CN(C)Cc1cc(C#CC2CC2)ccc1-c1cn(CC2CCCCO2)nn1] |
| I-359 | 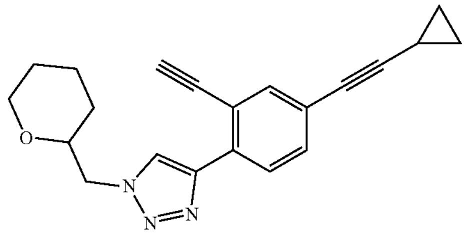 [SMILES: C#Cc1cc(C#CC2CC2)ccc1-c1cn(CC2CCCCO2)nn1] |

-continued
| Compound No. | Structure |
|---|---|
| I-361 | 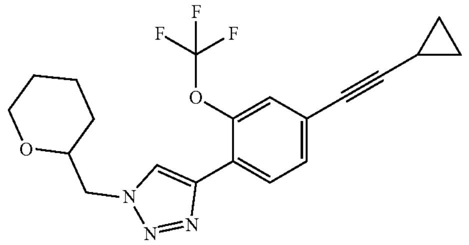 [SMILES: FC(F)(F)Oc1cc(C#CC2CC2)ccc1-c1cn(CC2CCCCO2)nn1] |
| I-362 | 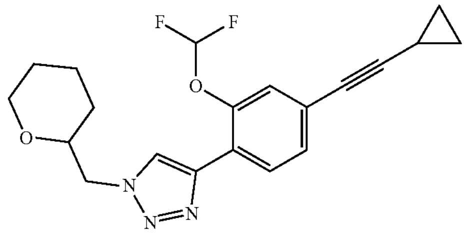 [SMILES: FC(F)Oc1cc(C#CC2CC2)ccc1-c1cn(CC2CCCCO2)nn1] |
| I-365 | 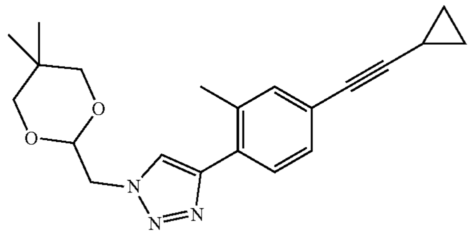 [SMILES: Cc1cc(C#CC2CC2)ccc1-c1cn(CC2OCC(C)(C)CO2)nn1] |
| I-367 | 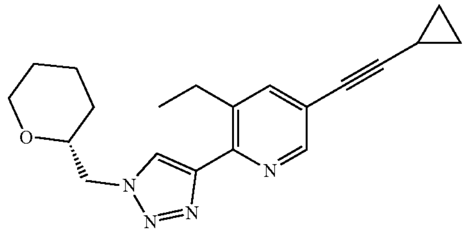 [SMILES: CCc1cc(C#CC2CC2)cnc1-c1cn(C[C@H]2CCCCO2)nn1] |
| I-369 | 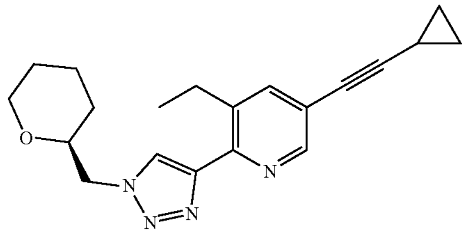 [SMILES: CCc1cc(C#CC2CC2)cnc1-c1cn(C[C@@H]2CCCCO2)nn1] |
| I-370 | 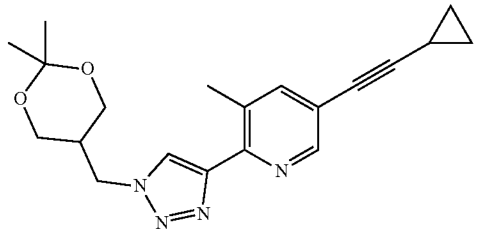 [SMILES: Cc1cc(C#CC2CC2)cnc1-c1cn(CC2COC(C)(C)OC2)nn1] |

-continued
| Compound No. | Structure |
| --- | --- |
| I-371 | 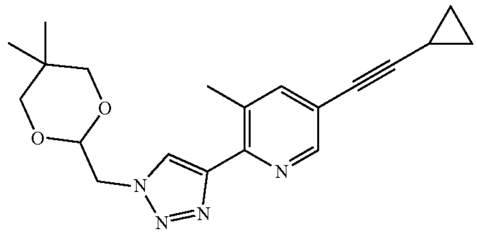 [SMILES: Cc1cc(C#CC2CC2)cnc1-c1cn(CC2OCC(C)(C)CO2)nn1] |
| I-374 | 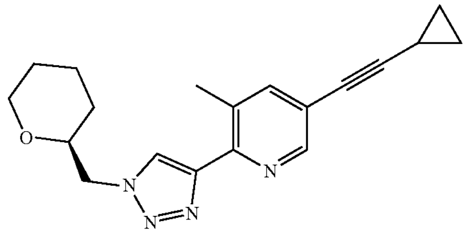 [SMILES: Cc1cc(C#CC2CC2)cnc1-c1cn(C[C@@H]2CCCCO2)nn1] |
| I-393 | 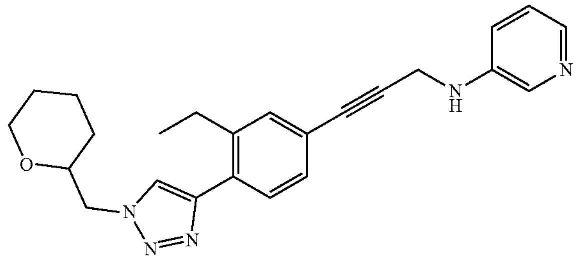 [SMILES: CCc1cc(C#CCNc2cccnc2)ccc1-c1cn(CC2CCCCO2)nn1] |
| I-394 | 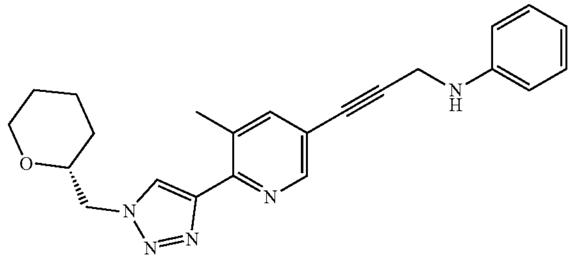 [SMILES: Cc1cc(C#CCNc2ccccc2)cnc1-c1cn(C[C@H]2CCCCO2)nn1] |
| I-402 | 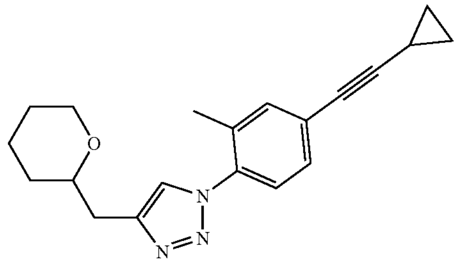 [SMILES: Cc1cc(C#CC2CC2)ccc1-n1cc(CC2CCCCO2)nn1] |
| I-413 | 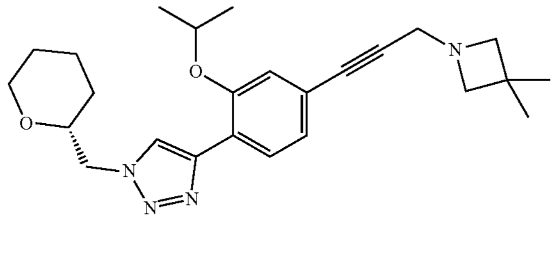 [SMILES: CC(C)Oc1cc(C#CCN2CC(C)(C)C2)ccc1-c1cn(C[C@H]2CCCCO2)nn1] |

-continued
| Compound No. | Structure |
|---|---|
| I-414 | 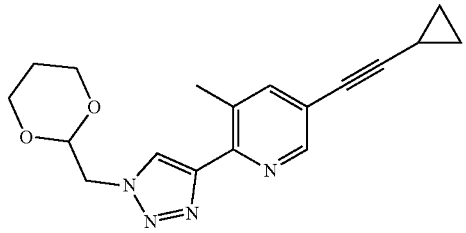 [SMILES: Cc1cc(C#CC2CC2)cnc1-c1cn(CC2OCCCO2)nn1] |
| I-455 | 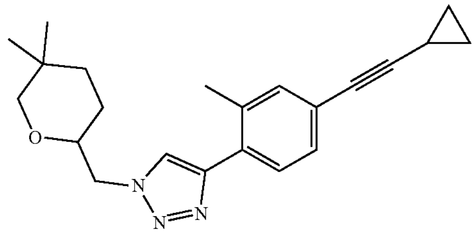 [SMILES: Cc1cc(C#CC2CC2)ccc1-c1cn(CC2CCC(C)(C)CO2)nn1] |
| I-462 | 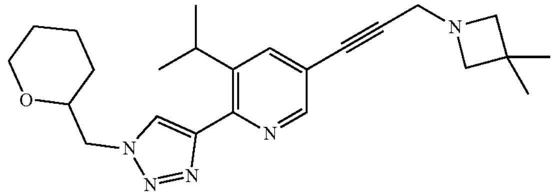 [SMILES: CC(C)c1cc(C#CCN2CC(C)(C)C2)cnc1-c1cn(CC2CCCCO2)nn1] |
| I-475 | 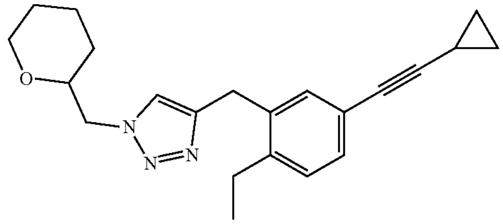 [SMILES: CCc1ccc(C#CC2CC2)cc1Cc1cn(CC2CCCCO2)nn1] |
| I-476 | 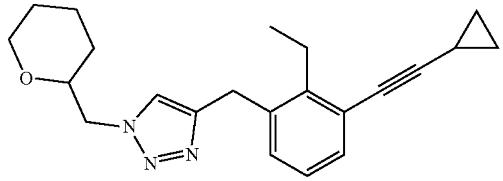 [SMILES: CCc1c(C#CC2CC2)cccc1Cc1cn(CC2CCCCO2)nn1] |
| I-478 | 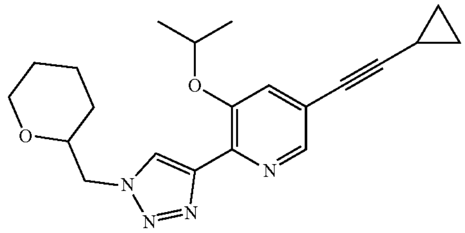 [SMILES: CC(C)Oc1cc(C#CC2CC2)cnc1-c1cn(CC2CCCCO2)nn1] |
| I-479 | 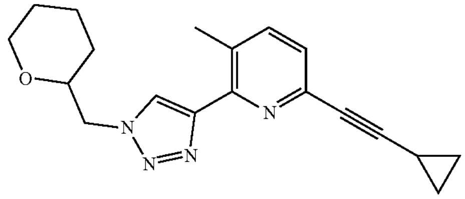 [SMILES: Cc1ccc(C#CC2CC2)nc1-c1cn(CC2CCCCO2)nn1] |

-continued
| Compound No. | Structure |
| --- | --- |
| I-497 | 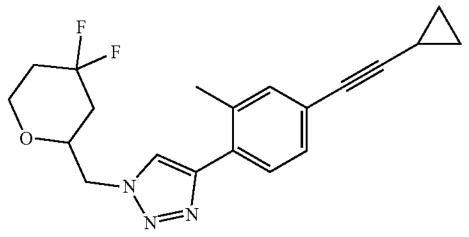 |
| I-498 | 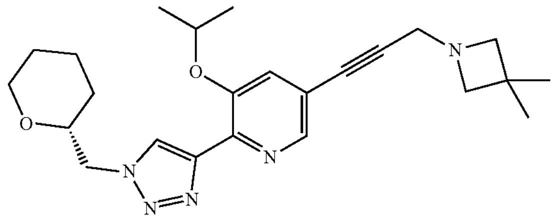 [SMILES: CC(C)Oc1cc(C#CCN2CC(C)(C)C2)cnc1-c1cn(C[C@H]2CCCCO2)nn1] |
| I-505 | 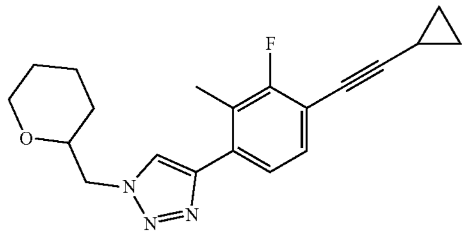 [SMILES: Cc1c(-c2cn(CC3CCCCO3)nn2)ccc(C#CC2CC2)c1F] |
| I-518 | 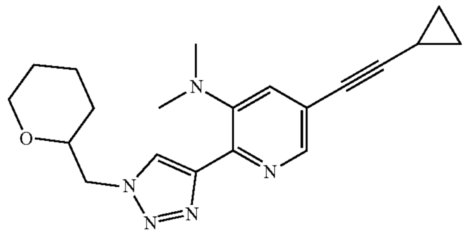 [SMILES: CN(C)c1cc(C#CC2CC2)cnc1-c1cn(CC2CCCCO2)nn1] |
| I-522 | 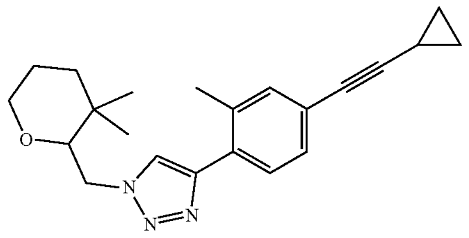 [SMILES: Cc1cc(C#CC2CC2)ccc1-c1cn(CC2OCCCC2(C)C)nn1] |
| I-535 | 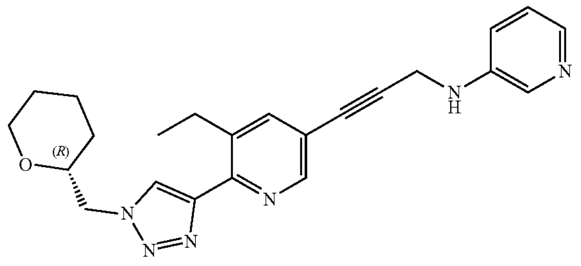 |

-continued
| Compound No. | Structure |
|---|---|
| I-554 | 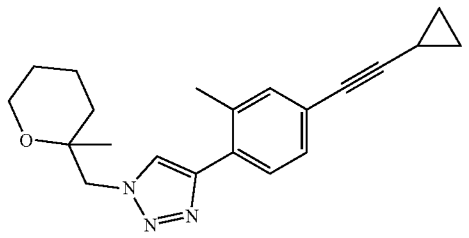 [SMILES: Cc1cc(C#CC2CC2)ccc1-c1cn(CC2(C)CCCCO2)nn1] |
| I-560 | 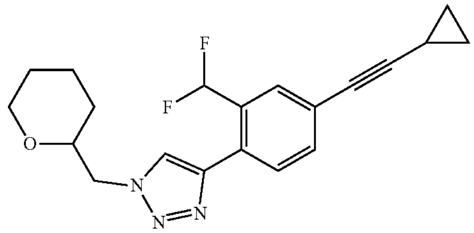 [SMILES: FC(F)c1cc(C#CC2CC2)ccc1-c1cn(CC2CCCCO2)nn1] |
| I-568 | 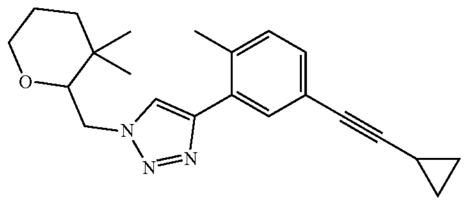 [SMILES: Cc1ccc(C#CC2CC2)cc1-c1cn(CC2OCCCC2(C)C)nn1] |
| I-575 | 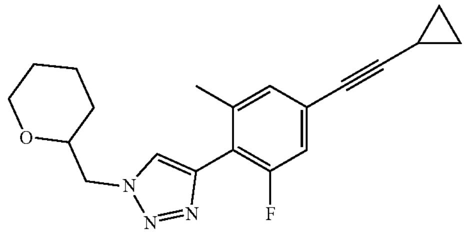 [SMILES: Cc1cc(C#CC2CC2)cc(F)c1-c1cn(CC2CCCCO2)nn1] |
| I-576 | 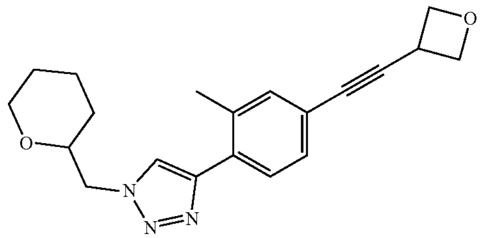 [SMILES: Cc1cc(C#CC2COC2)ccc1-c1cn(CC2CCCCO2)nn1] |
| I-596 | 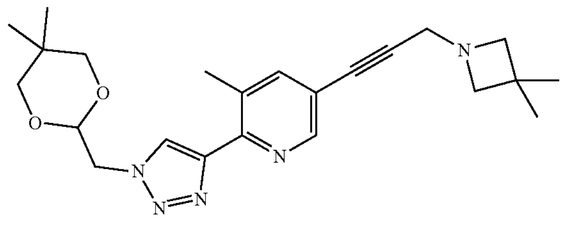 |

-continued
| Compound No. | Structure |
|---|---|
| I-599 | 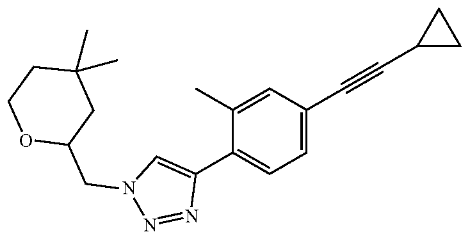 [SMILES: Cc1cc(C#CC2CC2)ccc1-c1cn(CC2CC(C)(C)CCO2)nn1] |
| I-610 | 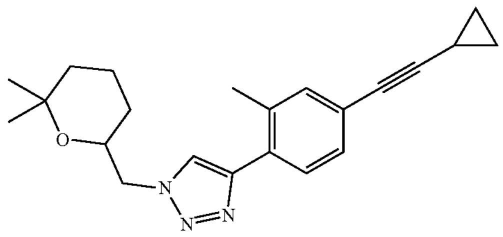 [SMILES: Cc1cc(C#CC2CC2)ccc1-c1cn(CC2CCCC(C)(C)O2)nn1] |
| I-619 | 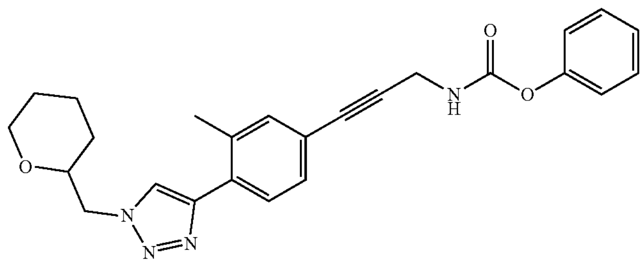 [SMILES: Cc1cc(C#CCNC(=O)Oc2ccccc2)ccc1-c1cn(CC2CCCCO2)nn1] |
| I-634 | 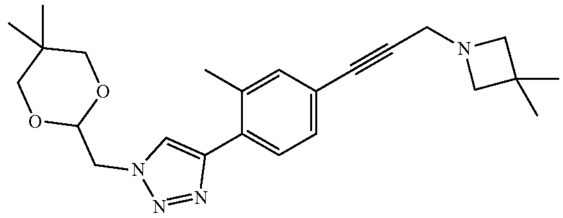 |
| I-651 | 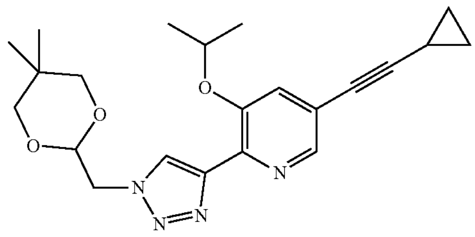 [SMILES: CC(C)Oc1cc(C#CC2CC2)cnc1-c1cn(CC2OCC(C)(C)CO2)nn1] |
| I-658 | 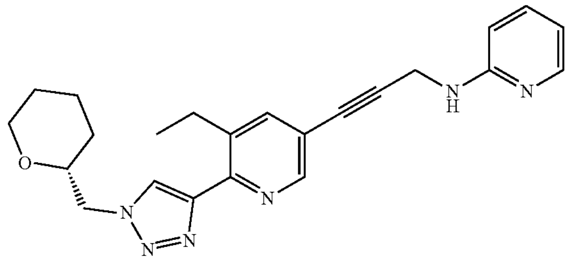 [SMILES: CCc1cc(C#CCNc2ccccn2)cnc1-c1cn(C[C@H]2CCCCO2)nn1] |

-continued
| Compound No. | Structure |
|---|---|
| I-659 | 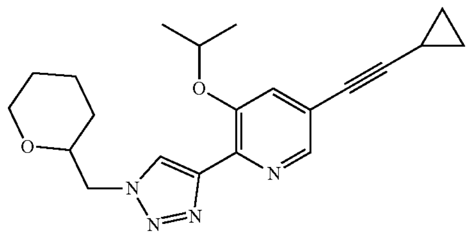 [SMILES: CC(C)Oc1cc(C#CC2CC2)cnc1-c1cn(CC2CCCCO2)nn1] |
| I-666 | 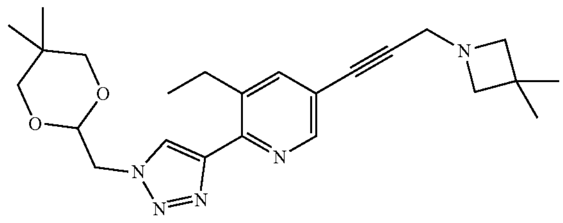 |
| I-670 | 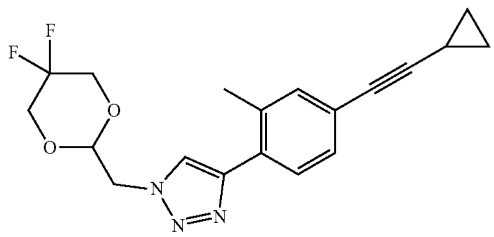 [SMILES: Cc1cc(C#CC2CC2)ccc1-c1cn(CC2OCC(F)(F)CO2)nn1] |
| I-676 | 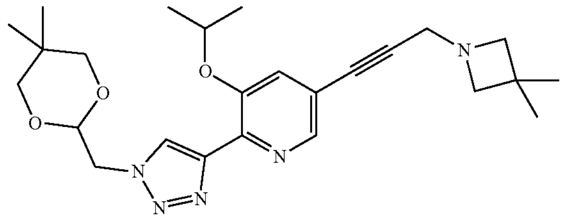 |
| I-686 | 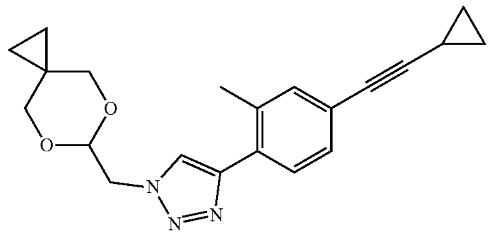 [SMILES: Cc1cc(C#CC2CC2)ccc1-c1cn(CC2OCC3(CC3)CO2)nn1] |
| I-697 | 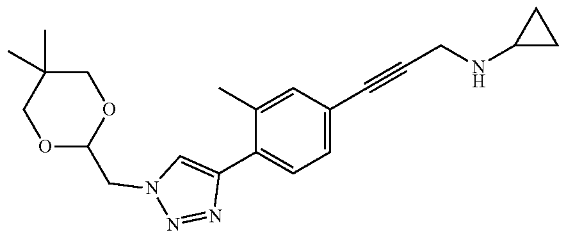 [SMILES: Cc1cc(C#CCNC2CC2)ccc1-c1cn(CC2OCC(C)(C)CO2)nn1] |

-continued
| Compound No. | Structure |
|---|---|
| I-700 | 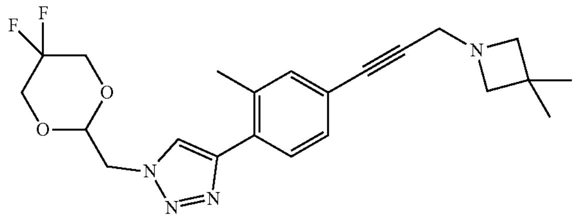 [SMILES: Cc1cc(C#CCN2CC(C)(C)C2)ccc1-c1cn(CC2OCC(F)(F)CO2)nn1] |
| I-708 | 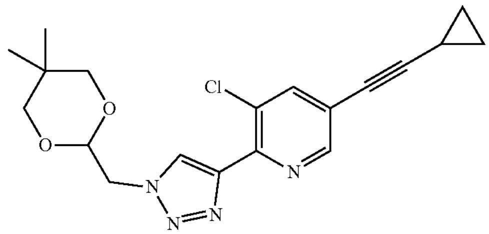 [SMILES: CC1(C)COC(Cn2cc(-c3ncc(C#CC4CC4)cc3Cl)nn2)OC1] |
| I-713 | 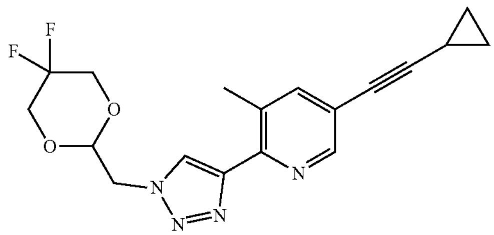 [SMILES: Cc1cc(C#CC2CC2)cnc1-c1cn(CC2OCC(F)(F)CO2)nn1] |
| I-719 | 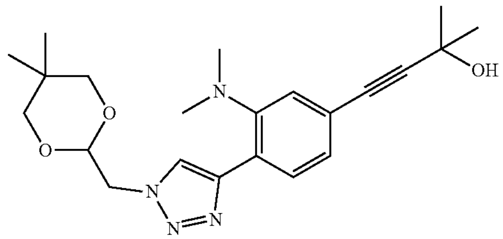 [SMILES: CN(C)c1cc(C#CC(C)(C)O)ccc1-c1cn(CC2OCC(C)(C)CO2)nn1] |
| I-722 | 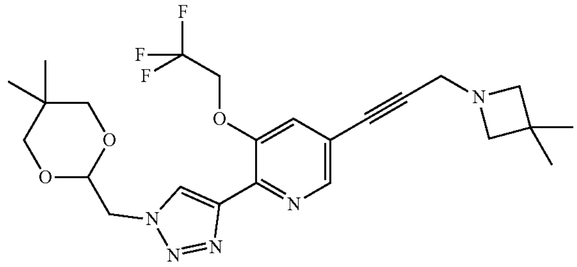 |
| I-727 | 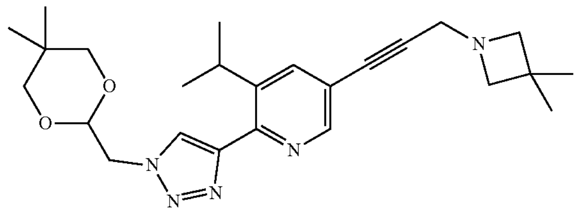 |

-continued
| Compound No. | Structure |
|---|---|
| I-736 | 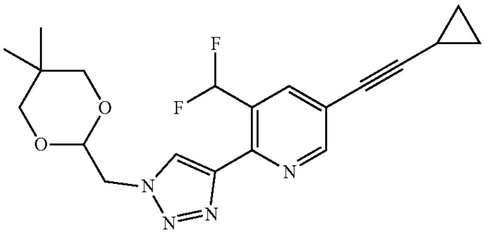 [SMILES: CC1(C)COC(Cn2cc(-c3ncc(C#CC4CC4)cc3C(F)F)nn2)OC1] |
| I-738 | 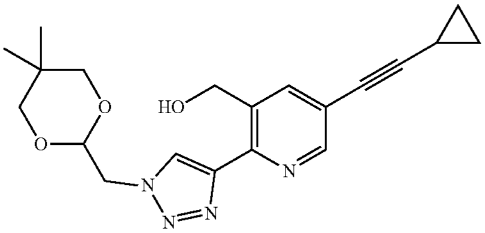 [SMILES: CC1(C)COC(Cn2cc(-c3ncc(C#CC4CC4)cc3CO)nn2)OC1] |
| I-750 | 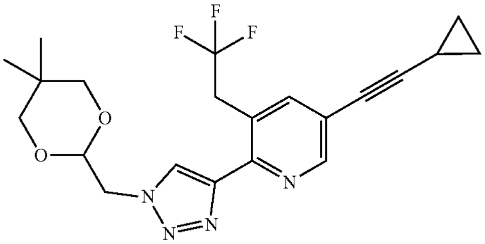 [SMILES: CC1(C)COC(Cn2cc(-c3ncc(C#CC4CC4)cc3CC(F)(F)F)nn2)OC1] |
| I-757 | 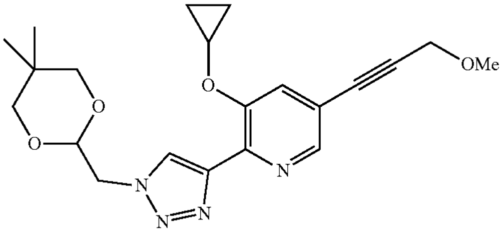 [SMILES: COCC#Cc1cnc(-c2cn(CC3OCC(C)(C)CO3)nn2)c(OC2CC2)c1] |
| I-762 | 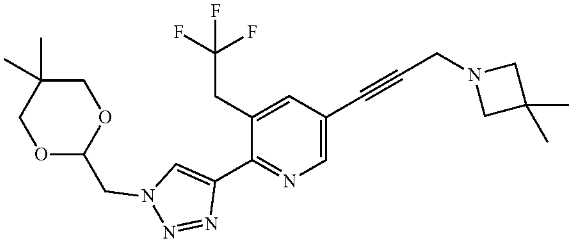 |
| I-771 | 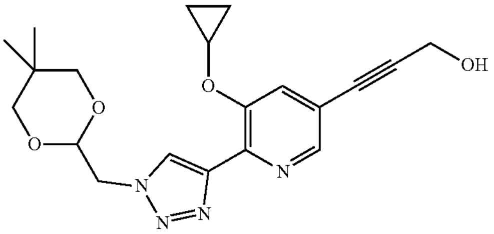 [SMILES: CC1(C)COC(Cn2cc(-c3ncc(C#CCO)cc3OC3CC3)nn2)OC1] |

-continued
| Compound No. | Structure |
|---|---|
| I-777 | 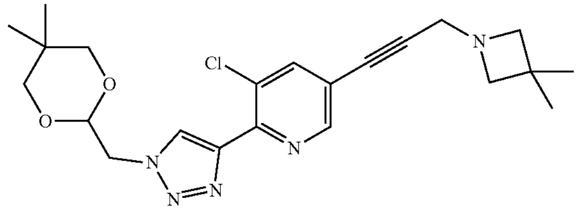 |
| I-789 | 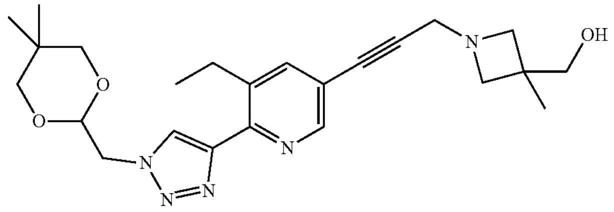 [SMILES: CCc1cc(C#CCN2CC(C)(CO)C2)cnc1-c1cn(CC2OCC(C)(C)CO2)nn1] |
| I-797 | 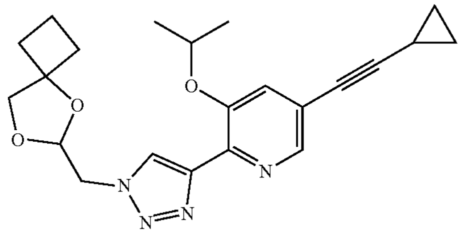 [SMILES: CC(C)Oc1cc(C#CC2CC2)cnc1-c1cn(CC2OCC3(CCC3)O2)nn1] |
| I-806 | 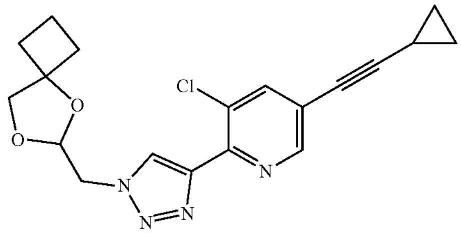 [SMILES: Clc1cc(C#CC2CC2)cnc1-c1cn(CC2OCC3(CCC3)O2)nn1] |
| I-815 | 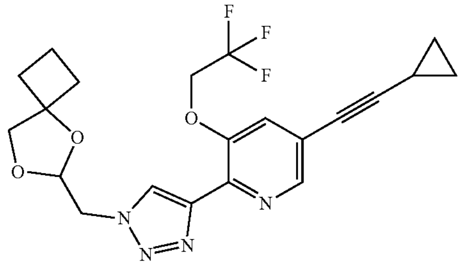 [SMILES: FC(F)(F)COc1cc(C#CC2CC2)cnc1-c1cn(CC2OCC3(CCC3)O2)nn1] |
| I-817 | 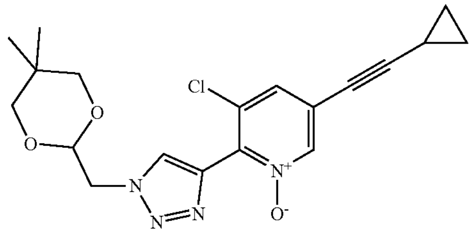 [SMILES: CC1(C)COC(Cn2cc(-c3c(Cl)cc(C#CC4CC4)c[n+]3[O-])nn2)OC1] |

-continued
| Compound No. | Structure |
|---|---|
| I-818 | 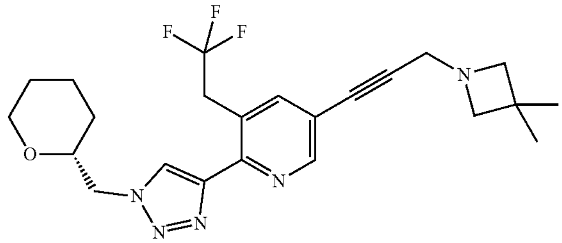 [SMILES: CC1(C)CN(CC#Cc2cnc(-c3cn(C[C@H]4CCCCO4)nn3)c(CC(F)(F)F)c2)C1] |
| I-819 | 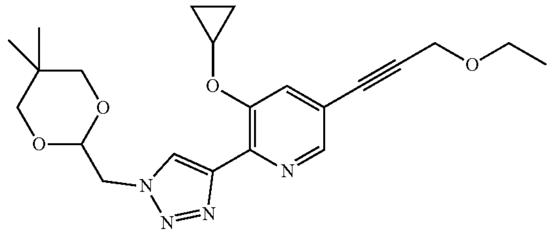 [SMILES: CCOCC#Cc1cnc(-c2cn(CC3OCC(C)(C)CO3)nn2)c(OC2CC2)c1] |
| I-821 | 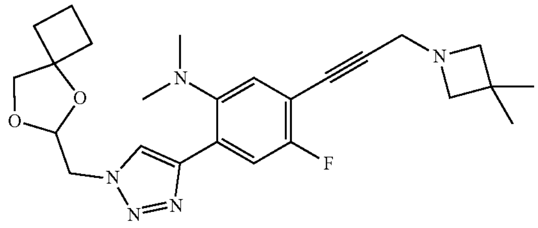 [SMILES: CN(C)c1cc(C#CCN2CC(C)(C)C2)c(F)cc1-c1cn(CC2OCC3(CCC3)O2)nn1] |
| I-822 | 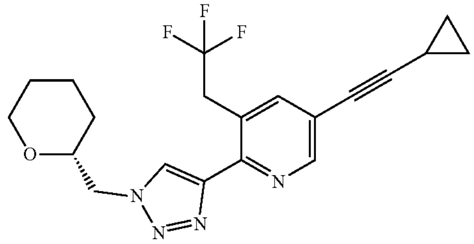 [SMILES: FC(F)(F)Cc1cc(C#CC2CC2)cnc1-c1cn(C[C@H]2CCCCO2)nn1] |
| I-833 | 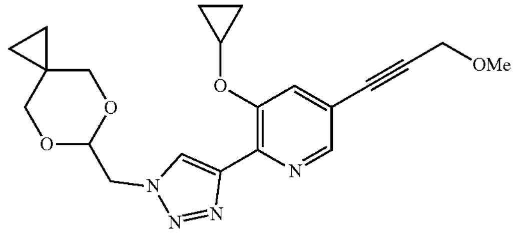 [SMILES: COCC#Cc1cnc(-c2cn(CC3OCC4(CC4)CO3)nn2)c(OC2CC2)c1] |
| I-851 | 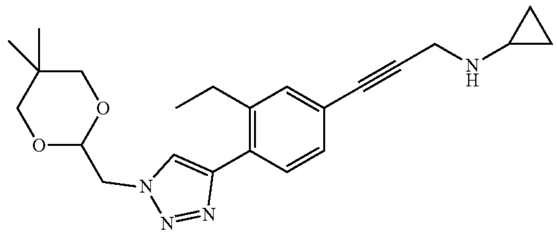 [SMILES: CCc1cc(C#CCNC2CC2)ccc1-c1cn(CC2OCC(C)(C)CO2)nn1] |

-continued
| Compound No. | Structure |
|---|---|
| I-865 | 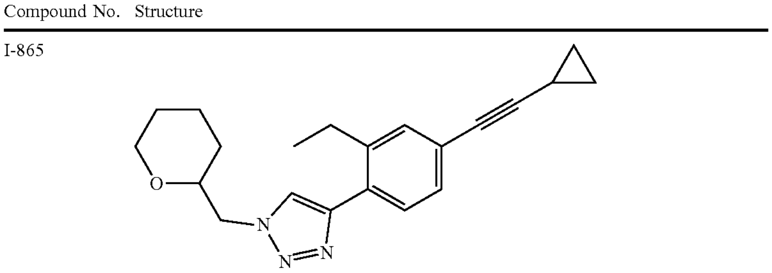 |
| I-866 | 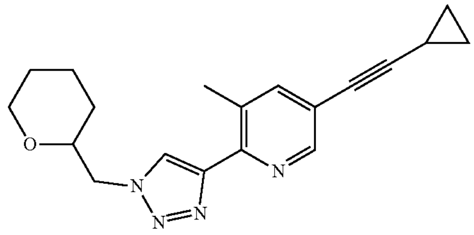 [SMILES: Cc1cc(C#CC2CC2)cnc1-c1cn(CC2CCCCO2)nn1] |
| I-877 | 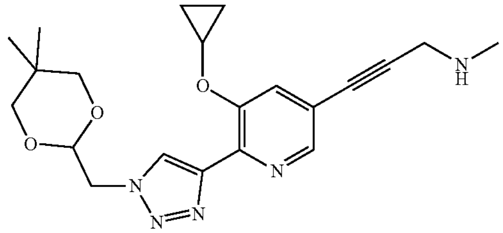 |
| I-878 | 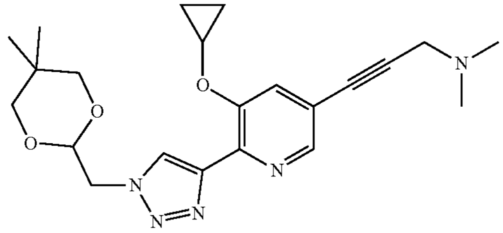 |
| I-883 | 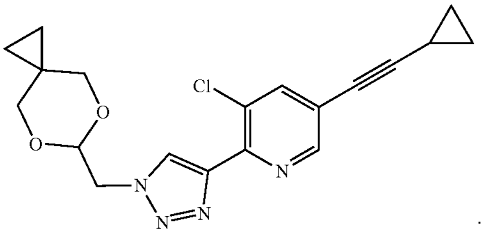 [SMILES: Clc1cc(C#CC2CC2)cnc1-c1cn(CC2OCC3(CC3)CO2)nn1] |
* * * * *